United States Patent
Winston et al.

(10) Patent No.: US 12,076,371 B2
(45) Date of Patent: *Sep. 3, 2024

(54) ACTIVATABLE CYTOKINE POLYPEPTIDES AND METHODS OF USE THEREOF

(71) Applicant: Werewolf Therapeutics, Inc., Cambridge, MA (US)

(72) Inventors: William Winston, West Newton, MA (US); Daniel Hicklin, Boston, MA (US); Jose Andres Salemeron-Garcia, Acton, MA (US); Heather Brodkin, West Newton, MA (US); Cynthia Seidel-Dugan, Belmont, MA (US)

(73) Assignee: Werewolf Therapeutics, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/166,700

(22) Filed: Feb. 9, 2023

(65) Prior Publication Data

US 2024/0033326 A1     Feb. 1, 2024

Related U.S. Application Data

(63) Continuation of application No. 17/934,811, filed on Sep. 23, 2022, which is a continuation of application No. 17/741,275, filed on May 10, 2022, which is a continuation of application No. PCT/US2020/060624, filed on Nov. 14, 2020.

(60) Provisional application No. 62/935,605, filed on Nov. 14, 2019.

(51) Int. Cl.

| | |
|---|---|
| A61K 47/64 | (2017.01) |
| A61K 35/17 | (2015.01) |
| A61K 38/17 | (2006.01) |
| A61K 38/20 | (2006.01) |
| A61K 38/21 | (2006.01) |
| A61K 47/65 | (2017.01) |
| A61K 47/68 | (2017.01) |
| A61P 31/12 | (2006.01) |
| A61P 35/00 | (2006.01) |
| C12N 15/63 | (2006.01) |

(52) U.S. Cl.
CPC .......... *A61K 38/2013* (2013.01); *A61K 35/17* (2013.01); *A61K 38/1774* (2013.01); *A61K 38/208* (2013.01); *A61K 38/212* (2013.01); *A61K 38/215* (2013.01); *A61K 38/217* (2013.01); *A61K 47/6425* (2017.08); *A61K 47/65* (2017.08); *A61K 47/6813* (2017.08); *A61K 47/6845* (2017.08); *A61P 31/12* (2018.01); *A61P 35/00* (2018.01); *C12N 15/63* (2013.01)

(58) Field of Classification Search
None
See application file for complete search history.

(56) References Cited

U.S. PATENT DOCUMENTS

| | | |
|---|---|---|
| 4,419,446 A | 12/1983 | Howley et al. |
| 4,560,655 A | 12/1985 | Baker |
| 4,601,978 A | 7/1986 | Karin |
| 4,657,866 A | 4/1987 | Kumar |
| 4,676,980 A | 6/1987 | Segal et al. |
| 4,767,704 A | 8/1988 | Cleveland |
| 4,816,567 A | 3/1989 | Cabilly et al. |
| 4,927,762 A | 5/1990 | Darfier |
| 4,965,199 A | 10/1990 | Capon et al. |
| 5,089,261 A | 2/1992 | Nitecki et al. |
| 5,122,464 A | 6/1992 | Wilson et al. |
| 5,122,469 A | 6/1992 | Mather et al. |
| 5,208,020 A | 5/1993 | Chari et al. |
| 5,264,365 A | 11/1993 | Georgiou |
| 5,416,064 A | 5/1995 | Chari et al. |
| 5,508,192 A | 4/1996 | Georgiou et al. |
| 5,571,894 A | 11/1996 | Weis et al. |
| 5,587,458 A | 12/1996 | King et al. |
| 5,624,821 A | 4/1997 | Winter et al. |
| 5,635,483 A | 6/1997 | Pettit et al. |
| 5,639,635 A | 6/1997 | Joly et al. |

(Continued)

FOREIGN PATENT DOCUMENTS

| | | |
|---|---|---|
| EP | 547163 B1 | 2/2002 |
| EP | 2639241 A2 | 9/2013 |

(Continued)

OTHER PUBLICATIONS

Giesen et al., 8O89Zr-labeled anti-PD-L1 CX-072 PET imaging in human xenograft and syngeneic tumors, Annals of Oncology, Feb. 27, 2019, vol. 30, Issue Supplement 1, Oxford Academic.

Gillies, et al "Improved circulating half-life and efficacy of an antibody-interleukin 2 immunocytokine based on reduced intracellular proteolysis" Clinical Cancer Research, the American Association for Cancer Research, US, 8(1) Jan. 2002, 210-216.

Gerber et al Preferential attachment of peritoneal tumor metastases to omental immune aggregates and possible role of a unique vascular microenvironment in metastatic survival and growth. Am J Pathol 169(5): 1739-1752.

(Continued)

*Primary Examiner* — Michail A Belyavskyi
(74) *Attorney, Agent, or Firm* — Ice Miller LLP

(57) ABSTRACT

The disclosure features fusion proteins that are conditionally active variants of a cytokine of interest. In one aspect, the full-length polypeptides of the invention have reduced or minimal cytokine-receptor activating activity even though they contain a functional cytokine polypeptide. Upon activation, e.g., by cleavage of a linker that joins a blocking moiety, e.g., a steric blocking polypeptide, in sequence to the active cytokine, the cytokine can bind its receptor and effect signaling. Typically, the fusion proteins further comprise an in vivo half-life extension element, which may be cleaved from the cytokine in the tumor microenvironment.

29 Claims, 223 Drawing Sheets

Specification includes a Sequence Listing.

(56) References Cited

U.S. PATENT DOCUMENTS

| | | |
|---|---|---|
| 5,641,870 A | 6/1997 | Rinderknecht et al. |
| 5,648,237 A | 7/1997 | Carter et al. |
| 5,648,260 A | 7/1997 | Winter et al. |
| 5,712,374 A | 1/1998 | Kunstmann et al. |
| 5,714,586 A | 2/1998 | Kunstmann et al. |
| 5,739,277 A | 4/1998 | Presta et al. |
| 5,767,285 A | 6/1998 | Hamann et al. |
| 5,770,701 A | 6/1998 | McGahren et al. |
| 5,770,710 A | 6/1998 | McGahren et al. |
| 5,773,001 A | 6/1998 | Hamann et al. |
| 5,780,588 A | 7/1998 | Pettit et al. |
| 5,834,597 A | 11/1998 | Tso et al. |
| 5,869,046 A | 2/1999 | Presta et al. |
| 5,877,296 A | 3/1999 | Hamann et al. |
| 5,891,693 A | 4/1999 | Bebbington et al. |
| 5,939,598 A | 8/1999 | Kucherlapati et al. |
| 6,027,888 A | 2/2000 | Georgiou et al. |
| 6,075,181 A | 6/2000 | Kucherlapati et al. |
| 6,083,715 A | 7/2000 | Georgiou et al. |
| 6,114,598 A | 9/2000 | Kucherlapati et al. |
| 6,150,584 A | 11/2000 | Kucherlapati et al. |
| 6,162,963 A | 12/2000 | Kucherlapati et al. |
| 6,165,745 A | 12/2000 | Ward et al. |
| 6,248,516 B1 | 6/2001 | Winter et al. |
| 6,602,684 B1 | 8/2003 | Umana et al. |
| 6,630,579 B2 | 10/2003 | Chari et al. |
| 6,670,147 B1 | 12/2003 | Heidtman et al. |
| 6,821,505 B2 | 11/2004 | Ward et al. |
| 6,942,853 B2 | 9/2005 | Chernajovsky et al. |
| 7,498,298 B2 | 3/2009 | Doronina et al. |
| 7,514,073 B2 | 4/2009 | Epstein et al. |
| 8,399,219 B2 | 3/2013 | Stagliano et al. |
| 8,734,774 B2 | 5/2014 | Frelinger et al. |
| 8,809,504 B2 | 8/2014 | Lauermann et al. |
| 8,969,538 B2 | 3/2015 | Rosen et al. |
| 9,206,243 B2 | 12/2015 | Monzon et al. |
| 9,487,590 B2 | 11/2016 | West et al. |
| 9,540,440 B2 | 1/2017 | Lowman et al. |
| 9,708,412 B2 | 7/2017 | Baeuerle et al. |
| 9,775,913 B2 | 10/2017 | Lauermann |
| 9,856,314 B2 | 1/2018 | Lowman et al. |
| 9,861,705 B2 | 1/2018 | Bossard et al. |
| 9,889,211 B2 | 2/2018 | Lowman et al. |
| 10,100,106 B2 | 10/2018 | Dubridge et al. |
| 10,513,549 B2 | 12/2019 | Stagliano et al. |
| 2002/0164328 A1 | 11/2002 | Shinkawa et al. |
| 2003/0139575 A1 | 7/2003 | Gillies et al. |
| 2003/0157108 A1 | 8/2003 | Presta et al. |
| 2003/0190311 A1 | 10/2003 | Dall'Acqua et al. |
| 2004/0014652 A1 | 1/2004 | Trouet et al. |
| 2004/0093621 A1 | 5/2004 | Shitara et al. |
| 2004/0109865 A1 | 6/2004 | Niwa et al. |
| 2004/0110282 A1 | 6/2004 | Kanda et al. |
| 2004/0110682 A1 | 6/2004 | Heidtmann et al. |
| 2004/0132140 A1 | 7/2004 | Satoh et al. |
| 2004/0136952 A1 | 7/2004 | Bhaskaran et al. |
| 2005/0014934 A1 | 1/2005 | Hinton et al. |
| 2006/0166329 A1 | 7/2006 | Rosen et al. |
| 2006/0205926 A1 | 9/2006 | Ross et al. |
| 2006/0236411 A1 | 10/2006 | Dreher et al. |
| 2007/0048282 A1 | 3/2007 | Rosen et al. |
| 2007/0269422 A1 | 11/2007 | Beirnaert et al. |
| 2010/0254944 A1 | 10/2010 | Subramanian et al. |
| 2011/0190209 A1 | 8/2011 | Culbertson et al. |
| 2013/0064788 A1 | 3/2013 | Barnes et al. |
| 2013/0089516 A1 | 11/2013 | Frelinger et al. |
| 2016/0152686 A1 | 6/2016 | Camphausen et al. |
| 2016/0354472 A1 | 12/2016 | Merchant et al. |
| 2017/0096472 A1 | 4/2017 | Rosen et al. |
| 2017/0240608 A1 | 8/2017 | Stagliano et al. |
| 2018/0016316 A1 | 1/2018 | Garcia et al. |
| 2018/0119128 A1 | 5/2018 | Metzner et al. |
| 2018/0134789 A1 | 5/2018 | Baeuerle et al. |
| 2018/0200346 A1 | 7/2018 | Ballance et al. |
| 2018/0344810 A1 | 12/2018 | Addepalli et al. |
| 2019/0008978 A1 | 1/2019 | Huang et al. |
| 2019/0225702 A1 | 7/2019 | Baeuerle et al. |
| 2019/0367576 A1* | 12/2019 | Winston .............. C07K 14/55 |
| 2020/0044052 A1* | 2/2020 | Bao .............. H01L 21/823842 |

FOREIGN PATENT DOCUMENTS

| | | |
|---|---|---|
| EP | 3134102 A4 | 11/2017 |
| EP | 3792277 A1 | 3/2021 |
| WO | 1987/00195 | 1/1987 |
| WO | 1990/03430 | 4/1990 |
| WO | 1991/01743 | 2/1991 |
| WO | 1993/08829 | 5/1993 |
| WO | 1993/16185 | 8/1993 |
| WO | 1994/11026 | 5/1994 |
| WO | 199429351 | 12/1994 |
| WO | 1996027011 | 9/1996 |
| WO | 1997/30087 | 8/1997 |
| WO | 1998/58964 | 12/1998 |
| WO | 1999/22764 | 5/1999 |
| WO | 1999/51642 | 10/1999 |
| WO | 2000/61739 | 10/2000 |
| WO | 2001/079271 A1 | 10/2001 |
| WO | 2002022833 A1 | 3/2002 |
| WO | 2002/43478 | 6/2002 |
| WO | 2002055098 A2 | 7/2002 |
| WO | 2002076489 | 10/2002 |
| WO | 2003/011878 | 2/2003 |
| WO | 2003/59934 A2 | 7/2003 |
| WO | 2003/084570 | 10/2003 |
| WO | 2003/085119 | 10/2003 |
| WO | 2003/106381 A2 | 12/2003 |
| WO | 2004/041865 | 5/2004 |
| WO | 2004/056312 | 7/2004 |
| WO | 2005/035586 | 4/2005 |
| WO | 2005/035778 | 4/2005 |
| WO | 2005/053742 | 6/2005 |
| WO | 2006/0166329 A1 | 7/2006 |
| WO | 20060166329 A1 | 7/2006 |
| WO | 2006/106905 A1 | 10/2006 |
| WO | 2006110728 A2 | 10/2006 |
| WO | 2009/025846 A2 | 2/2009 |
| WO | 2009103965 A1 | 8/2009 |
| WO | 2010020766 A2 | 2/2010 |
| WO | 2011011797 A2 | 1/2011 |
| WO | 2011/124718 | 10/2011 |
| WO | 2012/059486 | 5/2012 |
| WO | 2013/177187 A2 | 11/2013 |
| WO | 2013177187 A2 | 11/2013 |
| WO | 2014100014 A1 | 6/2014 |
| WO | 2016/200645 A1 | 12/2016 |
| WO | 2017156178 A1 | 9/2017 |
| WO | 2018/071918 | 4/2018 |
| WO | 2018071777 A1 | 4/2018 |
| WO | 2018136725 A1 | 4/2018 |
| WO | 2018160754 A2 | 9/2018 |
| WO | 2018160877 A1 | 9/2018 |
| WO | 2018204528 A1 | 11/2018 |
| WO | 2018204717 A1 | 11/2018 |
| WO | 2018213341 A1 | 11/2018 |
| WO | 2018236701 A1 | 12/2018 |
| WO | 2019036031 A2 | 2/2019 |
| WO | 2019051122 A1 | 3/2019 |
| WO | 2019094396 A1 | 5/2019 |
| WO | 2019/173832 A2 | 9/2019 |
| WO | 2019/214757 A1 | 11/2019 |
| WO | 2019/222294 A1 | 11/2019 |
| WO | 2019/222295 A1 | 11/2019 |
| WO | 2019222295 A1 | 11/2019 |
| WO | 2019/246392 | 12/2019 |
| WO | 2020069398 A1 | 2/2020 |
| WO | 2020/069398 A1 | 4/2020 |
| WO | 2020232305 A1 | 11/2020 |
| WO | 2020/252264 A1 | 12/2020 |
| WO | 2021/016599 A1 | 1/2021 |
| WO | 2021/030483 A1 | 2/2021 |
| WO | 2021202673 A1 | 7/2021 |

(56) References Cited

FOREIGN PATENT DOCUMENTS

| WO | 2021202675 A1 | 7/2021 |
|---|---|---|
| WO | 2021/202678 A1 | 10/2021 |
| WO | 2021202678 A1 | 10/2021 |

OTHER PUBLICATIONS

Geletu et al., Effect of Caveolin-1 upon Stat3-ptyr705 levels in breast and lung carcinoma cells., Biochem Cell Biol., Apr. 15, 2019, 1-19, Canadian Science Publishing.
Gao et al "High-throughput screening using patient-derived tumor xenografts to predict clinical trial drug response." Nature Medicine 2015; 21(11): 1318-1325.
Fercher et al., Evolution of the magic bullet: Single chain antibody fragments for the targeted delivery of immunomodulatory proteins, Exp Biol Med, Jan. 2018, 166-183, vol. 243, Issue 2, Sage Journals.
Erster et al., Site-specific targeting of antibody activity in vivo mediated by disease-associated proteases, Journal of Controlled Release, Aug. 10, 2012, 804-812, vol. 161, Issue 3, Elsevier, USA.
Drag et al., Emerging principles in protease-based drug discovery, Nat Rev Drug Discov., Nov. 5, 2010, 690-701, vol. 9, Issue 9, Springer Nature, USA.
Desnoyers et al., Tumor-Specific Activation of an EGFR-Targeting Probody Enhances Therapeutic Index, Science Translational Medicine, Oct. 16, 2013, , vol. 5, Issue 207, American Association for the Advancement of Science, USA.
Desbois et al IL-15 Trans-signaling with the superagonist RLI Promotes Effector/Memory CD8+ T cell responses and enhances antitumor activity of PD-1 antagonists. 2016 J Immunol 1-11.
Denise Skrombolas et al., Challenges and developing solutions for increasing the benefits of IL-2 treatment in tumor therapy, Expert Review of Clinical Immunology, vol. 10, No. 2, Feb. 1, 2014, pp. 207-217.
Deluca et al., Potentiation of PD-L1 blockade with a potency-matched dual cytokine-antibody fusion protein leads to cancer eradication in BALB/c-derived tumors but not in other mouse strains, Cancer Immunol Immunother, Sep. 6, 2018, 1381-1391, vol. 67, Issue 9, Springer.
Declerck et al., Proteases, extracellular matrix, and cancer: a workshop of the path B study section, Am J Pathol., Apr. 2004, 1131-1139, vol. 164, Issue 4, Elsevier, USA.
De Luca et al., Potency-matched Dual Cytokine-Antibody Fusion Proteins for Cancer Therapy. Mol Cancer Ther, Nov. 2017, 2442-2451, vol. 16, Issue 11, AACR, USA.
Darragh et al., Specific targeting of proteolytic activity for tumor detection in vivo, Cancer Res., Feb. 15, 2010, 1505-1512, vol. 70, Issue 5, AACR, USA.
Conlon et al "Redistribution, hyperproliferation, activation of natural killer cells and CD8 T cells, and cytokine production during first-in-human clinical trial of recombinant human interleukin-15 in patients with cancer." J Clin Oncol 2015; 33(1): 74-82.
Boulware et al., Protease specificity determination by using cellular libraries of peptide substrates (CLiPS), PNAS, May 16, 2006, 7583-7588, vol. 103, Issue 20, National Academy of Sciences, USA.
Boulware et al., Evolutionary optimization of peptide substrates for proteases that exhibit rapid hydrolysis kinetics, Biotechnol Bioeng., Jun. 15, 2010, 339-46, vol. 106, Issue 3, Wiley, USA.
Bessard et al High antitumor activity of RLI, an interleukin-15 (IL-15)-IL-15 receptor alpha fusion protein, in metastatic melanoma and colorectal cancer. Mol Cancer Ther 2009; 8(9): 2736-2745.
Berger et al "An Operational definition of epigenetics." Genes Dev 2009; 23: 781-783.
Agard et al., Methods for the proteomic identification of protease substrates, Curr Opin Chem Biol., Dec. 2009, 503-509, vol. 12, Issue 5-6, Elsevier, USA.
Afonina et al., Proteolytic Processing of Interleukin-1 Family Cytokines: Variations on a Common Theme, Immunity Review16 Jun. 2015, 991-1004, vol. 42, Issue 6, Elsevier, USA.

Adusumilli et al., New Cancer Immunotherapy Agents in Development: a report from an associated program of the 31stAnnual Meeting of the Society for Immunotherapy of Cancer, 2016, J Immunother Cancer, Jun. 20, 2017, 1-9, vol. 5, Issue 50, BioMed Central, USA.
Skrombolas, etl al. "Development of an Interleukin-12 Fusion Protein That Is Activated by Cleavage with Matrix Metalloproteinase 9," Journal of Interferon & Cytokine Research, 39(4):233-245 (2019).
Berger et al "Safety and immunologic effects of IL-15 administration in nonhuman primates." Blood 2009; 114(12): 2417-2426.
Skrombolas, et al. "Development of Protease Activated Interleukin-12 Cytokine Fusion Proteins for Tumor Immunotherapy (TUM7P. 946)," The Journal of Immunology; 203:28, 192 (1 Supplement) (2014).
Skrombolas, et al. "Development of an Interleukin-12 Fusion Protein That Is Activated by Cleavage with Matrix Metalloproteinase 9," Journal of Interferon & Cytokine Research, 39(4):233-245 (2019).
Zapata et al., "Engineering linear F(ab')2 fragments for efficient production in *Escherichia coli* and enhanced antiproliferative activity," Protein Eng., 8(10):1057-1062 (1995).
Yeung et al., "Engineering Human IgG1 Affinity to Human Neonatal Fc Receptor: Impact of Affinity Improvement on Pharmacokinetics in Primates," J. Immunol., 182:7667-7671 (2009).
Yaniv, "Enhancing elements for activation of eukaryotic promoters," Nature 297:17-18 (1982).
Yamane-Ohnuki et al., "Production of therapeutic antibodies with controlled fucosylation," MAbs, 1 (3):230-236 (2009).
Yamane-Ohnuki et al., "Establishment of FUT8 knockout Chinese hamster ovary cells: an ideal host cell line for producing completely defucosylated antibodies with enhanced antibody-dependent cellular cytotoxicity," Biotech. Bioeng., 87:614-22 (2004).
Vitetta et al., "Redesigning nature's poisons to create anti-tumor reagents," Science, 238: 1098-1104 (1987).
Verhoeven et al., "Reshaping human antibodies: grafting an antilysozyme activity," Science, 239:1534-1536. (1988).
Urlaub et al., "Isolation of Chinese hamster cell mutants deficient in dihydrofolate reductase activity," Proc. Natl. Acad. Sci. USA, 77:4216-4220 (1980).
Traunecker et al., "Bispecific single chain molecules (Janusins) target cytotoxic lymphocytes on HIV infected cells," Embo J., 10:3655-365 (1991).
Torgov et al., "Generation of an Intensely Potent Anthracycline by a Monoclonal Antibody-[3-Galactosidase Conjugate," Bioconj. Chem., 16:717-721 (2005).
Tomizuka et al., "Double trans-chromosomic mice: Maintenance of two individual human chromosome fragments containing Ig heavy and K loci and expression of fully human antibodies," Proc. Natl. Acad. Sci. USA, 97:722-727 (2000).
Suresh et al., "Bispecific monoclonal antibodies from hybrid hybridomas," Methods in Enzymology, 121:210-228 (1986).
Sties et al. (eds), Basic and Clinical Immunology, 8th Edition, Appleton & Lange, Nmwalk, CT,p. 71 and Chapter 6 (1994).
Sola et al., "Modulation of protein biophysical properties by chemical glycosylation: biochemical insights and biomedical implications," Cell. Mol. Life Sci., 64(16):2133-2152 (2007).
Simmons et al., "Expression of full-length immunoglobulins in *Escherichia coli*: rapid and efficient production of aglycosylated antibodies," J. Immunol. Methods, 263:133-147 (2002).
Shinkawa et al., The absence of fucose but not the presence of galactose or bisecting N-acetylglucosamine of human IgG1 complex-type oligosaccharides shows the critical role of enhancing antibody-dependent cellular cytotoxicity, J. Biol. Chem., 278(5):3466-73 (2003).
Shields et al.,"Lack of fucose on human IgG1 N-linked oligosaccharide improves binding to human Fcgamma RIii and antibody-dependent cellular toxicity," J. Biol. Chem., 277(30):26733-40 (2002).
Shields et al, "High resolution mapping of the binding site on human IgG1 for Fc gamma RI, Fc gamma RII, Fc gamma RIii, and FcRn and design of IgG1 variants with improved binding to the Fc gamma R," J. Biol. Chem., 276:6591-6604 (2001).

(56) References Cited

OTHER PUBLICATIONS

Schlapschy et al., "PASylation: a biological alternative to PEGylation for extending the plasma half-life of pharmaceutically active proteins," Protein Eng. Des. Sel., 26(8):489-501 (2013).

Sali et al. "Characterization of a Novel Human-Specific STING Agonist that Elicits Antiviral Activity Against Emerging Alphaviruses," PloS Pathog., 11(12):e1005324, 30 pages (2015).

Lehninger, in Biochemistry, second ed., pp. 73-75, Worth Publishers, New York (1975).

Lindmark et al., "Binding of immunoglobulins to protein A and immunoglobulin levels in mammalian sera," J. Immunol. Meth., 62:1-13 (1983).

Lode et al., "Targeted Therapy with a Novel Enediyene Antibiotic Calicheamicin -al 1 Effectively Suppresses Growth and Dissemination of Liver Metastases in a Syngeneic Model of Murine Neuroblastoma," Cancer Res., 58:2925-2928 (1998).

Lonberg, et al., "Antigen-specific human antibodies from mice comprising four distinct genetic modifications," Nature 368:856-859 (1994).

Mather et al., "Culture of testicular cells in hormone-supplemented serum-free medium," Annals N.Y. Acad. Sci., 383:44-68 (1982).

Mather, "Establishment and characterization of two distinct mouse testicular epithelial cell lines," Biol. Reprod. 23:243-251 (1980).

Merchant et al., "An efficient route to human bispecific IgG," Nat. Biotechnol., 16(7):677-681 (1998).

Milstein et al.,. "Hybrid hybridomas and their use in immunohistochemistry," Nature, 305:537 (1983).

Moore et al., "A novel bispecific antibody format enables simultaneous bivalent and monovalent co-engagement of distinct target antigens," MAbs., 3(6): 546-557 (2011).

Mori et al., "Engineering Chinese hamster ovary cells to maximize effector function of produced antibodies using FUT8 siRNA," Biotechnol. Bioeng. 88(7):901-908 (2004).

Morimoto et al., "Single-step purification of F(ab12 fragments of mouse monoclonal antibodies (immunoglobulins G1) by hydrophobic interaction high performance liquid chromatography using TSKgel Phenyl-5PW," Journal of Biochemical and Biophysical Methods, 24:107-117 (1992).

Nagy et al., "Stability of cytotoxic luteinizing hormone-releasing hormone conjugate (AN-152) containing doxorubicin 14-O-hemiglutarate in mouse and human serum in vitro: Implications for the design of preclinical studies," Proc. Natl. Acad. Sci. USA, 97:829-834 (2000).

Nilvebrant et al., "The albumin-binding domain as a scaffold for protein engineering," Comput. Struct. Biotechnol. J., 6:e201303009, 8 pages (2013).

Nygren et al.,"Analysis and use of the serum albumin binding domains of streptococcal protein G," J. Mal. Recogn., 1 (2):69-74 (1988).

Okazaki et al., "Fucose depletion from human IgG1 oligosaccharide enhances binding enthalpy and association rate between IgG1 and FcgammaRIIIa," J. Mal. Biol., 336:1239-1249 (2004).

Omasa et al., "Decrease in antithrombin III fucosylation by expressing GDP-fucose transporter siRNA in Chinese hamster ovary cells," J. Biosci. Bioeng., 106(2):168-173 (2008).

Podust et al., "Extension of in vivo half-life of biologically active molecules by XTEN protein polymers," J. Controlled Release, 240:52-66 (2016).

Proba et al., "Functional antibody single-chain fragments from the cytoplasm of *Escherichia coli*: influence of thioredoxin reductase (TrxB)," Gene, 159:203-7 (1995).

Ramm et al., "The periplasmic *Escherichia coli* peptidylprolyl cis, trans-isomerase FkpA II. Isomerase-independent chaperone activity in vitro," J. Biol. Chem., 275:17106-17113 (2000).

Reyes et al., "Expression of human 13-interferon cDNA under the control of a thymidine kinase promoter from herpes simplex virus," Nature, 297:598-601 (1982).

Riechmann et al., "Reshaping human antibodies for therapy," Nature, 332:323-327 (1988).

Ridgway et al., "Knobs-into-holes' engineering of antibody CH3 domains for heavy chain heterodimerization," Protein Eng., 9(7):617-621 (1996).

Ripka et al., "Two chinese hamster ovary glycosylation mutants affected in the conversion of GDP-man nose to GDP-fucose," Arch. Biochem. Biophys., 249:533-545 (1986).

Roux et al., "Comparisons of the ability of human IgG3 hinge mutants, IgM, IgE, and IgA2, to form small immune complexes: a role for flexibility and geometry," J Immunol, 161 :4083-90 (1998).

Cao, et al., "Next generation of tumor-activating type I IFN enhances anti-tumor immune responses to overcome therapy resistance", Nature Communications, 12:5866, pp. 1-11 (2021).

Puskas et al., "Development of an attenuated interleukin-2 fusion protein that can be activated by tumour-expressed proteases," Immunology, 133:206-220 (2011).

Dubowchik et al., "Doxorubicin Immunoconjugates Containing Bivalent, Lysosomally-Cleavable Dipeptide Linkages," Bioorg. & Med. Chem. Letters 12:1529-1532 (2002).

Xue et al, "A tumor-specific pro-IL-12 activates preexisting cytotoxic T cells to control established tumors" Science Immunology, vol. 7, Jan. 7, 2022, pp. 1-14.

Xue et al, "Supplementary Materials for A tumor-specific pro-IL-12 activates preexisting cytotoxic T cells to control established tumors" Science Immunology, vol. 7, (2022), pp. 1-26.

Arie et al. "Chaperone function of FkpA, a heat shock prolyl isomerase, in the periplasm of *Escherichia coli*,", Mol. Micro biol. 39:199-210 (2001).

Atwell et al., "Stable heterodimers from remodeling the domain interface of a homodimer using a phage display library," J. Mol. Biol., 270(1):26-35 (1997).

Bachmann, Cellular and Molecular Biology, vol. 2 (Washington, D.C.: American Society for Microbiology), pp. 1190-1219 (1987).

Barnes et al., "Methods for growth of cultured cells in serum-free medium," Anal. Biochem. 102:255 (1980).

Bass et al., "Hormone phage: an enrichment method for variant proteins with altered binding properties," Proteins, 8:309-314 (1990).

Bernett et al., "Potency-reduced Il 15/IL 15Ra heterodimeric Fe-fusions display enhanced in vivo activity through increased exposure," Xencor, AACR (2018) Abstract #5565.

Boerner et al., "Production of antigen-specific human monoclonal antibodies from in vitro-primed human splenocytes," J. Immunol., 147: 86 (1991).

Bothmann and Pluckthun. "Improving Expression of scFv Fragments by Coexpression of Periplasmic Chaperones," J. Biol. Chem. 275:17100-17105 (2000).

Brennan et al., "Preparation of bispecific antibodies by chemical recombination of monoclonal immunoglobulin G1 fragments," Science, 229:81 (1985).

Brodeur et al., Monoclonal Antibody Production Techniques and Applications, pp. 51-63 Marcel Dekker, Inc., New York, (1987).

Caescu et al., "Active site determinants of substrate recognition by the metalloproteinases TACE and ADAM10," Biochem. J., 424(1):79-88 (2010).

Carter et al., "High level *Escherichia coli* expression and production of a bivalent humanized antibody fragment," BiofTechnology 10: 163-167 (1992).

Carter et al., "Bispecific human IgG by design," J. Immunol. Methods, 248: 7-15 (2001).

Chapman et al. "Therapeutic antibody fragments with prolonged in vivo half-lives," Nature Biotechnol., 17:780-783 (1999).

Chari et al., "Immunoconjugates containing novel maytansinoids: promising anticancer drugs," Cancer Res. 52:127-131 (1992).

Chen et al., "Chaperone activity of DsbC," J. Biol. Chem. 274:19601-19605 (1999).

Choe et al. , "Fe-Binding Ligands of Immunoglobulin G: An Overview of High Affinity Proteins and Peptides," Materials 9(12): 994 (2016).

Cunningham and Wells ,"High-resolution epitope mapping of hGH-receptor interactions by alanine-scanning mutagenesis," Science, 244:1081-1085 (1989).

Davies et al., "Antibody-antigen complexes," Annual Rev Biochem. 59:439-473, (1990).

(56) References Cited

OTHER PUBLICATIONS

Dennis et al., "Albumin binding as a general strategy for improving the pharmacokinetics of proteins," JBC 277(38): 35035-35043 (2002).
Duncan and Winter, "The binding site for C1q on IgG," Nature 322:738-40 (1988).
Damodaran, "Protein PEGylation: An overview of chemistry and process considerations," European Pharmaceutical Review, 15(1): 18-26 (2010).
Firan, M., et al., "The MHC class I-related receptor, FcRn, plays an essential role in the maternofetal transfer of y-globulin in humans," Int. Immunol. 13: 993-1002 (2001).
Fishwild, D. et al., "High-avidity human IgG kappa monoclonal antibodies from a novel strain of minilocus transgenic mice," Nature Biotechnology 14: 845-851 (1996).
Graham et al., "Characteristics of a human cell line transformed by DNA from human adenovirus type 5," J. Gen Virol. 36:59 (1977).
Gunasekaran et al., "Enhancing antibody Fc heterodimer formation through electrostatic steering effects: applications to bispecific molecules and monovalent IgG," J Biol Chem., 285(25): 19637-19646 (2010).
Guss et al., "Structure of the IgG-binding regions of streptococcal protein G.," EMBO J. 5:15671575 (1986).
Guyer et al., "Immunoglobulin Binding by Mouse Intestinal Epithelial Cell Receptors," J. Immunol. 117:587 (1976).
Ham et al., "Media and Growth Requirements," Meth. Enz. 58:44 (1979).
Hara et al., "Overproduction of Penicillin-Binding Protein 7 Suppresses Thermosensitive Growth Defect at Low Osmolarity due to an spr Mutation of *Escherichia coli*," Microbial Drug Resistance, 2:63-72 (1996).
Hinman et al., "Preparation and characterization of monoclonal antibody conjugates of the calicheamicins: a novel and potent family of antitumor antibiotics," Cancer Res. 53:3336-3342 (1993).
Hudson et al., "Engineered antibodies," Nat. Med., 9:129-134 (2003).
Idusogie et al., "Mapping of the C1q Binding Site on Rituxan, a Chimeric Antibody with a Human IgG1 Fc," J. Immunol., 164:4178-4184, (2000).
Imai-Nishiya et al., "Double knockdown of a1,6-fucosyltransferase (FUT8) and GDP-mannose 4,6-dehydratase (GMD) in antibody-producing cells: a new strategy for generating fully non-fucosylated therapeutic antibodies with enhanced ADCC," BMC Biotechnol., 7:84, 13 pages (2007).
Jefferis et al., "Human immunoglobulin allotypes: Possible implications for immunogenicity," mAbs, 1 (4):332-8 (2009).
Jeffrey et al., "Dipeptide-based highly potent doxorubicin antibody conjugates," Bioorganic & Med. Chem. Letters, 16:358-362 (2006).
Jones et al., "Replacing the complementarity-determining regions in a human antibody with those from a mouse," Nature, 321 :522-525 (1986).
Kim et al., "Localization of the site of the murine IgG1 molecule that is involved in binding to the murine intestinal Fc receptor," European Journal of Immunology, 24:2429-2434 (1994).
King et al., "Monoclonal Antibody Conjugates of Doxorubicin Prepared with Branched Peptide Linkers: Inhibition of Aggregation by Methoxytriethyleneglycol Chains," J. Med. Chem., 45:4336-4343 (2002).
Klein et al., "Progress in overcoming the chain association issue in bispecific heterodimeric IgG antibodies," MAbs, 4(6):653-663 (2012).
Kontermann et al., "Bispecific antibodies," Drug Discovery Today, 20(7) :838-84 7 (2015).
Kozbor et al., "A human hybrid myeloma for production of human monoclonal antibodies," J. Immunol., 133:3001-5 (1984).
Kratz et al., "Prodrugs of anthracyclines in cancer chemotherapy," Current Med. Chem. 13:477-523 (2006).
Krieg et al., "Improved IL-2 immunotherapy by selective stimulation of IL-2 receptors on lymphocytes and endothelial cells," PNAS, 107(26):11906-11911 (2010).
Chen, et al., "Fusion protein linkers: Property, design and functionality", Advanced Drug Delivery Reviews, vol. 65, No. 10, (Sep. 1, 2012), pp. 1357-1369.
International Search Report and Written Opinion of PCT/US2020/060624 mailed May 20, 2021.

\* cited by examiner

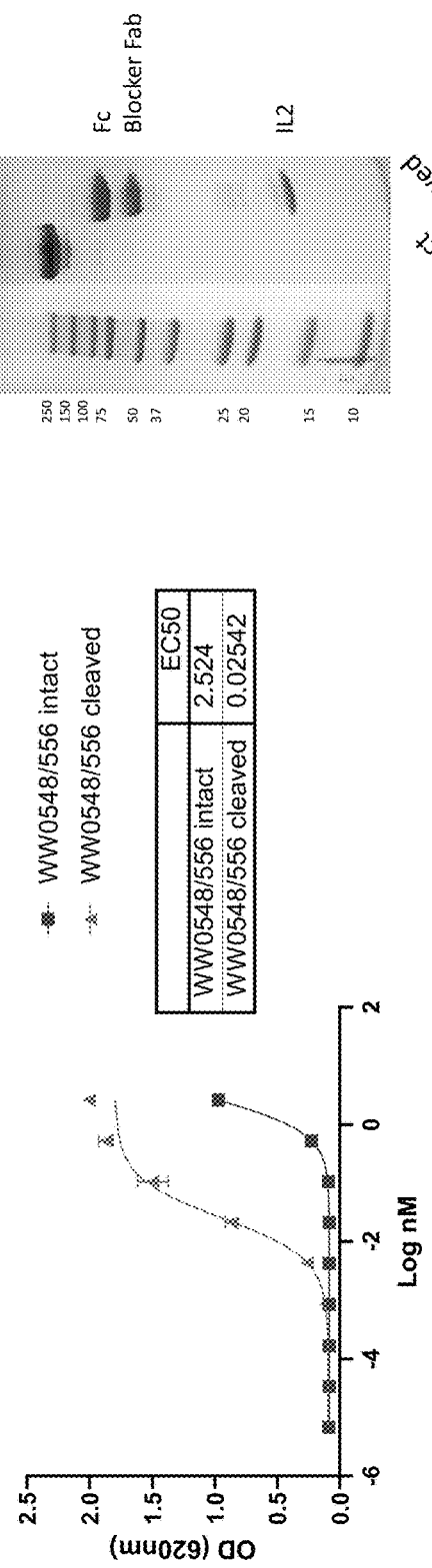
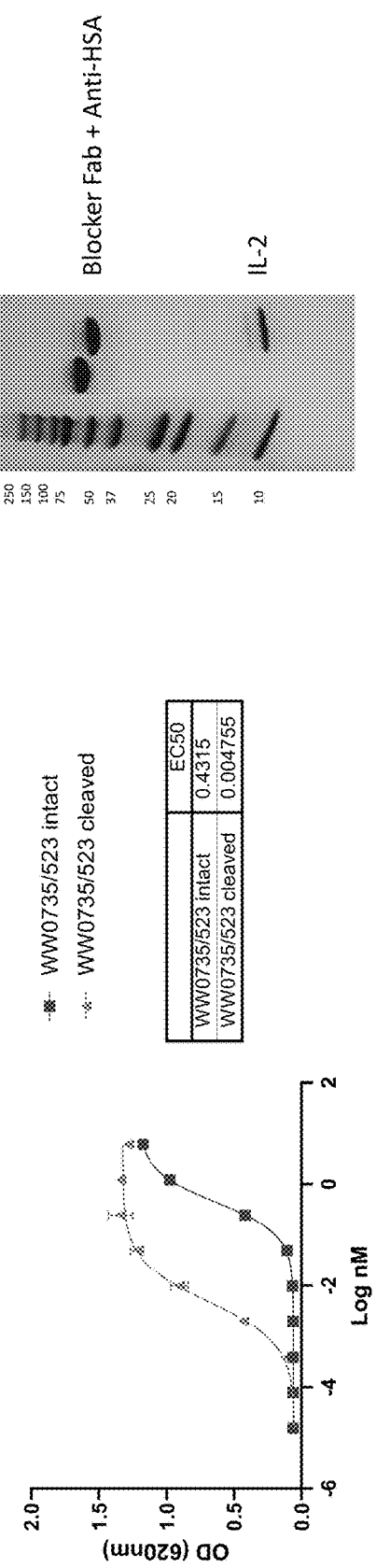
FIG. 1C
FIG. 1D

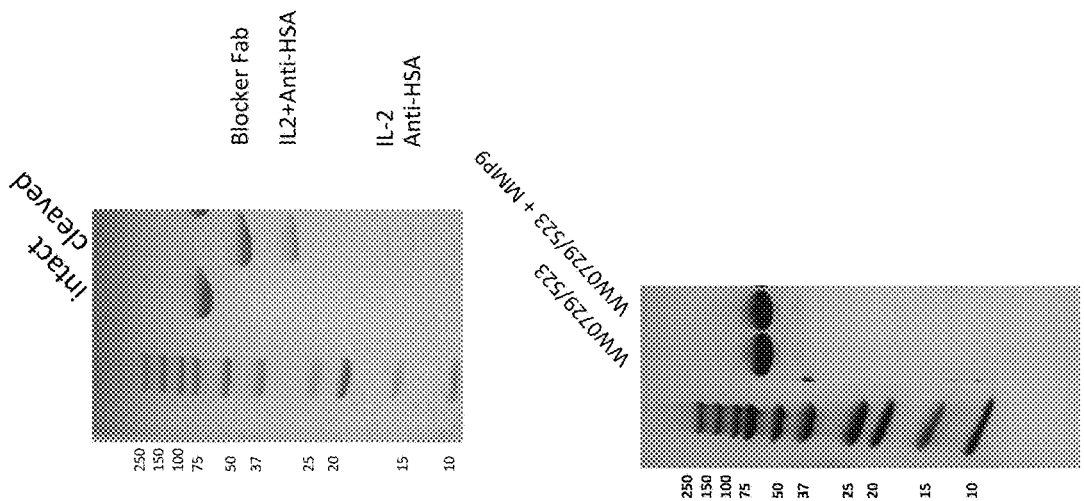
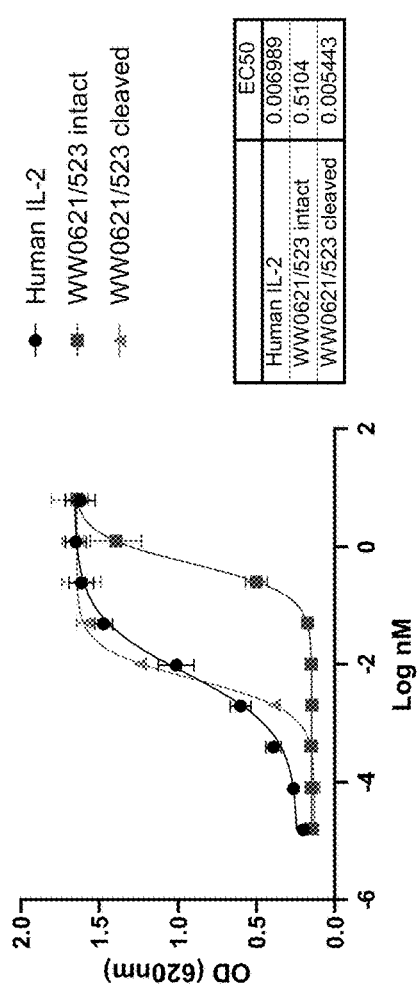
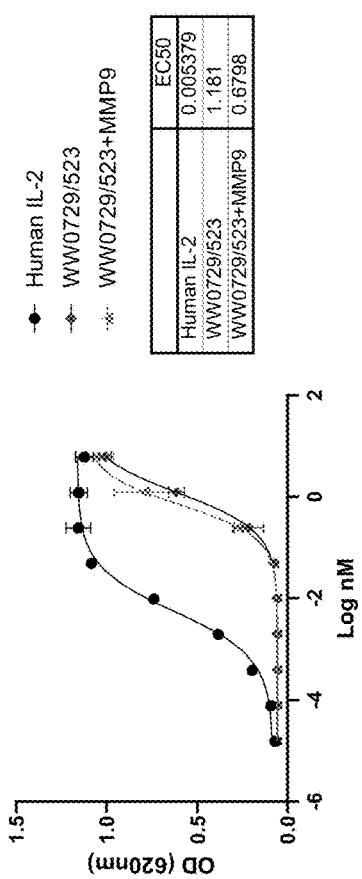
FIG. 1E
FIG. 1F

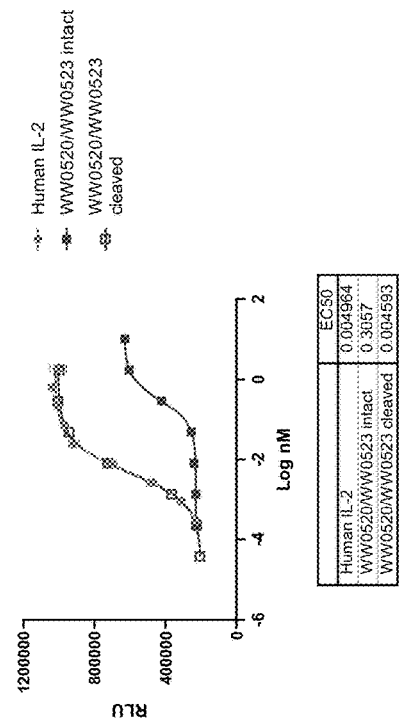
FIG. 2I
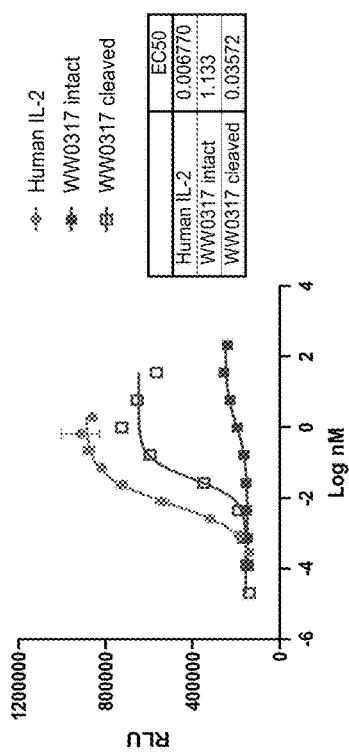
FIG. 2J
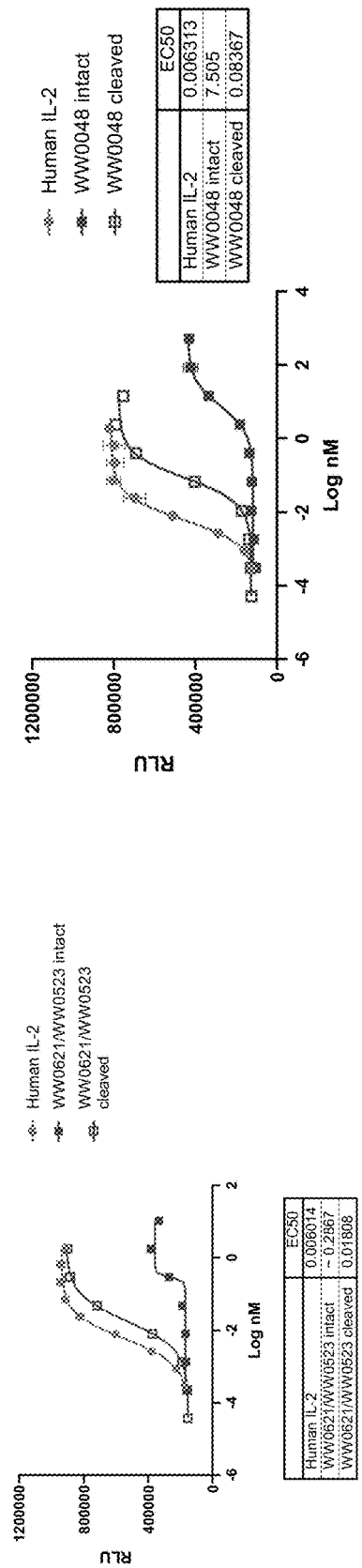
FIG. 2K
FIG. 2L

FIG. 7E
FIG. 7F
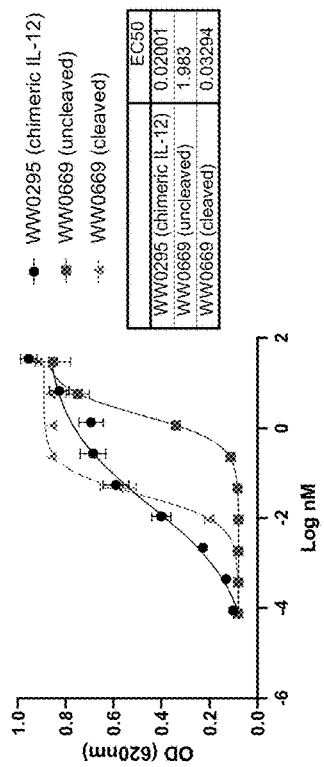
FIG. 7G

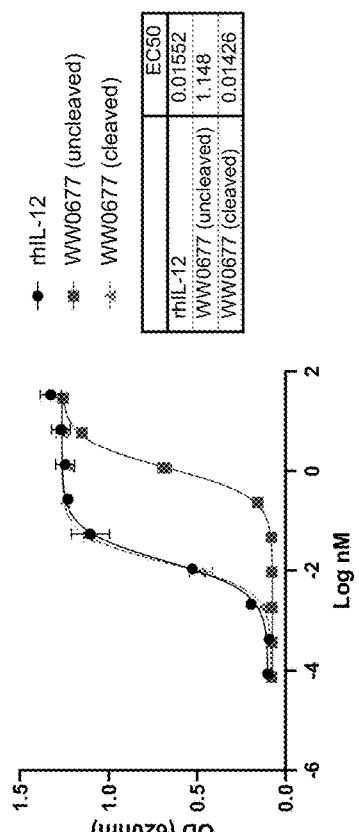
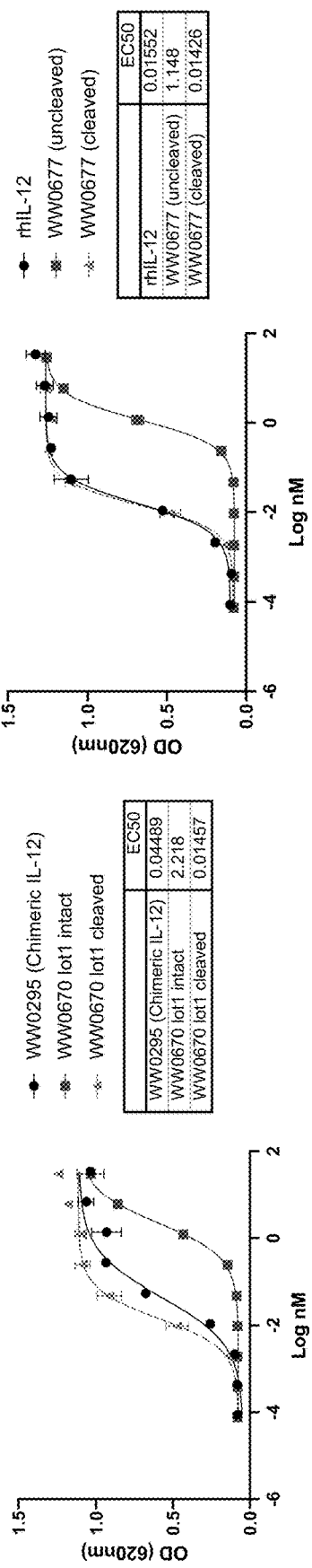
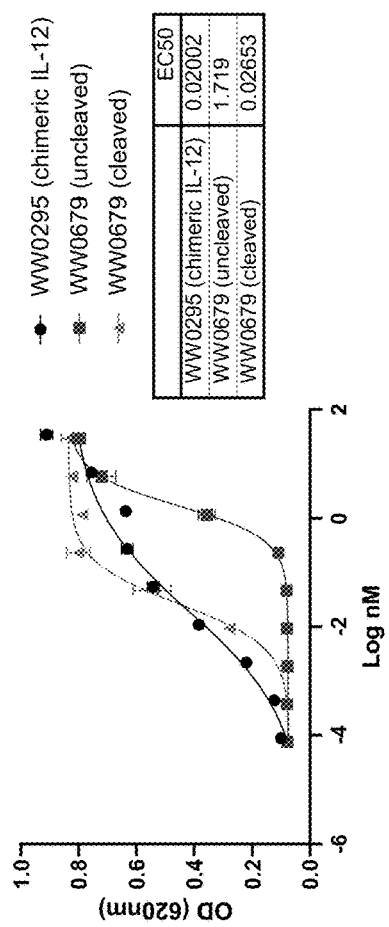
FIG. 7K
FIG. 7L
FIG. 7M

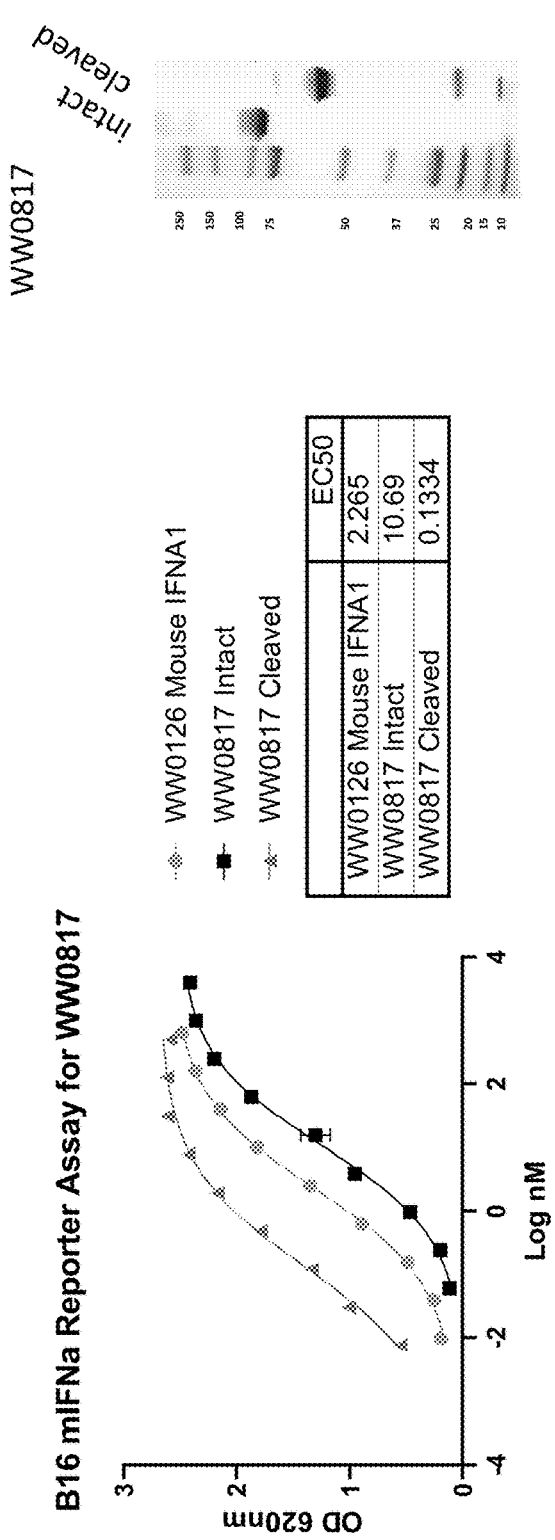
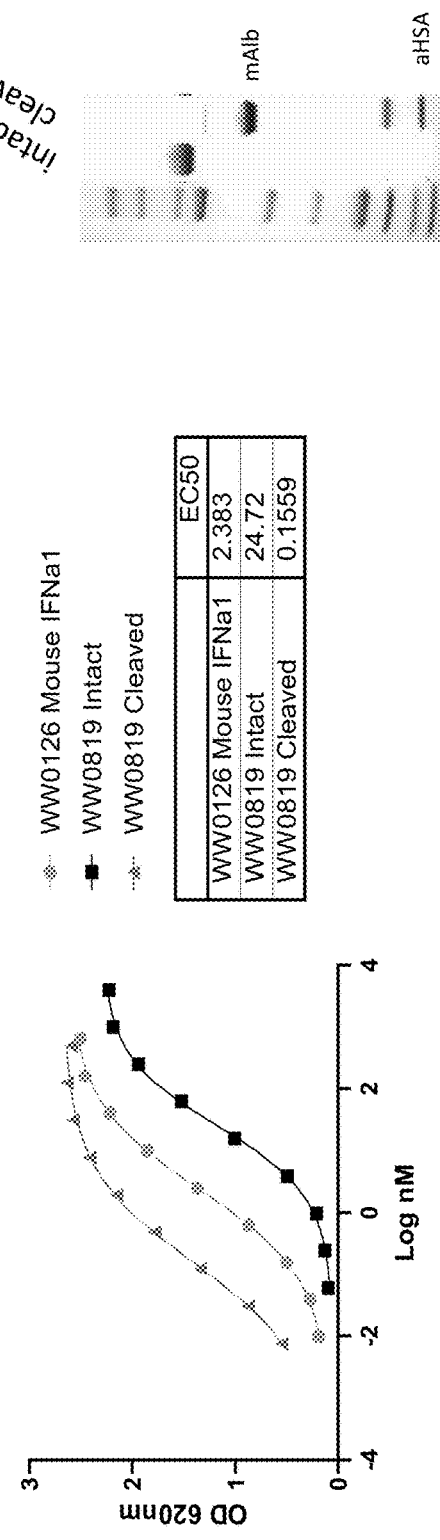
FIG. 10G
FIG. 10H

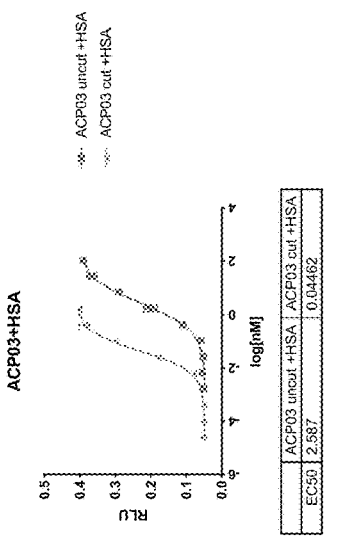
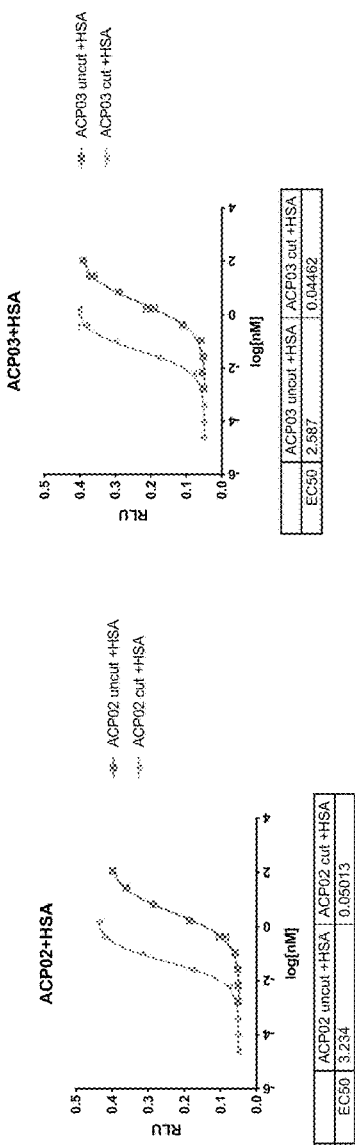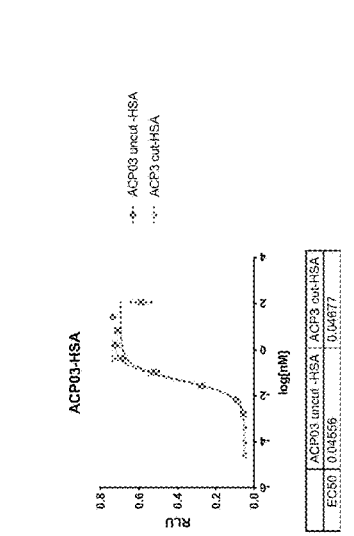
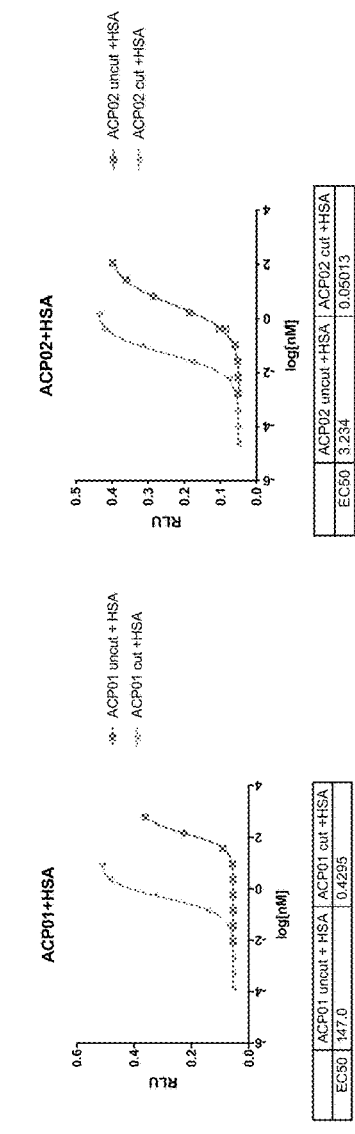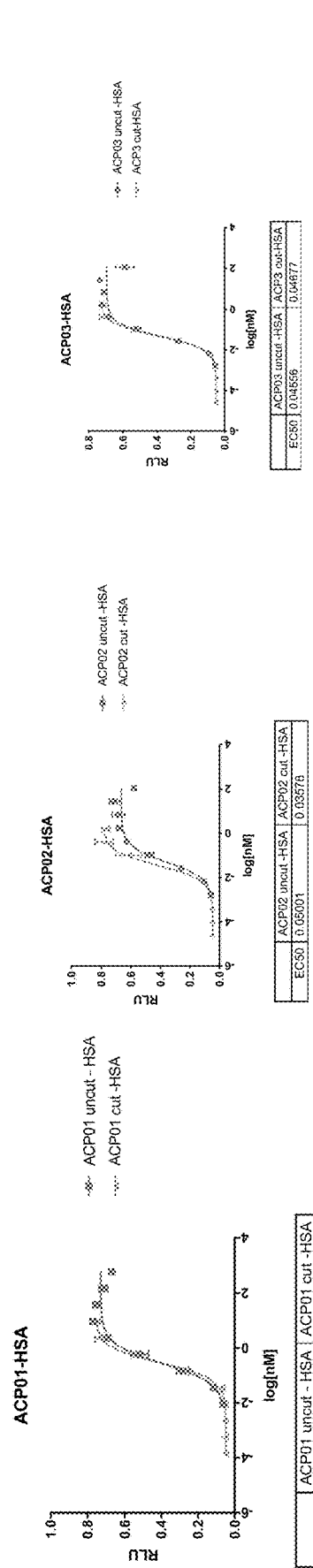
FIG. 17A  FIG. 17C  FIG. 17E
FIG. 17B  FIG. 17D  FIG. 17F

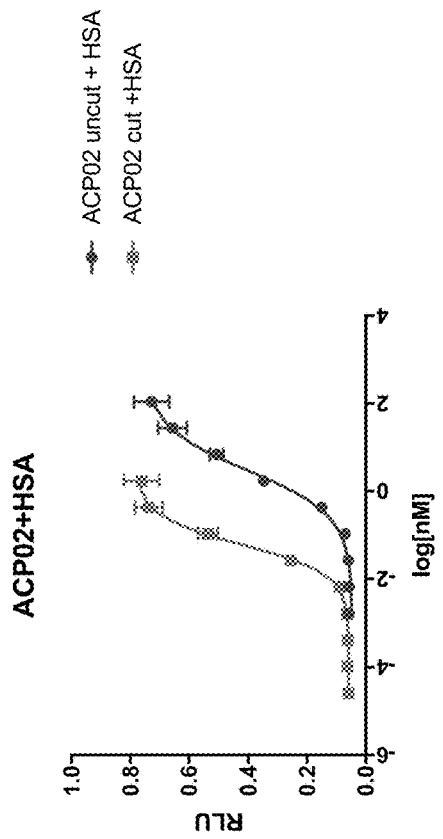
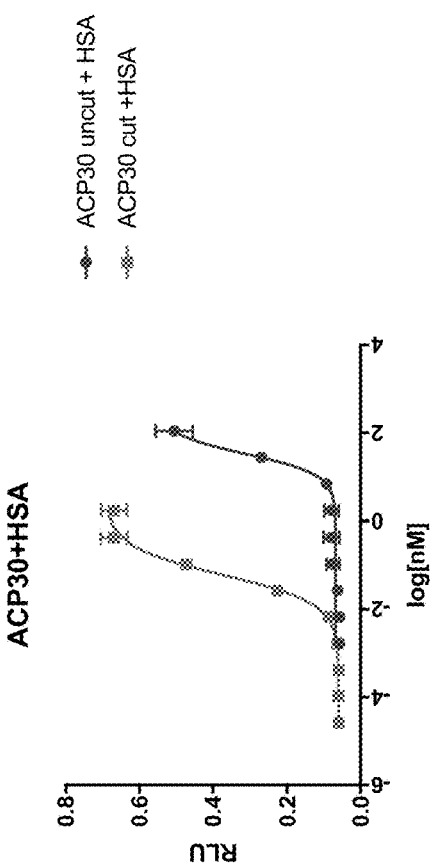
FIG. 19B
FIG. 19A

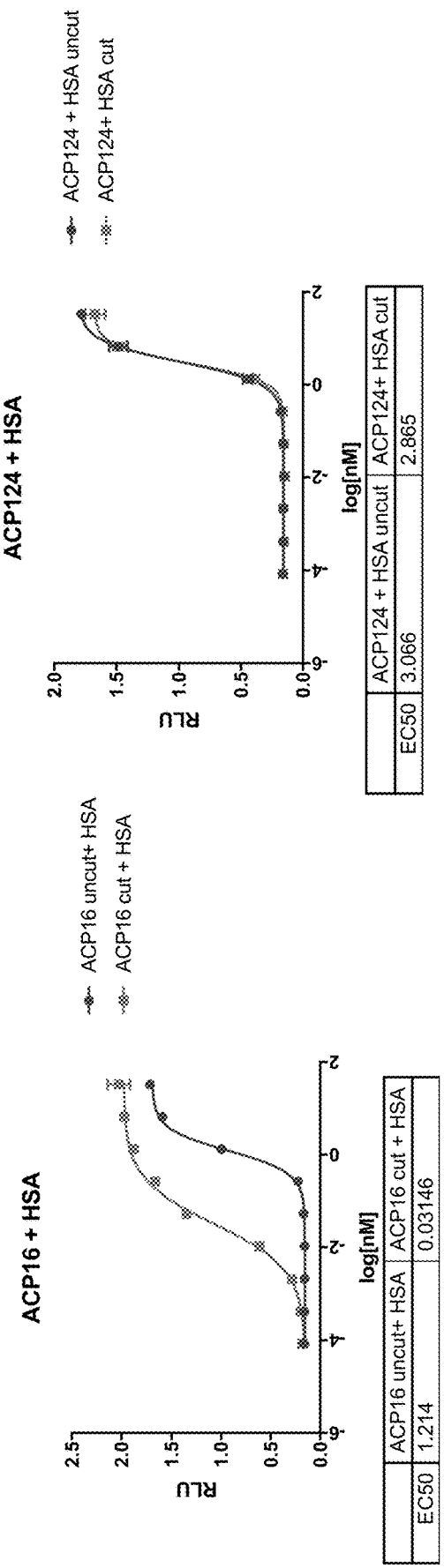

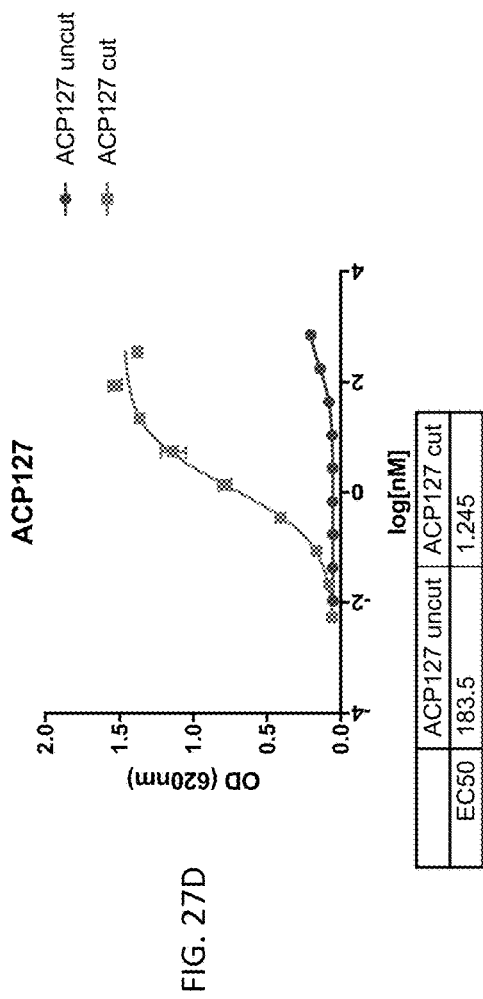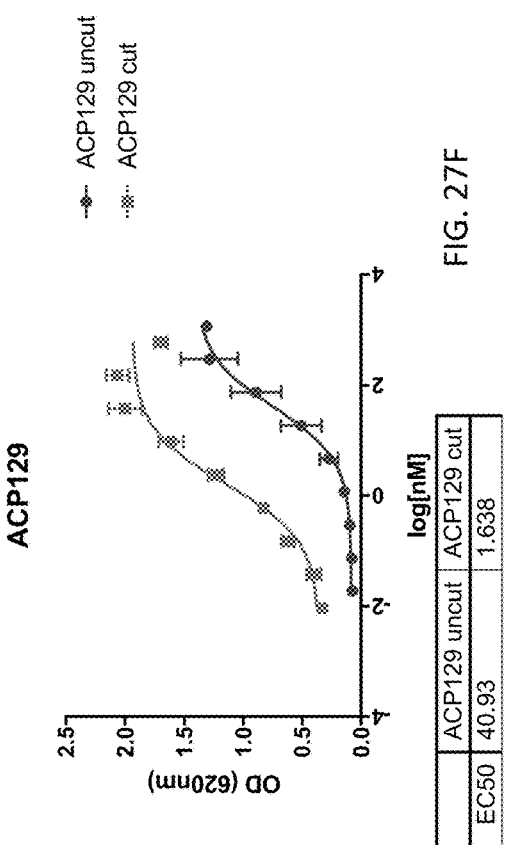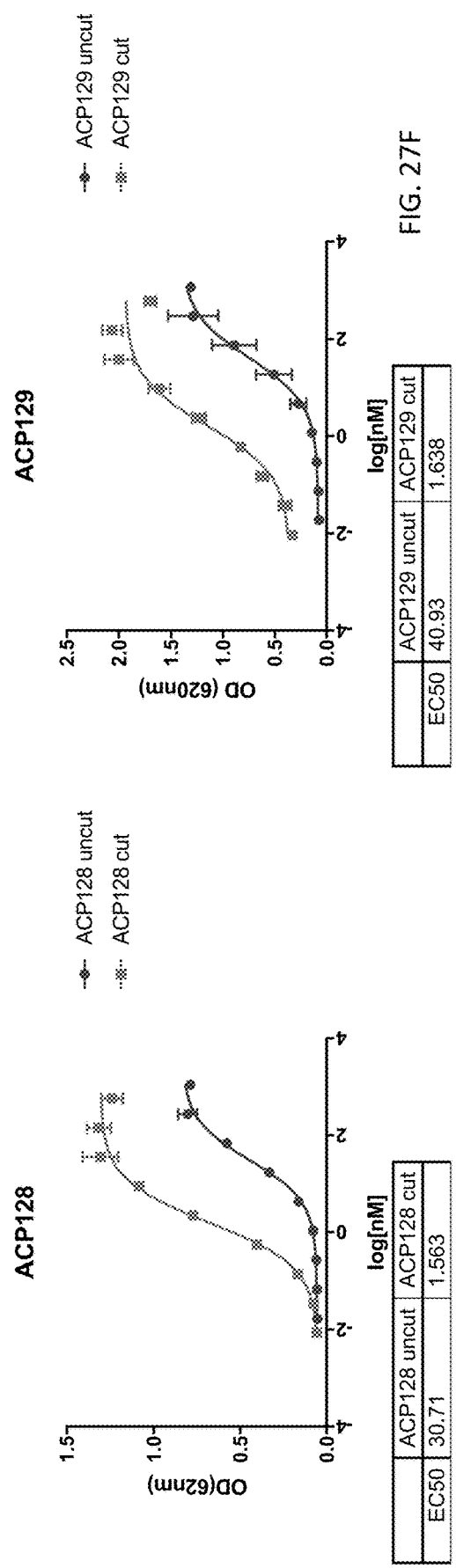
FIG. 27D
FIG. 27E
FIG. 27F

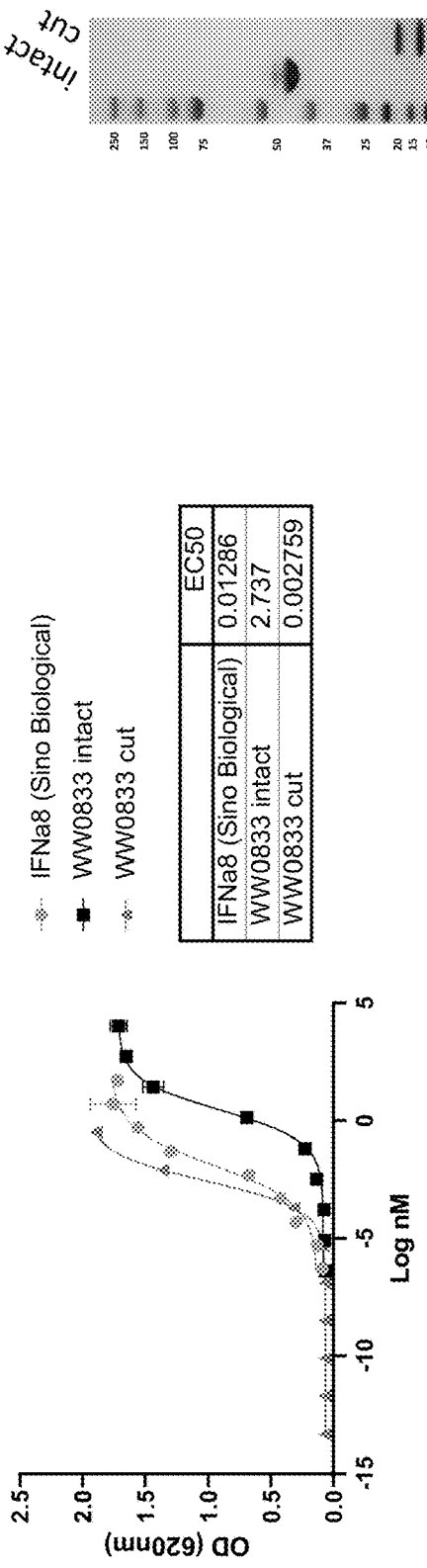
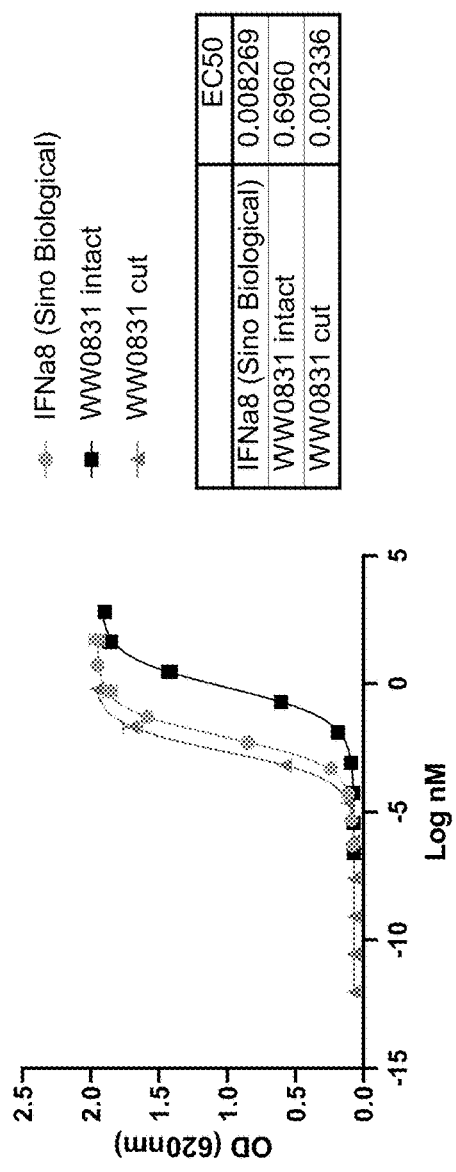
FIG. 36G
FIG. 36H

| Mouse serum Albumin | KD (nM) | kon (1/Ms) | kdis (1/s) |
|---|---|---|---|
| ACP16 | 2.6 | 4.3E+4 | 1.1E-4 |
| ACP10 | 0.38 | 2.5E+5 | 9.7E-5 |
| ACP11 | No binding | No binding | No binding |

| Human Serum Albumin | KD (nM) | kon (1/Ms) | kdis (1/s) |
|---|---|---|---|
| ACP16 | 4.3 | 3.4E+5 | 1.5E-3 |
| ACP10 | 4.4 | 2.8E+5 | 1.2E-3 |
| ACP11 | 79 | 3.1E+4 | 2.5E-3 |

FIG. 43

ACTIVATABLE CYTOKINE POLYPEPTIDES AND METHODS OF USE THEREOF

CROSS-REFERENCE TO RELATED APPLICATIONS

This application is a continuation of U.S. patent application Ser. No. 17/934,811 filed on Sep. 23, 2022, which is a continuation of U.S. patent application Ser. No. 17/741,275, filed on May 10, 2022, which is a continuation of International Patent Application No. PCT/US2020/060624, filed on Nov. 14, 2020, which claims the benefit of U.S. Provisional Application No. 62/935,605, filed on Nov. 14, 2019, each of which are incorporated herein by reference.

REFERENCE TO SEQUENCE LISTING SUBMITTED ELECTRONICALLY

The instant application contains a Sequence Listing which has been submitted electronically in XML format and is hereby incorporated by reference in its entirety. Said XML file, created on Feb. 8, 2023, is named "761146_300011_SL.xml" and is 887 KB.

BACKGROUND

The development of mature immunocompetent lymphoid cells from less-committed precursors, their subsequent antigen-driven immune responses, and the suppression of these and unwanted autoreactive responses are highly dependent and regulated by cytokines (including interleukin-2 [IL-2], IL-4, IL-7, IL-9, IL-15, and IL-21) that utilize receptors in the common γ-chain (γc) family (Rochman et al., 2009) and family members including IL-12, 18 and 23. IL-2 is essential for thymic development of Treg cells and critically regulates several key aspects of mature peripheral Treg and antigen-activated conventional T cells. Because of its potent T cell growth factor activity in vitro, IL-2 has been extensively studied in part because this activity offered a potential means to directly boost immunity, e.g., in cancer and AIDS-HIV patients, or a target to antagonize unwanted responses, e.g., transplantation rejection and autoimmune diseases. Although in vitro studies with IL-2 provided a strong rationale for these studies, the function of IL-2 in vivo is clearly much more complex as first illustrated in IL-2-deficient mice, where a rapid lethal autoimmune syndrome, not lack of immunity, was observed (Sadlack et al., 1993, 1995). Similar observations were later made when the gene encoding IL-2Rα (Il2ra) and IL-2Rβ (Il2rb) were individually ablated (Suzuki et al., 1995; Willerford et al., 1995).

The present invention refers to conditionally active and/or targeted cytokines for use in the treatment of cancer and other diseases dependent on immune up or down regulation. For example, the antitumoral activity of some cytokines is well known and described and some cytokines have already been used therapeutically in humans. Cytokines such as interleukin-2 (IL-2) and interferon α (IFNα) have shown positive antitumoral activity in patients with different types of tumors, such as kidney metastatic carcinoma, hairy cell leukemia, Kaposi sarcoma, melanoma, multiple myeloma, and the like. Other cytokines like IFNβ, the Tumor Necrosis Factor (TNF) α, TNFβ, IL-1, 4, 6, 12, 15 and the CSFs have shown a certain antitumoral activity on some types of tumors and therefore are the object of further studies.

SUMMARY

Provided herein are therapeutic proteins, nucleic acids (e.g., DNA, RNA, mRNA) that encode the proteins, and compositions and methods of using the proteins and nucleic acids for the treatment of a disease or disorder, such as proliferative disease, a tumorous disease, an inflammatory disease, an immunological disorder, an autoimmune disease, an infectious disease, a viral disease, an allergic reaction, a parasitic reaction, graft-versus-host disease and the like. In certain embodiments, the fusion protein the amino acid sequence of any one of SEQ ID NOs.: 193-271. Certain fusion proteins disclosed herein are referred to as ACP200-208, ACP211, ACP213-ACP215, ACP240-ACP245, ACP247, ACP284-ACP292, ACP296-ACP300, ACP302-ACP306, ACP309-ACP314, ACP336-ACP359, ACP371-ACP379, ACP383-ACP434, ACP439-ACP447, or ACP451-ACP471. This disclosure also relates to nucleic acids (e.g., DNA, RNA, mRNA) that encode the fusion proteins, methods of making fusion proteins, compositions comprising a fusion protein, as well as methods of using the fusion proteins to treat cancer including combination of two or more fusion proteins and one or more fusion protein in combination with another therapeutic agent.

The invention features fusion proteins that are conditionally active variants of a cytokine of interest. Cytokines of particular interest include IL-2, IL-12, and IFN. In one aspect, the full-length polypeptides of the invention have reduced or minimal cytokine-receptor activating activity even though they contain a functional cytokine polypeptide. Upon activation, e.g., by cleavage of a linker that joins a blocking moiety, e.g. a steric blocking polypeptide, in sequence to the active cytokine, the cytokine, e.g., IL-2, IL-7, IL-12, IL-15, IL-18, IL-21, IL-23, IFNalpha, IFNbeta, IFNgamma, TNFalpha, lymphotoxin, TGF-beta1, TGF-beta2, TGFbeta3, GM-CSF, CXCL10, CCL19, CCL20, CCL21 or functional fragment or mutein or functional variant or a subunit of any of the foregoing, can bind its receptor and effect signaling. If desired, the full-length polypeptides can include a blocking polypeptide moiety that also provides additional advantageous properties. For example, the full-length polypeptide can contain a blocking polypeptide moiety that also extends the serum half-life and/or targets the full-length polypeptide to a desired site of cytokine activity. Alternatively, the full-length fusion polypeptides can contain a serum half-life extension element and/or targeting domain that are distinct from the blocking polypeptide moiety. Preferably, the fusion protein contains at least one element or domain capable of extending in vivo circulating half-life. Preferably, this element is removed enzymatically in the desired body location (e.g., protease cleavage in the tumor microenvironment), restoring pharmacokinetic properties to the payload molecule (e.g., IL2, IL-12, IFNb or IFNa) substantially similar to the naturally occurring payload molecule. The fusion proteins may be targeted to a desired cell or tissue.

The fusion polypeptides typically comprise a cytokine polypeptide [A], a blocking moiety [D], optionally a half-life extension moiety [H], and a protease-cleavable polypeptide linker. The cytokine polypeptide and the blocking moiety and the optional half-life extension element when present are operably linked by the protease-cleavable polypeptide linker and the fusion polypeptide has attenuated cytokine receptor activating activity, e.g., the cytokine-receptor activating activity of the fusion polypeptide is at least about 10× less than the cytokine receptor activating activity of the polypeptide that contains the cytokine polypeptide that is produced by cleavage of the protease cleavable linker. Some preferred fusion polypeptides are of one of formula (I)— (VI):

[A]-[L1]-[H]-[L2]-[D]           (I);

[D]-[L2]-[H]-[L1]-[A]           (II);

[A]-[L1]-[D]-[L2]-[H]           (III);

[H]-[L2]-[D]-[L1]-[A]           (IV);

[H]-[L1]-[A]-[L2']-[D]          (V);

[D]-[L1]-[A]-[L2']-[H]          (VI);

wherein A is a cytokine polypeptide, D is a blocking moiety, H is a half-life extension moiety, L1 is a protease-cleavable polypeptide linker, L2 is a polypeptide linker that is optionally protease-cleavable, and L2' is a protease-cleavable polypeptide linker. L1 and L2 or L1 and L2' can be have the same or different amino acid sequence and or protease-cleavage site (when L2 is protease-cleavable) as desired.

In some aspects, the fusion proteins described herein are conditionally active variants of IL-12, IL-2, or IFN. In embodiments, the fusion protein can contain an IL-2 polypeptide. The fusion protein containing an IL-2 polypeptide can comprise or consist of the amino acid sequence of SEQ ID NOs. 257-300, 302-317, 325-353, 355-365, 366, 372-381, 383-385, 388-420, 579-608, and 636-646. The fusion proteins disclosed as SEQ ID NOs. 257-300, 302-317, 325-353, 355-365, 366, 372-381, 383-385, 388-420, 579-608, 636-646 are referred to herein as ACP289-ACP292, ACP296-ACP302, WW0301, ACP304-ACP306, ACP309-ACP313, WW0353, ACP414, ACP336-ACP398, WW0472-WW0477, ACP406-ACP426, ACP439-ACP447, ACP451-ACP471, WW0729, WW0734-WW0792, ACP101, ACP293-ACP295, ACP316-ACP335, ACP427-ACP438, and ACP448-ACP450. For example, the fusion protein can comprise the amino acid sequence of SEQ ID NO: 272. The fusion protein can comprise the amino acid sequence of SEQ ID NO: 286. The fusion protein can comprise the amino acid sequence of SEQ ID NO:362. The fusion protein can comprise the amino acid sequence of SEQ ID NO:336. The fusion protein can comprise the amino acid sequence of SEQ ID NO: 348. The fusion protein can comprise the amino acid sequence of SEQ ID NO: 363. The fusion protein can comprise the amino acid sequence of SEQ ID NO: 580.

In embodiments, the fusion protein can contain IL-12. The fusion protein containing an IL-12 polypeptide can comprise or consist of the amino acid sequence of any one of SEQ ID NOs. 368-371, 434-440, 453-519, or 523-538. The fusion proteins disclosed as SEQ ID NOs. 368-371, 434-440, 453-519, or 523-538 are referred to herein as ACP240-ACP245, ACP247, ACP285-ACP288, WW0641, WW0649-WW0652, WW0662-WW0725, WW0765-WW0772, and WW0796-WW0803. For example, the fusion protein can comprise the amino acid sequence of SEQ ID NO: 424. For example, the fusion protein can comprise the amino acid sequence of SEQ ID NO: 428. For example, the fusion protein can comprise the amino acid sequence of SEQ ID NO: 541. For example, the fusion protein can comprise the amino acid sequence of SEQ ID NO: 556. For example, the fusion protein can comprise the amino acid sequence of SEQ ID NO: 560. For example, the fusion protein can comprise the amino acid sequence of SEQ ID NO: 568. For example, the fusion protein can comprise the amino acid sequence of SEQ ID NO: 573.

In embodiments, the fusion protein contains IFN. The fusion protein containing an IFN polypeptide can comprise or consist of the amino acid sequence of any one of SEQ ID NOs. 421-430, and 539-578. The fusion proteins disclosed as SEQ ID NOs. 421-430, and 539-578 can be referred to herein as ACP200-ACP209, WW0644-WW0648, WW0781-WW0786, WW0815-WW0822, WW0831-WW0834, WW0737-WW0748, and WW0787-WW0790.

In some aspects, the fusion polypeptide disclosed herein can be covalently or non-covalently bonded to a second polypeptide chain. For example, a fusion polypeptide can dimerize (i.e., form a dimer) or a portion of a fusion polypeptide may associate with another polypeptide, for example, to form a functional binding site for a cytokine polypeptide or serum albumin. In certain embodiments, the second polypeptide chain and the blocking moiety on the fusion polypeptide are complementary and together form a functional binding site that has specificity for the cytokine polypeptide contained in the fusion polypeptide. Exemplary functional binding sites that can be formed by the blocking moiety of the fusion polypeptide and a complimentary second polypeptide include antigen binding sites of antibodies, such as a Fab fragment of an antibody or a portion thereof. For example, one chain of a Fab that binds the cytokine can be the blocking moiety of the fusion polypeptide, e.g., a VH-CH1, and the complementary VL-CL can be part of the second polypeptide. In such situations, the blocking moiety of the fusion protein i.e., VH-CH1 and the second polypeptide that comprises the complementary VL-CL, can associate to form a functional binding site with specificity for the cytokine polypeptide contained within the fusion protein (e.g., IL-2, IL-12, IFNalpha, IFNbeta) and attenuate cytokine polypeptide activity.

In embodiments, the fusion protein containing an IL-2 cytokine polypeptide can be bonded covalently or noncovalently to a second polypeptide chain. The second polypeptide chain can contain an antibody light chain VL-CL that comprises or consists of the amino acid sequence of SEQ ID NO: 263, 264, or 333. Such a second polypeptide can bond with a complimentary VH-CH1 polypeptide contained within the fusion protein, e.g., as contained within SEQ ID NOS: 362, 363, 325, 286, 579, 581, or 582. The second polypeptide chain disclosed as SEQ ID NOs. 263, 264, and 333 can be referred herein as WW0523 (ACP381), WW0524 (ACP382), or WW0556 (ACP414).

In embodiments, the fusion polypeptide can comprise or consist of the amino acid sequence of SEQ ID NOs. 362, 363, 325, 286, 579, 581, or 582 and the second polypeptide chain can comprise or consist of the amino acid sequence of SEQ ID NOs: 263, 264, or 333. The fusion polypeptide disclosed as SEQ ID NOs. 362, 363, 325, 286, 579, 581, or 582 can be referred to as WW0520 (ACP378), WW0521 (ACP379), WW0548 (ACP406), WW0621 (ACP457), WW0729, WW0735, or WW0736, and the second polypeptide chain disclosed as SEQ ID NOs. 263, 264, and 333 can be referred herein as WW0523 (ACP381), WW0524 (ACP382), or WW0556 (ACP414). For example, the fusion protein can comprise or consist the amino acid sequence of SEQ ID NO: 362 and the second polypeptide chain can comprise or consist the amino acid sequence of SEQ ID NO: 263. For example, the fusion protein can comprise or consist the amino acid sequence of SEQ ID NO: 362 and the second polypeptide chain can comprise or consist the amino acid sequence of SEQ ID NO: 264. For example, the fusion protein can comprise or consist the amino acid sequence of SEQ ID NO: 362 and the second polypeptide chain can comprise or consist the amino acid sequence of SEQ ID NO: 333. For example, the fusion protein can comprise or consist of an amino acid sequence of SEQ ID NO: 363 and the second polypeptide chain can comprise or consist of an amino acid sequence of SEQ ID NO: 263. For example, the fusion protein can comprise or consist of an amino acid sequence of SEQ ID No. 363 and the second polypeptide chain can comprise or consist of an amino acid sequence of SEQ ID NO: 264. For example, the fusion protein can comprise or consist of an amino acid sequence of SEQ ID NO: 363 and the second polypeptide chain can comprise or consist of an amino acid sequence of SEQ ID NO: 333. For example, the fusion protein can comprise or consist of an amino acid sequence of SEQ ID NO: 325 and the second polypeptide chain can comprise or consist of an amino acid sequence of SEQ ID NO: 264. For example, the fusion protein can comprise or consist of an amino acid sequence of SEQ ID NO: 325 and the second polypeptide chain can comprise or consist of an amino acid sequence of SEQ ID NO: 333. For example, the fusion protein can comprise or consist of an amino acid sequence of SEQ ID NO: 325 and the second polypeptide chain can comprise or consist of an amino acid sequence of SEQ ID NO: 263. For example, the fusion protein can comprise or consist of an amino acid sequence of SEQ ID NO: 286 and the second polypeptide chain can comprise or consist of an amino acid sequence of SEQ ID NO: 263. For example, the fusion protein can comprise or consist of an amino acid sequence of SEQ ID NO: 286 and the second polypeptide chain can comprise or consist of an amino acid sequence of SEQ ID NO: 264. For example, the fusion protein can comprise or consist of an amino acid sequence of SEQ ID NO: 286, and the second polypeptide can comprise or consist of an amino acid sequence of SEW ID NO: 333. For example, the fusion protein can comprise or consist of an amino acid sequence of SEQ ID NO: 579 and the second polypeptide chain can comprise or consist of an amino acid sequence of SEQ ID NO: 263. For example, the fusion protein can comprise or consist of an amino acid sequence of SEQ ID NO: 579 and the second polypeptide chain can comprise or consist of an amino acid sequence of SEQ ID NO: 264. For example, the fusion protein can comprise or consist of an amino acid sequence of SEQ ID NO: 579 and the second polypeptide chain can comprise or consist of an amino acid sequence of SEQ ID NO: 233. For example, the fusion protein can comprise or consist of SEQ ID NO: 581 and the second polypeptide chain can comprise or consist of SEQ ID NO.: 263. For example, the fusion protein can comprise or consist of SEQ ID NO: 581 and the second polypeptide chain can comprise or consist of SEQ ID NO.: 264. For example, the fusion protein can comprise or consist of SEQ ID NO: 581 and the second polypeptide chain can comprise or consist of SEQ ID NO.: 333. For example, the fusion protein can comprise or consist of SEQ ID NO: 582 and the second polypeptide chain can comprise or consist of SEQ ID NO: 263. For example, the fusion protein can comprise or consist of SEQ ID NO: 582 and the second polypeptide chain can comprise or consist of SEQ ID NO: 264. For example, the fusion protein can comprise or consist of SEQ ID NO: 582 and the second polypeptide chain can comprise or consist of SEQ ID NO: 333.

As described herein targeting is accomplished through the action of a blocking polypeptide moiety that also binds to a desired target, or through a targeting domain. The domain that recognizes a target antigen on a preferred target (for example a tumor-specific antigen), may be attached to the cytokine via a cleavable or non-cleavable linker. If attached by a non-cleavable linker, the targeting domain may further aid in retaining the cytokine in the tumor, and it may be considered a retention domain. The targeting domain does not necessarily need to be directly linked to the payload molecule, and it may be linked directly to another element of the fusion protein. This is especially true if the targeting domain is attached via a cleavable linker.

In one aspect is provided a fusion polypeptide comprising a cytokine polypeptide, or functional fragment, a mutein thereof, a functional variant thereof or a subunit thereof, and a blocking moiety, e.g., a steric blocking domain. The blocking moiety is fused to the cytokine polypeptide, directly or through a linker, and can be separated from the cytokine polypeptide by cleavage (e.g., protease mediated cleavage) of the fusion polypeptide at or near the fusion site or linker or in the blocking moiety. For example, when the cytokine polypeptide is fused to a blocking moiety through a linker that contains a protease cleavage site, the cytokine polypeptide is released from the blocking moiety and can bind its receptor, upon protease mediated cleavage of the linker. The linker is designed to be cleaved at the site of desired cytokine activity, for example in the tumor microenvironment, avoiding off-target cytokine activity and reducing overall toxicity of cytokine therapy.

The blocking moiety can also function as a serum half-life extension element. In some embodiments, the fusion polypeptide further comprises a separate serum half-life extension element. In some embodiments, the fusion polypeptide further comprises a targeting domain. In various embodiments, the serum half-life extension element is a water-soluble polypeptide such as optionally branched or multi-armed polyethylene glycol (PEG), full length human serum albumin (HSA) or a fragment that preserves binding to FcRn, an Fc fragment, or a nanobody that binds to FcRn directly or to human serum albumin.

In addition to serum half-life extension elements, the pharmaceutical compositions described herein preferably comprise at least one, or more targeting domains that bind to one or more target antigens or one or more regions on a single target antigen. It is contemplated herein that a polypeptide construct of the invention is cleaved, for example, in a disease-specific microenvironment or in the blood of a subject at the protease cleavage site and that the targeting domain(s) will bind to a target antigen on a target cell. At least one target antigen is involved in and/or associated with a disease, disorder or condition. Exemplary target antigens include those associated with a proliferative disease, a tumorous disease, an inflammatory disease, an immunological disorder, an autoimmune disease, an infectious disease, a viral disease, an allergic reaction, a parasitic reaction, a graft-versus-host disease or a host-versus-graft disease.

In some embodiments, a target antigen is a cell surface molecule such as a protein, lipid or polysaccharide. In some embodiments, a target antigen is a on a tumor cell, virally infected cell, bacterially infected cell, damaged red blood cell, arterial plaque cell, or fibrotic tissue cell.

Target antigens, in some cases, are expressed on the surface of a diseased cell or tissue, for example a tumor or a cancer cell. Target antigens for tumors include but are not limited to Fibroblast activation protein alpha (FAPa), Trophoblast glycoprotein (5T4), Tumor-associated calcium signal transducer 2 (Trop2), Fibronectin EDB (EDB-FN), fibronectin EIIIB domain, CGS-2, EpCAM, EGFR, HER-2, HER-3, c-Met, FOLR1, FAP, and CEA. Pharmaceutical compositions disclosed herein, also include proteins comprising two antigen binding domains that bind to two different target antigens known to be expressed on a diseased cell or tissue. Exemplary pairs of antigen binding domains include but are not limited to EGFR/CEA, EpCAM/CEA, and HER-2/HER-3.

In some embodiments, the targeting polypeptides independently comprise a scFv, a VH domain, a VL domain, a non-Ig domain, or a ligand that specifically binds to the target antigen. In some embodiments, the targeting polypeptides specifically bind to a cell surface molecule. In some embodiments, the targeting polypeptides specifically bind to a tumor antigen. In some embodiments, the targeting polypeptides specifically and independently bind to a tumor antigen selected from at least one of EpCAM, EGFR, HER-2, HER-3, cMet, CEA, and FOLR1. In some embodiments, the targeting polypeptides specifically and independently bind to two different antigens, wherein at least one of the antigens is a tumor antigen selected from EpCAM, EGFR, HER-2, HER-3, cMet, CEA, and FOLR1. In some embodiments, the targeting polypeptide serves as a retention domain and is attached to the cytokine via a non-cleavable linker.

As described herein, the cytokine blocking moiety can bind to the cytokine and thereby block activation of the cognate receptor of the cytokine.

This disclosure also related to nucleic acids, e.g., DNA, RNA, mRNA, that encode the conditionally active proteins described herein, as well as vectors and host cells that contain such nucleic acids.

This disclosure also relates to pharmaceutical compositions that contain a conditionally active protein, nucleic acid that encodes the conditionally active protein, and vectors and host cells that contain such nucleic acids. Typically, the pharmaceutical composition contains one or more physiologically acceptable carriers and/or excipients.

The disclosure also relates to therapeutic methods that include administering to a subject in need thereof an effective amount of a conditionally active protein, nucleic acid that encodes the conditionally active protein, vector or host cells that contain such a nucleic acid, and pharmaceutical compositions of any of the foregoing. Typically, the subject has, or is at risk of developing, a proliferative disease, a tumorous disease, an inflammatory disease, an immunological disorder, an autoimmune disease, an infectious disease, a viral disease, an allergic reaction, a parasitic reaction, a graft-versus-host disease or a host-versus-graft disease.

The disclosure also relates to the use of a conditionally active protein, nucleic acid that encodes the conditionally active protein, vector or host cells that contain such a nucleic acid, and pharmaceutical compositions of any of the foregoing, for treating a subject in need thereof. Typically, the subject has, or is at risk of developing, a proliferative disease, a tumorous disease, an inflammatory disease, an immunological disorder, an autoimmune disease, an infectious disease, a viral disease, an allergic reaction, a parasitic reaction, a graft-versus-host disease or a host-versus-graft disease.

The disclosure also relates to the use of a conditionally active protein, nucleic acid that encodes the conditionally active protein, vector or host cells that contain such a nucleic acid for the manufacture of a medicament for treating a disease, such as a proliferative disease, a tumorous disease, an inflammatory disease, an immunological disorder, an autoimmune disease, an infectious disease, a viral disease, an allergic reaction, a parasitic reaction, a graft-versus-host disease or a host-versus-graft disease.

BRIEF DESCRIPTION OF THE DRAWINGS

FIGS. 1A-1E are a series of graphs showing activity of IL-2 fusion proteins in a HEKBlue IL-2 reporter assay in the presence of HSA. Squares depict activity of the uncut IL-2 polypeptide (intact) and triangles depict the activity of the cut polypeptide (cleaved). Circles depict activity of control IL-2. EC50 for each IL-12. EC50 values for each are shown in the table. FIGS. 1A-1E also depict results of the protein cleavage assay for each IL-2 polypeptide. Constructs tested and depicted include WW0475 (FIG. 1A), WW0517 (FIG. 1B), WW0548/556 (FIG. 1C), WW0735/523 (FIG. 1D), and WW0621/523 (FIG. 1E). FIG. 1F is a graph showing activity of a non-cleavable control, WW0729/523. FIG. 1F also depicts results of a protein cleavage assay for the non-cleavable control.

FIGS. 2A-2L are a series of graphs showing activity of fusion proteins in an IL-2 luciferase reporter assay. Closed squares depict activity of the uncut IL-2 polypeptide (intact) and open squares depict the activity of the cut IL-2 polypeptide (cleaved). Circles depict activity of the control (human IL-2). EC50 values for each are shown in the table (human IL-2). EC50 values for each are shown in the table. Constructs tested and depicted include WW0521/WW0556 (FIG. 2A), WW0521/WW0524 (FIG. 2B), WW0521/WW0523 (FIG. 2C), WW0520/WW0524 (FIG. 2D), WW0517 (FIG. 2E), WW0516 (FIG. 2F), WW0417 (FIG. 2G), WW0317 (FIG. 2H), WW0317 (FIG. 2I), and WW0520/WW0523 (FIG. 2J), WW0621/WW0523 (FIG. 2K), WW0048 (FIG. 2L).

In FIGS. 3B, 3D, 3J squares and in FIGS. 3A, 3C, 3E, 3I triangles depict activity of the uncut IL-2 polypeptide (intact), and in FIGS. 3B, 3D, 3J triangles, and in FIGS. 3A, 3C and 3E-3I upside down triangles depict the activity of the cut polypeptide (cleaved). Circles (FIGS. 3B, 3D, 3J) or squares (FIGS. 3A, 3C, 3E-3I) depict activity of the control human IL-2. EC50 values for each are shown in the table. Constructs tests and depicted include WW0317 (FIG. 3A), WW0516 (FIG. 3B), WW0354 (FIG. 3C), WW0517 (FIG. 3D), WW0621/0523 (FIG. 3E), WW0521/524 (FIG. 3F), WW0520/0523 (FIG. 3G), WW0729/523 (FIG. 3H), and WW0735/523 (FIG. 3I), WW0520/524 (FIG. 3J).

FIG. 5A contains the data corresponding to vehicle treatment and fusion proteins WW0517 and WW0520/523. FIG. 5B contains the data corresponding to treatment with fusion proteins WW0548/0524, WW0548/0556, and WW0475. FIG. 5C contains the data corresponding to treatment with fusion proteins WW0619 and WW0621/0523.

FIG. 6A contains the data corresponding to vehicle treatment and fusion proteins WW0517 and WW0520/523. FIG. 6B contains the data corresponding to treatment with fusion proteins WW0548/0524, WW0548/0556, and WW0475. FIG. 6C contains the data corresponding to treatment with fusion proteins WW0619 and WW0621/0523.

FIGS. 7A-7Q depict IL-12/STAT4 activation in a comparison of human p40/murine p35 IL-12 or human IL-12 fusion proteins to chimeric IL-12 (mouse p35/human p40) or recombinant human IL-12 (control). Squares depict activity of the uncut IL-12 polypeptide (intact) and triangles depict the activity of the cut IL-12 polypeptide (cleaved). Circles depict activity of the control. EC50 values for each are shown in the table.

FIGS. 8A-8D depicts activation of IL-12 signaling in a comparison of a human p40/murine p35 IL12 or human IL12 fusion protein to control, chimeric IL-12 (human p40/murine p35 IL12) or recombinant human IL12. Squares depict activity of the uncut IL-12 polypeptide (intact) and triangles depict the activity of the cut IL-12 polypeptide (cleaved). Circles depict activity of the control chimeric IL-12 or recombinant human IL-12. EC50 values for each are shown in the table.

FIGS. 9A-9B depict activation of IL-12 signaling in a comparison of a human p40/murine p35 IL-12 fusion protein to recombinant human IL-12 (control). FIG. 9C depicts activation of IL-12 signaling in comparison of a human IL-12 (human p40/human p35 IL-12) fusion protein to recombinant human IL12. Closed squares depict activity of the uncut IL-12 polypeptide (intact) and open squares depict the activity of the cut polypeptide (cleaved). Circles depict activity of the control. EC50 values for each are shown in the table.

FIGS. 10A-10J are a series of graphs showing activity of fusion proteins in the B16-Blue IFN-α/β reporter assay. FIGS. 10A-10J depict activation of the IFN-α/β pathway in a comparison of mouse IFNα fusion protein to mouse IFNα (control). Squares depict activity of the uncut IFNα polypeptide (intact) and triangles depict the activity of the cut IFNα polypeptide (cleaved). Circles depict activity of the control (mouse IFNα). EC50 values for each are shown in the table. FIGS. 10A-10J also depict results of the protein cleavage assay for each IFNα fusion protein. Each IFNα fusion protein was run on an SDS-PAGE gel in both cleaved and uncleaved form. As can be seen in the gel, cleavage was complete.

FIGS. 17A-17F are a series of graphs showing activity of exemplary IFNγ fusion proteins compared to activity of mouse IFNγ control using B16 reporter assay. Each assay was performed with medium containing HSA (+HSA) or not containing HSA (-HSA). Each fusion protein comprises an anti-HSA binder, and both uncleaved and MMP9 protease cleaved versions of the fusion protein were used in each assay.

FIG. 18A) and ACP55 (IFN-γ fusion protein; 18B), were run on an SDS-PAGE gel in both cleaved and uncleaved form. As can be seen in the gel, cleavage was complete.

FIGS. 19A-19B are a series of graphs (FIGS. 19A and 19B) showing activity of exemplary IFNγ fusion proteins before and after protease cleavage using B16 reporter assay. Each assay was performed with culture medium containing HSA, and each fusion protein comprises an anti-HSA binder. Both uncleaved and MMP9 protease cleaved versions of the fusion protein were used in each assay.

FIG. 21A-C show the effect of IFNγ and IFNγ fusion proteins on tumor growth when injected intraperitoneally (IP) using different dosing levels and schedules (ug=micrograms, BID=twice daily, BIW=twice weekly, QW=weekly). FIG. 21D shows the effect of intratumoral (IT) injection of IFNγ and IL-2 on tumor growth.

FIG. 24A shows results of IL-2 constructs ACP132 and ACP133 with and without albumin. FIG. 24B shows results of IL-2 construct ACP16 cleaved and uncleaved. Results of a protein cleavage assay of ACP16 in cleaved and uncleaved forms is also depicted. FIG. 24C shows results of IL-2 construct ACP153 in cleaved and uncleaved forms. Results of a protein cleavage assay are also depicted. FIG. 24D illustrates the results from a HEK-Blue IL-2 assay using wild-type cytokine, intact fusion protein, and protease-cleaved fusion protein.

FIGS. 25A and 25B are two graphs showing analysis of ACP16 (FIG. 25A) and ACP124 (FIG. 25B) in a HEKBlue IL-2 reporter assay in the presence of HSA. Circles depict the activity of the uncut polypeptide; squares depict activity of the cut polypeptide.

FIG. 26A depicts IL-12/STAT4 activation in a comparison of ACP11 (a human p40/murine p35 IL12 fusion protein) to ACP04 (negative control). FIG. 26B is a graph showing analysis of ACP91 (a chimeric IL-12 fusion protein). Squares depict activity of the uncut ACP91 polypeptide, and triangles depict the activity of the cut polypeptide (ACP91+MMP9). EC50 values for each are shown in the table. FIG. 26C is a graph showing analysis of ACP136 (a chimeric IL-12 fusion protein). Squares depict activity of the uncut ACP136 polypeptide, and triangles depict the activity of the cut polypeptide (ACP136+MMP9). EC50 values for each are shown in the table insert.

FIGS. 27A-27F are a series of graphs showing that cleaved mouse IFNα1 polypeptides ACP31 (FIG. 27A), ACP125 (FIG. 27B), ACP126 (FIG. 27C), ACP127 (FIG. 27D), APC128 (FIG. 27E), and APC129 (FIG. 27F) are active in an B16-Blue IFN-α/β reporter assay.

FIG. 29A shows tumor volume over time in mice treated with 33 µg ACP31 (circles), 110 µg ACP31 (triangles), 330 µg ACP31 (diamonds), and as controls 1 µg murine wild type IFNα1 (dashed line, squares) and 10 µg mIFNα1 (dashed line, small circles). Vehicle alone is indicated by large open circles. The data show tumor volume decreasing over time in a dose-dependent manner in mice treated with ACP31. FIG. 29B shows tumor volume over time in mice treated with 17.5 µg ACP11 (squares), 175 µg ACP11 (triangles), 525 µg ACP11 (circles), and as controls 2 µg ACP04 (dashed line, triangles) and 10 µg ACP04 (dashed line, diamonds). Vehicle alone is indicated by large open circles. The data show tumor volume decreasing over time in a dose-dependent manner in mice treated with both ACP11 and ACP04 (a human p40/murine p35 IL12 fusion protein).

FIG. 31A shows tumor volume over time in mice treated with 4.4 µg ACP16 (squares), 17 µg ACP16 (triangles), 70 µg ACP16 (downward triangles), 232 µg ACP16 (dark circles), and as a comparator 12 µg wild type IL-2 (dashed line, triangles) and 36 µg wild type IL-2 (dashed line, diamonds). Vehicle alone is indicated by large open circles. The data show tumor volume decreasing over time in a dose-dependent manner in mice treated with ACP16 at higher concentrations. FIG. 31B shows tumor volume over time in mice treated with 17 µg ACP124 (squares), 70 µg ACP124 (triangles), 230 µg ACP124 (downward triangles), and 700 µg ACP124. Vehicle alone is indicated by large open circles. FIG. 31C shows tumor volume over time in mice treated with 17 µg ACP16 (triangles), 70 µg ACP16 (circles), 232 µg ACP16 (dark circles), and as a comparator 17 µg ACP124 (dashed line, triangles) 70 µg ACP124 (dashed line, diamonds), 230 µg ACP124 (dashed line, stars). Vehicle alone is indicated by dark downward triangles. The data show tumor volume decreasing over time in a dose-dependent manner in mice treated with ACP16, but not ACP124.

FIG. 34A shows data for mice treated with vehicle alone (gray line), 17 µg ACP16 (dark line), and 17 µg ACP124 (dashed line). FIG. 34B shows data for mice treated with vehicle alone (gray line), 70 µg ACP16 (dark line), and 70 µg ACP124 (dashed line). FIG. 34C shows data for mice treated with vehicle alone (gray line), 232 µg ACP16 (dark line), and 230 µg ACP124 (dashed line). FIG. 34D shows data for mice treated with vehicle alone (gray line), 232 µg ACP16 (dark line), and 700 µg ACP124 (dashed line).

FIGS. 36A-36H are a series of graphs showing activity of fusion proteins in the HEK-Blue IFN-α/β reporter assay. FIGS. 36A-36H depict activation of the IFN-α/β pathway in a comparison of human IFNα fusion protein) to control (human IFNα). Squares depict activity of the uncut IFNα polypeptide (intact) and triangles depict the activity of the cut IFNα polypeptide (cleaved). Circles depict activity of the control (human IFNα). EC50 values for each are shown in the table. Results confirm that the IFNα fusion proteins are active and inducible. FIGS. 36A-36H also depict results of the protein cleavage assay for each IFNα fusion protein. Each IFNα fusion protein was run on an SDS-PAGE gel in both cleaved and uncleaved form. As can be seen in the gel, cleavage was complete.

FIGS. 37A-37B depict activation of the IFN-α/β pathway in a comparison of a mouse IFNβ fusion protein to control (mouse IFNβ). FIGS. 37C-37D depict activation of the IFN-α/β pathway in a comparison of a human IFNβ fusion protein to control (human IFNβ). Squares depict activity of the uncut IFNβ polypeptide (intact) and triangles depict the activity of the cut IFNβ polypeptide (cleaved). Circles depict activity of the control. EC50 values for each are shown in the table. Results confirm that the IFNβ fusion proteins are active and inducible.

FIGS. 38A-38C depict activation of the IFNα pathway in a comparison of human IFNα fusion protein to control (human IFNα). Squares depict activity of the uncut IFNα polypeptide (intact) and triangles depict the activity of the cut IFNα polypeptide (cleaved). Circles depict activity of the control human IFNα. EC50 values for each are shown in the table. Analysis was performed based on quantification of CXCL-10 (IP-10). Results confirm that the IFNα fusion proteins are active and inducible.

FIG. 39A shows average tumor volume over time in mice treated with 369 µg WW0610 (square), 553 µg WW0610 (down triangle), 830 µg WW0610 (up triangle), and 1,245 µg WW0610 (circle). Vehicle alone is indicated by a black circle. FIG. 39B shows average tumor volume over time in mice treated with 1,231 µg WW0815 (square), 1,845 µg WW0815 (down triangle), 2,770 µg WW0815 (up triangle), and 4,154 µg WW0815 (circle). Vehicle alone is indicated by a black circle. FIG. 39C shows average tumor volume over time in mice treated with 4.6 µg WW0644 (square), 9.3 µg WW0644 (down triangle), 19 µg WW0644 (up triangle), and 37 µg WW0644 (circle). Vehicle alone is indicated by a black circle. FIG. 39D shows average tumor volume over time in mice treated with 31 µg WW0816 (square), 62 µg WW0816 (down triangle), 123 µg WW0816 (up triangle), and 247 µg WW0816 (circle). Vehicle alone is indicated by a black circle. FIG. 39E shows average tumor volume over time in mice treated with 110 µg WW0609 (square), 830 µg WW0609 (down triangle), and 1,320 µg WW0609 (up triangle). FIG. 39F shows average tumor volume over time in mice treated with 110 µg WW0610 (square), 830 µg WW0610 (down triangle), and 1,320 µg WW0610 (up triangle). FIG. 39G shows average tumor volume over time in mice treated with 0.3 µg WW0643 (square), 1.5 µg WW0643 (down triangle), 7.5 µg WW0643 (up triangle), and 37.5 µg WW0643 (diamond). Vehicle alone is indicated by a black circle.

FIG. 43 shows binding data of ACP16, ACP10, ACP11

FIG. 61A depicts activation of the IFN-α/β pathway for construct WW0609 in the presence and absence of albumin. FIG. 61B depicts activation of the IFN-α/β pathway for construct WW0643 in the presence and absence of albumin. Squares depict activity of the uncut IFNα polypeptide (intact) and triangles depict the activity of the cut IFNα polypeptide (cleaved). Circles depict activity of the control (mouse IFNα). EC50 values for each are shown in the table.

DETAILED DESCRIPTION

Figure 1A:
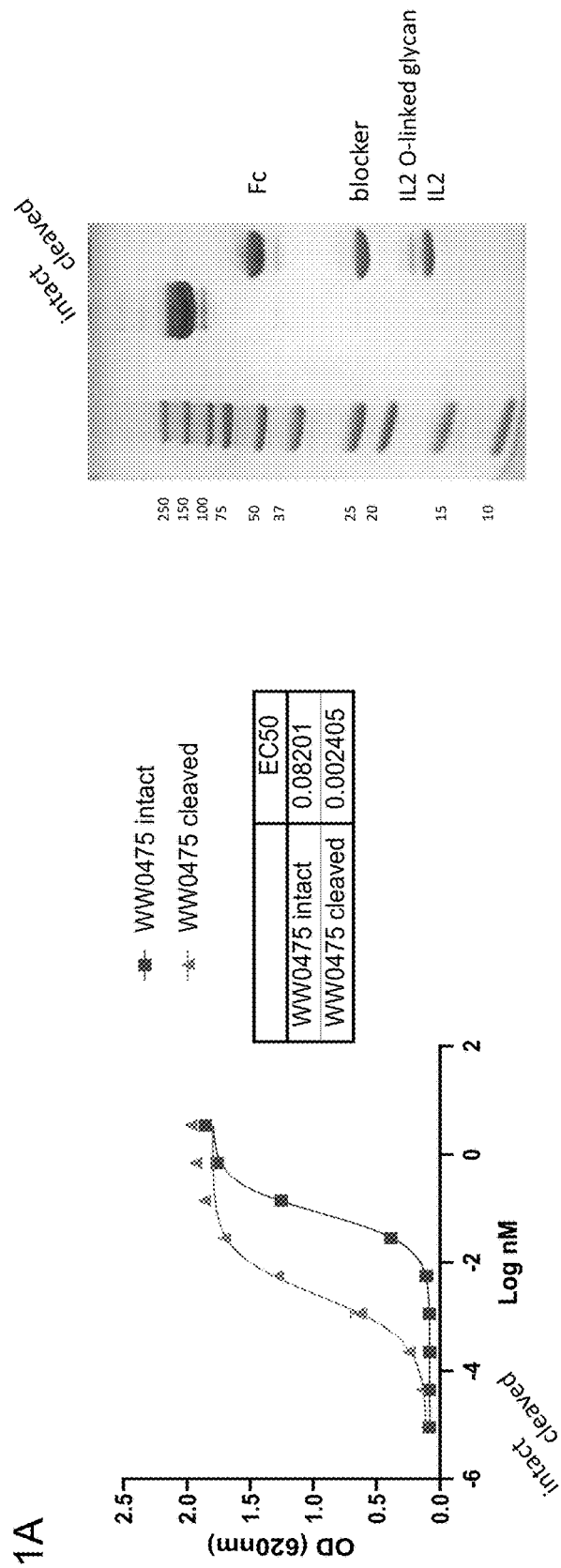
Figure 1B:
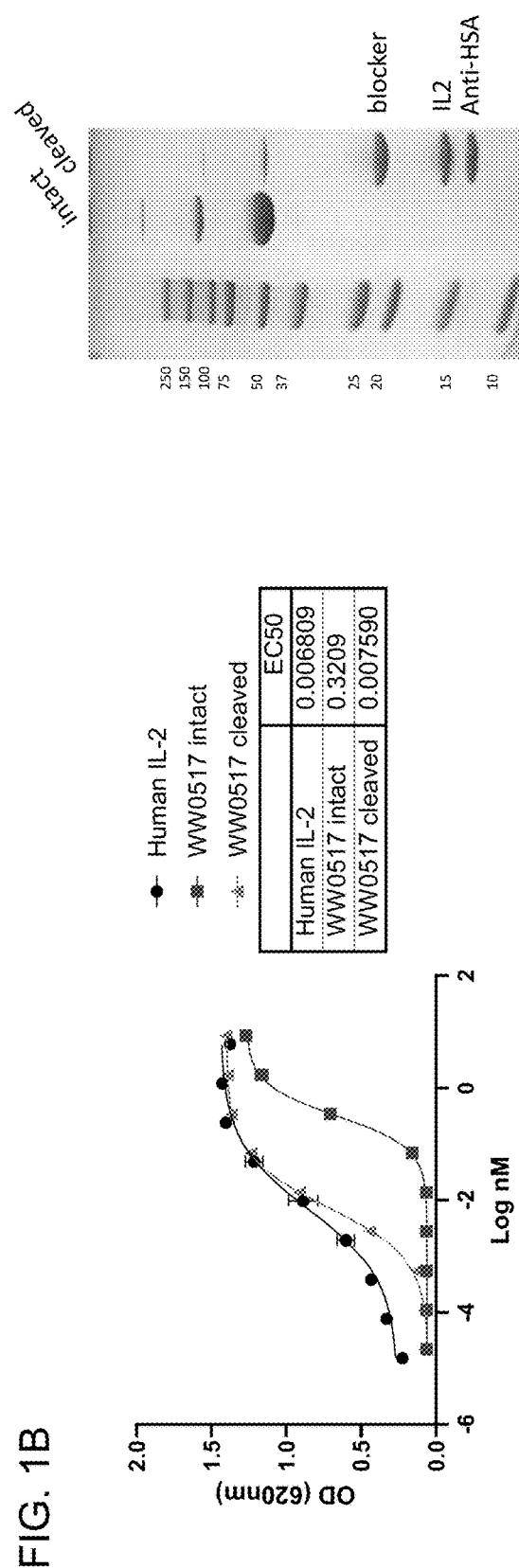
Figure 2A:
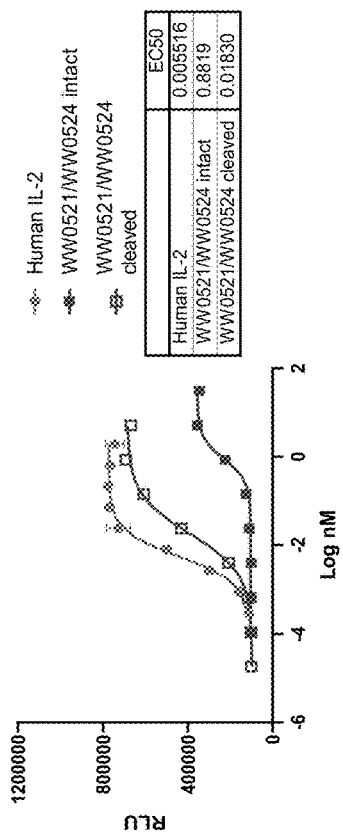
Figure 2B:
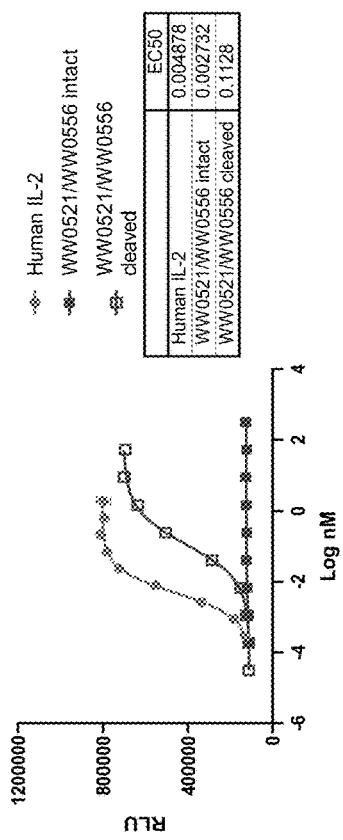
Figure 2C:
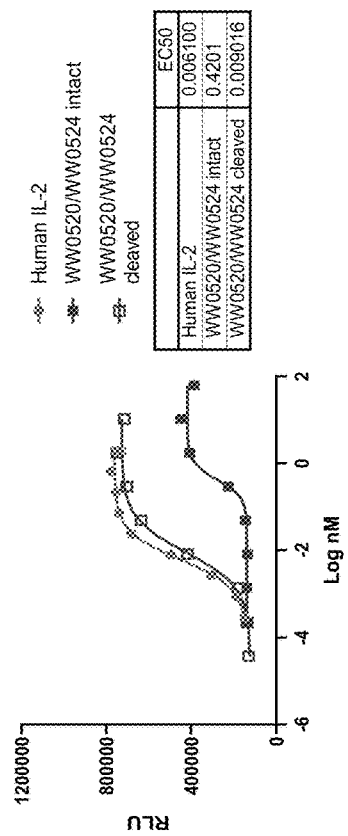
Figure 2D:
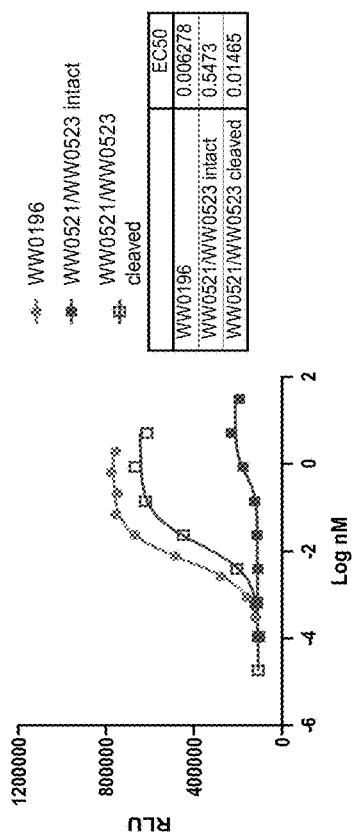
Figure 2E:
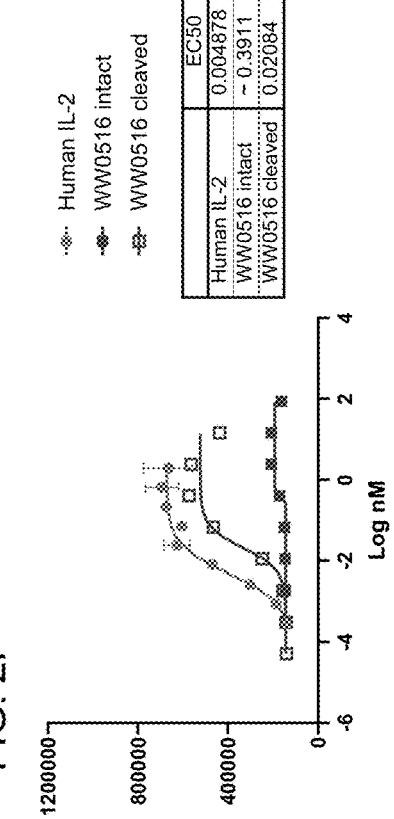
Figure 2F:
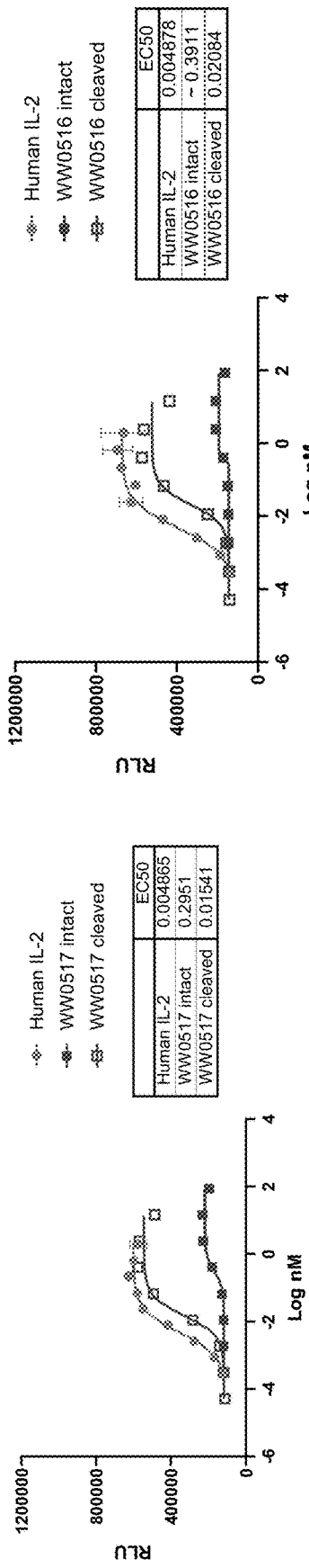
Figure 2G:
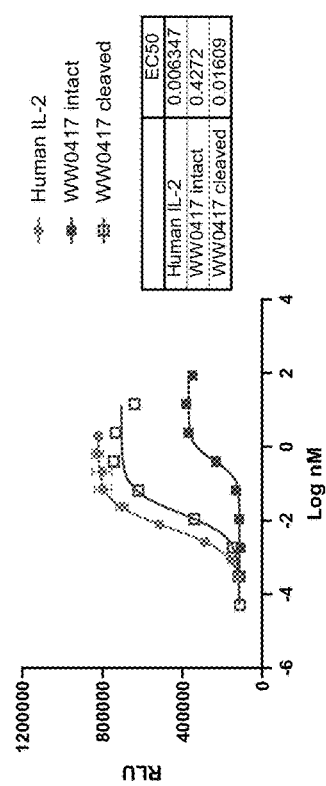
Figure 2H:
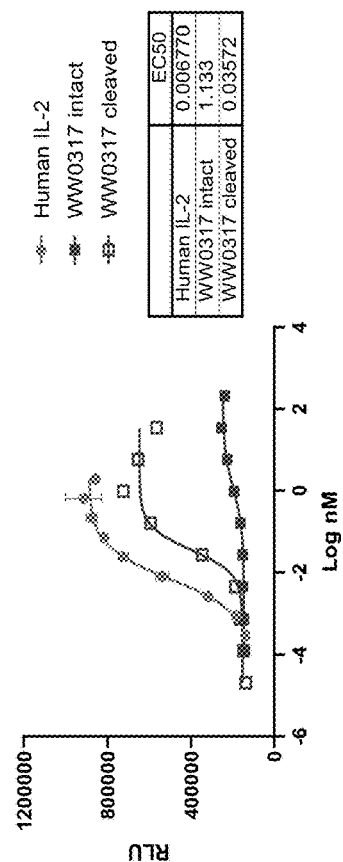
Figure 3A:
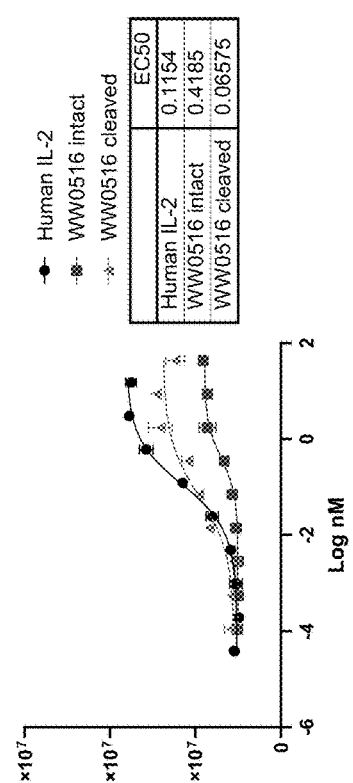
FIGS. 3A-3J are a series of graphs showing activity of fusion proteins in an IL-2 T-Blast assay.
Figure 3B:
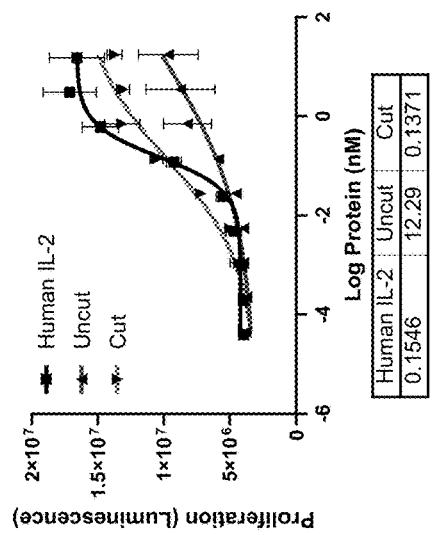
Figure 3C:
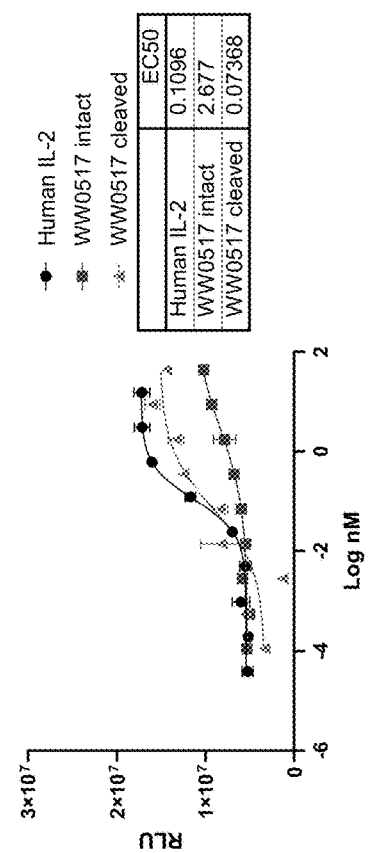
Figure 3D:
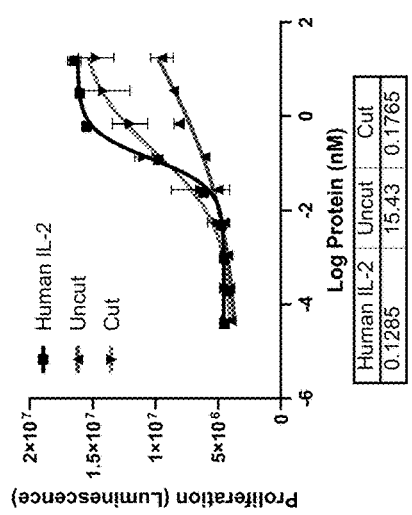
Figure 3E:
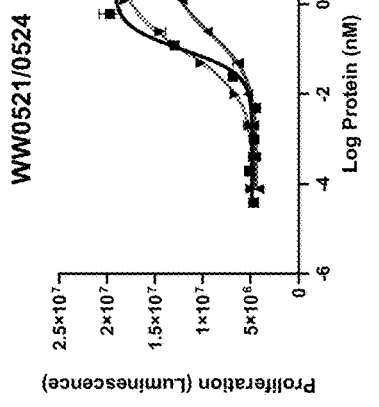
Figure 3F:
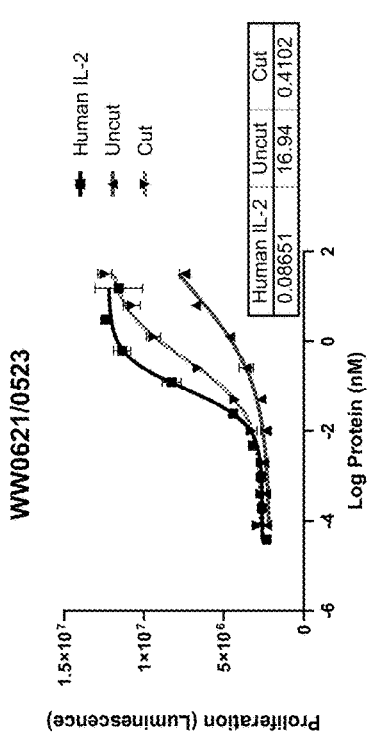
Figure 3G:
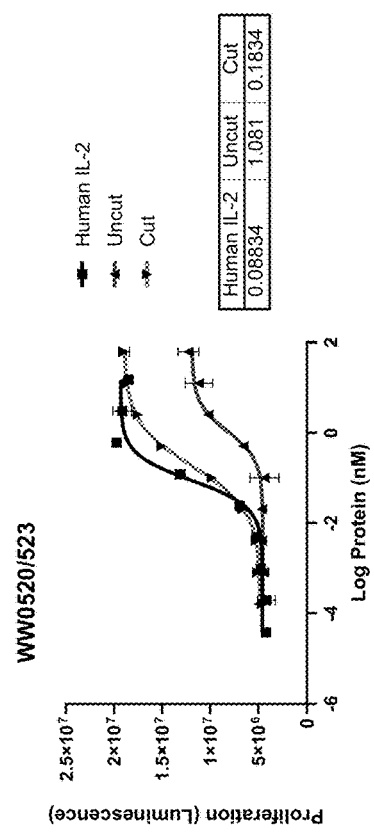
Figure 3H:
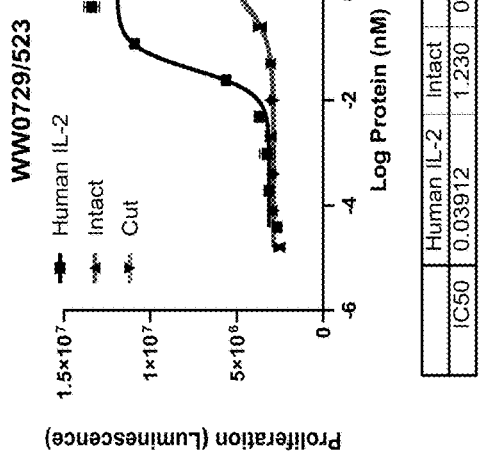
Figure 3I:
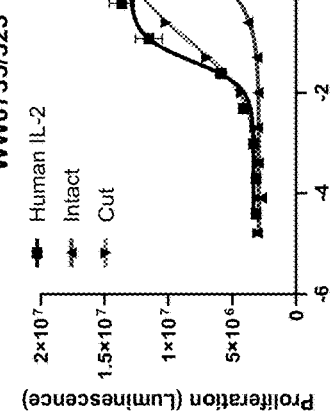
Figure 3J:
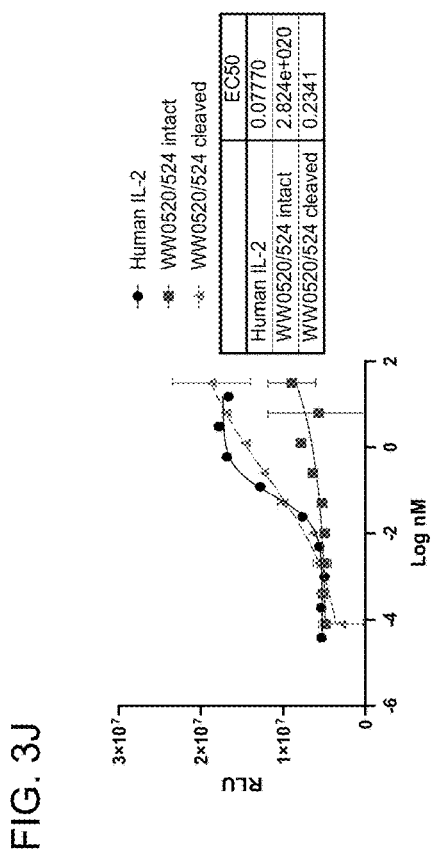
Figure 4A:
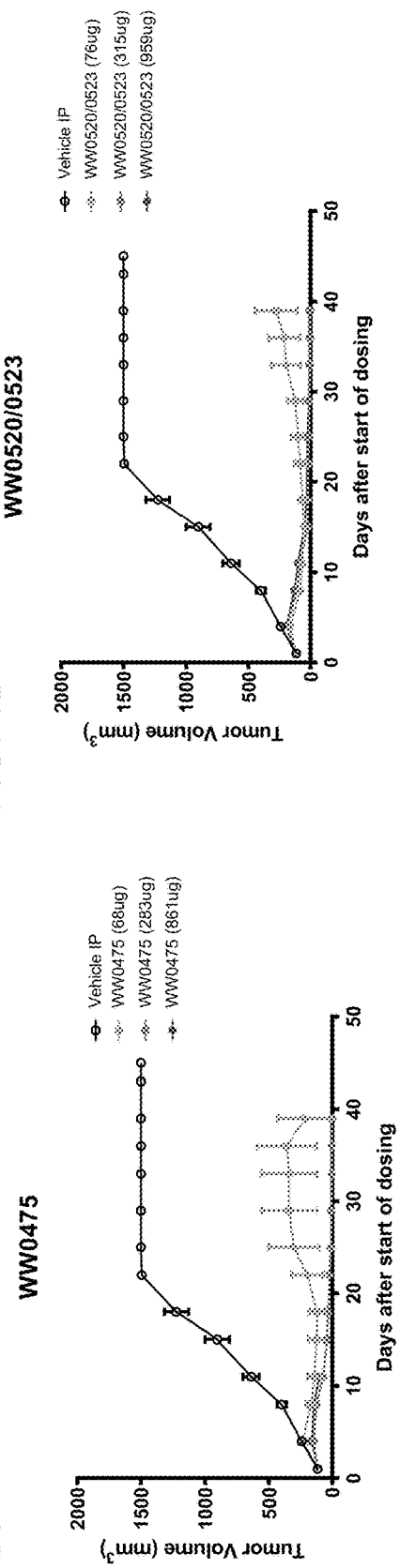
FIGS. 4A-4G are graphs that show results of analyzing WW0475, WW0520/0523, WW0548/0524, WW0548/0556, WW0517, WW0621/0523, and WW0619 IL-2 fusion proteins in a syngeneic MC38 mouse tumor model. Each graph shows average tumor volume (Mean+/−SEM) over time in mice treated with different doses of each of the fusion proteins as indicated. The data show tumor volume decreasing over time in a dose-dependent manner.
Figure 4B:
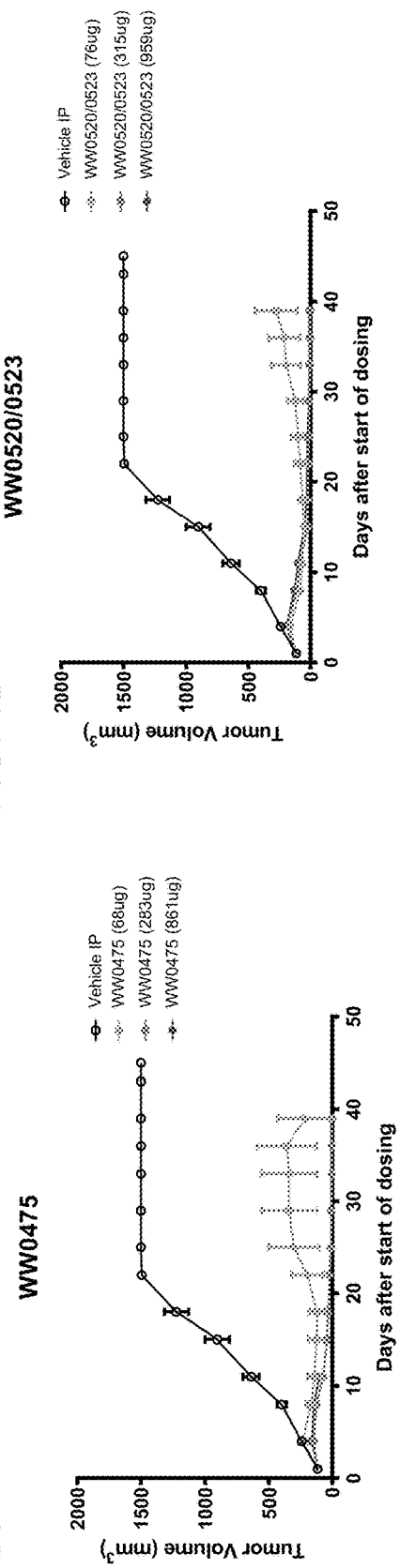
Figure 4C:
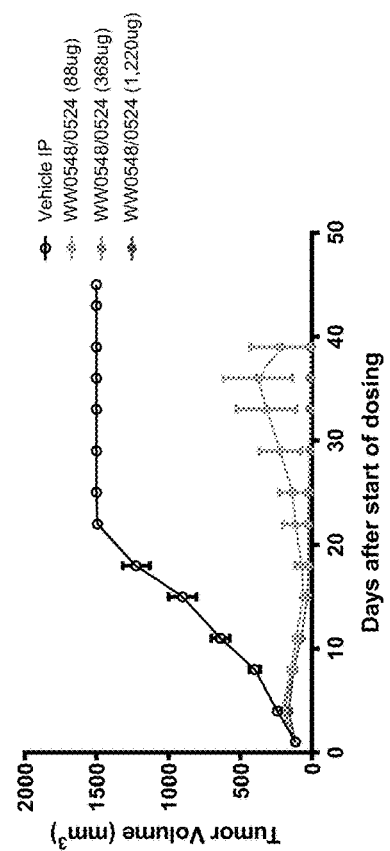
Figure 4D:
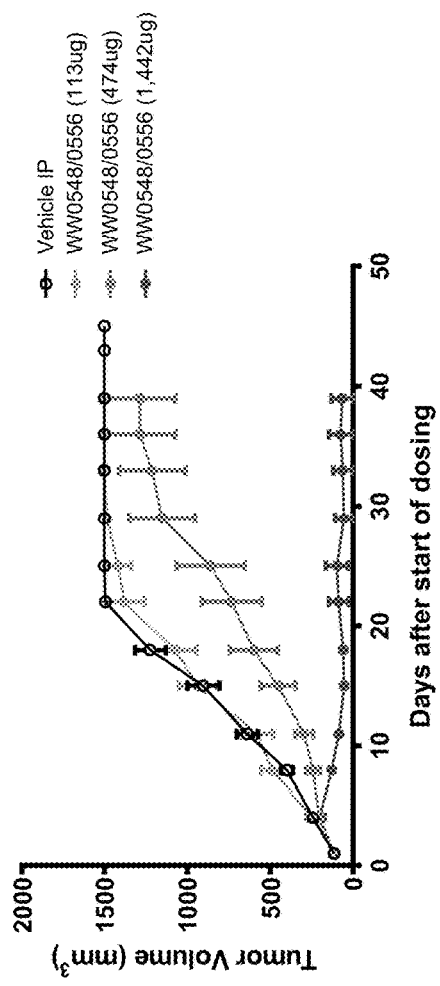
Figure 4E:
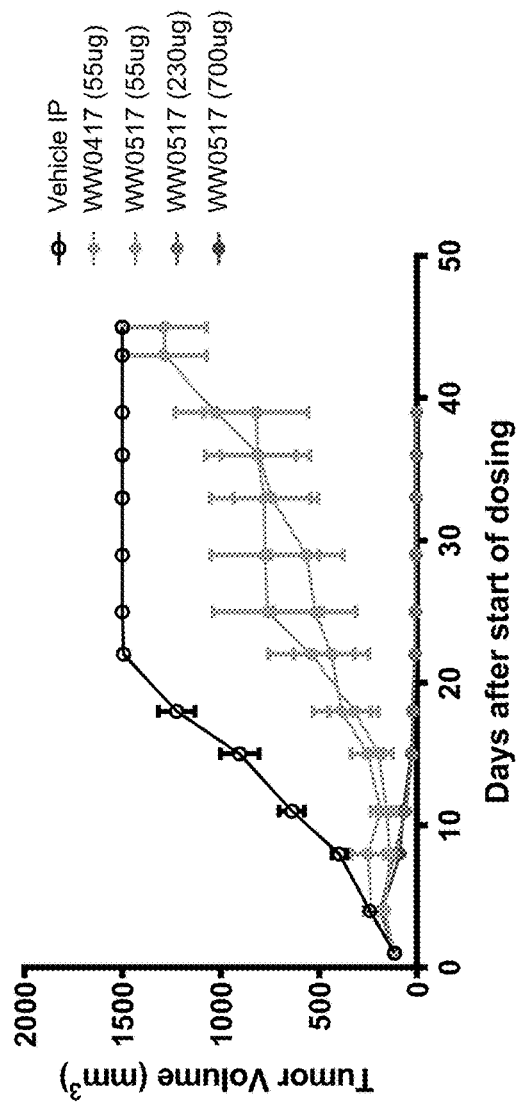
Figure 4F:
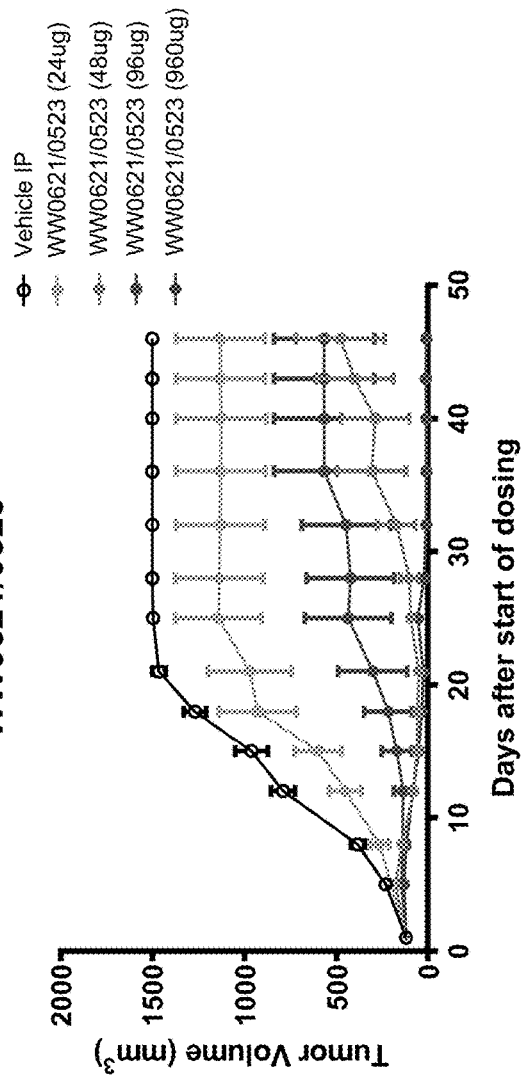
Figure 4G:
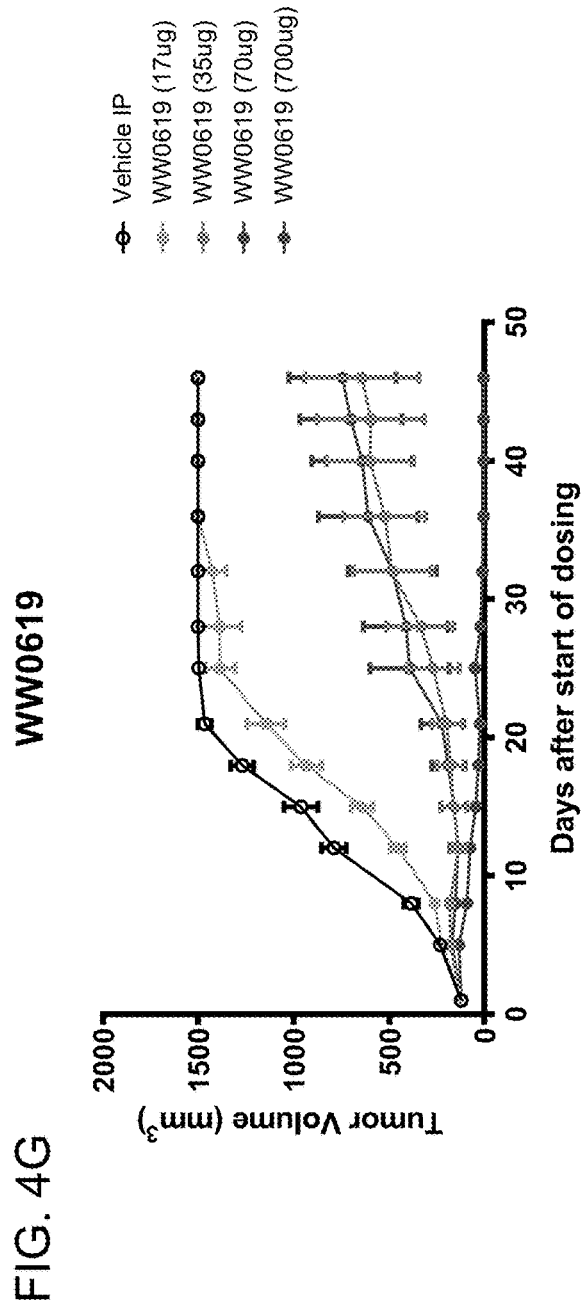

Disclosed herein are methods and compositions to engineer and use constructs comprising inducible cytokines. Cytokines are potent immune agonists, which lead to them being considered promising therapeutic agents for oncology. However, cytokines proved to have a very narrow therapeutic window. Cytokines have short serum half-lives and are also considered to be highly potent. Consequently, therapeutic administration of cytokines produced undesirable systemic effects and toxicities. These were exacerbated by the need to administer large quantities of cytokine in order to achieve the desired levels of cytokine at the intended site of cytokine action (e.g., a tumor). Unfortunately, due to the biology of cytokines and inability to effectively target and control their activity, cytokines did not achieve the hoped-for clinical advantages in the treatment of tumors.

Disclosed herein are fusion proteins that overcome the toxicity and short half-life problems that have severely limited the clinical use of cytokines in oncology. The fusion proteins contain cytokine polypeptides that have receptor agonist activity. But in the context of the fusion protein, the cytokine receptor agonist activity is attenuated, and the circulating half-life is extended. The fusion proteins include protease cleave sites, which are cleaved by proteases that are associated with a desired site of cytokine activity (e.g., a tumor), and are typically enriched or selectively present at the site of desired activity. Thus, the fusion proteins are preferentially (or selectively) and efficiently cleaved at the desired site of activity to limit cytokine activity substantially to the desired site of activity, such as the tumor microenvironment. Protease cleavage at the desired site of activity, such as in a tumor microenvironment, releases a form of the cytokine from the fusion protein that is much more active as a cytokine receptor agonist than the fusion protein (typically at least about 100× more active than the fusion protein). The form of the cytokine that is released upon cleavage of the fusion protein typically has a short half-life, which is often substantially similar to the half-life of the naturally occurring cytokine, further restricting cytokine activity to the tumor microenvironment. Even though the half-life of the fusion protein is extended, toxicity is dramatically reduced or eliminated because the circulating fusion protein is attenuated, and active cytokine is targeted to the tumor microenvironment. The fusion proteins described herein, for the first time, enable the administration of an effective therapeutic dose of a cytokine to treat tumors with the activity of the cytokine substantially limited to the tumor microenvironment, and dramatically reduces or eliminates unwanted systemic effects and toxicity of the cytokine.

The fusion proteins disclosed herein typically comprise a cytokine polypeptide [A], a blocking moiety [D], optionally a half-life extension moiety [H], and a protease-cleavable polypeptide linker. The cytokine polypeptide and the blocking moiety and the optional half-life extension element when present are operably linked by the protease-cleavable polypeptide linker and the fusion polypeptide has attenuated cytokine receptor activating activity, e.g., the cytokine-receptor activating activity of the fusion polypeptide is at least about 10× less than the cytokine receptor activating activity of the polypeptide that contains the cytokine polypeptide that is produced by cleavage of the protease cleavable linker. Some preferred fusion polypeptides are of one of formula (I)—(VI):

[A]-[L1]-[H]-[L2]-[D]     (I);

[D]-[L2]-[H]-[L1]-[A]     (II);

[A]-[L1]-[D]-[L2]-[H]     (III);

[H]-[L2]-[D]-[L1]-[A]     (IV);

[H]-[L1]-[A]-[L2']-[D]     (V);

[D]-[L1]-[A]-[L2']-[H]     (VI);

wherein [A] is a cytokine polypeptide, [D] is a blocking moiety, [H] is a half-life extension moiety, [L1] is a protease-cleavable polypeptide linker, [L2] is an polypeptide linker that is optionally protease-cleavable, and [L2'] is a protease-cleavable polypeptide linker. [L1] and [L2] or [L1] and [L2'] can be have the same or different amino acid sequence and or protease-cleavage site (when L2 is protease-cleavable) as desired.

This disclosure further relates to pharmaceutical compositions that contain the inducible fusion protein and an additional therapeutic agent, as well as nucleic acids that encode the polypeptides, and recombinant expression vectors and host sells for making such fusion proteins. Also provided herein are methods of using the disclosed fusion proteins in the treatment of diseases, conditions, and disorders.

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a difference over what is generally understood in the art. The techniques and procedures described or referenced herein are generally well understood and commonly employed using conventional methodologies by those skilled in the art, such as, for example, the widely utilized molecular cloning methodologies described in Sambrook et al., *Molecular Cloning: A Laboratory Manual* 4th ed. (2012) Cold Spring Harbor Laboratory Press, Cold Spring Harbor, NY. As appropriate, procedures involving the use of commercially available kits and reagents are generally carried out in accordance with manufacturer-defined protocols and conditions unless otherwise noted.

"Cytokine" is a well-known term of art that refers to any of a class of immunoregulatory proteins (such as interleukin or interferon) that are secreted by cells especially of the immune system and that are modulators of the immune system. Cytokine polypeptides that can be used in the fusion proteins disclosed herein include, but are not limited to transforming growth factors, such as TGF-α and TGF-β (e.g., TGFbeta1, TGFbeta2, TGFbeta3); interferons, such as interferon-α, interferon-β, interferon-γ, interferon-kappa and interferon-omega; interleukins, such as IL-1, IL-1α, IL-2, IL-3, IL-4, IL-5, IL-6, IL-7, IL-8, IL-9, IL-10, IL-11, IL-12, IL-13, IL-14, IL-15, IL-16, IL-17, IL-18, IL-21 and IL-25; tumor necrosis factors, such as tumor necrosis factor alpha and lymphotoxin; chemokines (e.g., C-X-C motif chemokine 10 (CXCL10), CCL19, CCL20, CCL21), and granulocyte macrophage-colony stimulating factor (GM-CS), as well as fragments of such polypeptides that active the cognate receptors for the cytokine (i.e., functional fragments of the foregoing). "Chemokine" is a term of art that refers to any of a family of small cytokines with the ability to induce directed chemotaxis in nearby responsive cells.

Cytokines are well-known to have short serum half-lives that frequently are only a few minutes or hours. Even forms of cytokines that have altered amino acid sequences intended to extend the serum half-life yet retain receptor agonist activity typically also have short serum half-lives. As used herein, a "short-half-life cytokine" refers to a cytokine that has a substantially brief half-life circulating in the serum of a subject, such as a serum half-life that is less than 10, less than 15, less than 30, less than 60, less than 90, less than 120, less than 240, or less than 480 minutes. As used herein, a short half-life cytokine includes cytokines which have not been modified in their sequence to achieve a longer than usual half-life in the body of a subject and polypeptides that have altered amino acid sequences intended to extend the serum half-life yet retain receptor agonist activity. This latter case is not meant to include the addition of heterologous protein domains, such as a bona fide half-life extension element, such as serum albumin.

"Sortases" are transpeptidases that modify proteins by recognizing and cleaving a carboxyl-terminal sorting signal embedded in or terminally attached to a target protein or peptide. Sortase A catalyzes the cleavage of the LPXTG motif (SEQ ID NO.: 442) (where X is any standard amino acid) between the Thr and Gly residue on the target protein, with transient attachment of the Thr residue to the active site Cys residue on the enzyme, forming an enzyme-thioacyl intermediate. To complete transpeptidation and create the peptide-monomer conjugate, a biomolecule with an N-terminal nucleophilic group, typically an oligoglycine motif, attacks the intermediate, displacing Sortase A and joining the two molecules.

As used herein, the term "steric blocker" refers to a polypeptide or polypeptide moiety that can be covalently bonded to a cytokine polypeptide directly or indirectly through other moieties such as linkers, for example in the form of a chimeric polypeptide (fusion protein), but otherwise does not covalently bond to the cytokine polypeptide. A steric blocker can non-covalently bond to the cytokine polypeptide, for example though electrostatic, hydrophobic, ionic or hydrogen bonding. A steric blocker typically inhibits or blocks the activity of the cytokine moiety due to its proximity to the cytokine moiety and comparative size. A steric blocker may also block by virtue of recruitment of a large protein binding partner. An example of this is an antibody which binds to serum albumin; while the antibody itself may or may not be large enough to block activation or binding on its own, recruitment of albumin allows for sufficient steric blocking.

As used and described herein, a "half-life extension element" is a part of the chimeric polypeptide that increases the serum half-life and improve pK, for example, by altering its size (e.g., to be above the kidney filtration cutoff), shape, hydrodynamic radius, charge, or parameters of absorption, biodistribution, metabolism, and elimination.

As used herein, the terms "activatable," "activate," "induce," and "inducible" refer to the ability of a protein, i.e., a cytokine, that is part of a fusion protein, to bind its receptor and effectuate activity upon cleavage of additional elements from the fusion protein.

As used herein, "plasmids" or "viral vectors" are agents that transport the disclosed nucleic acids into the cell without degradation and include a promoter yielding expression of the nucleic acid molecule and/or polypeptide in the cells into which it is delivered.

As used herein, the terms "peptide", "polypeptide", or "protein" are used broadly to mean two or more amino acids linked by a peptide bond. Protein, peptide, and polypeptide are also used herein interchangeably to refer to amino acid sequences. It should be recognized that the term polypeptide is not used herein to suggest a particular size or number of amino acids comprising the molecule and that a peptide of the invention can contain up to several amino acid residues or more.

As used throughout, "subject" can be a vertebrate, more specifically a mammal (e.g. a human, horse, cat, dog, cow, pig, sheep, goat, mouse, rabbit, rat, and guinea pig), birds, reptiles, amphibians, fish, and any other animal. The term does not denote a particular age or sex. Thus, adult and newborn subjects, whether male or female, are intended to be covered.

As used herein, "patient" or "subject" may be used interchangeably and can refer to a subject with a disease or disorder (e.g. cancer). The term patient or subject includes human and veterinary subjects.

As used herein the terms "treatment", "treat", or "treating" refers to a method of reducing the effects of a disease or condition or symptom of the disease or condition. Thus, in the disclosed method, treatment can refer to at least about 10%, at least about 20%, at least about 30%, at least about 40%, at least about 50%, at least about 60%, at least about 70%, at least about 80%, at least about 90%, or substantially complete reduction in the severity of an established disease or condition or symptom of the disease or condition. For example, a method for treating a disease is considered to be a treatment if there is a 10% reduction in one or more symptoms of the disease in a subject as compared to a control. Thus, the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition.

As used herein, the terms "prevent", "preventing", and "prevention" of a disease or disorder refers to an action, for example, administration of the chimeric polypeptide or nucleic acid sequence encoding the chimeric polypeptide, that occurs before or at about the same time a subject begins to show one or more symptoms of the disease or disorder, which inhibits or delays onset or exacerbation of one or more symptoms of the disease or disorder.

As used herein, references to "decreasing", "reducing", or "inhibiting" include a change of at least about 10%, of at least about 20%, of at least about 30%, of at least about 40%, of at least about 50%, of at least about 60%, of at least about 70%, of at least about 80%, of at least about 90% or greater as compared to a suitable control level. Such terms can include but do not necessarily include complete elimination of a function or property, such as agonist activity.

An "attenuated cytokine receptor agonist" is a cytokine receptor agonist that has decreased receptor agonist activity as compared to the cytokine receptor's naturally occurring agonist. An attenuated cytokine agonist may have at least about 10×, at least about 50×, at least about 100×, at least about 250×, at least about 500×, at least about 1000× or less agonist activity as compared to the receptor's naturally occurring agonist. When a fusion protein that contains a cytokine polypeptide as described herein is described as "attenuated" or having "attenuated activity", it is meant that the fusion protein is an attenuated cytokine receptor agonist.

An "intact fusion protein" is a fusion protein in which no domain has been removed, for example by protease cleavage. A domain may be removable by protease cleavage or other enzymatic activity, but when the fusion protein is "intact", this has not occurred.

As used herein "moiety" refers to a portion of a molecule that has a distinct function within that molecule, and that function may be performed by that moiety in the context of another molecule. A moiety may be a chemical entity with a particular function, or a portion of a biological molecule with a particular function. For example, a "blocking moiety" within a fusion protein is a portion of the fusion protein which is capable of blocking the activity of some or all of the fusion polypeptide. This may be a protein domain, such as serum albumin. Blocking may be accomplished by a steric blocker or a specific blocker. A steric blocker blocks by virtue of size and position and not based upon specific binding; an examples is serum albumin. A specific blocker blocks by virtue of specific interactions with the moiety to be blocked. A specific blocker must be tailored to the particular cytokine or active domain; a steric blocker can be used regardless of the payload, as long as it is large enough.

If desired a blocking moiety that is incorporated into a fusion proteins described herein can associate with another polypeptide to create a specific binding domain. For example, if a cytokine binding fragment of an antibody is used as the blocking moiety, the fusion polypeptide can include an scFv that is specific for the cytokine as the blocking moiety or the fusion polypeptide can comprise half of a Fab, for example VH-CH1 or VL-CL as the blocking moiety, which can associate with a complementary chain VL-CL or VH-CH1, respectively, to form an Fab fragment that specifically binds the cytokine. As further described herein, the blocking moiety may block activity of the fusion protein directly or when the blocking moiety associates with another polypeptide. For example, when an anti-HSA scFv binds HSA or when a VH-CH1 polypeptide associates with a complementary VL-CL polypeptide and then binds the cytokine polypeptide.

In general, the therapeutic use of cytokines is strongly limited by their systemic toxicity. TNF, for example, was originally discovered for its capacity of inducing the hemorrhagic necrosis of some tumors, and for its in vitro cytotoxic effect on different tumoral lines, but it subsequently proved to have strong pro-inflammatory activity, which can, in case of overproduction conditions, dangerously affect the human body. As the systemic toxicity is a fundamental problem with the use of pharmacologically active amounts of cytokines in humans, novel derivatives and therapeutic strategies are now under evaluation, aimed at reducing the toxic effects of this class of biological effectors while keeping their therapeutic efficacy.

IL-2 exerts both stimulatory and regulatory functions in the immune system and is, along with other members of the common γ chain (γc) cytokine family, central to immune homeostasis. IL-2 mediates its action by binding to IL-2 receptors (IL-2R), consisting of either trimeric receptors made of IL-2Rα (CD25), IL-2Rβ (CD122), and IL-2Rγ (γc, CD132) chains or dimeric βγ IL-2Rs (1, 3). Both IL-2R variants are able to transmit signal upon IL-2 binding. However, trimeric αβγ IL-2Rs have a roughly 10-100 times higher affinity for IL-2 than dimeric βγ IL-2Rs (3), implicating that CD25 confers high-affinity binding of IL-2 to its receptor but is not crucial for signal transduction. Trimeric IL-2Rs are found on activated T cells and CD4+ forkhead box P3 (FoxP3)+ T regulatory cells (Treg), which are sensitive to IL-2 in vitro and in vivo. Conversely, antigen-experienced (memory) CD8+, CD44 high memory-phenotype (MP) CD8+, and natural killer (NK) cells are endowed with high levels of dimeric βγ IL-2Rs, and these cells also respond vigorously to IL-2 in vitro and in vivo.

Expression of the high-affinity IL-2R is critical for endowing T cells to respond to low concentrations of IL-2 that is transiently available in vivo. IL-2Rα expression is absent on naive and memory T cells but is induced after antigen activation. IL-2Rβ is constitutively expressed by NK, NKT, and memory CD8+ T cells but is also induced on naive T cells after antigen activation. γc is much less stringently regulated and is constitutively expressed by all lymphoid cells. Once the high-affinity IL-2R is induced by antigen, IL-2R signaling upregulates the expression of IL-2Rα in part through Stat5-dependent regulation of Il2ra transcription (Kim et al., 2001). This process represents a mechanism to maintain expression of the high-affinity IL-2R and sustain IL-2 signaling while there remains a source of IL-2.

IL-2 is captured by IL-2Rα through a large hydrophobic binding surface surrounded by a polar periphery that results in a relatively weak interaction (Kd 10-8 M) with rapid on-off binding kinetics. However, the IL-2Rα-IL-2 binary complex leads to a very small conformational change in IL-2 that promotes association with IL-2Rβ through a distinct polar interaction between IL-2 and IL-2Rβ. The pseudo-high affinity of the IL2/α/β trimeric complex (i.e. Kd~300 pM) clearly indicates that the trimeric complex is more stable than either IL2 bound to the α chain alone (Kd=10 nM) or to the β chain alone (Kd=450 nM) as shown by Ciardelli's data. In any event, the IL2/α/β trimer then recruits the γ chain into the quaternary complex capable of signaling, which is facilitated by the large composite binding site on the IL2-bound β chain for the γ chain.

In other words, the ternary IL-2Rα-IL-2Rβ-IL-2 complex then recruits γc through a weak interaction with IL-2 and a stronger interaction with IL-2Rβ to produce a stable quaternary high-affinity IL-2R (Kd 10-11 M which is 10 pM). The formation of the high-affinity quaternary IL-2-IL-2R complex leads to signal transduction through the tyrosine kinases Jak1 and Jak3, which are associated with IL-2Rβ and γc, respectively (Nelson and Willerford, 1998). The quaternary IL-2-IL-2R complex is rapidly internalized, where IL-2, IL-2Rβ, and γc are rapidly degraded, but IL-2Rα is recycled to the cell surface (Hémar et al., 1995; Yu and Malek, 2001). Thus, those functional activities that require sustained IL-2R signaling require a continued source of IL-2 to engage IL-2Rα and form additional IL-2-IL-2R signaling complexes.

Interleukin-15 (IL-15), another member of the 4-alpha-helix bundle family of cytokines, has also emerged as an immunomodulator for the treatment of cancer. IL-15 is initially captured via IL-15Rα, which is expressed on antigen-presenting dendritic cells, monocytes and macrophages. IL-15 exhibits broad activity and induces the differentiation and proliferation of T, B and natural killer (NK) cells via signaling through the IL-15/IL-2-R-β (CD122) and the common γ chain (CD132). It also enhances cytolytic activity of CD8+ T cells and induces long-lasting antigen-experienced CD8+CD44 memory T cells. IL-15 stimulates differentiation and immunoglobulin synthesis by B cells and induces maturation of dendritic cells. It does not stimulate immunosuppressive T regulatory cells (Tregs). Thus, boosting IL-15 activity selectively in the tumor micro-environment could enhance innate and specific immunity and fight tumors (Waldmann et al., 2012). IL-15 was initially identified for its ability to stimulate T cell proliferation in an IL-2-like manner through common receptor components (IL-2R/15Rβ-γc) and signaling through JAK1/JAK3 and STAT3/STAT5. Like IL-2, IL-15 has been shown to stimulate proliferation of activated CD4−CD8−, CD4+CD8+, CD4+ and CD8+ T cells as well as facilitate the induction of cytotoxic T-lymphocytes, and the generation, proliferation and activation of NK cells (Waldmann et al., 1999). However, unlike IL-2 which is required to maintain forkhead box P3 (FOXP3)-expressing CD4+CD25+ Treg cells and for the retention of these cells in the periphery, IL-15 has little effect on Tregs (Berger et al., 2009). This is important as FOXP3-expressing CD4+CD25+ Tregs inhibit effector T cells, thereby inhibiting immune responses including those directed against the tumor. IL-2 also has a crucial role in initiating activation induced cell death (AICD), a process that leads to the elimination of self-reactive T cells, whereas IL-15 is an anti-apoptotic factor for T cells (Marks-Konczalik et al., 2000). IL-15 co-delivered with HIV peptide vaccines has been shown to overcome CD4+ T cell deficiency by promoting longevity of antigen-specific CD8+ T cells and blocking TRAIL-mediated apoptosis (Oh et al., 2008). Furthermore, IL-15 promotes the long-term maintenance of CD8+CD44hi memory T cells (Kanegane et al., 1996).

The importance of IL-15 and IL-15Rα to T and NK cell development is further highlighted by the phenotype of IL-15Rα$^{-/-}$ and IL-15$^{-/-}$ mice. Knockout mice demonstrate decreased numbers of total CD8+ T cells, and are deficient in memory-phenotype CD8+ T cells, NK cells, NK/T cells and some subsets of intestinal intraepithelial lymphocytes, indicating that IL-15 provides essential positive homeostatic functions for these subsets of cells (Lodolce et al., 1996; Kennedy et al., 1998). The similarities in the phenotypes of these two strains of knockout mice suggest the importance of IL-15Rα in maintaining physiologically relevant IL-15 signals.

IL-15 is presented in trans by the IL-15 receptor alpha-chain to the IL-15Rβγc complex displayed on the surface of T cells and natural killer (NK) cells (Han et al., 2011). The IL-15Ra-chain plays a role of chaperone protein, stabilizes, and increases IL-15 activity (Desbois et al., 2016). It has been shown that exogenous IL-15 may have a limited impact on patients with cancer due to its dependency on IL-15Ra frequently downregulated in cancer patients. Therefore, the fusion protein RLI, composed of the sushi+domain of IL15Ra coupled via a linker to IL-15, has been suggested as an alternative approach to IL15 therapy (Bessard et al., 2009). It was found that administration of soluble IL-15/IL-15Rα complexes greatly enhanced IL-15 serum half-life and bioavailability in vivo (Stoklasek et al., 2010).

In addition to the effects on T and NK cells, IL-15 also has several effects on other components of the immune system. IL-15 protects neutrophils from apoptosis, modulates phagocytosis and stimulates the secretion of IL-8 and IL-1R antagonist. It functions through the activation of JAK2, p38 and ERK1/2 MAPK, Syk kinase and the NF-kB transcriptional factor (Pelletier et al., 2002). In mast cells, IL-15 can act as a growth factor and an inhibitor of apoptosis. In these cells IL-15 activates the JAK2/STAT5 pathway without the requirement of γc binding (Tagaya et al., 1996). IL-15 also induces B lymphocyte proliferation and differentiation, and increases immunoglobulin secretion (Armitage et al., 1995). It also prevents Fas-mediated apoptosis and allows induction of antibody responses partially independent of CD4-help (Demerci et al., 2004; Steel et al., 2010). Monocytes, macrophages and dendritic cells effectively transcribe and translate IL-15. They also respond to IL-15 stimulation. Macrophages respond by increasing phagocytosis, inducing IL-8, IL-12 and MCP-1 expression, and secreting IL-6, IL-8 and TNF α (Budagian et al., 2006). Dendritic cells incubated with IL-15 demonstrate maturation with increased CD83, CD86, CD40, and MHC class II expression, are also resistant to apoptosis, and show enhanced interferon-γ secretion (Anguille et al., 2009).

IL-15 has also been shown to have effects on non-hematological cells including myocytes, adipocytes, endothelial and neural cells. IL-15 has an anabolic effect on muscle and may support muscle cell differentiation (Quinn et al., 1995). It stimulates myocytes and muscle fibers to accumulate contractile protein and is able to slow muscle wasting in rats with cancer-related cachexia (Figueras et al., 2004). IL-15 has also been shown to stimulate angiogenesis (Angiolillo et al., 1997) and induce microglial growth and survival (Hanisch et al., 1997).

Interleukin-7 (IL-7), also of the IL-2/IL-15 family, is a well-characterized pleiotropic cytokine, and is expressed by stromal cells, epithelial cells, endothelial cells, fibroblasts, smooth muscle cells and keratinocytes, and following activation, by dendritic cells (Alpdogan et al., 2005). Although it was originally described as a growth and differentiation factor for precursor B lymphocytes, subsequent studies have shown that IL-7 is critically involved in T-lymphocyte development and differentiation. Interleukin-7 signaling is essential for optimal CD8 T-cell function, homeostasis and establishment of memory (Schluns et al., 2000); it is required for the survival of most T-cell subsets, and its expression has been proposed to be important for regulating T-cell numbers.

IL-7 binds to a dimeric receptor, including IL-7Rα and γ$_c$ to form a ternary complex that plays fundamental roles in extracellular matrix remodeling, development, and homeostasis of T and B cells (Mazzucchelli and Durum, 2007). IL-7Rα also cross-reacts to form a ternary complex with thymic stromal lymphopoietin (TSLP) and its receptor (TSLPR), and activates the TSLP pathway, resulting in T and dendritic cell proliferation in humans and further B cell development in mice (Leonard, 2002). Tight regulation of the signaling cascades activated by the complexes are therefore crucial to normal cellular function. Under-stimulation of the IL-7 pathway caused by mutations in the IL-7Rα ectodomain inhibits T and B cell development, resulting in patients with a form of severe combined immunodeficiency (SCID) (Giliani et al., 2005; Puel et al., 1998).

IL-7 has a potential role in enhancing immune reconstitution in cancer patients following cytotoxic chemotherapy. IL-7 therapy enhances immune reconstitution and can augment even limited thymic function by facilitating peripheral expansion of even small numbers of recent thymic emigrants. Therefore, IL-7 therapy could potentially repair the immune system of patients who have been depleted by cytotoxic chemotherapy (Capitini et al., 2010).

Interleukin-12 (IL-12) is a disulfide-linked heterodimer of two separately encoded subunits (p35 and p40), which are linked covalently to give rise to the so-called bioactive heterodimeric (p70) molecule (Lieschke et al., 1997; Jana et al., 2014). Apart from forming heterodimers (IL-12 and IL-23), the p40 subunit is also secreted as a monomer (p40) and a homodimer (p402). It is known in the art that synthesis of the heterodimer as a single chain with a linker connecting the p35 to the p40 subunit preserves the full biological activity of the heterodimer. IL-12 plays a critical role in the early inflammatory response to infection and in the generation of Th1 cells, which favor cell-mediated immunity. It has been found that overproduction of IL-12 can be dangerous to the host because it is involved in the pathogenesis of a number of autoimmune inflammatory diseases (e.g. MS, arthritis, type 1 diabetes).

The IL-12 receptor (IL-12R) is a heterodimeric complex consisting of IL-12Rβ1 and IL-12Rβ2 chains expressed on the surface of activated T-cells and natural killer cells (Trinchieri et al., 2003). The IL-12Rβ1 chain binds to the IL-12p40 subunit, whereas IL-12p35 in association with IL-12Rβ2 confers an intracellular signaling ability (Benson et al., 2011). Signal transduction through IL-12R induces phosphorylation of Janus kinase (Jak2) and tyrosine kinase (Tyk2), that phosphorylate and activate signal transducer and activator of transcription (STAT)1, STAT3, STAT4, and STAT5. The specific cellular effects of IL-12 are due mainly to activation of STAT4. IL-12 induces natural killer and T-cells to produce cytokines, in particular interferon (IFN)γ, that mediate many of the proinflammatory activities of IL-12, including CD4+ T-cell differentiation toward the Th1 phenotype (Montepaone et al., 2014).

Regulatory T cells actively suppress activation of the immune system and prevent pathological self-reactivity and consequent autoimmune disease. Developing drugs and methods to selectively activate regulatory T cells for the treatment of autoimmune disease is the subject of intense research and, until the development of the present invention, which can selectively deliver active interleukins at the site of inflammation, has been largely unsuccessful. Regulatory T cells (Treg) are a class of CD4+CD25+ T cells that suppress the activity of other immune cells. Treg are central to immune system homeostasis, and play a major role in maintaining tolerance to self-antigens and in modulating the immune response to foreign antigens. Multiple autoimmune and inflammatory diseases, including Type 1 Diabetes (T1D), Systemic Lupus Erythematosus (SLE), and Graft-versus-Host Disease (GVHD) have been shown to have a deficiency of Treg cell numbers or Treg function.

Consequently, there is great interest in the development of therapies that boost the numbers and/or function of Treg cells. One treatment approach for autoimmune diseases being investigated is the transplantation of autologous, ex vivo-expanded Treg cells (Tang, Q., et al, 2013, Cold Spring Harb. Perspect. Med., 3:1-15). While this approach has shown promise in treating animal models of disease and in several early-stage human clinical trials, it requires personalized treatment with the patient's own T cells, is invasive, and is technically complex. Another approach is treatment with low dose Interleukin-2 (IL-2). Treg cells characteristically express high constitutive levels of the high affinity IL-2 receptor, IL2Rαβγ, which is composed of the subunits IL2Rα (CD25), IL2Rβ (CD122), and IL2Rγ (CD132), and Treg cell growth has been shown to be dependent on IL-2 (Malek, T. R., et al., 2010, Immunity, 33:153-65).

Conversely, immune activation has also been achieved using IL-2, and recombinant IL-2 (Proleukin®) has been approved to treat certain cancers. High-dose IL-2 is used for the treatment of patients with metastatic melanoma and metastatic renal cell carcinoma with a long-term impact on overall survival.

Clinical trials of low-dose IL-2 treatment of chronic GVHD (Koreth, J., et al., 2011, N Engl J Med., 365:2055-66) and HCV-associated autoimmune vasculitis patients (Saadoun, D., et al., 2011, N Engl J Med., 365:2067-77) have demonstrated increased Treg levels and signs of clinical efficacy. New clinical trials investigating the efficacy of IL-2 in multiple other autoimmune and inflammatory diseases have been initiated. The rationale for using so-called low dose IL-2 was to exploit the high IL-2 affinity of the trimeric IL-2 receptor which is constitutively expressed on Tregs while leaving other T cells which do not express the high affinity receptor in the inactivated state. Aldesleukin (marketed as Proleukin® by Prometheus Laboratories, San Diego, CA), the recombinant form of IL-2 used in these trials, is associated with high toxicity. Aldesleukin, at high doses, is approved for the treatment of metastatic melanoma and metastatic renal cancer, but its side effects are so severe that its use is only recommended in a hospital setting with access to intensive care (Web address: www.proleukin.com/assets/pdf/proleukin.pdf).

The clinical trials of IL-2 in autoimmune diseases have employed lower doses of IL-2 in order to target Treg cells, because Treg cells respond to lower concentrations of IL-2 than many other immune cell types due to their expression of IL2R alpha (Klatzmann D, 2015 Nat Rev Immunol. 15:283-94). However, even these lower doses resulted in safety and tolerability issues, and the treatments used have employed daily subcutaneous injections, either chronically or in intermittent 5-day treatment courses. Therefore, there is a need for an autoimmune disease therapy that potentiates Treg cell numbers and function, that targets Treg cells more specifically than IL-2, that is safer and more tolerable, and that is administered less frequently.

One approach that has been suggested for improving the therapeutic index of IL-2-based therapy for autoimmune diseases is to use variants of IL-2 that are selective for Treg cells relative to other immune cells. IL-2 receptors are expressed on a variety of different immune cell types, including T cells, NK cells, eosinophils, and monocytes, and this broad expression pattern likely contributes to its pleiotropic effect on the immune system and high systemic toxicity. In particular, activated T effector cells express IL2Rαβγ, as do pulmonary epithelial cells. But, activating T effector cells runs directly counter to the goal of down-modulating and controlling an immune response, and activating pulmonary epithelial cells leads to known dose-limiting side effects of IL-2 including pulmonary edema. In fact, the major side effect of high-dose IL-2 immunotherapy is vascular leak syndrome (VLS), which leads to accumulation of intravascular fluid in organs such as lungs and liver with subsequent pulmonary edema and liver cell damage. There is no treatment of VLS other than withdrawal of IL-2. Low-dose IL-2 regimens have been tested in patients to avoid VLS, however, at the expense of suboptimal therapeutic results.

According to the literature, VLS is believed to be caused by the release of proinflammatory cytokines from IL-2-activated NK cells. However, there is some evidence that pulmonary edema results from direct binding of IL-2 to lung endothelial cells, which expressed low to intermediate levels of functional αβγ IL-2Rs. And, the pulmonary edema associated with interaction of IL-2 with lung endothelial cells was abrogated by blocking binding to CD25 with an anti-CD25 monoclonal antibody (mAb), in CD25-deficient host mice, or by the use of CD122-specific IL-2/anti-IL-2 mAb (IL-2/mAb) complexes, thus preventing VLS.

Treatment with interleukin cytokines other than IL-2 has been more limited. IL-15 displays immune cell stimulatory activity similar to that of IL-2 but without the same inhibitory effects, thus making it a promising immunotherapeutic candidate. Clinical trials of recombinant human IL-15 for the treatment of metastatic malignant melanoma or renal cell cancer demonstrated appreciable changes in immune cell distribution, proliferation, and activation and suggested potential antitumor activity (Conlon et. al., 2014). IL-15 is currently in clinical trials to treat various forms of cancer. However, IL-15 therapy is known to be associated with undesired and toxic effects, such as exacerbating certain leukemias, graft-versus-host disease, hypotension, thrombocytopenia, and liver injury. (Mishra A., et al., Cancer Cell, 2012, 22(5):645-55; Alpdogan O. et al., Blood, 2005, 105 (2):866-73; Conlon K C et al., J Clin Oncol, 2015, 33(1): 74-82.)

IL-7 promotes lymphocyte development in the thymus and maintains survival of naive and memory T cell homeostasis in the periphery. Moreover, it is important for the organogenesis of lymph nodes (LN) and for the maintenance of activated T cells recruited into the secondary lymphoid organs (SLOs) (Gao et. al., 2015). In clinical trials of IL-7, patients receiving IL-7 showed increases in both CD4+ and CD8+ T cells, with no significant increase in regulatory T cell numbers as monitored by FoxP3 expression (Sportes et al., 2008). In clinical trials reported in 2006, 2008 and 2010, patients with different kinds of cancers such as metastatic melanoma or sarcoma were injected subcutaneously with different doses of IL-7. Little toxicity was seen except for transient fevers and mild erythema. Circulating levels of both CD4+ and CD8+ T cells increased significantly and the number of Treg reduced. TCR repertoire diversity increased after IL-7 therapy. However, the anti-tumor activity of IL-7 was not well evaluated (Gao et. al., 2015). Results suggest that IL-7 therapy could enhance and broaden immune responses.

IL-12 is a pleiotropic cytokine, the actions of which create an interconnection between the innate and adaptive immunity. IL-12 was first described as a factor secreted from PMA-induced EBV-transformed B-cell lines. Based on its actions, IL-12 has been designated as cytotoxic lymphocyte maturation factor and natural killer cell stimulatory factor. Due to bridging the innate and adaptive immunity and potently stimulating the production of IFNγ, a cytokine coordinating natural mechanisms of anticancer defense, IL-12 seemed ideal candidate for tumor immunotherapy in humans. However, severe side effects associated with systemic administration of IL-12 in clinical investigations and the very narrow therapeutic index of this cytokine markedly tempered enthusiasm for the use of this cytokine in cancer patients (Lasek et. al., 2014). Approaches to IL-12 therapy in which delivery of the cytokine is tumor-targeted, which may diminish some of the previous issues with IL-12 therapy, are currently in clinical trials for cancers.

The direct use of IL-2 as an agonist to bind the IL-2R and modulate immune responses therapeutically has been problematic due its well-documented therapeutic risks, e.g., its short serum half-life and high toxicity. These risks have also limited the therapeutic development and use of other cytokines. New forms of cytokines that reduce these risks are needed. Disclosed herein are compositions and methods comprising IL-2 and IL-15 and other cytokines, functional fragments and muteins of cytokines, variants, and subunits of cytokines as well as conditionally active cytokines designed to address these risks and provide needed immunomodulatory therapeutics.

The present invention is designed to address the shortcomings of direct IL-2 therapy and therapy using other cytokines, for example using cytokine blocking moieties, e.g. steric blocking polypeptides, serum half-life extending polypeptides, targeting polypeptides, linking polypeptides, including protease cleavable linkers, and combinations thereof. Cytokines, including interleukins (e.g., IL-2, IL-7, IL-12, IL-15, IL-18, IL-21 IL-23), interferons (IFNs, including IFNalpha, IFNbeta and IFNgamma), tumor necrosis factors (e.g., TNFalpha, lymphotoxin), transforming growth factors (e.g., TGFbeta1, TGFbeta2, TGFbeta3), chemokines (C-X-C motif chemokine 10 (CXCL10), CCL19, CCL20, CCL21), and granulocyte macrophage-colony stimulating factor (GM-CS) are highly potent when administered to patients. As used herein, "chemokine" means a family of small cytokines with the ability to induce directed chemotaxis in nearby responsive cells Cytokines can provide powerful therapy, but are accompanied by undesired effects that are difficult to control clinically and which have limited the clinical use of cytokines. This disclosure relates to new forms of cytokines that can be used in patients with reduced or eliminated undesired effects. In particular, this disclosure relates to pharmaceutical compositions including chimeric polypeptides (fusion proteins), nucleic acids encoding fusion proteins and pharmaceutical formulations of the foregoing that contain cytokines or active fragments or muteins of cytokines that have decreased cytokine receptor activating activity in comparison to the corresponding cytokine. However, under selected conditions or in a selected biological environment the chimeric polypeptides activate their cognate receptors, often with the same or higher potency as the corresponding naturally occurring cytokine. As described herein, this is typically achieved using a cytokine blocking moiety that blocks or inhibits the receptor activating function of the cytokine, active fragment or mutein thereof under general conditions but not under selected conditions, such as those present at the desired site of cytokine activity (e.g., an inflammatory site or a tumor).

The chimeric polypeptides and nucleic acids encoding the chimeric polypeptides can be made using any suitable method. For example, nucleic acids encoding a chimeric polypeptide can be made using recombinant DNA techniques, synthetic chemistry or combinations of these techniques, and expressed in a suitable expression system, such as in CHO cells. Chimeric polypeptides can similarly be made, for example by expression of a suitable nucleic acid, using synthetic or semi-synthetic chemical techniques, and the like. In some embodiments, the blocking moiety can be attached to the cytokine polypeptide via sortase-mediated conjugation. "Sortases" are transpeptidases that modify proteins by recognizing and cleaving a carboxyl-terminal sorting signal embedded in or terminally attached to a target protein or peptide. Sortase A catalyzes the cleavage of the LPXTG motif (SEQ ID No.: 442) (where X is any standard amino acid) between the Thr and Gly residue on the target protein, with transient attachment of the Thr residue to the active site Cys residue on the enzyme, forming an enzyme-thioacyl intermediate. To complete transpeptidation and create the peptide-monomer conjugate, a biomolecule with an N-terminal nucleophilic group, typically an oligoglycine motif, attacks the intermediate, displacing Sortase A and joining the two molecules.

To form the cytokine-blocking moiety fusion protein, the cytokine polypeptide is first tagged at the N-terminus with a polyglycine sequence, or alternatively, with at the C-terminus with a LPXTG motif (SEQ ID NO.: 442). The blocking moiety or other element has respective peptides attached that serve as acceptor sites for the tagged polypeptides. For conjugation to domains carrying a LPXTG (SEQ ID NO.: 442) acceptor peptide attached via its N-terminus, the polypeptide will be tagged with an N-terminal poly-glycine stretch. For conjugation to domain carrying a poly-glycine peptide attached via its C-terminus, the polypeptide will be tagged at its C-terminus with a LPXTG (SEQ ID NO.: 442) sortase recognition sequence. Recognizing poly-glycine and LPXTG (SEQ ID NO.: 442) sequences, sortase will form a peptide bond between polymer-peptide and tagged polypeptides. The sortase reaction cleaves off glycine residues as intermediates and occurs at room temperature.

A variety of mechanisms can be exploited to remove or reduce the inhibition caused by the blocking moiety. For example, the pharmaceutical compositions can include a cytokine moiety and a blocking moiety, e.g., a steric blocking moiety, with a protease cleavable linker comprising a protease cleavage site located between the cytokine and cytokine blocking moiety or within the cytokine blocking moiety. When the protease cleavage site is cleaved, the blocking moiety can dissociate from cytokine, and the cytokine can then activate cytokine receptor. A cytokine moiety can also be blocked by a specific blocking moiety, such as an antibody, which binds an epitope found on the relevant cytokine.

Any suitable linker can be used. For example, the linker can comprise glycine-glycine, a sortase-recognition motif, or a sortase-recognition motif and a peptide sequence $(Gly_4Ser)_n$ (SEQ ID NO.: 443) or $(Gly_3Ser)_n$, (SEQ ID NO.: 444) wherein n is 1, 2, 3, 4 or 5. Typically, the sortase-recognition motif comprises a peptide sequence LPXTG (SEQ ID NO.: 442), where X is any amino acid. In some embodiments, the covalent linkage is between a reactive lysine residue attached to the C-terminal of the cytokine polypeptide and a reactive aspartic acid attached to the N-terminal of the blocker or other domain. In other embodiments, the covalent linkage is between a reactive aspartic acid residue attached to the N-terminal of the cytokine polypeptide and a reactive lysine residue attached to the C-terminal of said blocker or other domain.

Accordingly, as described in detail herein, the cytokine blocking moieties used can be steric blockers. As used herein, a "steric blocker" refers to a polypeptide or polypeptide moiety that can be covalently bonded to a cytokine polypeptide directly or indirectly through other moieties such as linkers, for example in the form of a chimeric polypeptide (fusion protein), but otherwise does not covalently bond to the cytokine polypeptide. A steric blocker can non-covalently bond to the cytokine polypeptide, for example though electrostatic, hydrophobic, ionic or hydrogen bonding. A steric blocker typically inhibits or blocks the activity of the cytokine moiety due to its proximity to the cytokine moiety and comparative size. The steric inhibition of the cytokine moiety can be removed by spatially separating the cytokine moiety from the steric blocker, such as by enzymatically cleaving a fusion protein that contains a steric blocker and a cytokine polypeptide at a site between the steric blocker and the cytokine polypeptide.

As described in greater detail herein, the blocking function can be combined with or due to the presence of additional functional components in the pharmaceutical composition, such as a targeting domain, a serum half-life extension element, and protease-cleavable linking polypeptides. For example, a serum half-life extending polypeptide can also be a steric blocker.

In the interest of presenting a concise disclosure of the full scope of the invention, aspects of the invention are described in detail using the cytokine IL-2 as an exemplary cytokine. However, the invention and this disclosure are not limited to IL-2. It will be clear to a person of skill in the art that this disclosure, including the disclosed methods, polypeptides and nucleic acids, adequately describes and enables the use of other cytokines, fragments, variants, cytokine subunits, and muteins, such as IL-2, IL-7, IL-12, IL-15, IL-18, IL-21 IL-23, IFNalpha, IFNbeta, IFNgamma, TNFalpha, lymphotoxin, TGF-beta1, TGFbeta2, TGFbeta3, GM-CSF, CXCL10, CCL19, CCL20, CCL21 and functional fragments or muteins of any of the foregoing. Preferred cytokines for use in the fusion proteins disclosed herein are IL-2, IL-12, IFNalpha, IFNbeta, IFNgamma, muteins, functional variants, and functional fragments, or subunits of any of the foregoing. For example, the cytokine a IL-12 cytokine may be a p35 subunit, a p40 subunit, a heterodimer.

Various elements ensure the delivery and activity of IL-2 preferentially at the site of desired IL-2 activity and to severely limit systemic exposure to the interleukin via a blocking and/or a targeting strategy preferentially linked to a serum half-life extension strategy. In this serum half-life extension strategy, the blocked version of interleukin circulates for extended times (preferentially 1-2 or more weeks) but the activated version has the typical serum half-life of the interleukin.

By comparison to a serum half-life extended version, the serum half-life of IL-2 administered intravenously is only ~10 minutes due to distribution into the total body extracellular space, which is large, ~15 L in an average sized adult. Subsequently, IL-2 is metabolized by the kidneys with a half-life of ~2.5 hours. (Smith, K. "Interleukin 2 immunotherapy." *Therapeutic Immunology* 240 (2001)). By other measurements, IL-2 has a very short plasma half-life of 85 minutes for intravenous administration and 3.3 hours subcutaneous administration (Kirchner, G. I., et al., 1998, Br J Clin Pharmacol. 46:5-10). In some embodiments of this invention, the half-life extension element is linked to the interleukin via a linker which is cleaved at the site of action (e.g., by inflammation-specific or tumor-specific proteases) releasing the interleukin's full activity at the desired site and also separating it from the half-life extension of the uncleaved version. In such embodiments, the fully active and free interleukin would have very different pharmacokinetic (pK) properties—a half-life of hours instead of weeks. In addition, exposure to active cytokine is limited to the site of desired cytokine activity (e.g., an inflammatory site or tumor) and systemic exposure to active cytokine, and associated toxicity and side effects, are reduced.

Other cytokines envisioned in this invention have similar pharmacology (e.g. IL-15 as reported by Blood 2011 117: 4787-4795; doi: doi.org/10.1182/blood-2010-10-311456) as IL-2 and accordingly, the designs of this invention address the shortcomings of using these agents directly, and provide chimeric polypeptides that can have extended half-life and/or be targeted to a site of desired activity (e.g., a site of inflammation or a tumor).

If desired, IL-2 can be engineered to bind the IL-2R complex generally or one of the three IL-2R subunits specifically with an affinity that differs from that of the corresponding wild-type IL-2, for example toto selectively activate Tregs or Teff. For example, IL-2 polypeptides that are said to have higher affinity for the trimeric form of the IL-2 receptor relative to the dimeric beta/gamma form of the 11-2 receptor in comparison to wild type IL-2 can have an amino acid sequence that includes one of the following sets of mutations with respect to SEQ ID NO:1 (a mature IL-2 protein comprising amino acids 21-153 of human IL-2 having the Uniprot Accession No. P60568-1): (a) K64R, V69A, and Q74P; (b) V69A, Q74P, and T101A; (c) V69A, Q74P, and I128T; (d) N30D, V69A, Q74P, and F103S; (e) K49E, V69A, A73V, and K76E; (f) V69A, Q74P, T101A, and T133N; (g) N30S, V69A, Q74P, and I128A; (h) V69A, Q74P, N88D, and S99P; (i) N30S, V69A, Q74P, and I128T; (j) K9T, Q11R, K35R, V69A, and Q74P; (k) A1T, M46L, K49R, E61D, V69A, and H79R; (l) K48E, E68D, N71T, N90H, F103S, and I114V; (m) S4P, T10A, Q11R, V69A, Q74P, N88D, and T133A; (n) E15K, N30S Y31H, K35R, K48E, V69A, Q74P, and I92T; (o) N30S, E68D, V69A, N71A, Q74P, S75P, K76R, and N90H; (p) N30S, Y31C, T37A, V69A, A73V, Q74P, H79R, and I128T; (q) N26D, N29S, N30S, K54R, E67G, V69A, Q74P, and I92T; (r) K8R, Q13R, N26D, N30T, K35R, T37R, V69A, Q74P, and I92T; and (s) N29S, Y31H, K35R, T37A, K48E, V69A, N71R, Q74P, N88D, and I89V. This approach can also be applied to prepare muteins of other cytokines including interleukins (e.g., IL-2, IL-7, IL-12, IL-15, IL-18, IL-23), interferons (IFNs, including IFNalpha, IFNbeta and IFNgamma), tumor necrosis factors (e.g., TNFalpha, lymphotoxin), transforming growth factors (e.g., TGFbeta1, TGFbeta2, TGFbeta3) and granulocyte macrophage-colony stimulating factor (GM-CS). For example, muteins can be prepared that have desired binding affinity for a cognate receptor.

As noted above, any of the mutant IL-2 polypeptides disclosed herein can include the sequences described; they can also be limited to the sequences described and otherwise identical to SEQ ID NO:1. Moreover, any of the mutant IL-2 polypeptides disclosed herein can optionally include a substitution of the cysteine residue at position 125 with another residue (e.g., serine) and/or can optionally include a deletion of the alanine residue at position 1 of SEQ ID NO:1.

Another approach to improving the therapeutic index of an IL-2 based therapy is to optimize the pharmacokinetics of the molecule to maximally activate Treg cells. Early studies of IL-2 action demonstrated that IL-2 stimulation of human T cell proliferation in vitro required a minimum of 5-6 hours exposure to effective concentrations of IL-2 (Cantrell, D. A., et. al., 1984, Science, 224: 1312-1316). When administered to human patients, IL-2 has a very short plasma half-life of 85 minutes for intravenous administration and 3.3 hours subcutaneous administration (Kirchner, G. I., et al., 1998, Br J Clin Pharmacol. 46:5-10). Because of its short half-life, maintaining circulating IL-2 at or above the level necessary to stimulate T cell proliferation for the necessary duration necessitates high doses that result in peak IL-2 levels significantly above the EC50 for Treg cells or will require frequent administration. These high IL-2 peak levels can activate IL2Rβγ receptors and have other unintended or adverse effects, for example VLS as noted above. An IL-2 analog, or a multifunctional protein with IL-2 attached to a domain that enables binding to the FcRn receptor, with a longer circulating half-life than IL-2 can achieve a target drug concentration for a specified period of time at a lower dose than IL-2, and with lower peak levels. Such an IL-2 analog will therefore require either lower doses or less frequent administration than IL-2 to effectively stimulate Treg cells. Less frequent subcutaneous administration of an IL-2 drug will also be more tolerable for patients. A therapeutic with these characteristics will translate clinically into improved pharmacological efficacy, reduced toxicity, and improved patient compliance with therapy. Alternatively, IL-2 or muteins of IL-2 (herein, "IL-2*") can be selectively targeted to the intended site of action (e.g. sites of inflammation or a tumor). This targeting can be achieved by one of several strategies, including the addition of domains to the administered agent that comprise blockers of the IL-2 (or muteins) that are cleaved away or by targeting domains or a combination of the two.

In some embodiments, IL-2* partial agonists can be tailored to bind with higher or lower affinity depending on the desired target; for example, an IL-2* can be engineered to bind with enhanced affinity to one of the receptor subunits and not the others. These types of partial agonists, unlike full agonists or complete antagonists, offer the ability to tune the signaling properties to an amplitude that elicits desired functional properties while not meeting thresholds for undesired properties. Given the differential activities of the partial agonists, a repertoire of IL-2 variants could be engineered to exhibit an even finer degree of distinctive signaling activities, ranging from almost full to partial agonism to complete antagonism.

In some embodiments, the IL-2* has altered affinity for IL-2Rα. In some embodiments, the IL-2* has a higher affinity for IL-2Rα than wild-type IL-2. In other embodiments, the IL-2* has altered affinity for IL-2Rβ. In one embodiment, IL-2* has enhanced binding affinity for IL-2Rβ, e.g., the N-terminus of IL-2Rβ, that eliminates the functional requirement for IL-2Rα. In another embodiment, an IL-2* is generated that has increased binding affinity for IL-2Rβ but that exhibited decreased binding to IL-2Rγ, and thereby is defective IL-2Rβγ heterodimerization and signaling.

Blocking moieties, described in further detail below, can also be used to favor binding to or activation of one or more receptors. In one embodiment, blocking moieties are added such that IL-2Rβγ binding or activation is blocked but IL-2Rα binding or activation is not changed. In another embodiment, blocking moieties are added such that IL-2Rα binding or activation is diminished. In another embodiment, blocking moieties are added such that binding to and or activation of all three receptors is inhibited. This blocking may be relievable by removal of the blocking moieties in a particular environment, for example by proteolytic cleavage of a linker linking one or more blocking moieties to the cytokine.

A similar approach can be applied to improve other cytokines, particularly for use as immunostimulatory agents, for example for treating cancer. For example, in this aspect, the pharmacokinetics and/or pharmacodynamics of the cytokine (e.g., IL-2, IL-7, IL-12, IL-15, IL-18, IL-21 IL-23, IFNalpha, IFNbeta and IFNgamma, TNFalpha, lymphotoxin, TGFbeta1, TGFbeta2, TGFbeta3 GM-CSF, CXCL10, CCL19, CCL20, and CCL21 can be tailored to maximally activate effector cells (e.g., effect T cells, NK cells) and/or cytotoxic immune response promoting cells (e.g., induce dendritic cell maturation) at a site of desired activity, such as in a tumor, but preferably not systemically.

Thus, provided herein are pharmaceutical compositions comprising at least one cytokine polypeptide, such as interleukins (e.g., IL-2, IL-7, IL-12, IL-15, IL-18, IL-21, IL-23), interferons (IFNs, including IFNalpha, IFNbeta and IFNgamma), tumor necrosis factors (e.g., TNFalpha, lymphotoxin), transforming growth factors (e.g., TGFbeta1, TGFbeta2, TGFbeta3), chemokines (e.g. CXCL10, CCL19, CCL20, CCL21) and granulocyte macrophage-colony stimulating factor (GM-CS) or a functional fragment or mutein of any of the foregoing. The polypeptide typically also includes at least one linker amino acid sequence, wherein the amino acid sequence is in certain embodiments capable of being cleaved by an endogenous protease. In one embodiment, the linker comprises an amino acid sequence comprising HSSKLQ (SEQ ID NO.: 25), GPLGVRG (SEQ ID NO.: 445), IPVSLRSG (SEQ ID NO.: 446), VPLSLYSG (SEQ ID NO. 447), or SGESPAYYTA (SEQ ID NO. 448). In other embodiments, the chimeric polypeptide further contains a blocking moiety, e.g. a steric blocking polypeptide moiety, capable of blocking the activity of the interleukin polypeptide. The blocking moiety, for example, can comprise a human serum albumin (HSA) binding domain or an optionally branched or multi-armed polyethylene glycol (PEG). Alternatively, the pharmaceutical composition comprises a first cytokine polypeptide or a fragment thereof, and blocking moiety, e.g. a steric blocking polypeptide moiety, wherein the blocking moiety blocks the activity of the cytokine polypeptide on the cytokine receptor, and wherein the blocking moiety in certain embodiments comprises a protease cleavable domain. In some embodiments, blockade and reduction of cytokine activity is achieved simply by attaching additional domains with very short linkers to the N or C terminus of the interleukin domain. In such embodiments, it is anticipated the blockade is relieved by protease digestion of the blocking moiety or of the short linker that tethers the blocker to the interleukin. Once the domain is clipped or is released, it will no longer be able to achieve blockade of cytokine activity.

The pharmaceutical composition e.g., chimeric polypeptide can comprise two or more cytokines, which can be the same cytokine polypeptide or different cytokine polypeptides. For example, the two or more different types of cytokines have complementary functions. In some examples, a first cytokine is IL-2 and a second cytokine is IL-12. In some embodiments, each of the two or more different types of cytokine polypeptides have activities that modulate the activity of the other cytokine polypeptides. In some examples of chimeric polypeptides that contain two cytokine polypeptides, a first cytokine polypeptide is T-cell activating, and a second cytokine polypeptide is non-T-cell-activating. In some examples of chimeric polypeptides that contain two cytokine polypeptides, a first cytokine is a chemoattractant, e.g. CXCL10, and a second cytokine is an immune cell activator.

Preferably, the cytokine polypeptides (including functional fragments) that are included in the fusion proteins disclosed herein are not mutated or engineered to alter the properties of the naturally occurring cytokine, including receptor binding affinity and specificity or serum half-life. However, changes in amino acid sequence from naturally occurring (including wild type) cytokine are acceptable to facilitate cloning and to achieve desired expression levels, for example.

Blocking Moiety

The blocking moiety can be any moiety that inhibits the ability of the cytokine to bind and/or activate its receptor. The blocking moiety can inhibit the ability of the cytokine to bind and/or activate its receptor sterically blocking and/or by noncovalently binding to the cytokine. Examples of suitable blocking moieties include the full length or a cytokine-binding fragment or mutein of the cognate receptor of the cytokine. Antibodies and fragments thereof including, a polyclonal antibody, a recombinant antibody, a human antibody, a humanized antibody a single chain variable fragment (scFv), single-domain antibody such as a heavy chain variable domain (VH), a light chain variable domain (VL) and a variable domain of camelid-type nanobody (VHH), a dAb and the like that bind the cytokine can also be used. Other suitable antigen-binding domain that bind the cytokine can also be used, include non-immunoglobulin proteins that mimic antibody binding and/or structure such as, anticalins, affilins, affibody molecules, affimers, affitins, alphabodies, avimers, DARPins, fynomers, kunitz domain peptides, monobodies, and binding domains based on other engineered scaffolds such as SpA, GroEL, fibronectin, lipocallin and CTLA4 scaffolds. Further examples of suitable blocking polypeptides include polypeptides that sterically inhibit or block binding of the cytokine to its cognate receptor. Advantageously, such moieties can also function as half-life extending elements. For example, a peptide that is modified by conjugation to a water-soluble polymer, such as PEG, can sterically inhibit or prevent binding of the cytokine to its receptor. Polypeptides, or fragments thereof, that have long serum half-lives can also be used, such as serum albumin (human serum albumin), immunoglobulin Fc, transferrin and the like, as well as fragments and muteins of such polypeptides.

Antibodies and antigen-binding domains that bind to, for example, a protein with a long serum half-life such as HSA, immunoglobulin or transferrin, or to a receptor that is recycled to the plasma membrane, such as FcRn or transferrin receptor, can also inhibit the cytokine, particularly when bound to their antigen. Examples of such antigen-binding polypeptides include a single chain variable fragment (scFv), single-domain antibody such as a heavy chain variable domain (VH), a light chain variable domain (VL) and a variable domain of camelid-type nanobody (VHH), a dAb and the like. Other suitable antigen-binding domain that bind the cytokine can also be used, include non-immunoglobulin proteins that mimic antibody binding and/or structure such as, anticalins, affilins, affibody molecules, affimers, affitins, alphabodies, avimers, DARPins, fynomers, kunitz domain peptides, monobodies, and binding domains based on other engineered scaffolds such as SpA, GroEL, fibronectin, lipocallin and CTLA4 scaffolds.

In illustrative examples, when IL-2 is the cytokine in the chimeric polypeptide, the blocking moiety can be the full length or fragment or mutein of the alpha chain of IL-2 receptor (IL-2Rα) or beta (IL-2Rβ) or gamma chain of IL-2 receptor (IL-2Rγ), an anti-IL-2 single-domain antibody (dAb) or scFv, a Fab, an anti-CD25 antibody or fragment thereof, and anti-HSA dAb or scFv, and the like. As described further herein, when an antibody fragment is used to attenuate the activity of the cytokine polypeptide, the blocking moiety in the fusion protein can be a single chain antibody binding fragment, such as an scFv. The blocking moiety can also be half of a two-chain antigen binding fragment such as a VH-CH1, which associates with a complementary VL-CL on a second polypeptide for form an antibody binding site the binds the cytokine polypeptide.

In Vivo Half-Life Extension Elements

Preferably, the chimeric polypeptides comprise an in vivo half-life extension element. Increasing the in vivo half-life of therapeutic molecules with naturally short half-lives allows for a more acceptable and manageable dosing regimen without sacrificing effectiveness. As used herein, a "half-life extension element" is a part of the chimeric polypeptide that increases the in vivo half-life and improve pK, for example, by altering its size (e.g., to be above the kidney filtration cutoff), shape, hydrodynamic radius, charge, or parameters of absorption, biodistribution, metabolism, and elimination. An exemplary way to improve the pK of a polypeptide is by expression of an element in the polypeptide chain that binds to receptors that are recycled to the plasma membrane of cells rather than degraded in the lysosomes, such as the FcRn receptor on endothelial cells and transferrin receptor. Three types of proteins, e.g., human IgGs, HSA (or fragments), and transferrin, persist for much longer in human serum than would be predicted just by their size, which is a function of their ability to bind to receptors that are recycled rather than degraded in the lysosome. These proteins, or fragments of them that retain the FcRn binding are routinely linked to other polypeptides to extend their serum half-life. In one embodiment, the half-life extension element is a human serum albumin (HSA) binding domain. HSA (SEQ ID NO: 2) may also be directly bound to the pharmaceutical compositions or bound via a short linker. Fragments of HSA may also be used. HSA and fragments thereof can function as both a blocking moiety and a half-life extension element. Human IgGs and Fc fragments can also carry out a similar function.

The serum half-life extension element can also be antigen-binding polypeptide that binds to a protein with a long serum half-life such as serum albumin, transferrin and the like. Examples of such polypeptides include antibodies and fragments thereof including, a polyclonal antibody, a recombinant antibody, a human antibody, a humanized antibody a single chain variable fragment (scFv), single-domain antibody such as a heavy chain variable domain (VH), a light chain variable domain (VL) and a variable domain of camelid-type nanobody (VHH), a dAb and the like. Other suitable antigen-binding domain include non-immunoglobulin proteins that mimic antibody binding and/or structure such as, anticalins, affilins, affibody molecules, affimers, affitins, alphabodies, avimers, DARPins, fynomers, kunitz domain peptides, monobodies, and binding domains based on other engineered scaffolds such as SpA, GroEL, fibronectin, lipocallin and CTLA4 scaffolds. Further examples of antigen-binding polypeptides include a ligand for a desired receptor, a ligand-binding portion of a receptor, a lectin, and peptides that binds to or associates with one or more target antigens.

Some preferred serum half-life extension elements are polypeptides that comprise complementarity determining regions (CDRs), and optionally non-CDR loops. Advantageously, such serum half-life extension elements can extend the serum half-life of the cytokine, and also function as inhibitors of the cytokine (e.g., via steric blocking, non-covalent interaction or combination thereof) and/or as targeting domains. In some instances, the serum half-life extension elements are domains derived from an immunoglobulin molecule (Ig molecule) or engineered protein scaffolds that mimic antibody structure and/or binding activity. The Ig may be of any class or subclass (IgG1, IgG2, IgG3, IgG4, IgA, IgE, IgM etc). A polypeptide chain of an Ig molecule folds into a series of parallel beta strands linked by loops. In the variable region, three of the loops constitute the "complementarity determining regions" (CDRs) which determine the antigen binding specificity of the molecule. An IgG molecule comprises at least two heavy (H) chains and two light (L) chains inter-connected by disulfide bonds, or an antigen binding fragment thereof. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDRs) with are hypervariable in sequence and/or involved in antigen recognition and/or usually form structurally defined loops, interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. In some embodiments of this disclosure, at least some or all of the amino acid sequences of FR1, FR2, FR3, and FR4 are part of the "non-CDR loop" of the binding moieties described herein. A variable domain of an immunoglobulin molecule has several beta strands that are arranged in two sheets. The variable domains of both light and heavy immunoglobulin chains contain three hypervariable loops, or complementarity-determining regions (CDRs). The three CDRs of a V domain (CDR1, CDR2, CDR3) cluster at one end of the beta barrel. The CDRs are the loops that connect beta strands B-C, C'-C", and F-G of the immunoglobulin fold, whereas the bottom loops that connect beta strands AB, CC', C"-D and E-F of the immunoglobulin fold, and the top loop that connects the D-E strands of the immunoglobulin fold are the non-CDR loops. In some embodiments of this disclosure, at least some amino acid residues of a constant domain, CH1, CH2, or CH3, are part of the "non-CDR loop" of the binding moieties described herein. Non-CDR loops comprise, in some embodiments, one or more of AB, CD, EF, and DE loops of a C1-set domain of an Ig or an Ig-like molecule; AB, CC', EF, FG, BC, and EC' loops of a C2-set domain of an Ig or an Ig-like molecule; DE, BD, GF, A(A1A2)B, and EF loops of I (Intermediate)-set domain of an Ig or Ig-like molecule.

Within the variable domain, the CDRs are believed to be responsible for antigen recognition and binding, while the FR residues are considered a scaffold for the CDRs. However, in certain cases, some of the FR residues play an important role in antigen recognition and binding. Framework region residues that affect Ag binding are divided into two categories. The first are FR residues that contact the antigen, thus are part of the binding-site, and some of these residues are close in sequence to the CDRs. Other residues are those that are far from the CDRs in sequence, but are in close proximity to it in the 3-D structure of the molecule, e.g., a loop in heavy chain.

The binding moieties are any kinds of polypeptides. For example, in certain instances the binding moieties are natural peptides, synthetic peptides, or fibronectin scaffolds, or engineered bulk serum proteins. The bulk serum protein comprises, for example, albumin, fibrinogen, or a globulin. In some embodiments, the binding moieties are engineered scaffolds. Engineered scaffolds comprise, for example, sdAb, a scFv, a Fab, a VHH, a fibronectin type III domain, immunoglobulin-like scaffold (as suggested in Halaby et al., 1999. Prot Eng 12(7):563-571), DARPin, cystine knot peptide, lipocalin, three-helix bundle scaffold, protein G-related albumin-binding module, or a DNA or RNA aptamer scaffold.

In some cases, the serum half-life extending element comprises a binding site for a bulk serum protein. In some embodiments, the CDRs provide the binding site for the bulk serum protein. The bulk serum protein is, in some examples, a globulin, albumin, transferrin, IgG1, IgG2, IgG4, IgG3, IgA monomer, Factor XIII, Fibrinogen, IgE, or pentameric IgM. In some embodiments, the CDR form a binding site for an immunoglobulin light chain, such as an Igκ free light chain or an Igκ free light chain.

The serum half-life extension element can be any type of binding domain, including but not limited to, domains from a monoclonal antibody, a polyclonal antibody, a recombinant antibody, a human antibody, a humanized antibody. In some embodiments, the binding moiety is a single chain variable fragment (scFv), single-domain antibody such as a heavy chain variable domain (VH), a light chain variable domain (VL) and a variable domain (VHH) of camelid derived nanobody. In other embodiments, the binding moieties are non-Ig binding domains, i.e., antibody mimetic, such as anticalins, affilins, affibody molecules, affimers, affitins, alphabodies, avimers, DARPins, fynomers, kunitz domain peptides, and monobodies.

In other embodiments, the serum half-life extension element can be a water-soluble polymer or a peptide that is conjugated to a water-soluble polymer, such as PEG. "PEG," "polyethylene glycol" and "poly(ethylene glycol)" as used herein, are interchangeable and encompass any nonpeptidic water-soluble poly(ethylene oxide). The term "PEG" also means a polymer that contains a majority, that is to say, greater than 50%, of —OCH$_2$CH$_2$— repeating subunits. With respect to specific forms, the PEG can take any number of a variety of molecular weights, as well as structures or geometries such as "branched," "linear," "forked," "multifunctional," and the like, to be described in greater detail below. The PEG is not limited to a particular structure and can be linear (e.g., an end capped, e.g., alkoxy PEG or a bifunctional PEG), branched or multi-armed (e.g., forked PEG or PEG attached to a polyol core), a dendritic (or star) architecture, each with or without one or more degradable linkages. Moreover, the internal structure of the PEG can be organized in any number of different repeat patterns and can be selected from the group consisting of homopolymer, alternating copolymer, random copolymer, block copolymer, alternating tripolymer, random tripolymer, and block tripolymer. PEGs can be conjugated to polypeptide and peptides through any suitable method. Typically, a reactive PEG derivative, such as N-hydroxysuccinamidyl ester PEG, is reacted with a peptide or polypeptide that includes amino acids with a side chain that contains an amine, sulfhydryl, carboxylic acid or hydroxyl functional group, such as cysteine, lysine, asparagine, glutamine, theonine, tyrosine, serine, aspartic acid, and glutamic acid.

Targeting and Retention Domains

For certain applications, it may be desirable to maximize the amount of time the construct is present in its desired location in the body. This can be achieved by including one further domain in the chimeric polypeptide (fusion protein) to influence its movements within the body. For example, the chimeric nucleic acids can encode a domain that directs the polypeptide to a location in the body, e.g., tumor cells or a site of inflammation; this domain is termed a "targeting domain" and/or encode a domain that retains the polypeptide in a location in the body, e.g., tumor cells or a site of inflammation; this domain is termed a "retention domain". In some embodiments a domain can function as both a targeting and a retention domain. In some embodiments, the targeting domain and/or retention domain are specific to a protease-rich environment. In some embodiments, the encoded targeting domain and/or retention domain are specific for regulatory T cells (Tregs), for example targeting the CCR4 or CD39 receptors. Other suitable targeting and/or retention domains comprise those that have a cognate ligand that is overexpressed in inflamed tissues, e.g., the IL-1 receptor, or the IL-6 receptor. In other embodiments, the suitable targeting and/or retention domains comprise those who have a cognate ligand that is overexpressed in tumor tissue, e.g., Epcam, CEA or mesothelin. In some embodiments, the targeting domain is linked to the interleukin via a linker which is cleaved at the site of action (e.g. by inflammation or cancer specific proteases) releasing the interleukin full activity at the desired site. In some embodiments, the targeting and/or retention domain is linked to the interleukin via a linker which is not cleaved at the site of action (e.g. by inflammation or cancer specific proteases), causing the cytokine to remain at the desired site.

Antigens of choice, in some cases, are expressed on the surface of a diseased cell or tissue, for example a tumor or a cancer cell. Antigens useful for tumor targeting and retention include but are not limited to EpCAM, EGFR, HER-2, HER-3, c-Met, FOLR1, and CEA. Pharmaceutical compositions disclosed herein, also include proteins comprising two targeting and/or retention domains that bind to two different target antigens known to be expressed on a diseased cell or tissue. Exemplary pairs of antigen binding domains include but are not limited to EGFR/CEA, EpCAM/CEA, and HER-2/HER-3.

Suitable targeting and/or retention domains include antigen-binding domains, such as antibodies and fragments thereof including, a polyclonal antibody, a recombinant antibody, a human antibody, a humanized antibody a single chain variable fragment (scFv), single-domain antibody such as a heavy chain variable domain (VH), a light chain variable domain (VL) and a variable domain of camelid-type nanobody (VHH), a dAb and the like. Other suitable antigen-binding domain include non-immunoglobulin proteins that mimic antibody binding and/or structure such as, anticalins, affilins, affibody molecules, affimers, affitins, alphabodies, avimers, DARPins, fynomers, kunitz domain peptides, monobodies, and binding domains based on other engineered scaffolds such as SpA, GroEL, fibronectin, lipocallin and CTLA4 scaffolds. Further examples of antigen-binding polypeptides include a ligand for a desired receptor, a ligand-binding portion of a receptor, a lectin, and peptides that binds to or associates with one or more target antigens.

In some embodiments, the targeting and/or retention domains specifically bind to a cell surface molecule. In some embodiments, the targeting and/or retention domains specifically bind to a tumor antigen. In some embodiments, the targeting polypeptides specifically and independently bind to a tumor antigen selected from at least one of Fibroblast activation protein alpha (FAPa), Trophoblast glycoprotein (5T4), Tumor-associated calcium signal transducer 2 (Trop2), Fibronectin EDB (EDB-FN), fibronectin EIIIB domain, CGS-2, EpCAM, EGFR, HER-2, HER-3, cMet, CEA, and FOLR1. In some embodiments, the targeting polypeptides specifically and independently bind to two different antigens, wherein at least one of the antigens is a tumor antigen selected from EpCAM, EGFR, HER-2, HER-3, cMet, CEA, and FOLR1.

The targeting and/or retention antigen can be a tumor antigen expressed on a tumor cell. Tumor antigens are well known in the art and include, for example, EpCAM, EGFR, HER-2, HER-3, c-Met, FOLR1, PSMA, CD38, BCMA, and CEA. 5T4, AFP, B7-H3, Cadherin-6, CAIX, CD117, CD123, CD138, CD166, CD19, CD20, CD205, CD22, CD30, CD33, CD352, CD37, CD44, CD52, CD56, CD70, CD71, CD74, CD79b, DLL3, EphA2, FAP, FGFR2, FGFR3, GPC3, gpA33, FLT-3, gpNMB, HPV-16 E6, HPV-16 E7, ITGA2, ITGA3, SLC39A6, MAGE, mesothelin, Muc1, Muc16, NaPi2b, Nectin-4, P-cadherin, NY-ESO-1, PRLR, PSCA, PTK7, ROR1, SLC44A4, SLTRK5, SLTRK6, STEAP1, TIM1, Trop2, WT1.

The targeting and/or retention antigen can be an immune checkpoint protein. Examples of immune checkpoint proteins include but are not limited to CD27, CD137, 2B4, TIGIT, CD155, ICOS, HVEM, CD40L, LIGHT, TIM-1, OX40, DNAM-1, PD-L1, PD1, PD-L2, CTLA-4, CD8, CD40, CEACAM1, CD48, CD70, A2AR, CD39, CD73, B7-H3, B7-H4, BTLA, IDO1, IDO2, TDO, KIR, LAG-3, TIM-3, or VISTA.

The targeting and/or retention antigen can be a cell surface molecule such as a protein, lipid or polysaccharide. In some embodiments, a targeting and/or retention antigen is a on a tumor cell, virally infected cell, bacterially infected cell, damaged red blood cell, arterial plaque cell, inflamed or fibrotic tissue cell. The targeting and/or retention antigen can comprise an immune response modulator. Examples of immune response modulator include but are not limited to granulocyte-macrophage colony stimulating factor (GM-CSF), macrophage colony stimulating factor (M-CSF), granulocyte colony stimulating factor (G-CSF), interleukin 2 (IL-2), interleukin 3 (IL-3), interleukin 12 (IL-12), interleukin 15 (IL-15), B7-1 (CD80), B7-2 (CD86), GITRL, CD3, or GITR.

The targeting and/or retention antigen can be a cytokine receptor. Examples, of cytokine receptors include but are not limited to Type I cytokine receptors, such as GM-CSF receptor, G-CSF receptor, Type I IL receptors, Epo receptor, LIF receptor, CNTF receptor, TPO receptor; Type II Cytokine receptors, such as IFN-alpha receptor (IFNAR1, IFNAR2), IFB-beta receptor, IFN-gamma receptor (IFNGR1, IFNGR2), Type II IL receptors; chemokine receptors, such as CC chemokine receptors, CXC chemokine receptors, CX3C chemokine receptors, XC chemokine receptors; tumor necrosis receptor superfamily receptors, such as TNFRSF5/CD40, TNFRSF8/CD30, TNFRSF7/CD27, TNFRSF1A/TNFR1/CD120a, TNFRSF1B/TNFR2/CD120b; TGF-beta receptors, such as TGF-beta receptor 1, TGF-beta receptor 2; Ig super family receptors, such as IL-1 receptors, CSF-1R, PDGFR (PDGFRA, PDGFRB), SCFR.

Linkers

As stated above, the pharmaceutical compositions comprise one or more linker sequences. A linker sequence serves to provide flexibility between polypeptides, such that, for example, the blocking moiety is capable of inhibiting the activity of the cytokine polypeptide. The linker sequence can be located between any or all of the cytokine polypeptide, the serum half-life extension element, and/or the blocking moiety. As described herein at least one of the linkers is protease cleavable, and contains a (one or more) cleavage site for a (one or more) desired protease. Preferably, the desired protease is enriched or selectively expressed at the desired site of cytokine activity (e.g., the tumor microenvironment). Thus, the fusion protein is preferentially or selectively cleaved at the site of desired cytokine activity.

Suitable linkers can be of different lengths, such as from 1 amino acid (e.g., Gly) to 20 amino acids, from 2 amino acids to 15 amino acids, from 3 amino acids to 12 amino acids, including 4 amino acids to 10 amino acids, amino acids to 9 amino acids, 6 amino acids to 8 amino acids, or 7 amino acids to 8 amino acids, and may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 41, 42, 43, 44, 45, 46, 47, 48, 49, 50, 51, 52, 53, 54, 55, 56, 57, 58, 59, or 60 amino acids.

The orientation of the components of the pharmaceutical composition, are largely a matter of design choice and it is recognized that multiple orientations are possible and all are intended to be encompassed by this disclosure. For example, a blocking moiety can be located C-terminally or N-terminally to a cytokine polypeptide.

Proteases known to be associated with diseased cells or tissues include but are not limited to serine proteases, cysteine proteases, aspartate proteases, threonine proteases, glutamic acid proteases, metalloproteases, asparagine peptide lyases, serum proteases, cathepsins, Cathepsin B, Cathepsin C, Cathepsin D, Cathepsin E, Cathepsin K, Cathepsin L, kallikreins, hK1, hK10, hK15, plasmin, collagenase, Type IV collagenase, stromelysin, Factor Xa, chymotrypsin-like protease, trypsin-like protease, elastase-like protease, subtilisin-like protease, actinidain, bromelain, calpain, caspases, caspase-3, Mirl-CP, papain, HIV-1 protease, HSV protease, CMV protease, chymosin, renin, pepsin, matriptase, legumain, plasmepsin, nepenthesin, metalloexopeptidases, metalloendopeptidases, matrix metalloproteases (MMP), MMP1, MMP2, MMP3, MMP8, MMP9, MMP13, MMP11, MMP14, urokinase plasminogen activator (uPA), enterokinase, prostate-specific antigen (PSA, hK3), interleukin-1β converting enzyme, thrombin, FAP (FAP-a), dipeptidyl peptidase, meprins, granzymes and dipeptidyl peptidase IV (DPPIV/CD26). Proteases capable of cleaving amino acid sequences encoded by the chimeric nucleic acid sequences provided herein can, for example, be selected from the group consisting of a prostate specific antigen (PSA), a matrix metalloproteinase (MMP), an A Disintigrin and a Metalloproteinase (ADAM), a plasminogen activator, a cathepsin, a caspase, a tumor cell surface protease, and an elastase. The MMP can, for example, be matrix metalloproteinase 2 (MMP2) or matrix metalloproteinase 9 (MMP9).

Proteases useful in the methods disclosed herein are presented in Table 1, and exemplary proteases and their cleavage site are presented in Table 1a:

TABLE 1

Proteases relevant to inflammation and cancer

| Protease | Specificity | Other aspects |
| --- | --- | --- |
| Secreted by killer T cells: | | |
| Granzyme B (grB) | Cleaves after Asp residues (asp-ase) | Type of serine protease; strongly implicated in inducing perforin-dependent target cell apoptosis |
| Granzyme A (grA) | trypsin-like, cleaves after basic residues | Type of serine protease; |
| Granzyme H (grH) | Unknown substrate specificity | Type of serine protease; Other granzymes are also secreted by killer T cells, but not all are present in humans |
| Caspase-8 | Cleaves after Asp residues | Type of cysteine protease; plays essential role in TCR-induced cellular expansion-exact molecular role unclear |
| Mucosa-associated lymphoid tissue (MALT1) | Cleaves after arginine residues | Type of cysteine protease; likely acts both as a scaffold and proteolytically active enzyme in the CBM-dependent signaling pathway |
| Tryptase | Targets: angiotensin I, fibrinogen, prourokinase, TGFβ; preferentially cleaves proteins after lysine or arginine residues | Type of mast cell-specific serine protease; trypsin-like; resistant to inhibition by macromolecular protease inhibitors expressed in mammals due to their tetrameric structure, with all sites facing narrow central pore; also associated with inflammation |
| Associated with inflammation: | | |
| Thrombin | Targets: FGF-2, HB-EGF, Osteo-pontin, PDGF, VEGF | Type of serine protease; modulates activity of vascular growth factors, chemokines and extracellular proteins; strengthens VEGF-induced proliferation; induces cell migration; angiogenic factor; regulates hemostasis |

TABLE 1-continued

Proteases relevant to inflammation and cancer

| Protease | Specificity | Other aspects |
| --- | --- | --- |
| Chymase | Exhibit chymotrypsin-like specificity, cleaving proteins after aromatic amino acid residues | Type of mast cell-specific serine protease |
| Carboxypeptidase A (MC-CPA) | Cleaves amino acid residues from C-terminal end of peptides and proteins | Type of zinc-dependent metalloproteinase |
| Kallikreins | Targets: high molecular weight kininogen, pro-urokinase | Type of serine protease; modulate relaxation response; contribute to inflammatory response; fibrin degradation |
| Elastase | Targets: E-cadherin, GM-CSF, IL-1, IL-2, IL-6, IL8, p38$^{MAPK}$, TNFα, VE-cadherin | Type of neutrophil serine protease; degrades ECM components; regulates inflammatory response; activates pro-apoptotic signaling |
| Cathepsin G | Targets: EGF, ENA-78, IL-8, MCP-1, MMP-2, MT1-MMP, PAI-1, RANTES, TGFβ TNFα | Type of serine protease; degrades ECM components; chemo-attractant of leukocytes; regulates inflammatory response; promotes apoptosis |
| PR-3 | Targets: ENA-78, IL-8, IL-18, JNK, p38$^{MAPK}$, TNFα | Type of serine protease; promotes inflammatory response; activates pro-apoptotic signaling |
| Granzyme M (grM) | Cleaves after Met and other long, unbranched hydrophobic residues | Type of serine protease; only expressed in NK cells |
| Calpains | Cleave between Arg and Gly | Family of cysteine proteases; calcium-dependent; activation is involved in the process of numerous inflammation-associated diseases |

TABLE 1a

Exemplary Proteases and Protease Recognition Sequences

| Protease | Cleavage Domain Sequence | SEQ ID NO: |
| --- | --- | --- |
| MMP7 | KRALGLPG | 3 |
| MMP7 | (DE)$_8$RPLALWRS(DR)$_8$ | 4 |
| MMP9 | PR(S/T)(L/I)(S/T) | 5 |
| MMP9 | LEATA | 6 |
| MMP11 | GGAANLVRGG | 7 |
| MMP14 | SGRIGFLRTA | 8 |
| MMP | PLGLAG | 9 |
| MMP | PLGLAX | 10 |
| MMP | PLGC(me)AG | 11 |
| MMP | ESPAYYTA | 12 |
| MMP | RLQLICL | 13 |
| MMP | RLQLKAC | 14 |
| MMP2, MMP9, MMP14 | EP(Cit)G(Hof)YL | 15 |
| Urokinase plasminogen activator (uPA) | SGRSA | 16 |
| Urokinase plasminogen activator (uPA) | DAFK | 17 |
| Urokinase plasminogen activator (uPA) | GGGRR | 18 |
| Lysosomal Enzyme | GFLG | 19 |
| Lysosomal Enzyme | ALAL | 20 |
| Lysosomal Enzyme | FK | 21 |
| Cathepsin B | NLL | 22 |
| Cathepsin D | PIC(Et)FF | 23 |
| Cathepsin K | GGPRGLPG | 24 |
| Prostate Specific Antigen | HSSKLQ | 25 |
| Prostate Specific Antigen | HSSKLQL | 26 |
| Prostate Specific Antigen | HSSICLQEDA | 27 |
| Herpes Simplex Virus Protease | LVLASSSFGY | 28 |
| HIV Protease | GVSQNYPIVG | 29 |
| CMV Protease | GVVQASCRLA | 30 |
| Thrombin | F(Pip)RS | 31 |

TABLE 1a-continued

Exemplary Proteases and Protease Recognition Sequences

| Protease | Cleavage Domain Sequence | SEQ ID NO: |
|---|---|---|
| Thrombin | DPRSFL | 32 |
| Thrombin | PPRSFL | 33 |
| Caspase-3 | DEVD | 34 |
| Caspase-3 | DEVDP | 35 |
| Caspase-3 | KGSGDVEG | 36 |
| Interleukin 1β converting enzyme | GWEHDG | 37 |
| Enterokinase | EDDDDKA | 38 |
| FAP | KQEQNPGST | 39 |
| Kallikrein 2 | GKAFRR | 40 |
| Plasmin | DAFK | 41 |
| Plasmin | DVLK | 42 |
| Plasmin | DAFK | 43 |
| TOP | ALLLALL | 44 |

Provided herein are pharmaceutical compositions comprising polypeptide sequences. As with all peptides, polypeptides, and proteins, including fragments thereof, it is understood that additional modifications in the amino acid sequence of the chimeric polypeptides (amino acid sequence variants) can occur that do not alter the nature or function of the peptides, polypeptides, or proteins. Such modifications include conservative amino acid substitutions and are discussed in greater detail below.

The compositions provided herein have a desired function. The compositions are comprised of at least a cytokine polypeptide, such as IL-2, IL-7, IL-12, IL-15, IL-18, IL-21, IFNα, or IFNγ, or a chemokine, such as CXCL10, CCL19, CCL20, CCL21, a blocking moiety, e.g. a steric blocking polypeptide, and an optional serum half-life extension element, and an optional targeting polypeptide, with one or more linkers connecting each polypeptide in the composition. The first polypeptide, e.g., an IL-2 mutein, is provided to be an active agent. The blocking moiety is provided to block the activity of the interleukin. The linker polypeptide, e.g., a protease cleavable polypeptide, is provided to be cleaved by a protease that is specifically expressed at the intended target of the active agent. Optionally, the blocking moiety blocks the activity of the first polypeptide by binding the interleukin polypeptide. In some embodiments, the blocking moiety, e.g. a steric blocking peptide, is linked to the interleukin via a protease-cleavable linker which is cleaved at the site of action (e.g. by inflammation-specific or tumor-specific proteases) releasing the cytokine full activity at the desired site.

The protease cleavage site may be a naturally occurring protease cleavage site or an artificially engineered protease cleavage site. The artificially engineered protease cleavage site can be cleaved by more than one protease specific to the desired environment in which cleavage will occur, e.g. a tumor. The protease cleavage site may be cleavable by at least one protease, at least two proteases, at least three proteases, or at least four proteases.

In some embodiments, the linker comprises glycine-glycine, a sortase-recognition motif, or a sortase-recognition motif and a peptide sequence (Gly$_4$Ser)$_n$ (SEQ ID NO.: 443) or (Gly$_3$Ser)$_n$, (SEQ ID NO.: 444), wherein n is 1, 2, 3, 4 or 5. In one embodiment, the sortase-recognition motif comprises a peptide sequence LPXTG (SEQ ID NO.: 442), where X is any amino acid. In one embodiment, the covalent linkage is between a reactive lysine residue attached to the C-terminal of the cytokine polypeptide and a reactive aspartic acid attached to the N-terminal of the blocking or other moiety. In one embodiment, the covalent linkage is between a reactive aspartic acid residue attached to the N-terminal of the cytokine polypeptide and a reactive lysine residue attached to the C-terminal of the blocking or other moiety.

Cleavage and Inducibility

As described herein, the activity of the cytokine polypeptide the context of the fusion protein is attenuated, and protease cleavage at the desired site of activity, such as in a tumor microenvironment, releases a form of the cytokine from the fusion protein that is much more active as a cytokine receptor agonist than the fusion protein. For example, the cytokine-receptor activating (agonist) activity of the fusion polypeptide can be at least about 10×, at least about at least about 100×, at least about 250×, at least about 500×, or at least about 1000× less than the cytokine receptor activating activity of the cytokine polypeptide as a separate molecular entity. The cytokine polypeptide that is part of the fusion protein exists as a separate molecular entity when it contains an amino acid that is substantially identical to the cytokine polypeptide and does not substantially include additional amino acids and is not associated (by covalent or non-covalent bonds) with other molecules. If necessary, a cytokine polypeptide as a separate molecular entity may include some additional amino acid sequences, such as a tag or short sequence to aid in expression and/or purification.

In other examples, the cytokine-receptor activating (agonist) activity of the fusion polypeptide is at least about 10×, at least about 50×, at least about 100×, at least about 250×, at least about 500×, or about 1000× less than the cytokine receptor activating activity of the polypeptide that contains the cytokine polypeptide that is produced by cleavage of the protease cleavable linker in the fusion protein. In other words, the cytokine receptor activating (agonist) activity of the polypeptide that contains the cytokine polypeptide that is produced by cleavage of the protease cleavable linker in the fusion protein is at least about 10×, at least about 50×, at least about 100×, at least about 250×, at least about 500×, or at least about 1000× greater than the cytokine receptor activating activity of the fusion protein.

Polypeptide Variants and Amino Acid Substitutions

The polypeptides described herein can include components (e.g., the cytokine, the blocking moiety) that have the same amino acid sequence of the corresponding naturally occurring protein (e.g., IL-2, IL-15, HSA) or can have an amino acid sequence that differs from the naturally occurring protein so long as the desired function is maintained. It is understood that one way to define any known modifications and derivatives or those that might arise, of the disclosed proteins and nucleic acids that encode them is through defining the sequence variants in terms of identity to specific known reference sequences. Specifically disclosed are polypeptides and nucleic acids which have at least, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent identity to the chimeric polypeptides provided herein. For example, provided are polypeptides or nucleic acids that have at least, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent identity to the sequence of any of the nucleic acids or polypeptides described herein. Those of skill in the art readily understand how to determine the identity of two polypeptides or two nucleic acids. For example, the identity can be calculated after aligning the two sequences so that the identity is at its highest level.

Another way of calculating identity can be performed by published algorithms. Optimal alignment of sequences for comparison may be conducted by the local identity algorithm of Smith and Waterman Adv. Appl. Math. 2:482 (1981), by the identity alignment algorithm of Needleman and Wunsch, J. Mol. Biol. 48:443 (1970), by the search for similarity method of Pearson and Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of identity can be obtained for nucleic acids by, for example, the algorithms disclosed in Zuker, Science 244:48-52 (1989); Jaeger et al., Proc. Natl. Acad. Sci. USA 86:7706-7710 (1989); Jaeger et al., Methods Enzymol. 183:281-306 (1989), which are herein incorporated by reference for at least material related to nucleic acid alignment. It is understood that any of the methods typically can be used and that in certain instances the results of these various methods may differ, but the skilled artisan understands if identity is found with at least one of these methods, the sequences would be said to have the stated identity, and be disclosed herein.

Protein modifications include amino acid sequence modifications. Modifications in amino acid sequence may arise naturally as allelic variations (e.g., due to genetic polymorphism), may arise due to environmental influence (e.g., by exposure to ultraviolet light), or may be produced by human intervention (e.g., by mutagenesis of cloned DNA sequences), such as induced point, deletion, insertion and substitution mutants. These modifications can result in changes in the amino acid sequence, provide silent mutations, modify a restriction site, or provide other specific mutations. Amino acid sequence modifications typically fall into one or more of three classes: substitutional, insertional or deletional modifications. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. Typically, no more than about from 2 to 6 residues are deleted at any one site within the protein molecule. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional modifications are those in which at least one residue has been removed and a different residue inserted in its place. Such substitutions generally are made in accordance with the following Table 2 and are referred to as conservative substitutions.

TABLE 2

Exemplary amino acid substitutions

| Amino Acid | Exemplary Substitutions |
|---|---|
| Ala | Ser, Gly, Cys |
| Arg | Lys, Gln, Met, Ile |
| Asn | Gln, His, Glu, Asp |
| Asp | Glu, Asn, Gln |
| Cys | Ser, Met, Thr |
| Gln | Asn, Lys, Glu, Asp |
| Glu | Asp, Asn, Gln |
| Gly | Pro, Ala |
| His | Asn, Gln |
| Ile | Leu, Val, Met |
| Leu | Ile, Val, Met |
| Lys | Arg, Gln, Met, Ile |
| Met | Leu, Ile, Val |
| Phe | Met, Leu, Tyr, Trp, His |
| Ser | Thr, Met, Cys |
| Thr | Ser, Met, Val |
| Trp | Tyr, Phe |
| Tyr | Trp, Phe, His |
| Val | Ile, Leu, Met |

Modifications, including the specific amino acid substitutions, are made by known methods. For example, modifications are made by site specific mutagenesis of nucleotides in the DNA encoding the polypeptide, thereby producing DNA encoding the modification, and thereafter expressing the DNA in recombinant cell culture. Techniques for making substitution mutations at predetermined sites in DNA having a known sequence are well known, for example M13 primer mutagenesis and PCR mutagenesis.

Modifications can be selected to optimize binding. For example, affinity maturation techniques can be used to alter binding of the scFv by introducing random mutations inside the complementarity determining regions (CDRs). Such random mutations can be introduced using a variety of techniques, including radiation, chemical mutagens or error-prone PCR. Multiple rounds of mutation and selection can be performed using, for example, phage display.

The disclosure also relates to nucleic acids that encode the chimeric polypeptides described herein, and to the use of such nucleic acids to produce the chimeric polypeptides and for therapeutic purposes. For example, the invention includes DNA and RNA molecules (e.g., mRNA, self-replicating RNA) that encode a chimeric polypeptide and to the therapeutic use of such DNA and RNA molecules.

Exemplary Compositions

Exemplary fusion proteins of the invention combine the above described elements in a variety of orientations. The orientations described in this section are meant as examples and are not to be considered limiting.

In some embodiments, the fusion protein comprises a cytokine, a blocking moiety and a half-life extension element. In some embodiments, the cytokine is positioned between the half-life extension element and the blocking moiety. In some embodiments, the cytokine is N-terminal to the blocking moiety and the half-life extension element. In some such embodiments, the cytokine is proximal to the blocking moiety; in some such embodiments, the cytokine is proximal to the half-life extension element. At least one protease-cleavable linker must be included in all embodiments, such that the cytokine may be active upon cleavage. In some embodiments, the cytokine is C-terminal to the blocking moiety and the half-life extension element. Additional elements may be attached to one another by a cleavable linker, a non-cleavable linker, or by direct fusion.

In some embodiments, the blocking domains used are capable of extending half-life, and the cytokine is positioned between two such blocking domains. In some embodiments, the cytokine is positioned between two blocking domains, one of which is capable of extending half-life.

In some embodiments, two cytokines are included in the same construct. In some embodiments, the cytokines are connected to two blocking domains each (three in total in one molecule), with a blocking domain between the two cytokine domains. In some embodiments, one or more additional half-life extension domains may be included to optimize pharmacokinetic properties. In some cases, it is beneficial to include two of the same cytokine to facilitate dimerization. An example of a cytokine that works as a dimer is IFN.

In some embodiments, three cytokines are included in the same construct. In some embodiments, the third cytokine may function to block the other two in place of a blocking domain between the two cytokines.

Preferred half-life extension elements for use in the fusion proteins are human serum albumin (HSA), an antibody or antibody fragment (e.g., scFV, dAb) which binds serum albumin, a human or humanized IgG, or a fragment of any of the foregoing. In some preferred embodiments, the blocking moiety is human serum albumin (HSA), or an antibody or antibody fragment which binds serum albumin, an antibody which binds the cytokine and prevents activation of binding or activation of the cytokine receptor, another cytokine, or a fragment of any of the foregoing. In preferred embodiments comprising an additional targeting domain, the targeting domain is an antibody which binds a cell surface protein which is enriched on the surface of cancer cells, such as EpCAM, FOLR1, and Fibronectin.

In embodiments, the fusion protein can contain an IL-2 polypeptide. The fusion protein containing an IL-2 polypeptide can comprise or consist of the amino acid sequence of any one of SEQ ID NOs. 257-300, 302-317, 325-353, 355-365, 366, 372-381, 383-385, 388-420, 579-608 and 636-646. The fusion proteins disclosed as SEQ ID NOs. 257-300, 302-317, 325-353, 355-365, 366, 372-381, 383-385, 388-420, 579-608, and 636-646 are also referred to herein as ACP289-ACP292, ACP296-ACP302, WW0301, ACP304-ACP306, ACP309-ACP313, WW0353, ACP414, ACP336-ACP398, WW0472-WW0477, ACP406-ACP426, ACP439-ACP447, ACP451-ACP471, WW0729, WW0734-WW0792, ACP101, ACP293-ACP295, ACP316-ACP335, ACP427-ACP438, and ACP448-ACP450. For example, the fusion protein can comprise the amino acid sequence of SEQ ID NO: 272. The fusion protein can comprise the amino acid sequence of SEQ ID NO: 286. The fusion protein can comprise the amino acid sequence of SEQ ID NO:362. The fusion protein can comprise the amino acid sequence of SEQ ID NO:336. The fusion protein can comprise the amino acid sequence of SEQ ID NO: 348. The fusion protein can comprise the amino acid sequence of SEQ ID NO: 363. The fusion protein can comprise the amino acid sequence of SEQ ID NO: 580.

In embodiments, the fusion protein can contain an IL-12 polypeptide. The fusion protein containing an IL-12 polypeptide can comprise or consist of the amino acid sequence of any one of SEQ ID NOs. 368-371, 434-440, 453-519, or 523-538. The fusion proteins disclosed as SEQ ID NOs. 368-371, 434-440, 453-519, or 523-538 are referred to herein as ACP240-ACP245, ACP247, ACP285-ACP288, WW0641, WW0649-WW0652, WW0662-WW0725, WW0765-WW0772, and WW0796-WW0803. For example, the fusion protein can comprise the amino acid sequence of SEQ ID NO:459. The fusion protein can comprise the amino acid sequence of SEQ ID NO: 466. The fusion protein can comprise the amino acid sequence of SEQ ID NO: 484. The fusion protein can comprise the amino acid sequence of SEQ ID NO: 506.

In embodiments, the fusion protein contains an IFN (e.g., IFNgamma, IFNalpha, IFNbeta) polypeptide. In some examples the IFN polypeptide is an IFNalpha or an IFNbeta. The fusion protein containing an IFN polypeptide can comprise or consist of the amino acid sequence of SEQ ID NOs. 421-430, and 539-578. The fusion proteins disclosed as SEQ ID NOs. 421-430, and 539-578 can be referred to herein as ACP200-ACP209, WW0644-WW0648, WW0781-WW0786, WW0815-WW0822, WW0831-WW0834, WW0737-WW0748, and WW0787-WW0790. For example, the fusion protein can comprise the amino acid sequence of SEQ ID NO: 421. The fusion protein can comprise the amino acid sequence of SEQ ID NO: 428. The fusion protein can comprise the amino acid sequence of 541. The fusion protein can comprise the amino acid sequence of SEQ IND NO: 558. The fusion protein can comprise the amino acid sequence of SEQ ID NO: 577.

In some aspects, the fusion polypeptide disclosed herein can be covalently or non-covalently bonded to a second polypeptide chain. For example, a fusion polypeptide can dimerize (i.e. form a dimer) or a portion of a fusion polypeptide may associate with another polypeptide, for example, to form a functional binding site for a cytokine polypeptide or serum albumin. In certain embodiments, the second polypeptide chain and the blocking moiety on the fusion polypeptide are complementary and together form a functional binding site that has specificity for the cytokine polypeptide contained in the fusion polypeptide. Exemplary functional binding sites that can be formed by the blocking moiety of the fusion polypeptide and a complimentary second polypeptide include antigen binding sites of antibodies, such as a Fab fragment of an antibody or a portion thereof. For example, one chain of a Fab that binds the cytokine can be the blocking moiety of the fusion polypeptide, e.g., a VH-CH1, and the complementary VL-CL can be part of the second polypeptide. In such situations, the blocking moiety of the fusion protein i.e., VH-CH1 and the second polypeptide that comprises the complementary VL-CL, can associate to form a functional binding site with specificity for the cytokine polypeptide contained within the fusion protein (e.g., IL-2, IL-12, IFNalpha, IFNbeta) and attenuates cytokine polypeptide activity. At least a portion of the blocking moiety can be on the second polypeptide chain can comprise at least a portion of the blocking moiety that associates with the blocking moiety on the fusion polypeptide.

In embodiments, the fusion protein containing an IL-2 cytokine polypeptide can be bonded covalently or noncovalently to a second polypeptide chain. The second polypeptide chain can contain an antibody light chain VL-CL that comprises or consist of the amino acid sequence of SEQ ID NO: 263, 264, or 333. Such a second polypeptide can bond with a complimentary VH-CH1 polypeptide contained within the fusion protein, e.g., as contained within SEQ ID NOS: 362, 363, 325, 286, 579, 581, or 582. The second polypeptide chain disclosed as SEQ ID NOs. 263, 264, and 333 can be referred herein as WW0523 (ACP381), WW0524 (ACP382), or WW0556 (ACP414).

In embodiments, the fusion polypeptide can comprise or consist of the amino acid sequence of SEQ ID NOs. 362, 363, 325, 286, 579, 581, or 582 and the second polypeptide chain can comprise or consist of the amino acid sequence of SEQ ID NOs: 263, 264, or 333. The fusion polypeptide disclosed as SEQ ID NOs. 362, 363, 325, 286, 579, 581, or 582 can be referred to as WW0520 (ACP378), WW0521 (ACP379), WW0548 (ACP406), WW0621 (ACP457), WW0729, WW0735, or WW0736, and the second polypeptide chain disclosed as SEQ ID NOs. 263, 264, and 333 can be referred herein as WW0523 (ACP381), WW0524 (ACP382), or WW0556 (ACP414).

For example, the fusion protein can comprise or consist the amino acid sequence of SEQ ID NO: 362 and the second polypeptide chain can comprise or consist the amino acid sequence of SEQ ID NO: 263. For example, the fusion protein can comprise or consist the amino acid sequence of SEQ ID NO: 362 and the second polypeptide chain can comprise or consist the amino acid sequence of SEQ ID NO: 264. For example, the fusion protein can comprise or consist the amino acid sequence of SEQ ID NO: 362 and the second polypeptide chain can comprise or consist the amino acid sequence of SEQ ID NO: 333. For example, the fusion protein can comprise or consist of an amino acid sequence of SEQ ID NO: 363 and the second polypeptide chain can comprise or consist of an amino acid sequence of SEQ ID NO: 263. For example, the fusion protein can comprise or consist of an amino acid sequence of SEQ ID No. 363 and the second polypeptide chain can comprise or consist of an amino acid sequence of SEQ ID NO: 264. For example, the fusion protein can comprise or consist of an amino acid sequence of SEQ ID NO: 363 and the second polypeptide chain can comprise or consist of an amino acid sequence of SEQ ID NO: 333. For example, the fusion protein can comprise or consist of an amino acid sequence of SEQ ID NO: 325 and the second polypeptide chain can comprise or consist of an amino acid sequence of SEQ ID NO: 264. For example, the fusion protein can comprise or consist of an amino acid sequence of SEQ ID NO: 325 and the second polypeptide chain can comprise or consist of an amino acid sequence of SEQ ID NO: 333. For example, the fusion protein can comprise or consist of an amino acid sequence of SEQ ID NO: 325 and the second polypeptide chain can comprise or consist of an amino acid sequence of SEQ ID NO: 263. For example, the fusion protein can comprise or consist of an amino acid sequence of SEQ ID NO: 286 and the second polypeptide chain can comprise or consist of an amino acid sequence of SEQ ID NO: 263. For example, the fusion protein can comprise or consist of an amino acid sequence of SEQ ID NO: 286 and the second polypeptide chain can comprise or consist of an amino acid sequence of SEQ ID NO: 264. For example, the fusion protein can comprise or consist of an amino acid sequence of SEQ ID NO: 286, and the second polypeptide can comprise or consist of an amino acid sequence of SEW ID NO: 333. For example, the fusion protein can comprise or consist of an amino acid sequence of SEQ ID NO: 579 and the second polypeptide chain can comprise or consist of an amino acid sequence of SEQ ID NO: 263. For example, the fusion protein can comprise or consist of an amino acid sequence of SEQ ID NO: 579 and the second polypeptide chain can comprise or consist of an amino acid sequence of SEQ ID NO: 264. For example, the fusion protein can comprise or consist of an amino acid sequence of SEQ ID NO: 579 and the second polypeptide chain can comprise or consist of an amino acid sequence of SEQ ID NO: 233. For example, the fusion protein can comprise or consist of SEQ ID NO: 581 and the second polypeptide chain can comprise or consist of SEQ ID NO.: 263. For example, the fusion protein can comprise or consist of SEQ ID NO: 581 and the second polypeptide chain can comprise or consist of SEQ ID NO.: 264. For example, the fusion protein can comprise or consist of SEQ ID NO: 581 and the second polypeptide chain can comprise or consist of SEQ ID NO.: 333. For example, the fusion protein can comprise or consist of SEQ ID NO: 582 and the second polypeptide chain can comprise or consist of SEQ ID NO: 263. For example, the fusion protein can comprise or consist of SEQ ID NO: 582 and the second polypeptide chain can comprise or consist of SEQ ID NO: 264. For example, the fusion protein can comprise or consist of SEQ ID NO: 582 and the second polypeptide chain can comprise or consist of SEQ ID NO: 333.

Methods of treatment and Pharmaceutical Compositions

This disclosure also relates to pharmaceutical compositions that comprise one or more fusion proteins as disclosed herein, optionally in combination with another therapeutic agent, which are preferably immunomodulators or anti-cancer agents. The disclosure also relates to the use of such pharmaceutical compositions, and one or more fusion proteins, optionally in combination with another therapeutic agent in treatment of cancers.

The therapeutic combinations disclosed herein can comprise, for example, a fusion protein containing an IL-2 polypeptide, a fusion protein containing an IL-12 polypeptide, or a fusion protein containing an IFN polypeptide. Therapy can be provided using two or more fusion proteins. For example, the therapeutic combination can comprise a fusion protein containing an IL-2 polypeptide and a fusion protein containing an IL-12 polypeptide, a fusion protein containing an IL-2 polypeptide and a fusion protein containing an IFN polypeptide, a fusion protein containing an IL-12 polypeptide and a fusion protein containing an IFN polypeptide.

The therapeutic combinations disclosed herein can comprise a fusion polypeptide cytokine polypeptide [A], a blocking moiety [D], optionally a half-life extension moiety [H], and a protease-cleavable polypeptide linker; wherein the cytokine polypeptide and the blocking moiety and the optional half-life extension element when present are operably linked by the protease-cleavable polypeptide linker and the fusion polypeptide has attenuated cytokine receptor activating activity, wherein the cytokine-receptor activating activity of the fusion polypeptide is at least about 10× less than the cytokine receptor activating activity of the polypeptide that contains the cytokine polypeptide that is produced by cleavage of the protease cleavable linker. the fusion polypeptide has the formula:

[A]-[L1]-[H]-[L2]-[D]    (I);

[D]-[L2]-[H]-[L1]-[A]    (II);

[A]-[L1]-[D]-[L2]-[H]    (III);

[H]-[L2]-[D]-[L1]-[A]    (IV);

[H]-[L1]-[A]-[L2']-[D]    (V);

[D]-[L1]-[A]-[L2']-[H]    (VI);

wherein [A] is a cytokine polypeptide, [D] is a blocking moiety, [H] is a half-life extension moiety, [L1] is a protease-cleavable polypeptide linker, [L2] is an polypeptide linker that is optionally protease-cleavable, and [L2'] is a protease-cleavable polypeptide linker. The therapeutic compositions can comprise a second fusion polypeptide comprising at least one of each of: a second cytokine polypeptide [A], a blocking moiety [D] optionally a half-life extension element [H]; and a protease-cleavable polypeptide linker [L]; wherein the cytokine polypeptide and the cytokine blocking moiety and the optional half-life extension element when present are operably linked by the protease-cleavable polypeptide linker and the fusion polypeptide has attenuated cytokine receptor activating activity, wherein the cytokine-receptor activating activity of the fusion polypeptide is at least about 10× less than the cytokine receptor activating activity of the polypeptide that contains the cytokine polypeptide that is produced by cleavage of the protease cleavable linker. The second fusion polypeptide can have the formula:

[A]-[L1]-[H]-[L2]-[D]        (I);

[D]-[L2]-[H]-[L1]-[A]        (II);

[A]-[L1]-[D]-[L2]-[H]        (III);

[H]-[L2]-[D]-[L1]-[A]        (IV);

[H]-[L1]-[A]-[L2']-[D]       (V);

[D]-[L1]-[A]-[L2']-[H]       (VI);

wherein [A] is a cytokine polypeptide, [D] is a blocking moiety, [H] is a half-life extension moiety, [L1] is a protease-cleavable polypeptide linker, [L2] is an polypeptide linker that is optionally protease-cleavable, and [L2'] is a protease-cleavable polypeptide linker.

The therapeutic combinations disclosed herein can comprise a first fusion protein comprising an amino acid selected from the group consisting of SEQ ID NOs. 257-300, 302-317, 325-353, 355-365, 366, 372-381, 383-385, 388-420, 579-608, 636-646, 368-371, 434-440, 453-519, 523-538, 421-430, and 539-578 and a second fusion protein comprising an amino acid sequence selected from the group consisting of selected from the group consisting of SEQ ID NOs. 257-300, 302-317, 325-353, 355-365, 366, 372-381, 383-385, 388-420, 579-608, 636-646, 368-371, 434-440, 453-519, 523-538, 421-430, and 539-578. It is preferred that the first fusion protein and the second fusion protein are different. In some preferred embodiments, the therapeutic combination comprises a first fusion protein comprising an amino acid sequence selected from SEQ ID NO: 257-300, 302-317, 325-353, 355-365, 366, 372-381, 383-385, 388-420, 579-608, 636-646 and a second fusion protein comprising an amino acid sequence selected from SEQ ID NO: 368-371, 434-440, 453-519, 523-538, 421-430, and 539-578. In some preferred embodiments, the therapeutic combination comprises a first fusion proteins comprising an amino acid sequence selected from SEQ ID NO: 368-371, 434-440, 453-519, or 523-538 and a second fusion protein comprising an amino acid sequence selected from SEQ ID NO: 257-300, 302-317, 325-353, 355-365, 366, 372-381, 383-385, 388-420, 636-646, 579-608, 421-430, and 539-578. In some preferred embodiments, the therapeutic combination comprises a first fusion protein comprising an amino acid sequence selected from SEQ ID NO: 421-430, and 539-578 and a second fusion protein comprising an amino acid sequence selected from SEQ ID NOs. 257-300, 302-317, 325-353, 355-365, 366, 372-381, 383-385, 388-420, 579-608, 636-646, 368-371, 434-440, 453-519, 523-538, or combinations thereof.

The therapeutic combination disclosed herein can comprise a first fusion protein that is covalently or non-covalently bonded to a second polypeptide chain and a therapeutic agent. The therapeutic combination can comprise (i) a fusion polypeptide comprising an amino acid sequence selected from SEQ ID NOs. 362, 363, 325, 286, 579, 581, or 582 and a second polypeptide chain comprising the amino acid sequence of SEQ ID NOs: 263, 264, or 333, and (ii) a second therapeutic agent, wherein the second therapeutic agent is a second fusion polypeptide comprising an amino acid sequence selected from the group consisting of SEQ ID NOs. 257-300, 302-317, 325-353, 355-365, 366, 372-381, 383-385, 388-420, 579-608, 636-646, 368-371, 434-440, 453-519, 523-538, 421-430, 539-578, or combinations thereof. It is preferred that the first fusion protein and the second fusion protein are not the same.

In embodiments, the therapeutic combination can comprise an additional therapeutic agent (e.g., one, two, three, four, five, or more therapeutic agents). In embodiments, the therapeutic combination can comprise 2 or more fusion proteins and one or more therapeutic agents, preferably agents for treating cancer.

Other exemplary therapeutic agents include, but are not limited to chemotherapeutic agents (e.g., Adriamycin, Cerubidine, Bleomycin, Alkeran, Velban, Oncovin, Fluorouracil, Thiotepa, Methotrexate, Bisantrene, Noantrone, Thiguanine, Cytaribine, Procarabizine), immuno-oncology agents (e.g., anti-PD-L1, anti-CTLA4, anti-PD-1, anti-CD47, anti-GD2, VEGF inhibitor), antibody-drug conjugates, cellular therapies (e.g, CAR-T, T-cell therapy), oncolytic viruses, radiation therapy and/or small molecules.

Non-limiting examples of anti-cancer agents that can be used include acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alpha-2a; interferon alpha-2b; interferon alpha-n1 interferon alpha-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin;

mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinzolidine sulfate; vinzolidine sulfate; vorozole; zeniplatin; zinostatin; zorubicin hydrochloride.

Accordingly, this disclosure relates to a therapeutic combination of any of the fusions proteins disclosed herein (e.g., fusion proteins that comprise an IL-2 polypeptide, and IL-12 polypeptide or an IFN polypeptide) in combination with a chemotherapeutic agent, such as Adriamycin, Cerubidine, Bleomycin, Alkeran, Velban, Oncovin, Fluorouracil, Thiotepa, Methotrexate, Bisantrene, Noantrone, Thiguanine, Cytaribine, Procarabizine. This disclosure relates to a therapeutic combination of any of the fusions proteins disclosed herein (e.g., fusion proteins that comprise an IL-2 polypeptide, and IL-12 polypeptide or an IFN polypeptide) in combination with an antibody-drug conjugate. A variety of antibody drug conjugates that are suitable for use in cancer therapy are well known and typically include an antibody that binds to a cellular antigen that is preferentially express or expressed at high levels on tumor cells, and a cytotoxic drug. This disclosure relates to a therapeutic combination of any of the fusion proteins disclosed herein (e.g., fusion proteins that comprise an IL-2 polypeptide, and IL-12 polypeptide, or an IFN polypeptide) in combination with a cellular therapy, such as CAR-T or T-cell therapy. The disclosure relates to a therapeutic combination of the fusion proteins disclosed herein (e.g., fusion proteins that comprise an IL-2 polypeptide, and IL-12 polypeptide, or an IFN polypeptide) in combination with an oncolytic virus. Exemplary oncolytic viruses include, oncolytic adenoviruses, type 1 herpes simplex virus (HSV), polioviruses, measles virus (MV), Newcastle disease virus (NDV), reoviruses, vesicular stomatitis virus (VSV), and Zika virus. This disclosure relates to a therapeutic combination of any of the fusion proteins disclosed herein (e.g., fusion proteins that comprise an IL-2 polypeptide, and IL-12 polypeptide, or an IFN polypeptide) in combination with radiation therapy, such an external beam radiation or internal therapy radiation therapy.

This disclosure relates to a therapeutic combination of any of the fusion proteins disclosed herein (e.g., fusion proteins that comprise an IL-2 polypeptide, and IL-12 polypeptide, or an IFN polypeptide) in combination with cytokines (e.g., IL-2, IL-15), signal induction inhibitors (e.g., BRAF inhibitors or MEK inhibitors), checkpoint inhibitors (e.g., PDL-1, PD-1, CTLA-4), c-met inhibitors, kinase inhibitors (e.g., VGEF inhibitors), a proteasome inhibitor, mTOR inhibitor, angiogenesis inhibitor. In embodiments, any one of the fusion proteins disclosed herein (e.g., fusion proteins that comprise an IL-2 polypeptide, and IL-12 polypeptide, or an IFN polypeptide) can be combined with an anti-PD-L1 agent or an anti-PD-1 agent. Exemplary PD-1 and/or PD-L1 inhibitors include, but are not limited to Spartalizumab, Camrelizumab, Sintilimab, Tislelizumab, Toripalimab, Dostarlimab, INCMGA00012, AMP-224, and AMP-514). In embodiments, a fusion protein comprising the amino acid sequence selected from SEQ ID NO: 257-300, 302-317, 325-353, 355-365, 366, 372-381, 383-385, 388-420, 579-608, 636-646, 368-371, 434-440, 453-519, 523-538, 421-430, and 539-578 can be combined with a check-point inhibitor, such as PDL-1, PD-1, or CTL-4.

Further provided are methods of treating a subject with or at risk of developing an of a disease or disorder, such as proliferative disease, a tumorous disease, an inflammatory disease, an immunological disorder, an autoimmune disease, an infectious disease, a viral disease, an allergic reaction, a parasitic reaction, or graft-versus-host disease. The methods disclosed herein are preferably used to treat a subject having cancer. The methods administering to a subject in need thereof an effective amount of a fusion protein as disclosed herein that is typically administered as a pharmaceutical composition. In some embodiments, the method further comprises selecting a subject with or at risk of developing such a disease or disorder. The pharmaceutical composition preferably comprises a blocked cytokine, fragment, variant, subunit, or mutein thereof that is activated at a site of inflammation or a tumor. In one embodiment, the chimeric polypeptide comprises a cytokine polypeptide, fragment or mutein thereof and a serum half-life extension element. In another embodiment, the chimeric polypeptide comprises a cytokine polypeptide, variant, subunit, fragment or mutein thereof and a blocking moiety, e.g. a steric blocking polypeptide, wherein the steric blocking polypeptide is capable of sterically blocking the activity of the cytokine polypeptide, fragment or mutein thereof. In another embodiment, the chimeric polypeptide comprises a cytokine polypeptide, fragment or mutein thereof, a blocking moiety, and a serum half-life extension element.

Inflammation is part of the complex biological response of body tissues to harmful stimuli, such as pathogens, damaged cells, or irritants, and is a protective response involving immune cells, blood vessels, and molecular mediators. The function of inflammation is to eliminate the initial cause of cell injury, clear out necrotic cells and tissues damaged from the original insult and the inflammatory process, and to initiate tissue repair. Inflammation can occur from infection, as a symptom or a disease, e.g., cancer, atherosclerosis, allergies, myopathies, HIV, obesity, or an autoimmune disease. An autoimmune disease is a chronic condition arising from an abnormal immune response to a self-antigen. Autoimmune diseases that may be treated with the polypeptides disclosed herein include but are not limited to lupus, celiac disease, diabetes mellitus type 1, Graves disease, inflammatory bowel disease, multiple sclerosis, psoriasis, rheumatoid arthritis, and systemic lupus erythematosus.

The pharmaceutical composition can comprise one or more protease-cleavable linker sequences. The linker sequence serves to provide flexibility between polypeptides, such that each polypeptide is capable of inhibiting the activity of the first polypeptide. The linker sequence can be located between any or all of the cytokine polypeptide, fragment or mutein thereof, the blocking moiety, and serum half-life extension element. Optionally, the composition comprises, two, three, four, or five linker sequences. The linker sequence, two, three, or four linker sequences can be the same or different linker sequences. In one embodiment, the linker sequence comprises GGGGS (SEQ ID NO.: 449), GSGSGS (SEQ ID NO.: 450), or G(SGGG)$_2$SGGT (SEQ ID NO.: 451). In another embodiment, the linker comprises a protease-cleavable sequence selected from group consisting of HSSKLQ (SEQ ID NO.: 25), GPLGVRG (SEQ ID NO.: 445), IPVSLRSG (SEQ ID NO.: 446), VPLSLYSG (SEQ ID NO.: 447), and SGESPAYYTA (SEQ ID NO.: 448).

In some embodiments, the linker is cleaved by a protease selected from the group consisting of a kallikrein, thrombin, chymase, carboxypeptidase A, cathepsin G, an elastase, PR-3, granzyme M, a calpain, a matrix metalloproteinase (MMP), a plasminogen activator, a cathepsin, a caspase, a tryptase, or a tumor cell surface protease.

Suitable linkers can be of different lengths, such as from 1 amino acid (e.g., Gly) to 20 amino acids, from 2 amino acids to 15 amino acids, from 3 amino acids to 12 amino acids, including 4 amino acids to 10 amino acids, amino acids to 9 amino acids, 6 amino acids to 8 amino acids, or 7 amino acids to 8 amino acids, and may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 amino acids.

Further provided are methods of treating a subject with or at risk of developing cancer. The methods comprise administering to the subject in need thereof an effective amount of a chimeric polypeptide (a fusion protein) as disclosed herein that is typically administered as a pharmaceutical composition. In some embodiments, the method further comprises selecting a subject with or at risk of developing cancer. The pharmaceutical composition preferably comprises a blocked cytokine, fragment or mutein thereof that is activated at a tumor site.

The methods disclosed herein can be used for any suitable cancer including, hematological malignancy, solid tumors, sarcomas, carcinomas, and other solid and non-solid tumors. Illustrative suitable cancers include, for example, acute lymphoblastic leukemia (ALL), acute myeloid leukemia (AML), adrenocortical carcinoma, anal cancer, appendix cancer, astrocytoma, basal cell carcinoma, brain tumor, bile duct cancer, bladder cancer, bone cancer, breast cancer, bronchial tumor, carcinoma of unknown primary origin, cardiac tumor, cervical cancer, chordoma, colon cancer, colorectal cancer, craniopharyngioma, ductal carcinoma, embryonal tumor, endometrial cancer, ependymoma, esophageal cancer, esthesioneuroblastoma, fibrous histiocytoma, Ewing sarcoma, eye cancer, germ cell tumor, gallbladder cancer, gastric cancer, gastrointestinal carcinoid tumor, gastrointestinal stromal tumor, gestational trophoblastic disease, glioma, head and neck cancer, hepatocellular cancer, histiocytosis, Hodgkin lymphoma, hypopharyngeal cancer, intraocular melanoma, islet cell tumor, Kaposi sarcoma, kidney cancer, Langerhans cell histiocytosis, laryngeal cancer, lip and oral cavity cancer, liver cancer, lobular carcinoma in situ, lung cancer, macroglobulinemia, malignant fibrous histiocytoma, melanoma, Merkel cell carcinoma, mesothelioma, metastatic squamous neck cancer with occult primary, midline tract carcinoma involving NUT gene, mouth cancer, multiple endocrine neoplasia syndrome, multiple myeloma, mycosis fungoides, myelodysplastic syndrome, myelodysplastic/myeloproliferative neoplasm, nasal cavity and par nasal sinus cancer, nasopharyngeal cancer, neuroblastoma, non-small cell lung cancer, oropharyngeal cancer, osteosarcoma, ovarian cancer, pancreatic cancer, papillomatosis, paraganglioma, parathyroid cancer, penile cancer, pharyngeal cancer, pheochromocytomas, pituitary tumor, pleuropulmonary blastoma, primary central nervous system lymphoma, prostate cancer, rectal cancer, renal cell cancer, renal pelvis and ureter cancer, retinoblastoma, rhabdoid tumor, salivary gland cancer, Sezary syndrome, skin cancer, small cell lung cancer, small intestine cancer, soft tissue sarcoma, spinal cord tumor, stomach cancer, T-cell lymphoma, teratoid tumor, testicular cancer, throat cancer, thymoma and thymic carcinoma, thyroid cancer, urethral cancer, uterine cancer, vaginal cancer, vulvar cancer, and Wilms tumor.

Preferably, the tumor is a solid tumor. Colon cancer, lung cancer, melanoma, sarcoma, renal cell carcinoma, and breast cancer are of particular interest.

The method can further involve the administration of one or more additional agents to treat cancer, such as one or more cytokine fusion proteins described herein, chemotherapeutic agents (e.g., Adriamycin, Cerubidine, Bleomycin, Alkeran, Velban, Oncovin, Fluorouracil, Thiotepa, Methotrexate, Bisantrene, Noantrone, Thiguanine, Cytaribine, Procarabizine), immuno-oncology agents (e.g., anti-PD-L1, anti-CTLA4, anti-PD-1, anti-CD47, anti-GD2, VEGF inhibitor), cellular therapies (e.g, CAR-T, T-cell therapy), oncolytic viruses, radiation therapy and the like.

In embodiments, the fusion proteins described herein, can be administered with one or more additional cytokine fusion proteins that are inducible. For example, a fusion protein containing an IL-2 polypeptide, as described herein, may be administered with fusion protein containing an IL-12 polypeptide, an IFN polypeptide, a different IL-2 polypeptide or a combinations thereof. A fusion protein containing an IL-12 polypeptide, as described herein, may be administered with a fusion protein containing an IL-2 polypeptide, an IFN polypeptide, a different IL-12 polypeptide or a combinations thereof. A fusion protein containing an IFN polypeptide, as described herein, may be administered with a fusion protein containing an IL-2 polypeptide, an IL-12 polypeptide, an different IFN polypeptide, or a combinations thereof.

In some preferred embodiments, a first fusion protein comprising the amino acid sequence of any one of SEQ ID NOS: 257-300, 302-317, 325-353, 355-365, 366, 372-381, 383-385, 388-420, 579-608, and 636-646 can be administered with a second different fusion protein comprising an amino acid sequence of any one of SEQ ID NOs. 368-371, 434-440, 453-519, 523-538, 421-430, and 539-578. In some preferred embodiments, a first fusion proteins comprising the amino acid sequence of any one of 368-371, 434-440, 453-519, or 523-538 can be administered with a second different fusion protein comprising an amino acid sequence of any one of SEQ ID NOs. 257-300, 302-317, 325-353, 355-365, 366, 372-381, 383-385, 388-420, 579-608, 636-646, 421-430, and 539-578. In some preferred embodiments, a first fusion protein comprising the amino acid sequence of any one of SEQ ID NOs. 421-430, and 539-578 can be administered with a second different fusion protein comprising the amino acid sequence of any one of SEQ ID NOs. 257-300, 302-317, 325-353, 355-365, 366, 372-381, 383-385, 388-420, 579-608, 636-646, 368-371, 434-440, 453-519, 523-538, or combinations thereof.

Further exemplary agents that can be administered in combination with one or more inducible cytokine fusion proteins described herein include, but are not limited to cytokines (e.g., IL-2, IL-15), signal induction inhibitors (e.g., BRAF inhibitors or MEK inhibitors), checkpoint inhibitors (e.g., PDL-1, PD-1, CTLA-4), c-met inhibitors, kinase inhibitors (e.g., VGEF inhibitors), a proteasome inhibitor, mTOR inhibitor, angiogenesis inhibitor.

A preferred immuno-oncology agent is an anti-PD-L1 agent or an anti-PD-1. Exemplary PD-1 and/or PD-L1 inhibitors include, but are not limited to Spartalizumab, Camrelizumab, Sintilimab, Tislelizumab, Toripalimab, Dostarlimab, INCMGA00012, AMP-224, and AMP-514). In embodiments, a fusion protein disclosed as 257-300, 302-317, 325-353, 355-365, 366, 372-381, 383-385, 388-420, 579-608, 636-646, 368-371, 434-440, 453-519, 523-538, 421-430, and 539-578 can be administered in combination with a check-point inhibitor, such as PDL-1, PD-1, or CTL-4.

Provided herein are pharmaceutical formulations or compositions containing the chimeric polypeptides and a pharmaceutically acceptable carrier. The herein provided compositions are suitable for administration in vitro or in vivo. By pharmaceutically acceptable carrier is meant a material that is not biologically or otherwise undesirable, i.e., the material is administered to a subject without causing undesirable biological effects or interacting in a deleterious manner with the other components of the pharmaceutical formulation or composition in which it is contained. The carrier is selected to minimize degradation of the active ingredient and to minimize adverse side effects in the subject.

Suitable carriers and their formulations are described in *Remington: The Science and Practice of Pharmacy, 21$^{st}$* Edition, David B. Troy, ed., Lippicott Williams & Wilkins (2005). Typically, an appropriate amount of a pharmaceutically-acceptable salt is used in the formulation to render the formulation isotonic, although the formulate can be hypertonic or hypotonic if desired. Examples of the pharmaceutically-acceptable carriers include, but are not limited to, sterile water, saline, buffered solutions like Ringer's solution, and dextrose solution. The pH of the solution is generally about 5 to about 8 or from about 7 to 7.5. Other carriers include sustained release preparations such as semipermeable matrices of solid hydrophobic polymers containing the immunogenic polypeptides. Matrices are in the form of shaped articles, e.g., films, liposomes, or microparticles. Certain carriers may be more preferable depending upon, for instance, the route of administration and concentration of composition being administered. Carriers are those suitable for administration of the chimeric polypeptides or nucleic acid sequences encoding the chimeric polypeptides to humans or other subjects.

The pharmaceutical formulations or compositions are administered in a number of ways depending on whether local or systemic treatment is desired and on the area to be treated. The compositions are administered via any of several routes of administration, including topically, orally, parenterally, intravenously, intra-articularly, intraperitoneally, intramuscularly, subcutaneously, intracavity, transdermally, intrahepatically, intracranially, nebulization/inhalation, or by installation via bronchoscopy. In some embodiments, the compositions are administered locally (non-systemically), including intratumorally, intra-articularly, intrathecally, etc.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives are optionally present such as, for example, antimicrobials, anti-oxidants, chelating agents, and inert gases and the like.

Formulations for topical administration include ointments, lotions, creams, gels, drops, suppositories, sprays, liquids, and powders. Conventional pharmaceutical carriers, aqueous, powder, or oily bases, thickeners and the like are optionally necessary or desirable.

Compositions for oral administration include powders or granules, suspension or solutions in water or non-aqueous media, capsules, sachets, or tables. Thickeners, flavorings, diluents, emulsifiers, dispersing aids or binders are optionally desirable.

Optionally, the chimeric polypeptides or nucleic acid sequences encoding the chimeric polypeptides are administered by a vector. There are a number of compositions and methods which can be used to deliver the nucleic acid molecules and/or polypeptides to cells, either in vitro or in vivo via, for example, expression vectors. These methods and compositions can largely be broken down into two classes: viral based delivery systems and non-viral based delivery systems. Such methods are well known in the art and readily adaptable for use with the compositions and methods described herein. Such compositions and methods can be used to transfect or transduce cells in vitro or in vivo, for example, to produce cell lines that express and preferably secrete the encoded chimeric polypeptide or to therapeutically deliver nucleic acids to a subject. The components of the chimeric nucleic acids disclosed herein typically are operably linked in frame to encode a fusion protein.

As used herein, plasmid or viral vectors are agents that transport the disclosed nucleic acids into the cell without degradation and include a promoter yielding expression of the nucleic acid molecule and/or polypeptide in the cells into which it is delivered. Viral vectors are, for example, Adenovirus, Adeno-associated virus, herpes virus, Vaccinia virus, Polio virus, Sindbis, and other RNA viruses, including these viruses with the HIV backbone. Also preferred are any viral families which share the properties of these viruses which make them suitable for use as vectors. Retroviral vectors, in general are described by Coffin et al., Retroviruses, Cold Spring Harbor Laboratory Press (1997), which is incorporated by reference herein for the vectors and methods of making them. The construction of replication-defective adenoviruses has been described (Berkner et al., J. Virol. 61:1213-20 (1987); Massie et al., Mol. Cell. Biol. 6:2872-83 (1986); Haj-Ahmad et al., J. Virol. 57:267-74 (1986); Davidson et al., J. Virol. 61:1226-39 (1987); Zhang et al., Bio-Techniques 15:868-72 (1993)). The benefit and the use of these viruses as vectors is that they are limited in the extent to which they can spread to other cell types, since they can replicate within an initial infected cell, but are unable to form new infectious viral particles. Recombinant adenoviruses have been shown to achieve high efficiency after direct, in vivo delivery to airway epithelium, hepatocytes, vascular endothelium, CNS parenchyma, and a number of other tissue sites. Other useful systems include, for example, replicating and host-restricted non-replicating vaccinia virus vectors.

The provided polypeptides and/or nucleic acid molecules can be delivered via virus like particles. Virus like particles (VLPs) consist of viral protein(s) derived from the structural proteins of a virus. Methods for making and using virus like particles are described in, for example, Garcea and Gissmann, Current Opinion in Biotechnology 15:513-7 (2004).

The provided polypeptides can be delivered by subviral dense bodies (DBs). DBs transport proteins into target cells by membrane fusion. Methods for making and using DBs are described in, for example, Pepperl-Klindworth et al., Gene Therapy 10:278-84 (2003).

The provided polypeptides can be delivered by tegument aggregates. Methods for making and using tegument aggregates are described in International Publication No. WO 2006/110728.

Non-viral based delivery methods, can include expression vectors comprising nucleic acid molecules and nucleic acid sequences encoding polypeptides, wherein the nucleic acids are operably linked to an expression control sequence. Suitable vector backbones include, for example, those routinely used in the art such as plasmids, artificial chromosomes, BACs, YACs, or PACs. Numerous vectors and expression systems are commercially available from such corporations as Novagen (Madison, Wis.), Clonetech (Pal Alto, Calif.), Stratagene (La Jolla, Calif.), and Invitrogen/Life Technologies (Carlsbad, Calif.). Vectors typically contain one or more regulatory regions. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, and introns. Such vectors can also be used to make the chimeric polypeptides by expression is a suitable host cell, such as CHO cells.

Preferred promoters controlling transcription from vectors in mammalian host cells may be obtained from various sources, for example, the genomes of viruses such as polyoma, Simian Virus 40 (SV40), adenovirus, retroviruses, hepatitis B virus, and most preferably cytomegalovirus (CMV), or from heterologous mammalian promoters, e.g. β-actin promoter or EF1α promoter, or from hybrid or chimeric promoters (e.g., CMV promoter fused to the (3-actin promoter). Of course, promoters from the host cell or related species are also useful herein.

Enhancer generally refers to a sequence of DNA that functions at no fixed distance from the transcription start site and can be either 5' or 3' to the transcription unit. Furthermore, enhancers can be within an intron as well as within the coding sequence itself. They are usually between 10 and 300 base pairs (bp) in length, and they function in cis. Enhancers usually function to increase transcription from nearby promoters. Enhancers can also contain response elements that mediate the regulation of transcription. While many enhancer sequences are known from mammalian genes (globin, elastase, albumin, fetoprotein, and insulin), typically one will use an enhancer from a eukaryotic cell virus for general expression. Preferred examples are the SV40 enhancer on the late side of the replication origin, the cytomegalovirus early promoter enhancer, the polyoma enhancer on the late side of the replication origin, and adenovirus enhancers.

The promoter and/or the enhancer can be inducible (e.g. chemically or physically regulated). A chemically regulated promoter and/or enhancer can, for example, be regulated by the presence of alcohol, tetracycline, a steroid, or a metal. A physically regulated promoter and/or enhancer can, for example, be regulated by environmental factors, such as temperature and light. Optionally, the promoter and/or enhancer region can act as a constitutive promoter and/or enhancer to maximize the expression of the region of the transcription unit to be transcribed. In certain vectors, the promoter and/or enhancer region can be active in a cell type specific manner. Optionally, in certain vectors, the promoter and/or enhancer region can be active in all eukaryotic cells, independent of cell type. Preferred promoters of this type are the CMV promoter, the SV40 promoter, the β-actin promoter, the EF1α promoter, and the retroviral long terminal repeat (LTR).

The vectors also can include, for example, origins of replication and/or markers. A marker gene can confer a selectable phenotype, e.g., antibiotic resistance, on a cell. The marker product is used to determine if the vector has been delivered to the cell and once delivered is being expressed. Examples of selectable markers for mammalian cells are dihydrofolate reductase (DHFR), thymidine kinase, neomycin, neomycin analog G418, hygromycin, puromycin, and blasticidin. When such selectable markers are successfully transferred into a mammalian host cell, the transformed mammalian host cell can survive if placed under selective pressure. Examples of other markers include, for example, the E. coli lacZ gene, green fluorescent protein (GFP), and luciferase. In addition, an expression vector can include a tag sequence designed to facilitate manipulation or detection (e.g., purification or localization) of the expressed polypeptide. Tag sequences, such as GFP, glutathione S-transferase (GST), polyhistidine, c-myc, hemagglutinin, or FLAG™ tag (Kodak; New Haven, Conn.) sequences typically are expressed as a fusion with the encoded polypeptide. Such tags can be inserted anywhere within the polypeptide including at either the carboxyl or amino terminus.

As used herein, the terms peptide, polypeptide, or protein are used broadly to mean two or more amino acids linked by a peptide bond. Protein, peptide, and polypeptide are also used herein interchangeably to refer to amino acid sequences. It should be recognized that the term polypeptide is not used herein to suggest a particular size or number of amino acids comprising the molecule and that a peptide of the invention can contain up to several amino acid residues or more. As used throughout, subject can be a vertebrate, more specifically a mammal (e.g. a human, horse, cat, dog, cow, pig, sheep, goat, mouse, rabbit, rat, and guinea pig), birds, reptiles, amphibians, fish, and any other animal. The term does not denote a particular age or sex. Thus, adult and newborn subjects, whether male or female, are intended to be covered. As used herein, patient or subject may be used interchangeably and can refer to a subject with a disease or disorder (e.g. cancer). The term patient or subject includes human and veterinary subjects.

A subject at risk of developing a disease or disorder can be genetically predisposed to the disease or disorder, e.g., have a family history or have a mutation in a gene that causes the disease or disorder, or show early signs or symptoms of the disease or disorder. A subject currently with a disease or disorder has one or more than one symptom of the disease or disorder and may have been diagnosed with the disease or disorder.

The methods and agents as described herein are useful for both prophylactic and therapeutic treatment. For prophylactic use, a therapeutically effective amount of the chimeric polypeptides or chimeric nucleic acid sequences encoding the chimeric polypeptides described herein are administered to a subject prior to onset (e.g., before obvious signs of cancer or inflammation) or during early onset (e.g., upon initial signs and symptoms of cancer or inflammation). Prophylactic administration can occur for several days to years prior to the manifestation of symptoms of cancer or inflammation. Prophylactic administration can be used, for example, in the preventative treatment of subjects diagnosed with a genetic predisposition to cancer. Therapeutic treatment involves administering to a subject a therapeutically effective amount of the chimeric polypeptides or nucleic acid sequences encoding the chimeric polypeptides described herein after diagnosis or development of cancer or inflammation (e.g., an autoimmune disease). Prophylactic use may also apply when a patient is undergoing a treatment, e.g., a chemotherapy, in which inflammation is expected.

According to the methods taught herein, the subject is administered an effective amount of the agent (e.g., a chimeric polypeptide). The terms effective amount and effective dosage are used interchangeably. The term effective amount is defined as any amount necessary to produce a desired physiologic response. Effective amounts and schedules for administering the agent may be determined empirically, and making such determinations is within the skill in the art. The dosage ranges for administration are those large enough to produce the desired effect in which one or more symptoms of the disease or disorder are affected (e.g., reduced or delayed). The dosage should not be so large as to cause substantial adverse side effects, such as unwanted cross-reactions, anaphylactic reactions, and the like. Generally, the dosage will vary with the age, condition, sex, type of disease, the extent of the disease or disorder, route of administration, or whether other drugs are included in the regimen, and can be determined by any one of skill in the art. The dosage can be adjusted by the individual physician in the event of any contraindications. Dosages can vary and can be administered in one or more dose administrations daily, for one or several days. Guidance can be found in the literature for appropriate dosages for given classes of pharmaceutical products.

As used herein the terms treatment, treat, or treating refers to a method of reducing the effects of a disease or condition or symptom of the disease or condition. Thus, in the disclosed method, treatment can refer to a 10%, 20%, 30%, 40%, 50%, 60%, 70%, 80%, 90%, or 100% reduction in the severity of an established disease or condition or symptom of the disease or condition. For example, a method for treating a disease is considered to be a treatment if there is a 10% reduction in one or more symptoms of the disease in a subject as compared to a control. Thus, the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition.

As used herein, the terms prevent, preventing, and prevention of a disease or disorder refers to an action, for example, administration of the chimeric polypeptide or nucleic acid sequence encoding the chimeric polypeptide, that occurs before or at about the same time a subject begins to show one or more symptoms of the disease or disorder, which inhibits or delays onset or exacerbation of one or more symptoms of the disease or disorder. As used herein, references to decreasing, reducing, or inhibiting include a change of 10%, 20%, 30%, 40%, 50%, 60%, 70%, 80%, 90% or greater as compared to a control level. Such terms can include but do not necessarily include complete elimination.

IL-2 variants have been developed that are selective for IL2Rαβγ relative to IL2Rβγ (Shanafelt, A. B., et al., 2000, Nat Biotechnol. 18:1197-202; Cassell, D. J., et. al., 2002, Curr Pharm Des., 8:2171-83). These variants have amino acid substitutions which reduce their affinity for IL2RB. Because IL-2 has undetectable affinity for IL2RG, these variants consequently have reduced affinity for the IL2Rβγ receptor complex and reduced ability to activate IL2Rβγ-expressing cells, but retain the ability to bind IL2RA and the ability to bind and activate the IL2Rαβγ receptor complex.

One of these variants, IL2/N88R (Bay 50-4798), was clinically tested as a low-toxicity version of IL-2 as an immune system stimulator, based on the hypothesis that IL2Rβγ-expressing NK cells are a major contributor to toxicity. Bay 50-4798 was shown to selectively stimulate the proliferation of activated T cells relative to NK cells, and was evaluated in phase I/II clinical trials in cancer patients (Margolin, K., et. al., 2007, Clin Cancer Res., 13:3312-9) and HIV patients (Davey, R. T., et. al., 2008, J Interferon Cytokine Res., 28:89-100). These clinical trials showed that Bay 50-4798 was considerably safer and more tolerable than aldesleukin, and also showed that it increased the levels of CD4+CD25+ T cells, a cell population enriched in Treg cells. Subsequent to these trials, research in the field more fully established the identity of Treg cells and demonstrated that Treg cells selectively express IL2Rαβγ (reviewed in Malek, T. R., et al., 2010, Immunity, 33:153-65).

In addition, mutants can be made that selectively alter the affinity for the CD25 chain relative to native Il-2.

IL-2 can be engineered to produce mutants that bind the IL-2R complex generally or the IL-2Rα subunit specifically with an affinity that differs from that of the corresponding wild-type IL-2 or of a presently available mutant (referred to as C125S, as the cysteine residue at position 125 is replaced with a serine residue).

Accordingly, the present invention features mutant interleukin-2 (IL-2*) polypeptides that include an amino acid sequence that is at least 80% identical to wild-type IL-2 (e.g., 85, 87, 90, 97, 98, or 99% identical) and that bind, as compared to WT IL-2, with higher to the IL-2 trimeric receptor relative to the dimeric IL-2 receptor. Typically, the muteins will also bind an IL-2 receptor a subunit (IL-2Rα) with an affinity that is greater than the affinity with which wild type IL-2 binds the IL-2Rα. The amino acid sequence within mutant IL-2 polypeptides can vary from SEQ ID NO:1 (UniProtKB accession number P60568) by virtue of containing (or only containing) one or more amino acid substitutions, which may be considered conservative or non-conservative substitutions. Non-naturally occurring amino acids can also be incorporated. Alternatively, or in addition, the amino acid sequence can vary from SEQ ID NO:1 (which may be considered the "reference" sequence) by virtue of containing and addition and/or deletion of one or more amino acid residues. More specifically, the amino acid sequence can differ from that of SEQ ID NO:1 by virtue of a mutation at least one of the following positions of SEQ ID NO:1: 1, 4, 8, 9, 10, 11, 13, 15, 26, 29, 30, 31, 35, 37, 46, 48, 49, 54, 61, 64, 67, 68, 69, 71, 73, 74, 75, 76, 79, 88, 89, 90, 92, 99, 101, 103, 114, 125, 128, or 133 (or combinations thereof). As noted, as few as one of these positions may be altered, as may two, three, four, five, six, seven, eight, nine, ten, or 11 or more (including up to all) of the positions. For example, the amino acid sequence can differ from SEQ ID NO:1 at positions 69 and 74 and further at one or more of positions 30, and 128. The amino acid sequence can also differ from SEQ ID NO:2 (as disclosed in U.S. Pat. No. 7,569,215, incorporated herein by reference) at one of the following sets of positions: (a) positions 64, 69, and 74; (b) positions 69, 74, and 101; (c) positions 69, 74, and 128; (d) positions 30, 69, 74, and 103; (e) positions 49, 69, 73, and 76; (f) positions 69, 74, 101, and 133; (g) positions 30, 69, 74, and 128; (h) positions 69, 74, 88, and 99; (i) positions 30, 69, 74, and 128; (j) positions 9, 11, 35, 69, and 74; (k) positions 1, 46, 49, 61, 69, and 79; (l) positions 48, 68, 71, 90, 103, and 114; (m) positions 4, 10, 11, 69, 74, 88, and 133; (n) positions 15, 30 31, 35, 48, 69, 74, and 92; (0) positions 30, 68, 69, 71, 74, 75, 76, and 90; (p) positions 30, 31, 37, 69, 73, 74, 79, and 128; (q) positions 26, 29, 30, 54, 67, 69, 74, and 92; (r) positions 8, 13, 26, 30, 35, 37, 69, 74, and 92; and (s) positions 29, 31, 35, 37, 48, 69, 71, 74, 88, and 89. Aside from mutations at these positions, the amino acid sequence of the mutant IL-2 polypeptide can otherwise be identical to SEQ ID NO:1. With respect to specific substitutions, the amino acid sequence can differ from SEQ ID NO:1 by virtue of having one or more of the following mutations: A1T, S4P, K8R, K9T, T10A, Q11R, Q13R, E15K, N26D, N29S, N30S, N30D, N30T, Y31H, Y31C, K35R, T37A, T37R, M46L, K48E, K49R, K49E, K54R, E61D, K64R, E67G, E68D, V69A, N71T, N71A, N71R, A73V, Q74P, 575P, K76E, K76R, H79R, N88D, I89V, N90H, I92T, S99P, T101A, F103S, I114V, I128T, I128A, T133A, or T133N. Our nomenclature is consistent with that of the scientific literature, where the single letter code of the amino acid in the wild-type or reference sequence is followed by its position within the sequence and then by the single letter code of the amino acid with which it is replaced. Thus, A1T designates a substitution of the alanine residue a position 1 with threonine. Other mutant polypeptides within the scope of the invention include those that include a mutant of SEQ ID NO:2 having substitutions at V69 (e.g. A) and Q74 (e.g., P). For example, the amino acid sequence can include one of the following sets of mutations with respect to SEQ ID NO:2: (a) K64R, V69A, and Q74P; (b) V69A, Q74P, and T101A; (c) V69A, Q74P, and I128T; (d) N30D, V69A, Q74P, and F103S; (e) K49E, V69A, A73V, and K76E; (f) V69A, Q74P, T101A, and T133N; (g) N30S, V69A, Q74P, and I128A; (h) V69A, Q74P, N88D, and S99P; (i) N30S, V69A, Q74P, and I128T; (j) K9T, Q11R, K35R, V69A, and Q74P; (k) A1T, M46L, K49R, E61D, V69A, and H79R; (1) K48E, E68D, N71T, N90H, F103S, and I114V; (m) S4P, T10A, Q11R, V69A, Q74P, N88D, and T133A; (n) E15K, N30S Y31H, K35R, K48E, V69A, Q74P, and I92T; (o) N30S, E68D, V69A, N71A, Q74P, 575P, K76R, and N90H; (p) N30S, Y31C, T37A, V69A, A73V, Q74P, H79R, and I128T; (q) N26D, N29S, N30S, K54R, E67G, V69A, Q74P, and I92T; (r) K8R, Q13R, N26D, N30T, K35R, T37R, V69A, Q74P, and I92T; and (s) N29S, Y31H, K35R, T37A, K48E, V69A, N71R, Q74P, N88D, and I89V. SEQ ID NO:2 is disclosed in U.S. Pat. No. 7,569,215, which is incorporated herein by reference as an exemplary IL-2 polypeptide sequence that can be used in the invention.

As noted above, any of the mutant IL-2 polypeptides disclosed herein can include the sequences described; they can also be limited to the sequences described and otherwise identical to SEQ ID NO:1. Moreover, any of the mutant IL-2 polypeptides described herein can optionally include a substitution of the cysteine residue at position 125 with another residue (e.g., serine) and/or can optionally include a deletion of the alanine residue at position 1 of SEQ ID NO:1.

The mutant IL-2 polypeptides disclosed herein can bind to the IL-2Rα subunit with a $K_d$ of less than about 28 nM (e.g., less than about 25 nM; less than about 5 nM; about 1 nM; less than about 500 pM; or less than about 100 pM). More specifically, a mutant IL-2 polypeptide can have an affinity equilibrium constant less than 1.0 nM (e.g., about 0.8, 0.6, 0.4, or 0.2 nM). Affinity can also be expressed as a relative rate of dissociation from an IL-2Rα subunit or from an IL-2 receptor complex (e.g., a complex expressed on the surface of a cell or otherwise membrane bound). For example, the mutant IL-2 polypeptides can dissociate from, e.g., IL-2Rα, at a decreased rate relative to a wild-type polypeptide or to an IL-2 based therapeutic, e.g., IL-2*. Alternatively, affinity can be characterized as the time, or average time, an IL-2* polypeptide persists on, for example, the surface of a cell expressing an IL-2R. For example, an IL-2*polypeptide can persist on the receptor for at least about 2, 5, 10, 50, 100, or 250 times (or more).

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

EXAMPLES

The following are examples of methods and compositions of the invention. It is understood that various other embodiments may be practiced, given the general description provided herein.

Example 1: Detection of IL-2, IL-2 mutein, IL-2Rα and IL-2Rγ in Fusion Proteins by ELISA IL-2 mutein is detected with a commercially available antibody, e.g., the anti-IL-2 monoclonal (JES6-1A12) (BD Pharmingen; San Jose, Calif.). A positive control is used to show whether the monoclonal antibody recognizes the cytokine or mutein. Antibodies against IL-2Rα and IL-2Rγ chain are also used. Wells of a 96-well plate are coated with an antibody (2.5 µg/ml) in PBS. Wells are blocked with 5% non-fat milk in PBS with 0.2% Tween®20 (PBS-M-Tw) and fusion proteins are added for 1-2 hours at 37° C. After washing, an anti-IL-2 biotin-labeled antibody, e.g., JES5H4 (BD Pharmingen) is added and binding is detected using Strepavidin HRP (Southern Biotechnology Associates; Birmingham, Ala.). The ELISA plate is developed by adding 50 µl O-phenylenediamine (OPD) (Sigma-Aldrich) in 0.1M Citrate pH 4.5 and 0.04% $H_2O_2$, stopped by adding 50 µl/well 2N $H_2SO_4$ and the absorbance was read at 490 nm.

Example 2: Protease Cleavage of Fusion Protein by MMP9 Protease

One of skill in the art would be familiar with methods of setting up protein cleavage assay. 100 ug of protein in 1×PBS pH 7.4 were cleaved with 1 μg active MMP9 (Sigma catalog #SAE0078-50 or Enzo catalog BML-SE360) and incubated at room temperature for up to 16 hours. Digested protein is subsequently used in functional assays or stored at −80° C. prior to testing. Extent of cleavage was monitored by SDS PAGE using methods well known in the art. As shown in FIGS. 10, 13, 18A, 18B, 24B, 24C, and 27A full cleavage of the fusion proteins by MMP9 protease is seen.

Example 3: CTLL-2 Assay

CTLL2 cells (ATCC) were plated in suspension at a concentration of 500,000 cells/well in culture media with or without 40 mg/ml human serum albumin (HSA) and stimulated with a dilution series of recombinant hIL2 or activatable hIL2 for 72 hours at 37° C. and 5% $CO_2$. Activity of uncleaved and cleaved activatable hIL2 was tested. Cleaved activatable hIL2 was generated by incubation with active MMP9. Cell activity was assessed using a CellTiter-Glo (Promega) luminescence-based cell viability assay.

Example 4: Protease Cleavage of the IL-2/IL-2Rα/IL-2Rγ Chimeric Polypeptide Results in Increased Accessibility to Antibodies and Biologically Active IL-2 Mutein The IL-2 mutein fusion proteins are biochemically characterized before and after cleavage with a protease, e.g., PSA. Immunoblot analyses will show that the fusion proteins can be cleaved by PSA and that there is an increase in intensity of the predicted low molecular weight cleavage product of approximately 20 kDa reactive with an anti-IL-2 antibody after treatment of the samples with PSA. The degree of cleavage is dependent upon the amount of PSA as well as the time of incubation. Interestingly, when the fusion protein is analyzed before and after PSA treatment by ELISA, it was found that the apparent amount of IL-2 is increased after PSA cleavage. In this experiment, there is an approximately 2 or 4-fold increase in the apparent amount of IL-2 detected using this sandwich ELISA depending on the construct, suggesting that the antibody binding is partially hindered in the intact fusion protein. Aliquots of the same samples are also analyzed after PSA treatment using the CTLL-2 cell line that requires IL-2 for growth and survival and the viability of cells can be ascertained using the colorimetric MTT assay. In this assay, the more a supernatant can be diluted, the more biologically active IL-2 it contains, and there is an increase in the amount of biologically active IL-2 after PSA cleavage. The amount of IL-2 mutein increase will suggest that after PSA cleavage there is an increase in the predicted low molecular weight cleavage fragment of approximately 20 kDa reactive with an anti-IL-2 antibody, an increase in antibody accessibility, and most importantly, an increase in the amount of biologically active IL-2 mutein.

Example 5. In Vivo Delivery of a Protease Activated Fusion Protein Results in Decreased Tumor Growth The chimeric polypeptide is examined to determine if it could have biological effects in vivo. For these experiments a system is used in which tumor cells injected intraperitoneally rapidly and preferentially attach and grow initially on the milky spots, a series of organized immune aggregates found on the omentum (Gerber et al., Am. J. Pathol. 169: 1739-52 (2006)). This system offers a convenient way to examine the effects of fusion protein treatment on tumor growth since fusion proteins can be delivered intraperitoneally multiple times and tumor growth can be analyzed by examining the dissociated omental cells. For these experiments, the Colon 38 cell line, a rapidly growing tumor cell line that expresses both MMP2 and MMP9 in vitro, may be used. The omental tissue normally expresses a relatively small amount of MMP2 and MMP9, but, when Colon 38 tumor is present on the omentum, MMP levels increase. Using this tumor model, the ability of IL-2 mutein fusion proteins to affect tumor growth is examined. Colon 38 cells are injected intraperitoneally, allowed to attach and grow for 1 day, and then treated daily with fusion protein interaperitoneally. At day 7, the animals are sacrificed and the omenta examined for tumor growth using flow cytometry and by a colony-forming assay.

Example 6: Construction of an Exemplary Activatable IL2 Protein Targeting CD20

Generation of an Activatable IL2 Domain
An IL-2 polypeptide capable of binding to CD20 polypeptide present in a tumor or on a tumor cell is produced as follows. A nucleic acid is produced that contains nucleic acid sequences: (1) encoding an IFNγ polypeptide sequence and (2) one or more polypeptide linkers. Activatable interleukin plasmid constructs can have optional Flag, His or other affinity tags, and are electroporated into HEK293 or other suitable human or mammalian cell lines and purified. Validation assays include T cell activation assays using T cells responsive to IFNγ stimulation in the presence of a protease.
Generation of a scFv CD20 Binding Domain
CD20 is one of the cell surface proteins present on B-lymphocytes. CD20 antigen is found in normal and malignant pre-B and mature B lymphocytes, including those in over 90% of B-cell non-Hodgkin's lymphomas (NHL). The antigen is absent in hematopoietic stem cells, activated B lymphocytes (plasma cells) and normal tissue. As such, several antibodies mostly of murine origin have been described: 1F5, 2B8/C2B8, 2H7, and 1H4.
Human or humanized anti-CD20 antibodies are therefore used to generate scFv sequences for CD20 binding domains of an activatable interleukin protein. DNA sequences coding for human or humanized VL and VH domains are obtained, and the codons for the constructs are, optionally, optimized for expression in cells from *Homo sapiens*. The order in which the VL and VH domains appear in the scFv is varied (i.e., VL-VH, or VH-VL orientation), and three copies of the "G4S" (SEQ ID NO.: 449) or "$G_4S$" (SEQ ID NO.: 449) subunit $(G_4S)_3$ (SEQ ID NO.: 452) connect the variable domains to create the scFv domain. Anti-CD20 scFv plasmid constructs can have optional Flag, His or other affinity tags, and are electroporated into HEK293 or other suitable human or mammalian cell lines and purified. Validation assays include binding analysis by FACS, kinetic analysis using Proteon, and staining of CD20-expressing cells.
Cloning of DNA Expression Constructs Encoding the Activatable IL2 Protein
The activatable IL2 construct with protease cleavage site domains are used to construct an activatable interleukin protein in combination with an anti-CD20 scFv domain and a serum half-life extension element (e.g., a HSA binding peptide or VH domain). For expression of an activatable interleukin protein in CHO cells, coding sequences of all protein domains are cloned into a mammalian expression vector system. In brief, gene sequences encoding the activatable interleukin domain, serum half-life extension element, and CD20 binding domain along with peptide linkers L1 and L2 are separately synthesized and subcloned. The resulting constructs are then ligated together in the order of CD20 binding domain—L1—IL2 subunit 1—L2—protease cleavage domain—L3-IL2 subunit 2—L4—anti-CD20 scFv—L5—serum half-life extension element to yield a final construct. All expression constructs are designed to contain coding sequences for an N-terminal signal peptide and a C-terminal hexahistidine (6×His)-tag (SEQ ID NO. 354) to facilitate protein secretion and purification, respectively.

Expression of Activatable IL2 Proteins in Stably Transfected CHO Cells

A CHO cell expression system (Flp-In®, Life Technologies), a derivative of CHO-K1 Chinese Hamster ovary cells (ATCC, CCL-61) (Kao and Puck, Proc. Natl. Acad Sci USA 1968; 60(4):1275-81), is used. Adherent cells are subcultured according to standard cell culture protocols provided by Life Technologies.

For adaption to growth in suspension, cells are detached from tissue culture flasks and placed in serum-free medium. Suspension-adapted cells are cryopreserved in medium with 10% DMSO.

Recombinant CHO cell lines stably expressing secreted activatable interleukin proteins are generated by transfection of suspension-adapted cells. During selection with the antibiotic Hygromycin B viable cell densities are measured twice a week, and cells are centrifuged and resuspended in fresh selection medium at a maximal density of $0.1 \times 10^6$ viable cells/mL. Cell pools stably expressing activatable interleukin proteins are recovered after 2-3 weeks of selection at which point cells are transferred to standard culture medium in shake flasks. Expression of recombinant secreted proteins is confirmed by performing protein gel electrophoresis or flow cytometry. Stable cell pools are cryopreserved in DMSO containing medium.

Activatable IL2 proteins are produced in 10-day fed-batch cultures of stably transfected CHO cell lines by secretion into the cell culture supernatant. Cell culture supernatants are harvested after 10 days at culture viabilities of typically >75%. Samples are collected from the production cultures every other day and cell density and viability are assessed. On day of harvest, cell culture supernatants are cleared by centrifugation and vacuum filtration before further use.

Protein expression titers and product integrity in cell culture supernatants are analyzed by SDS-PAGE.

Purification of Activatable IL2 Proteins

Activatable IL2 proteins are purified from CHO cell culture supernatants in a two-step procedure. The constructs are subjected to affinity chromatography in a first step followed by preparative size exclusion chromatography (SEC) on Superdex 200 in a second step. Samples are buffer-exchanged and concentrated by ultrafiltration to a typical concentration of >1 mg/mL. Purity and homogeneity (typically >90%) of final samples are assessed by SDS PAGE under reducing and non-reducing conditions, followed by immunoblotting using an anti-HSA or anti idiotype antibody as well as by analytical SEC, respectively. Purified proteins are stored at aliquots at −80° C. until use.

Example 7: Determination of Antigen Affinity by Flow Cytometry

The activatable interleukin proteins of Example 6 are tested for their binding affinities to human $CD20^+$ cells and cynomolgus $CD20^+$ cells.

$CD20^+$ cells are incubated with 100 μL of serial dilutions of the activatable interleukin proteins of Example 1 and at least one protease. After washing three times with FACS buffer the cells are incubated with 0.1 mL of 10 μg/mL mouse monoclonal anti-idiotype antibody in the same buffer for 45 min on ice. After a second washing cycle, the cells are incubated with 0.1 mL of 15 μg/mL FITC-conjugated goat anti-mouse IgG antibodies under the same conditions as before. As a control, cells are incubated with the anti-His IgG followed by the FITC-conjugated goat anti-mouse IgG antibodies without the activatable IL2 proteins. The cells were then washed again and resuspended in 0.2 mL of FACS buffer containing 2 μg/mL propidium iodide (PI) in order to exclude dead cells. The fluorescence of $1 \times 10^4$ living cells is measured using a Beckman-Coulter FC500 MPL flow cytometer using the MXP software (Beckman-Coulter, Krefeld, Germany) or a Millipore Guava EasyCyte flow cytometer using the Incyte software (Merck Millipore, Schwalbach, Germany). Mean fluorescence intensities of the cell samples are calculated using CXP software (Beckman-Coulter, Krefeld, Germany) or Incyte software (Merck Millipore, Schwalbach, Germany). After subtracting the fluorescence intensity values of the cells stained with the secondary and tertiary reagents alone the values are then used for calculation of the $K_D$ values with the equation for one-site binding (hyperbola) of the GraphPad Prism (version 6.00 for Windows, GraphPad Software, La Jolla California USA).

CD20 binding and crossreactivity are assessed on the human $CD20^+$ tumor cell lines. The $K_D$ ratio of crossreactivity is calculated using the $K_D$ values determined on the CHO cell lines expressing either recombinant human or recombinant cynomolgus antigens.

Example 8: Cytotoxicity Assay

The activatable interleukin protein of Example 6 is evaluated in vitro on its mediation of immune response to $CD20^+$ target cells.

Fluorescence labeled $CD20^+$ REC-1 cells (a Mantle cell lymphoma cell line, ATCC CRL-3004) are incubated with isolated PBMC of random donors or CB15 T-cells (standardized T-cell line) as effector cells in the presence of the activatable IL2 protein of Example 5 and at least one protease. After incubation for 4 h at 37° C. in a humidified incubator, the release of the fluorescent dye from the target cells into the supernatant is determined in a spectrofluorimeter. Target cells incubated without the activatable IL2 protein of Example 1 and target cells totally lysed by the addition of saponin at the end of the incubation serve as negative and positive controls, respectively.

Based on the measured remaining living target cells, the percentage of specific cell lysis is calculated according to the following formula: [1−(number of living targets$_{(sample)}$/ number of living targets$_{(spontaneous)}$)]×100%. Sigmoidal dose response curves and $EC_{50}$ values are calculated by non-linear regression/4-parameter logistic fit using the GraphPad Software. The lysis values obtained for a given antibody concentration are used to calculate sigmoidal dose-response curves by 4 parameter logistic fit analysis using the Prism software.

Example 9: Pharmacokinetics of Activatable Interleukin Proteins

The activatable interleukin protein of Example 6 is evaluated for half-time elimination in animal studies.

The activatable IL2 protein is administered to cynomolgus monkeys as a 0.5 mg/kg bolus injection into the saphenous vein. Another cynomolgus monkey group receives a comparable IL2 construct in size, but lacking a serum half-life extension element. A third and fourth group receive an IL2 construct with serum half-life extension element and a cytokine with CD20 and serum half-life extension elements respectively, and both comparable in size to the activatable interleukin protein. Each test group consists of 5 monkeys. Serum samples are taken at indicated time points, serially diluted, and the concentration of the proteins is determined using a binding ELISA to CD20.

Pharmacokinetic analysis is performed using the test article plasma concentrations. Group mean plasma data for each test article conforms to a multi-exponential profile when plotted against the time post-dosing. The data are fit by a standard two-compartment model with bolus input and first-order rate constants for distribution and elimination phases. The general equation for the best fit of the data for i.v. administration is: $c(t)=Ae^{-\alpha t}+Be^{-\beta t}$, where c(t) is the plasma concentration at time t, A and B are intercepts on the Y-axis, and $\alpha$ and $\beta$ are the apparent first-order rate constants for the distribution and elimination phases, respectively. The $\alpha$-phase is the initial phase of the clearance and reflects distribution of the protein into all extracellular fluid of the animal, whereas the second or $\beta$-phase portion of the decay curve represents true plasma clearance. Methods for fitting such equations are well known in the art. For example, $A=D/V(\alpha-k21)/(\alpha-\beta)$, $B=D/V(\beta-k21)/(\alpha-\beta)$, and $\alpha$ and $\beta$ (for $\alpha>\beta$) are roots of the quadratic equation: $r^2+(k12+k21+k10)r+k21k10=0$ using estimated parameters of V=volume of distribution, k10=elimination rate, k12=transfer rate from compartment 1 to compartment 2 and k21=transfer rate from compartment 2 to compartment 1, and D=the administered dose.

Data analysis: Graphs of concentration versus time profiles are made using KaleidaGraph (KaleidaGraph™ V. 3.09 Copyright 1986-1997. Synergy Software. Reading, Pa.). Values reported as less than reportable (LTR) are not included in the PK analysis and are not represented graphically. Pharmacokinetic parameters are determined by compartmental analysis using WinNonlin software (WinNonlin® Professional V. 3.1 WinNonlin™ Copyright 1998-1999. Pharsight Corporation. Mountain View, Calif.). Pharmacokinetic parameters are computed as described in Ritschel W A and Kearns G L, 1999, IN: *Handbook Of Basic Pharmacokinetics Including Clinical Applications*, 5th edition, American Pharmaceutical Assoc., Washington, D.C.

It is expected that the activatable interleukin protein of Example 5 has improved pharmacokinetic parameters such as an increase in elimination half-time as compared to proteins lacking a serum half-life extension element.

Example 10: Xenograft Tumor Model

The activatable IL2 protein of Example 6 is evaluated in a xenograft model.

Female immune-deficient NOD/scid mice are sub-lethally irradiated (2 Gy) and subcutaneously inoculated with $4\times10^6$ Ramos RA1 cells into the right dorsal flank. When tumors reach 100 to 200 mm³, animals are allocated into 3 treatment groups. Groups 2 and 3 (8 animals each) are intraperitoneally injected with $1.5\times10^7$ activated human T-cells. Three days later, animals from Group 3 are subsequently treated with a total of 9 intravenous doses of 50 μg activatable interleukin protein of Example 1 (qd×9d). Groups 1 and 2 are only treated with vehicle. Body weight and tumor volume are determined for 30 days.

It is expected that animals treated with the activatable interleukin protein of Example 5 have a statistically significant delay in tumor growth in comparison to the respective vehicle-treated control group.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Example 11: Mouse IFNγ WEHI Cell Survival Assay

WEHI279 cells (ATCC) were plated in suspension at a concentration of 25,000 cells/well in culture media with or without 1.5% human serum albumin (HSA) and stimulated with a dilution series of recombinant mIFNγ or inducible mIFNγ for 72 hours at 37° C. and 5% $CO_2$. Activity of uncleaved and cleaved inducible mIFNγ was tested. Cleaved inducible mIFNg was generated by incubation with active MMP9. Cell survival was assessed using a CellTiter-Glo (Promega) luminescence-based cell viability assay. The EC50 values for cleaved inducible mIFNg molecules were at least 100× more potent than un-cleaved inducible mIFNg molecules. As shown in FIGS. 16A-16F, greater inducibility was seen in assays wherein the culture media contained human serum albumin.

Example 12: Mouse IFNγ B16 Reporter and Mouse IFNα/β B16 Reporter Cell Assays B16-Blue IFNγ cells (InvivoGen) were plated at a concentration of 75,000 cells/well in culture media with or without 1.5% human serum albumin (HSA) and stimulated with a dilution series of recombinant mIFNγ or inducible mIFNγ for 24 hours at 37° C. and 5% $CO_2$. Activity of uncleaved and cleaved inducible mIFNγ was tested. Cleaved inducible mIFNγ was generated by incubation with active MMP9. Supernatants were harvested, and SEAP activation was assessed by adding QUANTI-Blue Reagent (InvivoGen), incubating at 37° C. for 2 hours, and measuring absorbance at 620 nm. Results are shown in FIGS. 17A-17F, 19A, 19B, 22A, 22B, 23A, 23B, and 28A-28N. This experiment was repeated with for IFNα fusion proteins using B16-Blue IFNα/β cells. The EC50 values for cleaved inducible mIFNα molecules were at least 100× more potent than un-cleaved inducible mIFNα molecules.

B16-Blue IFN-α/β cells (InvivoGen) were plated in suspension at a density of 75,000 cells/well in culture media with or without 15 mg/ml mouse serum albumin (HSA) and stimulated with a dilution series of recombinant mouse IFNα (or IFNβ) and activatable mouse IFNα (or IFNβ) for 20-24 hours at 37° C. and 5% $CO_2$. Activity of uncleaved and cleaved activatable IFNα (or IFNβ) was tested. Cleaved inducible IFNα (or IFNβ) was generated by incubation with active recombinant protease. Stimulation of B16-Blue IFN-α/β cells with IFNα (or IFNβ) induces expression of Secreted Alkaline Phosphatase (SEAP) from an ISRE-ISG54-SEAP reporter. IFNα (or IFNβ) activity was assessed by quantification of SEAP activity using the reagent QUANTI-Blue (InvivoGen), a colorimetric based assay. Results are shown in FIGS. 10A-10J.

Example 13. In Vivo Delivery of a Protease Activated Fusion Protein Results in Decreased Tumor Growth The chimeric polypeptide is examined to determine if it could have biological effects in vivo. For these experiments a system is used in which tumor cells injected intraperitoneally rapidly and preferentially attach and grow initially on the milky spots, a series of organized immune aggregates found on the omentum (Gerber et al., Am. J. Pathol. 169: 1739-52 (2006)). This system offers a convenient way to examine the effects of fusion protein treatment on tumor growth since fusion proteins can be delivered intraperitoneally multiple times and tumor growth can be analyzed by examining the dissociated omental cells. For these experiments, the Colon 38 cell line, a rapidly growing tumor cell line that expresses both MMP2 and MMP9 in vitro, may be used. The omental tissue normally expresses a relatively small amount of MMP2 and MMP9, but, when Colon 38 tumor is present on the omentum, MMP levels increase. Using this tumor model, the ability of IFN fusion proteins to affect tumor growth is examined. Colon 38 cells are injected intraperitoneally, allowed to attach and grow for 1 day, and then treated daily with fusion protein interaperitoneally. At day 7, the animals are sacrificed and the omenta examined for tumor growth using flow cytometry and by a colony-forming assay.

Figure 21A:
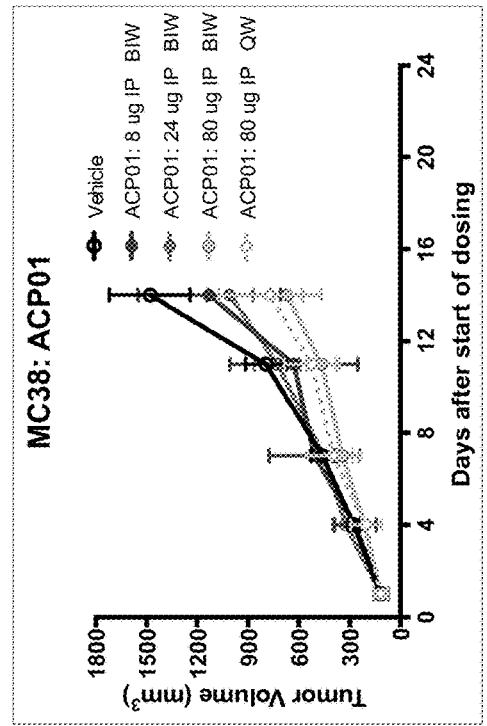
FIGS. 21A-21D are a series of graphs depicting the results of tumor growth studies using the MC38 cell line.
Figure 21C:
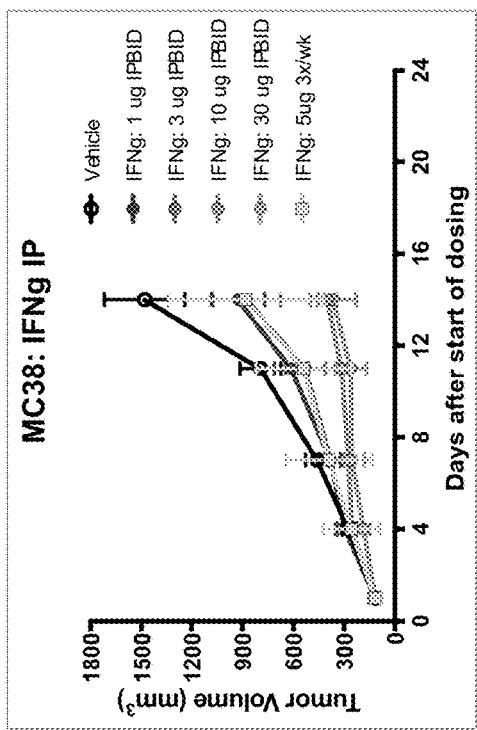
Figure 21B:
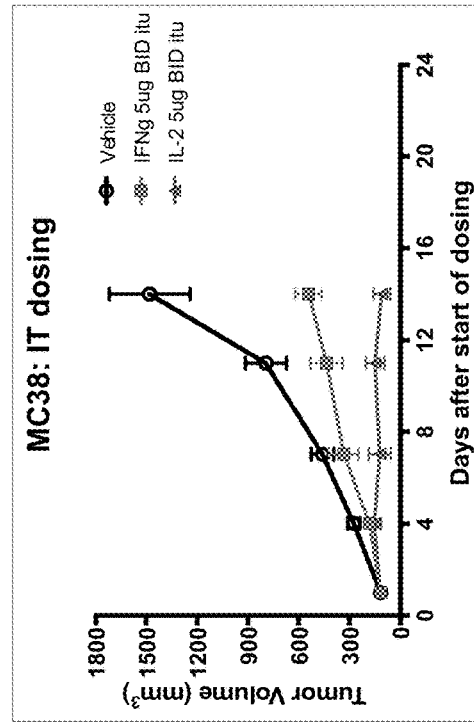
Figure 21D:
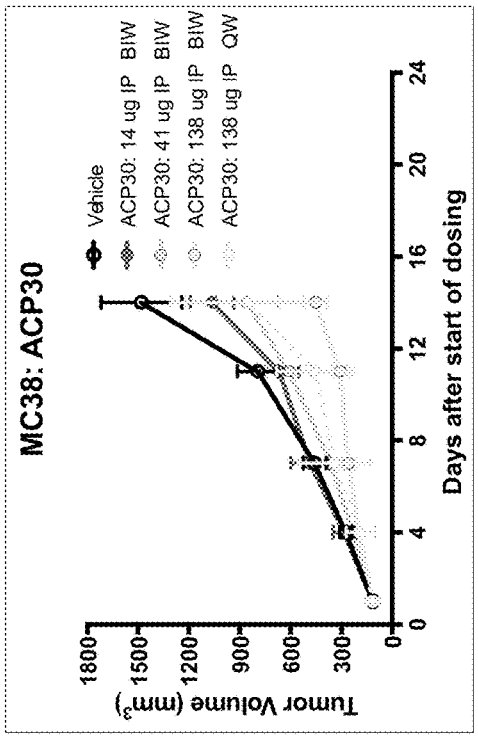
Figure 22B:
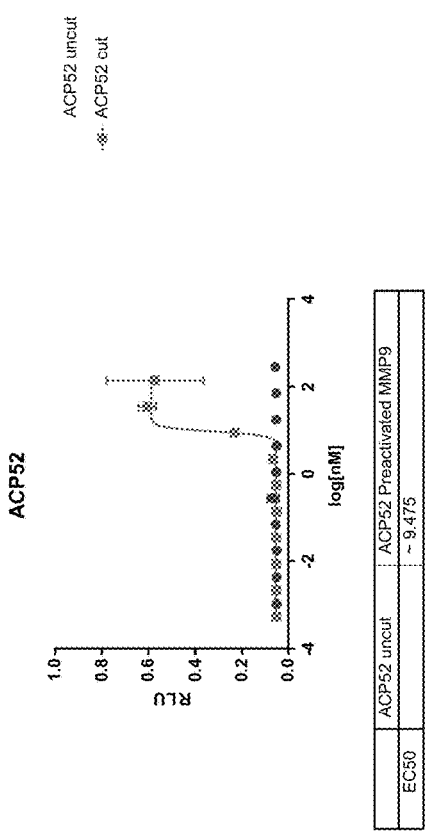
FIGS. 22A-22B are a series of graphs showing activity of exemplary IFNγ fusion proteins (ACP51 (FIG. 22A), and ACP52 (FIG. 22B)) cleaved by MMP9 protease compared to activity of uncleaved fusion proteins using B16 reporter assay. Each fusion protein comprises an anti-HSA binder and a tumor targeting domain.
Figure 22A:
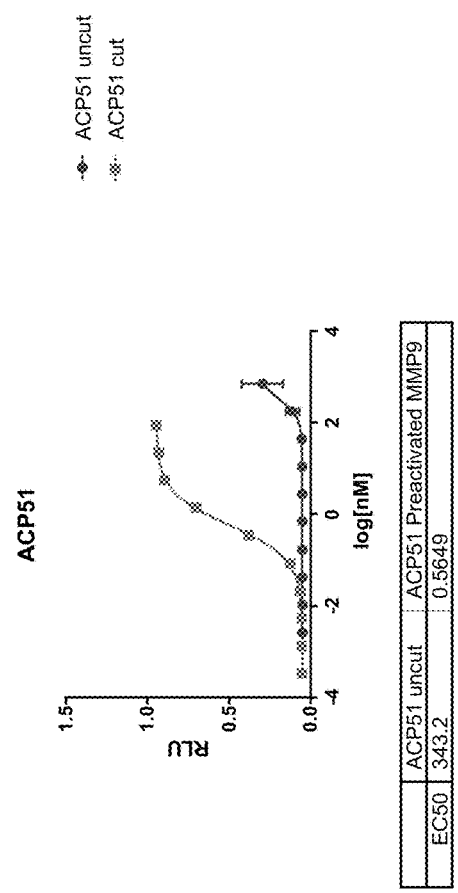
Figure 23B:
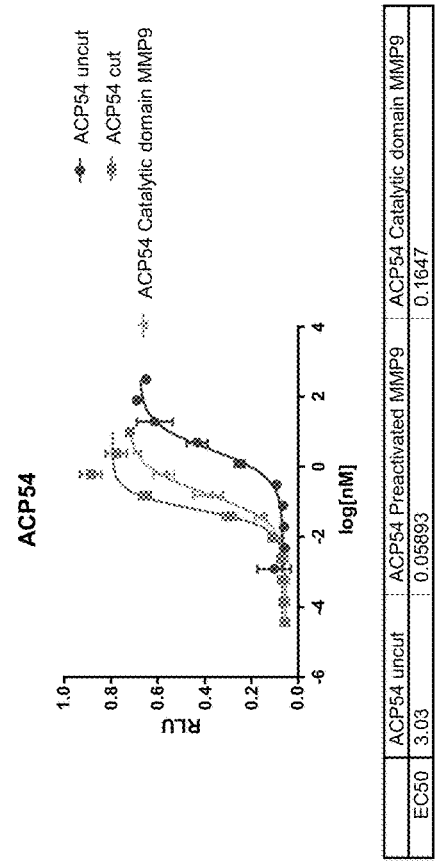
FIGS. 23A-23B are a series of graphs showing activity of exemplary IFNγ fusion proteins (ACP53 and ACP54) cleaved by MMP9 protease compared to activity of uncleaved fusion proteins using B16 reporter assay. Each fusion protein comprises IFNγ directly fused to albumin.
Figure 23A:
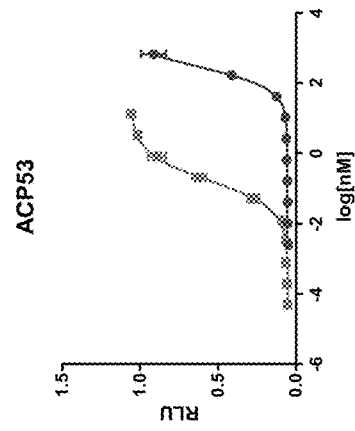
Figure 24A:
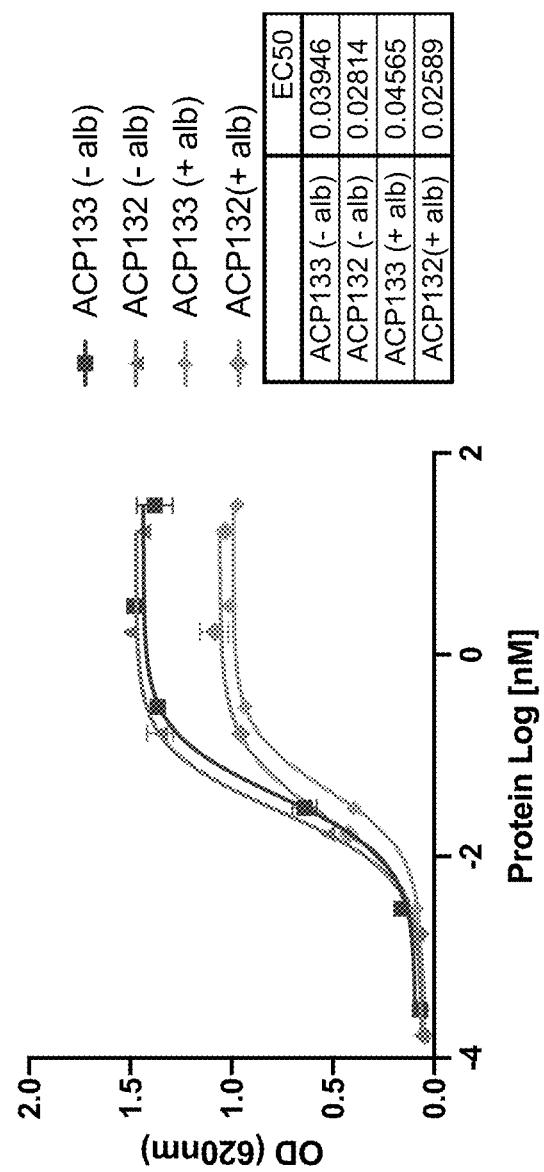
FIGS. 24A-24D are graphs depicting results from a HEK-Blue IL-2 reporter assay performed on IL-2 fusion proteins and recombinant human IL2 (Rec hIL-2). Analysis was performed based on quantification of Secreted Alkaline Phosphatase (SEAP) activity using the reagent QUANTI-Blue (InvivoGen).
Figure 24B:
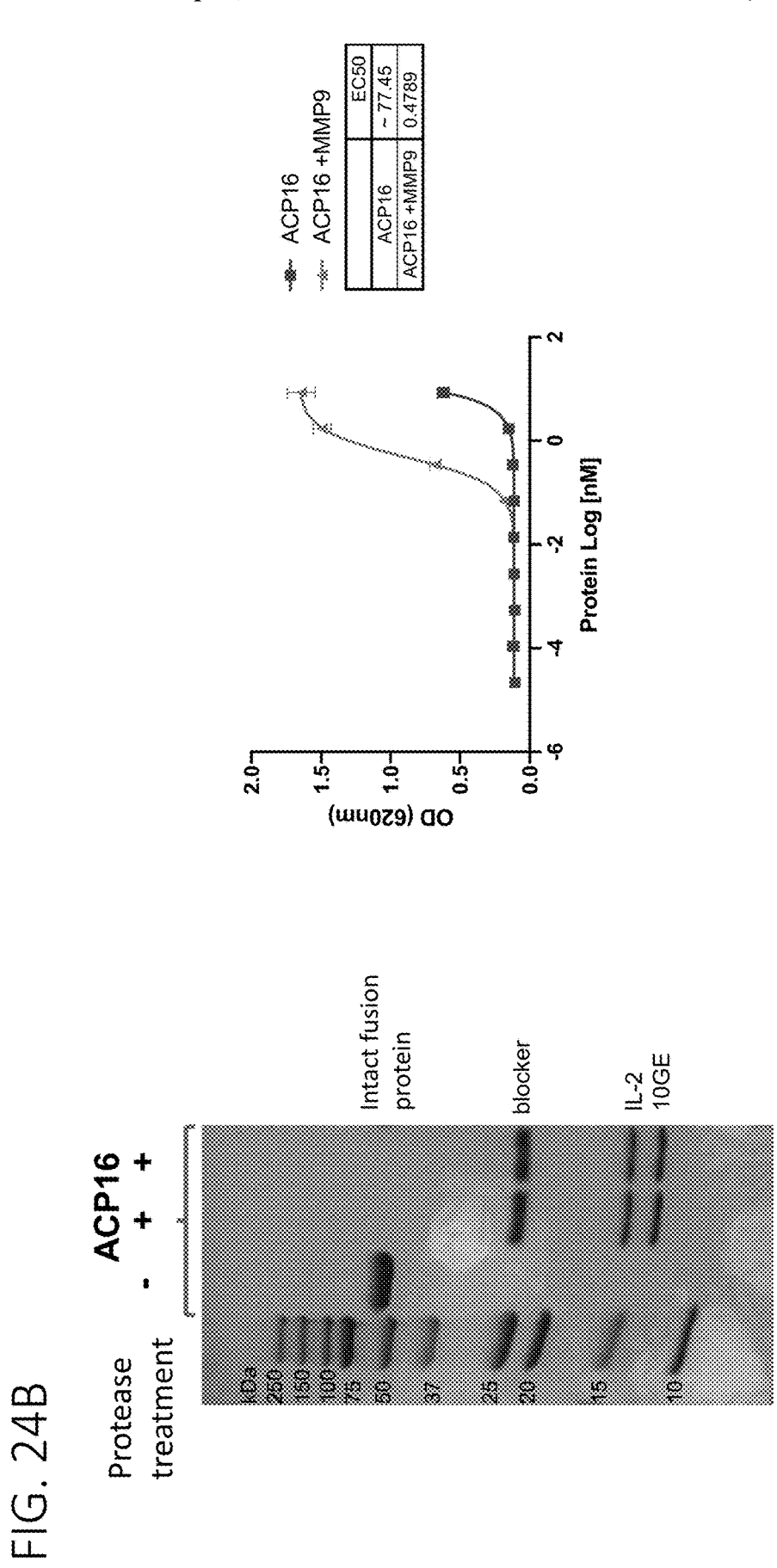
Figure 24C:
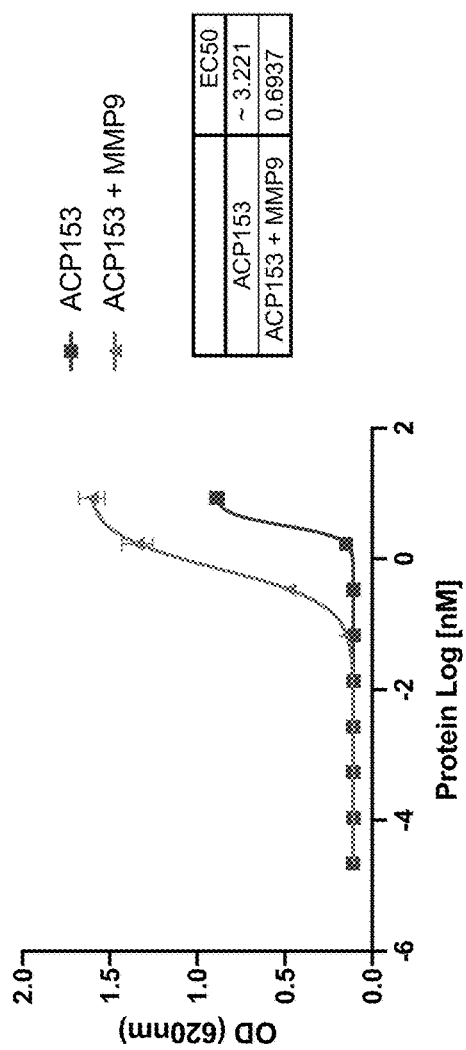
Figure 24C:
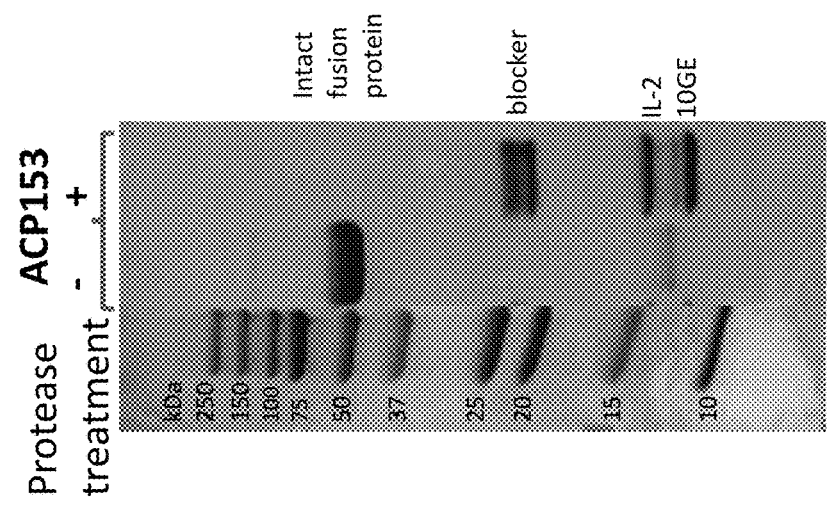
Figure 24D:
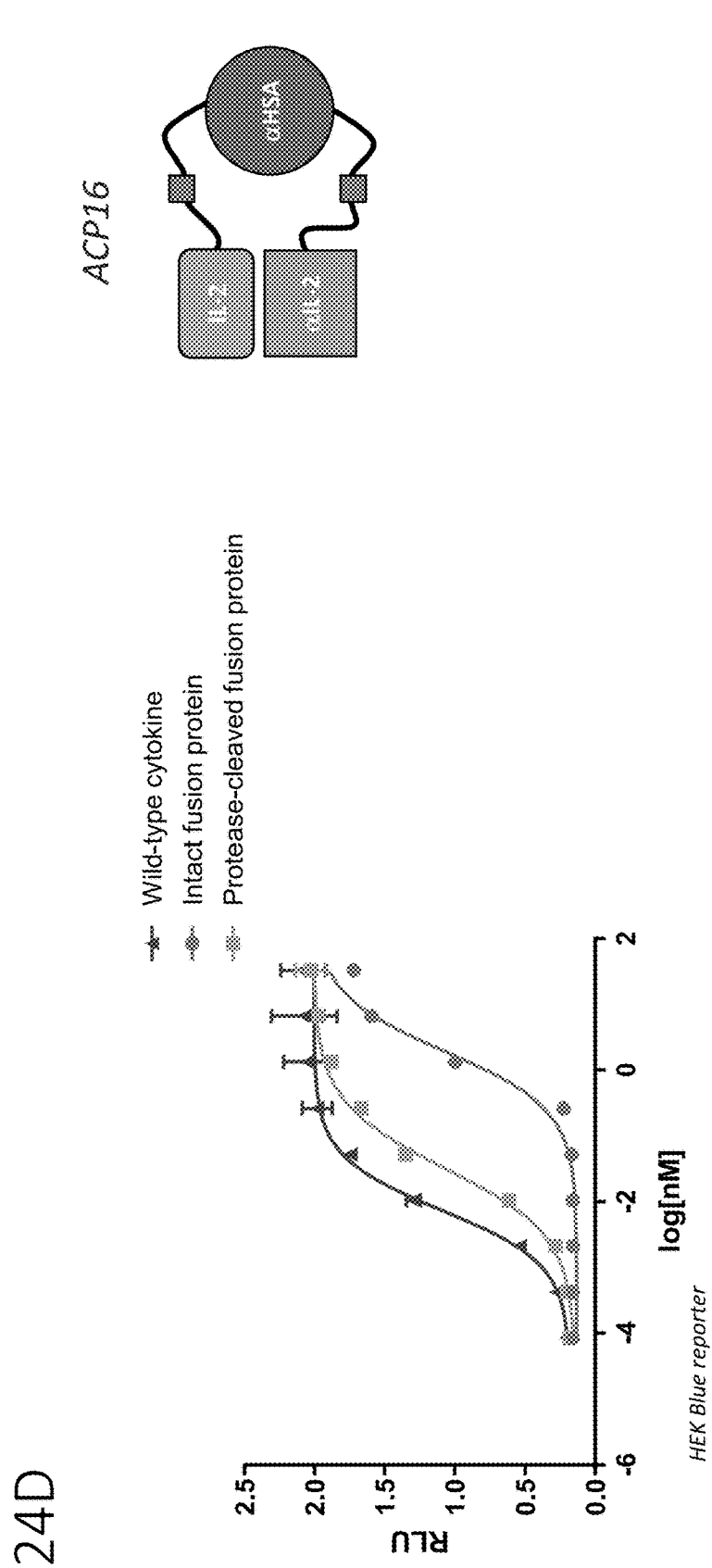
Figure 25C:
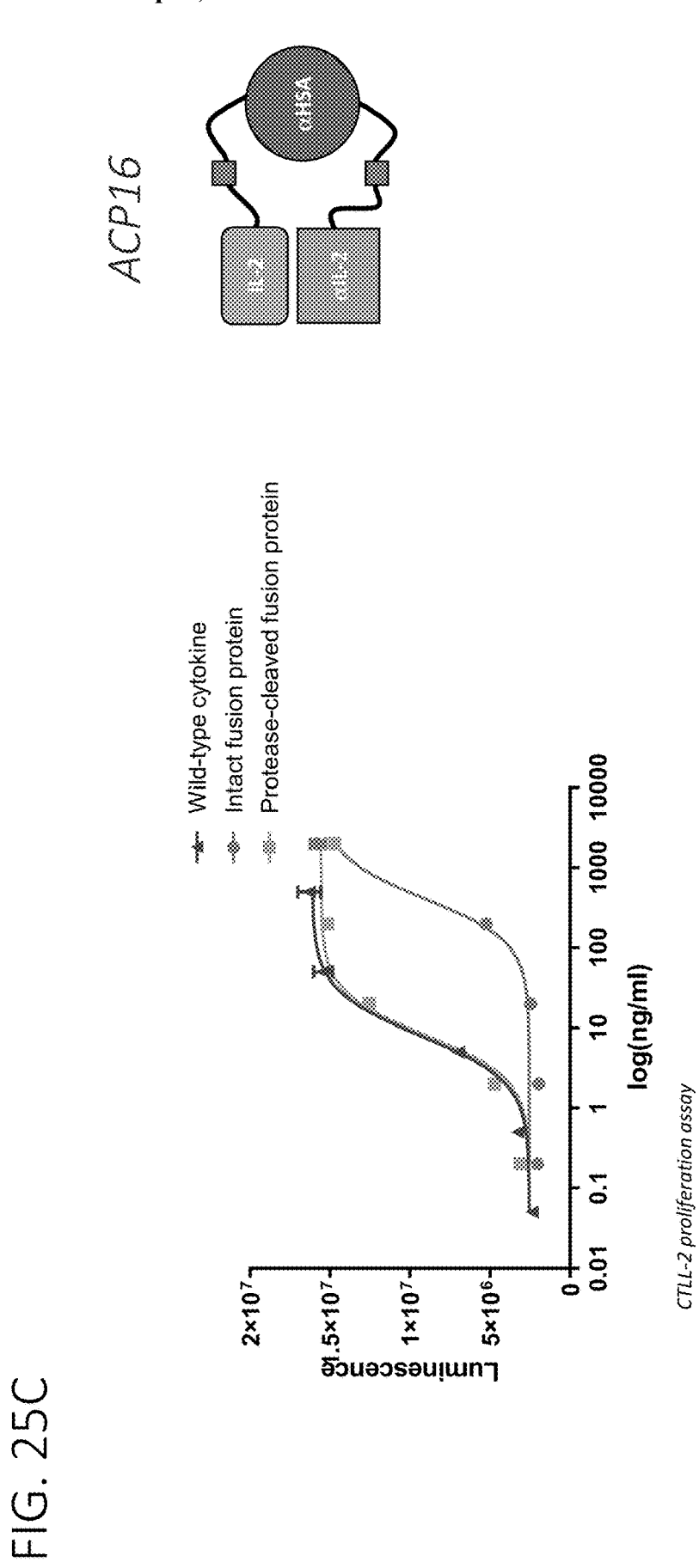
FIG. 25C is a graph showing results of a CTLL-2 proliferation assay. CTLL2 cells (ATCC) were plated in suspension at a concentration of 500,000 cells/well in culture media with or without 40 mg/ml human serum albumin (HSA) and stimulated with a dilution series of activatable hIL2 for 72 hours at 37° C. and 5% $CO_2$. Activity of uncleaved and cleaved activatable ACP16 was tested. Cleaved activatable hIL2 was generated by incubation with active MMP9. Cell activity was assessed using a CellTiter-Glo (Promega) luminescence-based cell viability assay. Circles depict intact fusion protein, and squares depict protease-cleaved fusion protein.
Figure 26A:
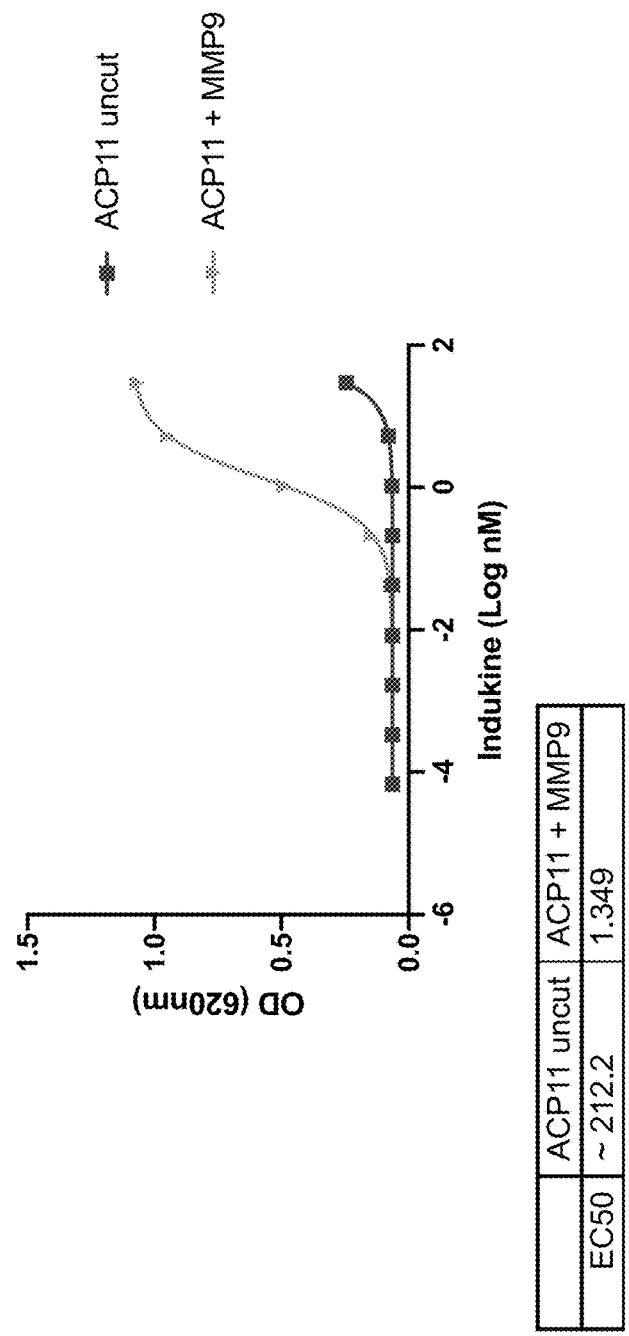
FIGS. 26A-26C are a series of graphs showing activity of fusion proteins in an HEKBlue IL-12 reporter assay.
Figure 26B:
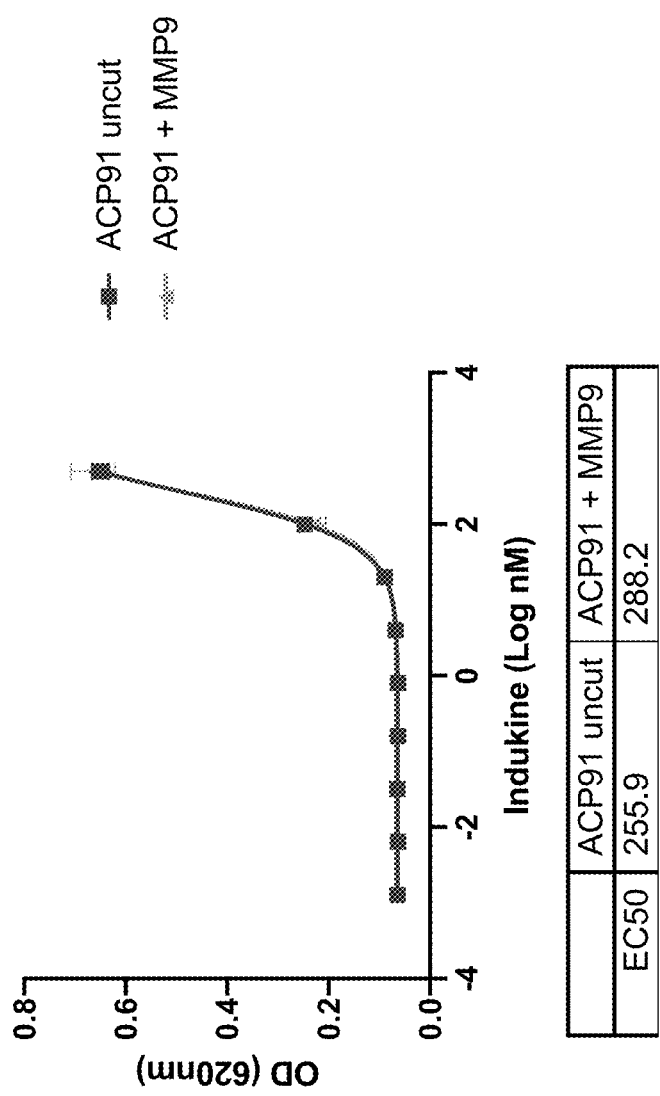
Figure 26C:
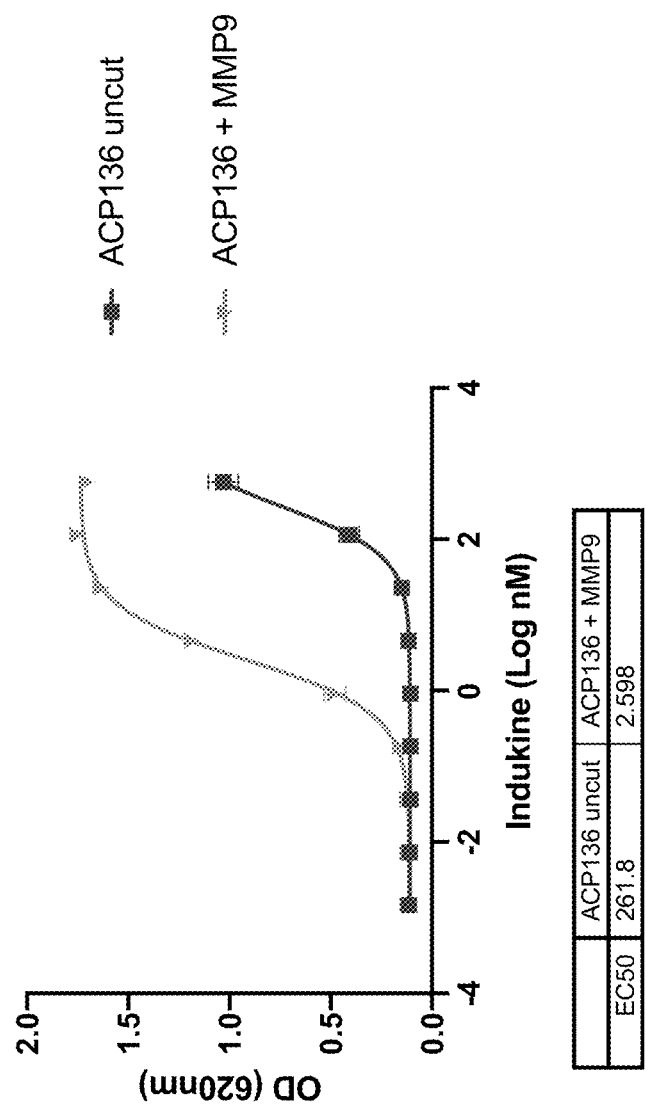
Figure 27A:
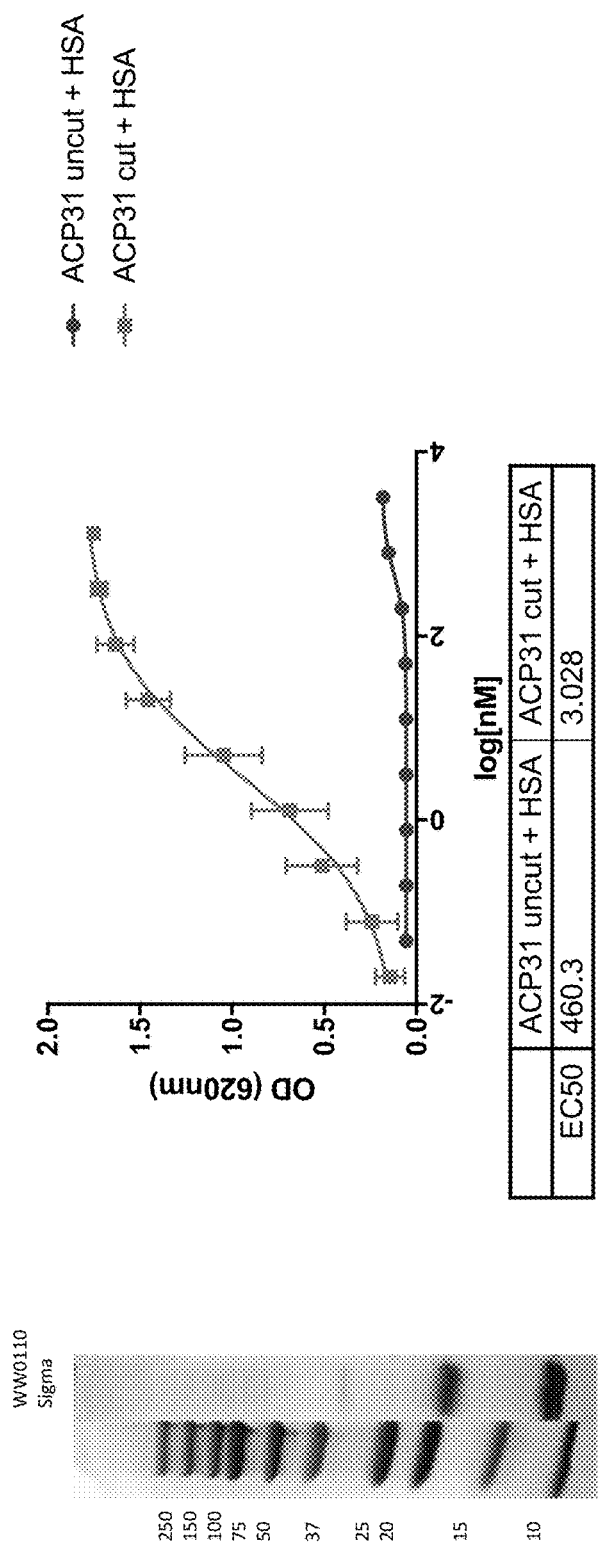
Figures 27B, 27C:
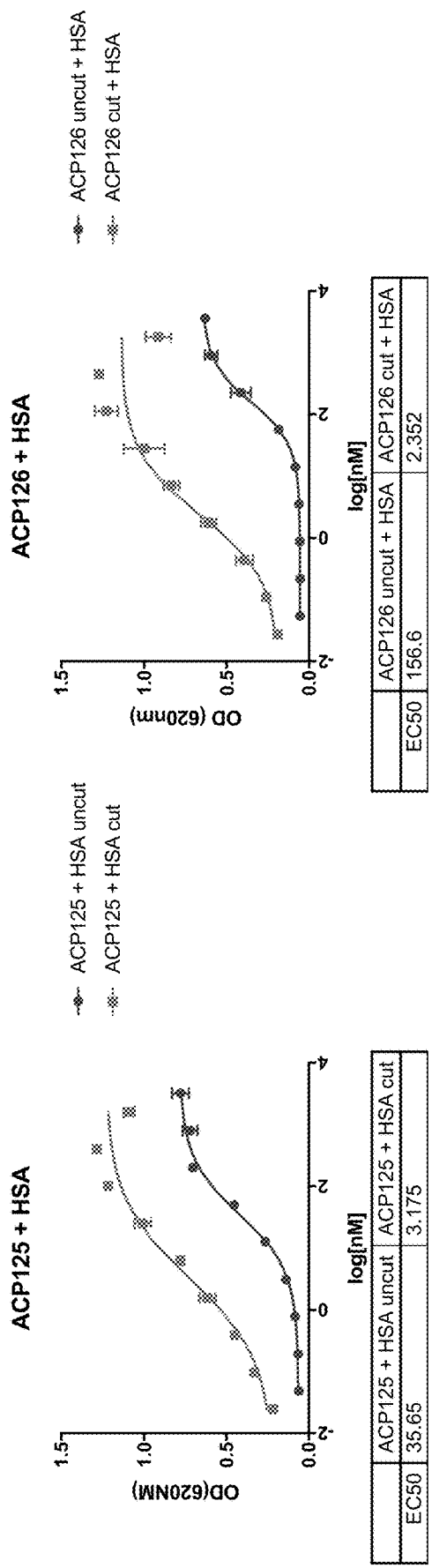
Figure 28B:
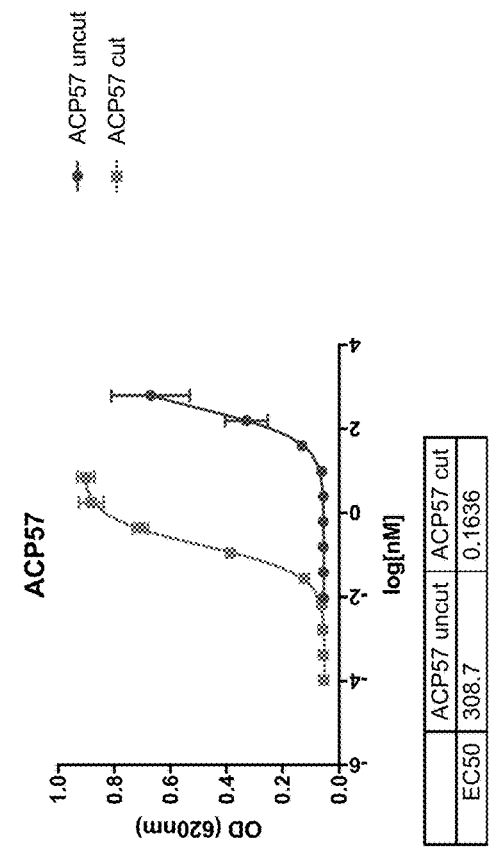
FIGS. 28A-28N are a series of graphs depicting the activity of ACP56 (FIG. 28A), ACP57 (FIG. 28B) ACP58 (FIG. 28C), ACP59 (FIG. 28D), ACP60 (FIG. 28E), ACP61+HSA (FIG. 28F), ACP30+HSA (FIG. 28G), ACP73 (FIG. 28H), ACP70+HSA (FIG. 28I), ACP71 (FIG. 28J), ACP72 (FIG. 28K), ACP 73 (FIG. 28L), ACP74 (FIG. 28M), and ACP75 (FIG. 28N) in a B16 IFNγ reporter assay. Each fusion was tested for its activity when cut (squares) and uncut (circles).
Figure 28A:
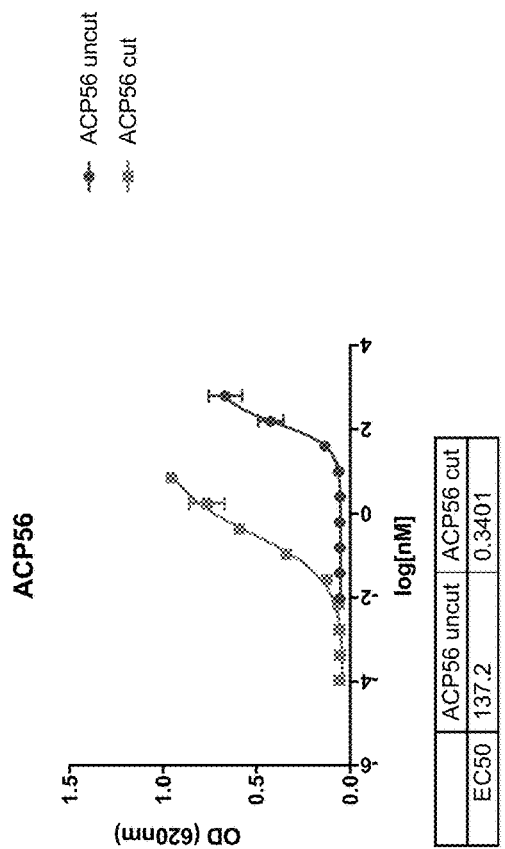
Figure 28D:
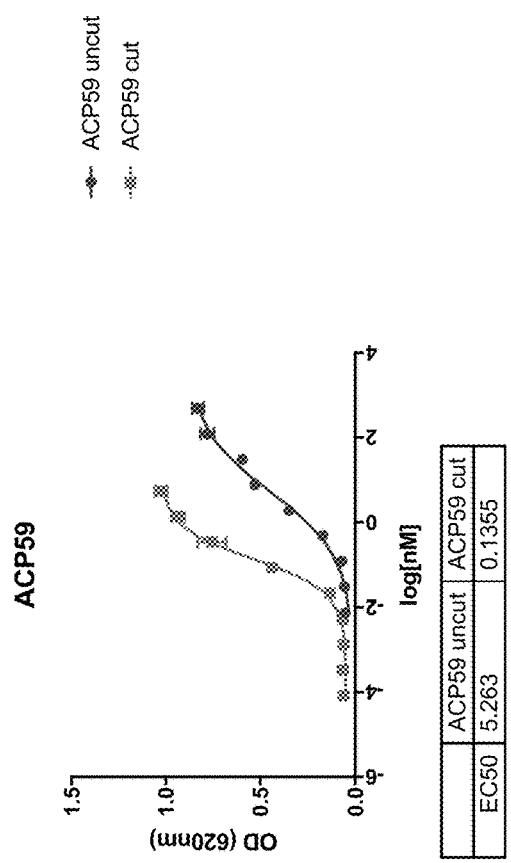
Figure 28C:
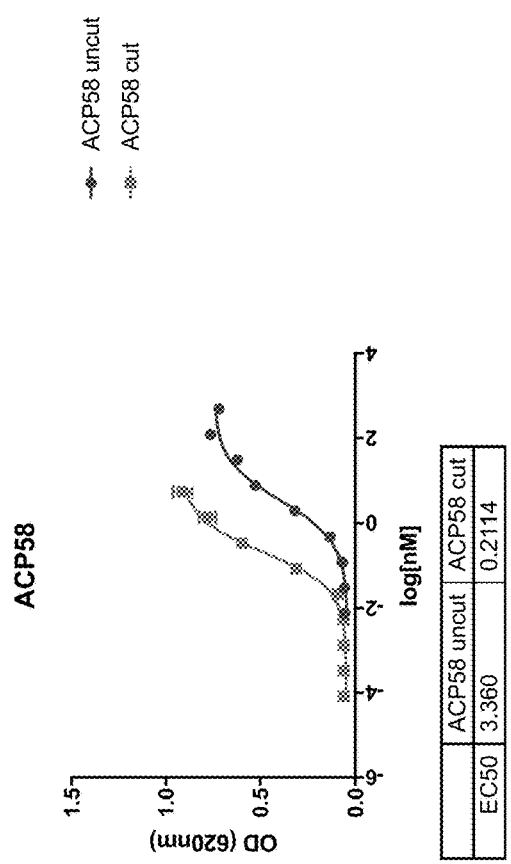
Figure 28E:
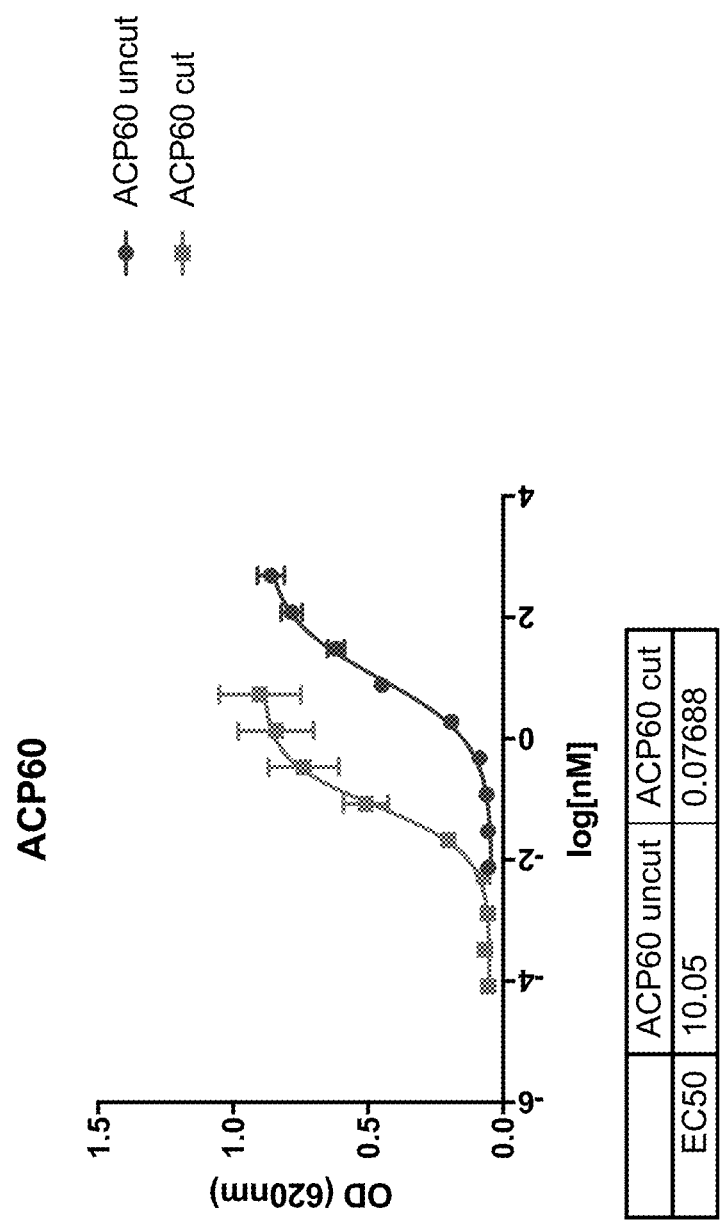
Figure 28F:
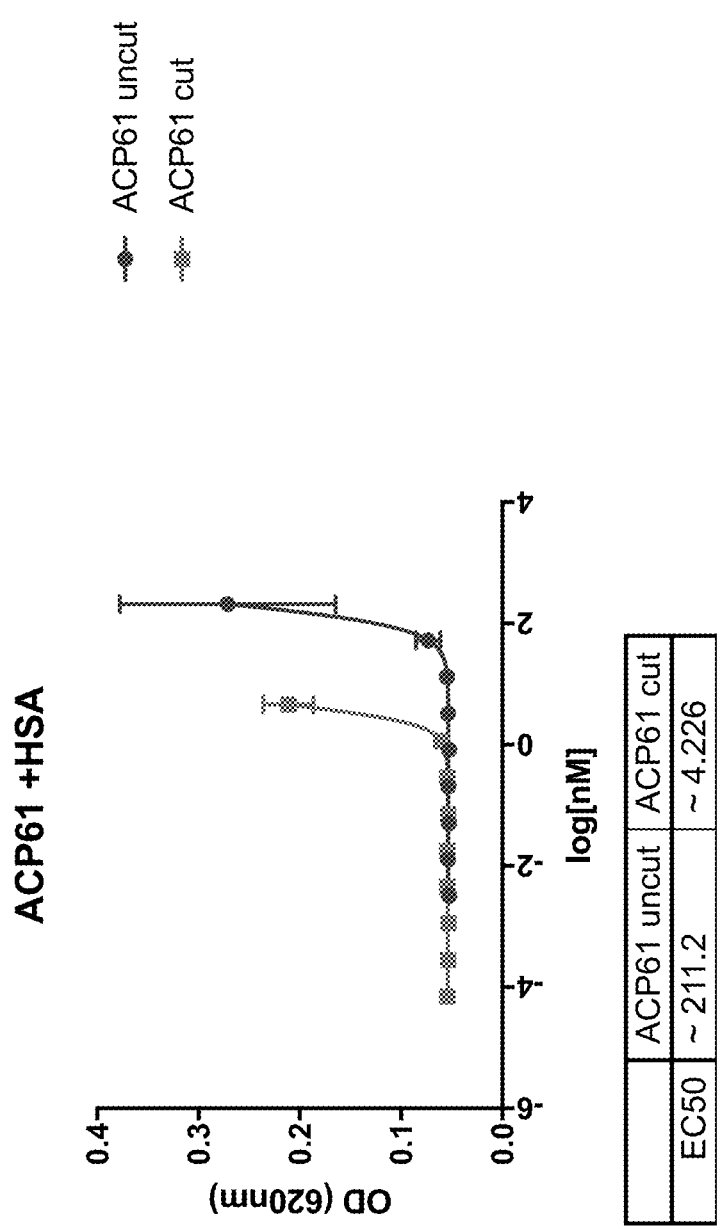
Figure 28G:
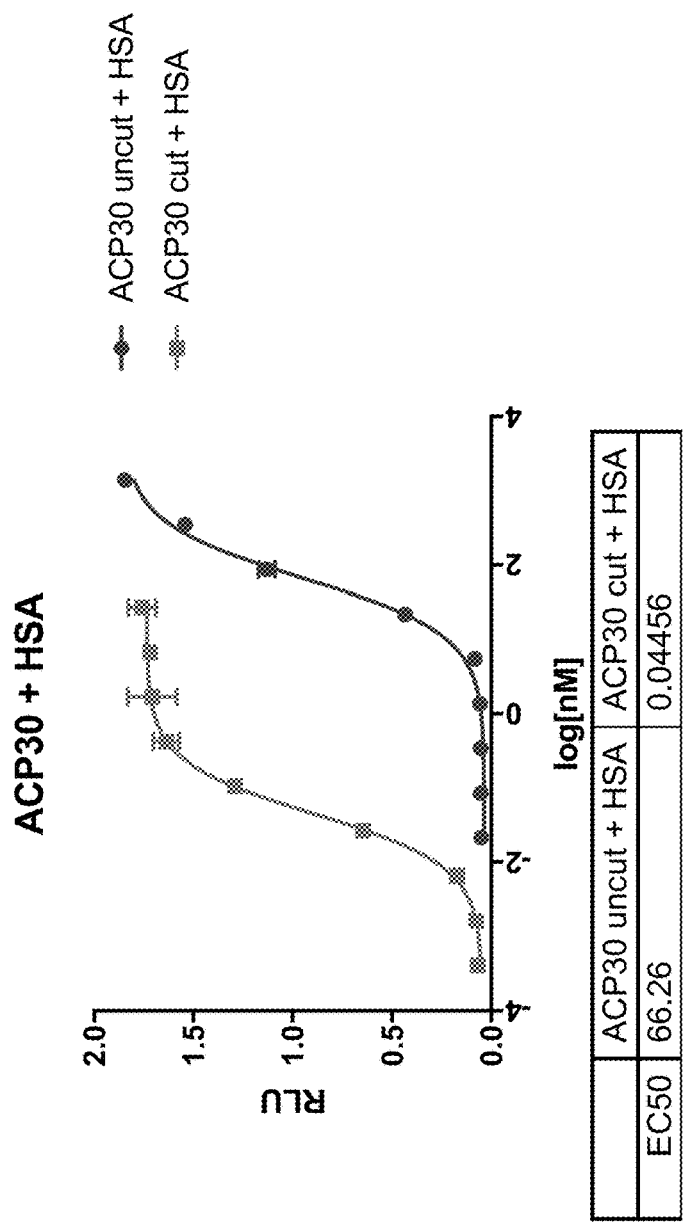
Figure 28H:
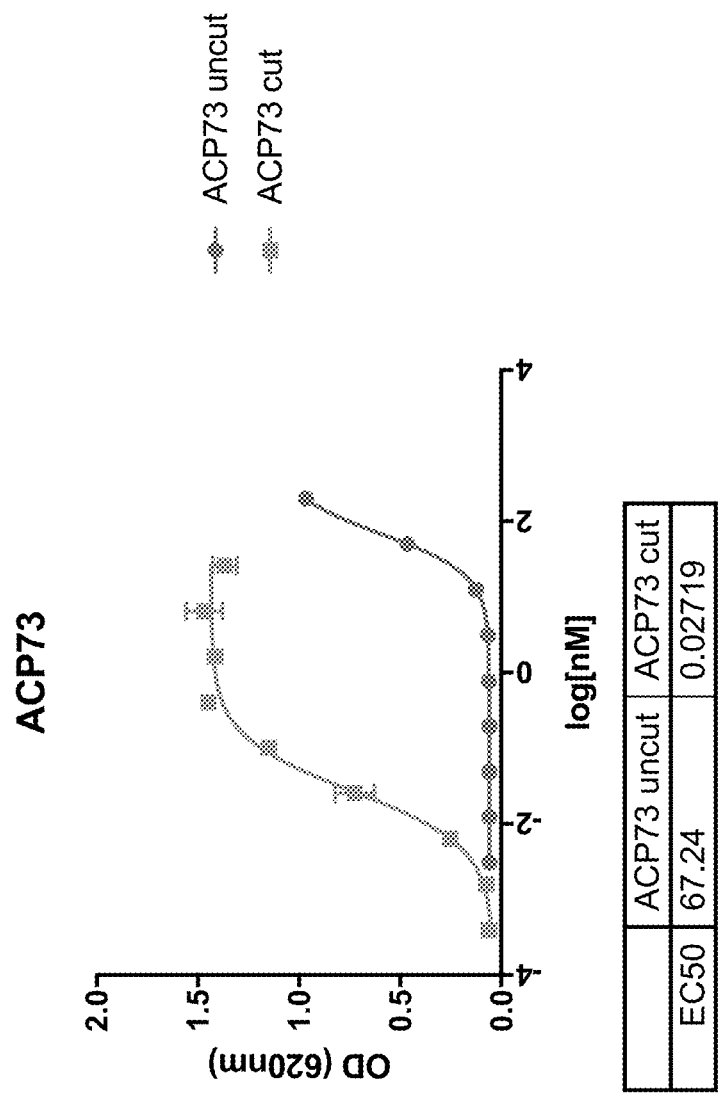
Figure 28I:
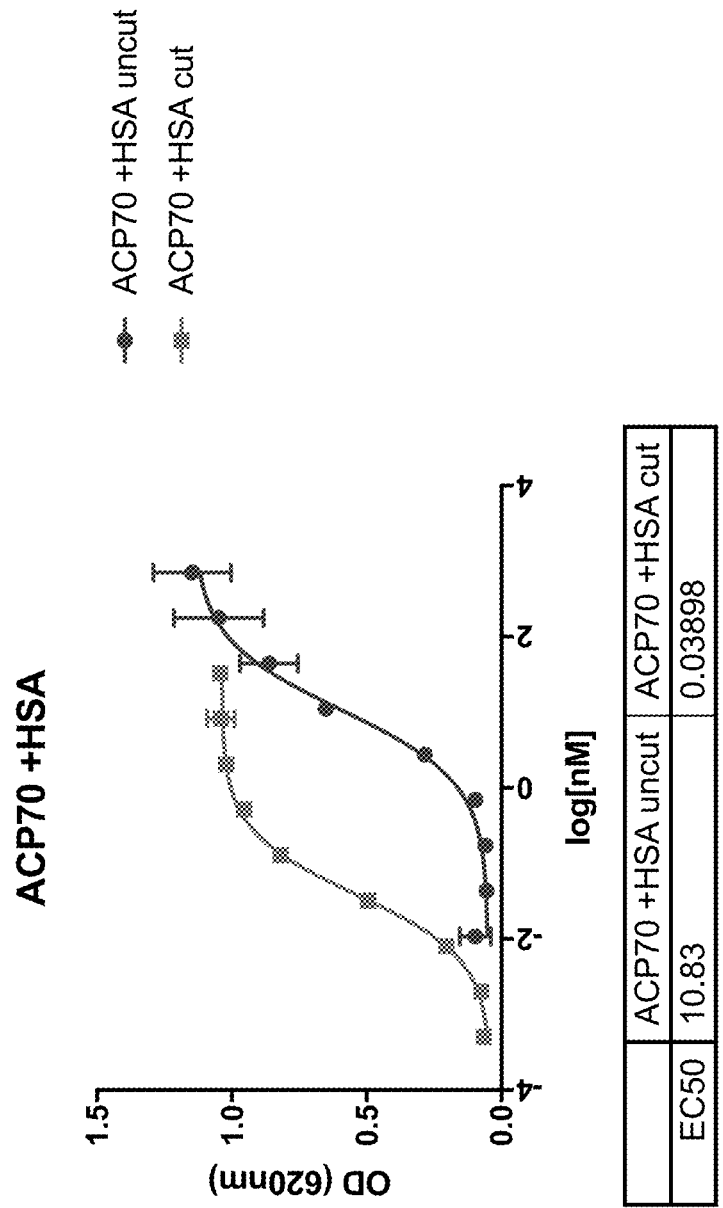
Figure 28J:
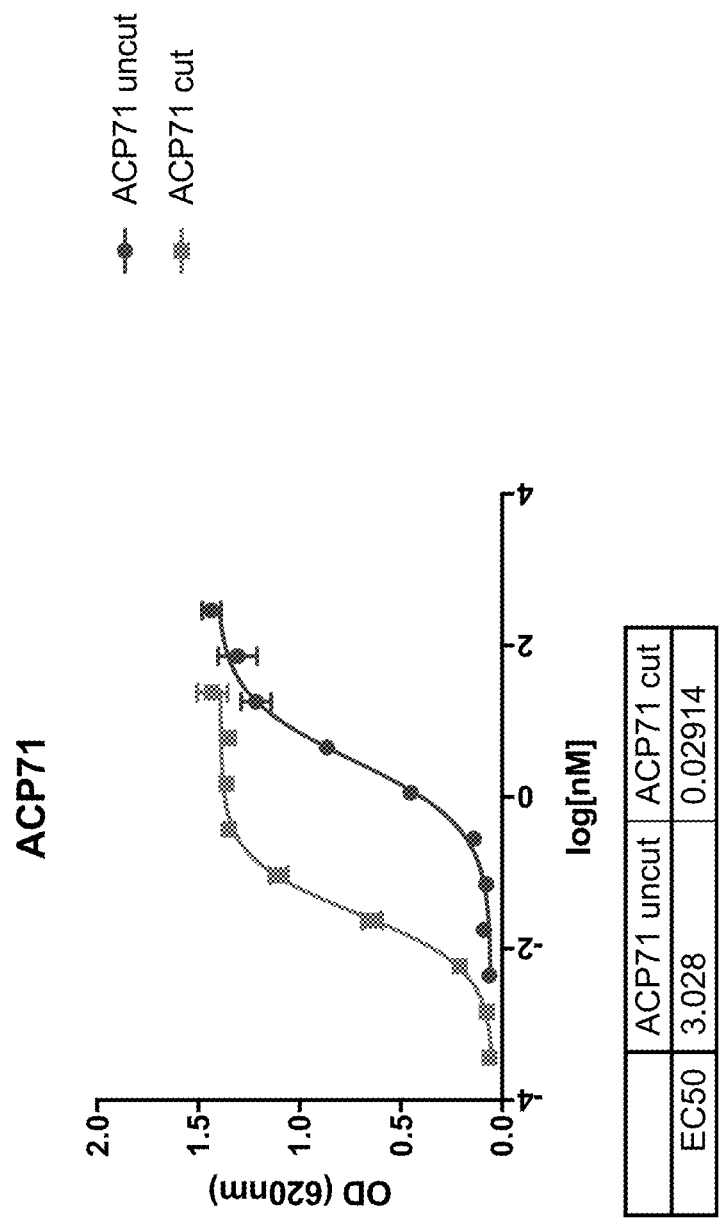
Figure 28K:
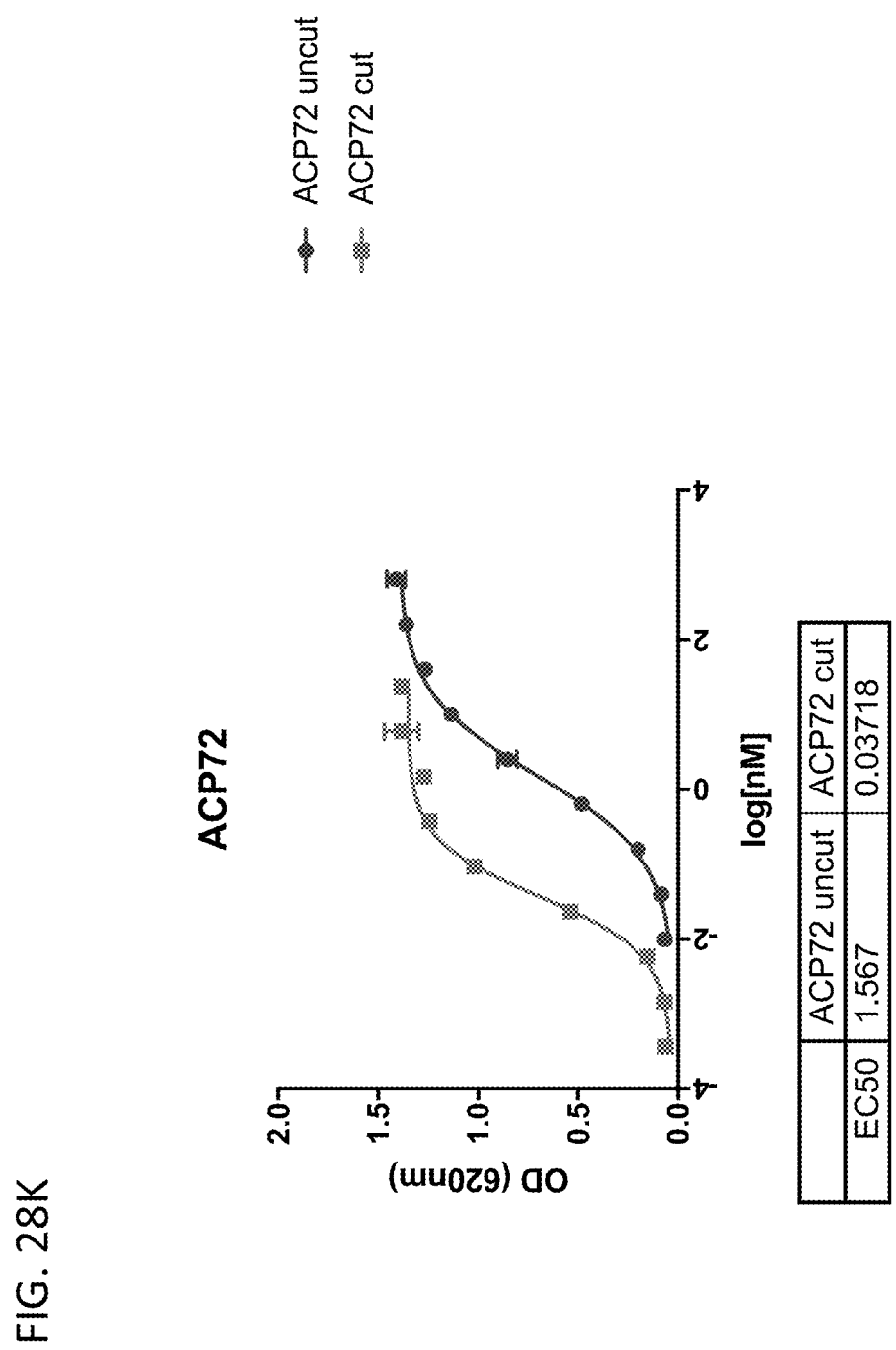
Figure 28L:
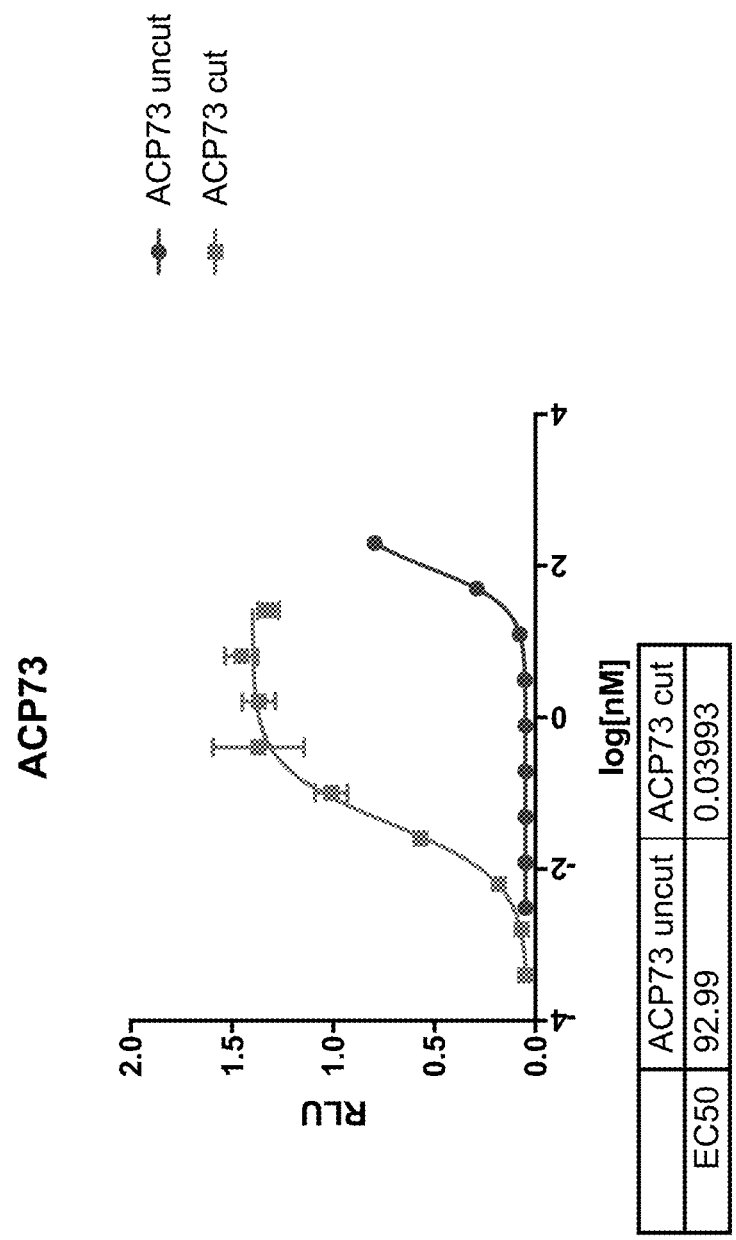
Figure 28M:
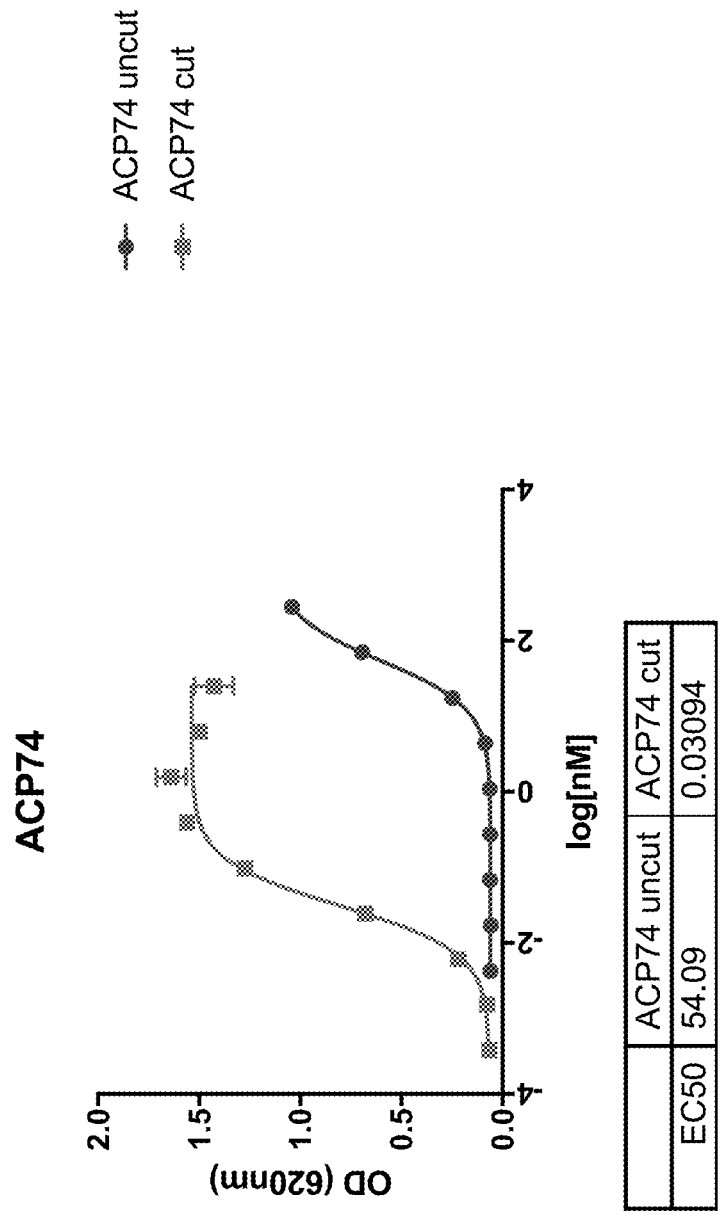
Figure 28N:
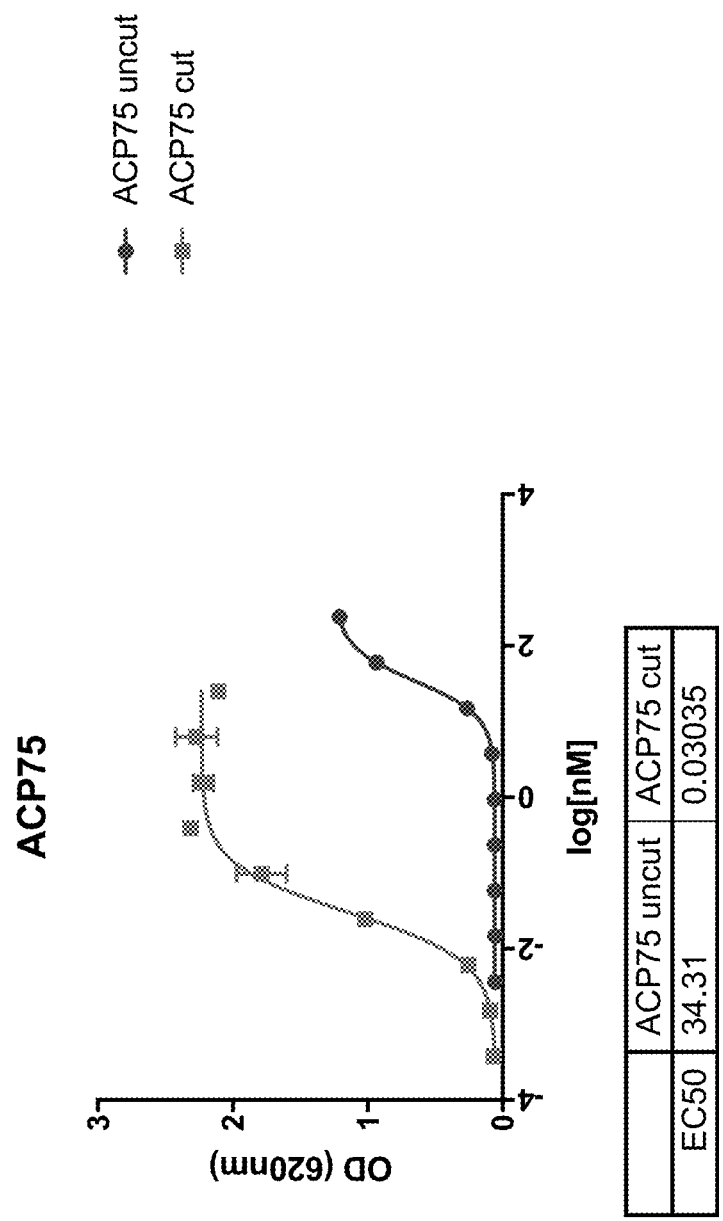

Example 13b: The Chimeric Polypeptide was Examined to Determine its Biological Effects In Vivo The MC38 cell line, a rapidly growing colon adenocarcinoma cell line that expresses MMP9 in vitro, was used. Using this tumor model, the ability of IFNγ fusion proteins to affect tumor growth was examined. MC38 cells were injected subcutaneously, allowed to grow for 10-14 days, and then treated with fusion protein twice weekly intraperitoneally for a total of four doses, at the levels shown in FIG. 21A-21C. As a comparator, wild-type mIFNγ was administered at the dose levels indicated, twice daily for 2 weeks on a 5 day on/2 day off schedule (10 total doses). Tumor growth and body weight were monitored approximately twice per week for two weeks.

Example 14: Construction of an Exemplary IFNγ Protein Targeting CD20

Generation of an Activatable Cytokine Domain

An IFNγ polypeptide capable of binding to CD20 polypeptide present in a tumor or on a tumor cell is produced as follows. A nucleic acid is produced that contains nucleic acid sequences: (1) encoding an IFN'γ, polypeptide sequence and (2) one or more polypeptide linkers. Activatable IFNγ plasmid constructs can have optional Flag, His or other affinity tags, and are electroporated into HEK293 or other suitable human or mammalian cell lines and purified. Validation assays include T cell activation assays using T cells responsive to IFNγ stimulation in the presence of a protease.

Generation of a scFv CD20 Binding Domain

CD20 is one of the cell surface proteins present on B-lymphocytes. CD20 antigen is found in normal and malignant pre-B and mature B lymphocytes, including those in over 90% of B-cell non-Hodgkin's lymphomas (NHL). The antigen is absent in hematopoietic stem cells, activated B lymphocytes (plasma cells) and normal tissue. As such, several antibodies mostly of murine origin have been described: 1F5, 2B8/C2B8, 2H7, and 1H4.

Human or humanized anti-CD20 antibodies are therefore used to generate scFv sequences for CD20 binding domains of an activatable IFNγ protein. DNA sequences coding for human or humanized VL and VH domains are obtained, and the codons for the constructs are, optionally, optimized for expression in cells from Homo sapiens. The order in which the VL and VH domains appear in the scFv is varied (i.e., VL-VH, or VH-VL orientation), and three copies of the "G4S" (SEQ ID NO.: 449) or "G$_4$S" (SEQ ID NO.: 449) subunit (G$_4$S)$_3$ (SEQ ID NO.: 452) connect the variable domains to create the scFv domain. Anti-CD20 scFv plasmid constructs can have optional Flag, His or other affinity tags, and are electroporated into HEK293 or other suitable human or mammalian cell lines and purified. Validation assays include binding analysis by FACS, kinetic analysis using Proteon, and staining of CD20-expressing cells.

Cloning of DNA Expression Constructs Encoding the Activatable IFNγ Protein

The activatable IFNγ construct with protease cleavage site domains are used to construct an activatable IFNγ protein in combination with an anti-CD20 scFv domain and a serum half-life extension element (e.g., a HSA binding peptide or VH domain), with the domains organized. For expression of an activatable IFNγ protein in CHO cells, coding sequences of all protein domains are cloned into a mammalian expression vector system. In brief, gene sequences encoding the activatable IFNγ domain, serum half-life extension element, and CD20 binding domain along with peptide linkers L1 and L2 are separately synthesized and subcloned. The resulting constructs are then ligated together in the order of CD20 binding domain—L1—IFNγ subunit 1—L2—protease cleavage domain—L3—IFNγ subunit2—L4—anti-CD20 scFv—L5—serum half-life extension element to yield a final construct. All expression constructs are designed to contain coding sequences for an N-terminal signal peptide and a C-terminal hexahistidine (6×His)-tag (SEQ ID NO.: 354) to facilitate protein secretion and purification, respectively.

Expression of Activatable IFNγ Proteins in Stably Transfected CHO Cells

A CHO cell expression system (Flp-In®, Life Technologies), a derivative of CHO-K1 Chinese Hamster ovary cells (ATCC, CCL-61) (Kao and Puck, Proc. Natl. Acad Sci USA 1968; 60(4):1275-81), is used. Adherent cells are subcultured according to standard cell culture protocols provided by Life Technologies.

For adaption to growth in suspension, cells are detached from tissue culture flasks and placed in serum-free medium. Suspension-adapted cells are cryopreserved in medium with 10% DMSO.

Recombinant CHO cell lines stably expressing secreted activatable IFNγ proteins are generated by transfection of suspension-adapted cells. During selection with the antibiotic Hygromycin B viable cell densities are measured twice a week, and cells are centrifuged and resuspended in fresh selection medium at a maximal density of $0.1 \times 10^6$ viable cells/mL. Cell pools stably expressing activatable IFNγ proteins are recovered after 2-3 weeks of selection at which point cells are transferred to standard culture medium in shake flasks. Expression of recombinant secreted proteins is confirmed by performing protein gel electrophoresis or flow cytometry. Stable cell pools are cryopreserved in DMSO containing medium.

Activatable IFNγ proteins are produced in 10-day fed-batch cultures of stably transfected CHO cell lines by secretion into the cell culture supernatant. Cell culture supernatants are harvested after 10 days at culture viabilities of typically >75%. Samples are collected from the production cultures every other day and cell density and viability are assessed. On day of harvest, cell culture supernatants are cleared by centrifugation and vacuum filtration before further use.

Protein expression titers and product integrity in cell culture supernatants are analyzed by SDS-PAGE.

Purification of Activatable IFNγ Proteins

Activatable IFNγ proteins are purified from CHO cell culture supernatants in a two-step procedure. The constructs are subjected to affinity chromatography in a first step followed by preparative size exclusion chromatography (SEC) on Superdex 200 in a second step. Samples are buffer-exchanged and concentrated by ultrafiltration to a typical concentration of >1 mg/mL. Purity and homogeneity (typically >90%) of final samples are assessed by SDS PAGE under reducing and non-reducing conditions, followed by immunoblotting using an anti-HSA or anti idiotype antibody as well as by analytical SEC, respectively. Purified proteins are stored at aliquots at −80° C. until use.

Example 15: Determination of Antigen Affinity by Flow Cytometry

The activatable IFNγ proteins of Example 1 are tested for their binding affinities to human CD20$^+$ cells and cynomolgus CD20$^+$ cells.

CD20$^+$ cells are incubated with 100 μL of serial dilutions of the activatable IFNγ proteins of Example 1 and at least one protease. After washing three times with FACS buffer the cells are incubated with 0.1 mL of 10 μg/mL mouse monoclonal anti-idiotype antibody in the same buffer for 45 min on ice. After a second washing cycle, the cells are incubated with 0.1 mL of 15 μg/mL FITC-conjugated goat anti-mouse IgG antibodies under the same conditions as before. As a control, cells are incubated with the anti-His IgG followed by the FITC-conjugated goat anti-mouse IgG antibodies without the activatable IFNγproteins. The cells were then washed again and resuspended in 0.2 mL of FACS buffer containing 2 μg/mL propidium iodide (PI) in order to exclude dead cells. The fluorescence of $1\times10^4$ living cells is measured using a Beckman-Coulter FC500 MPL flow cytometer using the MXP software (Beckman-Coulter, Krefeld, Germany) or a Millipore Guava EasyCyte flow cytometer using the Incyte software (Merck Millipore, Schwalbach, Germany). Mean fluorescence intensities of the cell samples are calculated using CXP software (Beckman-Coulter, Krefeld, Germany) or Incyte software (Merck Millipore, Schwalbach, Germany). After subtracting the fluorescence intensity values of the cells stained with the secondary and tertiary reagents alone the values are then used for calculation of the $K_D$ values with the equation for one-site binding (hyperbola) of the GraphPad Prism (version 6.00 for Windows, GraphPad Software, La Jolla California USA).

CD20 binding and crossreactivity are assessed on the human CD20$^+$ tumor cell lines. The $K_D$ ratio of crossreactivity is calculated using the $K_D$ values determined on the CHO cell lines expressing either recombinant human or recombinant cynomolgus antigens.

Example 16: Cytotoxicity Assay

The activatable IFNγ protein of Example 5 is evaluated in vitro on its mediation of immune response to CD20$^+$ target cells.

Fluorescence labeled CD20$^+$ REC-1 cells (a Mantle cell lymphoma cell line, ATCC CRL-3004) are incubated with isolated PBMC of random donors or CB15 T-cells (standardized T-cell line) as effector cells in the presence of the activatable IFNγ protein of Example 5 and at least one protease. After incubation for 4 h at 37° C. in a humidified incubator, the release of the fluorescent dye from the target cells into the supernatant is determined in a spectrofluorimeter. Target cells incubated without the activatable IFNγ protein of Example 5 and target cells totally lysed by the addition of saponin at the end of the incubation serve as negative and positive controls, respectively.

Based on the measured remaining living target cells, the percentage of specific cell lysis is calculated according to the following formula: [1−(number of living targets$_{(sample)}$/number of living targets$_{(spontaneous)}$)]×100%. Sigmoidal dose response curves and $EC_{50}$ values are calculated by non-linear regression/4-parameter logistic fit using the GraphPad Software. The lysis values obtained for a given antibody concentration are used to calculate sigmoidal dose-response curves by 4 parameter logistic fit analysis using the Prism software.

Example 17: Pharmacokinetics of Activatable IFNγ Proteins

The activatable IFNγ protein of Example 5 is evaluated for half-time elimination in animal studies.

The activatable IFNγ protein is administered to cynomolgus monkeys as a 0.5 mg/kg bolus injection into the saphenous vein. Another cynomolgus monkey group receives a comparable cytokine in size, but lacking a serum half-life extension element. A third and fourth group receive a cytokine with serum half-life extension elements and a cytokine with CD20 and serum half-life extension elements respectively, and both comparable in size to the activatable IFNγ protein. Each test group consists of 5 monkeys. Serum samples are taken at indicated time points, serially diluted, and the concentration of the proteins is determined using a binding ELISA to CD20.

Pharmacokinetic analysis is performed using the test article plasma concentrations. Group mean plasma data for each test article conforms to a multi-exponential profile when plotted against the time post-dosing. The data are fit by a standard two-compartment model with bolus input and first-order rate constants for distribution and elimination phases. The general equation for the best fit of the data for i.v. administration is: $c(t)=Ae^{-\alpha t}+Be^{-\beta t}$, where c(t) is the plasma concentration at time t, A and B are intercepts on the Y-axis, and α and β are the apparent first-order rate constants for the distribution and elimination phases, respectively. The α-phase is the initial phase of the clearance and reflects distribution of the protein into all extracellular fluid of the animal, whereas the second or β-phase portion of the decay curve represents true plasma clearance. Methods for fitting such equations are well known in the art. For example, A=D/V(α−k21)/(α−β), B=D/V(β−k21)/(α−β), and α and β (for α>β) are roots of the quadratic equation: $r^2+(k12+k21+k10)r+k21k10=0$ using estimated parameters of V=volume of distribution, k10=elimination rate, k12=transfer rate from compartment 1 to compartment 2 and k21=transfer rate from compartment 2 to compartment 1, and D=the administered dose. Data analysis: Graphs of concentration versus time profiles are made using KaleidaGraph (KaleidaGraph™ V. 3.09 Copyright 1986-1997. Synergy Software. Reading, Pa.). Values reported as less than reportable (LTR) are not included in the PK analysis and are not represented graphically. Pharmacokinetic parameters are determined by compartmental analysis using WinNonlin software (WinNonlin® Professional V. 3.1 WinNonlin™ Copyright 1998-1999. Pharsight Corporation. Mountain View, Calif.). Pharmacokinetic parameters are computed as described in Ritschel W A and Kearns G L, 1999, IN: *Handbook Of Basic Pharmacokinetics Including Clinical Applications,* 5th edition, American Pharmaceutical Assoc., Washington, D.C. It is expected that the activatable IFNγ protein of Example 5 has improved pharmacokinetic parameters such as an increase in elimination half-time as compared to proteins lacking a serum half-life extension element.

Example 18: Xenograft Tumor Model

The activatable IFNγ protein of Example 5 is evaluated in a xenograft model.

Female immune-deficient NOD/scid mice are sub-lethally irradiated (2 Gy) and subcutaneously inoculated with $4 \times 10^6$ Ramos RA1 cells into the right dorsal flank. When tumors reach 100 to 200 mm$^3$, animals are allocated into 3 treatment groups. Groups 2 and 3 (8 animals each) are intraperitoneally injected with $1.5 \times 10^7$ activated human T-cells. Three days later, animals from Group 3 are subsequently treated with a total of 9 intravenous doses of 50 µg activatable IFNγ protein of Example 5 (qd×9d). Groups 1 and 2 are only treated with vehicle. Body weight and tumor volume are determined for 30 days.

It is expected that animals treated with the activatable IFNγ protein of Example 5 have a statistically significant delay in tumor growth in comparison to the respective vehicle-treated control group.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Example 19: HEK-Blue Assay

HEK-Blue IL12 cells (InvivoGen) were plated in suspension at a concentration of 50,000 cells/well in culture media with or without 15 or 40 mg/ml human serum albumin (HSA) and stimulated with a dilution series of recombinant hIL12, chimeric IL12 (mouse p35/human p40) or activatable hIL12 for 20-24 hours at 37° C. and 5% $CO_2$. Activity of uncleaved and cleaved activatable hIL12 was tested. Cleaved inducible hIL12 was generated by incubation with active MMP9. IL12 activity was assessed by quantification of Secreted Alkaline Phosphatase (SEAP) activity using the reagent QUANTI-Blue (InvivoGen), a colorimetric based assay. Results are shown in FIGS. 7A-7Q, 11A-11B, 12A-12F, 15A-15D, and 26A-26D.

HEK-Blue IL2 cells (InvivoGen) were plated in suspension at a concentration of 50,000 cells/well in culture media with or without 15-40 mg/ml human serum albumin (HSA) and stimulated with a dilution series of recombinant hIL2 or activatable hIL2 for 24 hours at 37° C. and 5% $CO_2$. Activity of uncleaved and cleaved activatable hIL2 was tested. Cleaved inducible hIL2 was generated by incubation with active MMP9. IL12 activity was assessed by quantification of Secreted Alkaline Phosphatase (SEAP) activity using the reagent QUANTI-Blue (InvivoGen), a colorimetric based assay. Exemplary results are shown in FIGS. 1A-1F and FIGS. 24A-24D.

HEK-Blue IFN-a/b cells (InvivoGen) were plated in suspension at a density of 50,000 cells/well in culture media with or without 15 mg/ml human serum albumin (HSA) and stimulated with a dilution series of recombinant human IFNa (or IFNb) and activatable human IFNa (or IFNb) for 20-24 hours at 37° C. and 5% $CO_2$. Activity of uncleaved and cleaved activatable IFNa (or IFNb) was tested. Cleaved inducible IFNa (or IFNb) was generated by incubation with active recombinant protease. Stimulation of HEK-Blue IFN-α/β cells with IFNα (or IFNβ) induces expression of Secreted Alkaline Phosphatase (SEAP) from an ISG54-SEAP reporter. IFNα (or IFNβ) activity was assessed by quantification of SEAP activity using the reagent QUANTI-Blue (InvivoGen), a colorimetric based assay. Results are shown in FIGS. 36A-36H.

Example 20: Splenocyte T-Blast Assay

T-Blasts were induced from murine splenocytes with a 6-day incubation with PHA and a 24 hr incubation with recombinant hIL12. Tblasts were then plated in suspension at a concentration of 200,000 cells/well in culture media with or without 40 mg/ml human serum albumin (HSA) and stimulated with a dilution series of recombinant hIL12 or chimeric IL12 (mouse p35/human p40) or mouse IL12 for 72 hours at 37° C. and 5% $CO_2$. Activity of uncleaved and cleaved IL12 fusion proteins was tested. Cleaved inducible hIL12 was generated by incubation with active MMP9. IL12 activity was assessed by downstream quantification of IFNγ production using a mIFNγ alpha ELISA.

Example 21: In Vivo Delivery of a Protease Activated Fusion Protein Results in Decreased Tumor Growth The chimeric polypeptide is examined to determine if it could have biological effects in vivo. For these experiments a system is used in which tumor cells injected intraperitoneally rapidly and preferentially attach and grow initially on the milky spots, a series of organized immune aggregates found on the omentum (Gerber et al., Am. J. Pathol. 169: 1739-52 (2006)). This system offers a convenient way to examine the effects of fusion protein treatment on tumor growth since fusion proteins can be delivered intraperitoneally multiple times and tumor growth can be analyzed by examining the dissociated omental cells. For these experiments, the Colon 38 cell line, a rapidly growing tumor cell line that expresses both MMP2 and MMP9 in vitro, may be used. The omental tissue normally expresses a relatively small amount of MMP2 and MMP9, but, when Colon 38 tumor is present on the omentum, MMP levels increase.

Using this tumor model, the ability of IL-2 mutein fusion proteins to affect tumor growth is examined. Colon 38 cells are injected intraperitoneally, allowed to attach and grow for 1 day, and then treated daily with fusion protein interaperitoneally. At day 7, the animals are sacrificed and the omenta examined for tumor growth using flow cytometry and by a colony-forming assay.

Example 22: Construction of an Exemplary Activatable Interleukin Protein Targeting CD20

Generation of an Activatable Interleukin Domain

The human IL-12p35 chain canonical sequence is Uniprot Accession No. P29459. The human IL-12p40 chain canonical sequence is Uniprot Accession No. P29460. IL-12p35 and IL-12p40 are cloned into an expression construct. A protease cleavage site is included between the IL-12p35 and IL-12p40 domains. An IL-12 polypeptide capable of binding to CD20 polypeptide present in a tumor or on a tumor cell is produced as follows. A nucleic acid is produced that contains nucleic acid sequences: (1) encoding an IFNγ polypeptide sequence and (2) one or more polypeptide linkers. Activatable interleukin plasmid constructs can have optional Flag, His or other affinity tags, and are electroporated into HEK293 or other suitable human or mammalian cell lines and purified. Validation assays include T cell activation assays using T cells responsive to IL-12 stimulation in the presence of a protease.

Generation of a scFv CD20 Binding Domain

CD20 is one of the cell surface proteins present on B-lymphocytes. CD20 antigen is found in normal and malignant pre-B and mature B lymphocytes, including those in over 90% of B-cell non-Hodgkin's lymphomas (NHL). The antigen is absent in hematopoietic stem cells, activated B lymphocytes (plasma cells) and normal tissue. As such, several antibodies mostly of murine origin have been described: 1F5, 2B8/C2B8, 2H7, and 1H4.

Human or humanized anti-CD20 antibodies are therefore used to generate scFv sequences for CD20 binding domains of an activatable interleukin protein. DNA sequences coding for human or humanized VL and VH domains are obtained, and the codons for the constructs are, optionally, optimized for expression in cells from *Homo sapiens*. The order in which the VL and VH domains appear in the scFv is varied (i.e., VL-VH, or VH-VL orientation), and three copies of the "G4S" (SEQ ID NO.: 449) or "$G_4S$" (SEQ ID NO.: 449) subunit $(G_4S)_3$ (SEQ ID NO.: 452) connect the variable domains to create the scFv domain. Anti-CD20 scFv plasmid constructs can have optional Flag, His or other affinity tags, and are electroporated into HEK293 or other suitable human or mammalian cell lines and purified. Validation assays include binding analysis by FACS, kinetic analysis using Proteon, and staining of CD20-expressing cells.

Cloning of DNA Expression Constructs Encoding the Activatable Interleukin Protein The activatable interleukin construct with protease cleavage site domains are used to construct an activatable interleukin protein in combination with an anti-CD20 scFv domain and a serum half-life extension element (e.g., a HSA binding peptide or VH domain). For expression of an activatable interleukin protein in CHO cells, coding sequences of all protein domains are cloned into a mammalian expression vector system. In brief, gene sequences encoding the activatable interleukin domain, serum half-life extension element, and CD20 binding domain along with peptide linkers L1 and L2 are separately synthesized and subcloned. The resulting constructs are then ligated together in the order of CD20 binding domain—L1—IL-12p35—L2—protease cleavage domain—L3—IL-12p40—L4—anti-CD20 scFv—L5—serum half-life extension element to yield a final construct. All expression constructs are designed to contain coding sequences for an N-terminal signal peptide and a C-terminal hexahistidine (6×His)-tag (SEQ ID NO.: 354) to facilitate protein secretion and purification, respectively.

Expression of Activatable Interleukin Proteins in Stably Transfected CHO Cells

A CHO cell expression system (Flp-In®, Life Technologies), a derivative of CHO-K1 Chinese Hamster ovary cells (ATCC, CCL-61) (Kao and Puck, Proc. Natl. Acad Sci USA 1968; 60(4):1275-81), is used. Adherent cells are subcultured according to standard cell culture protocols provided by Life Technologies.

For adaption to growth in suspension, cells are detached from tissue culture flasks and placed in serum-free medium. Suspension-adapted cells are cryopreserved in medium with 10% DMSO.

Recombinant CHO cell lines stably expressing secreted activatable interleukin proteins are generated by transfection of suspension-adapted cells. During selection with the antibiotic Hygromycin B viable cell densities are measured twice a week, and cells are centrifuged and resuspended in fresh selection medium at a maximal density of $0.1\times10^6$ viable cells/mL. Cell pools stably expressing activatable interleukin proteins are recovered after 2-3 weeks of selection at which point cells are transferred to standard culture medium in shake flasks. Expression of recombinant secreted proteins is confirmed by performing protein gel electrophoresis or flow cytometry. Stable cell pools are cryopreserved in DMSO containing medium.

Activatable interleukin proteins are produced in 10-day fed-batch cultures of stably transfected CHO cell lines by secretion into the cell culture supernatant. Cell culture supernatants are harvested after 10 days at culture viabilities of typically >75%. Samples are collected from the production cultures every other day and cell density and viability are assessed. On day of harvest, cell culture supernatants are cleared by centrifugation and vacuum filtration before further use.

Protein expression titers and product integrity in cell culture supernatants are analyzed by SDS-PAGE.

Purification of Activatable Interleukin Proteins

Activatable interleukin proteins are purified from CHO cell culture supernatants in a two-step procedure. The constructs are subjected to affinity chromatography in a first step followed by preparative size exclusion chromatography (SEC) on Superdex 200 in a second step. Samples are buffer-exchanged and concentrated by ultrafiltration to a typical concentration of >1 mg/mL. Purity and homogeneity (typically >90%) of final samples are assessed by SDS PAGE under reducing and non-reducing conditions, followed by immunoblotting using an anti-HSA or anti idiotype antibody as well as by analytical SEC, respectively. Purified proteins are stored at aliquots at −80° C. until use.

Example 23: Determination of Antigen Affinity by Flow Cytometry

The activatable interleukin proteins of Example 5 are tested for their binding affinities to human $CD20^+$ cells and cynomolgus $CD20^+$ cells.

$CD20^+$ cells are incubated with 100 μL of serial dilutions of the activatable interleukin proteins of Example 5 and at least one protease. After washing three times with FACS buffer the cells are incubated with 0.1 mL of 10 μg/mL mouse monoclonal anti-idiotype antibody in the same buffer for 45 min on ice. After a second washing cycle, the cells are incubated with 0.1 mL of 15 μg/mL FITC-conjugated goat anti-mouse IgG antibodies under the same conditions as before. As a control, cells are incubated with the anti-His IgG followed by the FITC-conjugated goat anti-mouse IgG antibodies without the activatable interleukin proteins. The cells were then washed again and resuspended in 0.2 mL of FACS buffer containing 2 μg/mL propidium iodide (PI) in order to exclude dead cells. The fluorescence of $1\times10^4$ living cells is measured using a Beckman-Coulter FC500 MPL flow cytometer using the MXP software (Beckman-Coulter, Krefeld, Germany) or a Millipore Guava EasyCyte flow cytometer using the Incyte software (Merck Millipore, Schwalbach, Germany). Mean fluorescence intensities of the cell samples are calculated using CXP software (Beckman-Coulter, Krefeld, Germany) or Incyte software (Merck Millipore, Schwalbach, Germany). After subtracting the fluorescence intensity values of the cells stained with the secondary and tertiary reagents alone the values are then used for calculation of the $K_D$ values with the equation for one-site binding (hyperbola) of the GraphPad Prism (version 6.00 for Windows, GraphPad Software, La Jolla California USA).

CD20 binding and crossreactivity are assessed on the human CD20+ tumor cell lines. The $K_D$ ratio of crossreactivity is calculated using the $K_D$ values determined on the CHO cell lines expressing either recombinant human or recombinant cynomolgus antigens.

Example 24: Cytotoxicity Assay

The activatable interleukin protein of Example 5 is evaluated in vitro on its mediation of immune response to CD20+ target cells.

Fluorescence labeled CD20+ REC-1 cells (a Mantle cell lymphoma cell line, ATCC CRL-3004) are incubated with isolated PBMC of random donors or CB15 T-cells (standardized T-cell line) as effector cells in the presence of the activatable interleukin protein of Example 5 and at least one protease. After incubation for 4 h at 37° C. in a humidified incubator, the release of the fluorescent dye from the target cells into the supernatant is determined in a spectrofluorimeter. Target cells incubated without the activatable interleukin protein of Example 5 and target cells totally lysed by the addition of saponin at the end of the incubation serve as negative and positive controls, respectively.

Based on the measured remaining living target cells, the percentage of specific cell lysis is calculated according to the following formula: [1−(number of living targets$_{(sample)}$/number of living targets$_{(spontaneous)}$)]×100%. Sigmoidal dose response curves and $EC_{50}$ values are calculated by non-linear regression/4-parameter logistic fit using the GraphPad Software. The lysis values obtained for a given antibody concentration are used to calculate sigmoidal dose-response curves by 4 parameter logistic fit analysis using the Prism software.

Example 25: Pharmacokinetics of Activatable Interleukin Proteins

The activatable interleukin protein of Example 5 is evaluated for half-time elimination in animal studies.

The activatable interleukin protein is administered to cynomolgus monkeys as a 0.5 mg/kg bolus injection into the saphenous vein. Another cynomolgus monkey group receives a comparable cytokine in size, but lacking a serum half-life extension element. A third and fourth group receive a cytokine with serum half-life extension elements and a cytokine with CD20 and serum half-life extension elements respectively, and both comparable in size to the activatable interleukin protein. Each test group consists of 5 monkeys. Serum samples are taken at indicated time points, serially diluted, and the concentration of the proteins is determined using a binding ELISA to CD20.

Pharmacokinetic analysis is performed using the test article plasma concentrations. Group mean plasma data for each test article conforms to a multi-exponential profile when plotted against the time post-dosing. The data are fit by a standard two-compartment model with bolus input and first-order rate constants for distribution and elimination phases. The general equation for the best fit of the data for i.v. administration is: $c(t)=Ae^{-\alpha t}+Be^{-\beta t}$, where $c(t)$ is the plasma concentration at time t, A and B are intercepts on the Y-axis, and $\alpha$ and $\beta$ are the apparent first-order rate constants for the distribution and elimination phases, respectively. The $\alpha$-phase is the initial phase of the clearance and reflects distribution of the protein into all extracellular fluid of the animal, whereas the second or $\beta$-phase portion of the decay curve represents true plasma clearance. Methods for fitting such equations are well known in the art. For example, $A=D/V(\alpha-k21)/(\alpha-\beta)$, $B=D/V(\beta-k21)/(\alpha-\beta)$, and $\alpha$ and $\beta$ (for $\alpha>\beta$) are roots of the quadratic equation: $r^2+(k12+k21+k10)r+k21k10=0$ using estimated parameters of V=volume of distribution, k10=elimination rate, k12=transfer rate from compartment 1 to compartment 2 and k21=transfer rate from compartment 2 to compartment 1, and D=the administered dose.

Data analysis: Graphs of concentration versus time profiles are made using KaleidaGraph (KaleidaGraph™ V. 3.09 Copyright 1986-1997. Synergy Software. Reading, Pa.). Values reported as less than reportable (LTR) are not included in the PK analysis and are not represented graphically. Pharmacokinetic parameters are determined by compartmental analysis using WinNonlin software (WinNonlin® Professional V. 3.1 WinNonlin™ Copyright 1998-1999. Pharsight Corporation. Mountain View, Calif.). Pharmacokinetic parameters are computed as described in Ritschel W A and Kearns G L, 1999, IN: *Handbook Of Basic Pharmacokinetics Including Clinical Applications,* 5th edition, American Pharmaceutical Assoc., Washington, D.C.

It is expected that the activatable interleukin protein of Example 5 has improved pharmacokinetic parameters such as an increase in elimination half-time as compared to proteins lacking a serum half-life extension element.

Example 26: Xenograft Tumor Model

The activatable interleukin protein of Example 5 is evaluated in a xenograft model.

Female immune-deficient NOD/scid mice are sub-lethally irradiated (2 Gy) and subcutaneously inoculated with $4\times10^6$ Ramos RA1 cells into the right dorsal flank. When tumors reach 100 to 200 mm³, animals are allocated into 3 treatment groups. Groups 2 and 3 (8 animals each) are intraperitoneally injected with $1.5\times10^7$ activated human T-cells. Three days later, animals from Group 3 are subsequently treated with a total of 9 intravenous doses of 50 μg activatable interleukin protein of Example 5 (qd×9d). Groups 1 and 2 are only treated with vehicle. Body weight and tumor volume are determined for 30 days.

It is expected that animals treated with the activatable interleukin protein of Example 5 have a statistically significant delay in tumor growth in comparison to the respective vehicle-treated control group.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Example 27: MC38 Experiments

The MC38 cell line, a rapidly growing colon adenocarcinoma cell line that expresses MMP9 in vitro, was used. Using this tumor model, the ability of fusion proteins to affect tumor growth was examined.

Example 27a: MC38 IL-2POC

Agents and Treatment:

| Gr. | N | Agent | Formulation dose | Route | Schedule |
|---|---|---|---|---|---|
| 1# | 10 | Vehicle | — | ip | biwk × 3 |
| 2 | 7 | ACP16 | 700 µg/animal | ip | biwk × 3 |
| 3 | 7 | ACP16 | 230 µg/animal | ip | biwk × 3 |
| 4 | 7 | ACP16 | 70 µg/animal | ip | biwk × 3 |
| 5 | 7 | ACP16 | 55 ug/animal | ip | biwk × 3 |
| 6 | 7 | ACP16 | 17 µg/animal | ip | biwk × 3 |
| 7 | 7 | ACP132 | 361 µg/animal | ip | biwk × 3 |
| 8 | 7 | ACP132 | 119 µg/animal | ip | biwk × 3 |
| 9 | 7 | ACP132 | 36 µg/animal | ip | biwk × 3 |
| 10 | 7 | ACP132 | 28 µg/animal | ip | biwk × 3 |
| 11 | 7 | ACP132 | 9 µg/animal | ip | biwk × 3 |
| 12 | 7 | ACP21 | 540 µg/animal | ip | biwk × 3 |
| 13 | 7 | ACP21 | 177 µg/animal | ip | biwk × 3 |
| 14 | 7 | ACP21 | 54 µg/animal | ip | biwk × 3 |
| 15 | 7 | ACP21 | 42 µg/animal | ip | biwk × 3 |
| 16 | 7 | ACP21 | 13 µg/animal | ip | biwk × 3 |

ControlGroup

Procedures:

Mice were anaesthetized with isoflurane for implant of cells to reduce the ulcerations. 308 CR female C57BL/6 mice were set up with 5×10⁵ MC38 tumor cells in 0% Matrigel sc in flank. Cell Injection Volume was 0.1 mL/mouse. Mouse age at start date was 8 to 12 weeks. Pair matches were performed when tumors reach an average size of 100-150 mm³ and begin treatment. Body weights were taken at initiation and then biweekly to the end. Caliper measurements were taken biweekly to the end. Any adverse reactions were to be reported immediately. Any individual animal with a single observation of >than 30% body weight loss or three consecutive measurements of >25% body weight loss was euthanized. Any group with a mean body weight loss of >20% or >10% mortality stopped dosing; the group was not euthanized and recovery is allowed. Within a group with >20% weight loss, individuals hitting the individual body weight loss endpoint were euthanized. If the group treatment related body weight loss is recovered to within 10% of the original weights, dosing resumed at a lower dose or less frequent dosing schedule. Exceptions to non-treatment body weight % recovery were allowed on a case-by-case basis. Endpoint was tumor growth delay (TGD). Animals were monitored individually. The endpoint of the experiment was a tumor volume of 1500 mm³ or 45 days, whichever comes first. Responders were followed longer. When the endpoint was reached, the animals are to be euthanized.

Figure 35:
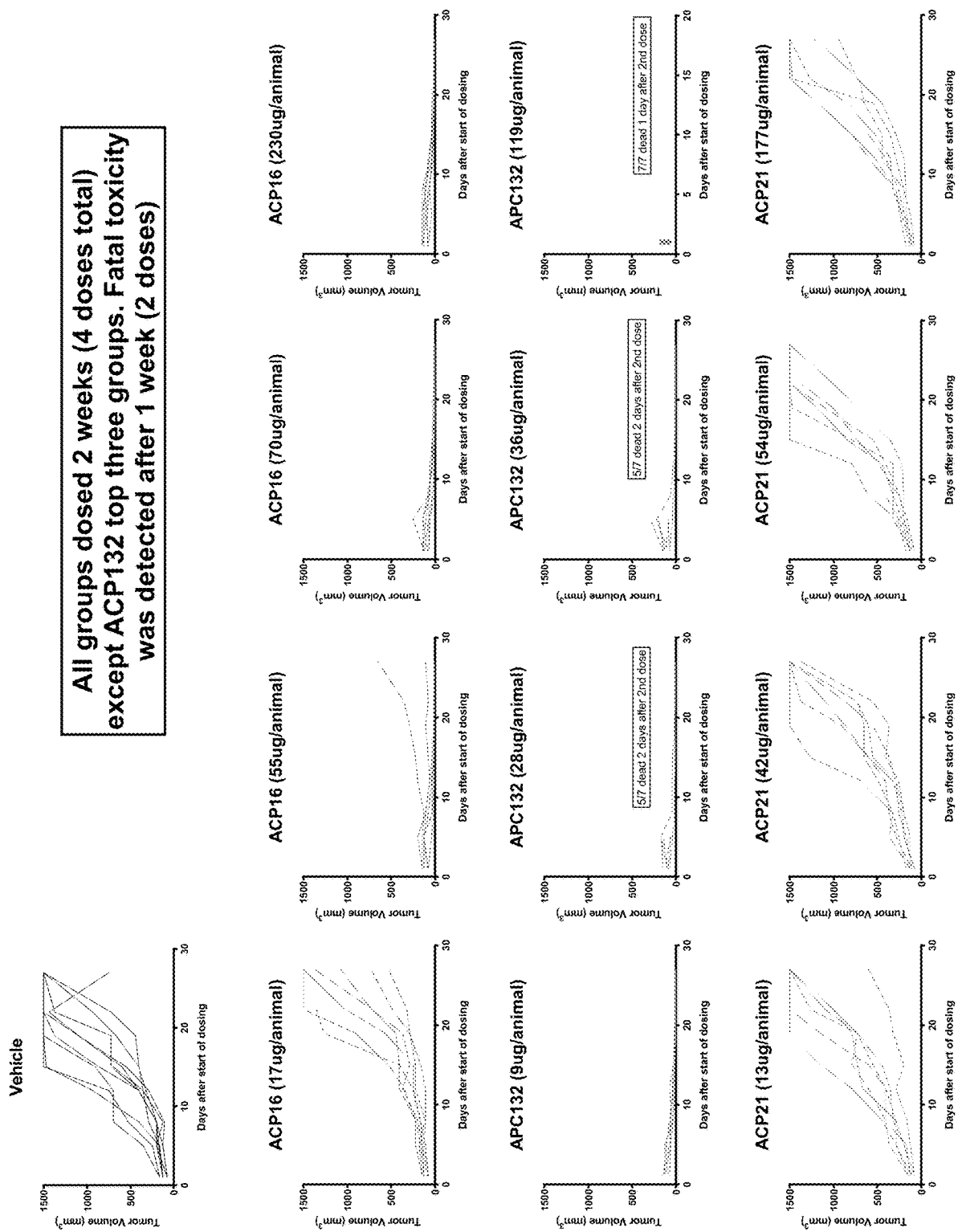
FIG. 35 a series of spaghetti plots showing activity of fusion proteins in an MC38 mouse xenograft model. All mouse groups were given four doses total except for the highest three doses of ACP132, wherein fatal toxicity was detected after 1 week/2 doses. Shown are vehicle alone (top), 17, 55, 70, and 230 µg ACP16 (top full row), 9, 28, 36, and 119 µg ACP132 (middle full row), and 13, 42, 54, and 177 µg ACP21 (bottom full row). Each line in the plots represents an individual animal.
Figure 36A:
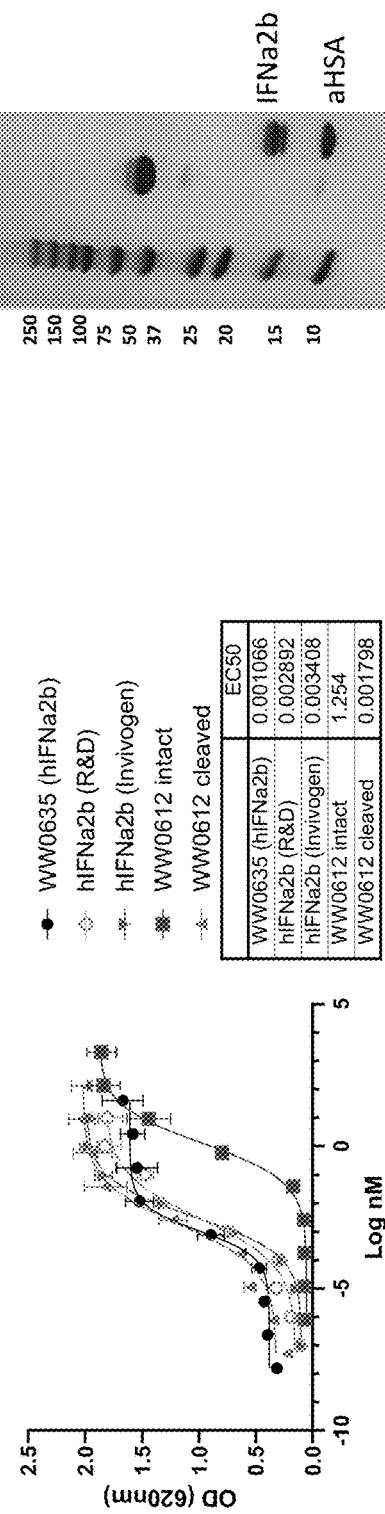
Figure 36B:
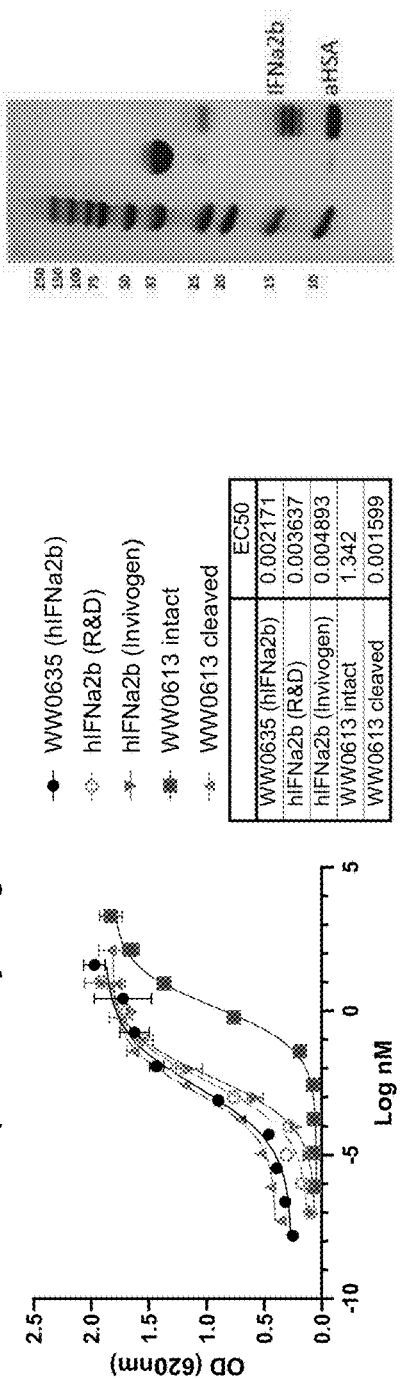
Figure 36C:
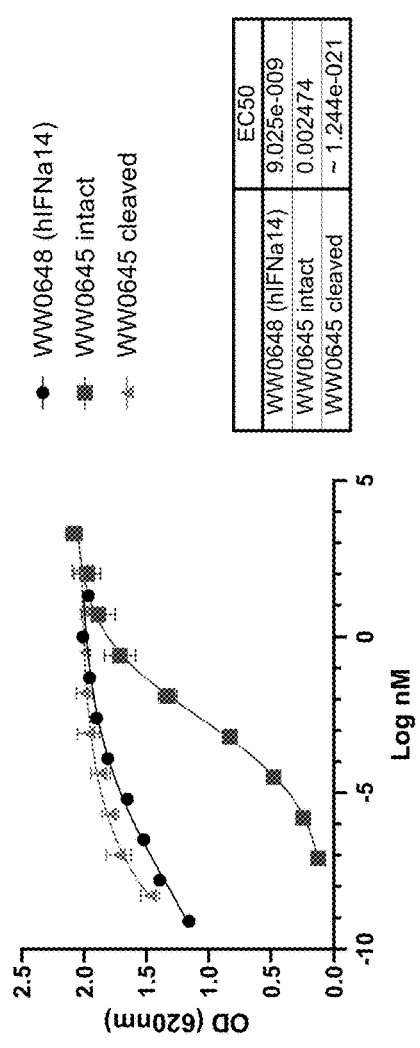
Figure 36D:
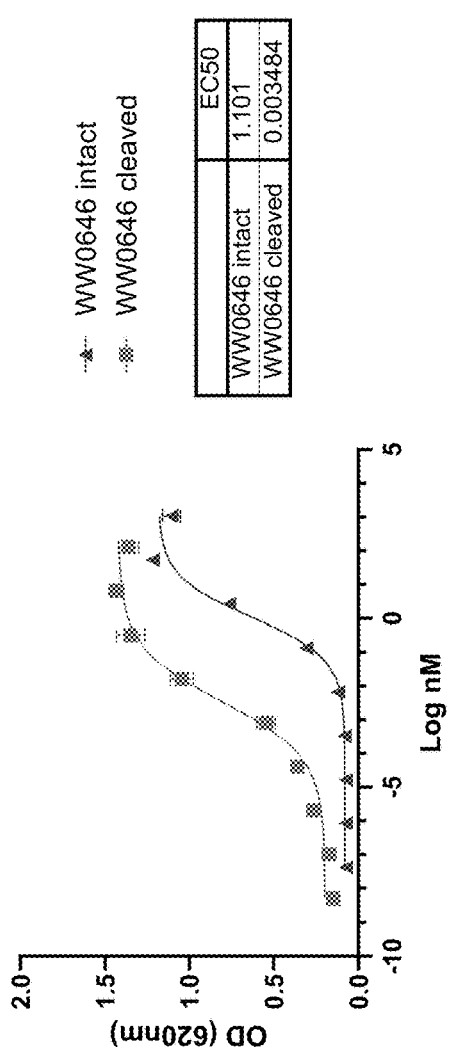
Figure 36E:
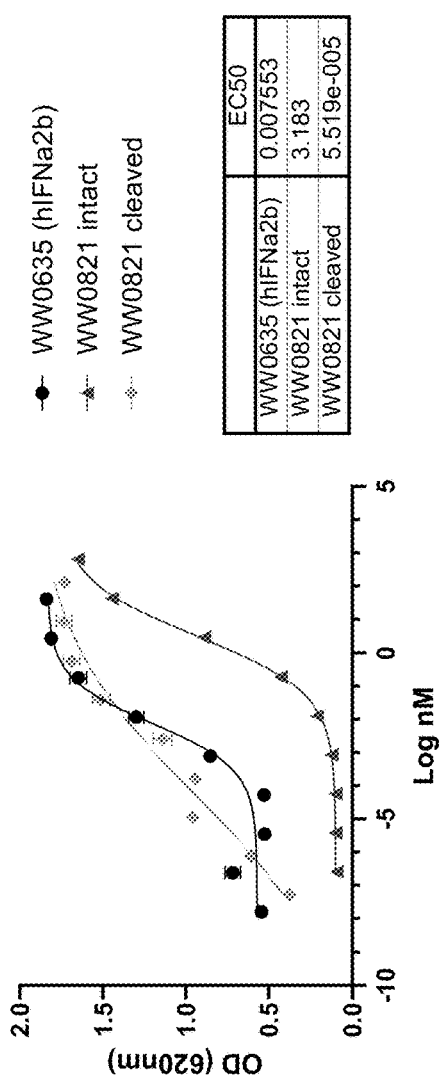
Figure 36F:
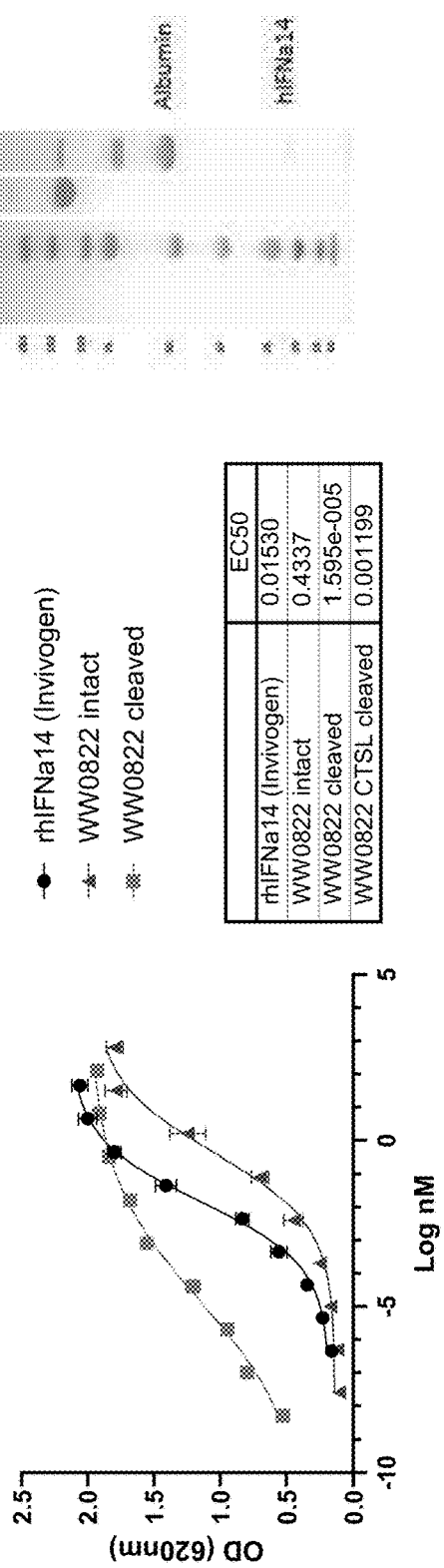
Figure 37A:
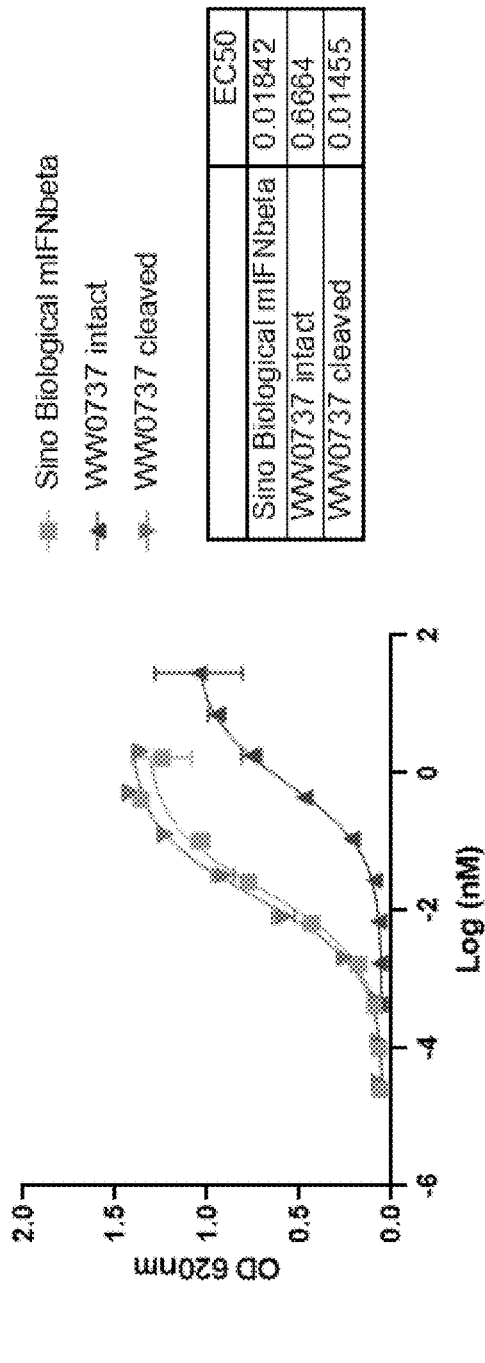
FIGS. 37A-37D are a series of graphs showing activity of fusion proteins in the HEK-Blue IFN-α/β reporter assay.
Figure 37B:
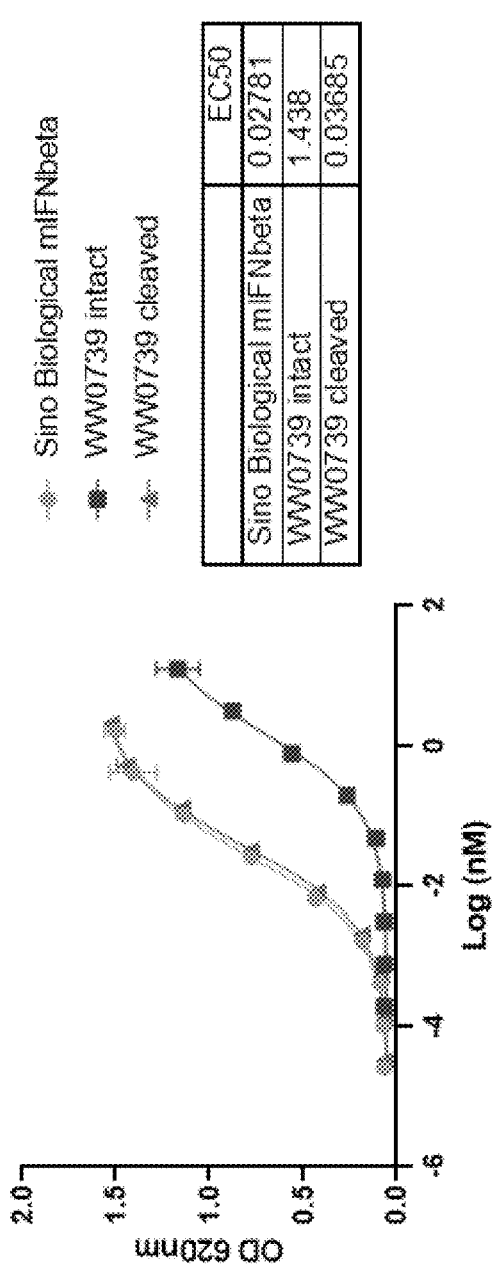
Figure 37C:
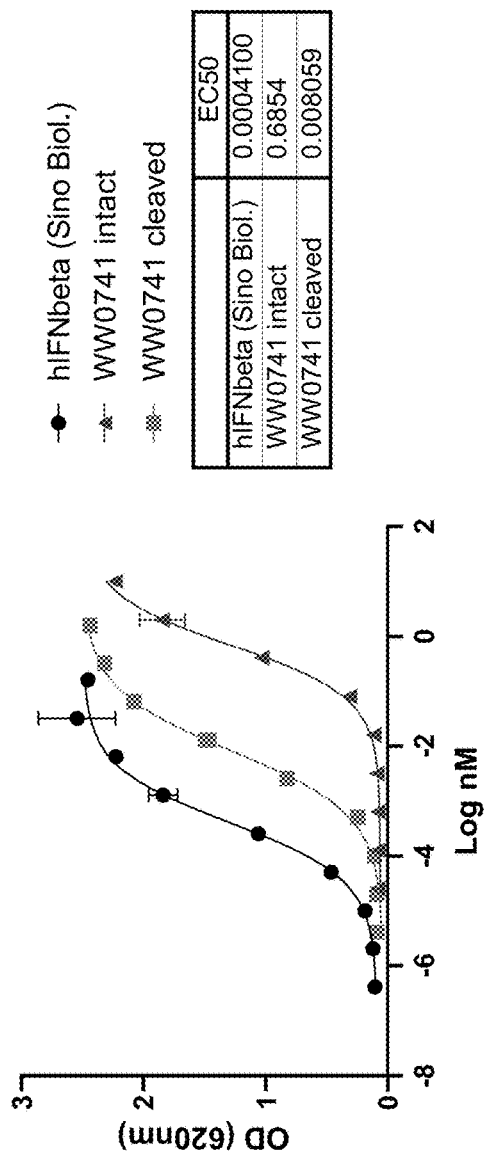
Figure 37D:
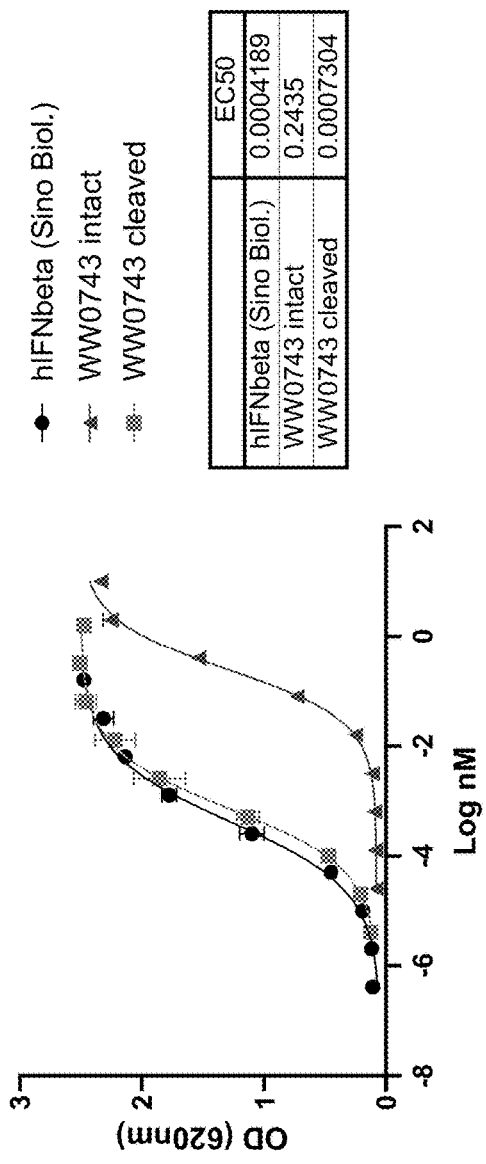

Results are shown in FIG. 35.

Example 27b: MC38 IL-2 POC. Treatment with ACP16, ACP124 and ACP130

Agents and Treatment:

| Gr. | N | Agent | Formulation dose | Route | Schedule |
|---|---|---|---|---|---|
| 1# | 12 | Vehicle | — | ip | biwk × 2 |
| 2 | 8 | ACP16 | 4.4 µg/animal | ip | biwk × 2 |
| 3 | 8 | ACP16 | 17 µg/animal | ip | biwk × 2 |
| 4 | 8 | ACP16 | 70 µg/animal | ip | biwk × 2 |
| 5 | 8 | ACP16 | 232 µg/animal | ip | biwk × 2 |
| 6 | 8 | ACP130 | 19 µg/animal | ip | biwk × 2 |
| 7 | 8 | ACP130 | 45 µg/animal | ip | biwk × 2 |
| 8 | 8 | ACP130 | 180 µg/animal | ip | biwk × 2 |
| 9 | 8 | ACP130 | 600 µg/animal | ip | biwk × 1 |
| 12 | 8 | ACP124 | 17 µg/animal | ip | biwk × 2 |
| 13 | 8 | ACP124 | 70 µg/animal | ip | biwk × 2 |
| 14 | 8 | ACP124 | 230 µg/animal | ip | biwk × 2 |
| 15 | 8 | ACP124 | 700 µg/animal | ip | biwk × 2 |
| 16 | 8 | IL-2-WTI | 12 µg/animal | ip | bid × 5 then 2-day pause then bid × 5 then 2-day pause |
| 17 | 8 | IL-2-WTI | 36 µg/animal | ip | bid × 5 then 2-day pause then bid × 5 then 2-day pause |

ControlGroup

Procedures:

Mice were anaesthetized with isoflurane for implant of cells to reduce the ulcerations. 308 CR female C57BL/6 mice were set up with 5×10⁵ MC38 tumor cells in 0% Matrigel sc in flank. Cell Injection Volume was 0.1 mL/mouse. Mouse age at start date was 8 to 12 weeks. Pair matches were performed when tumors reach an average size of 100-150 mm³ and begin treatment. Body weights were taken at initiation and then biweekly to the end. Caliper measurements were taken biweekly to the end. Any adverse reactions were to be reported immediately. Any individual animal with a single observation of >than 30% body weight loss or three consecutive measurements of >25% body weight loss was euthanized. Any group with a mean body weight loss of >20% or >10% mortality stopped dosing; the group was not euthanized and recovery is allowed. Within a group with >20% weight loss, individuals hitting the individual body weight loss endpoint were euthanized. If the group treatment related body weight loss is recovered to within 10% of the original weights, dosing resumed at a lower dose or less frequent dosing schedule. Exceptions to non-treatment body weight % recovery were allowed on a case-by-case basis. Endpoint was tumor growth delay (TGD). Animals were monitored individually. The endpoint of the experiment was a tumor volume of 1500 mm³ or 45 days, whichever comes first. Responders were followed longer. When the endpoint was reached, the animals are to be euthanized.

Results are shown in FIGS. 31A-31C and FIGS. 32B-32C. Survival curves are shown in FIGS. 34A-34D.

Example 27c: MC38 IFNα and IL-12

Agents and Treatment:

| Gr. | N | Agent | Formulation dose | Route | Schedule |
|---|---|---|---|---|---|
| 1# | 12 | Vehicle | — | ip | biwk × 3 |
| 2 | 8 | ACP11 | 17.5 µg/animal | ip | biwk × 3 |
| 3 | 8 | ACP11 | 175 µg/animal | ip | biwk × 3 |
| 4 | 8 | ACP11 | 525 µg/animal | ip | biwk × 3 |
| 5 | 8 | ACP31 | 33 µg/animal | ip | biwk × 3 |
| 6 | 8 | ACP31 | 110 µg/animal | ip | biwk × 3 |
| 7 | 8 | ACP31 | 330 µg/animal | ip | biwk × 3 |
| 8 | 8 | ACP131 | 1 µg/animal | ip | bid × 5 then 2-day pause then bid × 5 then 2-day pause |
| 9 | 8 | ACP131 | 10 µg/animal | ip | bid × 5 then 2-day pause then bid × 5 then 2-day pause |
| 10 | 8 | ACP131 | 30 µg/animal | ip | bid × 5 then 2-day pause then bid × 5 then 2-day pause |
| 11 | 8 | mIFNa1-WTI | 1 µg/animal | ip | bid × 5 then 2-day pause then bid × 5 then 2-day pause |
| 12 | 8 | mIFNa1-WTI | 10 µg/animal | ip | bid × 5 then 2-day pause then bid × 5 then 2-day pause |
| 13 | 8 | IL-12-HM-WTI | 2 µg/animal | ip | bid × 5 then 2-day pause then bid × 5 then 2-day pause |
| 14 | 8 | IL-12-HM-WTI | 10 µg/animal | ip | bid × 5 then 2-day pause then bid × 5 then 2-day pause |
| 15 | 8 | ACP131 | 5 µg/animal | itu | bid × 5 then 2-day pause then bid × 5 then 2-day pause |

ControlGroup

Figure 29A:
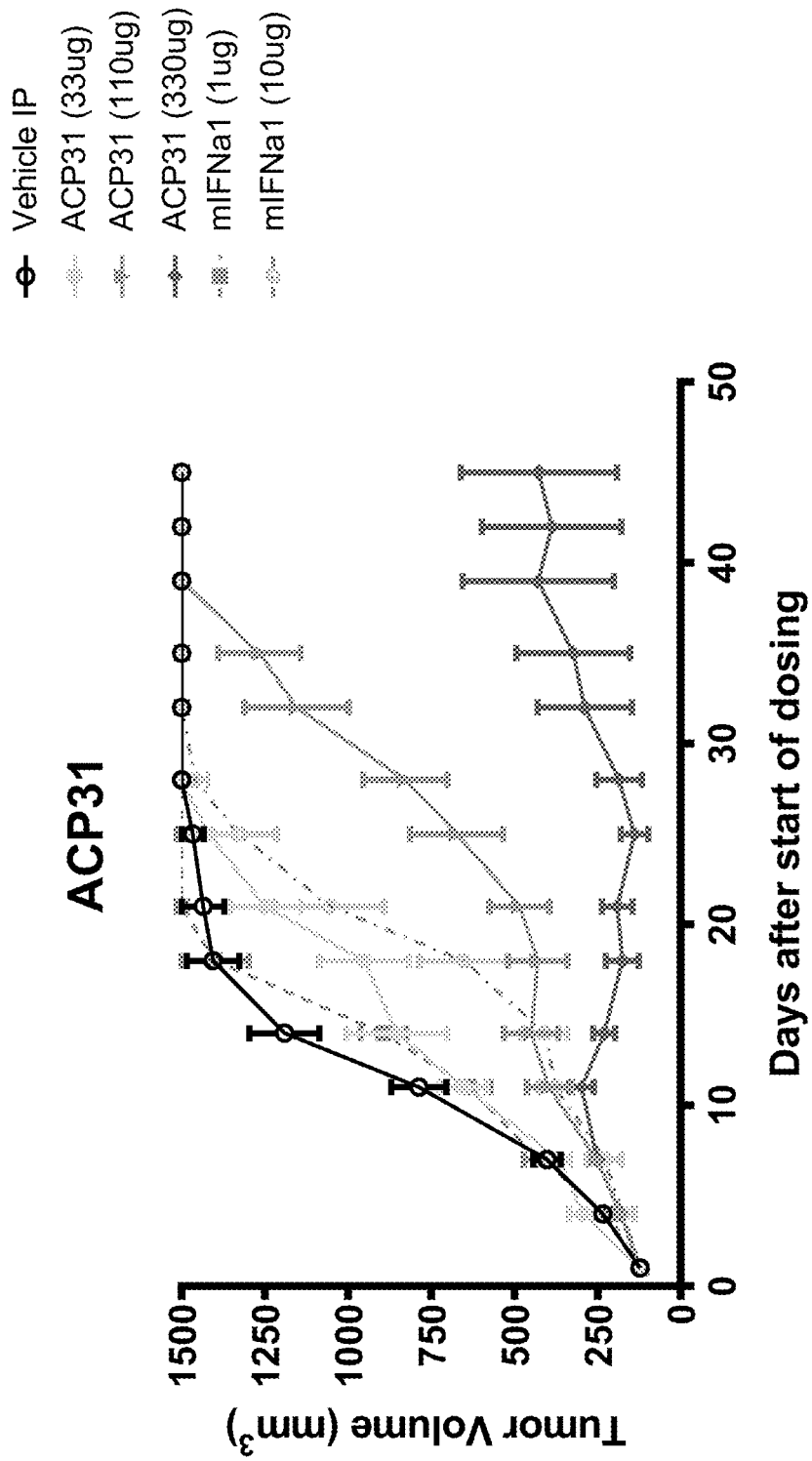
FIGS. 29A-29B are two graphs showing results of analyzing ACP31 (mouse IFNα1 fusion protein) and ACP11 (a human p40/murine p35 IL12 fusion protein) in a tumor xenograft model.
Figure 29B:
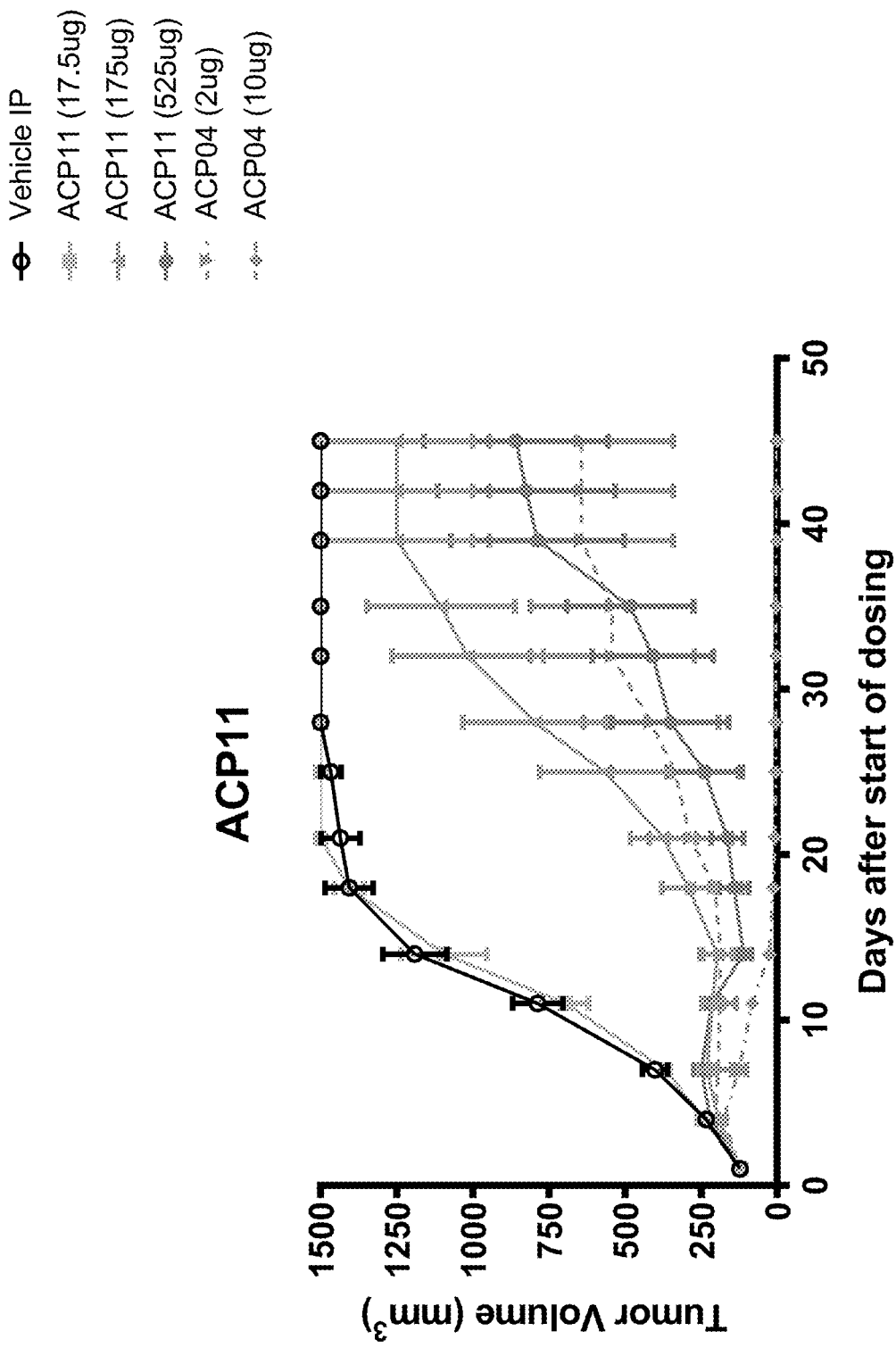
Figure 30A:
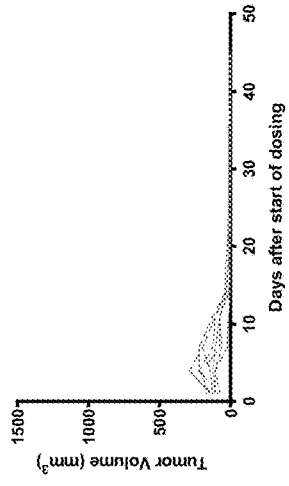
FIGS. 30A-30F are a series of spaghetti plots showing tumor volume over time in a mouse xenograft tumor model in mice each treated with vehicle alone (FIG. 30A), 2 µg ACP04 (FIG. 30B), 10 µg ACP04 (FIG. 30C), 17.5 µg ACP11 (FIG. 30D), 175 µg ACP11 (FIG. 30E), and 525 µg ACP11 (FIG. 30F). Each line represents a single mouse.
Figure 30B:
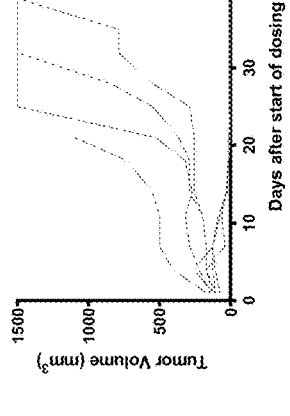
Figure 30C:
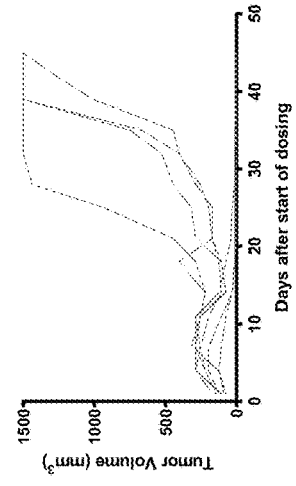
Figure 30D:
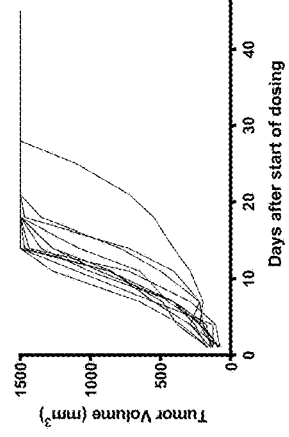
Figure 30E:
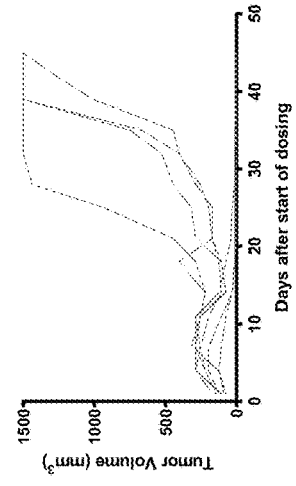
Figure 30F:
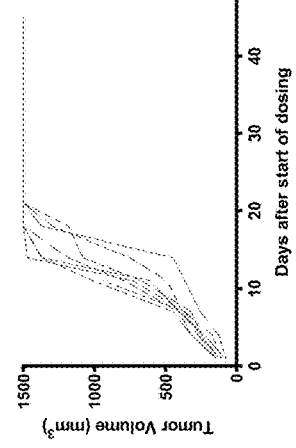
Figure 31A:
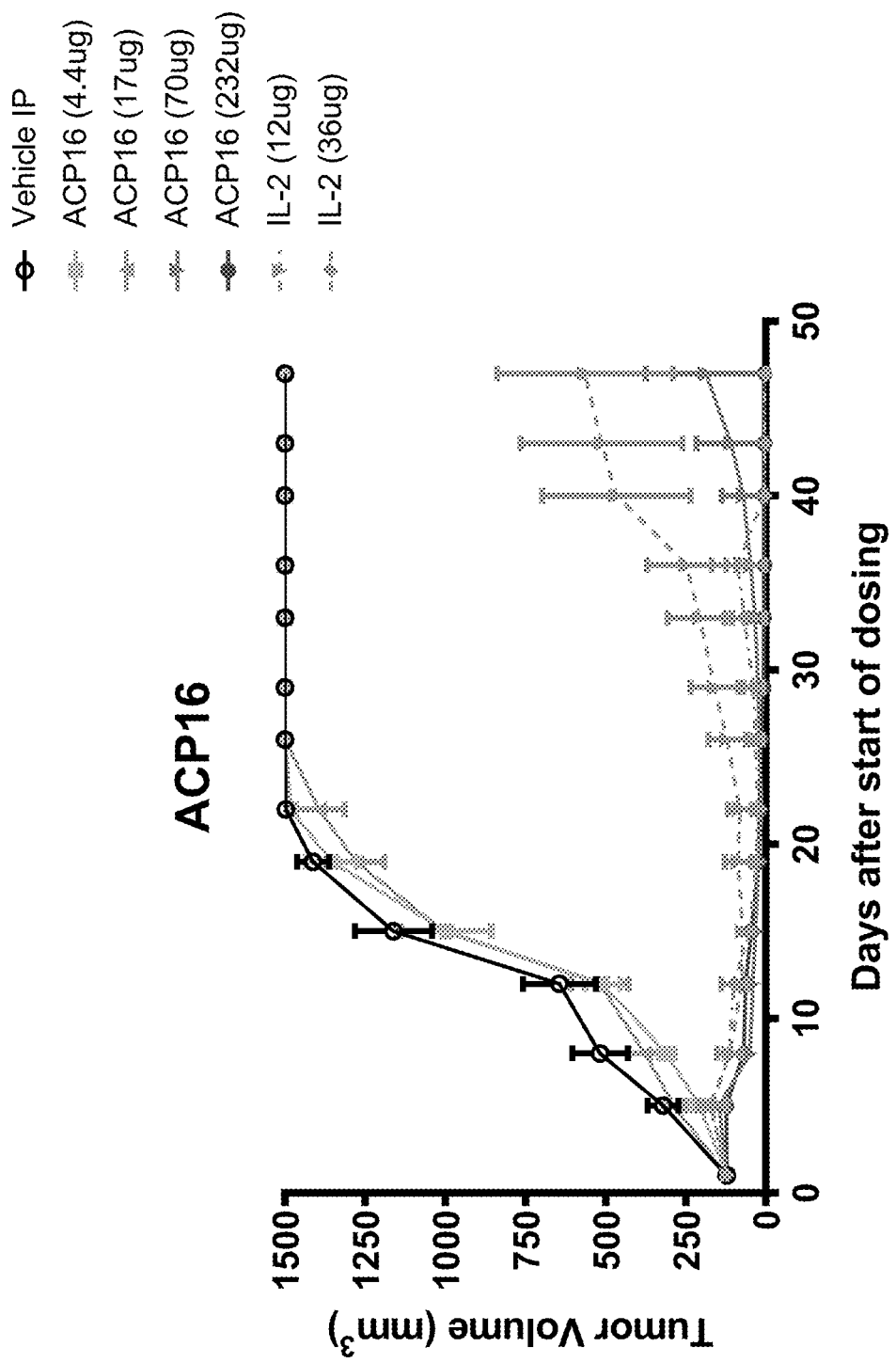
FIG. 31A-31C are three graphs showing results of analyzing ACP16 and ACP124 in a tumor xenograft model.
Figure 31B:
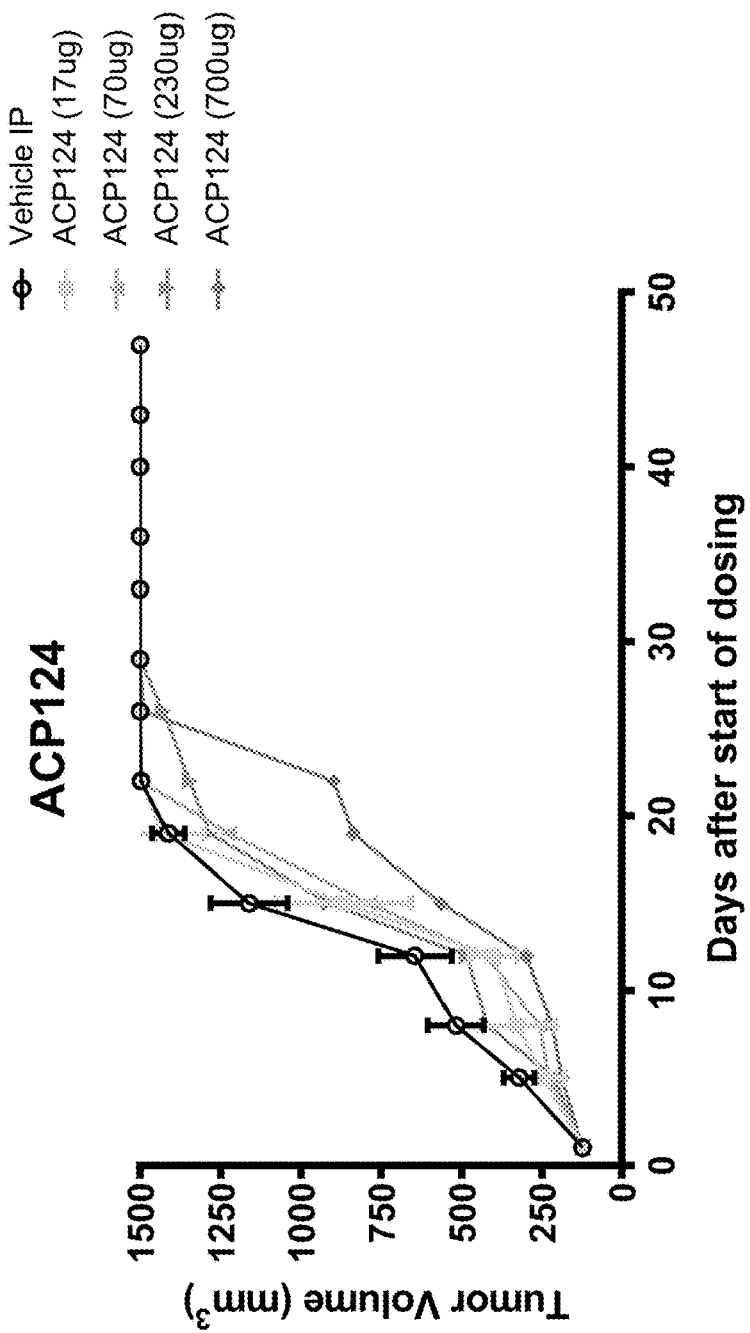
Figure 31C:
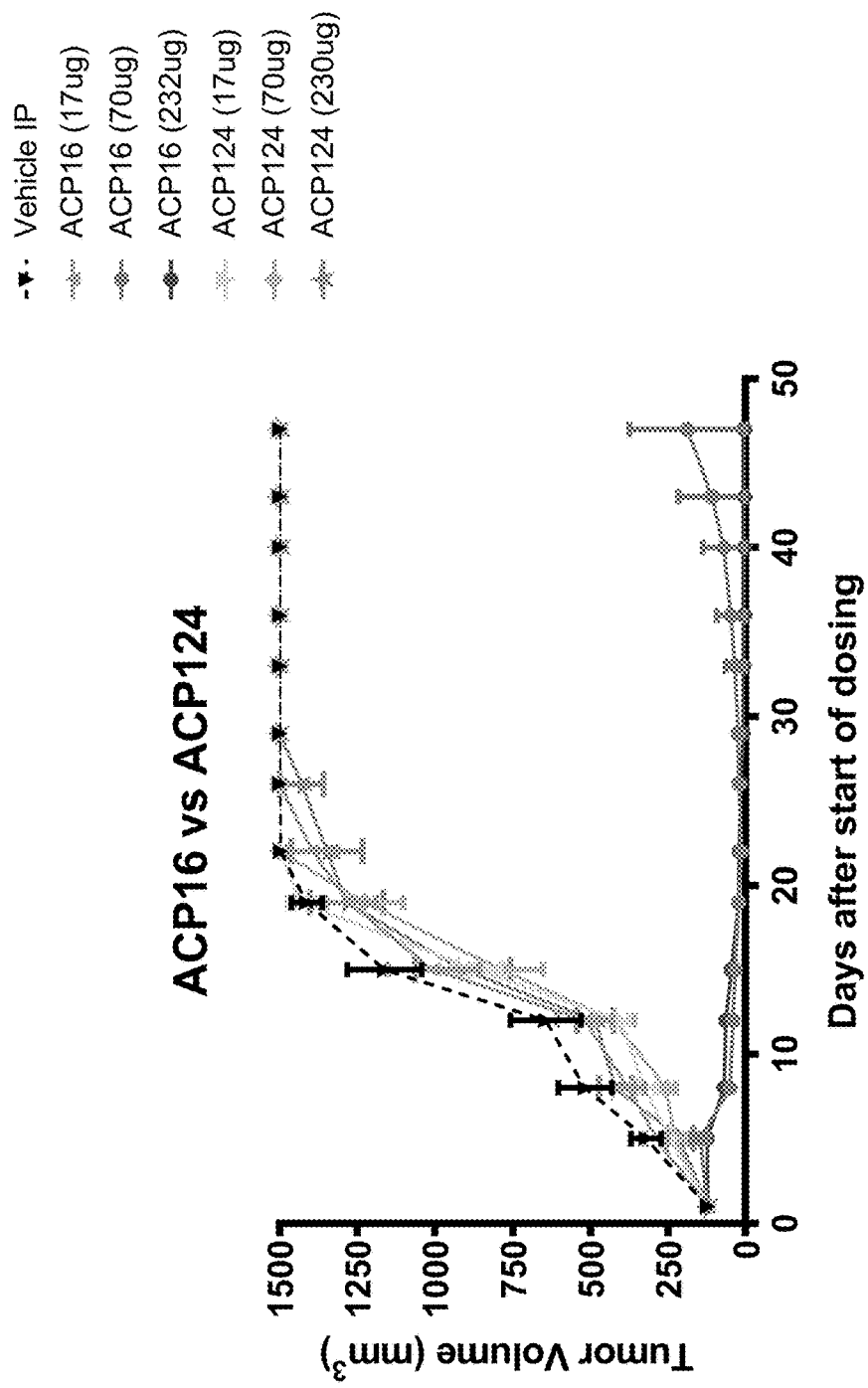
Figure 32A:
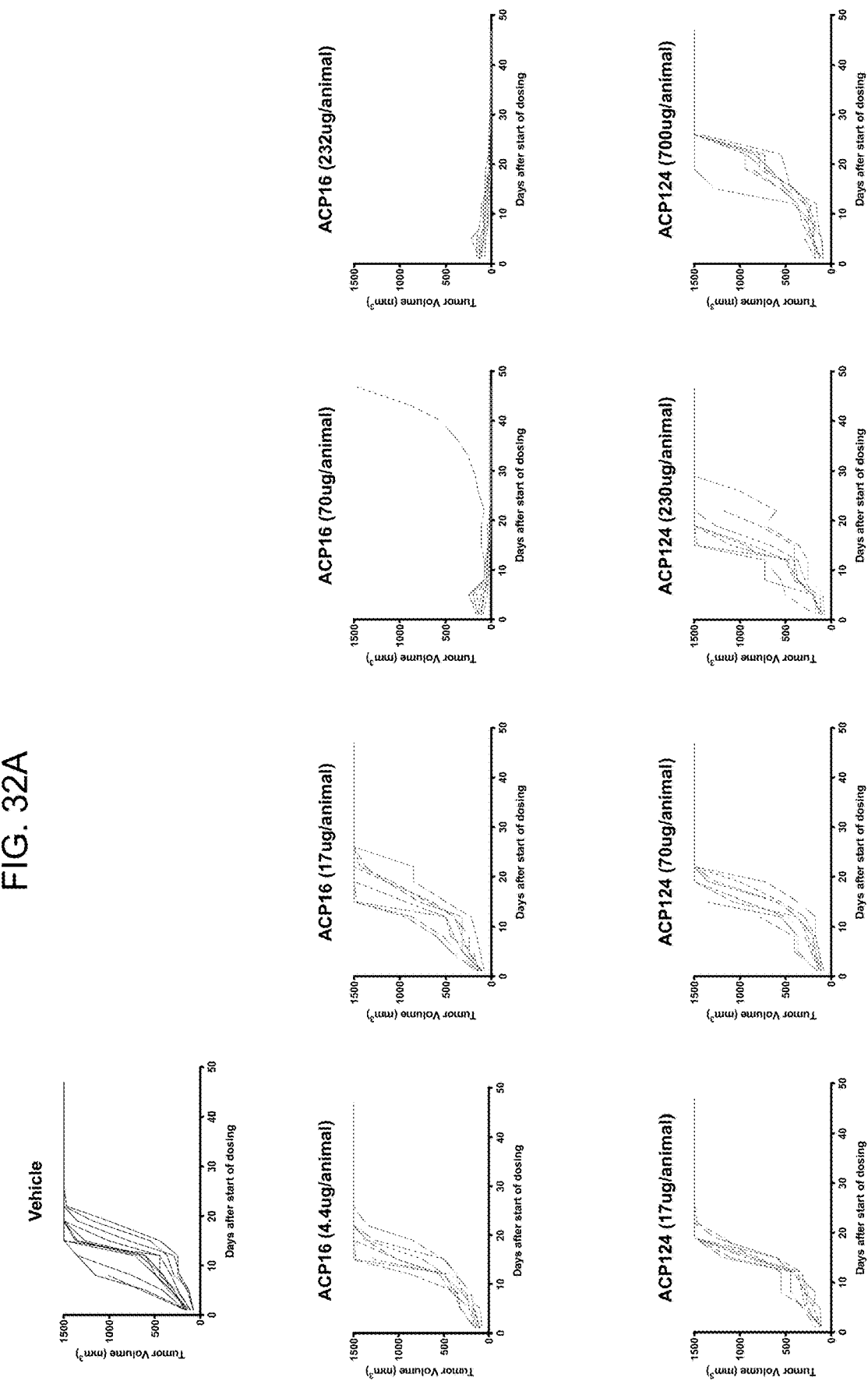
FIG. 32A-32B are a series of spaghetti plots showing activity of fusion proteins in an MC38 mouse xenograft model corresponding to the data shown in FIG. 31A-31C. Each line in the plots is a single mouse.
Figure 32B:
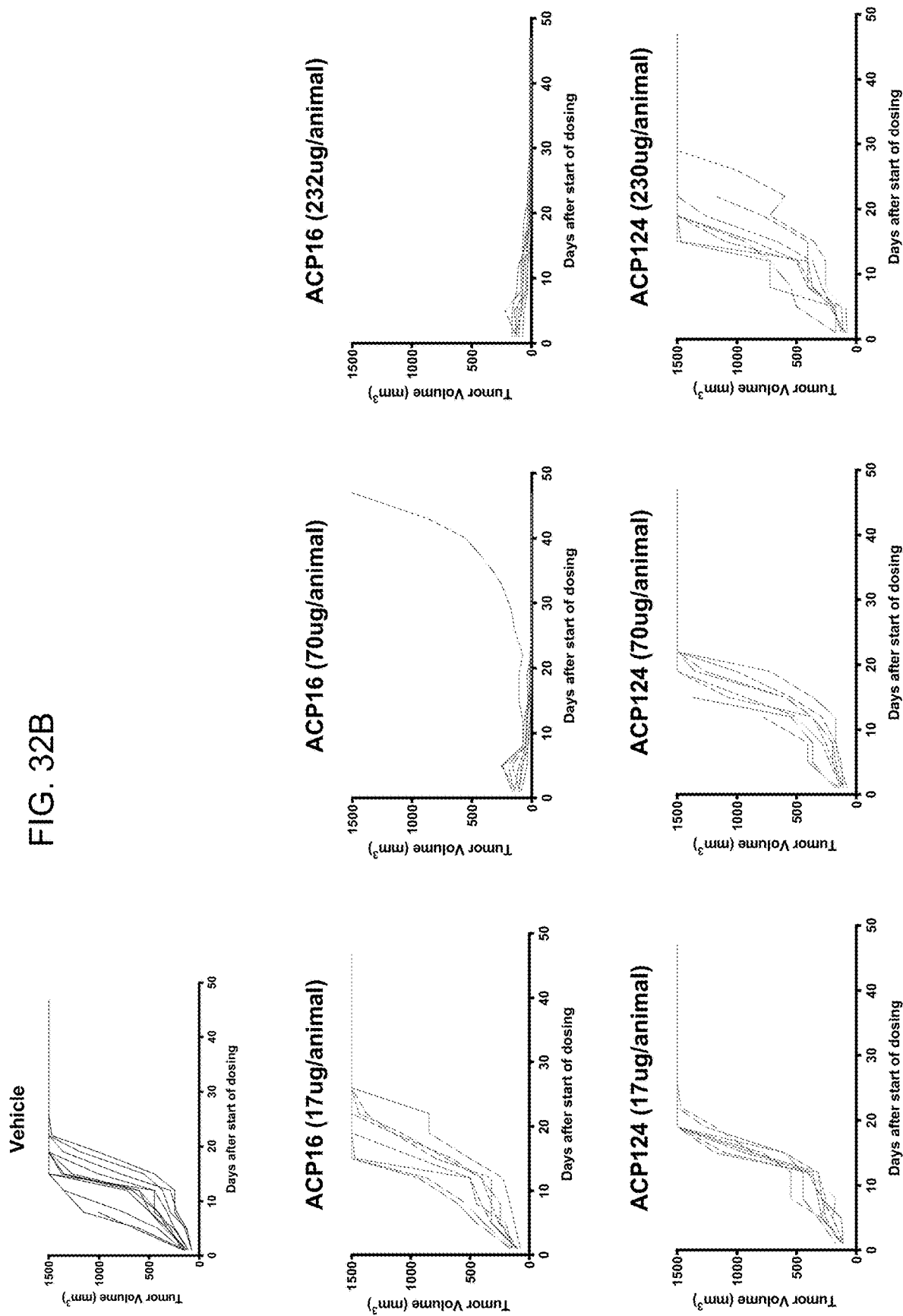

Procedures:

Mice were anaesthetized with isoflurane for implant of cells to reduce the ulcerations. 308 CR female C57BL/6 mice were set up with 5×10⁵ MC38 tumor cells in 0% Matrigel sc in flank. Cell Injection Volume was 0.1 mL/mouse. Mouse age at start date was 8 to 12 weeks. Pair matches were performed when tumors reach an average size of 100-150 mm³ and begin treatment. Body weights were taken at initiation and then biweekly to the end. Caliper measurements were taken biweekly to the end. Any adverse reactions were to be reported immediately. Any individual animal with a single observation of >than 30% body weight loss or three consecutive measurements of >25% body weight loss was euthanized. Any group with a mean body weight loss of >20% or >10% mortality stopped dosing; the group was not euthanized and recovery is allowed. Within a group with >20% weight loss, individuals hitting the individual body weight loss endpoint were euthanized. If the group treatment related body weight loss is recovered to within 10% of the original weights, dosing resumed at a lower dose or less frequent dosing schedule. Exceptions to non-treatment body weight % recovery were allowed on a case-by-case basis. Endpoint was tumor growth delay (TGD). Animals were monitored individually. The endpoint of the experiment was a tumor volume of 1500 mm³ or 45 days, whichever comes first. Responders were followed longer. When the endpoint was reached, the animals are to be euthanized. Results are show in in FIGS. 29A-29B, and 30.

Example 27d: Treatment with ACP16, ACP132, and ACP21

Agents and Treatment:

| Gr. | N | Agent | Formulation dose | Route | Schedule |
|---|---|---|---|---|---|
| 1# | 10 | Vehicle | — | ip | biwk × 2 |
| 2 | 7 | ACP16 | 17 μg/animal | ip | biwk × 2 |
| 3 | 7 | ACP16 | 55 μg/animal | ip | biwk × 2 |
| 4 | 7 | ACP16 | 70 μg/animal | ip | biwk × 2 |
| 5 | 7 | ACP16 | 230 μg/animal | ip | biwk × 2 |
| 6 | 7 | ACP132 | 9 μg/animal | ip | biwk × 2 |
| 7 | 7 | ACP132 | 28 μg/animal | ip | biwk × 1 |
| 8 | 7 | ACP132 | 36 μg/animal | ip | biwk × 1 |
| 9 | 7 | ACP132 | 119 μg/animal | ip | biwk × 1 |
| 10 | 7 | ACP21 | 13 μg/animal | ip | biwk × 2 |
| 11 | 7 | ACP21 | 42 μg/animal | ip | biwk × 2 |
| 12 | 7 | ACP21 | 54 μg/animal | ip | biwk × 2 |
| 13 | 7 | ACP21 | 177 μg/animal | ip | biwk × 2 |

Procedures:

Mice were anaesthetized with isoflurane for implant of cells to reduce the ulcerations. CR female C57BL/6 mice were set up with 5×10⁵ MC38 tumor cells in 0% Matrigel sc in flank. Cell Injection Volume was 0.1 mL/mouse. Mouse age at start date was 8 to 12 weeks. Pair matches were performed when tumors reach an average size of 100-150 mm³ and begin treatment. ACP16 was dosed at 17, 55, 70, or 230 μg/animal; ACP132 was dosed at 9, 28, 36, or 119 ug/animal; ACP21 was dosed at 13, 42, 54, or 177 μg/animal. Body weights were taken at initiation and then biweekly to the end. Caliper measurements were taken biweekly to the end. Any adverse reactions were to be reported immediately. Any individual animal with a single observation of >than 30% body weight loss or three consecutive measurements of >25% body weight loss was euthanized. Any group with a mean body weight loss of >20% or >10% mortality stopped dosing; the group was not euthanized and recovery is allowed. Within a group with >20% weight loss, individuals hitting the individual body weight loss endpoint were euthanized. If the group treatment related body weight loss is recovered to within 10% of the original weights, dosing resumed at a lower dose or less frequent dosing schedule. Exceptions to non-treatment body weight % recovery were allowed on a case-by-case basis. Endpoint was tumor growth delay (TGD). Animals were monitored individually. The endpoint of the experiment was a tumor volume of 1500 mm³ or 45 days, whichever comes first. Responders were followed longer. When the endpoint was reached, the animals are to be euthanized. Results are shown in FIG. 35.

Example 27e: MC38 Rechallenge

Cured mice (ACP16-treated) from Example 27b were rechallenged with tumor implantation to determine whether anti-tumor memory had been established from the initial treatments.

Agents and Treatment:

| Gr. | N | Agent | Formulation dose | Route | Schedule |
|---|---|---|---|---|---|
| 1# | 33 | No Treatment | — | — | — |
| 2 | 7 | ACP16 | 70 μg/animal | ip | (ACP16 biwk × 2) |
| 3 | 8 | ACP16 | 232 μg/animal | ip | (ACP16 biwk × 2) |
| 5 | 5 | IL-2-WTI | 12 μg/animal | ip | (IL-2-WTI bid × 5 then 2-day pause then bid × 5 then 2-day pause) |
| 6 | 7 | IL-2-WTI | 36 μg/animal | ip | (IL-2-WTI bid × 5 then 2-day pause then bid × 5 then 2-day pause) |

ControlGroup

Figure 33:
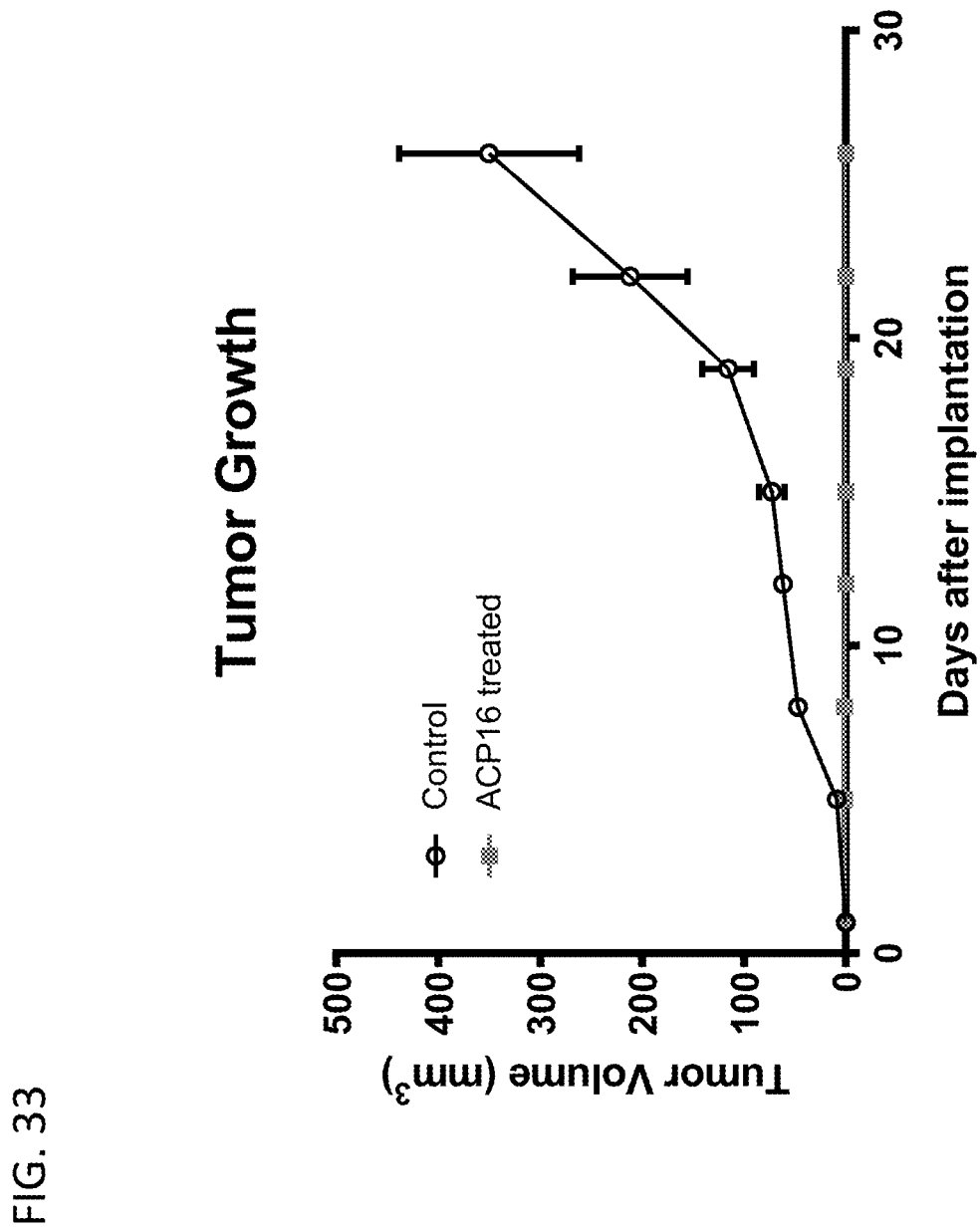
FIG. 33 is a graph showing tumor volume over time in a mouse xenograft model showing tumor growth in control mice (open circles) and AP16-treated mice (squares).
Figure 34A:
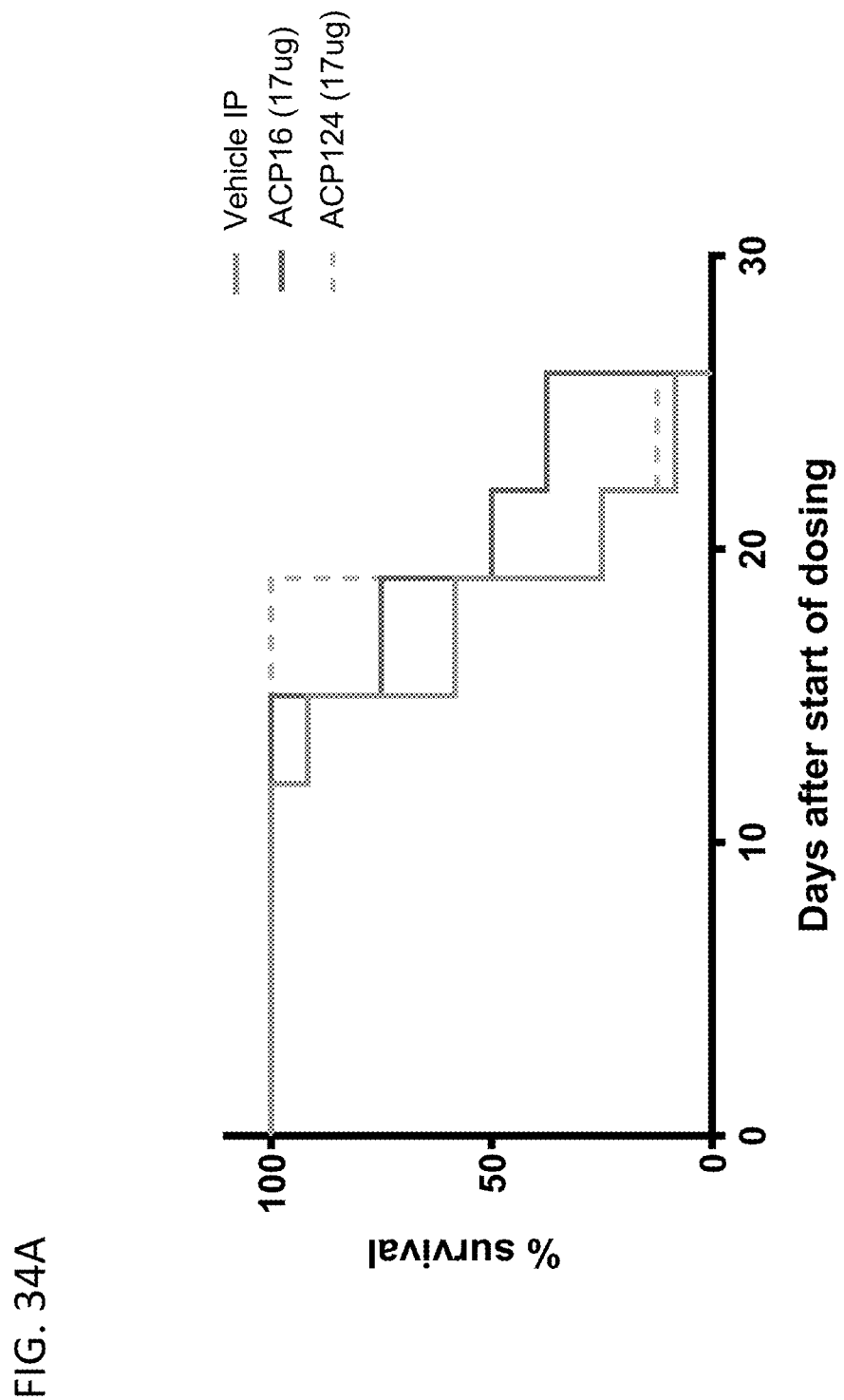
FIGS. 34A-34D are a series of survival plots showing survival of mice over time after treatment with cleavable fusion proteins.
Figure 34B:
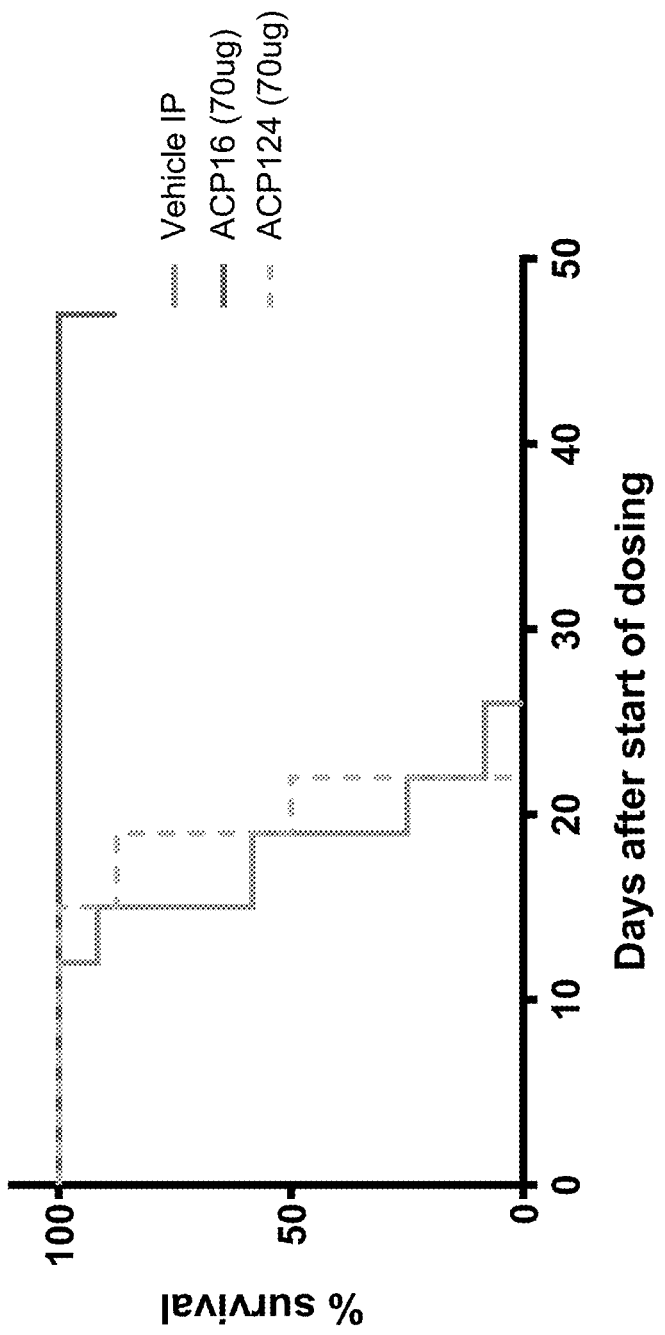
Figure 34C:
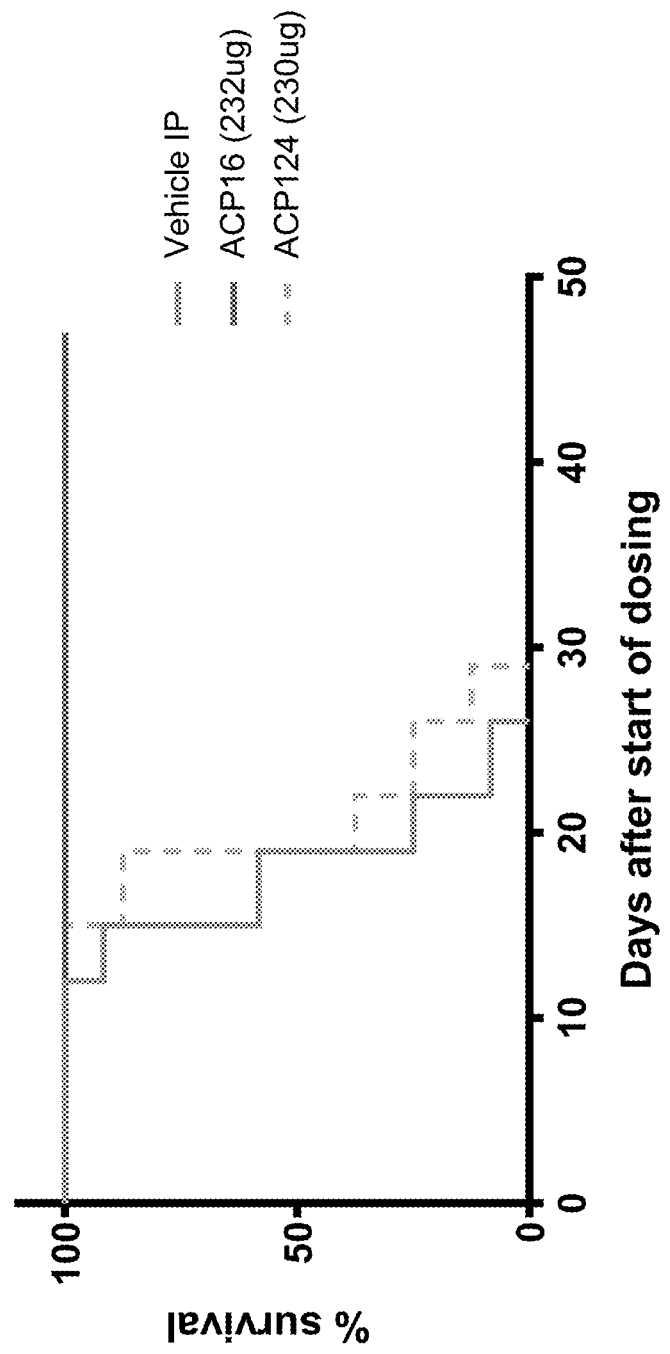
Figure 34D:
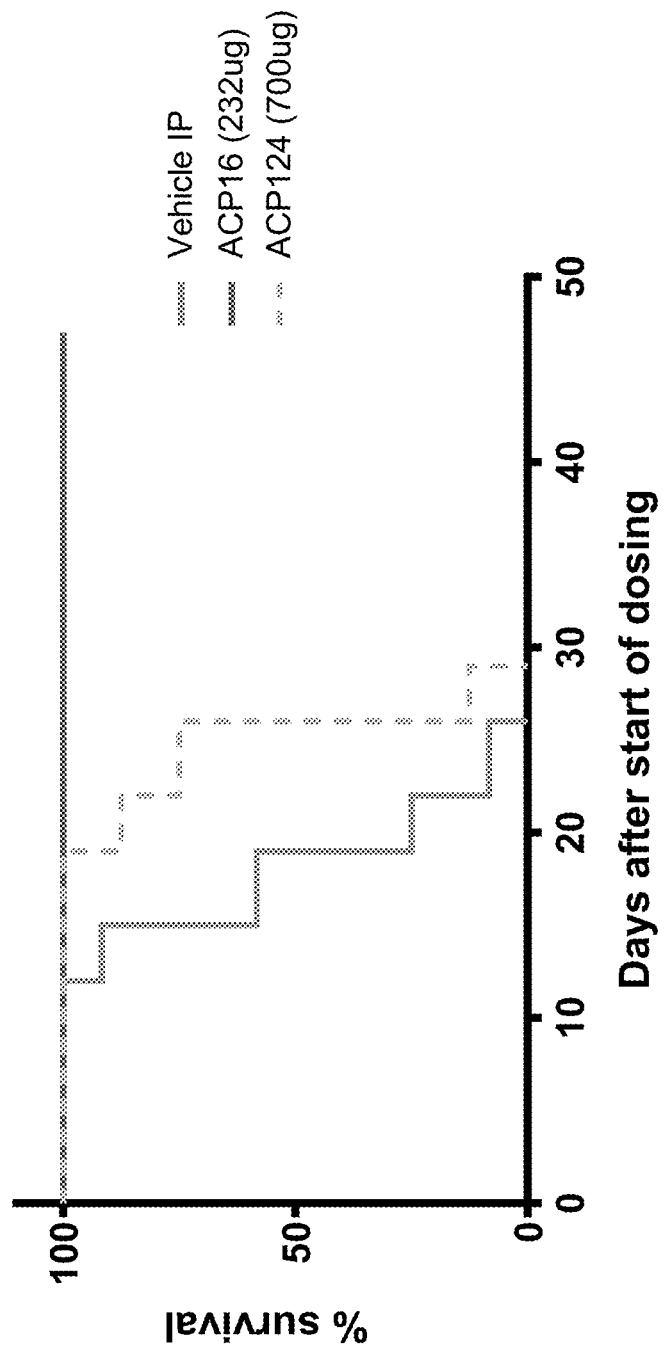

Procedures:

Mice were anaesthetized with isoflurane for implant of cells to reduce the ulcerations. This portion of the study began on the day of implant (Day 1). Group 1 consisted of 33 CR female C57BL/6 mice set up with 5×10⁵ MC38 tumor cells in 0% Matrigel subcutaneously in the flank. Groups 2-6 consisted of 33 CR female C57BL/6 mice set up with 5×10⁵ MC38 tumor cells in 0% Matrigel sc in the left flank. The tumors from the previous MC38 experiment (Example 27b) were implanted in the right flank of each animal. Cell Injection Volume was 0.1 mL/mouse. Age of control mice at initiation was 14 to 17 weeks. These mice were age matched to mice from the previous MC38 experiment (Example 27b). No dosing of active agent occurred during rechallenge. Body Weights were take biweekly until end, as were caliper measurements. Any adverse reactions or death were reported immediately. Any individual animal with a single observation of >than 30% body weight loss or three consecutive measurements of >25% body weight loss was euthanized. Endpoint was tumor growth delay (TGD). Animals were monitored individually. The endpoint of the experiment was a tumor volume of 1000 mm³ or 45 days, whichever comes first. Responders were followed longer when possible. When the endpoint is reached, the animals were euthanized. Results are shown in FIG. 33.

Example 27f: Treatment with ACP10, ACP11

Agents and Treatment:

| Gr. | N | Agent | Formulation dose | Route | Schedule |
|---|---|---|---|---|---|
| 1# | 12 | Vehicle | — | ip | biwk × 2 |
| 2 | 8 | ACP11 | 175 µg/animal | ip | biwk × 2 |
| 3 | 8 | ACP11 | 300 µg/animal | ip | biwk × 2 |
| 4 | 8 | ACP10 | 5 µg/animal | ip | biwk × 2 |
| 5 | 8 | ACP10 | 10 µg/animal | ip | biwk × 2 |
| 6 | 8 | ACP10 | 43 µg/animal | ip | biwk × 2 |
| 7 | 8 | ACP10 | 43 µg/animal | ip | qwk × 2 |
| 8 | 8 | ACP10 | 172 µg/animal | ip | biwk × 2 |
| 9 | 8 | IL-12-HM-WTI | 5 µg/animal | ip | bid for 5 days first day 1 dose then 2-day pause then bid for 5 days first day 1 dose then 2-day pause |
| 10 | 8 | IL-12-HM-WTI | 20 µg/animal | ip | bid for 5 days first day 1 dose then 2-day pause then bid for 5 days first day 1 dose then 2-day pause |

Procedures:

Mice were anaesthetized with isoflurane for implant of cells to reduce the ulcerations. CR female C57BL/6 mice were set up with 5×10⁵ MC38 tumor cells in 0% Matrigel sc in flank. Cell Injection Volume was 0.1 mL/mouse. Mouse age at start date was 8 to 12 weeks. Pair matches were performed when tumors reach an average size of 100-150 mm$^3$ and begin treatment. ACP11 was dosed at 175 or 300 µg/animal; ACP10 was dosed at 5, 10, 43, or 172 ug/animal; IL-12-HM-WTI was dosed at 5 or 20 ug/animal. Body weights were taken at initiation and then biweekly to the end. Caliper measurements were taken biweekly to the end. Any adverse reactions were to be reported immediately. Any individual animal with a single observation of >than 30% body weight loss or three consecutive measurements of >25% body weight loss was euthanized. Any group with a mean body weight loss of >20% or >10% mortality stopped dosing; the group was not euthanized and recovery is allowed. Within a group with >20% weight loss, individuals hitting the individual body weight loss endpoint were euthanized. If the group treatment related body weight loss is recovered to within 10% of the original weights, dosing resumed at a lower dose or less frequent dosing schedule. Exceptions to non-treatment body weight % recovery were allowed on a case-by-case basis. Endpoint was tumor growth delay (TGD). Animals were monitored individually. The endpoint of the experiment was a tumor volume of 1500 mm$^3$ or 45 days, whichever comes first. Responders were followed longer. When the endpoint was reached, the animals are to be euthanized. Results are shown in FIG. 45 and FIGS. 46A-46D.

Example 27g: Treatment with ACP16, APC153, ACP155, ACP156 and ACP292

Agents and Treatment:

| Gr. | N | Agent | Formulation dose | Route | Schedule |
|---|---|---|---|---|---|
| 1# | 12 | Vehicle | — | ip | biwk × 2 |
| 2 | 8 | ACP16 | 17 µg/animal | ip | biwk × 2 |
| 3 | 8 | ACP16 | 55 µg/animal | ip | biwk × 2 |
| 4 | 8 | ACP16 | 230 µg/animal | ip | biwk × 2 |
| 5 | 8 | ACP155 | 55 µg/animal | ip | biwk × 2 |
| 6 | 8 | ACP155 | 230 µg/animal | ip | biwk × 2 |
| 7 | 8 | ACP153 | 55 µg/animal | ip | biwk × 2 |
| 8 | 8 | ACP153 | 230 µg/animal | ip | biwk × 2 |
| 9 | 8 | ACP156 | 55 µg/animal | ip | biwk × 2 |
| 10 | 8 | ACP156 | 230 µg/animal | ip | biwk × 2 |
| 11 | 8 | ACP292 | 45 µg/animal | ip | biwk × 2 |
| 12 | 8 | ACP292 | 186 µg/animal | ip | biwk × 2 |

Procedures:

Mice were anaesthetized with isoflurane for implant of cells to reduce the ulcerations. CR female C57BL/6 mice were set up with 5×10⁵ MC38 tumor cells in 0% Matrigel sc in flank. Cell Injection Volume was 0.1 mL/mouse. Mouse age at start date was 8 to 12 weeks. Pair matches were performed when tumors reach an average size of 100-150 mm$^3$ and begin treatment. ACP16 was dosed at 17, 55 or 230 µg/animal; ACP153, ACP155 and ACP156 were dosed at 55 or 230 µg/animal; ACP292 was dosed at 45 or 186 µg/animal. Body weights were taken at initiation and then biweekly to the end. Caliper measurements were taken biweekly to the end. Any adverse reactions were to be reported immediately. Any individual animal with a single observation of >than 30% body weight loss or three consecutive measurements of >25% body weight loss was euthanized. Any group with a mean body weight loss of >20% or >10% mortality stopped dosing; the group was not euthanized and recovery is allowed. Within a group with >20% weight loss, individuals hitting the individual body weight loss endpoint were euthanized. If the group treatment related body weight loss is recovered to within 10% of the original weights, dosing resumed at a lower dose or less frequent dosing schedule. Exceptions to non-treatment body weight % recovery were allowed on a case-by-case basis. Endpoint was tumor growth delay (TGD). Animals were monitored individually. The endpoint of the experiment was a tumor volume of 1500 mm$^3$ or 45 days, whichever comes first. Responders were followed longer. When the endpoint was reached, the animals are to be euthanized. Results are shown in FIGS. 49A-49I.

Example 27h: Treatment with ACP16, APC302 and ACP314

Agents and Treatment:

| Gr. | N | Agent | Formulation dose | Route | Schedule |
|---|---|---|---|---|---|
| 1# | 12 | Vehicle | — | ip | biwk × 2 |
| 2 | 9 | ACP16 | 55 µg/animal | ip | biwk × 2 |
| 3 | 9 | ACP16 | 230 µg/animal | ip | biwk × 2 |
| 4 | 9 | ACP302 | 33 µg/animal | ip | biwk × 2 |
| 5 | 9 | ACP302 | 106 µg/animal | ip | biwk × 2 |
| 6 | 9 | ACP302 | 442 µg/animal | ip | biwk × 2 |
| 7 | 9 | ACP302 | 1,344 µg/animal | ip | biwk × 2 |
| 8 | 9 | ACP314 | 21 µg/animal | ip | biwk × 2 |
| 9 | 9 | ACP314 | 68 µg/animal | ip | biwk × 2 |
| 10 | 9 | ACP314 | 283 µg/animal | ip | biwk × 2 |
| 11 | 9 | ACP314 | 861 µg/animal | ip | biwk × 2 |

Figure 50A:
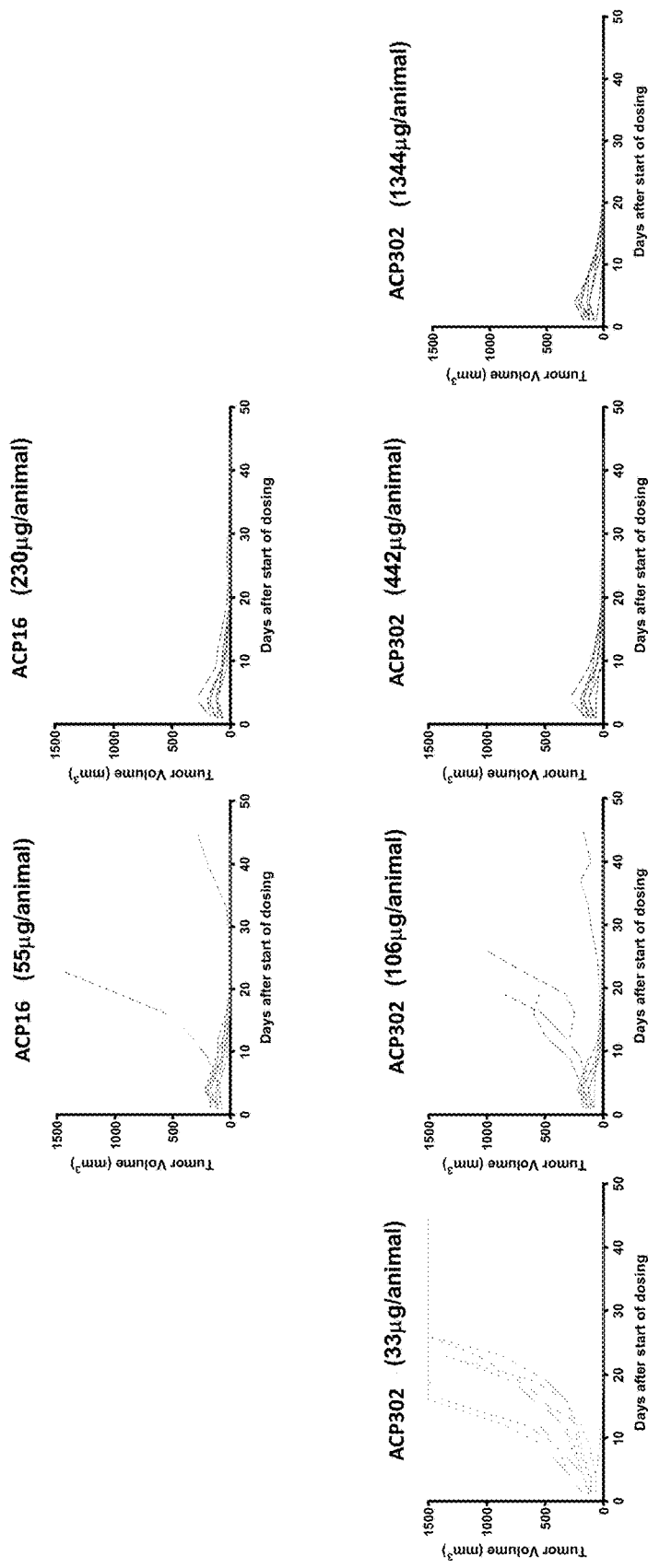
Figure 50B:
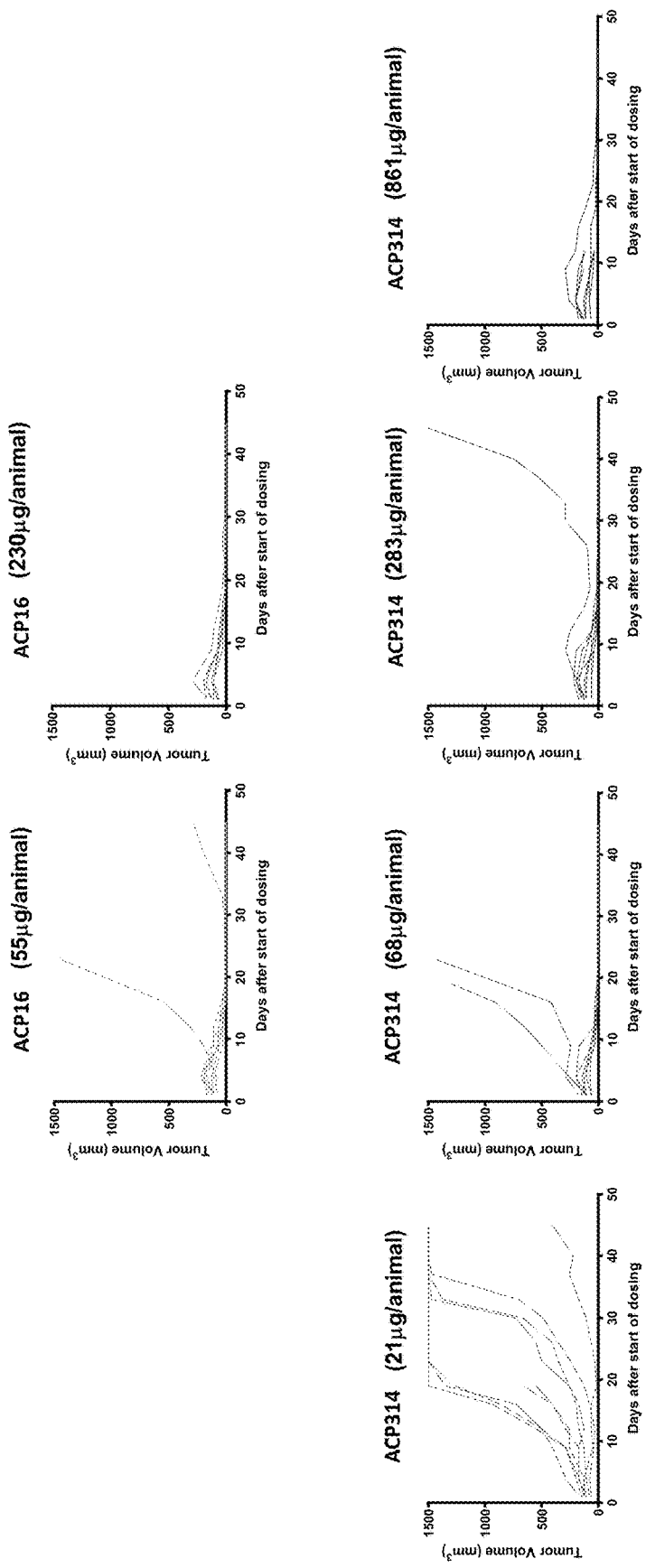

Procedures:

Mice were anaesthetized with isoflurane for implant of cells to reduce the ulcerations. CR female C57BL/6 mice were set up with $5 \times 10^5$ MC38 tumor cells in 0% Matrigel sc in flank. Cell Injection Volume was 0.1 mL/mouse. Mouse age at start date was 8 to 12 weeks. Pair matches were performed when tumors reach an average size of 100-150 mm³ and begin treatment. ACP16 was dosed at 55 or 230 µg/animal; ACP302 was dosed at 33, 106, 442 or 1344 ug/animal; ACP314 was dosed at 21, 68, 283 or 861 µg/animal. Body weights were taken at initiation and then biweekly to the end. Caliper measurements were taken biweekly to the end. Any adverse reactions were to be reported immediately. Any individual animal with a single observation of >than 30% body weight loss or three consecutive measurements of >25% body weight loss was euthanized. Any group with a mean body weight loss of >20% or >10% mortality stopped dosing; the group was not euthanized and recovery is allowed. Within a group with >20% weight loss, individuals hitting the individual body weight loss endpoint were euthanized. If the group treatment related body weight loss is recovered to within 10% of the original weights, dosing resumed at a lower dose or less frequent dosing schedule. Exceptions to non-treatment body weight % recovery were allowed on a case-by-case basis. Endpoint was tumor growth delay (TGD). Animals were monitored individually. The endpoint of the experiment was a tumor volume of 1500 mm³ or 45 days, whichever comes first. Responders were followed longer. When the endpoint was reached, the animals are to be euthanized. Results are shown in FIG. 50A-50B.

Example 27i: Treatment with ACP339

Agents and Treatment:

| Gr. | N | Agent | Formulation dose | Route | Schedule |
|---|---|---|---|---|---|
| 1# | 12 | Vehicle | — | ip | biwk × 2 |
| 2 | 9 | ACP339 | 55 µg/animal | ip | biwk × 2 |
| 3 | 9 | ACP339 | 230 µg/animal | ip | biwk × 2 |
| 4 | 9 | ACP339 | 700 µg/animal | ip | biwk × 2 |

Figure 51A:
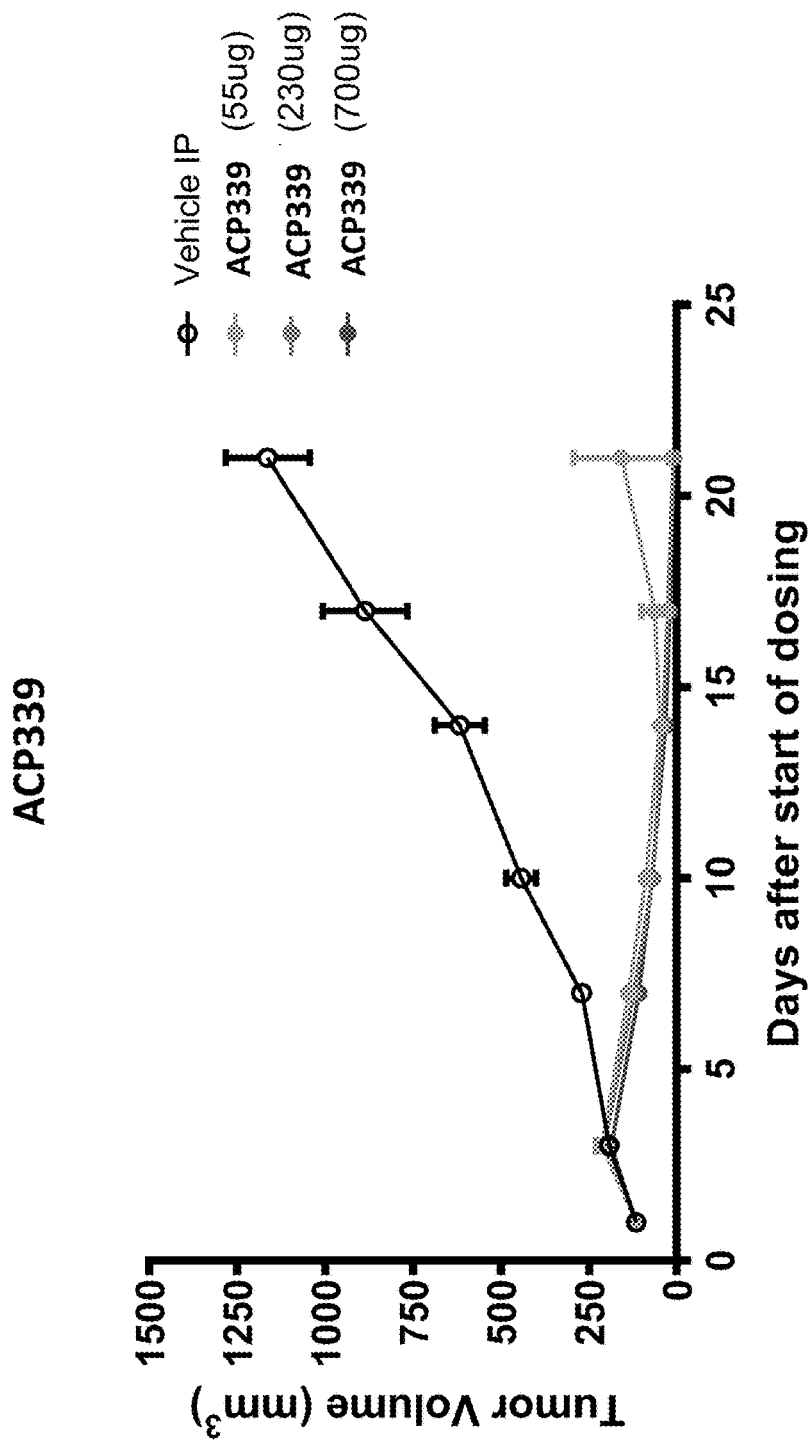
Figure 51B:
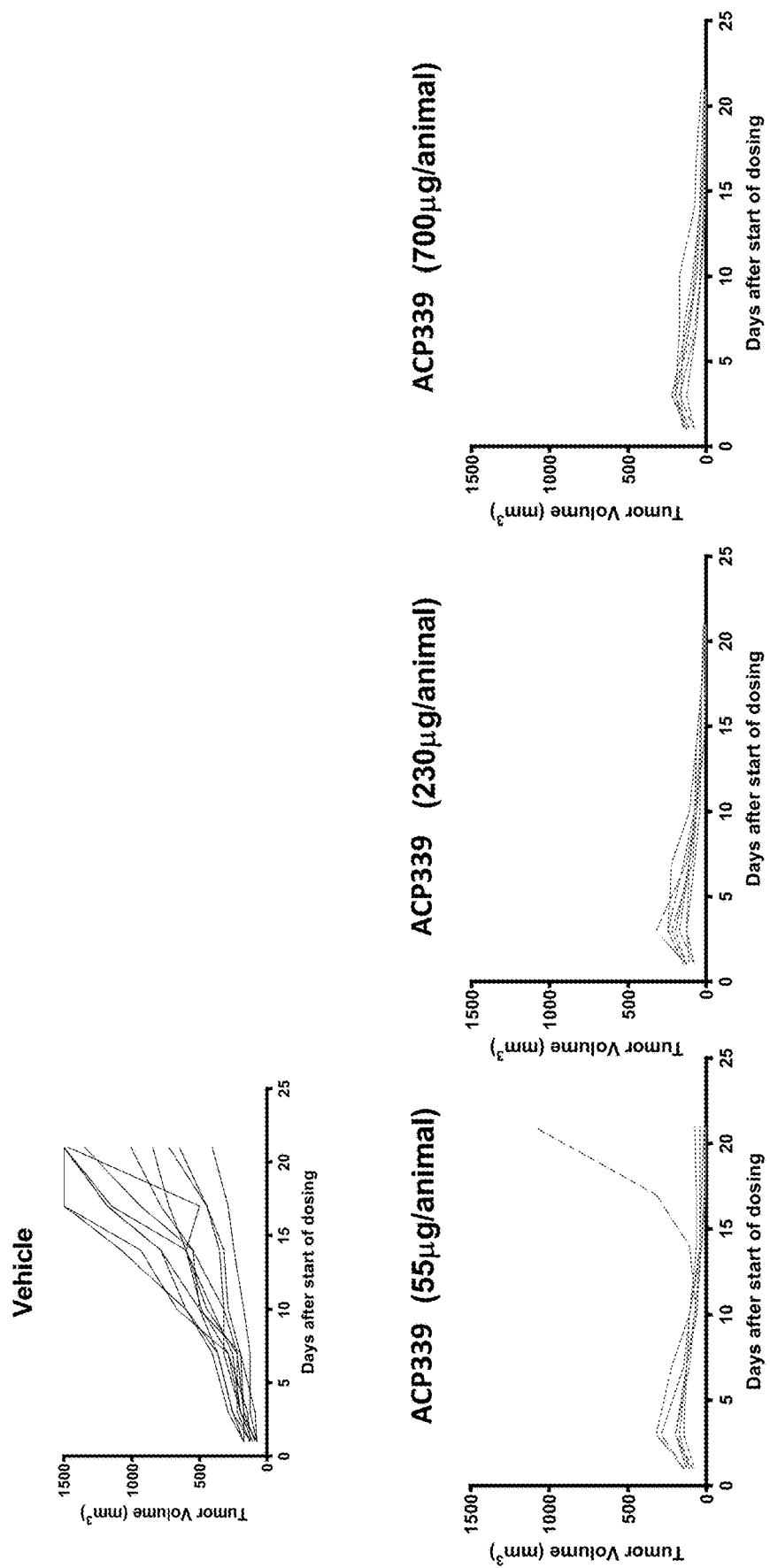
Figure 51C:
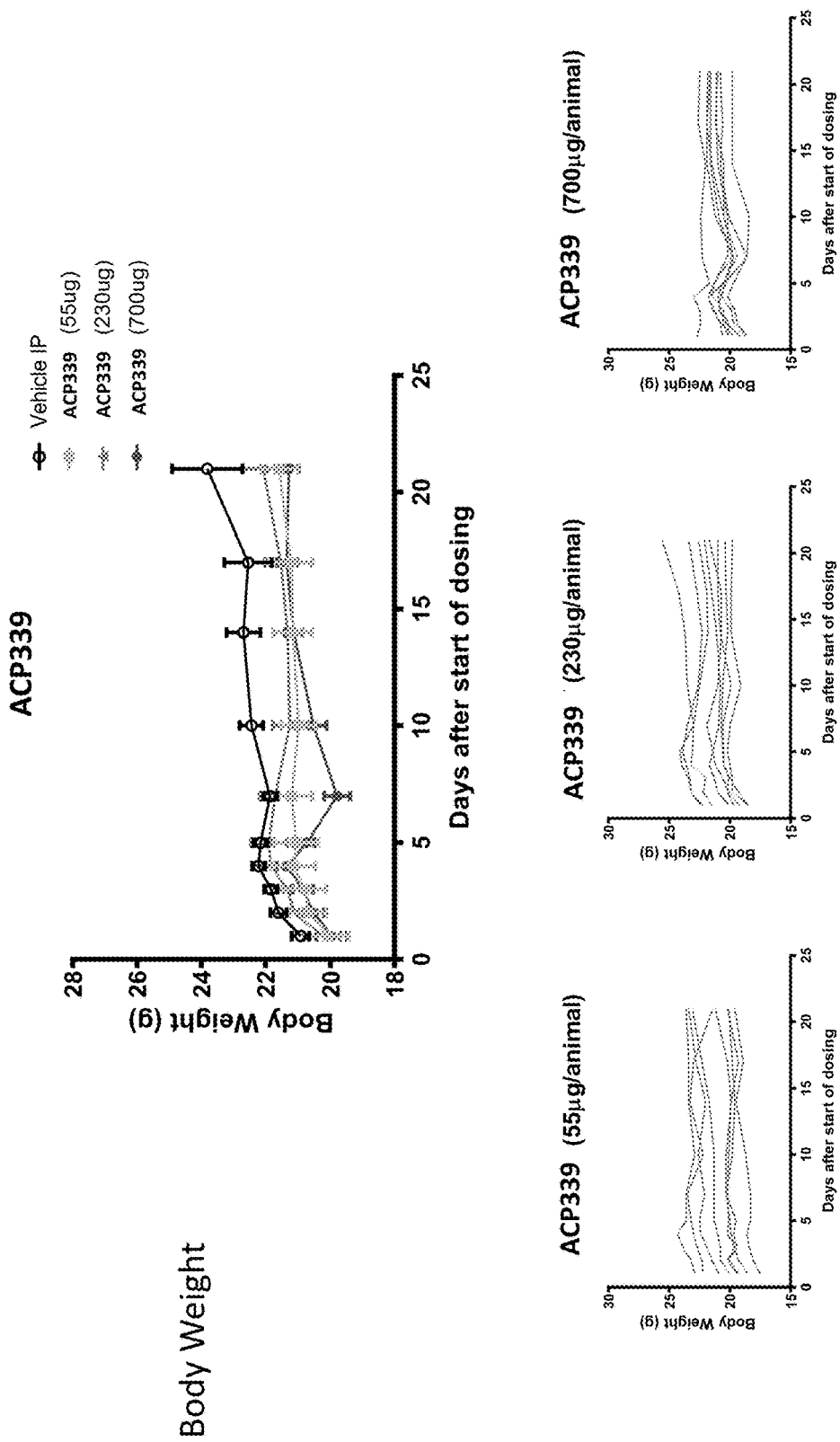
Figure 52A:
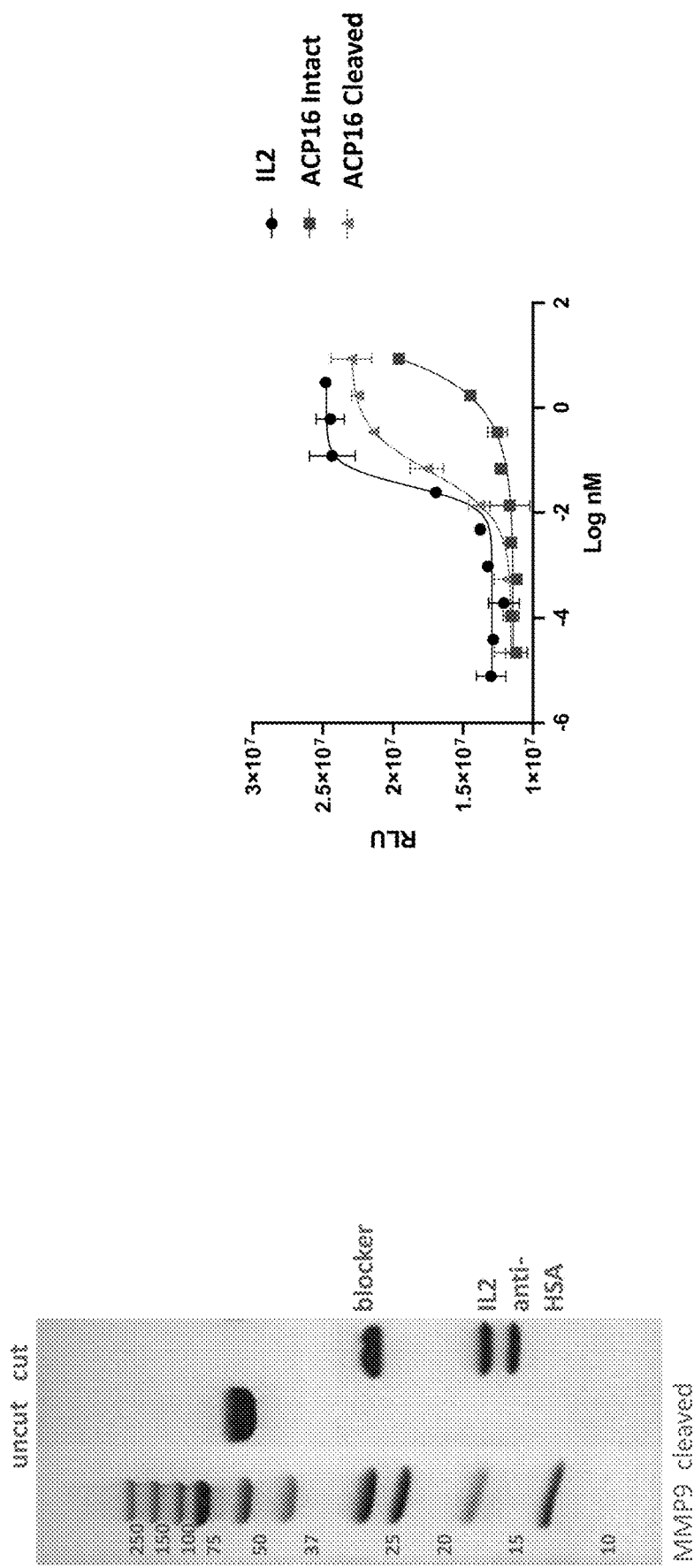
FIGS. 52A-52N, 53A, and 53B depict the activity of cytokine fusion proteins constructs.
Figure 52B:
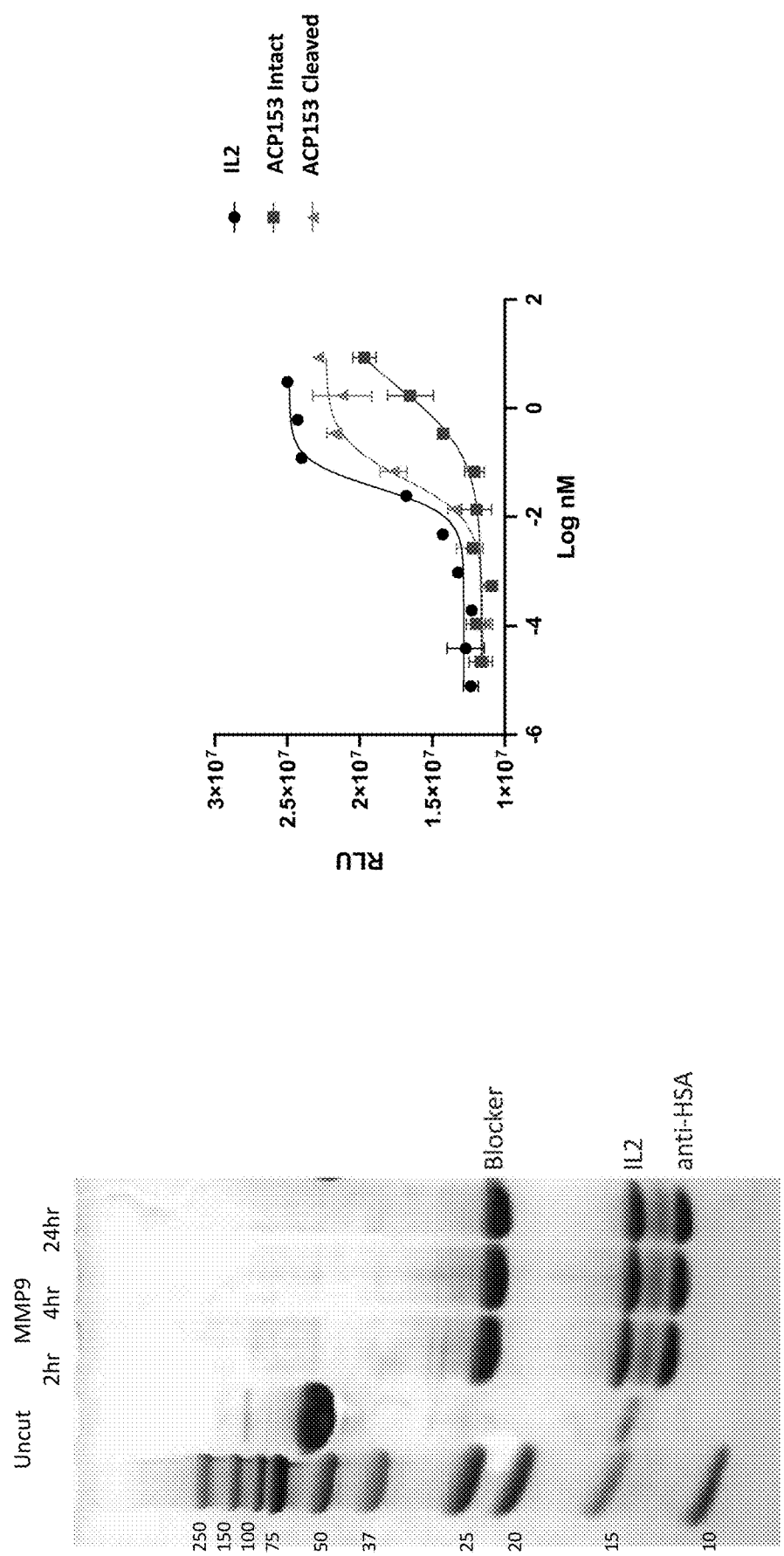
Figure 52C:
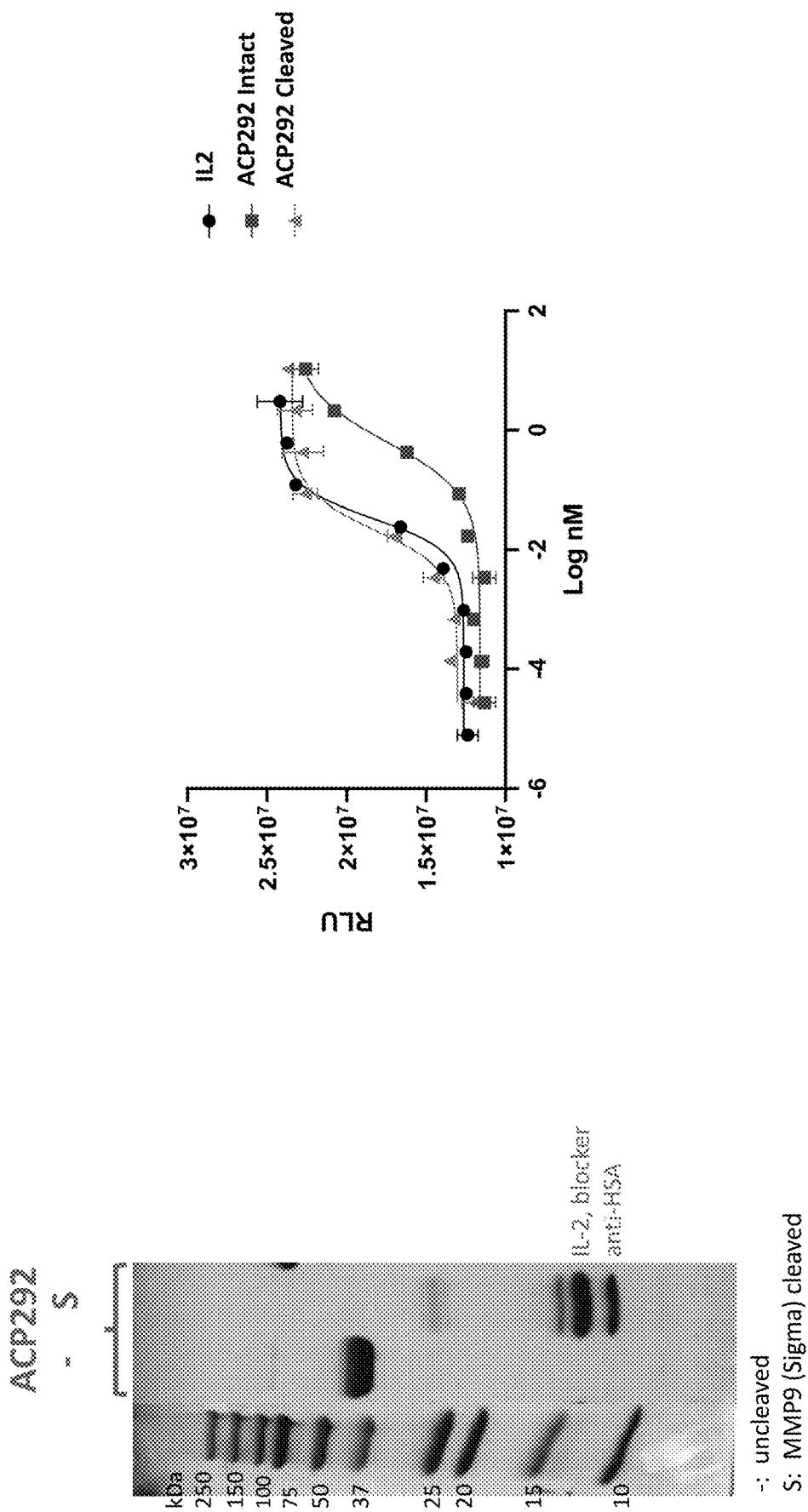
Figure 52D:
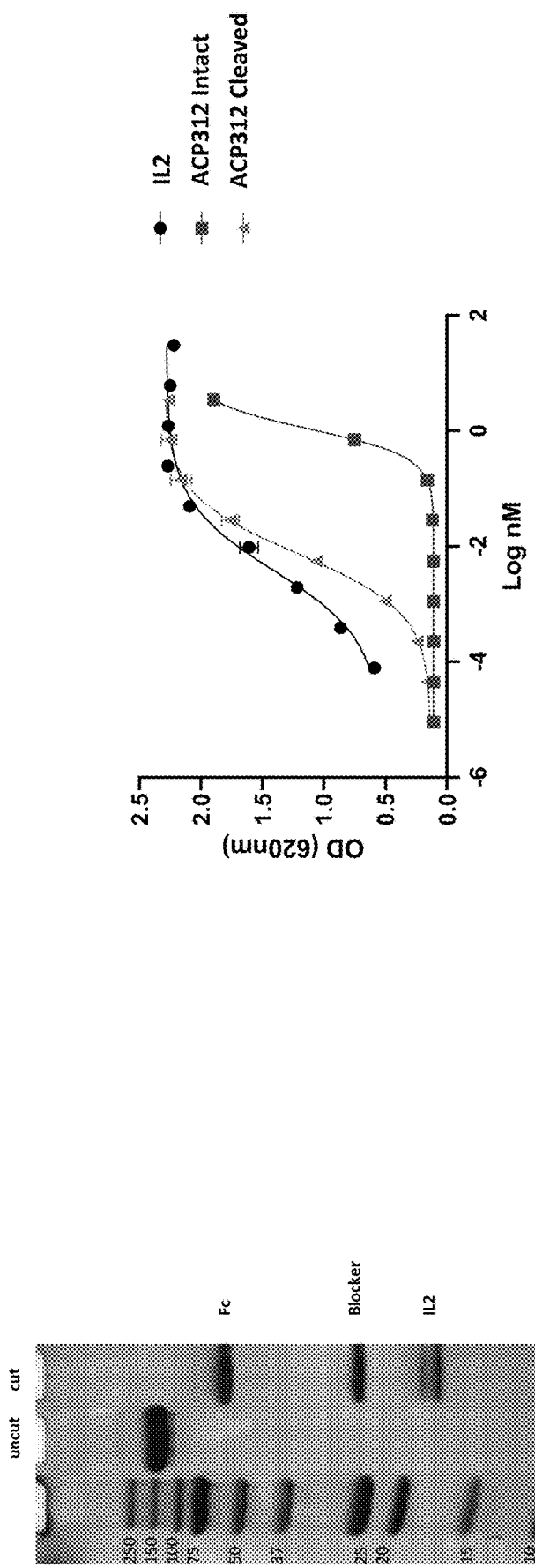
Figure 52E:
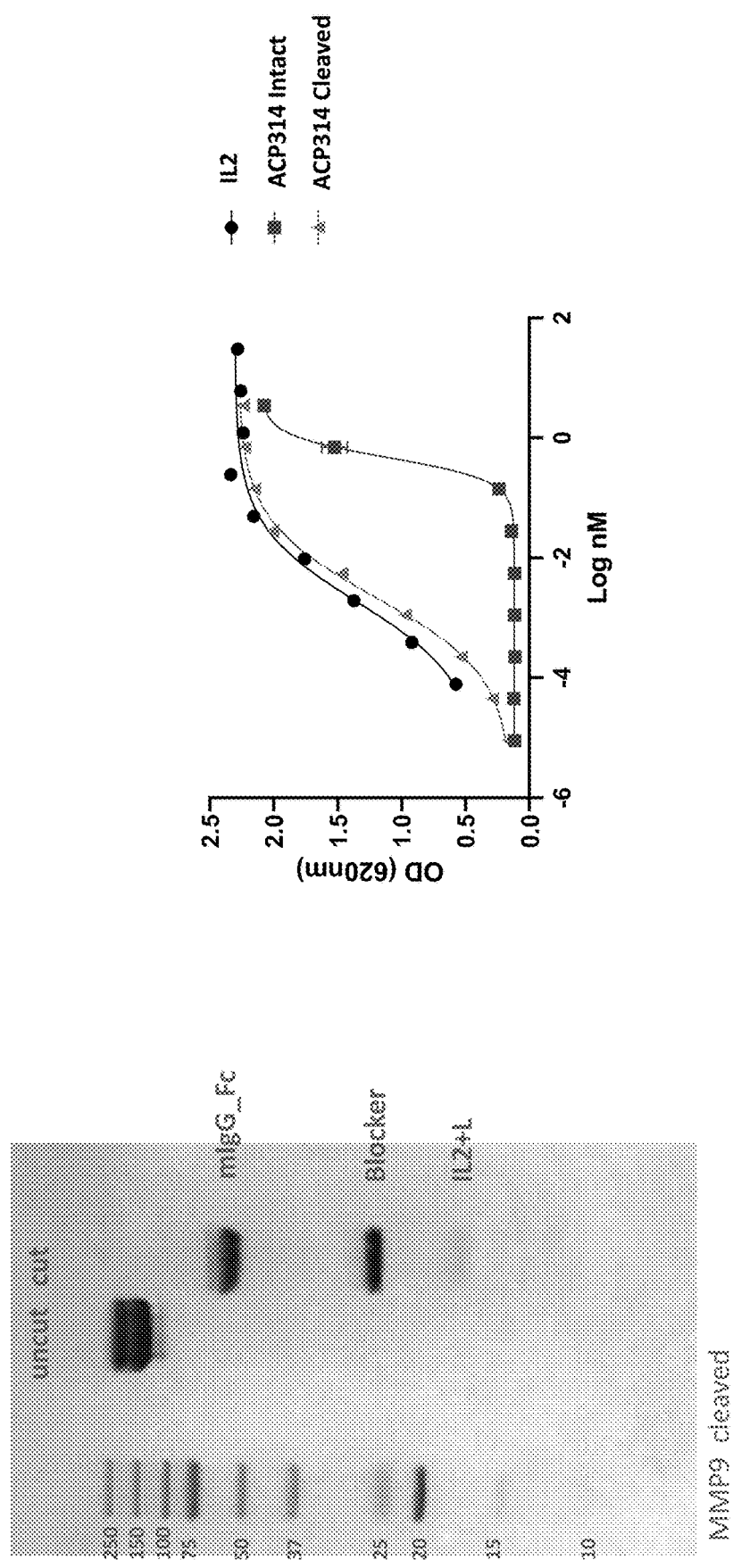
Figure 52F:
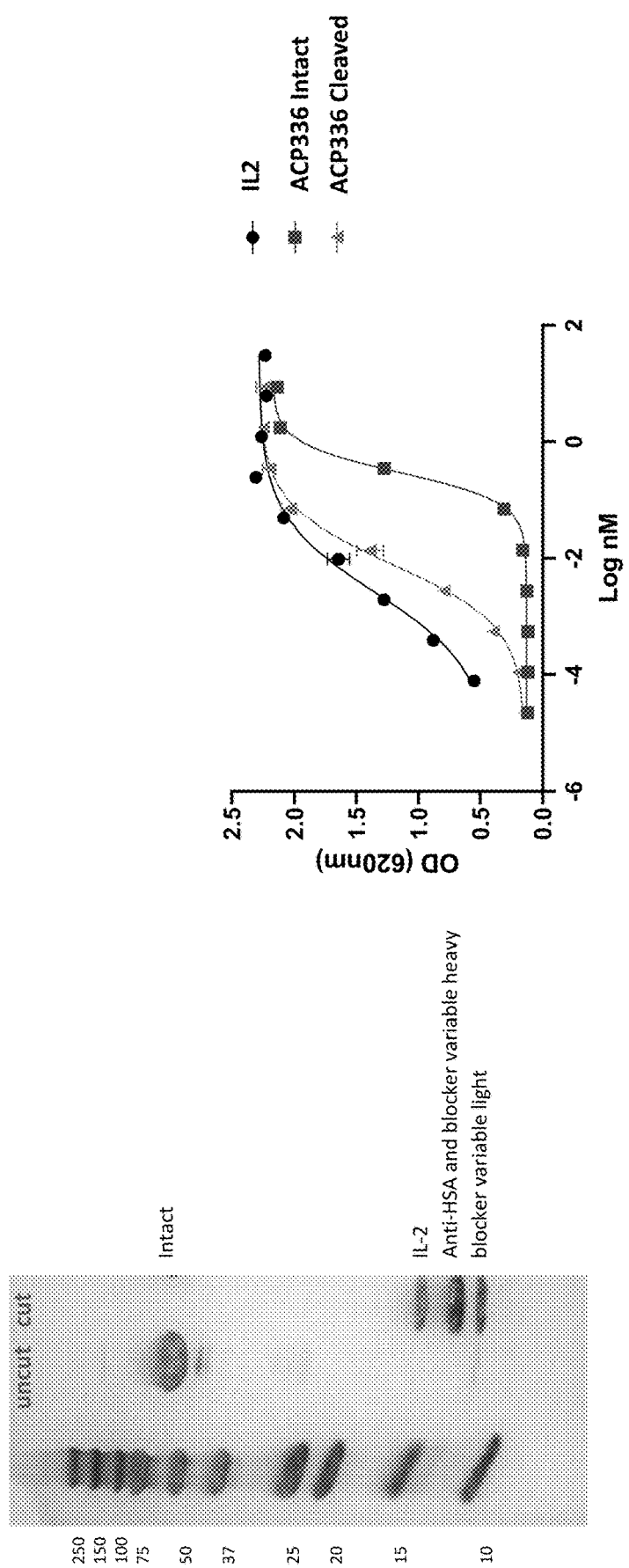
Figure 52G:
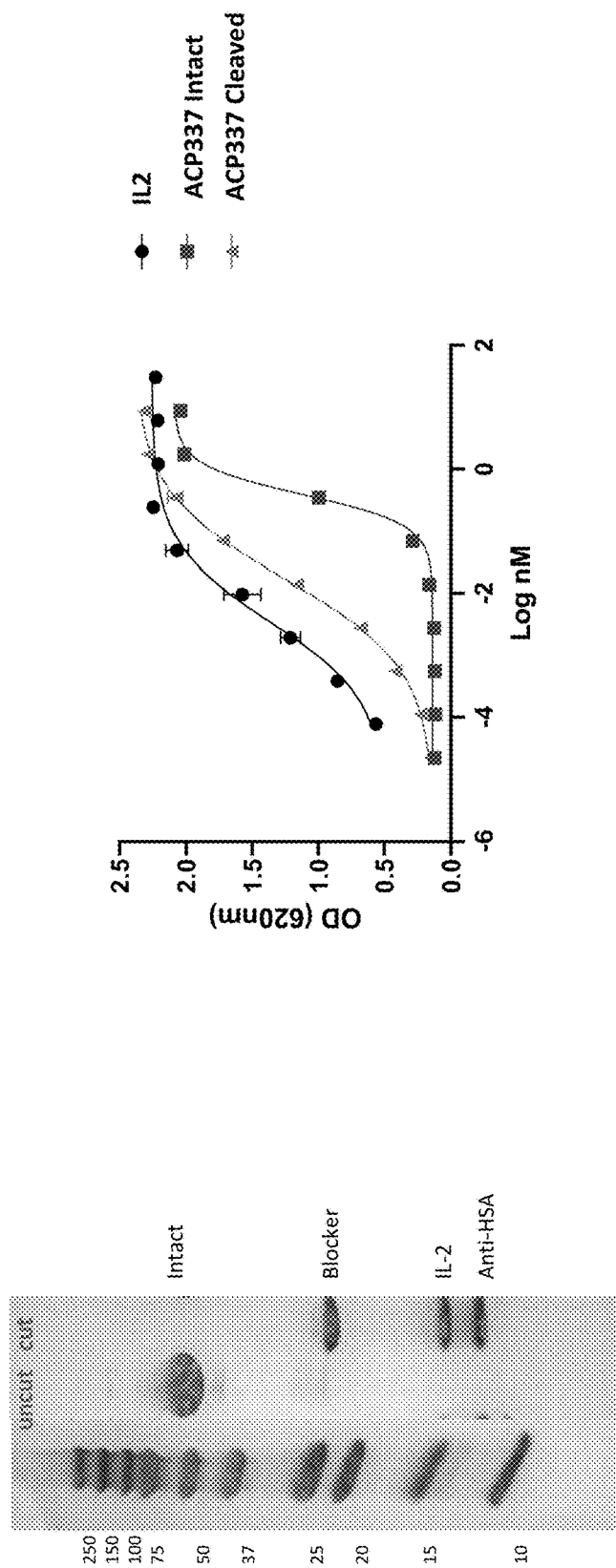
Figure 52H:
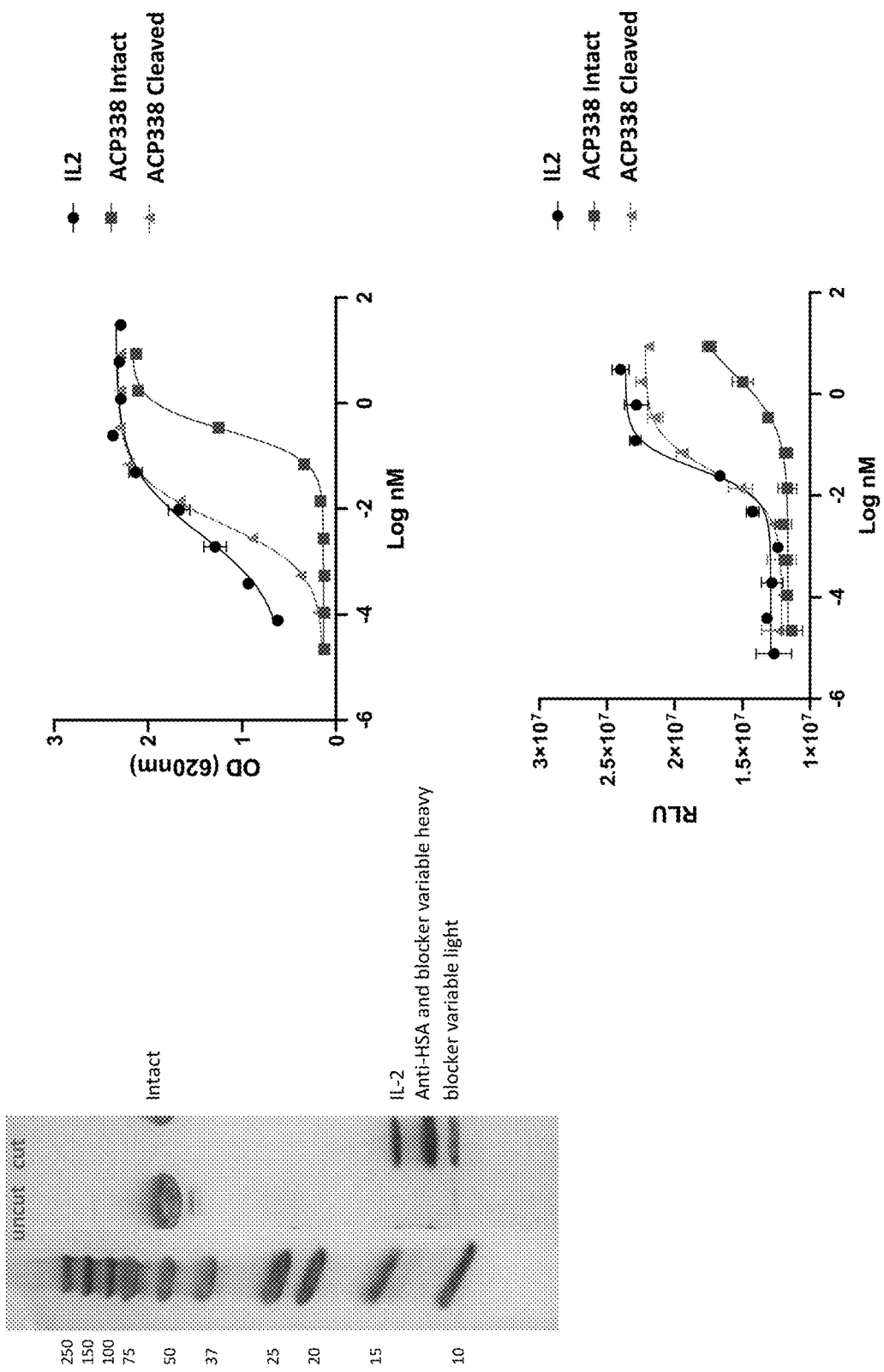
Figure 52I:
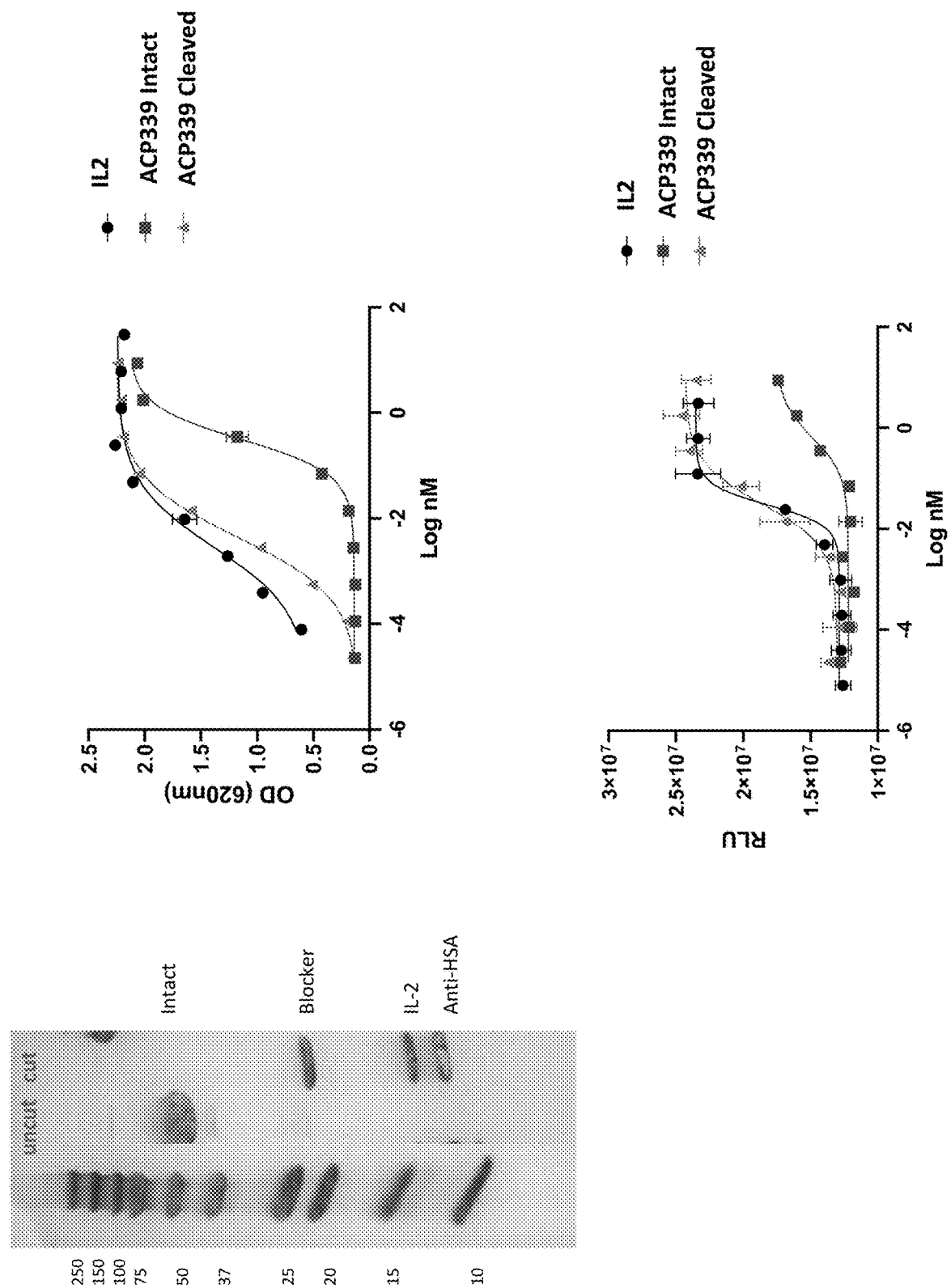
Figure 52J:
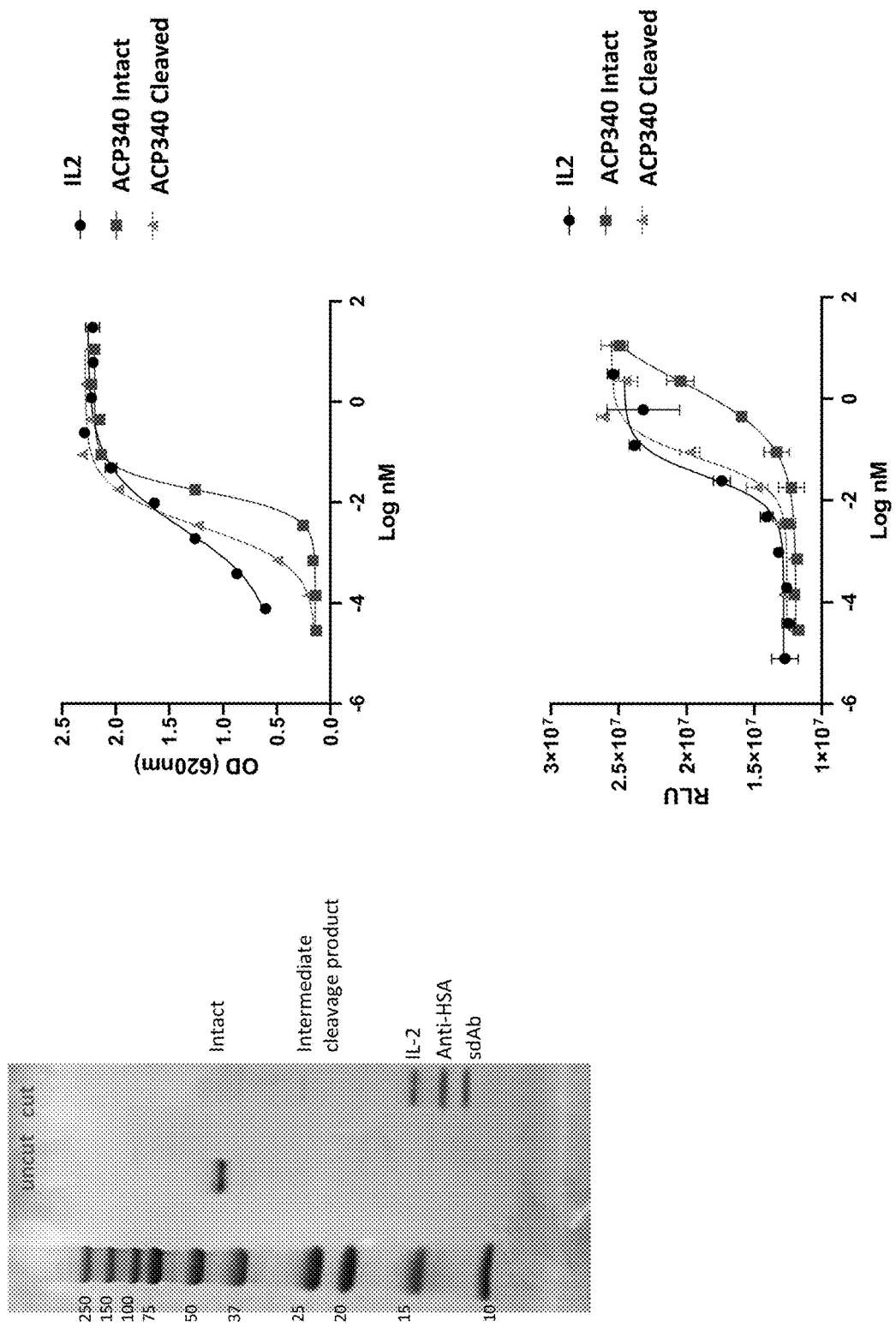
Figure 52K:
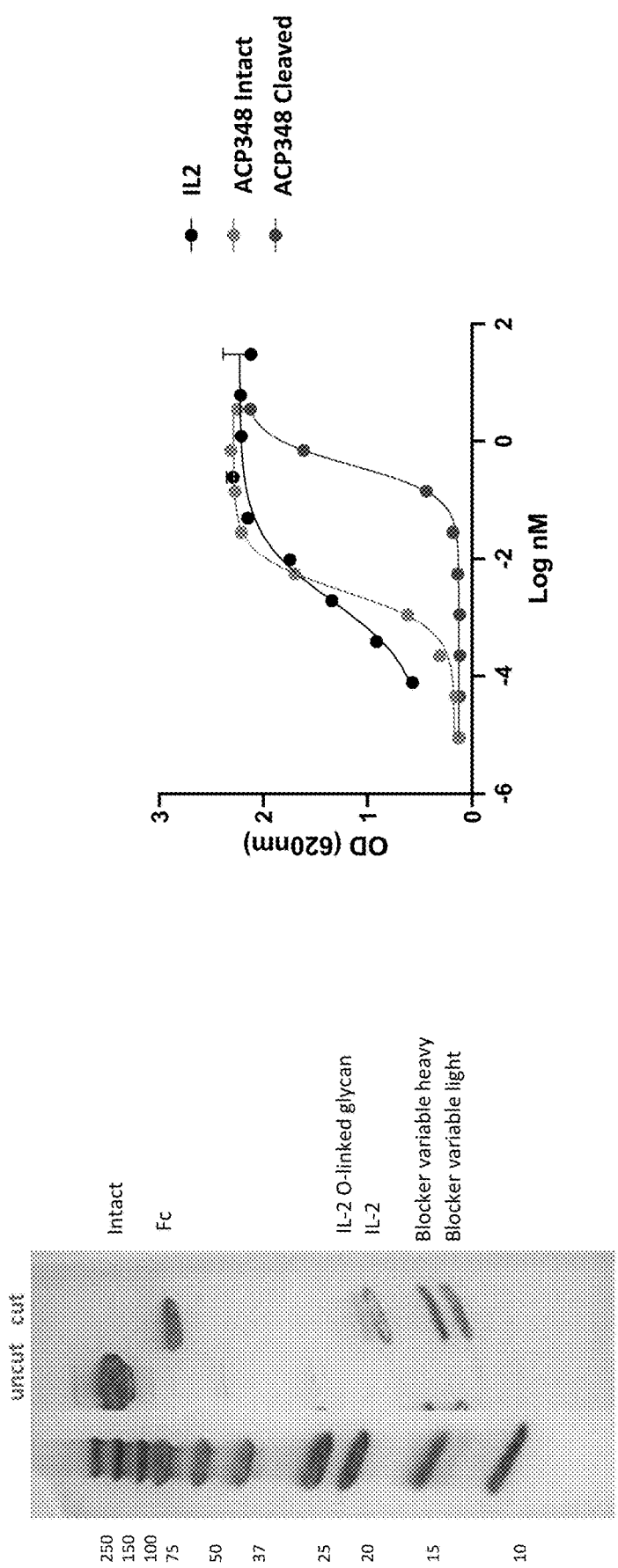
Figure 52L:
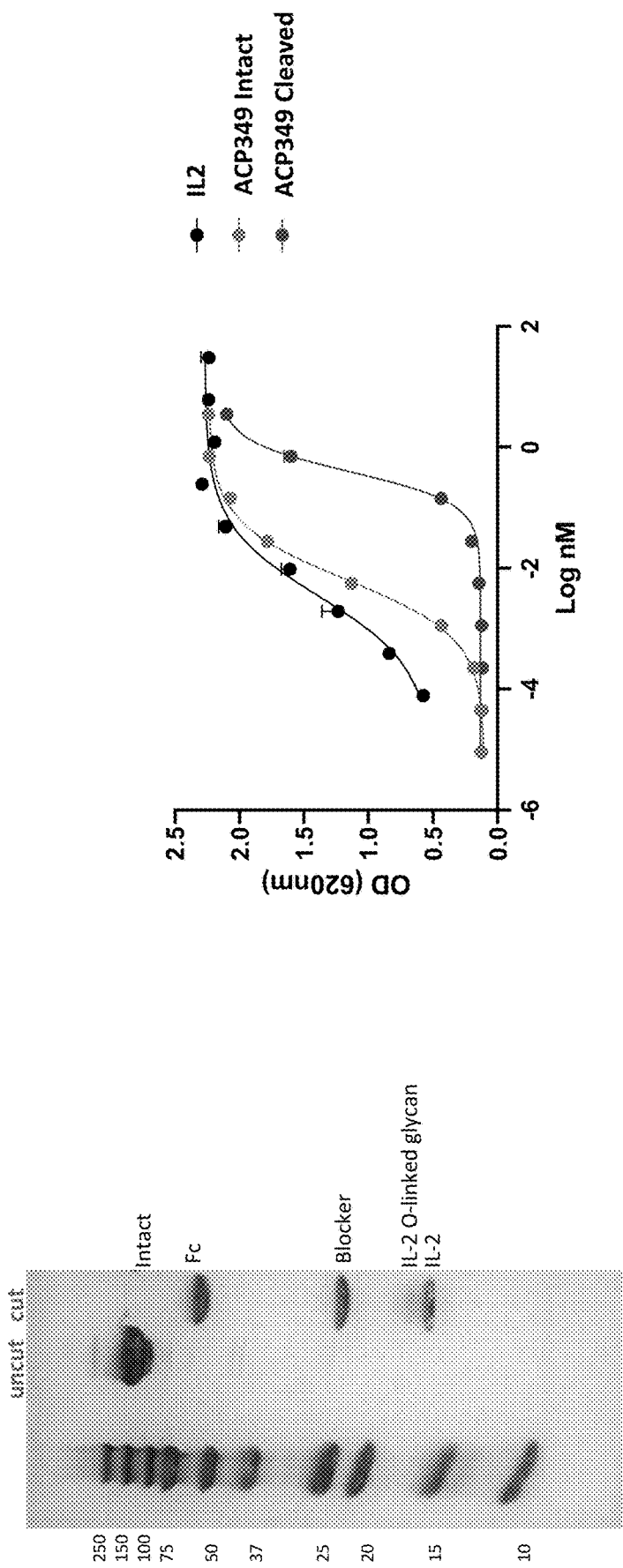
Figure 52M:
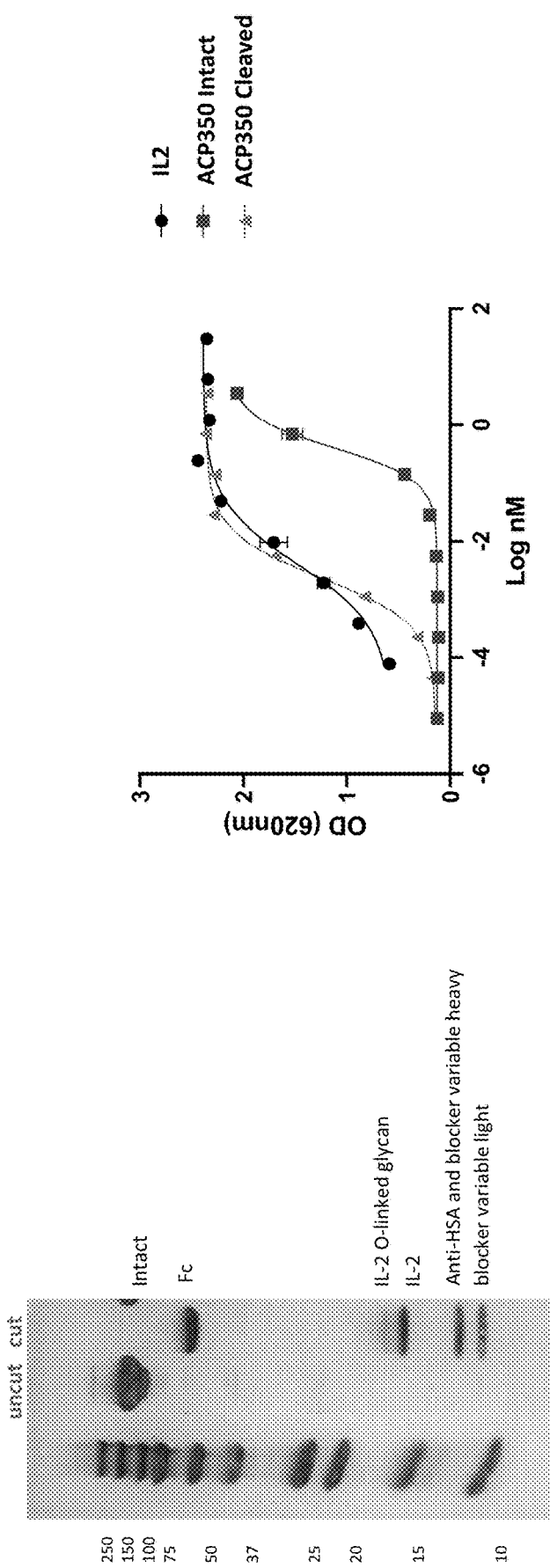
Figure 52N:
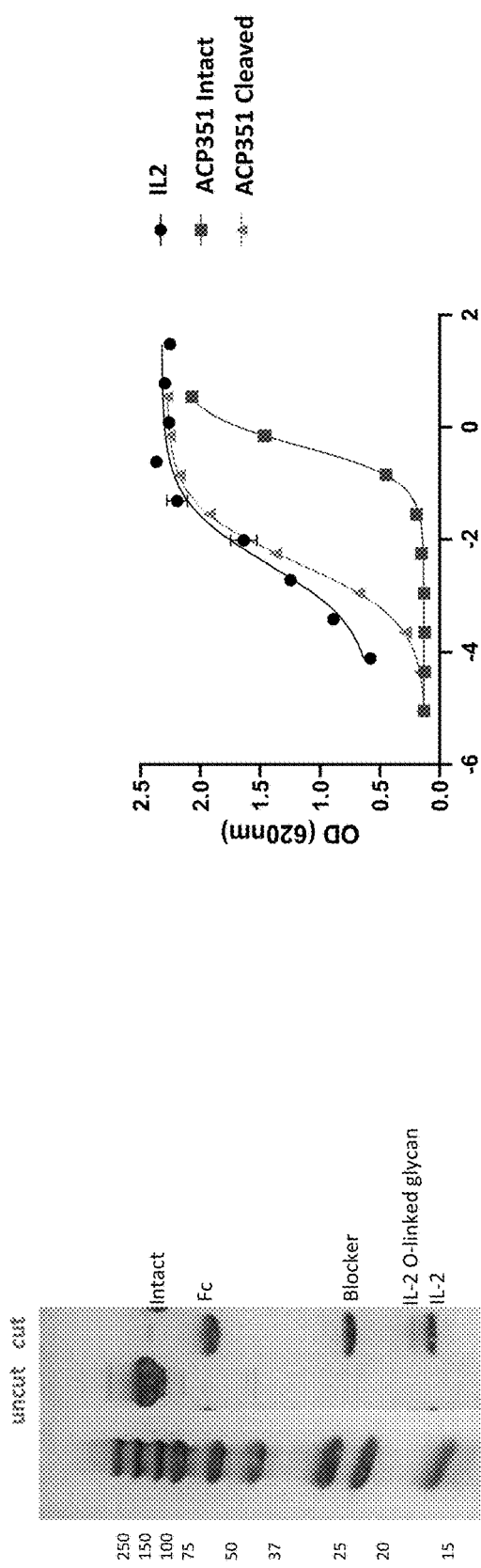
Figure 53A:
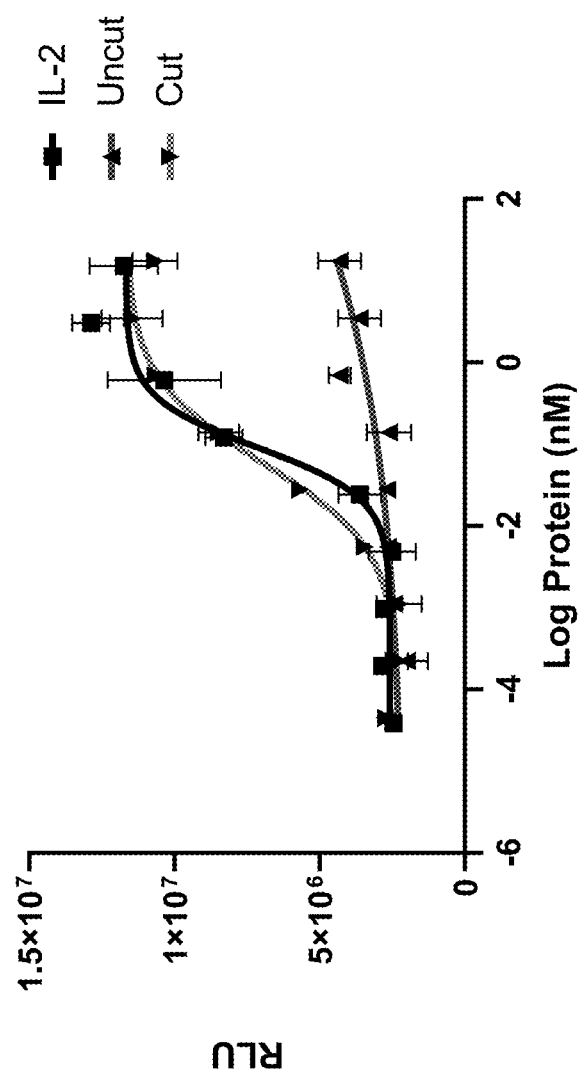
Figure 53B:
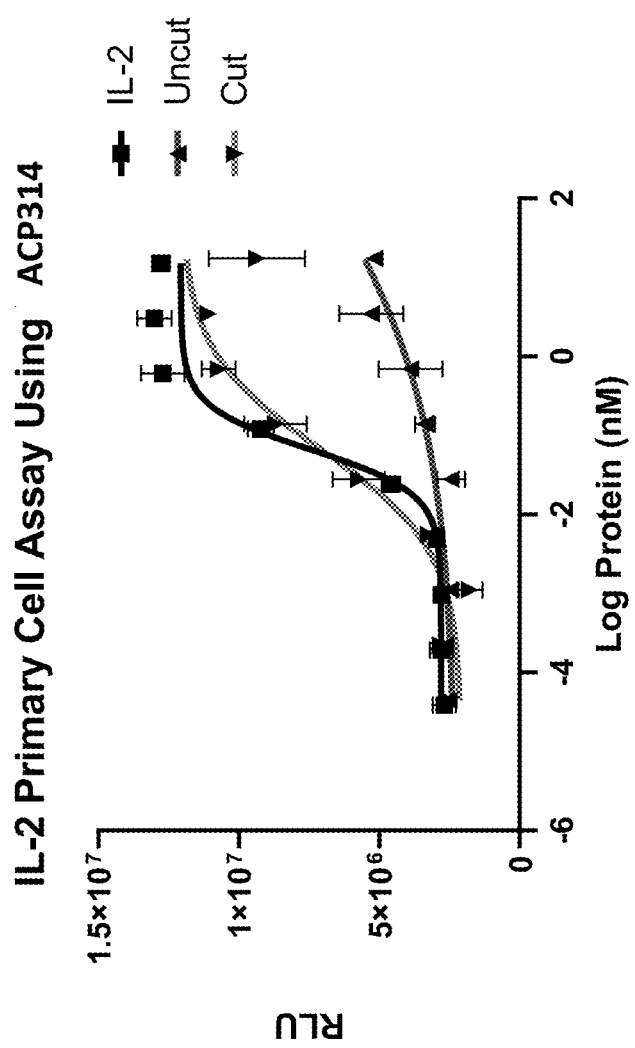
Figure 54A:
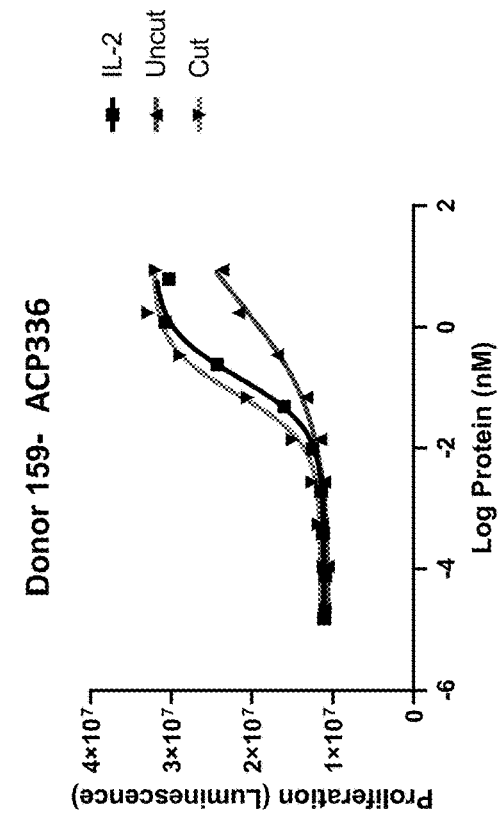
FIG. 54A-54N shows the results of proliferation assays comparing cut protein, uncut protein, and IL2 as a control.
Figure 54A:
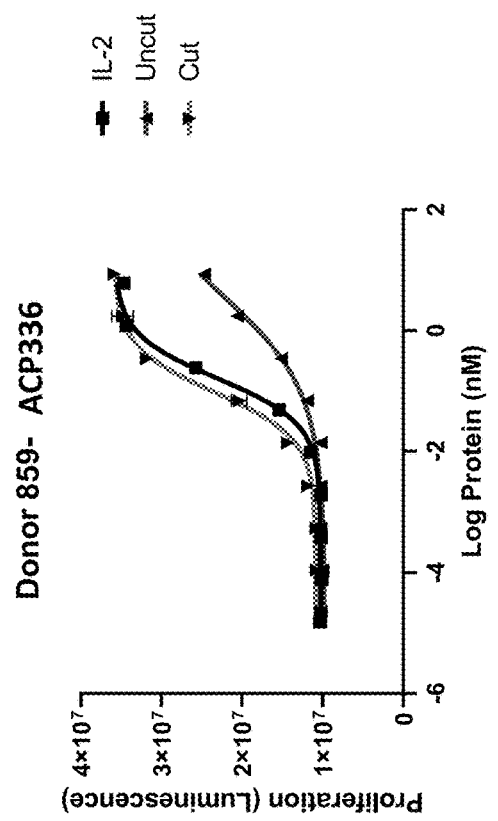
Figure 54B:
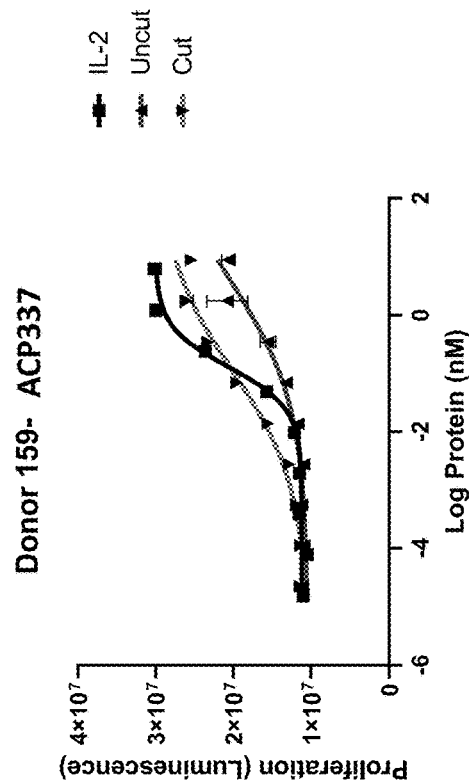
Figure 54B:
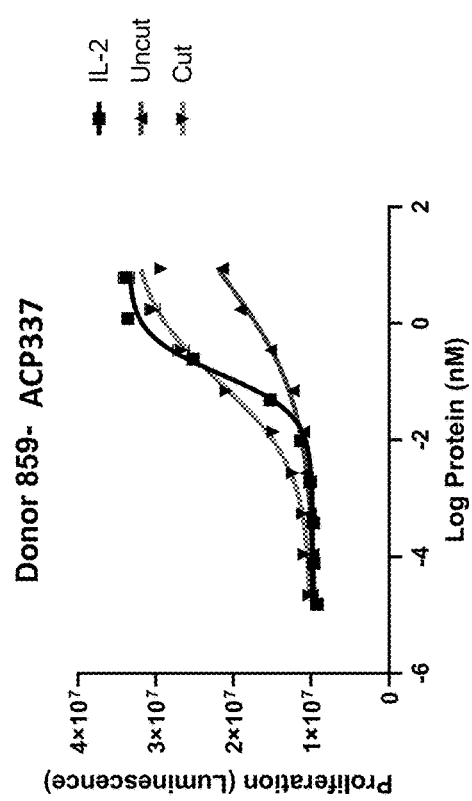
Figure 54C:
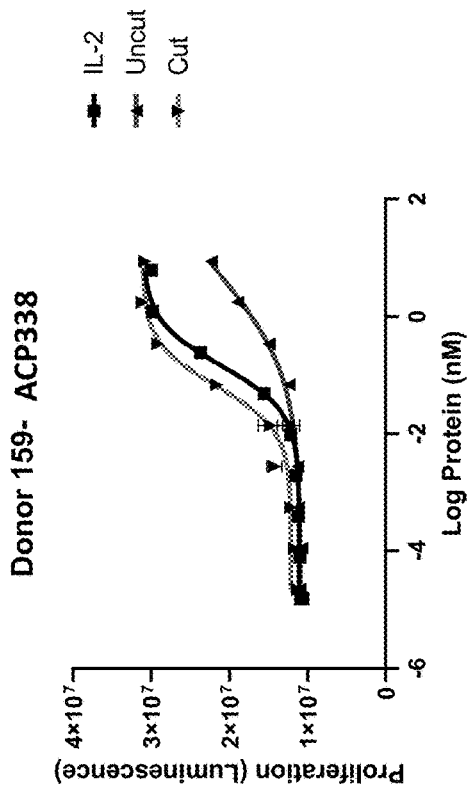
Figure 54C:
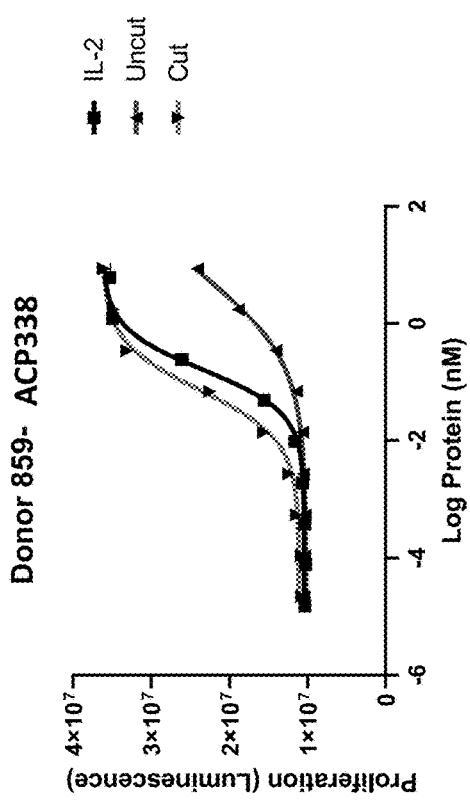
Figure 54D:
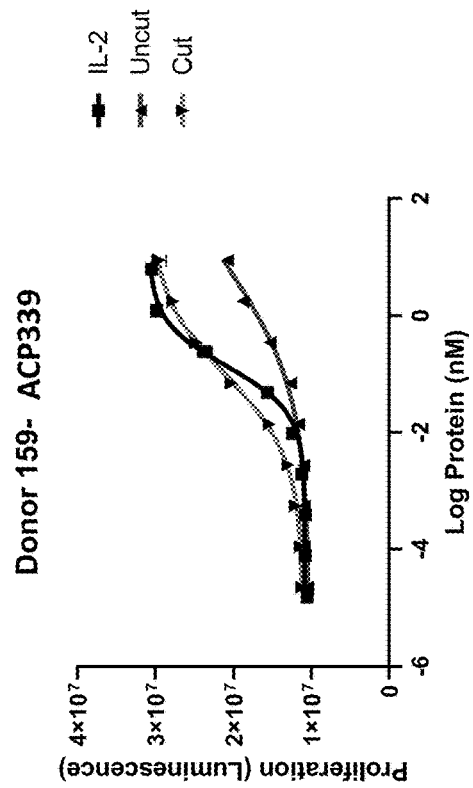
Figure 54D:
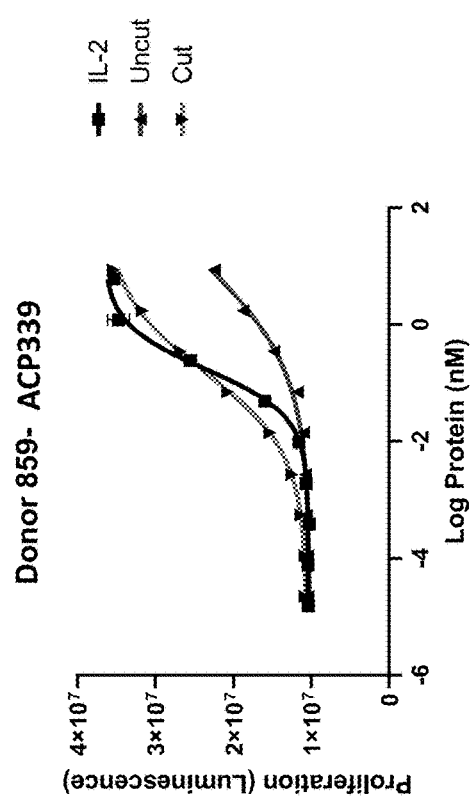
Figure 54E:
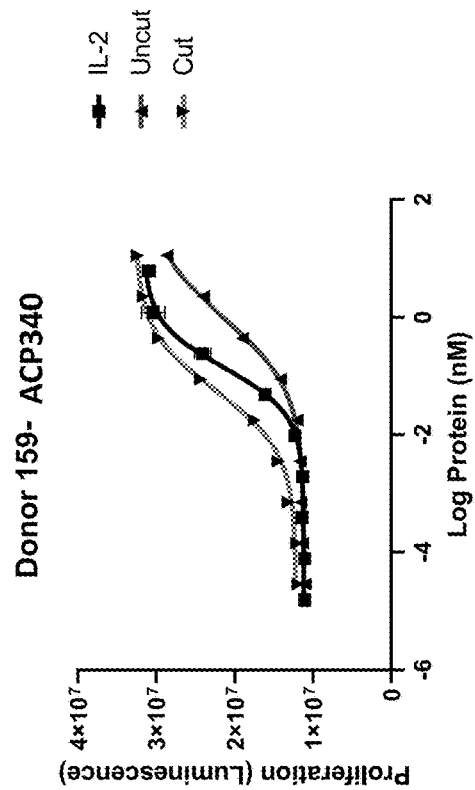
Figure 54E:
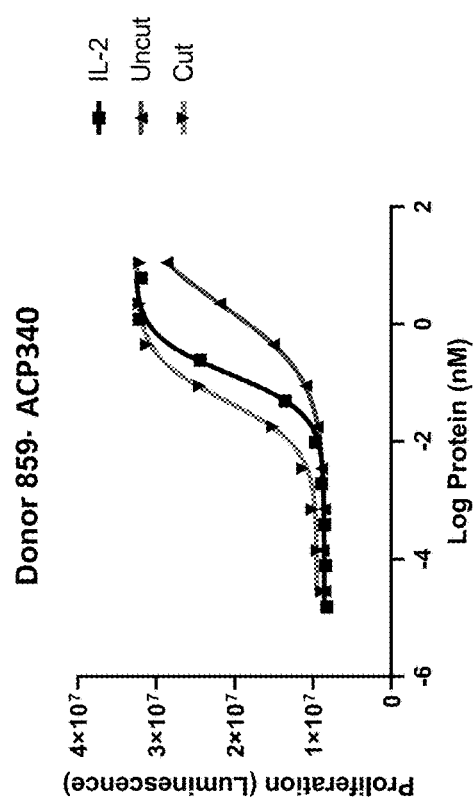
Figure 54F:
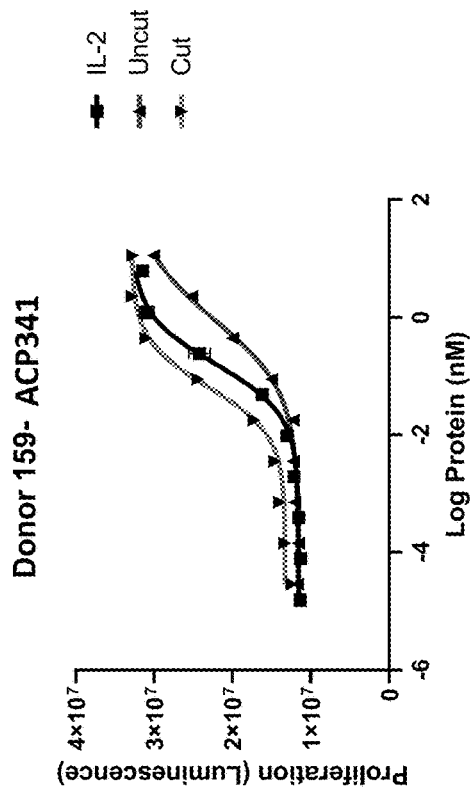
Figure 54F:
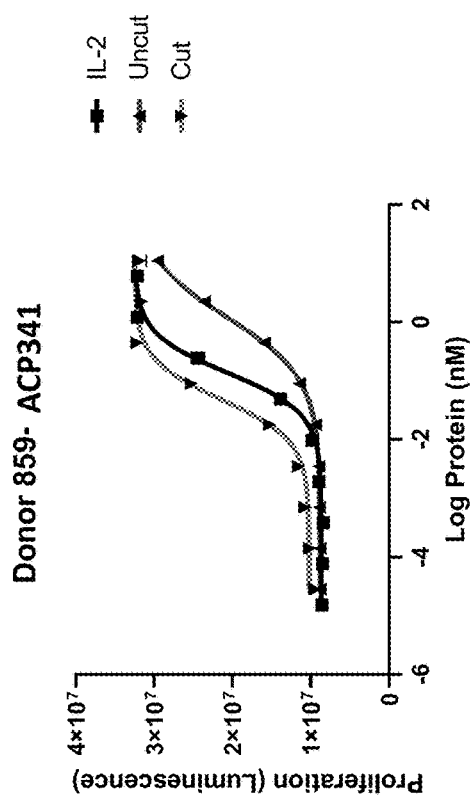
Figure 54G:
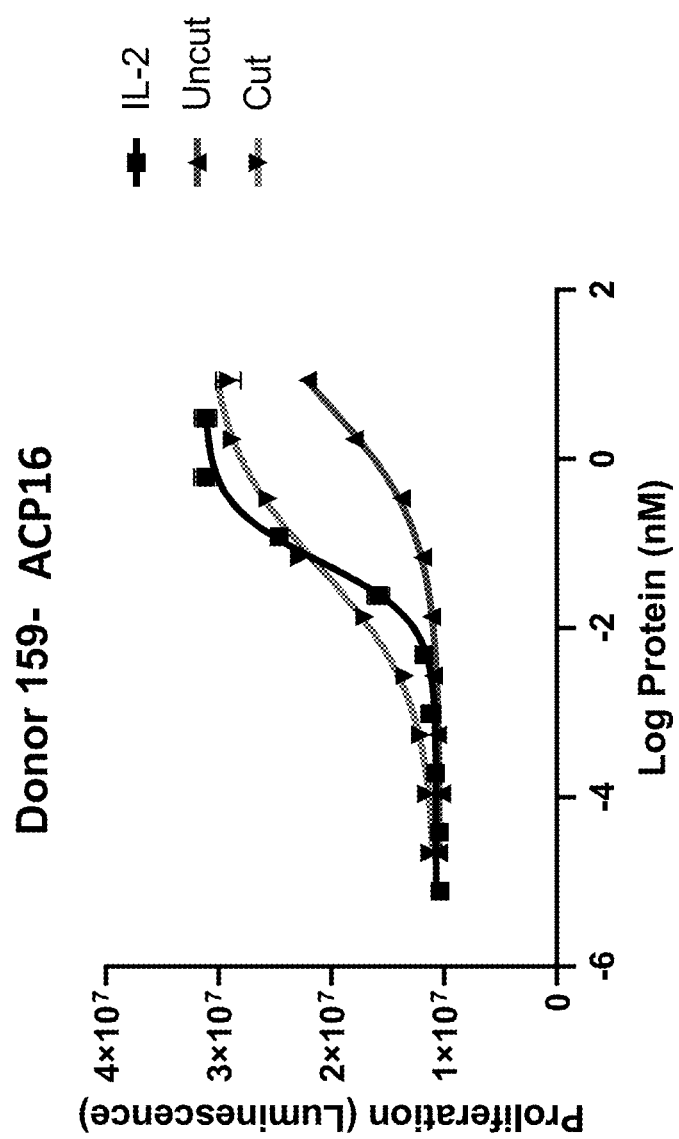
Figure 54H:
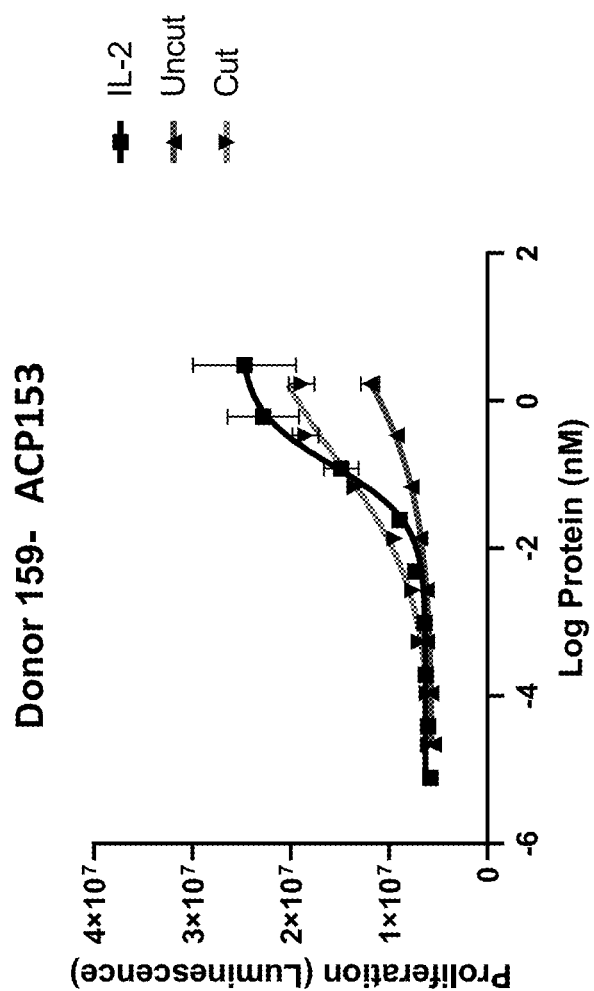
Figure 54I:
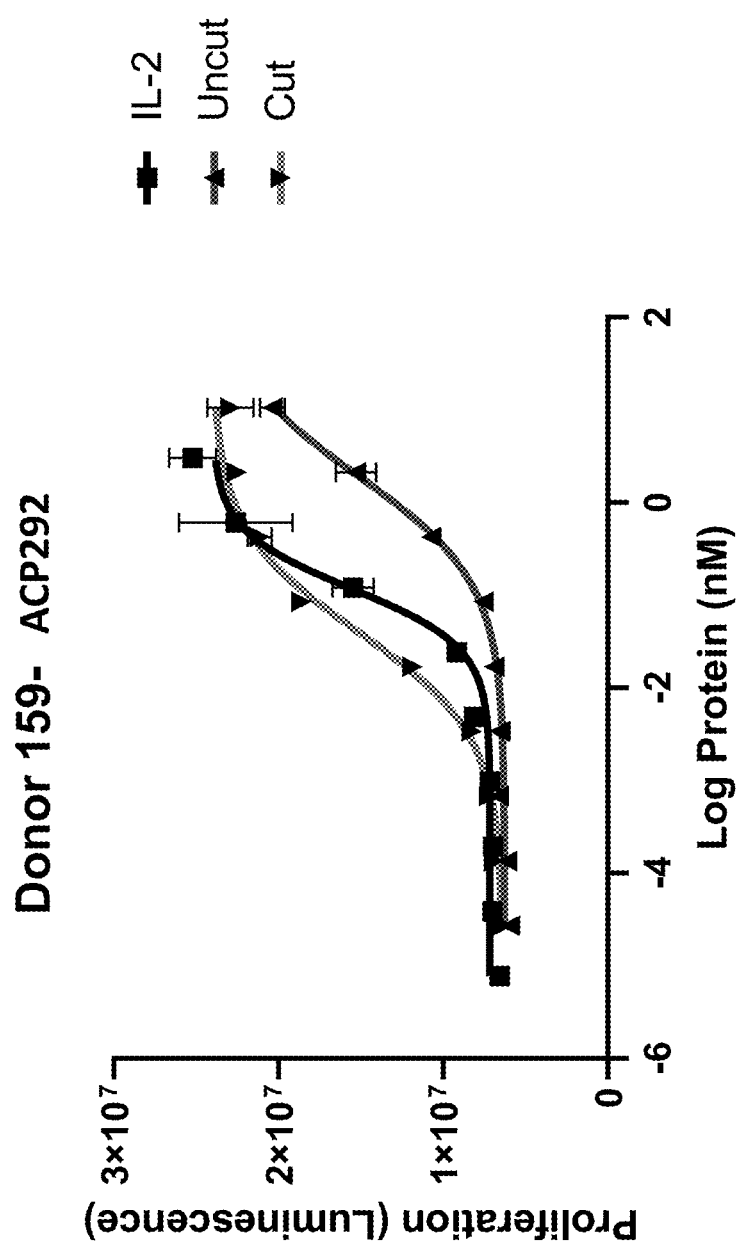
Figure 54J:
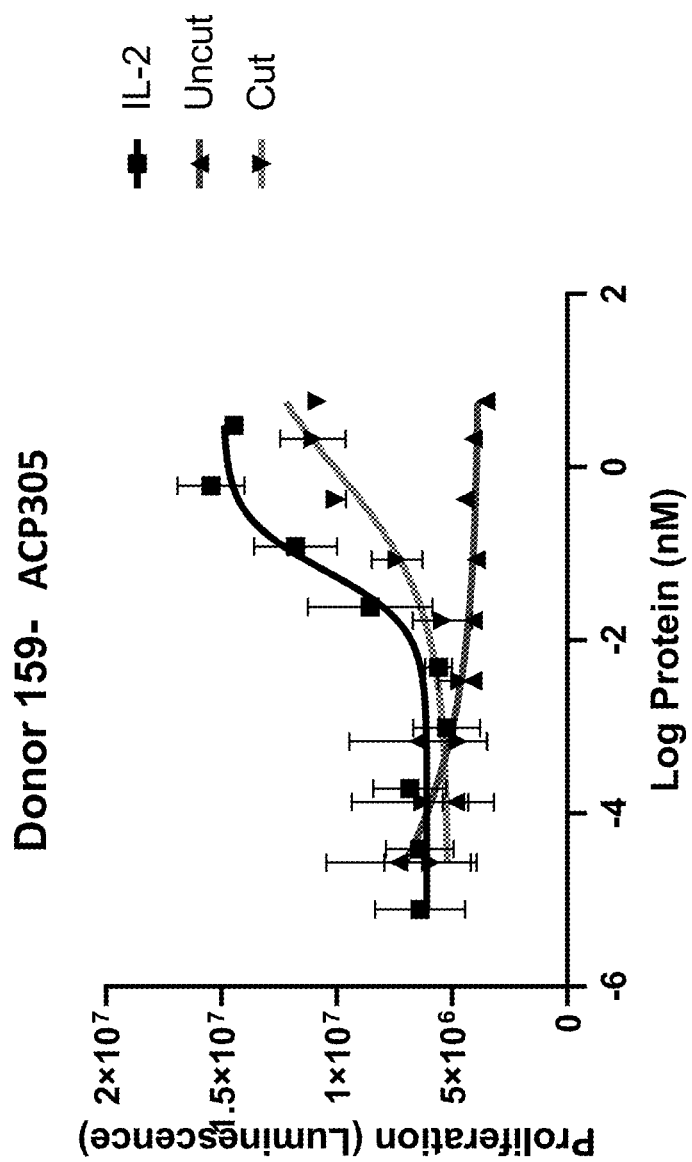
Figure 54K:
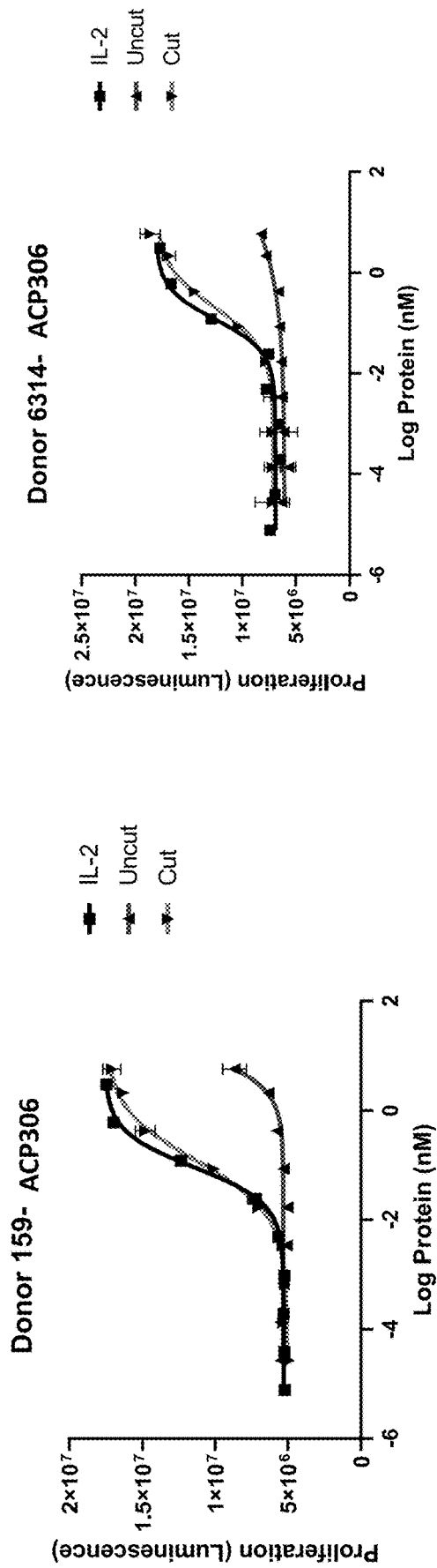
Figure 54L:
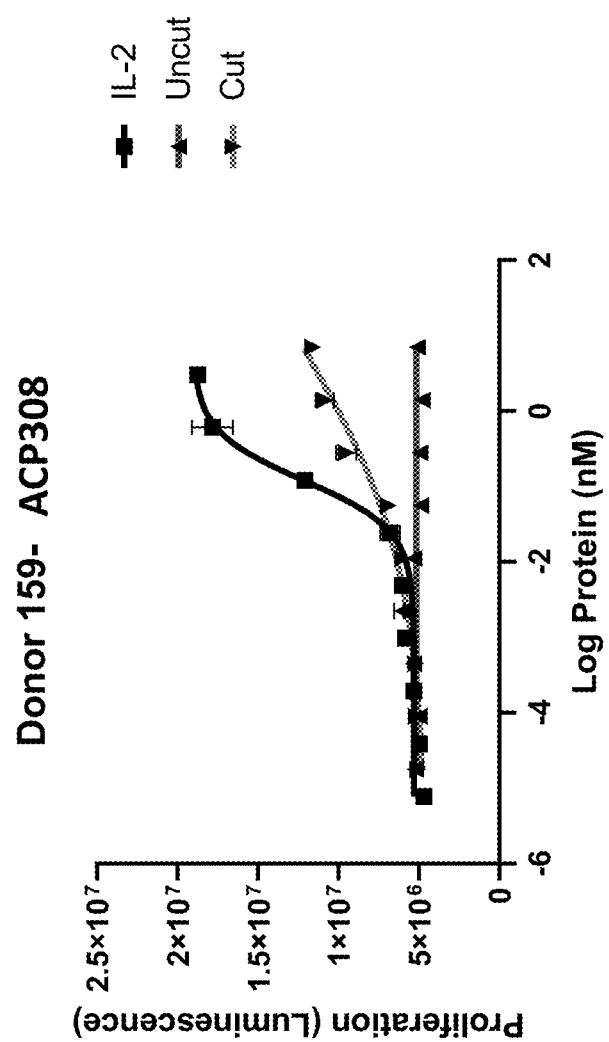
Figure 54M:
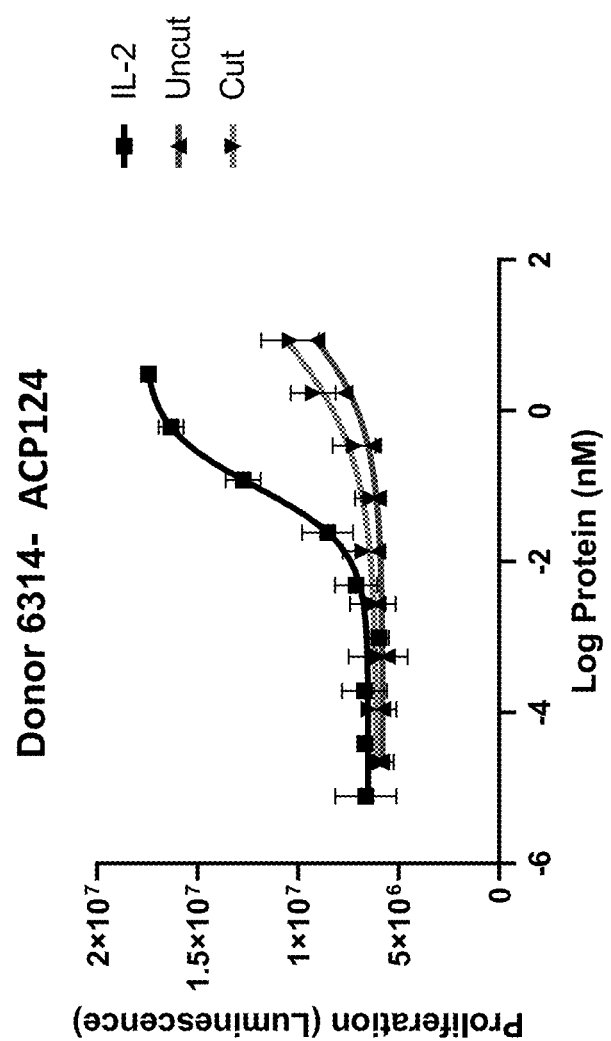
Figure 54N:
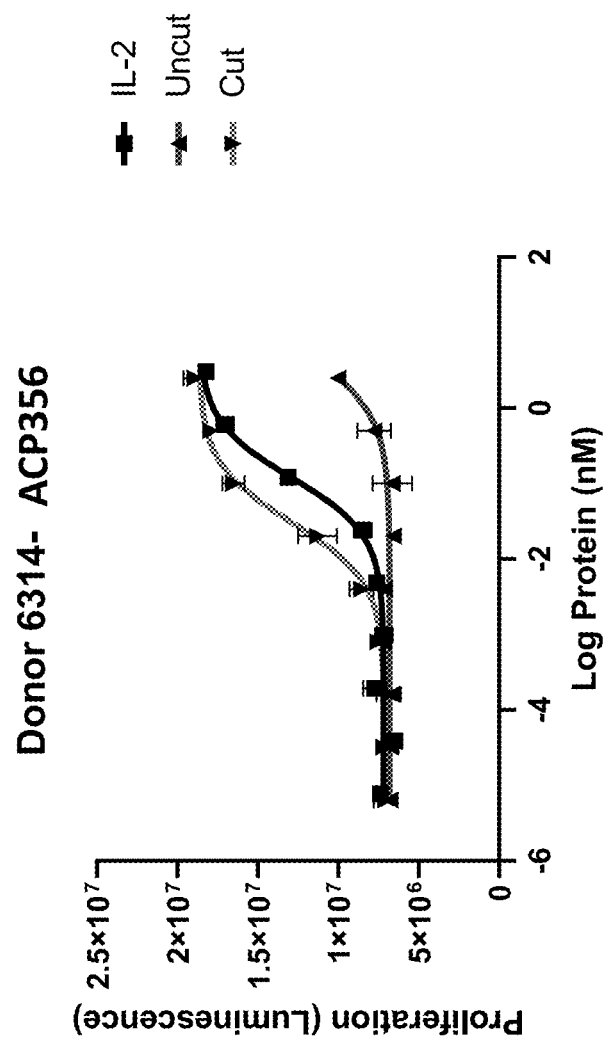
Figure 55A:
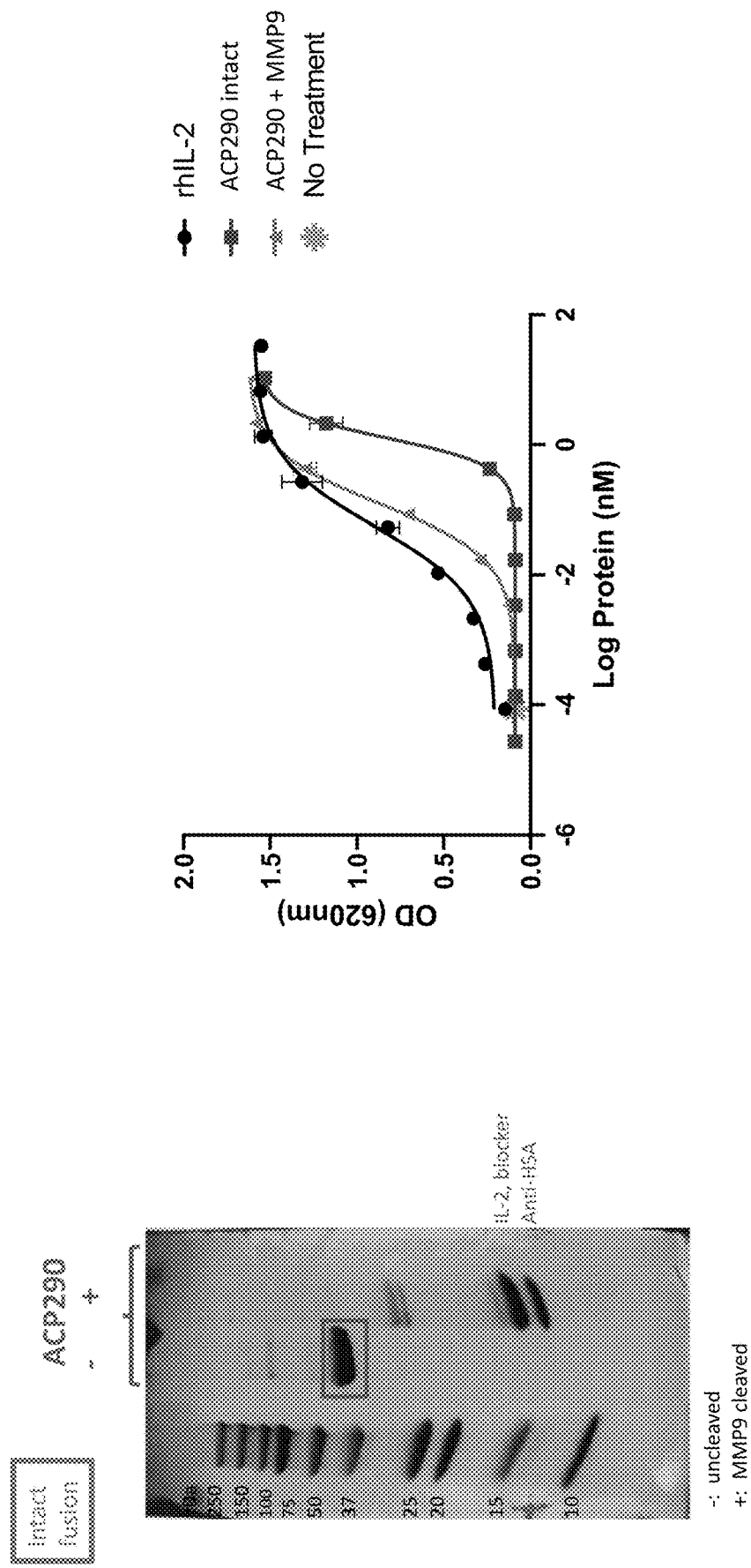
FIGS. 55A-55N shows the results of HekBlue IL2 reporter assays comparing activity of constructs with and without protease cleavage; IL-2 is included as a control.
Figure 55B:
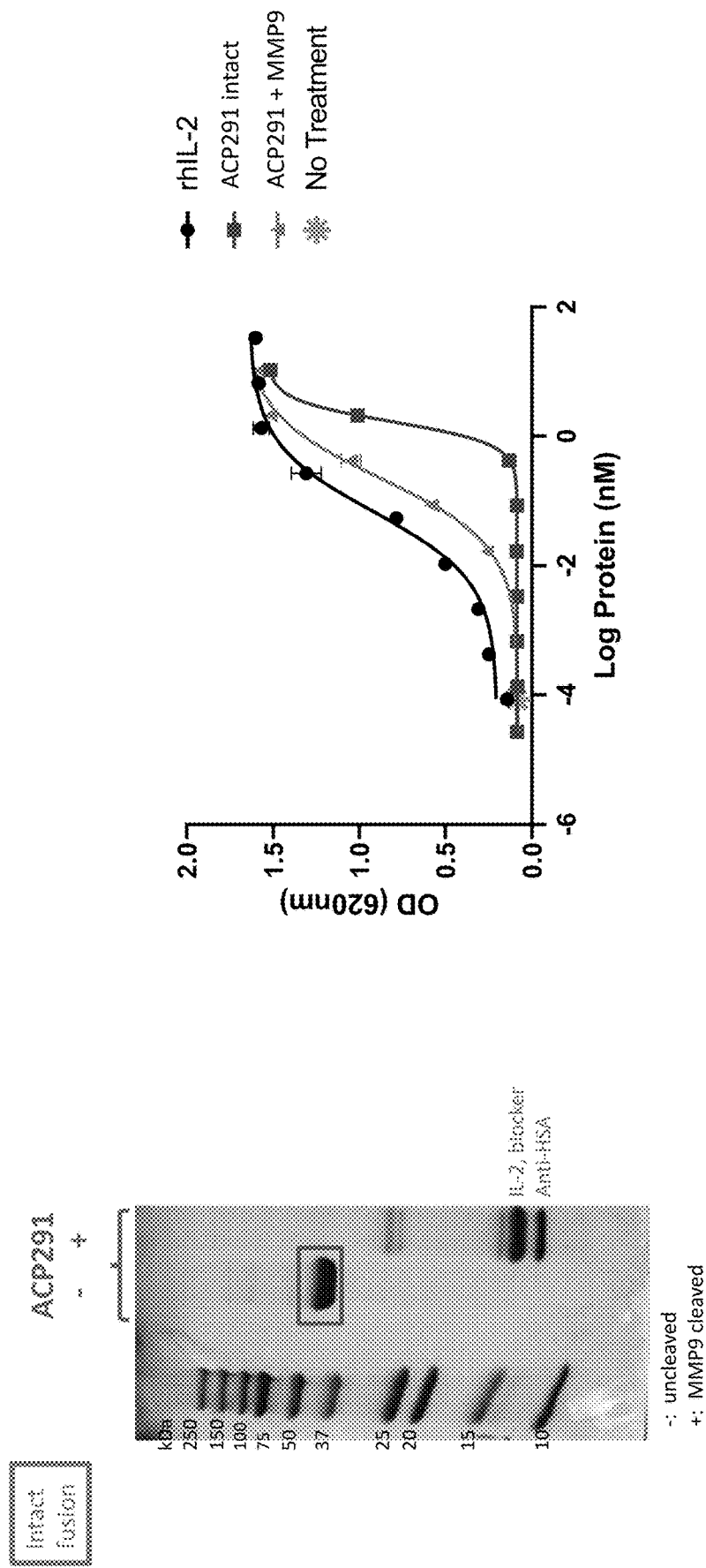
Figure 55C:
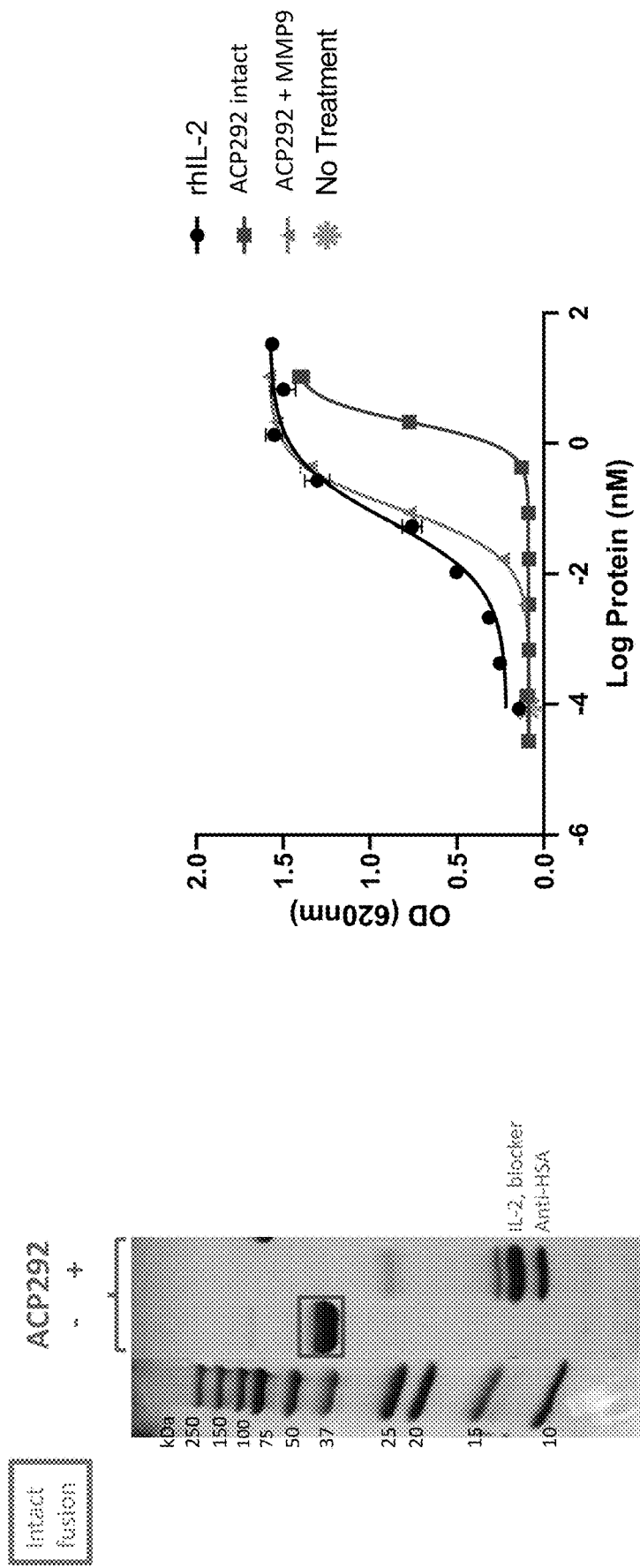
Figure 55D:
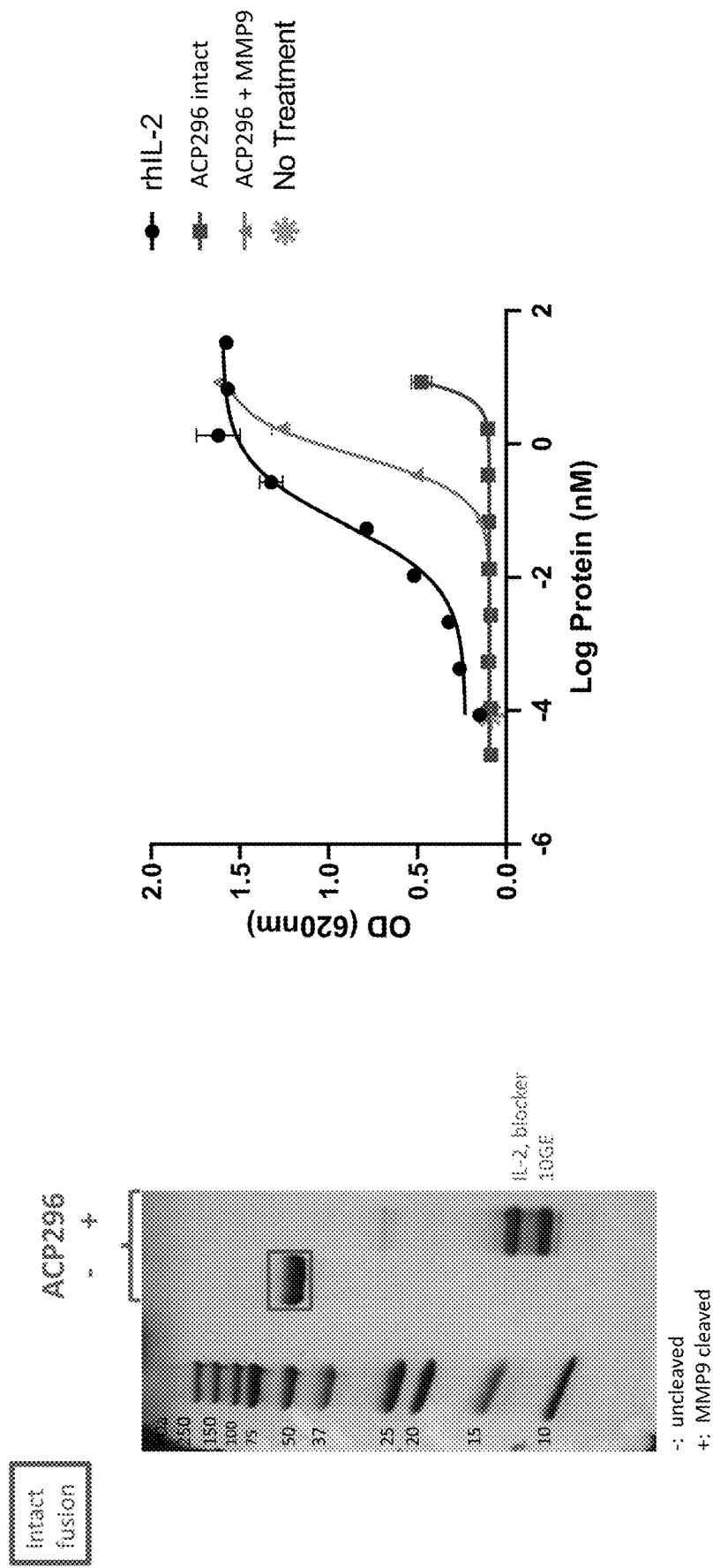
Figure 55E:
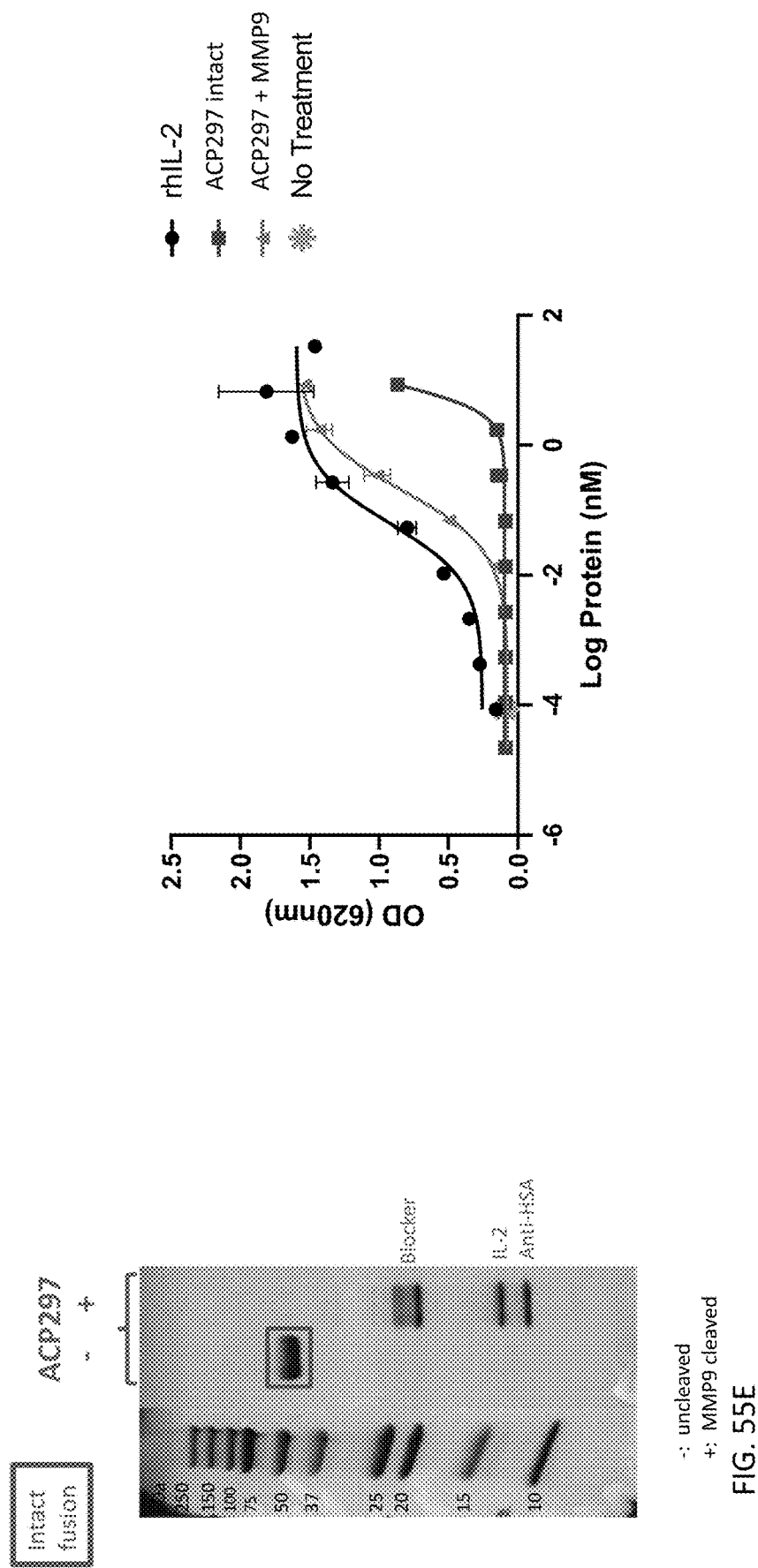
Figure 55F:
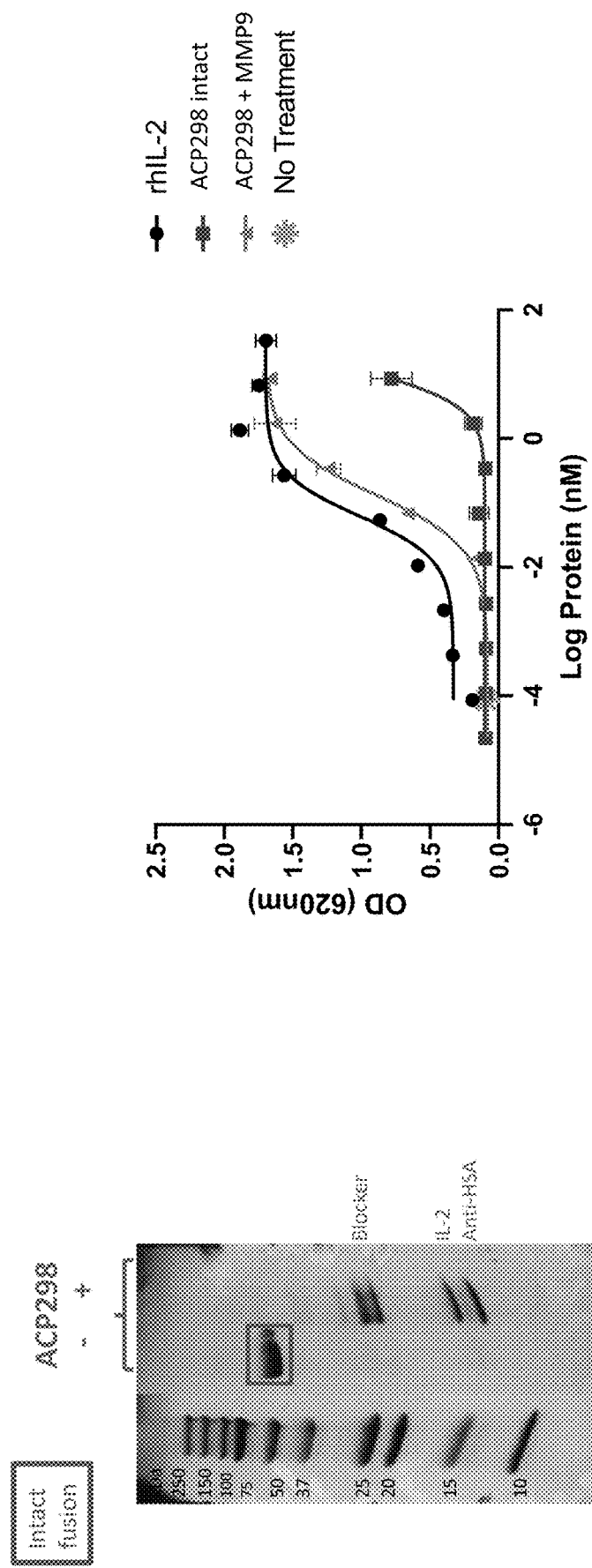
Figure 55G:
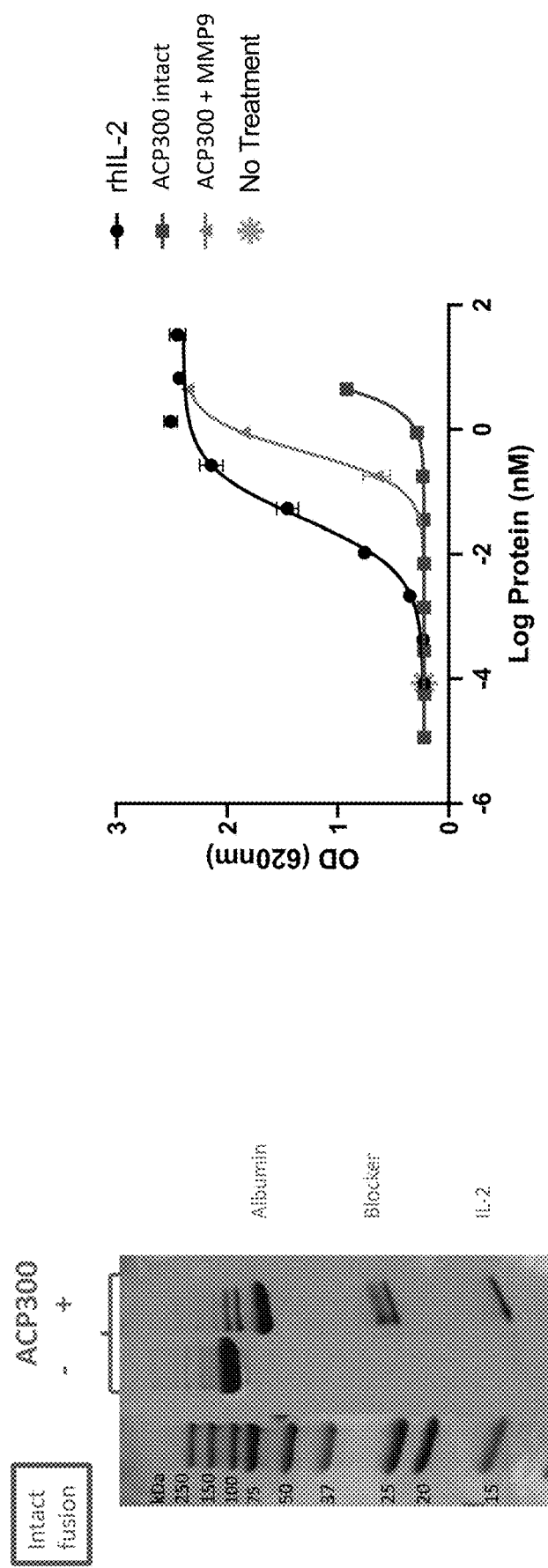
Figure 55H:
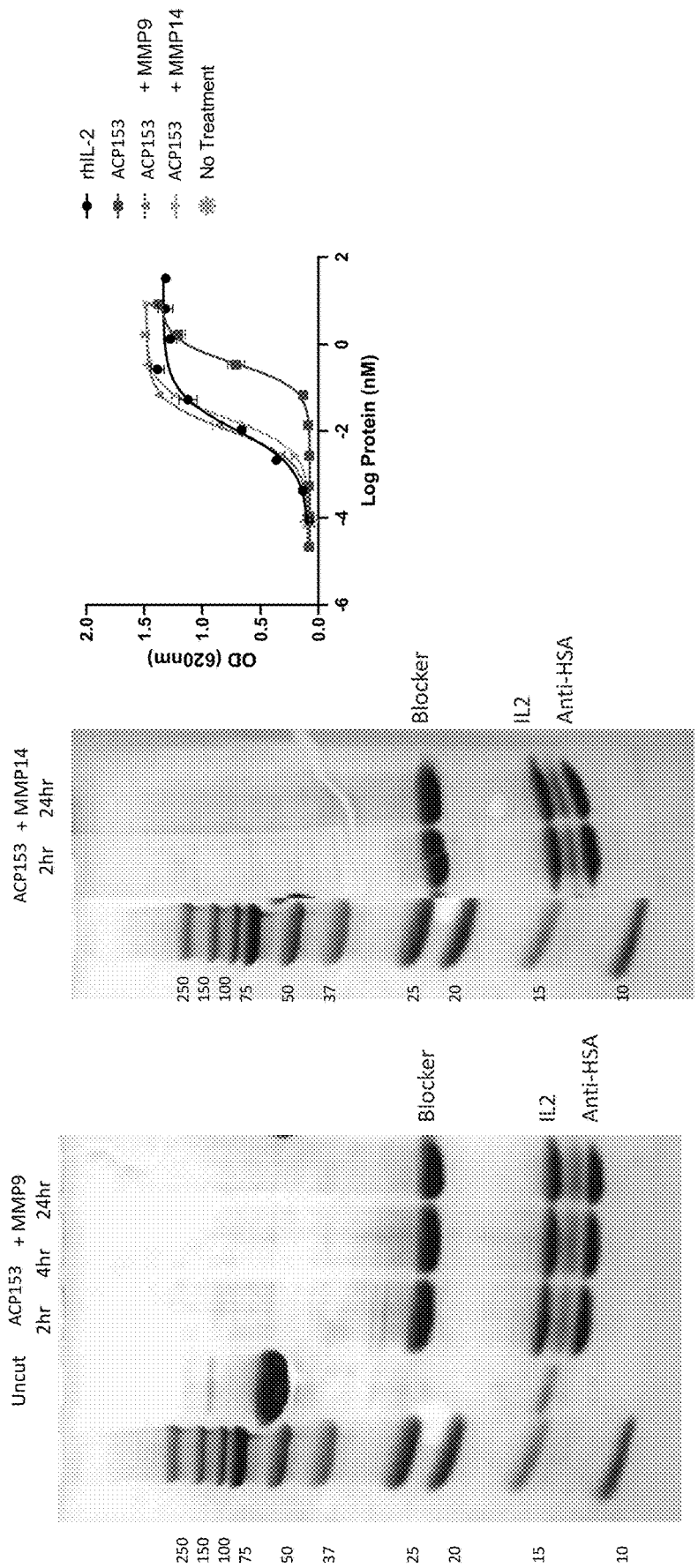
Figure 55I:
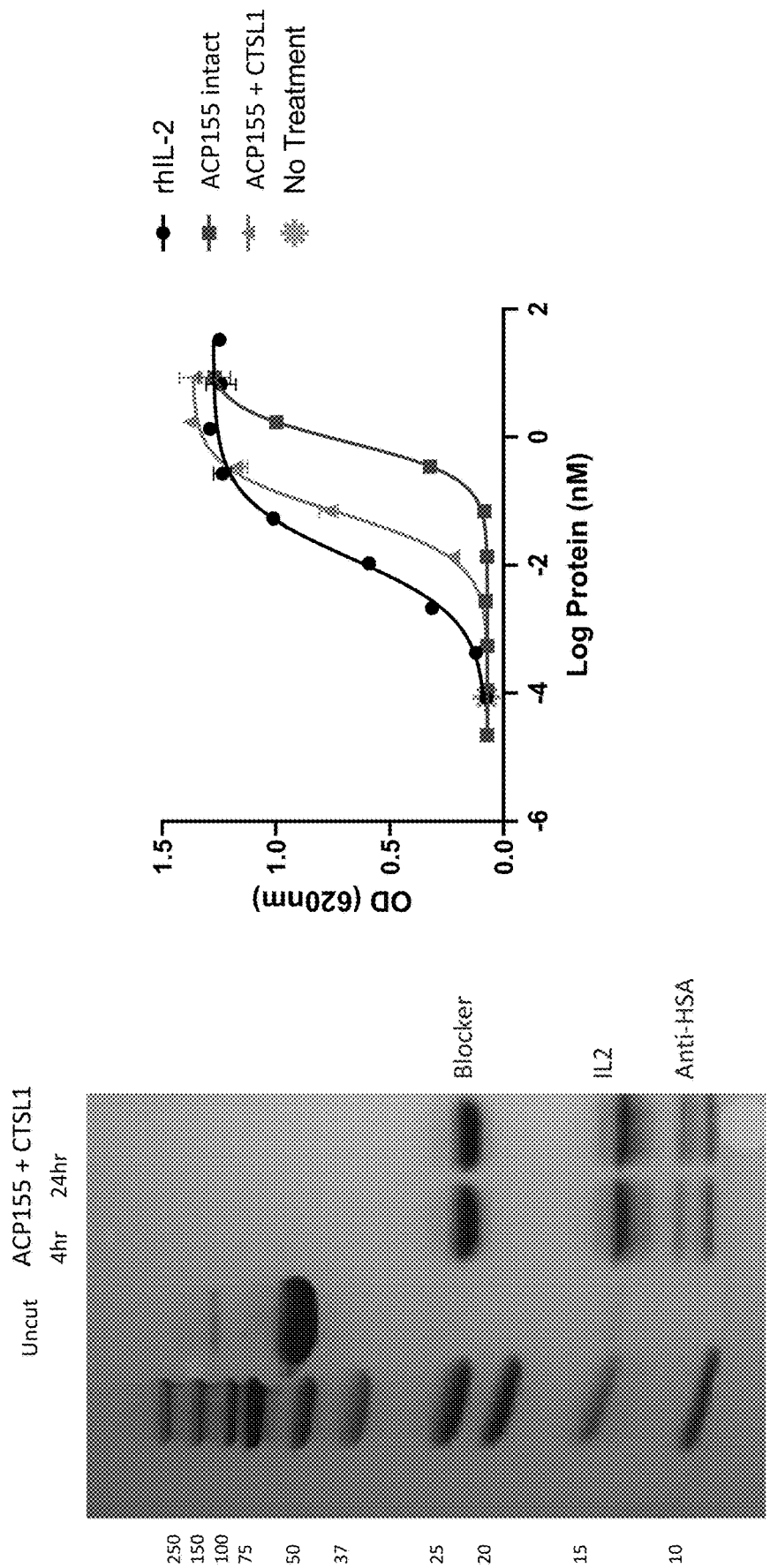
Figure 55J:
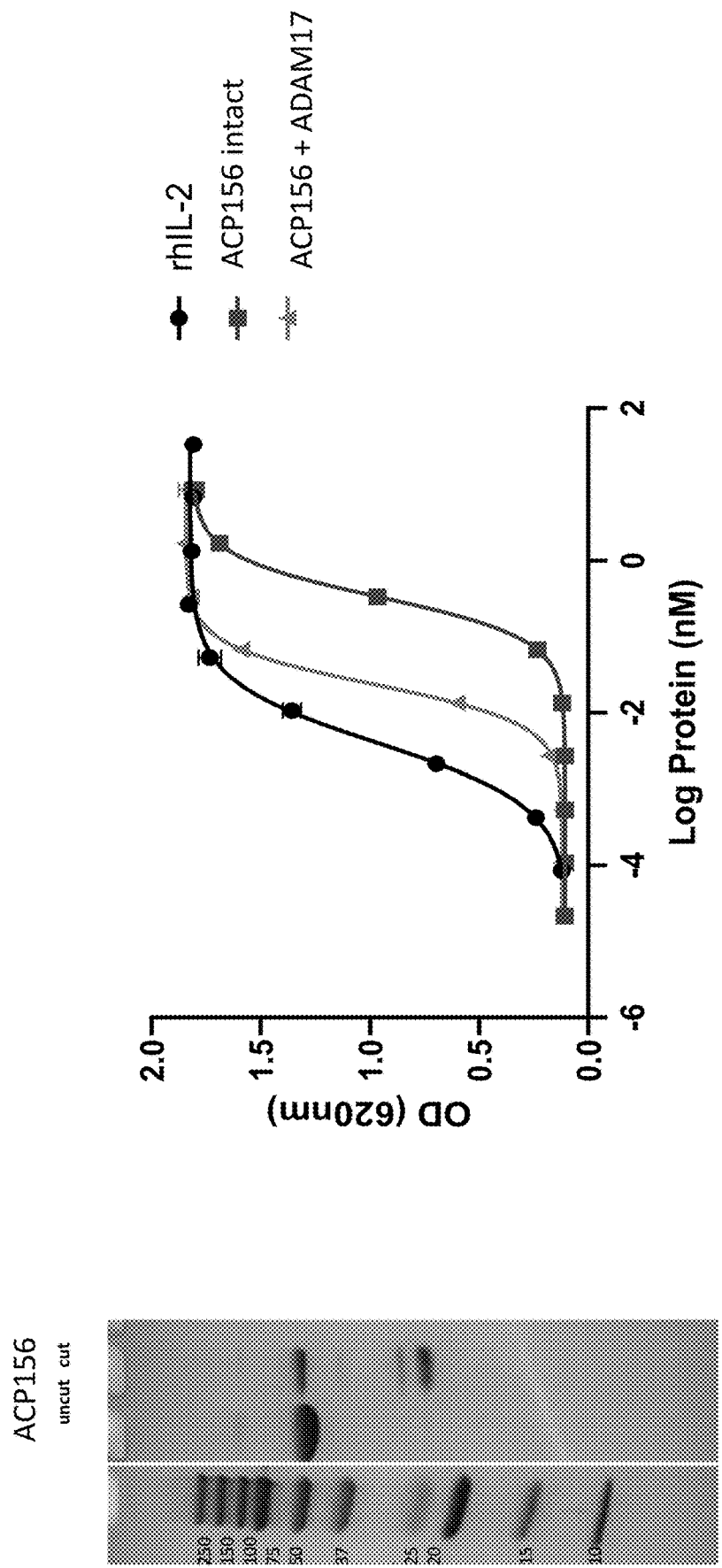
Figure 55K:
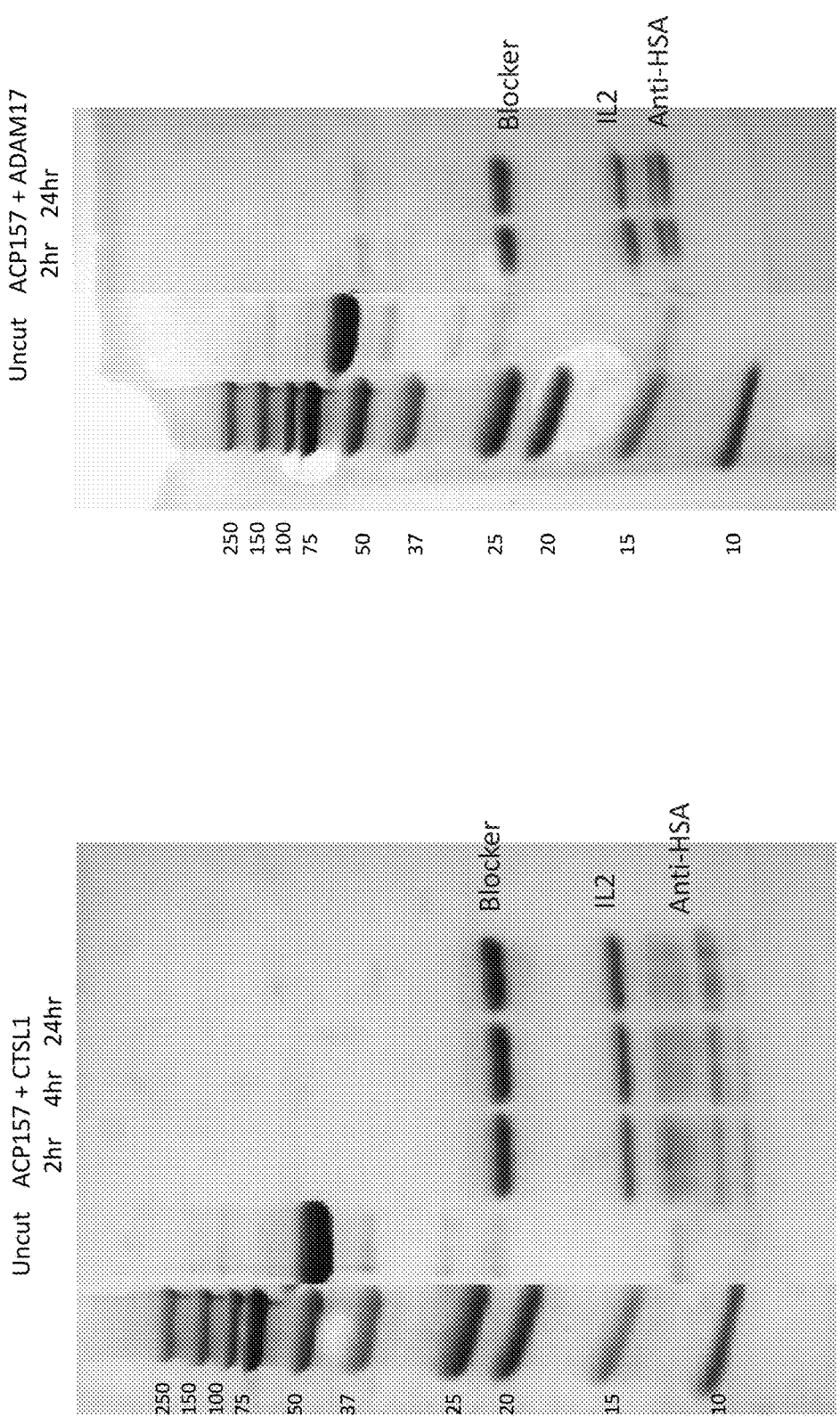
Figure 55L:
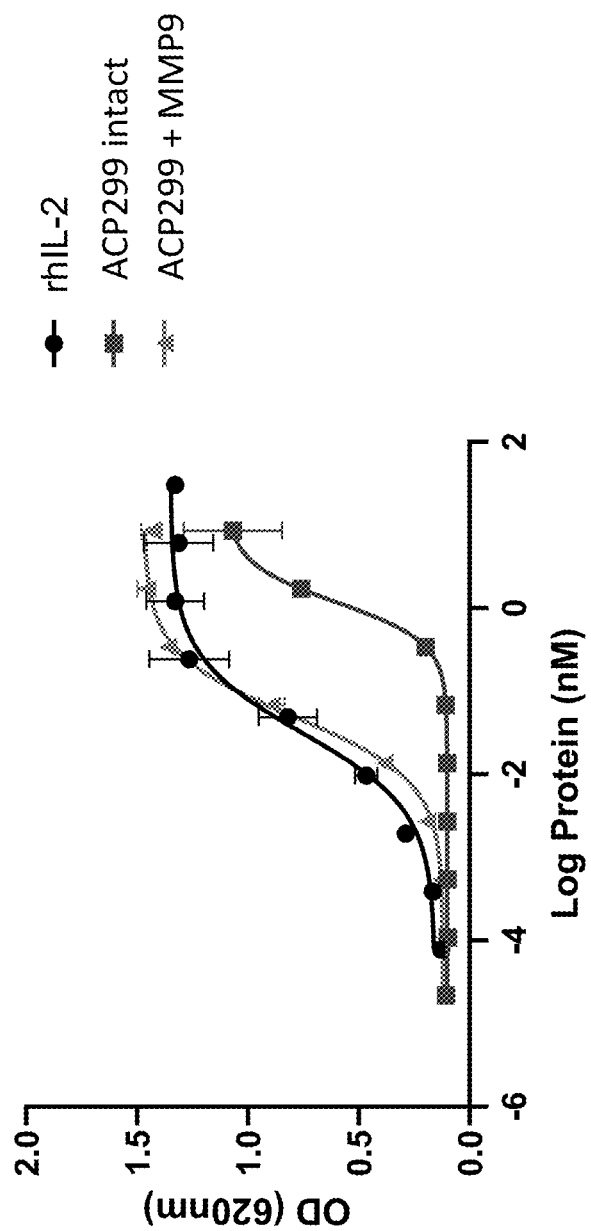
Figure 55M:
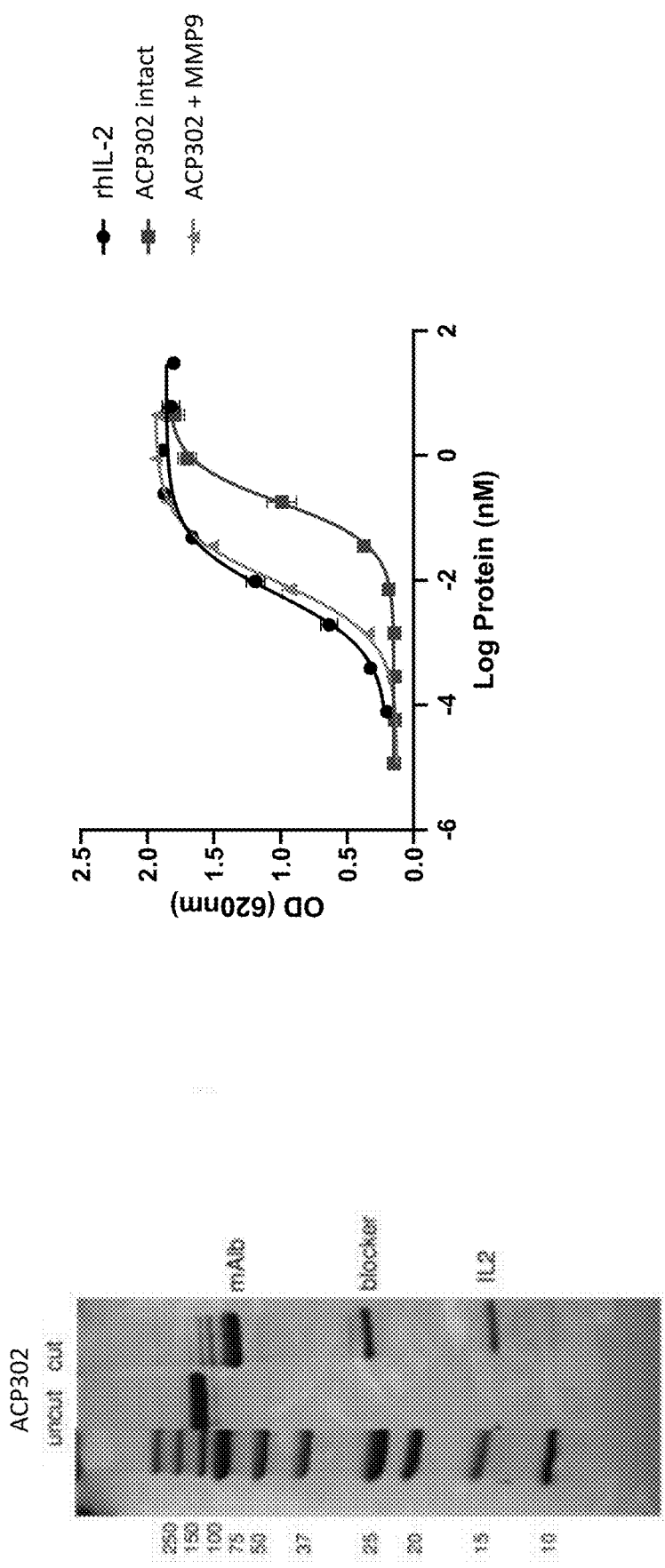
Figure 55N:
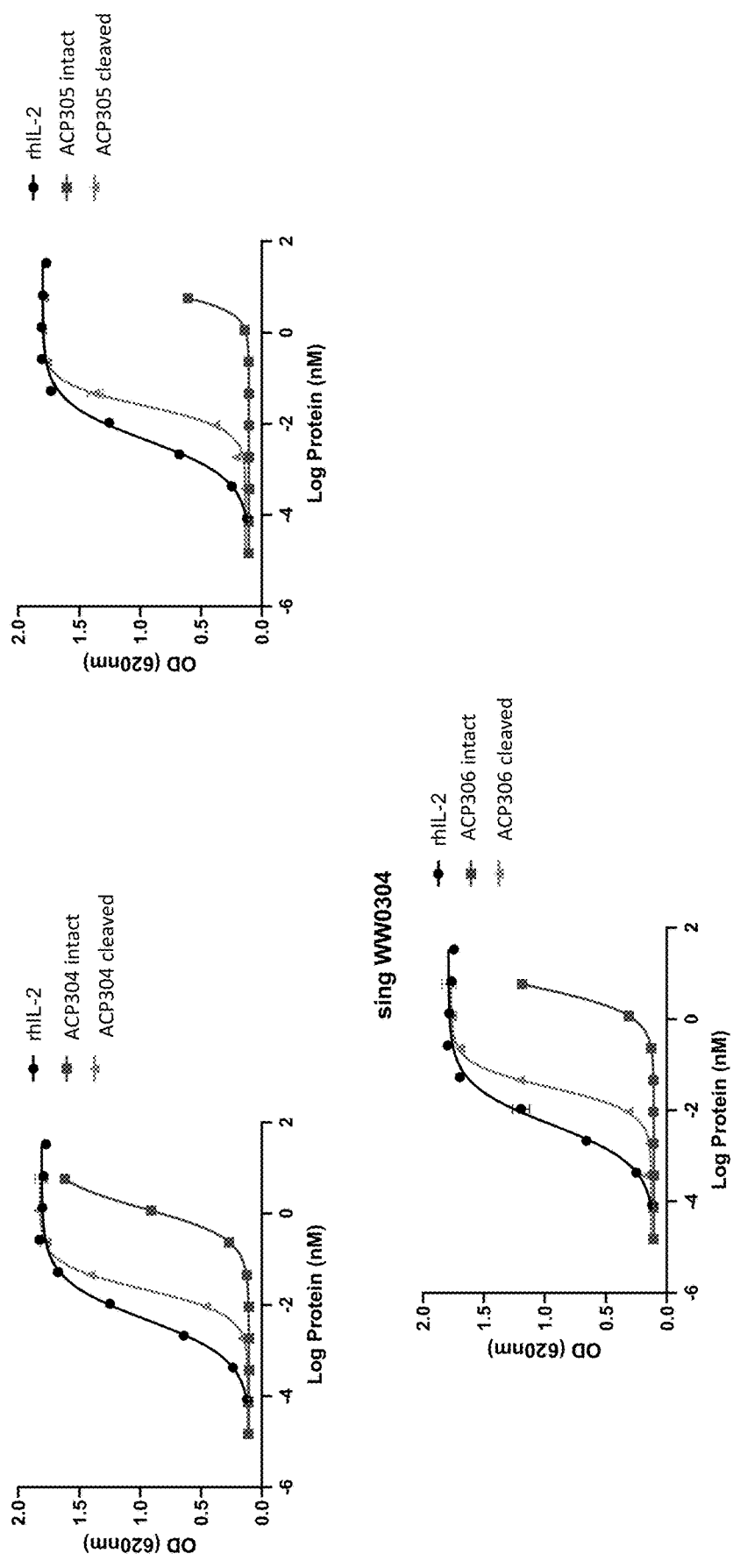
Figure 56:
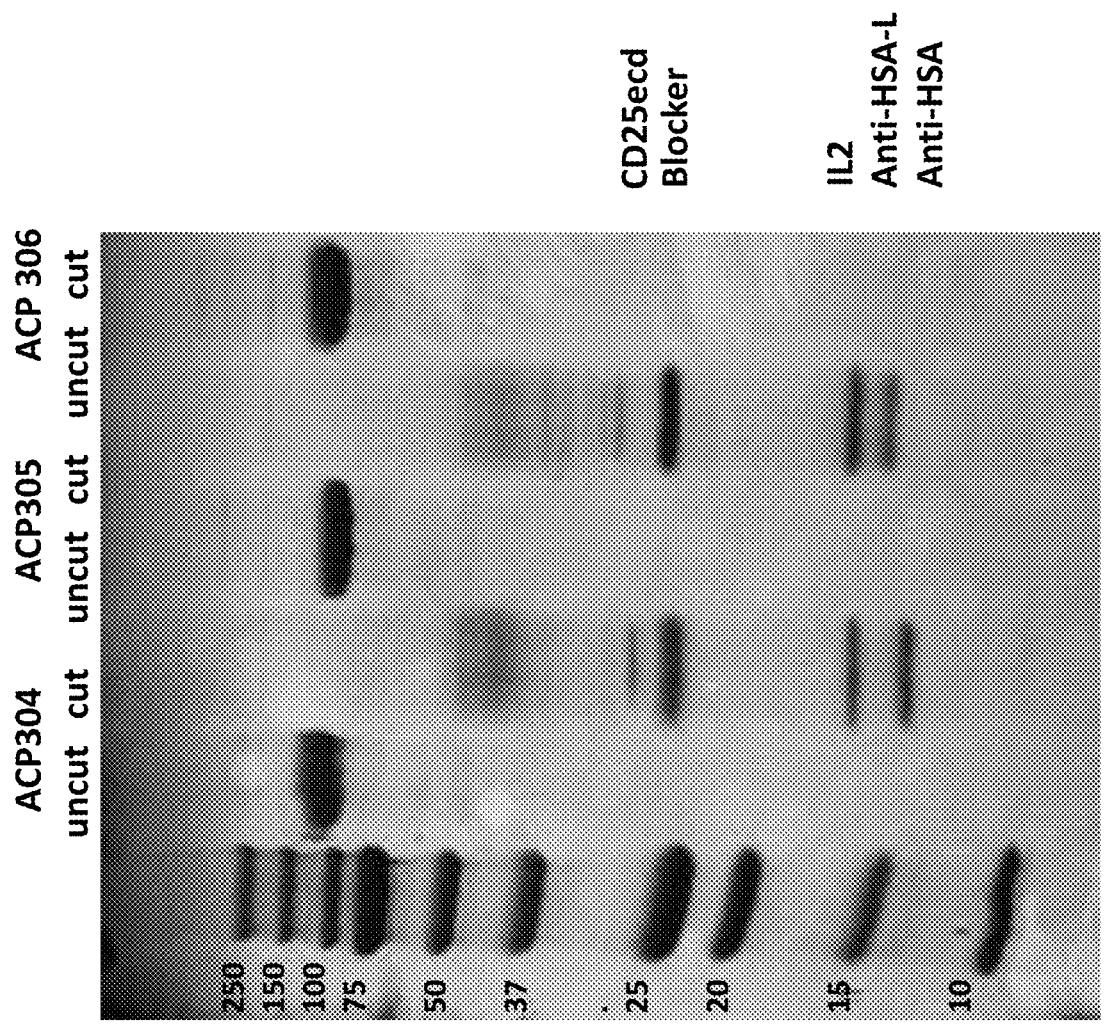
FIGS. 56, 57A-57D, 58, 59A-59Z depict the activity of cytokine fusion proteins constructs.
Figure 57A:
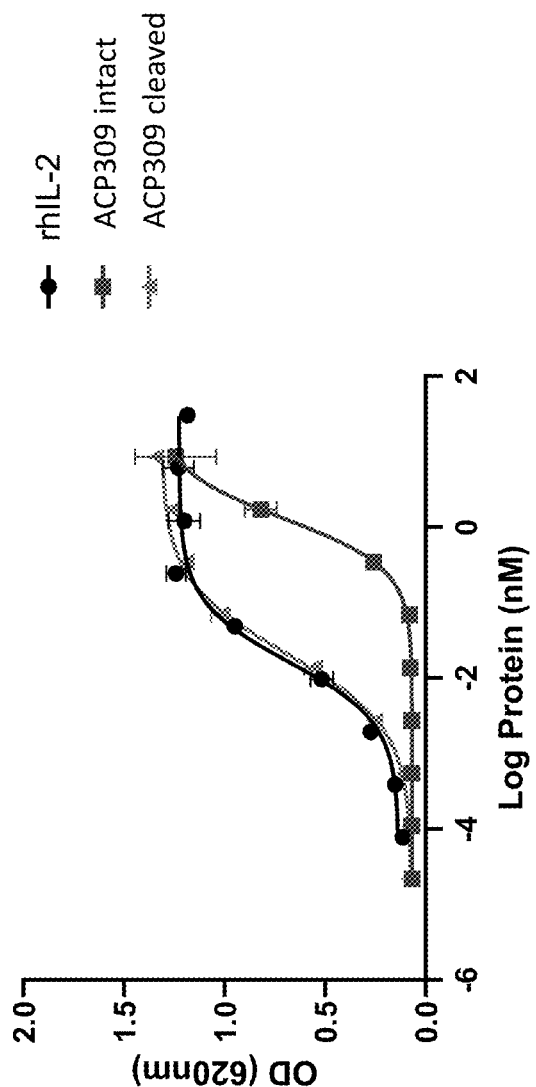
Figure 57B:
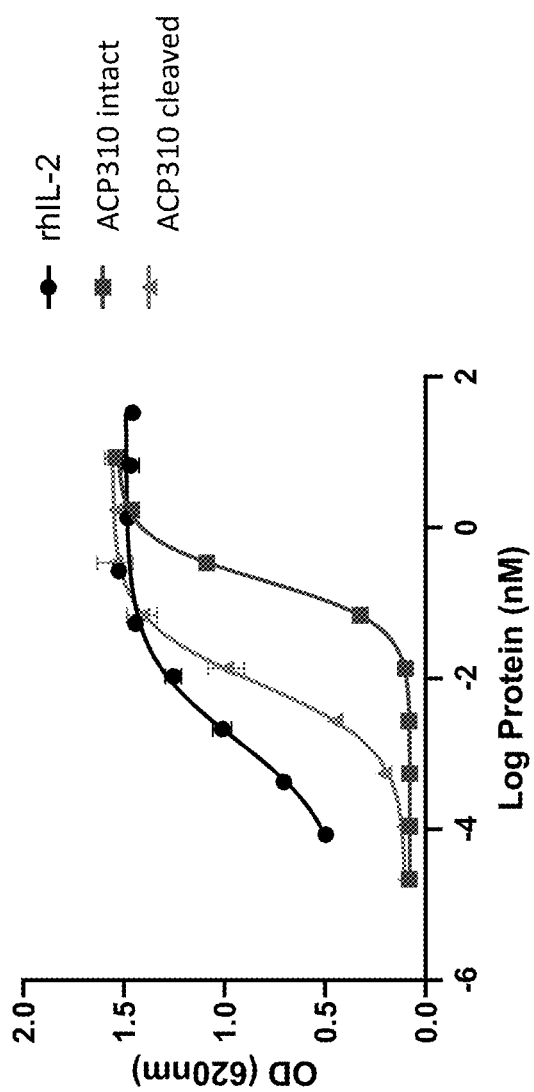
Figure 57C:
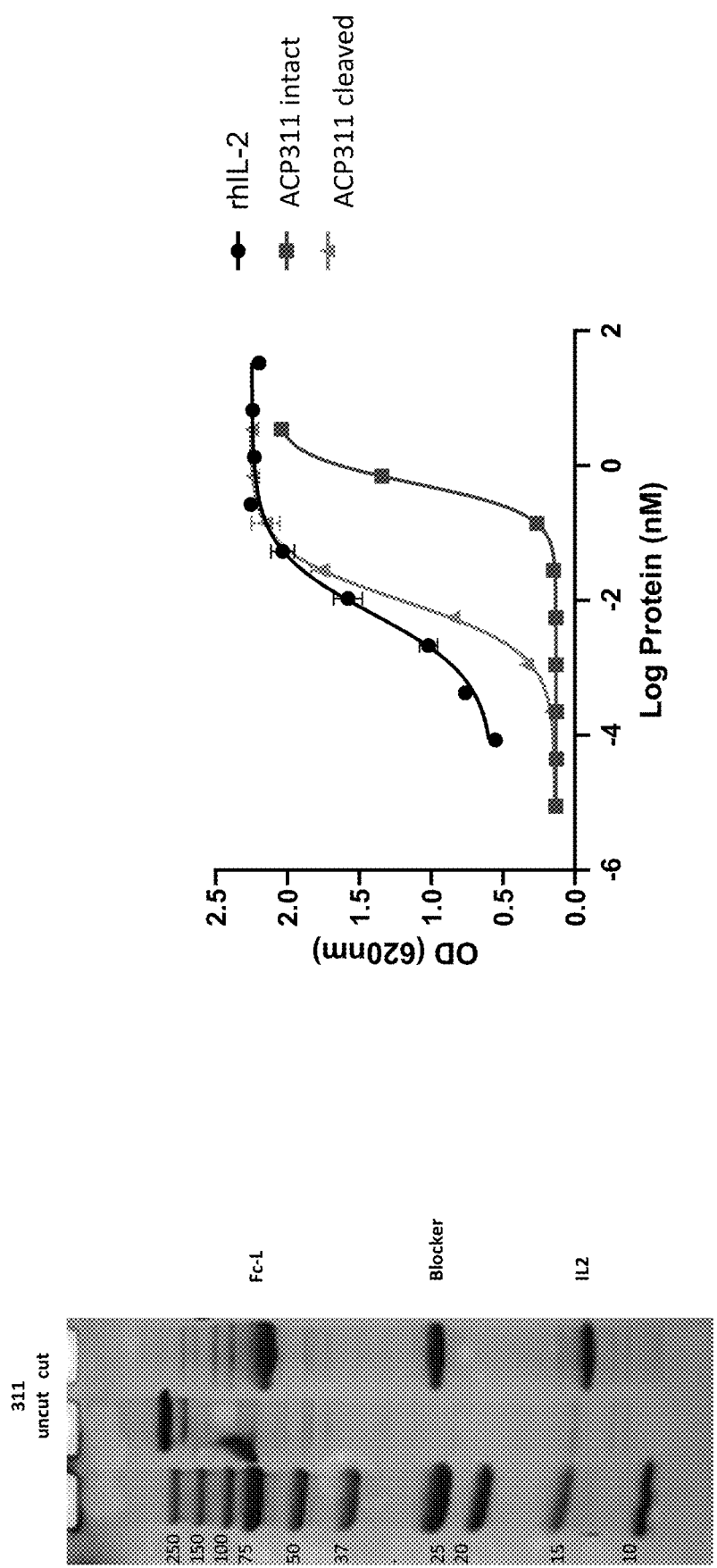
Figure 57D:
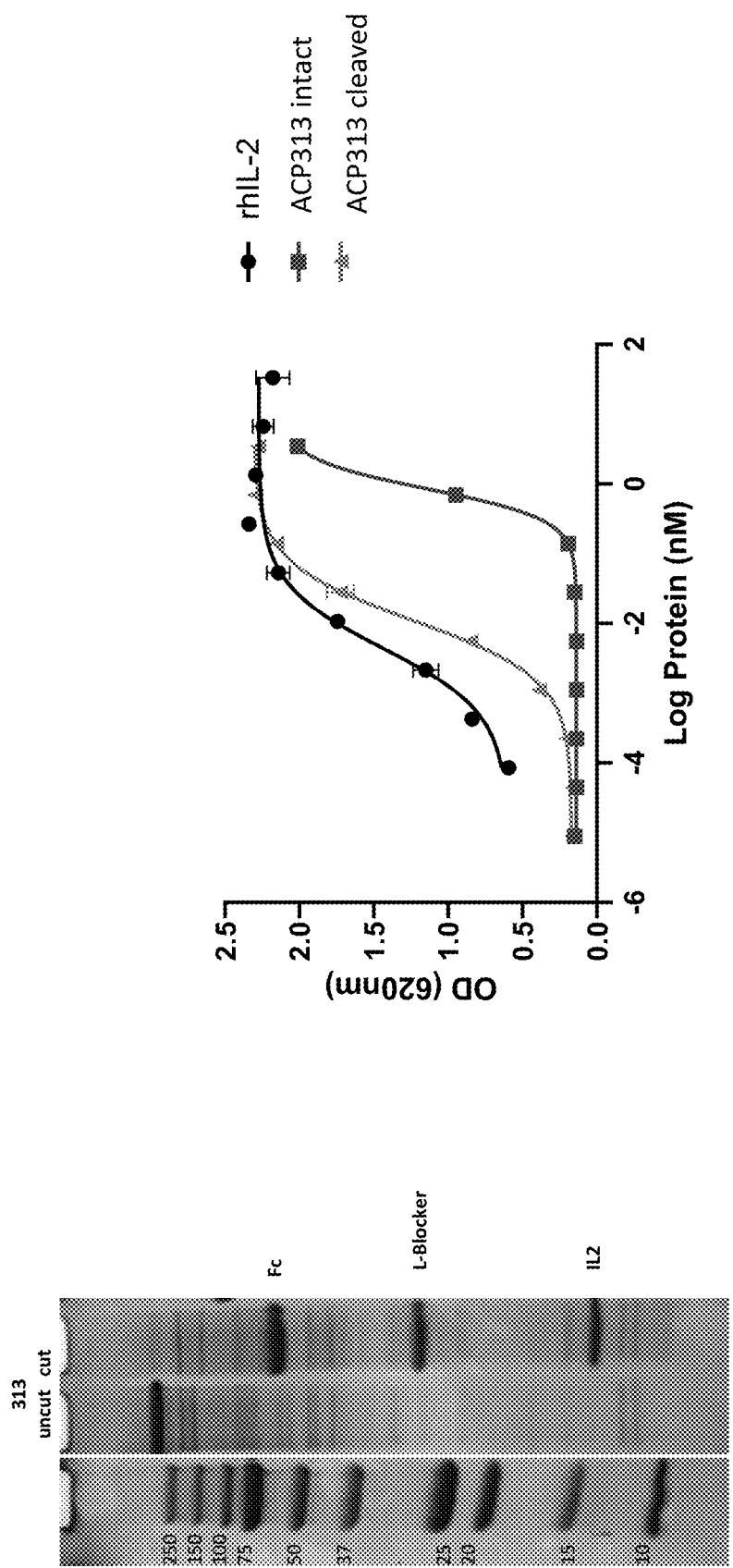
Figure 58:
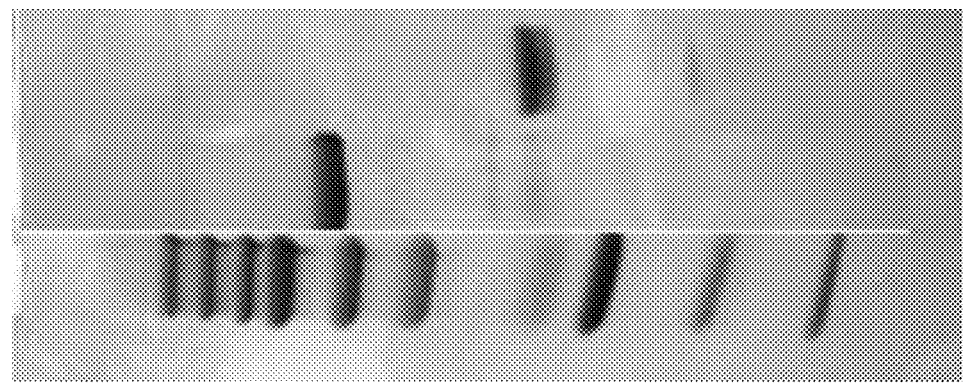
Figure 58:
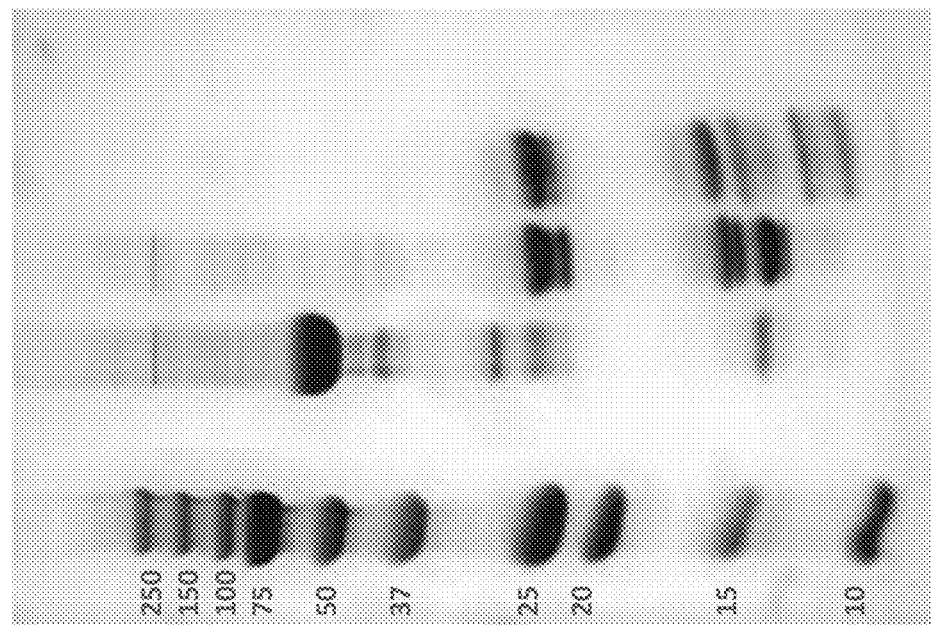
Figure 59A:
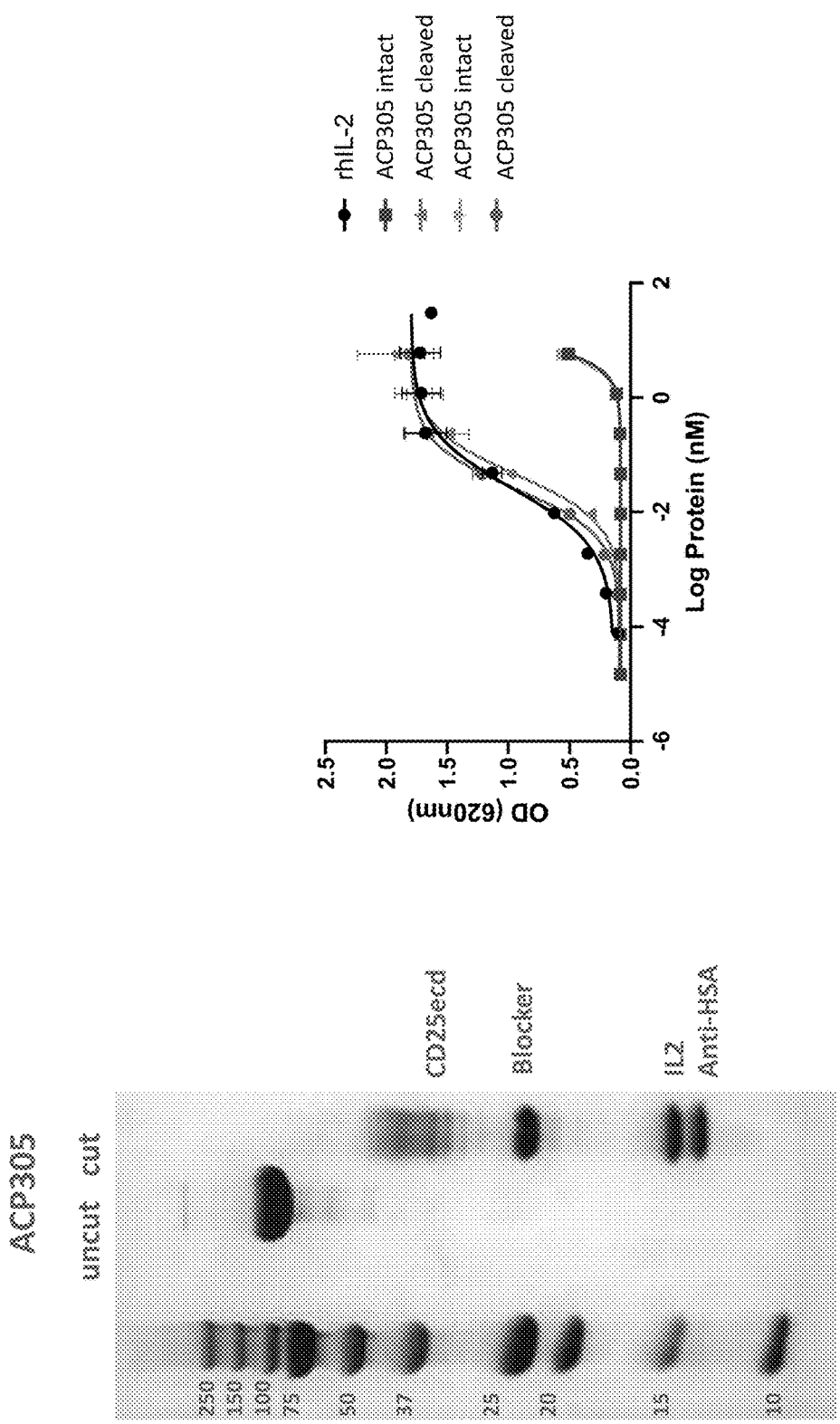
Figure 59B:
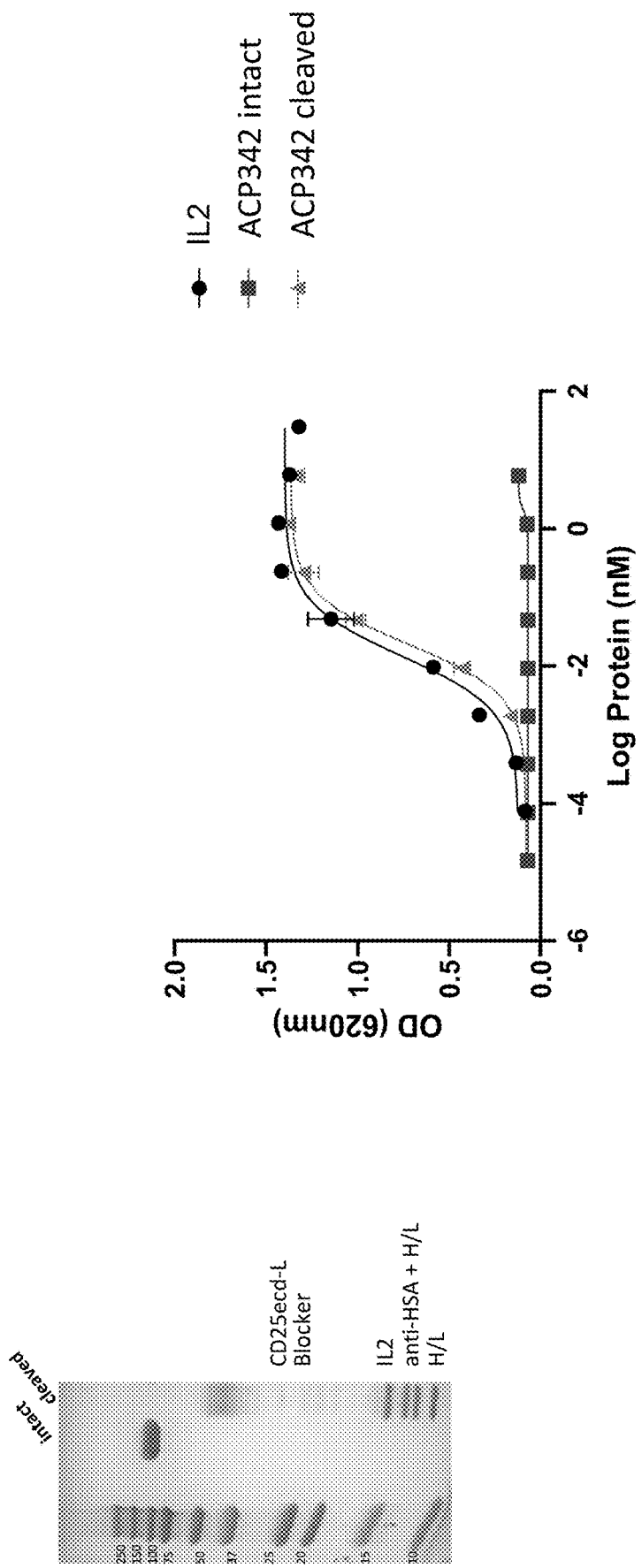
Figure 59C:
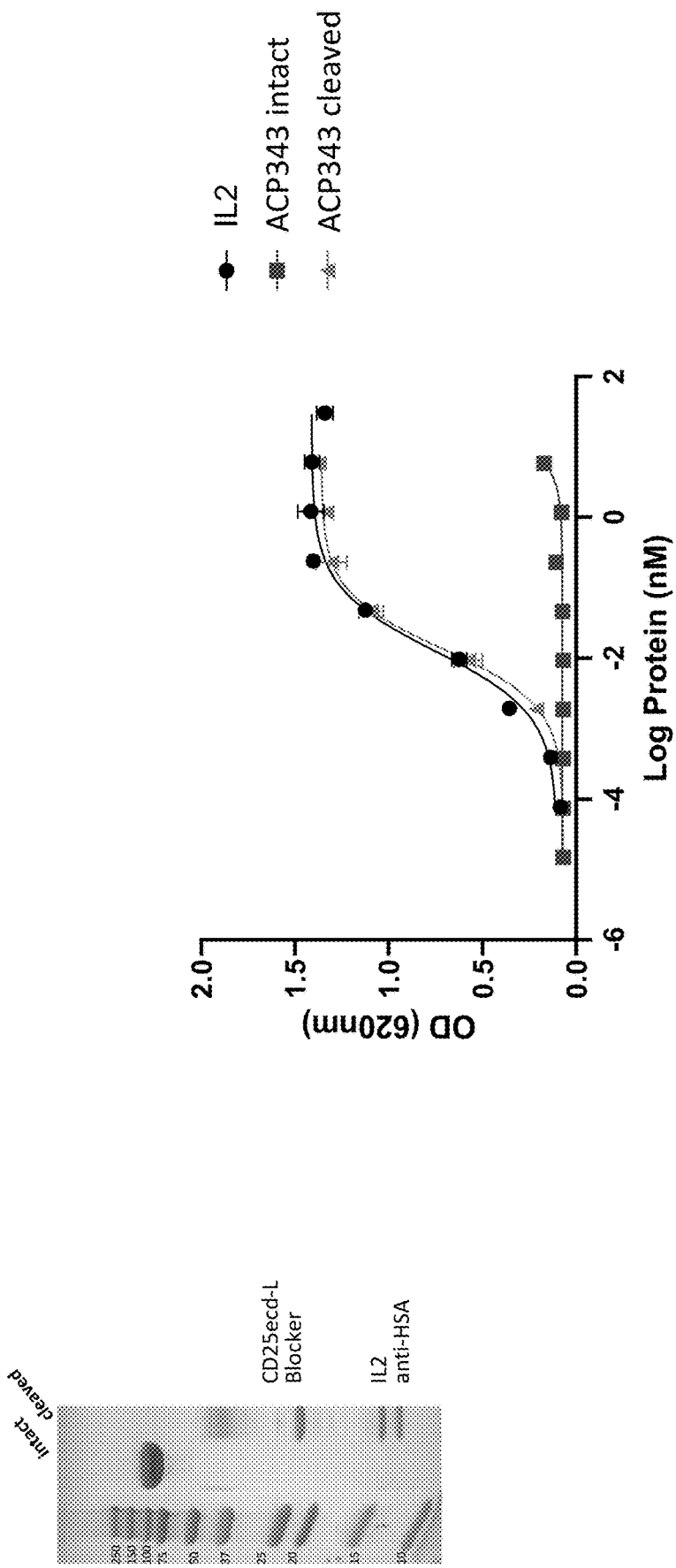
Figure 59D:
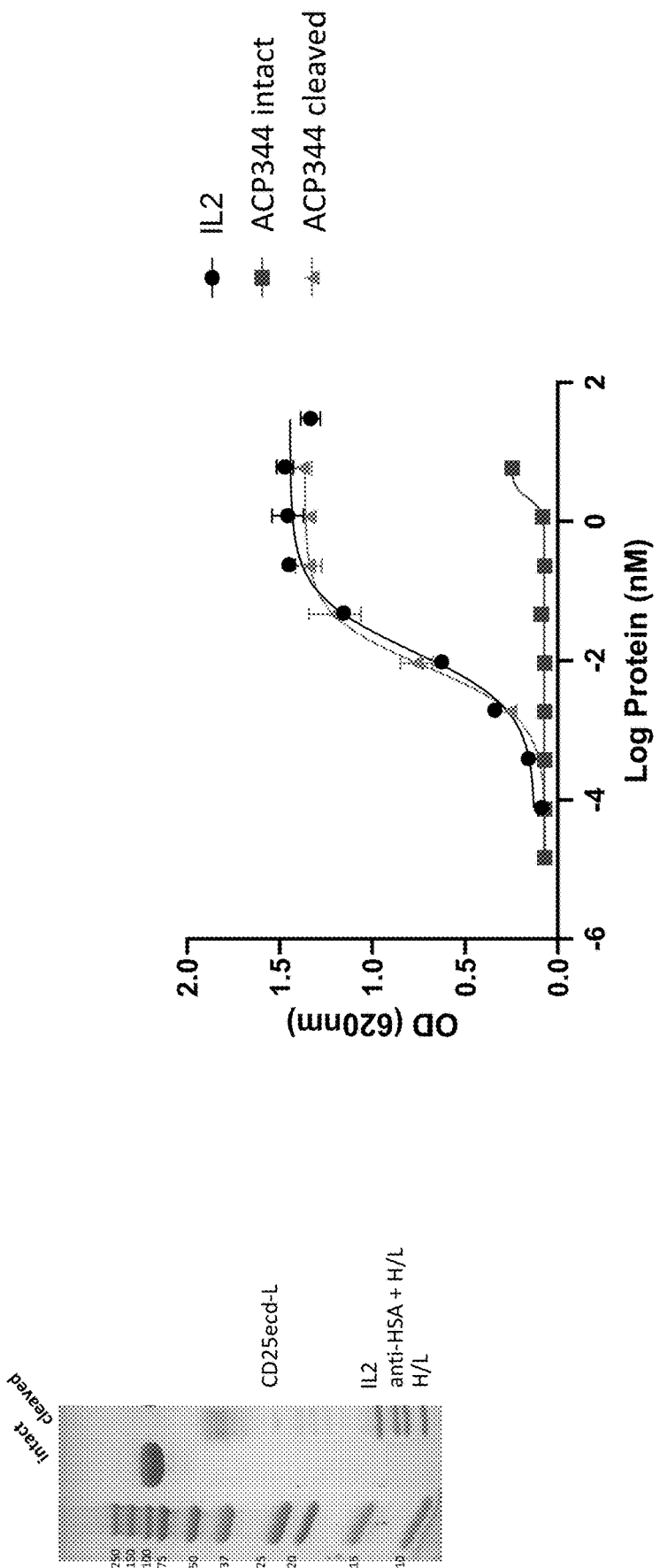
Figure 59E:
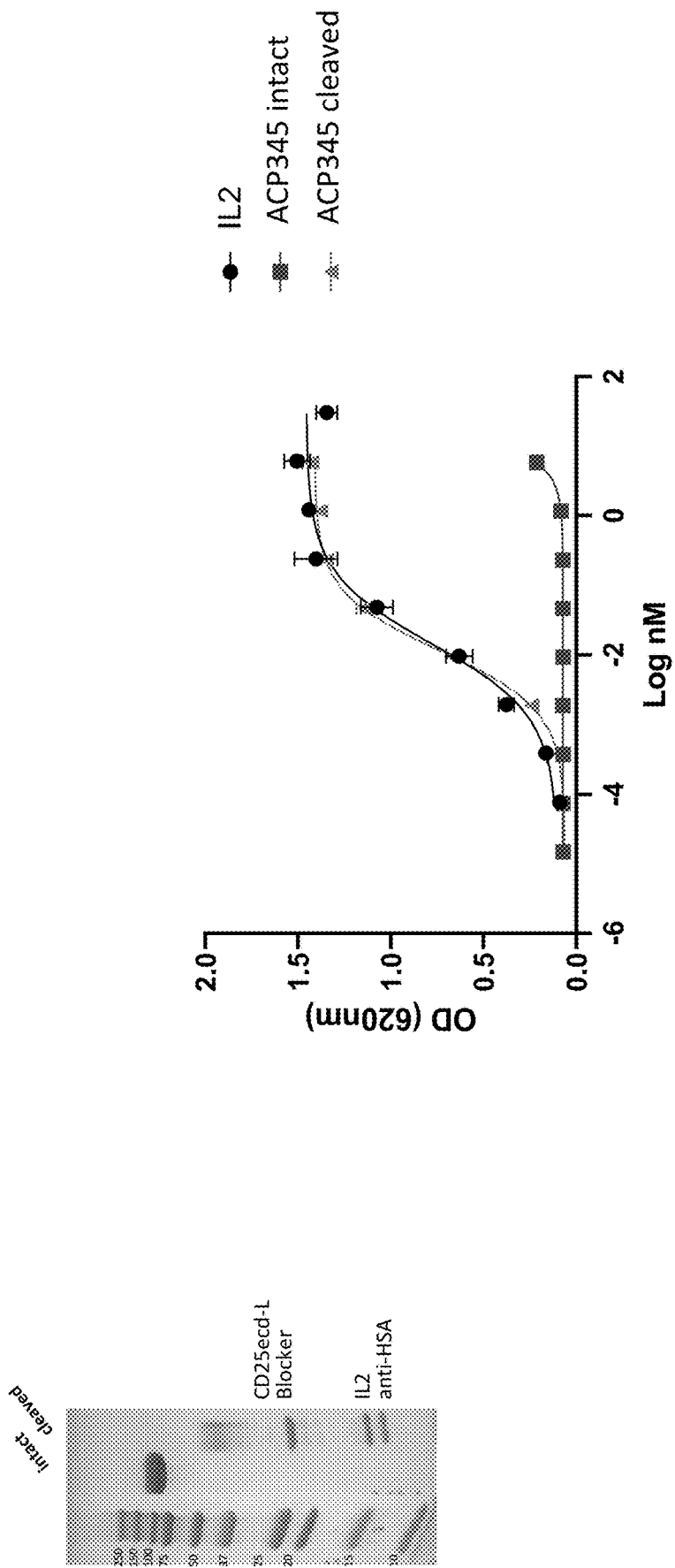
Figure 59F:
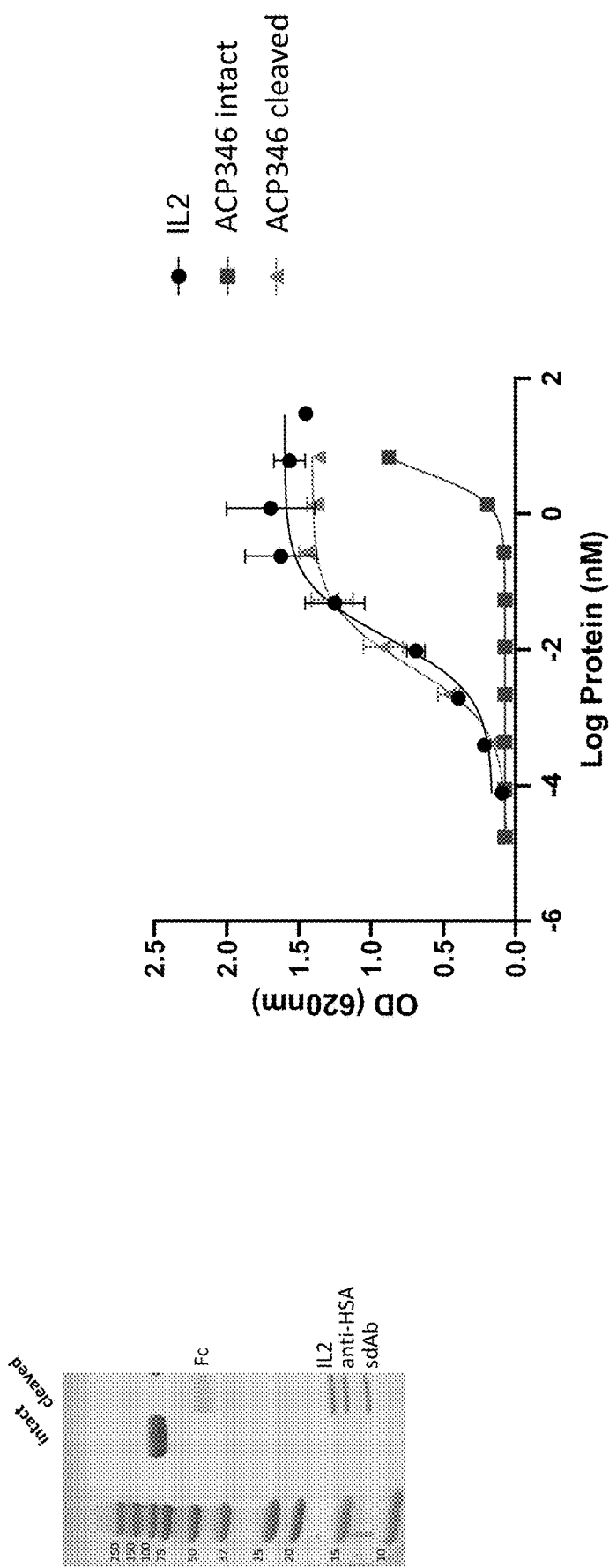
Figure 59G:
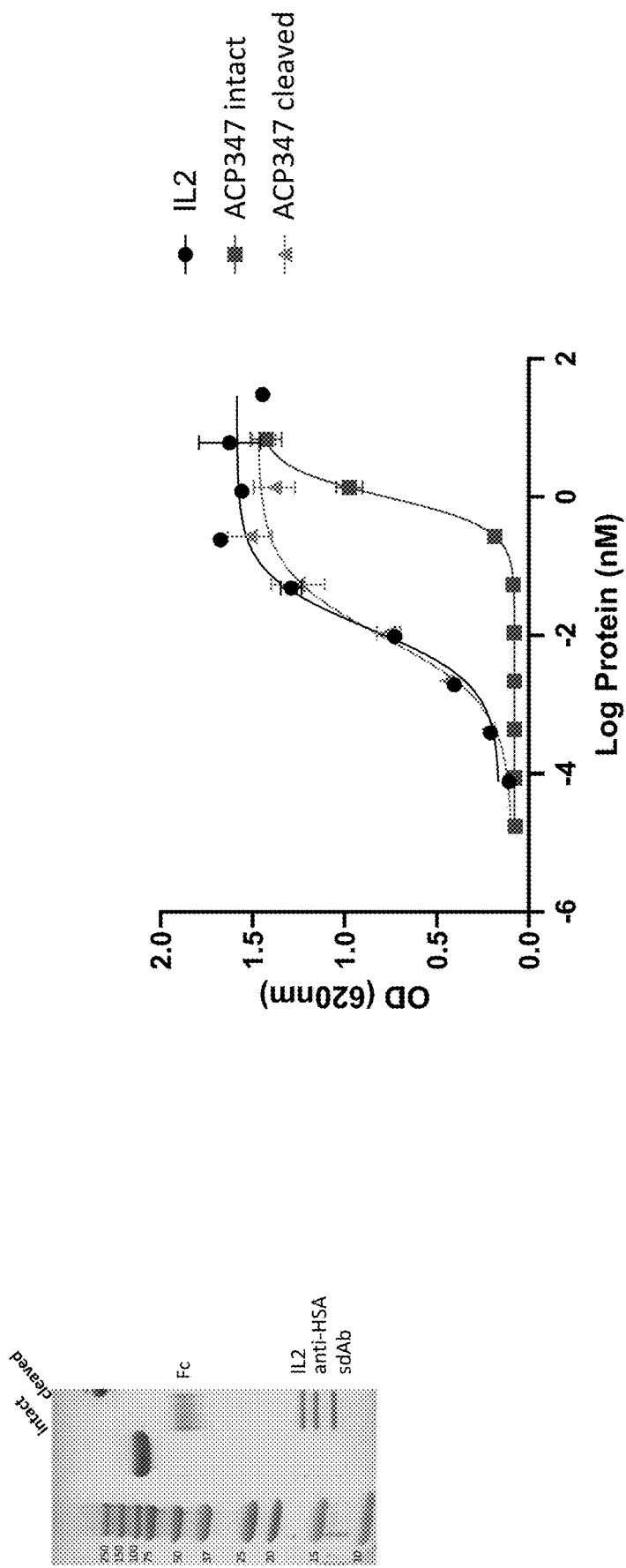
Figure 59H:
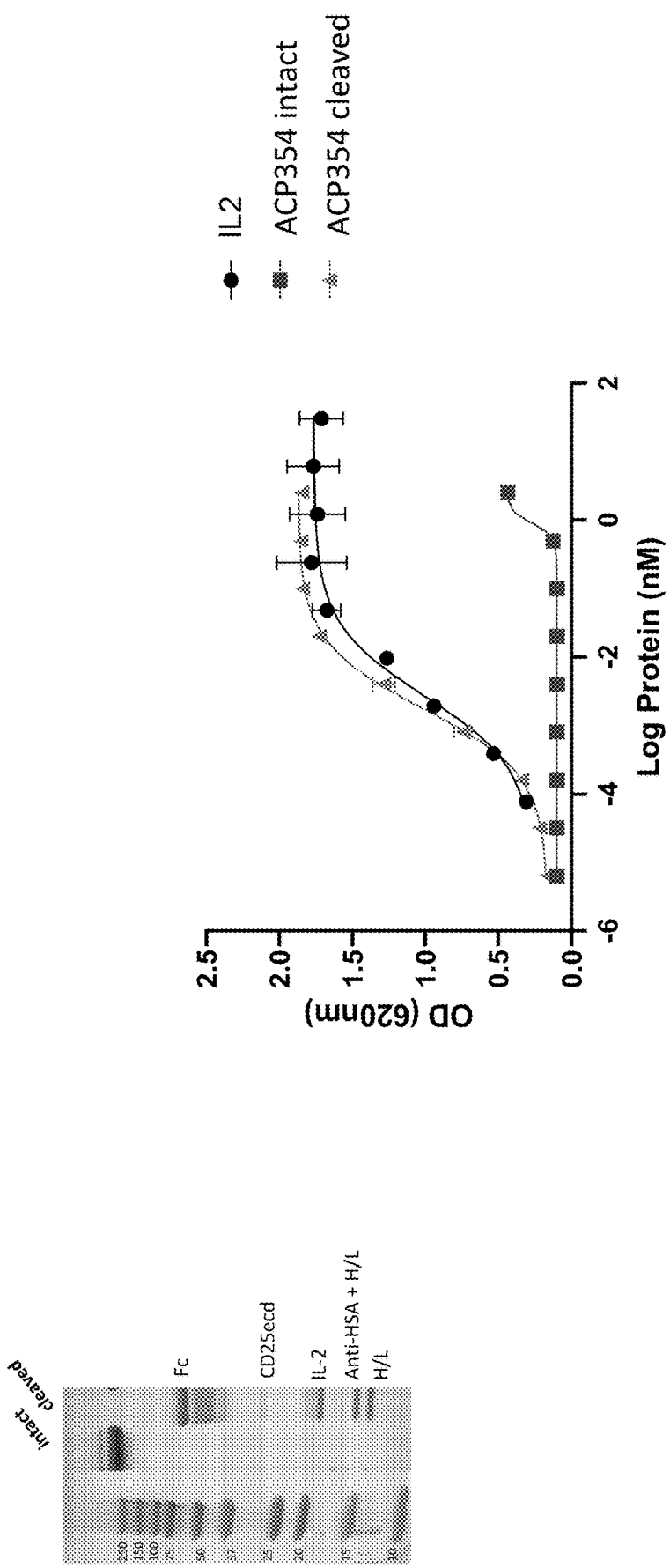
Figure 59I:
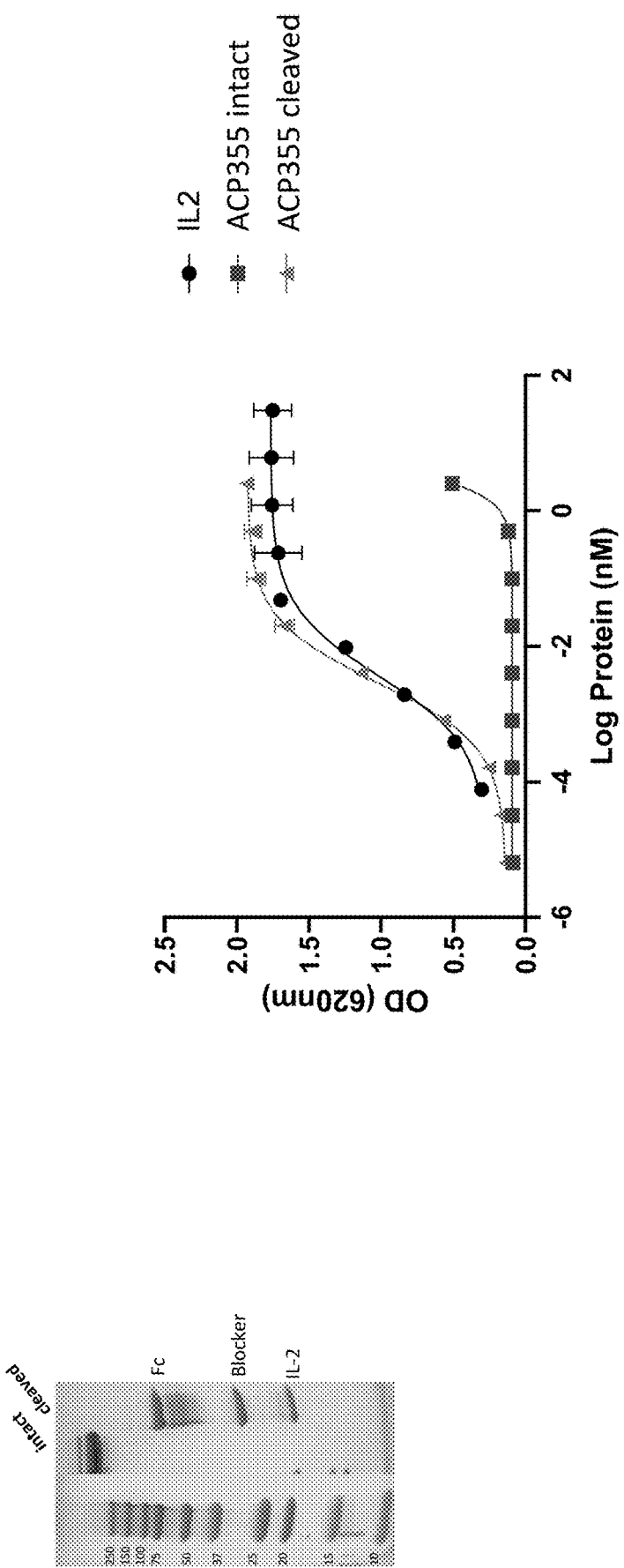
Figure 59J:
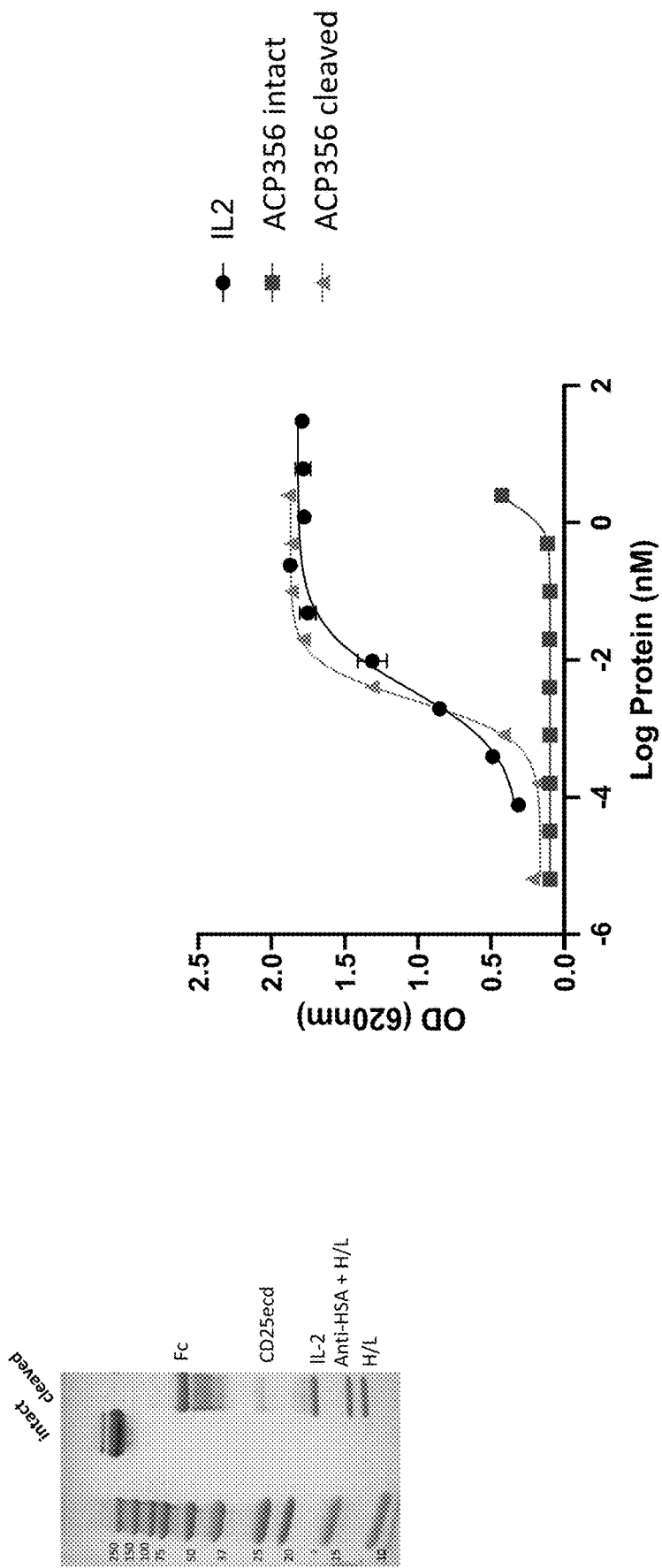
Figure 59K:
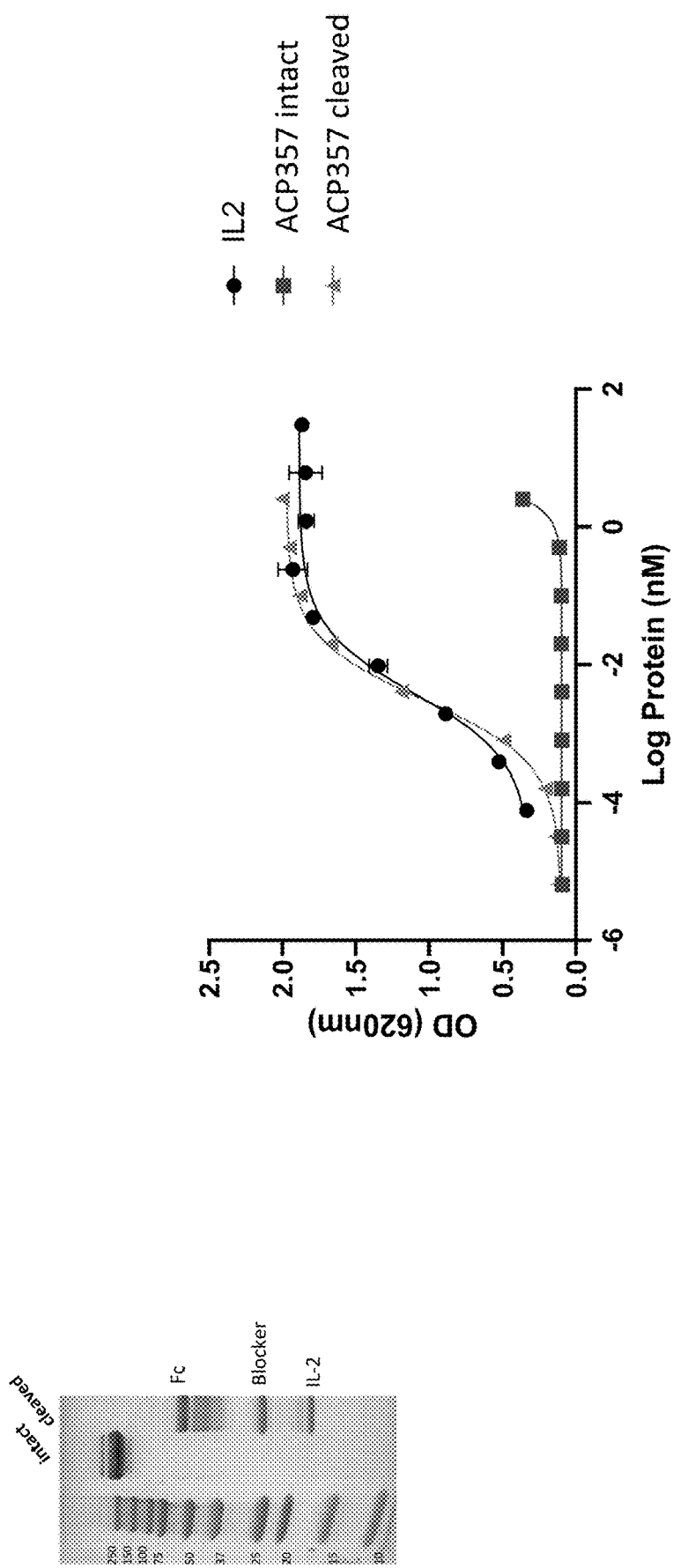
Figure 59L:
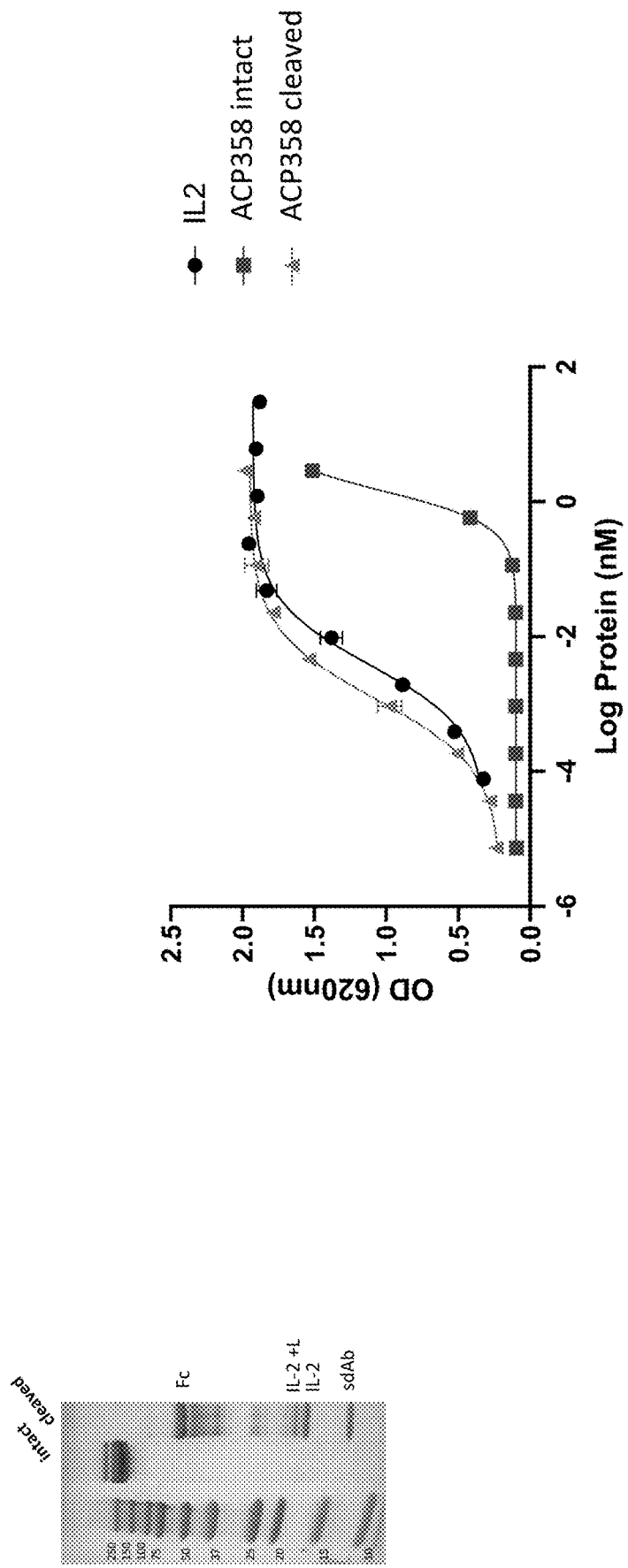
Figure 59M:
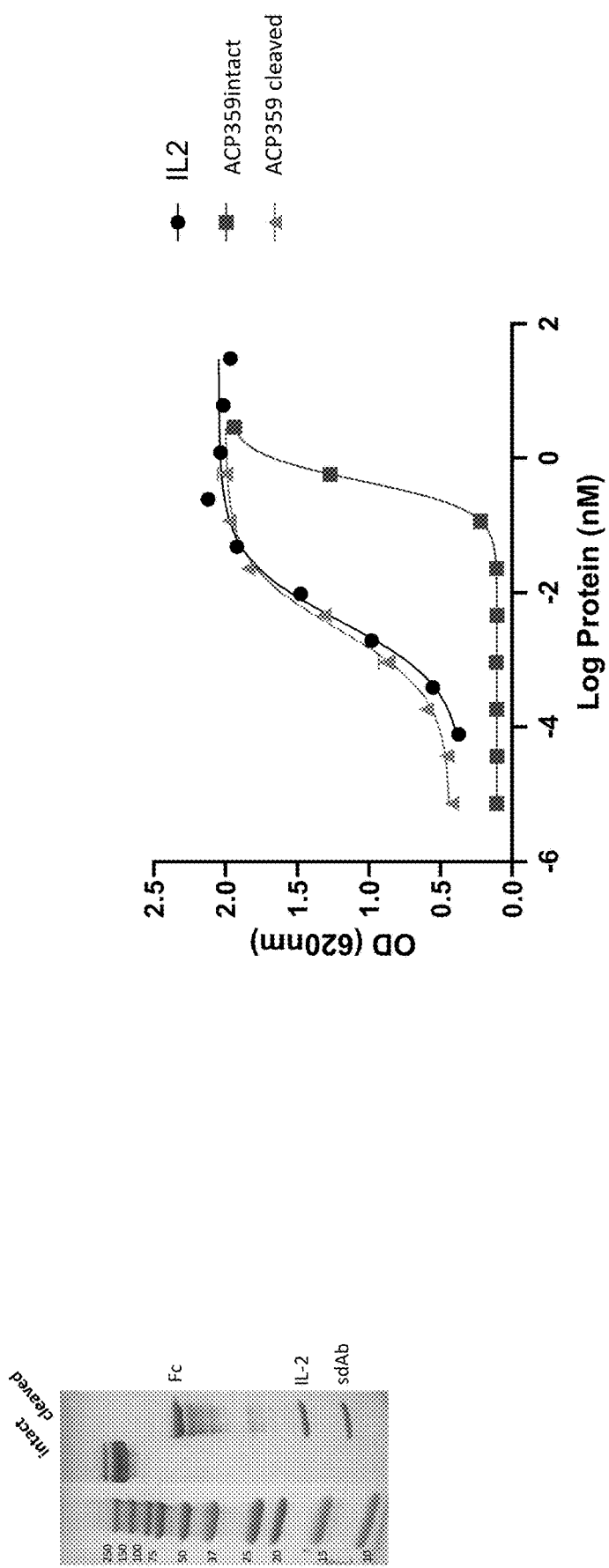
Figure 59N:
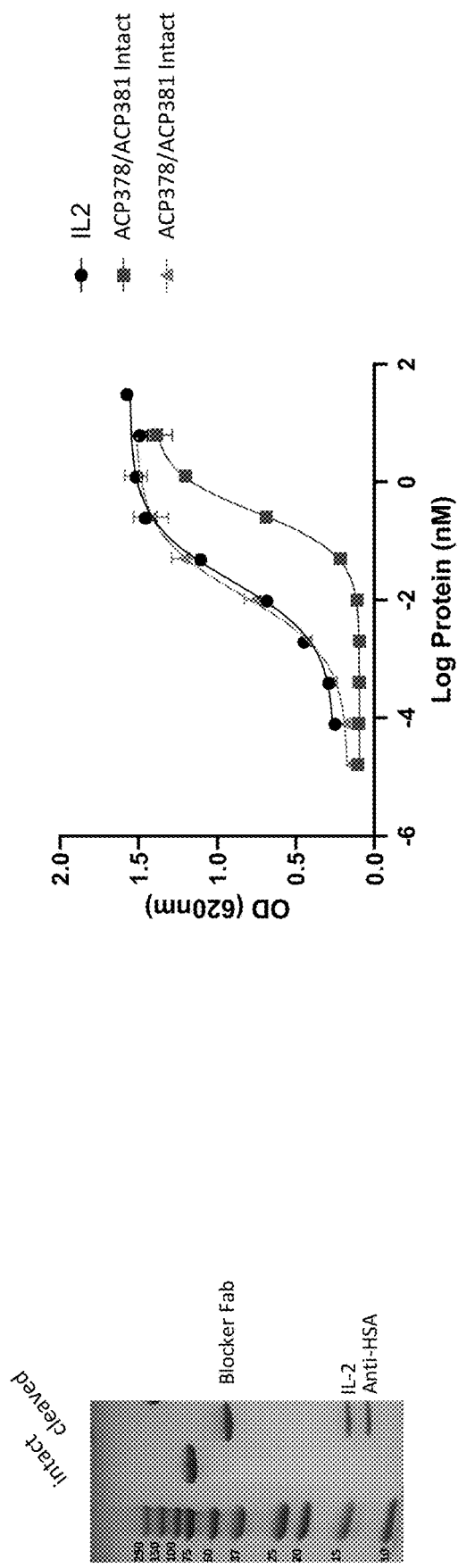
Figure 59O:
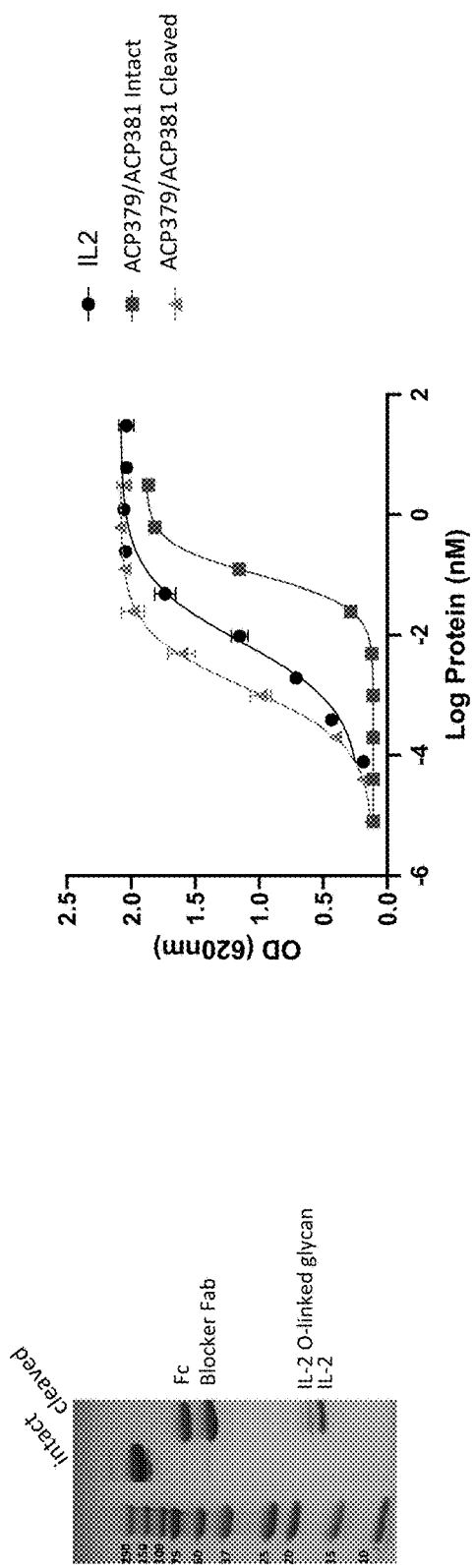
Figure 59P:
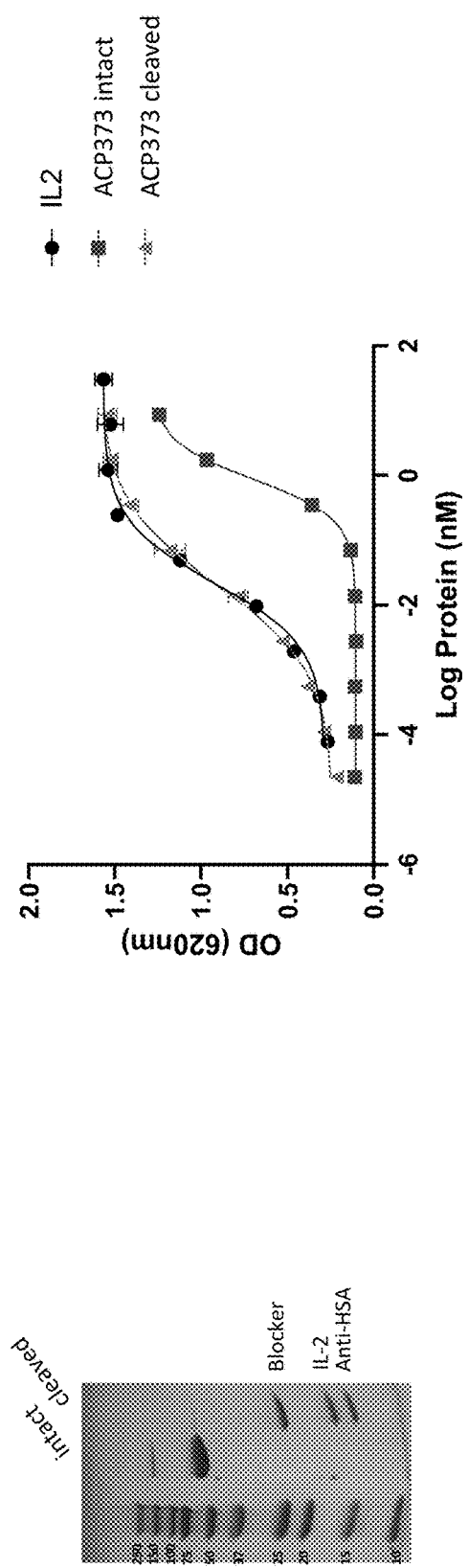
Figure 59Q:
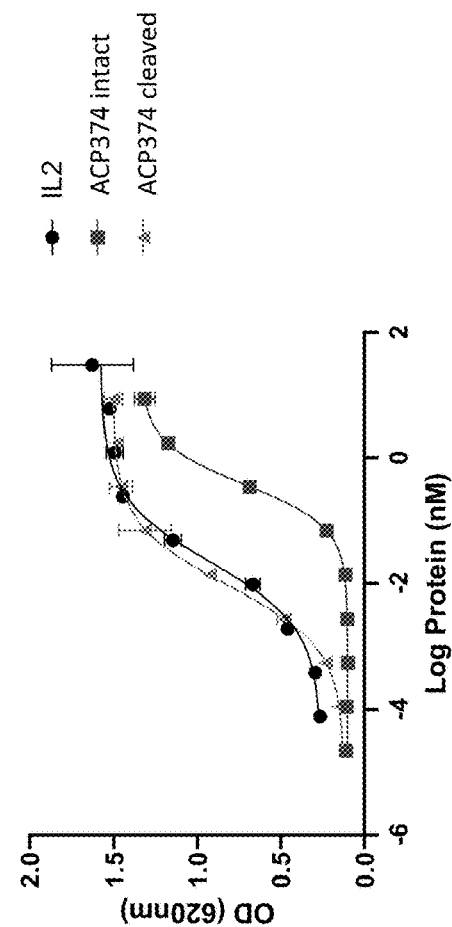
Figure 59Q:
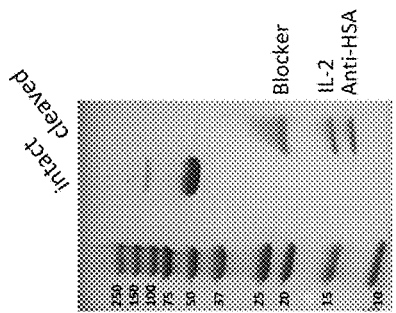
Figure 59R:
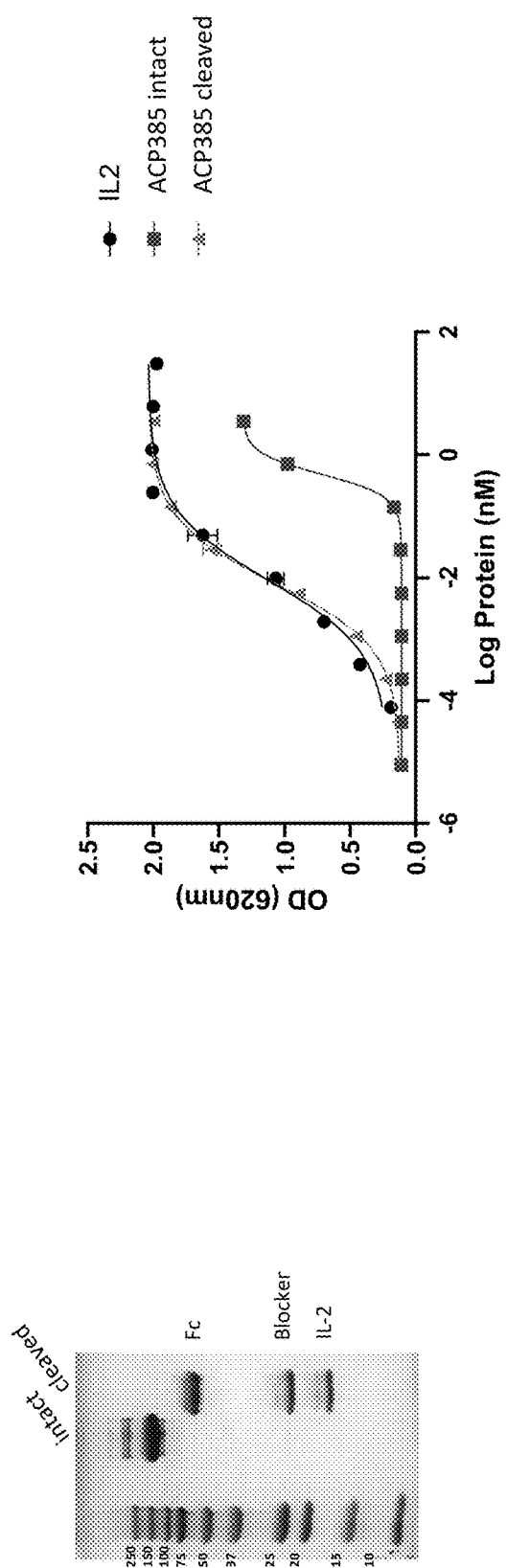
Figure 59S:
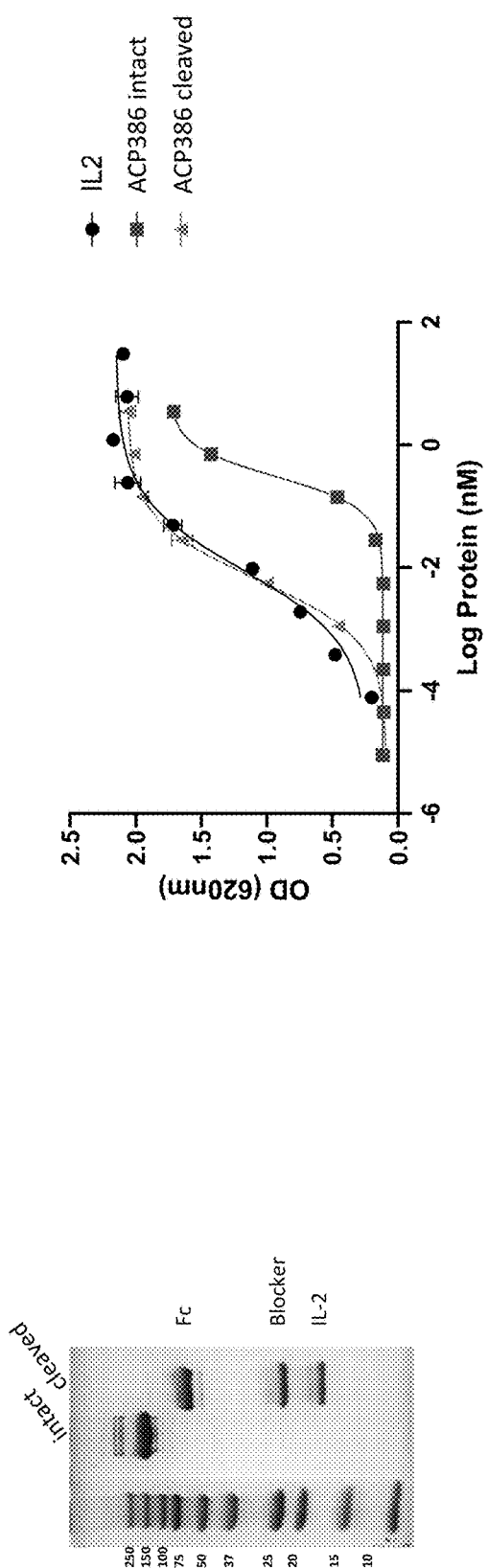
Figure 59T:
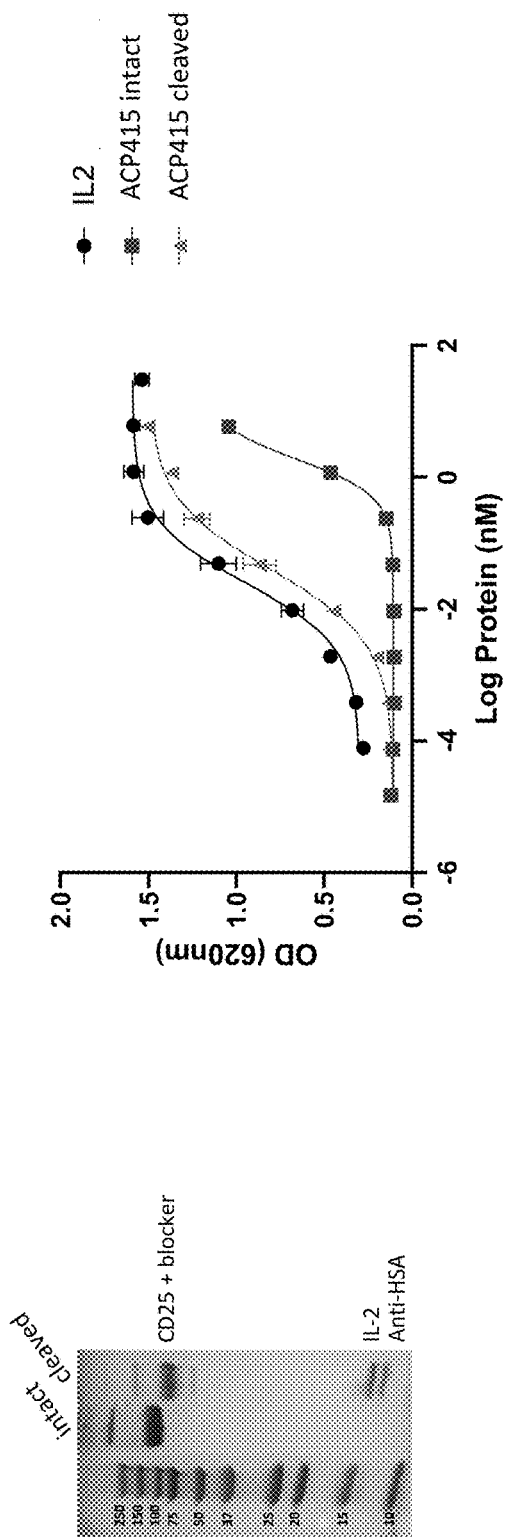
Figure 59U:
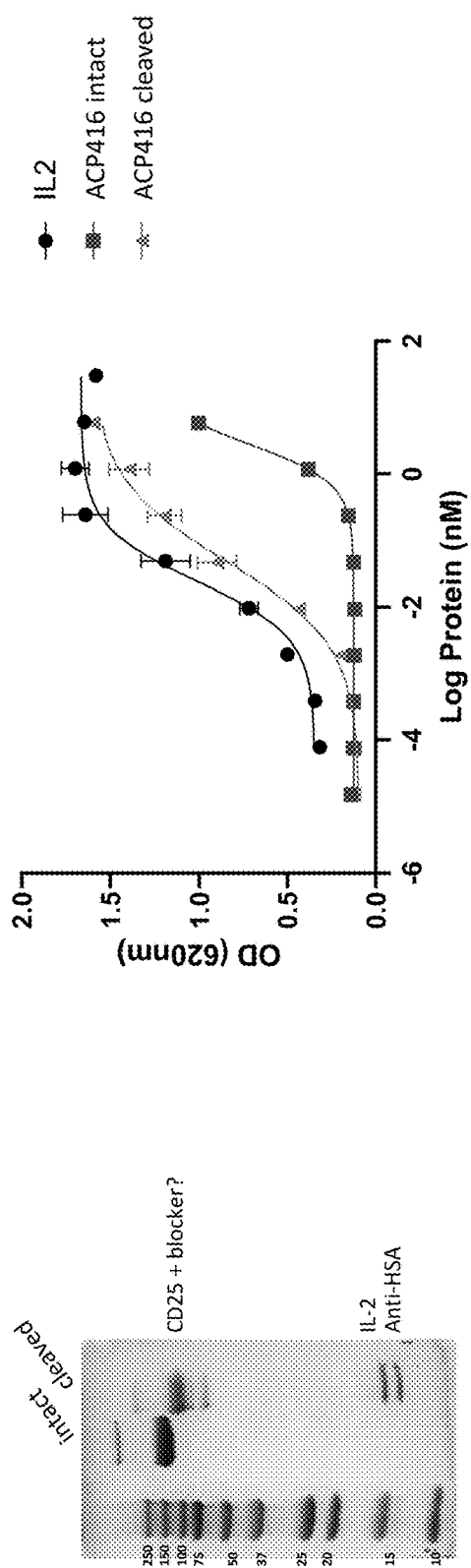
Figure 59V:
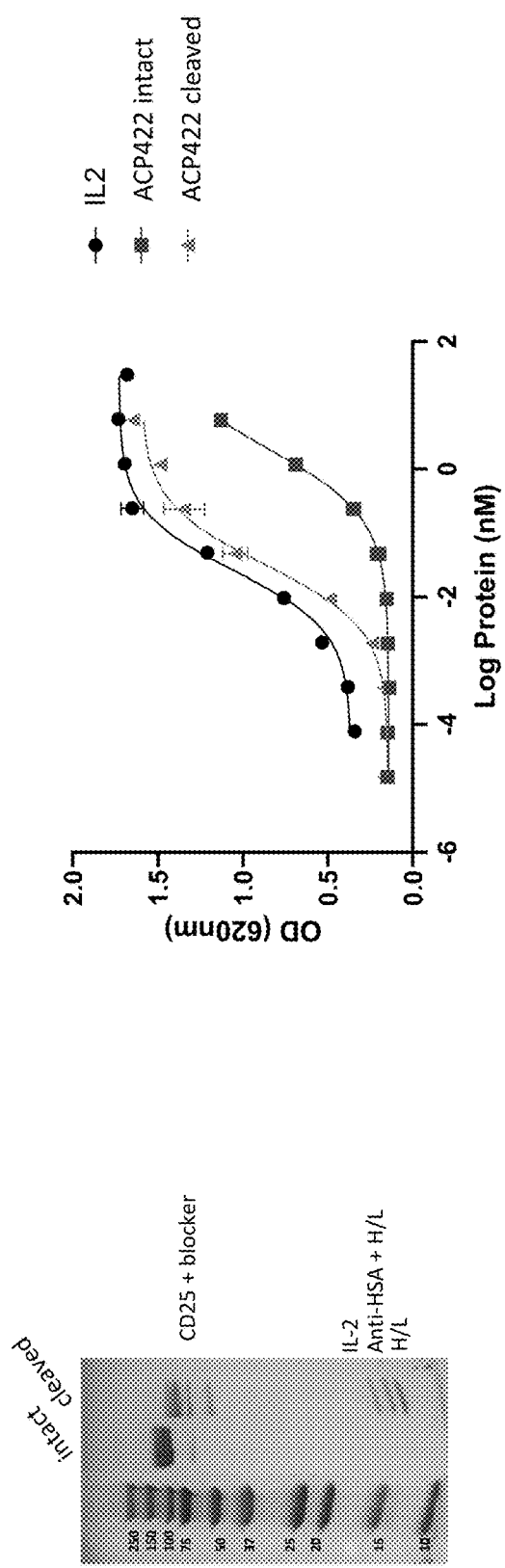
Figure 59W:
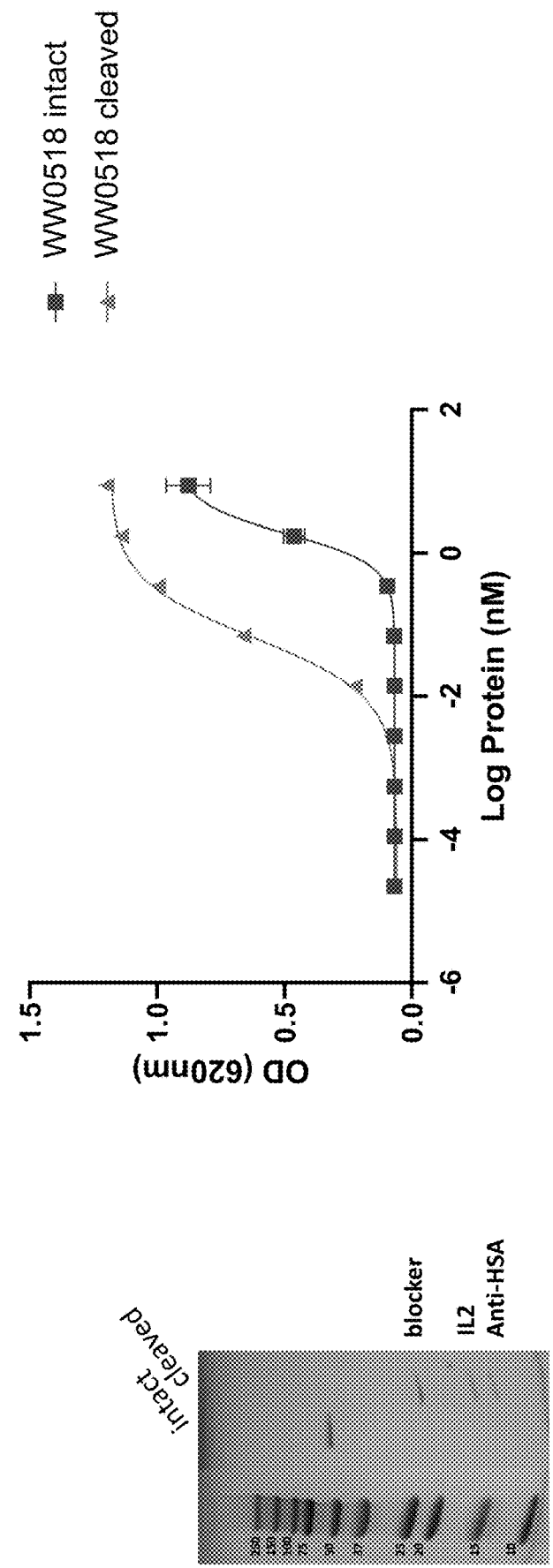
Figure 59X:
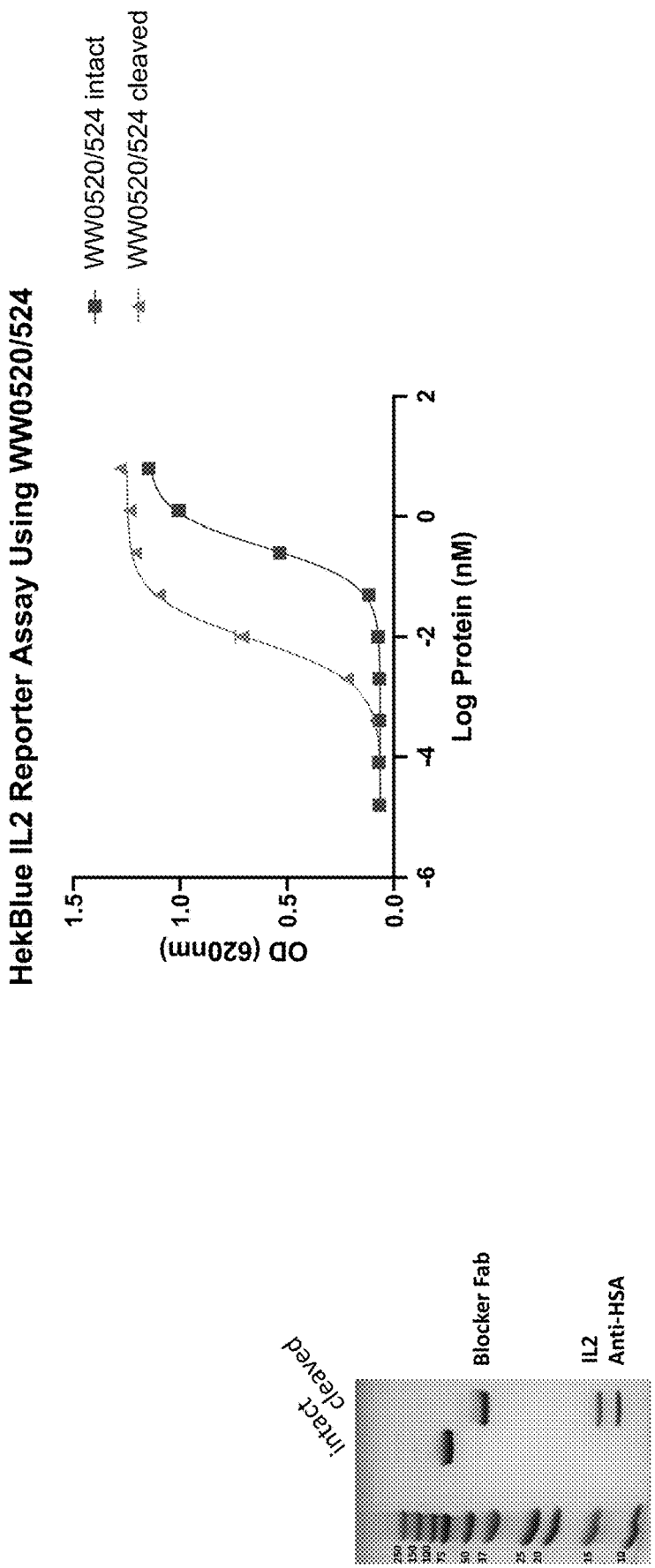
Figure 59Y:
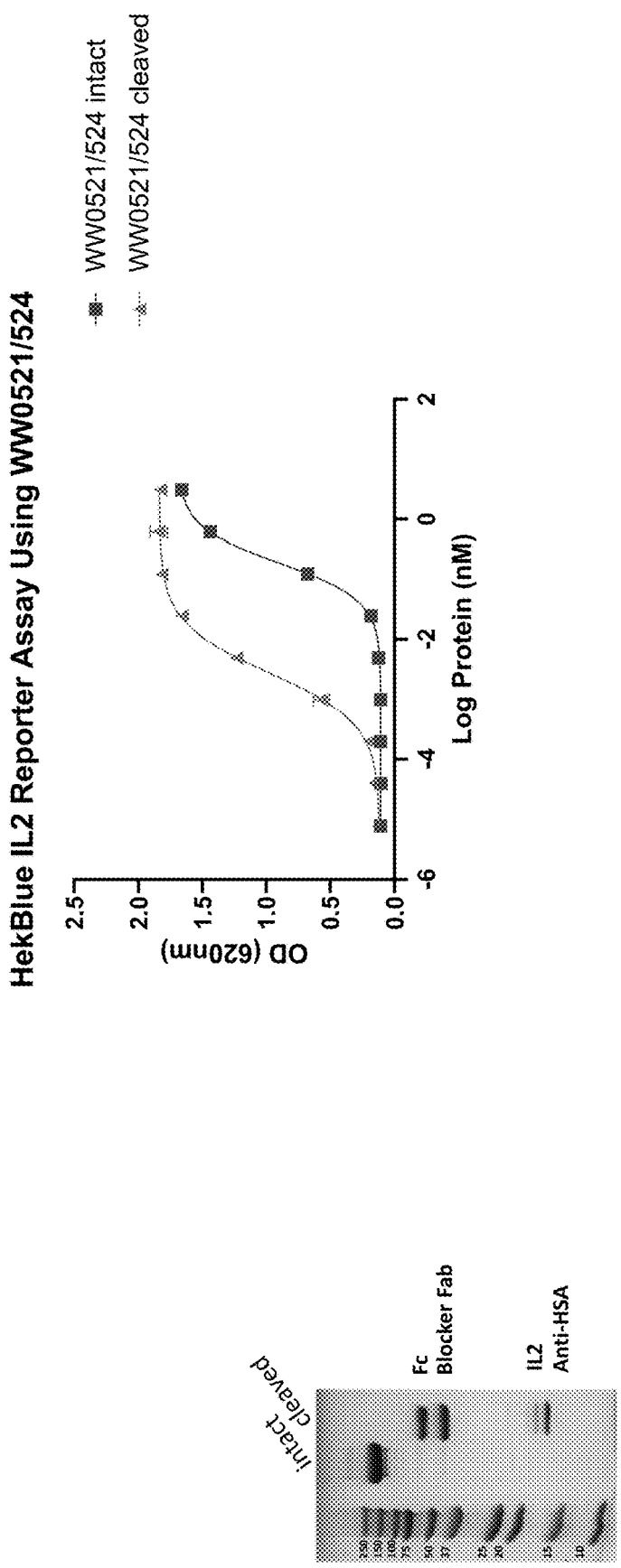
Figure 59Z:
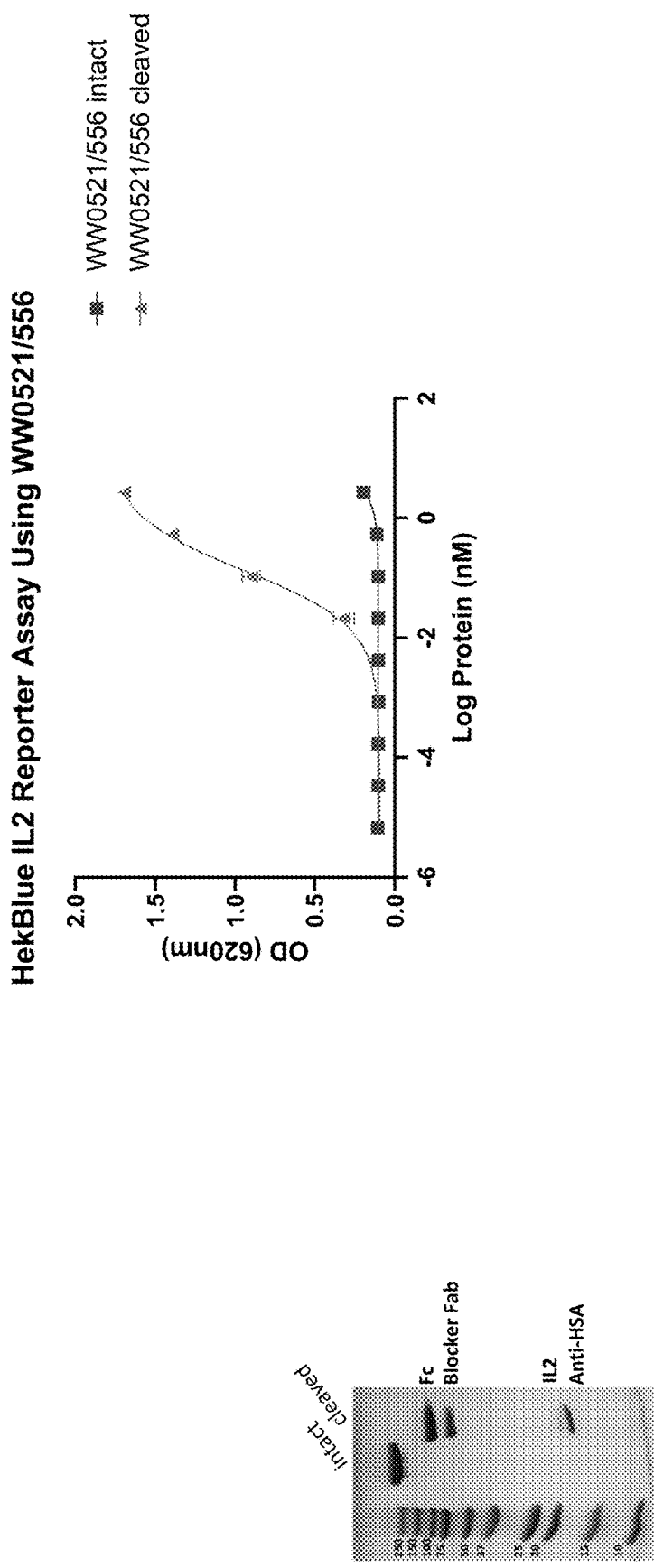
Figure 60A:
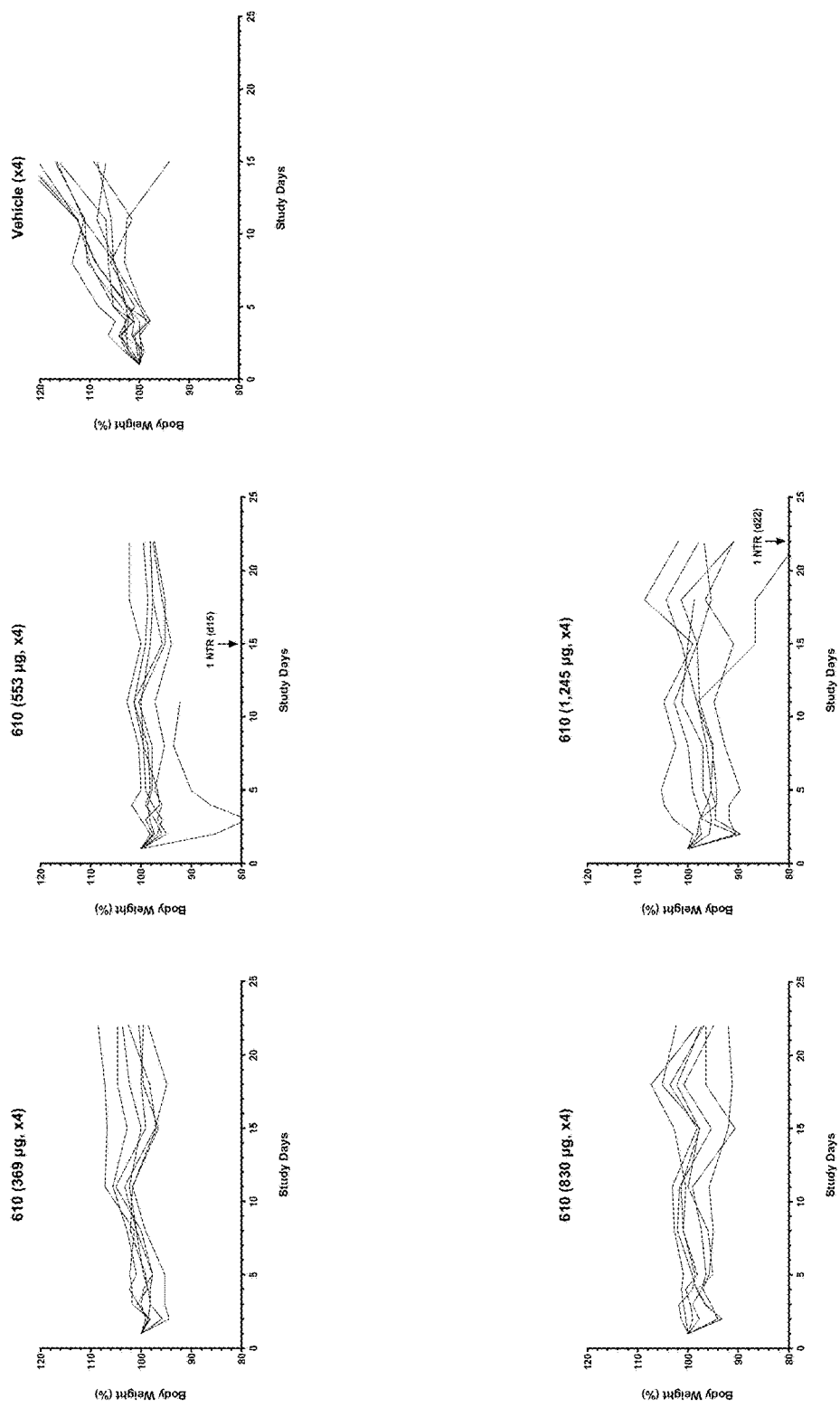
FIGS. 60A-60G shows a series of spider plots showing the impact of IFN fusion proteins on body weight in an MC38 mouse xenograft model corresponding to the data shown in FIGS. 41A-41G. Each line in the plots is the body weight over time for a single mouse.
Figure 60B:
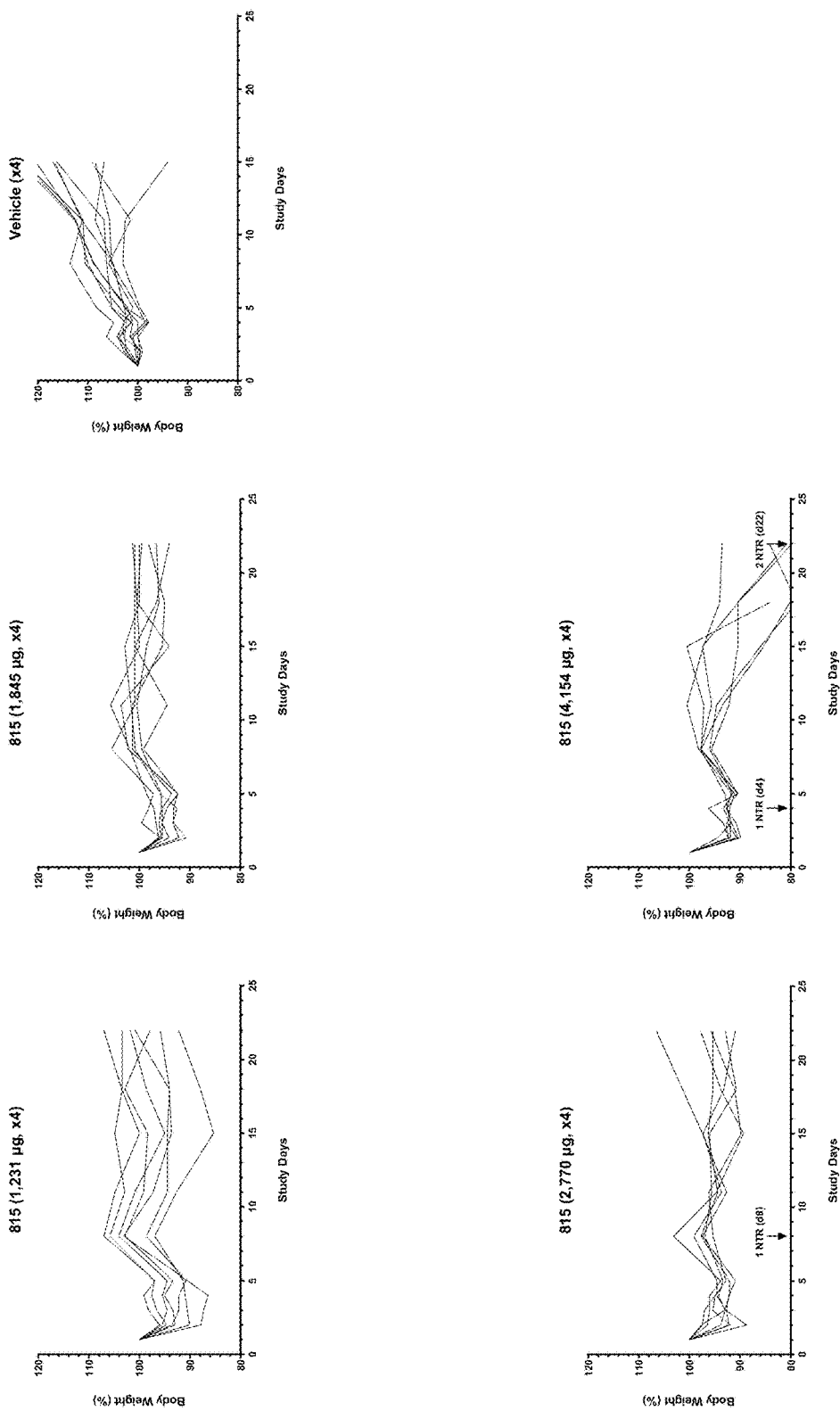
Figure 60C:
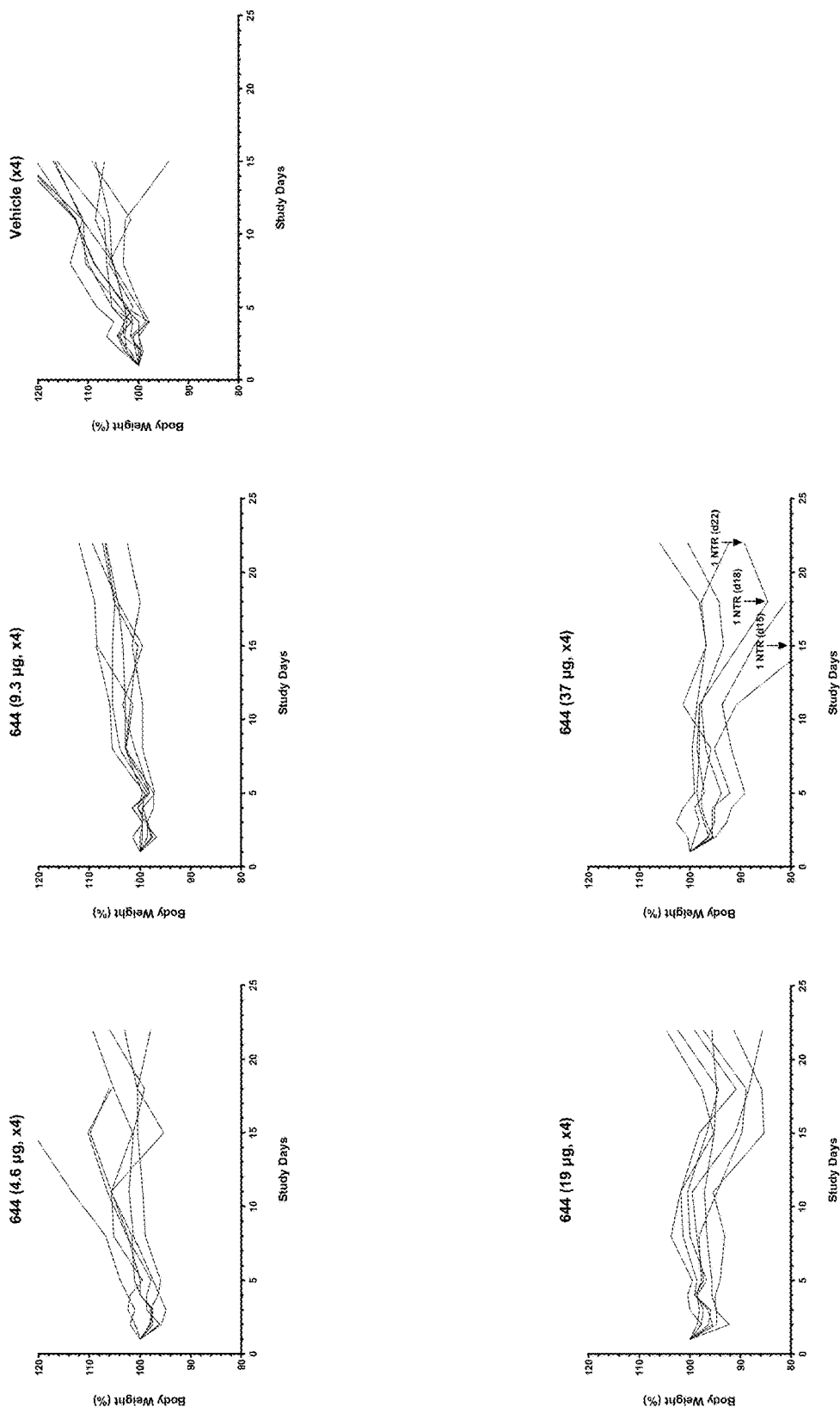
Figure 60D:
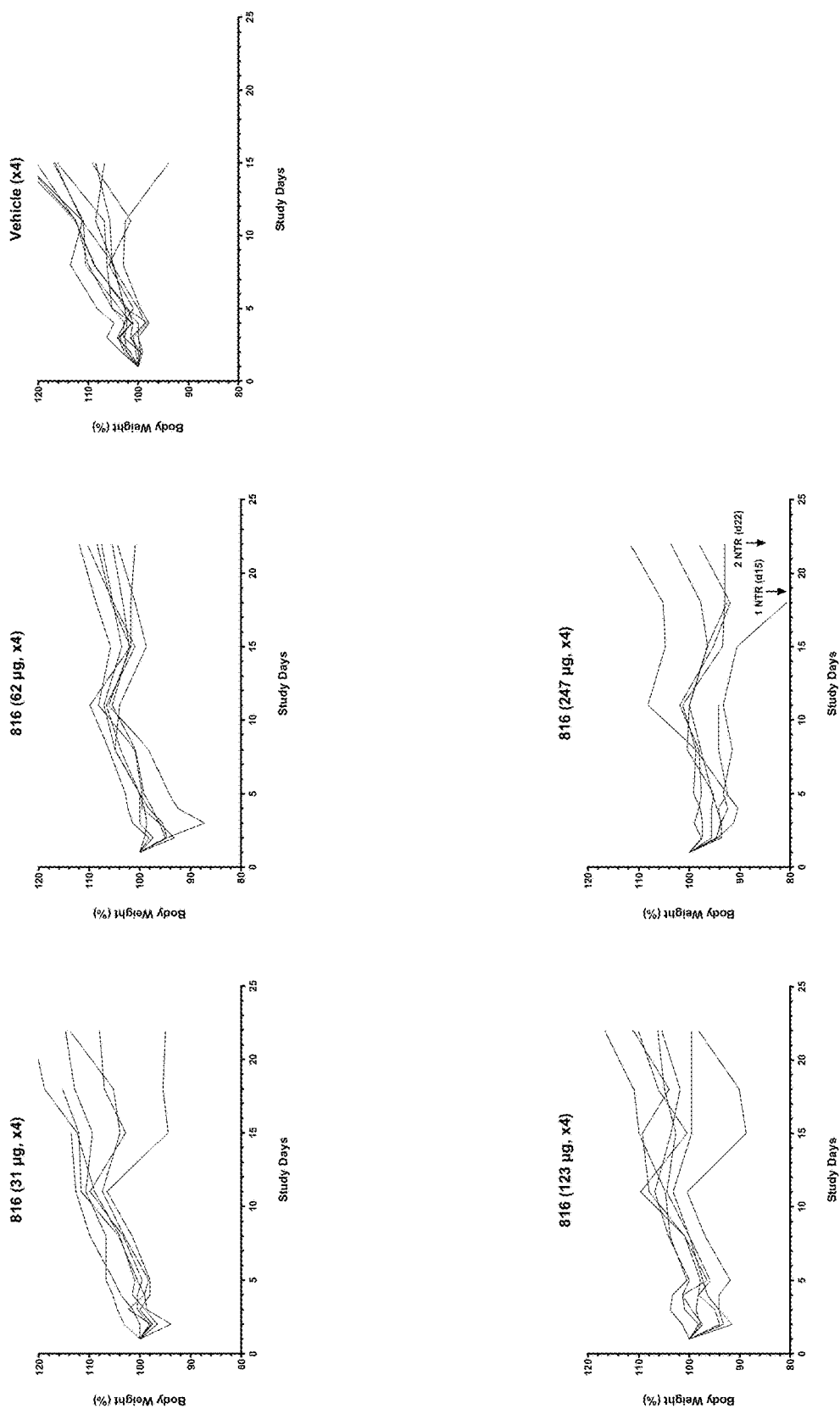
Figure 60E:
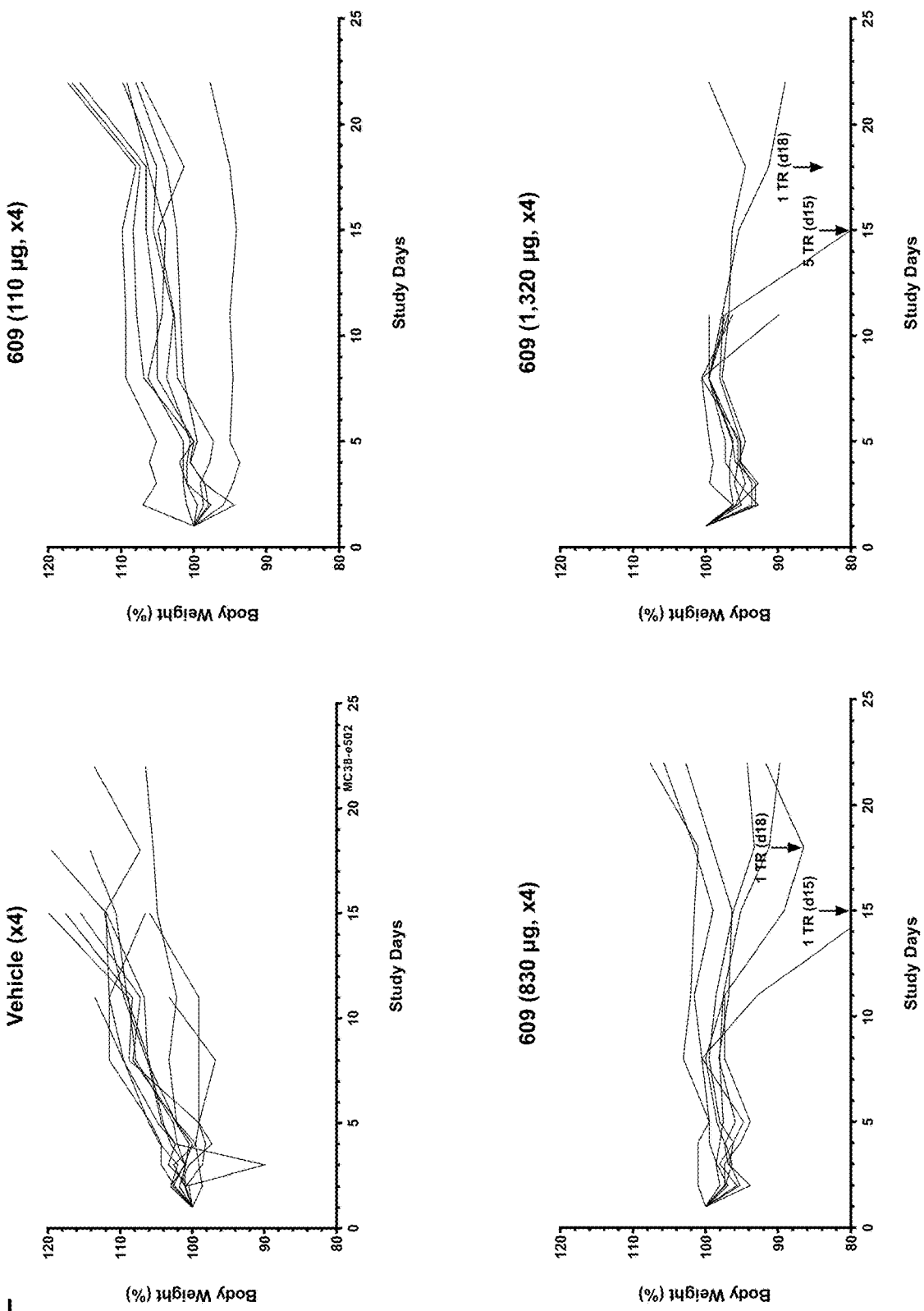
Figure 60F:
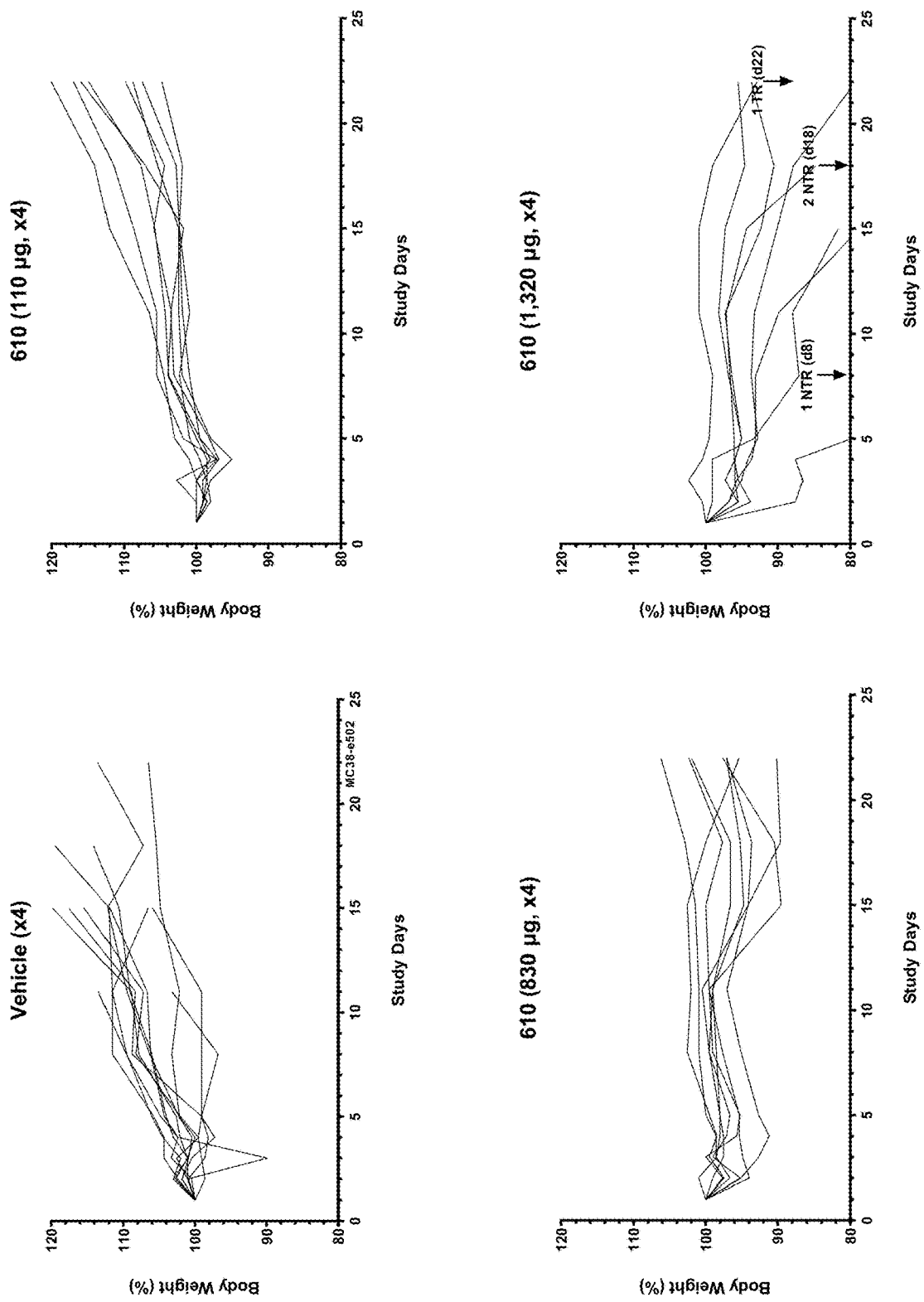
Figure 60G:
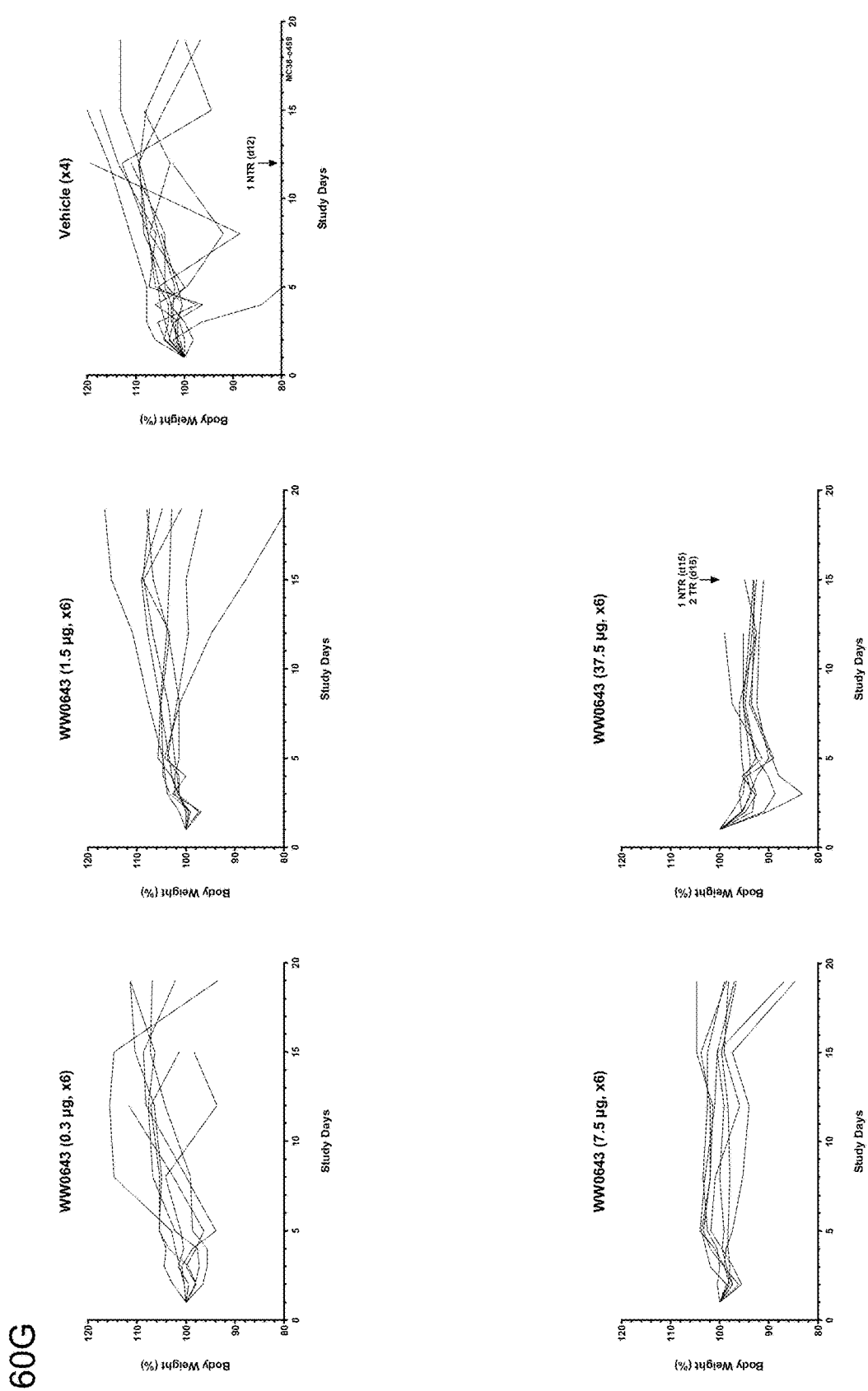
Figure 61A:
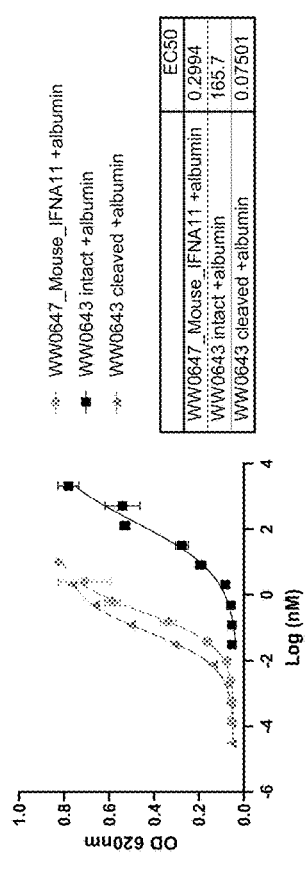
FIGS. 61A-61B are a series of graphs showing activity of fusion proteins in the B16-Blue IFN-α/β reporter assay.
Figure 61A:
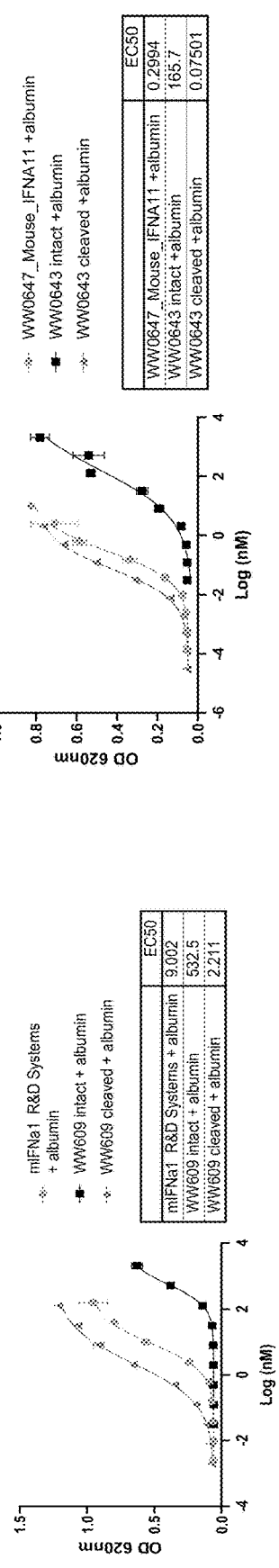
Figure 61A:
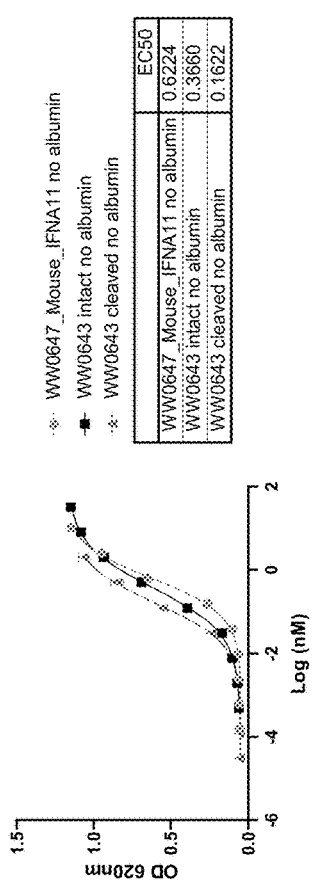
Figure 61B:
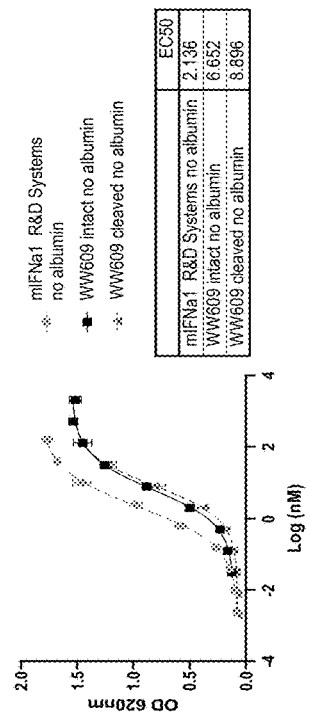

Procedures:

Mice were anaesthetized with isoflurane for implant of cells to reduce the ulcerations. CR female C57BL/6 mice were set up with $5 \times 10^5$ MC38 tumor cells in 0% Matrigel sc in flank. Cell Injection Volume was 0.1 mL/mouse. Mouse age at start date was 8 to 12 weeks. Pair matches were performed when tumors reach an average size of 100-150 mm³ and begin treatment. ACP339 was dosed at 55, 230 or 700 µg/animal. Body weights were taken at initiation and then biweekly to the end. Caliper measurements were taken biweekly to the end. Any adverse reactions were to be reported immediately. Any individual animal with a single observation of >than 30% body weight loss or three consecutive measurements of >25% body weight loss was euthanized. Any group with a mean body weight loss of >20% or >10% mortality stopped dosing; the group was not euthanized and recovery is allowed. Within a group with >20% weight loss, individuals hitting the individual body weight loss endpoint were euthanized. If the group treatment related body weight loss is recovered to within 10% of the original weights, dosing resumed at a lower dose or less frequent dosing schedule. Exceptions to non-treatment body weight % recovery were allowed on a case-by-case basis. Endpoint was tumor growth delay (TGD). Animals were monitored individually. The endpoint of the experiment was a tumor volume of 1500 mm³ or 45 days, whichever comes first. Responders were followed longer. When the endpoint was reached, the animals are to be euthanized. Results are shown in FIGS. 51A-51C.

Example 28: CT26 Experiments

The CT26 cell line, a rapidly growing colon adenocarcinoma cell line that expresses MMP9 in vitro, was used. Using this tumor model, the ability of fusion proteins to affect tumor growth was examined.

Example 28a: Treatment with ACP16 Alone or in Combination with Anti-PD1 Antibody Agents and Treatment:

| Gr. | N | Agent | Formulation dose | Route | Schedule |
|---|---|---|---|---|---|
| 1# | 12 | vehicle 1//vehicle 2 | na//na | ip//ip | days 1,4, 8,11//days 3,6, 10,13 |

| Gr. | N | Agent | Formulation dose | Route | Schedule |
|---|---|---|---|---|---|
| 2 | 10 | vehicle 1// ACP16 | na//70 µg/ animal | ip//ip | days 1,4, 8,11// days 3,6, 10,13 |
| 3 | 10 | vehicle 1// ACP16 | na// 232 µg/ animal | ip//ip | days 1,4, 8,11// days 3,6, 10,13 |
| 4 | 10 | vehicle 1// ACP16 | na// 500 µg/ animal | ip//ip | days 1,4, 8,11// days 3,6, 10,13 |
| 5 | 10 | anti-PD-1 RMP1-14// vehicle 2 | 200 µg/ animal//na | ip//ip | days 1,4, 8,11// days 3,6, 10,13 |
| 6 | 10 | anti-PD-1 RMP1-14// ACP16 | 200 µg/ animal// 70 µg/ animal | ip//ip | days 1,4, 8,11// days 3,6, 10,13 |
| 7 | 10 | anti-PD-1 RMP1-14// ACP16 | 200 µg/ animal// 232 µg/ animal | ip//ip | days 1,4, 8,11// days 3,6, 10,13 |
| 8 | 10 | anti-PD-1 RMP1-14// ACP16 | 200 µg/ animal// 500 µg/ animal | ip//ip | days 1,4, 8,11// days 3,6, 10,13 |
| 9 | 10 | vehicle 1// IL-2 | na//12 µg/ animal | ip//ip | days 1,4, 8,11// bid x 5 first day 1 dose per week x 2 |
| 10 | 10 | anti-PD-1 RMP1-14// IL-2 | 200 µg/ animal// 12 µg/ animal | ip//ip | days 1,4, 8,11// bid x 5 first day 1 dose per week x 2 |

Procedures:

Mice were anaesthetized with isoflurane for implant of cells to reduce the ulcerations. CR female BALB/c mice were set up with 3×10$^5$ CT26 tumor cells in 0% Matrigel sc in flank. Cell Injection Volume was 0.1 mL/mouse. Mouse age at start date was 8 to 12 weeks. Pair matches were performed when tumors reach an average size of 100-150 mm$^3$ and begin treatment. ACP16 was dosed at 70, 230 or 500 µg/animal with or without anti-PD-1 antibody (RMP1-14) at 200 µg/animal. Body weights were taken at initiation and then biweekly to the end. Caliper measurements were taken biweekly to the end. Any adverse reactions were to be reported immediately. Any individual animal with a single observation of >than 30% body weight loss or three consecutive measurements of >25% body weight loss was euthanized. Any group with a mean body weight loss of >20% or >10% mortality stopped dosing; the group was not euthanized and recovery is allowed. Within a group with >20% weight loss, individuals hitting the individual body weight loss endpoint were euthanized. If the group treatment related body weight loss is recovered to within 10% of the original weights, dosing resumed at a lower dose or less frequent dosing schedule. Exceptions to non-treatment body weight % recovery were allowed on a case-by-case basis.

Endpoint was tumor growth delay (TGD). Animals were monitored individually. The endpoint of the experiment was a tumor volume of 1500 mm$^3$ or 45 days, whichever comes first. Responders were followed longer. When the endpoint was reached, the animals are to be euthanized. Results are shown in FIGS. 47A-47D and FIGS. 48A-48B.

Example 29. Human Tblast Assay

IL-2 T-Blast Assay. Pre-stimulated T cells (T-blasts) were used to assess the activity of inducible IL-2 fusion proteins. T-Blasts were induced from human PBMCs with a 3-day incubation with PHA. Tblasts were then plated in suspension at a concentration of 50,000 or 75,000 cells/well in X-VIVO culture media (containing human serum albumin) and stimulated with a dilution series of recombinant IL-2 fusion proteins or human IL-2 for 72 hours at 37° C. and 5% $CO_2$. Activity of uncleaved and cleaved IL-2 fusion proteins was tested. Cleaved inducible IL-2 was generated by incubation with active MMP9. IL-2 activity was assessed measuring proliferation with CellTiter-Glo. Exemplary results are shown in FIG. 3A-3I.

IL-12 T-Blast Assay. T-Blasts were induced from human PBMCs through PHA stimulation for 72 hours. T-blasts were then washed and frozen prior use. For the assay, T-Blasts were thaw and plated in suspension at 100,000 cells/well in culture media containing human albumin and stimulated with a dilution series of recombinant hIL12 or chimeric IL12 (mouse p35/human p40) indukines or hIL12 indukines for 72 hours at 37° C. and 5% $CO_2$. Activity of uncleaved and cleaved IL12 fusion proteins was tested. Cleaved inducible hIL12 was generated by incubation with active MMP9 enzyme. IL12 activity was assessed by quantification of IFNγ production in supernatants using a hIFNγ Alpha-LISA kit. Exemplary results are shown in FIGS. 8A-8D.

Example 30. Luciferase Reporter Assay

IL-2 luciferase reporter cells (Promega), purchased from the manufacturer in a "Thaw and Use" format, were plated according to the manufacturer's directions and stimulated with a dilution series of recombinant hIL-2 or activatable hIL-2 for 6 hours at 37° C. and 5% $CO_2$. Activity of uncleaved and cleaved activatable IL-2 was tested. Cleaved inducible IL-2 was generated by incubation with active MMP9. IL-2 activity was assessed by quantification of luciferase activity using Bio-Glo™ Reagent (Promega), which allows for the measurement of luciferase activity by luminescence readout. Results are shown in FIGS. 2A-2J.

Figure 9B:
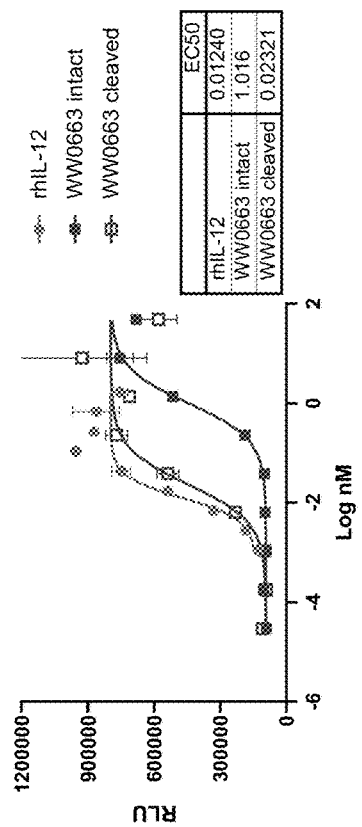
FIGS. 9A-9C are a series of graphs showing activity of fusion proteins in an IL-12 luciferase reporter assay.
Figure 9A:
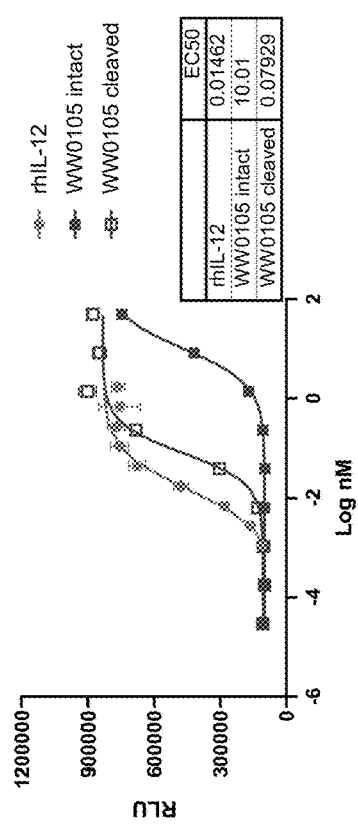
Figure 9C:
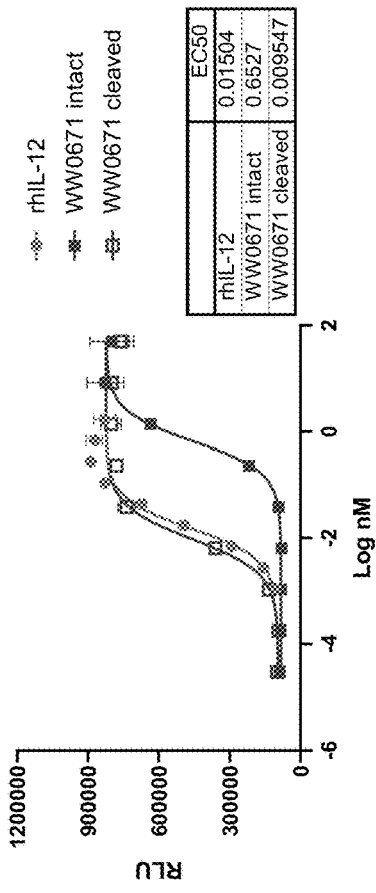
Figure 10A:
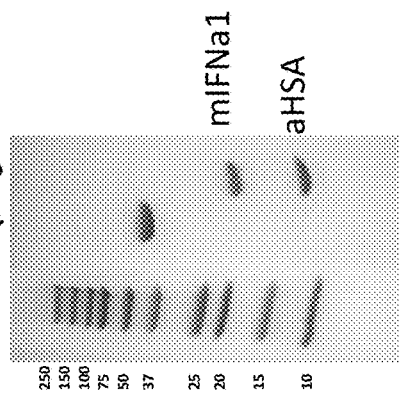
Figure 10A:
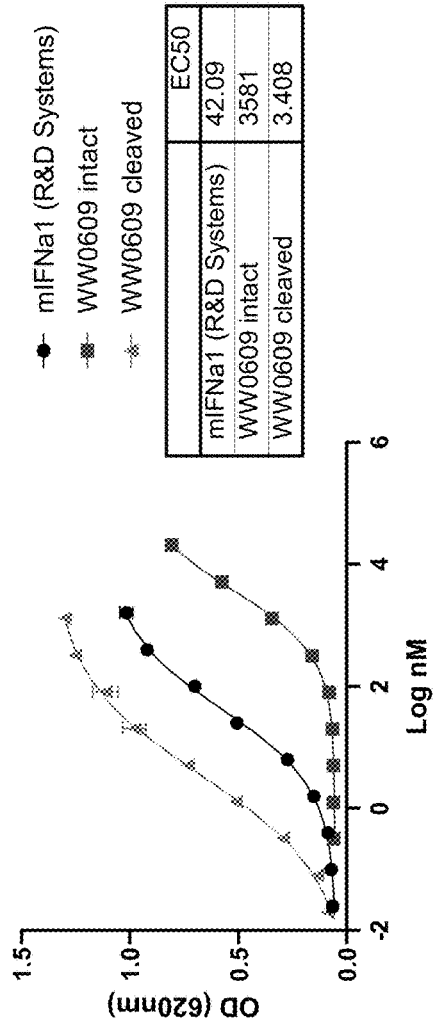
Figure 10B:
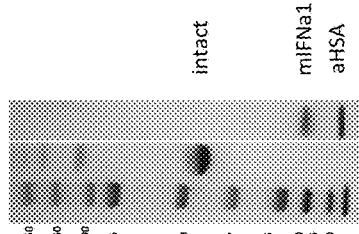
Figure 10B:
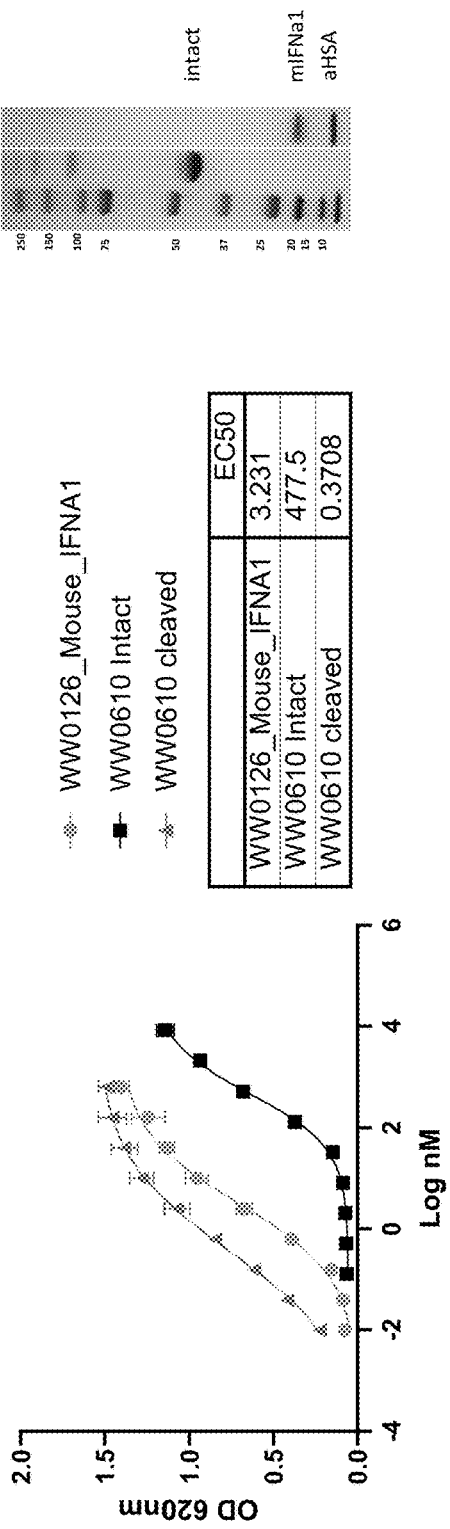
Figure 10C:
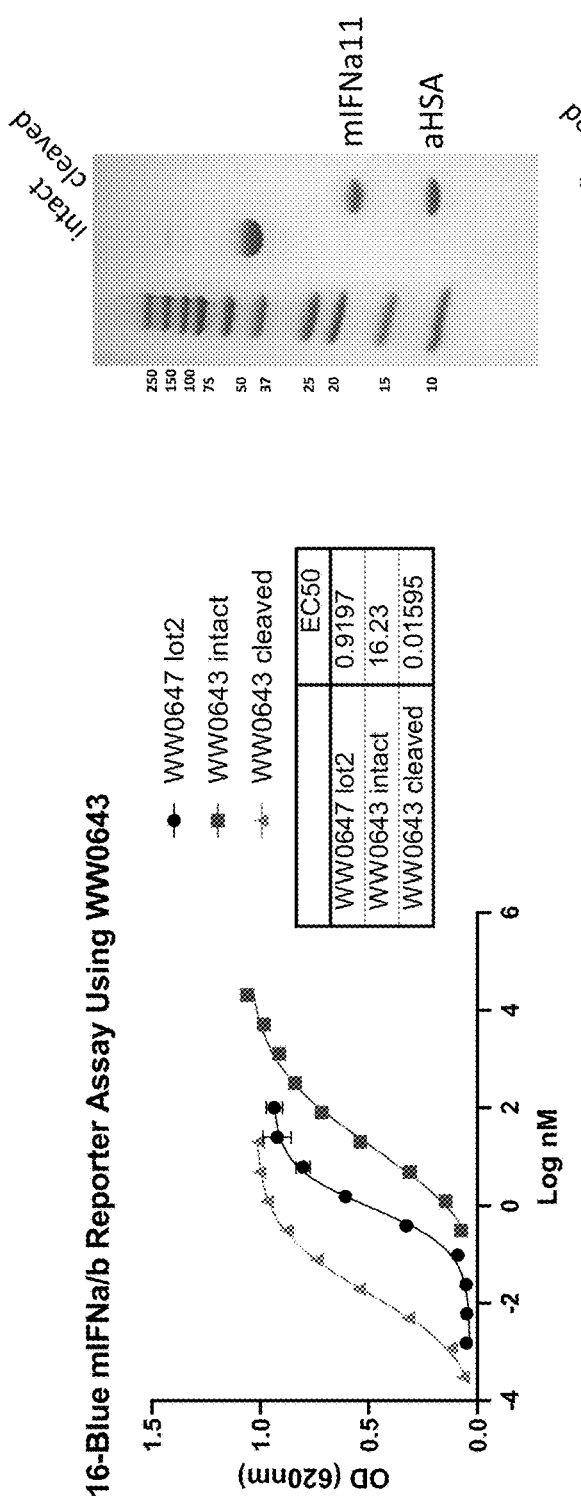
Figure 10D:
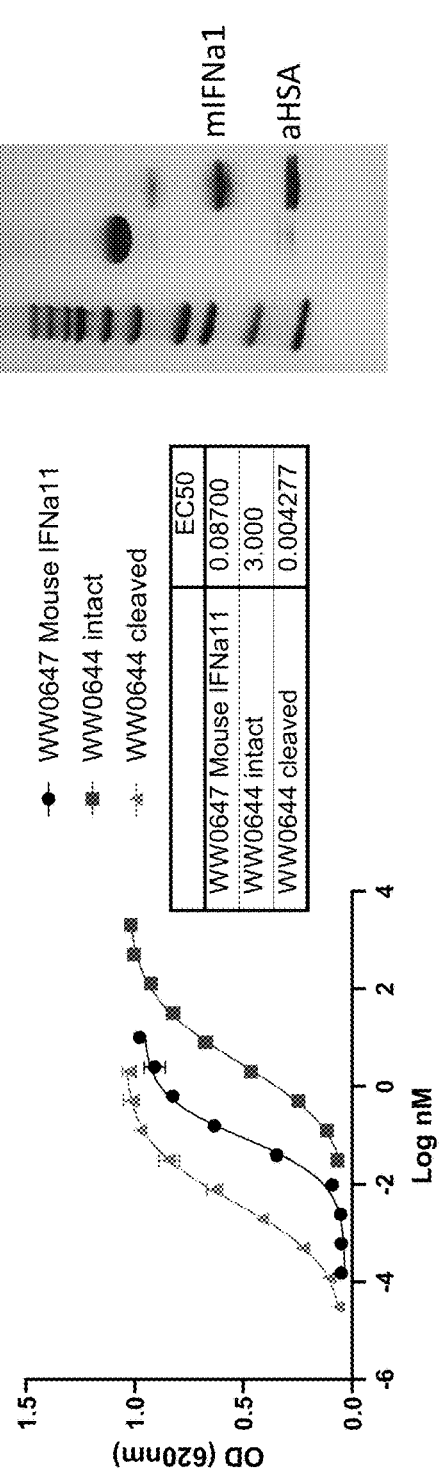
Figure 10E:
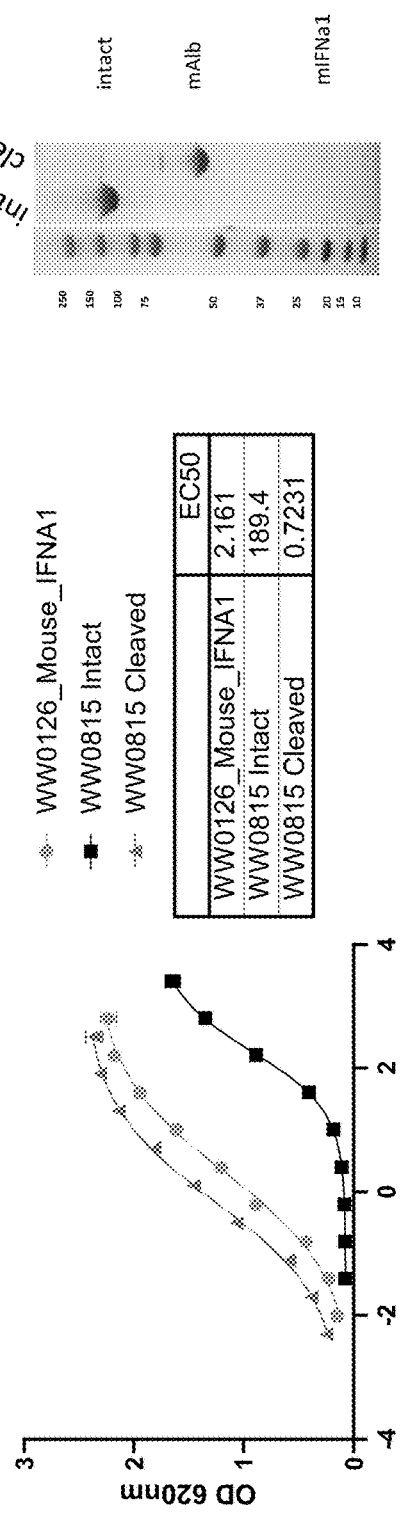
Figure 10F:
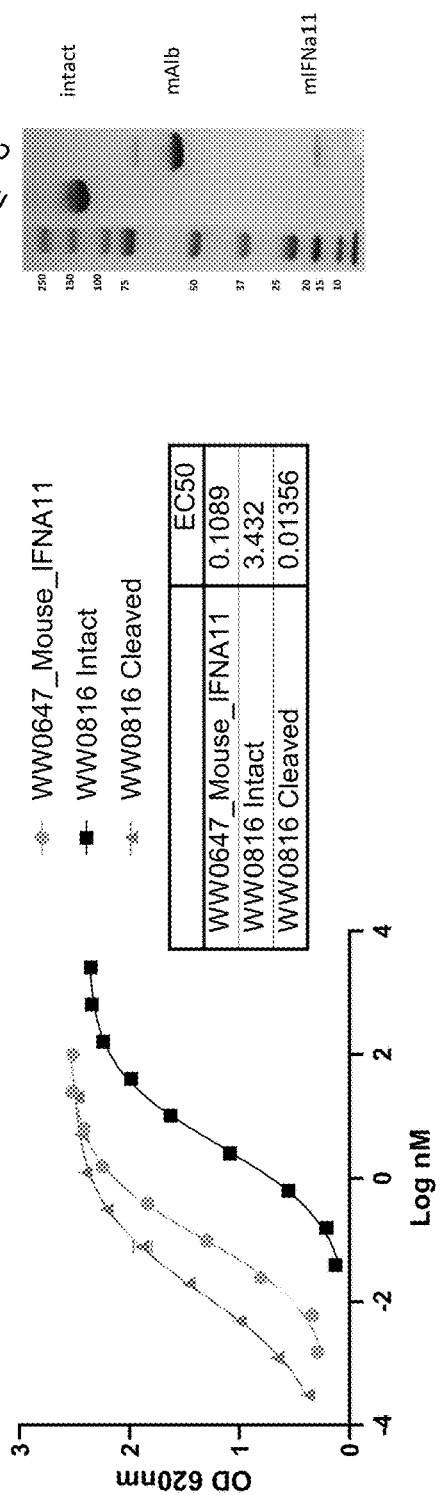
Figure 10I:
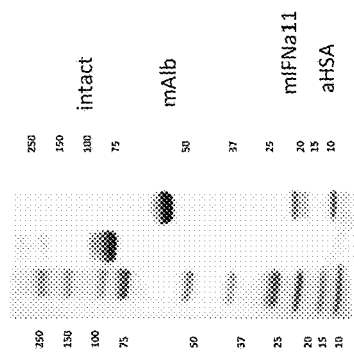
Figure 10I:
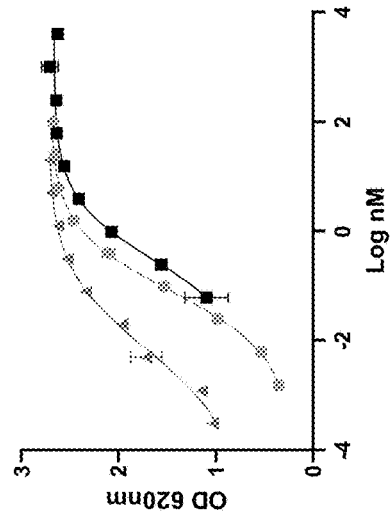
Figure 10J:
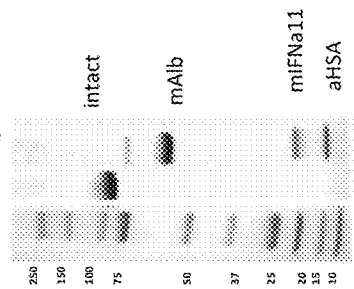
Figure 10J:
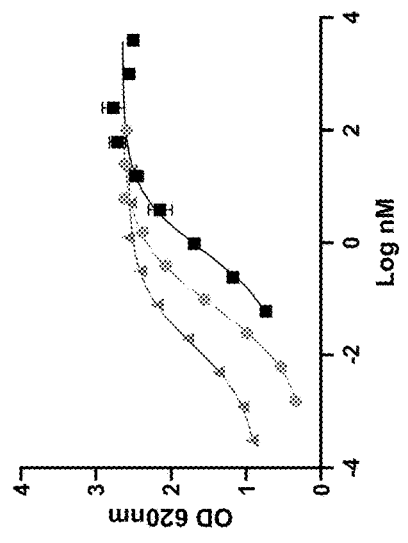
Figure 11B:
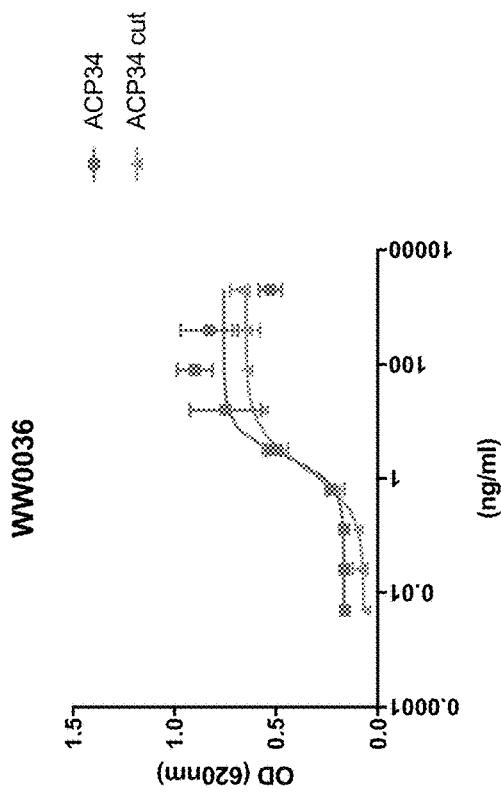
FIGS. 11A-11B are graphs depicting results from a HEK-Blue IL-12 reporter assay performed on human p40/murine p35 IL12 fusion proteins before and after protease cleavage. Constructs ACP35 (FIG. 11A) and ACP34 (FIG. 11B) were tested. Analysis was performed based on quantification of Secreted Alkaline Phosphatase (SEAP) activity using the reagent QUANTI-Blue® (InvivoGen). Results confirm that IL12 protein fusion proteins are active.
Figure 11A:
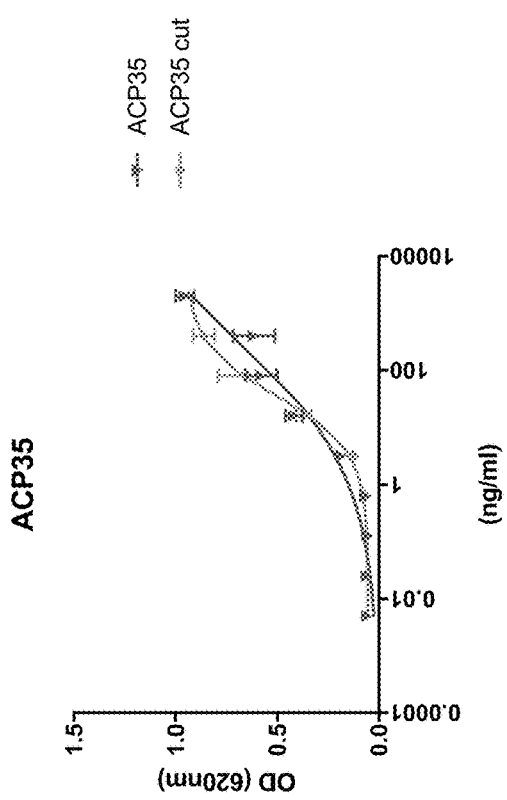
Figure 12C:
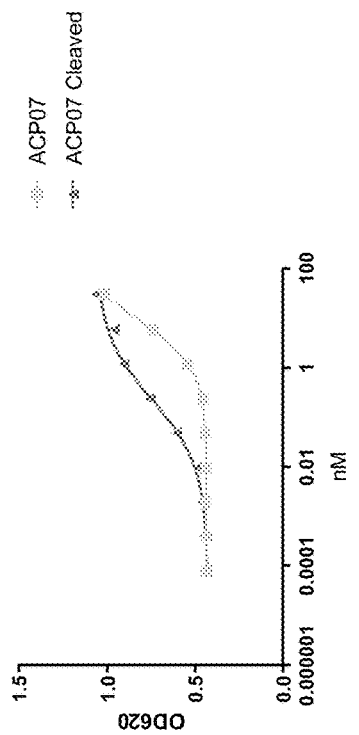
FIGS. 12A-12F show a series of graphs depicting the results of HEK-blue assay of four IL-12 fusion proteins, before and after cleavage by MMP9. Analysis was performed based on quantification of Secreted Alkaline Phosphatase (SEAP) activity using the reagent QUANTI-Blue (InvivoGen). The data show greater activity in the cleaved IL12 than in the full fusion protein. Constructs tested were ACP06 (FIG. 12A), ACP07 (FIG. 12C), ACP08 (FIG. 12B), ACP09 (FIG. 12D), ACP10 (FIG. 12E), ACP11 (FIG. 12F).
Figure 12D:
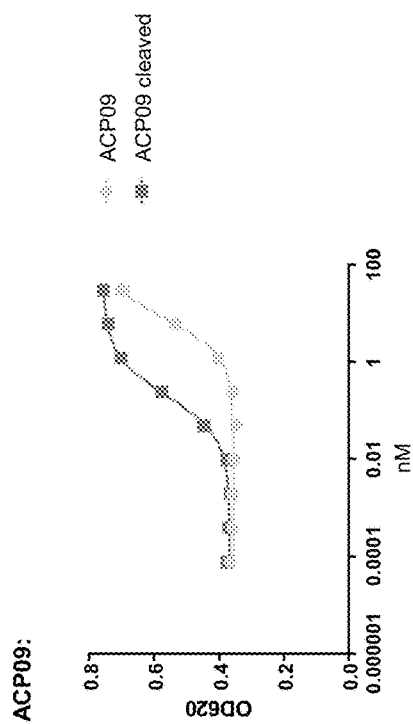
Figure 12A:
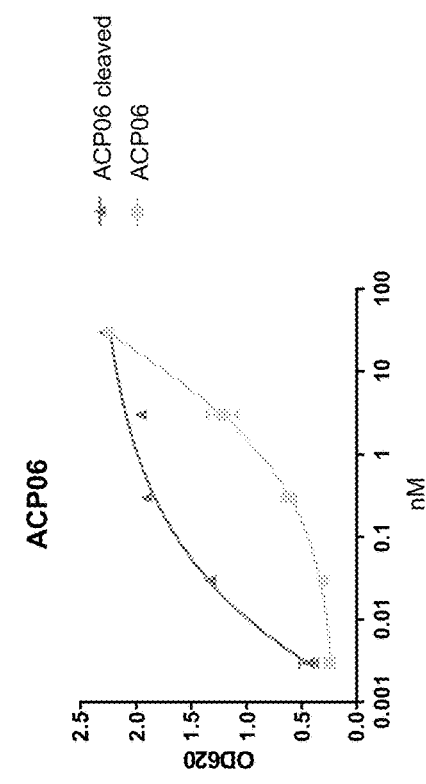
Figure 12B:
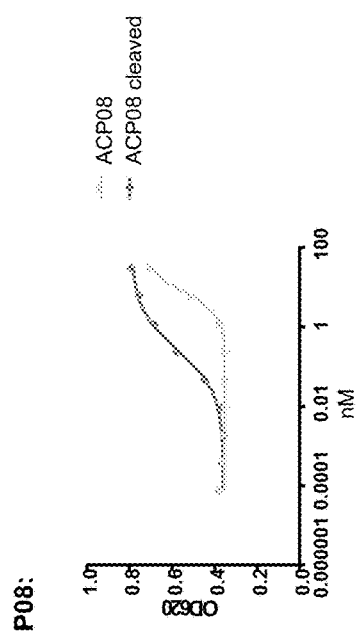
Figure 12F:
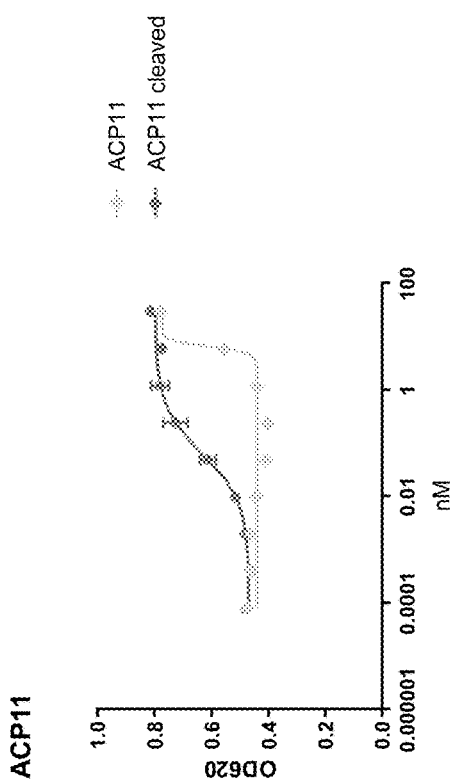
Figure 12E:
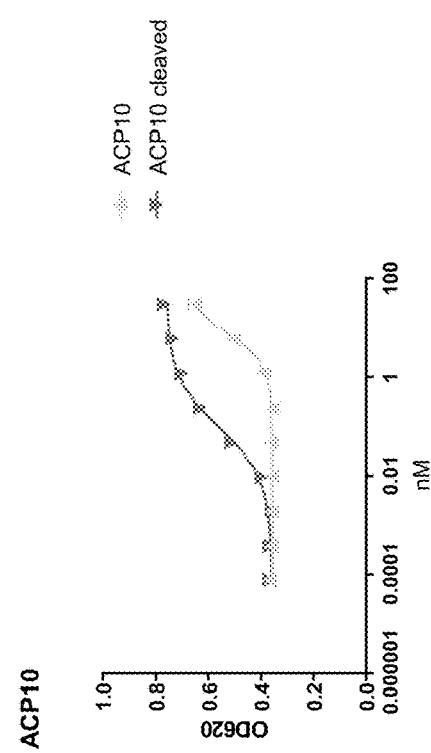
Figure 13:
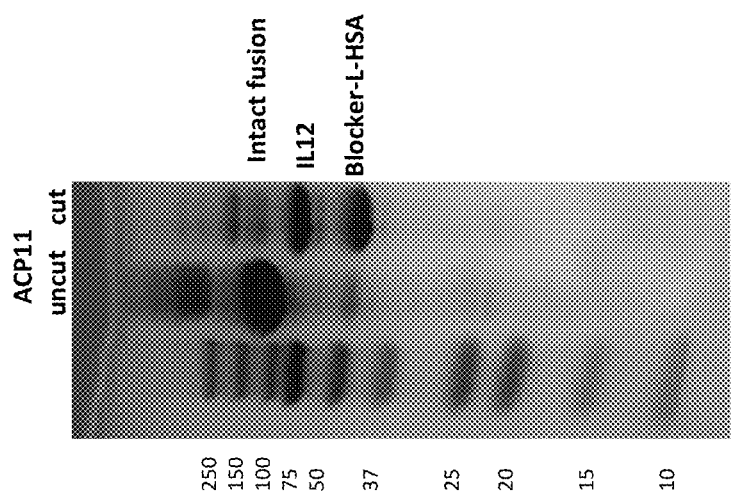
FIG. 13 shows results of protein cleavage assay. Fusion protein ACP11 was run on an SDS-PAGE gel in both cleaved and uncleaved form. As can be seen in the gel, cleavage was complete.
Figure 14:
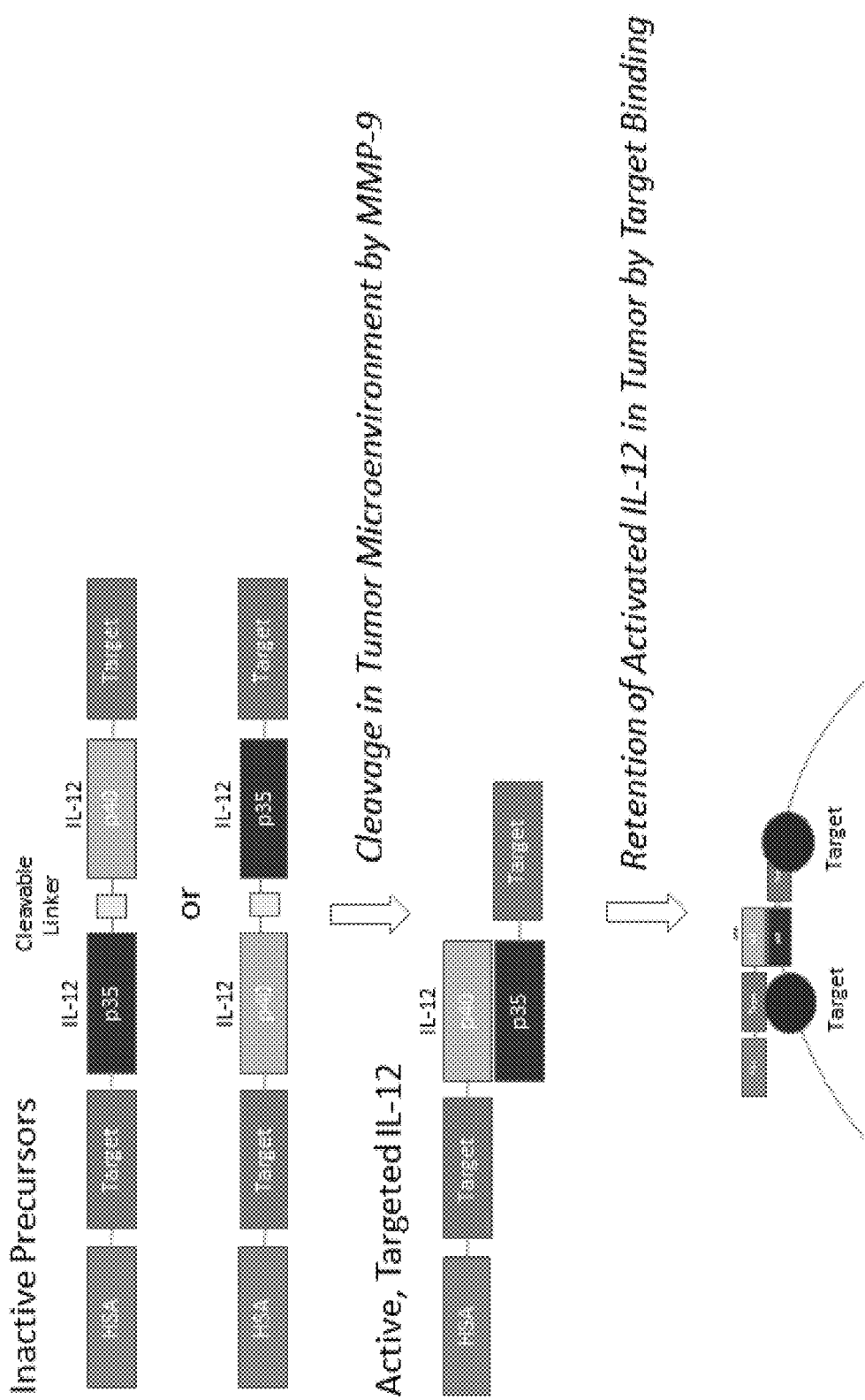
FIG. 14 is a schematic which depicts a non-limiting example of an inducible cytokine protein, wherein the construct is activated upon protease cleavage of a linker attached between two subunits of the cytokine.
Figure 15A:
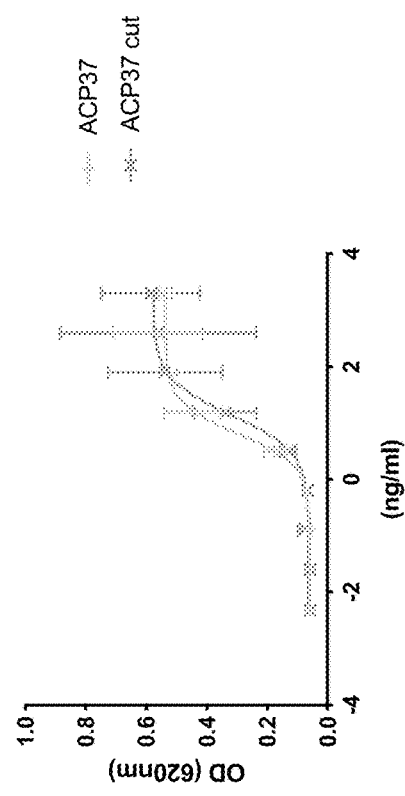
FIGS. 15A-15D are graphs depicting results from a HEK-Blue assay performed on human p40/murine p35 IL12 fusion proteins before and after protease cleavage. Results confirm that IL12 protein fusion proteins are active. Each proliferation assay was performed with HSA or without HSA.
Figure 15B:
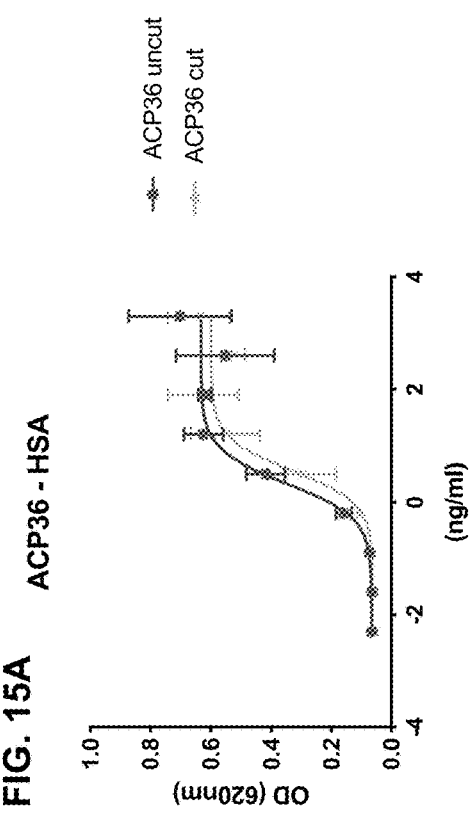
Figure 15C:
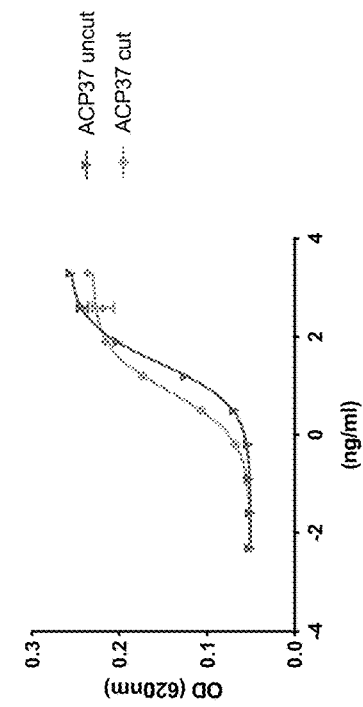
Figure 15D:
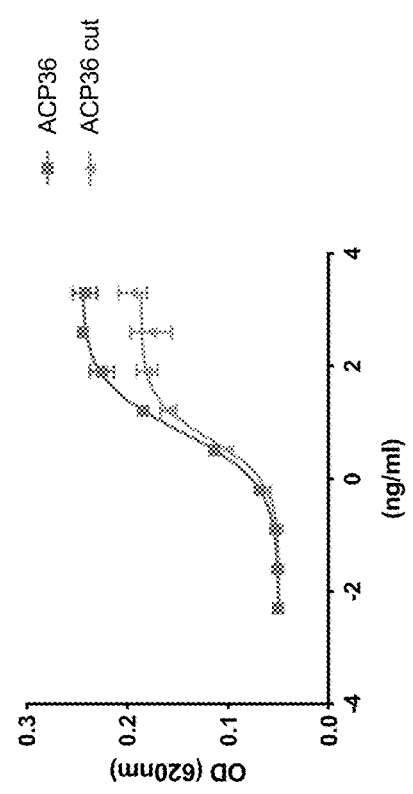
Figure 16A:
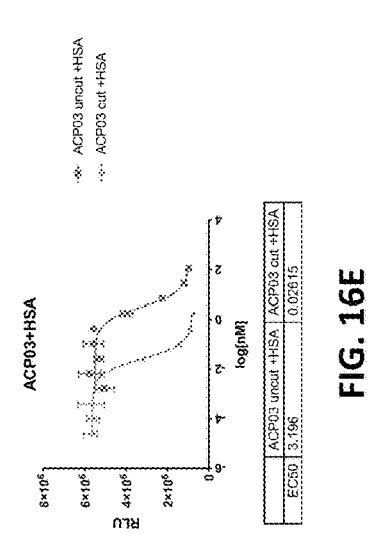
FIGS. 16A-16F are a series of graphs showing activity of exemplary IFNγ fusion proteins compared to activity of mouse IFNγ control using WEHI 279 cell survival assay. Each assay was performed with medium containing HSA (+HSA) or not containing HSA (-HSA). Each fusion protein comprises an anti-HSA binder, and both uncleaved and MMP9 protease cleaved versions of the fusion protein were used in each assay.
Figure 16B:
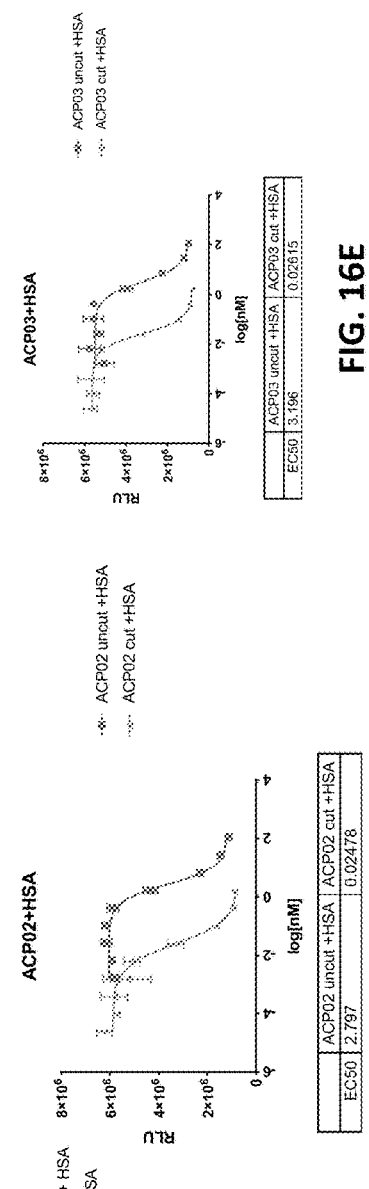
Figure 16C:
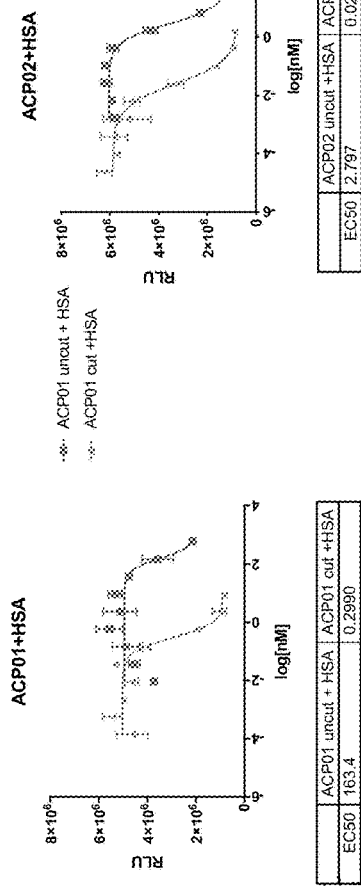
Figure 16D:
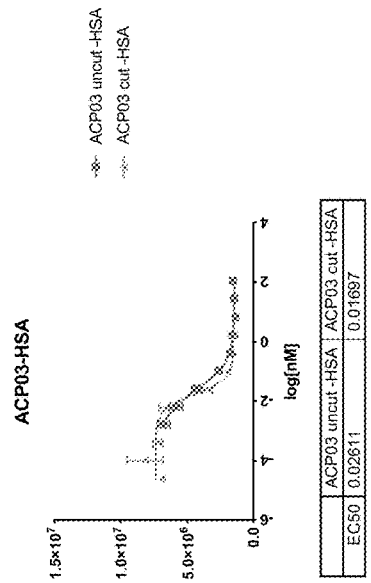
Figure 16E:
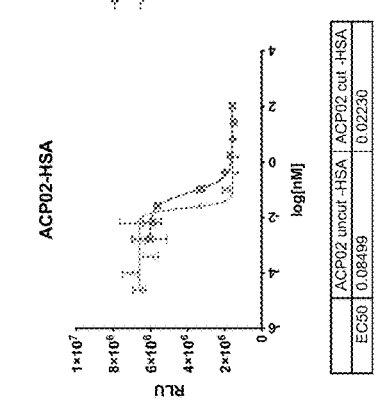
Figure 16F:
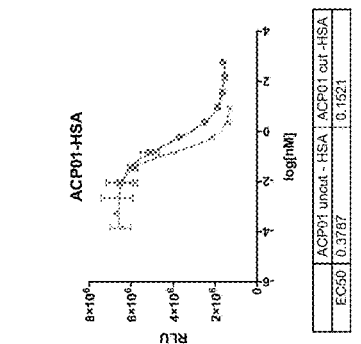
Figures 18A, 18B:
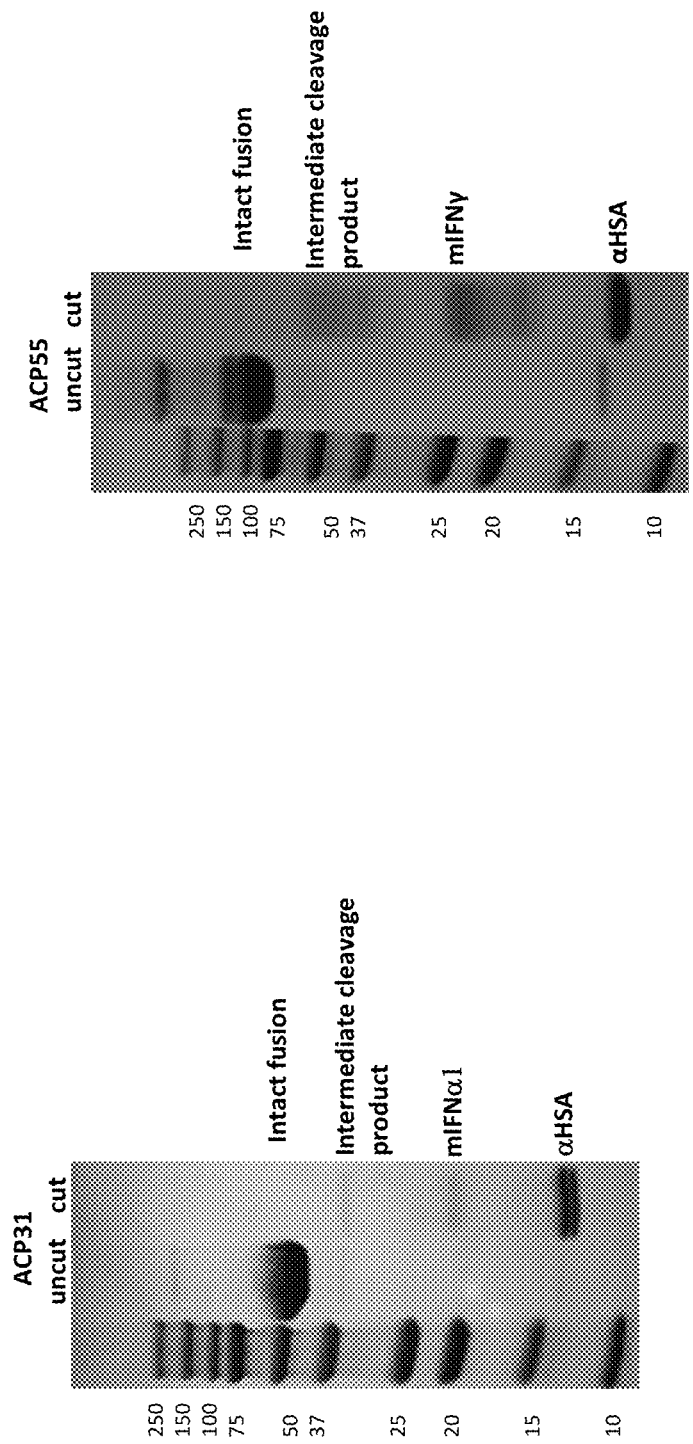
FIGS. 18A-18B show results of protein cleavage assay, as described in Example 2. Two constructs, ACP31 (IFN-α fusion protein.
Figure 20B:
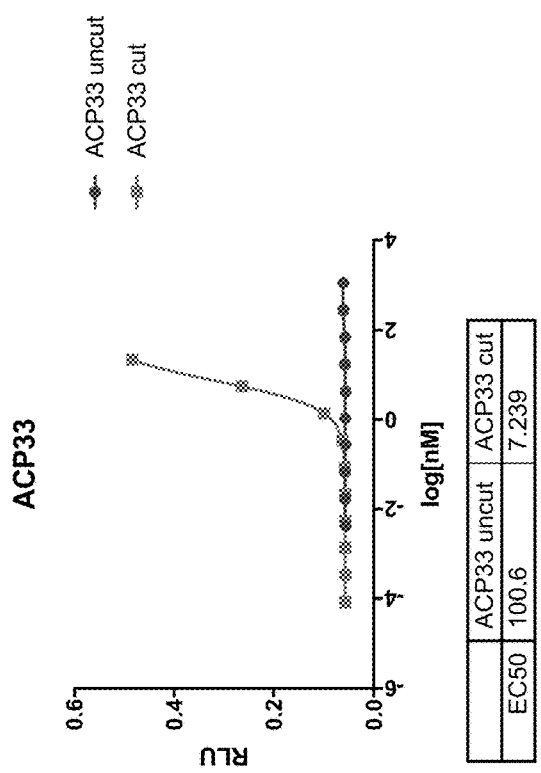
FIGS. 20A-20B are a series of graphs (FIG. 20A and FIG. 20B) showing activity of exemplary IFNα fusion proteins before and after cleavage using a B16 reporter assay. Each assay was performed with medium containing HSA, and each fusion protein comprises an anti-HSA binder. Both uncleaved and MMP9 protease cleaved versions of the fusion protein were used in each assay.
Figure 20A:
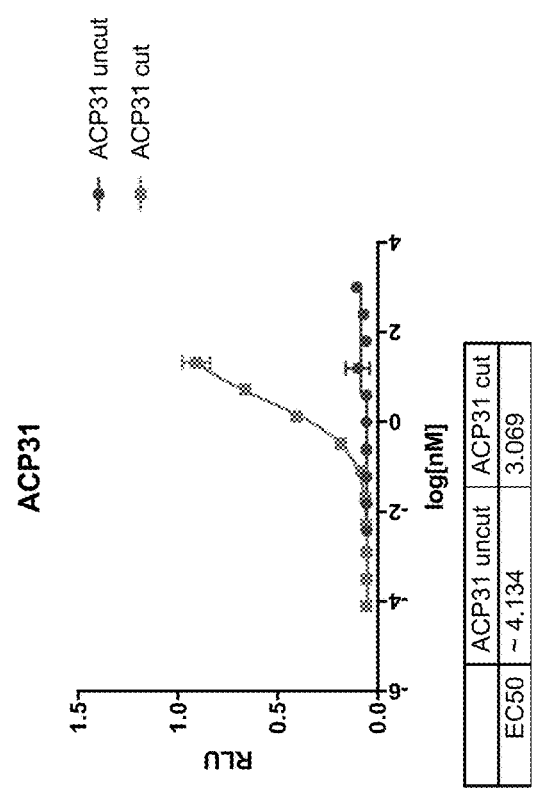

IL12 luciferase reporter cells (Promega), purchased from the manufacturer in a "Thaw and Use" format, were plated according to the manufacturer's directions and stimulated with a dilution series of recombinant hIL12 or activatable hIL12 for 6 hours at 37° C. and 5% $CO_2$. Activity of uncleaved and cleaved activatable IL12 was tested. Cleaved inducible IL12 was generated by incubation with active MMP9. IL12 activity was assessed by quantification of luciferase activity using Bio-Glo™ Reagent (Promega), which allows for the measurement of luciferase activity by luminescence readout. Results are shown in FIGS. 9A-9C.

Example 31. MC38 Experiments

Agents and Treatment

| Group | N | Agent | Dose | Route | Schedule |
|---|---|---|---|---|---|
| 1 | 12 | vehicle | — | ip | biwk × 2 |
| 2 | 8 | WW0417 | 55 µg/animal | ip | biwk × 2 |
| 3 | 8 | WW0517 | 55 µg/animal | ip | biwk × 2 |
| 4 | 8 | WW0517 | 230 µg/animal | ip | biwk × 2 |
| 5 | 8 | WW0517 | 700 µg/animal | ip | biwk × 2 |
| 6 | 8 | WWW0520/0523 | 76 µg/animal | ip | biwk × 2 |
| 7 | 8 | WWW0520/0523 | 315 µg/animal | ip | biwk × 2 |
| 8 | 8 | WWW0520/0523 | 959 µg/animal | ip | biwk × 2 |
| 9 | 8 | WWW0548/0524 | 88 µg/animal | ip | biwk × 2 |
| 10 | 8 | WWW0548/0524 | 368 µg/animal | ip | biwk × 2 |
| 11 | 8 | WWW0548/0524 | 1,120 µg/animal | ip | biwk × 2 |
| 12 | 8 | WWW0548/0556 | 113 µg/animal | ip | biwk × 2 |
| 13 | 8 | WWW0548/0556 | 474 µg/animal | ip | biwk × 2 |
| 14 | 8 | WWW0548/0556 | 1,442 µg/animal | ip | biwk × 2 |
| 15 | 8 | WW0475 | 68 µg/animal | ip | biwk × 2 |
| 16 | 8 | WW0475 | 283 µg/animal | ip | biwk × 2 |
| 17 | 8 | WW0475 | 861 µg/animal | ip | biwk × 2 |
| 10 | 8 | WW0619 | 17 µg/animal | ip | biwk × 2 |
| 11 | 8 | WW0619 | 35 µg/animal | ip | biwk × 2 |
| 12 | 8 | WW0619 | 70 µg/animal | ip | biwk × 2 |
| 13 | 8 | WW0619 | 700 µg/animal | ip | biwk × 2 |
| 14 | 8 | WW0621/0523 | 24 µg/animal | ip | biwk × 2 |
| 15 | 8 | WW0621/0523 | 48 µg/animal | ip | biwk × 2 |
| 16 | 8 | WW0621/0523 | 96 µg/animal | ip | biwk × 2 |
| 17 | 8 | WW0621/0523 | 960 µg/animal | ip | biwk × 2 |

Figure 5A:
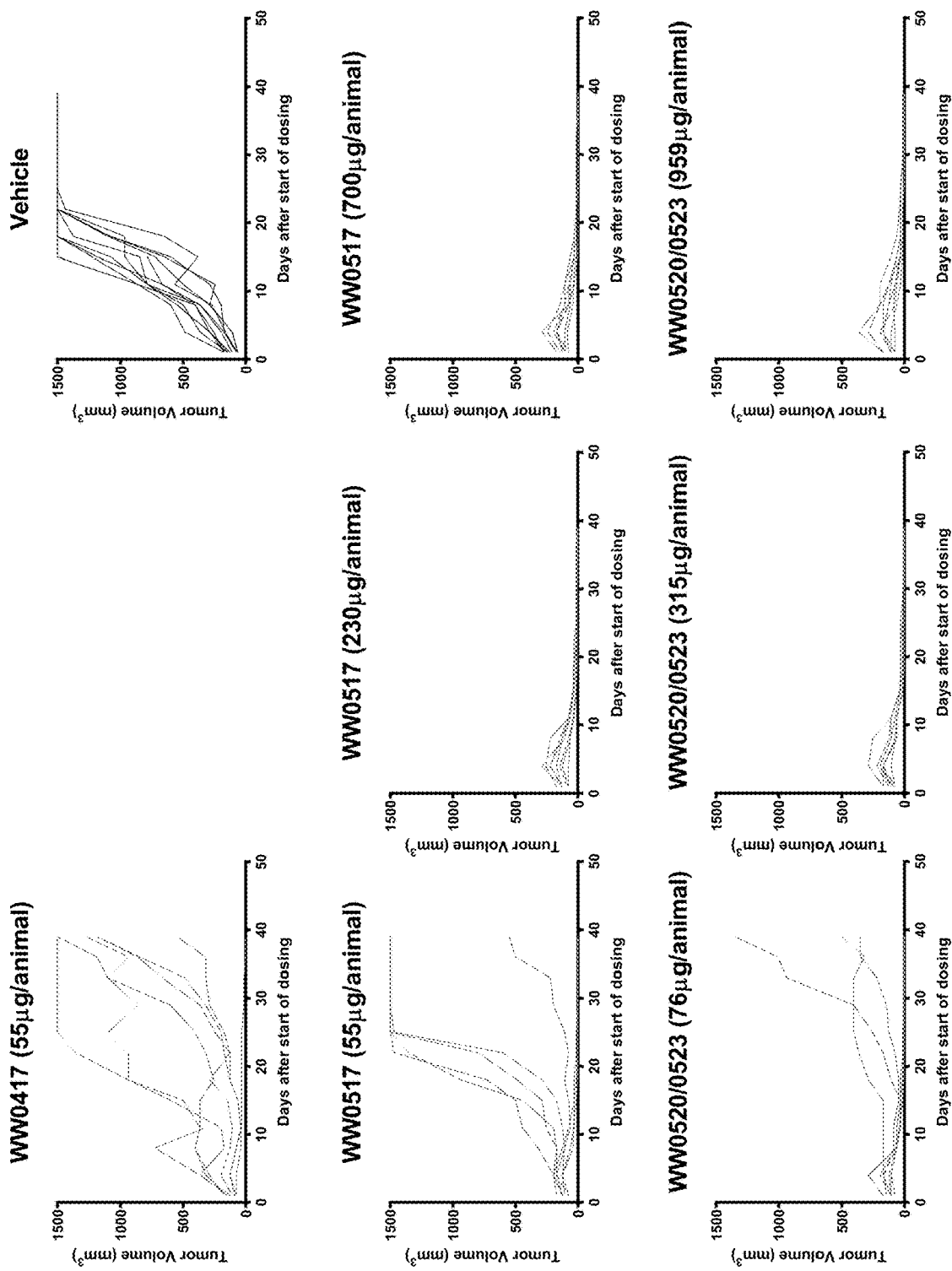
FIGS. 5A-5C are a series of spider plots showing activity of fusion proteins in the MC38 mouse syngeneic model corresponding to the data shown in FIG. 4A-4G. Each line in the plots is the tumor volume over time for a single mouse.
Figure 5B:
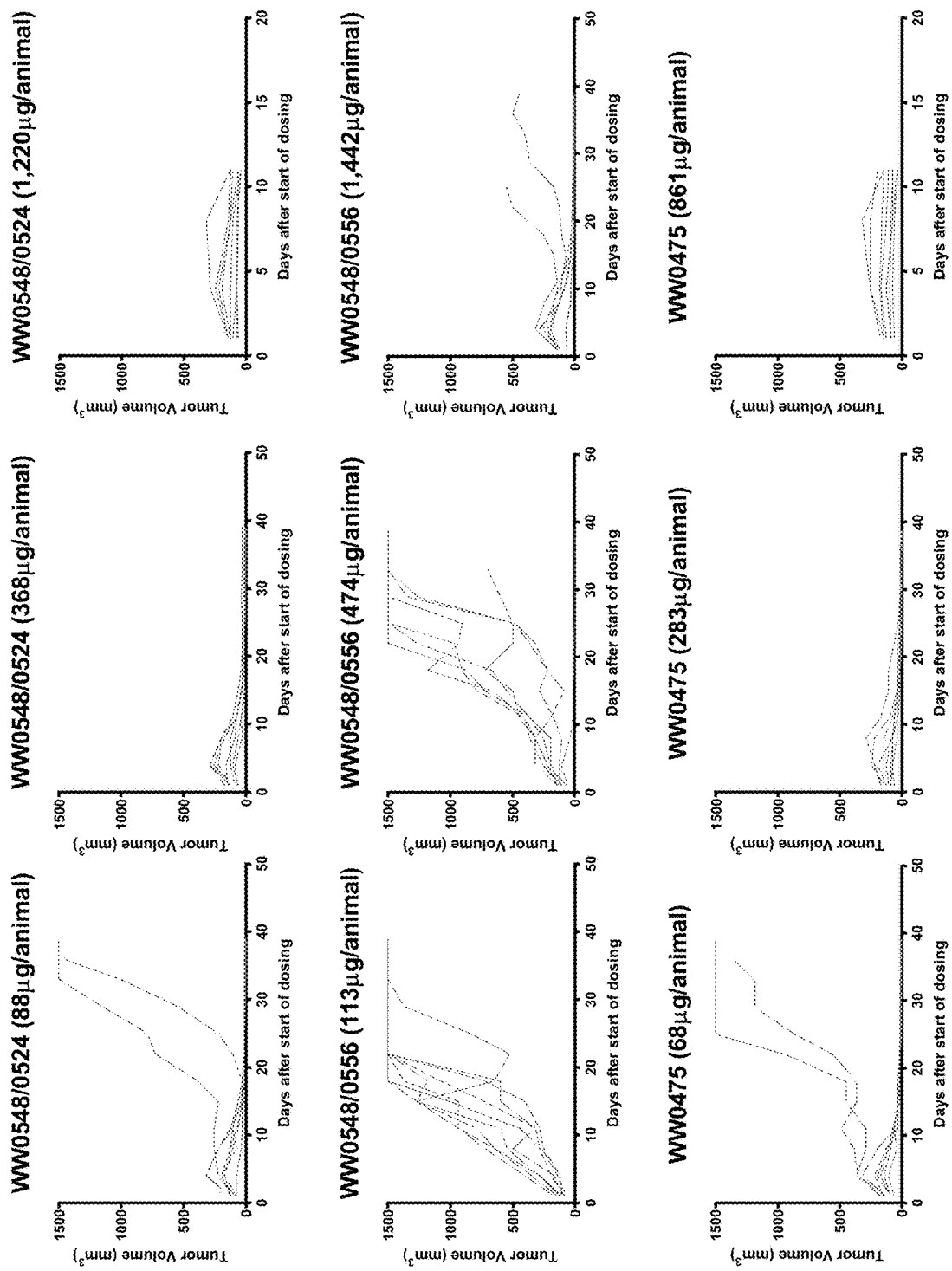
Figure 5C:
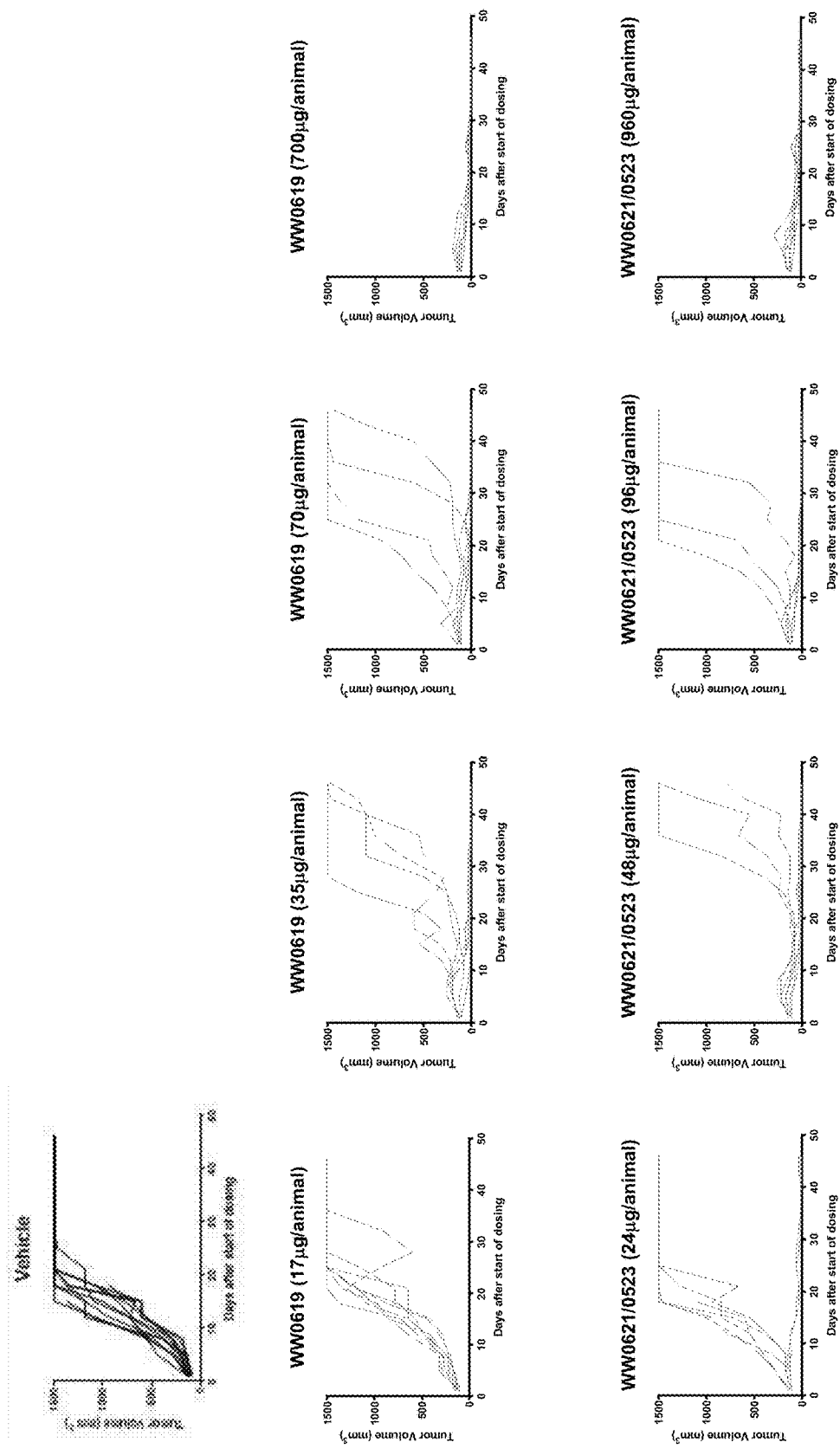
Figure 6A:
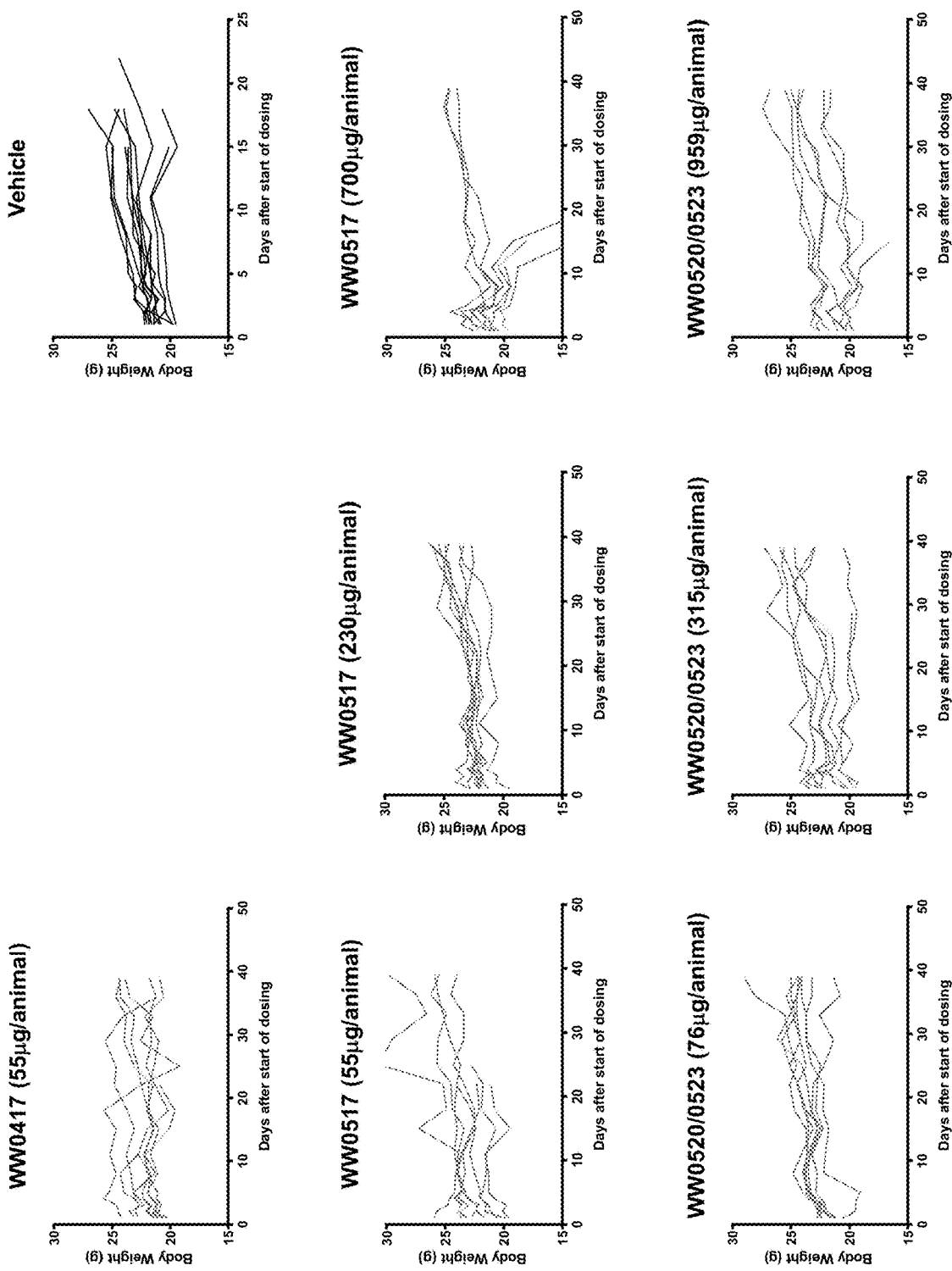
FIGS. 6A-6C are a series of spider plots showing the impact of fusion proteins on body weight in an MC38 mouse syngeneic model corresponding to the data shown in FIGS. 5A-5C. Each line in the plots is the body weight over time for a single mouse.
Figure 6B:
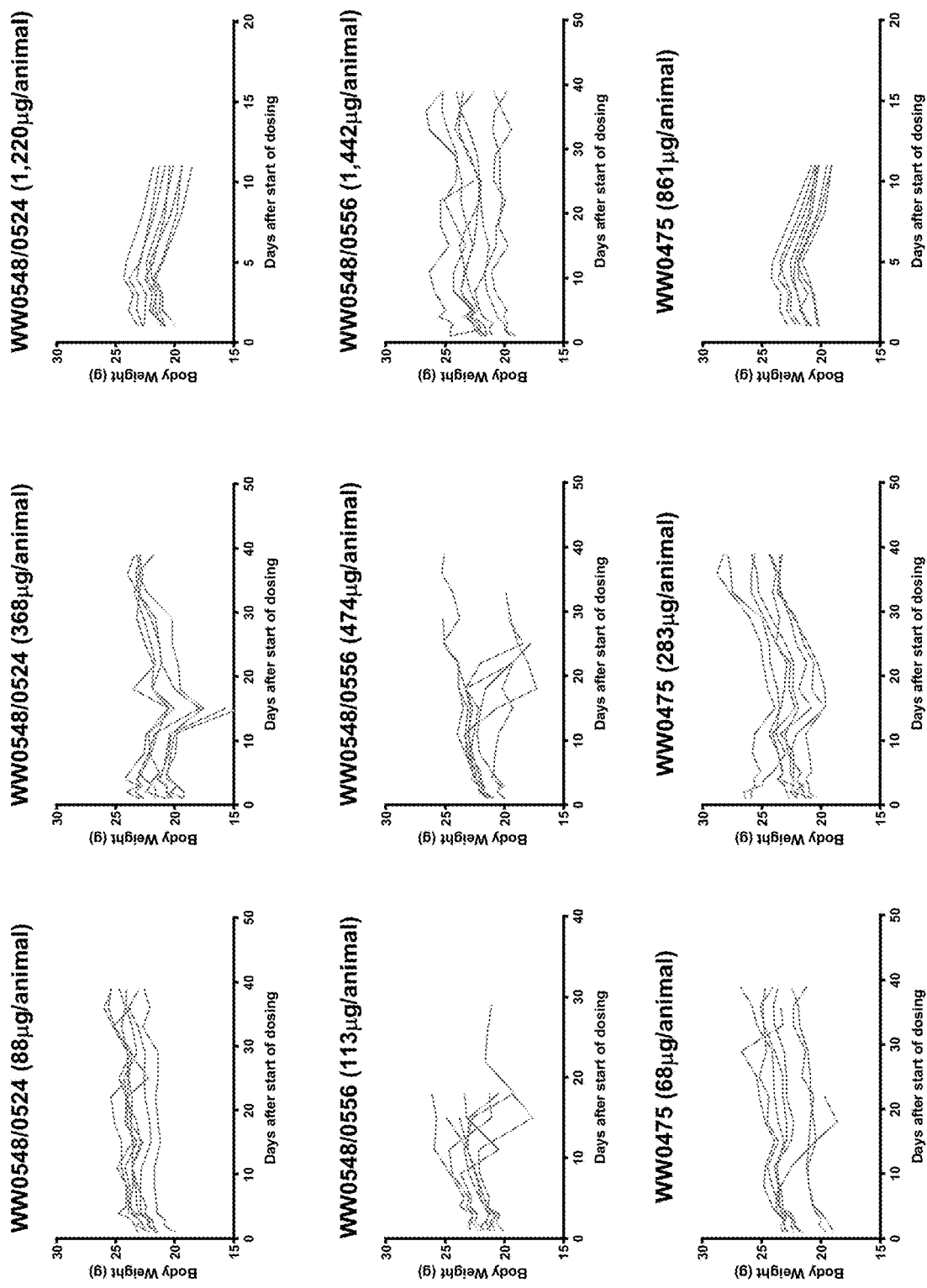
Figure 6C:
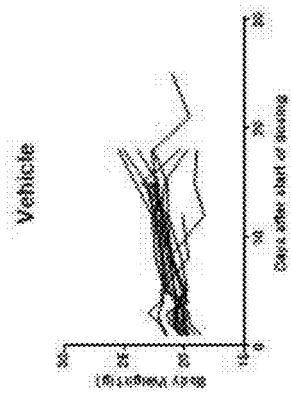
Figure 6C:
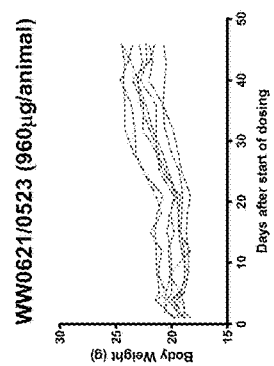
Figure 6C:
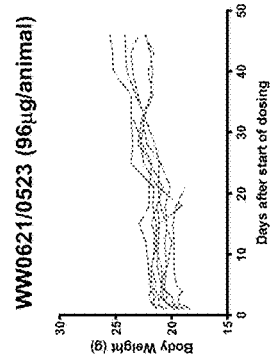
Figure 6C:
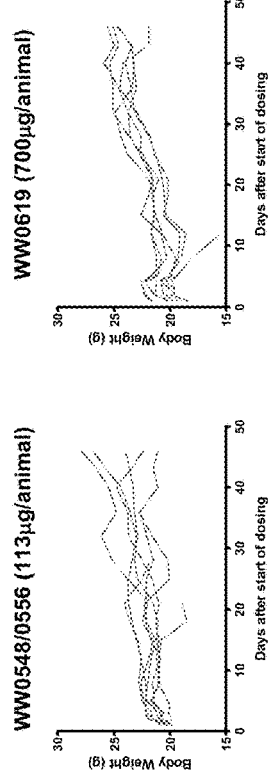
Figure 6C:
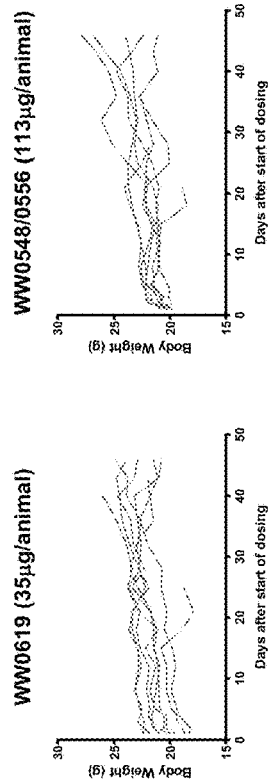
Figure 6C:
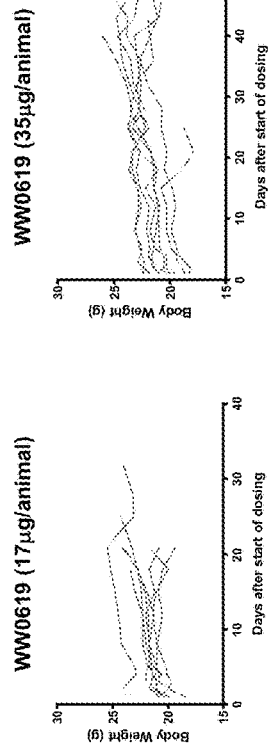
Figure 6C:
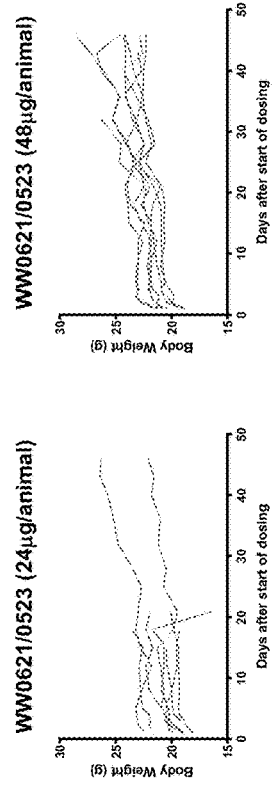
Figure 7A:
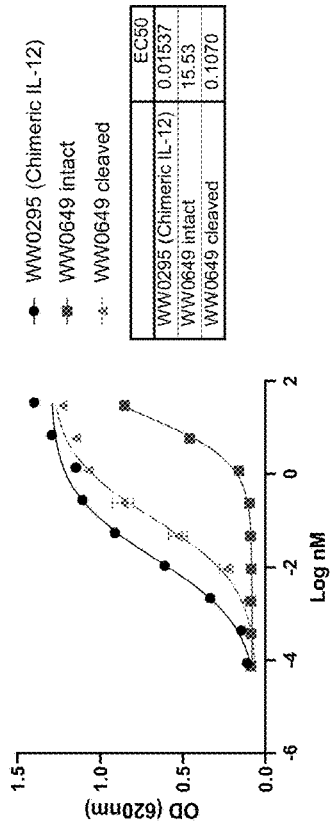
FIGS. 7A-7Q are a series of graphs showing activity of fusion proteins in an HEKBlue IL-12 reporter assay.
Figure 7B:
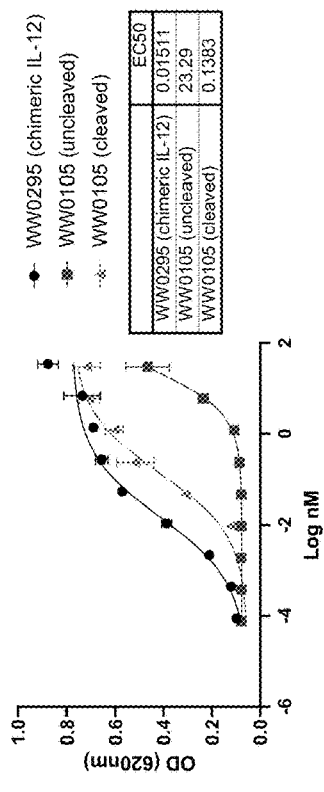
Figure 7C:
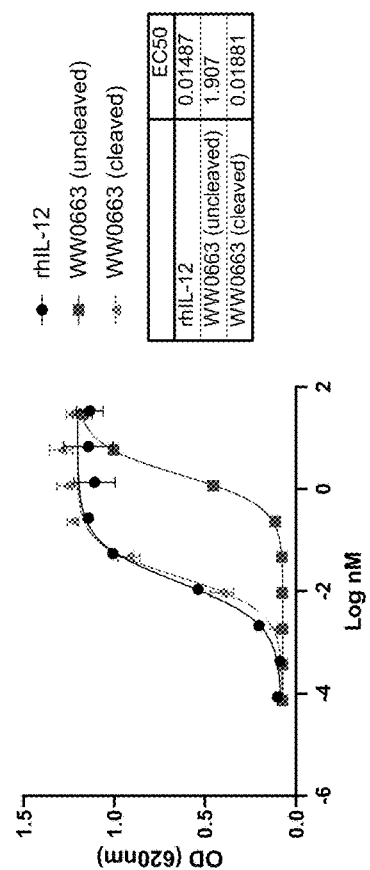
Figure 7D:
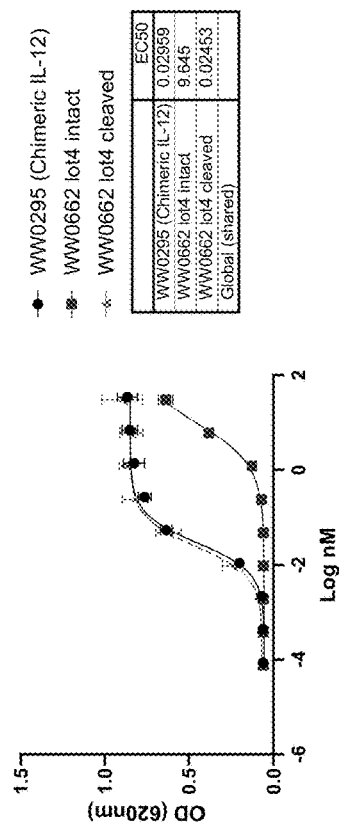
Figure 7H:
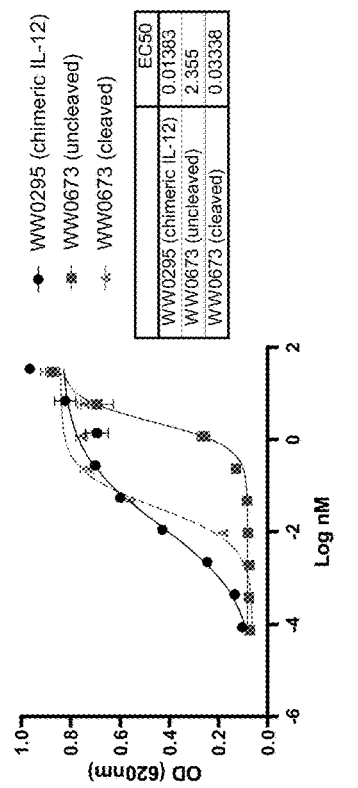
Figure 7I:
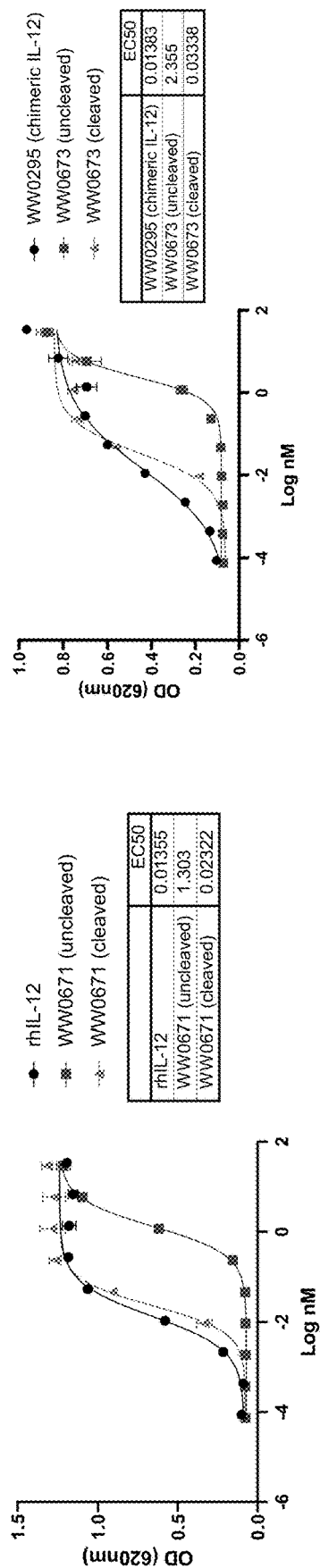
Figure 7J:
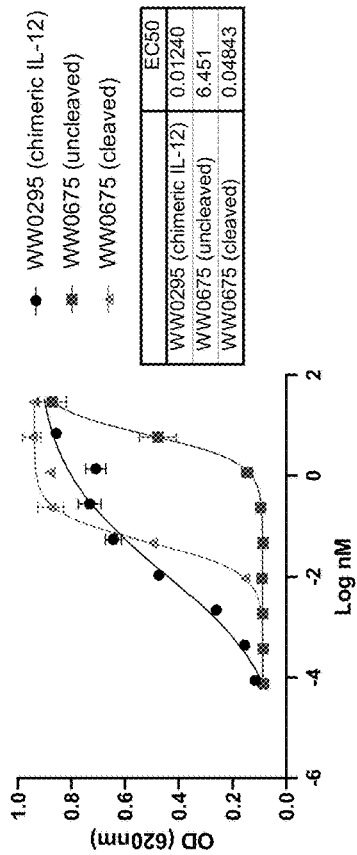
Figure 7O:
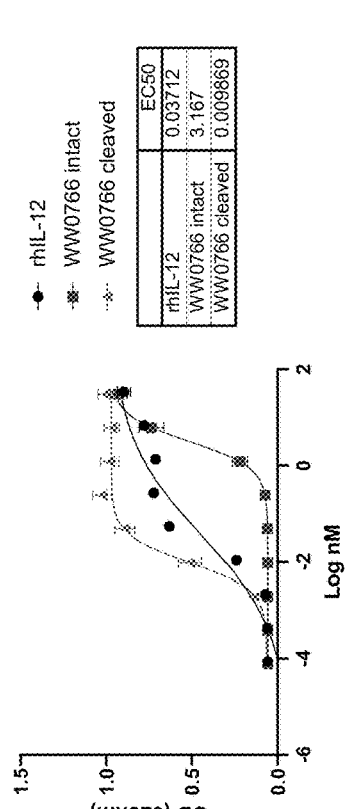
Figure 7Q:
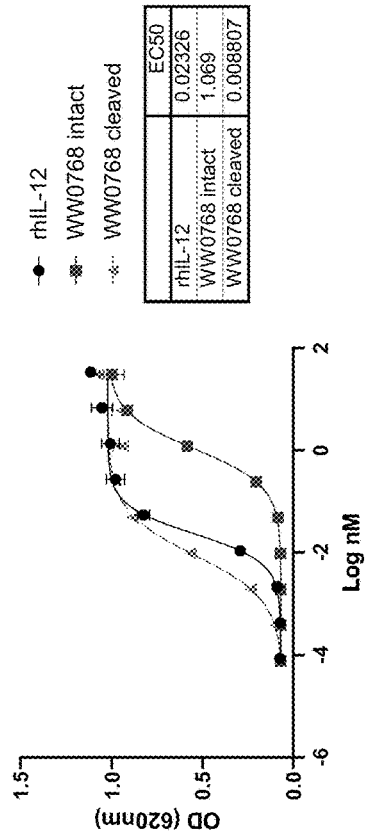
Figure 7N:
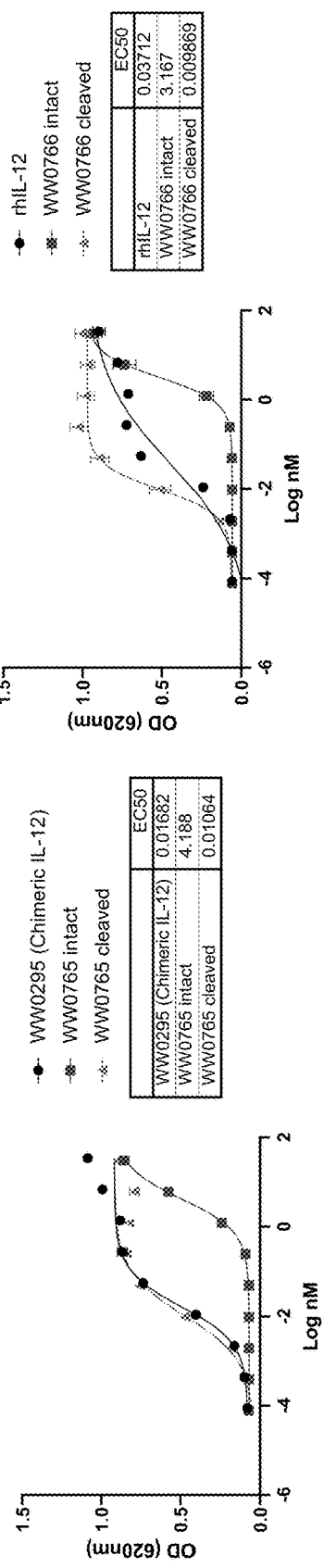
Figure 7P:
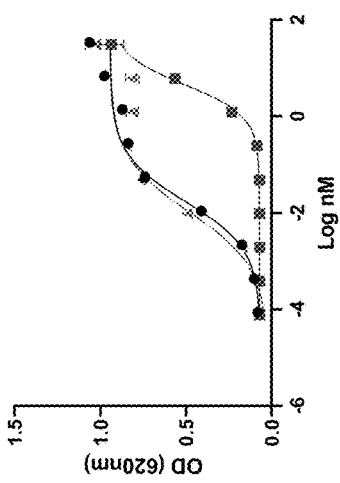
Figure 8B:
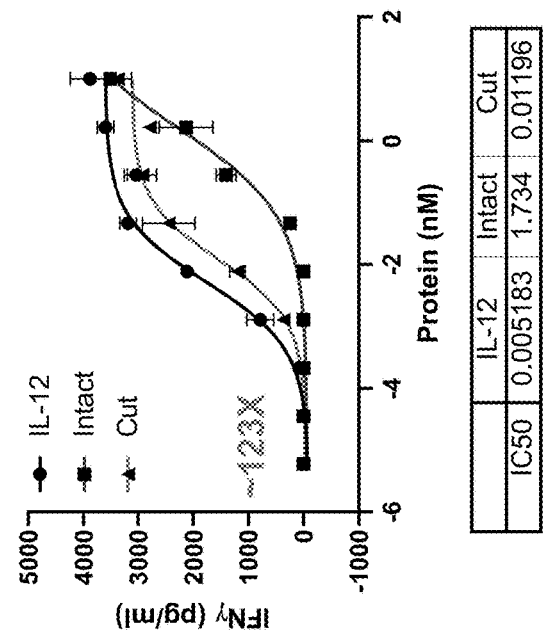
FIGS. 8A-8D are a series of graphs showing activity of fusion proteins in an IL12 T-Blast assay.
Figure 8D:
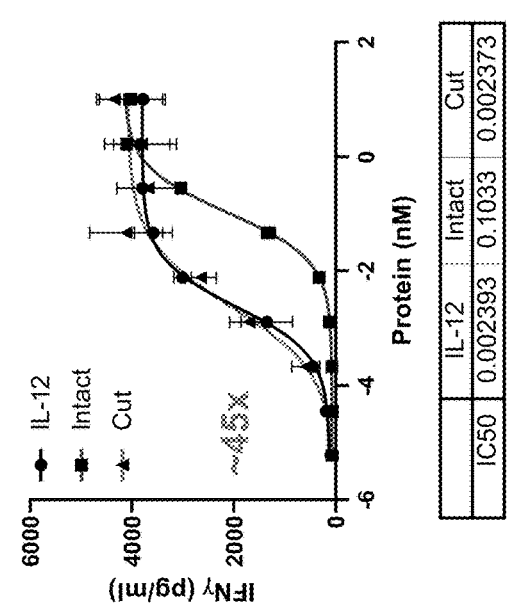
Figure 8A:
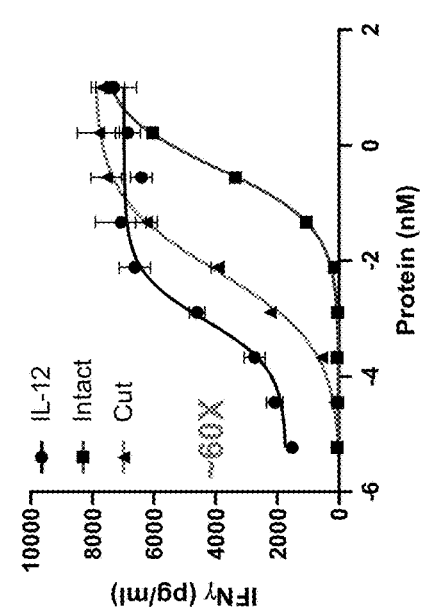
Figure 8C:
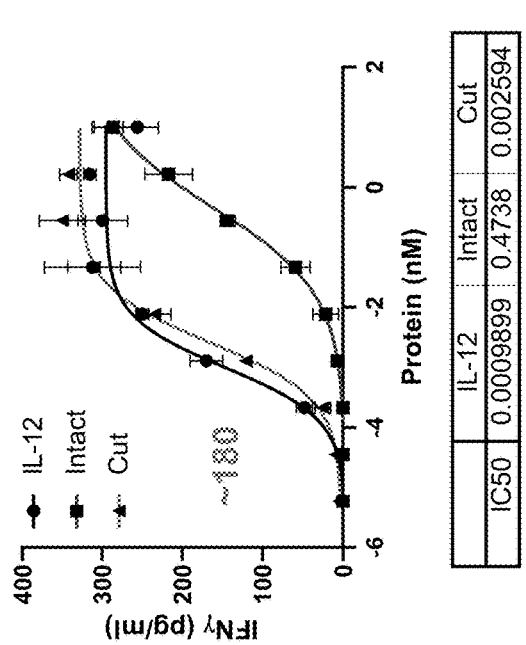

Procedures:

Mice were anaesthetized with isoflurane for implant of cells to reduce the ulcerations. 308 CR female C57BL/6 mice were set up with $5\times10^5$ MC38 tumor cells in 0% Matrigel sc in flank. Cell Injection Volume was 0.1 mL/mouse. Mouse age at start date was 8 to 12 weeks. Pair matches were performed when tumors reach an average size of 100-150 mm$^3$ and begin treatment. Body weights were taken at initiation and then biweekly to the end. Caliper measurements were taken biweekly to the end. Any adverse reactions were to be reported immediately. Any individual animal with a single observation of >than 30% body weight loss or three consecutive measurements of >25% body weight loss was euthanized. Any group with a mean body weight loss of >20% or >10% mortality stopped dosing; the group was not euthanized, and recovery is allowed. Within a group with >20% weight loss, individuals hitting the individual body weight loss endpoint were euthanized. If the group treatment related body weight loss is recovered to within 10% of the original weights, dosing resumed at a lower dose or less frequent dosing schedule. Exceptions to non-treatment body weight % recovery were allowed on a case-by-case basis. Endpoint was tumor growth delay (TGD). Animals were monitored individually. The endpoint of the experiment was a tumor volume of 1500 mm$^3$ or 45 days, whichever comes first. Responders were followed longer. When the endpoint was reached, the animals are to be euthanized. Results are shown in FIGS. 4-6.

Sample fusion protein constructs are detailed in Table 3. In table 3, "L" is an abbreviation of "linker", and "cleav. link." is an abbreviation of "cleavable linker". Other abbreviations "mIFNg" indicates mouse interferon gamma (IFNg); "hAlbumin" indicates human serum albumin (HSA); "mAlbumin" indicates mouse serum albumin.

Example 32. Human Interferon PBMC Assay

Figure 38A:
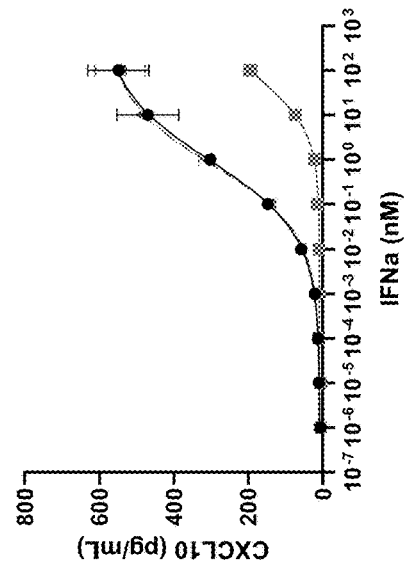
FIGS. 38A-38C are a series of graphs showing activity of fusion proteins in the human PBMCs assay.
Figure 38B:
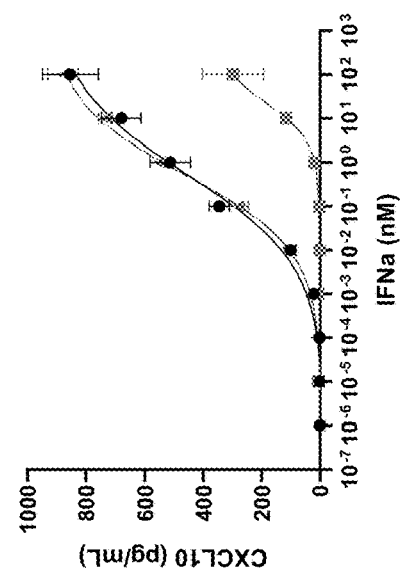
Figure 38C:
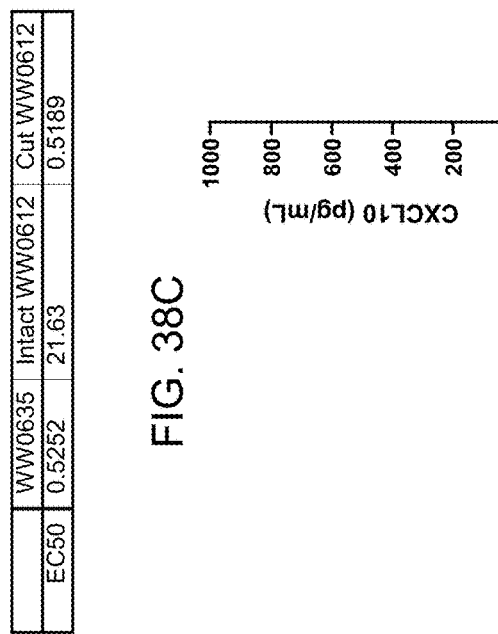
Figure 39B:
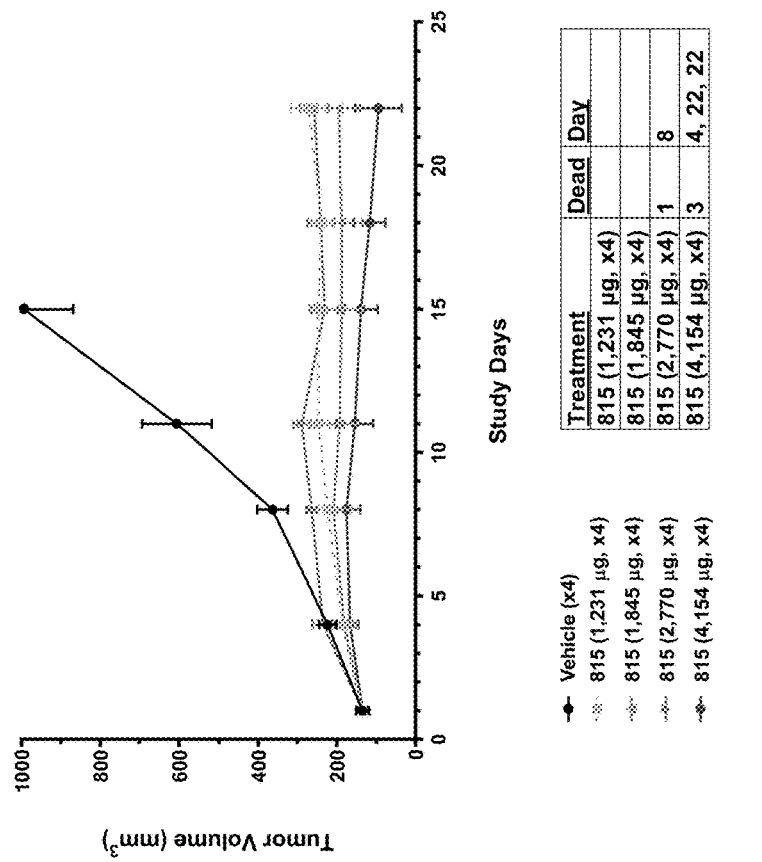
FIGS. 39A-39G show are results of analyzing IFN fusion proteins in syngeneic MC38 mouse tumor model.
Figure 39A:
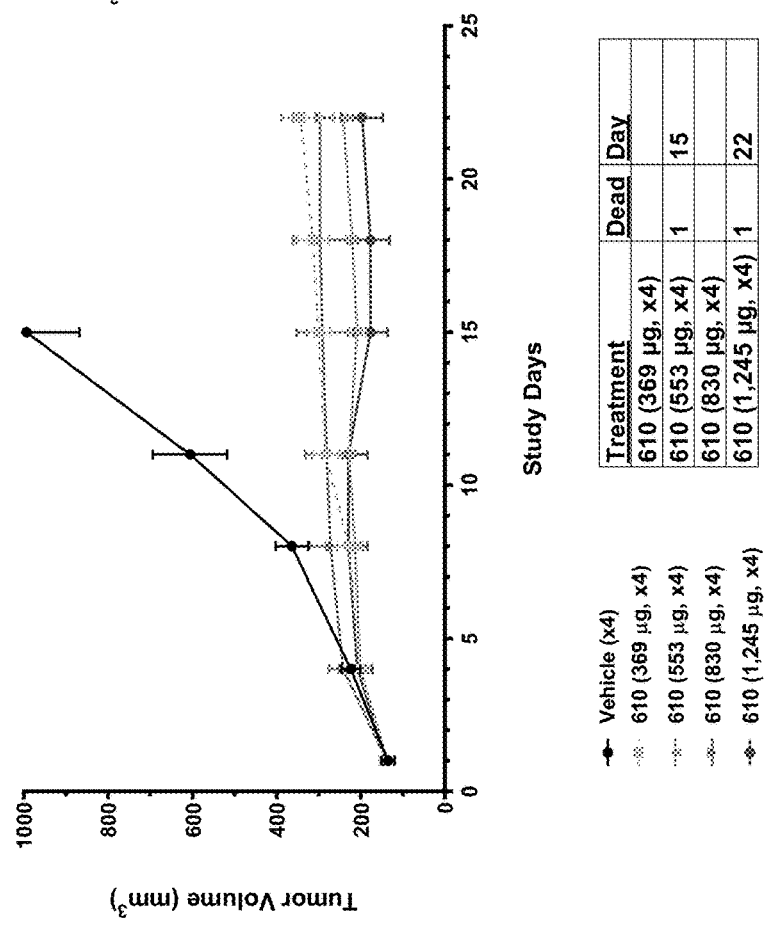
Figure 39C:
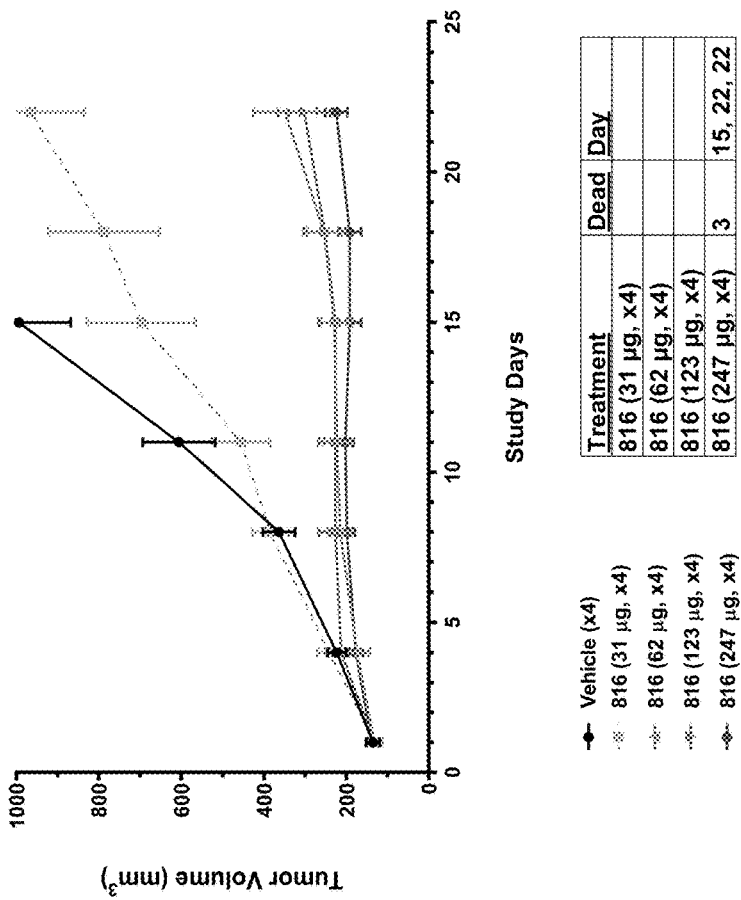
Figure 39D:
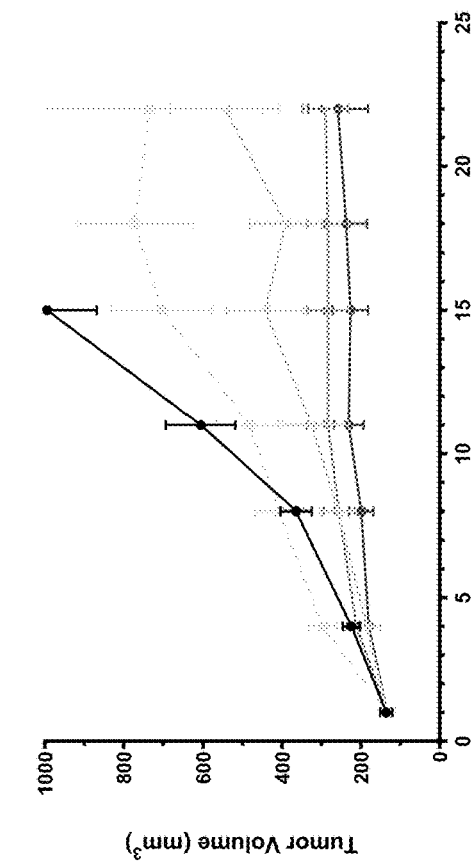
Figure 39E:
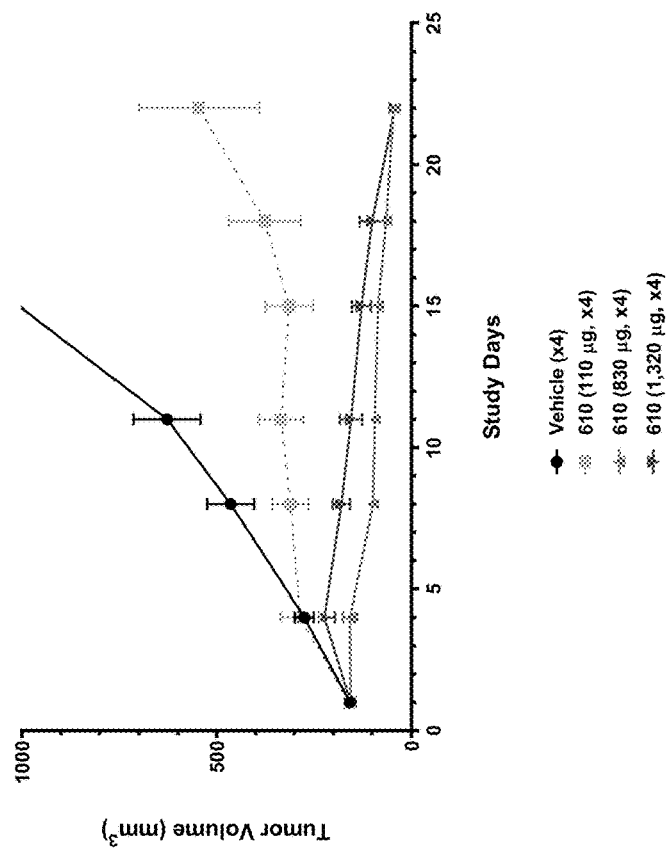
Figure 39F:
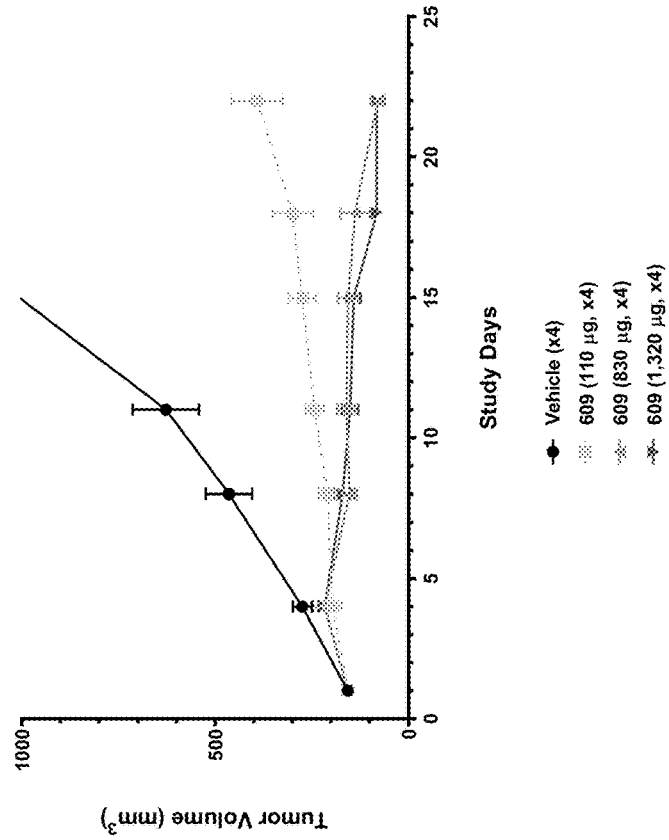
Figure 39G:
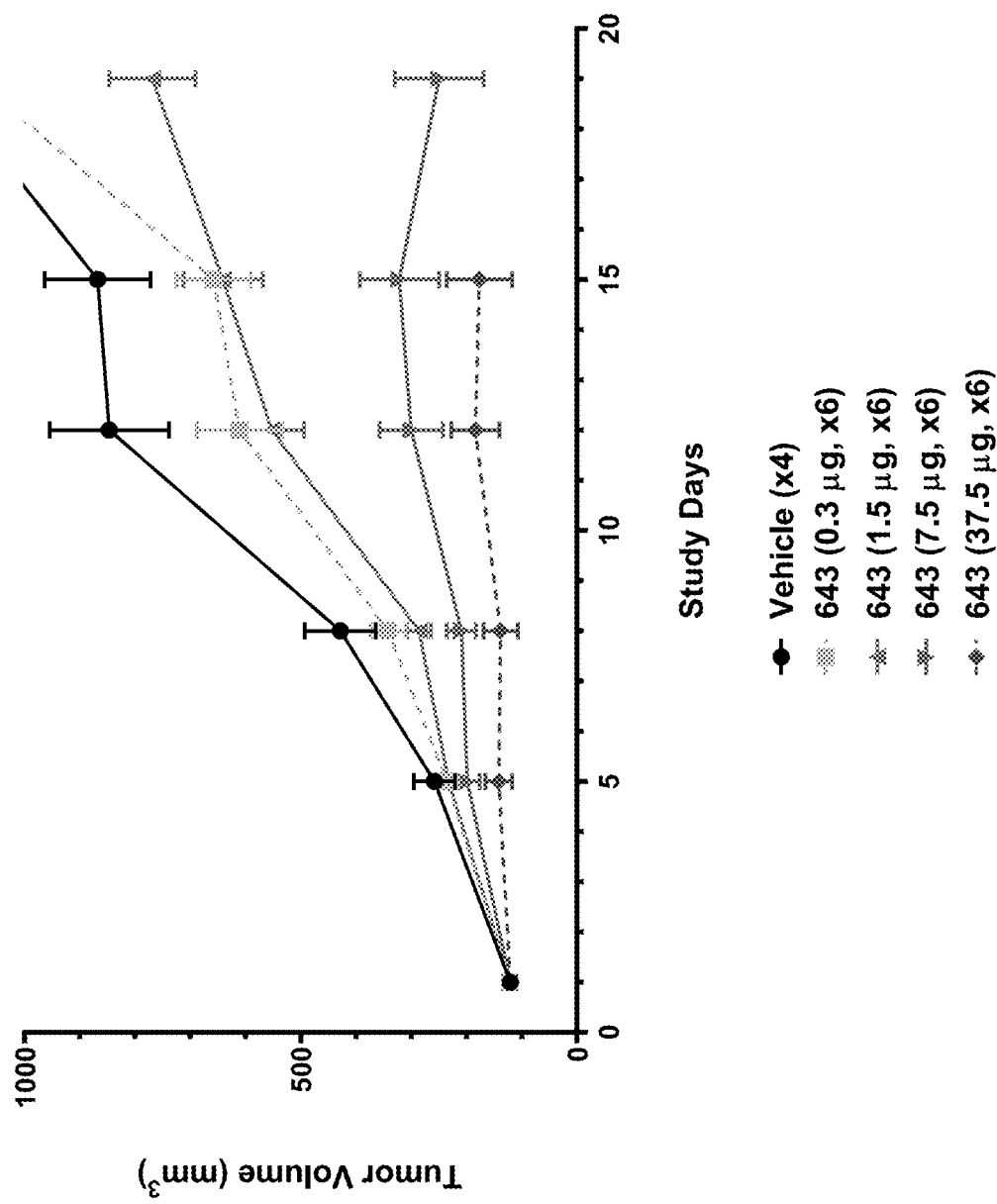
Figure 40A:
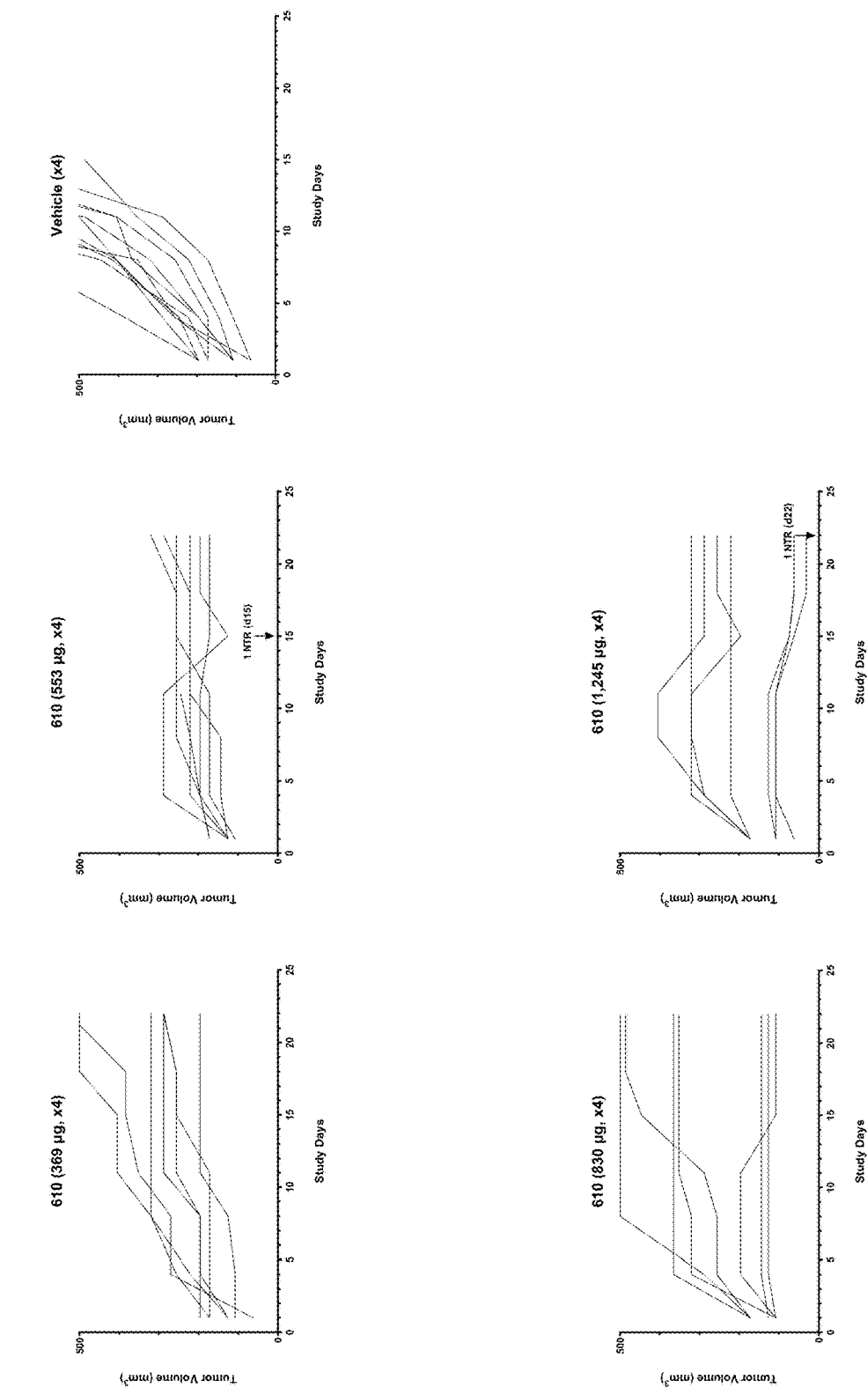
FIG. 40A-40G shows a series of spider plots showing activity of fusion proteins in an MC38 xenograft model corresponding to data in FIGS. 39A-39G. Each line in the plots is the tumor volume over time for a single mouse.
Figure 40B:
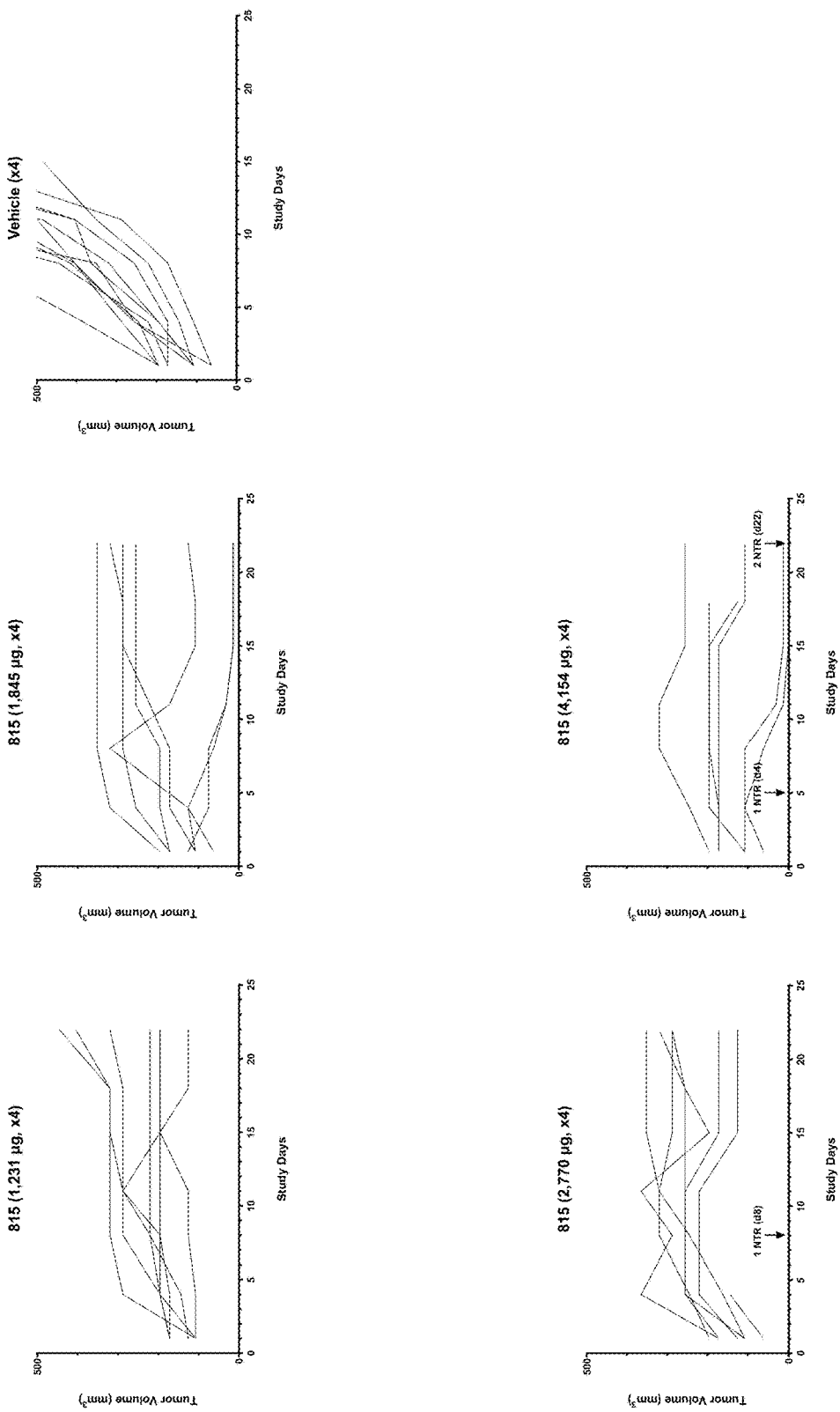
Figure 40C:
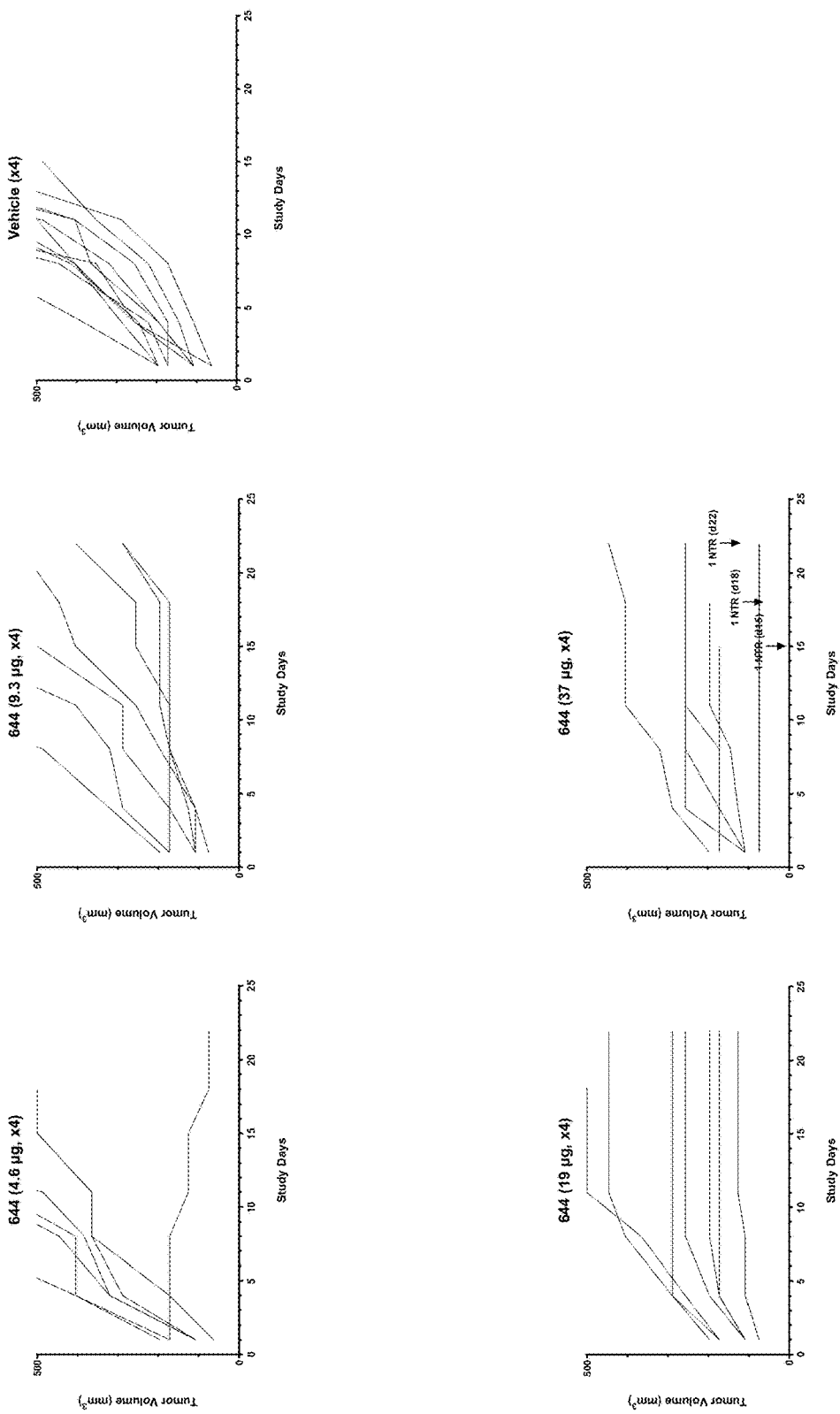
Figure 40D:
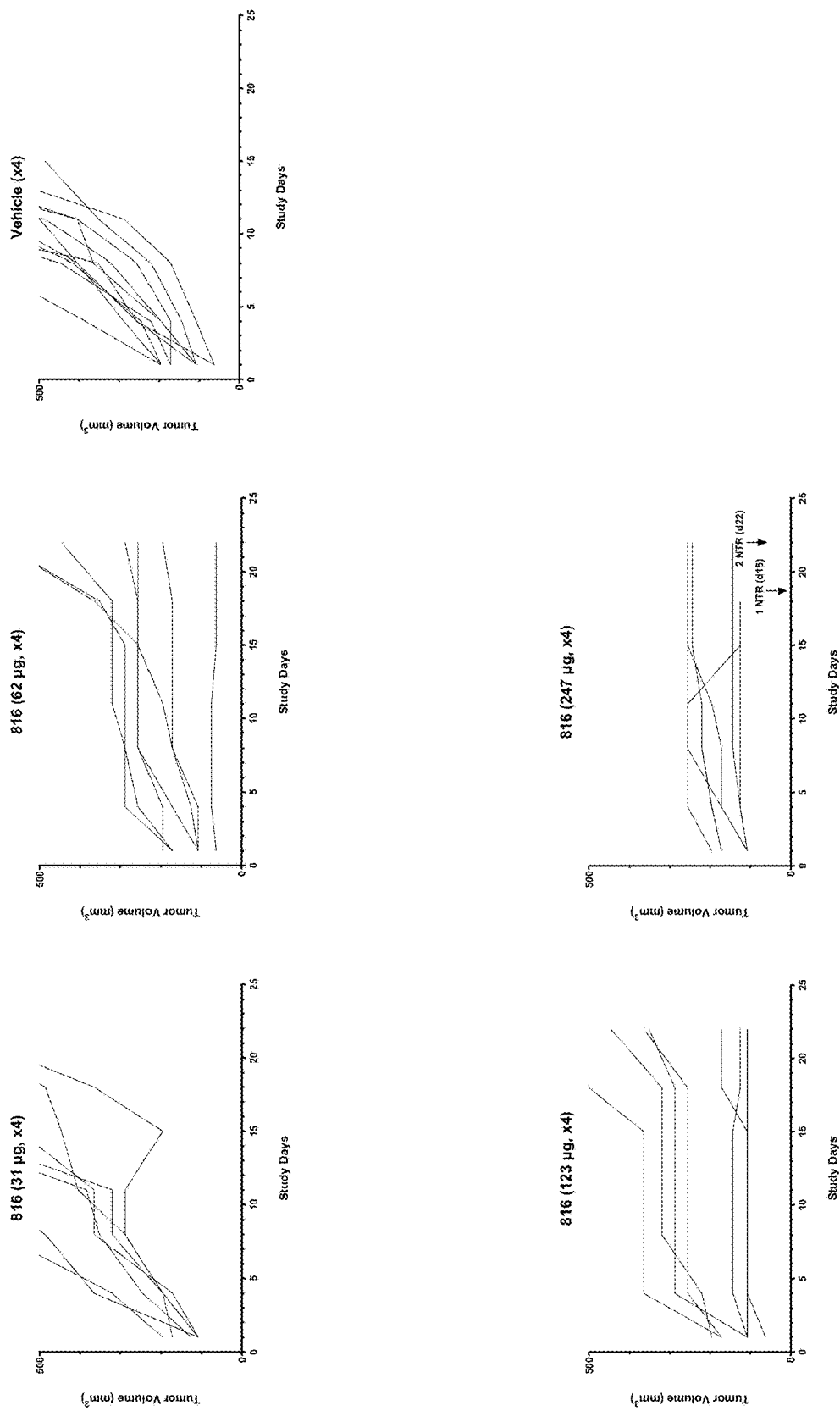
Figure 40E:
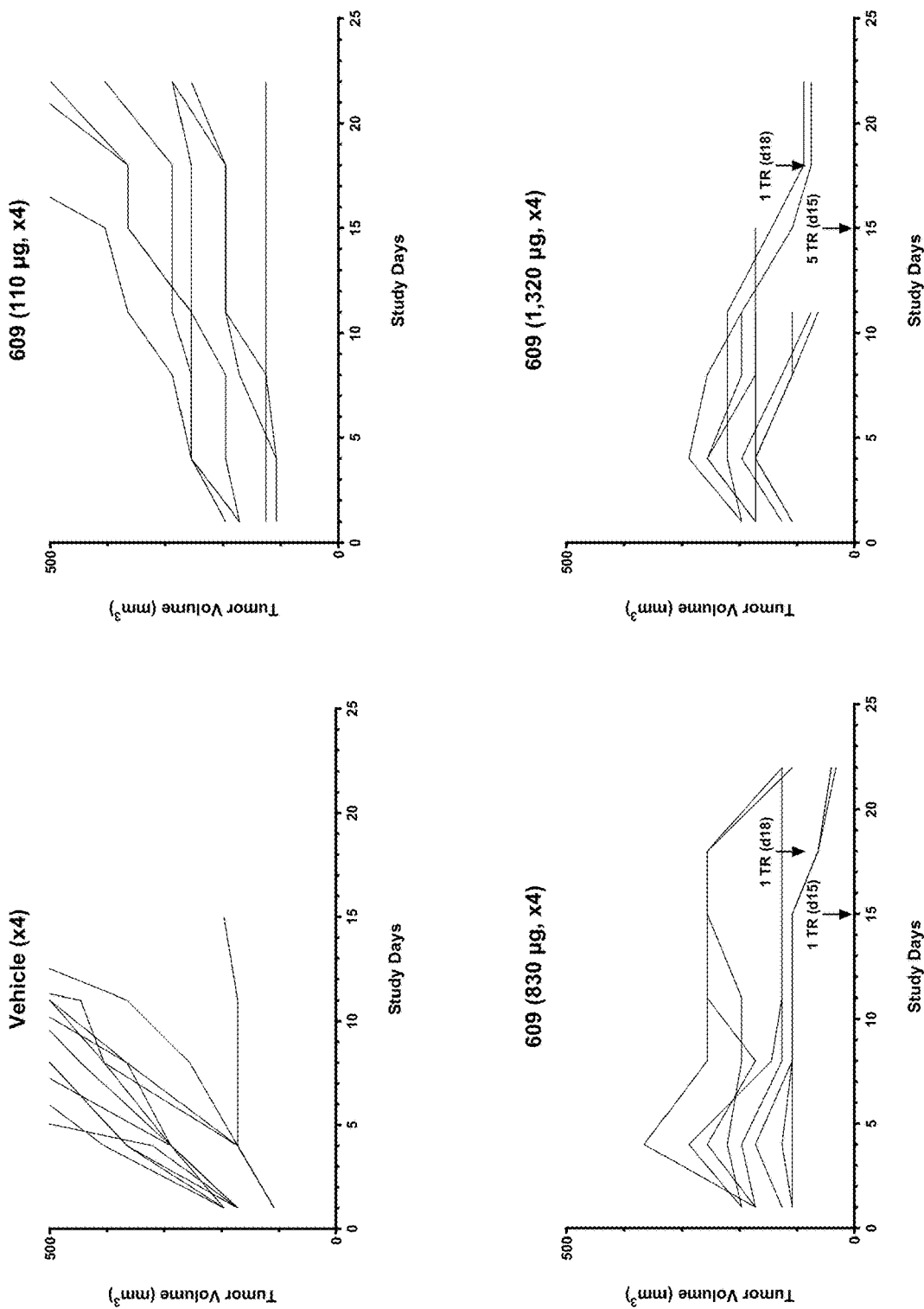
Figure 40F:
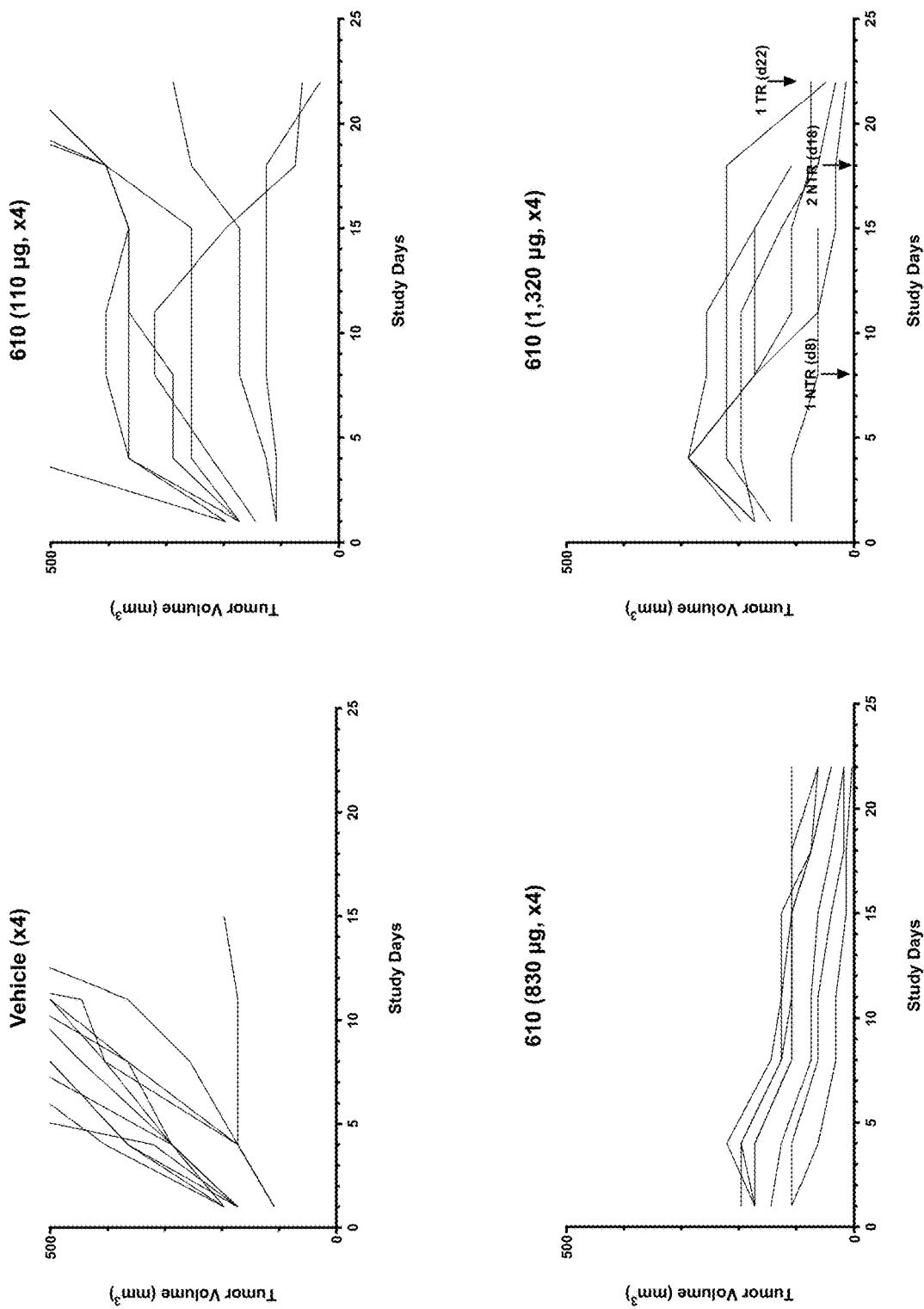
Figure 40G:
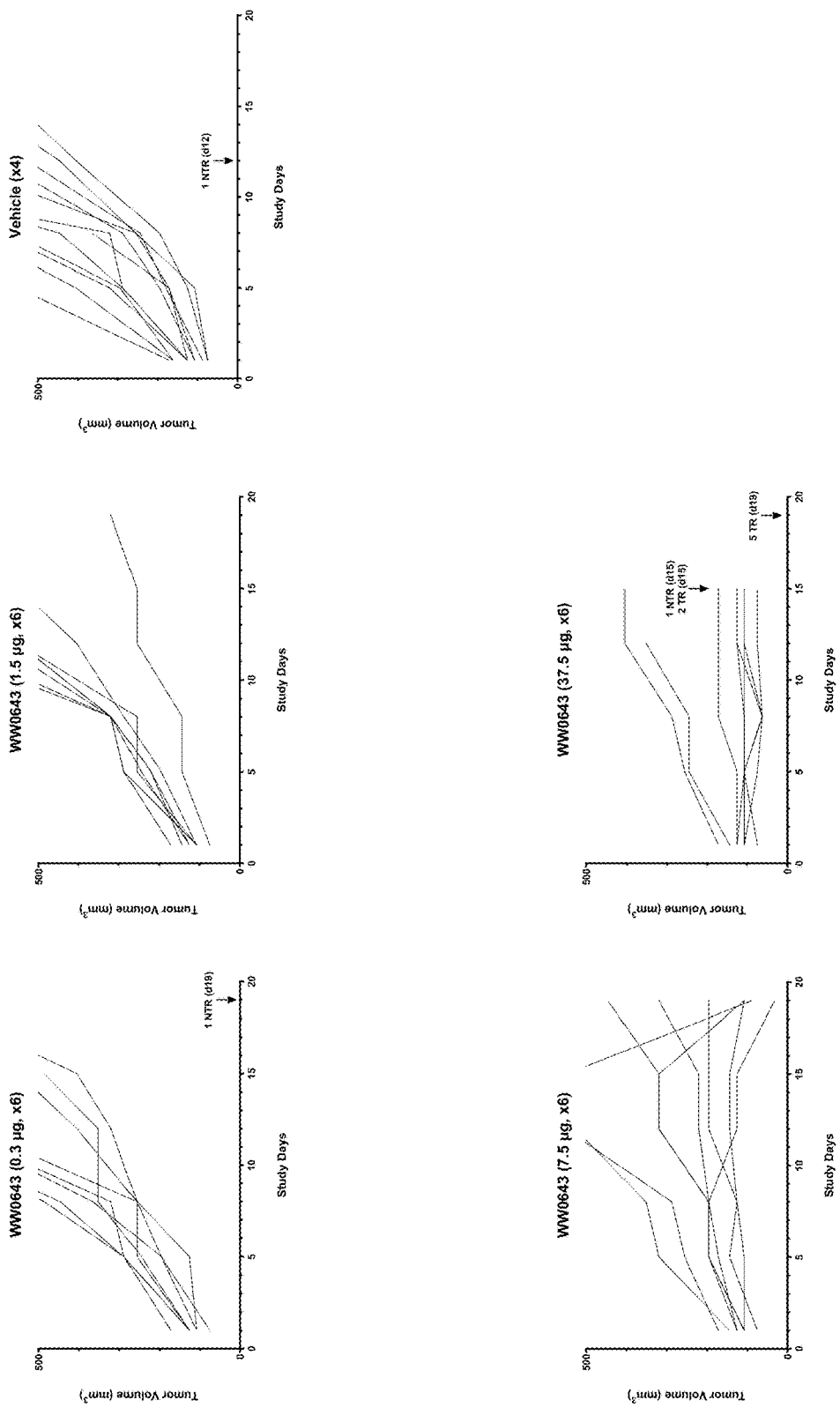
Figure 41A:
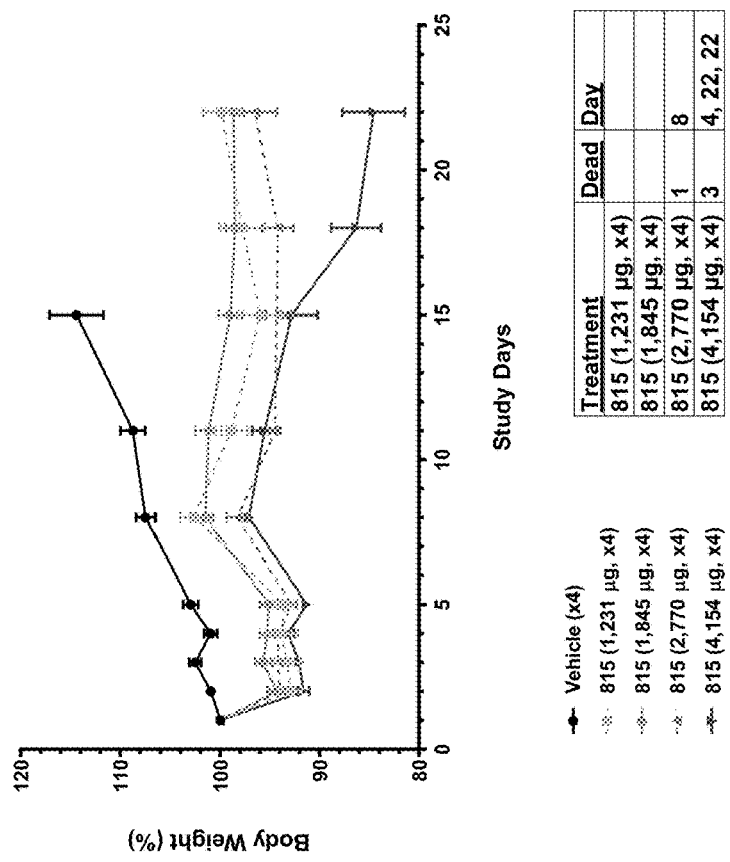
FIG. 41A-41G show average percent body weight over time in mice treated with the IFN fusion proteins in FIGS. 39A-39G.
Figure 41B:
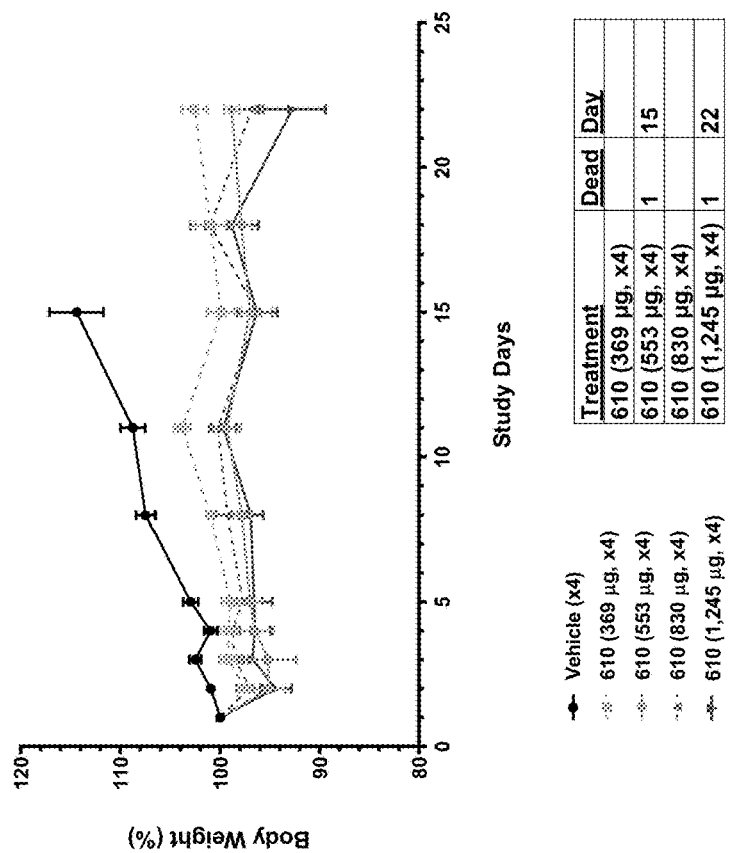
Figure 41D:
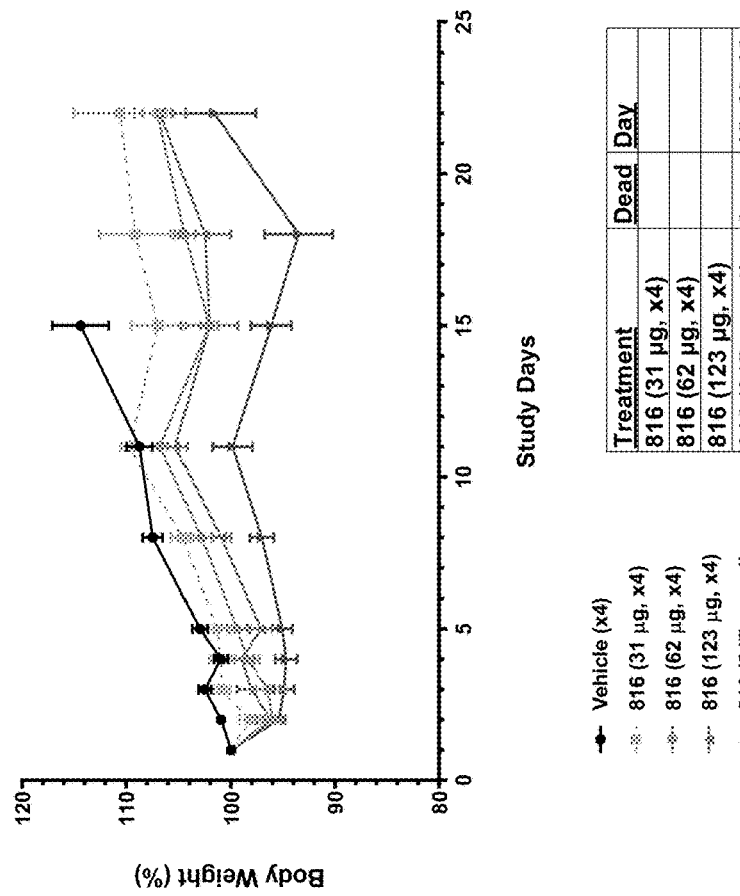
Figure 41C:
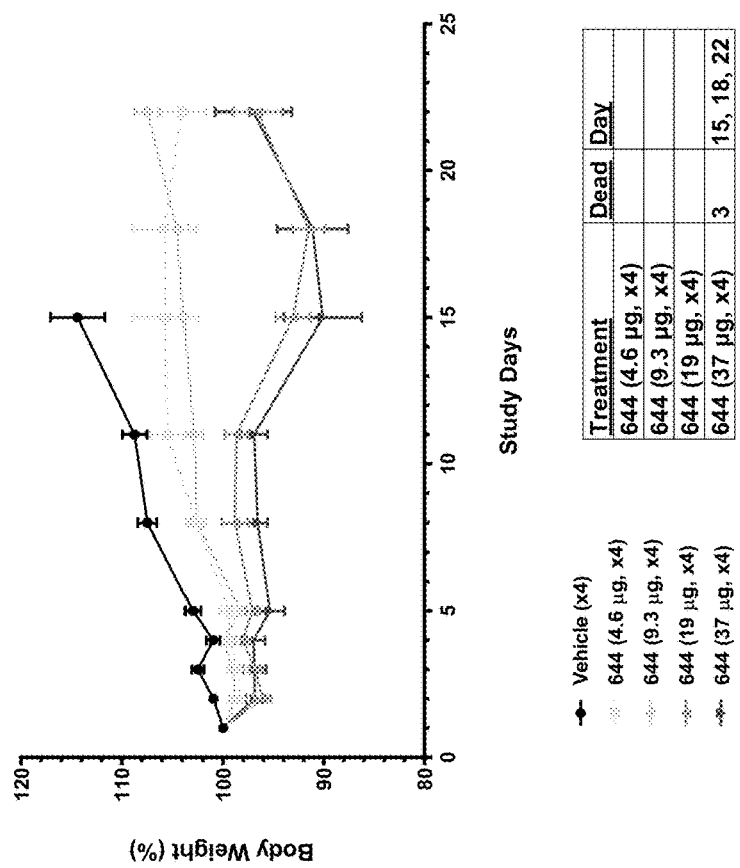
Figure 41E:
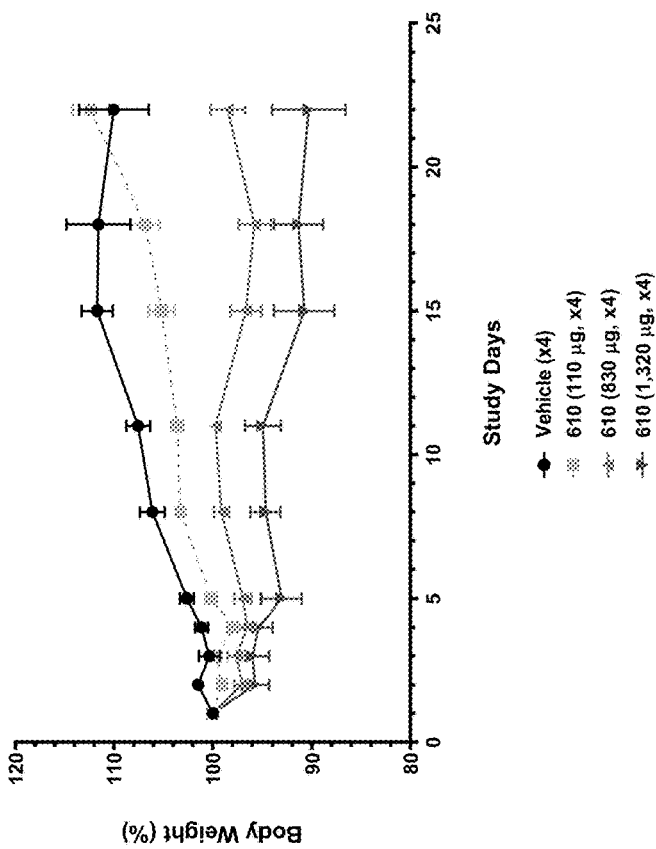
Figure 41F:
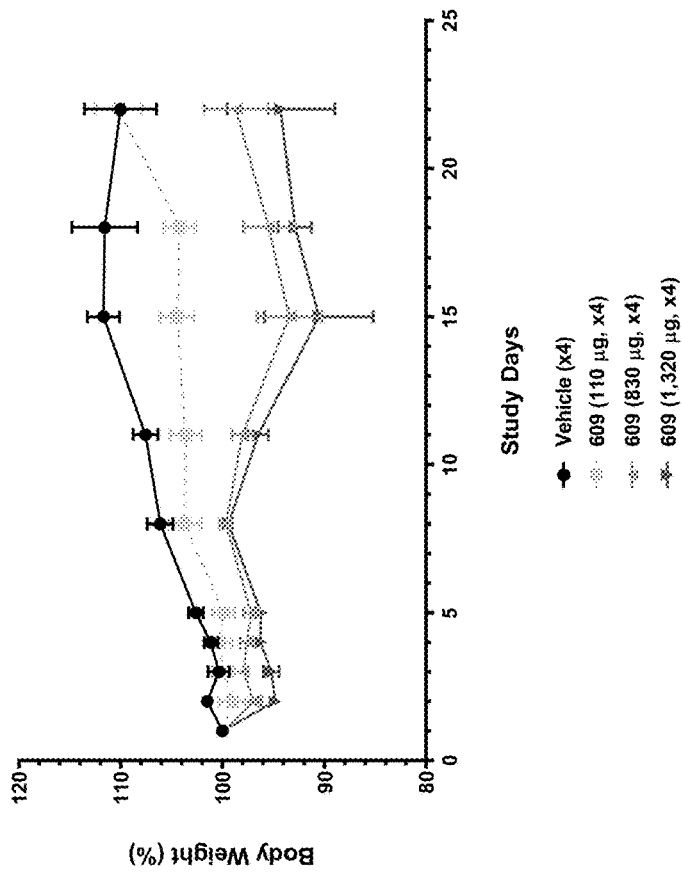
Figure 41G:
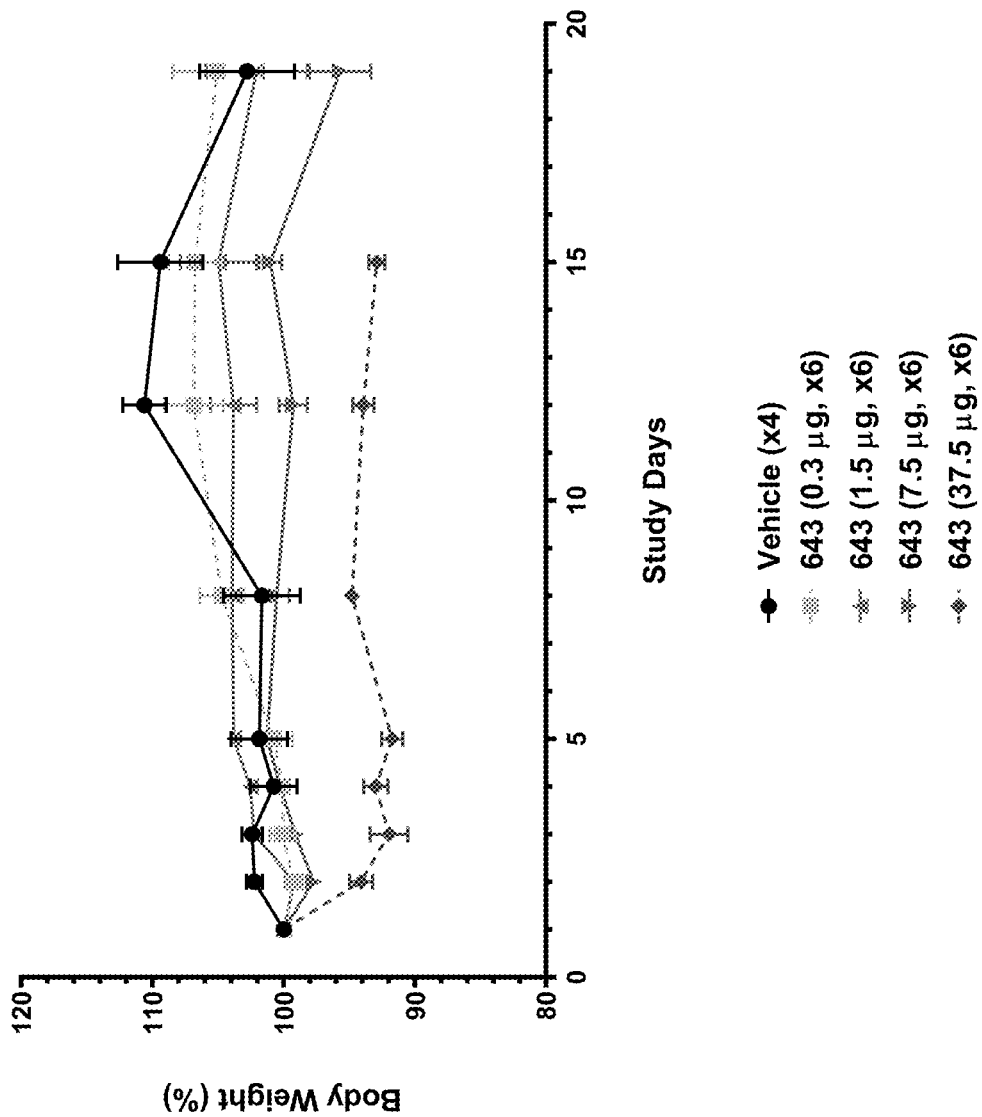
Figure 42A:
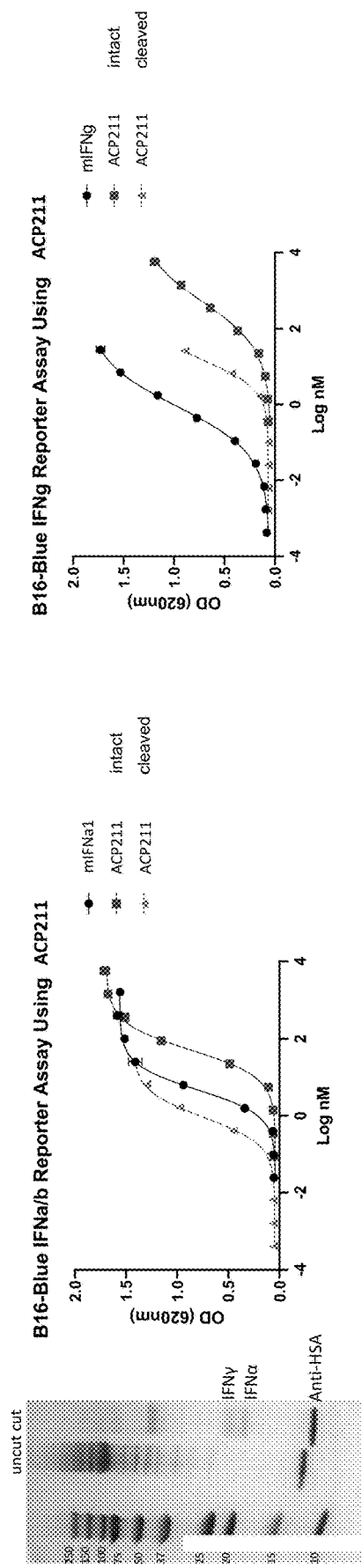
FIGS. 42A-42E shows the results of B16 IFN reporter assays. Inducible interferon constructs of interest were tested before and after cleavage. The relevant wildtype IFN was tested as a control.
Figure 42B:
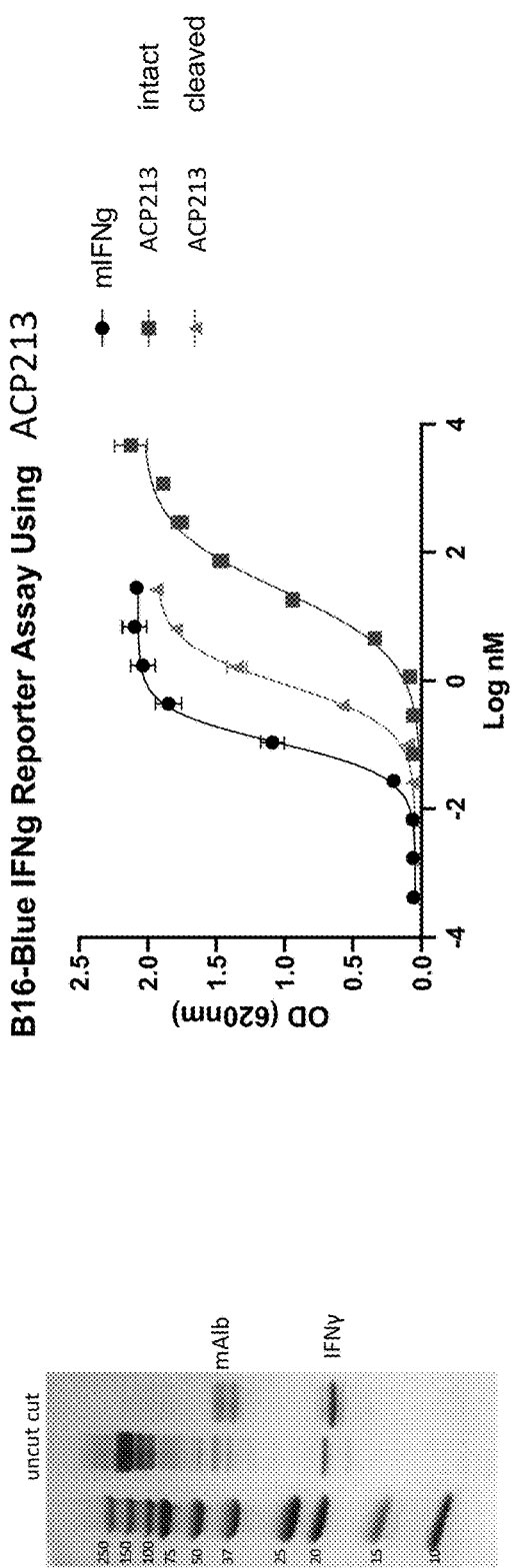
Figure 42C:
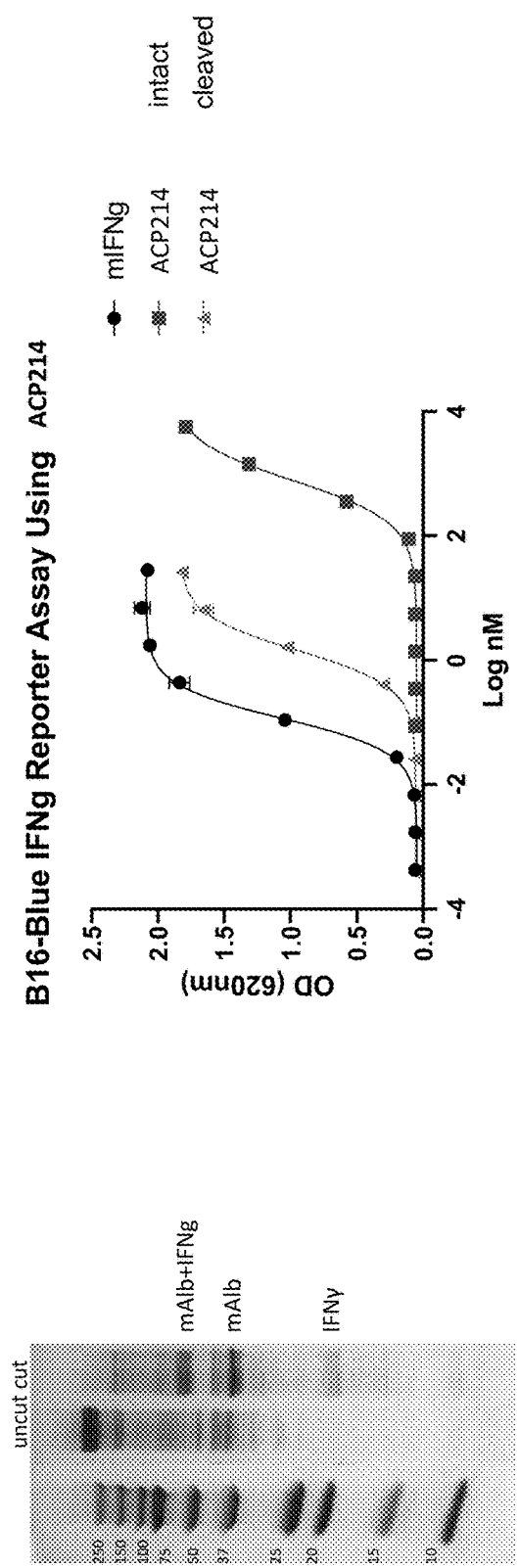
Figure 42D:
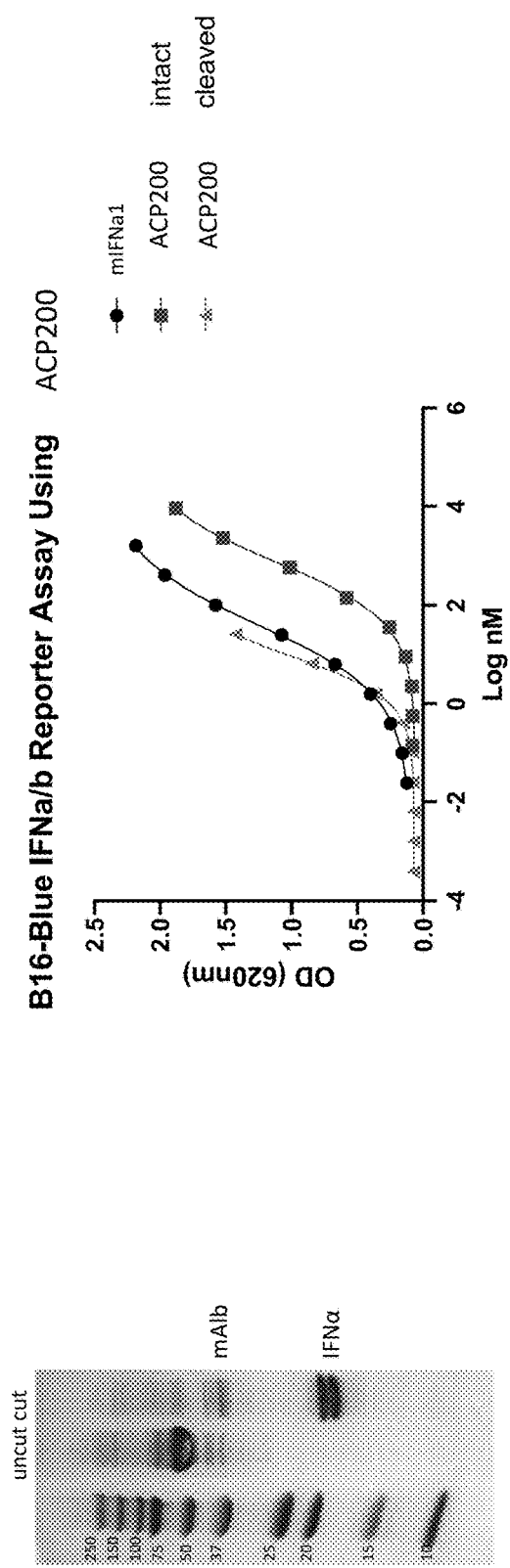
Figure 42E:
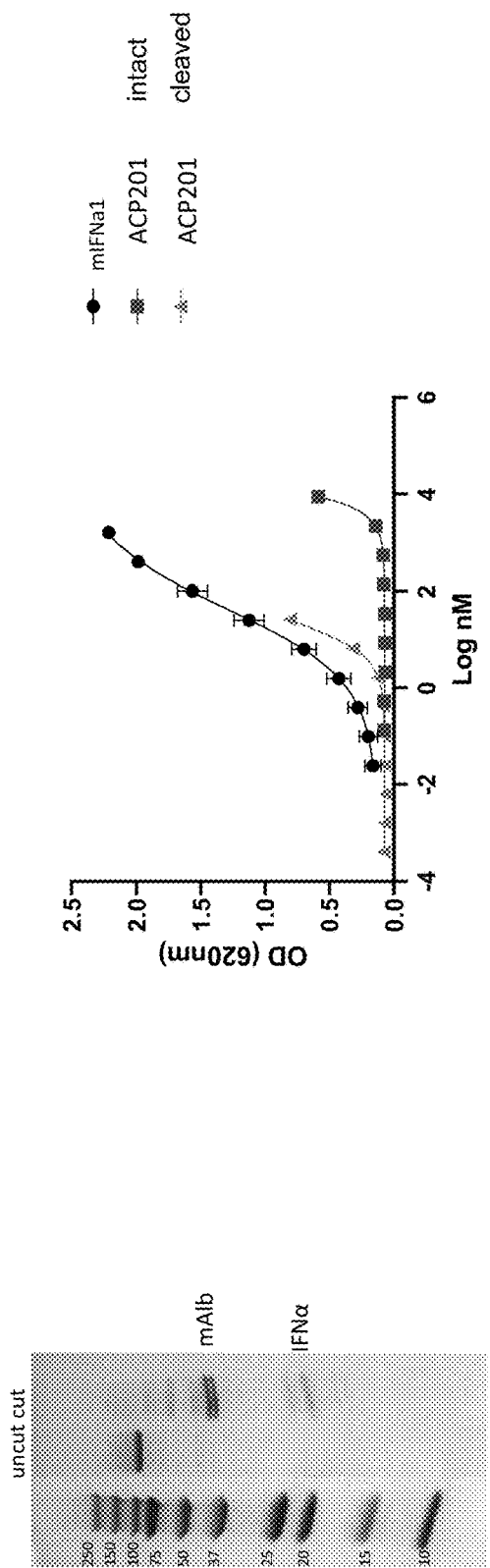
Figure 44A:
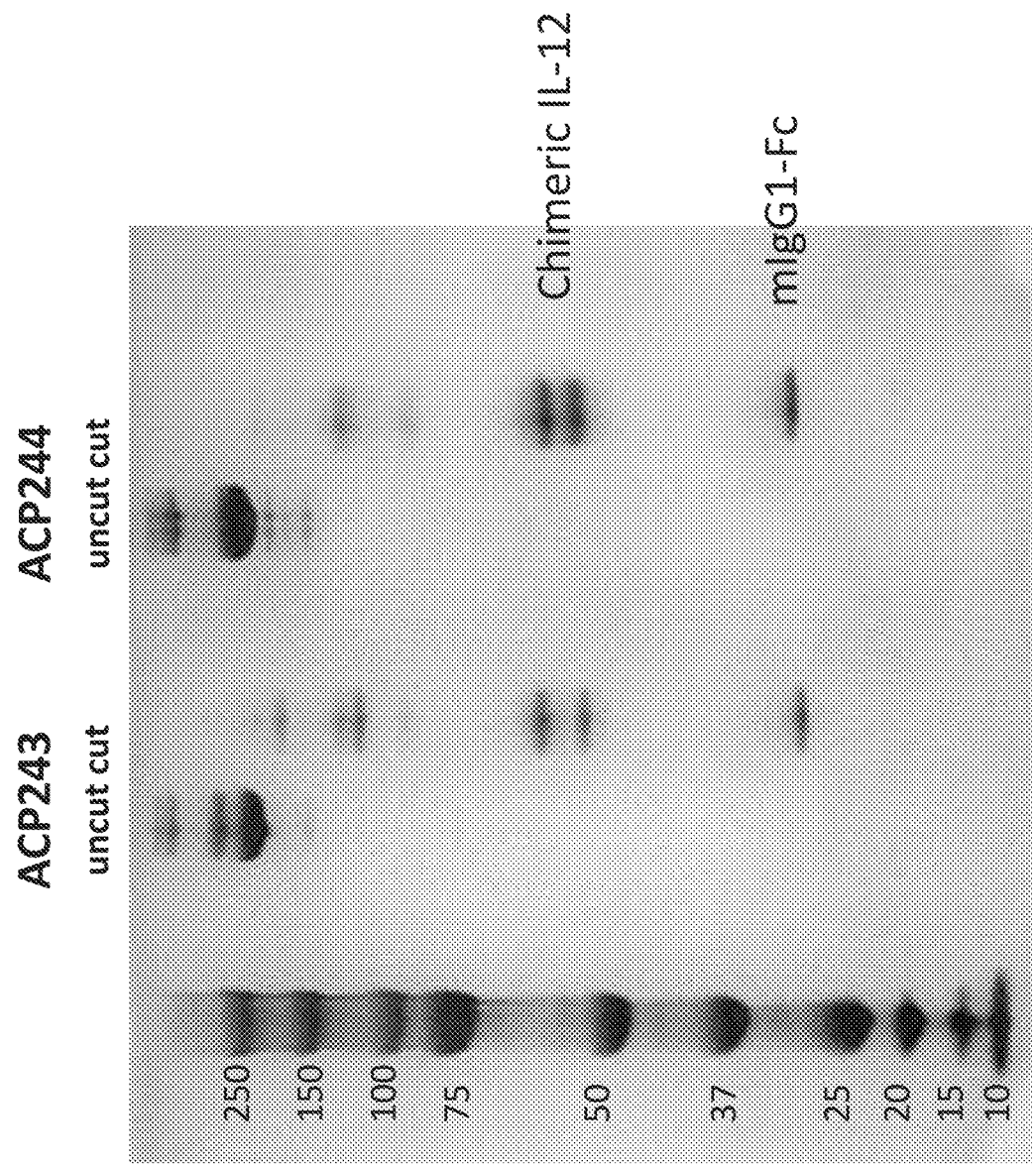
FIGS. 44A-44D depict the activity of cytokine fusion proteins constructs ACP243, ACP244, ACP243, ACP244, and ACP247.
Figure 44B:
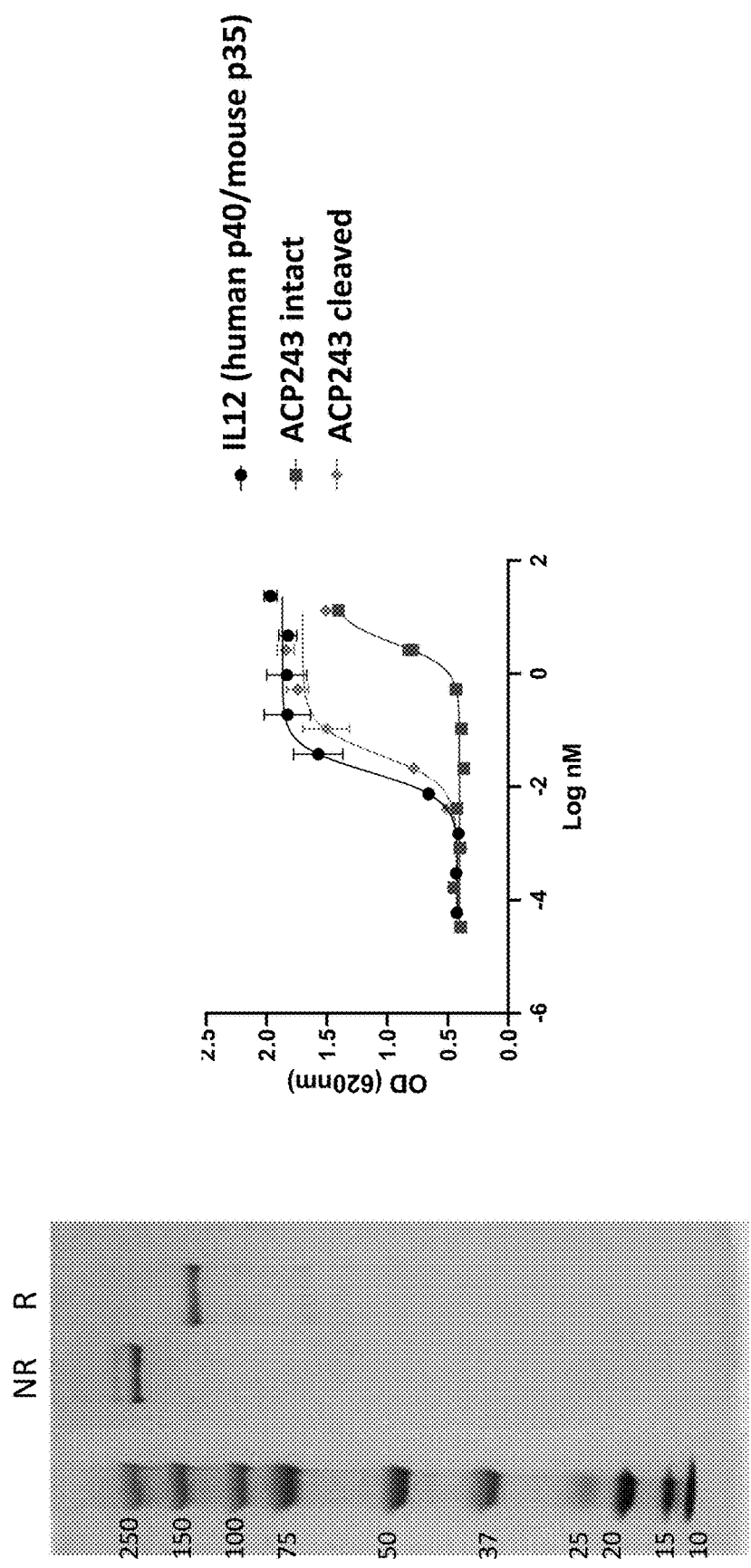
Figure 44C:
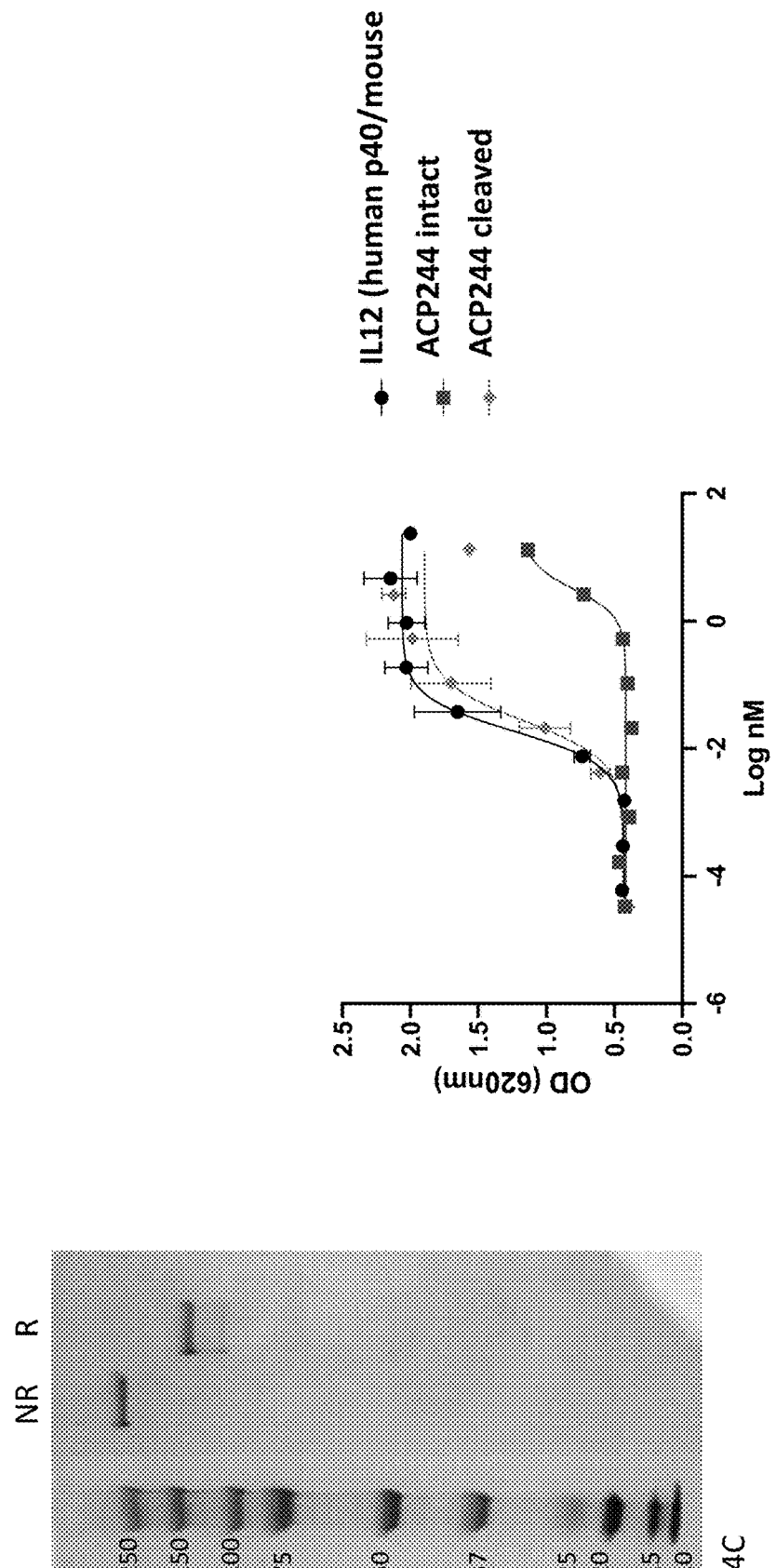
Figure 44D:
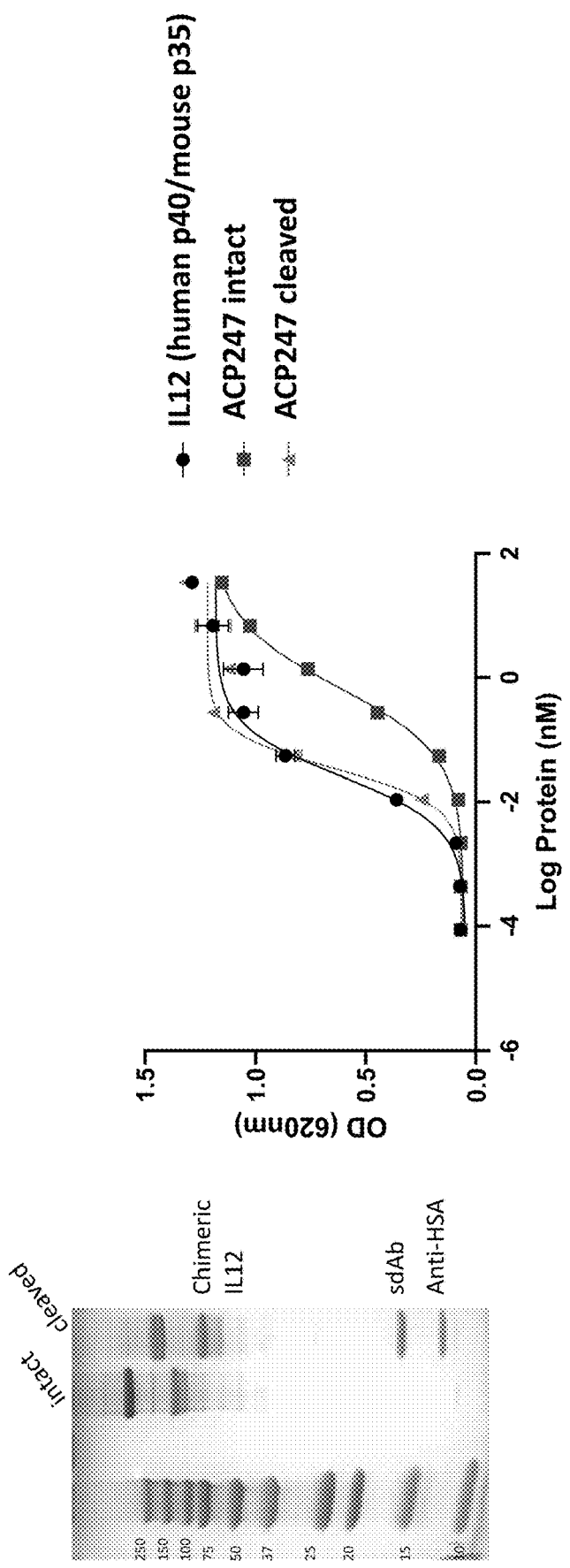
Figure 45:
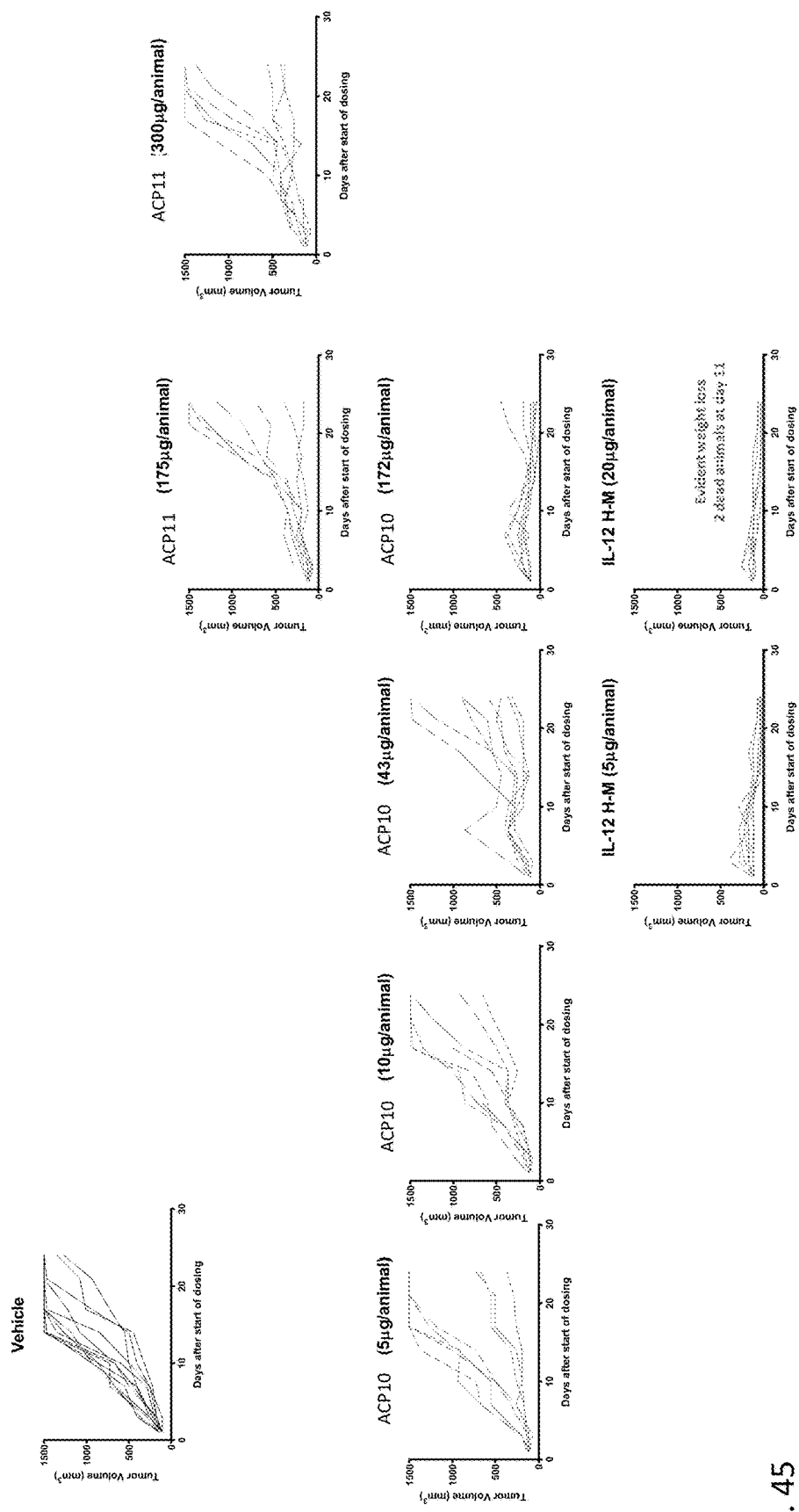
FIG. 45 shows a series of spider plots showing tumor volume over time during treatment with vehicle, IL-12, ACP11 or ACP10.
Figure 46A:
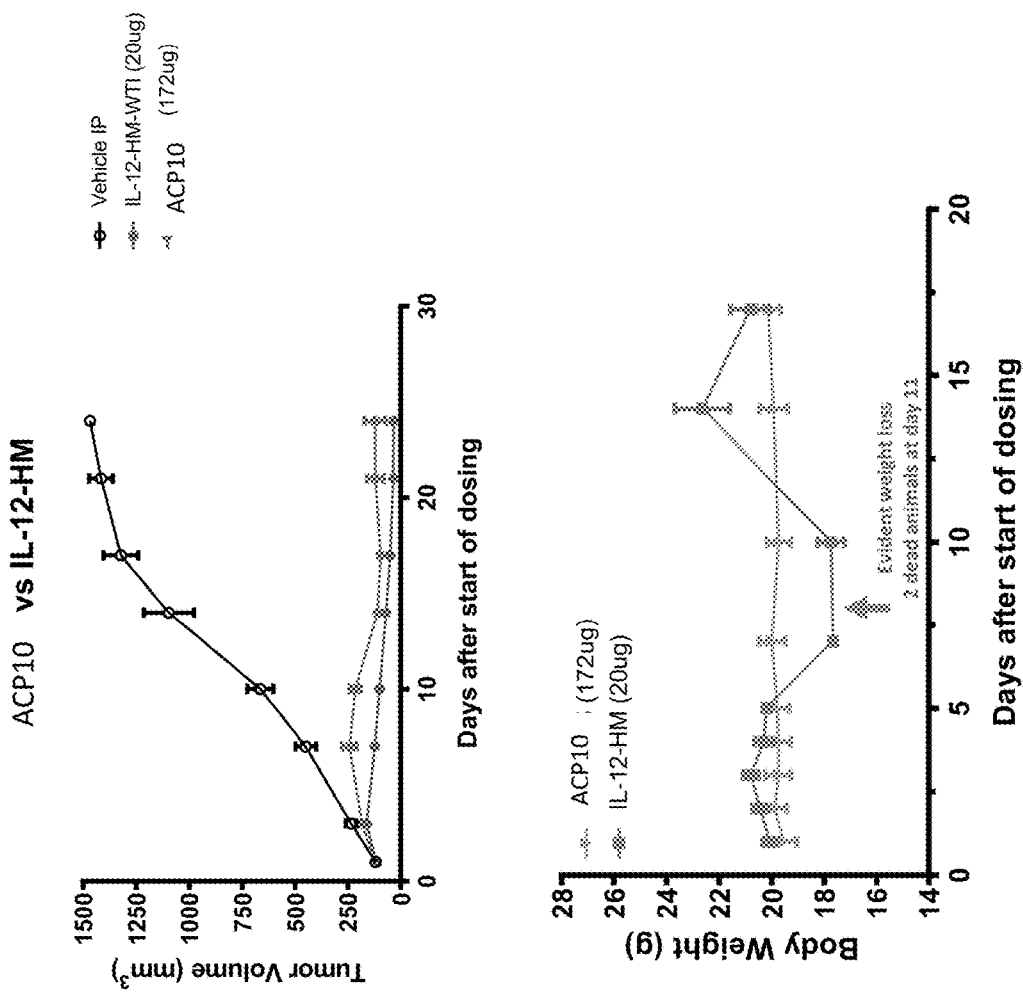
FIGS. 46A-46D, 47A-47D, 48A, 48B, 49A-49I, 50A, 50B, and 51A-51C shows data (tumor volume and/or body weight) for mice treated with cytokine fusion proteins constructs.
Figure 46B:
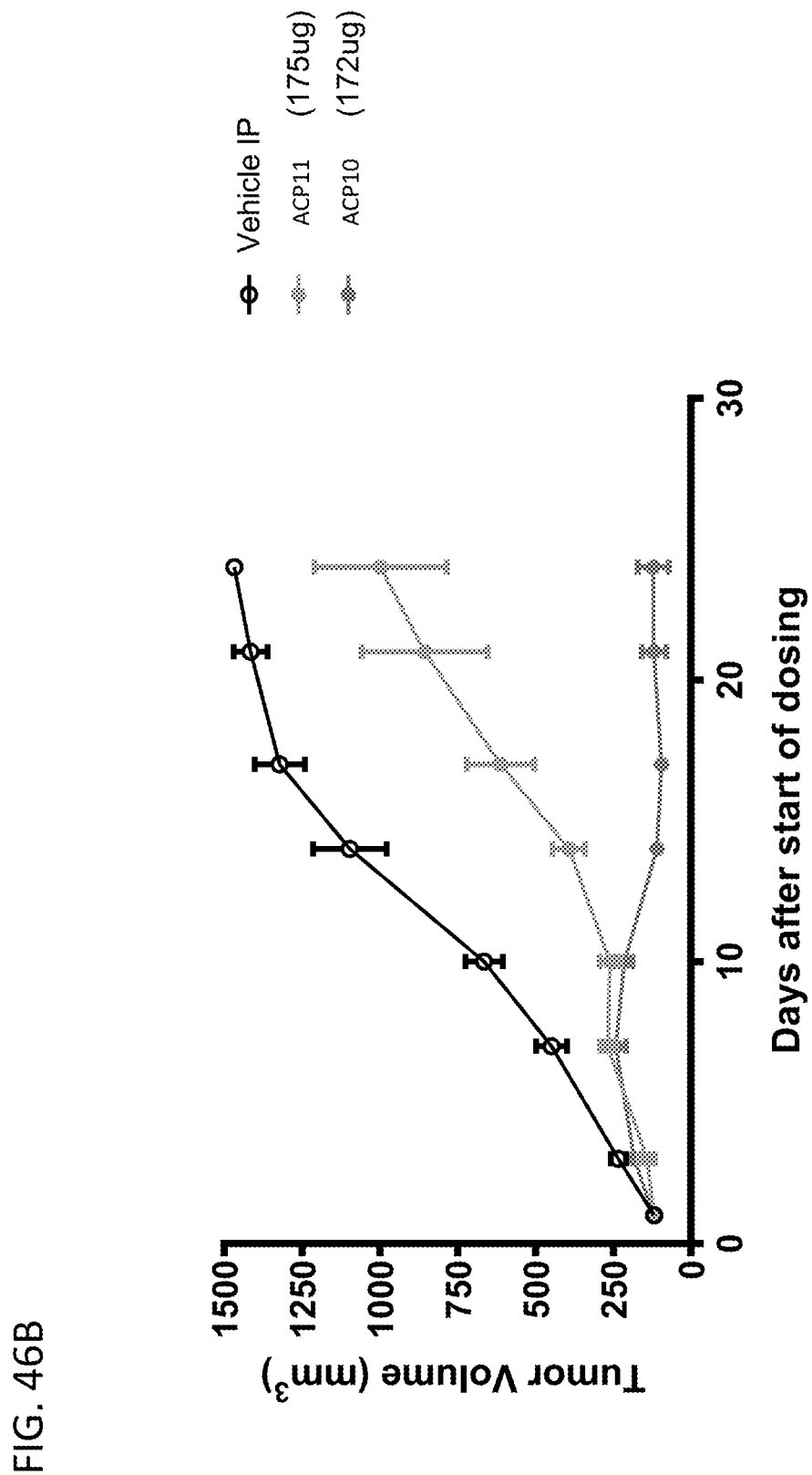
Figure 46C:
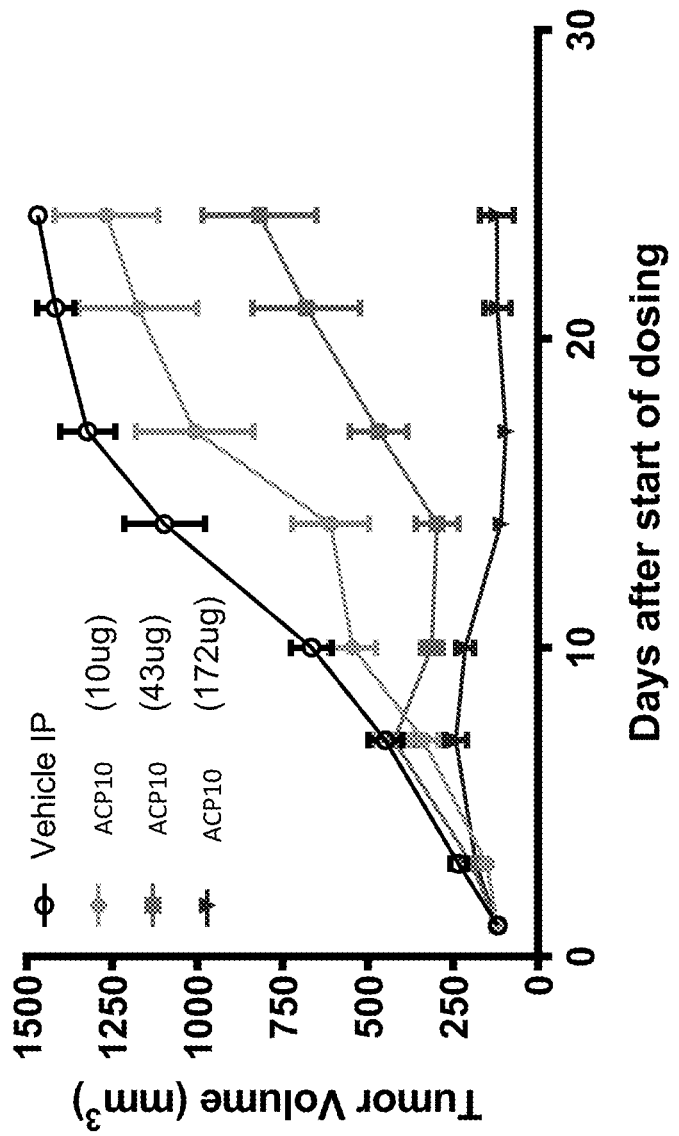
Figure 46D:
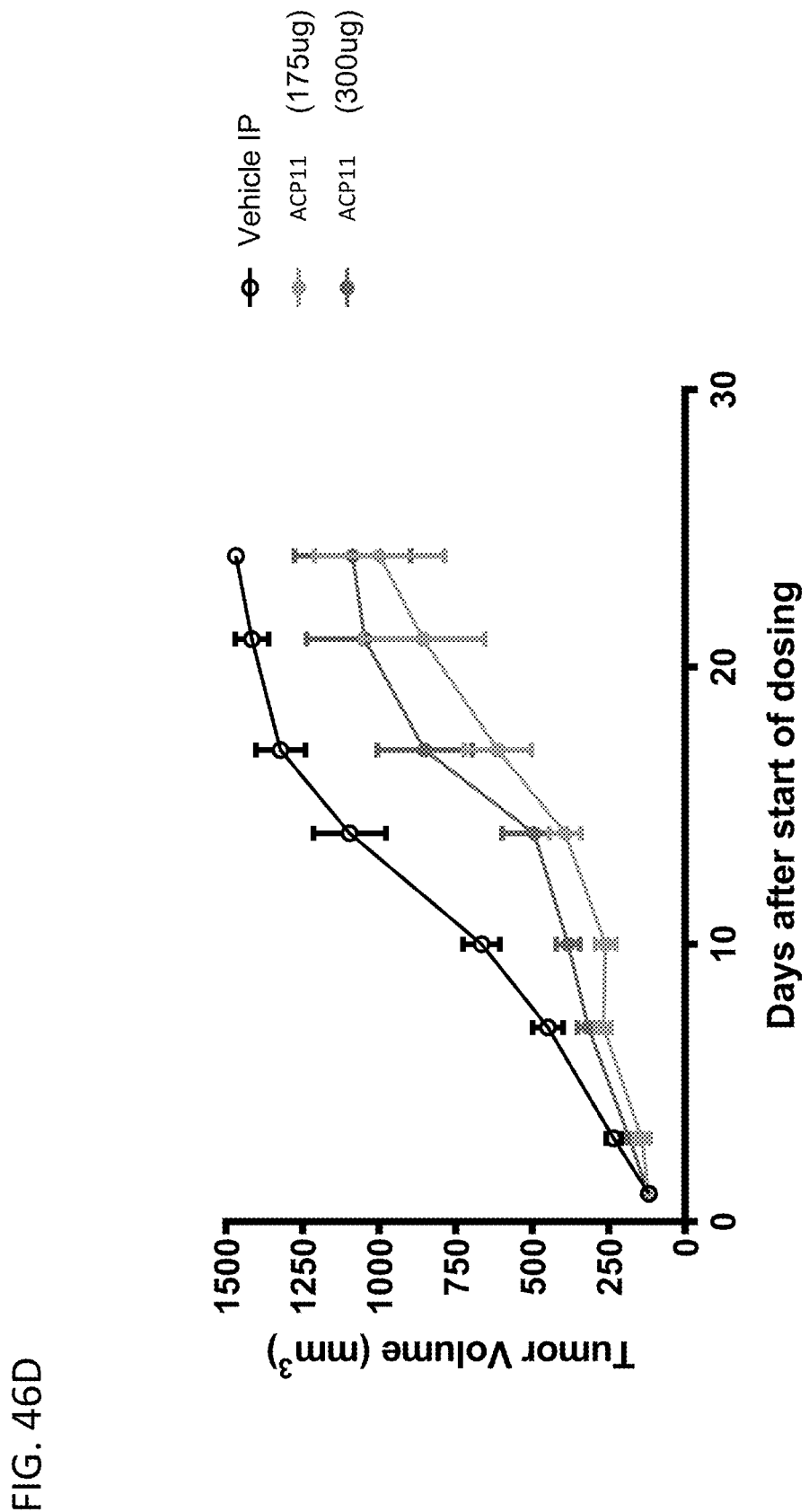
Figure 47A:
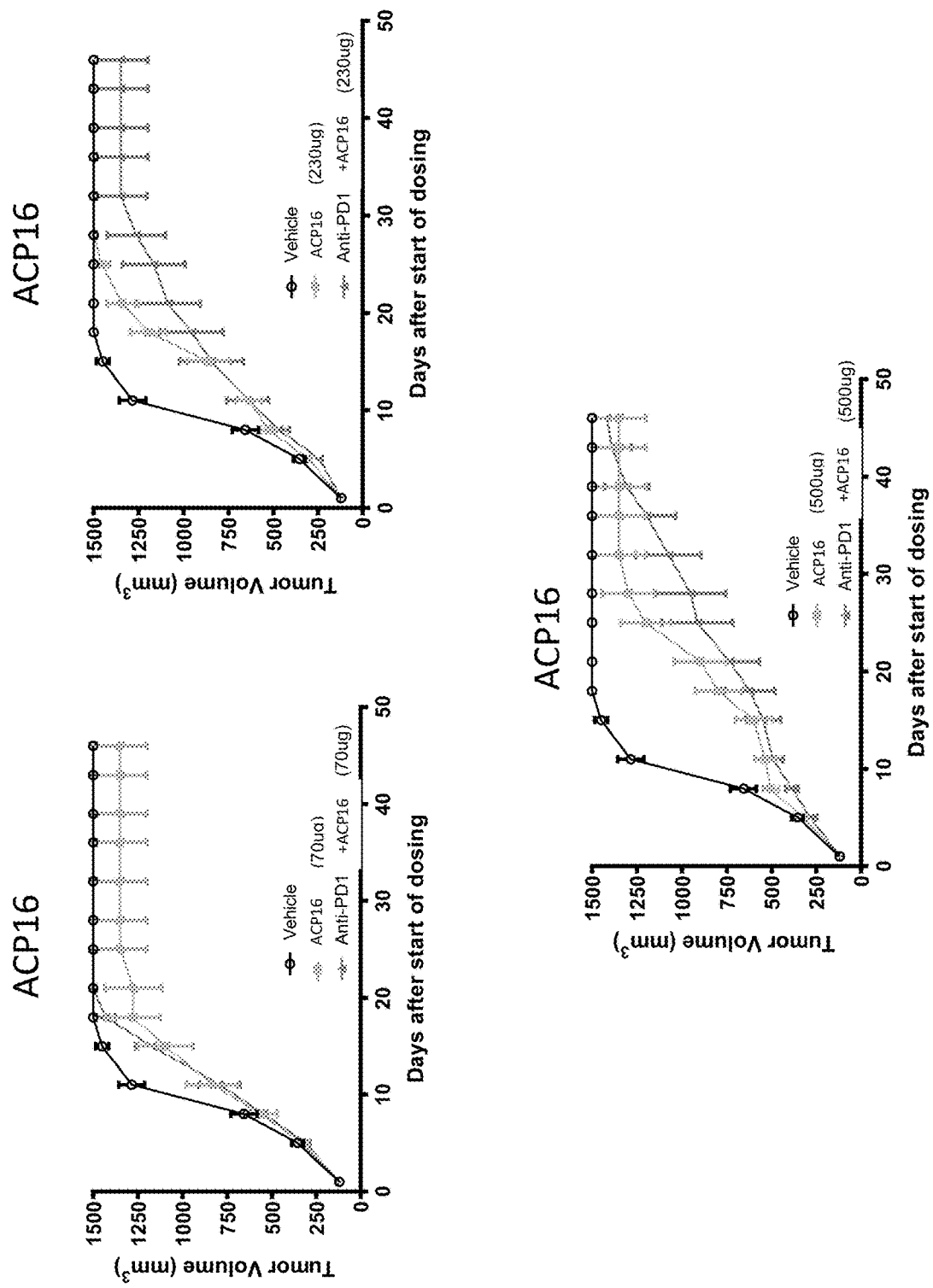
Figure 47B:
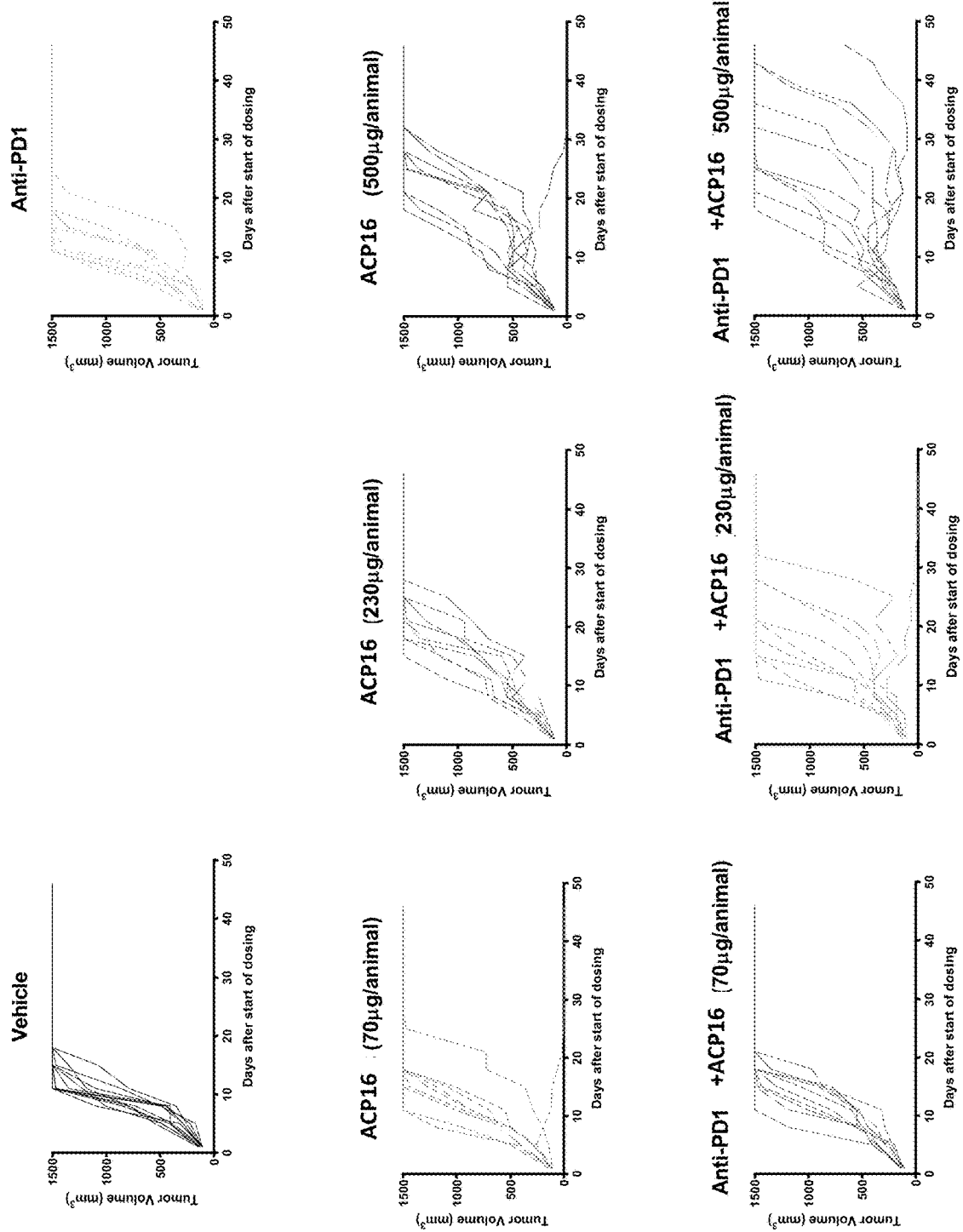
Figure 47C:
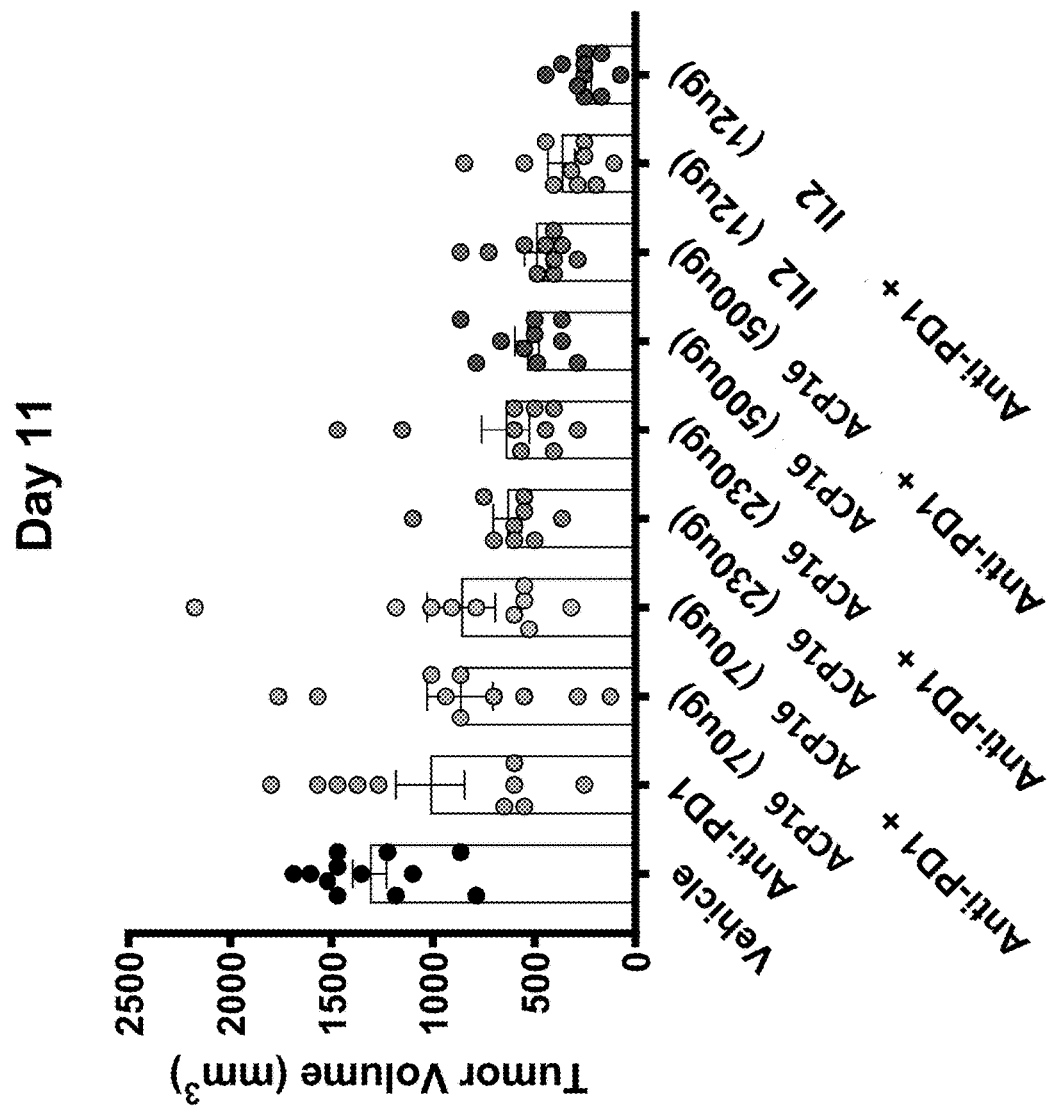
Figure 47D:
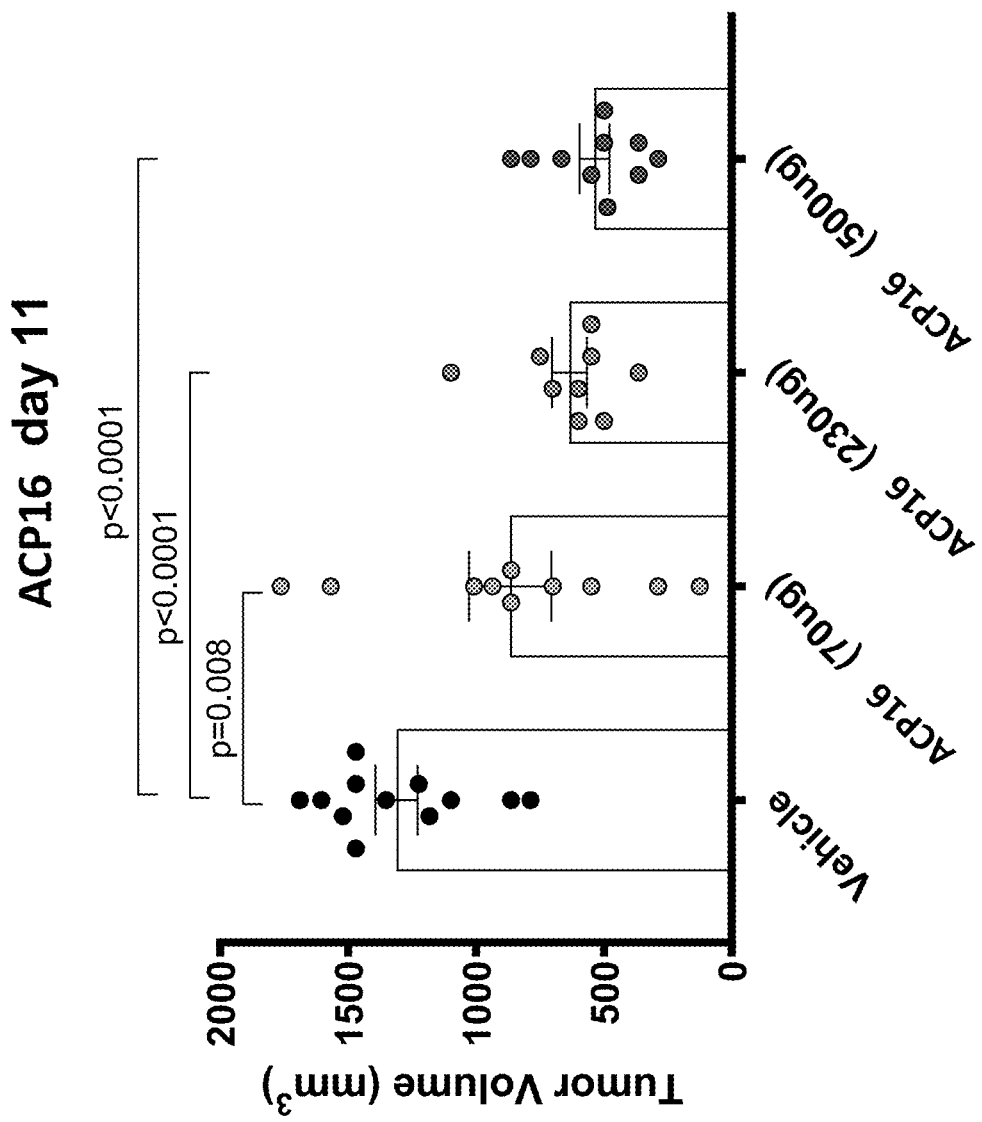
Figure 48A:
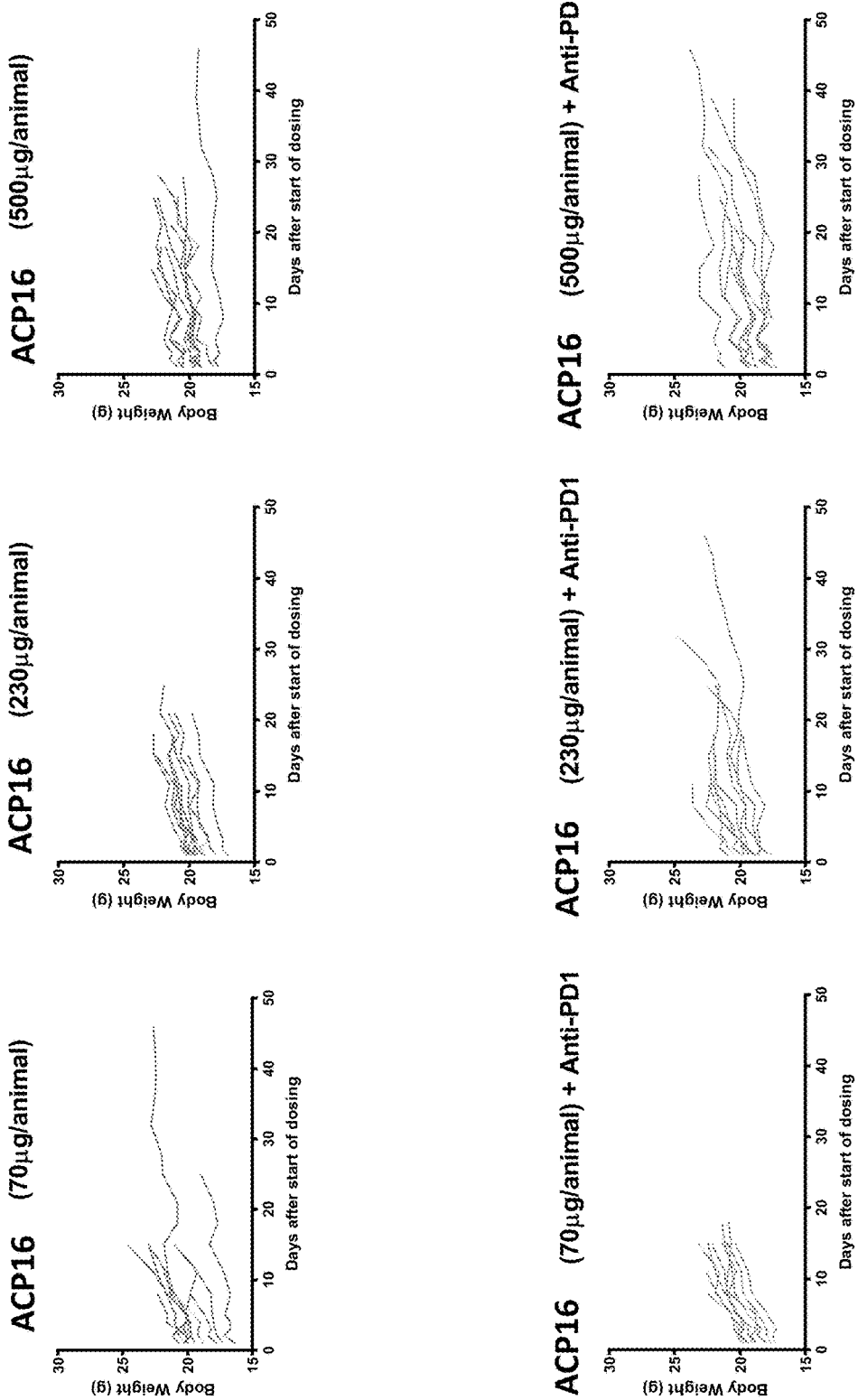
Figure 48B:
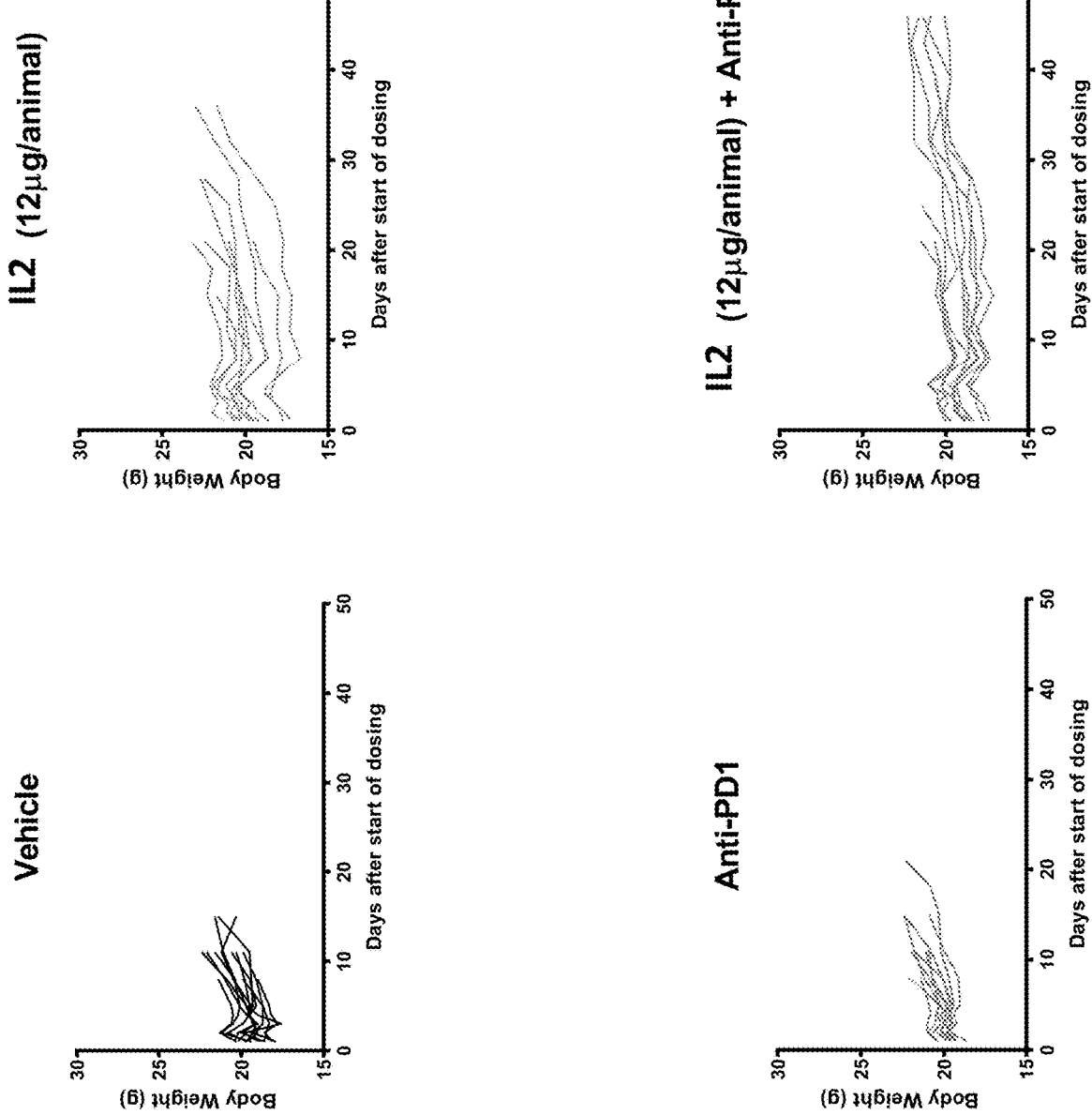
Figure 49A:
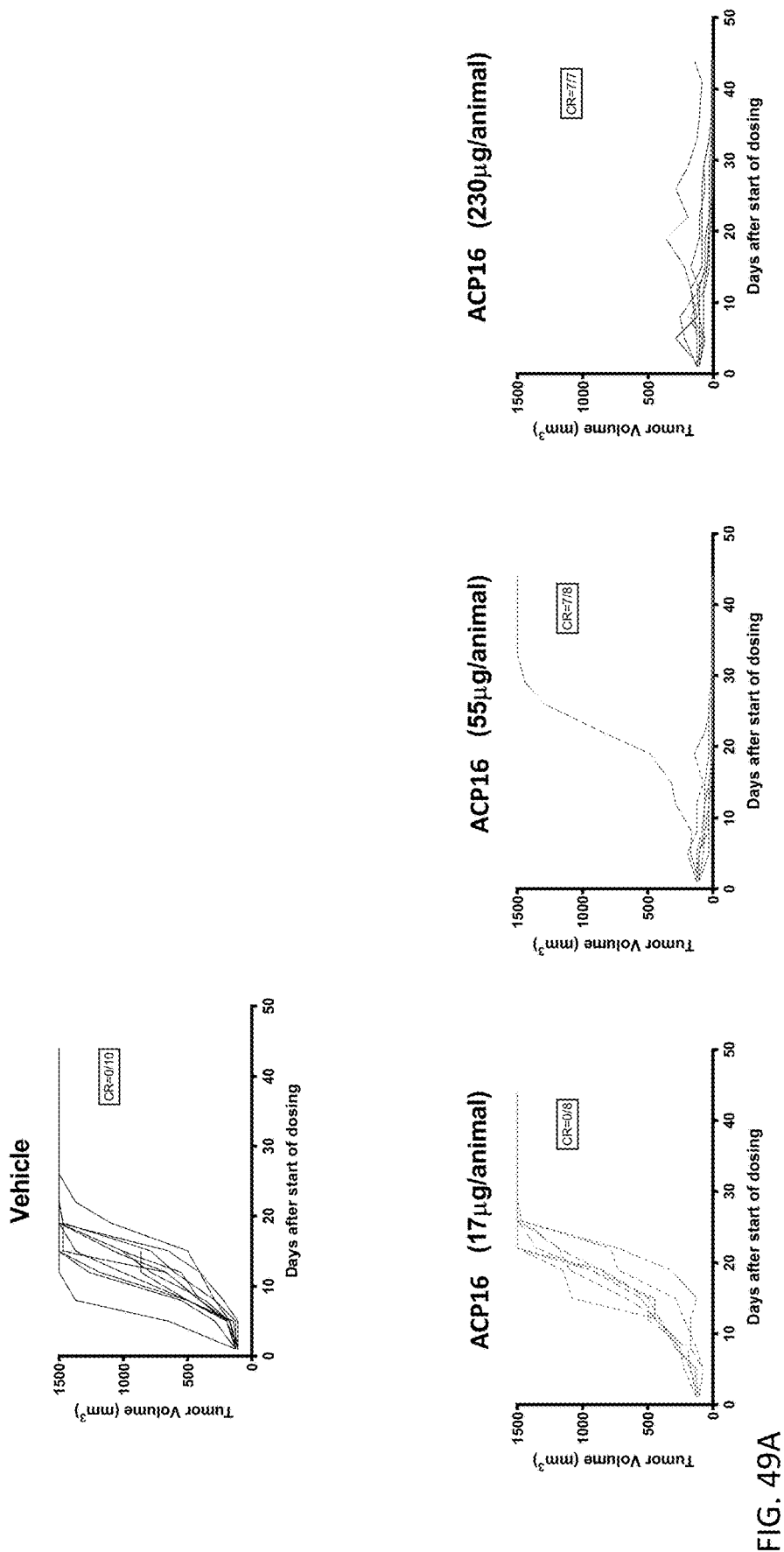
Figure 49B:
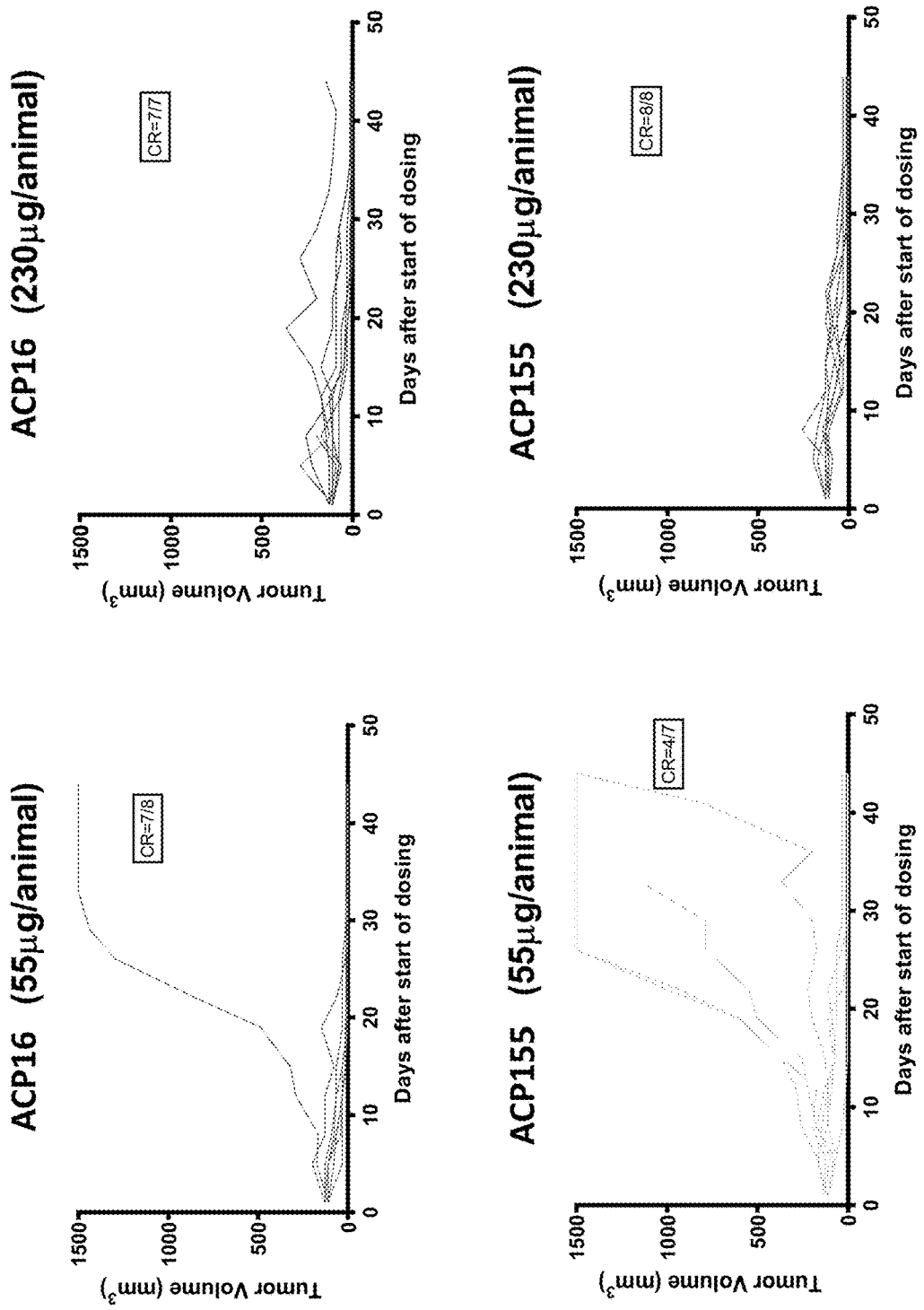
Figure 49C:
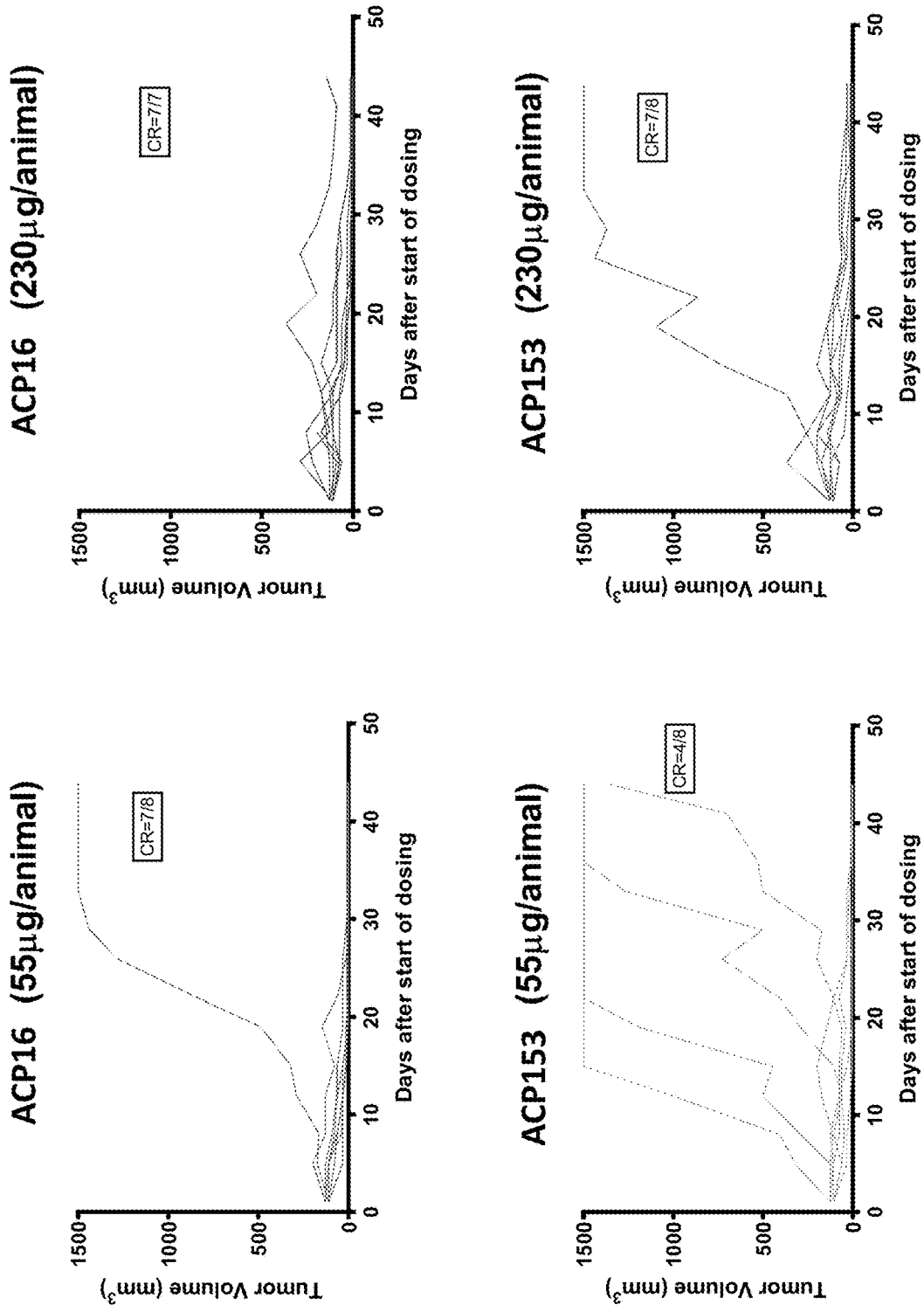
Figure 49D:
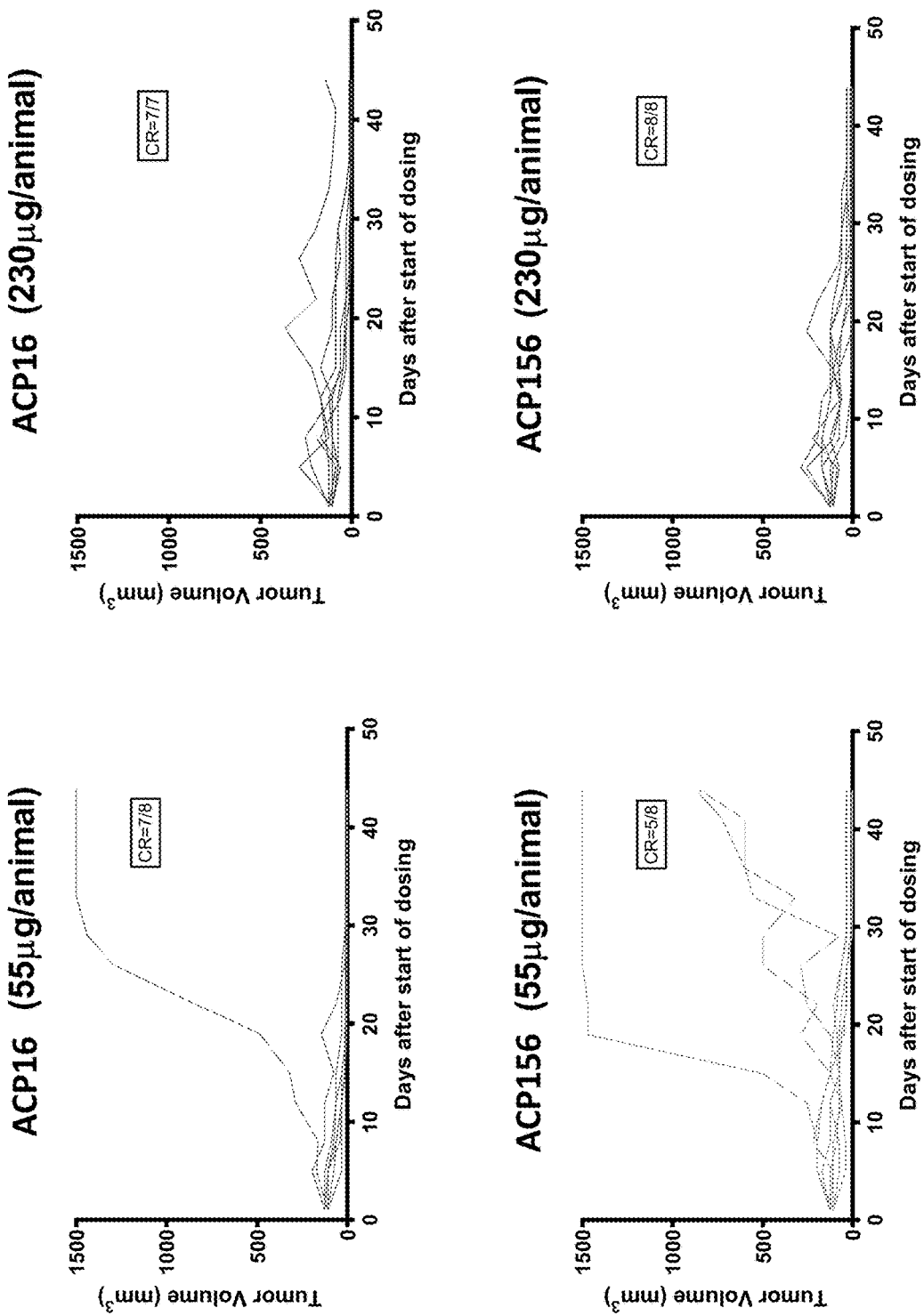
Figure 49E:
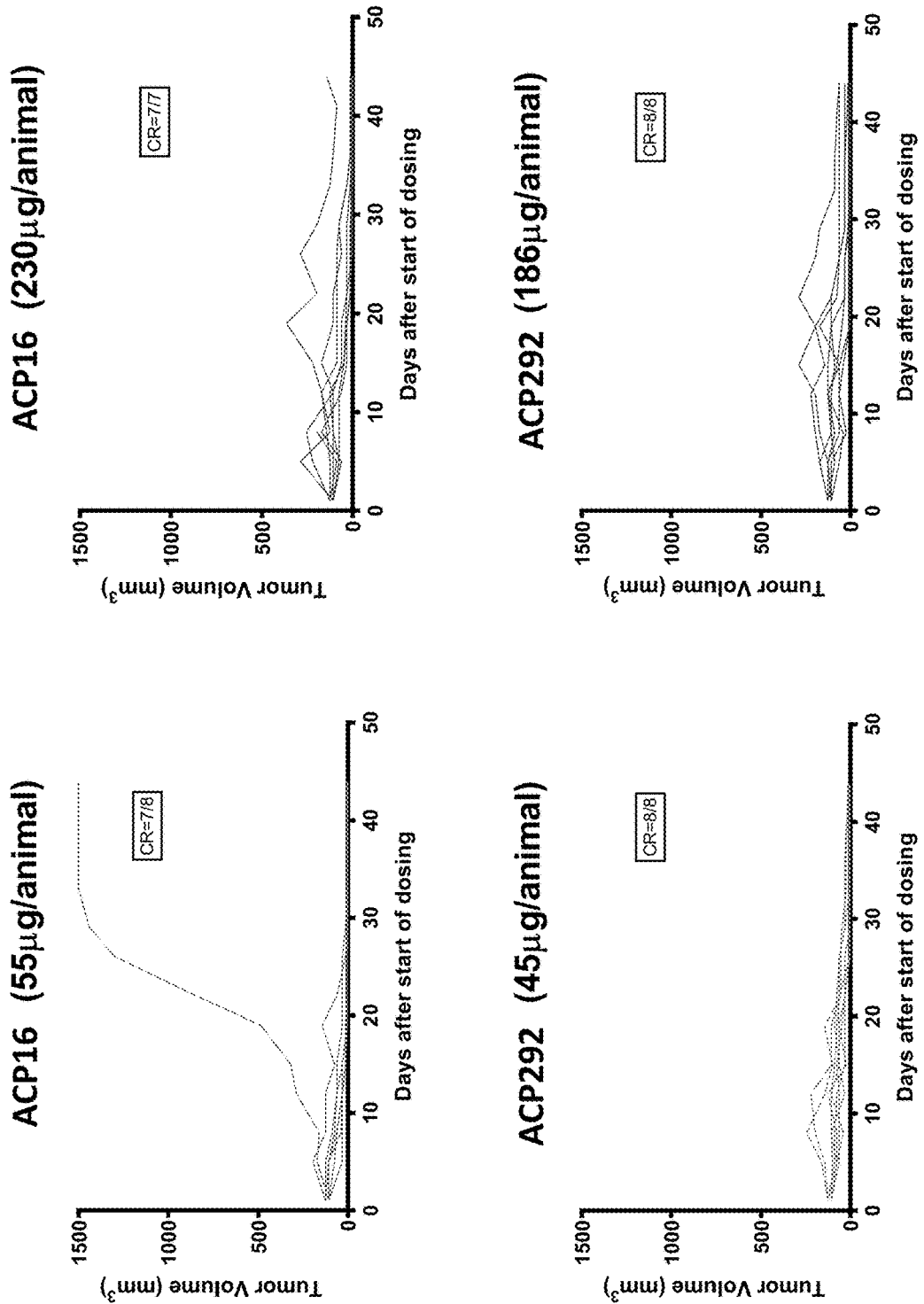
Figure 49F:
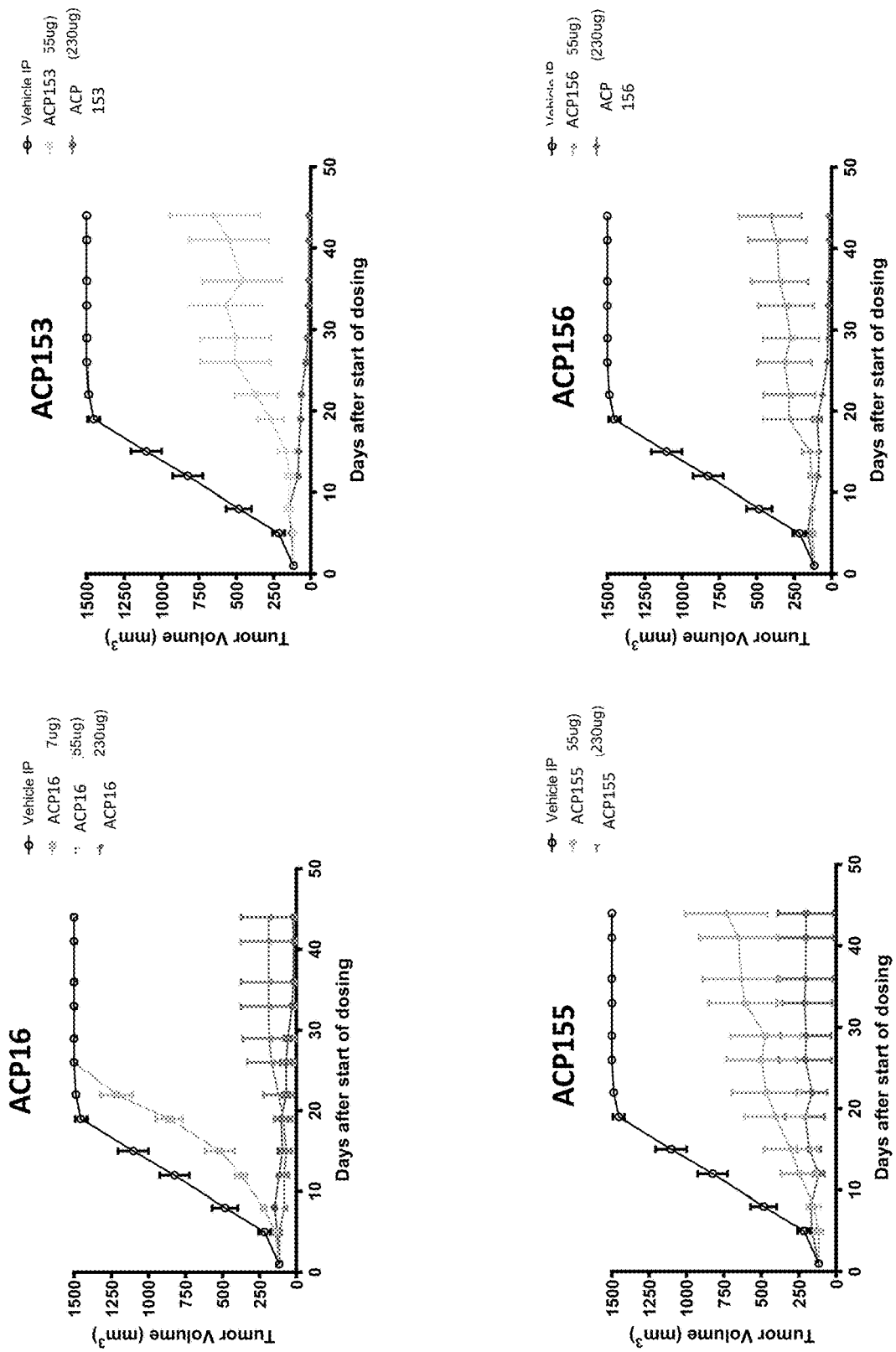
Figure 49G:
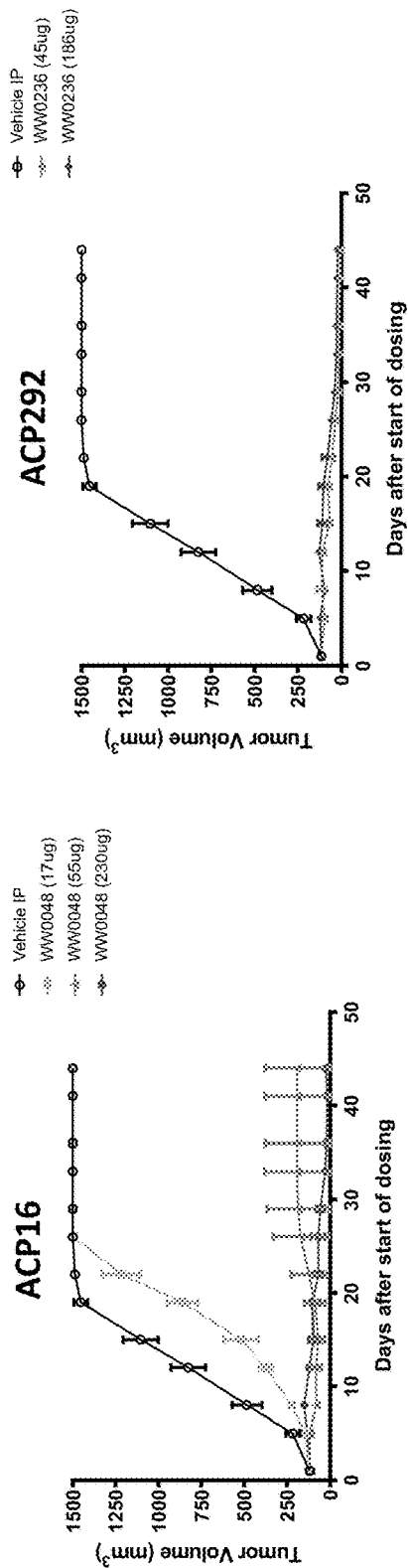
Figure 49H:
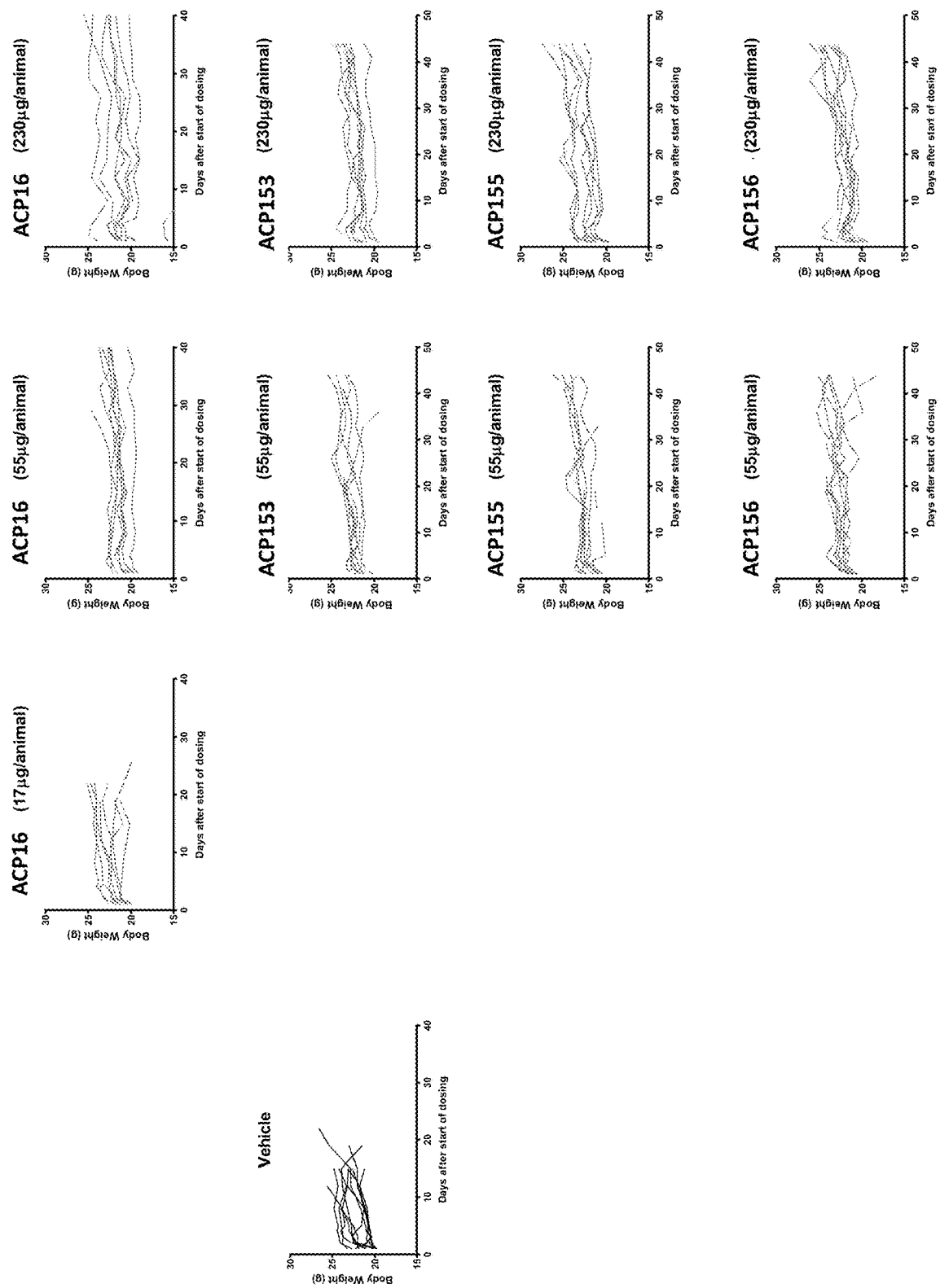
Figure 49I:
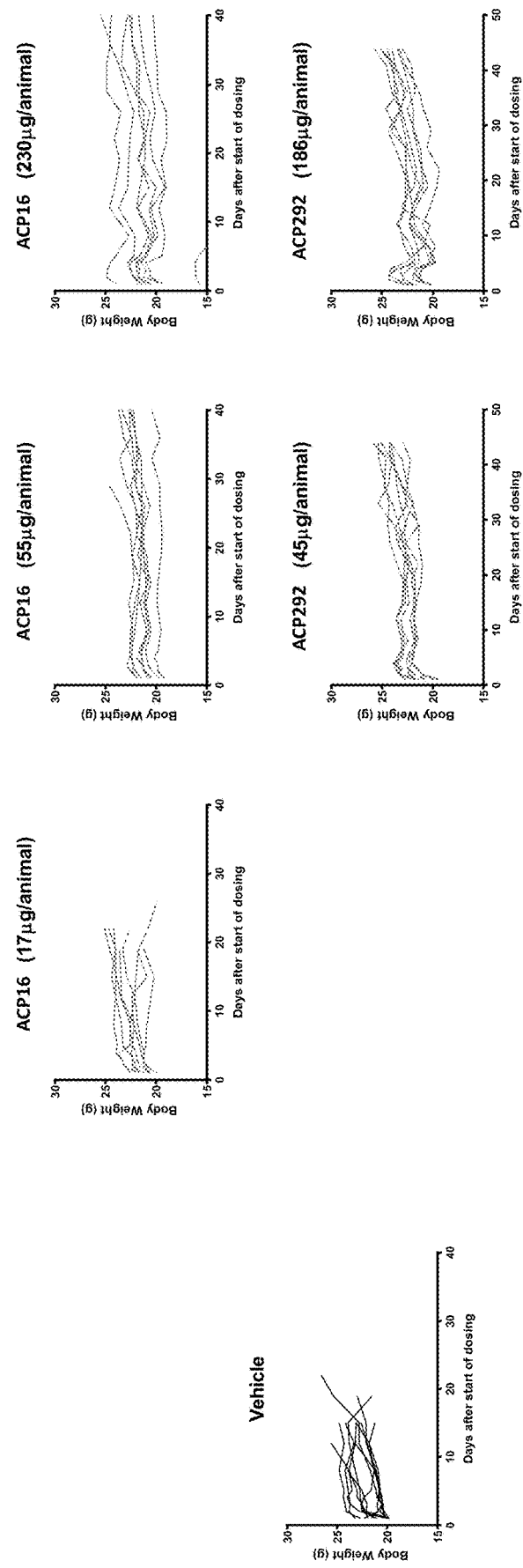

Human PBMCs were isolated form blood obtained from healthy donors. After isolation, PBMCs were cryopreserved until the assay was performed. For the assay, PBMCs were thawed and plated in suspension at 100,000 cells/well in X-Vivo media supplemented with 1.5% of human serum albumin. 96 well round bottom plates were used for the assay. Cells were stimulated with a dilution series of recombinant human IFNα and activatable human IFNα for 48 hours at 37° C. and 5% $CO_2$. Activity of uncleaved and cleaved activatable IFNα was tested. Cleaved inducible IFNα was generated by incubation with active recombinant protease. PBMC supernatants were collected and amounts of CXCL-10 (IP-10) produced were quantified using AlphaLISA as a measure of response. Results are shown in FIGS. 38A-38C.

TABLE 3

CONSTRUCT PERMUTATION TABLE ("6xHis" disclosed as SEQ ID NO: 354)

| Construct Name | Construct Description |
|---|---|
| ACP01 | (anti-HSA)-(cleav. link.)-mouse IFNg-(cleav. link.)-(anti-HSA)-6xHis |
| ACP02 | (anti-HSA)-(cleav. link.)-mouse IFNg-(cleav. link.)-mouse IFNg-(cleav. link.)-(anti-HSA)-6xHis |
| ACP03 | (anti-HSA)-(cleav. link.)-mouse IFNg-mouse IFNg-(cleav. link.)-(anti-HSA)-6xHis |
| ACP50 | (anti-EpCAM)-(anti-HSA)-(cleav. link.)-mouse IFNg-mouse IFNg-(cleav. link.)-(anti-HSA)-6xHis |
| ACP51 | (anti-EpCAM)-Linker-(anti-HSA)-(cleav. link.)-mIFNg-(cleav. link.)-(anti-HSA)-6xHis |
| ACP52 | (anti-HSA)-(cleav. link.)-mIFNg-(cleav. link.)-(anti-HSA)-Linker-(anti-EpCAM)-6xHis |
| ACP53 | mAlbumin-(cleav. link.)-mIFNg-(cleav. link.)-mAlbumin-6xHis |

TABLE 3-continued

CONSTRUCT PERMUTATION TABLE ("6xHis" disclosed as SEQ ID NO: 354)

| Construct Name | Construct Description |
|---|---|
| ACP54 | mAlbumin-(cleav. link.)-mIFNg-Linker-mIFNg-(cleav. link.)-mAlbumin-6xHis |
| ACP30 | (anti-HSA)-(cleav. link.)-mouse IFNg-(cleav. link.)-(anti-HSA)-(cleav. link.)-mouse IFNg-(cleav. link.)-(anti-HSA)-6xHis |
| ACP55 | (anti-HSA)-(cleav. link.)-mouse IFNg-(cleav. link.)-(anti-HSA)-(cleav. link.)-mouse IFNg-(cleav. link.)-(anti-HSA)-6xHis-C-tag |
| ACP56 | (anti-FOLR1)-Linker-(anti-HSA)-(cleav. link.)-mIFNg-(cleav. link.)-(anti-HSA)-6xHis |
| ACP57 | (anti-HSA)-(cleav. link.)-mIFNg-(cleav. link.)-(anti-HSA)-Linker-(anti-FOLR1)-6xHis |
| ACP58 | (anti-HSA)-(cleav. link.)-mIFNg-(cleav. link.)-mIFNg-(cleav. link.)-(anti-HSA)-Linker-(anti-EpCAM)-6xHis |
| ACP59 | (anti-FOLR1)-Linker-(anti-HSA)-(cleav. link.)-mIFNg-(cleav. link.)-mIFNg-(cleav. link.)-(anti-HSA)-6xHis |
| ACP60 | (anti-HSA)-(cleav. link.)-mIFNg-(cleav. link.)-mIFNg-(cleav. link.)-(anti-HSA)-Linker-(anti-FOLR1)-6xHis |
| ACP61 | (anti-HSA)-(cleav. link.)-mIFNg-(cleav. link.)-mIFNg-(cleav. link.)-(anti-HSA)-Linker-FN(CGS-2)-6xHis |
| ACP63 | anti-FN CGS-2 scFv (Vh/Vl)-6xHis |
| ACP69 | (anti-HSA)-(cleav. link.)-mouse IFNg-(cleav. link.)-(anti-HSA)-(cleav. link.)-mouse IFNg |
| ACP70 | mouse IFNg-(cleav. link.)-(anti-HSA)-(cleav. link.)-mouse IFNg-(cleav. link.)-(anti-HSA) |
| ACP71 | mouse IFNg-(cleav. link.)-mAlbumin-(cleav. link.)-mouse IFNg-(cleav. link.)-mAlbumin |
| ACP72 | mAlbumin-(cleav. link.)-mouse IFNg-(cleav. link.)-mAlbumin-(cleav. link.)-mouse IFNg |
| ACP73 | mAlbumin-(cleav. link.)-mouse IFNg-(cleav. link.)-mAlbumin-(cleav. link.)-mouse IFNg-(cleav. link.)-mAlbumin |
| ACP74 | mAlbumin-(cleav. link.)-mouse IFNg-(cleav. link.)-5mer linker-mAlbumin-5mer linker-(cleav. link.)-mouse IFNg-(cleav. link.)-mAlbumin |
| ACP75 | mAlbumin-(cleav. link.)-mouse IFNg-(cleav. link.)-10mer linker-mAlbumin-10mer linker-(cleav. link.)-mouse IFNg-(cleav. link.)-mAlbumin |
| ACP78 | (anti-HSA)-Linker-mouse_IFNg-Linker-(anti-HSA)-Linker-mouse_IFNg-Linker-(anti-HSA)_(non-cleavable_control) |
| ACP134 | Anti-HSA-(cleav. link.)-mouse_IFNg-(cleav. link.)-anti-HSA-(cleav. link.)-mouse_IFNg-(cleav. link.)-anti-HSA-L-anti-FOLR1 |
| ACP135 | Anti-FOLR1-L-HSA-(cleav. link.)-mouse_IFNg-(cleav. link.)-HSA-(cleav. link.)-mouse_IFNg-(cleav. link.)-HSA |
| ACP04 | human p40-murine p35-6xHis |
| ACP05 | human p40-human p35-6xHis |
| ACP34 | mouse p35-(cleav. link.)-mouse p40-6xHis |
| ACP35 | mouse p35-GS-(cleav. link.)-GS-mouse p40-6xHis |
| ACP36 | (anti-HSA)-(Cleav. Linker)-mouse p40-mouse p35-(Cleav. Linker)-(anti-HSA)-6xHis |
| ACP37 | (anti-EpCAM)-(anti-HSA)-(Cleav. Linker)-mouse p40-mouse p35-(Cleav. Linker)-(anti-HSA)-6xHis |
| ACP79 | (anti-EpCAM)-Linker-(anti-HSA)-(cleav. link.)-mIL12-(cleav. link.)-(Anti-HSA)-6xHis |
| ACP80 | (anti-HSA)-(cleav. link.)-mIL12-(cleav. link.)-(anti-HSA)-Linker-(anti-EpCAM)-6xHis |
| ACP06 | Blocker12-Linker-(cleav. link.)-human p40-Linker-mouse p35-(cleav. link.)-(anti-HSA)-6xHis |
| ACP07 | Blocker12-Linker-(cleav. link.)-human p40-Linker-mouse p35-(cleav. link.)-(anti-HSA)-Linker-(anti-FOLR1)-6xHis |
| ACP08 | (anti-FOLR1)-Linker-Blocker12-Linker-(cleav. link.)-human p40-Linker-mouse p35-(cleav. link.)-(anti-HSA)-6xHis |
| ACP09 | (anti-HSA)-Linker-Blocker12-Linker-(cleav. link.)-human p40-Linker-mouse p35-6xHis |
| ACP10 | (anti-HSA)-(cleav. link.)-human p40-L-mouse p35-(cleav. link.)-Linker-Blocker12-6xHis |
| ACP11 | Human_p40-Linker-mouse_p35-(cleav. link.)-Linker-Blocker12-Linker-(anti-HSA)-6xHis |
| ACP91 | human_p40-Linker-mouse_p35-Linker-Linker-Blocker-Linker-(anti-HSA)_(non-cleavable_control) |
| ACP136 | human p40-L-mouse p35-(cleav. link.)-Blocker |
| ACP138 | human_p40-L-mouse p35-(cleav. link.)-Blocker-L-(anti-HSA)-L-FOLR1 |
| ACP139 | Anti-FOLR1-L-human_p40-L-mouse p35-(cleav. link.)-Blocker12-L-(anti-HSA) |
| ACP140 | Anti-FOLR1-(cleav. link.)-human_p40-L-mouse p35-(cleav. link.)-Blocker12-L-(anti-HSA) |
| ACP12 | (anti-EpCAM)-IL2-(cleav. link.)-(anti-HSA)-blocker2-6xHis |

TABLE 3-continued

CONSTRUCT PERMUTATION TABLE ("6xHis" disclosed as SEQ ID NO: 354)

| Construct Name | Construct Description |
|---|---|
| ACP13 | (anti-EpCAM)-Blocker2-(anti-HSA)-(cleav. link.)-IL2-6xHis |
| ACP14 (WW0045) | Blocker2-Linker-(cleav. link.)-IL2-(cleav. link.)-(anti-HSA)-6xHis |
| ACP15 (WW0047) | Blocker2-Linker-(anti-HSA)-Linker-(cleav. link.)-IL2-6xHis |
| ACP16 (WW0048) | IL2-(cleav. link.)-(anti-HSA)-Linker-(cleav. link.)-Blocker2-6xHis |
| ACP17 | (anti-EpCAM)-Linker-IL2-(cleav. link.)-(anti-HSA)-Linker-(cleav. link.)-Blocker2-6xHis |
| ACP18 | (anti-EpCAM)-Linker-IL2-(cleav. link.)-(anti-HSA)-Linker-vh(cleav. link.)vl-6xHis |
| ACP19 | IL2-(cleav. link.)-Linker-Blocker2-Linker-(anti-HSA)-Linker-(anti-EpCAM)-6xHis |
| ACP20 (WW0056) | IL2-(cleav. link.)-Blocker2-6xHis |
| ACP21 (WW0057) | IL2-(cleav. link.)-Linker-Blocker2-6xHis |
| ACP22 | IL2-(cleav. link.)-Linker-blocker-(cleav. link.)-(anti-HSA)-Linker-(anti-EpCAM)-6xHis |
| ACP23 | (anti-FOLR1)-(cleav. link.)-Blocker2-Linker-(cleav. link.)-(anti-HSA)-(cleav. link.)-IL2-6xHis |
| ACP24 (WW0074) | (Blocker2)-(cleav. link.)-(IL2)-6xHis |
| ACP25 (WW0075) | Blocker2-Linker-(cleav. link.)-IL2-6xHis |
| ACP26 | (anti-EpCAM)-Linker-IL2-(cleav. link.)-(anti-HSA)-Linker-blocker(NARA1 Vh/Vl) |
| ACP27 | (anti-EpCAM)-Linker-IL2-(cleav. link.)-(anti-HSA)-Linker-blocker(NARA1 Vl/Vh) |
| ACP28 | IL2-(cleav. link.)-Linker-Blocker2-(NARA1 Vh/Vl)-Linker-(anti-HSA)-Linker-(anti-EpCAM) |
| ACP29 | IL2-(cleav. link.)-Linker-Blocker2-(NARA1 Vl/Vh)-Linker-(anti-HSA)-Linker-(anti-EpCAM) |
| ACP38 | IL2-(cleav. link.)-blocker-(anti-HSA)-(anti-EpCAM)-6xHis |
| ACP39 | (anti-EpCAM)-(cleav. link.)-(anti-HSA)-(cleav. link.)-Blocker2-(cleav. link.)-IL-2-6xHis |
| ACP40 (WW0076) | CD25ecd-Linker-(cleav. link.)-IL2-6xHis |
| ACP41 (WW0077) | IL2-(cleav. link.)-Linker-CD25ecd-6xHis |
| ACP42 (WW0078) | (anti-HSA)-Linker-CD25ecd-Linker-(cleav. link.)-IL2-6xHis |
| ACP43 (WW0079) | IL2-(cleav. link.)-Linker-CD25ecd-Linker-(anti-HSA)-6xHis |
| ACP44 (WW0080) | IL2-(cleav. link.)-Linker-CD25ecd-(cleav. link.)-(anti-HSA)-6xHis |
| ACP45 (WW0046) | (anti-HSA)-(cleav. link.)-Blocker2-Linker-(cleav. link.)-IL2-6xHis |
| ACP46 | IL2-(cleav. link.)-linkerL-vh(cleav. link.)vl-Linker-(anti-HSA)-L-(anti-EpCAM)-6xHis |
| ACP47 | (anti-EpCAM)-Linker-IL2-(Cleavable Linker)-(anti-HSA)-Linker-Blocker2-6xHis |
| ACP48 (WW0054) | IL2-(cleav. link.)-Blocker2-Linker-(anti-HSA)-6xHis |
| ACP49 (WW0055) | IL2-(cleav. link.)-Linker-Blocker2-Linker-(anti-HSA)-6xHis |
| ACP92 | (anti-HSA)-(16mer Cleav. Link.)-IL2-(16mer Cleav. Link.)-(anti-HSA)-6XHis |
| ACP93 | (anti-EpCAM)-(anti-HSA)-(anti-EpCAM)-Blocker2-(cleav. link.)-IL2-6xHis |
| ACP94 | (anti-EpCAM)-(anti-HSA)-Blocker2-(cleav. link.)-IL2-6xHis |
| ACP95 | (anti-EpCAM)-(anti-HSA)-(cleav. link.)-IL2-6xHis |
| ACP96 | (anti-EpCAM)-(16mer cleav. link.)-IL2-(16mer cleav. link.)-(anti-HSA) |
| ACP97 | (anti-EpCAM)-(anti-HSA)-(cleav. link.)-IL2-(cleav. link.)-(anti-HSA)-6xHis |
| ACP99 | (anti-EpCAM)-Linker-IL2-(cleav. link.)-(anti-HSA)-6xHis |
| ACP100 | (anti-EpCAM)-Linker-IL2-6xHis |
| ACP101 (WW0061) | IL2-(cleav. link.)-(anti-HSA)-6xHis |
| ACP102 | (anti-EpCAM)-(cleav. link.)-IL2-(cleav. link.)-(anti-HSA)-Linker-blocker-6xHis |
| ACP103 | IL2-(cleav. link.)-Linker-Blocker2-Linker-(anti-HSA)-Linker-(antiI-FOLR1)-6xHis |
| ACP104 | (anti-FOLR1)-IL2-(cleav. link.)-(anti-HSA)-Linker-Blocker2-6xHis |

TABLE 3-continued

CONSTRUCT PERMUTATION TABLE ("6xHis" disclosed as SEQ ID NO: 354)

| Construct Name | Construct Description |
|---|---|
| ACP105 | Blocker2-Linker-(cleav. link.)-IL2-(cleav. link.)-(anti-HSA)-Linker-(anti-FOLR1)-6xHis |
| ACP106 | (anti-FOLR1)-Linker-(anti-HSA)-(cleav. link.)-blocker-Linker-(cleav. link.)-IL2 -6xHis |
| ACP107 | Blocker2-Linker-(anti-HSA)-(cleav. link.)-IL2-Linker-(anti-FOLR1)-6xHis |
| ACP108 | (anti-EpCAM)-IL2-(Dually cleav. link.)-(anti-HSA)-Linker-blocker-6xHis |
| ACP117 | anti-FN CGS-2 scFv (Vh/Vl)-6xHis |
| ACP118 | NARA1 Vh/Vl non-cleavable |
| ACP119 | NARA1 Vh/Vl cleavable |
| ACP120 | NARA1 Vl/Vh non-cleavable |
| ACP121 | NARA1 Vl/Vh cleavable |
| ACP124 (WW0159) | IL2-Linker-(anti-HSA)-Linker-Linker-blocker_(non-cleavable_control) |
| ACP132 (WW0177) | IL2-L-HSA |
| ACP141 (WW0178) | IL2-L-human_Albumin |
| ACP142 (WW0179) | IL2-(cleav. link.)-human_Albumin |
| ACP144 | IL2-(cleav. link.)-HSA-(cleav.-link.)blocker-L-(anti-FOLR1) |
| ACP145 | Anti-FOLR1-L-IL2-(cleav. link.)-HSA-Linker-(cleav. link.)-blocker2 |
| ACP146 | Anti-FOLR1-(cleav. link)-IL2-(cleav. link.)-HSA-Linker-(cleav. link.)-blocker2 |
| ACP133 (WW0196) | IL2-6x His |
| ACP147 | IL2-(cleav. Linker)-(anti-HSA)-Linker-(cleav. link.)-blocker2-L-(anti-EpCAM) |
| ACP148 | (anti-EpCAM)-L-IL2-(cleav. link.)-(anti-HSA)-L-(cleav. Linker)-blocker2 |
| ACP149 | (anti-EpCAM)-(cleav. link.)-IL2-(cleav. Linker)-(anti-HSA)-L-(cleav. Linker)-blocker2 |
| ACP31 | (anti-HSA)-(cleav. link.)-mIFNa1-(cleav. link.)-(anti-HSA) |
| ACP32 | (anti-HSA)-(cleav. link.)-mIFNa1(N + C trunc)-(cleav. link.)-(anti-HSA) |
| ACP33 | (anti-HSA)-(cleav. link.)-mIFNa1(C trunc)-(cleav. link.)-(anti-HSA) |
| ACP131 | mIFNa1 |
| ACP125 | Anti-HSA-(cleav. link.)-mIFNa1 |
| ACP126 | mIFNa1-(cleav. link.)-(anti-HSA) |
| ACP127 | Mouse_Albumin-(cleav. Link.)-mIFNa1-(cleav link)-mouse_Albumin |
| ACP128 | Mouse_Albumin-(cleav. link.)-mIFNa1 |
| ACP129 | mIFNa1-(cleav. link.)-mAlb |
| ACP150 | (Anti-FOLR1)-L-(anti-HSA)-(cleav. Link.)-mIFNa1-(cleav. Link.)-(anti-HSA) |
| ACP151 | Anti-FOLR1-L-(anti-HSA)-(cleav. Link.)-mIFNa1-(cleav. Link.)-(anti-HSA)-L-(anti-FOLR1) |
| ACP152 | (anti-HSA)-L-mIFNa1-L-(anti-HSA)_(non-cleavable_control) |
| ACP153 (WW0201) | IL2-(cleav. link.)-(anti-HSA)-linker(cleav. link.)-blocker2 |
| ACP154 (WW0202) | IL2-(cleav. link.)-(anti-HSA)-linker(cleav. link.)-blocker2 |
| ACP155 (WW0203) | IL2-(cleav. link.)-(anti-HSA)-linker(cleav. link.)-blocker2 |
| ACP156 (WW0204) | IL2-X-anti-HSA-LX-blocker_(X = Linker4_Blocker = Vh-Vl) |
| ACP157 (WW0205) | IL2-X-anti-HSA-LX-blocker_(X = Linker5_Blocker = Vh-Vl) |
| ACP200 | mAlb(D3)-X-mouse-IFNa-X-mAlb(D3)_(X = Linker 1) |
| ACP201 | mAlb(D1-L-D3)-X-mouse-IFNa-X-mAlb(D1-L-D3)_(X = Linker 1) |
| ACP202 | HSA-X-mIFNa1-X-HSA_(X = Linker 1 + 17aa) |
| ACP203 | HSA-X-mIFNa1-X-HSA_(X = Linker 2) |
| ACP204 | HSA-X-mIFNa1-X-HSA_(X = Linker 3) |
| ACP205 | HSA-X-mIFNa1-X-HSA_(X = Linker 4) |
| ACP206 | HSA-X-Human_IFNA2b-X-HSA_(X = Linker 2) |
| ACP207 | HSA-X-Human_IFNA2b-X-HSA_(X = Linker 3) |
| ACP208 | HSA-X-Human_IFNA2b-X-HSA_(X = Linker 4) |
| ACP211 | HSA-X-mouse-IFNg-X-IFNa-X-mouse-IFNg-X-HSA_(X = Linker 1) |
| ACP213 | mAlb(D3)-X-mouse-IFNg-X-mAlb(D3)-X-mouse-IFNg-X-mAlb(D3)_(X = Linker 1) |

TABLE 3-continued

CONSTRUCT PERMUTATION TABLE ("6xHis" disclosed as SEQ ID NO: 354)

| Construct Name | Construct Description |
|---|---|
| ACP214 | mAlb(D1-L-D3)-X-mouse-IFNg-X-mAlb(D1-L-D3)-X-mouse-IFNg-X-mAlb(D1-L-D3)_(X = Linker 1) |
| ACP215 | HSA-X-mouse-IFNg-X-HSA-X-mouse-IFNg-X-HSA_(X = Linker 1 + 17aa) |
| ACP240 | HSA-L-human_p40-L-mouse_p35-LL-Blocker_(non-cleavable; Blocker = Vl/Vh) |
| ACP241 | mAlb-X-human_p40-L-mouse_p35-XL-Blocker_(X = Linker 1; Blocker = Vl/Vh) |
| ACP242 | human_p40-L-mouse_p35-XL-Blocker-X-mAlb_(X = Linker 1; Blocker = Vl/Vh) |
| ACP243 | mIgG1_Fc-X-human_p40-L-mouse_p35-XL-Blocker_(X = Linker 1; Blocker = Vl/Vh) |
| ACP244 | human_p40-L-mouse_p35-XL-Blocker-X-mIgG1_Fc_(X = Linker 1; Blocker = Vl/Vh) |
| ACP245 | HSA-X-human_p40-L-mouse_p35-XL-Blocker(cleavable)_ (X = Linker 1; Blocker = Vl-X-Vh) |
| ACP247 | HSA-X-human_p40-L-mouse_p35-XL-Blocker_(Blocker = 3CYT5; X = Linker 1) |
| ACP284 | HSA-X-mouse_p35-XL-Blocker_(Blocker = Vl/Vh; X = Linker 1) |
| ACP285 | HSA-X-human_p40_C199S-L-mouse_p35_C92S-XL-Blocker_ (Blocker = _Vl/Vh; X = Linker 1) |
| ACP286 | HSA-X-human_p40-L(4xG4S (SEQ ID NO: 453))-mouse_p35-XL-Blocker_(Blocker =Vl/Vh; X = Linker 1) |
| ACP287 | HSA-X-human_p40_mouse_p35-XL-Blocker_(Blocker = Vl/Vh_VH44-VL100 disulfide; X = Linker 1) |
| ACP288 | HSA-X-human_p40_mouse_p35-XL-Blocker_(Blocker = Vl/Vh_VH105-VL43_disulfide; X = Linker 1) |
| ACP289 (WW0233) | Geneart_WW0048_IL2-X-HSA-LX-blocker_Fusion_protein-6xHis |
| ACP290 (WW0234) | IL2-X-HSA-LX-blocker_(X = Linker 1; Blocker = 3TOW69) |
| ACP291 (WW0235) | IL2-X-HSA-LX-blocker_(X = Linker 1; Blocker = 3TOW85) |
| ACP292 (WW0236) | IL2-X-HSA-LX-blocker_(X = Linker 1; Blocker = 2TOW91) |
| ACP296 (WW0250) | IL2-X-HSA-LX-blocker(cleavable)_(X = Linker 1; Blocker = Vh-X-Vl) |
| ACP297 (WW0251) | IL2-X-HSA-LX-blocker(A46L)_(X = Linker 1; Blocker = Vh/Vl) |
| ACP298 (WW0252) | IL2-X-HSA-LX-blocker(A46G)_(X = Linker 1; Blocker = Vh/Vl) |
| ACP299 (WW0253) | IL2(Cys145Ser)-X-HSA-LX-blocker_(X = Linker 1; Blocker = Vh/Vl) |
| ACP300 (WW0255) | IL2-X-hAlb-LX-blocker_(X = Linker 1; Blocker = Vh/Vl) |
| ACP302 (WW0296) | IL2-X-mAlb-LX-blocker_(X = Linker 1; Blocker = Vh/Vl) |
| ACP303 | mAlb-X-IL2(Nterm-41)-X-mALB_(X = Linker 1) |
| ACP304 (WW0302) | IL2-X-HSA-LX-blocker-XL-CD25ecd_(X = Linker 1; Blocker = Vh/Vl) |
| ACP305 (WW0303) | CD25ecd-LX-IL2-X-HSA-LX-blocker_(X = Linker 1; Blocker = Vh/Vl) |
| ACP306 (WW0304) | IL2-XL-CD25ecd-X-HSA-LX-blocker_(X = Linker 1; Blocker = Vh/Vl) |
| ACP309 (WW0307) | IL2-X-HSA-LX-blocker(A46S)_(X = Linker 1; Blocker = Vh/Vl) |
| ACP310 (WW0308) | IL2-X-HSA-LX-blocker(QAPRL_FR2)_(X = Linker 1; Blocker = Vh/Vl) |
| ACP311 (WW0316) | IL2-X-IgG4_Fc(S228P)-LX-Blocker_(X = Linker 1; Blocker = Vh/Vl) |
| ACP312 (WW0317) | IgG4_Fc(S228P)-X-IL2-LX-Blocker_(X = Linker 1; Blocker = Vh/Vl) |
| ACP313 (WW0318) | IL2-XL-Blocker-X-IgG4_Fc(S228P)_(X = Linker 1; Blocker = Vh/Vl) |
| ACP314 (WW0354) | mIgG1_Fc-X-IL2-LX-Blocker_(X = Linker 1; Blocker = Vh/Vl) |
| ACP336 (WW0414) | IL2-X-anti-HSA-LX-blocker_(Blocker = VHVL.F2.high.A02_ Vh-X-Vl_A46S; X = Linker 2) |
| ACP337 (WW0415) | IL2-X-anti-HSA-LX-blocker_(Blocker = VHVL.F2.high.A02_ Vh/Vl_A46S; X = Linker 2) |
| ACP338 (WW0416) | IL2-X-anti-HSA-LX-blocker_(Blocker = VHVL.F2.high.F03_ Vh-X-Vl; X = Linker 2) |
| ACP339 (WW0417) | IL2-X-anti-HSA-LX-blocker_(Blocker = VHVL.F2.high.F03_ Vh/Vl; X = Linker 2) |

TABLE 3-continued

CONSTRUCT PERMUTATION TABLE ("6xHis" disclosed as SEQ ID NO: 354)

| Construct Name | Construct Description |
|---|---|
| ACP340 (WW0418) | IL2-X-anti-HSA-LX-blocker_(Blocker = Hu2TOW91_B; X = Linker 2) |
| ACP341 (WW0419) | IL2-X-anti-HSA-LX-blocker_(Blocker = Hu3TOW85_A; X = Linker 2) |
| ACP342 (WW0420) | CD25ecd_C213S-LX-IL2-X-anti-HSA-LX-blocker_(Blocker = VHVL.F2.high.A02_Vh-X-Vl_A46S; X = Linker 2) |
| ACP343 (WW0421) | CD25ecd_C213S-LX-IL2-X-anti-HSA-LX-blocker_(Blocker = VHVL.F2.high.A02_Vh/Vl_A46S; X = Linker 2) |
| ACP344 (WW0422) | CD25ecd_C213S-LX-IL2-X-anti-HSA-LX-blocker_(Blocker = VHVL.F2.high.F03_Vh-X-Vl; X = Linker 2) |
| ACP345 (WW0423) | CD25ecd_C213S-LX-IL2-X-anti-HSA-LX-blocker_(Blocker = VHVL.F2.high.F03_Vh/Vl; X =Linker 2) |
| ACP346 (WW0424) | CD25ecd_C213S-LX-IL2-X-anti-HSA-LX-blocker_(Blocker = Hu2TOW91_B; X = Linker 2) |
| ACP347 (WW0425) | CD25ecd_C213S-LX-IL2-X-anti-HSA-LX-blocker_(Blocker = Hu3TOW85_A; X = Linker 2) |
| ACP348 (WW0426) | IgG4_Fc(S228P)-X-IL-LX-Blocker_(Blocker = VHVL.F2.high.A02_Vh-X-Vl_A46S; X = Linker 2) |
| ACP349 (WW0427) | IgG4_Fc(S228P)-X-IL-LX-Blocker_(Blocker = VHVL.F2.high.A02_Vh\Vl_A46S; X = Linker2) |
| ACP350 (WW0428) | IgG4_Fc(S228P)-X-IL-LX-Blocker_(Blocker = VHVL.F2.high.F03_Vh-X-Vl; X = Linker 2) |
| ACP351 (WW0429) | IgG4_Fc(S228P)-X-IL-LX-Blocker_(Blocker = VHVL.F2.high.F03_Vh\Vl; X = Linker 2) |
| ACP352 (WW0430) | IgG4_Fc(S228P)-X-IL-LX-Blocker_(Blocker = Hu2TOW91_B; X = Linker 2) |
| ACP353 (WW0431) | IgG4_Fc(S228P)-X-IL-LX-Blocker_(Blocker = Hu3TOW85_A; X = Linker 2) |
| ACP354 (WW0432) | IgG4_Fc(S228P)-X-CD25ecd_C213S-LX-IL2-LX-Blocker_ (Blocker = VHVL.F2.high.A02_Vh-X-Vl_A46S; X = Linker 2) |
| ACP355 (WW0433) | IgG4_Fc(S228P)-X-CD25ecd_C213S-LX-IL2-LX-Blocker_(Blocker = VHVL.F2.high.A02_Vh\Vl_A46S; X = Linker 2) |
| ACP356 (WW0434) | IgG4_Fc(S228P)-X-CD25ecd_C213S-LX-IL2-LX-Blocker_ (Blocker = VHVL.F2.high.F03_Vh-X-Vl; X = Linker 2) |
| ACP357 (WW0435) | IgG4_Fc(S228P)-X-CD25ecd_C213S-LX-IL2-LX-Blocker_(Blocker = VHVL.F2.high.F03_Vh\Vl; X = Linker 2) |
| ACP358 (WW0436) | IgG4_Fc(S228P)-X-CD25ecd_C213S-LX-IL2-LX-Blocker_ (Blocker = Hu2TOW91_B; X =Linker 2) |
| ACP359 (WW0437) | IgG4_Fc(S228P)-X-CD25ecd_C213S-LX-IL2-LX-Blocker_ (Blocker = Hu3TOW85_A; X =Linker 2) |
| ACP371 (WW0513) | IL2-X-anti-HSA-LX-blocker_(Blocker = Vh/Vl_VH44-VL100_ disulfide; X = Linker 2) |
| ACP372 (WW0514) | IL2-X-anti-HSA-LX-blocker_(Blocker = Vh/Vl_VH105-VL43_ disulfide; X = Linker 2) |
| ACP373 (WW0515) | IL2-X-anti-HSA-LX-blocker_(Blocker = VHVL.F2.high.A02_ Vh/Vl_VH44-VL100_disulfide; X = Linker 2) |
| ACP374 (WW0516) | IL2-X-anti-HSA-LX-blocker_(Blocker = VHVL.F2.high.A02_ Vh/Vl_VH105-VL43_disulfide; X = Linker 2) |
| ACP375 (WW0517) | IL2-X-anti-HSA-LX-blocker_(Blocker = VHVL.F2.high.F03_ Vh/Vl_VH44-VL100_disulfide; X = Linker 2) |
| ACP376 (WW0521) | IL2-X-anti-HSA-LX-blocker_(Blocker = VHVL.F2.high.F03_ Vh/Vl_VH105-VL43_disulfide X =Linker 2) |
| ACP377 (WW0519) | IL2-X-anti-HSA-LX-blocker_(Blocker = Hu2TOW91_A; X = Linker 2) |
| ACP378 (WW0520) | IL2-X-anti-HSA-LX-Heavy_blocker_Fab_(Blocker = VH-CH1; X = Linker 2) |
| ACP379 (WW0521) | IgG4_Fc(S228P)-X-IL2-LX-Heavy_blocker_Fab_(Blocker = VH-CH1; X = Linker 2) |
| ACP383 (WW0525) | IgG4_Fc(S228P)-X-IL2-LX-blocker_(Blocker = Vh/Vl_ VH44-VL100_disulfide; X = LINKER 2) |
| ACP38 (WW05264) | IgG4_Fc(S228P)-X-IL2-LX-blocker_(Blocker = Vh/Vl_ VH105-VL43_disulfide; X = MMP14-1) |
| ACP385 (WW0527) | IgG4_Fc(S228P)-X-IL2-LX-blocker_(Blocker = VHVL.F2. high.A02_Vh/Vl_VH44-VL100_disulfide; X = LINKER 2) |
| ACP386 (WW0528) | IgG4_Fc(S228P)-X-IL2-LX-blocker_(Blocker = VHVL.F2. high.A02_Vh/Vl_VH105-VL43_disulfide; X = Linker 2) |
| ACP387 (WW0529) | IgG4_Fc(S228P)-X-IL2-LX-blocker_(Blocker = VHVL.F2. high.F03_Vh/Vl_VH44-VL100_disulfide; X = Linker 2) |
| ACP388 (WW0530) | IgG4_Fc(S228P)-X-IL2-LX-blocker_(Blocker = VHVL. F2.high.F03_Vh/Vl_VH105-VL43_disulfide; X = Linker 2) |
| ACP389 (WW0531) | IgG4_Fc(S228P)-X-IL2-LX-blocker_(Blocker = Hu2TOW91_ A; X = Linker 2) |

TABLE 3-continued

CONSTRUCT PERMUTATION TABLE ("6xHis" disclosed as SEQ ID NO: 354)

| Construct Name | Construct Description |
|---|---|
| ACP390 (WW0532) | IL2-X-anti-HSA-LX-blocker_(Blocker = VHVL.F2.high.A02_ Vh/Vl_A46S_VH44-VL100_disulfide; X = Linker 2) |
| ACP391 (WW0533) | IgG4_Fc(S228P)-X-IL2-LX-blocker_(Blocker = VHVL.F2. high.A02_Vh/Vl_A46S_VH44-VL100_disulfide; X = Linker 2) |
| ACP392 (WW0534) | IL2-XL-CD25ecd_C213S-X-HSA-LX-blocker_(Blocker = VHVL.F2.high.A02_Vh_G44C_Vl_A46S_G100C; X = Linker 2) |
| ACP393 (WW0535) | IL2-XL-CD25ecd_C213S-X-HSA-LX-blocker_(Blocker = VHVL.F2.high.A02_Vh_Q105C_Vl_A43C; X = Linker 2) |
| ACP394 (WW0536) | IL2-XL-CD25ecd_C213S-X-HSA-LX-blocker_(Blocker = VHVL.F2.high.F03_Vh_G44C_Vl_G100C; X = Linker 2) |
| ACP395 (WW0537) | IL2-XL-CD25ecd_C213S-X-HSA-LX-blocker_(Blocker = VHVL.F2.high.F03_Vh_Q105C_Vl_A43C; X = Linker 2) |
| ACP396 (WW0538) | IL2-XL-CD25ecd_C213S-X-HSA-LX-blocker_(Blocker = Hu2TOW91_A; X = Linker 2) |
| ACP397 (WW0539) | IL2-XL-CD25ecd_C213S-X-HSA-LX-blocker_(Blocker = Hu2TOW91_B; X = Linker 2) |
| ACP398 (WW0540) | IL2-XL-CD25ecd_C213S-X-HSA-LX-Heavy_blocker_Fab_ (Blocker = VH-CH1; X = Linker 2) |
| ACP399 | Blocker-XL-HSA-X-IL2(Nterm-41)-X-HSA_(Blocker = VHVL.F2.high.A02_Vh_G44C_Vl_A46S_G100C; X = Linker 2) |
| ACP400 | Blocker-XL-HSA-X-IL2(Nterm-41)-X-HSA_(Blocker = VHVL.F2.high.A02_Vh_Q105C_Vl_A43C; X = Linker 2) |
| ACP401 | Blocker-XL-HSA-X-IL2(Nterm-41)-X-HSA_(Blocker = VHVL.F2.high.F03_Vh_G44C_Vl_G100C; X = Linker 2) |
| ACP402 | Blocker-XL-HSA-X-IL2(Nterm-41)-X-HSA_(Blocker = VHVL.F2.high.F03_Vh_Q105C_Vl_A43C; X = Linker 2) |
| ACP403 | Blocker-XL-HSA-X-IL2(Nterm-41)-X-HSA_(Blocker = Hu2TOW91_A; X = Linker 2) |
| ACP404 | Blocker-XL-HSA-X-IL2(Nterm-41)-X-HSA_(Blocker = Hu2TOW91_B; X = Linker 2) |
| ACP405 | Heavy_Blocker_Fab-XL-HSA-X-IL2(Ntenn-41)-X-HSA_ (Blocker = VH-CH1; X = Linker 2) |
| ACP406 (WW0548) | mIgG1_Fc(S228P)-X-IL2-LX-Heavy_blocker_Fab_(Blocker = VH-CH1; X = Linker 2) |
| ACP407 (WW0549) | mIgG1_Fc(S228P)-X-IL2-LX-blocker_(Blocker = VHVL.F2. high.A02_Vh/Vl_VH44-VL100_disulfide; X = Linker 2) |
| ACP408 (WW0550) | mIgG1_Fc(S228P)-X-IL2-LX-blocker_(Blocker = VHVL.F2. high.A02_Vh/Vl_A46S_VH44-VL100_disulfide; X = Linker 2) |
| ACP409 (WW0551) | mIgG1_Fc(S228P)-X-IL2-LX-blocker_(Blocker = VHVL.F2. high.A02_Vh/Vl_VH105-VL43_disulfidel; X = Linker 2) |
| ACP410 (WW0552) | mIgG1_Fc(S228P)-X-IL2-LX-blocker_(Blocker = VHVL.F2. high.F03_Vh/Vl_VH44-VL100_disulfidel; X = Linker 2) |
| ACP411 (WW0553) | mIgG1_Fc(S228P)-X-IL2-LX-blocker_(Blocker = VHVL.F2. high.F03_Vh/Vl_VH105-VL43_disulfidel; X = Linker 2) |
| ACP412 (WW0554) | mIgG1_Fc(S228P)-X-IL2-LX-blocker_(Blocker = Hu2TOW91_A; X = Linker 2) |
| ACP413 (WW0555) | CD25_213S-L-Kappa_blocker_Fab_(Blocker = VHVL.F2.high. A02_A46S_Kappa) |
| ACP414 (WW0556) | CD25_213S-L-Kappa_blocker_Fab_(Blocker = VHVL.F2.high. F03_Kappa) |
| ACP415 (WW0557) | IL2-XL-blocker-L-CD25_213S-X-HSA_Blocker = VHVL.F2.high.A02_Vh_G44C_Vl_A46S_G100C; X = Linker 2) |
| ACP416 (WW0558) | IL2-XL-blocker-L-CD25_213S-X-HSA_(Blocker = VHVL.F2.high.A02_Vh_Q105C_Vl_A43C; X = Linker 2) |
| ACP417 (WW0559) | IL2-XL-blocker-L-CD25_213S-X-HSA_(Blocker = VHVL.F2.high.F03_Vh_G44C_Vl_G100C; X = Linker 2) |
| ACP418 (WW0560) | IL2-XL-blocker-L-CD25_213S-X-HSA_(Blocker = VHVL.F2.high.F03_Vh_Q105C_Vl_A43C; X = Linker 2) |
| ACP419 (WW0561) | IL2-XL-blocker-L-CD25_213S-X-HSA_(Blocker = Hu2TOW91_A; X = Linker 2) |
| ACP420 (WW0562) | IL2-XL-blocker-L-CD25_213S-X-HSA_(Blocker = Hu2TOW91_B; X = Linker 2) |

TABLE 3-continued

CONSTRUCT PERMUTATION TABLE ("6xHis" disclosed as SEQ ID NO: 354)

| Construct Name | Construct Description |
|---|---|
| ACP421 (WW0563) | HSA-X-blocker-L-CD25_213S-LX-IL2_(Blocker = VHVL.F2.high.A02_Vh_G44C_Vl_A46S_G100C; X = Linker 2) |
| ACP422 (WW0564) | HSA-X-blocker-L-CD25_213S-LX-IL2_(Blocker = VHVL.F2.high.A02_Vh_Q105C_Vl_A43C; X = Linker 2) |
| ACP423 (WW0565) | HSA-X-blocker-L-CD25_213S-LX-IL2_(Blocker = VHVL.F2.high.F03_Vh_G44C_Vl_G100C; X = Linker 2) |
| ACP424 (WW0566) | HSA-X-blocker-L-CD25_213S-LX-IL2_(Blocker = VHVL.F2.high.F03_Vh_Q105C_Vl_A43C; X = Linker 2) |
| ACP425 (WW0567) | HSA-X-blocker-L-CD25_213S-LX-IL2_(Blocker = Hu2TOW91_A; X = Linker 2) |
| ACP426 (WW0568) | HSA-X-blocker-L-CD25_213S-LX-IL2_(Blocker = Hu2TOW91_B; X = Linker 2) |
| ACP427 (WW0569) | IL2-X-anti-HSA-LX-Blocker1-L-Blocker2_(Blocker1 = VHVL.F2.high.A02_Vh_G44C_Vl_A46S_G100C, Blocker2 = Hu2TOW91_A; X = Linker 2) |
| ACP428 (WW0570) | IL2-X-anti-HSA-LX-Blocker1-L-Blocker2_(Blocker1 = VHVL.F2.high.A02_Vh_Q105C_Vl_A43C, Blocker2 = Hu2TOW91_A; X = Linker 2) |
| ACP429 (WW0571) | IL2-X-anti-HSA-LX-Blocker1-L-Blocker2_(Blocker1 = VHVL.F2.high.F03_Vh_G44C_Vl_G100C, Blocker2 = Hu2TOW91_A; X = Linker 2) |
| ACP430 (WW0572) | IL2-X-anti-HSA-LX-Blocker1-L-Blocker2_(Blocker1 = VHVL.F2.high.F03_Vh_Q105C_Vl_A43C, Blocker2 = Hu2TOW91_A; X = Linker 2) |
| ACP431 (WW0573) | IL2-X-anti-HSA-LX-Blocker1-L-Blocker2_(Blocker1 = VHVL.F2.high.A02_Vh_G44C_Vl_A46S_G100C, Blocker2 = Hu2TOW91_B; X = Linker 2) |
| ACP432 (WW0574) | IL2-X-anti-HSA-LX-Blocker1-L-Blocker2_(Blocker1 = VHVL.F2.high.A02_Vh_Q105C_Vl_A43C, Blocker2 = Hu2TOW91_B; X = Linker 2) |
| ACP433 (WW0575) | IL2-X-anti-HSA-LX-Blocker1-L-Blocker2_(Blocker1 = VHVL.F2.high.F03_Vh_G44C_Vl_G100C, Blocker2 = Hu2TOW91_B; X = Linker 2) |
| ACP434 (WW0576) | IL2-X-anti-HSA-LX-Blocker1-L-Blocker2_(Blocker1 = VHVL.F2.high.F03_Vh_Q105C_Vl_A43C, Blocker2 = Hu2TOW91_B; X = Linker 2) |
| ACP439 (WW0581) | IL2-X-anti-HSA-LX-blocker_(Blocker = VHVL.F2.high.C07_Vh/Vl; X = Linker 2) |
| ACP440 (WW0582) | IL2-X-anti-HSA-LX-blocker_(Blocker = VHVL.F2.high.C07_Vh/Vl_A46S; X = Linker 2) |
| ACP441 (WW0583) | IL2-X-anti-HSA-LX-blocker_(Blocker = VHVL.F2.high.C07_Vh/Vl_A46L; X = Linker 2) |
| ACP442 (WW0584) | IL2-X-anti-HSA-LX-blocker_(Blocker = VHVL.F2.high.C07_Vh/Vl_A46S_VH44-VL100_disulfide; X = Linker 2) |
| ACP443 (WW0585) | IL2-X-anti-HSA-LX-blocker_(Blocker = VHVL.F2.high.C07_Vh/Vl_A46L_VH44-VL100_disulfide; X = Linker 2) |
| ACP444 (WW0586) | IL2-X-anti-HSA-LX-blocker_(Blocker = VHVL.F2.high.C07_Vh/Vl_VH105-VL43_disulfide; X = Linker 2) |
| ACP445 (WW0587) | IL2-X-anti-HSA-LX-blocker_(Blocker = VHVL.F2.high.A02_Vh-X-Vl_A46L; X = Linker 2) |
| ACP446 (WW0588) | IL2-X-anti-HSA-LX-blocker_(Blocker = VHVL.F2.high.A02_Vh/Vl_A46L; X = Linker 2) |
| ACP447 (WW0589) | IL2-X-anti-HSA-LX-blocker_(Blocker = VHVL.F2.high.A02_Vh/Vl_A46L_VH44-VL100_disulfide; X = Linker 2) |
| ACP451 (WW0615) | IL2-X-anti-HSA-LX-blocker_(Blocker = VHVL.F2.high.A02_Vh/Vl_A46S; X = Linker 3) |
| ACP452 (WW0616) | IL2-X-anti-HSA-LX-blocker_(Blocker = VHVL.F2.high.F03_Vh/Vl; X = Linker 3) |
| ACP453 (WW0617) | IL2-X-anti-HSA-LX-blocker_(Blocker = VHVL.F2.high.A02_Vh/Vl_A46S_VH44-VL100_disulfide; X = Linker 3) |
| ACP454 (WW0618) | IL2-X-anti-HSA-LX-blocker_(Blocker = VHVL.F2.high.A02_Vh/Vl_VH105-VL43_disulfidel; X = Linker 3) |
| ACP455 (WW0619) | IL2-X-anti-HSA-LX-blocker_(Blocker = VHVL.F2.high.F03_Vh/Vl_VH44-VL100_disulfide; X = Linker 3) |
| ACP456 (WW0620) | IL2-X-anti-HSA-LX-blocker_(Blocker = VHVL.F2.high.F03_Vh/Vl_VH105-VL43_disulfideX = Linker 3) |
| ACP457 (WW0621) | IL2-X-anti-HSA-LX-Heavy_blocker_Fab_(Blocker = VH-CH1; X = Linker 3) |
| ACP458 (WW0622) | IgG4_Fc(S228P)-X-IL2-LX-Heavy_blocker_Fab_(Blocker = VH-CH1; X = Linker 3) |

TABLE 3-continued

CONSTRUCT PERMUTATION TABLE ("6xHis" disclosed as SEQ ID NO: 354)

| Construct Name | Construct Description |
|---|---|
| ACP459 (WW0623) | IgG4_Fc(S228P)-X-IL2-LX-Blocker_(Blocker = VHVL.F2.high.A02_Vh\Vl_A46S; X = Linker 3) |
| ACP460 (WW0624) | IgG4_Fc(S228P)-X-IL2-LX-Blocker_(Blocker = VHVL.F2.high.F03_Vh\Vl; X = Linker 3) |
| ACP461 (WW0625) | IgG4_Fc(S228P)-X-IL2-LX-blocker_(Blocker = VHVL.F2.high.A02_Vh/Vl_A46S_VH44-VL100_disulfide; X = Linker 3) |
| ACP462 (WW0626) | IgG4_Fc(S228P)-X-IL2-LX-blocker_(Blocker = VHVL.F2.high.A02_Vh/Vl_VH105-VL43_disulfide1; X = Linker 3) |
| ACP463 (WW0627) | IgG4_Fc(S228P)-X-IL2-LX-blocker_(Blocker = VHVL.F2.high.F03_Vh/Vl_VH44-VL100_disulfide1; X = Linker 3) |
| ACP464 (WW0628) | IgG4_Fc(S228P)-X-IL2-LX-blocker_(Blocker = VHVL.F2.high.F03_Vh/Vl_VH105-VL43_disulfide1; X = Linker 3) |
| ACP465 (WW0629) | mIgG1_Fc-X-IL2-LX-Blocker_(Blocker = VHVL.F2.high.A02_Vh\Vl_A46S; X = Linker 3) |
| ACP466 (WW0630) | mIgG1_Fc-X-IL2-LX-Blocker_(Blocker = VHVL.F2.high.F03_Vh\Vl; X = Linker 3) |
| ACP467 (WW0631) | mIgG1_Fc-X-IL2-LX-blocker_(Blocker = VHVL.F2.high.A02_Vh/Vl_A46S_VH44-VL100_disulfide; X = Linker 3) |
| ACP468 (WW0632) | mIgG1_Fc-X-IL2-LX-blocker_(Blocker = VHVL.F2.high.A02_Vh/Vl_VH105-VL43_disulfide1; X = Linker 3) |
| ACP469 (WW0633) | mIgG1_Fc-X-IL2-LX-blocker_(Blocker = VHVL.F2.high.F03_Vh/Vl_VH44-VL100_disulfide1; X = Linker 3) |
| ACP470 (WW0634) | mIgG1_Fc-X-IL2-LX-blocker_(Blocker = VHVL.F2.high.F03_Vh/Vl_VH105-VL43_disulfide1; X = Linker 3) |
| ACP471 (WW0642) | mIgG1_Fc-X-IL2-LX_Heavy_blocker_Fab_(Blocker = VH-CH1; X = Linker 3) |
| WW0301 | IL2-X-anti-HSA-LL-blocker_(X = Linker1_Blocker = Vh-Vl) |
| WW0353 | IL2-X-mIgG1_Fc-LX-Blocker_(X = Linker1_Blocker = Vh-Vl) |
| WW0355 | IL2-XL-Blocker-X-mIgG1_Fc_(X = Linker1_Blocker = Vh-Vl) |
| WW0365 | IL-2-L-anti-HSA-LX-Blocker_(instead_of_WW0048_IL2-X-anti-HSA-LX-blocker)_(X = Linker1) |
| WW0366 | IL-2-X-anti-HSA_(GeneArt_version_of_WW0061)_(X = Linker1) |
| WW0472 | mIgG1_Fc-X-IL2-LX-Blocker_(Blocker = VHVL.F2.high.A02_Vh-X-Vl_A46S_X = Linker2) |
| WW0473 | mIgG1_Fc-X-IL2-LX-Blocker_(Blocker = VHVL.F2.high.A02_Vh-Vl_A46S_X = Linker2) |
| WW0474 | mIgG1_Fc-X-IL2-LX-Blocker_(Blocker = VHVL.F2.high.F03_Vh-X-Vl_X = Linker2) |
| WW0475 | mIgG1_Fc-X-IL2-LX-Blocker_(Blocker = VHVL.F2.high.F03_Vh-Vl_X = Linker2) |
| WW0476 | mIgG1_Fc-X-IL2-LX-Blocker_(Blocker = Hu2TOW91_B_X = Linker2) |
| WW0477 | mIgG1_Fc-X-IL2-LX-Blocker_(Blocker = Hu3TOW85_A_X = Linker2) |
| WW0641 | anti-HSA-X-human_p40_mouse_p35-XL-Blocker_(Blocker = Vl/Vh_VH105-VL43_disulfide; X = Linker1) |
| WW0649 | anti-HSA-X-human_p40-L-mouse_p35-XL-Blocker_(Blocker = Vl/Vh_X = Linker2) |
| WW0650 | anti-HSA-X-human_p40-L-Human_p35-XL-Blocker_(Blocker = Vl/Vh_X = Linker2) |
| WW0651 | anti-HSA-X-human_p40-L-mouse_p35-XL-Blocker_(Blocker = Vl/Vh_X = Linker3) |
| WW0652 | anti-HSA-X-human_p40-L-Human_p35-XL-Blocker_(Blocker = Vl/Vh_X = Linker3) |
| WW0662 | anti-HSA-X-human_p40-L-mouse_p35-XL-Blocker_(Blocker = Opt1_Hv_D53E_D61E_Vl/Vh_X = Linker2) |
| WW0663 | anti-HSA-X-human_p40-L-human_p35-XL-Blocker_(Blocker = Opt1_Hv_D53E_D61E_Vl/Vh_X = Linker2) |
| WW0664 | anti-HSA-X-human_p40-L-mouse_p35-XL-Blocker_(Blocker = Opt2_Lv_N31E-Hv_D53E_D61E_Vl/Vh_X = Linker2) |
| WW0665 | anti-HSA-X-human_p40-L-human_p35-XL-Blocker_(Blocker = Opt2_Lv_N31E-Hv_D53E_D61E_Vl/Vh_X = Linker2) |
| WW0666 | anti-HSA-X-human_p40-L-mouse_p35-XL-Blocker_(Blocker = Opt3_LV_S30D-Hv_D53E_D61E_Vl/Vh_X = Linker2) |
| WW0667 | anti-HSA-X-human_p40-L-human_p35-XL-Blocker_(Blocker = Opt3_LV_S30D-Hv_D53E_D61E_Vl/Vh_X = Linker2) |
| WW0668 | anti-HSA-X-human_p40-L-mouse_p35-XL-Blocker_(Blocker = Opt4_LV_S30D_N31E_Vl/Vh_X = Linker2) |
| WW0669 | anti-HSA-X-human_p40-L-human_p35-XL-Blocker_(Blocker = Opt4_LV_S30D_N31E_Vl/Vh_X = Linker2) |
| WW0670 | anti-HSA-X-human_p40-L-mouse_p35-XL-Blocker_(Blocker = Opt5_Lv_S30D_N31E-Hv_D53E_D61E_Vl/Vh_X = Linker2) |
| WW0672 | anti-HSA-X-human_p40-L-mouse_p35-XL-Blocker_(Blocker = Opt6_Lv_R27E_T32D(LCharge_16(combo2))_Vl/Vh_X = Linker2) |

TABLE 3-continued

CONSTRUCT PERMUTATION TABLE ("6xHis" disclosed as SEQ ID NO: 354)

| Construct Name | Construct Description |
|---|---|
| WW0673 | anti-HSA-X-human_p40-L-human_p35-XL-Blocker_(Blocker = Opt6_Lv_R27E_T32D(LCharge_16(combo2))_Vl/Vh_X = Linker2) |
| WW0674 | anti-HSA-X-human_p40-L-mouse_p35-XL-Blocker_(Blocker = Opt7_Lv_S30E-Hv_D53E_D61E_Vl/Vh_X = Linker2) |
| WW0675 | anti-HSA-X-human_p40-L-human_p35-XL-Blocker_(Blocker = Opt7_Lv_S30E-Hv_D53E_D61E_Vl/Vh_X = Linker2) |
| WW0676 | anti-HSA-X-human_p40-L-mouse_p35-XL-Blocker_(Blocker = Opt8_Lv_S30E N31E_Vl/Vh_X = Linker2) |
| WW0677 | anti-HSA-X-human_p40-L-human_p35-XL-Blocker_(Blocker = Opt8_Lv_S30E N31E_Vl/Vh_X = Linker2) |
| WW0678 | anti-HSA-X-human_p40-L-mouse_p35-XL-Blocker_(Blocker = Opt9_Lv_N31E-Hv_D53E_Vl/Vh_X = Linker2) |
| WW0679 | anti-HSA-X-human_p40-L-human_p35-XL-Blocker_(Blocker = Opt9_Lv_N31E-Hv_D53E_Vl/Vh_X = Linker2) |
| WW0680 | anti-HSA-X-human_p40-L-mouse_p35-XL-Blocker_(Blocker = Opt1_Hv_D53E_D61E_Vl/Vh_X = Linker3 |
| WW0681 | anti-HSA-X-human_p40-L-human_p35-XL-Blocker_(Blocker = Opt1_Hv_D53E_D61E_Vl/Vh_X = Linker3) |
| WW0682 | anti-HSA-X-human_p40-L-mouse_p35-XL-Blocker_(Blocker = Opt2_Lv_N31E-Hv_D53E_D61E_Vl/Vh_X = Linker3 |
| WW0683 | anti-HSA-X-human_p40-L-human_p35-XL-Blocker_(Blocker = Opt2_Lv_N31E-Hv_D53E_D61E_Vl/Vh_X = Linker3) |
| WW0684 | anti-HSA-X-human_p40-L-mouse_p35-XL-Blocker_(Blocker = Opt3_LV_S30D-Hv_D53E_D61E_Vl/Vh_X = Linker3 |
| WW0685 | anti-HSA-X-human_p40-L-human_p35-XL-Blocker_(Blocker = Opt3_LV_S30D-Hv_D53E_D61E_Vl/Vh_X = Linker3 |
| WW0686 | anti-HSA-X-human_p40-L-mouse_p35-XL-Blocker_(Blocker = Opt4_LV_S30D_N31E_Vl/Vh_X = Linker3 |
| WW0687 | anti-HSA-X-human_p40-L-human_p35-XL-Blocker_(Blocker = Opt4_LV_S30D_N31E_Vl/Vh_X = Linker3) |
| WW0688 | anti-HSA-X-human_p40-L-mouse_p35-XL-Blocker_(Blocker = Opt5_Lv_S30D_N31E-Hv_D53E_D61E_Vl/Vh_X = Linker3 |
| WW0689 | anti-HSA-X-human_p40-L-human_p35-XL-Blocker_(Blocker = Opt5_Lv_S30D_N31E-Hv_D53E_D61E_Vl/Vh_X = Linker3) |
| WW0690 | anti-HSA-X-human_p40-L-mouse_p35-XL-Blocker_(Blocker = Opt6_Lv_R27E_T32D(LCharge_16(combo2))_Vl/Vh_X = Linker3 |
| WW0691 | anti-HSA-X-human_p40-L-human_p35-XL-Blocker_(Blocker = Opt6_Lv_R27E_T32D(LCharge_16(combo2))_Vl/Vh_X = Linker3 |
| WW0692 | anti-HSA-X-human_p40-L-mouse_p35-XL-Blocker_(Blocker = Opt7_Lv_S30E-Hv_D53E_D61E_Vl/Vh_X = Linker3 |
| WW0693 | anti-HSA-X-human_p40-L-human_p35-XL-Blocker_(Blocker = Opt7_Lv_S30E-Hv_D53E_D61E_Vl/Vh_X = Linker3) |
| WW0694 | anti-HSA-X-human_p40-L-mouse_p35-XL-Blocker_(Blocker = Opt8_Lv_S30E_N31E_Vl/Vh_X = Linker3 |
| WW0695 | anti-HSA-X-human_p40-L-human_p35-XL-Blocker_(Blocker = Opt8_Lv_S30E_N31E_Vl/Vh_X = Linker3) |
| WW0698 | anti-HSA-X-human_p40-L-mouse_p35-XL-Fab_Lambda_Blocker_(Blocker = Lambda_Fab_IGLC2-01_X = Linker2) |
| WW0699 | anti-HSA-X-human_p40-L-human_p35-XL-Fab_Lambda_Blocker_(Blocker = Lambda_Fab_IGLC2-01_X = Linker2) |
| WW0700 | anti-HSA-X-human_p40-L-mouse_p35-XL-Fab_Lambda_Blocker_(Blocker = Lambda_Fab_N31E_IGLC2-01_X = Linker2) |
| WW0701 | anti-HSA-X-human_p40-L-human_p35-XL-Fab_Lambda_Blocker_(Blocker = Lambda_Fab_N31E_IGLC2-01_X = Linker2) |
| WW0702 | anti-HSA-X-human_p40-L-mouse_p35-XL-Fab_Lambda_Blocker_(Blocker = Lambda_Fab_S30D_IGLC2-01_X = Linker2) |
| WW0703 | anti-HSA-X-human_p40-L-human_p35-XL-Fab_Lambda_Blocker_(Blocker = Lambda_Fab_S30D_IGLC2-01_X = Linker2) |
| WW0704 | anti-HSA-X-human_p40-L-mouse_p35-XL-Fab_Lambda_Blocker_(Blocker = Lambda_Fab_S30D_N31E_IGLC2-01_X = Linker2) |
| WW0705 | anti-HSA-X-human_p40-L-human_p35-XL-Fab_Lambda_Blocker_(Blocker = Lambda_Fab_S30D_N31E_IGLC2-01_X = Linker2) |

TABLE 3-continued

CONSTRUCT PERMUTATION TABLE ("6xHis" disclosed as SEQ ID NO: 354)

| Construct Name | Construct Description |
|---|---|
| WW0706 | anti-HSA-X-human_p40-L-mouse_p35-XL-Fab_Lambda_Blocker_(Blocker = Lambda_Fab_R27E_T32D_IGLC2-01_X = Linker2) |
| WW0707 | anti-HSA-X-human_p40-L-human_p35-XL-Fab_Lambda_Blocker_(Blocker = Lambda_Fab_R27E_T32D_IGLC2-01_X = Linker2) |
| WW0708 | anti-HSA-X-human_p40-L-mouse_p35-XL-Fab_Lambda_Blocker_(Blocker = Lambda_Fab_S30E_IGLC2-01_X = Linker2) |
| WW0709 | anti-HSA-X-human_p40-L-human_p35-XL-Fab_Lambda_Blocker_(Blocker = Lambda_Fab_S30E_IGLC2-01_X = Linker2) |
| WW0710 | anti-HSA-X-human_p40-L-mouse_p35-XL-Fab_Lambda_Blocker_(Blocker = Lambda_Fab_S30E_N31E_IGLC2-01_X = Linker2) |
| WW0711 | anti-HSA-X-human_p40-L-human_p35-XL-Fab_Lambda_Blocker_(Blocker = Lambda_Fab_S30E_N31E_IGLC2-01_X = Linker2) |
| WW0712 | anti-HSA-X-human_p40-L-mouse_p35-XL-Fab_Lambda_Blocker_(Blocker = Lambda_Fab_IGLC2-01_X = Linker3) |
| WW0713 | anti-HSA-X-human_p40-L-human_p35-XL-Fab_Lambda_Blocker_(Blocker = Lambda_Fab_IGLC2-01_X = Linker3) |
| WW0714 | anti-HSA-X-human_p40-L-mouse_p35-XL-Fab_Lambda_Blocker_(Blocker = Lambda_Fab_N31E_IGLC2-01_X = Linker3) |
| WW0715 | anti-HSA-X-human_p40-L-human_p35-XL-Fab_Lambda_Blocker_(Blocker = Lambda_Fab_N31E_IGLC2-01_X = Linker3) |
| WW0716 | anti-HSA-X-human_p40-L-mouse_p35-XL-Fab_Lambda_Blocker_(Blocker = Lambda_Fab_S30D_IGLC2-01_X = Linker3) |
| WW0717 | anti-HSA-X-human_p40-L-human_p35-XL-Fab_Lambda_Blocker_(Blocker = Lambda_Fab_S30D_IGLC2-01_X = Linker3) |
| WW0718 | anti-HSA-X-human_p40-L-mouse_p35-XL-Fab_Lambda_Blocker_(Blocker = Lambda_Fab_S30D_N31E_IGLC2-01_X = Linker3) |
| WW0719 | anti-HSA-X-human_p40-L-human_p35-XL-Fab_Lambda_Blocker_(Blocker = Lambda_Fab_S30D_N31E_IGLC2-01_X = Linker3) |
| WW0720 | anti-HSA-X-human_p40-L-mouse_p35-XL-Fab_Lambda_Blocker_(Blocker = Lambda_Fab_R27E_T32D_IGLC2-01_X = Linker3) |
| WW0721 | anti-HSA-X-human_p40-L-human_p35-XL-Fab_Lambda_Blocker_(Blocker = Lambda_Fab_R27E_T32D_IGLC2-01_X = Linker3) |
| WW0722 | anti-HSA-X-human_p40-L-mouse_p35-XL-Fab_Lambda_Blocker_(Blocker = Lambda_Fab_S30E_IGLC2-01_X = Linker3) |
| WW0723 | anti-HSA-X-human_p40-L-human_p35-XL-Fab_Lambda_Blocker_(Blocker = Lambda_Fab_S30E_IGLC2-01_X = Linker3) |
| WW0724 | anti-HSA-X-human_p40-L-mouse_p35-XL-Fab_Lambda_Blocker_(Blocker = Lambda_Fab_S30E_N31E_IGLC2-01_X = Linker3) |
| WW0725 | anti-HSA-X-human_p40-L-human_p35-XL-Fab_Lambda_Blocker_(Blocker = Lambda_Fab_S30E_N31E_IGLC2-01_X = Linker3) |
| WW0726 | Fab_Heavy_Blocker_(Blocker = IL-12_Heavy_Fab_IgG1_Fab) |
| WW0727 | Fab_Heavy_Blocker_(Blocker = IL-12_Heavy_Fab_D53E_D61E_IgG1_Fab) |
| WW0728 | Fab_Heavy_Blocker_(Blocker = IL-12_Heavy_Fab_D53E_IgG1_Fab) |
| WW0765 | human_p40-L-mouse_p35-X-anti-HSA-L-Blocker_(Blocker = Opt1_Hv_D53E_D61E_Vl/Vh_X = Linker2) |
| WW0766 | human_p40-L-human_p35-X-anti-HSA-L-Blocker_(Blocker = Opt1_Hv_D53E_D61E_Vl/Vh_X = Linker2) |
| WW0767 | human_p40-L-mouse_p35-X-anti-HSA-L-Blocker_(Blocker = Opt5_Lv_S30D_N31E-Hv_D53E_D61E_Vl/Vh_X = Linker2) |
| WW0768 | human_p40-L-human_p35-X-anti-HSA-L-Blocker_(Blocker = Opt5_Lv_S30D_N31E-Hv_D53E_D61E_Vl/Vh_X = Linker2) |
| WW0769 | human_p40-L-mouse_p35-X-anti-HSA-L-Fab_Lambda_Blocker_(Blocker = Lambda_Fab_IGLC2-01_X = Linker2) |

TABLE 3-continued

CONSTRUCT PERMUTATION TABLE ("6xHis" disclosed as SEQ ID NO: 354)

| Construct Name | Construct Description |
|---|---|
| WW0770 | human_p40-L-human_p35-X-anti-HSA-L-Fab_Lambda_Blocker_(Blocker = Lambda_Fab_IGLC2-01_X = Linker2) |
| WW0771 | human_p40-L-mouse_p35-X-anti-HSA-L-Fab_Lambda_Blocker_(Blocker = Lambda_Fab_S30D_N31E_IGLC2-01_X = Linker2) |
| WW0772 | human_p40-L-human_p35-X-anti-HSA-L-Fab_Lambda_Blocker_(Blocker = Lambda_Fab_S30D_N31E_IGLC2-01_X = Linker2) |
| WW0796 | human_p40-L-mouse_p35-X-anti-HSA-L-Blocker_(Blocker = Opt1_Hv_D53E_D61E_Vl-Vh_X = Linker3) |
| WW0797 | human_p40-L-human_p35-X-anti-HSA-L-Blocker_(Blocker = Opt1_Hv_D53E_D61E_Vl-Vh_X = Linker3) |
| WW0798 | human_p40-L-mouse_p35-X-anti-HSA-L-Blocker_(Blocker = Opt5_Lv_S30D_N31E-Hv_D53E_D61E_Vl-Vh_X = Linker3) |
| WW0799 | human_p40-L-human_p35-X-anti-HSA-L-Blocker_(Blocker = Opt5_Lv_S30D_N31E-Hv_D53E_D61E_Vl-Vh_X = Linker3) |
| WW0800 | human_p40-L-mouse_p35-X-anti-HSA-L-Fab_Lambda_Blocker_(Blocker = Lambda_Fab_IGLC2-01_X = Linker3) |
| WW0801 | human_p40-L-human_p35-X-anti-HSA-L-Fab_Lambda_Blocker_(Blocker = Lambda_Fab_IGLC2-01_X = Linker3) |
| WW0802 | human_p40-L-mouse_p35-X-anti-HSA-L-Fab_Lambda_Blocker_(Blocker = Lambda_Fab_S30D_N31E_IGLC2-01_X = Linker3) |
| WW0803 | human_p40-L-human_p35-X-anti-HSA-L-Fab_Lambda_Blocker_(Blocker = Lambda_Fab_S30D_N31E_IGLC2-01_X = Linker3) |
| WW0643 | HSA-X-mIFNa11-X-HSA_(X = Linker2) |
| WW0644 | HSA-X-mIFNa11-X-HSA_(X = Linker3) |
| WW0645 | HSA-X-Human_IFNA14-X-HSA_(X = Linker2) |
| WW0646 | HSA-X-Human_IFNA14-X-HSA_(X = Linker3) |
| WW0647 | Mouse_IFNA11 |
| WW0648 | Human_IFNA14 |
| WW0781 | HSA-X-Human_IFNA2b_T129E-X-HSA_(X = Linker2) |
| WW0782 | HSA-X-Human_IFNA14_N95D-X-HSA_(X = Linker2) |
| WW0783 | HSA-X-Human_IFNA14_N25D_S27P_N95D-X-HSA_(X = Linker2) |
| WW0784 | Human_IFNA2b_T129E |
| WW0785 | Human_IFNA14_N95D |
| WW0786 | Human_IFNA14_N25D_S27P_N95D |
| WW0815 | mAlb-X-mIFNa1-X-mAlb_(X = Linker3) |
| WW0816 | mAlb-X-mIFNa11-X-mAlb_(X = Linker3) |
| WW0817 | anti-HSA-X-mIFNa1-X-mAlb_(X = Linker3) |
| WW0818 | anti-HSA-X-mIFNa11-mAlb_(X = Linker3) |
| WW0819 | mAlb-X-mIFNa1-X-anti-HSA_(X = Linker3) |
| WW0820 | mAlb-X-mIFNa11-anti-HSA_(X = Linker3) |
| WW0821 | Alb-X-Human_IFNA2b-X-Alb_(X = Linker3) |
| WW0822 | Alb-X-Human_IFNA14-X-Alb_(X = Linker3) |
| WW0831 | Alb-X-IFNa8-X-Alb_(X = Linker3) |
| WW0832 | Alb-X-IFNa16-Alb_(X = Linker3) |
| WW0833 | Anti-HSA-X-IFNa8-X-anti-HSA_(X = Linker3) |
| WW0834 | Anti-HSA-X-IFNa16-x-anti-HSA_(X = Linker3) |
| WW0737 | HSA-X-mIFNb-X-HSA_(X = Linker2) |
| WW0738 | HSA-X-mIFNb-X-HSA_(X = Linker3) |
| WW0739 | HSA-X-mIFNb_C38S-X-HSA_(X = Linker2) |
| WW0740 | HSA-X-mIFNb_C38S-X-HSA_(X = Linker3) |
| WW0741 | HSA-X-Human_IFNB-X-HSA_(X = Linker2) |
| WW0742 | HSA-X-Human_IFNB-X-HSA_(X = Linker3) |
| WW0743 | HSA-X-Human_IFNB_C38S-X-HSA_(X = Linker2) |
| WW0744 | HSA-X-Human_IFNB_C38S-X-HSA_(X = Linker3) |
| WW0745 | Mouse_IFNb |
| WW0746 | Mouse_IFNb_C38S |
| WW0747 | Human_IFNB |
| WW0748 | Human_IFNAB_C38S |
| WW0787 | HSA-X-Human_IFNB_N101Q-X-HSA_(X = Linker2) |
| WW0788 | HSA-X-Human_IFNB_N101Q_C38S-X-HSA_(X = Linker2) |
| WW0789 | Human_IFNB_N101Q |
| WW0790 | Human_IFNB_C38S_N101Q |
| WW0729 | IL2-L-anti-HSA-LL-Heavy_blocker_Fab_(Blocker = VH-CH1_non-cleavable) |
| WW0734 | IL2-X-anti-HSA-LL-Heavy_blocker_Fab_(Blocker = VH-CH1_X = Linker1) |
| WW0735 | IL2-X-anti-HSA-LL-Heavy_blocker_Fab_(Blocker = VH-CH1_X = Linker2) |

TABLE 3-continued

CONSTRUCT PERMUTATION TABLE ("6xHis" disclosed as SEQ ID NO: 354)

| Construct Name | Construct Description |
|---|---|
| WW0736 | IL2-X-anti-HSA-LL-Heavy_blocker_Fab_(Blocker = VH-CH1_X = Linker3) |
| WW0792 | Anti-IL-2_Fab_Heavy_IgG1_Blocker_His_tag |
| WW0061 | IL2-X-anti-HSA_Fusion_(X = Linker1) |
| ACP293 (WW0237) | 3TOW69sdAb |
| ACP294 (WW0238) | 3TOW85sdAb |
| ACP295 (WW0239) | 2TOW91sdAb |
| ACP315 (WW0368) | Hu2TOW91_A |
| ACP316 (WW0369) | Hu2TOW91_B |
| ACP317 (WW0370) | Hu2TOW91_C |
| ACP318 (WW0371) | Hu2TOW91_D |
| ACP319 (WW0372) | HE_LM_2TOW91 |
| ACP320 (WW0373) | HE_L_2TOW91 |
| ACP321 (WW0374) | Hu3TOW85_A |
| ACP322 (WW0375) | Hu3TOW85_B |
| ACP323 (WW0376) | Hu3TOW85_C |
| ACP324 (WW0377) | Hu3TOW85_D |
| ACP325 (WW0378) | HE_LM_3TOW85 |
| ACP326 (WW0379) | HE_L_3TOW85 |
| ACP327 (WW0380) | HE_LM_R45L_3TOW85 |
| ACP328 (WW0381) | Hu3TOW69_A |
| ACP329 (WW0382) | Hu3TOW69_B |
| ACP330 (WW0383) | Hu3TOW69_C |
| ACP331 (WW0384) | Hu3TOW69_D |
| ACP332 (WW0385) | Hu3TOW69_E |
| ACP333 (WW0386) | HE_LM_3TOW69 |
| ACP334 (WW0387) | HE_L_3TOW69 |
| ACP335 (WW0388_ | HE_LM_R45L_3TOW69 |
| ACP360 (WW0438) | Vh-Vl_3xG4S_A46S ("3xG4S" is disclosed as SEQ ID NO: 452) |
| ACP361 (WW0439) | Vh-Vl_3xG4S_A46S ("3xG4S" is disclosed as SEQ ID NO: 452) |
| ACP362 (WW0440) | Vh-X-Vl_X = Linker2 |
| ACP363 (WW0441) | Vh-X-Vl_X = Linker2_A46S |
| ACP364 (WW0442) | VHVL.F2.high.A02_Vh-Vl_3xG4S ("3xG4S" is disclosed as SEQ ID NO: 452) |
| ACP365 (WW0443) | VHVL.F2.high.A02_Vh-Vl_3xG4S_A46S ("3xG4S" is disclosed as SEQ ID NO: 452) |
| ACP366 (WW0444) | VHVL.F2.high.A02_Vh-X-Vl_X = Linker2 |
| ACP367 (WW0445) | VHVL.F2.high.A02_Vh-X-Vl_X = Linker2_A46S |
| ACP368 (WW0446) | VHVL.F2.high.F03_Vh-Vl_3xG4S ("3xG4S" is disclosed as SEQ ID NO: 452) |
| ACP369 (WW0449) | VHVL.F2.high.F03_Vh-X-Vl_X = Linker2 |
| ACP370 (WW0450) | VHVL.F2.high.C07_Vh-Vl_3xG4S ("3xG4S" is disclosed as SEQ ID NO: 452) |

TABLE 3-continued

CONSTRUCT PERMUTATION TABLE ("6xHis" disclosed as SEQ ID NO: 354)

| Construct Name | Construct Description |
|---|---|
| ACP380 (WW0522) | Kappa_blocker_Fab_(Blocker = Kappa) |
| ACP381 (WW0523) | Kappa_blocker_Fab_(Blocker = VHVL.F2.high.A02_A46S_Kappa) |
| ACP382 (WW0524) | Kappa_blocker_Fab_(Blocker = VHVL.F2.high.F03_Kappa) |
| ACP434 (WW0576) | IL2-X-anti-HSA-LX-Blocker1-L-Blocker2_(Blocker1 = VHVL.F2.high.F03_Vh_Q105C_Vl_A43C_Blocker2 = Hu2TOW91_B_X =Linker2) |
| ACP435 (WW0577) | Kappa_blocker1_Fab-L-blocker2_(Blocker1 = VHVL.F2.high.A02_A46S_Kappa_Blocker2 = Hu2TOW91_A) |
| ACP436 (WW0578) | Kappa_blocker1_Fab-L-blocker2_(Blocker1 = VHVL.F2.high.A02_A46S_Kappa_Blocker2 = Hu2TOW91_B) |
| ACP437 (WW0579) | Kappa_blocker1_Fab-L-blocked_(Blocker1 = VHVL.F2.high.F03_Kappa_Blocker2 = Hu2TOW91_A) |
| ACP438 (WW0580) | Kappa_blocker1_Fab-L-blocker2_(Blocker1 = VHVL.F2.high.F03_Kappa_Blocker2 = Hu2TOW91_B) |
| ACP448 (WW0590) | Kappa_blocker_Fab_(Blocker = VHVL.F2.high.C07_A46S_Kappa) |
| ACP449 (WW0591) | Kappa_blocker_Fab_(Blocker = VHVL.F2.high.C07_A46L_Kappa) |
| ACP450 (WW0592) | Kappa_blocker_Fab_(Blocker = VHVL.F2.high.A02_A46L_Kappa) |

Sequence Table

| SEQ ID NO. | Name | Sequence |
|---|---|---|
| 1 | Human IL-2 | MYRMQLLSCI ALSLALVTNS APTSSSTKKT QLQLEHLLLD LQMILNGINN YKNPKLTRML TFKFYMPKKA TELKHLQCLE EELKPLEEVL NLAQSKNFHL RPRDLISNIN VIVLELKGSE TTFMCEYADE TATIVEFLNR WITFCQSIISTLT |
| 2 | Human serum albumin | MKWVTFISLL FLFSSAYSRG VFRRDAHKSE VAHRFKDLGE ENFKALVLIA FAQYLQQCPF EDHVKLVNEV TEFAKTCVAD ESAENCDKSL HTLFGDKLCT VATLRETYGE MADCCAKQEP ERNECFLQHK DDNPNLPRLV RPEVDVMCTA FHDNEETFLK KYLYEIARRH PYFYAPELLF FAKRYKAAFT ECCQAADKAA CLLPKLDELR DEGKASSAKQ GLKCASLQKF GERAFKAWAV ARLSQRFPKA EFAEVSKLVT DLTKVHTECC HGDLLECADD RADLAKYICE NQDSISSKLK ECCEKPLLEK SHCIAEVEND EMPADLPSLA ADFVGSKDVC KNYAEAKDVF LGMFLYEYAR RHPDYSVVLL LRLAKTYETT LEKCCAAADP HECYAKVFDE FKPLVEEPQN LIKQNCELFE QLGEYKFQNA LLVRYTKKVP QVSTPTLVEV SRNLGKVGSK CCKHPEAKRM PCAEDCLSVF LNQLCVLHEK TPVSDRVTKC CTESLVNGRPCFSALEVDETYVPKEFNAETFTFHADICTLSEKERQIKKQTALV ELVKHK PKATKEQLKAVMDDFAAFVEKCCKADDKET CFAEEGKKLVAASQAALGL |
| 45 | ACP12 (IL2 fusion protein) | QVQLQESGGGLVQAGGSLRLSCAASGRIFSIDIMSWYRQAPGKQRELVARITR GGTISYDDSVKGRFTISRDNAKNTVYLQMNSLKPEDTGVYYCNALYGTDYW GKGTQVTVSSggggsggggsggggsaptssstkktqlqlehllldlqmilnginnyknpklrmltfkfympkk atelkhlqcleeelkpleevlnlaqsknfhlrprdlisninvivlelkgsettfmceyadetative flnrwitfcqsiistltSGGPGPAGMKGLPGSEVQLVESGGGLVQPGNSLRLSCAASGFTFSKFGMSWVRQ APGKGLEWVSSISGSGRDTLYAESVKGRFTISRDNAKTTLYLQMNSLRPEDTA VYYCTIGGSLSVSSQGTLVTVSSggggsggggsggggsEVQLVESGGGLVQPGGSLR LSCAASGFTFSSYTLAWVRQAPGKGLEWVAAIDSSSYTYSPDTVRGRFTISRD NAKNSLYLQMNSLRAEDTAVYYCARDSNWDALDYWGQGTTVTVSSGGGGS GGGGSGGGGSDIQMTQSPSSLSASVGDRVTITCKASQNVGTNVGWYQQKPGK APKALIYSASFRYSGVPSRFSGSGSGTDFTLTISSLQPEDFATYYCQQYYTYPYT FGGGTKVEIKHHHHHH |
| 46 | ACP13 (IL2 fusion protein) | QVQLQESGGGLVQAGGSLRLSCAASGRIFSIDIMSWYRQAPGKQRELVARITR GGTISYDDSVKGRFTISRDNAKNTVYLQMNSLKPEDTGVYYCNALYGTDYW GKGTQVTVSSggggsggggsggggsEVQLVESGGGLVQPGGSLRLSCAASGFTFSSY TLAWVRQAPGKGLEWVAAIDSSSYTYSPDTVRGRFTISRDNAKNSLYLQMNS LRAEDTAVYYCARDSNWDALDYWGQGTTVTVSSGGGGSGGGGSGGGGSDI QMTQSPSSLSASVGDRVTITCKASQNVGTNVGWYQQKPGKAPKALIYSASFR |

| SEQ ID NO. | Name | Sequence |
|---|---|---|
| | | YSGVPSRFSGSGSGTDFTLTISSLQPEDFATYYCQQYTYPYTFGGGTKVEIKgg<br>ggsggggsggggsEVQLVESGGGLVQPGNSLRLSCAASGFTFSKFGMSWVRQAPGK<br>GLEWVSSISGSGRDTLYAESVKGRFTISRDNAKTTLYLQMNSLRPEDTAVYYC<br>TIGGSLSVSSQGTLVTVSSSGGPGPAGMKGLPGSaptssstkktqlqlehllldlqmilnginny<br>knpkltrmltkfympkkatelkhlqcleeelkpleevlnlaqsknfhlrprdlisninvivlelk<br>gsettfmceyadetativeflnrwitfcqsiistltHHHHHH |
| 47 | ACP14<br>(IL2 fusion protein)<br>WW0045 | EVQLVESGGGLVQPGGSLRLSCAASGFTFSSYTLAWVRQAPGKGLEWVAAID<br>SSSYTYSPDTVRGRFTISRDNAKNSLYLQMNSLRAEDTAVYYCARDSNWDAL<br>DYWGQGTTVTVSSGGGGSGGGGSGGGGSDIQMTQSPSSLSASVGDRVTITCK<br>ASQNVGTNVGWYQQKPGKAPKALIYSASFRYSGVPSRFSGSGSGTDFTLTISSL<br>QPEDFATYYCQQYTYPYTFGGGTKVEIKggggsggggsggggsggggsggggsSG<br>GPGPAGMKGLPGSaptssstkktqlqlehllldlqmilnginnyknpkltrmltfkfympkkatelkhlqcleee<br>lkpleevlnlaqsknfhlrprdlisninvivlelkgsettfmceyadetativeflnrwitfcqsiistltSGGPGPAGM<br>KGLPGSEVQLVESGGGLVQPGNSLRLSCAASGFTFSKFGMSWVRQAPGKGLE<br>WVSSISGSGRDTLYAESVKGRFTISRDNAKTTLYLQMNSLRPEDTAVYYCTIG<br>GSLSVSSQGTLVTVSSHHHHHH |
| 48 | ACP15<br>(IL2 fusion protein)<br>(WW0047) | EVQLVESGGGLVQPGGSLRLSCAASGFTFSSYTLAWVRQAPGKGLEWVAAID<br>SSSYTYSPDTVRGRFTISRDNAKNSLYLQMNSLRAEDTAVYYCARDSNWDAL<br>DYWGQGTTVTVSSGGGGSGGGGSGGGGSDIQMTQSPSSLSASVGDRVTITCK<br>ASQNVGTNVGWYQQKPGKAPKALIYSASFRYSGVPSRFSGSGSGTDFTLTISSL<br>QPEDFATYYCQQYTYPYTFGGGTKVEIKggggsggggsggggsggggsggggsggggsEV<br>QLVESGGGLVQPGNSLRLSCAASGFTFSKFGMSWVRQAPGKGLEWVSSISGS<br>GRDTLYAESVKGRFTISRDNAKTTLYLQMNSLRPEDTAVYYCTIGGSLSVSSQ<br>GTLVTVSSggggsggggsggggsSGGPGPAGMKGLPGSaptssstkktqlqlehllldlqmilnginn<br>yknpkltrmlifkfympkkatelkhlqcleeelkpleevlnlaqsknfhlrprdlisninvivlelkgsettfmceyadetat<br>iveflnrwitfcqsiistltHHHHHH |
| 49 | ACP16<br>(IL2 fusion protein)<br>(WW0048) | aptssstkktqlqlehllldlqmilnginnyknpkltrmltfkfympkkatelkhlqcleeelkpleevlnlaqsknfhlrpr<br>dlisninvivlelkgsetlfmceyadetativeflnrwitfcqsiistltSGGPGPAGMKGLPGSEVQLVES<br>GGGLVQPGNSLRLSCAASGFTFSKFGMSWVRQAPGKGLEWVSSISGSGRDTL<br>YAESVKGRFTISRDNAKTTLYLQMNSLRPEDTAVYYCTIGGSLSVSSQGTLVT<br>VSSggggsggggsggggsggggsggggsggggsSGGPGPAGMKGLPGSEVQLVESGGGLV<br>QPGGSLRLSCAASGFTFSSYTLAWVRQAPGKGLEWVAAIDSSSYTYSPDTVRG<br>RFTISRDNAKNSLYLQMNSLRAEDTAVYYCARDSNWDALDYWGQGTTVTVS<br>SGGGGSGGGGSGGGGSDIQMTQSPSSLSASVGDRVTITCKASQNVGTNVGWY<br>QQKPGKAPKALIYSASFRYSGVPSRFSGSGSGTDFTLTISSLQPEDFATYYCQQ<br>YTYPYTFGGGTKVEIKHHHHHH |
| 50 | ACP17<br>(IL2 fusion protein) | QVQLQESGGGLVQAGGSLRLSCAASGRIFSIDIMSWYRQAPGKQRELVARITR<br>GGTISYDDSVKGRFTISRDNAKNTVYLQMNSLKPEDTGVYYCNALYGTDYW<br>GKGTQVTVSSggggsggggsggggsaptssstkktqlqlehllldlqmilnginnyknpkltrmltfkympkk<br>atelkhlqcleeelkpleevlnlaqsknfhlrprdlisninvivlelkgsettfmceyadetativeflnrwitfc<br>qsiistltSGGPGPAGMKGLPGSEVQLVESGGGLVQPGNSLRLSCAASGFTFSKFGMSWVRQ<br>APGKGLEWVSSISGSGRDTLYAESVKGRFTISRDNAKTTLYLQMNSLRPEDTA<br>VYYCTIGGSLSVSSQGTLVTVSSggggsggggsggggsggggsggggsggggsSGGPGPAG<br>MKGLPGSEVQLVESGGGLVQPGGSLRLSCAASGFTFSSYTLAWVRQAPGKGL<br>EWVAAIDSSSYTYSPDTVRGRFTISRDNAKNSLYLQMNSLRAEDTAVYYCAR<br>DSNWDALDYWGQGTTVTVSSGGGGSGGGGSGGGGSDIQMTQSPSSLSASVG<br>DRVTITCKASQNVGTNVGWYQQKPGKAPKALIYSASFRYSGVPSRFSGSGSGT<br>DFTLTISSLQPEDFATYYCQQYTYPYTFGGGTKVEIKHHHHHH |
| 51 | ACP18<br>(IL2 fusion protein) | QVQLQESGGGLVQAGGSLRLSCAASGRIFSIDIMSWYRQAPGKQRELVARITR<br>GGTISYDDSVKGRFTISRDNAKNTVYLQMNSLKPEDTGVYYCNALYGTDYW<br>GKGTQVTVSSggggsggggsggggsaptssstkktqlqlehllldlqmilnginnyknpkltrmltfkfympkk<br>atelkhlqcleeelkpleevlnlaqsknfhlrprdlisninvivlelkgsettfmceyadetativeflnrwitf<br>cqsiistltSGGPGPAGMKGLPGSEVQLVESGGGLVQPGNSLRLSCAASGFTFSKFGMSWVRQ<br>APGKGLEWVSSISGSGRDTLYAESVKGRFTISRDNAKTTLYLQMNSLRPEDTA<br>VYYCTIGGSLSVSSQGTLVTVSSggggsggggsggggsggggsggggsggggsEVQLVESG<br>GGLVQPGGSLRLSCAASGFTFSSYTLAWVRQAPGKGLEWVAAIDSSSYTYSPD<br>TVRGRFTISRDNAKNSLYLQMNSLRAEDTAVYYCARDSNWDALDYWGQGTT<br>VTVSSsggpgpagmkglpgsDIQMTQSPSSLSASVGDRVTITCKASQNVGTNVGWY<br>QQKPGKAPKALIYSASFRYSGVPSRFSGSGSGTDFTLTISSLQPEDFATYYCQQ<br>YTYPYTFGGGTKVEIKHHHHHH |
| 52 | ACP19<br>(IL2 fusion protein) | aptssstkktqlqlehllldlqmilnginnyknpkltrmltfkfympkkatelkhlqcleeelkpleevl<br>nlaqsknfhlrprdlisninvivlelkgsettfmceyadetativeflnrwitfcqsiistltSGGPGPAG<br>MKGLPGSggggsggggsggggsggggsggggsggggsEVQLVESGGGLVQPGGSLRLSCAASGFTFSSYTLAWVR<br>QAPGKGLEWVAAIDSSSYTYSPDTVRGRFTISRDNAKNSLYLQMNSLRAEDTA<br>VYYCARDSNWDALDYWGQGTTVTVSSGGGGSGGGGSGGGGSDIQMTQSPSS<br>LSASVGDRVTITCKASQNVGTNVGWYQQKPGKAPKALIYSASFRYSGVPSRFS<br>GSGSGTDFTLTISSLQPEDFATYYCQQYTYPYTFGGGTKVEIKggggsggggsgggg |

-continued

Sequence Table

| SEQ ID NO. | Name | Sequence |
|---|---|---|
| | | gsEVQLVESGGGLVQPGNSLRLSCAASGFTFSKFGMSWVRQAPGKGLEWVSSI<br>SGSGRDTLYAESVKGRFTISRDNAKTTLYLQMNSLRPEDTAVYYCTIGGSLSV<br>SSQGTLVTVSSggggsggggsggggsQVQLQESGGGLVQAGGSLRLSCAASGRIFSID<br>IMSWYRQAPGKQRELVARITRGGTISYDDSVKGRFTISRDNAKNTVYLQMNSL<br>KPEDTGVYYCNALYGTDYWGKGTQVTVSSHHHHHH** |
| 53 | ACP20<br>(IL2 fusion protein)<br>(WW0056) | aptssstkktqlqlehllldlqmilnginnyknpkltrmltfkfympkkatelkhlqcleeelkpleev<br>lnlaqsknfhlrprdlisninvivlelkgsettfmceyadetativeflnrwitfcqsiistltSGGPGPA<br>GGGLVQPGGSLRLSCAASGFTFSSYTLAWVRQAPGKGLEWVAAIDSSSYTYSP<br>GMKGLPGSEVQLVESDTVRGRFTISRDNAKNSLYLQMNSLRAEDTAVYYCARDSNWDALDYWGQGT<br>TVTVSSGGGGSGGGGSGGGGSDIQMTQSPSSLSASVGDRVTITCKASQNVGTN<br>VGWYQQKPGKAPKALIYSASFRYSGVPSRFSGSGSGTDFTLTISSLQPEDFATY<br>YCQQYYTYPYTFGGGTKVEIKHHHHHH |
| 54 | ACP21<br>(IL2 fusion protein)<br>(WW0057) | aptssstkktqlqlehllldlqmilnginnyknpkltrmltfkfympkkatelkhlqcleeelkpleevlnlaqsknfhlrpr<br>dlisninvivlelkgsettfmceyadetativeflnrwitfcqsiistltSGGPGPAGMKGLPGSggggsggggs<br>ggggsggggsggggsEVQLVESGGGLVQPGGSLRLSCAASGFTFSSYTLAWVR<br>QAPGKGLEWVAAIDSSSYTYSPDTVRGRFTISRDNAKNSLYLQMNSLRAEDTA<br>VYYCARDSNWDALDYWGQTTVTVSSGGGGSGGGGSGGGGSDIQMTQSPSS<br>LSASVGDRVTITCKASQNVGTNVGWYQQKPGKAPKALIYSASFRYSGVPSRFS<br>GSGSGTDFTLTISSLQPEDFATYYCQQYYTYPYTFGGGTKVEIKHHHHHH |
| 55 | ACP22<br>(IL2 fusion protein) | aptssstkktqlqlehllldlqmilnginnyknpkltrmltfkfympkkatelkhlqcleeelkpleevlnlaqsknfhlrpr<br>dlisninvivlelkgsettfmceyadetativeflnrwitfcqsiistltSGGPGPAGMKGLPGSggggsggggs<br>ggggsggggsggggsEVQLVESGGGLVQPGGSLRLSCAASGFTFSSYTLAWVR<br>QAPGKGLEWVAAIDSSSYTYSPDTVRGRFTISRDNAKNSLYLQMNSLRAEDTA<br>VYYCARDSNWDALDYWGQTTVTVSSGGGGSGGGGSGGGGSDIQMTQSPSS<br>LSASVGDRVTITCKASQNVGTNVGWYQQKPGKAPKALIYSASFRYSGVPSRFS<br>GSGSGTDFTLTISSLQPEDFATYYCQQYYTYPYTFGGGTKVEIKSGGPGPAGM<br>KGLPGSEVQLVESGGGLVQPGNSLRLSCAASGFTFSKFGMSWVRQAPGKGLE<br>WVSSISGSGRDTLYAESVKGRFTISRDNAKTTLYLQMNSLRPEDTAVYYCTIG<br>GSLSVSSQGTLVTVSSggggsggggsggggsQVQLQESGGGLVQAGGSLRLSCAASG<br>RIFSIDIMSWYRQAPGKQRELVARITRGGTISYDDSVKGRFTISRDNAKNTVYL<br>QMNSLKPEDTGVYYCNALYGTDYWGKGTQVTVSSHHHHHH |
| 56 | ACP23<br>(IL2 fusion protein) | QVQLQESGGGLAQAGGSLSLSCAASGFTVSNSVMAWYRQTPGKQREFVAIIN<br>SVGSTNYADSVKGRFTISRDNAKNTVYLQMNNLKPEDTAVYVCNRNFDRIY<br>WGQGTQVTVSSSGGPGPAGMKGLPGSEVQLVESGGGLVQPGGSLRLSCAASG<br>FTFSSYTLAWVRQAPGKGLEWVAAIDSSSYTYSPDTVRGRFTISRDNAKNSLY<br>LQMNSLRAEDTAVYYCARDSNWDALDYWGQGTTVTVSSGGGGSGGGGSGG<br>GGSDIQMTQSPSSLSASVGDRVTITCKASQNVGTNVGWYQQKPGKAPKALIYS<br>ASFRYSGVPSRFSGSGSGTDFTLTISSLQPEDFATYYCQQYYTYPYTFGGGTKV<br>EIKggggsggggsggggsggggsggggsggggsSGGPGPAGMKGLPGSEVQLVESGGGLVQ<br>PGNSLRLSCAASGFTFSKFGMSWVRQAPGKGLEWVSSISGSGRDTLYAESVKG<br>RFTISRDNAKTTLYLQMNSLRPEDTAVYYCTIGGSLSVSSQGTLVTVSSSGGPGPAGMKG<br>LPGSaptssstldctqlqlehllldlqmilnginnyknpkltrmltfkfympkkatelkhlqcleeelkple<br>evlnlaqsknfhlrprdlisninvivlelkgsettfmceyadetativeflnrwitfcqsiistltHHHHHH |
| 57 | ACP24<br>(IL2 fusion protein)<br>(WW0074) | EVQLVESGGGLVQPGGSLRLSCAASGFTFSSYTLAWVRQAPGKGLEWVAAID<br>SSSYTYSPDTVRGRFTISRDNAKNSLYLQMNSLRAEDTAVYYCARDSNWDAL<br>DYWGQGTTVTVSSGGGGSGGGGSGGGGSDIQMTQSPSSLSASVGDRVTITCK<br>ASQNVGTNVGWYQQKPGKAPKALIYSASFRYSGVPSRFSGSGSGTDFTLTISSL<br>QPEDFATYYCQQYYTYPYTFGGGTKVEIKSGGPGPAGMKGLPGSaptssstkktqlql<br>ehllldlqmilnginnyknpkltrmltfkfympkkatelkhlqcleeelkpleevlnlaqsknf<br>hlrprdlisninvivlelkgsettfmceyadetativeflnrwitfcqsiistltHHHHHH |
| 58 | ACP25<br>(IL2 fusion protein)<br>(WW0075) | EVQLVESGGGLVQPGGSLRLSCAASGFTFSSYTLAWVRQAPGKGLEWVAAID<br>SSSYTYSPDTVRGRFTISRDNAKNSLYLQMNSLRAEDTAVYYCARDSNWDAL<br>DYWGQGTTVTVSSGGGGSGGGGSGGGGSDIQMTQSPSSLSASVGDRVTITCK<br>ASQNVGTNVGWYQQKPGKAPKALIYSASFRYSGVPSRFSGSGSGTDFTLTISSL<br>QPEDFATYYCQQYYTYPYTFGGGTKVEIKggggsggggsggggsggggsggggsggggsSG<br>GPGPAGMKGLPGSaptssstkktqlqlehllldlqmilnginnyknpkftrmltfkfympkkatelkhlqcleee<br>lkpleevlnlaqsknfhlrprdlisninvivlelkgsettfmceyadetativeflnrwitfcqsiistltHHHHHH |
| 59 | ACP26<br>(IL2 fusion protein) | QVQLQESGGGLVQAGGSLRLSCAASGRIFSIDIMSWYRQAPGKQRELVARITR<br>GGTISYDDSVKGRFTISRDNAKNTVYLQMNSLKPEDTGVYYCNALYGTDYW<br>GKGTQVTVSSggggsggggsggggsaptssstkktqlqlehllldlqmilnginnyknpkltrmltfkfympkk<br>atelkhlqcleeelkpleevlnlaqsknfhlrprdlisninvivlelkgsettfmceyadetativeflnrwi<br>tfcqsiistltSGGPGPAGMKGLPGSEVQLVESGGGLVQPGNSLRLSCAASGFTFSKFGMSWVRQ<br>APGKGLEWVSSISGSGRDTLYAESVKGRFTISRDNAKTTLYLQMNSLRPEDTA<br>VYYCTIGGSLSVSSQGTLVTVSSggggsggggsggggsggggsQVQLQQSGAELVRPGT<br>SVKVSCKASGYAFTNYLIEWVKQRPGQGLEWIGVINPGSGGTNYNEKFKGKA<br>TLTADKSSSTAYMQLSSLTSDDSAVYFCARWRGDGYYAYFDVWGAGTTTV |

| SEQ ID NO. | Name | Sequence |
|---|---|---|
| | | SSggggsggggsggggsDIVLTQSPASLAVSLGQRATISCKASQSVDYDGDSYMNWY QQKPGQPPKLLIYAASNLESGIPARFSGSGSGTDFTLNIHPVEEEDAATYYCQQ SNEDPYTFGGGTKLEIKHHHHHHEPEA |
| 60 | ACP27 (IL2 fusion protein) | QVQLQESGGGLVQAGGSLRLSCAASGRIFSIDIMSWYRQAPGKQRELVARITR GGTISYDDSVKGRFTISRDNAKNTVYLQMNSLKPEDTGVYYCNALYGTDYW GKGTQVTVSSggggsggggsggggsaptssstkktqlqlehllldlqmilnginnyknpkltrmltfkfklympkk atelkhlqcleeelkpleevlnlaqsknfhlrprdlisninvivlelkgsettfmceyadetativeflnrwitfc qsiistltSGGPGPAGMKGLPGSEVQLVESGGGLVQPGNSLRLSCAASGFTFSKFGMSWVRQ APGKGLEWVSSISGSGRDTLYAESVKGRFTISRDNAKTTLYLQMNSLRPEDTA VYYCTIGGSLSVSSQGTLVTVSSggggsggggsggggsggggsDIVLTQSPASLAVSLG QRATISCKASQSVDYDGDSYMNWYQQKPGQPPKLLIYAASNLESGIPARFSGS GSGTDFTLNIHPVEEEDAATYYCQQSNEDPYTFGGGTKLEIKggggsggggsggggs QVQLQQSGAELVRPGTSVKVSCKASGYAFTNYLIEWVKQRPGQGLEWIGVIN PGSGGTNYNEKFKGKATLTADKSSSTAYMQLSSLTSDDSAVYFCARWRGDG YYAYFDVWGAGTTVTVSSHHHHHHEPEA |
| 61 | ACP28 (IL2 fusion protein) | aptssstkktqlqlehllldlqmilnginnyknpkltrmltfkfympkkatelkhlqcleeelkpleevlnlaqsk nfhlrprdlisninvivlelkgsettfmceyadetativeflnrwitfcqsiistltSGGPGPAGMKGLPGSggg gsggggsggggsggggsggggsQVQLQQSGAELVRPGTSVKVSCKASGYAFTNYLIEWVKQRP GQGLEWIGVINPGSGGTNYNEKFKGKATLTADKSSSTAYMQLSSLTSDDSAV YFCARWRGDGYYAYFDVWGAGTTVTVSSggggsggggsggggsDIVLTQSPASLAV SLGQRATISCKASQSVDYDGDSYMNWYQQKPGQPPKLLIYAASNLESGIPARF SGSGSGTDFTLNIHPVEEEDAATYYCQQSNEDPYTFGGGTKLEIKggggsggggsgg ggsEVQLVESGGGLVQPGNSLRLSCAASGFTFSKFGMSWVRQAPGKGLEWVSS ISGSGRDTLYAESVKGRFTISRDNAKTTLYLQMNSLRPEDTAVYYCTIGGSLSV SSQGTLVTVSSggggsggggsggggsQVQLQESGGGLVQAGGSLRLSCAASGRIFSID IMSWYRQAPGKQRELVARITRGGTISYDDSVKGRFTISRDNAKNTVYLQMNSL KPEDTGVYYCNALYGTDYWGKGTQVTVSSHHHHHHEPEA |
| 62 | ACP29 (IL2 fusion protein) | aptssstkktqlqlehllldlqmilnginnyknpkltrmltfkfympkkatelkhlqcleeelkpleevlnla qsknfhlrprdlisninvivlelkgsettfmceyadetativeflnrwitfcqsiistltSGGPGPAGMKGLP GSggggsggggsggggsggggsggggsDIVLTQSPASLAVSLGQRATISCKASQSVDYDGDSYMNWYQ QKPGQPPKLLIYAASNLESGIPARFSGSGSGTDFTLNIHPVEEEDAATYYCQQS NEDPYTFGGGTKLEIKggggsggggsggggsQVQLQQSGAELVRPGTSVKVSCKASG YAFTNYLIEWVKQRPGQGLEWIGVINPGSGGTNYNEKFKGKATLTADKSSST AYMQLSSLTSDDSAVYFCARWRGDGYYAYFDVWGAGTTVTVSSggggsggggsg gggsEVQLVESGGGLVQPGNSLRLSCAASGFTFSKFGMSWVRQAPGKGLEWVS SISGSGRDTLYAESVKGRFTISRDNAKTTLYLQMNSLRPEDTAVYYCTIGGSLS VSSQGTLVTVSSggggsggggsggggsQVQLQESGGGLVQAGGSLRLSCAASGRIFSI DIMSWYRQAPGKQRELVARITRGGTISYDDSVKGRFTISRDNAKNTVYLQMN SLKPEDTGVYYCNALYGTDYWGKGTQVTVSSHHHHHHEPEA |
| 63 | IL2Ra | 10 20 30 40 50<br>MDSYLLMWGL LTFIMVPGCQ AELCDDDPPE IPHATFKAMA YKEGTMLNCE<br>60 70 80 90 100<br>CKRGFRRIKS GSLYMLCTGN SSHSSWDNQC QCTSSATRNT TKQVTPQPEE<br>110 120 130 140 150<br>QKERKTTEMQ SPMQPVDQAS LPGHCREPPP WENEATERIY HFVVGQMVYY<br>160 170 180 190 200<br>QCVQGYRALH RGPAESVCKM THGKTRWTQP QLICTGEMET SQFPGEEKPQ<br>210 220 230 240 250<br>ASPEGRPESE TSCLVTTTDF QIQTEMAATM ETSIFTTEYQ VAVAGCVFLL<br>260 270<br>ISVLLLSGLT WQRRQRKSRR TI |
| 64 | IL2Rb | 10 20 30 40 50<br>MAAPALSWRL PLLILLLPLA TSWASAAVNG TSQFTCFYNS RANISCVWSQ<br>60 70 80 90 100<br>DGALQDTSCQ VHAWPDRRRW NQTCELLPVS QASWACNLIL GAPDSQKLTT<br>110 120 130 140 150<br>VDIVTLRVLC REGVRWRVMA IQDFKPFENL RLMAPISLQV VHVETHRCNI<br>160 170 180 190 200<br>SWEISQASHY FERHLEFEAR TLSPGHTWEE APLLTLKQKQ EWICLETLTP<br>210 220 230 240 250<br>DTQYEFQVRV KPLQGEFTTW SPWSQPLAFR TKPAALGKDT IPWLGHLLVG<br>260 270 280 290 300<br>LSGAFGFIIL VYLLINCRNT GPWLKKVLKC NTPDSKFFS QLSSEHGGDV<br>310 320 330 340 350<br>QKWLSSPFPS SSFSPGGLAP EISPLEVLER DKVTQLLLQQ DKVPEPASLS<br>360 370 380 390 400<br>SNHSLTSCFT NQGYFFFHLP DALEIEACQV YFTYDPYSEE DPDEGVAGAP<br>410 420 430 440 450 |

| SEQ ID NO. | Name | Sequence |
|---|---|---|
| | | TGSSPQPLQP LSGEDDAYCT FPSRDDLLLF SPSLLGGPSP PSTAPGGSGA<br>  460      470      480      490      500<br>GEERMPPSLQ ERVPRDWDPQ PLGPPTPGVP DLVDFQPPPE LVLREAGEEV<br>  510      520      530      540      550<br>PDAGPREGVS FPWSRPPGQG EFRALNARLP LNTDAYLSLQ ELQGQDPTHL<br>V |
| 65 | IL2Rg |    10       20       30       40       50<br>MLKPSLPFTS LLFLQLPLLG VGLNTTILTP NGNEDTTADF FLTTMPTDSL<br>   60       70       80       90      100<br>SVSTLPLPEV QCFVFNVEYM NCTWNSSSEP QPTNLTLHYW YKNSDNDKVQ<br>  110      120      130      140      150<br>KCSHYLFSEE ITSGCQLQKK EIHLYQTFVV QLQDPREPRR QATQMLKLQN<br>  160      170      180      190      200<br>LVIPWAPENL TLHKLSESQL ELNWNNRFLN HCLEHLVQYR TDWDHSWTEQ<br>  210      220      230      240      250<br>SVDYRHKFSL PSVDGQKRYT FRVRSRFNPL CGSAQHWSEW SHPIHWGSNT<br>  260      270      280      290      300<br>SKENPFLFAL EAVVISVGSM GLIISLLCVY FWLERTMPRI PTLKNLEDLV<br>  310      320      330      340      350<br>TEYHGNFSAW SGVSKGLAES LQPDYSERLC LVSEIPPKGG ALGEGPGASP<br>  360<br>CNQHSPYWAP PCYTLKPET |
| 66 | ACP04 (human p40/murine p35 IL12 fusion protein) | iwelkkdvyvveldwypdapgemvvltcdtpeedgitwtldqssevlgsgktltiqvkefgdagqytchkggevlshs<br>llllhkkedgiwstdilkdqkepknktflrceaknysgrftcwwlttistdltfsvkssrgssdpqgvtcgaatlsaervrgd<br>nkeyeysvecqedsacpaaeeslpievmvdavhklkyenytssffirdiikpdppknlqlkplknsrqvevsweypdt<br>wstphsyfsltfcvqvqgkskrekkdwftdktsatvicrknasisvraqthyyssswsewasvpcsggggsggggsggggs<br>rvipvsgparclsqsrnllkttddmvktareklkhysctaedidheditrdqtstlktclplelhknesclatretsssttrgs<br>clppqktslmmticlgsiyedlkmyqtefqainaalqnhnhqqiildkgmlvaidelmqslnhngetlrqkppvgead<br>pyrvkmklcillhafstrvvtinrvmgylssaHHHHHH |
| 67 | ACP05 (human p40/murine p35 IL12 fusion protein) | iwelkkdvyvveldwypdapgemvvitcdtpeedgitwadqssevlgsgktltiqvkefgdagqytchkggevlshs<br>llllhkkedgiwstdilkdqkepknktflrceaknysgrftcwwlttistdltfsvkssrgssdpqgvtcgaatlsaervrgd<br>nkeyeysvecqedsacpaaeeslpievmvdavhklkyenytssffirdiikpdppknlqlkplknsrqvevsweypdt<br>wstphsyfsltfcvqvqgkskrekkdwftdktsatvicrknasisvraqthyyssswsewasvpcsggggsggggsgg<br>ggsrnlpvatpdpgmfpclhhsqnllraysnmlqkarqtlefypctseeidhedtkdktstveaclpleltknesclnsre<br>tsfitngsclasrktsfmmalclssiyedlkmyqvefktmnakllmdpkrqifldqnmlavidelmqalnfnsetvpqk<br>ssleepdfyktkiklcillhafriravtidrvmsylnasHHHHHH |
| 68 | ACP06 (human p40/murine p35 IL12 fusion protein) | QSVLTQPPSVSGAPGQRVTISCSGSRSNIGSNTVKWYQQLPGTAPKLLIYYNDQ<br>RPSGVPDRFSGSKSGTSASLAITGLQAEDEADYYCQSYDRYTHPALLFGTGTK<br>VTVLggggsggggsggggsggggsQVQLVESGGGVVQPGRSLRLSCAASGFTFSSYGMHWV<br>RQAPGKGLEWVAFIRYDGSNKYYADSVKGRFTISRDNSKNTLYLQMNSLRAE<br>DTAVYYCKTHGSHDNWGQGTMVTSSggggsggggsggggsggggsggggsggggsSGG<br>PGPAGMKGLPGSiwelkkdvyvveldwypdapgemvvltcdtpeedgitwtldqssevlgsgktltiqvkef<br>gdagqytchkggevlshsllllhkkedgiwstdilkdqkepknktflrceaknysgrftcwwlttistdltfsvkssrgssd<br>pqgvtcgaatlsaervrgdnkeyeysvecqedsacpaaeeslpievmvdavhklkyenytssffirdiikpdppknlql<br>kplknsrqvevsweypdtwstphsyfsltfcvqvqgkskrekkdrvftdktsatvicrknasisvraqthyyssswsew<br>asvpcsggggsggggsggggsggggsrvipvsgparclsqsrnllkttddmvktareklkhysctaedidheditrdqtstlktcl<br>plelhknesclatretsssttrgsclppqktslmmticlgsiyedlkmyqtefqainaalqnhnhqqiildkgmlvaidelm<br>qslnhngetlrqkppvgeadpyrvkmklcillhafstrvvtinrvmgylssaSGGPGPAGMKGLPGSEVQ<br>LVESGGGLVQPGNSLRLSCAASGFTFSKFGMSWVRQAPGKGLEWVSSISGSGR<br>DTLYAESVKGRFTISRDNAKTTLYLQMNSLRPEDTAVYYCTIGGSLSVSSQGT<br>LVTVSSHHHHHHEPEA |
| 69 | ACP07 (human p40/murine p35 IL12 fusion protein) | QSVLTQPPSVSGAPGQRVTISCSGSRSNIGSNTVKWYQQLPGTAPKLLIYYNDQ<br>RPSGVPDRFSGSKSGTSASLAITGLQAEDEADYYCQSYDRYTHPALLFGTGTK<br>VTVLggggsggggsggggsggggsQVQLVESGGGVVQPGRSLRLSCAASGFTFSSYGMHWV<br>RQAPGKGLEWVAFIRYDGSNKYYADSVKGRFTISRDNSKNTLYLQMNSLRAE<br>DTAVYYCKTHGSHDNWGQGTMVTSSggggsggggsggggsggggsggggsggggsSGG<br>PGPAGMKGLPGSiwelkkdvyvveldwypdapgemvvltcdtpeedgitwtldqssevlgsgktltiqvkef<br>gdagqytchkggevlshsllllhkkedgiwstdilkdqkepknktflrceaknysgrftcwwlttistdltfsvkssrgssd<br>pqgvtcgaatlsaervrgdnkeyeysvecqedsacpaaeeslpievmvdavificlkyenytssffirdiikpdppknlql<br>kplknsrqvevsweypdtwstphsyfshfcvqvqgkskrekkdrvftdktsatvicrknasisvraqchyyssswsew<br>asvpcsggggsggggsggggsggggsrvipvsgparclsqsrnllkttddmvktareklkhysctaedidheditrdqtstlktcl<br>plelhknesclatretsssttrgsclppqktslmmticlgsiyedlkmyqtefqainaalqnhnhqqiildkgmlvaidelm<br>qslnhngetlrqkppvgeadpyrvkmlcicillhafstrvvtinrvmgylssaSGGPGPAGMKGLPGSEVQ<br>LVESGGGLVQPGNSLRLSCAASGFTFSKFGMSWVRQAPGKGLEWVSSISGSGR<br>DTLYAESVKGRFTISRDNAKTTLYLQMNSLRPEDTAVYYCTIGGSLSVSSQGT<br>LVTVSSggggsggggsggggsggggsQVQLVESGGGLAQAGGSLSLSCAASGFTVSNSVMA<br>WYRQTPGKQREFVAIINSVGSTNYADSVKGRFTISRDNAKNTVYLQMNNLKP<br>EDTAVYVCNRNFDRIYWGQGTQVTVSSHHHHHHEPEA |

-continued

Sequence Table

| SEQ ID NO. | Name | Sequence |
|---|---|---|
| 70 | ACP08 (human p40/murine p35 IL12 fusion protein) | QVQLQESGGGLAQAGGSLSLSCAASGFTVSNSVMAWYRQTPGKQREFVAIIN SVGSTNYADSVKGRFTISRDNAKNTVYLQMNNLKPEDTAVYVCNRNFDRIY WGQGTQVTVSSggggsggggsggggsQSVLTQPPSVSGAPGQRVTISCSGSRSNIGSN TVKWYQQLPGTAPKLLIYYNDQRPSGVPDRFSGSKSGTSASLAITGLQAEDEA DYYCQSYDRYTHPALLFGTGTKVTVLggggsggggsggggsQVQLVESGGGVVQPG RSLRLSCAASGFTFSSYGMHWVRQAPGKGLEWVAFIRYDGSNKYYADSVKG RFTISRDNSKNTLYLQMNSLRAEDTAVYYCKTHGSHDNWGQGTMVTVSSggg gsggggsggggsggggsggggsggggsSGGPGPAGMKGLPGSiwelkkdvyvveldwypdapgemv vltcdtpeedgitwtldqssevlgsgktltiqvkefgdagqytchkggevlshsllllhkkedgiwstdilkdqkepknktf liceaknysgrftcwwlttistdiffsvkssrgssdpqgvtcgaatlsaervrgdnkeyeysvecqedsacpaaeeslpiev mvdavhklkyenytssffirdiikpdppknlqlkplknsrqvevsweypdtwstphsyfshfcvqvqgkskrekkdr vftdktsatvicrknasisvraqchyyssswseasvpcsggggsggggsggggsrvipvsgparclsqsrnllkttdd mvktareklkhysctaedidheditrdqtstlktclplelhknesclatretsstrgsclppqktslmmticlgsiyedlkm yqtefclainaalqnhnhqqiildkgmlvaidelmqslnhngetlrqkppvgeadpyrvkmklcillhafstrvvtinry mgylssaSGGPGPAGMKGLPGSEVQLVESGGGLVQPGNSLVQLVESGGGLVQPGNSLRLSCAASGFTFSKFG MSWVRQAPGKGLEWVSSISGSGRDTLYAESVKGRFTISRDNAKTTLYLQMNS LRPEDTAVYYCTIGGSLSVSSQGTLVTVSSHHHHHHEPEA |
| 71 | ACP09 (human p40/murine p35 IL12 fusion protein) | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSggggsggggsggggsQSVLTQPPSVSGAPGQRVTISCSGSRSNIGSNTV KWYQQLPGTAPKLLIYYNDQRPSGVPDRFSGSKSGTSASLAITGLQAEDEADY YCQSYDRYTHPALLFGTGTKVTVLggggsggggsggggsQVQLVESGGGVVQPGRS LRLSCAASGFTFSSYGMHWVRQAPGKGLEWVAFIRYDGSNKYYADSVKGRF TISRDNSKNTLYLQMNSLRAEDTAVYYCKTHGSHDNWGQGTMVTVSSggggsg ggggsggggsggggsggggsggggsSGGPGPAGMKGLPGSiwelkkdvyvveldwypdapgemvvltc dtpeedgitwadqssevlgsgktltiqvkefgdagqytchkggevlshslllhldcedgiwstdilkdqkepknktflrce aknysgrftcwwlttistdiffsvkssrgssdpqgvtcgaatlsaervrgdnkeyeysvecqedsacpaaeeslpievmv davhklkyenytssffirdiikpdppknlqlkplknsrqvevsweypdtwstphsyfslifcvqvqgkskrekkdrvftd ktsatvicrknasisvraqthyyssswsewasvpcsggggsggggsggggsrvipvsgparclsqsrnllkttddmvkt areklkhysctaedidheditrdqtstlktclplelhknesclatretsstrgsclppqktslmmticlgsiyedlkmyqtef qainaalqnhnhqqiildkgmlvaidelmqslnhngetlrqkppvgeadpyrvkmklcillhafstrvvtinrvmgyls saHHHHHHEPEA |
| 72 | ACP10 (human p40/murine p35 IL12 fusion protein) | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSSGGPGPAGMKGLPGSiwelkkdvyvveldwypdapgemvvltcdtpeedgitwtl dqssevlgsgktltiqvkefgdagqytchkggevlshsllllhkkedgiwstdilkdqkepknktflrceaknysgrftcw wittistdlifsvkssrgssdpqgvtcgaatlsaervrgdnkeyeysvecqedsacpaaeeslpievmvdavhklkyeny tssffirdiikpdppknlqlkplknsrqvevsweypdtwstphsyfsltfcvqvqgkskrekkdrvftdktsatvicrkna sisvraqthyyssswsewasvpcsggggsggggsggggsrvipvsgparclsqsrnllkttddmvktareklkhyscta edidheditrdqtstlktclplelhknesclatretsstrgsclppqktslmmticlgsiyedlkmyqtefqainaalqnhnh qqiildkgmlvaidelmqslnhngetlrqkppvgeadpyrvkmklcillhafstrvvtinrvmgylssaSGGPGPA GMKGLPGSggggsggggsggggsggggsggggsggggsQSVLTQPPSVSGAPGQRVTISCS GSRSNIGSNTVKWYQQLPGTAPKLLIYYNDQRPSGVPDRFSGSKSGTSASLAIT GLQAEDEADYYCQSYDRYTHPALLFGTGTKVTVLggggsggggsggggsQVQLVES GGGVVQPGRSLRLSCAASGFTFSSYGMHWVRQAPGKGLEWVAFIRYDGSNK YYADSVKGRFTISRDNSKNTLYLQMNSLRAEDTAVYYCKTHGSHDNWGQGT MVTVSSHHHHHHEPEA |
| 73 | ACP11 (human p40/murine p35 IL12 fusion protein) | iwelkkdvyvveldwypdapgemvvltcdtpeedgitwadqssevlgsgktltiqvkefgdagqytchkggevlshs llllhkkedgiwstdilkdqkepknktflrceaknysgrftcwwlttistdltfsvkssrgssdpqgvtcgaatlsaervrgd nkeyeysvecqedsacpaaeeslpievmvdavhklkyenytssffirdiikpdppknlqlkplknsrqvevsweypdt wstphsyfsltfcvqvqgkskrekkdivfldktsatvicrknasisvraqthyyssswsewasvpcsggggsggggsggggsr vipvsgparclsqsrnllkttddmvktareklkhysctaedidheditrdqtstlktclplelhknesclatretsstrgs clppqktslmmticlgsiyedlkmyqtefqainaalqnhnhqqiildkgmlvaidelmqslnhngetlrqkppvgead pyrvkmklcillhafstrvvtinrvmgylssaSGGPGPAGMKGLPGSggggsggggsggggsggggsggg gsggggsQSVLTQPPSVSGAPGQRVTISCSGSRSNIGSNTVKWYQQLPGTAPKLLI YYNDQRPSGVPDRFSGSKSGTSASLAITGLQAEDEADYYCQSYDRYTHPALLF GTGTKVTVLggggsggggsggggsQVQLVESGGGVVQPGRSLRLSCAASGFTFSSYG MHWVRQAPGKGLEWVAFIRYDGSNKYYADSVKGRFTISRDNSKNTLYLQMN SLRAEDTAVYYCKTHGSHDNWGQGTMVTVSSggggsggggsggggsggggsEVQLVESGG GLVQPGNSLRLSCAASGFTFSKFGMSWVRQAPGKGLEWVSSISGSGRDTLYA ESVKGRFTISRDNAKTTLYLQMNSLRPEDTAVYYCTIGGSLSVSSQGTLVTVSS HHHHHHEPEA |
| 74 | IL12 p40 human (Uniprot (Accession No. P29460) | MCHQQLVISW FSLVFLASPL VAIWELKKDV YVVELDWYPD APGEMVVLTC DTPEEDGITH TLDQSSEVLG SGKTLTIQVK EFGDAGQYTC HKGGEYLSHS LLLLHKKEDG IWSTDILKDQ KEPKNKTFLR CEAKNYSGRF TCWWLTTIST |

Sequence Table

| SEQ ID NO. | Name | Sequence |
|---|---|---|
| | | 160 170 180 190 200<br>DLTFSVKSSR GSSDPQGVTC GAATLSAERV RGDNKEYEYS VECQEDSACP<br>210 220 230 240 250<br>AAEESLPIEV MVDAVHKLKY ENYTSSFFIR DIIKPDPPKN LQLKPLKNSR<br>260 270 280 290 300<br>QVEVSWEVPD TWSTPHSYFS LTFCVQVQGK SKRSKKDRVF TDKTSATVIC<br>310 320<br>RKNASISVRA QDRYYSSSWS EWASVPCS |
| 75 | IL12p35 mouse (Uniprot Accession No. P43431) | 10 20 30 40 50<br>MCQSRYLLFL ATLALLNHLS LARVIPVSGP ARCLSQSRNL LKTTDDMVKT<br>60 70 80 90 100<br>AREKLKHYSC TAEDIDHEDI TRDQTSTLKT CLPLELHKNE SCLATRETSS<br>110 120 130 140 150<br>TTRGSCLPPQ KTSLMNTLCL GSIYEDLKMY QTEFQAINAA LQNHNHQQII<br>160 170 180 190 200<br>LDKGMLVAID ELMQSLNHNG ETLRQKPPVG EADPYRVKMK LCILLHAFST<br>210<br>RVVTINRVMG YLSSA |
| 76 | IL12Rb-2 | 10 20 30 40 50<br>MAHIFRGCSL AFMFIIIWLL IKAKIDACKR GDVIVKPSHV ILLGSTVNIT<br>60 70 80 90 100<br>CSLKPROGCF HYSPRNKLIL YKFSRPINFH HGHSLMSQVT GLPLGTTLEV<br>110 120 130 140 150<br>CKLACINSKE IQICGAEIFV GVAPEQPQNL SCIQKGEQGT VACIWERGPD<br>160 170 180 190 200<br>IHLYTEYTLQ LSGPKNLTWQ KQCKDIYCDY LDFGINLTPE SPESNFTAKV<br>210 220 230 240 250<br>IVANSLGSSS SLPSTFIFLD IVRPLPPWDI PIKFQKASVS RCTLYWRDEG<br>260 270 280 290 300<br>IVLLNRLRYR PSNSRLWNMV NVTKAKGRHD LLDLKPFTFY FFQISSKLHL<br>310 320 330 340 350<br>YKGSWSDWSE SLRAQTPEEE PTGMLDVWYM KRHIDYSRQQ ISLFWKNLSV<br>360 370 380 390 400<br>SEARGKILHY QVTLQELTGG KAMIQNITGH ISWITVIPPT GNWAVAVSAA<br>410 420 430 440 450<br>NSKGSSLPTR INIMNLCEAG LLAPRQVSAN SEGMDNILVT WQPPRKDPSA<br>460 470 480 490 500<br>YQEYVVEWRE LHPGGDTQVP LNWLRSRRYN VSALISENIK SYICYEIRVY<br>510 520 530 540 550<br>ALSGDQGGCS SILGNSKHKA PLSGPHINAI TEEKGSILIS WNSIPVQEQM<br>560 570 580 590 600<br>GCLLHYRIYW KERDSNSQPQ LCEIPYRVSQ NSHPINSLQP RVTYVLWMTA<br>610 620 630 640 650<br>LTAAGESSHG NEREECLQGK ANWMAFVAPS ICIAIIMVGI FSTFTFQQKV<br>660 670 680 690 700<br>FVLLAALRPQ NCSREIPDPA NSICAKKYPI AEEKTQLPLD RLLIDWPTPE<br>710 720 730 740 750<br>DPEPLVISEV LHQVIPVFRH PPCENWPQRE KGIQGHQASE KDMMHSASSP<br>760 770 780 790 800<br>PPPRALQAES RQLVELYKVL ESRGSDPKPE NPACPWTVLP AGDLPTHDGY<br>810 820 830 840 850<br>LPSNIDDLES HEAPLADSLE ELEPQHISLS VFPSSSLHPL IFSCGDKLTL<br>860<br>DQLKMRCDSL ML |
| 77 | IL-12Rb1 | 10 20 30 40 50<br>MEPLVTWVVP LLFLFLLSRQ GAACRTSECC FQDPPYPDAD SGSASGPRDL<br>60 70 80 90 100<br>RCYRISSDRY ECSWQYEGPT AGVSHFLRCC LSSGRCCYFA AGSATRLQFS<br>110 120 130 140 150<br>DQAGVSVLYT VTLWVESWAR NQTEKSPEVT LQLYNSVKYE PPLGDIKVSK<br>160 170 180 190 200<br>LAGQLRMEWE TPDNQVGAEV QFRHRTPSSP WKLGDCGPQD DDIESCLCPL<br>210 220 230 240 250<br>EMNVAQKFQL RRRQLGSQGS SWSKWSSPVC VPPENPPQPQ VRESVEQLGQ<br>260 270 280 290 300<br>DGRRRLTLKE QPTQLELPEG CQGLAPGIEV TYRLQHMLS CPCKAKATRT<br>310 320 330 340 350<br>LHLGKMPYLS GAAYNVAVIS SNQFGPGLNQ TWHIPADTHT EPVALNISVG<br>360 370 380 390 400<br>TNGTTMYWPA RAQSMTYCIE NQPVGQDGGL ATCSLTAPQD PDPAGMATYS |

Sequence Table

| SEQ ID NO. | Name | Sequence |
|---|---|---|
| | | 410 420 430 440 450<br>WSRESGAMGQ EKCYYITIFA SAHPEKLTLW STVLSTYKFG GNASAAGTPH<br>460 470 480 490 500<br>HVSVKNHSLD SVSVDWAPSL LSTCPGVLKE YVVRCRDEDS KQVSEHPVQP<br>510 520 530 540 550<br>TETQVTLSGL RAGVAYTQV RADTAWLRGV WSQPQRFSIE VQVSDWLIFF<br>560 570 580 590 600<br>ASLGSFLSIL LVGVLGYLGL NRAARHLCPP LPIPCASSAI EEPGGKETWQ<br>610 620 630 640 650<br>WINPVDFQEE ASLQEALVVE MSWDKGERTE PLEKTELPEG APELALDTEL<br>660<br>SLEDGDRCKA KM |
| 78 | IL-12p35 human (Uniprot accession no. P29459) | 10 20 30 40 50<br>MCHQQLVISW FSLVFLASPL VAIWELKKDV YVVELDWYPD APGEMVVLTC<br>60 70 80 90 100<br>DTPEEDDITW TLDQSSEVLG SGKTLTIQVK EFGDAGQYTC HKGGEVLSHS<br>110 120 130 140 150<br>LLLLHKKEDG IWSTDILKDQ KEPKNKTFLR CEAKNYSGRF TCWWLTTIST<br>160 170 180 190 200<br>DLTFSVKSSR GSSDPQGVTC GAATLSAERV RDGNKEYEYS VECQEDSACP<br>210 220 230 240 250<br>AAEESLPIEV MVDAVHKLYK ENYTSSFFIR DIIKPDPPKN LQLKPLKNSR<br>260 270 280 290 300<br>QVEVSWEYPD TWSTPHSYFS LTFCVQVQGK SKREKKDRVF TDKTSATVIC<br>310 320<br>RKNASISVRA QDRYYSSSWS EWASVPCS |
| 79 | IL-12p40 mouse (Uniprot accession no. P43432) | 10 20 30 40 50<br>MCPQKLTISW FAIVLLVSPL MAMWELEKDV YVVEVDWTPD APGETVNLTC<br>60 70 80 90 100<br>DTPEEDDITW TSDQRHGVIG SGKTLTITVK ELFDAGQYTC HKGGETLSKS<br>110 120 130 140 150<br>HLLLHKKENG IWSTEILKNF KNKTFLKCEA PNYSGRFTCS WLVQRNMDLK<br>160 170 180 190 200<br>FNIKSSSSSP DSRAVTCGMA SLSAEKVTLD QRDYEKYSVS CQEDVTCPTA<br>210 220 230 240 250<br>EETLPIELAL EARQQNKYEN YSTSFFIRDI IKPDPPKNLQ MKPLKNSQVE<br>260 270 280 290 300<br>VSWEYPDSWS TPHSYFSLKF FVRIQRKKEK MKETEEGCNQ KGAFLVEKTS<br>310 320 330<br>TEVQCKGGNV CVQAQDRYYN SSCSKWACVP CRVRS |
| 80 | ACP01 (mouse IFNg fusion protein) | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSGGPGPAGMKGLPGShgtvieslesInnyfnssgidveekslfldiwrnwqkdgdm<br>kilqsqiisfylrlfevlkdnqaisnnisvieshlittffsnskakkdafmsiakfevnnpqvqrqafnelirvvh<br>celpessLrkrkrsrcSGGPGPAGMKGLPGSEVQLVESGGGLVQPGNSLRLSCAASGFTFSKFG<br>MSWVRQAPGKGLEWVSSISGSGRDTLYAESVKGRFTISRDNAKTTLYLQMNS<br>LRPEDTAVYYCTIGGSLSVSSQGTLVTVSSHHHHHH |
| 81 | ACP02 (mouse IFNg fusion protein) | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSGGPGPAGMKGLPGShgtvieslesInnyfnssgidveekslfldiwrnwqkdgdmkilqsqiis<br>fylrlfevlkdnqaisnnisvieshlittffsnskakkdafmsiakfevnnpqvqrqafnelirvvhqllpessIr<br>krkrsrcSGGPGPAGMKGLPGShgtvieslesInnyfnssgidveekslfldiwrnwqkdgdmkilqsqiisf<br>ylrlfevlkdnqaisnnisvieshlittffsnskakkdafmsiakfevnnpqvqrqafnelirvvhqllpess<br>likrkrsrcSGGPGPAGMKGLPGSEVQLVESGGGLVQPGNSLRLSCAASGFTFSKFGMSWVR<br>QAPGKGLEWVSSISGSGRDTLYAESVKGRFTISRDNAKTTLYLQMNSLRPEDT<br>AVYYCTIGGSLSVSSQGTLVTVSSHHHHHH |
| 82 | ACP03 (mouse IFNg fusion protein) | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSGGPGPAGMKGLPGShgtvieslesInnyfnssgidveekslfldiwrnwqkdgdmilqsqiis<br>kfylrlfevlkdnqaisnnisvieshlittffsnskaldcdafmsiakfevnnpqvqrqafnelirvvhqllpessIr<br>krkrsrcggggsggggsggggshgtvieslesInnyfnssgidveekslfldiwrnwqkdgdmkilqsqiisfylrlfevl<br>kdnqaisnnisvieshlittffsnskaldcdafmsiakfevnnpqvqrqafnelirvvhqllpessIrkrkrsrcSGGPGP<br>AGMKGLPGSEVQLVESGGGLVQPGNSLRLSCAASGFTFSKFGMSWVRQAPGK<br>GLEWVSSISGSGRDTLYAESVKGRFTISRDNAKTTLYLQMNSLRPEDTAVYYC<br>TIGGSLSVSSQGTLVTVSSHHHHHH |
| 83 | Human IFN-g | 10 20 30 40 50<br>MKYTSYILAF QLCIVLGSLG CYCQDPYVKE AENLKKYFNA GHSDVADNGT |

Sequence Table

| SEQ ID NO. | Name | Sequence |
|---|---|---|
| | (Uniprot Accession No. P01579) | LFLGILKNWK EESDRKIMQS QIVSFYFKLF KNFKDDQSIQ KSVETIKEDM NVKFFNSNKK KRDDFEKLTN YSVTDLNVQR KAIHELIQVM AELSPAAKTG KRKRSQMLFR GRRASQ (positions 60–166) |
| 84 | Mouse IFNg (Uniprot Accession No. P01580) | MNATHCILAL QLFLMAVSGC YCHGTVIESL ESLNNYFNSS GIDVEEKSLF LDIWRNQQKD GDMKILQSQI ISFYLRLFEV LKDNQAISNN ISVIESHLIT TFFSNSKAKK DAFMSIAKFE VNNPQVQRQA FNELIRVVHQ LLPESSLRKR KRSRC |
| 85 | ACP30 (mouse IFNg fusion protein) | mdmrvpaqllglllwlrgarcEVQLVESGGGLVQPGNSLRLSCAASGFTFSKFGMSWVR QAPGKGLEWVSSISGSGRDTLYAESVKGRFTISRDNAKTTLYLQMNSLRPEDT AVYYCTIGGSLSVSSQGTLVTVSSSGGPGPAGMKGLPGShgtviesleslnnyfnssgidv eekslfldiwrnwqkdgdmkilqsqiisfylrlfevlkdnqaisnnisvieshlittffsnskaldcdafmsiakfevnnpq vqrqafnelirvvhqllpesslrkrkrsrcSGGPGPAGMKGLPGSEVQLVESGGGLVQPGNSLR LSCAASGFTFSKFGMSWVRQAPGKGLEWVSSISGSGRDTLYAESVKGRFTISR DNAKTTLYLQMNSLRPEDTAVYYCTIGGSLSVSSQGTLVTVSSSGGPGPAGM KGLPGShgtviesleslnnyfnssgidveekslfldiwrnwqkdgdmkilqsqiisfylrlfevlkdnqaisnnisvie shlittffsnskakkdafmsiakfevnnpqvqrqafnelirvvhcillpesslikrkrsrcSGGPGPAGMKGLPG SEVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSHHHHHH |
| 86 | ACP31 (mouse IFNa1 fusion protein) | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSSGGPGPAGMKGLPGScdlpqthnlinkraltlkqmrrlsplsclkdrkdfgfpqekvd aqqikkagaipvlseltqqilniftskdssaawnttlldsfendlhqqlndlqgclmqqvgvqefpltqedallavrkyfhri tvylrekkhspcawevvraevwralssanvlgrlreekSGGPGPAGMKGLPGSEVQLVESGGGL VQPGNSLRLSCAASGFTFSKFGMSWVRQAPGKGLEWVSSISGSGRDTLYAESV KGRFTISRDNAKTTLYLQMNSLRPEDTAVYYCTIGGSLSVSSQGTLVTVSSHH HHHEPEA |
| 87 | ACP32 (mouse IFNa1 fusion protein) | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSSGGPGPAGMKGLPGScdlpqthnlinkraltlkqmrrlsplsclkdrkdfgfpqekvd aqqikkagaipvlseltqqilniftskdssaawnttlldsfendlhqqlndlqgclmqqvgvqefpltqedallavrkyfhri tvylrekkhspcawevvraevwralsssanvSGGPGPAGMKGLPGSEVQLVESGGGLVQPGN SLRLSCAASGFTFSKFGMSWVRQAPGKGLEWVSSISGSGRDTLYAESVKGRFT ISRDNAKTTLYLQMNSLRPEDTAVYYCTIGGSLSVSSHHHHHE PEA |
| 88 | IFNgR1 | MALLFLLPLV MQGVSRAEMG TADLGPSSVP TPTNVTIESY NMNPIVYWEY QIMPQVPVFT VEVKNYGVKN SEWIDACINI SHYYCNISDH VGDPSNSLWV RVKARVGQKE SAYAKSEEFA VCRDGKIGPP KLDIRKEEKQ IMIDIFHPSV FVNGDEQEVD YDPETTCYIR VYNVYVRMNG SEIQYKILTQ KEDDCDEIQC QLAIPVSSLN SQYCVSAEGV LHVWGVTTEK SKEVCITIFN SSIKGSLWIP VVAALLLFLV LSLVFICFYI KKINPLKEKS IILPKSLISV VRSAILETKP ESKYVSLITS YQPFSLEKEV VCEEPLSPAT VPGMHTEDNP QKVEHTEELS SITEVVTTEE NIPDVVPGSH LTPIERESSS PLSSNQSEPG SIALMSYHSR NCSESDHSRN GFDTSSCLE SHSSLSDSEF PPNNKGEIKT EGQELITVIK APTSFGYDKP HVLVDLLVDD SGKESLTGYR PTEDSKEFS |
| 89 | IFNgR2 | MRPTLLWSLL LLLGVFAAAA AAPPDPLSQL PAPQHPKIRL YNAEQVLSWE PVALSNSTRP VVYQVQFKYI DSKWFTADIM SIGVNCTQIT ATECDFTAAS PSAGFPMDFN VTLRLRAELG ALHSAWVTMP WFQHYRNVTV GPPENIEVTP |

Sequence Table

| SEQ ID NO. | Name | Sequence |
|---|---|---|
| | | 160 170 180 190 200<br>GEGSLIIRFS SPFDIADTST AFFCYYVHYW EKGGIQQVKG PFRSNSISLD<br>210 220 230 240 250<br>NLKPSRVYCL QVQAQLLWNK SNIFRVGHLS NISCYEIMAD ASTELQQVIL<br>260 270 280 290 300<br>ISVGTFSLLS VLAGACFFLV LKYRGLIKYW FHTPPSIPLQ IEEYLKDPTQ<br>310 320 330<br>PILEALDKDS SPKDDVWDGV SIISFPEKEQ EDVLQTL |
| 90 | ACP51 Mouse IFG fusion protein | QVQLQESGGGLVQAGGSLRLSCAASGRIFSIDIMSWYRQAPGKQRELVARITR GGTISYDDSVKGRFTISRDNAKNTVYLQMNSLKPEDTGVYYCNALYGTDYW GKGTQVTVSSggggsggggsggggsEVQLVESGGGLVQPGNSLRLSCAASGFTFSKF GMSWVRQAPGKGLEWVSSISGSGRDTLYAESVKGRFTISRDNAKTTLYLQMN SLRPEDTAVYYCTIGGSLSVSSQGTLVTVSSSGGPGPAGMKGLPGShgtvieslesln nyfnssgidveeskslfldiwrnwqkdgdmkilqsqiisfylrlfevlkdnqaisnnisvieshlittffsnskakkdafmsi akfevnnpqvqrqafnelirvvhqllpessLrkrkrsrcSGGPGPAGMKGLPGSEVQLVESGGGLV QPGNSLRLSCAASGFTFSKFGMSWVRQAPGKGLEWVSSISGSGRDTLYAESVK GRFTISRDNAKTTLYLQMNSLRPEDTAVYYCTIGGSLSVSSQGTLVTVSSHHH HHH |
| 91 | ACP52 Mouse IFG fusion protein | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSSGGPGPAGMKGLPGShgtvieslesInnyfnssgidveekslfldiwrnwqkdgdm kilqsqiisfylrlfevlkdnqaisnnisvieshlittffsnskakkdafmsiakfevnnpqvqrqafnelirvvhq llpessLrkrkrsrcSGGPGPAGMKGLPGSEVQLVESGGGLVQPGNSLRLSCAASGFTFSKFG MSWVRQAPGKGLEWVSSISGSGRDTLYAESVKGRFTISRDNAKTTLYLQMNS LRPEDTAVYYCTIGGSLSVSSQGTLVTVSSSGGPGPAGMKGLPGSEVQLVESG GGLVQPGNSLRLSCAASGFTFSKFGMSWVRQAPGKGLEWVSSISGSGRDTLY AESVKGRFTISRDNAKTTLYLQMNSLRPEDTAVYYCTIGGSLSVSSQGTLVTV SSggggsggggsggggsQVQLQESGGGLVQAGGSLRLSCAASGRIFSIDIMSWYRQA PGKQRELVARITRGGTISYDDSVKGRFTISRDNAKNTVYLQMNSLKPEDTGVY YCNALYGTDYWGKGTQVTVSSHHHHHH |
| 92 | ACP53 Mouse IFG fusion protein | eahkseiahryndlgeqhfkglvliafsqylqkcsydehaklvqevtdfaktcvadesaancdkslhtlfgdklcaipnlr enygeladcctkqepemecflqlikddnpslppferpeaeamctsfkenpttfmghylhevarrlipyfyapellyyaeq yneiltqccaeadkescltpkldgvkekalvssvrqrmkcssmqkfgerafkawavarlsqtfpnadfaeitklatdltkv nkecchgdllecaddraelakymcenqatissklqtccdkpllkkahclsevehdtmpadlpaiaadfVedqevckny aeakdvflgtflyeyssrrhpdysvslllrlakkyeatlekccaeanppacygtvlaefqplveepknlvktncdlyeklgey gfqnailvrytqkapqvstpUveaamlgrvgtkcctlpedqrlpcvedylsailnrvcllhektpvsehvtkccsgslver rpcfsaltvdetyvpkefkaetftflisdictlpekekqikkqtalaelvkhkpkataeqlktvmddfaqfldtcckaadkdt cfstegpnlvtrckdalaSGGPGPAGMKGLPGShgtvieslesIinymyfiiissgidveekslfldiwrnwqkdgdmkilqsq iisfylrlfevlkdiiiqaismiisvieshlittffsiiiskakkdafmsiakfevmipqvqrqafnelirvvliqllpes slrkrkrsrcSGGPGPAGMKGLPGSeahkseiahiyndlgeqhfkglvliafsqylqkcsydehaklvqevtd faktcvadesaancdkslhtlfgdklcaipnlrenygeladcctkqepemecflqhkddnpslppferpeaeamctslk enpttfmghylhevarrhpyiyapellyyaeqyneiltqccaeadkescltpkldgvkekalvssvrqrmkcssmqkf gcrafkawavarlsqtfpnadfaeitklatdltkvnkecchgdllecaddrackikymccnqatissklqtccdkpllkka hclsevehdtmpadlpaiaadfVedqevcknyaeakdvflgtflyeyssrrhpdysvslllrlakkyeatlekccaeanpp acygtvlaefqplveepknlvktncdlyeklgeygfqnailvrytqkapqvstpUveaamlgrvgtkcctlpedqrlpcv edylsailnrvcllhcktpvsehvtkccsgslverrpcfsaltvdetyvpkefkaetftnisdictlpekekqikkqtalaelv klikpkalaeqlktvmddfaqfldtcckaadkdtcfstegpulvtrckdalaHHHHHH |
| 93 | ACP54 Mouse IFG fusion protein | eahkseiahiyndlgeqhfkglvliafsqylqkcsydehaklvqevtdfaktcvadesaancdkslhtlfgdklcaipnlr enygeladcctkqepemecflqhkddnpslppferpeaeamctsfkenpttfmghylhevarrhpyfyapellyyaeq yneiltqccaeadkescltpkldgvkekalvssviqrmkcssmqkfgerafkawavarlsqtfpnadfaeitklatdltkv nkecchgdllecaddraelakymcenqatissklqtccdkpllkkahclsevehdtmpadlpaiaadfVedqevckny aeakdvflgtflyeyssrrhpdysvslllrlakkyeatlekccaeanppacygtvlaefqplveepkiilvktncdlyeklgey gfqnailviytqkapqvstptiveaaarnlgrvgtkcctlpedqrlpcvedylsailmvcllhektpvsehvtkccsgslver rpcfsaltvdetyvpkefkaetftfhsdictlpekekqikkqtalaelvkhkpkataeqlktvmddfaqfldtcckaadkdt cfstegpnlvtrckdalaSGGPGPAGMKGLPGShgtviesleslIiinyfussgidveekslfldiwrnwqkdg mkilqsqiisfylrlfevlkdnqaismiisvieshlittffsnskakkdafnisiakfevmipqvqrqafnelirvvhqllpes slrkrkrsrcgggggsggggsggggshgtvieslesInnyfnssgidveekslfldiwmwqkdgdmkilqsqiisfylrlf evlkdnqaisnnisvieshlittffsnskakkdafmsiakfevnnpqvqrqafnelirvvhqllpesslrkrkrsrcSGGP GPAGMKGLPGSeahkseiahiyndlgeqhfkglvliafsqylqkcsydehaklvqevtdfaktcvadesaanc dkslhtlfgdklcaipiilrenygeladcclkqepeniecflqhkddnpslppferpeaeamctsfkenpttfmghylhev arrhpyfyapellyyaeqyneiltqccaeadkescltpkldgvkekalvssvrqnnkcssmqkfgerafkawavarlsq tfpnadfaeitklatdltkvnkecchgdllecaddraelakymcenqatissklqtccdkpllkkahclsevehdtmpadl paiaadfvedqevckiiyaeakdvflgtflyeyssrrhpdysvslllrlakkyeatlekccaeanppacygtvlaefqplvee pknlvktncdlyeklgeygfqnailviytqkapqvstptIveaamlgrvgtkcctlpedqrlpcvedylsailnrvcllhe ktpvsehvtkccsgslverrpcfsaltvdetyvpkefkaetftfhsdictlpekekqikkqtalaelvkhkpkataeqlktv mddfaqfldtcckaadkdtcfstegpnlvtrckdalaHHHHHH |
| 94 | ACP50 Mouse | mdmrvpaqllglllwlrgarcQVQLQESGGGLVQAGGSLRLSCAASGRIFSIDIMSWYR QAPGKQRELVARITRGGTISYDDSVKGRFTISRDNAKNTVYLQMNSLKPEDTG |

Sequence Table

| SEQ ID NO. | Name | Sequence |
|---|---|---|
|  | IFG fusion protein | VYYCNALYGTDYWGKGTQVTVSSggggsggggsggggsEVQLVESGGGLVQPGNSLRLSCAASGFTFSKFGMSWVRQAPGKGLEWVSSISGSGRDTLYAESVKGRFTISRDNAKTTLYLQMNSLRPEDTAVYYCTIGGSLSVSSQGTLVTVSSSGGPGPAGMKGLPGShgtvieslesinnyfrissgidveekslfldiwrnwqkdgdmkilqsqiisfylrlfevlkdnqaisnnisvieshlittffsnskaldcdafmsiakfevnnpqvqrqafnelirvvhqllpesslitcrlcrsreggggsggggsggggshgtvieslesinnyfussgidveekslfldiwrnwqkdgdmkilqsqiisfylrlfevlkdnqaisnnisvieshlittffsnskaklulafmsiakfevnnpqvqrqafnelirvvhqllpesslrkrkrsrcSGGPGPAGMKGLPGSEVQLVESGGGLVQPGNSLRLSCAASGFTFSKFGMSWVRQAPGKGLEWVSSISGSGRDTLYAESVKGRFTISRDNAKTTLYLQMNSLRPEDTAVYYCTIGGSLSVSSQGTLVTVSSHHHHHH |
| 95 | ACP55 Mouse IFG fusion protein | mdmrvpaqllglllwlrgarcEVQLVESGGGLVQPGNSLRLSCAASGFTFSKFGMSWVRQAPGKGLEWVSSISGSGRDTLYAESVKGRFTISRDNAKTTLYLQMNSLRPEDTAVYYCTIGGSLSVSSQGTLVTVSSSGGPGPAGMKGLPGShgtvieslesinnyfnssgidveekslfldiwrnwqkdgdmkilqsqiisfylrlfevlkdnqaisnnisvieshlittffsnskaldcdafmsiakfevnnpqvqrqafnelirvvhqllpesslrkrkrsrcSGGPGPAGMKGLPGSEVQLVESGGGLVQPGNSLRLSCAASGFTFSKFGMSWVRQAPGKGLEWVSSISGSGRDTLYAESVKGRFTISRDNAKTTLYLQMNSLRPEDTAVYYCTIGGSLSVSSQGTLVTVSSSGGPGPAGMKGLPGShgtvieslesinnyfrissgidveekslfldiwrnwqkdgdmkilqsqiisfylrlfevlkdnqaisnnisvieshlittffsnskakkdafmsiakfevnnpqvqrqafnelirvvhqllpesslrkrkrsrcSGGPGPAGMKGLPGSEVQLVESGGGLVQPGNSLRLSCAASGFTFSKFGMSWVRQAPGKGLEWVSSISGSGRDTLYAESVKGRFTISRDNAKTTLYLQMNSLRPEDTAVYYCTIGGSLSVSSQGTLVTVSSHHHHHH |
| 96 | ACP56 Mouse IFG fusion protein | mdmrvpaqllglllwlrgarcQVQLQESGGGLAQAGGSLSLSCAASGFTVSNSVMAWYRQTPGKQREFVAIINSVGSTNYADSVKGRFTISRDNAKNTVYLQMNNLKPEDTAVYYCNRNFDRIYWGQGTQVTVSSggggsggggsggggsEVQLVESGGGLVQPGNSLRLSCAASGFTFSKFGMSWVRQAPGKGLEWVSSISGSGRDTLYAESVKGRFTISRDNAKTTLYLQMNSLRPEDTAVYYCTIGGSLSVSSQGTLVTVSSSGGPGPAGMKGLPGShgtvieslesinnyfrissgidveekslfldiwrnwqkdgdmkilqsqiisfylrlfevlkdnqaisnnisvieshlittffsnskakkdafmsiakfevnnpqvqrqafnelirvvhqllpesslrkrkrsrcSGGPGPAGMKGLPGSEVQLVESGGGLVQPGNSLRLSCAASGFTFSKFGMSWVRQAPGKGLEWVSSISGSGRDTLYAESVKGRFTISRDNAKTTLYLQMNSLRPEDTAVYYCTIGGSLSVSSQGTLVTVSSHHHHHHEPEA |
| 97 | ACP57 Mouse IFG fusion protein | mdmrvpaqllglllwlrgarcEVQLVESGGGLVQPGNSLRLSCAASGFTFSKFGMSWVRQAPGKGLEWVSSISGSGRDTLYAESVKGRFTISRDNAKTTLYLQMNSLRPEDTAVYYCTIGGSLSVSSQGTLVTVSSSGGPGPAGMKGLPGShgtvieslesinnyfnssgidveekslfldiwrnwqkdgdmkilqsqiisfylrlfevlkdnqaisnnisvieshlittffsnskaldcdafmsiakfevnnpqvqrqafnelirvvhqllpesslrkrkrsrcSGGPGPAGMKGLPGSEVQLVESGGGLVQPGNSLRLSCAASGFTFSKFGMSWVRQAPGKGLEWVSSISGSGRDTLYAESVKGRFTISRDNAKTTLYLQMNSLRPEDTAVYYCTIGGSLSVSSQGTLVTVSSggggsggggsggggsQVQLQESGGGLAQAGGSLSLSCAASGFTVSNSVMAWYRQTPGKQREFVAIINSVGSTNYADSVKGRFTISRDNAKNTVYLQMNNLKPEDTAVYVCNRNFDRIYWGQGTQVTVSSHHHHHHEPEA |
| 98 | ACP58 Mouse IFG fusion protein | mdmrvpaqllglllwlrgarcEVQLVESGGGLVQPGNSLRLSCAASGFTFSKFGMSWVRIFGQAPGKGLEWVSSISGSGRDTLYAESVKGRFTISRDNAKTTLYLQMNSLRPEDTAVYYCTIGGSLSVSSQGTLVTVSSSGGPGPAGMKGLPGShgtvieslesinnyfnssgidveekslfldiwrnwqkdgdmkilqsqiisfylrlfevlkdnqaisnnisvieshlittffsnskaldcdafmsiakfevnnpqvqrqafnelirvvhqllpesshicrkrsrcSGGPGPAGMKGLPGShgtvieslesinnyfrissgidveekslfldiwrnwqkdgdmkilqsqiisfylrlfevlkdnqaisnnisvieshlittffsnskaldcdafmsiakfevnnpqvqrqafnelirvvhqllpesslrkrkrsrcSGGPGPAGMKGLPGSEVQLVESGGGLVQPGNSLRLSCAASGFTFSKFGMSWVRQAPGKGLEWVSSISGSGRDTLYAESVKGRFTISRDNAKTTLYLQMNSLRPEDTAVYYCTIGGSLSVSSQGTLVTVSSggggsggggsggggsQVQLQESGGGLVQAGGSLRLSCAASGRIFSIDIMSWYRQAPGKQRELVARITRGGTISYDDSVKGRFTISRDNAKNTVYLQMNSLKPEDTGVYYCNALYGTDYWGKGTQVTVSSHHHHHHEPEA |
| 99 | ACP59 Mouse IFG fusion protein | mdmrvpaqllglllwlrgarcQVQLQESGGGLAQAGGSLSLSCAASGFTVSNSVMAWYRQTPGKQREFVAIINSVGSTNYADSVKGRFTISRDNAKNTVYLQMNNLKPEDTAVYVCNRNFDRIYWGQGTQVTVSSggggsggggsggggsEVQLVESGGGLVQPGNSLRLSCAASGFTFSKFGMSWVRQAPGKGLEWVSSISGSGRDTLYAESVKGRFTISRDNAKTTLYLQMNSLRPEDTAVYYCTIGGSLSVSSQGTLVTVSSSGGPGPAGMKGLPGShgtvieslesinnyfrissgidveekslfldiwrnwqkdgdmkilqsqiisfylrlfevlkdnqaisnnisvieshlittffsnskakkdafmsiakfevnnpqvqrqafnelirvvhqllpesslrkrkrsrcSGGPGPAGMKGLPGShgtvieslesinnyfrissgidveekslfldiwrnwqkdgdmkilqsqiisfylrlfevlkdnqaisnnisvieshlittffsnskakkdafmsiakfevnnpqvqrqafnelirvvhqllpesslikrkrsrcSGGPGPAGMKGLPGSEVQLVESGGGLVQPGNSLRLSCAASGFTFSKFGMSWVRQAPGKGLEWVSSISGSGRDTLYAESVKGRFTISRDNAKTTLYLQMNSLRPEDTAVYYCTIGGSLSVSSQGTLVTVSSHHHHHHEPEA |

Sequence Table

| SEQ ID NO. | Name | Sequence |
|---|---|---|
| 100 | ACP60 Mouse IFG fusion protein | mdmrvpaqllglllwlrgarcEVQLVESGGGLVQPGNSLRLSCAASGFTFSKFGMSWVR QAPGKGLEWVSSISGSGRDTLYAESVKGRFTISRDNAKTTLYLQMNSLRPEDT AVYYCTIGGSLSVSSQGTLVTVSSSGGPGPAGMKGLPGShgtviesleslnnyfnssgidv eekslfldiwrnwqkdgdmkilqsqiisfylrlfevlkdnqaisnnisvieshlittffsnskaldcdafmsiakfevnnpq vqrqafnelirvvhqllpesshicrkrsrcSGGPGPAGMKGLPGShgtviesleslnnyfrissgidveekslfldi wrnwqkdgdmkilqsqiisfylrlfevlkdnqaisnnisvieshlittffsnskaldcdafmsiakfevnnpqvqrqafnel irvvhqllpesslikrkrsrcSGGPGPAGMKGLPGSEVQLVESGGGLVQPGNSLRLSCAAS GFTFSKFGMSWVRQAPGKGLEWVSSISGSGRDTLYAESVKGRFTISRDNAKTT LYLQMNSLRPEDTAVYYCTIGGSLSVSSQGTLVTVSSggggsggggsggggsQVQLQ ESGGGLAQAGGSLSLSCAASGFTVSNSVMAWYRQTPGKQREFVAIINSVGSTN YADSVKGRFTISRDNAKNTVYLQMNNLKPEDTAVYVCNRNFDRIYWGQGTQ VTVSSHHHHHHEPEA |
| 101 | ACP61 Mouse IFG fusion protein | mdmrvpaqllglllwlrgarcEVQLVESGGGLVQPGNSLRLSCAASGFTFSKFGMSWVR QAPGKGLEWVSSISGSGRDTLYAESVKGRFTISRDNAKTTLYLQMNSLRPEDT AVYYCTIGGSLSVSSQGTLVTVSSSGGPGPAGMKGLPGShgtviesleslnnyfnssgidv eekslfldiwrnwqkdgdmkilqsqiisfylrlfevlkdnqaisnnisvieshlittffsnskaldcdafmsiakfevnnpq vqrqafnelirvvhqllpesslikrkrsrcSGGPGPAGMKGLPGShgtviesleslnnyfnssgidveekslfldi wrnwqkdgdmkilqsqiisfylrlfevlkdnqaisnnisvieshlittffsnskaldcdafmsiakfevnnpqvqrqafnel irvvhqllpesslikrkrsrcSGGPGPAGMKGLPGSEVQLVESGGGLVQPGNSLRLSCAAS VGFTFSKFGMSWVRQAPGKGLEWVSSISGSGRDTLYAESVKGRFTISRDNAKTT LYLQMNSLRPEDTAVYYCTIGGSLSVSSQGTLVTVSSggggsggggsggggsEVQLV ESGGGLVQPGGSLRLSCAASGFTFSSYAMSWVRQAPGKGLEWVSAISGSGGS TYYADSVKGRFTISRDNSKNTLYLQMNSLRAEDTAVYYCARGVGAFRPYRKH EWGQGTLVTVSRggggsggggsggggsSSELTQDPAVSVALGQTVRITCQGDSLRSY YASWYQQKPGQAPVLVIYGKNNRPSGIPDRFSGSSSGNTASLTTTGAQAEDEA DYYCNSSPFEENLVVFGGGTKLTVLHHHHHHEPEA |
| 102 | ACP63 Anti-FN CGS-2 scFv | mdmrvpaqllglllwlrgarcEVQLVESGGGLVQPGGSLRLSCAASGFTFSSYAMSWVR QAPGKGLEWVSAISGSGGSTYYADSVKGRFTISRDNSKNTLYLQMNSLRAED TAVYYCARGVGAFRPYRKHEWGQGTLVTVSRggggsggggsggggsSSELTQDPAV SVALGQTVRITCQGDSLRSYYASWYQQKPGQAPVLVIYGKNNRPSGIPDRFSG SSSGNTASLTTTGAQAEDEADYYCNSSPFEHNLVVFGGGTKLTVLHHHHHHE PEA |
| 103 | ACP69 Mouse IFG fusion protein | mdmrvpaqllglllwlrgarcEVQLVESGGGLVQPGNSLRLSCAASGFTFSKFGMSWVR QAPGKGLEWVSSISGSGRDTLYAESVKGRFTISRDNAKTTLYLQMNSLRPEDT AVYYCTIGGSLSVSSQGTLVTVSSSGGPGPAGMKGLPGShgtviesleslnnyfnssgidv eekslfldiwrnwqkdgdmkilqsqiisfylrlfevlkdnqaisnnisvieshlittffsnskaldcdafmsiakfevnnpq vqrqafnelirvvhqllpesslikrkrsrcSGGPGPAGMKGLPGSEVQLVESGGGLVQPGNSLR LSCAASGFTFSKFGMSWVRQAPGKGLEWVSSISGSGRDTLYAESVKGRFTISR DNAKTTLYLQMNSLRPEDTAVYYCTIGGSLSVSSQGTLVTVSSSGGPGPAGM KGLPGShgtviesleslnnyfnssgidveekslfldiwrnwqkdgdmkilqsqiisfylrlfevlkdnqaisnnisvie shlittffsnskakkdafmsiakfevnnpqvqrqafnelirvvhqllpesshkrkrsrcHHHHHHEPEA |
| 104 | ACP70 Mouse IFG fusion protein | mdmrvpaqllglllwlrgarchgtviesleslnnyfnssgidveekslfkliwrnwqkdgdmkilqsqiisfylrlfevlk dnqaisnnisvieshlittffsnskakkdafmsiakfevnnpqvqrqafnelirvvhqllpesshkrkrsrcSGGPGP AGMKGLPGSEVQLVESGGGLVQPGNSLRLSCAASGFTFSKFGMSWVRQAPGK GLEWVSSISGSGRDTLYAESVKGRFTISRDNAKTTLYLQMNSLRPEDTAVYYC TIGGSLSVSSQGTLVTVSSSGGPGPAGMKGLPGShgtviesleslnnyfnssgidveekslfldi wrnwqkdgdmkilqsqiisfylrlfevlkdnqaisnnisvieshlittffsnskaldcdafmsiakfevnnpqvqrqafnel irvvhqllpesslikrkrsrcSGGPGPAGMKGLPGSEVQLVESGGGLVQPGNSLRLSCAAS GFTFSKFGMSWVRQAPGKGLEWVSSISGSGRDTLYAESVKGRFTISRDNAKTT LYLQMNSLRPEDTAVYYCTIGGSLSVSSQGTLVTVSSHHHHHHEPEA |
| 105 | ACP71 Mouse IFG fusion protein | mdmrvpaqllglllwlrgarchgtviesleslnnyfnssgidveekslfldiwrnwqkdgdmkilqsqiisfylrlfevlk dnqaisnnisvieshlittffsnskakkdafmsiakfevnnpqvqrqafnelirvvhqllpesshkrkrsrcSGGPGP AGMKGLPGSEAHKSEIAHRYNDLGEQHFKGLVLIAFSQYLQKCSYDEHAKLV QEVTDFAKTCVADESAANCDKSLHTLFGDKLCAIPNLRENYGELADCCTKQE PERNECFLQHKDDNPSLPPFERPEAEAMCTSFKENPTTFMGHYLHEVARRHPY FYAPELLYYAEQYNEILTQCCAEADKESCLTPKLDGVKEKALVSSVRQRMKC SSMQKFGERAFKAWAVARLSQTFPNADFAEITKLATDLTKVNKECCHGDLLE CADDRAELAKYMCENQATISSKLQTCCDKPLLKKAHCLSEVEHDTMPADLPA IAADFVEDQEVCKNYAEAKDVFLGlFLYEYSRRHPDYSVSLLLRLAKKYEAT LEKCCAEANPPACYGTVLAEFQPLVEEPKNLVKTNCDLYEKLGEYGFQNAILV RYTQKAPQVSTPTLVEAARNLGRVGTKCCTLPEDQRLPCVEDYLSAILNRVCL LHEKTPVSEHVIKCCSGSLVERRPCFSALTVDETYVPKEFKAETFTFHSDICTL PEKEKQIKKQTALAELVKHKPKATAEQLKTVMDDFAQFLDTCCKAADKDTCF STEGPNLVTRCKDALASGGPGPAGMKGLPGShgtviesleslnnyfassgidveekslfldiwrn wqkdgdmkilqsqiisfylrlfevlkdnqaisnnisvieshlittffsnskaldcdafmsiakfevnnpqvqr qafnelirvvhqllpesslrkrkrsrcSGGPGPAGMKGLPGSEAHKSEIAHRYNDLGEQHFKGLVLIAF SQYLQKCSYDEHAKLVQEVTDFAKTCVADESAANCDKSLHTLFGDKLCAIPN LRENYGELADCCTKQEPERNECFLQHKDDNPSLPPFERPEAEAMCTSFKENPT |

| SEQ ID NO. | Name | Sequence |
|---|---|---|
| | | TFMGHYLEVARRHPYFYAPELLYYAEQYNEILTQCCAEADKESCLTPKLDG<br>VKEKALVSSVRQRMKCSSMQKFGERAFKAWAVARLSQTFPNADFAEITKLAT<br>DLTKVNKECCHGDLLECADDRAELAKYMCENQATISSKLQTCCDKPLLKKAH<br>CLSEVEHDTMPADLPAIAADFVEDQEVCKNYAEAKDVFLGTFLYEYSRRHPD<br>YSVSLLLRLAKKYEATLEKCCAEANPPACYGTVLAEFQPLVEEPKNLVKTNC<br>DLYEKLGEYGFQNAILVRYTQKAPQVSTPTLVEAARNLGRVGTKCCTLPEDQ<br>RLPCVEDYLSAILNRVCLLHEKTPVSEHVTKCCSGSLVERRPCFSALTVDETYV<br>PKEFKAETFTFHSDICTLPEKEKQIKKQTALAELVKHKPKATAEQLKTVMDDF<br>AQFLDTCCKAADKDTCFSTEGPNLVTRCKDALAHHHHHHEPEA |
| 106 | ACP72 Mouse IFG fusion protein | mdmrvpaqllglllwlrgarcEAHKSEIAHRYNDLGEQHFKGLVLIAFSQYLQKCSYDE<br>HAKLVQEVTDFAKTCVADESAANCDKSLHTLFGDKLCAIPNLRENYGELADC<br>CTKQEPERNECFLQHKDDNPSLPPFERPEAEAMCTSFKENPTTFMGHYLEVA<br>RRHPYFYAPELLYYAEQYNEILTQCCAEADKESCLTPKLDGVKEKALVSSVRQ<br>RMKCSSMQKFGERAFKAWAVARLSQTFPNADFAEITKLATDLTKVNKECCH<br>GDLLECADDRAELAKYMCENQATISSKLQTCCDKPLLKKAHCLSEVEHDTMP<br>ADLPAIAADFVEDQEVCKNYAEAKDVFLGTFLYEYSRRHPDYSVSLLLRLAK<br>KYEATLEKCCAEANPPACYGTVLAEFQPLVEEPKNLVKTNCDLYEKLGEYGF<br>QNAILVRYTQKAPQVSTPTLVEAARNLGRVGTKCCTLPEDQRLPCVEDYLSAI<br>LNRVCLLHEKTPVSEHVTKCCSGSLVERRPCFSALTVDETYVPKEFKAETFTFH<br>SDICTLPEKEKQIKKQTALAELVKHKPKATAEQLKTVMDDFAQFLDTCCKAA<br>DKDTCFSTEGPNLVTRCKDALASGGPGPAGMKGLPGShgtvieslesInnythssgidveeksIfld<br>iwrnwqkdgdmkilqsqiisfylrlfevlkdnqaisnnisvieshlittffsnskakkdafmsiakfevnnpqvq<br>rqafnelirvvhqllpessIitcrkrsrcSGGPGPAGMKGLPGSEAHKSEIAHRYNDLGEQHFK<br>GLVLIAFSQYLQKCSYDEHAKLVQEVTDFAKTCVADESAANCDKSLHTLFGD<br>KLCAIPNLRENYGELADCCTKQEPERNECFLQHKDDNPSLPPFERPEAEAMCT<br>SFKENPTTFMGHYLHEVARRHPYFYAPELLYYAEQYNEILTQCCAEADKESCL<br>TPKLDGVKEKALVSSVRQRMKCSSMQKFGERAFKAWAVARLSQTFPNADFA<br>EITKLATDLTKVNKECCHGDLLECADDRAELAKYMCENQATISSKLQTCCDK<br>PLLKKAHCLSEVEHDTMPADLPAIAADFVEDQEVCKNYAEAKDVFLGTFLYE<br>YSRRHPDYSVSLLLRLAKKYEATLEKCCAEANPPACYGTVLAEFQPLVEEPKN<br>LVKTNCDLYEKLGEYGFQNAILVRYTQKAPQVSTPTLVEAARNLGRVGTKCC<br>TLPEDQRLPCVEDYLSAILNRVCLLHEKTPVSEHVTKCCSGSLVERRPCFSALT<br>VDETYVPKEFKAETFTFHSDICTLPEKEKQIKKQTALAELVKHKPKATAEQLK<br>TVMDDFAQFLDTCCKAADKDTCFSTEGPNLVTRCKDALASGGPGPAGMKGLPGShgtvie<br>sleslnnyfassgidveekslfldiwrnwqkdgdmkilqsqiisfylrlfevlkdnqaisnnisvieshlitt<br>ffsnskakkdafmsiakfevnnpqvqrqafnelirvvhqllpessIrkrkrsrcHHHHHHEPEA |
| 107 | ACP73 Mouse IFG fusion protein | mdmrvpaqllglllwlrgarcEAHKSEIAHRYNDLGEQHFKGLVLIAFSQYLQKCSYDE<br>HAKLVQEVTDFAKTCVADESAANCDKSLHTLFGDKLCAIPNLRENYGELADC<br>CTKQEPERNECFLQHKDDNPSLPPFERPEAEAMCTSFKENPTTFMGHYLEVA<br>RRHPYFYAPELLYYAEQYNEILTQCCAEADKESCLTPKLDGVKEKALVSSVRQ<br>RMKCSSMQKFGERAFKAWAVARLSQTFPNADFAEITKLATDLTKVNKECCH<br>GDLLECADDRAELAKYMCENQATISSKLQTCCDKPLLKKAHCLSEVEHDTMP<br>ADLPAIAADFVEDQEVCKNYAEAKDVFLGTFLYEYSRRHPDYSVSLLLRLAK<br>KYEATLEKCCAEANPPACYGTVLAEFQPLVEEPKNLVKTNCDLYEKLGEYGF<br>QNAILVRYTQKAPQVSTPTLVEAARNLGRVGTKCCTLPEDQRLPCVEDYLSAI<br>LNRVCLLHEKTPVSEHVTKCCSGSLVERRPCFSALTVDETYVPKEFKAETFTFH<br>SDICTLPEKEKQIKKQTALAELVKHKPKATAEQLKTVMDDFAQFLDTCCKAA<br>DKDTCFSTEGPNLVTRCKDALASGGPGPAGMKGLPGShgtvieslesInnythssgidvee<br>ksIfldiwrnwqkdgdmkilqsqiisfylrlfevlkdnqaisnnisvieshlittffsnskakkdafms<br>iakfevnnpqvqrqafnelirvvhqllpessIitcrkrsrcSGGPGPAGMKGLPGSEAHKSEIAHRYNDLGEQHFK<br>GLVLIAFSQYLQKCSYDEHAKLVQEVTDFAKTCVADESAANCDKSLHTLFGD<br>KLCAIPNLRENYGELADCCTKQEPERNECFLQHKDDNPSLPPFERPEAEAMCT<br>SFKENPTTFMGHYLHEVARRHPYFYAPELLYYAEQYNEILTQCCAEADKESCL<br>TPKLDGVKEKALVSSVRQRMKCSSMQKFGERAFKAWAVARLSQTFPNADFA<br>EITKLATDLTKVNKECCHGDLLECADDRAELAKYMCENQATISSKLQTCCDK<br>PLLKKAHCLSEVEHDTMPADLPAIAADFVEDQEVCKNYAEAKDVFLGTFLYE<br>YSRRHPDYSVSLLLRLAKKYEATLEKCCAEANPPACYGTVLAEFQPLVEEPKN<br>LVKTNCDLYEKLGEYGFQNAILVRYTQKAPQVSTPTLVEAARNLGRVGTKCC<br>TLPEDQRLPCVEDYLSAILNRVCLLHEKTPVSEHVTKCCSGSLVERRPCFSALT<br>VDETYVPKEFKAETFTFHSDICTLPEKEKQIKKQTALAELVKHKPKATAEQLK<br>TVMDDFAQFLDTCCKAADKDTCFSTEGPNLVTRCKDALASGGPGPAGMKGL<br>PGShgtvieslesInnyfrissgidveekslfldiwrnwqkdgdmkilqsqiisfylrlfevlkdnqaisnnisvieshlitt<br>ffsnskaldcdafmsiakfevnnpqvqrqafnelirvvhqllpessIrkrkrsrcSGGPGPAGMKGLPGSEA<br>HKSEIAHRYNDLGEQHFKGLVLIAFSQYLQKCSYDEHAKLVQEVTDFAKTCV<br>ADESAANCDKSLHTLFGDKLCAIPNLRENYGELADCCTKQEPERNECFLQH<br>DDNPSLPPFERPEAEAMCTSFKENPTTFMGHYLHEVARRHPYFYAPELLYYAE<br>QYNEILTQCCAEADKESCLTPKLDGVKEKALVSSVRQRMKCSSMQKFGERAF<br>KAWAVARLSQIFPNADFAEITKLATDLTKVNKECCHGDLLECADDRAELAKY<br>MCENQATISSKLQTCCDKPLLKKAHCLSEVEHDTMPADLPAIAADFVEDQEV<br>CKNYAEAKDVFLGTFLYEYSRRHPDYSVSLLLRLAKKYEATLEKCCAEANPP<br>ACYGTVLAEFQPLVEEPKNLVKTNCDLYEKLGEYGFQNAILVRYTQKAPQVS |

| SEQ ID NO. | Name | Sequence |
|---|---|---|
| | | TPTLVEAARNLGRVGTKCCTLPEDQRLPCVEDYLSAILNRVCLLHEKTPVSEH VTKCCSGSLVERRPCFSALTVDETYVPKEFKAETFTFHSDICTLPEKEKQIKKQ TALAELVKHKPKATAEQLKTVMDDFAQFLDTCCKAADKDTCFSTEGPNLVTR CKDALAHHHHHEPEA |
| 108 | ACP74 Mouse IFG fusion protein | mdmrvpaqllglllwlrgarcEAHKSEIAHRYNDLGEQHFKGLVLIAFSQYLQKCSYDE HAKLVQEVTDFAKTCVADESAANCDKSLHTLFGDKLCAIPNLRENYGELADC CTKQEPERNECFLQHKDDNPSLPPFERPEAEAMCTSFKENPTTFMGHYLHEVA RRHPYFYAPELLYYAEQYNEILTQCCAEADKESCLTPKLDGVKEKALVSSVRQ RMKCSSMQKFGERAFKAWAVARLSQTFPNADFAEITKLATDLTKVNKECCH GDLLECADDRAELAKYMCENQATISSKLQTCCDKPLLKKAHCLSEVEHDTMP ADLPAIAADFVEDQEVCKNYAEAKDVFLGTFLYEYSRRHPDYSVSLLLRLAK KYEATLEKCCAEANPPACYGTVLAEFQPLVEEPKNLVKTNCDLYEKLGEYGF QNAILVRYTQKAPQVSTPTLVEAARNLGRVGTKCCTLPEDQRLPCVEDYLSAI LNRVCLLHEKTPVSEHVTKCCSGSLVERRPCFSALTVDETYVPKEFKAETFTFH SDICTLPEKEKQIKKQTALAELVKHKPKATAEQLKTVMDDFAQFLDTCCKAA DKDTCFSTEGPNLVTRCKDALASGGPGPAGMKGLPGShgtviesleslnnythssgidvee kslfldiwrnwqkdgdmkilqsqiisfylrlfevlkdnqaisnnisvieshlittffsnskakkdafmsiakfevnnpqvq rqafnelirvvhqllpesslitcrkrsrcSGGPGPAGMKGLPGSggggsEAHKSEIAHRYNDLGEQ HFKGLVLIAFSQYLQKCSYDEHAKLVQEVTDFAKTCVADESAANCDKSLHTL FGDKLCAIPNLRENYGELADCCTKQEPERNECFLQHKDDNPSLPPFERPEAEA MCTSFKENPTTFMGHYLHEVARRHPYFYAPELLYYAEQYNEILTQCCAEADK ESCLTPKLDGVKEKALVSSVRQRMKCSSMQKFGERAFKAWAVARLSQTFPN ADFAEITKLATDLTKVNKECCHGDLLECADDRAELAKYMCENQATISSKLQT CCDKPLLKKAHCLSEVEHDTMPADLPAIAADFVEDQEVCKNYAEAKDVFLGT FLYEYSRRHPDYSVSLLLRLAKKYEATLEKCCAEANPPACYGTVLAEFQPLVE EPKNLVKTNCDLYEKLGEYGFQNAILVRYTQKAPQVSTPTLVEAARNLGRVG TKCCTLPEDQRLPCVEDYLSAILNRVCLLHEKTPVSEHVTKCCSGSLVERRPCF SALTVDETYVPKEFKAETFTFHSDICTLPEKEKQIKKQTALAELVKHKPKATAE QLKTVMDDFAQFLDTCCKAADKDTCFSTEGPNLVTRCKDALggggsSGGPGP AGMKGLPGShgtviesleslnnythssgidveekslfldiwrnwqk dgdmkilqsqiisfylrlfevlkdnqaisn nisvieshlittffsnslcaldcdafmsiakfevnnpqvqrqafne lirvvhqllpesslrkrkrsrcSGGPGPAGMK GLPGSEAHKSEIAHRYNDLGEQHFKGLVLIAFSQYLQKCSYDEHAKLVQEVTD FAKTCVADESAANCDKSLHTLFGDKLCAIPNLRENYGELADCCTKQEPERNEC FLQHKDDNPSLPPFERPEAEAMCTSFKENPTTFMGHYLHEVARRHPYFYAPEL LYYAEQYNEILTQCCAEADKESCLTPKLDGVKEKALVSSVRQRMKCSSMQKF GERAFKAWAVARLSQTFPNADFAEITKLATDLTKVNKECCHGDLLECADDRA ELAKYMCENQATISSKLQTCCDKPLLKKAHCLSEVEHDTMPADLPAIAADFVE DQEVCKNYAEAKDVFLGTFLYEYSRRHPDYSVSLLLRLAKKYEATLEKCCAE ANPPACYGTVLAEFQPLVEEPKNLVKTNCDLYEKLGEYGFQNAILVRYTQKA PQVSTPTLVEAARNLGRVGTKCCTLPEDQRLPCVEDYLSAILNRVCLLHEKTP VSEHVTKCCSGSLVERRPCFSALTVDETYVPKEFKAETFTFHSDICTLPEKEKQI KKQTALAELVKHKPKATAEQLKTVMDDFAQFLDTCCKAADKDTCFSTEGPN LVTRCKDALAHHHHHEPEA |
| 109 | ACP75 Mouse IFG fusion protein | mdmrvpaqllglllwlrgarcEAHKSEIAHRYNDLGEQHFKGLVLIAFSQYLQKCSYDE HAKLVQEVTDFAKTCVADESAANCDKSLHTLFGDKLCAIPNLRENYGELADC CTKQEPERNECFLQHKDDNPSLPPFERPEAEAMCTSFKENPTTFMGHYLHEVA RRHPYFYAPELLYYAEQYNEILTQCCAEADKESCLTPKLDGVKEKALVSSVRQ RMKCSSMQKFGERAFKAWAVARLSQTFPNADFAEITKLATDLTKVNKECCH GDLLECADDRAELAKYMCENQATISSKLQTCCDKPLLKKAHCLSEVEHDTMP ADLPAIAADFVEDQEVCKNYAEAKDVFLGTFLYEYSRRHPDYSVSLLLRLAK KYEATLEKCCAEANPPACYGTVLAEFQPLVEEPKNLVKTNCDLYEKLGEYGF QNAILVRYTQKAPQVSTPTLVEAARNLGRVGTKCCTLPEDQRLPCVEDYLSAI LNRVCLLHEKTPVSEHVTKCCSGSLVERRPCFSALTVDETYVPKEFKAETFTFH SDICTLPEKEKQIKKQTALAELVKHKPKATAEQLKTVMDDFAQFLDTCCKAA DKDTCFSTEGPNLVTRCKDALASGGPGPAGMKGLPGShgtviesleslnnyth ssgidveekslfldiwrnwqkdgdmkilqsqiisfylrlfevlkdnqaisnni svieshlittffsnskakkdafmsiakfevnnpqvqrqafnelirvvhq llpesshicrkrsrcSGGPGPAGMKGLPGSggggsggggsEAHKSEIAHRYND LGEQHFKGLVLIAFSQYLQKCSYDEHAKLVQEVTDFAKTCVADESAANCDKS LHTLFGDKLCAIPNLRENYGELADCCTKQEPERNECFLQHKDDNPSLPPFERPE AEAMCTSFKENPTTFMGHYLHEVARRHPYFYAPELLYYAEQYNEILTQCCAE ADKESCLTPKLDGVKEKALVSSVRQRMKCSSMQKFGERAFKAWAVARLSQT FPNADFAEITKLATDLTKVNKECCHGDLLECADDRAELAKYMCENQATISSKL QTCCDKPLLKKAHCLSEVEHDTMPADLPAIAADFVEDQEVCKNYAEAKDVFL GTFLYEYSRRHPDYSVSLLLRLAKKYEATLEKCCAEANPPACYGTVLAEFQPL VEEPKNLVKTNCDLYEKLGEYGFQNAILVRYTQKAPQVSTPTLVEAARNLGR VGTKCCTLPEDQRLPCVEDYLSAILNRVCLLHEKTPVSEHVTKCCSGSLVERR PCFSALTVDETYVPKEFKAETFTFHSDICTLPEKEKQIKKQTALAELVKHKPKA TAEQLKTVMDDFAQFLDTCCKAADKDTCFSTEGPNLVTRCKDALggggsgggg |

| SEQ ID NO. | Name | Sequence |
|---|---|---|
| | | sSGGPGPAGMKGLPGShgtviesleslnnythssgidveekslfldiwrnwq kdgdmkilqsqiisfylrlfevlkdnqaisnnisvieshlittffsnskakkda fmsiakfevnnpqvqrqafnelirvvhqllpesslikrkrsrcSGGP GPAGMKGLPGSEAHKSEIAHRYNDLGEQHFKGLVLIAFSQYLQKCSYDEHAK LVQEVTDFAKTCVADESAANCDKSLHTLFGDKLCAIPNLRENYGELADCCTK QEPERNECFLQHKDDNPSLPPFERPEAEAMCTSFKENPTTFMGHYLHEVARRH PYFYAPELLYYAEQYNEILTQCCAEADKESCLTPKLDGVKEKALVSSVRQRM KCSSMQKFGERAFKAWAVARLSQIFPNADFAEITKLATDLTKVNKECCHGDL LECADDRAELAKYMCENQATISSKLQTCCDKPLLKKAHCLSEVEHDTMPADL PAIAADFVEDQEVCKNYAEAKDVFLGIFLYEYSRRHPDYSVSLLLRLAKKYE ATLEKCCAEANPPACYGTVLAEFQPLVEEPKNLVKTNCDLYEKLGEYGFQNAI LVRYTQKAPQVSTPTLVEAARNLGRVGTKCCTLPEDQRLPCVEDYLSAILNRV CLLHEKTPVSEHVTKCCGSLVERRPCFSALTVDETYVPKEFKAETFTFHSDIC TLPEKEKQIKKQTALAELVKHKPKATAEQLKTVMDDFAQFLDTCCKAADKDT CFSTEGPNLVTRCKDALAHHHHHHEPEA |
| 110 | ACP78 Mouse IFG fusion protein | mdmrvpaqllglllwlrgarcEVQLVESGGGLVQPGNSLRLSCAASGFTFSKFGMSWVR QAPGKGLEWVSSISGSGRDTLYAESVKGRFTISRDNAKTTLYLQMNSLRPEDT AVYYCTIGGSLSVSSQGTLVTVSSggggsggggsggggs shgtviesleslnnythssgidveekslfldiwrnwqkdgdmkilqsqiisfylrlfe vlkdnqaisnnisvieshlittffsnskaldcdafmsiakfevnnpqvqrqafne lirvvhqllpesslrkrkrsreggggsggggsggggsEVQLVESGGGLVQPGNSLRLSCAASGFTF SKFGMSWVRQAPGKGLEWVSSISGSGRDTLYAESVKGRFTISRDNAKTTLYL QMNSLRPEDTAVYYCTIGGSLSVSSQGTLVTVSSggggsggggsggggsshgtviesleslnn ythssgidveekslildiwrnwqkdgdmkilqsqiisfylrlfevlkd nqaisnnisvieshlittffsnskakkdafmsiakfevnnpqvqrqafnelirvvhqllpesslrkrkrsreggggsgg ggsggggsEVQLVESGGGLVQPGNSLRLSCAASGFTFSKFGMSWVRQAPGKGLEWVSSISGSGRDTLYAESVKGRFTI SRDNAKTTLYLQMNSLRPEDTAVYYCTIGGSLSVSSQGTLVTVSSHHHHHHEPEA |
| 111 | ACP134 Mouse IFG fusion protein | mdmrvpaqllglllwlrgarcEVQLVESGGGLVQPGNSLRLSCAASGFTFSKFGMSWVR QAPGKGLEWVSSISGSGRDTLYAESVKGRFTISRDNAKTTLYLQMNSLRPEDT AVYYCTIGGSLSVSSQGTLVTVSSSGGPGPAGMKGLPGShgtviesleslnnyfnssgidv eekslfldiwrnwqkdgdmkilqsqiisfylrlfevlkdnqaisn nisvieshlittffsnskaldcdafmsiakfevnnpq vqrqafnelirvvhqllpesshkrkrsrcSGGPGPAGMKGLPGSEVQLVESGGGLVQPGNSLR LSCAASGFTFSKFGMSWVRQAPGKGLEWVSSISGSGRDTLYAESVKGRFTISR DNAKTTLYLQMNSLRPEDTAVYYCTIGGSLSVSSQGTLVTVSSSGGPGPAGM KGLPGShgtviesleslnnyfnssgidveekslfldiwrnwqkdgdmkilqsqiisfylrlfevlkdnqaisnnisvie shlittffsnskakkdafmsiakfevnnpqvqrqafnelirvvhqllpesshkrkrsrcSGGPGPAGMKGLPG SEVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSggggsggggsggggsQVQLQESGGGLAQAGGSLSLSCAASGFTVSNS VMAWYRQTPGKQREFVAIINSVGSTNYADSVKGRFTISRDNAKNTVYLQMNN LKPEDTAVYVCNRNFDRIYWGQGTQVTVSSHHHHHHEPEA |
| 112 | ACP135 Mouse IFG fusion protein | mdmrvpaqllglllwlrgarcQVQLQESGGGLAQAGGSLSLSCAASGFTVSNSVMAWY RQTPGKQREFVAIINSVGSTNYADSVKGRFTISRDNAKNTVYLQMNNLKPEDT AVYYCNRNFDRIYWGQGTQVTVSSggggsggggsggggsEVQLVESGGGLVQPGNS LRLSCAASGFTFSKFGMSWVRQAPGKGLEWVSSISGSGRDTLYAESVKGRFTI SRDNAKTTLYLQMNSLRPEDTAVYYCTIGGSLSVSSQGTLVTVSSSGGPGPAG MKGLPGShgtviesleslnnyfnssgidveekslfldiwrnwqkdgdmkilqsqiisfylrlfevlkdnqaisnnisv ieshlittffsnskakkdafmsiakfevnnpqvqrqafnelirvvhqllpesshkrkrsrcSGGPGPAGMKGLP GSEVQLVESGGGLVQPGNSLRLSCAASGFTFSKFGMSWVRQAPGKGLEWVSS ISGSGRDTLYAESVKGRFTISRDNAKTTLYLQMNSLRPEDTAVYYCTIGGSLSV SSQGTLVTVSSSGGPGPAGMKGLPGShgtviesleslnnyfnssgidveekslfldiwrnwqkdgd mkilqsqiisfylrlfevlkdnqaisnnisvieshlittffsnskakkda fmsiakfevnnpqvqrqafnelirvvhqllpesshkrkrsrcSGGPGPAGMKGLPGSEVQLVESGGGLVQP GNSLRLSCAASGFTFSKFGMSWVRQAPGKGLEWVSSISGSGRDTLYAESVKGRFTISRDNAKTTLYLQMN SLRPEDTAVYYCTIGGSLSVSSQGTLVTVSSHHHHHHEPEA |
| 113 | ACP34 Mouse IL-12 fusion protein | mdmrvpaqllglllwlrgarcrvipvsgparclsqsrnllkttddmvktareklkhysctaedidheditrdqtstlktclp lelhknesclatretssttrgsclppqktslmmticlgsiyedlkmyqtefqainaalqnhnhqqiildkgmlvaidelmq slnhngetlrqkppvgeadpyrvkmklcillhafstryvtinrvmgylssaSGGPGPAGMKGLPGSmwele kdvyvvevdwtpdapgetvnitcdtpeedditwtsdqrhgvigsgktltitykefldagqytchkggetlshshlllhkke ngiwsteilknfknktflkceapnysgrftcswlvqrnmdlkfnikssssspdsravtcgmaslsaekvtldqrdyekys vscqedvtcptaeetlpielalearqqnkyenystsffirdiikpdppknlqmkplknsqvevsweypdswstphsyfsl kffvriqrkkekmketeegcnqkgaflvektstevqckggnvcvqaqchyynsscskwacvpervrsHHHHHH |
| 114 | ACP35 Mouse IL-12 fusion protein | mdmrvpaqllglllwlrgarcrvipvsgparclsqsrnllkttddmvktareklkhysctaedidheditrdqtstlktclp lelhknesclatretssttrgsclppqktslmmticlgsiyedlkmyqtefqainaalqnhnhqqiildkgmlvaidelmq slnhngetlrqkppvgeadpyrvkmklcillhafstryvtinrvmgylssaggggsggggsggggsSGGPGPAG MKGLPGSggggsggggsggggsmwelekdvyvvevdwtpdapgetvnitcdtpeedditwtsdqrhgvigsg ktltitykefldagqytchkggetlshshlllhkkengiwsteilknfkatflkceapnysgrftcswlvqrnmdlkfnik |

| SEQ ID NO. | Name | Sequence |
|---|---|---|
| | | ssssspdsravtcgmaslsaekvtldqrdyekysyscqedvtcptaeetlpielalearqqnkyenystsffirdiikpdpp<br>knlqmkplknsqvevsweypdswstphsyfslkffvriqrkkekmketeegcnqkgaflvektstevqckggnvcv<br>qaqdryynsscskwacvpervrsHHHHHH |
| 115 | ACP36<br>Mouse IL-<br>12 fusion<br>protein | mdmrvpaqllglllwlrgarcEVQLVESGGGLVQPGNSLRLSCAASGFTFSKFGMSWVR<br>QAPGKGLEWVSSISGSGRDTLYAESVKGRFTISRDNAKTTLYLQMNSLRPEDT<br>AVYYCTIGGSLSVSSQGTLVTVSSSGGPGPAGMKGLPGSmwelekdvyvvevdwtpd<br>apgetvnhcdtpeedditwtsdqrhgvigsgktltitykefldagqytchkggetlshshlllhkkengiwsteilknfkn<br>kffikceapnysgrftcswlvqrnmdlkfniksssssspdsravtcgmaslsaekvtldqrdyekysyscqedvtcptaee<br>tlpielalearqqnkyenystsffirdiikpdppknlqmkplknsqvevsweypdswstphsyfslkffvriqrkkekm<br>keteegcnqkgaflvektstevqckggnvcvqaqchyynsscskwacvpervrsggggsggggsggggsrvipvsgparcl<br>sqsrifilkttddmvktareklkhysctaedidheditrdqtstlktclplelhknesclatretssttrgsclppqktsl<br>mmticlgsiyedlkmyqtefciainaalqnhnhqqiildkgmlvaidelmqslnhngetlrqkppvgeadpyrvkml<br>cillhafstryvtinrvmgylssaSGGPGPAGMKGLPGSEVQLVESGGGLVQPGNSLRLSC<br>AASGFTFSKFGMSWVRQAPGKGLEWVSSISGSGRDTLYAESVKGRFTISRDNA<br>KTTLYLQMNSLRPEDTAVYYCTIGGSLSVSSQGTLVTVSSHHHHHH |
| 116 | ACP37<br>Mouse IL-<br>12 fusion<br>protein | mdmrvpaqllglllwlrgarcQVQLQESGGGLVQAGGSLRLSCAASGRIFSIDIMSWYR<br>QAPGKQRELVARITRGGTISYDDSVKGRFTISRDNAKNTVYLQMNSLKPEDTG<br>VYYCNALYGTDYWKGTQVTVSSggggsggggsggggsEVQLVESGGGLVQPGNS<br>LRLSCAASGFTFSKFGMSWVRQAPGKGLEWVSSISGSGRDTLYAESVKGRFTI<br>SRDNAKTTLYLQMNSLRPEDTAVYYCTIGGSLSVSSQGTLVTVSSSGGPGPAG<br>MKGLPGSmwelekdvyvvevdwtpdapgetvnitcdtpeedditwtsdqrhgvigsgktltitykefldagqytc<br>hkggetlshshlllhkkengiwsteilknfknktflkceapnysgrftcswlvqrnmdlkfniksssspdsravtcgmas<br>Vlsaekvtldqrdyekysyscqedvtcptaeetlpielalearqqnkyenystsffirdiikpdppknlqmkplknsqvevs<br>weypdswstphsyfslkffvriqrkkekmketeegcnqkgaflvektstevqckggnvcvqaqchyynsscskwac<br>vpervrsggggsggggsggggsrvipvsgparclsqsnillkttddmvktareklkhysctaedidheditrdqtstlktcl<br>plelhknesclatretssttrgsclppqktslmmticlgsiyedlkmyqtefciainaalqnhnhqqiildkgmlvaidelm<br>qslnhngetlrqkppvgeadpyrvkmlcillhafstrvvtinrvmgylssaSGGPGPAGMKGLPGSEVQ<br>LVESGGGLVQPGNSLRLSCAASGFTFSKFGMSWVRQAPGKGLEWVSSISGSGR<br>DTLYAESVKGRFTISRDNAKTTLYLQMNSLRPEDTAVYYCTIGGSLSVSSQGT<br>LVTVSSHHHHHH |
| 117 | ACP79<br>Mouse IL-<br>12 fusion<br>protein | mdmrvpaqllglllwlrgarcQVQLQESGGGLVQAGGSLRLSCAASGRIFSIDIMSWYR<br>QAPGKQRELVARITRGGTISYDDSVKGRFTISRDNAKNTVYLQMNSLKPEDTG<br>VYYCNALYGTDYWKGTQVTVSSggggsggggsggggsEVQLVESGGGLVQPGNS<br>LRLSCAASGFTFSKFGMSWVRQAPGKGLEWVSSISGSGRDTLYAESVKGRFTI<br>SRDNAKTTLYLQMNSLRPEDTAVYYCTIGGSLSVSSQGTLVTVSSSGGPGPAG<br>MKGLPGSmwelekdvyvvevdwtpdapgetvnitcdtpeedditwtsdqrhgvigsgktltitykefldagqytc<br>hkggetlshshlllhkkengiwsteilknfknktflkceapnysgrftcswlvqrnmdlkfniksssspdsravtcgmas<br>lsaekvtldqrdyekysyscqedvtcptaeetlpielalearqqnkyenystsffirdiikpdppknlqmkplknsqvevs<br>weypdswstphsyfslkffvriqrkkekmketeegcnqkgaflvektstevqckggnvcvqaqchyynsscskwac<br>vpervrsggggsggggsggggsrvipvsgparclsqsnillkttddmvktareklkhysctaedidheditrdqtstlktcl<br>plelhknesclatretssttrgsclppqktslmmticlgsiyedlkmyqtefciainaalqnhnhqqiildkgmlvaidelm<br>qslnhngetlrqkppvgeadpyrvkmlcicillhafstrvvtinrvmgylssaSGGPGPAGMKGLPGSEVQ<br>LVESGGGLVQPGNSLRLSCAASGFTFSKFGMSWVRQAPGKGLEWVSSISGSGR<br>DTLYAESVKGRFTISRDNAKTTLYLQMNSLRPEDTAVYYCTIGGSLSVSSQGT<br>LVTVSSHHHHHH |
| 118 | ACP80<br>Mouse IL-<br>12 fusion<br>protein | mdmrvpaqllglllwlrgarcEVQLVESGGGLVQPGNSLRLSCAASGFTFSKFGMSWVR<br>QAPGKGLEWVSSISGSGRDTLYAESVKGRFTISRDNAKTTLYLQMNSLRPEDT<br>AVYYCTIGGSLSVSSQGTLVTVSSSGGPGPAGMKGLPGSmwelekdvyvvevdwtpd<br>apgetvnhcdtpeedditwtsdqrhgvigsgktltitykefldagqytchkggetlshshlllhkkengiwsteilknfkn<br>kffikceapnysgrftcswlvqrnmdlkfniksssssspdsravtcgmaslsaekvtldqrdyekysyscqedvtcptaee<br>tlpielalearqqnkyenystsffirdiikpdppknlqmkplknsqvevsweypdswstphsyfslkffvriqrkkekm<br>keteegcnqkgaflvektstevqckggnvcvqaqdwynsscskwacvpervrsggggsggggsggggsrvipvsgparc<br>lsqsnillkttddmvktareklkhysctaedidheditrdqtstlktclplelhknesclatretssttrgsclppqktsl<br>mmticlgsiyedlkmyqtefciainaalqnhnhqqiildkgmlvaidelmqslnhngetlrqkppvgeadpyrvkml<br>cillhafstrvvtinrvmgylssaSGGPGPAGMKGLPGSEVQLVESGGGLVQPGNSLRLSC<br>AASGFTFSKFGMSWVRQAPGKGLEWVSSISGSGRDTLYAESVKGRFTISRDNA<br>KTTLYLQMNSLRPEDTAVYYCTIGGSLSVSSQGTLVTVSSggggsggggsggggsQV<br>QLQESGGGLVQAGGSLRLSCAASGRIFSIDIMSWYRQAPGKQRELVARITRGG<br>TISYDDSVKGRFTISRDNAKNTVYLQMNSLKPEDTGVYYCNALYGTDYWGK<br>GTQVTVSSHHHHHH |
| 119 | ACP91<br>Chimeric<br>IL-12<br>fusion<br>protein | mdmrvpaqllglllwlrgarciwelkkdvyvveldwypdapgemvvitcdtpeedgitwildqssevlgsgkfltiqv<br>kefgdagqytchkggevlshsllllhkkedgiwstdilkdqkepknktflrceaknysgrftcwwlttistditfsvkssrg<br>ssdpqggvtcgaatlsaervrgdnkeyeysvecqedsacpaaeeslpievmvdavhklkyenytssffirdiikpdppkn<br>lqlkplknsrqvevsweypdtwstphsyfsltfcvqvqgkskrekkdrvftdktsatvicrknasisvraqchyysssws<br>ewasvpcsggggsggggsggggsrvipvsgparclsqsnillkttddmvktareklkhysctaedidheditrdqtstlkt<br>clplelhknesclatretssttrgsclppqktslmmticlgsiyedlkmyqtefqainaalqnhnhqqiildkgmlvaidel<br>mqslnhngetlrqkppvgeadpyrvkmklcillhafstivvtinrvmgylssagggsggggsggggsggggsgggg<br>sggggsggggsggggsggggsQSVLTQPPSVSGAPGQRVTISCSGSRSNIGSNTVKWYQ |

| SEQ ID NO. | Name | Sequence |
|---|---|---|
| | | QLPGTAPKLLIYYNDQRPSGVPDRFSGSKSGTSASLAITGLQAEDEADYYCQS<br>YDRYTHPALLFGTGTKVTVLggggsggggsggggsQVQLVESGGGVVQPGRSLRLS<br>CAASGFTFSSYGMHWVRQAPGKGLEWVAFIRYDGSNKYYADSVKGRFTISRD<br>NSKNTLYLQMNSLRAEDTAVYYCKTHGSHDNWGQGTMVTVSSggggsggggsgg<br>ggsEVQLVESGGGLVQPGNSLRLSCAASGFTFSKFGMSWVRQAPGKGLEWVSS<br>ISGSGRDTLYAESVKGRFTISRDNAKTTLYLQMNSLRPEDTAVYYCTIGGSLSV<br>SSQGTLVTVSSHHHHHHEPEA |
| 120 | ACP136<br>Chimeric<br>IL-12<br>fusion<br>protein | mdmrvpaqllglllwlrgarciwelkkdvyvveldwypdapgemvvitcdtpeedgitwtldqssevlgsgkfltiqv<br>kefgdagqytchkggevlshslllllhkkedgiwstdilkdqkepknktflrceaknysgrftcwwlttistditfsvkssrg<br>ssdpqgvtcgaatlsaervrgdnkeyeysvecqedsacpaaeeslpievmvdavhklIcyenytssffirdiikpdppkn<br>lqlkplknsrqvevsweypdtwstphsyfshfcvqvqgkskrekkdrvftdktsatvicrknasisvraqchyyssswsw<br>ewasvpcsggggsggggsggggsrvipvsgparclsqsnillkttddmvktareklkhysctaedidheditrdqtstlkt<br>clplelhIcnesclatretssttrgsclppqktslmmticlgsiyedlkmyqtefqainaalqnhnhqqiiildkgmlvaidel<br>mqslnhngetlrqkppvgeadpyrvkmklcillhafstrvvtinrvmgylssaSGGPGPAGMKGLPGSggg<br>gsggggsggggsggggsggggsggggsQSVLTQPPSVSGAPGQRVTISCSGSRSNIGSNTVK<br>WYQQLPGTAPKLLIYYNDQRPSGVPDRFSGSKSGTSASLAITGLQAEDEADYY<br>CQSYDRYTHPALLFGTGTKVTVLggggsggggsggggsQVQLVESGGGVVQPGRSL<br>RLSCAASGFTFSSYGMHWVRQAPGKGLEWVAFIRYDGSNKYYADSVKGRFTI<br>SRDNSKNTLYLQMNSLRAEDTAVYYCKTHGSHDNWGQGTMVTVSSHHHHH<br>HEPEA |
| 121 | ACP138<br>Chimeric<br>IL-12<br>fusion<br>protein | mdmrvpaqllglllwlrgarciwelkkdvyvveldwypdapgemvvlicdtpeedgitwtldqssevlgsgktltiqv<br>kefgdagqytchkggevlshsllllIckedgiwstdilkdqkepknktflrceaknysgrftcwwlttistditfsvkssrg<br>ssdpqgvtcgaatlsaervrgdnkeyeysvecqedsacpaaeeslpievmvdavhklIcyenytssffirdiikpdppkn<br>lqlkplknsrqvevsweypdtwstphsyfshfcvqvqgkskrekkdrvftdktsatvicrknasisvraqchyyssswsw<br>ewasvpcsggggsggggsggggsrvipvsgparclsqsnillkttddmvktareklkhysctaedidheditrdqtstlkt<br>clplelhIcnesclatretssttrgsclppqktslmmticlgsiyedlkmyqtefqainaalqnhnhqqiiildkgmlvaidel<br>mqslnhngetlrqkppvgeadpyrvkmklcillhafstrvvtinrvmgylssaSGGPGPAGMKGLPGSggg<br>gsggggsggggsggggsggggsggggsQSVLTQPPSVSGAPGQRVTISCSGSRSNIGSNTVK<br>WYQQLPGTAPKLLIYYNDQRPSGVPDRFSGSKSGTSASLAITGLQAEDEADYY<br>CQSYDRYTHPALLFGTGTKVTVLggggsggggsggggsQVQLVESGGGVVQPGRSL<br>RLSCAASGFTFSSYGMHWVRQAPGKGLEWVAFIRYDGSNKYYADSVKGRFTI<br>SRDNSKNTLYLQMNSLRAEDTAVYYCKTHGSHDNWGQGTMVTVSSggggsggg<br>gsggggsEVQLVESGGGLVQPGNSLRLSCAASGFTFSKFGMSWVRQAPGKGLEW<br>VSSISGSGRDTLYAESVKGRFTISRDNAKTTLYLQMNSLRPEDTAVYYCTIGGS<br>LSVSSQGTLVTVSSggggsggggsggggsQVQLQESGGGLAQAGGSLSLSCAASGFT<br>VSNSVMAWYRQTPGKQREFVAIINSVGSTNYADSVKGRFTISRDNAKNTVYL<br>QMNNLKPEDTAVYVCNRNFDRIYWGQGTQVTVSSHHHHHHEPEA |
| 122 | ACP139<br>Chimeric<br>IL-12<br>fusion<br>protein | mdmrvpaqllglllwlrgarcQVQLQESGGGLAQAGGSLSLSCAASGFTVSNSVMAWY<br>RQTPGKQREFVAIINSVGSTNYADSVKGRFTISRDNAKNTVYLQMNNLKPEDT<br>AVYVCNRNFDRIYWGQGTQVTVSSggggsggggsggggsiwelIckdvyvveldwypdapgem<br>vvitcdtpeedgitwadqssevlgsgktltiqvkefgdagqytchkggevlshsllllhldcedgiwstdilkdqkepknk<br>tflrceaknysgrftcwwlttistclitfsvkssrgssdpqgvtcgaatlsaervrgdnkeyeysvecqedsacpaaeeslpie<br>vmvdavhklIcyenytssffirdiikpdppknlqlkplknsrqvevsweypdtwstphsyfsltfcvqvqgkskrekkd<br>rvftdktsatvicrknasisvraqdryyssswsewasvpcsggggsggggsggggsrvipvsgparclsqsrnllkttdd<br>mvktareklkhysctaedidheditrdqtstlktclplelhknesclatretssttrgsclppqktslmmticlgsiyedlkm<br>yqtefgainaalqnhnhqqiiildkgmlvaidelmqslnhngetlrqkppvgeadpyrvkmklcillhafstrvvtinry<br>mgylssaSGGPGPAGMKGLPGSggggsggggsggggsggggsggggsggggsQSVLTQPPSVS<br>GAPGQRVTISCSGSRSNIGSNTVKWYQQLPGTAPKLLIYYNDQRPSGVPDRFS<br>GSKSGTSASLAITGLQAEDEADYYCQSYDRYTHPALLFGTGTKVTVLggggsggg<br>gsggggsQVQLVESGGGVVQPGRSLRLSCAASGFTFSSYGMHWVRQAPGKGLE<br>WVAFIRYDGSNKYYADSVKGRFTISRDNSKNTLYLQMNSLRAEDTAVYYCKT<br>HGSHDNWGQGTMVTVSSggggsggggsggggsEVQLVESGGGLVQPGNSLRLSCA<br>ASGFTFSKFGMSWVRQAPGKGLEWVSSISGSGRDTLYAESVKGRFTISRDNAK<br>TTLYLQMNSLRPEDTAVYYCTIGGSLSVSSQGTLVTVSSHHHHHHEPEA |
| 123 | ACP140<br>Chimeric<br>IL-12<br>fusion<br>protein | mdmrvpaqllglllwlrgarcQVQLQESGGGLAQAGGSLSLSCAASGFTVSNSVMAWY<br>RQTPGKQREFVAIINSVGSTNYADSVKGRFTISRDNAKNTVYLQMNNLKPEDT<br>AVYVCNRNFDRIYWGQGTQVTVSSSGGPGPAGMKGLPGSiwelkkcIvyvveldwyp<br>dapgemvvitcdtpeedgitwtldqssevlgsgktltiqvkefgdagqytchkggevlshslllllhIckedgiwstdilkdq<br>kepknktttflrceaknysgrftcwwlttistdiffsvkssrgssdpqgvtcgaatlsaervrgdnkeyeysvecqedsacpa<br>aeeslpievmvdavhklIcyenytssffirdiikpdppknlqlkplknsrqvevsweypdtwstphsyfsltfcvqvqgk<br>skrekkdrvftdktsatvicrknasisvraqchyyssswsewasvpcsggggsggggsggggsrvipvsgparclsqsr<br>nllkttddmvktareklkhysctaedidheditrdqtstlktclplelhIcnesclatretssttrgsclppqktslmmticlgsi<br>yedlkmyqtefgainaalqnhnhqqiiildkgmlvaidelmqslnhngetlrqkppvgeadpyrvkmklcillhafstry<br>vtinrvmgylssaSGGPGPAGMKGLPGSggggsggggsggggsggggsggggsggggsQSVLTQP<br>PSVSGAPGQRVTISCSGSRSNIGSNTVKWYQQLPGTAPKLLIYYNDQRPSGVPD<br>RFSGSKSGTSASLAITGLQAEDEADYYCQSYDRYTHPALLFGTGTKVTVLgggg<br>sggggsggggsQVQLVESGGGVVQPGRSLRLSCAASGFTFSSYGMHWVRQAPGKG<br>LEWVAFIRYDGSNKYYADSVKGRFTISRDNSKNTLYLQMNSLRAEDTAVYYC<br>KTHGSHDNWGQGTMVTVSSggggsggggsggggsEVQLVESGGGLVQPGNSLRLSC |

Sequence Table

| SEQ ID NO. | Name | Sequence |
|---|---|---|
| | | AASGFTFSKFGMSWVRQAPGKGLEWVSSISGSGRDTLYAESVKGRFTISRDNA KTTLYLQMNSLRPEDTAVYYCTIGGSLSVSSQGTLVTVSSHHHHHHEPEA |
| 124 | ACP38 IL-2 fusion protein | mdmrvpaqllglllwlrgarcaptssstkktqlqlehllldlqmilnginnyknpkltrmltfkfympkkatelkhlqcle eelkpleevinlaqsknfhlrprdlisninvivlelkgsetlfmceyadetativeflnrwitfcqsiistltSGGPGPAG MKGLPGSEVQLVESGGGLVQPGGSLRLSCAASGFTFSSYTLAWVRQAPGKGL EWVAAIDSSSYTYSPDTVRGRFTISRDNAKNSLYLQMNSLRAEDTAVYYCAR DSNWDALDYWGQGTTVTVSSGGGGSGGGGSGGGGSDIQMTQSPSSLSASVG DRVTITCKASQNVGTNVGWYQQKPGKAPKALIYSASFRYSGVPSRFSGSGSGT DFTLTISSLQPEDFATYYCQQYYTYPYTFGGGTKVEIKggggsggggsggggsEVQLV ESGGGLVQPGNSLRLSCAASGFTFSKFGMSWVRQAPGKGLEWVSSISGSGRDT LYAESVKGRFTISRDNAKTTLYLQMNSLRPEDTAVYYCTIGGSLSVSSQGTLV TVSSggggsggggsggggsQVQLQESGGGLVQAGGSLRLSCAASGRlFSIDIMSWYR QAPGKQRELVARITRGGTISYDDSVKGRFTISRDNAKNTVYLQMNSLKPEDTG VYYCNALYGTDYWGKGTQVTVSSHHHHHH |
| 125 | ACP39 IL-2 fusion protein | mdmrvpaqllglllwlrgarcQVQLQESGGGLVQAGGSLRLSCAASGRIFSIDIMSWYR QAPGKQRELVARITRGGTISYDDSVKGRFTISRDNAKNTVYLQMNSLKPEDTG VYYCNALYGTDYWGKGTQVTVSSSGGPGPAGMKGLPGSEVQLVESGGGLVQ PGNSLRLSCAASGFTFSKFGMSWVRQAPGKGLEWVSSISGSGRDTLYAESVKG RFTISRDNAKTTLYLQMNSLRPEDTAVYYCTIGGSLSVSSQGTLVTVSSSGGPG PAGMKGLPGSEVQLVESGGGLVQPGGSLRLSCAASGFTFSSYTLAWVRQAPG KGLEWVAAIDSSSYTYSPDTVRGRFTISRDNAKNSLYLQMNSLRAEDTAVYY CARDSNWDALDYWGQGTTVTVSSGGGGSGGGGSGGGGSDIQMTQSPSSLSA SVGDRVTITCKASQNVGTNVGWYQQKPGKAPKALIYSASFRYSGVPSRFSGSG SGTDFTLTISSLQPEDFATYYCQQYYTYPYTFGGGTKVEIKSGGPGPAGMKGL PGSaptssstkktqlqlehllldlqmilnginnyknpkltrmltfklympkkatelkhlqcleeelkpleevinlaqsknf hlrprdlisninvivlelkgsetlfmceyadetativeflnrwitfcqsiistltHHHHHH** |
| 126 | ACP40 IL-2 fusion | mdmrvpaqllglllwlrgarcelcddddppeiphatfkamaykegtmlncecrkgfrriksgslymktgnsshsswd nqcqctssatrntttkqvtpqeeqkerkttemqspmqpvdqaslpghcrepppweneateriyhfvvgqmvyyqcv qgyralhrgpaesvckmthgktrwtqpqlictgemetsqfpgeekpqaspegrpesetsclvtddfqiqtemaatmets proteiniftteyqggggsggggsggggsggggsggggsSGGPGPAGMKGLPGSaptssstkktqlqlehllld lqmilnginnyknpkltrmlffidympldcatelkhlqcleeelkpleevinlaqsknfhlrprdlisninvivlelkgsettf mceyadetativeflnrwitfcqsiistltHHHHHH |
| 127 | ACP41 IL-2 fusion protein (WW0076) | mdmrvpaqllglllwlrgarcaptssstkktqlqlehllldlqmilnginnyknpkltrmltfkfympkkatelkhlqcle eelkpleevinlaqsknfhlrprdlisninvivlelkgsetlfmceyadetativeflnrwitfcqsiistltSGGPGPAG MKGLPGSggggsggggsggggsggggsggggsggggselcddddppeiphallkamaykegtmlnceckrgfr riksgslymlctgnsshsswdnqcqctssatrntttkqvtpqeeqkerkttemqspmqpvdqaslpghcrepppwen eateriyhfvvgqmvyyqcvqgyralhrgpaesvclunthgktrwtqpqlictgemetsqfpgeekpqaspegrpese tsclvtdclfqiqtemaatmetsifftteyqHHHHHH |
| 128 | ACP42 IL-2 fusion protein (WW0078) | mdmrvpaqllglllwlrgarcEVQLVESGGGLVQPGNSLRLSCAASGFTFSKFGMSWVR QAPGKGLEWVSSISGSGRDTLYAESVKGRFTISRDNAKTTLYLQMNSLRPEDT AVYYCTIGGSLSVSSQGTLVTVSSggggsggggsggggsggggselcddddppeiphatfkamaykegtmln ceckrgfrriksgslymktgnsshsswdnqcqctssatrntttkqvtpqeeqkerkttemqspmqpvdqaslpghcre pppweneateriyhfvvgqmvyyqcvqgyralhrgpaesvckmthgktrwtqpqlictgemetsqfpgeekpqasp egrpesetsclvtdclfqiqtemaatmetsifftteyqggggsggggsggggsggggsggggsggggsSGGPGPAG MKGLPGSaptssstkktqlqlehllldlqmilnginnyknpkltrmltfkfympkkatelkhlqcleeelkpleevinl aqsknfblrprdlisninvivlelkgsetlfmceyadetativeflnrwitfcqsiistltHHHHHH |
| 129 | ACP43 IL-2 fusion protein (WW0079) | mdmrvpaqllglllwlrgarcaptssstkktqlqlehllldlqmilnginnyknpkltrmltfkfympkkatelkhlqcle eelkpleevinlaqsknfhlrprdlisninvivlelkgsetlfmceyadetativeflnrwitfcqsiistltSGGPGPAG MKGLPGSggggsggggsggggsggggsggggsggggselcddddppeiphallkamaykegtmlnceckrgfr riksgslymlctgnsshsswdnqcqctssatrntttkqvtpqeeqkerkttemqspmqpvdqaslpghcrepppwen eateriyhfvvgqmvyyqcvqgyralhrgpaesvclunthgktrwtqpqlictgemetsqfpgeekpqaspegrpese tsclvtddfqiqtemaatmetsifftteyqggggsggggsggggsggggsEVQLVESGGGLVQPGNSLRLSCA ASGFTFSKFGMSWVRQAPGKGLEWVSSISGSGRDTLYAESVKGRFTISRDNAK TTLYLQMNSLRPEDTAVYYCTIGGSLSVSSQGTLVTVSSHHHHHH |
| 130 | ACP44 IL-2 fusion protein (WW0080) | mdmrvpaqllglllwlrgarcaptssstkktqlqlehllldlqmilnginnyknpkltrmltfkfympkkatelkhlqcle eelkpleevinlaqsknfhlrprdlisninvivlelkgsettfmceyadetativeflnrwitfcqsiistltSGGPGPAG MKGLPGSggggsggggsggggsggggsggggsggggselcddddppeiphatikamaykegtmlnceckrgfr riksgslymlctgnsshsswdnqcqctssatrntttkqvtpqeeqkerkttemqspmqpvdqaslpghcrepppwen eateriyhfvvgqmvyyqcvqgyralhrgpaesvckmthgktrwtqpqlictgemetsqfpgeekpqaspegrpese tsclvtddfqiqtemaatmetsifftteyqSGGPGPAGMKGLPGSEVQLVESGGGLVQPGNSLR LSCAASGFTFSKFGMSWVRQAPGKGLEWVSSISGSGRDTLYAESVKGRFTISR DNAKTTLYLQMNSLRPEDTAVYYCTIGGSLSVSSQGTLVTVSSHHHHHH |
| 131 | ACP45 IL-2 fusion | mdmrvpaqllglllwlrgarcEVQLVESGGGLVQPGNSLRLSCAASGFTFSKFGMSWVR QAPGKGLEWVSSISGSGRDTLYAESVKGRFTISRDNAKTTLYLQMNSLRPEDT AVYYCTIGGSLSVSSQGTLVTVSSSGGPGPAGMKGLPGSEVQLVESGGGLVQP |

| SEQ ID NO. | Name | Sequence |
|---|---|---|
| | protein WW0046 | proteinGGSLRLSCAASGFTFSSYTLAWVRQAPGKGLEWVAAIDSSSYTYSPDTVRGRF<br>TISRDNAKNSLYLQMNSLRAEDTAVYYCARDSNWDALDYWGQGTTVTVSSG<br>GGGSGGGGSGGGGSDIQMTQSPSSLSASVGDRVTITCKASQNVGTNVGWYQQ<br>KPGKAPKALIYSASFRYSGVPSRFSGSGSGTDFTLTISSLQPEDFATYYCQQYY<br>TYPYTFGGGTKVEIKggggsggggsggggsggggsggggsggggsSGGPGPAGMKGLPGSa<br>ptssstkktqlqlehllldlqmilnginnyknpkihmltfkfympkkatelkhlqcleeelkpleevinlaqsknfhlrprd<br>lisninvivlelkgsettfmceyadetativeflnrwitfcqsiistltHHHHHH |
| 132 | ACP46 IL-2 fusion protein | mdmrvpaqllglllwlrgarcaptssstkktqlqlehllldlqmilnginnyknpkltrmltfkfympkkatelkhlqcle<br>eelkpleevinlaqsknfhlrprdlisninvivlelkgsettfmceyadetativeflnrwitfcqsiistltSGGPGPAG<br>MKGLPGSggggsggggsggggsggggsggggsggggsEVQLVESGGGLVQPGGSLRLSCA<br>ASGFTFSSYTLAWVRQAPGKGLEWVAAIDSSSYTYSPDTVRGRFTISRDNAKN<br>SLYLQMNSLRAEDTAVYYCARDSNWDALDYWGQGTTVTVSSsggpgpagmkglp<br>gsDIQMTQSPSSLSASVGDRVTITCKASQNVGTNVGWYQQKPGKAPKALIYSA<br>SFRYSGVPSRFSGSGSGTDFTLTISSLQPEDFATYYCQQYYTYPYTFGGGTKVEI<br>KggggsggggsggggsEVQLVESGGGLVQPGNSLRLSCAASGFTFSKFGMSWVRQA<br>PGKGLEWVSSISGSGRDTLYAESVKGRFTISRDNAKTTLYLQMNSLRPEDTAV<br>YYCTIGGSLSVSSQGTLVTVSSggggsggggsggggsQVQLQESGGGLVQAGGSLRL<br>SCAASGRIFSIDIMSWYRQAPGKQRELVARITRGGTISYDDSVKGRFTISRDNA<br>KNTVYLQMNSLKPEDTGVYYCNALYGTDYWGKGTQVTVSSHHHHHH |
| 133 | ACP47 IL-2 fusion protein | mdmrvpaqllglllwlrgarcQVQLQESGGGLVQAGGSLRLSCAASGRIFSIDIMSWYR<br>QAPGKQRELVARITRGGTISYDDSVKGRFTISRDNAKNTVYLQMNSLKPEDTG<br>VYYCNALYGTDYWGKGTQVTVSSggggsggggsggggsaptssstkktqlqlehllldlqmilngin<br>proteinnyknpkltrmltfkylympldcatelkhlqcleeelkpleevinlaqsknfhlrprd<br>lisninvivlelkgsettfmceyadet<br>ativeflnrwitfcqsiistltSGGPGPAGMKGLPGSEVQLVESGGGLVQPGNSLRLSCAAS<br>GFTFSKFGMSWVRQAPGKGLEWVSSISGSGRDTLYAESVKGRFTISRDNAKTT<br>LYLQMNSLRPEDTAVYYCTIGGSLSVSSQGTLVTVSSggggsggggsggggsggggsgg<br>ggsggggsEVQLVESGGGLVQPGGSLRLSCAASGFTFSSYTLAWVRQAPGKGLE<br>WVAAIDSSSYTYSPDTVRGRFTISRDNAKNSLYLQMNSLRAEDTAVYYCARD<br>SNWDALDYWGQGTTVTVSSGGGGSGGGGSGGGGSDIQMTQSPSSLSASVGD<br>RVTITCKASQNVGTNVGWYQQKPGKAPKALIYSASFRYSGVPSRFSGSGSGTD<br>FTLTISSLQPEDFATYYCQQYYTYPYTFGGGTKVEIKHHHHHH |
| 134 | ACP48 IL-2 fusion protein (WW0054) | mdmrvpaqllglllwlrgarcaptssstkktqlqlehllldlqmilnginnyknpkltrmltfkfympkkatelkhlqcle<br>eelkpleevinlaqsknfhlrprdlisninvivlelkgsettfmceyadetativeflnrwitfcqsiistltSGGPGPAG<br>MKGLPGSEVQLVESGGGLVQPGGSLRLSCAASGFTFSSYTLAWVRQAPGKGL<br>EWVAAIDSSSYTYSPDTVRGRFTISRDNAKNSLYLQMNSLRAEDTAVYYCAR<br>DSNWDALDYWGQGTTVTVSSGGGGSGGGGSGGGGSDIQMTQSPSSLSASVG<br>DRVTITCKASQNVGTNVGWYQQKPGKAPKALIYSASFRYSGVPSRFSGSGSGT<br>DFTLTISSLQPEDFATYYCQQYYTYPYTFGGGTKVEIKggggsggggsggggsEVQLV<br>ESGGGLVQPGNSLRLSCAASGFTFSKFGMSWVRQAPGKGLEWVSSISGSGRDT<br>LYAESVKGRFTISRDNAKTTLYLQMNSLRPEDTAVYYCTIGGSLSVSSQGTLV<br>TVSSHHHHHH |
| 135 | ACP49 IL-2 fusion protein (WW0055) | mdmrvpaqllglllwlrgarcaptssstkktqlqlehllldlqmilnginnyknpkltrmltfkfympkkatelkhlqcle<br>eelkpleevinlaqsknfhlrprdlisninvivlelkgsettfmceyadetativeflnrwitfcqsiistltSGGPGPAG<br>MKGLPGSggggsggggsggggsggggsggggsggggsEVQLVESGGGLVQPGGSLRLSCA<br>ASGFTFSSYTLAWVRQAPGKGLEWVAAIDSSSYTYSPDTVRGRFTISRDNAKN<br>SLYLQMNSLRAEDTAVYYCARDSNWDALDYWGQGTTVTVSSGGGGSGGGG<br>SGGGGSDIQMTQSPSSLSASVGDRVTITCKASQNVGTNVGWYQQKPGKAPKA<br>LIYSASFRYSGVPSRFSGSGSGTDFTLTISSLQPEDFATYYCQQYYTYPYTFGGG<br>TKVEIKggggsggggsggggsEVQLVESGGGLVQPGNSLRLSCAASGFTFSKFGMSW<br>VRQAPGKGLEWVSSISGSGRDTLYAESVKGRFTISRDNAKTTLYLQMNSLRPE<br>DTAVYYCTIGGSLSVSSQGTLVTVSSHHHHHH |
| 136 | ACP92 IL-2 fusion protein | mdmrvpaqllglllwlrgarcEVQLVESGGGLVQPGNSLRLSCAASGFTFSKFGMSWVR<br>QAPGKGLEWVSSISGSGRDTLYAESVKGRFTISRDNAKTTLYLQMNSLRPEDT<br>proteinAVYYCTIGGSLSVSSQGTLVTVSSSGGPGPAGMKGLPGSaptssstkktqlqlehllldlqm<br>ilnginnyknpklirmltfkfympkkatelkhlqcleeelkpleevinlaqsknfhlrprdlisninvivlelkgsettfmce<br>yadetativeflnrwitfcqsiistltSGGPGPAGMKGLPGSEVQLVESGGGLVQPGNSLRLSC<br>AASGFTFSKFGMSWVRQAPGKGLEWVSSISGSGRDTLYAESVKGRFTISRDNA<br>KTTLYLQMNSLRPEDTAVYYCTIGGSLSVSSQGTLVTVSSHHHHHH |
| 137 | ACP93 IL-2 fusion protein | mdmrvpaqllglllwlrgarcQVQLQESGGGLVQAGGSLRLSCAASGRIFSIDIMSWYR<br>QAPGKQRELVARITRGGTISYDDSVKGRFTISRDNAKNTVYLQMNSLKPEDTG<br>VYYCNALYGTDYWGKGTQVTVSSgsgsgsgsgsgsgsEVQLVESGGGLVQPGNS<br>LRLSCAASGFTFSKFGMSWVRQAPGKGLEWVSSISGSGRDTLYAESVKGRFTI<br>SRDNAKTTLYLQMNSLRPEDTAVYYCTIGGSLSVSSQGTLVTVSSgsgsgsgsgsgs<br>gsgsQVQLQESGGGLVQAGGSLRLSCAASGRIFSIDIMSWYRQAPGKQRELVAR<br>ITRGGTISYDDSVKGRFTISRDNAKNTVYLQMNSLKPEDTGVYYCNALYGTD<br>YWGKGTQVTVSSgsgsgsgsgsgsgsgsEVQLVESGGGLVQPGGSLRLSCAASGFTFS |

-continued

Sequence Table

| SEQ ID NO. | Name | Sequence |
|---|---|---|
| | | SYTLAWVRQAPGKGLEWVAAIDSSSYTYSPDTVRGRFTISRDNAKNSLYLQM NSLRAEDTAVYYCARDSNWDALDYWGQGTTVTVSSGGGGSGGGGSGGGGS DIQMTQSPSSLSASVGDRVTITCKASQNVGTNVGWYQQKPGKAPKALIYSASF RYSGVPSRFSGSGSGTDFTLTISSLQPEDFATYYCQQYYTYPYTFGGGTKVEIK SGGPGPAGMKGLPGSaptssstkktqlqlehllldlqmilnginnyknpkltrmltfkfympkkatelkhlqcl eeelkpleevinlaqsknfhlrprdlisninvivlelkgsettfmceyadetativeflnrwilfcqsiistltHHHHHH |
| 138 | ACP94 IL-2 fusion protein | mdmrvpaqllglllwlrgarcQVQLQESGGGLVQAGGSLRLSCAASGRIFSIDIMSWYR QAPGKQRELVARITRGGTISYDDSVKGRFTISRDNAKNTVYLQMNSLKPEDTG VYYCNALYGTDYWGKGTQVTVSSgsgsgsgsgsgsgsgsEVQLVESGGGLVQPGNS LRLSCAASGFTFSKFGMSWVRQAPGKGLEWVSSISGSGRDTLYAESVKGRFTI SRDNAKTTLYLQMNSLRPEDTAVYYCTIGGSLSVSSQGTLVTVSSgsgsgsgsgsgs gsgsEVQLVESGGGLVQPGGSLRLSCAASGFTFSSYTLAWVRQAPGKGLEWVA AIDSSSYTYSPDTVRGRFTISRDNAKNSLYLQMNSLRAEDTAVYYCARDSNW DALDYWGQGTTVTVSSGGGGSGGGGSGGGGSDIQMTQSPSSLSASVGDRVTI TCKASQNVGTNVGWYQQKPGKAPKALIYSASFRYSGVPSRFSGSGSGTDFTLT ISSLQPEDFATYYCQQYYTYPYTFGGGTKVEIKSGGPGPAGMKGLPGSaptssstk ktqlqlehllldlqmilnginnyknpkltrmltfkfympkkatelkhlqcleeelkpleevinlaqsknfblrprdlisninv ivlelkgsettfmceyadetativeflnrwitfcqsiistltHHHHHH |
| 139 | ACP95 IL-2 fusion protein | mdmrvpaqllglllwlrgarcQVQLQESGGGLVQAGGSLRLSCAASGRIFSIDIMSWYR QAPGKQRELVARITRGGTISYDDSVKGRFTISRDNAKNTVYLQMNSLKPEDTG VYYCNALYGTDYWGKGTQVTVSSgsgsgsgsgsgsgsgsEVQLVESGGGLVQPGNS LRLSCAASGFTFSKFGMSWVRQAPGKGLEWVSSISGSGRDTLYAESVKGRFTI SRDNAKTTLYLQMNSLRPEDTAVYYCTIGGSLSVSSQGTLVTVSSSGGPGPAG MKGLPGSaptssstkktqlqlehllldlqmilnginnyknpkltrmltfkfympkkatelkhlqcleeelkpleevinl aqsknfblrprdlisninvivlelkgsettfmceyadetativeflnrwitfcqsiistltHHHHHH |
| 140 | ACP96 IL-2 fusion protein | mdmrvpaqllglllwlrgarcQVQLQESGGGLVQAGGSLRLSCAASGRIFSIDIMSWYR QAPGKQRELVARITRGGTISYDDSVKGRFTISRDNAKNTVYLQMNSLKPEDTG VYYCNALYGTDYWGKGTQVTVSSSGGPGPAGMKGLPGSaptssstkktqlqlehllldlq milnginnyknpklirmltfkfympkkatelkhlqcleeelkpleevinlaqsknfhlrprdlisninvivlelkgsettfm ceyadetativeflnrwitfcqsiistltSGGPGPAGMKGLPGSEVQLVESGGGLVQPGNSLRL SCAASGFTFSKFGMSWVRQAPGKGLEWVSSISGSGRDTLYAESVKGRFTISRD NAKTTLYLQMNSLRPEDTAVYYCTIGGSLSVSSQGTLVTVSSHHHHHH |
| 141 | ACP97 IL-2 fusion protein | mdmrvpaqllglllwlrgarcQVQLQESGGGLVQAGGSLRLSCAASGRIFSIDIMSWYR QAPGKQRELVARITRGGTISYDDSVKGRFTISRDNAKNTVYLQMNSLKPEDTG VYYCNALYGTDYWGKGTQVTVSSggggsggggsggggsEVQLVESGGGLVQPGNS LRLSCAASGFTFSKFGMSWVRQAPGKGLEWVSSISGSGRDTLYAESVKGRFTI SRDNAKTTLYLQMNSLRPEDTAVYYCTIGGSLSVSSQGTLVTVSSSGGPGPAG MKGLPGSaptsssticktqlqlehllldlqmilnginnyknpkltrmltfkfympkkatelklilqcleeelkpleevinl aqsknfhlrprdlisninvivlelkgsettfmceyadetativeflnrwitfcqsiistltSGGPGPAGMKGLPGS EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSHHHHHH |
| 142 | ACP99 IL-2 fusion protein | mdmrvpaqllglllwlrgarcQVQLQESGGGLVQAGGSLRLSCAASGRIFSIDIMSWYR QAPGKQRELVARITRGGTISYDDSVKGRFTISRDNAKNTVYLQMNSLKPEDTG VYYCNALYGTDYWGKGTQVTVSSggggsggggsggggsaptsssticktqlqlehllldlqmilngin nyknpkltrmltficfympkkatelkhlqcleeelkpleevinlaqsknfhlrprdlisninvivlelkgsettfmceyadet ativeflnrwitfcqsiistltSGGPGPAGMKGLPGSEVQLVESGGGLVQPGNSLRLSCAAS GFTFSKFGMSWVRQAPGKGLEWVSSISGSGRDTLYAESVKGRFTISRDNAKTT LYLQMNSLRPEDTAVYYCTIGGSLSVSSQGTLVTVSSHHHHHH |
| 143 | ACP100 IL-2 fusion protein | mdmrvpaqllglllwlrgarcQVQLQESGGGLVQAGGSLRLSCAASGRIFSIDIMSWYR QAPGKQRELVARITRGGTISYDDSVKGRFTISRDNAKNTVYLQMNSLKPEDTG VYYCNALYGTDYWGKGTQVTVSSggggsggggsggggsaptsssticktqlqlehllldlqmilngin nyknpkltrinifficfympldcatelkhlqcleeelkpleevinlaqsknfhlrprdlisninvivlelkgset tfmceyadetativeflnrwitfcqsiistltHHHHHH |
| 144 | ACP101 (WW0061) IL-2 fusion protein | mdmrvpaqllglllwlrgarcaptsssticktqlqlehllldlqmilnginnyknpkltrmlafympkkatelkhlqcle eelkpleevinlaqsknfhlrprdlisninvivlelkgsettfmceyadetativeflnrwitfcqsiistltSGGPGPAG MKGLPGSEVQLVESGGGLVQPGNSLRLSCAASGFTFSKFGMSWVRQAPGKGL EWVSSISGSGRDTLYAESVKGRFTISRDNAKTTLYLQMNSLRPEDTAVYYCTI GGSLSVSSQGTLVTVSSHHHHHH |
| 145 | ACP102 IL-2 fusion protein | mdmrvpaqllglllwlrgarcQVQLQESGGGLVQAGGSLRLSCAASGRIFSIDIMSWYR QAPGKQRELVARITRGGTISYDDSVKGRFTISRDNAKNTVYLQMNSLKPEDTG VYYCNALYGTDYWGKGTQVTVSSSGGPGPAGMKGLPGSaptsssticktqlqlehllldlq milnginnyknpkltrmlafympkkatelkhlqcleeelkpleevinlaqsknfhliprdlisninvivlelkgsettfm ceyadetativeflnrwitfcqsiistltSGGPGPAGMKGLPGSEVQLVESGGGLVQPGNSLRL SCAASGFTFSKFGMSWVRQAPGKGLEWVSSISGSGRDTLYAESVKGRFTISRD |

Sequence Table

| SEQ ID NO. | Name | Sequence |
|---|---|---|
| | | NAKTTLYLQMNSLRPEDTAVYYCTIGGSLSVSSQGTLVTVSSggggsggggsggggs<br>ggggsggggsggggsEVQLVESGGGLVQPGGSLRLSCAASGFTFSSYTLAWVRQAPG<br>KGLEWVAAIDSSSYTYSPDTVRGRFTISRDNAKNSLYLQMNSLRAEDTAVYY<br>CARDSNWDALDYWGQGTTVTVSSGGGGSGGGGSGGGGSDIQMTQSPSSLSA<br>SVGDRVTITCKASQNVGTNVGWYQQKPGKAPKALIYSASFRYSGVPSRFSGSG<br>SGTDFTLTISSLQPEDFATYYCQQYYTYPYTFGGGTKVEIKHHHHHH |
| 146 | ACP103 IL-2 fusion protein | mdmrvpaqllglllwlrgarcaptsssticktqlqlehllldlqmilnginnyknpkltrmltfk<br>fympkkatelkhlqcleeelkpleevinlaqsknfhlrprdlisninvivlelkgsettfmcey<br>adetativeflnrwitfcqsiistltSGGPGPAGMKGLPGSggggsggggsggggsggggsggggsg<br>gggsEVQLVESGGGLVQPGGSLRLSCAASGFTFSSYTLAWVRQAPGKGLEWVAAIDSSSYTYSPDTVR<br>GRFTISRDNAKNSLYLQMNSLRAEDTAVYYCARDSNWDALDYWGQGTTVTVSSGGGGSGGGG<br>SGGGGSDIQMTQSPSSLSASVGDRVTITCKASQNVGTNVGWYQQKPGKAPKA<br>LIYSASFRYSGVPSRFSGSGSGTDFTLTISSLQPEDFATYYCQQYYTYPYTFGGG<br>TKVEIKggggsggggsggggsEVQLVESGGGLVQPGNSLRLSCAASGFTFSKFGMSW<br>VRQAPGKGLEWVSSISGSGRDTLYAESVKGRFTISRDNAKTTLYLQMNSLRPE<br>DTAVYYCTIGGSLSVSSQGTLVTVSSggggsggggsggggsggggsQVQLQESGGGLAQAGG<br>SLSLSCAASGFTVSNSVMAWYRQTPGKQREFVAIINSVGSTNYADSVKGRFTIS<br>RDNAKNTVYLQMNNLKPEDTAVYVCNRNFDRIYWGQGTQVTVSSHHHHHH |
| 147 | ACP104 IL-2 fusion protein | mdmrvpaqllglllwlrgarcQVQLQESGGGLAQAGGSLSLSCAASGFTVSNSVMAWY<br>RQTPGKQREFVAIINSVGSTNYADSVKGRFTISRDNAKNTVYLQMNNLKPEDT<br>AVYVCNRNFDRIYWGQGTQVTVSSaptsssticktqlqlehllldlqmilnginnyknpkltrmltfkfy<br>mpkkatelkhlilqcleeelkpleevnlnlaqsknflilrprdlisninvlnlaqsknflilrprdlisninvivlelkgsettfmceyadetati<br>veflnrvvitfcqsiieflnrwitfcqsiistltSGGPGPAGMKGLPGSEVQLVESGGGLVQPGNSLRLSC<br>AASGFTFSKFGMSWVRQAPGKGLEWVSSISGSGRDTLYAESVKGRFTISRDNAKTTLYLQMNSLR<br>PEDTAVYYCTIGGSLSVSSQGTLVTVSSggggsggggsggggsggggsggggsggggsEVQL<br>VESGGGLVQPGGSLRLSCAASGFTFSSYTLAWVRQAPGKGLEWVAAIDSSSYT<br>YSPDTVRGRFTISRDNAKNSLYLQMNSLRAEDTAVYYCARDSNWDALDYWG<br>QGTTVTVSSGGGGSGGGGSGGGGSDIQMTQSPSSLSASVGDRVTITCKASQNV<br>GTNVGWYQQKPGKAPKALIYSASFRYSGVPSRFSGSGSGTDFTLTISSLQPEDF<br>ATYYCQQYYTYPYTFGGGTKVEIKHHHHHH |
| 148 | ACP105 IL-2 fusion protein | mdmrvpaqllglllwlrgarcEVQLVESGGGLVQPGGSLRLSCAASGFTFSSYTLAWVR<br>QAPGKGLEWVAAIDSSSYTYSPDTVRGRFTISRDNAKNSLYLQMNSLRAEDTA<br>VYYCARDSNWDALDYWGQGTTVTVSSGGGGSGGGGSGGGGSDIQMTQSPSS<br>LSASVGDRVTITCKASQNVGTNVGWYQQKPGKAPKALIYSASFRYSGVPSRFS<br>GSGSGTDFTLTISSLQPEDFATYYCQQYYTYPYTFGGGTKVEIKggggsggggsggg<br>gsggggsggggsggggsSGGPGPAGMKGLPGSaptsssticktqlqlehllldlqmilnginnyknpkltrml<br>tflcfympkkatelkhlqcleeelkpleevinlaqsknfhlrprdlisninvivlelkgsettfmceyadeta<br>tiveflnrwitfcqsiistltSGGPGPAGMKGLPGSEVQLVESGGGLVQPGNSLRLSCAASGFTFSKFG<br>MSWVRQAPGKGLEWVSSISGSGRDTLYAESVKGRFTISRDNAKTTLYLQMNS<br>LRPEDTAVYYCTIGGSLSVSSQGTLVTVSSggggsggggsggggsggggsQVQLQESGGGLA<br>QAGGSLSLSCAASGFTVSNSVMAWYRQTPGKQREFVAIINSVGSTNYADSVK<br>GRFTISRDNAKNTVYLQMNNLKPEDTAVYVCNRNFDRIYWGQGTQVTVSSH<br>HHHHH |
| 149 | ACP106 IL-2 fusion protein | mdmrvpaqllglllwlrgarcQVQLQESGGGLAQAGGSLSLSCAASGFTVSNSVMAWY<br>RQTPGKQREFVAIINSVGSTNYADSVKGRFTISRDNAKNTVYLQMNNLKPEDT<br>AVYVCNRNFDRIYWGQGTQVTVSSggggsggggsggggsggggsEVQLVESGGGLVQPGNS<br>LRLSCAASGFTFSKFGMSWVRQAPGKGLEWVSSISGSGRDTLYAESVKGRFTI<br>SRDNAKTTLYLQMNSLRPEDTAVYYCTIGGSLSVSSQGTLVTVSSSGGPGPAG<br>MKGLPGSEVQLVESGGGLVQPGGSLRLSCAASGFTFSSYTLAWVRQAPGKGL<br>EWVAAIDSSSYTYSPDTVRGRFTISRDNAKNSLYLQMNSLRAEDTAVYYCAR<br>DSNWDALDYWGQGTTVTVSSGGGGSGGGGSGGGGSDIQMTQSPSSLSASVG<br>DRVTITCKASQNVGTNVGWYQQKPGKAPKALIYSASFRYSGVPSRFSGSGSGT<br>DFTLTISSLQPEDFATYYCQQYYTYPYTFGGGTKVEIKggggsggggsggggsggggsgg<br>ggsggggsSGGPGPAGMKGLPGSaptsssticktqlqlehllldlqmilnginnyknpkltrmltfkfympkk<br>atelkhlqcleeelkpleevinlaqsknfhlrprdlisninvivlelkgsettfmceyadetativeflnrwil<br>fcqsiistltHHHHHH |
| 150 | ACP107 IL-2 fusion protein | mdmrvpaqllglllwlrgarcEVQLVESGGGLVQPGGSLRLSCAASGFTFSSYTLAWVR<br>QAPGKGLEWVAAIDSSSYTYSPDTVRGRFTISRDNAKNSLYLQMNSLRAEDTA<br>VYYCARDSNWDALDYWGQGTTVTVSSGGGGSGGGGSGGGGSDIQMTQSPSS<br>LSASVGDRVTITCKASQNVGTNVGWYQQKPGKAPKALIYSASFRYSGVPSRFS<br>GSGSGTDFTLTISSLQPEDFATYYCQQYYTYPYTFGGGTKVEIKggggsggggsggg<br>gsggggsggggsggggsEVQLVESGGGLVQPGNSLRLSCAASGFTFSKFGMSWVRQA<br>PGKGLEWVSSISGSGRDTLYAESVKGRFTISRDNAKTTLYLQMNSLRPEDTAV<br>YYCTIGGSLSVSSQGTLVTVSSSGGPGPAGMKGLPGSaptsssticktqlqlehllldlqmilng<br>innyknpkltrmltfkfympkkatelkhlqcleeelkpleevinlaqsknfhliprdlisninvivlelkgse<br>ettfmceyadtativeflnrwitfcqsiistltggggsggggsggggsQVQLQESGGGLAQAGGSLSLSCAASGFT<br>VSNSVMAWYRQTPGKQREFVAIINSVGSTNYADSVKGRFTISRDNAKNTVYL<br>QMNNLKPEDTAVYVCNRNFDRIYWGQGTQVTVSSHHHHHH |

Sequence Table

| SEQ ID NO. | Name | Sequence |
|---|---|---|
| 151 | ACP108 IL-2 fusion protein | mdmrvpaqllglllwlrgarcQVQLQESGGGLVQAGGSLRLSCAASGRIFSIDIMSWYR QAPGKQRELVARITRGGTISYDDSVKGRFTISRDNAKNTVYLQMNSLKPEDTG VYYCNALYGTDYWGKGTQVTVSSggggsggggsggggsaptssssticktqlqlehllldlqmilngin nyknpkltrmltfklympldcatelkhlqcleeelkpleevinlaqsknfhlrprdlisninvivlelkgsett fmceyadetativeflnrwitfcqsiistltSGGPGPAGMKGLPGSrgetgpaaPGSEVQLVESGGGLVQPGNS LRLSCAASGFTFSKFGMSWVRQAPGKGLEWVSSISGSGRDTLYAESVKGRFTI SRDNAKTTLYLQMNSLRPEDTAVYYCTIGGSLSVSSQGTLVTVSSggggsggggsg gggsggggsggggsggggsEVQLVESGGGLVQPGGSLRLSCAASGFTFSSYTLAWVRQ APGKGLEWVAAIDSSSYTYSPDTVRGRFTISRDNAKNSLYLQMNSLRAEDTAV YYCARDSNWDALDYWGQGTTVTVSSGGGGSGGGGSGGGGSDIQMTQSPSSL SASVGDRVTITCKASQNVGTNVGWYQQKPGKAPKALIYSASFRYSGVPSRFSG SGSGTDFTLTISSLQPEDFATYYCQQYYTYPYTFGGGTKVEIKHHHHHH |
| 152 | ACP117 Anti-FN CGS-2 scFv | mdmrvpaqllglllwlrgarcEVQLVESGGGLVQPGGSLRLSCAASGFTFSSYAMSWVR QAPGKGLEWVSAISGSGGSTYYADSVKGRFTIRDNSKNTLYLQMNSLRAED PEATAVYYCARGVGAFRPYRKHEWGQGTLVTVSRggggsggggsggggsSSELTQDPAV SVALGQTVRITCQGDSLRSYYASWYQQKPGQAPVLVIYGKNNRPSGIPDRFSG SSSGNTASLTTTGAQAEDEADYYCNSSPFEHNLVVFGGGTKLTVLHHHHHHEPEA |
| 153 | ACP118 NARA1 Vh/Vl non-cleavable | mdmrvpaqllglllwlrgarcQVQLQQSGAELVRPGTSVKVSCKASGYAFTNYLIEWV KQRPGQGLEWIGVINPGSGGTNYNEKFKGKATLTADKSSSTAYMQLSSLTSD DSAVYFCARWRGDGYYAYFDVWGAGTTVTVSSggggsggggsggggsDIVLTQSP ASLAVSLGQRATISCKASQSVDYDGDSYMNWYQQKPGQPPKLLIYAASNLES GIPARFSGSGSGTDFTLNIHPVEEEDAATYYCQQSNEDPYTFGGGTKLEIKHHH HHEPEA |
| 154 | ACP119 NARA1 Vh/Vl cleavable | mdmrvpaqllglllwlrgarcQVQLQQSGAELVRPGTSVKVSCKASGYAFTNYLIEWV KQRPGQGLEWIGVINPGSGGTNYNEKFKGKATLTADKSSSTAYMQLSSLTSD DSAVYFCARWRGDGYYAYFDVWGAGTTVTVSSSGGPGPAGMKGLPGSDIVL TQSPASLAVSLGQRATISCKASQSVDYDGDSYMNWYQQKPGQPPKLLIYAAS NLESGIPARFSGSGSGTDFTLNIHPVEEEDAATYYCQQSNEDPYTFGGGTKLEI KHHHHHHEPEA |
| 155 | ACP120 NARA1 Vl/Vh non-cleavable | mdmrvpaqllglllwlrgarcDIVLTQSPASLAVSLGQRATISCKASQSVDYDGDSYMN WYQQKPGQPPKLLIYAASNLESGIPARFSGSGSGTDFTLNIHPVEEEDAATYYC QQSNEDPYTFGGGTKLEIKggggsggggsggggsggggsQVQLQQSGAELVRPGTSVKVSCK ASGYAFTNYLIEWVKQRPGQGLEWIGVINPGSGGTNYNEKFKGKATLTADKS SSTAYMQLSSLTSDDSAVYFCARWRGDGYYAYFDVWGAGTTVTVSSHHHHH HEPEA |
| 156 | ACP121 NARA1 Vl/Vh cleavable | mdmrvpaqllglllwlrgarcDIVLTQSPASLAVSLGQRATISCKASQSVDYDGDSYMN WYQQKPGQPPKLLIYAASNLESGIPARFSGSGSGTDFTLNIHPVEEEDAATYYC QQSNEDPYTFGGGTKLEIKSGGPGPAGMKGLPGSQVQLQQSGAELVRPGTSV KVSCKASGYAFTNYLIEWVKQRPGQGLEWIGVINPGSGGTNYNEKFKGKATL TADKSSSTAYMQLSSLTSDDSAVYFCARWRGDGYYAYFDVWGAGTTVTVSS HHHHHHEPEA |
| 157 | ACP124 IL-2 fusion protein (WW0159) | mdmrvpaqllglllwlrgarcaptsssstkktqlqlehllldlqmilnginnyknpkltrmilfkfympkkatelkhlqcle eelkpleevinlaqsknfhlrprdlisninvivlelkgsetlfmceyadetativeflnrwitfcqsiistligggsggggsg gggsEVQLVESGGGLVQPGNSLRLSCAASGFTFSKFGMSWVRQAPGKGLEWVS SISGSGRDTLYAESVKGRFTISRDNAKTTLYLQMNSLRPEDTAVYYCTIGGSLS VSSQGTLVTVSSHHHHHHEPEA |
| 158 | ACP132 IL-2 fusion protein (WW0177) | mdmrvpaqllglllwlrgarcaptsssstkktqlqlehllldlqmilnginnyknpkltrmilfkfympkkatelkhlqcle eelkpleevinlaqsknfhlrprdlisninvivlelkgsetlfmceyadetativeflnrwitfcqsiistligggsggggsg gggsdahksevahrfkdlgeenfkalvliafaqylqqcpfedhvklvnevtefaktcvadesaencdkslhtlfgdklctv atlretygemadccakqepernecflqhkddnpnlprlvrpevdvmctafhdneeffildcylyeiarrhpyfyapellff akrykaafteccqqaadkaaclIIpkldelrdegkassakqrlkcaslqkfgerafkawavarlsqrfpkaefaevsklvtdlt kyhteccchgdllecaddradlakyicenqdsissklkeccekpllekshciaevendempadlpslaadfveskdvckn yaeakdvflgmflyeyarrhpdysvvillrlaktyyettlekccaaadphecyakvfdefkplveepqnlikqncelfeqlg eykfqnallviytldwpqvstptivevsrnlgkvgskccckhpeakrmpcaedylsvvinqlcvlhektpvsdrvtkcct esknrrpcfsalevdetyvpkefnaetflfhadictlsekerqildcqtalvelvldikpkatkeqlkavmddfaafvekcc kaddketcfaeegkklvaasqaallglHHHHHHEPEA |
| 159 | ACP141 IL-2 fusion protein (WW0178) | mdmrvpaqllglllwlrgarcaptsssstkktqlqlehllldlqmilnginnyknpkltrmilfkfympkkatelkhlqcle eelkpleevinlaqsknfhlrprdlisninvivlelkgsetlfmceyadetativeflnrwitfcqsiistligggsggggsg gggsdahksevahrfkdlgeenfkalvliafaqylqqcpfedhvklvnevtefaktcvadesaencdkslhtlfgdklctv atlretygemadccakqepernecflqhkddnpnlprlvrpevdvmctafhdneeffildcylyeiarrhpyfyapellff akrykaafteccqqaadkaaclIIpkldelrdegkassakqrlkcaslqkfgerafkawavarlsqrfpkaefaevsklvtdlt kyhteccchgdllecaddradlakyicenqdsissklkeccekpllekshciaevendempadlpslaadfveskdvckn yaeakdvflgmflyeyarrhpdysvvillrlaktyyettlekccaaadphecyakvfdefkplveepqnlikqncelfeqlg eykfqnallviytldwpqvstptivevsrnlgkvgskccckhpeakrmpcaedylsvvinqlcvlhektpvsdrvtkcct |

-continued

Sequence Table

| SEQ ID NO. | Name | Sequence |
|---|---|---|
| | | esknrrpcfsalevdetyvpkefnaetflfhadictlsekerqildcqtalvelvldikpkatkeqlkavmddfaafvekcc<br>kaddketcfaeegkklvaasqaalglHHHHHHEPEA |
| 160 | ACP142<br>IL-2 fusion<br>protein<br>(WW0179) | mdmrvpaqllglllwlrgarcaptssstIcktqlqlehllldlqmilnginnyknpkltrmilflcfympkkatelkhlqcle<br>eelkpleevinlaqsknfhlrprdlisninvivlelkgsetlfmceyadetativeflnrwitfcqsiistltSGGPGPAG<br>MKGLPGSdaliksevahrfkdlgeenfkalvliafaqylqqcpfedhvklvnevtefaktcvadesaencdkslhtlf<br>gdkletvatlretygemadccakqepernecflqhkddnpnlprlvrpevdvmctafhdneeffildcylyeiarrhpyf<br>yapellffakrykaafteccqaadkaacllpkldelrdegkassakqrlkcaslqkfgerafkawavarlsqrfpkaefaev<br>sklvtdltkvhtecchgdllecaddradlakyicenqdsissklkeccekpllekshciaevendempadlpslaadfves<br>kdvcknyaeakdvflgmflyeyarrhpdysvvillrlaktyettlekccaaadphecyakvfdefkplveepqnlikqn<br>celfeqlgeykfqnallviytkkvpqvstptivevsrnlgIcvgskcckhpeakrmpcaedylsvvinqlcvlhektpvs<br>drytkcctesknripcfsalevdetyvpkefnaelftfhadictlsekerqildcqtalvelvkhkpkatkeqlkavmdclfa<br>afvekcckaddketcfaeegkklvaasqaalglHHHHHHEPEA |
| 161 | ACP144<br>IL-2 fusion<br>protein | mdmrvpaqllglllwlrgarcaptssstIcktqlqlehllldlqmilnginnyknpkltrmilflcfympkkatelkhlqcle<br>eelkpleevinlaqsknfhlrprdlisninvivlelkgsetlfmceyadetativeflnrwitfcqsiistltSGGPGPAG<br>MKGLPGSEVQLVESGGGLVQPGNSLRLSCAASGFTFSKFGMSWVRQAPGKGL<br>EWVSSISGSGRDTLYAESVKGRFTISRDNAKTTLYLQMNSLRPEDTAVYYCTI<br>GGSLSVSSQGTLVTVSSggggsggggsggggsggggsggggsggggsSGGPGPAGMKGLPG<br>SEVQLVESGGGLVQPGGSLRLSCAASGFTFSSYTLAWVRQAPGKGLEWVAAI<br>DSSSYTYSPDTVRGRFTISRDNAKNSLYLQMNSLRAEDTAVYYCARDSNWDA<br>LDYWGQGTTVTVSSGGGGSGGGGSGGGGSDIQMTQSPSSLSASVGDRVTITC<br>KASQNVGTNVGWYQQKPGKAPKALIYSASFRYSGVPSRFSGSGSGTDFTLTIS<br>SLQPEDFATYYCQQYYTYPYTFGGGTKVEIKggggsggggsggggsQVQLQESGGG<br>LAQAGGSLSLSCAASGFTVSNSVMAWYRQTPGKQREFVAIINSVGSTNYADS<br>VKGRFTISRDNAKNTVYLQMNNLKPEDTAVYVCNRNFDRIYWGQGTQVTVS<br>SHHHHHHEPEA |
| 162 | ACP145<br>IL-2 fusion<br>protein | mdmrvpaqllglllwlrgarcQVQLQESGGGLAQAGGSLSLSCAASGFTVSNSVMAWY<br>RQTPGKQREFVAIINSVGSTNYADSVKGRFTISRDNAKNTVYLQMNNLKPEDT<br>AVYVCNRNFDRIYWGQGTQVTVSSggggsggggsggggsaptssstldctqlqlehllldlqmilngi<br>nnyknpkltrmltfkfympldcatelkhlqcleeelkpleevinlaqsknflilrprdlisninvivlelkgsetlfmceyade<br>tativeflnrwitfcqsiistltSGGPGPAGMKGLPGSEVQLVESGGGLVQPGNSLRLSCAAS<br>GFTFSKFGMSWVRQAPGKGLEWVSSISGSGRDTLYAESVKGRFTISRDNAKTT<br>LYLQMNSLRPEDTAVYYCTIGGSLSVSSQGTLVTVSSggggsggggsggggsggggsgg<br>ggsggggsSGGPGPAGMKGLPGSEVQLVESGGGLVQPGGSLRLSCAASGFTFSSY<br>TLAWVRQAPGKGLEWVAAIDSSSYTYSPDTVRGRFTISRDNAKNSLYLQMNS<br>LRAEDTAVYYCARDSNWDALDYWGQGTTVTVSSGGGGSGGGGSGGGGSDI<br>QMTQSPSSLSASVGDRVTITCKASQNVGTNVGWYQQKPGKAPKALIYSASFR<br>YSGVPSRFSGSGSGTDFTLTISSLQPEDFATYYCQQYYTYPYTFGGGTKVEIKH<br>HHHHHEPEA |
| 163 | ACP146<br>IL-2 fusion<br>protein | mdmrvpaqllglllwlrgarcQVQLQESGGGLAQAGGSLSLSCAASGFTVSNSVMAWY<br>RQTPGKQREFVAIINSVGSTNYADSVKGRFTISRDNAKNTVYLQMNNLKPEDT<br>AVYVCNRNFDRIYWGQGTQVTVSSSGGPGPAGMKGLPGSaptssstkktqlqlehllldlqmilnginn<br>ykiipkltrmltfkfSmpkkatelklilqcleeelkpleevlnlaqsknflilrprdlisninvivlelkgsettfm<br>ceyadetativeflnrwitfcqsiistltSGGPGPAGMKGLPGSEVQLVESGGGLVQPGNSLRL<br>SCAASGFTFSKFGMSWVRQAPGKGLEWVSSISGSGRDTLYAESVKGRFTISRD<br>NAKTTLYLQMNSLRPEDTAVYYCTIGGSLSVSSQGTLVTVSSggggsggggsggggs<br>ggggsggggsggggsSGGPGPAGMKGLPGSEVQLVESGGGLVQPGGSLRLSCAASG<br>FTFSSYTLAWVRQAPGKGLEWVAAIDSSSYTYSPDTVRGRFTISRDNAKNSLY<br>LQMNSLRAEDTAVYYCARDSNWDALDYWGQGTTVTVSSGGGGSGGGGSGG<br>GGSDIQMTQSPSSLSASVGDRVTITCKASQNVGTNVGWYQQKPGKAPKALIYS<br>ASFRYSGVPSRFSGSGSGTDFTLTISSLQPEDFATYYCQQYYTYPYTFGGGTKV<br>EIKHHHHHHEPEA |
| 164 | ACP133<br>(WW0196)<br>IL-2-6xHis<br>("6xHis"<br>disclosed<br>as SEQ ID<br>NO.: 354) | mdmrvpaqllglllwlrgarcaptssstkktqlqlehllldlqmilnginnyknpkltrmilfkfympkkatelkhlqcle<br>eelkpleevinlaqsknfhlrprdlisninvivlelkgsetlfmceyadetativeflnrwitfcqsiistltHHHHHH |
| 165 | ACP147<br>IL-2 fusion<br>protein | mdmrvpaqllglllwlrgarcaptssstkktqlqlehllldlqmilnginnyknpkltrmltfkfympkkatelkhlqcle<br>eelkpleevinlaqsknfhlrprdlisninvivlelkgsettfmceyadetativeflnrwitfcqsiistltSGGPGPAG<br>MKGLPGSEVQLVESGGGLVQPGNSLRLSCAASGFTFSKFGMSWVRQAPGKGL<br>EWVSSISGSGRDTLYAESVKGRFTISRDNAKTTLYLQMNSLRPEDTAVYYCTI<br>GGSLSVSSQGTLVTVSSggggsggggsggggsggggsggggsggggsSGGPGPAGMKGLPG<br>SEVQLVESGGGLVQPGGSLRLSCAASGFTFSSYTLAWVRQAPGKGLEWVAAI<br>DSSSYTYSPDTVRGRFTISRDNAKNSLYLQMNSLRAEDTAVYYCARDSNWDA<br>LDYWGQGTTVTVSSGGGGSGGGGSGGGGSDIQMTQSPSSLSASVGDRVTITC<br>KASQNVGTNVGWYQQKPGKAPKALIYSASFRYSGVPSRFSGSGSGTDFTLTIS |

Sequence Table

| SEQ ID NO. | Name | Sequence |
|---|---|---|
| | | SLQPEDFATYYCQQYYTYPYTFGGGTKVEIKggggsggggsggggsQVQLQESGGG<br>LVQAGGSLRLSCAASGRIFSIDIMSWYRQAPGKQRELVARITRGGTISYDDSVK<br>GRFTISRDNAKNTVYLQMNSLKPEDTGVYYCNALYGTDYWGKGTQVTVSSH<br>HHHHHEPEA |
| 166 | ACP148 IL-2 fusion protein | mdmrvpaqllglllwlrgarcQVQLQESGGGLVQAGGSLRLSCAASGRIFSIDIMSWYR<br>QAPGKQRELVARITRGGTISYDDSVKGRFTISRDNAKNTVYLQMNSLKPEDTG<br>VYYCNALYGTDYWGKGTQVTVSSggggsggggsggggsggggsaptsssticktqlqlehllldlqmilngin<br>nyknpkltrmlificlympldcatelkhlqcleeelkpleevinlaqsknfhlrprdlisninvivlelkgsettfmceyadet<br>ativeflnrwitfcqsiistltSGGPGPAGMKGLPGSEVQLVESGGGLVQPGNSLRLSCAAS<br>GFTFSKFGMSWVRQAPGKGLEWVSSISGSGRDTLYAESVKGRFTISRDNAKTT<br>LYLQMNSLRPEDTAVYYCTIGGSLSVSSQGTLVTVSSggggsggggsggggsggggsgg<br>ggsggggsSGGPGPAGMKGLPGSEVQLVESGGGLVQPGGSLRLSCAASGFTFSSY<br>TLAWVRQAPGKGLEWVAAIDSSSYTYSPDTVRGRFTISRDNAKNSLYLQMNS<br>LRAEDTAVYYCARDSNWDALDYWGQGTTVTVSSGGGGSGGGGSGGGGSDI<br>QMTQSPSSLSASVGDRVTITCKASQNVGTNVGWYQQKPGKAPKALIYSASFR<br>YSGVPSRFSGSGSGTDFTLTISSLQPEDFATYYCQQYYTYPYTFGGGTKVEIKH<br>HHHHHEPEA |
| 167 | ACP149 IL-2 fusion protein | mdmrvpaqllglllwlrgarcQVQLQESGGGLVQAGGSLRLSCAASGRIFSIDIMSWYR<br>QAPGKQRELVARITRGGTISYDDSVKGRFTISRDNAKNTVYLQMNSLKPEDTG<br>VYYCNALYGTDYWGKGTQVTVSSSGGPGPAGMKGLPGSaptsssticktqlqlehllldlq<br>milnginnyknpkltrmlafympkkatelkhlqcleeelkpleevinlaqsknfhlrprdlisninvivlelkgsettfm<br>ceyadetativeflnrwitfcqsiistltSGGPGPAGMKGLPGSEVQLVESGGGLVQPGNSLRL<br>SCAASGFTFSKFGMSWVRQAPGKGLEWVSSISGSGRDTLYAESVKGRFTISRD<br>NAKTTLYLQMNSLRPEDTAVYYCTIGGSLSVSSQGTLVTVSSggggsggggsggggs<br>ggggsggggsggggsSGGPGPAGMKGLPGSEVQLVESGGGLVQPGGSLRLSCAASG<br>FTFSSYTLAWVRQAPGKGLEWVAAIDSSSYTYSPDTVRGRFTISRDNAKNSLY<br>LQMNSLRAEDTAVYYCARDSNWDALDYWGQGTTVTVSSGGGGSGGGGSGG<br>GGSDIQMTQSPSSLSASVGDRVTITCKASQNVGTNVGWYQQKPGKAPKALIYS<br>ASFRYSGVPSRFSGSGSGTDFTLTISSLQPEDFATYYCQQYYTYPYTFGGGTKV<br>EIKHHHHHHEPEA |
| 168 | ACP33 Mouse IFNa-fusion protein | mdmrvpaqllglllwlrgarcEVQLVESGGGLVQPGNSLRLSCAASGFTFSKFGMSWVR<br>QAPGKGLEWVSSISGSGRDTLYAESVKGRFTISRDNAKTTLYLQMNSLRPEDT<br>AVYYCTIGGSLSVSSQGTLVTVSSSGGPGPAGMKGLPGScdlpqthnlrnkraltllvqmrr<br>lsplsclkdrkdfgfpqekvdaqqildcaqaipvlseltqqilniftskdssaawntttlldsfendlhqqlndlqgclmqqvg<br>vqefpltqedallavrkythritvylrekkhspcawevvraevwralssssanvlSGGPGPAGMKGLPGSEV<br>QLVESGGGLVQPGNSLRLSCAASGFTFSKFGMSWVRQAPGKGLEWVSSISGS<br>GRDTLYAESVKGRFTISRDNAKTTLYLQMNSLRPEDTAVYYCTIGGSLSVSSQ<br>GTLVTVSSHHHHHHEPEA |
| 169 | ACP131 Mouse IFNa | mdmrvpaqllglllwlrgarcallpqthnlinkralfilvqmrrlsplsclkdrkcifgfpqekvdaqqildcaqaipvlsel<br>tqqilniftskdssaawntttlldsfendlhqqlndlqgclmqqvgvqefpltqedallavrkyfhritvylrekkhspcawe<br>vvraevwralssssanvlgrlreekHHHHHHEPEA |
| 170 | ACP125 Mouse IFNa-fusion protein | mdmrvpaqllglllwlrgarcEVQLVESGGGLVQPGNSLRLSCAASGFTFSKFGMSWVR<br>QAPGKGLEWVSSISGSGRDTLYAESVKGRFTISRDNAKTTLYLQMNSLRPEDT<br>AVYYCTIGGSLSVSSQGTLVTVSSSGGPGPAGMKGLPGScdlpqthnlrnkraltllvqmrr<br>lsplsclkdrkdfgfpqekvdaqqikkactaipvlseltqqilniftskdssaawntttlldsfcndlhqqlndlqgclmqqvg<br>vqefpltqedallavrIcyfhritvylrekkhspcawevvraevwralsssanvlgrlreekHHHHHHEPEA |
| 171 | ACP126 Mouse IFNa-fusion protein | mdmrvpaqllginiwlrgarccdlpqthnlrnkraltllvqmrrlsplsclkdrkdfgfpqekvdaqqikkaqaipvlel<br>tqqilniftskdssaawntttlldsfcndlhqqlndlqgclmqqvgvqefpltqedallavrkyfhritvylrekkhspcawe<br>vvraevwralsssanvlgrlreekSGGPGPAGMKGLPGSEVQLVESGGGLVQPGNSLRLSC<br>AASGFTFSKFGMSWVRQAPGKGLEWVSSISGSGRDTLYAESVKGRFTISRDNA<br>KTTLYLQMNSLRPEDTAVYYCTIGGSLSVSSHHHHHHEPEA |
| 172 | ACP127 Mouse IFNa-fusion protein | mdmrvpaqllglllwlrgarcEAHKSEIAHRYNDLGEQHFKGLVLIAFSQYLQKCSYDE<br>HAKLVQEVTDFAKTCVADESAANCDKSLHTLFGDKLCAIPNLRENYGELADC<br>CTKQEPERNECFLQHKDDNPSLPPFERPEAEAMCTSFKENPTTFMGHYLHEVA<br>RRHPYFYAPELLYYAEQYNEILTQCCAEADKESCLTPKLDGVKEKALVSSVRQ<br>RMKCSSMQKFGERAFKAWAVARLSQTFPNADFAEITKLATDLTKVNKECCH<br>GDLLECADDRAELAKYMCENQATISSKLQTCCDKPLLKKAHCLSEVEHDTMP<br>ADLPAIAADFVEDQEVCKNYAEAKDVFLGTFLYEYSRRHPDYSVSLLLRLAK<br>KYEATLEKCCAEANPPACYGTVLAEFQPLVEEPKNLVKTNCDLYEKLGEYGF<br>QNAILVRYTQKAPQVSTPTLVEAARNLGRVGTKCCTLPEDQRLPCVEDYLSAI<br>LNRVCLLHEKTPVSEHVTKCCSGSLVERRPCFSALTVDETYVPKEFKAETFTFH<br>SDICTLPEKEKQIKKQTALAELVKHKPKATAEQLKTVMDDFAQFLDTCCKAA<br>DKDTCFSTEGPNLVTRCKDALASGGPGPAGMKGLPGScdlpqthnlinkraltllvqmrrls<br>plsclkdrkcifgfpqekvdaqqikkactaipvlseltqqilniftskdssaawntttlldsfcndlhqqlndlqgclmqqgv<br>qefpltqedallavrkythritvylrekkhspcawevvraevwralsssanvlgrlreekSGGPGPAGMKGLP<br>GSEAHKSEIAHRYNDLGEQHFKGLVLIAFSQYLQKCSYDEHAKLVQEVTDFA |

Sequence Table

| SEQ ID NO. | Name | Sequence |
|---|---|---|
| | | KTCVADESAANCDKSLHTLFGDKLCAIPNLRENYGELADCCTKQEPERNECFL<br>QHKDDNPSLPPFERPEAEAMCTSFKENPTTFMGHYLHEVARRHPYFYAPELLY<br>YAEQYNEILTQCCAEADKESCLTPKLDGVKEKALVSSVRQRMKCSSMQKFGE<br>RAFKAWAVARLSQTFPNADFAEITKLATDLTKVNKECCHGDLLECADDRAEL<br>AKYMCENQATISSKLQTCCDKPLLKKAHCLSEVEHDTMPADLPAIAADFVED<br>QEVCKNYAEAKDVFLGTFLYEYSRRHPDYSVSLLLRLAKKYEATLEKCCAEA<br>NPPACYGTVLAEFQPLVEEPKNLVKTNCDLYEKLGEYGFQNAILVRYTQKAP<br>QVSTPTLVEAARNLGRVGTKCCTLPEDQRLPCVEDYLSAILNRVCLLHEKTPV<br>SEHVTKCCSGSLVERRPCFSALTVDETYVPKEFKAETFTFHSDICTLPEKEKQIK<br>KQTALAELVKHKPKATAEQLKTVMDDFAQFLDTCCKAADKDTCFSTEGPNL<br>VTRCKDALAHHHHHHEPEA |
| 173 | ACP128<br>Mouse<br>IFNa-<br>fusion<br>protein | mdmrvpaqllglllwlrgarcEAHKSEIAHRYNDLGEQHFKGLVLIAFSQYLQKCSYDE<br>HAKLVQEVTDFAKTCVADESAANCDKSLHTLFGDKLCAIPNLRENYGELADC<br>CTKQEPERNECFLQHKDDNPSLPPFERPEAEAMCTSFKENPTTFMGHYLHEVA<br>RRHPYFYAPELLYYAEQYNEILTQCCAEADKESCLTPKLDGVKEKALVSSVRQ<br>RMKCSSMQKFGERAFKAWAVARLSQTFPNADFAEITKLATDLTKVNKECCH<br>GDLLECADDRAELAKYMCENQATISSKLQTCCDKPLLKKAHCLSEVEHDTMP<br>ADLPAIAADFVEDQEVCKNYAEAKDVFLGTFLYEYSRRHPDYSVSLLLRLAK<br>KYEATLEKCCAEANPPACYGTVLAEFQPLVEEPKNLVKTNCDLYEKLGEYGF<br>QNAILVRYTQKAPQVSTPTLVEAARNLGRVGTKCCTLPEDQRLPCVEDYLSAI<br>LNRVCLLHEKTPVSEHVTKCCSGSLVERRPCFSALTVDETYVPKEFKAETFTFH<br>SDICTLPEKEKQIKKQTALAELVKHKPKATAEQLKTVMDDFAQFLDTCCKAA<br>DKDTCFSTEGPNLVTRCKDALASGGPGPAGMKGLPGScdlpqthnlinkraltllvqmrrls<br>plsclkdrkcifgfpqekvdaqqikkactaipvlseltqqilniftskdssaawnttlldsfcndlhqqlndlqgclmqqvgv<br>qefpltqedallavrkythritvylrekkhspcawevvraevwralsssanvlgrlreekHHHHHHEPEA |
| 174 | ACP129<br>Mouse<br>IFNa-<br>fusion<br>protein | mdmrvpaqllglllwlrgarccdlpqtlmlmkraltllvqmrrlsplsclkdrkdfgfpqekvdaqqikkactaipvlsel<br>tqqilniftskdssaawnttlldsfcndlhqqlndlqgclmqqvgvqefpltqedallavrIcyfhritvylrekkhspcawe<br>vvraevwralsssanvlgrlreekSGGPGPAGMKGLPGSEAHKSEIAHRYNDLGEQHFKGL<br>VLIAFSQYLQKCSYDEHAKLVQEVTDFAKTCVADESAANCDKSLHTLFGDKL<br>CAIPNLRENYGELADCCTKQEPERNECFLQHKDDNPSLPPFERPEAEAMCTSF<br>KENPTTFMGHYLHEVARRHPYFYAPELLYYAEQYNEILTQCCAEADKESCLTP<br>KLDGVKEKALVSSVRQRMKCSSMQKFGERAFKAWAVARLSQTFPNADFAEIT<br>KLATDLTKVNKECCHGDLLECADDRAELAKYMCENQATISSKLQTCCDKPLL<br>KKAHCLSEVEHDTMPADLPAIAADFVEDQEVCKNYAEAKDVFLGTFLYEYSR<br>RHPDYSVSLLLRLAKKYEATLEKCCAEANPPACYGTVLAEFQPLVEEPKNLVK<br>TNCDLYEKLGEYGFQNAILVRYTQKAPQVSTPTLVEAARNLGRVGTKCCTLP<br>EDQRLPCVEDYLSAILNRVCLLHEKTPVSEHVTKCCSGSLVERRPCFSALTVDE<br>TYVPKEFKAETFTFHSDICTLPEKEKQIKKQTALAELVKHKPKATAEQLKTVM<br>DDFAQFLDTCCKAADKDTCFSTEGPNLVTRCKDALAHHHHHHEPEA |
| 175 | ACP150<br>Mouse<br>IFNa-<br>fusion<br>protein | mdmrvpaqllglllwlrgarcQVQLQESGGGLAQAGGSLSLSCAASGFTVSNSVMAWY<br>RQTPGKQREFVAIINSVGSTNYADSVKGRFTISRDNAKNTVYLQMNNLKPEDT<br>AVYYCNRNFDRIYWGQGTQVTVSSggggsggggsggggsEVQLVESGGGLVQPGNS<br>LRLSCAASGFTFSKFGMSWVRQAPGKGLEWVSSISGSGRDTLYAESVKGRFTI<br>SRDNAKTTLYLQMNSLRPEDTAVYYCTIGGSLSVSSQGTLVTVSSSGGPGPAG<br>MKGLPGScdlpqthnlinkraltllvqmrrlsplsclkdrkclfgfpqekvdaqqikkapipvlseltqqilniftskd<br>ssaawnttlldsfcndlhqqlndlqgclmqqvgvqefpltqedallavrkythritvylrekichspcawevvraevwral<br>sssanylgrlreekSGGPGPAGMKGLPGSEVQLVESGGGLVQPGNSLRLSCAASGFTF<br>SKFGMSWVRQAPGKGLEWVSSISGSGRDTLYAESVKGRFTISRDNAKTTLYL<br>QMNSLRPEDTAVYYCTIGGSLSVSSQGTLVTVSSHHHHHHEPEA |
| 176 | ACP151<br>Mouse<br>IFNa-<br>fusion<br>protein | mdmrvpaqllglllwlrgarcEVQLVESGGGLVQPGNSLRLSCAASGFTFSKFGMSWVR<br>QAPGKGLEWVSSISGSGRDTLYAESVKGRFTISRDNAKTTLYLQMNSLRPEDT<br>AVYYCTIGGSLSVSSQGTLVTVSSSGGPGPAGMKGLPGScdlpqthnlinkraltllvqmrr<br>lsplsclkdrkdfgfpqekvdaqqikkaqaipvlseltqqilniftskdssaawnttlldsfcndlhqqlndlqgclmqqvg<br>vqefpltqedallavrkyfhritvylrekkhspcawevvraevwralsssanylgrlreekSGGPGPAGMKGLP<br>GSEVQLVESGGGLVQPGNSLRLSCAASGFTFSKFGMSWVRQAPGKGLEWVSS<br>ISGSGRDTLYAESVKGRFTISRDNAKTTLYLQMNSLRPEDTAVYYCTIGGSLSV<br>SSQGTLVTVSSggggsggggsggggsQVQLQESGGGLAQAGGSLSLSCAASGFTVSN<br>SVMAWYRQTPGKQREFVAIINSVGSTNYADSVKGRFTISRDNAKNTVYLQMN<br>NLKPEDTAVYVCNRNFDRIYWGQGTQVTVSSHHHHHHEPEA |
| 177 | ACP152<br>Mouse<br>IFNa-<br>fusion<br>protein | mdmrvpaqllglllwlrgarcEVQLVESGGGLVQPGNSLRLSCAASGFTFSKFGMSWVR<br>QAPGKGLEWVSSISGSGRDTLYAESVKGRFTISRDNAKTTLYLQMNSLRPEDT<br>AVYYCTIGGSLSVSSQGTLVTVSSggggsggggsggggscdlpqthnlinkraltllvqmrrlsplscl<br>kdrkdfgfpqekvdaqqikkacjaipvlseltqqilniftskdssaawnttlldsfcndlhqqlndlqgclmqqvgvqefpl<br>tqedallavrkyfhritvylrekkhspcawevvraevwralsssanylgrlreekggggsggggsggggsEVQLVE<br>SGGGGLVQPGNSLRLSCAASGFTFSKFGMSWVRQAPGKGLEWVSSISGSGRDTL<br>YAESVKGRFTISRDNAKTTLYLQMNSLRPEDTAVYYCTIGGSLSVSSQGTLVT<br>VSSHHHHHHEPEA |

Sequence Table

| SEQ ID NO. | Name | Sequence |
|---|---|---|
| 178 | ACP153 (WW0201) (IL-2 Conjugate) | mdmrvpaqllglllwlrgarcaptsssildctqlqlehllldlqmilnginnyknpkltrmltfkfympkkatelkhlqcle eelkpleevinlaqsknfhlrprdlisninvivlelkgsetifmceyadetativeflnrwitfcqsiistltsgGPAGL YAQpgsEVQLVESGGGLVQPGNSLRLSCAASGFTFSKFGMSWVRQAPGKGLE WVSSISGSGRDTLYAESVKGRFTISRDNAKTTLYLQMNSLRPEDTAVYYCTIG GSLSVSSQGTLVTVSSggggsggggsggggsggggsggggsggggssggpGPAGLYAQpgsEV QLVESGGGLVQPGGSLRLSCAASGFTFSSYTLAWVRQAPGKGLEWVAAIDSSS YTYSPDTVRGRFTISRDNAKNSLYLQMNSLRAEDTAVYYCARDSNWDALDY WGQGTTVTVSSGGGGSGGGGSGGGGSDIQMTQSPSSLSASVGDRVTITCKAS QNVGTNVGWYQQKPGKAPKALIYSASFRYSGVPSRFSGSGSGTDFTLTISSLQP EDFATYYCQQYYTYPYTFGGGTKVEIKHHHHHHEPEA |
| 179 | ACP154 (WW0202) (IL-2 Conjugate) | mdmrvpaqllglllwlrgarcaptsssildctqlqlehllldlqmilnginnyknpkltrmltfkfympkkatelkhlqcle eelkpleevinlaqsknfhlrprdlisninvivlelkgsetifmceyadetativeflnrwitfcqsiistltsggpPGGPA GIGpgsEVQLVESGGGLVQPGNSLRLSCAASGFTFSKFGMSWVRQAPGKGLEW VSSISGSGRDTLYAESVKGRFTISRDNAKTTLYLQMNSLRPEDTAVYYCTIGGS LSVSSQGTLVTVSSggggsggggsggggsggggsggggsggggssggpPGGPAGIGpgsEVQLV ESGGGLVQPGGSLRLSCAASGFTFSSYTLAWVRQAPGKGLEWVAAIDSSSYTY SPDTVRGRFTISRDNAKNSLYLQMNSLRAEDTAVYYCARDSNWDALDYWGQ GTTVTVSSGGGGSGGGGSGGGGSDIQMTQSPSSLSASVGDRVTITCKASQNVG TNVGWYQQKPGKAPKALIYSASFRYSGVPSRFSGSGSGTDFTLTISSLQPEDFA TYYCQQYYTYPYTFGGGTKVEIKHHHHHHEPEA |
| 180 | ACP155 (WW0203) (IL-2 Conjugate) | mdmrvpaqllglllwlrgarcaptssstkktqlqlehllldlqmilnginnyknpkltrmilfkfympkkatelkhlqcle eelkpleevinlaqsknfhlrprdlisninvivlelkgsetfmceyadetativeflnrwitfcqsiistltsggpALFKSS FPpgsEVQLVESGGGLVQPGNSLRLSCAASGFTFSKFGMSWVRQAPGKGLEWV SSISGSGRDTLYAESVKGRFTISRDNAKTTLYLQMNSLRPEDTAVYYCTIGGSL SVSSQGTLVTVSSggggsggggsggggsggggsggggsggggssggpALFKSSFPpgsEVQLVE SGGGLVQPGGSLRLSCAASGFTFSSYTLAWVRQAPGKGLEWVAAIDSSSYTYS PDTVRGRFTISRDNAKNSLYLQMNSLRAEDTAVYYCARDSNWDALDYWGQG TTVTVSSGGGGSGGGGSGGGGSDIQMTQSPSSLSASVGDRVTITCKASQNVGT NVGWYQQKPGKAPKALIYSASFRYSGVPSRFSGSGSGTDFTLTISSLQPEDFAT YYCQQYYTYPYTFGGGTKVEIKHHHHHHEPEA |
| 181 | ACP156 (WW0204) (IL-2 Conjugate) | mdmrvpaqllglllwlrgarcaptssstkktqlqlehllldlqmilnginnyknpkltrmilfkfympkkatelkhlqcle eelkpleevinlaqsknfhlrprdlisninvivlelkgsettfmceyadetativeflnrwitfcqsiistltsggpPLAQK LKSSpgsEVQLVESGGGLVQPGNSLRLSCAASGFTFSKFGMSWVRQAPGKGLE WVSSISGSGRDTLYAESVKGRFTISRDNAKTTLYLQMNSLRPEDTAVYYCTIG GSLSVSSQGTLVTVSSggggsggggsggggsggggsggggsggggssggpPLAQKLKSSpgsEV QLVESGGGLVQPGGSLRLSCAASGFTFSSYTLAWVRQAPGKGLEWVAAIDSSS YTYSPDTVRGRFTISRDNAKNSLYLQMNSLRAEDTAVYYCARDSNWDALDY WGQGTTVTVSSGGGGSGGGGSGGGGSDIQMTQSPSSLSASVGDRVTITCKAS QNVGTNVGWYQQKPGKAPKALIYSASFRYSGVPSRFSGSGSGTDFTLTISSLQP EDFATYYCQQYYTYPYTFGGGTKVEIKHHHHHHEPEA |
| 182 | ACP157 (WW0205) (IL-2 Conjugate) | mdmrvpaqllglllwlrgarcaptssstkktqlqlehllldlqmilnginnyknpkltrmilfkfympkkatelkhlqcle eelkpleevinlaqsknfhlrprdlisninvivlelkgsettfmceyadetativeflnrwitfcqsiistltsggpPGGPA GIGalfkssfpPLAQKLKSSpgsEVQLVESGGGLVQPGNSLRLSCAASGFTFSKFGM SWVRQAPGKGLEWVSSISGSGRDTLYAESVKGRFTISRDNAKTTLYLQMNSL RPEDTAVYYCTIGGSLSVSSQGTLVTVSSggggsggggsggggsggggsggggsggggssggp PGGPAGIGalfkssfpPLAQKLKSSpgsEVQLVESGGGLVQPGGSLRLSCAASGFTFS SYTLAWVRQAPGKGLEWVAAIDSSSYTYSPDTVRGRFTISRDNAKNSLYLQM NSLRAEDTAVYYCARDSNWDALDYWGQGTTVTVSSGGGGSGGGGSGGGGS DIQMTQSPSSLSASVGDRVTITCKASQNVGTNVGWYQQKPGKAPKALIYSASF RYSGVPSRFSGSGSGTDFTLTISSLQPEDFATYYCQQYYTYPYTFGGGTKVEIK HHHHHHEPEA |
| 183 | | Not assigned |
| 184 | | Not assigned |
| 185 | | Not assigned |
| 186 | | Not assigned |
| 187 | | Not assigned |
| 188 | | Not assigned |
| 189 | | Not assigned |
| 190 | | Not assigned |
| 191 | Blocker 2 (IL2 blocker) | mdmrvpaqllglllwlrgarcEVQLVESGGGLVQPGGSLRLSCAASGFTFSSYTLAWVR QAPGKGLEWVAAIDSSSYTYSPDTVRGRFTISRDNAKNSLYLQMNSLRAEDTA VYYCARDSNWDALDYWGQGTTVTVSSggggsggggsggggsggggsDIQMTQSPSSLSASV GDRVTITCKASQNVGTNVGWYQQKPGKAPKALIYSASFRYSGVPSRFSGSGSG TDFTLTISSLQPEDFATYYCQQYYTYPYTFGGGTKVEIKHHHHHH |

Sequence Table

| SEQ ID NO. | Name | Sequence |
|---|---|---|
| 192 | Blocker 12 (IL-12 blocker) | mdmrvpaqllglllwlrgarcQSVLTQPPSVSGAPGQRVTISCSGSRSNIGSNTVKWYQQ<br>LPGTAPKLLIYYNDQRPSGVPDRFSGSKSGTSASLAITGLQAEDEADYYCQSY<br>DRYTHPALLFGTGTKVTVLggggsggggsggggsQVLVESGGGVVQPGRSLRLSC<br>AASGFTFSSYGMHWVRQAPGKGLEWVAFIRYDGSNKYYADSVKGRFTISRDN<br>SKNTLYLQMNSLRAEDTAVYYCKTHGSHDNWGQGTMVTVSSHHHHHH |
| 193 | Human_IFNA2b | cdlpqthslgsrrtlmllaqmrrislfsclkdrhdfgfpqeefgnqfqkaetipvlhemiqqifhlfstkdssaawdetlldk<br>fytelyqqlndleacviqgvgvtetplmkedsilavrkyfqritlylkekkyspcawevvraeimrsfslstnlqesliske<br>HHHHHH** |
| 194 | ACP239-geneart | iwelkkdvyvveldwypdapgemvvltcdtpeedgitwtldqssevlgsgktltiqvkefgdagqytchkggevlshs<br>llllhkkedgiwstdilkdqkepknkffirceaknysgrftcwwlttistdltfsvkssrgssdpqgvtcgaatlsaervrgd<br>nkeyeysvecqedsacpaaeeslpievmvdavhklkyenytssffirdiikpdppknlqlkplknsrqvevsweypdt<br>wstphsyfshfcvqvqgkskrekkdwftdktsatvicrknasisvraqdryyssswsewasvpcsggggsggggsggggsr<br>vipvsgparclsqsrnllkttddmvktareklkhysctaedidheditrdqtstlktclplelhknesclatretsstttrgs<br>clppqktslmmticlgsiyedlkmyqtefqainaalqnhnhqqiildkgmlvaidelmqslnhngetlrqkppvgead<br>pyrvkmklcillhafstrvvtinrvmgylssahhhhhh |
| 195 | 3CYT5_sdAb | QVQLQESGGGLVQAGGSLRLSCAASGRTFSSVYDMGWFRQAPGKDREFVARI<br>TESARNTRYADSVRGRFTISRDNAKNTVYLQMNNLELEDAAVYYCAADPQT<br>VVVGTPDYWGQGTQVTVSSAAAYPYDVPDYGSHHHHHH |
| 196 | ACP248 | QSVLTQPPSVSGAPGQRVTISCtGSsSNIGSNTVKWYQQLPGTAPKLLIYgNDQR<br>PSGVPDRFSGSKSGTSASLAITGLQAEDEADYYCQSYDRYTHPAyvFGTGTKVT<br>VLggggsggggsggggsQVQLVESGGGVVQPGRSLRLSCAASGFTFSSYGMHWVRQ<br>APGKGLEWVAFIRYDGSNKYYADSVKGRFTISRDNSKNTLYLQMNSLRAEDT<br>AVYYCKTHGSHDNWGQGTMVTVSSHHHHHH |
| 197 | ACP249 | QSVLTQPPSVSGAPGQRVTISCtGSsSNIGSNTVKWYQQLPGTAPKLLIYYNDQ<br>RPSGVPDRFSGSKSGTSASLAITGLQAEDEADYYCQSYDRYTHPAyvFGTGTK<br>VTVLggggsggggsggggsQVQLVESGGGVVQPGRSLRLSCAASGFTFSSYGMHWV<br>RQAPGKGLEWVAFIRYDGSNKYYADSVKGRFTISRDNSKNTLYLQMNSLRAE<br>DTAVYYCKTHGSHDNWGQGTMVTVSSHHHHHH |
| 198 | ACP250 | QSVLTQPPSVSGAPGQRVTISCSGSRSNIGSNTVKWYQQLPGTAPKLLIYYNDQ<br>RPSGVPDRFSGSKSGTSASLAITGLQAEDEADYYCQSYDRYTHPALLFGTGTK<br>VTVLggggsggggsggggsQVQLVESGGGVVQPGRSLRLSCAASGFTFSSYaMHWV<br>RQAPGKGLEWVAvIsYDGSNKYYADSVKGRFTISRDNSKNTLYLQMNSLRAE<br>DTAVYYCarHGSHDNWGQGTMVTVSSHHHHHH |
| 199 | ACP251 | QSVLTQPPSVSGAPGQRVTISCSGSRSNIGSNTVKWYQQLPGTAPKLLIYYNDQ<br>RPSGVPDRFSGSKSGTSASLAITGLQAEDEADYYCQSYDRYTHPALLFGTGTK<br>VTVLggggsggggsggggsQVQLVESGGGVVQPGRSLRLSCAASGFTFSSYGMHWV<br>RQAPGKGLEWVAFIRYeGSNKYYADSVKGRFTISRDNSKNTLYLQMNSLRAE<br>DTAVYYCKTHGSHDNWGQGTMVTVSSHHHHHH |
| 200 | ACP252 | QSVLTQPPSVSGAPGQRVTISCSGSRSNIGSNTVKWYQQLPGTAPKLLIYYNDQ<br>RPSGVPDRFSGSKSGTSASLAITGLQAEDEADYYCQSYDRYTHPALLFGTGTK<br>VTVLggggsggggsggggsQVQLVESGGGVVQPGRSLRLSCAASGFTFSSYGMHWV<br>RQAPGKGLEWVAFIRYDGSNKYYAeSVKGRFTISRDNSKNTLYLQMNSLRAE<br>DTAVYYCKTHGSHDNWGQGTMVTVSSHHHHHH |
| 201 | ACP253 | QSVLTQPPSVSGAPGQRVTISCSGSRSNIGSqTVKWYQQLPGTAPKLLIYYNDQ<br>RPSGVPDRFSGSKSGTSASLAITGLQAEDEADYYCQSYeRYTHPALLFGTGTKV<br>TVLggggsggggsggggsQVQLVESGGGVVQPGRSLRLSCAASGFTFSSYGMHWVR<br>QAPGKGLEWVAFIRYDGSNKYYADSVKGRFTISRDNSKNTLYLQMNSLRAED<br>TAVYYCKTHGSHDNWGQGTMVTVSSHHHHHH |
| 202 | ACP254 | QSVLTQPPSVSGAPGQRVTISCSGSRSNIGSqTVKWYQQLPGTAPKLLIYYNDQ<br>RPSGVPDRFSGSKSGTSASLAITGLQAEDEADYYCQSYsRYTHPALLFGTGTKV<br>TVLggggsggggsggggsQVQLVESGGGVVQPGRSLRLSCAASGFTFSSYGMHWVR<br>QAPGKGLEWVAFIRYDGSNKYYADSVKGRFTISRDNSKNTLYLQMNSLRAED<br>TAVYYCKTHGSHDNWGQGTMVTVSSHHHHHH |
| 203 | ACP255 | QSVLTQPPSVSGAPGQRVTISCSGSeSNIGSNTVKWYQQLPGTAPKLLIYYNDQ<br>RPSGVPDRFSGSKSGTSASLAITGLQAEDEADYYCQSYDRYTHPALLFGTGTK<br>VTVLggggsggggsggggsQVQLVESGGGVVQPGRSLRLSCAASGFTFSSYGMHWV<br>RQAPGKGLEWVAFIRYDGSNKYYADSVKGRFTISRDNSKNTLYLQMNSLRAE<br>DTAVYYCKTHGSHDNWGQGTMVTVSSHHHHHH |
| 204 | ACP256 | QSVLTQPPSVSGAPGQRVTISCSGSsSNIGSNTVKWYQQLPGTAPKLLIYYNDQ<br>RPSGVPDRFSGSKSGTSASLAITGLQAEDEADYYCQSYDRYTHPALLFGTGTK<br>VTVLggggsggggsggggsQVQLVESGGGVVQPGRSLRLSCAASGFTFSSYGMHWV |

Sequence Table

| SEQ ID NO. | Name | Sequence |
|---|---|---|
| | | RQAPGKGLEWVAFIRYDGSNKYYADSVKGRFTISRDNSKNTLYLQMNSLRAE<br>DTAVYYCKTHGSHDNWGQGTMVTVSSHHHHHH |
| 205 | ACP257 | QSVLTQPPSVSGAPGQRVTISCSGSRSNIGdNTVKWYQQLPGTAPKLLIYYNDQ<br>RPSGVPDRFSGSKSGTSASLAITGLQAEDEADYYCQSYDRYTHPALLFGTGTK<br>VTVLggggsggggsggggsQVQLVESGGGVVQPGRSLRLSCAASGFTFSSYGMHWV<br>RQAPGKGLEWVAFIRYDGSNKYYADSVKGRFTISRDNSKNTLYLQMNSLRAE<br>DTAVYYCKTHGSHDNWGQGTMVTVSSHHHHHH |
| 206 | ACP258 | QSVLTQPPSVSGAPGQRVTISCSGSRSNIGeNTVKWYQQLPGTAPKLLIYYNDQ<br>RPSGVPDRFSGSKSGTSASLAITGLQAEDEADYYCQSYDRYTHPALLFGTGTK<br>VTVLggggsggggsggggsQVQLVESGGGVVQPGRSLRLSCAASGFTFSSYGMHWV<br>RQAPGKGLEWVAFIRYDGSNKYYADSVKGRFTISRDNSKNTLYLQMNSLRAE<br>DTAVYYCKTHGSHDNWGQGTMVTVSSHHHHHH |
| 207 | ACP259 | QSVLTQPPSVSGAPGQRVTISCSGSRSNIGSdTVKWYQQLPGTAPKLLIYYNDQ<br>RPSGVPDRFSGSKSGTSASLAITGLQAEDEADYYCQSYDRYTHPALLFGTGTK<br>VTVLggggsggggsggggsQVQLVESGGGVVQPGRSLRLSCAASGFTFSSYGMHWV<br>RQAPGKGLEWVAFIRYDGSNKYYADSVKGRFTISRDNSKNTLYLQMNSLRAE<br>DTAVYYCKTHGSHDNWGQGTMVTVSSHHHHHH |
| 208 | ACP260 | QSVLTQPPSVSGAPGQRVTISCSGSRSNIGSeTVKWYQQLPGTAPKLLIYYNDQ<br>RPSGVPDRFSGSKSGTSASLAITGLQAEDEADYYCQSYDRYTHPALLFGTGTK<br>VTVLggggsggggsggggsQVQLVESGGGVVQPGRSLRLSCAASGFTFSSYGMHWV<br>RQAPGKGLEWVAFIRYDGSNKYYADSVKGRFTISRDNSKNTLYLQMNSLRAE<br>DTAVYYCKTHGSHDNWGQGTMVTVSSHHHHHH |
| 209 | ACP261 | QSVLTQPPSVSGAPGQRVTISCSGSRSNIGSNdVKWYQQLPGTAPKLLIYYNDQ<br>RPSGVPDRFSGSKSGTSASLAITGLQAEDEADYYCQSYDRYTHPALLFGTGTK<br>VTVLggggsggggsggggsQVQLVESGGGVVQPGRSLRLSCAASGFTFSSYGMHWV<br>RQAPGKGLEWVAFIRYDGSNKYYADSVKGRFTISRDNSKNTLYLQMNSLRAE<br>DTAVYYCKTHGSHDNWGQGTMVTVSSHHHHHH |
| 210 | ACP262 | QSVLTQPPSVSGAPGQRVTISCSGSRSNIGSNTVdWYQQLPGTAPKLLIYYNDQ<br>RPSGVPDRFSGSKSGTSASLAITGLQAEDEADYYCQSYDRYTHPALLFGTGTK<br>VTVLggggsggggsggggsQVQLVESGGGVVQPGRSLRLSCAASGFTFSSYGMHWV<br>RQAPGKGLEWVAFIRYDGSNKYYADSVKGRFTISRDNSKNTLYLQMNSLRAE<br>DTAVYYCKTHGSHDNWGQGTMVTVSSHHHHHH |
| 211 | ACP263 | QSVLTQPPSVSGAPGQRVTISCSGSRSNIGSNTVeWYQQLPGTAPKLLIYYNDQ<br>RPSGVPDRFSGSKSGTSASLAITGLQAEDEADYYCQSYDRYTHPALLFGTGTK<br>VTVLggggsggggsggggsQVQLVESGGGVVQPGRSLRLSCAASGFTFSSYGMHWV<br>RQAPGKGLEWVAFIRYDGSNKYYADSVKGRFTISRDNSKNTLYLQMNSLRAE<br>DTAVYYCKTHGSHDNWGQGTMVTVSSHHHHHH |
| 212 | ACP264 | QSVLTQPPSVSGAPGQRVTISCSGSRSNIGSNTVKWYQQLPGTAPKLLIYYNDQ<br>dPSGVPDRFSGSKSGTSASLAITGLQAEDEADYYCQSYDRYTHPALLFGTGTK<br>VTVLggggsggggsggggsQVQLVESGGGVVQPGRSLRLSCAASGFTFSSYGMHWV<br>RQAPGKGLEWVAFIRYDGSNKYYADSVKGRFTISRDNSKNTLYLQMNSLRAE<br>DTAVYYCKTHGSHDNWGQGTMVTVSSHHHHHH |
| 213 | ACP265 | QSVLTQPPSVSGAPGQRVTISCSGSRSNIGSNTVKWYQQLPGTAPKLLIYYNDQ<br>ePSGVPDRFSGSKSGTSASLAITGLQAEDEADYYCQSYDRYTHPALLFGTGTK<br>VTVLggggsggggsggggsQVQLVESGGGVVQPGRSLRLSCAASGFTFSSYGMHWV<br>RQAPGKGLEWVAFIRYDGSNKYYADSVKGRFTISRDNSKNTLYLQMNSLRAE<br>DTAVYYCKTHGSHDNWGQGTMVTVSSHHHHHH |
| 214 | ACP266 | QSVLTQPPSVSGAPGQRVTISCSGSRSNIGSNTVKWYQQLPGTAPKLLIYYNDQ<br>RPdGVPDRFSGSKSGTSASLAITGLQAEDEADYYCQSYDRYTHPALLFGTGTK<br>VTVLggggsggggsggggsQVQLVESGGGVVQPGRSLRLSCAASGFTFSSYGMHWV<br>RQAPGKGLEWVAFIRYDGSNKYYADSVKGRFTISRDNSKNTLYLQMNSLRAE<br>DTAVYYCKTHGSHDNWGQGTMVTVSSHHHHHH |
| 215 | ACP267 | QSVLTQPPSVSGAPGQRVTISCSGSRSNIGSNTVKWYQQLPGTAPKLLIYYNDQ<br>RPSGVPDRFSGSKSGTSASLAITGLQAEDEADYYCQSYDeYTHPALLFGTGTK<br>VTVLggggsggggsggggsQVQLVESGGGVVQPGRSLRLSCAASGFTFSSYGMHWV<br>RQAPGKGLEWVAFIRYDGSNKYYADSVKGRFTISRDNSKNTLYLQMNSLRAE<br>DTAVYYCKTHGSHDNWGQGTMVTVSSHHHHHH |

Sequence Table

| SEQ ID NO. | Name | Sequence |
|---|---|---|
| 216 | ACP268 | QSVLTQPPSVSGAPGQRVTISCSGSRSNIGSNTVKWYQQLPGTAPKLLIYYNDQ<br>RPSGVPDRFSGSKSGTSASLAITGLQAEDEADYYCQSYDRYTdPALLFGTGTK<br>VTVLggggsggggsggggsQVQLVESGGGVVQPGRSLRLSCAASGFTFSSYGMHWV<br>RQAPGKGLEWVAFIRYDGSNKYYADSVKGRFTISRDNSKNTLYLQMNSLRAE<br>DTAVYYCKTHGSHDNWGQGTMVTVSSHHHHHH |
| 217 | ACP269 | QSVLTQPPSVSGAPGQRVTISCSGSeSNIGSNTVKWYQQLPGTAPKLLIYYNDQ<br>ePSGVPDRFSGSKSGTSASLAITGLQAEDEADYYCQSYDeYTHPALLFGTGTKV<br>TVLggggsggggsggggsQVQLVESGGGVVQPGRSLRLSCAASGFTFSSYGMHWVR<br>QAPGKGLEWVAFIRYDGSNKYYADSVKGRFTISRDNSKNTLYLQMNSLRAED<br>TAVYYCKTHGSHDNWGQGTMVTVSSHHHHHH |
| 218 | ACP270 | QSVLTQPPSVSGAPGQRVTISCSGSeSNIGSNdVKWYQQLPGTAPKLLIYYNDQ<br>RPSGVPDRFSGSKSGTSASLAITGLQAEDEADYYCQSYDRYTHPALLFGTGTK<br>VTVLggggsggggsggggsQVQLVESGGGVVQPGRSLRLSCAASGFTFSSYGMHWV<br>RQAPGKGLEWVAFIRYDGSNKYYADSVKGRFTISRDNSKNTLYLQMNSLRAE<br>DTAVYYCKTHGSHDNWGQGTMVTVSSHHHHHH |
| 219 | ACP271 | QSVLTQPPSVSGAPGQRVTISCSGSRSNIGSNTVKWYQQLPGTAPKLLIYYNDQ<br>RPSGVPDRFSGSKSGTSASLAITGLQAEDEADYYCQSYDRYTHPALLFGTGTK<br>VTVLggggsggggsggggsQVQLVESGGGVVQPGRSLRLSCAASGFTFeSYGMHWV<br>RQAPGKGLEWVAFIRYDGSNKYYADSVKGRFTISRDNSKNTLYLQMNSLRAE<br>DTAVYYCKTHGSHDNWGQGTMVTVSSHHHHHH |
| 220 | ACP272 | QSVLTQPPSVSGAPGQRVTISCSGSRSNIGSNTVKWYQQLPGTAPKLLIYYNDQ<br>RPSGVPDRFSGSKSGTSASLAITGLQAEDEADYYCQSYDRYTHPALLFGTGTK<br>VTVLggggsggggsggggsQVQLVESGGGVVQPGRSLRLSCAASGFTFSeYGMHWV<br>RQAPGKGLEWVAFIRYDGSNKYYADSVKGRFTISRDNSKNTLYLQMNSLRAE<br>DTAVYYCKTHGSHDNWGQGTMVTVSSHHHHHH |
| 221 | ACP273 | QSVLTQPPSVSGAPGQRVTISCSGSRSNIGSNTVKWYQQLPGTAPKLLIYYNDQ<br>RPSGVPDRFSGSKSGTSASLAITGLQAEDEADYYCQSYDRYTHPALLFGTGTK<br>VTVLggggsggggsggggsQVQLVESGGGVVQPGRSLRLSCAASGFTFSdYGMHWV<br>RQAPGKGLEWVAFIRYDGSNKYYADSVKGRFTISRDNSKNTLYLQMNSLRAE<br>DTAVYYCKTHGSHDNWGQGTMVTVSSHHHHHH |
| 222 | ACP274 | QSVLTQPPSVSGAPGQRVTISCSGSRSNIGSNTVKWYQQLPGTAPKLLIYYNDQ<br>RPSGVPDRFSGSKSGTSASLAITGLQAEDEADYYCQSYDRYTHPALLFGTGTK<br>VTVLggggsggggsggggsQVQLVESGGGVVQPGRSLRLSCAASGFTFSSYGMHWV<br>RQAPGKGLEWVAFIeYDGSNKYYADSVKGRFTISRDNSKNTLYLQMNSLRAE<br>DTAVYYCKTHGSHDNWGQGTMVTVSSHHHHHH |
| 223 | ACP275 | QSVLTQPPSVSGAPGQRVTISCSGSRSNIGSNTVKWYQQLPGTAPKLLIYYNDQ<br>RPSGVPDRFSGSKSGTSASLAITGLQAEDEADYYCQSYDRYTHPALLFGTGTK<br>VTVLggggsggggsggggsQVQLVESGGGVVQPGRSLRLSCAASGFTFSSYGMHWV<br>RQAPGKGLEWVAFIdYDGSNKYYADSVKGRFTISRDNSKNTLYLQMNSLRAE<br>DTAVYYCKTHGSHDNWGQGTMVTVSSHHHHHH |
| 224 | ACP276 | QSVLTQPPSVSGAPGQRVTISCSGSRSNIGSNTVKWYQQLPGTAPKLLIYYNDQ<br>RPSGVPDRFSGSKSGTSASLAITGLQAEDEADYYCQSYDRYTHPALLFGTGTK<br>VTVLggggsggggsggggsQVQLVESGGGVVQPGRSLRLSCAASGFTFSSYGMHWV<br>RQAPGKGLEWVAFIRYDGSNdYYADSVKGRFTISRDNSKNTLYLQMNSLRAE<br>DTAVYYCKTHGSHDNWGQGTMVTVSSHHHHHH |
| 225 | ACP277 | QSVLTQPPSVSGAPGQRVTISCSGSRSNIGSNTVKWYQQLPGTAPKLLIYYNDQ<br>RPSGVPDRFSGSKSGTSASLAITGLQAEDEADYYCQSYDRYTHPALLFGTGTK<br>VTVLggggsggggsggggsQVQLVESGGGVVQPGRSLRLSCAASGFTFSSYGMHWV<br>RQAPGKGLEWVAFIRYDGSNeYYADSVKGRFTISRDNSKNTLYLQMNSLRAE<br>DTAVYYCKTHGSHDNWGQGTMVTVSSHHHHHH |
| 226 | ACP278 | QSVLTQPPSVSGAPGQRVTISCSGSRSNIGSNTVKWYQQLPGTAPKLLIYYNDQ<br>RPSGVPDRFSGSKSGTSASLAITGLQAEDEADYYCQSYDRYTHPALLFGTGTK<br>VTVLggggsggggsggggsQVQLVESGGGVVQPGRSLRLSCAASGFTFSSYGMHWV<br>RQAPGKGLEWVAFIRYDGSNKYYADSVeGRFTISRDNSKNTLYLQMNSLRAE<br>DTAVYYCKTHGSHDNWGQGTMVTVSSHHHHHH |
| 227 | ACP279 | QSVLTQPPSVSGAPGQRVTISCSGSRSNIGSNTVKWYQQLPGTAPKLLIYYNDQ<br>RPSGVPDRFSGSKSGTSASLAITGLQAEDEADYYCQSYDRYTHPALLFGTGTK<br>VTVLggggsggggsggggsQVQLVESGGGVVQPGRSLRLSCAASGFTFSSYGMHWV<br>RQAPGKGLEWVAFIRYDGSNKYYADSVKGRFTISRDNSKNTLYLQMNSLRAE<br>DTAVYYCKTHGSeDNWGQGTMVTVSSHHHHHH |

-continued

Sequence Table

| SEQ ID NO. | Name | Sequence |
|---|---|---|
| 228 | ACP280 | QSVLTQPPSVSGAPGQRVTISCSGSRSNIGSNTVKWYQQLPGTAPKLLIYYNDQ<br>RPSGVPDRFSGSKSGTSASLAITGLQAEDEADYYCQSYDRYTHPALLFGTGTK<br>VTVLggggsggggsggggsQVQLVESGGGVVQPGRSLRLSCAASGFTFSSYGMHWV<br>RQAPGKGLEWVAFIeYDGSNKYYADSVeGRFTISRDNSKNTLYLQMNSLRAED<br>TAVYYCKTHGSHDNWGQGTMVTVSSHHHHHH |
| 229 | ACP281 | QSVLTQPPSVSGAPGQRVTISCSGSRSNIGSNTVKWYQQLPGTAPKLLIYYNDQ<br>RPSGVPDRFSGSKSGTSASLAITGLQAEDEADYYCQSYDRYTHPALLFGTGTK<br>VTVLggggsggggsggggsQVQLVESGGGVVQPGRSLRLSCAASGFTFSSYGMHWV<br>RQAPGKGLEWVAFIeYDGSNKYYADSVeGRFTISRDNSKNTLYLQMNSLRAED<br>TAVYYCKTHGSeDNWGQGTMVTVSSHHHHHH |
| 230 | ACP282 | QSVLTQPPSVSGAPGQRVTISCSGSRSNIGSNTVKWYQQLPGTAPKLLIYYNDQ<br>RPSGVPDRFSGSKSGTSASLAITGLQAEDEADYYCQSYDRYTHPALLFGTGTK<br>VTVLggggsggggsggggsQVQLVESGGGVVQPGRSLRLSCAASGFTFSSYGMHWV<br>RQAPGKGLEWVAFIRYDGSNKYYADSVKGRFTISRDNSKNTLYLQMNSLRAE<br>DTAVYYCKTHGSHDNWGQGTMVTVSSHHHHHH |
| 231 | ACP283 (WW0617) | iwelkkdvyvveldwypdapgemvvitcdtpeedgitwddqssevlgsgktltiqvkefgdagqytchkggevlshs<br>sgrftcwwlttistdltfsvkssrgssdpqgvtcgaatlsaervrgdllllhkkedgiwstdilkdqkepknktflrceakny<br>nkeyeysvecqedsacpaaeeslpievmvdavhklkyenytssffirdiikpdppknlqlkplknsrqvevsweypdt<br>wstphsyfshfcvqvqgkskrekkdrvftdktsatvicrknasisvraqdryyssswsewasvpcs |
| 232 | 3TOW69 sdAb | QVQLQESGGGLVQTGGSLRLSCTTSGTIFSGYTMGWYRQAPGEQRELVAVISG<br>GGDTNYADSVKGRFTISRDNTKDTMYLQMNSLKPEDTAVYYCYSREVTPPW<br>KLYWGQGTQVTVSSAAAYPYDVPDYGSHHHHHH |
| 233 | 3TOW85 sdAb | QVQLQESGGGLVQEGGSLRLSCAASERIFSTDVMGWYRQAAEKQRELVAVVS<br>ARGTTNYLDAVKGRFTISRDNARNTLTLQMNDLKPEDTASYYCYVRETTSPW<br>RIYWGQGTQVTVSSAAAYPYDVPDYGSHHHHHH |
| 234 | 2TOW91 sdAb | QVQLQESGGGLVQAGGSLRLSCAASGSlFSANAMGWYRQAPGKQRELVAVIS<br>SGGSTNYADSVKGRFTISRDNAKNTVYLQMNSLKPEDTAVYYCMYSGSYYY<br>TPNDYWGQGTQVTVSSAAAYPYDVPDYGSHHHHHH |
| 235 | ACP301 | evqlvesgggglvqpggslrlscaasgftfssytlawvrqapgkglewvaaidsssytyspdtvrgrftisrdnaknslylq<br>mnslraedtavyycardsnwdaldywgqgttvtvssggggsggggsggggsdiqmtqspsslsasvgdrvtitckasq<br>nvgtnvgwyqqkpgkapkaliysasflysgvpsrfsgsgsgtdftltisslqpecifatyycqqyytypylfgggtkveik<br>hhhhhh |
| 236 | Hu2TOW91_A | evqllesggglvqpggslrlscaasGSIFSANAMGwYrqapgkgQReLvAVISSGGSTNYADSVK<br>GrftisrdnskntVylqmnslraedtavyycMYSGSYYYTPNDYwgqgtivtvssAAAYPYDVPD<br>YGSHHHHHH** |
| 237 | Hu2TOW91_B | evqllesggglvqpggslrlscaasGSIFSANAMGwYrqapgkgleLvAVISSGGSTNYADSVKG<br>rftisrdnskntVylqmnslraedtavyycMYSGSYYYTPNDYwgqgtivtvssAAAYPYDVPDY<br>GSHHHHHH** |
| 238 | Hu2TOW91_C | evqllesggglvqpggslrlscaasGSIFSANAMGwvrqapgkglewvsVISSGGSTNYADSVKGrf<br>tisrdnskntlylqmnslraedtavyycMYSGSYYYTPNDYwgqgtivtvssAAAYPYDVPDYGS<br>HHHHHH** |
| 239 | Hu2TOW91_D | QvqllesggglvqpggslrlscaasGSIFSANAMGwYrqapgkQReLvAVISSGGSTNYADSVK<br>GrftisrdnskntVylqmnslraedtavyycMYSGSYYYTPNDYwgqgtivtvssAAAYPYDVPD<br>YGSHHHHHH** |
| 240 | HE_LM_ 2TOW91 | evqllesggglvqpggslrlscaasgSIfsANamGwYrqapgkgReLvAVissggstNyadsvkgrftisrdns<br>kntVylqmnslraedtavyycMYSGSYYYTPNDYwgqgtivtvssAAAYPYDVPDYGSHHH<br>HHH** |
| 241 | HE_LM_ 2TOW91 | QvqllesggglvqAggslrlscaasgSIfsANamGwYrqapgkQReLvAVissggstNyadsvkgrftisrdn<br>skntVylqmnslraedtavyycMYSGSYYYTPNDYwgqgtivtvssAAAYPYDVPDYGSHHH<br>HHH** |
| 242 | Hu3TOW85_A | evqllesggglvqpggslrlscaasERIFSTDVMGwYrqapgkQReLvAVVSARGTTNYLDAV<br>KGrftisrdnskntlylqmnslraedtavyycYVRETTSPWRIYwgqgtivtvssAAAYPYDVPDYG<br>SHHHHHH** |
| 243 | Hu3TOW85_B | evqllesggglvqpggslrlscaasERIFSTDVMGwYrqapgkgleLvAVVSARGTTNYLDAVK<br>GrftisrdnskntlylqmnslraedtavyycYVRETTSPWRIYwgqgtivtvssAAAYPYDVPDYGS<br>HHHHHH** |

-continued

Sequence Table

| SEQ ID NO. | Name | Sequence |
|---|---|---|
| 244 | Hu3TOW85_C | evqllesggglvqpggslrlscaasERIFSTDVMGwvrqapgkglewvsVVSARGTTNYLDAVKGrftisrdnskntlylqmnslraedtavyycYVRETTSPWRIYwgqgtivtvssAAAYPYDVPDYGSHHHHHH** |
| 245 | Hu3TOW85_D | QvqllesggglvqpggslrlscaasERIFSTDVMGwYrqapgkQReLvAVVSARGTTNYLDAVKGrftisrdnskntlylqmnslraedtavyycYVRETTSPWRIYwgqgtivtvssAAAYPYDVPDYGSHHHHHH** |
| 246 | HE_LM_3TO1T85 | evqllesggglvqpggslrlscaasERIfsTDVmGwYrqapgkgReLvAVVsARgTtNyLdsvkgrftisrdnskntlylqmnslraedtavyycYVRETTSPWRIywgqgtivtvssAAAYPYDVPDYGSHHHHHH** |
| 247 | HE_L_3TOW85 | QvqllesggglvqEggslrlscaasERIfsTDVmGwYrqaAgkQReLvAVVsARgTtNyLdAvkgrftisrdnskntlylqmnslraedtaSyycYVRETTSPWRIywgqgtivtvssAAAYPYDVPDYGSHHHHHH** |
| 248 | HE_LM_R45L_3TOW85 | evqllesggglvqpggslrlscaasERIfsTDVmGwYrqapgkgleLvAVVsARgTtNyLdsvkgrftisrdnskntlylqmnslraedtavyycYVRETTSPWRIywgqgtivtvssAAAYPYDVPDYGSHHHHHH** |
| 249 | Hu3TOW69_A | evqllesggglvqpggslrlscaTsGTIFSGYTMGwYrqapgkQReLvAVISGGGDTNYADSVKGrftisrdnskDtMylqmnslraedtavyycYSREVTPPWKLYwgqgtivtvssAAAYPYDVPDYGSHHHHHH** |
| 250 | Hu3TOW69_B | evqllesggglvqpggslrlscaTsGTIFSGYTMGwYrqapgkgleLvAVISGGGDTNYADSVKGrftisrdnskDtMylqmnslraedtavyycYSREVTPPWKLYwgqgtivtvssAAAYPYDVPDYGSHHHHHH** |
| 251 | Hu3TOW69_C | evqllesggglvqpggslrlscaasGTIFSGYTMGwvrqapgkglewvsVISGGGDTNYADSVKGrftisrdnskntlylqmnslraedtavyycYSREVTPPWKLYwgqgtivtvssAAAYPYDVPDYGSHHHHHH** |
| 252 | Hu3TOW69_D | QvqllesggglvqpggslrlscaTsGTIFSGYTMGwYrqapgkQReLvAVISGGGDTNYADSVKGrftisrdnskDtMylqmnslraedtavyycYSREVTPPWKLYwgqgtivtvssAAAYPYDVPDYGSHHHHHH** |
| 253 | Hu3TOW69_E | evqllesggglvqpggslrlscaTsGTIFSGYTMGwYrqapgkQReLvAVISGGGDTNYADSVKGrftisrdnskntMylqmnslraedtavyycYSREVTPPWKLYwgqgtivtvssAAAYPYDVPDYGSHHHHHH** |
| 254 | HE_LM_3TO1T69 | evqllesggglvqpggslrlscaTsgTIfsGyTmGwYrqapgkgReLvAVisGggDtNyadsvkgrftisrdnskntMylqmnslraedtavyycYSREVTPPWKLYwgqgtivtvssAAAYPYDVPDYGSHHHHHH** |
| 255 | HE_L_3TOW69 | QvqllesggglvqTggslrlscaTsgTIfsGyTmGwYrqapgkQReLvAVisGggDtNyadsvkgrftisrdnskDtMylqmnslraedtavyycYSREVTPPWKLYwgqgtivtvssAAAYPYDVPDYGSHHHHHH** |
| 256 | HE_LM_R45L_3TOW69 | evqllesggglvqpggslrlscaTsgTIfsGyTmGwYrqapgkgleLvAVisGggDtNyadsvkgrftisrdnskntMylqmnslraedtavyycYSREVTPPWKLYwgqgtivtvssAAAYPYDVPDYGSHHHHHH** |
| 257 | ACP363 (WW0441) | EVQLVESGGGLVQPGGSLRLSCAASGFTFSSYTLAWVRQAPGKGLEWVAAIDSSSYTYSPDTVRGRFTISRDNAKNSLYLQMNSLRAEDTAVYYCARDSNWDALDYWGQGTTVTVSSggggsggggsggggsDIQMTQSPSSLSASVGDRVTITCKAREKLWSAVAWYQQKPGKAPKALIYSASFRYSGVPSRFSGSGSGTDFTLTISSLQPEDFATYYCQQYYTYPYTFGGGTKVEIKHHHHHH |
| 258 | ACP364 (WW0442) | EVQLVESGGGLVQPGGSLRLSCAASGFTFSSYTLAWVRQAPGKGLEWVAAIDSSSYTYSPDTVRGRFTISRDNAKNSLYLQMNSLRAEDTAVYYCARDSNWDALDYWGQGTTVTVSSggggsggggsggggsDIQMTQSPSSLSASVGDRVTITCKAREKLWSAVAWYQQKPGKAPKsLIYSASFRYSGVPSRFSGSGSGTDFTLTISSLQPEDFATYYCQQYYTYPYTFGGGTKVEIKHHHHHH |
| 259 | ACP367 (WW0445) | EVQLVESGGGLVQPGGSLRLSCAASGFTFSSYTLAWVRQAPGKGLEWVAAIDSSSYTYSPDTVRGRFTISRDNAKNSLYLQMNSLRAEDTAVYYCARDSNWDALDYWGQGTTVTVSSggggsggggsggggsDIQMTQSPSSLSASVGDRVTITCKVTEKVWGNVAWYQQKPGKAPISLIYSPSLRKSGVPSRFSGSGSGTDFTLTISSLQPEDFATYYCQQYYTYPYTFGGGTKVEIKHHHHHH |
| 260 | ACP369 (WW0449) | EVQLVESGGGLVQPGGSLRLSCAASGFTFSSYTLAWVRQAPGKGLEWVAAIDSSSYTYSPDTVRGRFTISRDNAKNSLYLQMNSLRAEDTAVYYCARDSNWDALDYWGQGTTVTVSSggggsggggsggggsDIQMTQSPSSLSASVGDRVTITCKSSEKL |

| SEQ ID NO. | Name | Sequence |
|---|---|---|
| | | WANVAWYQQKPGKAPKALIYSASFRYSGVPSRFSGSGSGTDFTLTISSLQPED<br>FATYYCQQYYTYPYTFGGGTKVEIKHHHHHH |
| 261 | ACP370<br>(WW0450) | EVQLVESGGGLVQPGGSLRLSCAASGFTFSSYTLAWVRQAPGKGLEWVAAID<br>SSSYTYSPDTVRGRFTISRDNAKNSLYLQMNSLRAEDTAVYYCARDSNWDAL<br>DYWGQGTTVTVSSggggsggggsggggsDIQMTQSPSSLSASVGDRVTITCKSSEKL<br>WANVAWYQQKPGKAPKsLIYSASFRYSGVPSRFSGSGSGTDFTLTISSLQPEDF<br>ATYYCQQYYTYPYTFGGGTKVEIKHHHHHH |
| 262 | ACP380<br>(WW0522) | DIQMTQSPSSLSASVGDRVTITCKASQNVGTNVGWYQQKPGKAPKALIYSASF<br>RYSGVPSRFSGSGSGTDFTLTISSLQPEDFATYYCQQYYTYPYTFGGGTKVEIKr<br>tvaapsvfifppsdeqlksgtasvvellnnfypreakvqwkvdnalqsgnsqesvteqdskdstyslsstltlskadyekh<br>kvyacevthqglsspvtksfnrgec |
| 263 | ACP381<br>(WW0523) | DIQMTQSPSSLSASVGDRVTITCKAREKLWSAVAWYQQKPGKAPKsLIYSASF<br>RYSGVPSRFSGSGSGTDFTLTISSLQPEDFATYYCQQYYTYPYTFGGGTKVEIKr<br>tvaapsvfifppsdeqlksgtasvvellnnfypreakvqwkvdnalqsgnsqesvteqdskdstyslsstltlskadyekh<br>kvyacevthqglsspvtksfnrgec |
| 264 | ACP382<br>(WW0524) | DIQMTQSPSSLSASVGDRVTITCKVTEKVWGNVAWYQQKPGKAPISLIYSPSL<br>RKSGVPSRFSGSGSGTDFTLTISSLQPEDFATYYCQQYYTYPYTFGGGTKVEIKr<br>tvaapsvfifppsdeqlksgtasvvellnnfypreakvqwkvdnalqsgnsqesvteqdskdstyslsstltlskadyekh<br>kvyacevthqglsspvtksfnrgec |
| 265 | ACP435 | DIQMTQSPSSLSASVGDRVTITCKAREKLWSAVAWYQQKPGKAPKsLIYSASF<br>RYSGVPSRFSGSGSGTDFTLTISSLQPEDFATYYCQQYYTYPYTFGGGTKVEIKr<br>tvaapsvfifppsdeqlksgtasvvellnnfypreakvqwkvdnalqsgnsqesvteqdskdstyslsstltlskadyekh<br>kvyacevthqglsspvtksfnrgecggggsggggsggggsggggsggggsggggsevqllesggglvqpggslrlsca<br>asgsifsanamgwyrqapgkglrirelvavissggstnyadsvkgrftisrdnskntvylqmnslraedtavyycmysgsy<br>yytpndywgqgtivtvss** |
| 266 | ACP436<br>(WW0578) | DIQMTQSPSSLSASVGDRVTITCKAREKLWSAVAWYQQKPGKAPKsLIYSASF<br>RYSGVPSRFSGSGSGTDFTLTISSLQPEDFATYYCQQYYTYPYTFGGGTKVEIKr<br>tvaapsvfifppsdeqlksgtasvvellnnfypreakvqwkvdnalqsgnsqesvteqdskdstyslsstltlskadyekh<br>kvyacevthqglsspvtksfnrgecggggsggggsggggsggggsggggsggggsevqllesggglvqpggslrlsca<br>asgsifsanamgwyrqapgkglelvavissggstnyadsvkgrftisrdnskntvylqmnslraedtavyycmysgsy<br>yytpndywgqgtivtvss** |
| 267 | ACP437<br>(WW0579) | DIQMTQSPSSLSASVGDRVTITCKVTEKVWGNVAWYQQKPGKAPISLIYSPSL<br>RKSGVPSRFSGSGSGTDFTLTISSLQPEDFATYYCQQYYTYPYTFGGGTKVEIKr<br>tvaapsvfifppsdeqlksgtasvvellnnfypreakvqwkvdnalqsgnsqesvteqdskdstyslsstltlskadyekh<br>kvyacevthqglsspvtksfnrgecggggsggggsggggsggggsggggsggggsevqllesggglvqpggslrlsca<br>asgsifsanamgwyrqapglairelvavissggstnyadsvkgrftisrdnskntvylqmnslraedtavyycmysgsy<br>yytpndywgqgtivtvss** |
| 268 | ACP438<br>(WW0580) | DIQMTQSPSSLSASVGDRVTITCKVTEKVWGNVAWYQQKPGKAPISLIYSPSL<br>RKSGVPSRFSGSGSGTDFTLTISSLQPEDFATYYCQQYYTYPYTFGGGTKVEIKr<br>tvaapsvfifppsdeqlksgtasvvellnnfypreakvqwkvdnalqsgnsqesvteqdskdstyslsstltlskadyekh<br>kvyacevthqglsspvtksfnrgecggggsggggsggggsggggsggggsggggsevqllesggglvqpggslrlsca<br>asgsifsanamgwyrqapgkglelvavissggstnyadsvkgrftisrdnskntvylqmnslraedtavyycmysgsy<br>yytpndywgqgtivtvss** |
| 269 | ACP448<br>(WW0590) | DIQMTQSPSSLSASVGDRVTITCKSSEKLWANVAWYQQKPGKAPKsLIYSASF<br>RYSGVPSRFSGSGSGTDFTLTISSLQPEDFATYYCQQYYTYPYTFGGGTKVEIKr<br>tvaapsvfifppsdeqlksgtasvvcllnnfypreakvqwkvdnalqsgnsqesvteqdskdstyslsstltlskadyekh<br>kvyacevthqglsspvtksfnrgec** |
| 270 | ACP449<br>(WW0591) | DIQMTQSPSSLSASVGDRVTITCKSSEKLWANVAWYQQKPGKAPKLLIYSASF<br>RYSGVPSRFSGSGSGTDFTLTISSLQPEDFATYYCQQYYTYPYTFGGGTKVEIKr<br>tvaapsvfifppsdeqlksgtasvvcllnnfypreakvqwkvdnalqsgnsqesvteqdskdstyslsstltlskadyekh<br>kvyacevthqglsspvtksfnrgec** |
| 271 | ACP450<br>(WW0592) | DIQMTQSPSSLSASVGDRVTITCKAREKLWSAVAWYQQKPGKAPKLLIYSASF<br>RYSGVPSRFSGSGSGTDFTLTISSLQPEDFATYYCQQYYTYPYTFGGGTKVEIKr<br>tvaapsvfifppsdeqlksgtasvvcllnnfypreakvqwkvdnalqsgnsqesvteqdskdstyslsstltlskadyekh<br>kvyacevthqglsspvtksfnrgec** |
| 272 | ACP439<br>(WW0581) | aptssstkktqlqlehllldlqmilnginnyknpkltrmltfkfympkkatelkhlqcleeelkpleevinlaqsknfhlrpr<br>dlisninvivlelkgsettfmceyadetativeflnrwitfcqsiistltsggpPAGLYAQpgsEVQLVESGG<br>GLVQPGNSLRLSCAASGFTFSKFGMSWVRQAPGKGLEWVSSISGSGRDTLYA<br>ESVKGRFTISRDNAKTTLYLQMNSLRPEDTAVYYCTIGGSLSVSSQGTLVTVSS<br>ggggsggggsggggsggggsggggsggggssggpPAGLYAQpgsEVQLVESGGGLVQPGGS<br>LRLSCAASGFTFSSYTLAWVRQAPGKGLEWVAAIDSSSYTYSPDTVRGRFTISR |

Sequence Table

| SEQ ID NO. | Name | Sequence |
|---|---|---|
| | | DNAKNSLYLQMNSLRAEDTAVYYCARDSNWDALDYWGQGTTVTVSSGGGG<br>SGGGGSGGGGSDIQMTQSPSSLSASVGDRVTITCKSSEKLWANVAWYQQKPG<br>KAPKALIYSASFRYSGVPSRFSGSGSGTDFTLTISSLQPEDFATYYCQQYYTYP<br>YTFGGGTKVEIK |
| 273 | ACP440 (WW0582) | aptssstkktqlqlehllldlqmilnginnyknpkltrmltfkfympkkatelkhlqcleeelkpleevinlaqsknfhlrpr<br>dlisninvivlelkgsettfmceyadetativeflnrwitfcqsiistltsggpGPAGLYAQpgsEVQLVESGG<br>GLVQPGNSLRLSCAASGFTFSKFGMSWVRQAPGKGLEWVSSISGSGRDTLYA<br>ESVKGRFTISRDNAKTTLYLQMNSLRPEDTAVYYCTIGGSLSVSSQGTLVTVSS<br>ggggsggggsggggsggggsggggsggggssggpGPAGLYAQpgsEVQLVESGGGLVQPGGS<br>LRLSCAASGFTFSSYTLAWVRQAPGKGLEWVAAIDSSSYTYSPDTVRGRFTISR<br>DNAKNSLYLQMNSLRAEDTAVYYCARDSNWDALDYWGQGTTVTVSSGGGG<br>SGGGGSGGGGSDIQMTQSPSSLSASVGDRVTITCKSSEKLWANVAWYQQKPG<br>KAPKsLIYSASFRYSGVPSRFSGSGSGTDFTLTISSLQPEDFATYYCQQYYTYPY<br>TFGGGTKVEIK |
| 274 | ACP441 (WW0583) | aptssstkktqlqlehllldlqmilnginnyknpkltrmltfkfympkkatelkhlqcleeelkpleevinlaqsknfhlrpr<br>dlisninvivlelkgsettfmceyadetativeflnrwitfcqsiistltsggpGPAGLYAQpgsEVQLVESGG<br>GLVQPGNSLRLSCAASGFTFSKFGMSWVRQAPGKGLEWVSSISGSGRDTLYA<br>ESVKGRFTISRDNAKTTLYLQMNSLRPEDTAVYYCTIGGSLSVSSQGTLVTVSS<br>ggggsggggsggggsggggsggggsggggssggpGPAGLYAQpgsEVQLVESGGGLVQPGGS<br>LRLSCAASGFTFSSYTLAWVRQAPGKGLEWVAAIDSSSYTYSPDTVRGRFTISR<br>DNAKNSLYLQMNSLRAEDTAVYYCARDSNWDALDYWGQGTTVTVSSGGGG<br>SGGGGSGGGGSDIQMTQSPSSLSASVGDRVTITCKSSEKLWANVAWYQQKPG<br>KAPKLLIYSASFRYSGVPSRFSGSGSGTDFTLTISSLQPEDFATYYCQQYYTYPY<br>TFGGGTKVEIK |
| 275 | ACP442 (WW0584) | aptssstkktqlqlehllldlqmilnginnyknpkltrmltfkfympkkatelkhlqcleeelkpleevinlaqsknfhlrpr<br>dlisninvivlelkgsettfmceyadetativeflnrwitfcqsiistltsggpGPAGLYAQpgsEVQLVESGG<br>GLVQPGNSLRLSCAASGFTFSKFGMSWVRQAPGKGLEWVSSISGSGRDTLYA<br>ESVKGRFTISRDNAKTTLYLQMNSLRPEDTAVYYCTIGGSLSVSSQGTLVTVSS<br>ggggsggggsggggsggggsggggsggggssggpGPAGLYAQpgsEVQLVESGGGLVQPGGS<br>LRLSCAASGFTFSSYTLAWVRQAPGKcLEWVAAIDSSSYTYSPDTVRGRFTISR<br>DNAKNSLYLQMNSLRAEDTAVYYCARDSNWDALDYWGQGTTVTVSSGGGG<br>SGGGGSGGGGSDIQMTQSPSSLSASVGDRVTITCKSSEKLWANVAWYQQKPG<br>KAPKsLIYSASFRYSGVPSRFSGSGSGTDFTLTISSLQPEDFATYYCQQYYTYPY<br>TFGcGTKVEIK |
| 276 | ACP443 (WW0585) | aptssstkktqlqlehllldlqmilnginnyknpkltrmltfkfympkkatelkhlqcleeelkpleevinlaqsknfhlrpr<br>dlisninvivlelkgsettfmceyadetativeflnrwitfcqsiistltsggpGPAGLYAQpgsEVQLVESGG<br>GLVQPGNSLRLSCAASGFTFSKFGMSWVRQAPGKGLEWVSSISGSGRDTLYA<br>ESVKGRFTISRDNAKTTLYLQMNSLRPEDTAVYYCTIGGSLSVSSQGTLVTVSS<br>ggggsggggsggggsggggsggggsggggssggpGPAGLYAQpgsEVQLVESGGGLVQPGGS<br>LRLSCAASGFTFSSYTLAWVRQAPGKcLEWVAAIDSSSYTYSPDTVRGRFTISR<br>DNAKNSLYLQMNSLRAEDTAVYYCARDSNWDALDYWGQGTTVTVSSGGGG<br>SGGGGSGGGGSDIQMTQSPSSLSASVGDRVTITCKSSEKLWANVAWYQQKPG<br>KAPKLLIYSASFRYSGVPSRFSGSGSGTDFTLTISSLQPEDFATYYCQQYYTYPY<br>TFGcGTKVEIK |
| 277 | ACP444 (WW0586) | aptsssticktqlqlehllldlqmilnginnyknpkltrmltfkfympkkatelkhlqcleeelkpleevinlaqsknfhlrpr<br>dlisninvivlelkgsettfmceyadetativeflnrwiticqsiistltsggpGPAGLYAQpgsEVQLVESGG<br>GLVQPGNSLRLSCAASGFTFSKFGMSWVRQAPGKGLEWVSSISGSGRDTLYA<br>ESVKGRFTISRDNAKTTLYLQMNSLRPEDTAVYYCTIGGSLSVSSQGTLVTVSS<br>ggggsggggsggggsggggsggggsggggssggpGPAGLYAQpgsEVQLVESGGGLVQPGGS<br>LRLSCAASGFTFSSYTLAWVRQAPGKGLEWVAAIDSSSYTYSPDTVRGRFTISR<br>DNAKNSLYLQMNSLRAEDTAVYYCARDSNWDALDYWGcGTTVTVSSGGGG<br>SGGGGSGGGGSDIQMTQSPSSLSASVGDRVTITCKSSEKLWANVAWYQQKPG<br>KcPKALIYSASFRYSGVPSRFSGSGSGTDFTLTISSLQPEDFATYYCQQYYTYPY<br>TFGGGTKVEIK |
| 278 | ACP445 (WW0587) | aptsssticktqlqlehllldlqmilnginnyknpkltrmltfkfympkkatelkhlqcleeelkpleevinlaqsknfhlrpr<br>dlisninvivlelkgsettfmceyadetativeflnrwiticqsiistltsggpGPAGLYAQpgsEVQLVESGG<br>GLVQPGNSLRLSCAASGFTFSKFGMSWVRQAPGKGLEWVSSISGSGRDTLYA<br>ESVKGRFTISRDNAKTTLYLQMNSLRPEDTAVYYCTIGGSLSVSSQGTLVTVSS<br>ggggsggggsggggsggggsggggsggggssggpGPAGLYAQpgsEVQLVESGGGLVQPGGS<br>LRLSCAASGFTFSSYTLAWVRQAPGKGLEWVAAIDSSSYTYSPDTVRGRFTISR<br>DNAKNSLYLQMNSLRAEDTAVYYCARDSNWDALDYWGQGTTVTVSSggpG<br>PAGLYAQpgsDIQMTQSPSSLSASVGDRVTITCKAREKLWSAVAWYQQPGKA<br>PKLLIYSASFRYSGVPSRFSGSGSGTDFTLTISSLQPEDFATYYCQQYYTYPYTF<br>GGGTKVEIK |
| 279 | ACP446 (WW0588) | aptsssticktqlqlehllldlqmilnginnyknpkltrmltfkfympkkatelkhlqcleeelkpleevinlaqsknfhlrpr<br>dlisninvivlelkgsettfmceyadetativeflnrwiticqsiistltsggpGPAGLYAQpgsEVQLVESGG |

Sequence Table

| SEQ ID NO. | Name | Sequence |
|---|---|---|
| | | GLVQPGNSLRLSCAASGFTFSKFGMSWVRQAPGKGLEWVSSISGSGRDTLYA<br>ESVKGRFTISRDNAKTTLYLQMNSLRPEDTAVYYCTIGGSLSVSSQGTLVTVSS<br>ggggsggggsggggsggggsggggsggggssggpGPAGLYAQpgsEVQLVESGGGLVQPGGS<br>LRLSCAASGFTFSSYTLAWVRQAPGKGLEWVAAIDSSSYTYSPDTVRGRFTISR<br>DNAKNSLYLQMNSLRAEDTAVYYCARDSNWDALDYWGQGTTVTVSSGGGG<br>SGGGGSGGGGSDIQMTQSPSSLSASVGDRVTITCKAREKLWSAVAWYQQKPG<br>KAPKLLIYSASFRYSGVPSRFSGSGSGTDFTLTISSLQPEDFATYYCQQYYTYPY<br>TFGGGTKVEIK |
| 280 | ACP447<br>(WW0589) | aptsssticktqlqlehllldlqmilnginnyknpkltrmltfkfympkkatelkhlqcleeelkpleevinlaqsknfhlrpr<br>dlisninivlvlelkgsettfmceyadetativeflnrwiticqsiistltsggpGPAGLYAQpgsEVQLVESGG<br>GLVQPGNSLRLSCAASGFTFSKFGMSWVRQAPGKGLEWVSSISGSGRDTLYA<br>ESVKGRFTISRDNAKTTLYLQMNSLRPEDTAVYYCTIGGSLSVSSQGTLVTVSS<br>ggggsggggsggggsggggsggggsggggssggpGPAGLYAQpgsEVQLVESGGGLVQPGGS<br>LRLSCAASGFTFSSYTLAWVRQAPGKcLEWVAAIDSSSYTYSPDTVRGRFTISR<br>DNAKNSLYLQMNSLRAEDTAVYYCARDSNWDALDYWGQGTTVTVSSGGGG<br>SGGGGSGGGGSDIQMTQSPSSLSASVGDRVTITCKAREKLWSAVAWYQQKPG<br>KAPKLLIYSASFRYSGVPSRFSGSGSGTDFTLTISSLQPEDFATYYCQQYYTYPY<br>TFGcGTKVEIK |
| 281 | ACP451<br>(WW0615) | aptsssticktqlqlehllldlqmilnginnyknpkltrmltfkfympkkatelkhlqcleeelkpleevinlaqsknfhlrpr<br>dlisninivlvlelkgsettfmceyadetativeflnrwiticqsiistltsggpALFKSSFPpgsEVQLVESGGG<br>LVQPGNSLRLSCAASGFTFSKFGMSWVRQAPGKGLEWVSSISGSGRDTLYAES<br>VKGRFTISRDNAKTTLYLQMNSLRPEDTAVYYCTIGGSLSVSSQGTLVTVSSgg<br>ggsggggsggggsggggsggggsggggssggpALFKSSFPpgsEVQLVESGGGLVQPGGSLRL<br>SCAASGFTFSSYTLAWVRQAPGKGLEWVAAIDSSSYTYSPDTVRGRFTISRDN<br>AKNSLYLQMNSLRAEDTAVYYCARDSNWDALDYWGQGTTVTVSSGGGGSG<br>GGGSGGGGSDIQMTQSPSSLSASVGDRVTITCKAREKLWSAVAWYQQKPGKA<br>PKsLIYSASFRYSGVPSRFSGSGSGTDFTLTISSLQPEDFATYYCQQYYTYPYTF<br>GGGTKVEIK** |
| 282 | ACP452<br>(WW0616) | aptsssticktqlqlehllldlqmilnginnyknpkltrmltfkfympkkatelkhlqcleeelkpleevinlaqsknfhlrpr<br>dlisninivlvlelkgsettfmceyadetativeflnrwitfcqsiistltsggpALFKSSFPpgsEVQLVESGGG<br>LVQPGNSLRLSCAASGFTFSKFGMSWVRQAPGKGLEWVSSISGSGRDTLYAES<br>VKGRFTISRDNAKTTLYLQMNSLRPEDTAVYYCTIGGSLSVSSQGTLVTVSSgg<br>ggsggggsggggsggggsggggsggggssggpALFKSSFPpgsEVQLVESGGGLVQPGGSLRL<br>SCAASGFTFSSYTLAWVRQAPGKGLEWVAAIDSSSYTYSPDTVRGRFTISRDN<br>AKNSLYLQMNSLRAEDTAVYYCARDSNWDALDYWGQGTTVTVSSGGGGSG<br>GGGSGGGGSDIQMTQSPSSLSASVGDRVTITCKVTEKVWGNVAWYQQKPGK<br>APISLIYSPSLRKSGVPSRFSGSGSGTDFTLTISSLQPEDFATYYCQQYYTYPYTF<br>GGGTKVEIK** |
| 283 | ACP453<br>(WW0617) | aptsssticktqlqlehllldlqmilnginnyknpkltrmltfkfympkkatelkhlqcleeelkpleevinlaqsknfhlrpr<br>dlisninivlvlelkgsettfmceyadetativeflnrwitfcqsiistltsggpALFKSSFPpgsEVQLVESGGG<br>LVQPGNSLRLSCAASGFTFSKFGMSWVRQAPGKGLEWVSSISGSGRDTLYAES<br>VKGRFTISRDNAKTTLYLQMNSLRPEDTAVYYCTIGGSLSVSSQGTLVTVSSgg<br>ggsggggsggggsggggsggggsggggssggpALFKSSFPpgsEVQLVESGGGLVQPGGSLRL<br>SCAASGFTFSSYTLAWVRQAPGKcLEWVAAIDSSSYTYSPDTVRGRFTISRDNA<br>KNSLYLQMNSLRAEDTAVYYCARDSNWDALDYWGQGTTVTVSSGGGGSGG<br>GGSGGGGSDIQMTQSPSSLSASVGDRVTITCKAREKLWSAVAWYQQKPGKAP<br>KsLIYSASFRYSGVPSRFSGSGSGTDFTLTISSLQPEDFATYYCQQYYTYPYTFG<br>cGTKVEIK** |
| 284 | ACP454<br>(WW0618) | aptsssticktqlqlehllldlqmilnginnyknpkltrmltfkfympkkatelkhlqcleeelkpleevinlaqsknfhlrpr<br>dlisninivlvlelkgsettfmceyadetativeflnrwitfcqsiistltsggpALFKSSFPpgsEVQLVESGGG<br>LVQPGNSLRLSCAASGFTFSKFGMSWVRQAPGKGLEWVSSISGSGRDTLYAES<br>VKGRFTISRDNAKTTLYLQMNSLRPEDTAVYYCTIGGSLSVSSQGTLVTVSSgg<br>ggsggggsggggsggggsggggsggggssggpALFKSSFPpgsEVQLVESGGGLVQPGGSLRL<br>SCAASGFTFSSYTLAWVRQAPGKGLEWVAAIDSSSYTYSPDTVRGRFTISRDN<br>AKNSLYLQMNSLRAEDTAVYYCARDSNWDALDYWGcGTTVTVSSGGGGSG<br>GGSGGGGSDIQMTQSPSSLSASVGDRVTITCKAREKLWSAVAWYQQKPGKc<br>PKALIYSASFRYSGVPSRFSGSGSGTDFTLTISSLQPEDFATYYCQQYYTYPYTF<br>GGGTKVEIK** |
| 285 | ACP455<br>(WW0619) | aptsssticktqlqlehllldlqmilnginnyknpkltrmltfkfympkkatelkhlqcleeelkpleevinlaqsknfhlrpr<br>dlisninivlvlelkgsettfmceyadetativeflnrwitfcqsiistltsggpALFKSSFPpgsEVQLVESGGG<br>LVQPGNSLRLSCAASGFTFSKFGMSWVRQAPGKGLEWVSSISGSGRDTLYAES<br>VKGRFTISRDNAKTTLYLQMNSLRPEDTAVYYCTIGGSLSVSSQGTLVTVSSgg<br>ggsggggsggggsggggsggggsggggssggpALFKSSFPpgsEVQLVESGGGLVQPGGSLRL<br>SCAASGFTFSSYTLAWVRQAPGKcLEWVAAIDSSSYTYSPDTVRGRFTISRDNA |

Sequence Table

| SEQ ID NO. | Name | Sequence |
|---|---|---|
| | | KNSLYLQMNSLRAEDTAVYYCARDSNWDALDYWGQGTTVTVSSGGGGSGG<br>GGSGGGGSDIQMTQSPSSLSASVGDRVTITCKVTEKVWGNVAWYQQKPGKA<br>PISLIYSPSLRKSGVPSRFSGSGSGTDFTLTISSLQPEDFATYYCQQYYTYPYTFG<br>cGTKVEIK** |
| 441 | ACP456<br>(WW0620) | aptssssticktqlqlehllldlqmilnginnyknpkltrmltfkfympkkatelkhlqcleeelkpleevinlaqsknfhlrpr<br>dlisninvivlelkgsettfmceyadetativeflnrwitfcqsiistltsggpALFKSSFPpgsEVQLVESGGG<br>LVQPGNSLRLSCAASGFTFSKFGMSWVRQAPGKGLEWVSSISGSGRDTLYAES<br>VKGRFTISRDNAKTTLYLQMNSLRPEDTAVYYCTIGGSLSVSSQGTLVTVSSgg<br>ggsggggsggggsggggsggggsggggsggggssggpALFKSSFPpgsEVQLVESGGGLVQPGGSLRL<br>SCAASGFTFSSYTLAWVRQAPGKGLEWVAAIDSSSYTYSPDTVRGRFTISRDN<br>AKNSLYLQMNSLRAEDTAVYYCARDSNWDALDYWGcGTTVTVSSGGGGSG<br>GGGSGGGGSDIQMTQSPSSLSASVGDRVTITCKVTEKVWGNVAWYQQKPGKc<br>PISLIYSPSLRKSGVPSRFSGSGSGTDFTLTISSLQPEDFATYYCQQYYTYPYTFG<br>GGTKVEIK** |
| 286 | ACP457<br>(WW0621) | aptssssticktqlqlehllldlqmilnginnyknpkltrmltfkfympkkatelkhlqcleeelkpleevinlaqsknfhlrpr<br>dlisninvivlelkgsettfmceyadetativeflnrwitfcqsiistltsggpALFKSSFPpgsEVQLVESGGG<br>LVQPGNSLRLSCAASGFTFSKFGMSWVRQAPGKGLEWVSSISGSGRDTLYAES<br>VKGRFTISRDNAKTTLYLQMNSLRPEDTAVYYCTIGGSLSVSSQGTLVTVSSgg<br>ggsggggsggggsggggsggggsggggsggggssggpALFKSSFPpgsEVQLVESGGGLVQPGGSLRL<br>SCAASGFTFSSYTLAWVRQAPGKGLEWVAAIDSSSYTYSPDTVRGRFTISRDN<br>AKNSLYLQMNSLRAEDTAVYYCARDSNWDALDYWGQGTTVTVSSastkgpsvfp<br>lapssskstsggtaalgclvkdyfpepvtvswnsgaltsgvhtfpavlqssglyslssvvtvpssslgtqtyicnvnhkpsnt<br>kvdkrvepksc** |
| 287 | ACP458<br>(WW0622) | eskygppcppcpapeflggpsvflfppkpkdtlmisrtpevtcvvvdvsqedpevqfnwyvdgvevhnaktkpree<br>qfnstyrvvsyltvlhqdwlngkeykckvsnkglpssiektiskakgqprepqvytlppsqeemtknqvsltclvkgfy<br>psdiavewesngqpennykappvldsdgsfflysrltvdksrwqegnvfscsvmhealhnhytqkslslslgksggp<br>ALFKSSFPpgsaptsssstkktqlqlehllldlqmilnginnyknpkltrmltfklympkkatelkhlqcleeelkplee<br>vinlaqsknfhlrprdlisninvivlelkgsettfmceyadetativeflnrwitfcqsiistltggggsggggsggggsggg<br>gsggggsggggssggpALFKSSFPpgsEVQLVESGGGLVQPGGSLRLSCAASGFTFSSY<br>TLAWVRQAPGKGLEWVAAIDSSSYTYSPDTVRGRFTISRDNAKNSLYLQMNS<br>LRAEDTAVYYCARDSNWDALDYWGQGTTVTVSSastkgpsvfplapssskstsggtaalgclv<br>kdyfpepvtvswnsgaltsgvhtfpavlqssglyslssvvtvpssslgtqtyicnvnhkpsntkvdkrvepksc** |
| 288 | ACP459<br>(WW0623) | eskygppcppcpapeflggpsvflfppkpkdtlmisrtpevtcvvvdvsqedpevqfnwyvdgvevhnaktkpree<br>qfnstyrvvsyltvlhqdwlngkeykckvsnkglpssiektiskakgqprepqvytlppsqeemtknqvsltclvkgfy<br>psdiavewesngqpennykappvldsdgsfflysrltvdksrwqegnvfscsvmhealhnhytqkslslslgksggp<br>ALFKSSFPpgsaptsssstkktqlqlehllldlqmilnginnyknpkltrmltfklympkkatelkhlqcleeelkplee<br>vinlaqsknfhlrprdlisninvivlelkgsettfmceyadetativeflnrwitfcqsiistltggggsggggsggggsggg<br>gsggggsggggssggpALFKSSFPpgsEVQLVESGGGLVQPGGSLRLSCAASGFTFSSY<br>TLAWVRQAPGKGLEWVAAIDSSSYTYSPDTVRGRFTISRDNAKNSLYLQMNS<br>LRAEDTAVYYCARDSNWDALDYWGQGTTVTVSSGGGGSGGGGSGGGGSDI<br>QMTQSPSSLSASVGDRVTITCKAREKLWSAVAWYQQKPGKAPKsLIYSASFRY<br>SGVPSRFSGSGSGTDFTLTISSLQPEDFATYYCQQYYTYPYTFGGGTKVEIK** |
| 289 | ACP460<br>(WW0624) | eskygppcppcpapeflggpsvflfppkpkdtlmisrtpevtcvvvdvsqedpevqfnwyvdgvevhnaktkpree<br>qfnstyrvvsyltvlhqdwlngkeykckvsnkglpssiektiskakgqprepqvytlppsqeemtknqvsltclvkgfy<br>psdiavewesngqpennykappvldsdgsfflysrltvdksrwqegnvfscsvmhealhnhytqkslslslgksggp<br>ALFKSSFPpgsaptsssstkktqlqlehllldlqmilnginnyknpkltrmltfklympkkatelkhlqcleeelkplee<br>vinlaqsknfhlrprdlisninvivlelkgsettfmceyadetativeflnrwitfcqsiistltggggsggggsggggsggg<br>gsggggsggggssggpALFKSSFPpgsEVQLVESGGGLVQPGGSLRLSCAASGFTFSSY<br>TLAWVRQAPGKGLEWVAAIDSSSYTYSPDTVRGRFTISRDNAKNSLYLQMNS<br>LRAEDTAVYYCARDSNWDALDYWGQGTTVTVSSGGGGSGGGGSGGGGSDI<br>QMTQSPSSLSASVGDRVTITCKVTEKVWGNVAWYQQKPGKAPISLIYSPSLRK<br>SGVPSRFSGSGSGTDFTLTISSLQPEDFATYYCQQYYTYPYTFGGGTKVEIK** |
| 290 | ACP461<br>(WW0625) | eskygppcppcpapeflggpsvflfppkpkdtlmisrtpevtcvvvdvsqedpevqfnwyvdgvevhnaktkpree<br>qfnstyrvvsyltvlhqdwlngkeykckvsnkglpssiektiskakgqprepqvytlppsqeemtknqvsltclvkgfy<br>psdiavewesngqpennykappvldsdgsfflysrltvdksrwqegnvfscsvmhealhnhytqkslslslgksggp<br>ALFKSSFPpgsaptsssstkktqlqlehllldlqmilnginnyknpkltrmltfklympkkatelkhlqcleeelkplee<br>vinlaqsknfhlrprdlisninvivlelkgsettfmceyadetativeflnrwitfcqsiistltggggsggggsggggsggg<br>gsggggsggggssggpALFKSSFPpgsEVQLVESGGGLVQPGGSLRLSCAASGFTFSSY<br>TLAWVRQAPGKcLEWVAAIDSSSYTYSPDTVRGRFTISRDNAKNSLYLQMNSL<br>RAEDTAVYYCARDSNWDALDYWGQGTTVTVSSGGGGSGGGGSGGGGSDIQ<br>MTQSPSSLSASVGDRVTITCKAREKLWSAVAWYQQKPGKAPKsLIYSASFRYS<br>GVPSRFSGSGSGTDFTLTISSLQPEDFATYYCQQYYTYPYTFGcGTKVEIK** |
| 291 | ACP462<br>(WW0626) | eskygppcppcpapeflggpsvflfppkpkdtlmisrtpevtcvvvdvsqedpevqfnwyvdgvevhnaktkpree<br>qfnstyrvvsyltvlhqdwlngkeykckvsnkglpssiektiskakgqprepqvytlppsqeemtknqvsltclvkgfy<br>psdiavewesngqpennykappvldsdgsfflysrltvdksrwqegnvfscsvmhealhnhytqkslslslgksggp<br>ALFKSSFPpgsaptsssstkktqlqlehllldlqmilnginnyknpkltrmltfklympkkatelkhlqcleeelkplee |

Sequence Table

| SEQ ID NO. | Name | Sequence |
|---|---|---|
| | | vinlaqsknfhlrprdlisninvivlelkgsettfmceyadetativeflnrwitfcqsiiistltggggsggggsggggsggg<br>gsggggsggggssggpALFKSSFPpgsEVQLVESGGGLVQPGGSLRLSCAASGFTFSSY<br>TLAWVRQAPGKGLEWVAAIDSSSYTYSPDTVRGRFTISRDNAKNSLYLQMNS<br>LRAEDTAVYYCARDSNWDALDYWGcGTTVTVSSGGGGSGGGGSGGGGSDIQ<br>MTQSPSSLSASVGDRVTITCKAREKLWSAVAWYQQKPGKcPKALIYSASFRYS<br>GVPSRFSGSGSGTDFTLTISSLQPEDFATYYCQQYYTYPYTFGGGTKVEIK** |
| 292 | ACP463 (WW0627) | eskygppcppcpapeflggpsvflfppkpkdtlmisrtpevtcvvvdvsqedpevqfnwyvdgvevhnaktkpree<br>qfnstyrvvsyltvlhqdwlngkeykckvsnkglpssiektiskakgqprepqvytlppsqeemtknqvsltclvkgfy<br>psdiavewesngqpennykappvldsdgsfflysrltvdksrwqegnvfscsvmhealhnhytqkslslslgksggp<br>ALFKSSFPpgsaptssstkktqlqlehllldlqmilnginnyknpkltrmltfklympkkatelkhlqcleeeelkplee<br>vinlaqsknfhlrprdlisninvivlelkgsettfmceyadetativeflnrwitfcqsiiistltggggsggggsggggsggg<br>gsggggsggggssggpALFKSSFPpgsEVQLVESGGGLVQPGGSLRLSCAASGFTFSSY<br>TLAWVRQAPGKcLEWVAAIDSSSYTYSPDTVRGRFTISRDNAKNSLYLQMNSL<br>RAEDTAVYYCARDSNWDALDYWGQGTTVTVSSGGGGSGGGGSGGGGSDIQ<br>MTQSPSSLSASVGDRVTITCKVTEKVWGNVAWYQQKPGKAPISLIYSPSLRKS<br>GVPSRFSGSGSGTDFTLTISSLQPEDFATYYCQQYYTYPYTFGcGTKVEIK** |
| 293 | ACP464 (WW0628) | eskygppcppcpapeflggpsvflfppkpkdtlmisrtpevtcyvvvdvsqedpevqfnwyydgvevhnaktkpree<br>qfnstyrvvsyltvlhqdwingkeykcicvsnkglpssiektiskakgqprepqvytlpmqvsltclvkgfy<br>psdiavewesngqpennykappvldsdgsfflysrltvdksrwqegnvfscsvmhealhnhytqkslslslgkssgp<br>ALFKSSFPpgsaptssssticktqlqlehllldlqmilnginnyknpkltrmlfficfymmpkkatelkhlqcleeeelkplee<br>vinlaqsknfhlrprdlisninvivlelkgsettfmceyadetativeflnrwilfcqsiiistltggggsggggsggggsggg<br>gsggggsggggssggpALFKSSFPpgsEVQLVESGGGLVQPGGSLRLSCAASGFTFSSY<br>TLAWVRQAPGKGLEWVAAIDSSSYTYSPDTVRGRFTISRDNAKNSLYLQMNS<br>LRAEDTAVYYCARDSNWDALDYWGcGTTVTVSSGGGGSGGGGSGGGGSDIQ<br>MTQSPSSLSASVGDRVTITCKVTEKVWGNVAWYQQKPGKcPISLIYSPSLRKS<br>GVPSRFSGSGSGTDFTLTISSLQPEDFATYYCQQYYTYPYTFGGGTKVEIK** |
| 294 | ACP465 (WW0629) | vprdcgckpcictypevssvfifppkpkdvltitltpkvtcyvvdiskddpevqfswfvddvevhtaqtqpreeqfnsif<br>rsyselpimhqdwingkefkcrynsaafpapiektisktkgrpkapqvytipppkeqmakdkvsltcmitcapeditv<br>ewqwngqpaenykntqpimdtdgsyfvyskllnvqksnweagniftcsvlheglhnhhtekslshspgksggpAL<br>FKSSFPpgsaptsssticktqlqlehllldlqmilnginnyknpklbnillfldympkkatelkhlqcleeeelkpleevin<br>laqsknfhlrprdlisninvivlelkgsettfmceyadetativeflnrwilfcqsiiistltggggsggggsggggsggggsg<br>gggsggggssggpALFKSSFPpgsEVQLVESGGGLVQPGGSLRLSCAASGFTFSSYTL<br>AWVRQAPGKGLEWVAAIDSSSYTYSPDTVRGRFTISRDNAKNSLYLQMNSLR<br>AEDTAVYYCARDSNWDALDYWGQGTTVTVSSGGGGSGGGGSGGGGSDIQM<br>TQSPSSLSASVGDRVTITCKAREKLWSAVAWYQQKPGKAPKsLIYSASFRYSG<br>VPSRFSGSGSGTDFTLTISSLQPEDFATYYCQQYYTYPYTFGGGTKVEIK** |
| 295 | ACP466 (WW0630) | vprdcgckpcictypevssvfifppkpkdvltitltpkvtcyvvdiskddpevqfswfvddvevhtaqtqpreeqfnsif<br>rsyselpimhqdwingkefkcrynsaafpapiektisktkgrpkapqvytipppkeqmakdkvsltcmitcapeditv<br>ewqwngqpaenykntqpimdtdgsyfvyskllnvqksnweagniftcsvlheglhnhhtekslshspgksggpAL<br>FKSSFPpgsaptsssticktqlqlehllldlqmilnginnyknpklbnillfldympkkatelkhlqcleeeelkpleevin<br>laqsknfhlrprdlisninvivlelkgsettfmceyadetativeflnrwilfcqsiiistltggggsggggsggggsggggsg<br>gggsggggssggpALFKSSFPpgsEVQLVESGGGLVQPGGSLRLSCAASGFTFSSYTL<br>AWVRQAPGKGLEWVAAIDSSSYTYSPDTVRGRFTISRDNAKNSLYLQMNSLR<br>AEDTAVYYCARDSNWDALDYWGQGTTVTVSSGGGGSGGGGSGGGGSDIQM<br>TQSPSSLSASVGDRVTITCKVTEKVWGNVAWYQQKPGKAPISLIYSPSLRKSG<br>VPSRFSGSGSGTDFTLTISSLQPEDFATYYCQQYYTYPYTFGGGTKVEIK** |
| 296 | ACP467 (WW0631) | vprdcgckpcictypevssvfifppkpkdvltitltpkvtcyvvdiskddpevqfswfvddvevhtaqtqpreeqfnsif<br>rsyselpimhqdwingkefkcrynsaafpapiektisktkgrpkapqvytipppkeqmakdkvsltcmitcapeditv<br>ewqwngqpaenykntqpimdtdgsyfvyskllnvqksnweagniftcsvlheglhnhhtekslshspgksggpAL<br>FKSSFPpgsaptsssticktqlqlehllldlqmilnginnyknpklbnillfldympkkatelkhlqcleeeelkpleevin<br>laqsknfhlrprdlisninvivlelkgsettfmceyadetativeflnrwilfcqsiiistltggggsggggsggggsggggsg<br>gggsggggssggpALFKSSFPpgsEVQLVESGGGLVQPGGSLRLSCAASGFTFSSYTL<br>AWVRQAPGKcLEWVAAIDSSSYTYSPDTVRGRFTISRDNAKNSLYLQMNSLR<br>AEDTAVYYCARDSNWDALDYWGQGTTVTVSSGGGGSGGGGSGGGGSDIQM<br>TQSPSSLSASVGDRVTITCKAREKLWSAVAWYQQKPGKAPKsLIYSASFRYSG<br>VPSRFSGSGSGTDFTLTISSLQPEDFATYYCQQYYTYPYTFGcGTKVEIK** |
| 297 | ACP468 (WW0632) | vprdcgckpcictypevssvfifppkpkdvltitltpkvtcyvvdiskddpevqfswfvddvevhtaqtqpreeqfnsif<br>rsyselpimhqdwingkefkcrynsaafpapiektisktkgrpkapqvytipppkeqmakdkvsltcmitcapeditv<br>ewqwngqpaenykntqpimdtdgsyfvyskllnvqksnweagniftcsvlheglhnhhtekslshspgksggpAL<br>FKSSFPpgsaptsssticktqlqlehllldlqmilnginnyknpklbnillfldympkkatelkhlqcleeeelkpleevin<br>laqsknfhlrprdlisninvivlelkgsettfmceyadetativeflnrwilfcqsiiistltggggsggggsggggsggggsg<br>gggsggggssggpALFKSSFPpgsEVQLVESGGGLVQPGGSLRLSCAASGFTFSSYTL<br>AWVRQAPGKGLEWVAAIDSSSYTYSPDTVRGRFTISRDNAKNSLYLQMNSLR<br>AEDTAVYYCARDSNWDALDYWGcGTTVTVSSGGGGSGGGGSGGGGSDIQMT<br>QSPSSLSASVGDRVTITCKAREKLWSAVAWYQQKPGKcPKALIYSASFRYSGV<br>PSRFSGSGSGTDFTLTISSLQPEDFATYYCQQYYTYPYTFGGGTKVEIK** |

Sequence Table

| SEQ ID NO. | Name | Sequence |
|---|---|---|
| 298 | ACP469 (WW0633) | vprdcgckpcictypevssvfifppkpkdvltitltpkvtcyvvdiskddpevqfswfvddvevhtaqtqpreeqfnsif<br>rsyselpimhqdwingkefkcrynsaafpapiektisktkgrpkapqvytipppkeqmakdkvsltcmitcapeditv<br>ewqwngqpaenykntqpimdtdgsyfvysklnvqksnweagniftcsvlheglhnhhtekslshspgksggpAL<br>FKSSFPpgsaptsssktktqlqlehllldlqmilngiimyknpklliiiiltfkfympkkatelkhlqcleeelkpleevin<br>laqsknfhlrprdlisnininvivlelkgsettfmceyadetativeflnrwilfcqsiiistltggggsggggsggggsggggsg<br>gggsggggssggpALFKSSFPpgsEVQLVESGGGLVQPGGSLRLSCAASGFTFSSYTL<br>AWVRQAPGKcLEWVAAIDSSSYTYSPDTVRGRFTISRDNAKNSLYLQMNSLR<br>AEDTAVYYCARDSNWDALDYWGQGTTVTVSSGGGGSGGGGSGGGGSDIQM<br>TQSPSSLSASVGDRVTITCKVTEKVWGNVAWYQQKPGKAPISLIYSPSLRKSG<br>VPSRFSGSGSGTDFTLTISSLQPEDFATYYCQQYYTYPYTFGcGTKVEIK** |
| 299 | ACP470 (WW0634) | vprdcgckpcictypevssvfifppkpkdvltitltpkvtcyvvdiskddpevqfswfvddvevhtaqtqpreeqfnslf<br>rsyselpimhqdwingkefkcrynsaafpapiektisktkgrpkapqvytipppkeqmakdkvsltcmitcapeditv<br>ewqwngqpaenykntqpimdtdgsyfvysklnvqksnweagntftcsvlheglhnhhtekslshspgksggpAL<br>FKSSFPpgsaptsssticktqlqlehllldlqmilnginnyknpklbnillfldympkkatelkhlqcleeelkpleevin<br>laqsknfhlrprdlisnininvivlelkgsettfmceyadetativeflnrwilfcqsiiistltggggsggggsggggsggggsg<br>gggsggggssggpALFKSSFPpgsEVQLVESGGGLVQPGGSLRLSCAASGFTFSSYTL<br>AWVRQAPGKGLEWVAAIDSSSYTYSPDTVRGRFTISRDNAKNSLYLQMNSLR<br>AEDTAVYYCARDSNWDALDYWGcGTTVTVSSGGGGSGGGGSGGGGSDIQMT<br>QSPSSLSASVGDRVTITCKVTEKVWGNVAWYQQKPGKcPISLIYSPSLRKSGVP<br>SRFSGSGSGTDFTLTISSLQPEDFATYYCQQYYTYPYTFGGGTKVEIK** |
| 300 | ACP471 (WW0642) | mdmrvpaqllglllwlrgarcvprdcgckpcictvpevssvfifppkpkdvltitltpkvtcvvvdiskddpevqfswf<br>vddveyhtaqtqpreeqfnslfrsyselpimhqdwingkefkcrynsaafpapiektisktkgrpkapqvytipppkeq<br>makdkvsltcmitdffpeditvewqwngqpaenykntqpimdtdgsyfvysklnvqknweagntftcsvlheglh<br>nhhhtekslshspgksggpALFKSSFPpgsaptsssticktqlqlehllldlqmilnginnyknpkltrmllfldympk<br>katelkhlqcleeelkpleevinlaqsknfhlrprdlisnininvivlelkgsettfmceyadetativeflnrwilfcqsiiistltg<br>gggsggggsggggsggggsggggssggpALFKSSFPpgsEVQLVESGGGLVQPGGSLR<br>LSCAASGFTFSSYTLAWVRQAPGKGLEWVAAIDSSSYTYSPDTVRGRFTISRD<br>NAKNSLYLQMNSLRAEDTAVYYCARDSNWDALDYWGQGTTVTVSSastkgpsv<br>fplapssksstsggtaalgclykdyfpepvtvswnsgaltsgvhtipavlqssglyslssvvtvpssslgtqtyicnvnhkps<br>nticvdkrvepksc** |
| 301 | ACP382 (WW0524) | DIQMTQSPSSLSASVGDRVTITCKVTEKVWGNVAWYQQKPGKAPISLIYSPSL<br>RKSGVPSRFSGSGSGTDFTLTISSLQPEDFATYYCQQYYTYPYTFGGGTKVEIKr<br>tvaapsvfifppsdeqlksgtasvvcllnaypreakvqwkvdnalqsgnsqesvteqdskdstyslsstltlskadyekh<br>kvyacevthqglsspvtksfnrgec** |
| 302 | ACP383 (WW0525) | eskygppcppcpapefIggpsvflfppkpkdtlmisrtpevtcyvvdvsqedpevqfnwyydgvevhnaktkpree<br>qfnstyrvvsyltvlhqdwingkeykcicvsnkglpssiektiskakgqprepqvytlppsqeemtlmqvsltclvkgfy<br>psdiavewesngqpennykappvldsdgsfflysrltvdksrwqegnvfscsvmhealhnhytqkslslslgksggp<br>GPAGLYAQpgsaptsssticktqlqlehllldlqmilnginnyknpkltrmllfklympldcatelkhlqcleeelkpl<br>eevinlaqsknfhlrprdlisnininvivlelkgsettfmceyadetativeflnrwilfcqsiiistltggggsggggsggggsgg<br>ggsggggsggggssggpGPAGLYAQpgsEVQLVESGGGLVQPGGSLRLSCAASGFTFS<br>SYTLAWVRQAPGKcLEWVAAIDSSSYTYSPDTVRGRFTISRDNAKNSLYLQM<br>NSLRAEDTAVYYCARDSNWDALDYWGQGTTVTVSSGGGGSGGGGSGGGGS<br>DIQMTQSPSSLSASVGDRVTITCKASQNVGTNVGWYQQKPGKAPKALIYSASF<br>RYSGVPSRFSGSGSGTDFTLTISSLQPEDFATYYCQQYYTYPYTFGcGTKVEIK** |
| 303 | ACP384 (WW0526) | eskygppcppcpapefIggpsvflfppkpkdtlmisrtpevtcyvvdvsqedpevqfnwyydgvevhnaktkpree<br>qfnstyrvvsyltvlhqdwingkeykcicvsnkglpssiektiskakgqprepqvytlppsqeemtlmqvsltclvkgfy<br>psdiavewesngqpennykappvldsdgsfflysrltvdksrwqegnvfscsvmhealhnhytqkslslslgksggp<br>GPAGLYAQpgsaptsssticktqlqlehllldlqmilnginnyknpkltrmlltfkfympldcatelkhlqcleeelkpl<br>eevinlaqsknfhlrprdlisnininvivlelkgsettfmceyadetativeflnrwilfcqsiiistltggggsggggsggggsgg<br>ggsggggsggggssggpGPAGLYAQpgsEVQLVESGGGLVQPGGSLRLSCAASGFTFS<br>SYTLAWVRQAPGKGLEWVAAIDSSSYTYSPDTVRGRFTISRDNAKNSLYLQM<br>NSLRAEDTAVYYCARDSNWDALDYWGcGTTVTVSSGGGGSGGGGSGGGGSD<br>IQMTQSPSSLSASVGDRVTITCKASQNVGTNVGWYQQKPGKcPKALIYSASFR<br>YSGVPSRFSGSGSGTDFTLTISSLQPEDFATYYCQQYYTYPYTFGGGTKVEIK** |
| 304 | ACP385 (WW0527) | eskygppcppcpapefIggpsvflfppkpkdtlmisrtpevtcyvvdvsqedpevqfnwyydgvevhnaktkpree<br>qfnstyrvvsyltvlhqdwingkeykcicvsnkglpssiektiskakgqprepqvytlppsqeemtlmqvsltclvkgfy<br>psdiavewesngqpennykappvldsdgsfflysrltvdksrwqegnvfscsvmhealhnhytqkslslslgksggp<br>GPAGLYAQpgsaptsssticktqlqlehllldlqmilnginnyknpkltrmllfklympldcatelkhlqcleeelkpl<br>eevinlaqsknfhlrprdlisnininvivlelkgsettfmceyadetativeflnrwilfcqsiiistltggggsggggsggggsgg<br>ggsggggsggggssggpGPAGLYAQpgsEVQLVESGGGLVQPGGSLRLSCAASGFTFS<br>SYTLAWVRQAPGKcLEWVAAIDSSSYTYSPDTVRGRFTISRDNAKNSLYLQM<br>NSLRAEDTAVYYCARDSNWDALDYWGQGTTVTVSSGGGGSGGGGSGGGGS<br>DIQMTQSPSSLSASVGDRVTITCKAREKLWSAVAWYQQKPGKAPKALIYSASF<br>RYSGVPSRFSGSGSGTDFTLTISSLQPEDFATYYCQQYYTYPYTFGcGTKVEIK** |
| 305 | ACP386 (WW0528) | eskygppcppcpapefIggpsvflfppkpkdtlmisrtpevtcvvvdvsqedpevqfnwyydgvevhnaktkpree<br>qfnstyrvvsyltvlhqdwingkeykckcvsnkglpssiektiskakgqprepqvytlppsqeemtlmqvsltclvkgfy |

Sequence Table

| SEQ ID NO. | Name | Sequence |
|---|---|---|
| | | psdiavewesngqpennykttppvldsdgsfflysrltvdksrwqegnvfscsvmhealhnhytqkslslslgksggp GPAGLYAQpgsaptssstIcktqlqlehllldlqmilnginnyknpkltrmltfkfympldcatelkhlqcleeelkpl eevinlaqsknfldrprdlisninvivlelkgsettfmceyadetativeflnrwitfcqsiistltggggsggggsggggsgg ggsggggsggggssggpGPAGLYAQpgsEVQLVESGGGLVQPGGSLRLSCAASGFTFS SYTLAWVRQAPGKGLEWVAAIDSSSYTYSPDTVRGRFTISRDNAKNSLYLQM NSLRAEDTAVYYCARDSNWDALDYWGcGTTVTVSSGGGGSGGGGSGGGGSD IQMTQSPSSLSASVGDRVTITCKAREKLWSAVAWYQQKPGKcPKALIYSASFR YSGVPSRFSGSGSGTDFTLTISSLQPEDFATYYCQQYYTYPYTFGGGTKVEIK** |
| 306 | ACP387 (WW0529) | eskygppcppcpapeflggpsvflfppkpkdtlmisrtpevtcvvvdvsqedpevqfnwyvdgvevhnaktkpree qfnstyrvvsyltvlhqdwingkeykckvsnkglpssiektiskakgqprepqvytlppsqeemtlmqvsltclvkgfy psdiavewesngqpennykttppvldsdgsfflysrltvdksrwqegnvfscsvmhealhnhytqkslslslgksggp GPAGLYAQpgsaptssstIcktqlqlehllldlqmilnginnyknpkltrmltfkfympldcatelkhlqcleeelkpl eevinlaqsknfldrprdlisninvivlelkgsettfmceyadetativeflnrwitfcqsiistltggggsggggsggggsgg ggsggggsggggssggpGPAGLYAQpgsEVQLVESGGGLVQPGGSLRLSCAASGFTFS SYTLAWVRQAPGKcLEWVAAIDSSSYTYSPDTVRGRFTISRDNAKNSLYLQM NSLRAEDTAVYYCARDSNWDALDYWGQGTTVTVSSGGGGSGGGGSGGGGS DIQMTQSPSSLSASVGDRVTITCKVTEKVWGNVAWYQQKPGKAPISLIYSPSL RKSGVPSRFSGSGSGTDFTLTISSLQPEDFATYYCQQYYTYPYTFGcGTKVEIK** |
| 307 | ACP388 (WW0530) | eskygppcppcpapeflggpsvflfppkpkdtlmisrtpevtcvvvdvsqedpevqfnwyvdgvevhnaktkpree qfnstyrvvsyltvlhqdwingkeykckvsnkglpssiektiskakgqprepqvytlppsqeemtlmqvsltclvkgfy psdiavewesngqpennykttppvldsdgsfflysrltvdksrwqegnvfscsvmhealhnhytqkslslslgksggp GPAGLYAQpgsaptssstIcktqlqlehllldlqmilnginnyknpkltrmlfficfympldcatelkhlqcleeelkpl eevinlaqsknfldrprdlisninvivlelkgsettfmceyadetativeflnrwitfcqsiistltggggsggggsggggsgg ggsggggsggggssggpGPAGLYAQpgsEVQLVESGGGLVQPGGSLRLSCAASGFTFS SYTLAWVRQAPGKGLEWVAAIDSSSYTYSPDTVRGRFTISRDNAKNSLYLQM NSLRAEDTAVYYCARDSNWDALDYWGcGTTVTVSSGGGGSGGGGSGGGGSD IQMTQSPSSLSASVGDRVTITCKVTEKVWGNVAWYQQKPGKcPISLIYSPSLRK SGVPSRFSGSGSGTDFTLTISSLQPEDFATYYCQQYYTYPYTFGGGTKVEIK** |
| 308 | ACP389 (WW0531) | eskygppcppcpapeflggpsvflfppkpkdtlmisrtpevtcvvvdvsqedpevqfnwyvdgvevhnaktkpree qfnstyrvvsyltvlhqdwingkeykckvsnkglpssiektiskakgqprepqvytlppsqeemtlmqvsltclvkgfy psdiavewesngqpennykttppvldsdgsfflysrltvdksrwqegnvfscsvmhealhnhytqkslslslgksggp GPAGLYAQpgsaptssstIcktqlqlehllldlqmilnginnyknpkltrmltfkfympldcatelkhlqcleeelkpl eevinlaqsknfldrprdlisninvivlelkgsettfmceyadetativeflnrwitfcqsiistltggggsggggsggggsgg ggsggggsggggssggpGPAGLYAQpgsevqllesgggvlqpgsslrlscaasgsifsanamgwyrqapgkqr elvavaissggstnyadsvkgrftisrdnskntvylqmnstraedtavyycmysgsyyytpndywgqgtivtvss** |
| 309 | ACP390 (WW0532) | aptssstkktqlqlehllldlqmilnginnyknpkltrmltfkfympkkatelkhlqcleeelkpleevinlaqsknfhlrpr dlisninvivlelkgsettfmceyadetativeflnrwitfcqsiistltsggpGPAGLYAQpgsEVQLVESGG GLVQPGNSLRLSCAASGFTFSKFGMSWVRQAPGKGLEWVSSISGSGRDTLYA ESVKGRFTISRDNAKTTLYLQMNSLRPEDTAVYYCTIGGSLSVSSQGTLVTVSS ggggsggggsggggsggggsggggsggggsggggssggpGPAGLYAQpgsEVQLVESGGGLVQPGGS LRLSCAASGFTFSSYTLAWVRQAPGKcLEWVAAIDSSSYTYSPDTVRGRFTISR DNAKNSLYLQMNSLRAEDTAVYYCARDSNWDALDYWGQGTTVTVSSGGGG SGGGGSGGGGSDIQMTQSPSSLSASVGDRVTITCKAREKLWSAVAWYQQKPG KAPKsLIYSASFRYSGVPSRFSGSGSGTDFTLTISSLQPEDFATYYCQQYYTYPY TFGcGTKVEIK** |
| 310 | ACP391 (WW0533) | eskygppcppcpapeflggpsvflfppkpkdtlmisrtpevtcvvvdvsqedpevqfnwyvdgvevhnaktkpree qfnstyrvvsyltvlhqdwingkeykckvsnkglpssiektiskakgqprepqvytlppsqeemtlmqvsltclvkgfy psdiavewesngqpennykttppvldsdgsfflysrltvdksrwqegnvfscsvmhealhnhytqkslslslgksggp GPAGLYAQpgsaptssstkktqlqlehllldlqmilnginnyknpkltrmlfficfympldcatelkhlqcleeelkpl eevinlaqsknfhlrprdlisninvivlelkgsettfmceyadetativeflnrwitfcqsiistligggsggggsggggsgg ggsggggsggggssggpGPAGLYAQpgsEVQLVESGGGLVQPGGSLRLSCAASGFTFS SYTLAWVRQAPGKcLEWVAAIDSSSYTYSPDTVRGRFTISRDNAKNSLYLQM NSLRAEDTAVYYCARDSNWDALDYWGQGTTVTVSSGGGGSGGGGSGGGGS DIQMTQSPSSLSASVGDRVTITCKAREKLWSAVAWYQQKPGKAPKsLIYSASF RYSGVPSRFSGSGSGTDFTLTISSLQPEDFATYYCQQYYTYPYTFGcGTKVEIK** |
| 311 | ACP392 (WW0534) | aptssstkktqlqlehllldlqmilnginnyknpkltrmltfkfympkkatelkhlqcleeelkpleevinlaqsknfhlrpr dlisninvivlelkgsettfmceyadetativeflnrwitfcqsiistltsggpGPAGLYAQpgsggggsggggsggg gsggggsggggsggggsselcdddppeiphatfkamaykegtmlnceckrgfrriksgslymlctgnsshsswdnqc qctssatrnttkqvtpqpeeqkerkttemqspmqpvdqaslpghcrepppweneateriyhfvvgqmvyyqcvqgy ralhrgpaesvckmthgkrtwtqpqlictgemetsqfpgeekpqasepgrpesetsSlvtncifqiqtemaatmetsifttt eyqsggpGPAGLYAQpgsEVQLVESGGGLVQPGNSLRLSCAASGFTFSKFGMSWV RQAPGKGLEWVSSISGSGRDTLYAESVKGRFTISRDNAKTTLYLQMNSLRPED TAVYYCTIGGSLSVSSQGTLVTVSSggggsggggsggggsggggsggggsggggssggpGPAG LYAQpgsEVQLVESGGGLVQPGGSLRLSCAASGFTFSSYTLAWVRQAPGKcLE |

| SEQ ID NO. | Name | Sequence |
|---|---|---|
| | | WVAAIDSSSYTYSPDTVRGRFTISRDNAKNSLYLQMNSLRAEDTAVYYCARD<br>SNWDALDYWGQGTTVTVSSGGGGSGGGGSGGGGSDIQMTQSPSSLSASVGD<br>RVTITCKAREKLWSAVAWYQQKPGKAPKsLIYSASFRYSGVPSRFSGSGSTD<br>FTLTISSLQPEDFATYYCQQYTYPYTFGcGTKVEIK** |
| 312 | ACP393<br>(WW0535) | aptssstkktqlqlehllldlqmilnginnyknpkltrmltfkfympkkatelkhlqcleeelkpleevinlaqsknfhlrpr<br>dlisninvivlelkgsettfmceyadetativeflnrwitfcqsiistltsggpGPAGLYAQpgsggggsggggsggg<br>gsggggsggggsggggselcdddppeiphatfkamaykegtmlnceckrgfrriksgslymlctgnsshsswdnqc<br>qctssatrnttkqvtpqpeeqkerkttemqspmqpvdqaslpghcrepppweneateriyhfvvgqmvyyqcvqgy<br>ralhrgpaesvckmthgktrwtqpqlictgemetsqfpgeekpqaspegrpesetsSlvtncifqiqtemaatmetsifttt<br>eyqsggpGPAGLYAQpgsEVQLVESGGGLVQPGNSLRLSCAASGFTFSKFGMSWV<br>RQAPGKGLEWVSSISGSGRDTLYAESVKGRFTISRDNAKTTLYLQMNSLRPED<br>TAVYYCTIGGSLSVSSQGTLVTVSSggggsggggsggggsggggsggggsggggssggpGPAG<br>LYAQpgsEVQLVESGGGLVQPGGSLRLSCAASGFTFSSYTLAWVRQAPGKGLE<br>WVAAIDSSSYTYSPDTVRGRFTISRDNAKNSLYLQMNSLRAEDTAVYYCARD<br>SNWDALDYWGQGTTVTVSSGGGGSGGGGSGGGGSDIQMTQSPSSLSASVGDR<br>VTITCKAREKLWSAVAWYQQKPGKcPKALIYSASFRYSGVPSRFSGSGSTDF<br>TLTISSLQPEDFATYYCQQYTYPYTFGGGTKVEIK** |
| 313 | ACP394<br>(WW0536) | aptssstkktqlqlehllldlqmilnginnyknpkltrmltfkfympkkatelkhlqcleeelkpleevinlaqsknfhlrpr<br>dlisninvivlelkgsettfmceyadetativeflnrwitfcqsiistltsggpGPAGLYAQpgsggggsggggsggg<br>gsggggsggggsggggselcdddppeiphatfkamaykegtmlnceckrgfrriksgslymlctgnsshsswdnqc<br>qctssatrnttkqvtpqpeeqkerkttemqspmqpvdqaslpghcrepppweneateriyhfvvgqmvyyqcvqgy<br>ralhrgpaesvckmthgktrwtqpqlictgemetsqfpgeekpqaspegrpesetsSlvtncifqiqtemaatmetsifttt<br>eyqsggpGPAGLYAQpgsEVQLVESGGGLVQPGNSLRLSCAASGFTFSKFGMSWV<br>RQAPGKGLEWVSSISGSGRDTLYAESVKGRFTISRDNAKTTLYLQMNSLRPED<br>TAVYYCTIGGSLSVSSQGTLVTVSSggggsggggsggggsggggsggggsggggssggpGPAG<br>LYAQpgsEVQLVESGGGLVQPGGSLRLSCAASGFTFSSYTLAWVRQAPGKcLE<br>WVAAIDSSSYTYSPDTVRGRFTISRDNAKNSLYLQMNSLRAEDTAVYYCARD<br>SNWDALDYWGQGTTVTVSSGGGGSGGGGSGGGGSDIQMTQSPSSLSASVGD<br>RVTITCKVTEKVWGNVAWYQQKPGKAPISLIYSPSLRKSGVPSRFSGSGSTD<br>FTLTISSLQPEDFATYYCQQYTYPYTFGcGTKVEIK** |
| 314 | ACP395<br>(WW0537) | aptssstkktqlqlehllldlqmilnginnyknpkltrmltfkfympkkatelkhlqcleeelkpleevinlaqsknfhlrpr<br>dlisninvivlelkgsettfmceyadetativeflnrwitfcqsiistltsggpGPAGLYAQpgsggggsggggsggg<br>gsggggsggggsggggselcdddppeiphatfkamaykegtmlnceckrgfrriksgslymlctgnsshsswdnqc<br>qctssatrnttkqvtpqpeeqkerkttemqspmqpvdqaslpghcrepppweneateriyhfvvgqmvyyqcvqgy<br>ralhrgpaesvckmthgktrwtqpqlictgemetsqfpgeekpqaspegrpesetsSlvtncifqiqtemaatmetsifttt<br>eyqsggpGPAGLYAQpgsEVQLVESGGGLVQPGNSLRLSCAASGFTFSKFGMSWV<br>RQAPGKGLEWVSSISGSGRDTLYAESVKGRFTISRDNAKTTLYLQMNSLRPED<br>TAVYYCTIGGSLSVSSQGTLVTVSSggggsggggsggggsggggsggggsggggssggpGPAG<br>LYAQpgsEVQLVESGGGLVQPGGSLRLSCAASGFTFSSYTLAWVRQAPGKGLE<br>WVAAIDSSSYTYSPDTVRGRFTISRDNAKNSLYLQMNSLRAEDTAVYYCARD<br>SNWDALDYWGcGTTVTVSSGGGGSGGGGSGGGGSDIQMTQSPSSLSASVGDR<br>VTITCKVTEKVWGNVAWYQQKPGKcPISLIYSPSLRKSGVPSRFSGSGSGTDFT<br>LTISSLQPEDFATYYCQQYTYPYTFGGGTKVEIK** |
| 315 | ACP396<br>(WW0538) | aptssstkktqlqlehllldlqmilnginnyknpkltrmltfkfympkkatelkhlqcleeelkpleevinlaqsknfhlrpr<br>dlisninvivlelkgsettfmceyadetativeflnrwitfcqsiistltsggpGPAGLYAQpgsggggsggggsggg<br>gsggggsggggsggggselcdddppeiphatfkamaykegtmlnceckrgfrriksgslymlctgnsshsswdnqc<br>qctssatrnttkqvtpqpeeqkerkttemqspmqpvdqaslpghcrepppweneateriyhfvvgqmvyyqcvqgy<br>ralhrgpaesvckmthgktrwtqpqlictgemetsqfpgeekpqaspegrpesetsSlytttclfqiqtemaatmetsifttt<br>eyqsggpGPAGLYAQpgsEVQLVESGGGLVQPGNSLRLSCAASGFTFSKFGMSWV<br>RQAPGKGLEWVSSISGSGRDTLYAESVKGRFTISRDNAKTTLYLQMNSLRPED<br>TAVYYCTIGGSLSVSSQGTLVTVSSggggsggggsggggsggggsggggsggggssggpGPAG<br>LYAQpgsevqllesggglvqpggslrlscaasgsifsanamgwyrqapgkqrelvavissggstnyadsvkgrftisr<br>dnskntvylqmnslraedtavyycmysgsyyytpndywgqgtivtvss** |
| 316 | ACP397<br>(WW0539) | aptssstkktqlqlehllldlqmilnginnyknpkltrmltfkfympkkatelkhlqcleeelkpleevinlaqsknfhlrpr<br>dlisninvivlelkgsettfmceyadetativeflnrwitfcqsiistltsggpGPAGLYAQpgsggggsggggsggg<br>gsggggsggggsggggselcdddppeiphatfkamaykegtmlnceckrgfrriksgslymlctgnsshsswdnqc<br>qctssatrnttkqvtpqpeeqkerkttemqspmqpvdqaslpghcrepppweneateriyhfvvgqmvyyqcvqgy<br>ralhrgpaesvckmthgktrwtqpqlictgemetsqfpgeekpqaspegrpesetsSlytttclfqiqtemaatmetsifttt<br>eyqsggpGPAGLYAQpgsEVQLVESGGGLVQPGNSLRLSCAASGFTFSKFGMSWV<br>RQAPGKGLEWVSSISGSGRDTLYAESVKGRFTISRDNAKTTLYLQMNSLRPED<br>TAVYYCTIGGSLSVSSQGTLVTVSSggggsggggsggggsggggsggggsggggssggpGPAG<br>LYAQpgsevqllesggglvqpggslrlscaasgsifsanamgwyrqapgkglelvavissggstnyadsvkgrftisr<br>dnskntvylqmnslraedtavyycmysgsyyytpndywgqgtivtvss** |
| 317 | ACP398<br>(WW0540) | aptssstkktqlqlehllldlqmilnginnyknpkltrmltfkfympkkatelkhlqcleeelkpleevinlaqsknfhlrpr<br>dlisninvivlelkgsettfmceyadetativeflnrwitfcqsiistltsggpGPAGLYAQpgsggggsggggsggg<br>gsggggsggggsggggselcdddppeiphatfkamaykegtmlnceckrgfrriksgslymlctgnsshsswdnqc<br>qctssatrnttkqvtpqpeeqkerkttemqspmqpvdqaslpghcrepppweneateriyhfvvgqmvyyqcvqgy |

Sequence Table

| SEQ ID NO. | Name | Sequence |
|---|---|---|
| | | ralhrgpaesvckmthgktrwtqpqlictgemetsqfpgeekpqaspegrpesetsSlytttclfqiqtemaatmetsifttt eyqsggpGPAGLYAQpgsEVQLVESGGGLVQPGNSLRLSCAASGFTFSKFGMSWV RQAPGKGLEWVSSISGSGRDTLYAESVKGRFTISRDNAKTTLYLQMNSLRPED TAVYYCTIGGSLSVSSQGTLVTVSSggggsggggsggggsggggsggggsggggsggggssggpGPAG LYAQpgsEVQLVESGGGLVQPGGSLRLSCAASGFTFSSYTLAWVRQAPGKGLE WVAAIDSSSYTYSPDTVRGRFTISRDNAKNSLYLQMNSLRAEDTAVYYCARD SNWDALDYWGQGTTVTVSSastkgpsvfplapssksstsggtaalgclvkdyfpepvtvswnsgaltsgv htfpavlqssglyslssvvtvpssslgtqtyicnvnhkpsntkvdkrvepksc** |
| 318 | ACP399 | EVQLVESGGGLVQPGGSLRLSCAASGFTFSSYTLAWVRQAPGKcLEWVAAIDS SSYTYSPDTVRGRFTISRDNAKNSLYLQMNSLRAEDTAVYYCARDSNWDALD YWGQGTTVTVSSGGGGSGGGGSGGGGSDIQMTQSPSSLSASVGDRVTITCKA REKLWSAVAWYQQKPGKAPKsLIYSASFRYSGVPSRFSGSGSGTDFTLTISSLQ PEDFATYYCQQYYTYPYTFGcGTKVEIKsggpGPAGLYAQpgsggggsggggsggggsg gggsggggsggggsEVQLVESGGGLVQPGNSLRLSCAASGFTFSKFGMSWVRQAPG KGLEWVSSISGSGRDTLYAESVKGRFTISRDNAKTTLYLQMNSLRPEDTAVYY CTIGGSLSVSSQGTLVTVSSsggpGPAGLYAQpgsfficlympkkatelkhlqcleeelkpleevinl aqsknfhlrprdlisninvivlelkgsetlfmceyadetativeflnrwitfcqsiistltGGssstldctqlqle hllldlqmilnginnyknpkltrmlsggpGPAGLYAQpgsEVQLVESGGGLVQPGNSLRLSCAASGFTFS KFGMSWVRQAPGKGLEWVSSISGSGRDTLYAESVKGRFTISRDNAKTTLYLQ MNSLRPEDTAVYYCTIGGSLSVSSQGTLVTVSS** |
| 319 | ACP400 | EVQLVESGGGLVQPGGSLRLSCAASGFTFSSYTLAWVRQAPGKGLEWVAAID SSSYTYSPDTVRGRFTISRDNAKNSLYLQMNSLRAEDTAVYYCARDSNWDAL DYWGcGTTVTVSSGGGGSGGGGSGGGGSDIQMTQSPSSLSASVGDRVTITCKA REKLWSAVAWYQQKPGKcPKALIYSASFRYSGVPSRFSGSGSGTDFTLTISSLQ PEDFATYYCQQYYTYPYTFGGGTKVEIKsggpGPAGLYAQpgsggggsggggsggggsg gggsggggsggggsEVQLVESGGGLVQPGNSLRLSCAASGFTFSKFGMSWVRQAPG KGLEWVSSISGSGRDTLYAESVKGRFTISRDNAKTTLYLQMNSLRPEDTAVYY CTIGGSLSVSSQGTLVTVSSsggpGPAGLYAQpgsfficlympkkatelkhlqcleeelkpleevinl aqsknfhlrprdlisninvivlelkgsetlfmceyadetativeflnrwitfcqsiistltGGssstldctqlq lehllldlqmilnginnyknpkltrmlsggpGPAGLYAQpgsEVQLVESGGGLVQPGNSLRLSCAASGFTFS KFGMSWVRQAPGKGLEWVSSISGSGRDTLYAESVKGRFTISRDNAKTTLYLQ MNSLRPEDTAVYYCTIGGSLSVSSQGTLVTVSS** |
| 320 | ACP401 | EVQLVESGGGLVQPGGSLRLSCAASGFTFSSYTLAWVRQAPGKcLEWVAAIDS SSYTYSPDTVRGRFTISRDNAKNSLYLQMNSLRAEDTAVYYCARDSNWDALD YWGQGTTVTVSSGGGGSGGGGSGGGGSDIQMTQSPSSLSASVGDRVTITCKV TEKVWGNVAWYQQKPGKAPISLIYSPSLRKSGVPSRFSGSGSGTDFTLTISSLQ PEDFATYYCQQYYTYPYTFGcGTKVEIKsggpGPAGLYAQpgsggggsggggsggggsg gggsggggsggggsEVQLVESGGGLVQPGNSLRLSCAASGFTFSKFGMSWVRQAPG KGLEWVSSISGSGRDTLYAESVKGRFTISRDNAKTTLYLQMNSLRPEDTAVYY CTIGGSLSVSSQGTLVTVSSsggpGPAGLYAQpgsdklympkkatelkhlqcleeelkpleevinl aqsknfhlrprdlisninvivlelkgsetifmceyadetativeflnrwitfcqsiistltGGssstkktqlqlehll ldlqmilnginnyknpkltrmlsggpGPAGLYAQpgsEVQLVESGGGLVQPGNSLRLSCAASGFTFS KFGMSWVRQAPGKGLEWVSSISGSGRDTLYAESVKGRFTISRDNAKTTLYLQ MNSLRPEDTAVYYCTIGGSLSVSSQGTLVTVSS** |
| 321 | ACP402 | EVQLVESGGGLVQPGGSLRLSCAASGFTFSSYTLAWVRQAPGKGLEWVAAID SSSYTYSPDTVRGRFTISRDNAKNSLYLQMNSLRAEDTAVYYCARDSNWDAL DYWGcGTTVTVSSGGGGSGGGGSGGGGSDIQMTQSPSSLSASVGDRVTITCKV TEKVWGNVAWYQQKPGKcPISLIYSPSLRKSGVPSRFSGSGSGTDFTLTISSLQP EDFATYYCQQYYTYPYTFGGGTKVEIKsggpGPAGLYAQpgsggggsggggsggggsgg ggsggggsggggsEVQLVESGGGLVQPGNSLRLSCAASGFTFSKFGMSWVRQAPGK GLEWVSSISGSGRDTLYAESVKGRFTISRDNAKTTLYLQMNSLRPEDTAVYYC TIGGSLSVSSQGTLVTVSSsggpGPAGLYAQpgstfklympkkatelkhlqcleeelkpleevinla qsknfldrprdlisninvivlelkgsellfmceyadetativeflnrwitfcqsiistltGGssstkktqlqlehlll dlqmilnginnyknpkltrmlsggpGPAGLYAQpgsEVQLVESGGGLVQPGNSLRLSCAASGFTFS KFGMSWVRQAPGKGLEWVSSISGSGRDTLYAESVKGRFTISRDNAKTTLYLQ MNSLRPEDTAVYYCTIGGSLSVSSQGTLVTVSS** |
| 322 | ACP403 | evqllesggglvqpggslrlscaasgsifsanamgwyrqapgkqrelvavissggstnyadsvkgrftisrdnskntvyl qmnslraedtavyycmysgsyyytpndywgqgtivtvsssggpGPAGLYAQpgsggggsggggsggggsg gggsggggsggggsEVQLVESGGGLVQPGNSLRLSCAASGFTFSKFGMSWVRQAPG KGLEWVSSISGSGRDTLYAESVKGRFTISRDNAKTTLYLQMNSLRPEDTAVYY CTIGGSLSVSSQGTLVTVSSsggpGPAGLYAQpgsdklympkkatelkhlqcleeelkpleevinl aqsknfhlrprdlisninvivlelkgsetifmceyadetativeflnrwideqsiistltGGssstkktqlqlehllldlqmiln ginnyknpkltrmlsggpGPAGLYAQpgsEVQLVESGGGLVQPGNSLRLSCAASGFTFS KFGMSWVRQAPGKGLEWVSSISGSGRDTLYAESVKGRFTISRDNAKTTLYLQ MNSLRPEDTAVYYCTIGGSLSVSSQGTLVTVSS** |
| 323 | ACP404 | evqllesggglvqpggslrlscaasgsifsanamgwyrqapgkglelvavissggstnyadsvkgrftisrdnskntvyl qmnslraedtavyycmysgsyyytpndywgqgtivtvsssggpGPAGLYAQpgsggggsggggsggggsg |

Sequence Table

| SEQ ID NO. | Name | Sequence |
|---|---|---|
| | | gggsggggsggggsEVQLVESGGGLVQPGNSLRLSCAASGFTFSKFGMSWVRQAPG<br>KGLEWVSSISGSGRDTLYAESVKGRFTISRDNAKTTLYLQMNSLRPEDTAVYY<br>CTIGGSLSVSSQGTLVTVSSsggpGPAGLYAQpgsdklympkkatelkhlqcleeelkpleevinl<br>aqsknfhlrprdlisninvivlelkgsetifmceyadetativeflnrwideqsiistltGGssstkktqlqlehlllldlqmiln<br>ginnyknpkltrmlsggpGPAGLYAQpgsEVQLVESGGGLVQPGNSLRLSCAASGFTFS<br>KFGMSWVRQAPGKGLEWVSSISGSGRDTLYAESVKGRFTISRDNAKTTLYLQ<br>MNSLRPEDTAVYYCTIGGSLSVSSQGTLVTVSS** |
| 324 | ACP405 | EVQLVESGGGLVQPGGSLRLSCAASGFTFSSYTLAWVRQAPGKGLEWVAAID<br>SSSYTYSPDTVRGRFTISRDNAKNSLYLQMNSLRAEDTAVYYCARDSNWDAL<br>DYWGQGTTVTVSSastkgpsvfplapsskstsggtaalgclvkdyfpepvtvswnsgaltsgvhtfpavlqss<br>glyslssvvtvpssslgtqtyicnvnhkpsntkvdkrvepkscsggpGPAGLYAQpgsggggsggggsggggs<br>ggggsggggsggggsEVQLVESGGGLVQPGNSLRLSCAASGFTFSKFGMSWVRQAP<br>GKGLEWVSSISGSGRDTLYAESVKGRFTISRDNAKTTLYLQMNSLRPEDTAVY<br>YCTIGGSLSVSSQGTLVTVSSsggpGPAGLYAQpgstildympkkatelkhlqcleeelkpleevl<br>nlaqsknfhlrprdlisninvivlelkgsettfmceyadetativeflnrwitfcqsiistltGGssstkktqlq<br>lehlllldlqmilnginnyknpkltrmlsggpGPAGLYAQpgsEVQLVESGGGLVQPGNSLRLSCAASGFTF<br>SKFGMSWVRQAPGKGLEWVSSISGSGRDTLYAESVKGRFTISRDNAKTTLYL<br>QMNSLRPEDTAVYYCTIGGSLSVSSQGTLVTVSS** |
| 325 | ACP406 (WW0548) | vprdcgckpcictypevssvfifppkpkdvltitltpkvtcvvdiskddpevqfswfvddvevhtaqtqpreeqfnstf<br>rsyselpimhqdwingkefkcrynsaafpapiektisktkgrpkapqvytipppkeqmakdkvsltcmitdffpeditv<br>ewqwngqpaenyknqtpimdtdgsyfyysklnvqksnweagniftcsvlheglhnhhteksIshspgksggpGP<br>AGLYAQpgsaptsssticktqlqlehlldlqmilnginnyknpkltrmifficfympkkatelkhlqcleeelkpleev<br>lnlaqsknfhlrprdlisninvivlelkgsettfmceyadetativeflnrwilfcqsiistltggggsggggsggggsggggs<br>ggggsggggssggpGPAGLYAQpgsEVQLVESGGGLVQPGGSLRLSCAASGFTFSSYT<br>LAWVRQAPGKGLEWVAAIDSSSYTYSPDTVRGRFTISRDNAKNSLYLQMNSL<br>RAEDTAVYYCARDSNWDALDYWGQGTTVTVSSastkgpsvfplapssksstsggtaalgclvk<br>dyfpepvtvswnsgaltsgvhdpavlqssglyslssvvtvpssslgtqtyicnvnhkpsnticvdlavepksc** |
| 326 | ACP407 (WW0549) | vprdcgckpcictypevssvfifppkpkdvltitltpkvtcvvdiskddpevqfswfvddvevhtaqtqpreeqfnsif<br>rsyselpimhqdwingkefkcrynsaafpapiektisktkgrpkapqvytipppkeqmakdkvsltcmitcapeditv<br>ewqwngqpaenyknqtpimdtdgsyfyysklnvqksnweagniftcsvlheglhnhhteksIshspgksggpGP<br>AGLYAQpgsaptsssticktqlqlehlldlqmilnginnyknpkltrmifficfympkkatelkhlqcleeelkpleev<br>lnlaqsknfhlrprdlisninvivlelkgsettfmceyadetativeflnrwilfcqsiistltggggsggggsggggsggggs<br>ggggsggggssggpGPAGLYAQpgsEVQLVESGGGLVQPGGSLRLSCAASGFTFSSYT<br>LAWVRQAPGKcLEWVAAIDSSSYTYSPDTVRGRFTISRDNAKNSLYLQMNSLR<br>AEDTAVYYCARDSNWDALDYWGQGTTVTVSSGGGGSGGGGSGGGGSDIQM<br>TQSPSSLSASVGDRVTITCKAREKLWSAVAWYQQKPGKAPKALIYSASFRYSG<br>VPSRFSGSGSGTDFTLTISSLQPEDFATYYCQQYYTYPYTFGcGTKVEIK** |
| 327 | ACP408 (WW0550) | vprdcgckpcictypevssvfifppkpkdvltitltpkvtcvvdiskddpevqfswfvddvevhtaqtqpreeqfnsif<br>rsyselpimhqdwingkefkcrynsaafpapiektisktkgrpkapqvytipppkeqmakdkvsltcmitcapeditv<br>ewqwngqpaenyknqtpimdtdgsyfyysklnvqksnweagniftcsvlheglhnhhteksIshspgksggpGP<br>AGLYAQpgsaptsssticktqlqlehlldlqmilnginnyknpkltrmifficfympkkatelkhlqcleeelkpleev<br>lnlaqsknfhlrprdlisninvivlelkgsettfmceyadetativeflnrwilfcqsiistltggggsggggsggggsggggs<br>ggggsggggssggpGPAGLYAQpgsEVQLVESGGGLVQPGGSLRLSCAASGFTFSSYT<br>LAWVRQAPGKcLEWVAAIDSSSYTYSPDTVRGRFTISRDNAKNSLYLQMNSLR<br>AEDTAVYYCARDSNWDALDYWGQGTTVTVSSGGGGSGGGGSGGGGSDIQM<br>TQSPSSLSASVGDRVTITCKAREKLWSAVAWYQQKPGKAPKsLIYSASFRYSG<br>VPSRFSGSGSGTDFTLTISSLQPEDFATYYCQQYYTYPYTFGcGTKVEIK** |
| 328 | ACP409 (WW0551) | vprdcgckpcictypevssvfifppkpkdvltitltpkvtcvvdiskddpevqfswfvddvevhtaqtqpreeqfnsif<br>rsyselpimhqdwingkefkcrynsaafpapiektisktkgrpkapqvytipppkeqmakdkvsltcmitcapeditv<br>ewqwngqpaenyknqtpimdtdgsyfyysklnvqksnweagniftcsvlheglhnhhteksIshspgksggpGP<br>AGLYAQpgsaptsssticktqlqlehlldlqmilnginnyknpkltrmifficfympkkatelkhlqcleeelkpleev<br>lnlaqsknfhlrprdlisninvivlelkgsettfmceyadetativeflnrwilfcqsiistltggggsggggsggggsggggs<br>ggggsggggssggpGPAGLYAQpgsEVQLVESGGGLVQPGGSLRLSCAASGFTFSSYT<br>LAWVRQAPGKGLEWVAAIDSSSYTYSPDTVRGRFTISRDNAKNSLYLQMNSL<br>RAEDTAVYYCARDSNWDALDYWGcGTTVTVSSGGGGSGGGGSGGGGSDIQ<br>MTQSPSSLSASVGDRVTITCKAREKLWSAVAWYQQKPGKcPKALIYSASFRYS<br>GVPSRFSGSGSGTDFTLTISSLQPEDFATYYCQQYYTYPYTFGGGTKVEIK** |
| 329 | ACP410 (WW0552) | vprdcgckpcictypevssvfifppkpkdvltitltpkvtcvvdiskddpevqfswfvddvevhtaqtqpreeqfnsif<br>rsyselpimhqdwingkefkcrynsaafpapiektisktkgrpkapqvytipppkeqmakdkvsltcmitcapeditv<br>ewqwngqpaenyknqtpimdtdgsyfyysklnvqksnweagniftcsvlheglhnhhteksIshspgksggpGP<br>AGLYAQpgsaptsssticktqlqlehlldlqmilnginnyknpkltrmifficfympkkatelkhlqcleeelkpleev<br>lnlaqsknfhlrprdlisninvivlelkgsettfmceyadetativeflnrwilfcqsiistltggggsggggsggggsggggs<br>ggggsggggssggpGPAGLYAQpgsEVQLVESGGGLVQPGGSLRLSCAASGFTFSSYT<br>LAWVRQAPGKcLEWVAAIDSSSYTYSPDTVRGRFTISRDNAKNSLYLQMNSLR<br>AEDTAVYYCARDSNWDALDYWGQGTTVTVSSGGGGSGGGGSGGGGSDIQM<br>TQSPSSLSASVGDRVTITCKVTEKVWGNVAWYQQKPGKAPISLIYSPSLRKSG<br>VPSRFSGSGSGTDFTLTISSLQPEDFATYYCQQYYTYPYTFGcGTKVEIK** |

| SEQ ID NO. | Name | Sequence |
|---|---|---|
| 330 | ACP411 (WW0553) | vprdcgckpcictypevssvfifppkpkdvltitltpkvtcwvdiskddpevqfswfvddvevhtaqtqpreeqfnsif rsyselpimhqdwingkefkcrynsaafpapiektisktkgrpkapqvytippppkeqmakdkvsltcmitcapeditv ewqwngqpaenyknqpimdtdgsyfyysklnvqksnweagniftcsvlheglhnhhteksIshspgksggpGP AGLYAQpgsaptssssticktqlqlehllldlqmilnginnyknpkltrmifficfympkkatelkhlqcleeelkpleev lnlaqsknfhlrprdlisninvivlelkgsettfmceyadetativeflnrwilfcqsiistltggggsggggsggggsggggs ggggsggggssggpGPAGLYAQpgsEVQLVESGGGLVQPGGSLRLSCAASGFTFSSYT LAWVRQAPGKGLEWVAAIDSSSYTYSPDTVRGRFTISRDNAKNSLYLQMNSL RAEDTAVYYCARDSNWDALDYWGcGTTVTVSSGGGGSGGGGSGGGGSDIQ MTQSPSSLSASVGDRVTITCKVTEKVWGNVAWYQQKPGKcPISLIYSPSLRKS GVPSRFSGSGSGTDFTLTISSLQPEDFATYYCQQYYTYPYTFGGGTKVEIK** |
| 331 | ACP412 (WW0554) | vprdcgckpcictypevssvfifppkpkdvltitltpkvtcwvdiskddpevqfswfvddvevhtaqtqpreeqfnstf rsyselpimhqdwhigkefkcrynsaafpapiektisktkgrpkapqvytippppkeqmakdkvsltcmitclffpeditv ewqwngqpaenyknqpimdtdgsyfvysklnvqksnweagntftcsvlheglhnhhteksIshspgksggpGP AGLYAQpgsaptssssticktqlqlehllldlqmilnginnyknpkltrmlafympkkatelkhlqcleeelkpleev lnlaqsknfhlrprdlisninvivlelkgsettfmceyadetativeflnrwitfcqsiistltggggsggggsggggsggggs ggggsggggssggpGPAGLYAQpgsevqllesgggIvqpggslrlscaasgsifsanamgwyrqapgkqrelv avissggstnyadsvkgrftisrdnskntvylqmnslraedtavyycmysgsyyytpndywgqgtivtvss** |
| 332 | ACP413 (WW0555) | elcdddppeiphafficamaykegtmlnceckrgfrriksgslymlctgnsshsswdnqcqctssatrnttkqvtpqpee qkerkttemqspmqpvdqaslpghcrepppweneateriyhfvvgqmvyyqcvqgyralhrgpaesvckmthgk trwtqpqlictgemetsqfpgeekpqaspegrpesetsSlvtttclfqiqtemaatmetsiffteyqggggsggggsgggg sggggsggggsggggsDIQMTQSPSSLSASVGDRVTITCKAREKLWSAVAWYQQKPG KAPKsLIYSASFRYSGVPSRFSGSGSGTDFTLTISSLQPEDFATYYCQQYYTYPY TFGGGTKVEIKrtvaapsvfifppsdeqlksgtasvvcllnnfypreakvqwkvdnalqsgnsqesvteqdskd styslssstifiskadyekhkvyacevthqglsspvtksfnrgec** |
| 333 | ACP414 (WW0556) | elcdddppeiphatfkamaykegtmlnceckrgfrriksgslymlctgnsshsswdnqcqctssatrnttkqvtpqpee qkerkttemqspmqpvdqaslpghcrepppweneateriyhfvvgqmvyyqcvqgyralhrgpaesvckmthgk trwtqpqlictgemetsqfpgeekpqaspegrpesetsSlvtttclfqiqtemaatmetsiffteyqggggsggggsgggg sggggsggggsggggsDIQMTQSPSSLSASVGDRVTITCKVTEKVWGNVAWYQQKP GKAPISLIYSPSLRKSGVPSRFSGSGSGTDFTLTISSLQPEDFATYYCQQYYTYP YTFGGGTKVEIKrtvaapsvfifppsdeqlksgtasvvcllnaypreakvqwkvdnalqsgnsqesvteqds kdstyslssstltlskadyekhkvyacevthqglsspvtksfnrgec** |
| 334 | ACP415 (WW0557) | aptssssticktqlqlehllldlqmilnginnyknpkltrmltfkfympkkatelkhlqcleeelkpleevinlaqsknfhlrpr dlisninvivlelkgsettfmceyadetativeflnrwitfcqsiistltsggpGPAGLYAQpgsggggsggggsggg gsggggsggggsggggsEVQLVESGGGLVQPGGSLRLSCAASGFTFSSYTLAWVRQA PGKcLEWVAAIDSSSYTYSPDTVRGRFTISRDNAKNSLYLQMNSLRAEDTAVY YCARDSNWDALDYWGQGTTVTVSSGGGGSGGGGSGGGGSDIQMTQSPSSLS ASVGDRVTITCKAREKLWSAVAWYQQKPGKAPKsLIYSASFRYSGVPSRFSGS GSGTDFTLTISSLQPEDFATYYCQQYYTYPYTFGcGTKVEIKggggsggggsggggsgg ggsggggsggggsggggsggggsggggselcdddppeiphatfkamaykegtmlnceckrgfrriksgslymlctg nsshsswdnqcqctssatrnttkqvtpqpeeqkerkttemqspmqpvdqaslpghcrepppweneateriyhfvvgq mvyyqcvqgyralhrgpaesvckmthgktrwtqpqlictgemetsqfpgeekpqaspegrpesetsSlvMdfqiqte maatmetsiffteyqsggpGPAGLYAQpgsEVQLVESGGGLVQPGNSLRLSCAASGFTFS KFGMSWVRQAPGKGLEWVSSISGSGRDTLYAESVKGRFTISRDNAKTTLYLQ MNSLRPEDTAVYYCTIGGSLSVSSQGTLVTVSS** |
| 335 | ACP416 (WW0558) | aptssssticktqlqlehllldlqmilnginnyknpkltrmltfkfympkkatelkhlqcleeelkpleevinlaqsknfhlrpr dlisninvivlelkgsettfmceyadetativeflnrwitfcqsiistltsggpGPAGLYAQpgsggggsggggsggg gsggggsggggsggggsEVQLVESGGGLVQPGGSLRLSCAASGFTFSSYTLAWVRQA PGKGLEWVAAIDSSSYTYSPDTVRGRFTISRDNAKNSLYLQMNSLRAEDTAVY YCARDSNWDALDYWGcGTTVTVSSGGGGSGGGGSGGGGSDIQMTQSPSSLSA SVGDRVTITCKAREKLWSAVAWYQQKPGKcPKALIYSASFRYSGVPSRFSGSG SGTDFTLTISSLQPEDFATYYCQQYYTYPYTFGGGTKVEIKggggsggggsggggsgggg ggggsggggsggggsggggsggggselcdddppeiphatfkamaykegtmlnceckrgfrriksgslymlctgns shsswdnqcqctssatrnttkqvtpqpeeqkerkttemqspmqpvdqaslpghcrepppweneateriyhfvvgqm vyyqcvqgyralhrgpaesvckmthgktrwtqpqlictgemetsqfpgeekpqaspegrpesetsSlvtttdfqiqtem aatmetsiffteyqsggpGPAGLYAQpgsEVQLVESGGGLVQPGNSLRLSCAASGFTFSK FGMSWVRQAPGKGLEWVSSISGSGRDTLYAESVKGRFTISRDNAKTTLYLQM NSLRPEDTAVYYCTIGGSLSVSSQGTLVTVSS** |
| 336 | ACP417 (WW0559) | aptssssticktqlqlehllldlqmilnginnyknpkltrmltfkfympkkatelkhlqcleeelkpleevinlaqsknfhlrpr dlisninvivlelkgsettfmceyadetativeflnrwitfcqsiistltsggpGPAGLYAQpgsggggsggggsggg gsggggsggggsggggsEVQLVESGGGLVQPGGSLRLSCAASGFTFSSYTLAWVRQA PGKcLEWVAAIDSSSYTYSPDTVRGRFTISRDNAKNSLYLQMNSLRAEDTAVY YCARDSNWDALDYWGQGTTVTVSSGGGGSGGGGSGGGGSDIQMTQSPSSLS ASVGDRVTITCKVTEKVWGNVAWYQQKPGKAPISLIYSPSLRKSGVPSRFSGS GSGTDFTLTISSLQPEDFATYYCQQYYTYPYTFGcGTKVEIKggggsggggsggggsggg ggsggggsggggsggggsggggsggggselcdddppeiphatfkamaykegtmlnceckrgfrriksgslymlctg nsshsswdnqcqctssatrnttkqvtpqpeeqkerkttemqspmqpvdqaslpghcrepppweneateriyhfvvgq |

| SEQ ID NO. | Name | Sequence |
|---|---|---|
| | | mvyyqcvqgyralhrgpaesvckmthgktrwtqpqlictgemetsqfpgeekpqaspegrpesetsSlvMdfqiqte maatmetsiftteyqsggpGPAGLYAQpgsEVQLVESGGGLVQPGNSLRLSCAASGFTFS KFGMSWVRQAPGKGLEWVSSISGSGRDTLYAESVKGRFTISRDNAKTTLYLQ MNSLRPEDTAVYYCTIGGSLSVSSQGTLVTVSS** |
| 337 | ACP418 (WW0560) | aptssstkktqlqlehllldlqmilnginnyknpkltrmltfkfympkkatelkhlqcleeelkpleevinlaqsknfhlrpr dlisninvivlelkgsettfmceyadetativeflnrwitfcqsiistltsggpGPAGLYAQpgsggggsggggsggg gsggggsggggsggggsEVQLVESGGGLVQPGGSLRLSCAASGFTFSSYTLAWVRQA PGKGLEWVAAIDSSSYTYSPDTVRGRFTISRDNAKNSLYLQMNSLRAEDTAVY YCARDSNWDALDYWGcGTTVTVSSGGGGSGGGGSGGGGSDIQMTQSPSSLSA SVGDRVTITCKVTEKVWGNVAWYQQKPGKcPISLIYSPSLRKSGVPSRFSGSGS GTDFTLTISSLQPEDFATYYCQQYYTYPYTFGGGTKVEIKggggsggggsggggsgggg sggggsggggsggggsggggsggggsggggselcdddppeiphatikamaykegtmlnceckrgfrriksgslymlctgnss hsswdnqcqctssatrntttkqvtpqpeeqkerkttemqspmqpvdqaslpghcrepppweneateriyhfvvgqmv yyyqcvqgyralhrgpaesvckmthgktrwtqpqlictgemetsqfpgeekpqaspegrpesetsSlvtddfqiqtema atmetsifteyqsggpGPAGLYAQpgsEVQLVESGGGLVQPGNSLRLSCAASGFTFSKF GMSWVRQAPGKGLEWVSSISGSGRDTLYAESVKGRFTISRDNAKTTLYLQMN SLRPEDTAVYYCTIGGSLSVSSQGTLVTVSS** |
| 338 | ACP419 (WW0561) | aptssstkktqlqlehllldlqmilnginnyknpkltrmltfkfympkkatelkhlqcleeelkpleevinlaqsknfhlrpr dlisninvivlelkgsettfmceyadetativeflnrwitfcqsiistltsggpGPAGLYAQpgsggggsggggsggg gsggggsggggsggggsevqllesggglvqpggslrlscaasgsifsanamgwyrqapgkqrelvavissggstnyad svkgrftisrdnskntvylqmnslraedtavyycmysgsyyytpndywgqgtivtvssggggsggggsggggsggg gsggggsggggsggggsggggsggggsggggselcdddppeiphatfkamaykegtmlnceckrgfrriksgslymlctgns shsswdnqcqctssatrntttkqvtpqpeeqkerkttemqspmqpvdqaslpghcrepppweneateriyhfvvgqm vyyqcvqgyralhrgpaesvckmthgktrwtqpqlictgemetsqfpgeekpqaspegrpesetsSlvtddfqiqtem aatmetsiftteyqsggpGPAGLYAQpgsEVQLVESGGGLVQPGNSLRLSCAASGFTFSK FGMSWVRQAPGKGLEWVSSISGSGRDTLYAESVKGRFTISRDNAKTTLYLQM NSLRPEDTAVYYCTIGGSLSVSSQGTLVTVSS** |
| 339 | ACP420 (WW0562) | aptssstkktqlqlehllldlqmilnginnyknpkltrmltfkfympkkatelkhlqcleeelkpleevinlaqsknfhlrpr dlisninvivlelkgsettfmceyadetativeflnrwitfcqsiistltsggpGPAGLYAQpgsggggsggggsggg gsggggsggggsggggsevqllesggglvqpggslrlscaasgsifsanamgwyrqapgkglelvavissggstnyad svkgrftisrdnskntvylqmnslraedtavyycmysgsyyytpndywgqgtivtvssggggsggggsggggsggg gsggggsggggsggggsggggsggggsggggselcdddppeiphatfkamaykegtmlnceckrgfrriksgslymlctgns shsswdnqcqctssatrntttkqvtpqpeeqkerkttemqspmqpvdqaslpghcrepppweneateriyhfvvgqm vyyqcvqgyralhrgpaesvckmthgktrwtqpqlictgemetsqfpgeekpqaspegrpesetsSlvtddfqiqtem aatmetsiftteyqsggpGPAGLYAQpgsEVQLVESGGGLVQPGNSLRLSCAASGFTFSK FGMSWVRQAPGKGLEWVSSISGSGRDTLYAESVKGRFTISRDNAKTTLYLQM NSLRPEDTAVYYCTIGGSLSVSSQGTLVTVSS** |
| 340 | ACP421 (WW0563) | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSsggpGPAGLYAQpgsEVQLVESGGGLVQPGGSLRLSCAASGFTFS SYTLAWVRQAPGKcLEWVAAIDSSSYTYSPDTVRGRFTISRDNAKNSLYLQM NSLRAEDTAVYYCARDSNWDALDYWGQGTTVTVSSGGGGSGGGGSGGGGS DIQMTQSPSSLSASVGDRVTITCKAREKLWSAVAWYQQKPGKAPKsLIYSASF RYSGVPSRFSGSGSGTDFTLTISSLQPEDFATYYCQQYYTYPYTFGcGTKVEIKg gggsggggsggggsggggsggggsggggsggggsggggselcdddppeiphatfkamaykegtmlncec krgfrriksgslymlctgnsshsswdnqcqctssatrntttkqvtpqpeeqkerkttemqspmqpvdqaslpghcrepp pweneateriyhfvvgqmvyyqcvqgyralhrgpaesvckmthgktrwtqpqlictgemetsqfpgeekpqaspeg rpesetsSlvtddfqiqtemaatmetsifteyqggggsggggsggggsggggsggggsggggssgpGPAGLY AQpgsaptssstkktqlqlehllldlqmilnginnyknpkltrmlafympkkatelkhlqcleeelkpleevinlaqsk nfhlrprdlisninvivlelkgsettfmceyadetativeflnrwitieqsiistlt** |
| 341 | ACP422 (WW0564) | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSsggpGPAGLYAQpgsEVQLVESGGGLVQPGGSLRLSCAASGFTFS SYTLAWVRQAPGKGLEWVAAIDSSSYTYSPDTVRGRFTISRDNAKNSLYLQM NSLRAEDTAVYYCARDSNWDALDYWGcGTTVTVSSGGGGSGGGGSGGGGSD IQMTQSPSSLSASVGDRVTITCKAREKLWSAVAWYQQKPGKcPKALIYSASFR YSGVPSRFSGSGSGTDFTLTISSLQPEDFATYYCQQYYTYPYTFGGGTKVEIKgg ggsggggsggggsggggsggggsggggsggggsggggselcdddppeiphatfkamaykegtmlnceck rgfrriksgslymlctgnsshsswdnqcqctssatrntttkqvtpqpeeqkerkttemqspmqpvdqaslpghcreppp weneateriyhfvvgqmvyyqcvqgyralhrgpaesvckmthgktrwtqpqlictgemetsqfpgeekpqaspegr pesetsSlyttclfqiqtemaatmetsifteyqggggsggggsggggsggggsggggsggggssgpGPAGLYA Qpgsaptssstkktqlqlehllldlqmilnginnyknpkltrmlfficfympkkatelkhlqcleeelkpleevinlaqsknf hlrprdlisninvivlelkgsetlfmceyadetativeflnrwitfcqsiistlt** |
| 342 | ACP423 (WW0565) | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSsggpGPAGLYAQpgsEVQLVESGGGLVQPGGSLRLSCAASGFTFS SYTLAWVRQAPGKcLEWVAAIDSSSYTYSPDTVRGRFTISRDNAKNSLYLQM |

Sequence Table

| SEQ ID NO. | Name | Sequence |
|---|---|---|
| | | NSLRAEDTAVYYCARDSNWDALDYWGQGTTVTVSSGGGGSGGGGSGGGGS<br>DIQMTQSPSSLSASVGDRVTITCKVTEKVWGNVAWYQQKPGKAPISLIYSPSL<br>RKSGVPSRFSGSGSGTDFTLTISSLQPEDFATYYCQQYYTYPYTFGcGTKVEIKg<br>gggsggggsggggsggggsggggsggggsggggsggggsggggsggggsselcdddppeiphatfkamaykegtmlncec<br>krgfrriksgslymktgnsshsswdnqcqctssatrntttkqvtpqpeeqkerkttemqspmqpvdqaslpghcrepp<br>pweneateriyhfvvgqmvyyqcvqgyralhrgpaesvckmthgktrwtqpqlictgemetsqfpgeekpqaspeg<br>rpesetsSlvMdfqiqtemaatmetsifttteyqgggsggggsggggsggggsggggsggggsggggssggpPAGLY<br>AQpgsaptssstkktqlqlehllldlqmilnginnyknpkltrmltfkfympkkatelkhlqcleeelkpleevinlaqsk<br>nfhlrprdlisninivlvelkgsetlfmceyadetativeflnrwitfcqsiistlt** |
| 343 | ACP424<br>(WW0566) | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsEVQLVESGGGLVQPGGSLRLSCAASGFTFS<br>SYTLAWVRQAPGKGLEWVAAIDSSSYTYSPDTVRGRFTISRDNAKNSLYLQM<br>NSLRAEDTAVYYCARDSNWDALDYWGcGTTVTVSSGGGGSGGGGSGGGGSD<br>IQMTQSPSSLSASVGDRVTITCKVTEKVWGNVAWYQQKPGKcPISLIYSPSLRK<br>SGVPSRFSGSGSGTDFTLTISSLQPEDFATYYCQQYYTYPYTFGGGTKVEIKggg<br>gsggggsggggsggggsggggsggggsggggsggggsggggsselcdddppeiphatikamaykegtmlnceckr<br>gfrriksgslymktgnsshsswdnqcqctssatrntttkqvtpqpeeqkerkttemqspmqpvdqaslpghcrepppw<br>eneateriyhfvvgqmvyyqcvqgyralhrgpaesvckmthgktrwtqpqlictgemetsqfpgeekpqaspegrpe<br>setsSlytttclfqiqtemaatmetsifttteyqgggsggggsggggsggggsggggsggggsggggssggpGPAGLYAQ<br>pgsaptssstkktqlqlehllldlqmilnginnyknpkltrmltfklympldcatelkhlqcleeelkpleevinlaqsknfh<br>lrprdlisninivlvelkgsetlfmceyadetativeflnrwitfcqsiistlt** |
| 344 | ACP425<br>(WW0567) | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsevqllesgggglvqpggslrlscaasgsifsanamgwyrqapgkq<br>relvavissggstnyadsvkgrftisrdnskntvylqmnslraedtavyycmysgsyyytpndywgqgtivtvssggg<br>gsggggsggggsggggsggggsggggsggggsggggsggggsselcdddppeiphatikamaykegtmlnceckr<br>gfrriksgslymlctgnsshsswdnqcqctssatrntttkqvtpqpeeqkerkttemqspmqpvdqaslpghcrepppw<br>eneateriyhfvvgqmvyyqcvqgyralhrgpaesvckmthgktrwtqpqlictgemetsqfpgeekpqaspegrpe<br>setsSlytttclfqiqtemaatmetsifttteyqgggsggggsggggsggggsggggsggggsggggssggpGPAGLYAQ<br>pgsaptssstkktqlqlehllldlqmilnginnyknpkltrmltfklympldcatelkhlqcleeelkpleevinlaqsknfh<br>lrprdlisninivlvelkgsettfmceyadetativeflnrwitfcqsiistlt** |
| 345 | ACP426<br>(WW0568) | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsevqllesgggglvqpggslrlscaasgsifsanamgwyrqapgkg<br>lelvavissggstnyadsvkgrftisrdnskntvylqmnslraedtavyycmysgsyyytpndywgqgtivtvssgggg<br>sggggsggggsggggsggggsggggsggggsggggsggggsselcdddppeiphatfkamaykegtmlnceckrgf<br>rriksgslymlctgnsshsswdnqcqctssatrntttkqvtpqpeeqkerkttemqspmqpvdqaslpghcrepppwe<br>neateriyhfvvgqmvyyqcvqgyralhrgpaesvckmthgktrwtqpqlictgemetsqfpgeekpqaspegrpes<br>etsSlytttclfqiqtemaatmetsifttteyqgggsggggsggggsggggsggggsggggssggpGPAGLYAQp<br>gsaptssstkktqlqlehllldlqmilnginnyknpkltrmltfkfympkkatelkhlqcleeelkpleevinlaqsknfhlr<br>prdlisninivlvelkgsetlfmceyadetativeflnrwitfcqsiistlt** |
| 346 | ACP427<br>(WW0569) | aptssstkktqlqlehllldlqmilnginnyknpkltrmltfkfympkkatelkhlqcleeelkpleevinlaqsknfhlrpr<br>dlisninivlvelkgsettfmceyadetativeflnrwitfcqsiistltsggpGPAGLYAQpgsEVQLVESGG<br>GLVQPGNSLRLSCAASGFTFSKFGMSWVRQAPGKGLEWVSSISGSGRDTLYA<br>ESVKGRFTISRDNAKTTLYLQMNSLRPEDTAVYYCTIGGSLSVSSQGTLVTVSS<br>ggggsggggsggggsggggsggggsggggsggggssggpGPAGLYAQpgsEVQLVESGGGLVQPGGS<br>LRLSCAASGFTFSSYTLAWVRQAPGKcLEWVAAIDSSSYTYSPDTVRGRFTISR<br>DNAKNSLYLQMNSLRAEDTAVYYCARDSNWDALDYWGQGTTVTVSSGGGG<br>SGGGGSGGGGSDIQMTQSPSSLSASVGDRVTITCKAREKLWSAVAWYQQKPG<br>KAPKsLIYSASFRYSGVPSRFSGSGSGTDFTLTISSLQPEDFATYYCQQYYTYPY<br>TFGcGTKVEIKggggsggggsggggsggggsggggsggggsggggsevqllesgggglvqpggslrlscaasgsifsana<br>mgwyrqapgkqrelvavissggstnyadsvkgrftisrdnskntvylqmnslraedtavyycmysgsyyytpndyw<br>gqgtlvtvss** |
| 347 | ACP428<br>(WW0570) | aptssstkktqlqlehllldlqmilnginnyknpkltrmltfkfympkkatelkhlqcleeelkpleevinlaqsknfhlrpr<br>dlisninivlvelkgsettfmceyadetativeflnrwitfcqsiistltsggpGPAGLYAQpgsEVQLVESGG<br>GLVQPGNSLRLSCAASGFTFSKFGMSWVRQAPGKGLEWVSSISGSGRDTLYA<br>ESVKGRFTISRDNAKTTLYLQMNSLRPEDTAVYYCTIGGSLSVSSQGTLVTVSS<br>ggggsggggsggggsggggsggggsggggsggggssggpGPAGLYAQpgsEVQLVESGGGLVQPGGS<br>LRLSCAASGFTFSSYTLAWVRQAPGKGLEWVAAIDSSSYTYSPDTVRGRFTISR<br>DNAKNSLYLQMNSLRAEDTAVYYCARDSNWDALDYWGcGTTVTVSSGGGG<br>SGGGGSGGGGSDIQMTQSPSSLSASVGDRVTITCKAREKLWSAVAWYQQKPG<br>KcPKALIYSASFRYSGVPSRFSGSGSGTDFTLTISSLQPEDFATYYCQQYYTYPY<br>TFGGGTKVEIKggggsggggsggggsggggsggggsggggsggggsevqllesgggglvqpggslrlscaasgsifsan<br>amgwyrqapgkqrelvavissggstnyadsvkgrftisrdnskntvylqmnslraedtavyycmysgsyyytpndy<br>wgqgtlvtvss** |

Sequence Table

| SEQ ID NO. | Name | Sequence |
|---|---|---|
| 348 | ACP429 (WW0571) | aptssstkktqlqlehllldlqmilnginnyknpkltrmltfkfympkkatelkhlqcleeelkpleevinlaqsknfhlrpr dlisninvivlelkgsettfmceyadetativeflnrwitfcqsiistltsggpGPAGLYAQpgsEVQLVESGG GLVQPGNSLRLSCAASGFTFSKFGMSWVRQAPGKGLEWVSSISGSGRDTLYA ESVKGRFTISRDNAKTTLYLQMNSLRPEDTAVYYCTIGGSLSVSSQGTLVTVSS ggggsggggsggggsggggsggggsggggssggpGPAGLYAQpgsEVQLVESGGGLVQPGGS LRLSCAASGFTFSSYTLAWVRQAPGKcLEWVAAIDSSSYTYSPDTVRGRFTISR DNAKNSLYLQMNSLRAEDTAVYYCARDSNWDALDYWGQTTVTVSSGGGG SGGGGSGGGGSDIQMTQSPSSLSASVGDRVTITCKVTEKVWGNVAWYQQKP GKAPISLIYSPSLRKSGVPSRFSGSGSGTDFTLTISSLQPEDFATYYCQQYYTYP YTFGcGTKVEIKggggsggggsggggsggggsggggsggggsggggsevqllesggglvqpggslrlscaasgsifsa namgwyrqapgkqrelvavissggstnyadsvkgrftisrdnskntvylqmnslraedtavyycmysgsyyytpndy wgqgtlvtvss** |
| 349 | ACP430 (WW0572) | aptssstkktqlqlehllldlqmilnginnyknpkltrmltfkfympkkatelkhlqcleeelkpleevinlaqsknfhlrpr dlisninvivlelkgsettfmceyadetativeflnrwitfcqsiistltsggpGPAGLYAQpgsEVQLVESGG GLVQPGNSLRLSCAASGFTFSKFGMSWVRQAPGKGLEWVSSISGSGRDTLYA ESVKGRFTISRDNAKTTLYLQMNSLRPEDTAVYYCTIGGSLSVSSQGTLVTVSS ggggsggggsggggsggggsggggsggggssggpGPAGLYAQpgsEVQLVESGGGLVQPGGS LRLSCAASGFTFSSYTLAWVRQAPGKGLEWVAAIDSSSYTYSPDTVRGRFTISR DNAKNSLYLQMNSLRAEDTAVYYCARDSNWDALDYWGcGTTVTVSSGGGG SGGGGSGGGGSDIQMTQSPSSLSASVGDRVTITCKVTEKVWGNVAWYQQKP GKcPISLIYSPSLRKSGVPSRFSGSGSGTDFTLTISSLQPEDFATYYCQQYYTYPY TFGGGTKVEIKggggsggggsggggsggggsggggsggggsggggsevqllesggglvqpggslrlscaasgsifsan amgwyrqapgkqrelvavissggstnyadsvkgrftisrdnskntvylqmnslraedtavyycmysgsyyytpndy wgqgtlvtvss** |
| 350 | ACP431 (WW0573) | aptssstkktqlqlehllldlqmilnginnyknpkltrmltfkfympkkatelkhlqcleeelkpleevinlaqsknfhlrpr dlisninvivlelkgsettfmceyadetativeflnrwitfcqsiistltsggpGPAGLYAQpgsEVQLVESGG GLVQPGNSLRLSCAASGFTFSKFGMSWVRQAPGKGLEWVSSISGSGRDTLYA ESVKGRFTISRDNAKTTLYLQMNSLRPEDTAVYYCTIGGSLSVSSQGTLVTVSS ggggsggggsggggsggggsggggsggggssggpGPAGLYAQpgsEVQLVESGGGLVQPGGS LRLSCAASGFTFSSYTLAWVRQAPGKcLEWVAAIDSSSYTYSPDTVRGRFTISR DNAKNSLYLQMNSLRAEDTAVYYCARDSNWDALDYWGQTTVTVSSGGGG SGGGGSGGGGSDIQMTQSPSSLSASVGDRVTITCKAREKLWSAVAWYQQKPG KAPKsLIYSASFRYSGVPSRFSGSGSGTDFTLTISSLQPEDFATYYCQQYYTYPY TFGcGTKVEIKggggsggggsggggsggggsggggsggggsggggsevqllesggglvqpggslrlscaasgsifsana mgwyrqapgkglelvavissggstnyadsvkgrftisrdnskntvylqmnslraedtavyycmysgsyyytpndyw gqgtlvtvss** |
| 351 | ACP432 (WW0574) | aptssstkktqlqlehllldlqmilnginnyknpkltrmltfkfympkkatelkhlqcleeelkpleevinlaqsknfhlrpr dlisninvivlelkgsettfmceyadetativeflnrwitfcqsiistltsggpGPAGLYAQpgsEVQLVESGG GLVQPGNSLRLSCAASGFTFSKFGMSWVRQAPGKGLEWVSSISGSGRDTLYA ESVKGRFTISRDNAKTTLYLQMNSLRPEDTAVYYCTIGGSLSVSSQGTLVTVSS ggggsggggsggggsggggsggggsggggssggpGPAGLYAQpgsEVQLVESGGGLVQPGGS LRLSCAASGFTFSSYTLAWVRQAPGKGLEWVAAIDSSSYTYSPDTVRGRFTISR DNAKNSLYLQMNSLRAEDTAVYYCARDSNWDALDYWGcGTTVTVSSGGGG SGGGGSGGGGSDIQMTQSPSSLSASVGDRVTITCKAREKLWSAVAWYQQKPG KcPKALIYSASFRYSGVPSRFSGSGSGTDFTLTISSLQPEDFATYYCQQYYTYPY TFGGGTKVEIKggggsggggsggggsggggsggggsggggsggggsevqllesggglvqpggslrlscaasgsifsan amgwyrqapgkglelvavissggstnyadsvkgrftisrdnskntvylqmnslraedtavyycmysgsyyytpndy wgqgtivtvss** |
| 352 | ACP433 (WW0575) | aptssstkktqlqlehllldlqmilnginnyknpkltrmltfkfympkkatelkhlqcleeelkpleevinlaqsknfhlrpr dlisninvivlelkgsettfmceyadetativeflnrwitfcqsiistltsggpGPAGLYAQpgsEVQLVESGG GLVQPGNSLRLSCAASGFTFSKFGMSWVRQAPGKGLEWVSSISGSGRDTLYA ESVKGRFTISRDNAKTTLYLQMNSLRPEDTAVYYCTIGGSLSVSSQGTLVTVSS ggggsggggsggggsggggsggggsggggssggpGPAGLYAQpgsEVQLVESGGGLVQPGGS LRLSCAASGFTFSSYTLAWVRQAPGKcLEWVAAIDSSSYTYSPDTVRGRFTISR DNAKNSLYLQMNSLRAEDTAVYYCARDSNWDALDYWGQTTVTVSSGGGG SGGGGSGGGGSDIQMTQSPSSLSASVGDRVTITCKVTEKVWGNVAWYQQKP GKAPISLIYSPSLRKSGVPSRFSGSGSGTDFTLTISSLQPEDFATYYCQQYYTYP YTFGcGTKVEIKggggsggggsggggsggggsggggsggggsggggsevqllesggglvqpggslrlscaasgsifsa namgwyrqapgkglelvavissggstnyadsvkgrftisrdnskntvylqmnslraedtavyycmysgsyyytpndy wgqgtlvtvss** |
| 353 | ACP434 (WW0576) | aptssstkktqlqlehllldlqmilnginnyknpkltrmltfkfympkkatelkhlqcleeelkpleevinlaqsknfhlrpr dlisninvivlelkgsettfmceyadetativeflnrwitfcqsiistltsggpGPAGLYAQpgsEVQLVESGG GLVQPGNSLRLSCAASGFTFSKFGMSWVRQAPGKGLEWVSSISGSGRDTLYA ESVKGRFTISRDNAKTTLYLQMNSLRPEDTAVYYCTIGGSLSVSSQGTLVTVSS ggggsggggsggggsggggsggggsggggssggpGPAGLYAQpgsEVQLVESGGGLVQPGGS LRLSCAASGFTFSSYTLAWVRQAPGKGLEWVAAIDSSSYTYSPDTVRGRFTISR DNAKNSLYLQMNSLRAEDTAVYYCARDSNWDALDYWGcGTTVTVSSGGGG SGGGGSGGGGSDIQMTQSPSSLSASVGDRVTITCKVTEKVWGNVAWYQQKP |

| SEQ ID NO. | Name | Sequence |
|---|---|---|
| | | GKcPISLIYSPSLRKSGVPSRFSGSGSGTDFTLTISSLQPEDFATYYCQQYTYPY<br>TFGGGTKVEIKggggsggggsggggsggggsggggsggggsggggsevqllesgggglvqpggslrlscaasgsifsan<br>amgwyrqapgkglelvavissggstnyadsvkgrftisrdnskntvylqmnslraedtavyycmysgsyyytpndy<br>wgqgtlvtvss** |
| 265 | ACP435<br>(WW0577) | DIQMTQSPSSLSASVGDRVTITCKAREKLWSAVAWYQQKPGKAPKsLIYSASF<br>RYSGVPSRFSGSGSGTDFTLTISSLQPEDFATYYCQQYTYPYTFGGGTKVEIKr<br>tvaapsvfifppsdeqlksgtasvvellnaypreakvqwkvdnalqsgnsqesvteqdskdstyslsstltlskadyekh<br>kvyacevthqglsspvtksfmgecggggsggggsggggsggggsggggsggggsevqllesgggglvqpggslrlsca<br>asgsifsanamgwyrqapgkqrelvavissggstnyadsvkgrftisrdnskntvylqmnslraedtavyycmysgsy<br>yytpndywgqgtlvtvss** |
| 355 | ACP371<br>(WW0513) | aptssstkktqlqlehllldlqmilnginnyknpkltrmltfkfympkkatelkhlqcleeelkpleevinlaqsknfhlrpr<br>dlisninvivlelkgsettfmceyadetativeflnrwitfcqsiistltsggpPAGLYAQpgsEVQLVESGG<br>GLVQPGNSLRLSCAASGFTFSKFGMSWVRQAPGKGLEWVSSISGSGRDTLYA<br>ESVKGRFTISRDNAKTTLYLQMNSLRPEDTAVYYCTIGGSLSVSSQGTLVTVSS<br>ggggsggggsggggsggggsggggsggggssggpGPAGLYAQpgsEVQLVESGGGLVQPGGS<br>LRLSCAASGFTFSSYTLAWVRQAPGKcLEWVAAIDSSSYTYSPDTVRGRFTISR<br>DNAKNSLYLQMNSLRAEDTAVYYCARDSNWDALDYWGQGTTVTVSSGGGG<br>SGGGGSGGGGSDIQMTQSPSSLSASVGDRVTITCKASQNVGTNVGWYQQKPG<br>KAPKALIYSASFRYSGVPSRFSGSGSGTDFTLTISSLQPEDFATYYCQQYTYP<br>YTFGcGTKVEIK** |
| 356 | ACP372<br>(WW0514) | aptssstkktqlqlehllldlqmilnginnyknpkltrmltfkfympkkatelkhlqcleeelkpleevinlaqsknfhlrpr<br>dlisninvivlelkgsettfmceyadetativeflnrwitfcqsiistltsggpPAGLYAQpgsEVQLVESGG<br>GLVQPGNSLRLSCAASGFTFSKFGMSWVRQAPGKGLEWVSSISGSGRDTLYA<br>ESVKGRFTISRDNAKTTLYLQMNSLRPEDTAVYYCTIGGSLSVSSQGTLVTVSS<br>ggggsggggsggggsggggsggggsggggssggpGPAGLYAQpgsEVQLVESGGGLVQPGGS<br>LRLSCAASGFTFSSYTLAWVRQAPGKGLEWVAAIDSSSYTYSPDTVRGRFTISR<br>DNAKNSLYLQMNSLRAEDTAVYYCARDSNWDALDYWGcGTTVTVSSGGGG<br>SGGGGSGGGGSDIQMTQSPSSLSASVGDRVTITCKASQNVGTNVGWYQQKPG<br>KcPKALIYSASFRYSGVPSRFSGSGSGTDFTLTISSLQPEDFATYYCQQYTYPY<br>TFGGGTKVEIK** |
| 357 | ACP373<br>(WW0515) | aptssstkktqlqlehllldlqmilnginnyknpkltrmltfkfympkkatelkhlqcleeelkpleevinlaqsknfhlrpr<br>dlisninvivlelkgsettfmceyadetativeflnrwitfcqsiistltsggpPAGLYAQpgsEVQLVESGG<br>GLVQPGNSLRLSCAASGFTFSKFGMSWVRQAPGKGLEWVSSISGSGRDTLYA<br>ESVKGRFTISRDNAKTTLYLQMNSLRPEDTAVYYCTIGGSLSVSSQGTLVTVSS<br>ggggsggggsggggsggggsggggsggggssggpGPAGLYAQpgsEVQLVESGGGLVQPGGS<br>LRLSCAASGFTFSSYTLAWVRQAPGKcLEWVAAIDSSSYTYSPDTVRGRFTISR<br>DNAKNSLYLQMNSLRAEDTAVYYCARDSNWDALDYWGQGTTVTVSSGGGG<br>SGGGGSGGGGSDIQMTQSPSSLSASVGDRVTITCKAREKLWSAVAWYQQKPG<br>KAPKALIYSASFRYSGVPSRFSGSGSGTDFTLTISSLQPEDFATYYCQQYTYP<br>YTFGcGTKVEIK** |
| 358 | ACP374<br>(WW0516) | aptssstkktqlqlehllldlqmilnginnyknpkltrmltfkfympkkatelkhlqcleeelkpleevinlaqsknfhlrpr<br>dlisninvivlelkgsettfmceyadetativeflnrwitfcqsiistltsggpPAGLYAQpgsEVQLVESGG<br>GLVQPGNSLRLSCAASGFTFSKFGMSWVRQAPGKGLEWVSSISGSGRDTLYA<br>ESVKGRFTISRDNAKTTLYLQMNSLRPEDTAVYYCTIGGSLSVSSQGTLVTVSS<br>ggggsggggsggggsggggsggggsggggssggpGPAGLYAQpgsEVQLVESGGGLVQPGGS<br>LRLSCAASGFTFSSYTLAWVRQAPGKGLEWVAAIDSSSYTYSPDTVRGRFTISR<br>DNAKNSLYLQMNSLRAEDTAVYYCARDSNWDALDYWGcGTTVTVSSGGGG<br>SGGGGSGGGGSDIQMTQSPSSLSASVGDRVTITCKAREKLWSAVAWYQQKPG<br>KcPKALIYSASFRYSGVPSRFSGSGSGTDFTLTISSLQPEDFATYYCQQYTYPY<br>TFGGGTKVEIK** |
| 359 | ACP375<br>(WW0517) | aptssstkktqlqlehllldlqmilnginnyknpkltrmltfkfympkkatelkhlqcleeelkpleevinlaqsknfhlrpr<br>dlisninvivlelkgsettfmceyadetativeflnrwitfcqsiistltsggpPAGLYAQpgsEVQLVESGG<br>GLVQPGNSLRLSCAASGFTFSKFGMSWVRQAPGKGLEWVSSISGSGRDTLYA<br>ESVKGRFTISRDNAKTTLYLQMNSLRPEDTAVYYCTIGGSLSVSSQGTLVTVSS<br>ggggsggggsggggsggggsggggsggggssggpGPAGLYAQpgsEVQLVESGGGLVQPGGS<br>LRLSCAASGFTFSSYTLAWVRQAPGKcLEWVAAIDSSSYTYSPDTVRGRFTISR<br>DNAKNSLYLQMNSLRAEDTAVYYCARDSNWDALDYWGQGTTVTVSSGGGG<br>SGGGGSGGGGSDIQMTQSPSSLSASVGDRVTITCKVTEKVWGNVAWYQQKP<br>GKAPISLIYSPSLRKSGVPSRFSGSGSGTDFTLTISSLQPEDFATYYCQQYTYP<br>YTFGcGTKVEIK** |
| 360 | ACP376<br>(WW0521) | aptssstkktqlqlehllldlqmilnginnyknpkltrmltfkfympkkatelkhlqcleeelkpleevinlaqsknfhlrpr<br>dlisninvivlelkgsettfmceyadetativeflnrwitfcqsiistltsggpPAGLYAQpgsEVQLVESGG<br>GLVQPGNSLRLSCAASGFTFSKFGMSWVRQAPGKGLEWVSSISGSGRDTLYA<br>ESVKGRFTISRDNAKTTLYLQMNSLRPEDTAVYYCTIGGSLSVSSQGTLVTVSS<br>ggggsggggsggggsggggsggggsggggssggpGPAGLYAQpgsEVQLVESGGGLVQPGGS<br>LRLSCAASGFTFSSYTLAWVRQAPGKGLEWVAAIDSSSYTYSPDTVRGRFTISR |

Sequence Table

| SEQ ID NO. | Name | Sequence |
|---|---|---|
| | | DNAKNSLYLQMNSLRAEDTAVYYCARDSNWDALDYWGcGTTVTVSSGGGG SGGGGSGGGGSDIQMTQSPSSLSASVGDRVTITCKVTEKVWGNVAWYQQKP GKcPISLIYSPSLRKSGVPSRFSGSGSGTDFTLTISSLQPEDFATYYCQQYYTYPY TFGGGTKVEIK** |
| 361 | ACP377 (WW0519) | aptssstkktqlqlehllldlqmilnginnyknpkltrmltfkfympkkatelkhlqcleeelkpleevinlaqsknfhlrpr dlisninvivlelkgsettfmceyadetativeflnrwitfcqsiistltsggpGPAGLYAQpgsEVQLVESGG GLVQPGNSLRLSCAASGFTFSKFGMSWVRQAPGKGLEWVSSISGSGRDTLYA ESVKGRFTISRDNAKTTLYLQMNSLRPEDTAVYYCTIGGSLSVSSQGTLVTVSS ggggsggggsggggsggggsggggsggggssggpGPAGLYAQpgsevqllesggglvqpggslrlscaasgsi fsanamgwyrqapgkqrelvavissggstnyadsvkgrftisrdnskntvylqmnslraedtavyycmysgsyyytp ndywgqgtivtvss** |
| 362 | ACP378 (WW0520) | aptssstkktqlqlehllldlqmilnginnyknpkltrmltfkfympkkatelkhlqcleeelkpleevinlaqsknfhlrpr dlisninvivlelkgsettfmceyadetativeflnrwitfcqsiistltsggpGPAGLYAQpgsEVQLVESGG GLVQPGNSLRLSCAASGFTFSKFGMSWVRQAPGKGLEWVSSISGSGRDTLYA ESVKGRFTISRDNAKTTLYLQMNSLRPEDTAVYYCTIGGSLSVSSQGTLVTVSS ggggsggggsggggsggggsggggsggggssggpGPAGLYAQpgsEVQLVESGGGLVQPGGS LRLSCAASGFTFSSYTLAWVRQAPGKGLEWVAAIDSSSYTYSPDTVRGRFTISR DNAKNSLYLQMNSLRAEDTAVYYCARDSNWDALDYWGQGTTVTVSSastkgps vfplapssskstsggtaalgclvkdyfpepvtswnsgaltsgvhtfpavlqssglyslssvvtvpssslgtqtyicnvnhkp sntkvdkrvepksc** |
| 363 | ACP379 (WW0521) | eskygppcppcpapeflggpsvflfppkpkdtlmisrtpevtcvvvdvsqedpevqfnwyvdgvevhnaktkpree qfnstyrvvsyltvlhqdwingkeykckvsnkglpssiektiskakgqprepqvytlppsqeemtlmqvsltclvkgfy psdiavewesngqpennykttppvldsdgsfflysrltvdksrwqegnvfscsvmhealhnhytqkslslslgksggp GPAGLYAQpgsaptssstkktqlqlehllldlqmilnginnyknpkltrmlffficfympldcatelkhlqcleeelkpl eevinlaqsknfhlrprdlisninvivlelkgsetlfmceyadetativeflnrwitfcqsiistltggggsggggsggggsgg ggsggggsggggsggggssggpGPAGLYAQpgsEVQLVESGGGLVQPGGSLRLSCAASGFTFS SYTLAWVRQAPGKGLEWVAAIDSSSYTYSPDTVRGRFTISRDNAKNSLYLQM NSLRAEDTAVYYCARDSNWDALDYWGQGTTVTVSSastkgpsvfplapssskstsggtaal gclvkdyfpepvtswnsgaltsgvhtfpavlqssglyslssvvtvpssslgtqtyicnvnhkpsntkvdkrvepksc** |
| 364 | ACP368 (WW0446) | EVQLVESGGGLVQPGGSLRLSCAASGFTFSSYTLAWVRQAPGKGLEWVAAID SSSYTYSPDTVRGRFTISRDNAKNSLYLQMNSLRAEDTAVYYCARDSNWDAL DYWGQGTTVTVSSsggpGPAGLYAQpgsDIQMTQSPSSLSASVGDRVTITCKVTE KVWGNVAWYQQKPGKAPISLIYSPSLRKSGVPSRFSGSGSGTDFTLTISSLQPE DFATYYCQQYYTYPYTFGGGTKVEIKHHHHHH |
| 365 | ACP365 (WW0443) | EVQLVESGGGLVQPGGSLRLSCAASGFTFSSYTLAWVRQAPGKGLEWVAAID SSSYTYSPDTVRGRFTISRDNAKNSLYLQMNSLRAEDTAVYYCARDSNWDAL DYWGQGTTVTVSSsggpGPAGLYAQpgsDIQMTQSPSSLSASVGDRVTITCKARE KLWSAVAWYQQKPGKAPKALIYSASFRYSGVPSRFSGSGSGTDFTLTISSLQPE DFATYYCQQYYTYPYTFGGGTKVEIKHHHHHH |
| 366 | ACP366 (WW0444) | EVQLVESGGGLVQPGGSLRLSCAASGFTFSSYTLAWVRQAPGKGLEWVAAID SSSYTYSPDTVRGRFTISRDNAKNSLYLQMNSLRAEDTAVYYCARDSNWDAL DYWGQGTTVTVSSsggpGPAGLYAQpgsDIQMTQSPSSLSASVGDRVTITCKARE KLWSAVAWYQQKPGKAPKsLIYSASFRYSGVPSRFSGSGSGTDFTLTISSLQPE DFATYYCQQYYTYPYTFGGGTKVEIKHHHHHH |
| 367 | ACP284 | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSSGGPGPAGMKGLPGSwipvsgparclsquallkttddmvktareklkhysctaedi dheditrdqtststlktclplelhknesclatretssttrgsclppqktslmmticlgsiyedlkmyqtefqainaalqnhnhqqi ildkgmlvaidelmqslahngetlrqkppvgeadpyrvkmklcillhafstrvvtinrvmgylssaSGGPGPAG MKGLPGSggggsggggsggggsggggsggggsggggsggggsQSVLTQPPSVSGAPGQRVTISCSGS RSNIGSNTVKWYQQLPGTAPKLLIYYNDQRPSGVPDRFSGSKSGTSASLAITGL QAEDEADYYCQSYDRYTHPALLFGTGTKVTVLggggsggggsggggsggggsQVQLVESGG GVVVQPGRSLRLSCAASGFTFSSYGMHWVRQAPGKGLEWVAFIRYDGSNKYY ADSVKGRFTISRDNSKNTLYLQMNSLRAEDTAVYYCKTHGSHDNWGQGTMV TVSS |
| 368 | ACP285 | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSSGGPGPAGMKGLPGSiwelkkdvyvveldwypdapgemvvltcdtpeedgitwtl dqssevlgsgktltiqvkefgdagqytchkggevlshsllllhkkedgiwstdilkdqkepknktflrcealmysgrftcw wittistdilfsvkssrgssdpqgvtcgaatlsaervrgdnkeyeysvecqedsaSpaaeeslpievmvdavhklkyeny tssffirdiikpdppknlqlkplknsrqvevsweypdtwstphsyfsltkvqvqgkskrekkdrvftdktsatvicrkna sisvramthyyssswsewasvpcsggggsggggsggggsrvipvsgparclsquallkttddmvktareklkhyscta edidheditrdqtststlktclplelhknesSlatretssttrgsclppqktslmmticlgsiyedllanyqtefqainaalqnhnh qqiildkgmlvaidelmqslahngetlrqkppvgeadpyrvkmklcillhafstrvvtinrvmgylssaSGGPGPA GMKGLPGSggggsggggsggggsggggsggggsggggsQSVLTQPPSVSGAPGQRVTISCS |

-continued

Sequence Table

| SEQ ID NO. | Name | Sequence |
|---|---|---|
| | | GSRSNIGSNTVKWYQQLPGTAPKLLIYYNDQRPSGVPDRFSGSKSGTSASLAIT<br>GLQAEDEADYYCQSYDRYTHPALLFGTGTKVTVLggggsggggsggggsQVQLVES<br>GGGVVQPGRSLRLSCAASGFTFSSYGMHWVRQAPGKGLEWVAFIRYDGSNK<br>YYADSVKGRFTISRDNSKNTLYLQMNSLRAEDTAVYYCKTHGSHDNWGQGT<br>MVTVSS |
| 369 | ACP286 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSSGGPGPAGMKGLPGSiwelkkdvyvveldwypdapgemvvltcdtpeedgitwtl<br>dqssevlgsgktltiqvkefgdagqytchkggevlshsllllhkkedgiwstdilkdqkepknktflrcealmysgrftcw<br>wittistdlifsvkssrgssdpqgvtcgaatlsaervrgdnkeyeysvecqedsacpaaeeslpievmvdavhklkyeny<br>tssffirdiikpdpppknlqlkplknsrqvevsweypdtwstphsyfsltfcvqvqgkskrekkdrvftdktsatvicrkna<br>sisvracichyyssswsewasvpcsggggsggggsggggsggggsrvipvsgparclsqsrffilkttddmvktareklk<br>hysctaediddheditrdqtstlktclplelhknesclatretssttrgsclppqktslmmticlgsiyedlkmyqtefclainaal<br>qnhnhqqiiildkgmlvaidelmqslnhngetlrqkppvgeadpyrvkmklcillhafstrvvtinrvmgylssaSGG<br>PGPAGMKGLPGSggggsggggsggggsggggsggggsQSVLTQPPSVSGAPGQRVT<br>ISCSGSRSNIGSNTVKWYQQLPGTAPKLLIYYNDQRPSGVPDRFSGSKSGTSAS<br>LAITGLQAEDEADYYCQSYDRYTHPALLFGTGTKVTVLggggsggggsggggsQVQ<br>LVESGGGVVQPGRSLRLSCAASGFTFSSYGMHWVRQAPGKGLEWVAFIRYDG<br>SNKYYADSVKGRFTISRDNSKNTLYLQMNSLRAEDTAVYYCKTHGSHDNWG<br>QGTMVTVSS |
| 370 | ACP287 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSSGGPGPAGMKGLPGSiwelkkdvyvveldwypdapgemvvltcdtpeedgitwtl<br>dqssevlgsgkiltiqvkefgdagqytchkggevlshsllllhkkedgiwstdilkdqkepknktflrcealmysgrftcw<br>wittistditfsvkssrgssdpqgvtcgaatlsaervrgdnkeyeysvecqedsacpaaeeslpievmvdavhklkyeny<br>tssffirdiikpdppknlqlkplknsrqvevsweypdtwstphsyfslffevqvqgkskrekkdrvftdktsatvicrkna<br>sisvracichyyssswsewasvpcsggggsggggsggggsggggsrvipvsgparclsqsmllkttddmvktareklkhysctA<br>ediddheditrdqtstlktclplelhknesclatretssttrgsclppqktslmmticlgsiyedlkmyqtefqainaalqnhnh<br>qqiiildkgmlvaidelmqslnhngetlrqkppvgeadpyrvkmklcillhafstrvvtinrvmgylssaSGGPGPA<br>GMKGLPGSggggsggggsggggsggggsggggsggggsQSVLTQPPSVSGAPGQRVTISCS<br>GSRSNIGSNTVKWYQQLPGTAPKLLIYYNDQRPSGVPDRFSGSKSGTSASLAIT<br>GLQAEDEADYYCQSYDRYTHPALLFGcGTKVTVLggggsggggsggggsQVQLVES<br>GGGVVQPGRSLRLSCAASGFTFSSYGMHWVRQAPGKcLEWVAFIRYDGSNKY<br>YADSVKGRFTISRDNSKNTLYLQMNSLRAEDTAVYYCKTHGSHDNWGQGTM<br>VTVSS |
| 371 | ACP288 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSSGGPGPAGMKGLPGSiwelkkdvyvveldwypdapgemvvltcdtpeedgitwtl<br>dqssevlgsgkiltiqvkefgdagqytchkggevlshsllllhkkedgiwstdilkdqkepknktflrcealmysgrftcw<br>wittistdlifsvkssrgssdpqgvtcgaatlsaervrgdnkeyeysvecqedsacpaaeeslpievmvdavhklkyeny<br>tssffirdiikpdppknlqlkplknsrqvevsweypdtwstphsyfsltfcvqvqgkskrekkdrvftdktsatvicrkna<br>sisvracichyyssswsewasvpcsggggsggggsggggsggggsrvipvsgparclsqsmllkttddmvktareklkhysctA<br>ediddheditrdqtstlktclplelhknesclatretssttrgsclppqktslmmticlgsiyedlkmyqtefqainaalqnhnh<br>qqiiildkgmlvaidelmqslnhngetlrqkppvgeadpyrvkmkillhafstrvvtinrvmgylssaSGGPGPA<br>GMKGLPGSggggsggggsggggsggggsggggsggggsQSVLTQPPSVSGAPGQRVTISCS<br>GSRSNIGSNTVKWYQQLPGTcPKLLIYYNDQRPSGVPDRFSGSKSGTSASLAIT<br>GLQAEDEADYYCQSYDRYTHPALLFGTGTKVTVLggggsggggsggggsQVQLVES<br>GGGVVQPGRSLRLSCAASGFTFSSYGMHWVRQAPGKGLEWVAFIRYDGSNK<br>YYADSVKGRFTISRDNSKNTLYLQMNSLRAEDTAVYYCKTHGSHDNWGcGT<br>MVTVSS |
| 372 | ACP289 (WW0233) | aptssstkktqlqlehllldlqmilnginnyknpkltrmltfkfympkkatelkhlqcleeelkpleevinlaqsknfhlrpr<br>dlisninvivlelkgsettfmceyadetativeflnrwirdeqsiistltsggpgpagmkglpgsevqlvesggglvqpgns<br>lrlscaasgftfgiskfgmswvrqapgkglewvssisgsgrdtlyaesvkgrftisrdnakttlylqmnslrpedtavyyctig<br>gslsyssqgtivtvssggggsggggsggggsggggsggpgpagmkglpgsevqlvesggglvqpg<br>gslrlscaasgftfssytlawvrqapgkglewvaaidsssytyspdtvrgrftisrdnaknslylqmnslraedtavyycar<br>dsnwdaldywgqgttvtvssggggsggggsggggsdiqmtqspsslsasvgdrvtitckasqnvgtnvgwyqqkpg<br>kapkaliysasfrysgvpsrfsgsgsgtdftltisslqpedfatyycqqyytypyttggtkveikhhhhhh |
| 373 | ACP290 (WW0234) | aptssstkktqlqlehllldlqmilnginnyknpkltrmltfkfympkkatelkhlqcleeelkpleevinlaqsknfhlrpr<br>dlisninvivlelkgsettfmceyadetativeflnrwirdeqsiistltsggpgpagmkglpgsevqlvesggglvqpgns<br>lrlscaasgftfgiskfgmswvrqapgkglewvssisgsgrdtlyaesvkgrftisrdnakttlylqmnslrpedtavyyctig<br>gslsyssqgtivtvssggggsggggsggggsggggsggggsggggsggpgpagmkglpgQVQLQESGGG<br>LVQTGGSLRLSCTTSGTIFSGYTMGWYRQAPGEQRELVAVISGGDTNYADS<br>VKGRFTISRDNTKDTMYLQMSLKPEDTAVYYCSREVTPPWKLYWGQGTQ<br>VTVSSAAAYPYDVPDYGSHHHHHH |
| 374 | ACP291 (WW0235) | aptssstkktqlqlehllldlqmilnginnyknpkltrmltfkfympkkatelkhlqcleeelkpleevinlaqskahlrpr<br>dlisninvivlelkgsettfmceyadetativeflnrwitieqsiistltsggpgpagmkglpgsevqlvesggglvqpgns<br>lrlscaasgitfgiskfgmswvrqapgkglewvssisgsgrdtlyaesvkgrftisrdnakttlylqmnslrpedtavyyctig |

Sequence Table

| SEQ ID NO. | Name | Sequence |
|---|---|---|
| | | gslsyssqgtivtvssggggsggggsggggsggggsggggsggggsggggssggpgpagmkglpgQVQLQESGGG<br>LVQEGGSLRLSCAASERIFSTDVMGWYRQAAEKQRELVAVVSARGTTNYLDA<br>VKGRFTISRDNARNTLTLQMNDLKPEDTASYYCYVRETTSPWRIYWGQGTQV<br>TVSSAAAYPYDVPDYGSHHHHHH |
| 375 | ACP292<br>(WW0236) | aptssstkktqlqlehllldlqmilnginnyknpkltrmltildympldcatelkhlqcleeelkpleevinlaqsknfhlrpr<br>dlisninvivlelkgsettfmceyadetativeflnrwiticqsiistltsggpgpagmkglpgsevqlvesggglvqpgns<br>lrlscaasgfifskfgmswvrqapgkglewvssisgsgrdtlyaesvkgrftisrdnakttlylqmnslrpedtavyyctig<br>gslsyssqgtivtvssggggsggggsggggsggggsggggsggggsggggssggpgpagmkglpgQVQLQESGGG<br>LVQAGGSLRLSCAASGSIFSANAMGWYRQAPGKQRELVAVISSGGSTNYADS<br>VKGRFTISRDNAKNTVYLQMNSLKPEDTAVYYCMYSGSYYYTPNDYWGQGT<br>QVTVSSAAAYPYDVPDYGSHHHHHH |
| 376 | ACP296<br>(WW0250) | aptssstkktqlqlehllldlqmilnginnyknpkltrmltfkfympkkatelkhlqcleeelkpleevinlaqsknfhlrpr<br>dlisninvivlelkgsettfmceyadetativeflnrwiticqsiistltSGGPGPAGMKGLPGSEVQLVES<br>GGGLVQPGNSLRLSCAASGFTFSKFGMSWVRQAPGKGLEWVSSISGSGRDTL<br>YAESVKGRFTISRDNAKTTLYLQMNSLRPEDTAVYYCTIGGSLSVSSQGTLVT<br>VSSggggsggggsggggsggggsggggsggggsSGGPGPAGMKGLPGSEVQLVESGGGLV<br>QPGGSLRLSCAASGFTFSSYTLAWVRQAPGKGLEWVAAIDSSSYTYSPDTVRG<br>RFTISRDNAKNSLYLQMNSLRAEDTAVYYCARDSNWDALDYWGQGTTVTVS<br>SGGGPGPAGMKGLPGSDIQMTQSPSSLSASVGDRVTITCKASQNVGTNVGWY<br>QQKPGKAPKALIYSASFRYSGVPSRFSGSGSGTDFTLTISSLQPEDFATYYCQQ<br>YYTYPYTFGGGTKVEIKHHHHHHEPEA** |
| 377 | ACP297<br>(WW0251) | aptssstkktqlqlehllldlqmilnginnyknpkltrmltfkfympkkatelkhlqcleeelkpleevinlaqsknfhlrpr<br>dlisninvivlelkgsettfmceyadetativeflnrwiticqsiistltSGGPGPAGMKGLPGSEVQLVES<br>GGGLVQPGNSLRLSCAASGFTFSKFGMSWVRQAPGKGLEWVSSISGSGRDTL<br>YAESVKGRFTISRDNAKTTLYLQMNSLRPEDTAVYYCTIGGSLSVSSQGTLVT<br>VSSggggsggggsggggsggggsggggsggggsSGGPGPAGMKGLPGSEVQLVESGGGLV<br>QPGGSLRLSCAASGFTFSSYTLAWVRQAPGKGLEWVAAIDSSSYTYSPDTVRG<br>RFTISRDNAKNSLYLQMNSLRAEDTAVYYCARDSNWDALDYWGQGTTVTVS<br>SGGGGSGGGGSGGGGSDIQMTQSPSSLSASVGDRVTITCKASQNVGTNVGWY<br>QQKPGKAPKLLIYSASFRYSGVPSRFSGSGSGTDFTLTISSLQPEDFATYYCQQ<br>YYTYPYTFGGGTKVEIKHHHHHHEPEA** |
| 378 | ACP298<br>(WW0252) | aptssstkktqlqlehllldlqmilnginnyknpkltrmltfkfympkkatelkhlqcleeelkpleevinlaqsknfhlrpr<br>dlisninvivlelkgsettfmceyadetativeflnrwiticqsiistltSGGPGPAGMKGLPGSEVQLVES<br>GGGLVQPGNSLRLSCAASGFTFSKFGMSWVRQAPGKGLEWVSSISGSGRDTL<br>YAESVKGRFTISRDNAKTTLYLQMNSLRPEDTAVYYCTIGGSLSVSSQGTLVT<br>VSSggggsggggsggggsggggsggggsggggsSGGPGPAGMKGLPGSEVQLVESGGGLV<br>QPGGSLRLSCAASGFTFSSYTLAWVRQAPGKGLEWVAAIDSSSYTYSPDTVRG<br>RFTISRDNAKNSLYLQMNSLRAEDTAVYYCARDSNWDALDYWGQGTTVTVS<br>SGGGGSGGGGSGGGGSDIQMTQSPSSLSASVGDRVTITCKASQNVGTNVGWY<br>QQKPGKAPKGLIYSASFRYSGVPSRFSGSGSGTDFTLTISSLQPEDFATYYCQQ<br>YYTYPYTFGGGTKVEIKHHHHHHEPEA** |
| 379 | ACP299<br>(WW0253) | aptssstkktqlqlehllldlqmilnginnyknpkltrmltfkfympkkatelkhlqcleeelkpleevinlaqsknfhlrpr<br>dlisninvivlelkgsettfmceyadetativeflnrwitiSqsiistltSGGPGPAGMKGLPGSEVQLVES<br>GGGLVQPGNSLRLSCAASGFTFSKFGMSWVRQAPGKGLEWVSSISGSGRDTL<br>YAESVKGRFTISRDNAKTTLYLQMNSLRPEDTAVYYCTIGGSLSVSSQGTLVT<br>VSSggggsggggsggggsggggsggggsggggsSGGPGPAGMKGLPGSEVQLVESGGGLV<br>QPGGSLRLSCAASGFTFSSYTLAWVRQAPGKGLEWVAAIDSSSYTYSPDTVRG<br>RFTISRDNAKNSLYLQMNSLRAEDTAVYYCARDSNWDALDYWGQGTTVTVS<br>SGGGGSGGGGSGGGGSDIQMTQSPSSLSASVGDRVTITCKASQNVGTNVGWY<br>QQKPGKAPKALIYSASFRYSGVPSRFSGSGSGTDFTLTISSLQPEDFATYYCQQ<br>YYTYPYTFGGGTKVEIKHHHHHHEPEA** |
| 380 | ACP300<br>(WW0255) | aptssstkktqlqlehllldlqmilnginnyknpkltrmltfkfympkkatelkhlqcleeelkpleevinlaqsknfhlrpr<br>dlisninvivlelkgsettfmceyadetativeflnrwiticqsiistltSGGPGPAGMKGLPGSdahksevahrf<br>kdlgeenfkalvliafaqylqqcpfedhvklvnevtefaktcvadesaencdkslhtlfgdklctvatlretygemadcca<br>kqepernecflqhkddnpnlprlvrpevdvmctafhdneeffildcylyeiarrhpyfyapellffakrykaafteccqaa<br>dkaacllpkldelrdegkassakqrlkcaslqkfgerafkawavarlsqrfpkaefaevsklvtdltkvhtecchgdlleca<br>ddradlakyicenqdsissklkeccekpllekshciaevendempadlpslaacIfveskdvcknyaeakdvflgmfly<br>eyarrhpdysvvlllrlaktyettlekccaaadphecyalcvfdefkplveepqnlikqncelfeqlgeykfqnallviyildc<br>vpqvstptivevsralglcvgskcchpeakrmpcaedylsvvinqlcvlhektpvsdrytkccteslvarrpcfsalevd<br>etyvpkefnaafthadictlsekerqikkqtalvelvlchkpkatkeqlkavmddfaafvekcckaddketcfaeegldc<br>lvaasqaalglggggsggggsggggsggggsggggsggggsSGGPGPAGMKGLPGSEVQLVESGG<br>GLVQPGSLRLSCAASGFTFSSYTLAWVRQAPGKGLEWVAAIDSSSYTYSPDT<br>VRGRFTISRDNAKNSLYLQMNSLRAEDTAVYYCARDSNWDALDYWGQGTTV<br>TVSSGGGGSGGGGSGGGGSDIQMTQSPSSLSASVGDRVTITCKASQNVGTNVG<br>WYQQKPGKAPKALIYSASFRYSGVPSRFSGSGSGTDFTLTISSLQPEDFATYYC<br>QQYYTYPYTFGGGTKVEIKHHHHHHEPEA** |

Sequence Table

| SEQ ID NO. | Name | Sequence |
|---|---|---|
| 381 | ACP302 (WW0296) | aptsssildctqlqlehllldlqmilnginnyknpkltrmltfkfympkkatelkhlqcleeelkpleevinlaqsknfhlrpr dlisninvivlelkgsettfmceyadetativeflnrwiticqsiistltSGGPGPAGMKGLPGSEAHKSEIA HRYNDLGEQHFKGLVLIAFSQYLQKCSYDEHAKLVQEVTDFAKTCVADESAA NCDKSLHTLFGDKLCAIPNLRENYGELADCCTKQEPERNECFLQHKDDNPSLP PFERPEAEAMCTSFKENPTTFMGHYLHEVARRHPYFYAPELLYYAEQYNEILT QCCAEADKESCLTPKLDGVKEKALVSSVRQRMKCSSMQKFGERAFKAWAVA RLSQTFPNADFAEITKLATDLTKVNKECCHGDLLECADDRAELAKYMCENQA TISSKLQTCCDKPLLKKAHCLSEVEHDTMPADLPAIAADFVEDQEVCKNYAEA KDVFLGTFLYEYSRRHPDYSVSLLLRLAKKYEATLEKCCAEANPPACYGTVL AEFQPLVEEPKNLVKTNCDLYEKLGEYGFQNAILVRYTQKAPQVSTPTLVEAA RNLGRVGTKCCTLPEDQRLPCVEDYLSAILNRVCLLHEKTPVSEHVTKCCSGS LVERRPCFSALTVDETYVPKEFKAETFTFHSDICTLPEKEKQIKKQTALAELVK HKPKATAEQLKTVMDDFAQFLDTCCKAADKDTCFSTEGPNLVTRCKDALAgg ggsggggsggggsggggsggggsggggsSGGPGPAGMKGLPGSEVQLVESGGGLVQPGGS LRLSCAASGFTFSSYTLAWVRQAPGKGLEWVAAIDSSSYTYSPDTVRGRFTISR DNAKNSLYLQMNSLRAEDTAVYYCARDSNWDALDYWGQTTVTVSSGGGG SGGGGSGGGGSDIQMTQSPSSLSASVGDRVTITCKASQNVGTNVGWYQQKPG KAPKALIYSASFRYSGVPSRFSGSGSGTDFTLTISSLQPEDFATYYCQQYYTYP YTFGGGTKVEIKHHHHHH** |
| 382 | ACP303 | EAHKSEIAHRYNDLGEQHFKGLVLIAFSQYLQKCSYDEHAKLVQEVTDFAKT CVADESAANCDKSLHTLFGDKLCAIPNLRENYGELADCCTKQEPERNECFLQH KDDNPSLPPFERPEAEAMCTSFKENPTTFMGHYLHEVARRHPYFYAPELLYYA EQYNEILTQCCAEADKESCLTPKLDGVKEKALVSSVRQRMKCSSMQKFGERA FKAWAVARLSQTFPNADFAEITKLATDLTKVNKECCHGDLLECADDRAELAK YMCENQATISSKLQTCCDKPLLKKAHCLSEVEHDTMPADLPAIAADFVEDQE VCKNYAEAKDVFLGTFLYEYSRRHPDYSVSLLLRLAKKYEATLEKCCAEANP PACYGTVLAEFQPLVEEPKNLVKTNCDLYEKLGEYGFQNAILVRYTQKAPQV STPTLVEAARNLGRVGTKCCTLPEDQRLPCVEDYLSAILNRVCLLHEKTPVSE HVTKCCSGSLVERRPCFSALTVDETYVPKEFKAETFTFHSDICTLPEKEKQIKK QTALAELVKHKPKATAEQLKTVMDDFAQFLDTCCKAADKDTCFSTEGPNLVT RCKDALASGGPGPAGMKGLPGSfficfympldcatelkhlqcleeelkpleevinlaqsknfhlrprdlis ninvivlelkgsettfmceyadetativeflnrwilfcqsiistltGGssssticktqlqlehllldlqmilnginnyknpkltrm ISGGPGPAGMKGLPGSEAHKSEIAHRYNDLGEQHFKGLVLIAFSQYLQKCSYD EHAKLVQEVTDFAKTCVADESAANCDKSLHTLFGDKLCAIPNLRENYGELAD CCTKQEPERNECFLQHKDDNPSLPPFERPEAEAMCTSFKENPFITMGHYLHEV ARRHPYFYAPELLYYAEQYNEILTQCCAEADKESCLTPKLDGVKEKALVSSVR QRMKCSSMQKFGERAFKAWAVARLSQlFPNADFAEITKLATDLTKVNKECC HGDLLECADDRAELAKYMCENQATISSKLQTCCDKPLLKKAHCLSEVEHDTM PADLPAIAADFVEDQEVCKNYAEAKDVFLG1FLYEYSRRHPDYSVSLLLRLAK KYEATLEKCCAEANPPACYGTVLAEFQPLVEEPKNLVKTNCDLYEKLGEYGF QNAILVRYTQKAPQVSTPTLVEAARNLGRVGTKCCTLPEDQRLPCVEDYLSAI LNRVCLLHEKTPVSEHVTKCCSGSLVERRPCFSALTVDETYVPKEFKAETFTFH SDICTLPEKEKQIKKQTALAELVKHKPKATAEQLKTVMDDFAQFLDTCCKAA DKDTCFSTEGPNLVTRCKDALAHHHHHH** |
| 383 | ACP304 (WW0302) | aptsssildctqlqlehllldlqmilnginnyknpkltrmltfkfympkkatelkhlqcleeelkpleevinlaqsknfhlrpr dlisninvivlelkgsettfmceyadetativeflnrwiticqsiistltSGGPGPAGMKGLPGSEVQLVES GGGLVQPGNSLRLSCAASGFTFSKFGMSWVRQAPGKGLEWVSSISGSGRDTL YAESVKGRFTISRDNAKTTLYLQMNSLRPEDTAVYYCTIGGSLSVSSQGTLVT VSSggggsggggsggggsggggsggggsggggsSGGPGPAGMKGLPGSEVQLVESGGGLV QPGGSLRLSCAASGFTFSSYTLAWVRQAPGKGLEWVAAIDSSSYTYSPDTVRG RFTISRDNAKNSLYLQMNSLRAEDTAVYYCARDSNWDALDYWGQTTVTVS SGGGGSGGGGSGGGGSDIQMTQSPSSLSASVGDRVTITCKASQNVGTNVGWY QQKPGKAPKALIYSASFRYSGVPSRFSGSGSGTDFTLTISSLQPEDFATYYCQQ YYTYPYTFGGGTKVEIKSGGPGPAGMKGLPGSggggsggggsggggsggggsggggsggg gselcdddppeiphatfkamaykegtmlnceckrgfrriksgslymktgnsshsswdnqcqctssatrnttkqvtpqp eeqkerkttemqspmqpvdqaslpghcrepppweneateriyhfvvgqmvyyqcvqgyralhrgpaesvclunth gktrwtqpqlictgemetsqfpgeekpqaspegrpesetsclvtltdfqiqtemaatmetsiftteyqHHHHHH** |
| 384 | ACP305 (WW0303) | elcdddppeiphatfkamaykegtmlnceckrgfrriksgslymktgnsshsswdnqcqctssatrnttkqvtpqpee qkerkttemqspmqpvdqaslpghcrepppweneateriyhfvvgqmvyyqcvqgyralhrgpaesvckmthgk trwtqpqlictgemetsqfpgeekpqaspegrpesetsclvtttdfqiqtemaatmetsifftteyqggggsggggsggggs sggggsggggsggggsSGGPGPAGMKGLPGSaptssstlthqlqlehllldlqmilnginnyknpkltrmllf kfympkkatelkhlqcleeelkpleevinlaqsknfhlrprdlisninvivlelkgsettfmceyadetativeflnrwitfc qsiistltSGGPGPAGMKGLPGSEVQLVESGGGLVQPGNSLRLSCAASGFTFSKFG MSWVRQAPGKGLEWVSSISGSGRDTLYAESVKGRFTISRDNAKTTLYLQMNS LRPEDTAVYYCTIGGSLSVSSQGTLVTVSSggggsggggsggggsggggsggggsggggsSG GPGPAGMKGLPGSEVQLVESGGGLVQPGGSLRLSCAASGFTFSSYTLAWVRQ APGKGLEWVAAIDSSSYTYSPDTVRGRFTISRDNAKNSLYLQMNSLRAEDTAV YYCARDSNWDALDYWGQTTVTVSSGGGGSGGGGSGGGGSDIQMTQSPSSL SASVGDRVTITCKASQNVGTNVGWYQQKPGKAPKALIYSASFRYSGVPSRFSG SGSGTDFTLTISSLQPEDFATYYCQQYYTYPYTFGGGTKVEIKHHHHHH** |

Sequence Table

| SEQ ID NO. | Name | Sequence |
|---|---|---|
| 385 | ACP306 (WW0304) | aptssstkktqlqlehllldlqmilnginnyknpkltrmltfkfympkkatelkhlqcleeelkpleevinlaqsknfhlrpr<br>dlisninvivlelkgsettfmceyadetativeflnrwitfcqsiistltSGGPGPAGMKGLPGSggggsggggs<br>ggggsggggsggggsggggsggggselcdddpeiphatfkamaykegtmlncecekrgfrriksgslymktgnsshsswd<br>nqcqctssatrnttkqvtpqpeeqkerkttemqspmqpvdqaslpghcrepppweneateriyhfvvgqmvyyqcv<br>qgyralhrgpaesvckmthgktrwtqpqlictgemetsqfpgeekpqaspegrpesetsclvtttdfqiqtemaatmets<br>iftteyqSGGPGPAGMKGLPGSEVQLVESGGGLVQPGNSLRLSCAASGFTFSKFG<br>MSWVRQAPGKGLEWVSSISGSGRDTLYAESVKGRFTISRDNAKTTLYLQMNS<br>LRPEDTAVYYCTIGGSLSVSSQGTLVTVSSggggsggggsggggsggggsggggsggggsSG<br>GPGPAGMKGLPGSEVQLVESGGGLVQPGGSLRLSCAASGFTFSSYTLAWVRQ<br>APGKGLEWVAAIDSSSYTYSPDTVRGRFTISRDNAKNSLYLQMNSLRAEDTAV<br>YYCARDSNWDALDYWGQGTTVTVSSGGGGSGGGGSGGGGSDIQMTQSPSSL<br>SASVGDRVTITCKASQNVGTNVGWYQQKPGKAPKALIYSASFRYSGVPSRFSG<br>SGSGTDFTLTISSLQPEDFATYYCQQYYTYPYTFGGGTKVEIKHHHHHH** |
| 386 | ACP307 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSGGPGPAGMKGLPGSfficlympldcatelkhlqcleeelkpleevinlaqsknfhlrpr<br>dlisninvivlelkgsettfmceyadetativeflnrwitfcqsiistitGGssstkktqlqlehllldlqmilnginnyknpkl<br>trmlSGGPGPAGMKGLPGSEVQLVESGGGLVQPGNSLRLSCAASGFTFSKFGMS<br>WVRQAPGKGLEWVSSISGSGRDTLYAESVKGRFTISRDNAKTTLYLQMNSLR<br>PEDTAVYYCTIGGSLSVSSQGTLVTVSSggggsggggsggggsggggsggggsggggsSGGP<br>GPAGMKGLPGSEVQLVESGGGLVQPGGSLRLSCAASGFTFSSYTLAWVRQAP<br>GKGLEWVAAIDSSSYTYSPDTVRGRFTISRDNAKNSLYLQMNSLRAEDTAVY<br>YCARDSNWDALDYWGQGTTVTVSSGGGGSGGGGSGGGGSDIQMTQSPSSLS<br>ASVGDRVTITCKASQNVGTNVGWYQQKPGKAPKALIYSASFRYSGVPSRFSGS<br>GSGTDFTLTISSLQPEDFATYYCQQYYTYPYTFGGGTKVEIKHHHHHH** |
| 387 | ACP308 | EVQLVESGGGLVQPGSLRLSCAASGFTFSSYTLAWVRQAPGKGLEWVAAID<br>SSSYTYSPDTVRGRFTISRDNAKNSLYLQMNSLRAEDTAVYYCARDSNWDAL<br>DYWGQGTTVTVSSGGGGSGGGGSGGGGSDIQMTQSPSSLSASVGDRVTITCK<br>ASQNVGTNVGWYQQKPGKAPKALIYSASFRYSGVPSRFSGSGSGTDFTLTISSL<br>QPEDFATYYCQQYYTYPYTFGGGTKVEIKSGGPGPAGMKGLPGSggggsggggsg<br>ggggsggggsggggsggggsEVQLVESGGGLVQPGNSLRLSCAASGFTFSKFGMSWVR<br>QAPGKGLEWVSSISGSGRDTLYAESVKGRFTISRDNAKTTLYLQMNSLRPEDT<br>AVYYCTIGGSLSVSSQGTLVTVSSSGGPGPAGMKGLPGStfkfympkkatelkhlqcleee<br>lkpleevinlaqsknfhlrprdlisninvivlelkgsettfmceyadetativeflnrwitfcqsiistltGGssstkktqlqle<br>hllldlqmilnginnyknpkltrmlSGGPGPAGMKGLPGSEVQLVESGGGLVQPGNSLRLS<br>CAASGFTFSKFGMSWVRQAPGKGLEWVSSISGSGRDTLYAESVKGRFTISRDN<br>AKTTLYLQMNSLRPEDTAVYYCTIGGSLSVSSQGTLVTVSSHHHHHH** |
| 388 | ACP309 (WW0307) | aptssstkktqlqlehllldlqmilnginnyknpkltrmltfkfympkkatelkhlqcleeelkpleevinlaqsknfhlrpr<br>dlisninvivlelkgsetfmceyadetativeflnrwitfcqsiistltSGGPGPAGMKGLPGSEVQLVES<br>GGGLVQPGNSLRLSCAASGFTFSKFGMSWVRQAPGKGLEWVSSISGSGRDTL<br>YAESVKGRFTISRDNAKTTLYLQMNSLRPEDTAVYYCTIGGSLSVSSQGTLVT<br>VSSggggsggggsggggsggggsggggsggggsSGGPGPAGMKGLPGSEVQLVESGGGLV<br>QPGGSLRLSCAASGFTFSSYTLAWVRQAPGKGLEWVAAIDSSSYTYSPDTVRG<br>RFTISRDNAKNSLYLQMNSLRAEDTAVYYCARDSNWDALDYWGQGTTVTVS<br>SGGGGSGGGGSGGGGSDIQMTQSPSSLSASVGDRVTITCKASQNVGTNVGWY<br>QQKPGKAPKSLIYSASFRYSGVPSRFSGSGSGTDFTLTISSLQPEDFATYYCQQY<br>YTYPYTFGGGTKVEIKHHHHHH** |
| 389 | ACP310 (WW0308) | aptssstkktqlqlehllldlqmilnginnyknpkltrmltfkfympkkatelkhlqcleeelkpleevinlaqsknfhlrpr<br>dlisninvivlelkgsetfmceyadetativeflnrwitfcqsiistltSGGPGPAGMKGLPGSEVQLVES<br>GGGLVQPGNSLRLSCAASGFTFSKFGMSWVRQAPGKGLEWVSSISGSGRDTL<br>YAESVKGRFTISRDNAKTTLYLQMNSLRPEDTAVYYCTIGGSLSVSSQGTLVT<br>VSSggggsggggsggggsggggsggggsggggsSGGPGPAGMKGLPGSEVQLVESGGGLV<br>QPGGSLRLSCAASGFTFSSYTLAWVRQAPGKGLEWVAAIDSSSYTYSPDTVRG<br>RFTISRDNAKNSLYLQMNSLRAEDTAVYYCARDSNWDALDYWGQGTTVTVS<br>SGGGGSGGGGSGGGGSDIQMTQSPSSLSASVGDRVTITCKASQNVGTNVGWY<br>QQKPGQAPRLLIYSASFRYSGVPSRFSGSGSGTDFTLTISSLQPEDFATYYCQQY<br>YTYPYTFGGGTKVEIKHHHHHH** |
| 390 | ACP311 (WW0316) | aptssstkktqlqlehllldlqmilnginnyknpkltrmltfkfympkkatelkhlqcleeelkpleevinlaqsknfhlrpr<br>dlisninvivlelkgsettfmceyadetativeflnrwitfcqsiistltSGGPGPAGMKGLPGSeskygppcpp<br>cpapefglgppsvflfppkpkdtlmisrtpevtcvvvdvsqedpevqfnwyvdgvevhnaktkpreeqfnstyrvvsvl<br>tvlhqdwlngkeykckvsnkglpssiektiskakgqprepqvytlppsqeemtknqvsltclvkgfypsdiavewesn<br>gqpennykttppvldsdgsfflysrltvdksrwqegnvfscsvmhealhnhytqkslslslgkggggsggggsggggs<br>ggggsggggsggggsSGGPGPAGMKGLPGSEVQLVESGGGLVQPGGSLRLSCAASG<br>FTFSSYTLAWVRQAPGKGLEWVAAIDSSSYTYSPDTVRGRFTISRDNAKNSLY |

Sequence Table

| SEQ ID NO. | Name | Sequence |
|---|---|---|
| | | LQMNSLRAEDTAVYYCARDSNWDALDYWGQGTTVTVSSGGGGSGGGGSGG<br>GGSDIQMTQSPSSLSASVGDRVTITCKASQNVGTNVGWYQQKPGKAPKALIYS<br>ASFRYSGVPSRFSGSGSGTDFTLTISSLQPEDFATYYCQQYYTYPYTFGGGTKV<br>EIKHHHHHH** |
| 391 | ACP312 (WW0317) | eskygppcppcpapeflggpsvflfppkpkdtlmisrtpevtcvvvdvsqedpevqfnwyvdgvevhnaktkpree<br>qfnstyrvvsyltvlhqdwhigkeykckvsnkglpssiektiskakgqprepqvytlppsqeemtknqvsltclvkgfy<br>psdiavewesngqpennyklippvldsdgsfflysrltvdksrwqegnvfscsvmhealhnhytqkslslslgkSGG<br>PGPAGMKGLPGSaptssstkktqlqlehllldlqmilnginnyknpkltrmltfkflympkkatelkhlqcleeeel<br>kpleevinlaqsknfblrprdlisninvivlelkgsellfmceyadetativeflnrwitfcqsiistlliggggsggggsgggg<br>sggggsggggsggggsSGGPGPAGMKGLPGSEVQLVESGGGLVQPGGSLRLSCAASG<br>FTFSSYTLAWVRQAPGKGLEWVAAIDSSSYTYSPDTVRGRFTISRDNAKNSLY<br>LQMNSLRAEDTAVYYCARDSNWDALDYWGQGTTVTVSSGGGGSGGGGSGG<br>GGSDIQMTQSPSSLSASVGDRVTITCKASQNVGTNVGWYQQKPGKAPKALIYS<br>ASFRYSGVPSRFSGSGSGTDFTLTISSLQPEDFATYYCQQYYTYPYTFGGGTKV<br>EIKHHHHHH** |
| 392 | ACP313 (WW0318) | aptssstkktqlqlehllldlqmilnginnyknpkltrmltfkfympkkatelkhlqcleeeelkpleevinlaqsknfhlrpr<br>dlisninvivlelkgsettfmceyadetativeflnrwitfcqsiistltSGGPGPAGMKGLPGSggggsggggs<br>ggggsggggsggggsggggsEVQLVESGGGLVQPGGSLRLSCAASGFTFSSYTLAWVR<br>QAPGKGLEWVAAIDSSSYTYSPDTVRGRFTISRDNAKNSLYLQMNSLRAEDTA<br>VYYCARDSNWDALDYWGQGTTVTVSSGGGGSGGGGSGGGGSDIQMTQSPSS<br>LSASVGDRVTITCKASQNVGTNVGWYQQKPGKAPKALIYSASFRYSGVPSRFS<br>GSGSGTDFTLTISSLQPEDFATYYCQQYYTYPYTFGGGTKVEIKSGGPGPAGM<br>KGLPGSeskygppcppcpapeflggpsvflfppkpkdtlmisrtpevtcvvvdvsqedpevqfnwyvdgvevh<br>naktkpreeqfnstyrvvsyltvlhqdwhigkeykckvsnkglpssiektiskakgqprepqvytlppsqeemtknqv<br>sliclvkgypsdiavewesngqpennyklippvldsdgsfflysrltvdksrwqegnvfscsvmhealhnhytqkslsl<br>slgkHHHHHH** |
| 393 | ACP314 (WW0354) | vprdcgckpcictypevssvfifppkpkdvltitltpkvtcvvvdiskddpevqfswfvddvevhtaqtqpreeqfnslf<br>rsyselpimhqdwingkefkcrynsaafpapiektisktkgrpkapqvytipppkeqmakdkvsltcmitclffpeditv<br>ewqwngqpaenykntqpimdtdgsyfyysklnvqksnweagnIftcsvlheglhnhhtekslshspgkSGGPG<br>PAGMKGLPGSaptsssstIcktqlqlehllldlqmilnginnyknpkltrmlffidympkkatelkhlqcleeeelkple<br>evinlaqsknfhlrprdlisninvivlelkgsetlfmceyadetativeflnrwilfcqsiistltggggsggggsggggsgg<br>ggsggggsggggsSGGPGPAGMKGLPGSEVQLVESGGGLVQPGGSLRLSCAASGFT<br>FSSYTLAWVRQAPGKGLEWVAAIDSSSYTYSPDTVRGRFTISRDNAKNSLYLQ<br>MNSLRAEDTAVYYCARDSNWDALDYWGQGTTVTVSSGGGGSGGGGSGGGG<br>SDIQMTQSPSSLSASVGDRVTITCKASQNVGTNVGWYQQKPGKAPKALIYSAS<br>FRYSGVPSRFSGSGSGTDFTLTISSLQPEDFATYYCQQYYTYPYTFGGGTKVEI<br>KHHHHHH** |
| 394 | ACP336 (WW0414) | aptssstkktqlqlehllldlqmilnginnyknpkltrmltfkfympkkatelkhlqcleeeelkpleevinlaqsknfhlrpr<br>dlisninvivlelkgsetlfmceyadetativeflnrwilfcqsiistltsggpGPAGLYAQpgsEVQLVESGG<br>GLVQPGNSLRLSCAASGFTFSKFGMSWVRQAPGKGLEWVSSISGSGRDTLYA<br>ESVKGRFTISRDNAKTTLYLMNSLRPEDTAVYYCTIGGSLSVSSQGTLVTVSS<br>ggggsggggsggggsggggsggggsggggssggpGPAGLYAQpgsEVQLVESGGGLVQPGGS<br>LRLSCAASGFTFSSYTLAWVRQAPGKGLEWVAAIDSSSYTYSPDTVRGRFTISR<br>DNAKNSLYLQMNSLRAEDTAVYYCARDSNWDALDYWGQGTTVTVSSsggpG<br>PAGLYAQpgsDIQMTQSPSSLSASVGDRVTITCKAREKLWSAVAWYQQKPGKA<br>PKsLIYSASFRYSGVPSRFSGSGSGTDFTLTISSLQPEDFATYYCQQYYTYPYTF<br>GGGTKVEIK** |
| 395 | ACP337 (WW0415) | aptssstkktqlqlehllldlqmilnginnyknpkltrmltfkfympkkatelkhlqcleeeelkpleevinlaqsknfhlrpr<br>dlisninvivlelkgsetlfmceyadetativeflnrwilfcqsiistltsggpGPAGLYAQpgsEVQLVESGG<br>GLVQPGNSLRLSCAASGFTFSKFGMSWVRQAPGKGLEWVSSISGSGRDTLYA<br>ESVKGRFTISRDNAKTTLYLMNSLRPEDTAVYYCTIGGSLSVSSQGTLVTVSS<br>ggggsggggsggggsggggsggggsggggssggpGPAGLYAQpgsEVQLVESGGGLVQPGGS<br>LRLSCAASGFTFSSYTLAWVRQAPGKGLEWVAAIDSSSYTYSPDTVRGRFTISR<br>DNAKNSLYLQMNSLRAEDTAVYYCARDSNWDALDYWGQGTTVTVSSGGGG<br>SGGGGSGGGGSDIQMTQSPSSLSASVGDRVTITCKAREKLWSAVAWYQQKPG<br>KAPKsLIYSASFRYSGVPSRFSGSGSGTDFTLTISSLQPEDFATYYCQQYYTYPY<br>TFGGGTKVEIK** |
| 396 | ACP338 (WW0416) | aptssstkktqlqlehllldlqmilnginnyknpkltrmltfkfympkkatelkhlqcleeeelkpleevinlaqsknfhlrpr<br>dlisninvivlelkgsetlfmceyadetativeflnrwilfcqsiistltsggpGPAGLYAQpgsEVQLVESGG<br>GLVQPGNSLRLSCAASGFTFSKFGMSWVRQAPGKGLEWVSSISGSGRDTLYA<br>ESVKGRFTISRDNAKTTLYLMNSLRPEDTAVYYCTIGGSLSVSSQGTLVTVSS<br>ggggsggggsggggsggggsggggsggggsggggssggpGPAGLYAQpgsEVQLVESGGGLVQPGGS<br>LRLSCAASGFTFSSYTLAWVRQAPGKGLEWVAAIDSSSYTYSPDTVRGRFTISR<br>DNAKNSLYLQMNSLRAEDTAVYYCARDSNWDALDYWGQGTTVTVSSsggpG<br>PAGLYAQpgsDIQMTQSPSSLSASVGDRVTITCKVTEKVWGNVAWYQQKPGK<br>APISLIYSPSLRKSGVPSRFSGSGSGTDFTLTISSLQPEDFATYYCQQYYTYPYTF<br>GGGTKVEIK** |

-continued

Sequence Table

| SEQ ID NO. | Name | Sequence |
|---|---|---|
| 397 | ACP339 (WW0417) | aptssstkktqlqlehllldlqmilnginnyknpkltrmltfkfympkkatelkhlqcleeelkpleevinlaqsknfhlrpr dlisninvivlelkgsetlfmceyadetativeflnrwilfcqsiistltsggpGPAGLYAQpgsEVQLVESGG GLVQPGNSLRLSCAASGFTFSKFGMSWVRQAPGKGLEWVSSISGSGRDTLYA ESVKGRFTISRDNAKTTLYLQMNSLRPEDTAVYYCTIGGSLSVSSQGTLVTVSS ggggsggggsggggsggggsggggsggggssggpGPAGLYAQpgsEVQLVESGGGLVQPGGS LRLSCAASGFTFSSYTLAWVRQAPGKGLEWVAAIDSSSYTYSPDTVRGRFTISR DNAKNSLYLQMNSLRAEDTAVYYCARDSNWDALDYWGQGTTVTVSSGGGG SGGGGSGGGGSDIQMTQSPSSLSASVGDRVTITCKVTEKVWGNVAWYQQKP GKAPISLIYSPSLRKSGVPSRFSGSGSGTDFTLTISSLQPEDFATYYCQQYYTYP YTFGGGTKVEIK** |
| 398 | ACP340 (WW0418) | aptssstkktqlqlehllldlqmilnginnyknpkltrmltfkfympkkatelkhlqcleeelkpleevinlaqsknfhlrpr dlisninvivlelkgsettfmceyadetativeflnrwitfcqsiistltsggpGPAGLYAQpgsEVQLVESGG GLVQPGNSLRLSCAASGFTFSKFGMSWVRQAPGKGLEWVSSISGSGRDTLYA ESVKGRFTISRDNAKTTLYLQMNSLRPEDTAVYYCTIGGSLSVSSQGTLVTVSS ggggsggggsggggsggggsggggsggggssggpGPAGLYAQpgsevqllesggglvqpggslrlscaasgsi fsanamgwyrqapgkglelvavissggstnyadsvkgrftisrdnskntvylqmnslraedtavyycmysgsyyytp ndywgqgtlvtvss** |
| 399 | ACP341 (WW0419) | aptssstkktqlqlehllldlqmilnginnyknpkltrmltfkfympkkatelkhlqcleeelkpleevinlaqsknfhlrpr dlisninvivlelkgsettfmceyadetativeflnrwitfcqsiistltsggpGPAGLYAQpgsEVQLVESGG GLVQPGNSLRLSCAASGFTFSKFGMSWVRQAPGKGLEWVSSISGSGRDTLYA ESVKGRFTISRDNAKTTLYLQMNSLRPEDTAVYYCTIGGSLSVSSQGTLVTVSS ggggsggggsggggsggggsggggsggggssggpGPAGLYAQpgsevqllesggglvqpggslrlscaaseri fstdvmgwyrqapgkqrelvavvsargttnyldavkgrftisrdnskntlylqmnslraedtavyycyvrettspwriy wgqgtlvtvss** |
| 400 | ACP342 (WW0420) | elcdddppeiphatfkamaykegtmlnceckrgfrriksgslymlctgnsshsswdnqcqctssatrnttkqvtpqee qkerkttemqspmqpvdqaslpghcrepppweneateriyhfvvgqmvyyqcvqgyralhrgpaesvckmthgk trwtqpqlictgemetsqfpgeekpqaspegrpesetsSlvtdclfqiqtemaatmetsifteyqggggsggggsgggg sggggsggggsggggssggpGPAGLYAQpgsaptssstkktqlqlehllldlqmilnginnyknpkltrmltfkfy mpkkatelkhlqcleeelkpleevinlaqsknfhlrprdlisninvivlelkgsetlfmceyadetativeflnrwitfcqsii stltsggpGPAGLYAQpgsEVQLVESGGGLVQPGNSLRLSCAASGFTFSKFGMSWV RQAPGKGLEWVSSISGSGRDTLYAESVKGRFTISRDNAKTTLYLQMNSLRPED TAVYYCTIGGSLSVSSQGTLVTVSSggggsggggsggggsggggsggggsggggssggpGPAG LYAQpgsEVQLVESGGGLVQPGGSLRLSCAASGFTFSSYTLAWVRQAPGKGLE WVAAIDSSSYTYSPDTVRGRFTISRDNAKNSLYLQMNSLRAEDTAVYYCARD SNWDALDYWGQGTTVTVSSsggpGPAGLYAQpgsDIQMTQSPSSLSASVGDRVT ITCKAREKLWSAVAWYQQKPGKAPKsLIYSASFRYSGVPSRFSGSGSGTDFTLT ISSLQPEDFATYYCQQYYTYPYTFGGGTKVEIK** |
| 401 | ACP343 (WW0421) | elcdddppeiphatfkamaykegtmlnceckrgfrriksgslymlctgnsshsswdnqcqctssatrnttkqvtpqee qkerkttemqspmqpvdqaslpghcrepppweneateriyhfvvgqmvyyqcvqgyralhrgpaesvckmthgk trwtqpqlictgemetsqfpgeekpqaspegrpesetsSlvtdclfqiqtemaatmetsifteyqggggsggggsgggg sggggsggggsggggssggpGPAGLYAQpgsaptssstkktqlqlehllldlqmilnginnyknpkltrmltfkfy mpkkatelkhlqcleeelkpleevinlaqsknfhlrprdlisninvivlelkgsetlfmceyadetativeflnrwitfcqsii stltsggpGPAGLYAQpgsEVQLVESGGGLVQPGNSLRLSCAASGFTFSKFGMSWV RQAPGKGLEWVSSISGSGRDTLYAESVKGRFTISRDNAKTTLYLQMNSLRPED TAVYYCTIGGSLSVSSQGTLVTVSSggggsggggsggggsggggsggggsggggssggpGPAG LYAQpgsEVQLVESGGGLVQPGGSLRLSCAASGFTFSSYTLAWVRQAPGKGLE WVAAIDSSSYTYSPDTVRGRFTISRDNAKNSLYLQMNSLRAEDTAVYYCARD SNWDALDYWGQGTTVTVSSGGGGSGGGGSGGGGSDIQMTQSPSSLSASVGD RVTITCKAREKLWSAVAWYQQKPGKAPKsLIYSASFRYSGVPSRFSGSGSGTD FTLTISSLQPEDFATYYCQQYYTYPYTFGGGTKVEIK** |
| 402 | ACP344 (WW0422) | elcdddppeiphatfkamaykegtmlnceckrgfrriksgslymlctgnsshsswdnqcqctssatrnttkqvtpqee qkerkttemqspmqpvdqaslpghcrepppweneateriyhfvvgqmvyyqcvqgyralhrgpaesvckmthgk trwtqpqlictgemetsqfpgeekpqaspegrpesetsSlvtdclfqiqtemaatmetsifteyqggggsggggsgggg sggggsggggsggggssggpGPAGLYAQpgsaptssstkktqlqlehllldlqmilnginnyknpkltrmilfkfy mpkkatelkhlqcleeelkpleevinlaqsknfhlrprdlisninvivlelkgsetlfmceyadetativeflnrwitfcqsii stltsggpGPAGLYAQpgsEVQLVESGGGLVQPGNSLRLSCAASGFTFSKFGMSWV RQAPGKGLEWVSSISGSGRDTLYAESVKGRFTISRDNAKTTLYLQMNSLRPED TAVYYCTIGGSLSVSSQGTLVTVSSggggsggggsggggsggggsggggsggggssggpGPAG LYAQpgsEVQLVESGGGLVQPGGSLRLSCAASGFTFSSYTLAWVRQAPGKGLE WVAAIDSSSYTYSPDTVRGRFTISRDNAKNSLYLQMNSLRAEDTAVYYCARD SNWDALDYWGQGTTVTVSSsggpGPAGLYAQpgsDIQMTQSPSSLSASVGDRVT ITCKVTEKVWGNVAWYQQKPGKAPISLIYSPSLRKSGVPSRFSGSGSGTDFTLT ISSLQPEDFATYYCQQYYTYPYTFGGGTKVEIK** |
| 403 | ACP345 (WW0423) | elcdddppeiphatfkamaykegtmlnceckrgfrriksgslymlctgnsshsswdnqcqctssatrnttkqvtpqee qkerkttemqspmqpvdqaslpghcrepppweneateriyhfvvgqmvyyqcvqgyralhrgpaesvckmthgk trwtqpqlictgemetsqfpgeekpqaspegrpesetsSlvtdclfqiqtemaatmetsifteyqggggsggggsgggg |

Sequence Table

| SEQ ID NO. | Name | Sequence |
|---|---|---|
| | | sggggsggggsggggsggggssggpGPAGLYAQpgsaptssstkktqlqlehllldlqmilnginnyknpkltrmltfkfy mpkkatelkhlqcleeeelkpleevinlaqsknfblrprdlisninvivlelkgsetlfmceyadetativeflnrwilleqsii stltsggpGPAGLYAQpgsEVQLVESGGGLVQPGNSLRLSCAASGFTFSKFGMSWV RQAPGKGLEWVSSISGSGRDTLYAESVKGRFTISRDNAKTTLYLQMNSLRPED TAVYYCTIGGSLSVSSQGTLVTVSSggggsggggsggggsggggsggggsggggssggpGPAG LYAQpgsEVQLVESGGGLVQPGGSLRLSCAASGFTFSSYTLAWVRQAPGKGLE WVAAIDSSSYTYSPDTVRGRFTISRDNAKNSLYLQMNSLRAEDTAVYYCARD SNWDALDYWGQGTTVTVSSGGGGSGGGGSGGGGSDIQMTQSPSSLSASVGD RVTITCKVTEKVWGNVAWYQQKPGKAPISLIYSPSLRKSGVPSRFSGSGSGTD FTLTISSLQPEDFATYYCQQYYTYPYTFGGGTKVEIK** |
| 404 | ACP346 (WW0424) | elcdddppeiphatflcamaykegtmlnceckrgfrriksgslymktgnsshsswdnqcqctssatrnttkqvtpqpee qkerkttemqspmqpvdqaslpghcrepppweneateriyhfvvgqmvyyqcvqgyralhrgpaesvckmthgk trwtqpqlictgemetsqfpgeekpqaspegrpesetsSlvtttclfqiqtemaatmetsifftteyqggggsggggsgggg sggggsggggsggggsggggssggpGPAGLYAQpgsaptssstlcktqlqlehllldlqmilnginnyknpkltrmilflcfy mpkkatelkhlqcleeeelkpleevinlaqsknfblrprdlisninvivlelkgsetlfmceyadetativeflnrwilleqsii stltsggpGPAGLYAQpgsEVQLVESGGGLVQPGNSLRLSCAASGFTFSKFGMSWV RQAPGKGLEWVSSISGSGRDTLYAESVKGRFTISRDNAKTTLYLQMNSLRPED TAVYYCTIGGSLSVSSQGTLVTVSSggggsggggsggggsggggsggggsggggssggpGPAG LYAQpgsevqllesgggglvqpggslrlscaasgsifsanamgwyrqapgkglelvavissggstnyadsvkgrftisr dnskntvylqmnslraedtavyycmysgsyyytpndywqgqtlvtvss** |
| 405 | ACP347 (WW0425) | elcdddppeiphatflcamaykegtmlnceckrgfrriksgslymktgnsshsswdnqcqctssatrnttkqvtpqpee qkerkttemqspmqpvdqaslpghcrepppweneateriyhfvvgqmvyyqcvqgyralhrgpaesvckmthgk trwtqpqlictgemetsqfpgeekpqaspegrpesetsSlvtttclfqiqtemaatmetsifftteyqggggsggggsgggg sggggsggggsggggsggggssggpGPAGLYAQpgsaptssstlcktqlqlehllldlqmilnginnyknpkltrmilflcfy mpkkatelkhlqcleeeelkpleevinlaqsknfblrprdlisninvivlelkgsetlfmceyadetativeflnrwilleqsii stltsggpGPAGLYAQpgsEVQLVESGGGLVQPGNSLRLSCAASGFTFSKFGMSWV RQAPGKGLEWVSSISGSGRDTLYAESVKGRFTISRDNAKTTLYLQMNSLRPED TAVYYCTIGGSLSVSSQGTLVTVSSggggsggggsggggsggggsggggsggggssggpGPAG LYAQpgsevqllesgggglvqpggslrlscaaserifstdvmgwyrqapgkqrelvavvsargttnyldavkgrftisrd nskntlylqmnslraedtavyycyvrettspwriywgqgtlvtvss** |
| 406 | ACP348 (WW0426) | eskygppcppcpapefIggpsvflfppkpkdtlmisrtpevtcvvvdvsqedpevqfnwydgvevhnaktkpree qfnstyrvvsyltvlhqdwlhigkeykcicvsnkglpssiektiskakgqprepqvytlppsqeemilmqvsltclvkgfy psdiavewesngqpennykappvldsdgsfflysrltvdksrwqegnvfscsvmhealhnhytqkslslslgksggp GPAGLYAQpgsaptssticktqlqlehllldlqmilnginnyknpkltrmltfkfymplcatelkhlqcleeeelkpl eevinlaqsknfhlrprdlisninvivlelkgsetlfmceyadetativeflnrwitfcqsiistligggggsggggsggggsgg ggsggggsggggssggpGPAGLYAQpgsEVQLVESGGGLVQPGGSLRLSCAASGFTFS SYTLAWVRQAPGKGLEWVAAIDSSSYTYSPDTVRGRFTISRDNAKNSLYLQM NSLRAEDTAVYYCARDSNWDALDYWGQGTTVTVSSsggpGPAGLYAQpgsDIQ MTQSPSSLSASVGDRVTITCKAREKLWSAVAWYQQKPGKAPKsLIYSASFRYS GVPSRFSGSGSGTDFTLTISSLQPEDFATYYCQQYYTYPYTFGGGTKVEIK** |
| 407 | ACP349 (WW0427) | eskygppcppcpapefIggpsvflfppkpkdtlmisrtpevtcvvvdvsqedpevqfnwydgvevhnaktkpree qfnstyrvvsyltvlhqdwlhigkeykcicvsnkglpssiektiskakgqprepqvytlppsqeemilmqvsltclvkgfy psdiavewesngqpennykappvldsdgsfflysrltvdksrwqegnvfscsvmhealhnhytqkslslslgksggp GPAGLYAQpgsaptssticktqlqlehllldlqmilnginnyknpkltrmilfkIympldcatelkhlqcleeeelkpl eevinlaqsknfhlrprdlisninvivlelkgsetlfmceyadetativeflnrwitfcqsiistligggggsggggsggggsgg ggsggggsggggssggpGPAGLYAQpgsEVQLVESGGGLVQPGGSLRLSCAASGFTFS SYTLAWVRQAPGKGLEWVAAIDSSSYTYSPDTVRGRFTISRDNAKNSLYLQM NSLRAEDTAVYYCARDSNWDALDYWGQGTTVTVSSGGGGSGGGGSGGGGS DIQMTQSPSSLSASVGDRVTITCKAREKLWSAVAWYQQKPGKAPKsLIYSASF RYSGVPSRFSGSGSGTDFTLTISSLQPEDFATYYCQQYYTYPYTFGGGTKVEIK** |
| 408 | ACP350 (WW0428) | eskygppcppcpapefIggpsvflfppkpkdtlmisrtpevtcvvvdvsqedpevqfnwydgvevhnaktkpree qfnstyrvvsyltvlhqdwlhigkeykcicvsnkglpssiektiskakgqprepqvytlppsqeemilmqvsltclvkgfy psdiavewesngqpennykappvldsdgsfflysrltvdksrwqegnvfscsvmhealhnhytqkslslslgksggp GPAGLYAQpgsaptssticktqlqlehllldlqmilnginnyknpkltrmltfkfymplcatelkhlqcleeeelkpl eevinlaqsknfhlrprdlisninvivlelkgsetlfmceyadetativeflnrwitfcqsiistligggggsggggsggggsgg ggsggggsggggssggpGPAGLYAQpgsEVQLVESGGGLVQPGGSLRLSCAASGFTFS SYTLAWVRQAPGKGLEWVAAIDSSSYTYSPDTVRGRFTISRDNAKNSLYLQM NSLRAEDTAVYYCARDSNWDALDYWGQGTTVTVSSsggpGPAGLYAQpgsDIQ MTQSPSSLSASVGDRVTITCKVTEKVWGNVAWYQQKPGKAPISLIYSPSLRKS GVPSRFSGSGSGTDFTLTISSLQPEDFATYYCQQYYTYPYTFGGGTKVEIK** |
| 409 | ACP351 (WW0429) | eskygppcppcpapefIggpsvflfppkpkdtlmisrtpevtcvvvdvsqedpevqfnwydgvevhnaktkpree qfnstyrvvsyltvlhqdwlhigkeykcvsnkglpssiektiskakgqprepqvytlppsqeemilmqvsltclvkgfy psdiavewesngqpennykttppvldsdgsfflysrltvdksrwqegnvfscsvmhealhnhytqkslslslgksggp GPAGLYAQpgsaptssstkktqlqlehllldlqmilnginnyknpkltrmltfkfymplcatelkhlqcleeeelkpl eevinlaqsknfhlrprdlisninvivlelkgsettfmceyadetativeflnrwitfcqsiistligggggsggggsggggsgg ggsggggsggggssggpGPAGLYAQpgsEVQLVESGGGLVQPGGSLRLSCAASGFTFS SYTLAWVRQAPGKGLEWVAAIDSSSYTYSPDTVRGRFTISRDNAKNSLYLQM |

Sequence Table

| SEQ ID NO. | Name | Sequence |
|---|---|---|
| | | NSLRAEDTAVYYCARDSNWDALDYWGQGTTVTVSSGGGGSGGGGSGGGGS DIQMTQSPSSLSASVGDRVTITCKVTEKVWGNVAWYQQKPGKAPISLIYSPSL RKSGVPSRFSGSGSGTDFTLTISSLQPEDFATYYCQQYYTYPYTFGGGTKVEIK** |
| 410 | ACP352 (WW0430) | eskygppcppcpapeflggpsvflfppkpkdtlmisrtpevtcvvvdvsqedpevqfnwyvdgvevhnaktkpree qfnstyrvvsyltvlhqdwhigkeykckvsnkglpssiektiskakgqprepqvytlppsqeemilmqvsltclvkgfy psdiavewesngqpennyktttppvldsdgsfflysrltvdksrwqegnvfscsvmhealhnhytqkslslslgksggp GPAGLYAQpgsaptssstkktqlqlehllldlqmilnginnyknpkltrmltfklympldcatelkhlqcleeelkpl eevinlaqsknfhlrprdlisninvivlelkgsettfmceyadetativeflnrwitfcqsiistliggggsggggsggggsgg ggsggggsggggssggpGPAGLYAQpgsevqllesggglvqpggslrlscaasgsifsanamgwyrqapgkgl elvavissggstnyadsvkgrftisrdnskntvylqmnslraedtavyycmysgsyyytpndywgqgtlvtvss** |
| 411 | ACP353 (WW0431) | eskygppcppcpapeflggpsvflfppkpkdtlmisrtpevtcvvvdvsqedpevqfnwyvdgvevhnaktkpree qfnstyrvvsyltvlhqdwhigkeykckvsnkglpssiektiskakgqprepqvytlppsqeemilmqvsltclvkgfy psdiavewesngqpennyktttppvldsdgsfflysrltvdksrwqegnvfscsvmhealhnhytqkslslslgksggp GPAGLYAQpgsaptssstkktqlqlehllldlqmilnginnyknpkltrmltfkfympldcatelkhlqcleeelkpl eevinlaqsknfhlrprdlisninvivlelkgsettfmceyadetativeflnrwitfcqsiistliggggsggggsggggsgg ggsggggsggggssggpGPAGLYAQpgsevqllesggglvqpggslrlscaaserifstdvmgwyrqapgkqr elvavvsargttnyldavkgrftisrdnkntlylqmnslraedtavyycyvrettspwriywgqgtlvtvss** |
| 412 | ACP354 (WW0432) | eskygppcppcpapeflggpsvflfppkpkdtlmisrtpevtcvvvdvsqedpevqfnwyvdgvevhnaktkpree qfnstyrvvsyltvlhqdwhigkeykckvsnkglpssiektiskakgqprepqvytlppsqeemilmqvsltclvkgfy psdiavewesngqpennyktttppvldsdgsfflysrltvdksrwqegnvfscsvmhealhnhytqkslslslgksggp GPAGLYAQpgselcdddppeiphalfkamaykegtmlnceckrgfrriksgslymlctgnsshsswdnqcqcts satrnttkqvtpqpeeqkerkttemqspmqpvdqaslpghcrepppweneateriyhfvvgqmvyyqcvqgyralh rgpaesvckmthgktrwtqpqlictgemetsqfpgeekpqaspegrpesetsSlvtddfqiqtemaatmetsiftteyq ggggsggggsggggsggggsggggsggggsggggssggpGPAGLYAQpgsaptssstkktqlqlehllldlqmilngin nyknpkltrmltfkfympkkatelkhlqcleeelkpleevinlaqsknfblrprdlisninvivlelkgsettfmceyadet ativeflnrwitfcqsiistliggggsggggsggggsggggsggggsggggsggggssggpGPAGLYAQpgsEVQLV ESGGGLVQPGGSLRLSCAASGFTFSSYTLAWVRQAPGKGLEWVAAIDSSSYTY SPDTVRGRFTISRDNAKNSLYLQMNSLRAEDTAVYYCARDSNWDALDYWGQ GTTVTVSSsggpGPAGLYAQpgsDIQMTQSPSSLSASVGDRVTITCKAREKLWSA VAWYQQKPGKAPKsLIYSASFRYSGVPSRFSGSGSGTDFTLTISSLQPEDFATY YCQQYYTYPYTFGGGTKVEIK** |
| 413 | ACP355 (WW0433) | eskygppcppcpapeflggpsvflfppkpkdtlmisrtpevtcvvvdvsqedpevqfnwyvdgvevhnaktkpree qfnstyrvvsyltvlhqdwhigkeykckvsnkglpssiektiskakgqprepqvytlppsqeemilmqvsltclvkgfy psdiavewesngqpennyktttppvldsdgsfflysrltvdksrwqegnvfscsvmhealhnhytqkslslslgksggp GPAGLYAQpgselcdddppeiphalfkamaykegtmlnceckrgfrriksgslymlctgnsshsswdnqcqcts satrnttkqvtpqpeeqkerkttemqspmqpvdqaslpghcrepppweneateriyhfvvgqmvyyqcvqgyralh rgpaesvckmthgktrwtqpqlictgemetsqfpgeekpqaspegrpesetsSlvtddfqiqtemaatmetsiftteyq ggggsggggsggggsggggsggggsggggsggggssggpGPAGLYAQpgsaptssstkktqlqlehllldlqmilngin nyknpkltrmltfkfympkkatelkhlqcleeelkpleevinlaqsknfhlrprdlisninvivlelkgsettfmceyadet ativeflnrwitfcqsiistliggggsggggsggggsggggsggggsggggsggggssggpGPAGLYAQpgsEVQLV ESGGGLVQPGGSLRLSCAASGFTFSSYTLAWVRQAPGKGLEWVAAIDSSSYTY SPDTVRGRFTISRDNAKNSLYLQMNSLRAEDTAVYYCARDSNWDALDYWGQ GTTVTVSSGGGGSGGGGSGGGGSDIQMTQSPSSLSASVGDRVTITCKAREKLW SAVAWYQQKPGKAPKsLIYSASFRYSGVPSRFSGSGSGTDFTLTISSLQPEDFAT YYCQQYYTYPYTFGGGTKVEIK** |
| 414 | ACP356 (WW0434) | eskygppcppcpapeflggpsvflfppkpkdtlmisrtpevtcvvvdvsqedpevqfnwyvdgvevhnaktkpree qfnstyrvvsyltvlhqdwhigkeykckvsnkglpssiektiskakgqprepqvytlppsqeemtknqvsltclvkgfy psdiavewesngqpennykappvldsdgsfflysrltvdksrwqegnvfscsvmhealhnhytqkslslslgksggp GPAGLYAQpgselcdddppeiphalfkamaykegtmlnceckrgfrriksgslymlctgnsshsswdnqcqcts satrnttkqvtpqpeeqkerkttemqspmqpvdqaslpghcrepppweneateriyhfvvgqmvyyqcvqgyralh rgpaesvclunthgktrwtqpqlictgemetsqfpgeekpqaspegrpesetsSlytttdfqiqtemaatmetsiftteyq ggggsggggsggggsggggsggggsggggsggggssggpGPAGLYAQpgsaptssstkktqlqlehllldlqmilngin nyknpkltrmlfficfympldcatelkhlqcleeelkpleevinlaqsknfhlrprdlisninvivlelkgsettfmceyadet ativeflnrwitfcqsiistltggggsggggsggggsggggsggggsggggsggggssggpGPAGLYAQpgsEVQLV ESGGGLVQPGGSLRLSCAASGFTFSSYTLAWVRQAPGKGLEWVAAIDSSSYTY SPDTVRGRFTISRDNAKNSLYLQMNSLRAEDTAVYYCARDSNWDALDYWGQ GTTVTVSSsggpGPAGLYAQpgsDIQMTQSPSSLSASVGDRVTITCKVTEKVWGN VAWYQQKPGKAPISLIYSPSLRKSGVPSRFSGSGSGTDFTLTISSLQPEDFATYY CQQYYTYPYTFGGGTKVEIK** |
| 415 | ACP357 (WW0435) | eskygppcppcpapeflggpsvflfppkpkdtlmisrtpevtcvvvdvsqedpevqfnwyvdgvevhnaktkpree qfnstyrvvsyltvlhqdwhigkeykckvsnkglpssiektiskakgqprepqvytlppsqeemtknqvsltclvkgfy psdiavewesngqpennykappvldsdgsfflysrltvdksrwqegnvfscsvmhealhnhytqkslslslgksggp GPAGLYAQpgselcdddppeiphalfkamaykegtmlnceckrgfrriksgslymlctgnsshsswdnqcqcts satrnttkqvtpqpeeqkerkttemqspmqpvdqaslpghcrepppweneateriyhfvvgqmvyyqcvqgyralh rgpaesvclunthgktrwtqpqlictgemetsqfpgeekpqaspegrpesetsSlytttdfqiqtemaatmetsiftteyq ggggsggggsggggsggggsggggsggggsggggssggpGPAGLYAQpgsaptssstkktqlqlehllldlqmilngin nyknpkltrmlfficfympkkatelkhlqcleeelkpleevinlaqsknfhlrprdlisninvivlelkgsettfmceyadet |

Sequence Table

| SEQ ID NO. | Name | Sequence |
|---|---|---|
| | | ativeflnrwitfcqsiistltggggsggggsggggsggggsggggsggggssggpGPAGLYAQpgsEVQLV<br>ESGGGLVQPGGSLRLSCAASGFTFSSYTLAWVRQAPGKGLEWVAAIDSSSYTY<br>SPDTVRGRFTISRDNAKNSLYLQMNSLRAEDTAVYYCARDSNWDALDYWGQ<br>GTTVTVSSGGGGSGGGGSGGGGSDIQMTQSPSSLSASVGDRVTITCKVTEKV<br>WGNVAWYQQKPGKAPISLIYSPSLRKSGVPSRFSGSGSGTDFTLTISSLQPEDF<br>ATYYCQQYTYPYTFGGGTKVEIK** |
| 416 | ACP358<br>(WW0436) | eskygppcppcpapeflggpsvflfppkpkdtlmisrtpevtcvvvdvsqedpevqfnwyvdgvevhnakttkpree<br>qfnstyrvvsyltvlhqdwhigkeykckvsnkglpssiektiskakgqprepqvytlppsqeemtknqvsltclvkgfy<br>psdiavewesngqpennykappvldsdgsfflysrltvdksrwqegnvfscsvmhealhnhytqkslslslgksggp<br>GPAGLYAQpgselcdddppeiphalfkamaykegtmlnceckrgfrriksgslymlctgnsshsswdnqcqcts<br>satrnttkqvtpqpeeqkerkttemqspmqpvdqaslpghcrepppweneateriyhfvvgqmvyyqcvqgyralh<br>rgpaesvclunthgktrwtqpqlictgemetsqfpgeekpqaspegrpesetsSlytttdfqiqtemaatmetsifttey<br>qggggsggggsggggsggggsggggsggggssggpGPAGLYAQpgsaptssstkktqlqlehllldlqmilngin<br>nyknpkltrmlfficfympldcatelkhlqcleeelkpleevinlaqsknfhlrprdlisninvivlelkgsettfmceyadet<br>ativeflnrwitfcqsiistltggggsggggsggggsggggsggggsggggssggpGPAGLYAQpgsevqllesg<br>gglvqpggslrlscaasgsifsanamgwyrqapgklelvavissgggstnyadsvkgrftisrdnskntvylqmnslrae<br>dtavyycmysgsyyytpndywgqgtlvtvss** |
| 417 | ACP359<br>(WW0437) | eskygppcppcpapeflggpsvflfppkpkdtlmisrtpevtcvvvdvsqedpevqfnwyvdgvevhnakttkpree<br>qfnstyrvvsyltvlhqdwhigkeykckvsnkglpssiektiskakgqprepqvytlppsqeemtknqvsltclvkgfy<br>psdiavewesngqpennykappvldsdgsfflysrltvdksrwqegnvfscsvmhealhnhytqkslslslgksggp<br>GPAGLYAQpgselcdddppeiphatfkamaykegtmlnceckrgfrriksgslymlctgnsshsswdnqcqcts<br>satrnttkqvtpqpeeqkerkttemqspmqpvdqaslpghcrepppweneateriyhfvvgqmvyyqcvqgyralh<br>rgpaesvclunthgktrwtqpqlictgemetsqfpgeekpqaspegrpesetsSlytttdfqiqtemaatmetsifttey<br>qggggsggggsggggsggggsggggsggggssggpGPAGLYAQpgsaptssstkktqlqlehllldlqmilngin<br>nyknpkltrmlfficfympldcatelkhlqcleeelkpleevinlaqsknfhlrprdlisninvivlelkgsettfmceyadet<br>ativeflnrwitfcqsiistltggggsggggsggggsggggsggggsggggssggpGPAGLYAQpgsevqllesg<br>gglvqpggslrlscaaserifstdvmgwyrqapgkqrelvavvsargttnyldavkgrftisrdnskntlylqmnslraed<br>tavyycyvrettspwriywgqgtlvtvss** |
| 418 | ACP360<br>(WW0438) | EVQLVESGGGLVQPGGSLRLSCAASGFTFSSYTLAWVRQAPGKGLEWVAAID<br>SSSYTYSPDTVRGRFTISRDNAKNSLYLQMNSLRAEDTAVYYCARDSNWDAL<br>DYWGQGTTVTVSSggggsggggsggggsDIQMTQSPSSLSASVGDRVTITCKASQNV<br>GTNVGWYQQKPGKAPKsLIYSASFRYSGVPSRFSGSGSGTDFTLTISSLQPEDF<br>ATYYCQQYTYPYTFGGGTKVEIKHHHHHH** |
| 419 | ACP361<br>(WW0439) | EVQLVESGGGLVQPGGSLRLSCAASGFTFSSYTLAWVRQAPGKGLEWVAAID<br>SSSYTYSPDTVRGRFTISRDNAKNSLYLQMNSLRAEDTAVYYCARDSNWDAL<br>DYWGQGTTVTVSSsggpGPAGLYAQpgsDIQMTQSPSSLSASVGDRVTITCKASQ<br>NVGTNVGWYQQKPGKAPKALIYSASFRYSGVPSRFSGSGSGTDFTLTISSLQPE<br>DFATYYCQQYTYPYTFGGGTKVEIKHHHHHH** |
| 420 | ACP362<br>(WW0440) | EVQLVESGGGLVQPGGSLRLSCAASGFTFSSYTLAWVRQAPGKGLEWVAAID<br>SSSYTYSPDTVRGRFTISRDNAKNSLYLQMNSLRAEDTAVYYCARDSNWDAL<br>DYWGQGTTVTVSSsggpGPAGLYAQpgsDIQMTQSPSSLSASVGDRVTITCKASQ<br>NVGTNVGWYQQKPGKAPKsLIYSASFRYSGVPSRFSGSGSGTDFTLTISSLQPE<br>DFATYYCQQYTYPYTFGGGTKVEIKHHHHHH** |
| 421 | ACP200 | lveepknlyktncdlyekleygyfqnailvlytqkapqvstptiveaarnlgrvgtkccltlpedqrlpcvedylsailnrycl<br>lhektpvsehytkccsgslverrpcfsaltvdetyvpkefkaaftfhsdictlpekekqikkqtalaelvkhkpkataeqlk<br>tvmdclfaqfldtcckaadkdtcfstegpnlvtrckdalaSGGPGPAGMKGLPGScdlpqthnlinkraltllyq<br>mrrlsplsclkdrkclfgfpqekvdaqqikkaqaipvlseltqqilniftskdssaawnttlldsfcndlhqqlndlqgclmq<br>qvgvqefpltqedallavrkyfhrityylrelcichspcawevvraevwralsssanylgrlreekSGGPGPAGMK<br>GLPGSlveepknlyktncdlyekleygyfqnailvrytqkapqvstptiveaarnlgrvgtkccltlpedqrlpcvedyl<br>sailnrycllhektpvsehytkccsgslverrpcfsaltvdetyvpkefkaelftihsdictlpekekqikkqtalaelvklikp<br>kataeqlktvmddfaqfldtcckaadkdtcfstegpnlvtrckdalaHHHHHH** |
| 422 | ACP201 | eahkseialuyndlgeqhfkglvliafsqylqkcsydehaklvqevtdfaktcvadesaancdkslhtlfgdklcaipnlr<br>enygeladcctkqepernecflqhkddnpslppferpeaeamctsfkenptlfmghylhevarrhpyfyapellyyaeq<br>yneiltqccaeadkescltpkldgykekalvssvrqGGGGSGGGGSGGSlveepknlyktncdlyekleygf<br>qnailvlytqkapqvstptiveaarnlgrvgtkccltlpedqrlpcvedylsailnrycllhektpvsehytkccsgslverrp<br>cfsaltvdetyvpkefkaallfhsdictlpekekqikkqtalaelvklikpkataeqlktvmddfaqfldtcckaadkdtcf<br>stegpnlvtrckdalaSGGPGPAGMKGLPGScdlpqtmlinkraltllvqmrrlsplsclkdrkdfgfpqekv<br>daqqikkagaipvlseltqqilniftskdssaawnifildsfcndlhqqlndlqgclmqqvgvqefpltqedallavrkyfh<br>rityylrekkhspcawevvraevwralsssanylgrlreekSGGPGPAGMKGLPGSeahkseialllyndlge<br>qhflcglvliafsqylqkcsydehaklvqevtclfaktcvadesaancdkslhtlfgdklcaipnlrenygeladcctkqepe<br>rnecflqhkddnpslppferpeaeamctsfkenptlfmghylhevarrhpyfyapellyyaeqyneiltqccaeadkes<br>cltpkldgykekalvssvrqGGGGSGGGGSGGSlveepknlyktncdlyekleygyfqnailviytqkapqvs<br>tptiveaarnlgrvgtkccltlpedqrlpcvedylsailnrycllhektpvsehytkccsgslverrpcfsaltvdetyvpkefk<br>aellfihsdictlpekekqikkqtalaelvklikpkataeqlktvmddfaqfldtcckaadkdtcfstegpnlvtrckdalaH<br>HHHHH** |

Sequence Table

| SEQ ID NO. | Name | Sequence |
|---|---|---|
| 423 | ACP202 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSggggsgggsGGPGPAGMKGLPGSggggsgggscdlpqamlinkraltllvqmrrls<br>plsclkdrkclfgfpqekvdaqqikkagaipvlseltqqilniftskdssaawnttlldsfcndlhqqlndlqgclmqqvgv<br>qefpltqedallavrkyfhrityylrelcichspcawevvraevwralsssanylgrlreekggggsgggsGGPGPAG<br>MKGLPGSggggsgggsEVQLVESGGGLVQPGNSLRLSCAASGFTFSKFGMSWVR<br>QAPGKGLEWVSSISGSGRDTLYAESVKGRFTISRDNAKTTLYLQMNSLRPEDT<br>AVYYCTIGGSLSVSSQGTLVTVSSHHHHHH** |
| 424 | ACP203 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsgggpGPAGLYAQpgscdlpqtmlinkraltllvqmrrlsplsclkdrkdfgfpqekvdaq<br>qikkagaipvlseltqqilniftskdssaawnifildsfcndlhqqlndlqgclmqqvgvqefpltqedallavrkyfhritv<br>ylrelcichspcawevvraevwralsssanylgrlreeksggpGPAGLYAQpgsEVQLVESGGGLVQP<br>GNSLRLSCAASGFTFSKFGMSWVRQAPGKGLEWVSSISGSGRDTLYAESVKG<br>RFTISRDNAKTTLYLQMNSLRPEDTAVYYCTIGGSLSVSSQGTLVTVSS** |
| 425 | ACP204 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsgggpALFKSSFPpgscdlpqthnlinkraltllvqmrrlsplsclkdrkdfgfpqekvdaqqi<br>klcaqaipvlseltqqilniftskdssaawnttlldsfcndlhqqlndlqgclmqqvgvqefpltqedallavrkyfhrityyl<br>rekkhspcawevvraevwralsssanylgrlreeksggpALFKSSFPpgsEVQLVESGGGLVQPGNS<br>LRLSCAASGFTFSKFGMSWVRQAPGKGLEWVSSISGSGRDTLYAESVKGRFTI<br>SRDNAKTTLYLQMNSLRPEDTAVYYCTIGGSLSVSSQGTLVTVSS** |
| 426 | ACP205 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsgggpPLAQKLKSSpgscdlpqthnlinkraltllvqmrrlsplsclkdrkdfgfpqekvdaq<br>qikkagaipvlseltqqilniftskdssaawnifildsfcndlhqqlndlqgclmqqvgvqefpltqedallavrkyfhritv<br>ylrelcichspcawevvraevwralsssanylgrlreeksggpPLAQKLKSSpgsEVQLVESGGGLVQP<br>GNSLRLSCAASGFTFSKFGMSWVRQAPGKGLEWVSSISGSGRDTLYAESVKG<br>RFTISRDNAKTTLYLQMNSLRPEDTAVYYCTIGGSLSVSSQGTLVTVSS** |
| 427 | ACP206 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsgggpGPAGLYAQpgscdlpqthslgsrrtlmllaqmrrislfsclkdrhdfgfpqeefgnqf<br>qkaetipvlhemiqqifnlfstkdssaawdetlldkfytelyqqlndleacviqgvgvtetplmkedsilavrkyfqritlyl<br>kekkyspcawevvraeimrsfslstnlqesliskesggpGPAGLYAQpgsEVQLVESGGGLVQPGN<br>SLRLSCAASGFTFSKFGMSWVRQAPGKGLEWVSSISGSGRDTLYAESVKGRFT<br>ISRDNAKTTLYLQMNSLRPEDTAVYYCTIGGSLSVSSQGTLVTVSS** |
| 428 | ACP207 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsgggpALFKSSFPpgscdlpqthslgsrrtlmllaqmrrislfsclkdrhdfgfpqeefgnqfq<br>kaetipvlhemiqqifnlfstkdssaawdetlldkfytelyqqlndleacviqgvgvtetplmkedsilavrkyfqritlylk<br>ekkyspcawevvraeimrsfslstnlqesliskesggpALFKSSFPpgsEVQLVESGGGLVQPGNSL<br>RLSCAASGFTFSKFGMSWVRQAPGKGLEWVSSISGSGRDTLYAESVKGRFTIS<br>RDNAKTTLYLQMNSLRPEDTAVYYCTIGGSLSVSSQGTLVTVSS** |
| 429 | ACP208 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsgggpPLAQKLKSSpgscdlpqthslgsrrtlmllaqmrrislfsclkdrhdfgfpqeefgnqf<br>qkaetipvlhemiqqifnlfstkdssaawdetlldkfytelyqqlndleacviqgvgvtetplmkedsilavrkyfqritlyl<br>kekkyspcawevvraeimrsfslstnlqesliskesggpPLAQKLKSSpgsEVQLVESGGGLVQPG<br>NSLRLSCAASGFTFSKFGMSWVRQAPGKGLEWVSSISGSGRDTLYAESVKGRF<br>TISRDNAKTTLYLQMNSLRPEDTAVYYCTIGGSLSVSSQGTLVTVSS** |
| 430 | ACP211 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSSGGPGPAGMKGLPGShgtviesleslnnyfnssgidveeekslfldiwrnwqkdgdm<br>kilqsqiisfylrlfevlkdnqaisnnisvieshlittffsnskakkdafmsiakfevnnpqvqrqafnelirvvhqllpesslr<br>krkrsrcSGGPGPAGMKGLPGScdlpqthnlinkraltllvqmrrlsplsclkdrkclfgfpqekvdaqqikka<br>qaipvlseltqqilniftskdssaawnttlldsfcndlhqqlndlqgclmqqvgvqefpltqedallavrkyfhritvylrek<br>khspcawevvraevwralsssanvlgrlreekSGGPGPAGMKGLPGShgtviesleslnnyfnssgidveek<br>slfldiwrnwqkdgdmkilqsqiisfylrlfevlkdnqaisnnisvieshlittffsnskaldcdafmsiakfevnnpqvqr<br>qafnelirvvhqllpesshkrkrsrcSGGPGPAGMKGLPGSEVQLVESGGGLVQPGNSLRLS<br>CAASGFTFSKFGMSWVRQAPGKGLEWVSSISGSGRDTLYAESVKGRFTISRDN<br>AKTTLYLQMNSLRPEDTAVYYCTIGGSLSVSSQGTLVTVSSHHHHHH |
| 431 | ACP213 | lveepknlvktncdlyeklgeygfqnailviytqkapqvstptiveaarnlgrvgtkccctlpedqrlpcvedylsailnrvcl<br>lhektpvsehytkccsgslverrpcfsaltvdetyvpkefkaelftfhsdictlpekeqikkqtalaelvkhkpkataeqlk<br>tvmdclfaqfldtcckaadkdtcfstegpnlvtrckdalaSGGPGPAGMKGLPGShgtviesleslnnyfnssgi<br>dveekslfldiwrnwqkdgdmkilqsqiisfylrlfevlkdnqaisnnisvieshlittffsnskaldcdafmsiakfevnn |

-continued

Sequence Table

| SEQ ID NO. | Name | Sequence |
|---|---|---|
| | | pqvqrqafnelirvvhqllpesshkrkrsrcSGGPGPAGMKGLPGSlveepknlvktncdlyeklgeygfqn ailvlytqkapqvstptiveaarnlgrvgtkccstlpedqrlpcvedylsailnrycllhektpvsehvtkccsgslverrpcfs altvdetyvpkefkaelft-fhsdictlpekekqikkqtalaelvklikpkataeqlktvmddfaqfldtcckaadkdtcfste gpnlvtrckdalaSGGPGPAGMKGLPGShgtviesleslnnyfnssgidveekslfldiwrnwqkdgdmkil qsqiisfylrlfevlkdnqaisnnisvieshlittffsnskakkdafmsiakfevnnpqvqrqafnelirvvhqllpesshkr krsrcSGGPGPAGMKGLPGSlveepknlvktncdlyeklgeygfqnailviytqkapqvstptiveaarnlgr vgtkccstlpedqrlpcvedylsailnrycllhektpvsehvtkccsgslverrpcfsaltvdetyvpkefkaelftfhsdictl pekekqikkqtalaelvklikpkataeqlktvmddfaqfldtcckaadkdtcfstegpnlvtrckdalaHHHHHH** |
| 432 | ACP214 | eahkseialllyndlgeqhflcglvliafsqylqkcsydehaklvqevtdfaktcvadesaancdkslhtlfgdklcaipnlr enygeladcctkqepernecflqhkddnpslppferpeaeamctsfkenpttfmghylhevarrhpyfyapellyyaeq yneiltqccaeadkescltpkldgvkekalvssvrqGGGSGGGGGSGGSlveepknlvktncdlyeklgeygf qnailvlytqkapqvstptiveaarnlgrvgtkccstlpedqrlpcvedylsailnrycllhektpvsehytkccsgslverrp cfsaltvdetyvpkefkaetflfhsdictlpekekqikkqtalaelvkhkpkataeqlktvmddfaqfldtcckaadkdtcf stegpnlvtrckdalaSGGPGPAGMKGLPGShgtviesleslnnyfnssgidveekslfldiwrnwqkdgdm kilqsqiisfylrlfevlkdnqaisnnisvieshlittffsnskakkdafmsiakfevnnpqvqrqafnelirvvhqllpesslr krkrsrcSGGPGPAGMKGLPGSeahkseialuyndlgeqhfkglvliafsqylqkcsydehaklvqevtdfa ktcvadesaancdkslhtlfgdklcaipnlrenygeladcctkqepernecflqhkddnpslppferpeaeamctsfken pttfmghylhevarrhpyfyapellyyaeqyneiltqccaeadkescltpkldgvkekalvssvrqGGGGSGGGG SGGSlveepknlvktncdlyeklgeygfqnailviytqkapqvstptiveaarnlgrvgtkccstlpedqrlpcvedylsa ilnrycllhektpvsehytkccsgslverrpcfsaltvdetyvpkefkaelftfhsdictlpekekqikkqtalaelvkhkpk ataeqlktvmddfaqfldtcckaadkdtcfstegpnlvtrckdalaSGGPGPAGMKGLPGShgtviesleslnn yfnssgidveekslfldiwrnwqkdgdmkilqsqiisfylrlfevlkdnqaisnnisvieshlittffsnskakkdafmsia kfevnnpqvqrqafnelirvvhqllpesslrlukrsrcSGGPGPAGMKGLPGSeahkseiahryndlgeqhflc glvliafsqylqkcsydehaklvqevtdfaktcvadesaancdkslhtlfgdklcaipnlrenygeladcctkqepernec flqhkddnpslppferpeaeamctsfkenptlfmghylhevarrhpyfyapellyyaeqyneiltqccaeadkescltpk ldukekalvssvrqGGGGSGGGGSGGSlveepknlvktncdlyeklgeygfqnailviytqkapqvstptiv eaarnlgrvgtkccstlpedqrlpcvedylsailnrycllhektpvsehytkccsgslverrpcfsaltvdetyvpkefkaelft fhsdictlpekekqikkqtalaelvkhkpkataeqlktvmddfaqfldtcckaadkdtcfstegpnlvtrckdalaHHH HHH** |
| 433 | ACP215 | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSggggsgggSGGPGPAGMKGLPGSggggsgggshgtviesleslnnyfnssgidvee kslfldiwrnwqkdgdmkilqsqiisfylrlfevlkdnqaisnnisvieshlittffsnskakkdafmsiakfevnnpqvq rqafnelirvvhqllpesshkrkrsrcggggsgggSGGPGPAGMKGLPGSggggsgggsEVQLVESG GGLVQPGNSLRLSCAASGFTFSKFGMSWVRQAPGKGLEWVSSISGSGRDTLY AESVKGRFTISRDNAKTTLYLQMNSLRPEDTAVYYCTIGGSLSVSSQGTLVTV SSggggsgggSGGPGPAGMKGLPGSggggsgggshgtviesleslnnyfnssgidveekslfldiwrnwq kdgdmkilqsqiisfylrlfevlkdnqaisnnisvieshlitlffsnskaldcdafmsiakfevnnpqvqrqafneffivvhq llpesshkrkrsrcggggsgggSGGPGPAGMKGLPGSggggsgggsEVQLVESGGGLVQPGN SLRLSCAASGFTFSKFGMSWVRQAPGKGLEWVSSISGSGRDTLYAESVKGRFT ISRDNAKTTLYLQMNSLRPEDTAVYYCTIGGSLSVSSQGTLVTVSSHHHHHH** |
| 434 | ACP240 | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSggggsggggsggggsiwelkkdvyvveldwypdapgemvvltcdtpeedgitwtldqssevl gsgktltiqvkefgdagqytchkggevlshsllllhkkedgiwstdilkdqkepknktflrceaknysgrftcwwlttistd llfsvksssrgsdpqgvtcgaatlsaervrgdnkeyeysvecqedsacpaaeeslpievmvdavhklkyenytssffirdi ikpdppknlqlkplknsrqvevsweypdtwstphsyfsitfcvqvqgkskrekkdrvftdkisatvicrknasisvraqd iyysssswsewasvpcsggggsggggsggggsrvipvsgparclsqsrnlltttddmvktareklkhysctaedidhedi trdqtstlktclplelhknesclatretssttrgsclppqktslmmticlgsiyedlkmyqtefqainaalqnhnhqqiildkg mlvaidelmqslnhngetlrqkppvgeadpyrvkmklcillhafstryvtimvmgylssaggggsggggsggggsg ggggsggggsggggsggggsggggsggggsQSVLTQPPSVSGAPGQRVTISCSGSRSNIGSNT VKWYQQLPGTAPKLLIYYNDQRPSGVPDRFSGSKSGTSASLAITGLQAEDEAD YYCQSYDRYTHPALLFGTGTKVTVLggggsggggsggggsQVQLVESGGGVVQPGR SLRLSCAASGFTFSSYGMHWVRQAPGKGLEWVAFIRYDGSNKYYADSVKGR FTISRDNSKNTLYLQMNSLRAEDTAVYYCKTHGSHDNWGQGTMVTVSSHHH HHH |
| 435 | ACP241 | EAHKSEIAHRYNDLGEQHFKGLVLIAFSQYLQKCSYDEHAKLVQEVTDFAKT CVADESAANCDKSLHTLFGDKLCAIPNLRENYGELADCCTKQEPERNECFLQH KDDNPSLPPFERPEAEAMCTSFKENPTTFMGHYLHEVARRHPYFYAPELLYYA EQYNEILTQCCAEADKESCLTPKLDGVKEKALVSSVRQRMKCSSMQKFGERA FKAWAVARLSQTFPNADFAEITKLATDLTKVNKECCHGDLLECADDRAELAK YMCENQATISSKLQTCCDKPLLKKAHCLSEVEHDTMPADLPAIAADFVEDQE VCKNYAEAKDVFLGTFLYEYSRRHPDYSVSLLLRLAKKYEATLEKCCAEANP PACYGTVLAEFQPLVEEPKNLVKTNCDLYEKLGEYGFQNAILVRYTQKAPQV STPTLVEAARNLGRVGTKCCTLPEDQRLPCVEDYLSAILNRVCLLHEKTPVSE HVTKCCSGSLVERRPCFSALTVDETYVPKEFKAETFTFHSDICTLPEKEKQIKK QTALAELVKHKPKATAEQLKTVMDDFAQFLDTCCKAADKDTCFSTEGPNLVT RCKDALASGGPGPAGMKGLPGSiwelkkdvyvveldwypdapgemvvitcdtpeedgitwadqs sevlgsgktltiqvkefgdagqytchkggevlshsllllhkkedgiwstdilkdqkepknktflrceaknysgrftcwwltt |

| SEQ ID NO. | Name | Sequence |
|---|---|---|
| | | istdltfsvkssrgssdpqgvtcgaatlsaervrgdnkeyeysvecqedsacpaaeeslpievmvdavhklkyenytssf firdiiikpdppknlqlkplknsrqvevsweypdtwstphsyfsltfcvqvqgkskrekkdrvftdktsatvicrknasisv raqthyyssswsewasvpcsggggsggggsggggsrvipvsgparclsqsrifilkttddmvktareklkhysctaedi dheditrdqtstlktctclplelhknesclatretsstrrgsclppqktslmmticlgsiyedlkmyqtefqainaalqnhnhqqi ildkgmlvaidelmqslnhngetlrqkppvgeadpyrvkmklcillhafstryvtinrvmgylssaSGGPGPAG MKGLPGSggggsggggsggggsggggsggggsggggsQSVLTQPPSVSGAPGQRVTISCSGS RSNIGSNTVKWYQQLPGTAPKLLIYYNDQRPSGVPDRFSGSKSGTSASLAITGL QAEDEADYYCQSYDRYTHPALLFGTGTKVTVLggggsggggsggggsQVQLVESGG GVVQPGRSLRLSCAASGFTFSSYGMHWVRQAPGKGLEWVAFIRYDGSNKYY ADSVKGRFTISRDNSKNTLYLQMNSLRAEDTAVYYCKTHGSHDNWGQGTMV TVSSHHHHHH** |
| 436 | ACP242 | iwelkkdvyvveldwypdapgemvvitcdtpeedgitwtldqssevlgsgktltiqvkefgdagqytchkggevlshs llllhkkedgiwstdilkdqkepknktflrceaknysgrftcwwlttistdltfsvkssrgssdpqgvtcgaatlsaervrgd nkeyeysvecqedsacpaaeeslpievmvdavhklkyenytssffirdiikpdppknlqlkplknsrqvevsweypdt wstphsyfsltkvqvqgkskrekkdivftdktsatvicrknasisvraqthyyssswsewasvpcsggggsggggsgg ggsrvipvsgparclsqsrnllkttddmvktareklkhysctaedidheditrdqtstlktctclplelhknesclatretss ttrgsclppqktslmmticlgsiyedlkmyqtefqainaalqnhnhqqiildkgmlvaidelmqslnhngetlrqkppvgead pyrvkmklcillhafstryvtinrvmgylssaSGGPGPAGMKGLPGSggggsggggsggggsggggsgg gsggggsQSVLTQPPSVSGAPGQRVTISCSGSRSNIGSNTVKWYQQLPGTAPKLLI YYNDQRPSGVPDRFSGSKSGTSASLAITGLQAEDEADYYCQSYDRYTHPALLF GTGTKVTVLggggsggggsggggsQVQLVESGGGVVQPGRSLRLSCAASGFTFSSYG MHWVRQAPGKGLEWVAFIRYDGSNKYYADSVKGRFTISRDNSKNTLYLQMN SLRAEDTAVYYCKTHGSHDNWGQGTMVTVSSSGGPGPAGMKGLPGSEAHKS EIAHRYNDLGEQHFKGLVLIAFSQYLQKCSYDEHAKLVQEVTDFAKTCVADE SAANCDKSLHTLFGDKLCAIPNLRENYGELADCCTKQEPERNECFLQHKDDNP SLPPFERPEAEAMCTSFKENPTTFMGHYLHEVARRHPYFYAPELLYYAEQYNE ILTQCCAEADKESCLTPKLDGVKEKALVSSVRQRMKCSSMQKFGERAFKAWA VARLSQTFPNADFAEITKLATDLTKVNKECCHGDLLECADDRAELAKYMCEN QATISSKLQTCCDKPLLKKAHCLSEVEHDTMPADLPAIAADFVEDQEVCKNY AEAKDVFLGTFLYEYSRRHPDYSVSLLLRLAKKYEATLEKCCAEANPPACYG TVLAEFQPLVEEPKNLVKTNCDLYEKLGEYGFQNAILVRYTQKAPQVSTPTLV EAARNLGRVGTKCCTLPEDQRLPCVEDYLSAILNRVCLLHEKTPVSEHVTKCC SGSLVERRPCFSALTVDETYVPKEFKAETFTFHSDICTLPEKEKQIKKQTALAEL VKHKPKATAEQLKTVMDDFAQFLDTCCKAADKDTCFSTEGPNLVTRCKDAL AHHHHHH** |
| 437 | ACP243 | vprdcgckpcictypevssvfifppkpkdvititltpkvtcvvvdiskddpevqfswfvddvevhtaqtqpreeqfnstf rsyselpimhqdvwingkefkcrynsaafpapiektisktkgrpkapqvytippkeqmakdkvsltcmitclffpeditv ewqwngqpaenyknrqpimdtdgsyfvyskinvqksnweagniftcsvlheglhnhhtekslshspgkSGGPG PAGMKGLPGSiwellckdvyvveldwypdapgemvvitcdtpeedgitwtldqssevlgsgktltiqvkefgda gqytchkggevlshslllllhkkedgiwstdilkdqkepknktflrceaknysgrftcwwlttistdltfsvkssrgssdpqg vtcgaatlsaervrgdnkeyeysvecqedsacpaaeeslpievmvdavhklkyenytssffirdiikpdppknlqlkplk nsrqvevsweypdtwstphsyfsltfcvqvqgkskrekkdrvftdktsatvicrknasisvraqthyyssswsewasvp csggggsggggsggggsrvipvsgparclsqsrifilkttddmvktareklkhysctaedidheditrdqtstlktclplelh knesclatretsstrrgsclppqktslmmticlgsiyedlkmyqtefqainaalqnhnhqqiildkgmlvaidelmqslnh ngetlrqkppvgeadpyrvkmklcillhafstrvvtinrvmgylssaSGGPGPAGMKGLPGSggggsgggg sggggsggggsggggsQSVLTQPPSVSGAPGQRVTISCSGSRSNIGSNTVKWYQ QLPGTAPKLLIYYNDQRPSGVPDRFSGSKSGTSASLAITGLQAEDEADYYCQS YDRYTHPALLFGTGTKVTVLggggsggggsggggsQVQLVESGGGVVQPGRSLRLS CAASGFTFSSYGMHWVRQAPGKGLEWVAFIRYDGSNKYYADSVKGRFTISRD NSKNTLYLQMNSLRAEDTAVYYCKTHGSHDNWGQGTMVTVSSHHHHHH** |
| 438 | ACP244 | iwelkkdvyvveldwypdapgemvvitcdtpeedgitwtldqssevlgsgktltiqvkefgdagqytchkggevlshs llllhkkedgiwstdilkdqkepknktflrceaknysgrftcwwlttistdltfsvkssrgssdpqgvtcgaatlsaervrgd nkeyeysvecqedsacpaaeeslpievmvdavhklkyenytssffirdiikpdppknlqlkplknsrqvevsweypdt wstphsyfsltkvqvqgkskrekkdwftdktsatvicrknasisvraqthyyssswsewasvpcsggggsggggsgg ggsrvipvsgparclsqsrnllkttddmvktareklkhysctaedidheditrdqtstlktclplelhknesclatretsst trgsclppqktslmmticlgsiyedlkmyqtefqainaalqnhnhqqiildkgmlvaidelmqslnhngetlrqkppvgead pyrvkmklcillhafstrvvtinrvmgylssaSGGPGPAGMKGLPGSggggsggggsggggsggggsggg gsggggsQSVLTQPPSVSGAPGQRVTISCSGSRSNIGSNTVKWYQQLPGTAPKLLI YYNDQRPSGVPDRFSGSKSGTSASLAITGLQAEDEADYYCQSYDRYTHPALLF GTGTKVTVLggggsggggsggggsQVQLVESGGGVVQPGRSLRLSCAASGFTFSSYG MHWVRQAPGKGLEWVAFIRYDGSNKYYADSVKGRFTISRDNSKNTLYLQMN SLRAEDTAVYYCKTHGSHDNWGQGTMVTVSSSGGPGPAGMKGLPGSvprdcgc kpcictypevssvfifppkpkdvltitltpkvtcwvdiskddpevqfswfvddvevhtaqtqpreeqfnstfrsyselpi mhqdvwhigkefkcrynsaafpapiektisktkgrpkapqvytippkeqmakdkvsltcmitdffpeditvewqwn gqpaenyknrqpimdtdgsyfvysklnvqksnweagntftcsvlheglhnhhtekslshspgkHHHHHH** |
| 439 | ACP245 | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGGSLSVS SQGTLVTVSSSGGPGPAGMKGLPGSiwelkkdvyvveldwypdapgemvvltcdtpeedgitwtl dqssevlgsgkiltiqvkefgdagqytchkggevlshslllllhkkedgiwstdilkdqkepknkffirceaknysgrftcw |

Sequence Table

| SEQ ID NO. | Name | Sequence |
|---|---|---|
| | | wittistdiffsvkssrgssdpqgvtcgaatlsaervrgdnkeyeysvecqedsacpaaeeslpievmvdavhklkyeny tssffirdiikpdppknlqlkplknsrqvevsweypdtwstphsyfsltkvqvqgkskrekkdrvftdktsatvicrkna sisvraqthyyssswsewasvpcsggggsggggsrvipvsgparclsqunllkttddmvktareklkhyscta edidheditrdqtstlktclplelhknesclatretsstfrgsclppqktslmmticlgsiyedlkmyqtefqainaalqnhnh qqiildkgmlvaidelmqslnhngetlrqkppvgeadpyrvkmklcillhafstrvvtinrvmgylssaSGGPGPA GMKGLPGSggggsggggsggggsggggsggggsggggsQSVLTQPPSVSGAPGQRVTISCS GSRSNIGSNTVKWYQQLPGTAPKLLIYYNDQRPSGVPDRFSGSKSGTSASLAIT GLQAEDEADYYCQSYDRYTHPALLFGTGTKVTVLSGGPGPAGMKGLPGSQV QLVESGGGVVQPGRSLRLSCAASGFTFSSYGMHWVRQAPGKGLEWVAFIRYD GSNKYYADSVKGRFTISRDNSKNTLYLQMNSLRAEDTAVYYCKTHGSHDNW GQGTMVTVSSHHHHHH |
| 440 | ACP247 | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSSGGPGPAGMKGLPGSiwelkkdvyvveldwypdapgemvvltcdtpeedgitwtl dqssevlgsgkiltiqvkefgdagqytchkggevlshslllllhkkedgiwstdilkdqkepknkifirceaknysgrftcw wittistdlifsvkssrgssdpqgvtcgaatlsaervrgdnkeyeysvecqedsacpaaeeslpievmvdavhklkyeny tssffirdiikpdppknlqlkplknsrqvevsweypdtwstphsyfsltkvqvqgkskrekkdrvftdktsatvicrkna sisvraqthyyssswsewasvpcsggggsggggsggggsrvipvsgparclsqsrnllkttddmvktareklkhyscta edidheditrdqtstlktclplelhknesclatretsstfrgsclppqktslmmticlgsiyedlkmyqtefqainaalqnhnh qqiildkgmlvaidelmqslnhngetlrqkppvgeadpyrvkmklcillhafstrvvtinrvmgylssaSGGPGPA GMKGLPGSggggsggggsggggsggggsggggsggggsQVQLQESGGGLVQAGGSLRLSC AASGRTFSSVYDMGWFRQAPGKDREFVARITESARNTRYADSVRGRFTISRDN AKNTVYLQMNNLELEDAAVYYCAADPQTVVVGTPDYWGQGTQVTVSSHHH HHH |
| 636 | WW0301 | APTSSSTKKTQLQLEHLLLDLQMILNGINNYKNPKLTRMLTFKFYMPKKATEL KHLQCLEEELKPLEEVLNLAQSKNFHLRPRDLISNINVIVLELKGSETTFMCEY ADETATIVEFLNRWITFCQSIISTLTSGGPGPAGMKGLPGSEVQLVESGGGLVQ PGNSLRLSCAASGFTFSKFGMSWVRQAPGKGLEWVSSISGSGRDTLYAESVKG RFTISRDNAKTTLYLQMNSLRPEDTAVYYCTIGGSLSVSSQGTLVTVSSGGGGS GGGGSGGGGSGGGGSGGGGSGGGGSGGGGSGGGGSEVQLVESGGGL VQPGGSLRLSCAASGFTFSSYTLAWVRQAPGKGLEWVAAIDSSSYTYSPDTVR GRFTISRDNAKNSLYLQMNSLRAEDTAVYYCARDSNWDALDYWGQGTTVTV SSGGGGSGGGGSGGGGSDIQMTQSPSSLSASVGDRVTITCKASQNVGTNVGW YQQKPGKAPKALIYSASFRYSGVPSRFSGSGSGTDFTLTISSLQPEDFATYYCQ QYYTYPYTFGGGTKVEIKHHHHHH |
| 637 | WW0353 | APTSSSTKKTQLQLEHLLLDLQMILNGINNYKNPKLTRMLTFKFYMPKKATEL KHLQCLEEELKPLEEVLNLAQSKNFHLRPRDLISNINVIVLELKGSETTFMCEY ADETATIVEFLNRWITFCQSIISTLTSGGPGPAGMKGLPGSVPRDCGCKPCICTV PBVSSVFIFPPKPKDVLTITLTPKVTCVVVDISKDDPEVQFSWFVDDVEVHTAQ TQPREEQFNSTFRSVSELPIMHQDWLNGKEFKCRVNSAAFPAPIEKTISKTKGR PKAPQVYTIPPPKEQMAKDKVSLTCMITDFFPEDITVEWQWNGQPAENYKNT QPIMDTDGSYFVYSKLNVQKSNWEAGNTFTCSVLHEGLHNHHTEKSLSHSPG KGGGGSGGGGSGGGGSGGGGSGGGGSGGGGSSGGPGPAGMKGLPGSEVQLV ESGGGLVQPGGSLRLSCAASGFTFSSYTLAWVRQAPGKGLEWVAAIDSSSYTY SPDTVRGRFTISRDNAKNSLYLQMNSLRAEDTAVYYCARDSNWDALDYWGQ GTTVTVSSGGGGSGGGGSGGGGSDIQMTQSPSSLSASVGDRVTITCKASQNVG TNVGWYQQKPGKAPKALIYSASFRYSGVPSRFSGSGSGTDFTLTISSLQPEDFA TYYCQQYYTYPYTFGGGTKVEIKHHHHHH |
| 638 | WW0355 | APTSSSTKKTQLQLEHLLLDLQMILNGINNYKNPKLTRMLTFKFYMPKKATEL KHLQCLEEELKPLEEVLNLAQSKNFHLRPRDLISNINVIVLELKGSETTFMCEY ADETATIVEFLNRWITFCQSIISTLTSGGPGPAGMKGLPGSGGGGSGGGGSGGG GSGGGGSGGGGSGGGGSEVQLVESGGGLVQPGGSLRLSCAASGFTFSSYTLA WVRQAPGKGLEWVAAIDSSSYTYSPDTVRGRFTISRDNAKNSLYLQMNSLRA EDTAVYYCARDSNWDALDYWGQGTTVTVSSGGGGSGGGGSGGGGSDIQMT QSPSSLSASVGDRVTITCKASQNVGTNVGWYQQKPGKAPKALIYSASFRYSGV PSRFSGSGSGTDFTLTISSLQPEDFATYYCQQYYTYPYTFGGGTKVEIKSGGPG PAGMKGLPGSVPRDCGCKPCICTVPEVSSVFIFPPKPKDVLTITLTPKVTCVVV DISKDDPEVQFSWFVDDVEVHTAQTQPREEQFNSlFRSVSELPIMHQDWLNGK EFKCRVNSAAFPAPIEKTISKTKGRPKAPQVYTIPPPKEQMAKDKVSLTCMITD FFPEDITVEWQWNGQPAENYKNTQPIMDTDGSYFVYSKLNVQKSNWEAGNT FTCSVLHEGLHNHHTEKSLSHSPGKHHHHHH |
| 639 | WW0365 | APTSSSTKKTQLQLEHLLLDLQMILNGINNYKNPKLTRMLTFKFYMPKKATEL KHLQCLEEELKPLEEVLNLAQSKNFHLRPRDLISNINVIVLELKGSETTFMCEY ADETATIVEFLNRWITFCQSIISTLTGGGSGGGSGGGSGGGSEVQLVESGGGLV QPGNSLRLSCAASGFTFSKFGMSWVRQAPGKGLEWVSSISGSGRDTLYAESVK GRFTISRDNAKTTLYLQMNSLRPEDTAVYYCTIGGSLSVSSQGTLVTVSSGGG GSGGGGSGGGGSGGGGSGGGGSSGGPGPAGMKGLPGSEVQLVESGG GLVQPGGSLRLSCAASGFTFSSYTLAWVRQAPGKGLEWVAAIDSSSYTYSPDT |

| SEQ ID NO. | Name | Sequence |
|---|---|---|
| | | VRGRFTISRDNAKNSLYLQMNSLRAEDTAVYYCARDSNWDALDYWGQGTTV TVSSGGGGSGGGGSGGGGSDIQMTQSPSSLSASVGDRVTITCKASQNVGTNVG WYQQKPGKAPKALIYSASFRYSGVPSRFSGSGSTDFTLTISSLQPEDFATYYC QQYYTYPYTFGGGTKVEIKHHHHHHEPEA |
| 640 | WW0366 | APTSSSTKKTQLQLEHLLLDLQMILNGINNYKNPKLTRMLTFKFYMPKKATEL KHLQCLEEELKPLEEVLNLAQSKNFHLRPRDLISNINVIVLELKGSETTFMCEY ADETATIVEFLNRWITFCQSIISTLTSGGPGPAGMKGLPGSEVQLVESGGGLVQ PGNSLRLSCAASGFTFSKFGMSWVRQAPGKGLEWVSSISGSGRDTLYAESVKG RFTISRDNAKTTLYLQMNSLRPEDTAVYYCTIGGSLSVSSQGTLVTVSSHHHH HHEPEA |
| 641 | WW0472 | VPRDCGCKPCICTVPEVSSVFIFPPKPKDVLTITLTPKVTCVVVDISKDDPEVQF SWFVDDVEVHTAQTQPREEQFNSTFRSVSELPIMHQDWLNGKEFKCRVNSAA FPAPIEKTISKTKGRPKAPQVYTIPPPKEQMAKDKVSLTCMITDFFPEDITVEWQ WNGQPAENYKNTQPIMDTDGSYFVYSKLNVQKSNWEAGNTFTCSVLHEGLH NHHHTEKSLSHSPGKSGGPGPAGLYAQPGSAPTSSSTKKTQLQLEHLLLDLQMI LNGINNYKNPKLTRMLTFKFYMPKKATELKHLQCLEEELKPLEEVLNLAQSK NFHLRPRDLISNINVIVLELKGSETTFMCEYADETATIVEFLNRWITFCQSIISTL TGGGGSGGGGSGGGGSGGGGSGGGGSGGGGSSGGPGPAGLYAQPGSEVQLV ESGGGLVQPGGSLRLSCAASGFTFSSYTLAWVRQAPGKGLEWVAAIDSSSYTY SPDTVRGRFTISRDNAKNSLYLQMNSLRAEDTAVYYCARDSNWDALDYWGQ GTTVTVSSGGPGPAGLYAQPGSDIQMTQSPSSLSASVGDRVTITCKAREKLW SAVAWYQQKPGKAPKSLIYSASFRYSGVPSRFSGSGSGTDFTLTISSLQPEDFA TYYCQQYYTYPYTFGGGTKVEIK |
| 642 | WW0473 | VPRDCGCKPCICTVPEVSSVFIFPPKPKDVLTITLTPKVTCVVVDISKDDPEVQF SWFVDDVEVHTAQTQPREEQFNSTFRSVSELPIMHQDWLNGKEFKCRVNSAA FPAPIEKTISKTKGRPKAPQVYTIPPPKEQMAKDKVSLTCMITDFFPEDITVEWQ WNGQPAENYKNTQPIMDTDGSYFVYSKLNVQKSNWEAGNTFTCSVLHEGLH NHHHTEKSLSHSPGKSGGPGPAGLYAQPGSAPTSSSTKKTQLQLEHLLLDLQMI LNGINNYKNPKLTRMLTFKFYMPKKATELKHLQCLEEELKPLEEVLNLAQSK NFHLRPRDLISNINVIVLELKGSETTFMCEYADETATIVEFLNRWITFCQSIISTL TGGGGSGGGGSGGGGSGGGGSGGGGSGGGGSSGGPGPAGLYAQPGSEVQLV ESGGGLVQPGGSLRLSCAASGFTFSSYTLAWVRQAPGKGLEWVAAIDSSSYTY SPDTVRGRFTISRDNAKNSLYLQMNSLRAEDTAVYYCARDSNWDALDYWGQ GTTVTVSSGGGGSGGGGSGGGGSDIQMTQSPSSLSASVGDRVTITCKAREKLW SAVAWYQQKPGKAPKSLIYSASFRYSGVPSRFSGSGSGTDFTLTISSLQPEDFA TYYCQQYYTYPYTFGGGTKVEIK |
| 643 | WW0474 | VPRDCGCKPCICTVPEVSSVFIFPPKPKDVLTITLTPKVTCVVVDISKDDPEVQF SWFVDDVEVHTAQTQPREEQFNSTFRSVSELPIMHQDWLNGKEFKCRVNSAA FPAPIEKTISKTKGRPKAPQVYTIPPPKEQMAKDKVSLTCMITDFFPEDITVEWQ WNGQPAENYKNTQPIMDTDGSYFVYSKLNVQKSNWEAGNTFTCSVLHEGLH NHHHTEKSLSHSPGKSGGPGPAGLYAQPGSAPTSSSTKKTQLQLEHLLLDLQMI LNGINNYKNPKLTRMLTFKFYMPKKATELKHLQCLEEELKPLEEVLNLAQSK NFHLRPRDLISNINVIVLELKGSETTFMCEYADETATIVEFLNRWITFCQSIISTL TGGGGSGGGGSGGGGSGGGGSGGGGSGGGGSSGGPGPAGLYAQPGSEVQLV ESGGGLVQPGGSLRLSCAASGFTFSSYTLAWVRQAPGKGLEWVAAIDSSSYTY SPDTVRGRFTISRDNAKNSLYLQMNSLRAEDTAVYYCARDSNWDALDYWGQ GTTVTVSSSGGPGPAGLYAQPGSDIQMTQSPSSLSASVGDRVTITCKVTEKVW GNVAWYQQKPGKAPISLIYSPSLRKSGVPSRFSGSGSGTDFTLTISSLQPEDFAT YYCQQYYTYPYTFGGGTKVEIK |
| 644 | WW0475 | VPRDCGCKPCICTVPEVSSVFIFPPKPKDVLTITLTPKVTCVVVDISKDDPEVQF SWFVDDVEVHTAQTQPREEQFNSTFRSVSELPIMHQDWLNGKEFKCRVNSAA FPAPIEKTISKTKGRPKAPQVYTIPPPKEQMAKDKVSLTCMITDFFPEDITVEWQ WNGQPAENYKNTQPIMDTDGSYFVYSKLNVQKSNWEAGNTFTCSVLHEGLH NHHHTEKSLSHSPGKSGGPGPAGLYAQPGSAPTSSSTKKTQLQLEHLLLDLQMI LNGINNYKNPKLTRMLTFKFYMPKKATELKHLQCLEEELKPLEEVLNLAQSK NFHLRPRDLISNINVIVLELKGSETTFMCEYADETATIVEFLNRWITFCQSIISTL TGGGGSGGGGSGGGGSGGGGSGGGGSGGGGSSGGPGPAGLYAQPGSEVQLV ESGGGLVQPGGSLRLSCAASGFTFSSYTLAWVRQAPGKGLEWVAAIDSSSYTY SPDTVRGRFTISRDNAKNSLYLQMNSLRAEDTAVYYCARDSNWDALDYWGQ GTTVTVSSGGGGSGGGGSGGGGSDIQMTQSPSSLSASVGDRVTITCKVTEKV WGNVAWYQQKPGKAPISLIYSPSLRKSGVPSRFSGSGSGTDFTLTISSLQPEDF ATYYCQQYYTYPYTFGGGTKVEIK |
| 645 | WW0476 | VPRDCGCKPCICTVPEVSSVFIFPPKPKDVLTITLTPKVTCVVVDISKDDPEVQF SWFVDDVEVHTAQTQPREEQFNSTFRSVSELPIMHQDWLNGKEFKCRVNSAA FPAPIEKTISKTKGRPKAPQVYTIPPPKEQMAKDKVSLTCMITDFFPEDITVEWQ WNGQPAENYKNTQPIMDTDGSYFVYSKLNVQKSNWEAGNTFTCSVLHEGLH NHHHTEKSLSHSPGKSGGPGPAGLYAQPGSAPTSSSTKKTQLQLEHLLLDLQMI |

Sequence Table

| SEQ ID NO. | Name | Sequence |
|---|---|---|
| | | LNGINNYKNPKLTRMLTFKFYMPKKATELKHLQCLEEELKPLEEVLNLAQSK<br>NFHLRPRDLISNINVIVLELKGSETTFMCEYADETATIVEFLNRWITFCQSIISTL<br>TGGGGSGGGGSGGGGSGGGGSGGGGSGGGGSSGGPGPAGLYAQPGSEVQLL<br>ESGGGLVQPGGSLRLSCAASGSIFSANAMGWYRQAPGKGLELVAVISSGGSTN<br>YADSVKGRFTISRDNSKNTVYLQMNSLRAEDTAVYYCMYSGSYYYTPNDYW<br>GQGTLVTVSS |
| 646 | WW0477 | VPRDCGCKPCICTVPEVSSVFIFPPKPKDVLTITLTPKVTCVVVDISKDDPEVQF<br>SWFVDDVEVHTAQTQPREEQFNSTFRSVSELPIMHQDWLNGKEFKCRVNSAA<br>FPAPIEKTISKTKGRPKAPQVYTIPPPKEQMAKDKVSLTCMITDFFPEDITVEWQ<br>WNGQPAENYKNTQPIMDTDGSYFVYSKLNVQKSNWEAGNTFTCSVLHEGLH<br>NHHTEKSLSHSPGKSGGPGPAGLYAQPGSAPTSSSTKKTQLQLEHLLLDLQMI<br>LNGINNYKNPKLTRMLTFKFYMPKKATELKHLQCLEEELKPLEEVLNLAQSK<br>NFHLRPRDLISNINVIVLELKGSETTFMCEYADETATIVEFLNRWITFCQSIISTL<br>TGGGGSGGGGSGGGGSGGGGSGGGGSGGGGSSGGPGPAGLYAQPGSEVQLL<br>ESGGGLVQPGGSLRLSCAASERIFSTDVMGWYRQAPGKQRELVAVVSARGTT<br>NYLDAVKGRFTISRDNSKNTLYLQMNSLRAEDTAVYYCYVRETTSPWRIYWG<br>QGTLVTVSS |
| 647 | WW0649 Monomeric IL-12 (chimeric) poly-peptide, anti-HSA sdAb, scFv Blocker, 2 cleavage sites | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggPAGLYAQPgsiwelkkdvyvveldwypdapgemvvltcdtpeedgitwildqs<br>sevlgsgktltiqvkefgdagqytchkggevlshsllllhldcedgiwstdilkdqkepluildflrceaknysgrftcwwltt<br>istdlifsvkssrgssdpqgvtcgaatlsaervrgdnkeyeysvecqedsacpaaeeslpievmvdavhklkyenytssf<br>firdiikpdppknlqlkplknsrqvevsweypdtwstphsyfsitfcvqvqgkskrekkdrvftdktsatvicrknasisv<br>raqdiyysssswsewasvpcsggggsggggsggggsrvipvsgparclsqsrnllktttddmvktareklkhysctaedi<br>dheditrdqtstlktcplelhknesclatretssttrgsclppqktslmmticlgsiyedlkmyqtefqainaalqnhnhqqi<br>ildkgmlvaidelmqslnhngetlrqkppvgeadpyrvkmklcillhafstrvvtinrvmgylssasggpGPAGLY<br>AQpgsggggsggggsggggsggggsggggsQSVLTQPPSVSGAPGQRVTISCSGSRSN<br>IGSNTVKWYQQLPGTAPKLLIYYNDQRPSGVPDRFSGSKSGTSASLAITGLQAE<br>DEADYYCQSYDRYTHPALLFGTGTKVTVLggggsggggsggggsQVQLVESGGGVV<br>QPGRSLRLSCAASGFTFSSYGMHWVRQAPGKGLEWVAFIRYDGSNKYYADS<br>VKGRFTISRDNSKNTLYLQMNSLRAEDTAVYYCKTHGSHDNWGQGTMVTVSS** |
| 454 | WW0650 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggPAGLYAQPgsiwelkkdvyvveldwypdapgemvvltcdtpeedgitwildqs<br>sevlgsgktltiqvkefgdagqytchkggevlshsllllhldcedgiwstdilkdqkepluildflrceaknysgrftcwwltt<br>istdlifsvkssrgssdpqgvtcgaatlsaervrgdnkeyeysvecqedsacpaaeeslpievmvdavhklkyenytssf<br>firdiikpdppknlqlkplknsrqvevsweypdtwstphsyfsitfcvqvqgkskrekkdrvftdktsatvicrknasisv<br>raqdiyyssswsewasvpcsggggsggggsggggsrnlpvatpdpgmfpclhhsqnllraysnmlqkarqtlefypc<br>tseeeidheditkdktstveaclpleltknesclnsretsfitngsclasrktsfmmalclssiyedlkmyqvefktmnakllm<br>dpkrqifldqnmlavidelmqalnfnsetvpqkssleepdfykttkiklcillhafriravtidrvmsylnassggpGPA<br>GLYAQpgsggggsggggsggggsggggsggggsggggsQSVLTQPPSVSGAPGQRVTISCSG<br>SRSNIGSNTVKWYQQLPGTAPKLLIYYNDQRPSGVPDRFSGSKSGTSASLAITG<br>LQAEDEADYYCQSYDRYTHPALLFGTGTKVTVLggggsggggsggggsQVQLVESG<br>GGVVQPGRSLRLSCAASGFTFSSYGMHWVRQAPGKGLEWVAFIRYDGSNKY<br>YADSVKGRFTISRDNSKNTLYLQMNSLRAEDTAVYYCKTHGSHDNWGQGTM<br>VTVSS** |
| 455 | WW0651 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpALFKSSFPpgsiwelkkdvyvveldwypdapgemvvitcdtpeedgitwildqss<br>evlgsglaltiqvkefgdagqytchkggevlshslllllhkkedgiwstdilkdqkepknktflrceaknysgrftcwwltti<br>stdiffsvkssrgssdpqgvtcgaatlsaervrgdnkeyeysvecqedsacpaaeeslpievmvdavhklkyenytssff<br>irdiikpdppknlqlkplknsrqvevsweypdtwstphsyfsitfcvqvqgkskrekkdrvftdktsatvicrknasisvr<br>aqdiyyssswsewasvpcsggggsggggsggggsrvipvsgparclsqsrnllktttddmvktareklkhysctaedid<br>heditrdqtstlktcplelhknesclatretssttrgsclppqktslmmticlgsiyedlkmyqtefqainaalqnhnhqqiil<br>dkgmlvaidelmqslnhngetlrqkppvgeadpyrvkmklcillhafstrvvtinrvmgylssasggpALFKSSF<br>PpgsggggsggggsggggsggggsggggsQSVLTQPPSVSGAPGQRVTISCSGSRSNI<br>GSNTVKWYQQLPGTAPKLLIYYNDQRPSGVPDRFSGSKSGTSASLAITGLQAE<br>DEADYYCQSYDRYTHPALLFGTGTKVTVLggggsggggsggggsQVQLVESGGGVV<br>QPGRSLRLSCAASGFTFSSYGMHWVRQAPGKGLEWVAFIRYDGSNKYYADS<br>VKGRFTISRDNSKNTLYLQMNSLRAEDTAVYYCKTHGSHDNWGQGTMVTVSS** |
| 456 | WW0652 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsgggpALFKSSFPpgsiwelkkdvyvveldwypdapgemvvitcdtpeedgitwildqss<br>evlgsglaltiqvkefgdagqytchkggevlshslllllhkkedgiwstdilkdqkepknktflrceaknysgrftcwwltti<br>stdiffsvkssrgssdpqgvtcgaatlsaervrgdnkeyeysvecqedsacpaaeeslpievmvdavhklkyenytssff<br>irdiikpdppknlqlkplknsrqvevsweypdtwstphsyfsitfcvqvqgkskrekkdrvftdktsatvicrknasisvr<br>aqdiyyssswsewasvpcsggggsggggsggggsrnlpvatpdpgmfpclhhsqnllraysnmlqkarqtlefypct<br>seeidheditkdktstveaclpleltknesclnsretsfitngsclasrktsfmmalclssiyedlkmyqvefktmnakllm |

Sequence Table

| SEQ ID NO. | Name | Sequence |
|---|---|---|
| | | dpkrqifldqnmlavidelmqalnfnsetvpqkssleepdfyktkiklcillhafriravtidrvmsylnassggpALFK<br>SSFPpgsggggsggggsggggsggggsggggsggggsQSVLTQPPSVSGAPGQRVTISCSGSRS<br>NIGSNTVKWYQQLPGTAPKLLIYYNDQRPSGVPDRFSGSKSGTSASLAITGLQ<br>AEDEADYYCQSYDRYTHPALLFGTGTKVTVLggggsggggsggggsQVQLVESGGG<br>VVQPGRSLRLSCAASGFTFSSYGMHWVRQAPGKGLEWVAFIRYDGSNKYYA<br>DSVKGRFTISRDNSKNTLYLQMNSLRAEDTAVYYCKTHGSHDNWGQGTMVT<br>VSS** |
| 457 | WW0662 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsiwelkkdvyvveldwypdapgemvvitcdtpeedgitwtldqs<br>sevlgsgktltiqvkefgdagqytchkggevlshsllllhIckedgiwstdilkdqkepknkiflrceaknysgrftcwwltt<br>istdlifsvkssrgssdpqgvtcgaatlsaervrgdnkeyeysvecqedsacpaaeeslpievmvdavhklkyenytssf<br>firdiikpdppknlqlkplknsrqvevsweypdtwstphsyfsltfcvqvqgkskrekkdrvftdktsatvicrknasisv<br>raqchyyssswsewasvpcsggggsggggsggggsrvipvsgparclsqsrffilkttddmvktareklkhysctaedi<br>dheditrdqtstlktclplelhkneslclatretssttrgsclppqktslmmticlgsiyedlkmyqtefqainaalqnhnhqqi<br>ildkgmlvaidelmqslnhngethqkppvgeadpyrvkmklcillhafstryvtinrvmgylssasggpGPAGLY<br>AQpgsggggsggggsggggsggggsggggsggggsQSVLTQPPSVSGAPGQRVTISCSGSRSN<br>IGSNTVKWYQQLPGTAPKLLIYYNDQRPSGVPDRFSGSKSGTSASLAITGLQAE<br>DEADYYCQSYDRYTHPALLFGTGTKVTVLggggsggggsggggsQVQLVESGGGVV<br>QPGRSLRLSCAASGFTFSSYGMHWVRQAPGKGLEWVAFIRYeGSNKYYAeSV<br>KGRFTISRDNSKNTLYLQMNSLRAEDTAVYYCKTHGSHDNWGQGTMVTVSS** |
| 458 | WW0663 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsiwelkkdvyvveldwypdapgemvvitcdtpeedgitwtldqs<br>sevlgsgktltiqvkefgdagqytchkggevlshsllllhIckedgiwstdilkdqkepknkiflrceaknysgrftcwwltt<br>istdlifsvkssrgssdpqgvtcgaatlsaervrgdnkeyeysvecqedsacpaaeeslpievmvdavhklkyenytssf<br>firdiikpdppknlqlkplknsrqvevsweypdtwstphsyfsltfcvqvqgkskrekkdrvftdktsatvicrknasisv<br>raqchyyssswsewasvpcsggggsggggsggggsrnlpvatpdpgmfpclhhsqnllraysnmlqkarqtlefypc<br>tseeidheditkdktstveaclplelktknesclnsretsfitngsclasrktsfmmalcissiyedlkmyqvefktmnakllm<br>dpkrqifldqnmlavidelmqalnfnsetvpqkssleepdfyktkiklcillhafriravtidrvmsylnassggpGPA<br>GLYAQpgsggggsggggsggggsggggsggggsggggsQSVLTQPPSVSGAPGQRVTISCSG<br>SRSNIGSNTVKWYQQLPGTAPKLLIYYNDQRPSGVPDRFSGSKSGTSASLAITG<br>LQAEDEADYYCQSYDRYTHPALLFGTGTKVTVLggggsggggsggggsQVQLVESG<br>GGVVQPGRSLRLSCAASGFTFSSYGMHWVRQAPGKGLEWVAFIRYeGSNKYY<br>AeSVKGRFTISRDNSKNTLYLQMNSLRAEDTAVYYCKTHGSHDNWGQGTMV<br>TVSS** |
| 459 | WW0664 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsiwelkkdvyvveldwypdapgemvvitcdtpeedgitwtldqs<br>sevlgsgktltiqvkefgdagqytchkggevlshsllllhIckedgiwstdilkdqkepknkiflrceaknysgrftcwwltt<br>istdlifsvkssrgssdpqgvtcgaatlsaervrgdnkeyeysvecqedsacpaaeeslpievmvdavhklkyenytssf<br>firdiikpdppknlqlkplknsrqvevsweypdtwstphsyfsltfcvqvqgkskrekkdrvftdktsatvicrknasisv<br>raqchyyssswsewasvpcsggggsggggsggggsrvipvsgparclsqsrffilkttddmvktareklkhysctaedi<br>dheditrdqtstlktclplelhkneslclatretssttrgsclppqktslmmticlgsiyedlkmyqtefqainaalqnhnhqqi<br>ildkgmlvaidelmqslnhngethqkppvgeadpyrvkmklcillhafstryvtinrvmgylssasggpGPAGLY<br>AQpgsggggsggggsggggsggggsggggsggggsQSVLTQPPSVSGAPGQRVTISCSGSRSN<br>IGSeTVKWYQQLPGTAPKLLIYYNDQRPSGVPDRFSGSKSGTSASLAITGLQAE<br>DEADYYCQSYDRYTHPALLFGTGTKVTVLggggsggggsggggsQVQLVESGGGVV<br>QPGRSLRLSCAASGFTFSSYGMHWVRQAPGKGLEWVAFIRYeGSNKYYAeSV<br>KGRFTISRDNSKNTLYLQMNSLRAEDTAVYYCKTHGSHDNWGQGTMVTVSS** |
| 460 | WW0665 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsiwelkkdvyvveldwypdapgemvvitcdtpeedgitwtldqs<br>sevlgsgktltiqvkefgdagqytchkggevlshsllllhIckedgiwstdilkdqkepknkiflrceaknysgrftcwwltt<br>istdlifsvkssrgssdpqgvtcgaatlsaervrgdnkeyeysvecqedsacpaaeeslpievmvdavhklkyenytssf<br>firdiikpdppknlqlkplknsrqvevsweypdtwstphsyfsltfcvqvqgkskrekkdrvftdktsatvicrknasisv<br>raqchyyssswsewasvpcsggggsggggsggggsrnlpvatpdpgmfpclhhsqnllraysnmlqkarqtlefypc<br>tseeidheditkdktstveaclplelktknesclnsretsfitngsclasrktsfmmalcissiyedlkmyqvefktmnakllm<br>dpkrqifldqnmlavidelmqalnfnsetvpqkssleepdfyktkiklcillhafriravtidrvmsylnassggpGPA<br>GLYAQpgsggggsggggsggggsggggsggggsggggsQSVLTQPPSVSGAPGQRVTISCSG<br>SRSNIGSeTVKWYQQLPGTAPKLLIYYNDQRPSGVPDRFSGSKSGTSASLAITG<br>LQAEDEADYYCQSYDRYTHPALLFGTGTKVTVLggggsggggsggggsQVQLVESG<br>GGVVQPGRSLRLSCAASGFTFSSYGMHWVRQAPGKGLEWVAFIRYeGSNKYY<br>AeSVKGRFTISRDNSKNTLYLQMNSLRAEDTAVYYCKTHGSHDNWGQGTMV<br>TVSS** |
| 461 | WW0666 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsiwelkkdvyvveldwypdapgemvvltcdtpeedgitwtldqs |

Sequence Table

| SEQ ID NO. | Name | Sequence |
|---|---|---|
| | | sevlgsgktltiqvkefgdagqytchkggevlshsllllhkkedgiwstdilkdqkepknkiflrceaknysgrftcwwltt<br>istdlifsvkssrgssdpqgvtcgaatlsaervrgdnkeyeysvecqedsacpaaeeslpievmvdavhklkyenytssf<br>firdiikpdppknlqlkplknsrqvevsweypdtwstphsyfsitfcvqvqgkskrekkdrvftdktsatvicrknasisv<br>raqdryyssswsewasvpcsggggsggggsggggsrvipvsgparclsqsrifilkttddmvktareklkhysctaedi<br>dheditrdqtstlktclplelhknesclatretssttrgsclppqktslmmticlgsiyedlkmyqtefqainaalqnhnhqqi<br>ildkgmlvaidelmqslnhngetlrqkppvgeadpyrvkmklcillhafstrvvtinrvmgylssasggpGPAGLY<br>AQpgsggggsggggsggggsggggsggggsQSVLTQPPSVSGAPGQRVTISCSGSRSN<br>IGdNTVKWYQQLPGTAPKLLIYYNDQRPSGVPDRFSGSKSGTSASLAITGLQAE<br>DEADYYCQSYDRYTHPALLFGTGTKVTVLggggsggggsggggsQVQLVESGGGVV<br>QPGRSLRLSCAASGFTFSSYGMHWVRQAPGKGLEWVAFIRYeGSNKYYAeSV<br>KGRFTISRDNSKNTLYLQMNSLRAEDTAVYYCKTHGSHDNWGQGTMVTVSS** |
| 462 | WW0667 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsiwelkkdvyvveldwypdapgemvvltcdtpeedgitwtldqs<br>sevlgsgktltiqvkefgdagqytchkggevlshsllllhkkedgiwstdilkdqkepknkiflrceaknysgrftcwwltt<br>istdlifsvkssrgssdpqgvtcgaatlsaervrgdnkeyeysvecqedsacpaaeeslpievmvdavhklkyenytssf<br>firdiikpdppknlqlkplknsrqvevsweypdtwstphsyfsitfcvqvqgkskrekkdrvftdktsatvicrknasisv<br>raqdryyssswsewasvpcsggggsggggsggggsrnlpvatpdpgmfpclhhsqnllraysnmlqkarqtlefypc<br>tseeidheditkdktstveaclpleltknesclnsretsfitngsclasrktsfmmalclssiyedlkmyqvefktmnakllm<br>dpkrqifldqnmlavidelmqalnfnsetvpqkssleepdfyktkiklcillhafriravtidrvmsylnassggpGPA<br>GLYAQpgsggggsggggsggggsggggsggggsggggsQSVLTQPPSVSGAPGQRVTISCSG<br>SRSNIGdNTVKWYQQLPGTAPKLLIYYNDQRPSGVPDRFSGSKSGTSASLAITG<br>LQAEDEADYYCQSYDRYTHPALLFGTGTKVTVLggggsggggsggggsQVQLVESG<br>GGVVQPGRSLRLSCAASGFTFSSYGMHWVRQAPGKGLEWVAFIRYeGSNKYY<br>AeSVKGRFTISRDNSKNTLYLQMNSLRAEDTAVYYCKTHGSHDNWGQGTMV<br>TVSS** |
| 463 | WW0668 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsiwelkkdvyvveldwypdapgemvvltcdtpeedgitwtldqs<br>sevlgsgktltiqvkefgdagqytchkggevlshsllllhkkedgiwstdilkdqkepknkiflrceaknysgrftcwwltt<br>istdlifsvkssrgssdpqgvtcgaatlsaervrgdnkeyeysvecqedsacpaaeeslpievmvdavhklkyenytssf<br>firdiikpdppknlqlkplknsrqvevsweypdtwstphsyfsitfcvqvqgkskrekkdrvftdktsatvicrknasisv<br>raqdryyssswsewasvpcsggggsggggsggggsrvipvsgparclsqsrifilkttddmvktareklkhysctaedi<br>dheditrdqtstlktclplelhknesclatretssttrgsclppqktslmmticlgsiyedlkmyqtefqainaalqnhnhqqi<br>ildkgmlvaidelmqslnhngetlrqkppvgeadpyrvkmklcillhafstrvvtinrvmgylssasggpGPAGLY<br>AQpgsggggsggggsggggsggggsggggsggggsQSVLTQPPSVSGAPGQRVTISCSGSRSN<br>IGdeTVKWYQQLPGTAPKLLIYYNDQRPSGVPDRFSGSKSGTSASLAITGLQAE<br>DEADYYCQSYDRYTHPALLFGTGTKVTVLggggsggggsggggsQVQLVESGGGVV<br>QPGRSLRLSCAASGFTFSSYGMHWVRQAPGKGLEWVAFIRYDGSNKYYADS<br>VKGRFTISRDNSKNTLYLQMNSLRAEDTAVYYCKTHGSHDNWGQGTMVTVSS** |
| 464 | WW0669 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsiwelkkdvyvveldwypdapgemvvltcdtpeedgitwtldqs<br>sevlgsgktltiqvkefgdagqytchkggevlshsllllhkkedgiwstdilkdqkepknkiflrceaknysgrftcwwltt<br>istdlifsvkssrgssdpqgvtcgaatlsaervrgdnkeyeysvecqedsacpaaeeslpievmvdavhklkyenytssf<br>firdiikpdppknlqlkplknsrqvevsweypdtwstphsyfsitfcvqvqgkskrekkdrvftdktsatvicrknasisv<br>raqdryyssswsewasvpcsggggsggggsggggsrnlpvatpdpgmfpclhhsqnllraysnmlqkarqtlefypc<br>tseeidheditkdktstveaclpleltknesclnsretsfitngsclasrktsfmmalclssiyedlkmyqvefktmnakllm<br>dpkrqifldqnmlavidelmqalnfnsetvpqkssleepdfyktkiklcillhafriravtidrvmsylnassggpGPA<br>GLYAQpgsggggsggggsggggsggggsggggsggggsQSVLTQPPSVSGAPGQRVTISCSG<br>SRSNIGdeTVKWYQQLPGTAPKLLIYYNDQRPSGVPDRFSGSKSGTSASLAITG<br>LQAEDEADYYCQSYDRYTHPALLFGTGTKVTVLggggsggggsggggsQVQLVESG<br>GGVVQPGRSLRLSCAASGFTFSSYGMHWVRQAPGKGLEWVAFIRYDGSNKY<br>YADSVKGRFTISRDNSKNTLYLQMNSLRAEDTAVYYCKTHGSHDNWGQGTM<br>VTVSS** |
| 465 | WW0670 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsiwelkkdvyvveldwypdapgemvvltcdtpeedgitwtldqs<br>sevlgsgktltiqvkefgdagqytchkggevlshsllllhkkedgiwstdilkdqkepknkiflrceaknysgrftcwwltt<br>istdlifsvkssrgssdpqgvtcgaatlsaervrgdnkeyeysvecqedsacpaaeeslpievmvdavhklkyenytssf<br>firdiikpdppknlqlkplknsrqvevsweypdtwstphsyfsitfcvqvqgkskrekkdrvftdktsatvicrknasisv<br>raqdryyssswsewasvpcsggggsggggsggggsrvipvsgparclsqsrifilkttddmvktareklkhysctaedi<br>dheditrdqtstlktclplelhknesclatretssttrgsclppqktslmmticlgsiyedlkmyqtefqainaalqnhnhqqi<br>ildkgmlvaidelmqslnhngetlrqkppvgeadpyrvkmklcillhafstrvvtinrvmgylssasggpGPAGLY<br>AQpgsggggsggggsggggsggggsggggsggggsQSVLTQPPSVSGAPGQRVTISCSGSRSN<br>IGdeTVKWYQQLPGTAPKLLIYYNDQRPSGVPDRFSGSKSGTSASLAITGLQAE<br>DEADYYCQSYDRYTHPALLFGTGTKVTVLggggsggggsggggsQVQLVESGGGVV<br>QPGRSLRLSCAASGFTFSSYGMHWVRQAPGKGLEWVAFIRYeGSNKYYAeSV<br>KGRFTISRDNSKNTLYLQMNSLRAEDTAVYYCKTHGSHDNWGQGTMVTVSS** |

| SEQ ID NO. | Name | Sequence |
|---|---|---|
| 466 | WW0671 | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSsggpGPAGLYAQpgsiwelkkdvyvveldwypdapgemvvltcdtpeedgitwtldqs sevlgsgktltiqvkefgdagqytchkggevlshsllllhkkedgiwstdilkdqkepknkiflrceaknysgrftcwwltt istdlifsvkssrgssdpqgvtcgaatlsaervrgdnkeyeysvecqedsacpaaeeslpievmvdavhklkyenytssf firdiikpdppknlqlkplknsrqvevsweypdtwstphsyfsitfcvqvqgkskrekkdrvftdktsatvicrknasisv raqdryyssswseawasvpcsggggsggggsggggsrnlpvatpdpgmfpclhhsqnllraysnmlqkarqtlefypc tseeidheditkdktstveaclpleltknesclnsretsfitngsclasrktsfmmalclssiyedlkmyqvefktmnakllm dpkrqifldqnmlavidelmqalnfnsetvpqkssleepdfyktkiklcillhafriravtidrvmsylnassggpGPA GLYAQpgsggggsggggsggggsggggsggggsggggsQSVLTQPPSVSGAPGQRVTISCSG SRSNIGdeTVKWYQQLPGTAPKLLIYYNDQRPSGVPDRFSGSKSGTSASLAITG LQAEDEADYYCQSYDRYTHPALLFGTGTKVTVLggggsggggsggggsQVQLVESG GGVVQPGRSLRLSCAASGFTFSSYGMHWVRQAPGKGLEWVAFIRYeGSNKYY AeSVKGRFTISRDNSKNTLYLQMNSLRAEDTAVYYCKTHGSHDNWGQGTMV TVSS** |
| 467 | WW0672 | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSsggpGPAGLYAQpgsiwelkkdvyvveldwypdapgemvvltcdtpeedgitwtldqs sevlgsgktltiqvkefgdagqytchkggevlshsllllhkkedgiwstdilkdqkepknkiflrceaknysgrftcwwltt istdlifsvkssrgssdpqgvtcgaatlsaervrgdnkeyeysvecqedsacpaaeeslpievmvdavhklkyenytssf firdiikpdppknlqlkplknsrqvevsweypdtwstphsyfsitfcvqvqgkskrekkdrvftdktsatvicrknasisv raqdryyssswseawasvpcsggggsggggsggggsrvipvsgparclsqsrifilktttddmvktareklkhysctaedi dheditrdqtstlktclplelhknesclatretssttrgsclppqktslmmticlgsiyedlkmyqtefqainaalqnhnhqqi ildkgmlvaidelmqslnhngetlrqkppvgeadpyrvkmklcillhafstrvvtinrvmgylssasggpGPAGLY AQpgsggggsggggsggggsggggsggggsggggsQSVLTQPPSVSGAPGQRVTISCSGSeSN IGSNdVKWYQQLPGTAPKLLIYYNDQRPSGVPDRFSGSKSGTSASLAITGLQAE DEADYYCQSYDRYTHPALLFGTGTKVTVLggggsggggsggggsQVQLVESGGGVV QPGRSLRLSCAASGFTFSSYGMHWVRQAPGKGLEWVAFIRYDGSNKYYADS VKGRFTISRDNSKNTLYLQMNSLRAEDTAVYYCKTHGSHDNWGQGTMVTVSS** |
| 468 | WW0673 | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSsgggpGPAGLYAQpgsiwelkkdvyvveldwypdapgemvvltcdtpeedgitwtldqs sevlgsgktltiqvkefgdagqytchkggevlshsllllhkkedgiwstdilkdqkepknkiflrceaknysgrftcwwltt istdlifsvkssrgssdpqgvtcgaatlsaervrgdnkeyeysvecqedsacpaaeeslpievmvdavhklkyenytssf firdiikpdppknlqlkplknsrqvevsweypdtwstphsyfsitfcvqvqgkskrekkdrvftdktsatvicrknasisv raqdryyssswseawasvpcsggggsggggsggggsrnlpvatpdpgmfpclhhsqnllraysnmlqkarqtlefypc tseeidheditkdktstveaclpleltknesclnsretsfitngsclasrktsfmmalclssiyedlkmyqvefktmnakllm dpkrqifldqnmlavidelmqalnfnsetvpqkssleepdfyktkiklcillhafriravtidrvmsylnassggpGPA GLYAQpgsggggsggggsggggsggggsggggsggggsQSVLTQPPSVSGAPGQRVTISCSG SeSNIGSNdVKWYQQLPGTAPKLLIYYNDQRPSGVPDRFSGSKSGTSASLAITG LQAEDEADYYCQSYDRYTHPALLFGTGTKVTVLggggsggggsggggsQVQLVESG GGVVQPGRSLRLSCAASGFTFSSYGMHWVRQAPGKGLEWVAFIRYDGSNKY YADSVKGRFTISRDNSKNTLYLQMNSLRAEDTAVYYCKTHGSHDNWGQGTM VTVSS** |
| 469 | WW0674 | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSsggpGPAGLYAQpgsiwelkkdvyvveldwypdapgemvvltcdtpeedgitwtldqs sevlgsgktltiqvkefgdagqytchkggevlshsllllhkkedgiwstdilkdqkepknkiflrceaknysgrftcwwltt istdlifsvkssrgssdpqgvtcgaatlsaervrgdnkeyeysvecqedsacpaaeeslpievmvdavhklkyenytssf firdiikpdppknlqlkplknsrqvevsweypdtwstphsyfsitfcvqvqgkskrekkdrvftdktsatvicrknasisv raqdryyssswseawasvpcsggggsggggsggggsrvipvsgparclsqsrifilktttddmvktareklkhysctaedi dheditrdqtstlktclplelhknesclatretssttrgsclppqktslmmticlgsiyedlkmyqtefqainaalqnhnhqqi ildkgmlvaidelmqslnhngetlrqkppvgeadpyrvkmklcillhafstrvvtinrvmgylssasggpGPAGLY AQpgsggggsggggsggggsggggsggggsggggsQSVLTQPPSVSGAPGQRVTISCSGSRSN IGeNTVKWYQQLPGTAPKLLIYYNDQRPSGVPDRFSGSKSGTSASLAITGLQAE DEADYYCQSYDRYTHPALLFGTGTKVTVLggggsggggsggggsQVQLVESGGGVV QPGRSLRLSCAASGFTFSSYGMHWVRQAPGKGLEWVAFIRYeGSNKYYAeSV KGRFTISRDNSKNTLYLQMNSLRAEDTAVYYCKTHGSHDNWGQGTMVTVSS** |
| 470 | WW0675 | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSsggpGPAGLYAQpgsiwelkkdvyvveldwypdapgemvvltcdtpeedgitwtldqs sevlgsgktltiqvkefgdagqytchkggevlshsllllhkkedgiwstdilkdqkepknkiflrceaknysgrftcwwltt istdlifsvkssrgssdpqgvtcgaatlsaervrgdnkeyeysvecqedsacpaaeeslpievmvdavhklkyenytssf firdiikpdppknlqlkplknsrqvevsweypdtwstphsyfsitfcvqvqgkskrekkdrvftdktsatvicrknasisv raqdryyssswseawasvpcsggggsggggsggggsrnlpvatpdpgmfpclhhsqnllraysnmlqkarqtlefypc tseeidheditkdktstveaclpleltknesclnsretsfitngsclasrktsfmmalclssiyedlkmyqvefktmnakllm dpkrqifldqnmlavidelmqalnfnsetvpqkssleepdfyktkiklcillhafriravtidrvmsylnassggpGPA GLYAQpgsggggsggggsggggsggggsggggsggggsQSVLTQPPSVSGAPGQRVTISCSG |

-continued

Sequence Table

| SEQ ID NO. | Name | Sequence |
|---|---|---|
| | | SRSNIGeNTVKWYQQLPGTAPKLLIYYNDQRPSGVPDRFSGSKSGTSASLAITG<br>LQAEDEADYYCQSYDRYTHPALLFGTGTKVTVLggggsggggsggggsQVQLVESG<br>GGVVQPGRSLRLSCAASGFTFSSYGMHWVRQAPGKGLEWVAFIRYeGSNKYY<br>AeSVKGRFTISRDNSKNTLYLQMNSLRAEDTAVYYCKTHGSHDNWGQGTMV<br>TVSS** |
| 471 | WW0676 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsiwelkkdvyvveldwypdapgemvvltcdtpeedgitwtldqs<br>sevlgsgktltiqvkefgdagqytchkggevlshsllllhkkedgiwstdilkdqkepknkiflrceaknysgrftcwwltt<br>istdlifsvkssrgssdpqgvtcgaatlsaervrgdnkeyeysvecqedsacpaaeeslpievmvdavhklkyenytssf<br>firdiikpdppknlqlkplknsrqvevsweypdtwstphsyfsltfcvqvqgkskrekkdrvftdktsatvicrknasisv<br>raqdryyssswsewasvpcsgggsggggsggggsrvipvsgparclsqsrifilkttddmvktareklkhysctaedi<br>dheditrdqtstlktclplelhknesclatretssttrgsclppqktslmmticlgsiyedlkmyqtefqainaalqnhnhqqi<br>ildkgmlvaidelmqslnhngetlrqkppvgeadpyrvkmklcillhafstrvvtinrvmgylssasggpGPAGLY<br>AQpgsggggsggggsggggsggggsggggsggggsQSVLTQPPSVSGAPGQRVTISCSGSRSN<br>IGeeTVKWYQQLPGTAPKLLIYYNDQRPSGVPDRFSGSKSGTSASLAITGLQAE<br>DEADYYCQSYDRYTHPALLFGTGTKVTVLggggsggggsggggsQVQLVESGGGVV<br>QPGRSLRLSCAASGFTFSSYGMHWVRQAPGKGLEWVAFIRYDGSNKYYADS<br>VKGRFTISRDNSKNTLYLQMNSLRAEDTAVYYCKTHGSHDNWGQGTMVTVSS** |
| 472 | WW0677 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsiwelkkdvyvveldwypdapgemvvltcdtpeedgitwtldqs<br>sevlgsgktltiqvkefgdagqytchkggevlshsllllhkkedgiwstdilkdqkepknkiflrceaknysgrftcwwltt<br>istdlifsvkssrgssdpqgvtcgaatlsaervrgdnkeyeysvecqedsacpaaeeslpievmvdavhklkyenytssf<br>firdiikpdppknlqlkplknsrqvevsweypdtwstphsyfsltfcvqvqgkskrekkdrvftdktsatvicrknasisv<br>raqdryyssswsewasvpcsggggsggggsggggsrnlpvatpdpgmfpclhhsqnllraysnmlqkarqtlefypc<br>tseeidheditkdktstveaclpleltknesclnsretsfitngsclasrktsfmmalcissiyedlkmyqvefktmnakllm<br>dpkrqifldqnmlavidelmqalnfnsetvpqkssleepdfyktkiklcillhafriravtidrvmsylnassggpGPA<br>GLYAQpgsggggsggggsggggsggggsggggsggggsQSVLTQPPSVSGAPGQRVTISCSGSRSN<br>SRSNIGeeTVKWYQQLPGTAPKLLIYYNDQRPSGVPDRFSGSKSGTSASLAITGL<br>QAEDEADYYCQSYDRYTHPALLFGTGTKVTVLggggsggggsggggsQVQLVESGG<br>GVVQPGRSLRLSCAASGFTFSSYGMHWVRQAPGKGLEWVAFIRYDGSNKYY<br>ADSVKGRFTISRDNSKNTLYLQMNSLRAEDTAVYYCKTHGSHDNWGQGTMV<br>TVSS** |
| 473 | WW0678 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsiwelkkdvyvveldwypdapgemvvitcdtpeedgitwtldqs<br>sevlgsgktltiqvkefgdagqytchkggevlshsllllhIckedgiwstdilkdqkepknkiflrceaknysgrftcwwltt<br>istdlifsvkssrgssdpqgvtcgaatlsaervrgdnkeyeysvecqedsacpaaeeslpievmvdavhklkyenytssf<br>firdiikpdppknlqlkplknsrqvevsweypdtwstphsyfsltfcvqvqgkskrekkdrvftdktsatvicrknasisv<br>raqdryyssswsewasvpcsgggsggggsggggsrvipvsgparclsqsrifilkttddmvktareklkhysctaedi<br>dheditrdqtstlktclplelhknesclatretssttrgsclppqktslmmticlgsiyedlkmyqtefqainaalqnhnhqqi<br>ildkgmlvaidelmqslnhngetlrqkppvgeadpyrvkmklcillhafstryvtinrvmgylssasggpGPAGLY<br>AQpgsggggsggggsggggsggggsggggsggggsQSVLTQPPSVSGAPGQRVTISCSGSRSN<br>IGSeTVKWYQQLPGTAPKLLIYYNDQRPSGVPDRFSGSKSGTSASLAITGLQAE<br>DEADYYCQSYDRYTHPALLFGTGTKVTVLggggsggggsggggsQVQLVESGGGVV<br>QPGRSLRLSCAASGFTFSSYGMHWVRQAPGKGLEWVAFIRYeGSNKYYADSV<br>KGRFTISRDNSKNTLYLQMNSLRAEDTAVYYCKTHGSHDNWGQGTMVTVSS** |
| 474 | WW0679 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsiwelkkdvyvveldwypdapgemvvitcdtpeedgitwtldqs<br>sevlgsgktltiqvkefgdagqytchkggevlshsllllhIckedgiwstdilkdqkepknktflrceaknysgrftcwwltt<br>istdlifsvkssrgssdpqgvtcgaatlsaervrgdnkeyeysvecqedsacpaaeeslpievmvdavhklkyenytssf<br>firdiikpdppknlqlkplknsrqvevsweypdtwstphsyfsltfcvqvqgkskrekkdrvftdktsatvicrknasisv<br>raqdryyssswsewasvpcsgggsggggsggggsrnlpvatpdpgmfpclhhsqnllraysnmlqkarqtlefypc<br>tseeidheditkdktstveaclpleltknesclnsretsfitngsclasrktsfmmalcissiyedlkmyqvefktmnakllm<br>dpkrqifldqnmlavidelmqalnfnsetvpqkssleepdfyktkiklcillhafriravtidrvmsylnassggpGPA<br>GLYAQpgsggggsggggsggggsggggsggggsggggsQSVLTQPPSVSGAPGQRVTISCSCG<br>SRSNIGSeTVKWYQQLPGTAPKLLIYYNDQRPSGVPDRFSGSKSGTSASLAITG<br>LQAEDEADYYCQSYDRYTHPALLFGTGTKVTVLggggsggggsggggsQVQLVESG<br>GGVVQPGRSLRLSCAASGFTFSSYGMHWVRQAPGKGLEWVAFIRYeGSNKYY<br>ADSVKGRFTISRDNSKNTLYLQMNSLRAEDTAVYYCKTHGSHDNWGQGTMV<br>TVSS** |
| 475 | WW0680 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpALFKSSFPpgsiwelkkdvyvveldwypdapgemvvitcdtpeedgitwtldqss<br>evlgsgktltiqvkefgdagqytchkggevlshsllllhkkedgiwstdilkdqkepknktflrceaknysgrftcwwltti<br>stdiffsvkssrgssdpqgvtcgaatlsaervrgdnkeyeysvecqedsacpaaeeslpievmvdavhklkyenytssff |

| SEQ ID NO. | Name | Sequence |
|---|---|---|
| | | irdiikpdppknlqlkplknsrqvevsweypdtwstphsyfsltfcvqvqgkskrekkdrvftdktsatvicrknasisvr<br>aqdryyssswsewasvpcsggggsggggsggggsrvipvsgparclsqsrnllkttddmvktareklkhysctaedid<br>heditrdqtstlktclplelhknesclatretsstrgsclppqktslmmticlgsiyedlkmyqtefqainaalqnhnhqqiil<br>dkgmlvaidelmqslnhngetlrqkppvgeadpyrvkmklcillhafstryvtinrvmgylssasgspALFKSSF<br>PpgsggggsggggsggggsggggsggggsggggsQSVLTQPPSVSGAPGQRVTISCSGSRSNI<br>GSNTVKWYQQLPGTAPKLLIYYNDQRPSGVPDRFSGSKSGTSASLAITGLQAE<br>DEADYYCQSYDRYTHPALLFGTGTKVTVLggggsggggsggggsQVQLVESGGGVV<br>QPGRSLRLSCAASGFTFSSYGMHWVRQAPGKGLEWVAFIRYeGSNKYYAeSV<br>KGRFTISRDNSKNTLYLQMNSLRAEDTAVYYCKTHGSHDNWGQGTMVTVSS** |
| 476 | WW0681 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpALFKSSFPpgsiwelkkdvyvveldwypdapgemvvlicdtpeedgitwtldqss<br>evlgssgktltiqvkefgdagqytchkggevlshsllllhkkedgiwstdilkdqkepknktflrceaknysgrftcwwltti<br>stdltfsvkssrgssdpqgvtcgaatlsaervrgdnkeyeysvecqedsacpaaeeslpievmvdavhklkyenytssff<br>irdiikpdppknlqlkplknsrqvevsweypdtwstphsyfsltfcvqvqgkskrekkdrvftdktsatvicrknasisvr<br>aqthyyssswsewasvpcsggggsggggsggggsrnlpvatpdpgmfpclhhsqnllraysnmlqkarqtlefypct<br>seeeidheditkdktstveaclpleltknesclnsretsfitngsclasrktsfmmalclssiyedlkmyqvefktmnakllm<br>dpkrqifldqnmlavidelmqalnfnsetvpqksssleepdfyktkiklcillhafriravtidrvmsylnasssggpALFK<br>SSFPpgsggggsggggsggggsggggsggggsggggsQSVLTQPPSVSGAPGQRVTISCSGSRS<br>NIGSNTVKWYQQLPGTAPKLLIYYNDQRPSGVPDRFSGSKSGTSASLAITGLQ<br>AEDEADYYCQSYDRYTHPALLFGTGTKVTVLggggsggggsggggsQVQLVESGGG<br>VVQPGRSLRLSCAASGFTFSSYGMHWVRQAPGKGLEWVAFIRYeGSNKYYAe<br>SVKGRFTISRDNSKNTLYLQMNSLRAEDTAVYYCKTHGSHDNWGQGTMVTV<br>SS** |
| 477 | WW0682 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpALFKSSFPpgsiwelkkdvyvveldwypdapgemvvlicdtpeedgitwtldqss<br>evlgssgktltiqvkefgdagqytchkggevlshsllllhkkedgiwstdilkdqkepknktflrceaknysgrftcwwltti<br>stdltfsvkssrgssdpqgvtcgaatlsaervrgdnkeyeysvecqedsacpaaeeslpievmvdavhklkyenytssff<br>irdiikpdppknlqlkplknsrqvevsweypdtwstphsyfsltfcvqvqgkskrekkdrvftdktsatvicrknasisvr<br>aqthyyssswsewasvpcsggggsggggsggggsrvipvsgparclsqsrnllkttddmvktareklkhysctaedid<br>heditrdqtstlktclplelhknesclatretsstrgsclppqktslmmticlgsiyedlkmyqtefciainaalqnhnhqqiil<br>dkgmlvaidelmqslnhngetlrqkppvgeadpyrvkmklcillhafstrvvtinrvmgylssasgspALFKSSF<br>PpgsggggsggggsggggsggggsggggsggggsQSVLTQPPSVSGAPGQRVTISCSGSRSNI<br>GSeTVKWYQQLPGTAPKLLIYYNDQRPSGVPDRFSGSKSGTSASLAITGLQAE<br>DEADYYCQSYDRYTHPALLFGTGTKVTVLggggsggggsggggsQVQLVESGGGVV<br>QPGRSLRLSCAASGFTFSSYGMHWVRQAPGKGLEWVAFIRYeGSNKYYAeSV<br>KGRFTISRDNSKNTLYLQMNSLRAEDTAVYYCKTHGSHDNWGQGTMVTVSS** |
| 635 | WW0683 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpALFKSSFPpgsiwelkkdvyvveldwypdapgemvvlicdtpeedgitwtldqss<br>evlgssgktltiqvkefgdagqytchkggevlshsllllhkkedgiwstdilkdqkepknktflrceaknysgrftcwwltti<br>stdltfsvkssrgssdpqgvtcgaatlsaervrgdnkeyeysvecqedsacpaaeeslpievmvdavhklkyenytssff<br>irdiikpdppknlqlkplknsrqvevsweypdtwstphsyfsltfcvqvqgkskrekkdrvftdktsatvicrknasisvr<br>aqthyyssswsewasvpcsggggsggggsggggsrnlpvatpdpgmfpclhhsqnllraysnmlqkarqtlefypct<br>seeeidheditkdktstveaclpleltknesclnsretsfitngsclasrktsfmmalclssiyedlkmyqvefktmnakllm<br>dpkrqifldqnmlavidelmqalnfnsetvpqksssleepdfyktkiklcillhafriravtidrvmsylnasssggpALFK<br>SSFPpgsggggsggggsggggsggggsggggsggggsQSVLTQPPSVSGAPGQRVTISCSGSRS<br>NIGSeTVKWYQQLPGTAPKLLIYYNDQRPSGVPDRFSGSKSGTSASLAITGLQA<br>EDEADYYCQSYDRYTHPALLFGTGTKVTVLggggsggggsggggsQVQLVESGGGVV<br>QPGRSLRLSCAASGFTFSSYGMHWVRQAPGKGLEWVAFIRYeGSNKYYAeS<br>VKGRFTISRDNSKNTLYLQMNSLRAEDTAVYYCKTHGSHDNWGQGTMVTVSS** |
| 478 | WW0684 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpALFKSSFPpgsiwelkkdvyvveldwypdapgemvvlicdtpeedgitwtldqss<br>evlgssgktltiqvkefgdagqytchkggevlshsllllhkkedgiwstdilkdqkepknktflrceaknysgrftcwwltti<br>stdltfsvkssrgssdpqgvtcgaatlsaervrgdnkeyeysvecqedsacpaaeeslpievmvdavhklkyenytssff<br>irdiikpdppknlqlkplknsrqvevsweypdtwstphsyfsltfcvqvqgkskrekkdrvftdktsatvicrknasisvr<br>aqthyyssswsewasvpcsggggsggggsggggsrvipvsgparclsqsrnllkttddmvktareklkhysctaedid<br>heditrdqtstlktclplelhknesclatretsstrgsclppqktslmmticlgsiyedlkmyqtefciainaalqnhnhqqiil<br>dkgmlvaidelmqslnhngetlrqkppvgeadpyrvkmklcillhafstrvvtinrvmgylssasgspALFKSSF<br>PpgsggggsggggsggggsggggsggggsggggsQSVLTQPPSVSGAPGQRVTISCSGSRSNI<br>GdNTVKWYQQLPGTAPKLLIYYNDQRPSGVPDRFSGSKSGTSASLAITGLQAE<br>DEADYYCQSYDRYTHPALLFGTGTKVTVLggggsggggsggggsQVQLVESGGGVV<br>QPGRSLRLSCAASGFTFSSYGMHWVRQAPGKGLEWVAFIRYeGSNKYYAeSV<br>KGRFTISRDNSKNTLYLQMNSLRAEDTAVYYCKTHGSHDNWGQGTMVTVSS** |
| 479 | WW0685 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS |

Sequence Table

| SEQ ID NO. | Name | Sequence |
|---|---|---|
| | | SQGTLVTVSSsggpALFKSSFPpgsiwelkkdvyvveldwypdapgemvvlicdtpeedgitwtldqss evlgsgktltiqvkefgdagqytchkggevlshslllllhkkedgiwstdilkdqkepknktflrceaknysgrftcwltti stdllfsvkssrgssdpqgvtcgaatlsaervrgdnkeyeysvecqedsacpaaeeslpievmvdavhklkyenytssff irdiikpdppknlqlkplknsrqvevsweypdtwstphsyfsltfcvqvqgkskrekkdrvftdktsatvicrknasisvr aqdlyyssswsewasvpcsggggsggggsggggsrnlpvatpdpgmfpclhhsqnllraysnmlqkarqtlefypct seeidheditkdktstveaclpleltknesclnsretsfitngsclasrktsfmmalclssiyedlkmyqvefktmnakllm dpkrqifldqnmlavidelmqalnfnsetvpqkssleepdfyktkiklcillhafriravtidrvmsylnassggpALFK SSFPpgsggggsggggsggggsggggsggggsggggsQSVLTQPPSVSGAPGQRVTISCSGSRS NIGdNTVKWYQQLPGTAPKLLIYYNDQRPSGVPDRFSGSKSGTSASLAITGLQA EDEADYYCQSYDRYTHPALLFGTGTKVTVLggggsggggsggggsQVQLVESGGGV VQPGRSLRLSCAASGFTFSSYGMHWVRQAPGKGLEWVAFIRYeGSNKYYAes VKGRFTISRDNSKNTLYLQMNSLRAEDTAVYYCKTHGSHDNWGQGTMVTVSS** |
| 480 | WW0686 | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSsggpALFKSSFPpgsiwelkkdvyvveldwypdapgemvvlicdtpeedgitwtldqss evlgsgktltiqvkefgdagqytchkggevlshslllllhkkedgiwstdilkdqkepknktflrceaknysgrftcwltti stdllfsvkssrgssdpqgvtcgaatlsaervrgdnkeyeysvecqedsacpaaeeslpievmvdavhklkyenytssff irdiikpdppknlqlkplknsrqvevsweypdtwstphsyfsltfcvqvqgkskrekkdrvftdktsatvicrknasisvr aqdlyyssswsewasvpcsggggsggggsggggsrvipvsgparclsqsrnllkttddmvktareklkhysctaedid heditrdqtstlktclplelhknesclatretssttrgsclppqktslmmticlgsiyedlkmyqtefqainaalqnhnhqqiil dkgmlvaidelmqslnhngetlrqkppvgeadpyrvkmklcillhafstrvvtinrvmgylssasggpALFKSSF PpgsggggsggggsggggsggggsggggsggggsQSVLTQPPSVSGAPGQRVTISCSGSRSNI GdeTVKWYQQLPGTAPKLLIYYNDQRPSGVPDRFSGSKSGTSASLAITGLQAED EADYYCQSYDRYTHPALLFGTGTKVTVLggggsggggsggggsQVQLVESGGGVVQ PGRSLRLSCAASGFTFSSYGMHWVRQAPGKGLEWVAFIRYDGSNKYYADSV KGRFTISRDNSKNTLYLQMNSLRAEDTAVYYCKTHGSHDNWGQGTMVTVSS** |
| 481 | WW0687 | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSsggpALFKSSFPpgsiwelkkdvyvveldwypdapgemvvlicdtpeedgitwtldqss evlgsgktltiqvkefgdagqytchkggevlshslllllhkkedgiwstdilkdqkepknktflrceaknysgrftcwltti stdllfsvkssrgssdpqgvtcgaatlsaervrgdnkeyeysvecqedsacpaaeeslpievmvdavhklkyenytssff irdiikpdppknlqlkplknsrqvevsweypdtwstphsyfsltfcvqvqgkskrekkdrvftdktsatvicrknasisvr aqdlyyssswsewasvpcsggggsggggsggggsrnlpvatpdpgmfpclhhsqnllraysnmlqkarqtlefypct seeidheditkdktstveaclpleltknesclnsretsfitngsclasrktsfmmalclssiyedlkmyqvefktmnakllm dpkrqifldqnmlavidelmqalnfnsetvpqkssleepdfyktkiklcillhafriravtidrvmsylnassggpALFK SSFPpgsggggsggggsggggsggggsggggsggggsQSVLTQPPSVSGAPGQRVTISCSGSRS NIGdeTVKWYQQLPGTAPKLLIYYNDQRPSGVPDRFSGSKSGTSASLAITGLQA EDEADYYCQSYDRYTHPALLFGTGTKVTVLggggsggggsggggsQVQLVESGGGV VQPGRSLRLSCAASGFTFSSYGMHWVRQAPGKGLEWVAFIRYDGSNKYYAD SVKGRFTISRDNSKNTLYLQMNSLRAEDTAVYYCKTHGSHDNWGQGTMVTV SS** |
| 482 | WW0688 | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSsggpALFKSSFPpgsiwelkkdvyvveldwypdapgemvvlicdtpeedgitwtldqss evlgsgktltiqvkefgdagqytchkggevlshslllllhkkedgiwstdilkdqkepknktflrceaknysgrftcwltti stdllfsvkssrgssdpqgvtcgaatlsaervrgdnkeyeysvecqedsacpaaeeslpievmvdavhklkyenytssff irdiikpdppknlqlkplknsrqvevsweypdtwstphsyfsltfcvqvqgkskrekkdrvftdktsatvicrknasisvr aqdlyyssswsewasvpcsggggsggggsggggsrvipvsgparclsqsrnllkttddmvktareklkhysctaedid heditrdqtstlktclplelhknesclatretssttrgsclppqktslmmticlgsiyedlkmyqtefqainaalqnhnhqqiil dkgmlvaidelmqslnhngetlrqkppvgeadpyrvkmklcillhafstrvvtinrvmgylssasggpALFKSSF PpgsggggsggggsggggsggggsggggsggggsQSVLTQPPSVSGAPGQRVTISCSGSRSNI GdeTVKWYQQLPGTAPKLLIYYNDQRPSGVPDRFSGSKSGTSASLAITGLQAED EADYYCQSYDRYTHPALLFGTGTKVTVLggggsggggsggggsQVQLVESGGGVVQ PGRSLRLSCAASGFTFSSYGMHWVRQAPGKGLEWVAFIRYeGSNKYYAeSVK GRFTISRDNSKNTLYLQMNSLRAEDTAVYYCKTHGSHDNWGQGTMVTVSS** |
| 483 | WW0689 | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSsggpALFKSSFPpgsiwelkkdvyvveldwypdapgemvvitcdtpeedgitwtldqss evlgsgktltiqvkefgdagqytchkggevlshsllllhlckedgiwstdilkdqkepknklflrceaknysgrftcwltti stdiffsvkssrgssdpqgvtcgaatlsaervrgdnkeyeysvecqedsacpaaeeslpievmvdavhklkyenytssff irdiikpdppknlqlkplknsrqvevsweypdtwstphsyfsllfcvqvqgkskrekkdryftdktsatvicrknasisvr aqdwyssswsewasvpcsggggsggggsggggsrnlpvatpdpgmfpclhhsqnllraysnmlqkarqtlefypct seeidheditkdktstveaclpleltknesclnsretsfitngsclasrktsfmmalclssiyedllunyqveflamnakllm dpkrqindqnmlavidelmqalnfnsetvpqkssleepdfyktkiklcillhafriravtidrvmsylnassggpALFK SSFPpgsggggsggggsggggsggggsggggsggggsQSVLTQPPSVSGAPGQRVTISCSGSRS NIGdeTVKWYQQLPGTAPKLLIYYNDQRPSGVPDRFSGSKSGTSASLAITGLQA EDEADYYCQSYDRYTHPALLFGTGTKVTVLggggsggggsggggsQVQLVESGGGV VQPGRSLRLSCAASGFTFSSYGMHWVRQAPGKGLEWVAFIRYeGSNKYYAes VKGRFTISRDNSKNTLYLQMNSLRAEDTAVYYCKTHGSHDNWGQGTMVTVSS** |

| SEQ ID NO. | Name | Sequence |
|---|---|---|
| 484 | WW0690 | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSsggpALFKSSFPpgsiwelkkdvyvveldwypdapgemvvitcdtpeedgitwtldqss evlgsgktltiqvkefgdagqytchkggevlshsllllhlckedgiwstdilkdqkepknklflrceaknysgrftcwwltti stdiffsvkssrgssdpqgvtcgaatlsaervrgdnkeyeysvecqedsacpaaeeslpievmvdavhklkyenytssff irdiikpdppknlqlkplknsrqvevsweypdtwstphsyfsllfcvqvqgkskrekkdryftdktsatvicrknasisvr aqdwyssswsewasvpcsggggsggggsggggsrvipvsgparclsqsnillkttddmvktarekllkhysctaedid heditrdqtstlktclplelhknesclatretsstrgsclppqktslmmticlgsiyedlkmyqtefriainaalqnhnhqqiil dkgmlvaidelmqslnhngetlrqkppvgeadpyrvkmklcillhafstrvvtinrvmgylssasggpALFKSSF PpgsggggsggggsggggsggggsggggsggggsQSVLTQPPSVSGAPGQRVTISCSGSeSNIG SNdVKWYQQLPGTAPKLLIYYNDQRPSGVPDRFSGSKSGTSASLAITGLQAED EADYYCQSYDRYTHPALLFGTGTKVTVLggggsggggsggggsQVQLVESGGGVVQ PGRSLRLSCAASGFTFSSYGMHWVRQAPGKGLEWVAFIRYDGSNKYYADSV KGRFTISRDNSKNTLYLQMNSLRAEDTAVYYCKTHGSHDNWGQGTMVTVSS** |
| 485 | WW0691 | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSsggpALFKSSFPpgsiwelkkdvyvveldwypdapgemvvitcdtpeedgitwtldqss evlgsgktltiqvkefgdagqytchkggevlshsllllhlckedgiwstdilkdqkepknklflrceaknysgrftcwwltti stdiffsvkssrgssdpqgvtcgaatlsaervrgdnkeyeysvecqedsacpaaeeslpievmvdavhklkyenytssff irdiikpdppknlqlkplknsrqvevsweypdtwstphsyfsiticvqvqgkskrekkdryftdktsatvicrknasisvr aqdwyssswsewasvpcsggggsggggsggggsrnlpvatpdpgmfpclhhsqnllraysnmlqkarqtlefypct seeidheditkdktstveaclplelttknesclnsretsfitngsclasrktsfmmalclssiyedllunyqveflamnakllm dpkrqindqnmlavidelmqalnfnsetvpqksslleepdfyktkiklcillhafriravtidrvmsylnassggpALFK SSFPpgsggggsggggsggggsggggsggggsggggsQSVLTQPPSVSGAPGQRVTISCSGSeS NIGSNdVKWYQQLPGTAPKLLIYYNDQRPSGVPDRFSGSKSGTSASLAITGLQA EDEADYYCQSYDRYTHPALLFGTGTKVTVLggggsggggsggggsggggsQVQLVESGGGV VQPGRSLRLSCAASGFTFSSYGMHWVRQAPGKGLEWVAFIRYDGSNKYYAD SVKGRFTISRDNSKNTLYLQMNSLRAEDTAVYYCKTHGSHDNWGQGTMVTV SS** |
| 486 | WW0692 | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSsggpALFKSSFPpgsiwelkkdvyvveldwypdapgemvvitcdtpeedgitwtldqss evlgsgktltiqvkefgdagqytchkggevlshsllllhlckedgiwstdilkdqkepknklflrceaknysgrftcwwltti stdiffsvkssrgssdpqgvtcgaatlsaervrgdnkeyeysvecqedsacpaaeeslpievmvdavhklkyenytssff irdiikpdppknlqlkplknsrqvevsweypdtwstphsyfsiticvqvqgkskrekkdryftdktsatvicrknasisvr aqdwyssswsewasvpcsggggsggggsggggsrvipvsgparclsqsnillkttddmvktarekllkhysctaedid heditrdqtstlktclplelhknesclatretsstrgsclppqktslmmticlgsiyedlkmyqtefriainaalqnhnhqqiil dkgmlvaidelmqslnhngethqkppvgeadpyrvkmklcillhafstryvtinrvmgylssasggpALFKSSF PpgsggggsggggsggggsggggsggggsggggsQSVLTQPPSVSGAPGQRVTISCSGSRSNI GeNTVKWYQQLPGTAPKLLIYYNDQRPSGVPDRFSGSKSGTSASLAITGLQAE DEADYYCQSYDRYTHPALLFGTGTKVTVLggggsggggsggggsQVQLVESGGGVV QPGRSLRLSCAASGFTFSSYGMHWVRQAPGKGLEWVAFIRYeSNKYYAeSV KGRFTISRDNSKNTLYLQMNSLRAEDTAVYYCKTHGSHDNWGQGTMVTVSS** |
| 487 | WW0693 | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSsggpALFKSSFPpgsiwelkkdvyvveldwypdapgemvvitcdtpeedgitwtldqss evlgsgktltiqvkefgdagqytchkggevlshsllllhkkedgiwstdilkdqkepknktflrceaknysgrftcwwltti stcliffsvkssrgssdpqgvtcgaatlsaervrgdnkeyeysvecqedsacpaaeeslpievmvdavhklkyenytssff irdiikpdppknlqlkplknsrqvevsweypdtwstphsyfsltfcvqvqgkskrekkdrvftdktsatvicrknasisvr aqchyyssswsewasvpcsggggsggggsggggsrnlpvatpdpgmfpclhhsqnllraysnmlqkarqtlefypct seeidheditkdktstveaclplelttknesclnsretsfitngsclasrktsfmmalclssiyedllunyqveflamnakllm dpkrqifldqnmlavidelmqalnfnsetvpqksslleepdfyktkiklcillhafriravtidrvmsylnassggpALFK SSFPpgsggggsggggsggggsggggsggggsggggsQSVLTQPPSVSGAPGQRVTISCSGSRS NIGeNTVKWYQQLPGTAPKLLIYYNDQRPSGVPDRFSGSKSGTSASLAITGLQA EDEADYYCQSYDRYTHPALLFGTGTKVTVLggggsggggsggggsQVQLVESGGGV VQPGRSLRLSCAASGFTFSSYGMHWVRQAPGKGLEWVAFIRYeGSNKYYAeS VKGRFTISRDNSKNTLYLQMNSLRAEDTAVYYCKTHGSHDNWGQGTMVTVSS** |
| 488 | WW0694 | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSsggpALFKSSFPpgsiwelkkdvyvveldwypdapgemvvitcdtpeedgitwtldqss evlgsgktltiqvkefgdagqytchkggevlshsllllhkkedgiwstdilkdqkepknktflrceaknysgrftcwwltti stcliffsvkssrgssdpqgvtcgaatlsaervrgdnkeyeysvecqedsacpaaeeslpievmvdavhklkyenytssff irdiikpdppknlqlkplknsrqvevsweypdtwstphsyfsltfcvqvqgkskrekkdryftdktsatvicrknasisvr aqchyyssswsewasvpcsggggsggggsggggsrvipvsgparclsqsmllkttddmvktarekllkhysctaedid heditrdqtstlktclplelhknesclatretsstrgsclppqktslmmticlgsiyedlkmyqtefqainaalqnhnhqqiil dkgmlvaidelmqslnhngethqkppvgeadpyrvkmklcillhafstryvtinrvmgylssasggpALFKSSF PpgsggggsggggsggggsggggsggggsggggsQSVLTQPPSVSGAPGQRVTISCSGSRSNI GeeTVKWYQQLPGTAPKLLIYYNDQRPSGVPDRFSGSKSGTSASLAITGLQAED |

Sequence Table

| SEQ ID NO. | Name | Sequence |
|---|---|---|
| | | EADYYCQSYDRYTHPALLFGTGTKVTVLggggsggggsggggsQVQLVESGGGVVQ<br>PGRSLRLSCAASGFTFSSYGMHWVRQAPGKGLEWVAFIRYDGSNKYYADSV<br>KGRFTISRDNSKNTLYLQMNSLRAEDTAVYYCKTHGSHDNWGQGTMVTVSS** |
| 489 | WW0695 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVSSQGTLVTVSS<br>sggpALFKSSFPpgsiwelkkdvyvveldwypdapgemvvitcdtpeedgitwtldqss<br>evlgsgktltiqvkefgdagqytchkggevlshsllllhkkedgiwstdilkdqkepknktflrceaknysgrftcwwltti<br>stcliffsvkssrgssdpqgvtcgaatlsaervrgdnkeyeysvecqedsacpaaeeslpievmvdavhklkyenytssff<br>irdiikpdppknlqlkplknsrqvevsweypdtwstphsyfsltfcvqvqgkskrekkdrvftdktsatvicrknasisvr<br>aqchyyssswewasvpcsggggsggggsggggsrnlpvatpdpgmfpclhhsqnllraysnmlqkarqtlefypct<br>seeidheditkdktstveaclpleltknesclnsretsfitngsclasrktsfmmalclssiyedllunyqveflamnakllm<br>dpkrqifldqnmlavidelmqalnfnsetvpqkssleepdfyktkiklcillhafriravtidrvmsylnasssggpALFK<br>SSFPpgsggggsggggsggggsggggsggggsggggsQSVLTQPPSVSGAPGQRVTISCSGSRS<br>NIGeeTVKWYQQLPGTAPKLLIYYNDQRPSGVPDRFSGSKSGTSASLAITGLQA<br>EDEADYYCQSYDRYTHPALLFGTGTKVTVLggggsggggsggggsQVQLVESGGGV<br>VQPGRSLRLSCAASGFTFSSYGMHWVRQAPGKGLEWVAFIRYDGSNKYYAD<br>SVKGRFTISRDNSKNTLYLQMNSLRAEDTAVYYCKTHGSHDNWGQGTMVTV<br>SS** |
| 490 | WW0696 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpALFKSSFPpgsiwelkkdvyvveldwypdapgemvvitcdtpeedgitwtldqss<br>evlgsgktltiqvkefgdagqytchkggevlshsllllhkkedgiwstdilkdqkepknktflrceaknysgrftcwwltti<br>stcliffsvkssrgssdpqgvtcgaatlsaervrgdnkeyeysvecqedsacpaaeeslpievmvdavhklkyenytssff<br>irdiikpdppknlqlkplknsrqvevsweypdtwstphsyfsitfcvqvqgkskrekkdrvftdktsatvicrknasisvr<br>aqdlyyssswewasvpcsggggsggggsggggsrvipvsgparclsqsrnllkttddmvktareklkhysctaedid<br>heditrdqtstlktcplelhknesclatretsstttrgsclppqktslmmticlgsiyedlkmyqtefciainaalqnhnhqqiil<br>dkgmlvaidelmqslnhngetlrqkppvgeadpyrvkmklcillhafstrvvtinrvmgylssasggpALFKSSF<br>PpgsggggsggggsggggsggggsggggsggggsggggsQSVLTQPPSVSGAPGQRVTISCSGSRSNI<br>GSeTVKWYQQLPGTAPKLLIYYNDQRPSGVPDRFSGSKSGTSASLAITGLQAE<br>DEADYYCQSYDRYTHPALLFGTGTKVTVLggggsggggsggggsQVQLVESGGGVV<br>QPGRSLRLSCAASGFTFSSYGMHWVRQAPGKGLEWVAFIRYeSNKYYADSV<br>KGRFTISRDNSKNTLYLQMNSLRAEDTAVYYCKTHGSHDNWGQGTMVTVSS** |
| 491 | WW0697 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpALFKSSFPpgsiwelkkdvyvveldwypdapgemvvlicdtpeedgitwtldqss<br>evlgsgktltiqvkefgdagqytchkggevlshsllllhkkedgiwstdilkdqkepknktflrceaknysgrftcwwltti<br>stdiffsvkssrgssdpqgvtcgaatlsaervrgdnkeyeysvecqedsacpaaeeslpievmvdavhklkyenytssff<br>irdiikpdppknlqlkplknsrqvevsweypdtwstphsyfsitfcvqvqgkskrekkdrvftdktsatvicrknasisvr<br>aqdlyyssswewasvpcsggggsggggsggggsrnlpvatpdpgmfpclhhsqnllraysnmlqkarqtlefypct<br>seeidheditkdktstveaclpleltknesclnsretsfitngsclasrktsfmmalclssiyedlkmyqvefktmnakllm<br>dpkrqifldqnmlavidelmqalnfnsetvpqkssleepdfyktkiklcillhafriravtidrvmsylnasssggpALFK<br>SSFPpgsggggsggggsggggsggggsggggsggggsQSVLTQPPSVSGAPGQRVTISCSGSRS<br>NIGSeTVKWYQQLPGTAPKLLIYYNDQRPSGVPDRFSGSKSGTSASLAITGLQA<br>EDEADYYCQSYDRYTHPALLFGTGTKVTVLggggsggggsggggsQVQLVESGGGV<br>VQPGRSLRLSCAASGFTFSSYGMHWVRQAPGKGLEWVAFIRYeGSNKYYADS<br>VKGRFTISRDNSKNTLYLQMNSLRAEDTAVYYCKTHGSHDNWGQGTMVTVSS** |
| 492 | WW0698 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsiwelkkdvyvveldwypdapgemvvtcdtpeedgitwtldqs<br>sevlgsgktltiqvkefgdagqytchkggevlshsllllhkkedgiwstdilkdqkepknkiflrceaknysgrftcwwltt<br>istdlifsvkssrgssdpqgvtcgaatlsaervrgdnkeyeysvecqedsacpaaeeslpievmvdavhklkyenytssf<br>firdiikpdppknlqlkplknsrqvevsweypdtwstphsyfsitfcvqvqgkskrekkdrvftdktsatvicrknasisv<br>raqdlyyssswewasvpcsggggsggggsggggsrvipvsgparclsqsrifilkttddmvktareklkhysctaedi<br>dheditrdqtstlktcplelhknesclatretsstttrgsclppqktslmmticlgssiyedlkmyqtefqainaalqnhnhqqi<br>ildkgmlvaidelmqslnhngetlrqkppvgeadpyrvkmklcillhafstrvvtinrvmgylssasggpGPAGLY<br>AQpgsggggsggggsggggsggggsggggsggggsggggsQSVLTQPPSVSGAPGQRVTISCSGSRSN<br>IGSNTVKWYQQLPGTAPKLLIYYNDQRPSGVPDRFSGSKSGTSASLAITGLQAE<br>DEADYYCQSYDRYTHPALLFGTGTKVTVLgqpkaapsvtlfppsseelqankatlyclisdfypg<br>avtvawkadsspvkagvettlpskqsnnkyaassylsltpeqwkshrsyscqvthegstvektvaptecs** |
| 493 | WW0699 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsiwelkkdvyvveldwypdapgemvvtcdtpeedgitwtldqs<br>sevlgsgktltiqvkefgdagqytchkggevlshsllllhkkedgiwstdilkdqkepknkiflrceaknysgrftcwwltt<br>istdlifsvkssrgssdpqgvtcgaatlsaervrgdnkeyeysvecqedsacpaaeeslpievmvdavhklkyenytssf<br>firdiikpdppknlqlkplknsrqvevsweypdtwstphsyfsitfcvqvqgkskrekkdrvftdktsatvicrknasisv<br>raqdlyyssswewasvpcsggggsggggsggggsrnlpvatpdpgmfpclhhsqnllraysnmlqkarqtlefypc<br>tseeidheditkdktstveaclpleltknesclnsretsfitngsclasrktsfmmalclssiyedlkmyqvefktmnakllm<br>dpkrqifldqnmlavidelmqalnfnsetvpqkssleepdfyktkiklcillhafriravtidrvmsylnasssggpGPA |

| SEQ ID NO. | Name | Sequence |
|---|---|---|
| | | GLYAQpgsggggsggggsggggsggggsggggsggggsQSVLTQPPSVSGAPGQRVTISCSG<br>SRSNIGSNTVKWYQQLPGTAPKLLIYYNDQRPSGVPDRFSGSKSGTSASLAITG<br>LQAEDEADYYCQSYDRYTHPALLFGTGTKVTVLgqpkaapsvtlfppsseelqankatlycli<br>sdfypgavtvawkadsspvkagvettlpskqsnnkyaassylsltpeqwkshrsyscqvthegstvektvaptecs** |
| 494 | WW0700 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsiwelkkdvyvveldwypdapgemvvltcdtpeedgitwtldqs<br>sevlgsgktltiqvkefgdagqytchkggevlshsllllhkkedgiwstdilkdqkepknkiflrceaknysgrftcwwltt<br>istdlifsvkssrgssdpqgvtcgaatlsaervrgdnkeyeysvecqedsacpaaeeslpievmvdavhklkyenytssf<br>firdiikpdppknlqlkplknsrqvevsweypdtwstphsyfsitfcvqvqgkskrekkdrvftdktsatvicrknasisv<br>raqdryyssswseawasvpcsggggsggggsggggsrvipvsgparclsqsrifilkttddmvktareklkhysctaedi<br>dheditrdqtstlktclplelhkneslatretssttrgsclppqktslmmticlgsiyedlkmyqtefqainaalqnhnhqqi<br>ildkgmlvaidelmqslnhngetlrqkppvgeadpyrvkmklcillhafstrvvtinrvmgylssasggpGPAGLY<br>AQpgsggggsggggsggggsggggsggggsggggsQSVLTQPPSVSGAPGQRVTISCSGSRSN<br>IGSeTVKWYQQLPGTAPKLLIYYNDQRPSGVPDRFSGSKSGTSASLAITGLQAE<br>DEADYYCQSYDRYTHPALLFGTGTKVTVLgqpkaapsvtlfppsseelqankatlyclisdfypg<br>avtvawkadsspvkagvettlpskqsnnkyaassylsltpeqwkshrsyscqvthegstvektvaptecs** |
| 495 | WW0701 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsiwelkkdvyvveldwypdapgemvvltcdtpeedgitwtldqs<br>sevlgsgktltiqvkefgdagqytchkggevlshsllllhkkedgiwstdilkdqkepknkffirceaknysgrftcwwltt<br>istdlifsvkssrgssdpqgvtcgaatlsaervrgdnkeyeysvecqedsacpaaeeslpievmvdavhklkyenytssf<br>firdiikpdppknlqlkplknsrqvevsweypdtwstphsyfsitfcvqvqgkskrekkdrvftdktsatvicrknasisv<br>raqdryyssswseawasvpcsggggsggggsggggsrnlpvatpdpgmfpclhhsqnllraysnmlqkarqtlefypc<br>tseeidheditkdktstveaclplelktknesclnsretsfitngsclasrktsfmmalclssiyedlkmyqvefktmnakllm<br>dpkrqifldqnmlavidelmqalnfnsetvpqkssleepdfyktkiklcillhafriravtidrvmsylnassggpGPA<br>GLYAQpgsggggsggggsggggsggggsggggsggggsQSVLTQPPSVSGAPGQRVTISCSG<br>SRSNIGSeTVKWYQQLPGTAPKLLIYYNDQRPSGVPDRFSGSKSGTSASLAITG<br>LQAEDEADYYCQSYDRYTHPALLFGTGTKVTVLgqpkaapsvtlfppsseelqankatlycli<br>sdfypgavtvawkadsspvkagvettlpskqsnnkyaassylsltpeqwkshrsyscqvthegstvektvaptecs** |
| 496 | WW0702 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsiwelkkdvyvveldwypdapgemvvltcdtpeedgitwtldqs<br>sevlgsgktltiqvkefgdagqytchkggevlshsllllhkkedgiwstdilkdqkepknkffirceaknysgrftcwwltt<br>istdlifsvkssrgssdpqgvtcgaatlsaervrgdnkeyeysvecqedsacpaaeeslpievmvdavhklkyenytssf<br>firdiikpdppknlqlkplknsrqvevsweypdtwstphsyfsitfcvqvqgkskrekkdrvftdktsatvicrknasisv<br>raqdryyssswseawasvpcsggggsggggsggggsrvipvsgparclsqsrifilkttddmvktareklkhysctaedi<br>dheditrdqtstlktclplelhkneslatretssttrgsclppqktslmmticlgsiyedlkmyqtefqainaalqnhnhqqi<br>ildkgmlvaidelmqslnhngetlrqkppvgeadpyrvkmklcillhafstrvvtinrvmgylssasggpGPAGLY<br>AQpgsggggsggggsggggsggggsggggsggggsQSVLTQPPSVSGAPGQRVTISCSGSRSN<br>IGdNTVKWYQQLPGTAPKLLIYYNDQRPSGVPDRFSGSKSGTSASLAITGLQAE<br>DEADYYCQSYDRYTHPALLFGTGTKVTVLgqpkaapsvtlfppsseelqankatlyclisdfypg<br>avtvawkadsspvkagvettlpskqsnnkyaassylsltpeqwkshrsyscqvthegstvektvaptecs** |
| 497 | WW0703 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsiwelkkdvyvveldwypdapgemvvltcdtpeedgitwtldqs<br>sevlgsgktltiqvkefgdagqytchkggevlshsllllhkkedgiwstdilkdqkepknkffirceaknysgrftcwwltt<br>istdlifsvkssrgssdpqgvtcgaatlsaervrgdnkeyeysvecqedsacpaaeeslpievmvdavhklkyenytssf<br>firdiikpdppknlqlkplknsrqvevsweypdtwstphsyfsitIfcvqvqgkskrekkdrvftdktsatvicrknasisv<br>raqdryyssswseawasvpcsggggsggggsggggsrnlpvatpdpgmfpclhhsqnllraysnmlqkarqtlefypc<br>tseeidheditkdktstveaclplelktknesclnsretsfitngsclasrktsfmmalclssiyedlkmyqvefktmnakllm<br>dpkrqifldqnmlavidelmqalnfnsetvpqkssleepdfyktkiklcillhafriravtidrvmsylnassggpGPA<br>GLYAQpgsggggsggggsggggsggggsggggsggggsQSVLTQPPSVSGAPGQRVTISCSG<br>SRSNIGdNTVKWYQQLPGTAPKLLIYYNDQRPSGVPDRFSGSKSGTSASLAITG<br>LQAEDEADYYCQSYDRYTHPALLFGTGTKVTVLgqpkaapsvtlfppsseelqankatlycli<br>sdfypgavtvawkadsspvkagvettlpskqsnnkyaassylsltpeqwkshrsyscqvthegstvektvaptecs** |
| 498 | WW0704 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsiwelkkdvyvveldwypdapgemvvltcdtpeedgitwtldqs<br>sevlgsgktltiqvkefgdagqytchkggevlshsllllhkkedgiwstdilkdqkepknkffirceaknysgrftcwwltt<br>istdlifsvkssrgssdpqgvtcgaatlsaervrgdnkeyeysvecqedsacpaaeeslpievmvdavhklkyenytssf<br>firdiikpdppknlqlkplknsrqvevsweypdtwstphsyfsitfcvqvqgkskrekkdrvftdktsatvicrknasisv<br>raqdryyssswseawasvpcsggggsggggsggggsrvipvsgparclsqsrifilkttddmvktareklkhysctaedi<br>dheditrdqtstlktclplelhkneslatretssttrgsclppqktslmmticlgsiyedlkmyqtefqainaalqnhnhqqi<br>ildkgmlvaidelmqslnhngetlrqkppvgeadpyrvkmklcillhafstrvvtinrvmgylssasggpGPAGLY<br>AQpgsggggsggggsggggsggggsggggsggggsQSVLTQPPSVSGAPGQRVTISCSGSRSN<br>IGdeTVKWYQQLPGTAPKLLIYYNDQRPSGVPDRFSGSKSGTSASLAITGLQAE<br>DEADYYCQSYDRYTHPALLFGTGTKVTVLgqpkaapsvtlfppsseelqankatlyclisdfypg |

| SEQ ID NO. | Name | Sequence |
|---|---|---|
| | | avtvawkadsspvkagvettlpskqsnnkyaassylsltpeqwkshrsyscqvthegstvektvaptecs** |
| 499 | WW0705 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsiwelkkdvyvveldwypdapgemvvltcdtpeedgitwtldqs<br>sevlgsgktltiqvkefgdagqytchkggevlshslllhkkedgiwstdilkdqkepknktflrceaknysgrftcwwltt<br>istdlifsvkssrgssdpqgvtcgaatlsaervrgdnkeyeysvecqedsacpaaeeslpievmvdavhklkyenytssf<br>firdiikpdppknlqlkplknsrqvevsweypdtwstphsyfsitfcvqvqgkskrekkdrvftdktsatvicrknasisv<br>raqdryyssswsewasvpcsggggsggggsggggsrnlpvatpdpgmfpclhhsqnllraysnmlqkarqtlefypc<br>tseeidheditkdktstveaclpleltknesclnsretsfitngsclasrktsfmmalclssiyedlkmyqvefktmnakllm<br>dpkrqifldqnmlavidelmqalnfnsetvpqkssleepdfyktkiklcillhafriravtidrvmsylnassggpGPA<br>GLYAQpgsggggsggggsggggsggggsggggsQSVLTQPPSVSGAPGQRVTISCSG<br>SRSNIGdeTVKWYQQLPGTAPKLLIYYNDQRPSGVPDRFSGSKSGTSASLAITG<br>LQAEDEADYYCQSYDRYTHPALLFGTGTKVTVLgqpkaapsvtlfppsseelqankatlycli<br>sdfypgavtvawkadsspvkagvettlpskqsnnkyaassylsltpeqwkshrsyscqvthegstvektvaptecs** |
| 500 | WW0706 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsiwelkkdvyvveldwypdapgemvvltcdtpeedgitwtldqs<br>sevlgsgktltiqvkefgdagqytchkggevlshslllhkkedgiwstdilkdqkepknktflrceaknysgrftcwwltt<br>istdlifsvkssrgssdpqgvtcgaatlsaervrgdnkeyeysvecqedsacpaaeeslpievmvdavhklkyenytssf<br>firdiikpdppknlqlkplknsrqvevsweypdtwstphsyfsitfcvqvqgkskrekkdrvftdktsatvicrknasisv<br>raqdryyssswsewasvpcsggggsggggsggggsrvipvsgparclsqsrifilkttddmvktareklkhysctaedi<br>dheditrdqtstlktclplelhknesclatretssttrgsclppqktslmmticlgsiyedlkmyqtefqainaalqnhnhqqi<br>ildkgmlvaidelmqslnhngetlrqkppvgeadpyrvkmklcillhafstrvvtinrvmgylssasggpGPAGLY<br>AQpgsggggsggggsggggsggggsggggsggggsQSVLTQPPSVSGAPGQRVTISCSGSeSN<br>IGSNdVKWYQQLPGTAPKLLIYYNDQRPSGVPDRFSGSKSGTSASLAITGLQAE<br>DEADYYCQSYDRYTHPALLFGTGTKVTVLgqpkaapsvtlfppsseelqankatlyclisclfypg<br>avtvawkadsspvkagvettlpskqsnnkyaassylsltpeqwkshrsyscqvthegstvektvaptecs** |
| 501 | WW0707 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsiwelkkdvyvveldwypdapgemvvltcdtpeedgitwtldqs<br>sevlgsgktltiqvkefgdagqytchkggevlshslllhkkedgiwstdilkdqkepknkffirceaknysgrftcwwltt<br>istdlifsvkssrgssdpqgvtcgaatlsaervrgdnkeyeysvecqedsacpaaeeslpievmvdavhklkyenytssf<br>firdiikpdppknlqlkplknsrqvevsweypdtwstphsyfsitfcvqvqgkskrekkdrvftdktsatvicrknasisv<br>raqdryyssswsewasvpcsggggsggggsggggsrnlpvatpdpgmfpclhhsqnllraysnmlqkarqtlefypc<br>tseeidheditkdktstveaclpleltknesclnsretsfitngsclasrktsfmmalclssiyedlkmyqvefktmnakllm<br>dpkrqifldqnmlavidelmqalnfnsetvpqkssleepdfyktkiklcillhafriravtidrvmsylnassggpGPA<br>GLYAQpgsggggsggggsggggsggggsggggsggggsQSVLTQPPSVSGAPGQRVTISCSG<br>SeSNIGSNdVKWYQQLPGTAPKLLIYYNDQRPSGVPDRFSGSKSGTSASLAITG<br>LQAEDEADYYCQSYDRYTHPALLFGTGTKVTVLgqpkaapsvtlfppsseelqankatlycli<br>sdfypgavtvawkadsspvkagvettlpskqsnnkyaassylsltpeqwkshrsyscqvthegstvektvaptecs** |
| 502 | WW0708 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsiwelkkdvyvveldwypdapgemvvltcdtpeedgitwtldqs<br>sevlgsgktltiqvkefgdagqytchkggevlshslllhkkedgiwstdilkdqkepknkffirceaknysgrftcwwltt<br>istdlifsvkssrgssdpqgvtcgaatlsaervrgdnkeyeysvecqedsacpaaeeslpievmvdavhklkyenytssf<br>firdiikpdppknlqlkplknsrqvevsweypdtwstphsyfsitfcvqvqgkskrekkdrvftdktsatvicrknasisv<br>raqdryyssswsewasvpcsggggsggggsggggsggggsrvipvsgparclsqsrifilkttddmvktareklkhysctaedi<br>dheditrdqtstlktclplelhknesclatretssttrgsclppqktslmmticlgsiyedlkmyqtefqainaalqnhnhqqi<br>ildkgmlvaidelmqslnhngetlrqkppvgeadpyrvkmklcillhafstrvvtinrvmgylssasggpGPAGLY<br>AQpgsggggsggggsggggsggggsggggsggggsggggsQSVLTQPPSVSGAPGQRVTISCSGSRSN<br>IGeNTVKWYQQLPGTAPKLLIYYNDQRPSGVPDRFSGSKSGTSASLAITGLQAE<br>DEADYYCQSYDRYTHPALLFGTGTKVTVLgqpkaapsvtlfppsseelqankatlyclisdfypg<br>avtvawkadsspvkagvettlpskqsnnkyaassylsltpeqwkshrsyscqvthegstvektvaptecs** |
| 503 | WW0709 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsiwelkkdvyvveldwypdapgemvvltcdtpeedgitwtldqs<br>sevlgsgktltiqvkefgdagqytchkggevlshslllhkkedgiwstdilkdqkepknkffirceaknysgrftcwwltt<br>istdlifsvkssrgssdpqgvtcgaatlsaervrgdnkeyeysvecqedsacpaaeeslpievmvdavhklkyenytssf<br>firdiikpdppknlqlkplknsrqvevsweypdtwstphsyfsitfcvqvqgkskrekkdrvftdktsatvicrknasisv<br>raqthyyssswsewasvpcsggggsggggsggggsrnlpvatpdpgmfpclhhsqnllraysnmlqkarqtlefypc<br>tseeidheditkdktstveaclpleltknesclnsretsfitngsclasrktsfmmalclssiyedlkmyqvefktmnakllm<br>dpkrqifldqnmlavidelmqalnfnsetvpqkssleepdfyktkiklcillhafriravtidrvmsylnassggpGPA<br>GLYAQpdsggggsggggsggggsggggsggggsggggsQSVLTQPPSVSGAPGQRVTISCSG<br>SRSNIGeNTVKWYQQLPGTAPKLLIYYNDQRPSGVPDRFSGSKSGTSASLAITG<br>LQAEDEADYYCQSYDRYTHPALLFGTGTKVTVLgqpkaapsvtlfppsseelqankatlycli<br>sdfypgavtvawkadsspvkagvettlpskqsnnkyaassylsltpeqwkshrsyscqvthegstvektvaptecs** |

Sequence Table

| SEQ ID NO. | Name | Sequence |
|---|---|---|
| 504 | WW0710 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsiwelkkdvyvveldwypdapgemvvltcdtpeedgitwtldqs<br>sevlgsgktltiqvkefgdagqytchkggevlshsllllhkkedgiwstdilkdqkepknkffirceaknysgrftcwwltt<br>istdlifsvkssrgssdpqgvtcgaatlsaervrgdnkeyeysvecqedsacpaaeeslpievmvdavhklkyenytssf<br>firdiikpdppknlqlkplknsrqvevsweypdtwstphsyfsitfcvqvqgkskrekkdrvftdktsatvicrknasisv<br>raqthyyssswsewasvpcsggggsggggsggggsrvipvsgparclsqsrnllkttddmvktareklkhysctaedi<br>dheditrdqtstlktclplelhknesclatretssttrgsclppqktslmmticlgsiyedlkmyqtefqainaalqnhnhqqi<br>ildkgmlvaidelmqslnhngetlrqkppvgeadpyrvkmklcillhafstrvvtinrvmgylssasggpGPAGLY<br>AQpgsggggsggggsggggsggggsggggsggggsQSVLTQPPSVSGAPGQRVTISCSGSRSN<br>IGeeTVKWYQQLPGTAPKLLIYYNDQRPSGVPDRFSGSKSGTSASLAITGLQAE<br>DEADYYCQSYDRYTHPALLFGTGTKVTVLgqpkaapsvtlfppsseelqankatlycliscifypg<br>avtvawkadsspvkagvettlpskqsnnkyaassylsltpeqwkshrsyscqvthegstvektvaptecs** |
| 505 | WW0711 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsiwelkkdvyvveldwypdapgemvvltcdtpeedgitwtldqs<br>sevlgsgktltiqvkefgdagqytchkggevlshsllllhkkedgiwstdilkdqkepknkffirceaknysgrftcwwltt<br>istdlifsvkssrgssdpqgvtcgaatlsaervrgdnkeyeysvecqedsacpaaeeslpievmvdavhklkyenytssf<br>firdiikpdppknlqlkplknsrqvevsweypdtwstphsyfsitfcvqvqgkskrekkdrvftdktsatvicrknasisv<br>raqthyyssswsewasvpcsggggsggggsggggsrnlpvatpdpgmfpclhhsqnllraysnmlqkarqtlefypc<br>tseeidheditkdktstveaclpleltknesclnsretsfitngsclasrktsfmmalclssiyedlkmyqvefktmnakllm<br>dpkrqifldqnmlavidelmqalnfnsetvpqkssleepdfyktkiklcillhafriravtidrvmsylnassggpGPA<br>GLYAQpgsggggsggggsggggsggggsggggsQSVLTQPPSVSGAPGQRVTISCSG<br>SRSNIGeeTVKWYQQLPGTAPKLLIYYNDQRPSGVPDRFSGSKSGTSASLAITGL<br>QAEDEADYYCQSYDRYTHPALLFGTGTKVTVLgqpkaapsvtlfppsseelqankatlyclis<br>dfypgavtvawkadsspvkagvettlpskqsnnkyaassylsltpeqwkshrsyscqvthegstvektvaptecs** |
| 506 | WW0712 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpALFKSSFPpgsiwelkkdvyvveldwypdapgemvvltcdtpeedgitwtldqss<br>evlgsgktltiqvkefgdagqytchkggevlshsllllhkkedgiwstdilkdqkepknktflrceaknysgrftcwltti<br>stdiffsvkssrgssdpqgvtcgaatlsaervrgdnkeyeysvecqedsacpaaeeslpievmvdavhklkyenytssff<br>irdiikpdppknlqlkplknsrqvevsweypdtwstphsyfsitfcvqvqgkskrekkdrvftdktsatvicrknasisvr<br>aqthyyssswsewasvpcsggggsggggsggggsrvipvsgparclsqsrnllkttddmvktareklkhysctaedid<br>heditrdqtstlktclplelhknesclatretssttrgsclppqktslmmticlgsiyedlkmyqtefciainaalqnhnhqqiil<br>dkgmlvaidelmqslnhngetlrqkppvgeadpyrvkmklcillhafstrvvtinrvmgylssasggpALFKSSF<br>PpgsggggsggggsggggsggggsggggsggggsQSVLTQPPSVSGAPGQRVTISCSGSRSNI<br>GSNTVKWYQQLPGTAPKLLIYYNDQRPSGVPDRFSGSKSGTSASLAITGLQAE<br>DEADYYCQSYDRYTHPALLFGTGTKVTVLgqpkaapsvtlfppsseelqankatlycliscifypg<br>avtvawkadsspvkagvettlpskqsnnkyaassylsltpeqwkshrsyscqvthegstvektvaptecs** |
| 507 | WW0713 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpALFKSSFPpgsiwelkkdvyvveldwypdapgemvvlicdtpeedgitwtldqss<br>evlgsgktltiqvkefgdagqytchkggevlshsllllhkkedgiwstdilkdqkepknktflrceaknysgrftcwltti<br>stdllfsvkssrgssdpqgvtcgaatlsaervrgdnkeyeysvecqedsacpaaeeslpievmvdavhklkyenytssff<br>irdiikpdppknlqlkplknsrqvevsweypdtwstphsyfsltfcvqvqgkskrekkdrvftdktsatvicrknasisvr<br>aqdfyyssswsewasvpcsggggsggggsggggsrnlpvatpdpgmfpclhhsqnllraysnmlqkarqtlefypct<br>seeidheditkdktstveaclpleltknesclnsretsfitngsclasrktsfmmalclssiyedlkmyqvefktmnakllm<br>dpkrqifldqnmlavidelmqalnfnsetvpqkssleepdfyktkiklcillhafriravtidrvmsylnassggpALFK<br>SSFPpgsggggsggggsggggsggggsggggsggggsQSVLTQPPSVSGAPGQRVTISCSGSRS<br>NIGSNTVKWYQQLPGTAPKLLIYYNDQRPSGVPDRFSGSKSGTSASLAITGLQ<br>AEDEADYYCQSYDRYTHPALLFGTGTKVTVLgqpkaapsvtlfppsseelqankatlycliscif<br>ypgavtvawkadsspvkagvetttpskqsnnkyaassylsltpeqwkshrsyscqvthegstvektvaptecs** |
| 508 | WW0714 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpALFKSSFPpgsiwelkkdvyvveldwypdapgemvvlicdtpeedgitwtldqss<br>evlgsgktltiqvkefgdagqytchkggevlshsllllhkkedgiwstdilkdqkepknktflrceaknysgrftcwltti<br>stdllfsvkssrgssdpqgvtcgaatlsaervrgdnkeyeysvecqedsacpaaeeslpievmvdavhklkyenytssff<br>irdiikpdppknlqlkplknsrqvevsweypdtwstphsyfsltfcvqvqgkskrekkdrvftdktsatvicrknasisvr<br>aqdfyyssswsewasvpcsggggsggggsggggsrvipvsgparclsqsrfdlkttddmvktareklkhysctaedid<br>heditrdqtstlktclplelhknesclatretssttrgsclppqktslmmticlgsiyedlkmyqtefciainaalqnhnhqqiil<br>dkgmlvaidelmqslnhngetlrqkppvgeadpyrvkmklcillhafstrvvtinrvmgylssasggpALFKSSF<br>PpgsggggsggggsggggsggggsggggsggggsQSVLTQPPSVSGAPGQRVTISCSGSRSNI<br>GSeTVKWYQQLPGTAPKLLIYYNDQRPSGVPDRFSGSKSGTSASLAITGLQAE<br>DEADYYCQSYDRYTHPALLFGTGTKVTVLgqpkaapsvtlfppsseelqankatlycliscifypg<br>avtvawkadsspvkagvettlpskqsnnkyaassylsltpeqwkshrsyscqvthegstvektvaptecs** |
| 509 | WW0715 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpALFKSSFPpgsiwelkkdvyvveldwypdapgemvvlicdtpeedgitwtldqss |

Sequence Table

| SEQ ID NO. | Name | Sequence |
|---|---|---|
| | | evlgsgktltiqvkefgdagqytchkggevlshsllllhkkedgiwstdilkdqkepknktflrceaknysgrftcwwltti stdllfsvkssrgssdpqgvtcgaatlsaervrgdnkeyeysvecqedsacpaaeeslpievmvdavhklkyenytssff irdiikpdppknlqlkplknsrqvevsweypdtwstphsyfsltfcvqvqgkskrekkdrvftdktsatvicrknasisvr aqdfyyssswsewasvpcsggggsggggsggggsrnlpvatpdpgmfpclhhsqnllraysnmlqkarqtlefypct seeidheditkdktstveaclpleltknesclnsretsfitngsclasrktsfmmalcssiyedlkmyqvefktmnakllm dpkrqifldqnmlavidelmqalnfnsetvpqkssleepdfyktkiklcillhafriravtidrvmsylnassggpALFK SSFPpgsggggsggggsggggsggggsggggsQSVLTQPPSVSGAPGQRVTISCSGSRS NIGSeTVKWYQQLPGTAPKLLIYYNDQRPSGVPDRFSGSKSGTSASLAITGLQA EDEADYYCQSYDRYTHPALLFGTGTKVTVLgqpkaapsvtlfppsseelqankatlyclisdfyp gavttvawkadsspvkagvetttpskqsnnkyaassylsltpeqwkshrsyscqvthegstvektvaptecs** |
| 510 | WW0716 | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSsggpALFKSSFPpgsiwelkkdvyvveldwypdapgemvvlicdtpeedgitwtldqss evlgsgktltiqvkefgdagqytchkggevlshsllllhkkedgiwstdilkdqkepknktflrceaknysgrftcwwltti stdllfsvkssrgssdpqgvtcgaatlsaervrgdnkeyeysvecqedsacpaaeeslpievmvdavhklkyenytssff irdiikpdppknlqlkplknsrqvevsweypdtwstphsyfsltfcvqvqgkskrekkdrvftdktsatvicrknasisvr aqdfyyssswsewasvpcsggggsggggsggggsrvipvsgparclsqsrfdlkttddmvktareklkhysctaedid heditrdqtstlktclplelhknesclatretssttrgsclppqktslmmticlgsiyedlkmyqtefciainaalqnhnhqqiil dkgmlvaidelmqslnhngetlrqkppvgeadpyrvkmklcillhafstrvvtinrvmgylssasggpALFKSSF PpgsggggsggggsggggsggggsggggsggggsQSVLTQPPSVSGAPGQRVTISCSGSRSNI GdNTVKWYQQLPGTAPKLLIYYNDQRPSGVPDRFSGSKSGTSASLAITGLQAE DEADYYCQSYDRYTHPALLFGTGTKVTVLgqpkaapsvtlfppsseelqankatlyclisdfypg avttvawkadsspvkagvettlpskqsnnkyaassylsltpeqwkshrsyscqvthegstvektvaptecs** |
| 511 | WW0717 | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSsggpALFKSSFPpgsiwelkkdvyvveldwypdapgemvvlicdtpeedgitwtldqss evlgsgktltiqvkefgdagqytchkggevlshsllllhkkedgiwstdilkdqkepknktflrceaknysgrftcwwltti stdllfsvkssrgssdpqgvtcgaatlsaervrgdnkeyeysvecqedsacpaaeeslpievmvdavhklkyenytssff irdiikpdppknlqlkplknsrqvevsweypdtwstphsyfsltfcvqvqgkskrekkdrvftdktsatvicrknasisvr aqdlyyssswsewasvpcsggggsggggsggggsrnlpvatpdpgmfpclhhsqnllraysnmlqkarqtlefypct seeidheditkdktstveaclpleltknesclnsretsfitngsclasrktsfmmalcssiyedlkmyqvefktmnakllm dpkrqifldqnmlavidelmqalnfnsetvpqkssleepdfyktkiklcillhafriravtidrvmsylnassggpALFK SSFPpgsggggsggggsggggsggggsggggsggggsQSVLTQPPSVSGAPGQRVTISCSGSRS NIGdNTVKWYQQLPGTAPKLLIYYNDQRPSGVPDRFSGSKSGTSASLAITGLQA EDEADYYCQSYDRYTHPALLFGTGTKVTVLgqpkaapsvtlfppsseelqankatlyclisdfyp gavttvawkadsspvkagvetttpskqsnnkyaassylsltpeqwkshrsyscqvthegstvektvaptecs** |
| 512 | WW0718 | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSsgggpALFKSSFPpgsiwelkkdvyvveldwypdapgemvvlicdtpeedgitwtldqss evlgsgktltiqvkefgdagqytchkggevlshsllllhkkedgiwstdilkdqkepknktflrceaknysgrftcwwltti stdltfsvkssrgssdpqgvtcgaatlsaervrgdnkeyeysvecqedsacpaaeeslpievmvdavhklkyenytssff irdiikpdppknlqlkplknsrqvevsweypdtwstphsyfsltfcvqvqgkskrekkdrvftdktsatvicrknasisvr aqdlyyssswsewasvpcsggggsggggsggggsrvipvsgparclsqsrnllkttddmvktareklkhysctaedid heditrdqtstlktclplelhknesclatretssttrgsclppqktslmmticlgsiyedlkmyqtefciainaalqnhnhqqiil dkgmlvaidelmqslnhngetlrqkppvgeadpyrvkmklcillhafstrvvtinrvmgylssasggpALFKSSF PpgsggggsggggsggggsggggsggggsggggsQSVLTQPPSVSGAPGQRVTISCSGSRSNI GdeTVKWYQQLPGTAPKLLIYYNDQRPSGVPDRFSGSKSGTSASLAITGLQAED EADYYCQSYDRYTHPALLFGTGTKVTVLgqpkaapsvtlfppsseelqankativclisdfypga vttvawkadsspvkagvetttpskqsnnkyaassylsltpeqwkshrsyscqvthegstvektvaptecs** |
| 513 | WW0719 | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSsggpALFKSSFPpgsiwelkkdvyvveldwypdapgemvvlicdtpeedgitwtldqss evlgsgktltiqvkefgdagqytchkggevlshsllllhkkedgiwstdilkdqkepknktflrceaknysgrftcwwltti stdltfsvkssrgssdpqgvtcgaatlsaervrgdnkeyeysvecqedsacpaaeeslpievmvdavhklkyenytssff irdiikpdppknlqlkplknsrqvevsweypdtwstphsyfsltfcvqvqgkskrekkdrvftdktsatvicrknasisvr aqdlyyssswsewasvpcsggggsggggsggggsrnlpvatpdpgmfpclhhsqnllraysnmlqkarqtlefypct seeidheditkdktstveaclpleltknesclnsretsfitngsclasrktsfmmalcssiyedlkmyqvefktmnakllm dpkrqifldqnmlavidelmqalnfnsetvpqkssleepdfyktkiklcillhafriravtidrvmsylnassggpALFK SSFPpgsggggsggggsggggsggggsggggsggggsQSVLTQPPSVSGAPGQRVTISCSGSRS NIGdeTVKWYQQLPGTAPKLLIYYNDQRPSGVPDRFSGSKSGTSASLAITGLQA EDEADYYCQSYDRYTHPALLFGTGTKVTVLgqpkaapsvtlfppsseelqankatlyclisdfyp gavttvawkadsspvkagvetttpskqsnnkyaassylsltpeqwkshrsyscqvthegstvektvaptecs** |
| 514 | WW0720 | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSsggpALFKSSFPpgsiwelkkdvyvveldwypdapgemvvlicdtpeedgitwtldqss evlgsgktltiqvkefgdagqytchkggevlshsllllhkkedgiwstdilkdqkepknktflrceaknysgrftcwwltti stdltfsvkssrgssdpqgvtcgaatlsaervrgdnkeyeysvecqedsacpaaeeslpievmvdavhklkyenytssff irdiikpdppknlqlkplknsrqvevsweypdtwstphsyfsltfcvqvqgkskrekkdrvftdktsatvicrknasisvr |

| SEQ ID NO. | Name | Sequence |
|---|---|---|
| | | aqdlyyssswsewasvpcsggggsggggsggggsrvipvsgparclsqsrnllkttddmvktareklkhysctaedid<br>heditrdqtstlktclplelhknesclatretssttrgsclppqktslmmticlgsiyedlkmyqtefqainaalqnhnhqqiil<br>dkgmlvaidelmqslnhngetlrqkppvgeadpyrvkmklcillhafstrvvtinrvmgylssasggpALFKSSF<br>PpgsggggsggggsggggsggggsggggsQSVLTQPPSVSGAPGQRVTISCSGSGeSNIG<br>SNdVKWYQQLPGTAPKLLIYYNDQRPSGVPDRFSGSKSGTSASLAITGLQAED<br>EADYYCQSYDRYTHPALLFGTGTKVTVLgqpkaapsvtlfppsseelqankativclisdfypga<br>vtvawkadsspvkagvetttpskqsnnkyaassylsltpeqwkshrsyscqvthegstvektvaptecs** |
| 515 | WW0721 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpALFKSSFPpgsiwelkkdvyvveldwypdapgemvvlicdtpeedgitwtldqss<br>evlgsgktltiqvkefgdagqytchkggevlshslllllhkkedgiwstdilkdqkepknktflrceaknysgrftcwwltti<br>stdltfsvkssrgssdpqgvtcgaatlsaervrgdnkeyeysvecqedsacpaaeeslpievmvdavhklkyenytssff<br>irdiikpdppknlqlkplknsrqvevsweypdtwstphsyfsltfcvqvqgkskrekkdrvftdktsatvicrknasisvr<br>aqdlyyssswsewasvpcsggggsggggsggggsrnlpvatpdpgmfpclhhsqnllraysnmlqkarqtlefypct<br>seeeidheditkdktstveaclplelthknesclnsretsfitngsclasrktsfmmalclssiyedlkmyqvefktmnakllm<br>dpkrqifldqnmlavidelmqalnfnsetvpqkssleepdfyktkiklcillhafriravtidrvmsylnassggpALFK<br>SSFPpgsggggsggggsggggsggggsggggsggggsQSVLTQPPSVSGAPGQRVTISCSGSeS<br>NIGSNdVKWYQQLPGTAPKLLIYYNDQRPSGVPDRFSGSKSGTSASLAITGLQA<br>EDEADYYCQSYDRYTHPALLFGTGTKVTVLgqpkaapsvtlfppsseelqankatlyclisdfyp<br>gavtvawkadsspvkagvetttpskqsnnkyaassylsltpeqwkshrsyscqvthegstvektvaptecs** |
| 516 | WW0722 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsgALFKSSFPpgsiwelkkdvyvveldwypdapgemvvlicdtpeedgitwtldqss<br>evlgsgktltiqvkefgdagqytchkggevlshslllllhkkedgiwstdilkdqkepknktflrceaknysgrftcwwltti<br>stdltfsvkssrgssdpqgvtcgaatlsaervrgdnkeyeysvecqedsacpaaeeslpievmvdavhklkyenytssff<br>irdiikpdppknlqlkplknsrqvevsweypdtwstphsyfsltfcvqvqgkskrekkdrvftdktsatvicrknasisvr<br>aqdlyyssswsewasvpcsggggsggggsggggsrvipvsgparclsqsrnllkttddmvktareklkhysctaedid<br>heditrdqtstlktclplelhknesclatretssttrgsclppqktslmmticlgsiyedlkmyqtefciainaalqnhnhqqiil<br>dkgmlvaidelmqslnhngetlrqkppvgeadpyrvkmklcillhafstrvvtinrvmgylssasggpALFKSSF<br>PpgsggggsggggsggggsggggsggggsggggsQSVLTQPPSVSGAPGQRVTISCSGSRSNI<br>GeNTVKWYQQLPGTAPKLLIYYNDQRPSGVPDRFSGSKSGTSASLAITGLQAE<br>DEADYYCQSYDRYTHPALLFGTGTKVTVLgqpkaapsvtlfppsseelqankatlyclisdfypg<br>avtvawkadsspvkagvettlpskqsnnkyaassylsltpeqwkshrsyscqvthegstvektvaptecs** |
| 517 | WW0723 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpALFKSSFPpgsiwelkkdvyvveldwypdapgemvvlicdtpeedgitwtldqss<br>evlgsgktltiqvkefgdagqytchkggevlshslllllhkkedgiwstdilkdqkepknktflrceaknysgrftcwwltti<br>stdltfsvkssrgssdpqgvtcgaatlsaervrgdnkeyeysvecqedsacpaaeeslpievmvdavhklkyenytssff<br>irdiikpdppknlqlkplknsrqvevsweypdtwstphsyfsltfcvqvqgkskrekkdrvftdktsatvicrknasisvr<br>aqdlyyssswsewasvpcsggggsggggsggggsrnlpvatpdpgmfpclhhsqnllraysnmlqkarqtlefypct<br>seeidheditkdktstveaclplelthknesclnsretsfitngsclasrktsfmmalclssiyedlkmyqvefktmnakllm<br>dpkrqifldqnmlavidelmqalnfnsetvpqkssleepdfyktkiklcillhafriravtidrvmsylnassggpALFK<br>SSFPpgsggggsggggsggggsggggsggggsggggsQSVLTQPPSVSGAPGQRVTISCSGSRS<br>NIGeNTVKWYQQLPGTAPKLLIYYNDQRPSGVPDRFSGSKSGTSASLAITGLQA<br>EDEADYYCQSYDRYTHPALLFGTGTKVTVLgqpkaapsvtlfppsseelqankatlyclisdfyp<br>gavtvawkadsspvkagvetttpskqsnnkyaassylsltpeqwkshrsyscqvthegstvektvaptecs** |
| 518 | WW0724 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpALFKSSFPpgsiwelkkdvyvveldwypdapgemvvlicdtpeedgitwtldqss<br>evlgsgktltiqvkefgdagqytchkggevlshslllllhkkedgiwstdilkdqkepknktflrceaknysgrftcwwltti<br>stdltfsvkssrgssdpqgvtcgaatlsaervrgdnkeyeysvecqedsacpaaeeslpievmvdavhklkyenytssff<br>irdiikpdppknlqlkplknsrqvevsweypdtwstphsyfsltfcvqvqgkskrekkdrvftdktsatvicrknasisvr<br>aqdlyyssswsewasvpcsggggsggggsggggsrvipvsgparclsqsrnllkttddmvktareklkhysctaedid<br>heditrdqtstlktclplelhknesclatretssttrgsclppqktslmmticlgsiyedlkmyqtefciainaalqnhnhqqiil<br>dkgmlvaidelmqslnhngetlrqkppvgeadpyrvkmklcillhafstrvvtinrvmgylssasggpALFKSSF<br>PpgsggggsggggsggggsggggsggggsggggsQSVLTQPPSVSGAPGQRVTISCSGSRSNI<br>GeeTVKWYQQLPGTAPKLLIYYNDQRPSGVPDRFSGSKSGTSASLAITGLQAED<br>EADYYCQSYDRYTHPALLFGTGTKVTVLgqpkaapsvtlfppsseelqankativclisdfypga<br>vtvawkadsspvkagvetttpskqsnnkyaassylsltpeqwkshrsyscqvthegstvektvaptecs** |
| 519 | WW0725 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpALFKSSFPpgsiwelkkdvyvveldwypdapgemvvlicdtpeedgitwtldqss<br>evlgsgktltiqvkefgdagqytchkggevlshslllllhkkedgiwstdilkdqkepknktflrceaknysgrftcwwltti<br>stdltfsvkssrgssdpqgvtcgaatlsaervrgdnkeyeysvecqedsacpaaeeslpievmvdavhklkyenytssff<br>irdiikpdppknlqlkplknsrqvevsweypdtwstphsyfsltfcvqvqgkskrekkdrvftdktsatvicrknasisvr<br>aqdryyssswsewasvpcsggggsggggsggggsrnlpvatpdpgmfpclhhsqnllraysnmlqkarqtlefypct<br>seeidheditkdktstveaclplelthknesclnsretsfitngsclasrktsfmmalclssiyedlkmyqvefktmnakllm<br>dpkrqifldqnmlavidelmqalnfnsetvpqkssleepdfyktkiklcillhafriravtidrvmsylnassggpALFK |

| SEQ ID NO. | Name | Sequence |
|---|---|---|
| | | SSFPpgsggggsggggsggggsggggsggggsggggsggggsQSVLTQPPSVSGAPGQRVTISCSGSRS<br>NIGeeTVKWYQQLPGTAPKLLIYYNDQRPSGVPDRFSGSKSGTSASLAITGLQA<br>EDEADYYCQSYDRYTHPALLFGTGTKVTVLgqpkaapsvtlfppsseelqankatlyclisdfyp<br>gavtvawkadsspvkagvetttpskqsnnkyaassylsltpeqwkshrsyscqvthegstvektvaptecs** |
| 520 | WW0726 | QVQLVESGGGVVQPGRSLRLSCAASGFTFSSYGMHWVRQAPGKGLEWVAFIR<br>YDGSNKYYADSVKGRFTISRDNSKNTLYLQMNSLRAEDTAVYYCKTHGSHD<br>NWGQGTMVTVSSastkgpsvfplapsskstsggtaalgclvkdyfpepvtvswnsgaltsgvhtfpavlqssgl<br>yslssvvtvpssslgtqtyicnvnhkpsntkvdkrvepksc** |
| 521 | WW0727 | QVQLVESGGGVVQPGRSLRLSCAASGFTFSSYGMHWVRQAPGKGLEWVAFIR<br>YeGSNKYYAeSVKGRFTISRDNSKNTLYLQMNSLRAEDTAVYYCKTHGSHDN<br>WGQGTMVTVSSastkgpsvfplapsskstsggtaalgclvkdyfpepvtvswnsgaltsgvhtfpavlqssgly<br>slssvvtvpssslgtqtyicnvnhkpsntkvdkrvepksc** |
| 522 | WW0728 | QVQLVESGGGVVQPGRSLRLSCAASGFTFSSYGMHWVRQAPGKGLEWVAFIR<br>YeGSNKYYADSVKGRFTISRDNSKNTLYLQMNSLRAEDTAVYYCKTHGSHDN<br>WGQGTMVTVSSastkgpsvfplapsskstsggtaalgclvkdyfpepvtvswnsgaltsgvhtfpavlqssgly<br>slssvvtvpssslgtqtyicnvnhkpsntkvdkrvepksc** |
| 523 | WW0765 | iwelkkdvyvveldwypdapgemvvlicdtpeedgitwildqssevlgsgktltiqvkefgdagqytchkggevlshs<br>llllhkkedgiwstdilkdqkepknktflrceaknysgrftcwwlttistdltfsvkssrgssdpqgvtcgaatlsaervrgd<br>nkeyeysvecqedsacpaaeeslpievmvdavhklkyenytssffirdiikpdppknlqlkplknsrqvevsweypdt<br>wstphsyfshfcvqvqgkskrekkchvftdktsatvicrknasisvraqdryyssswsewasvpcsggggsggggsgg<br>ggsrvipvsgparclsqsrnllktttddmvktareklkhysctaedidheditrdqtstlktclplelhknesclatretssttrgs<br>clppqktslmmticlgsiyedlkmyqtefqainaalqnhnhqqiildkgmlvaidelmqslnhngetlrqkppvgead<br>pyrvkmklcillhafstryvtinrvmgylssasgpGPAGLYAQpgsEVQLVESGGGLVQPGNSL<br>RLSCAASGFTFSKFGMSWVRQAPGKGLEWVSSISGSGRDTLYAESVKGRFTIS<br>RDNAKTTLYLQMNSLRPEDTAVYYCTIGGSLSVSSQGTLVTVSSggggsggggsgg<br>ggsggggsggggsggggsQSVLTQPPSVSGAPGQRVTISCSGSRSNIGSNTVKWYQQLP<br>GTAPKLLIYYNDQRPSGVPDRFSGSKSGTSASLAITGLQAEDEADYYCQSYDR<br>YTHPALLFGTGTKVTVLggggsggggsggggsQVQLVESGGGVVQPGRSLRLSCAA<br>SGFTFSSYGMHWVRQAPGKGLEWVAFIRYeGSNKYYAeSVKGRFTlSRDNSKN<br>TLYLQMNSLRAEDTAVYYCKTHGSHDNWGQGTMVTVSS** |
| 524 | WW0766 | iwelkkdvyvveldwypdapgemvvitcdtpeedgitwtldqssevlgsgktltiqvkefgdagqytchkggevlshs<br>llllhkkedgiwstdilkdqkepknktflrceaknysgrftcwwlttistdltfsvkssrgssdpqgvtcgaatlsaervrgd<br>nkeyeysvecqedsacpaaeeslpievmvdavhklkyenytssffirdiikpdppknlqlkplknsrqvevsweypdt<br>wstphsyfshfcvqvqgkskrekkchvftdktsatvicrknasisvraqdryyssswsewasvpcsggggsggggsgg<br>ggsrnlpvatpdpgmfpclhhsqnllraysnmlqkarqtlefypctseeidheditkdktstveaclpleltknesclnsre<br>tsfitngsclasrktsfmmalclssiyedlkmyqvefktmnakllmdpkrqifldqnmlavidelmqalnfnsetvpqk<br>ssleepdfyktkiklcillhafriravtidrvmsylnassggpGPAGLYAQpgsEVQLVESGGGLVQPG<br>NSLRLSCAASGFTFSKFGMSWVRQAPGKGLEWVSSISGSGRDTLYAESVKGRF<br>TISRDNAKTTLYLQMNSLRPEDTAVYYCTIGGSLSVSSQGTLVTVSSggggsgggg<br>sggggsggggsggggsggggsQSVLTQPPSVSGAPGQRVTISCSGSRSNIGSNTVKWYQ<br>QLPGTAPKLLIYYNDQRPSGVPDRFSGSKSGTSASLAITGLQAEDEADYYCQS<br>YDRYTHPALLFGTGTKVTVLggggsggggsggggsQVQLVESGGGVVQPGRSLRLS<br>CAASGFTFSSYGMHWVRQAPGKGLEWVAFIRYeGSNKYYAeSVKGRFTISRD<br>NSKNTLYLQMNSLRAEDTAVYYCKTHGSHDNWGQGTMVTVSS** |
| 525 | WW0767 | iwelkkdvyvveldwypdapgemvvitcdtpeedgitwildqssevlgsgktltiqvkefgdagqytchkggevlshs<br>llllhkkedgiwstdilkdqkepknktflrceaknysgrftcwwlttistdltfsvkssrgssdpqgvtcgaatlsaervrgd<br>nkeyeysvecqedsacpaaeeslpievmvdavhklkyenytssffirdiikpdppknlqlkplknsrqvevsweypdt<br>wstphsyfshfcvqvqgkskrekkchvftdktsatvicrknasisvraqdryyssswsewasvpcsggggsggggsgg<br>ggsrvipvsgparclsqsrnllktttddmvktareklkhysctaedidheditrdqtstlktclplelhknesclatretssttrgs<br>clppqktslmmticlgsiyedlkmyqtefqainaalqnhnhqqiildkgmlvaidelmqslnhngetlrqkppvgead<br>pyrvkmklcillhafstrvvtinrvmgylssasgpGPAGLYAQpgsEVQLVESGGGLVQPGNSL<br>RLSCAASGFTFSKFGMSWVRQAPGKGLEWVSSISGSGRDTLYAESVKGRFTIS<br>RDNAKTTLYLQMNSLRPEDTAVYYCTIGGSLSVSSQGTLVTVSSggggsggggsgg<br>ggsggggsggggsggggsQSVLTQPPSVSGAPGQRVTISCSGSRSNIGdeTVKWYQQLP<br>GTAPKLLIYYNDQRPSGVPDRFSGSKSGTSASLAITGLQAEDEADYYCQSYDR<br>YTHPALLFGTGTKVTVLggggsggggsggggsQVQLVESGGGVVQPGRSLRLSCAA<br>SGFTFSSYGMHWVRQAPGKGLEWVAFIRYeGSNKYYAeSVKGRFTlSRDNSKN<br>TLYLQMNSLRAEDTAVYYCKTHGSHDNWGQGTMVTVSS** |
| 526 | WW0768 | iwelkkdvyvveldwypdapgemvvitcdtpeedgitwtldqssevlgsgktltiqvkefgdagqytchkggevlshs<br>llllhkkedgiwstdilkdqkepknktflrceaknysgrftcwwlttistdltfsvkssrgssdpqgvtcgaatlsaervrgd<br>nkeyeysvecqedsacpaaeeslpievmvdavhklkyenytssffirdiikpdppknlqlkplknsrqvevsweypdt<br>wstphsyfshfcvqvqgkskrekkchvftdktsatvicrknasisvraqdryyssswsewasvpcsggggsggggsgg<br>ggsrnlpvatpdpgmfpclhhsqnllraysnmlqkarqtlefypctseeidheditkdktstveaclpleltknesclnsre<br>tsfitngsclasrktsfmmalclssiyedlkmyqvefktmnakllmdpkrqifldqnmlavidelmqalnfnsetvpqk<br>ssleepdfyktkiklcillhafriravtidrvmsylnassggpGPAGLYAQpgsEVQLVESGGGLVQPG<br>NSLRLSCAASGFTFSKFGMSWVRQAPGKGLEWVSSISGSGRDTLYAESVKGRF |

Sequence Table

| SEQ ID NO. | Name | Sequence |
|---|---|---|
| | | TISRDNAKTTLYLQMNSLRPEDTAVYYCTIGGSLSVSSQGTLVTVSSggggsggggs<br>sggggsggggsggggsggggsQSVLTQPPSVSGAPGQRVTISCSGSRSNIGdeTVKWYQQ<br>LPGTAPKLLIYYNDQRPSGVPDRFSGSKSGTSASLAITGLQAEDEADYYCQSY<br>DRYTHPALLFGTGTKVTVLggggsggggsggggsQVQLVESGGGVVQPGRSLRLSC<br>AASGFTFSSYGMHWVRQAPGKGLEWVAFIRYeGSNKYYAeSVKGRFTISRDNS<br>KNTLYLQMNSLRAEDTAVYYCKTHGSHDNWGQGTMVTVSS** |
| 527 | WW0769 | iwelkkdvyvveldwypdapgemvvitcdtpeedgitwildqssevlgsgktltiqvkefgdagqytchkggevlshs<br>llllhkkedgiwstdilkdqkepknktflrceaknysgrftcwwlttistdltfsvkssrgssdpqgvtcgaatlsaervrgd<br>nkeyeysvecqedsacpaaeeslpievmvdavhklkyenytssffirdiikpdppknlqlkplknsrqvevsweypdt<br>wstphsyfshfcvqvqgkskrekkchvftdktsatvicrknasisvraqdryyssswsewasvpcsggggsggggsgg<br>ggsrvipvsgparclsqsrnllkttddmvktarekllkhysctaedidheditrdqtstlktclplelhhknesclatretsstttrgs<br>clppqktslmmticlgsiyedlkmyqtefqainaalqnhnhqqiildkgmlvaidelmqslnhngetlrqkppvgead<br>pyryvkmklcilllhafstrvvtinrvmgylssasgpGPAGLYAQpgsEVQLVESGGGLVQPGNSL<br>RLSCAASGFTFSKFGMSWVRQAPGKGLEWVSSISGSGRDTLYAESVKGRFTIS<br>RDNAKTTLYLQMNSLRPEDTAVYYCTIGGSLSVSSQGTLVTVSSggggsggggs<br>ggsggggsggggsggggsQSVLTQPPSVSGAPGQRVTISCSGSRSNIGSNTVKWYQQLP<br>GTAPKLLIYYNDQRPSGVPDRFSGSKSGTSASLAITGLQAEDEADYYCQSYDR<br>YTHPALLFGTGTKVTVLgqpkaapsvtlfppsseelqankatlyclisdfypgavtvawkadsspvkagv<br>etttpskqsnnkyaassylsltpeqwkshrsyscqvthegstvektvaptecs** |
| 528 | WW0770 | iwelkkdvyvveldwypdapgemvvitcdtpeedgitwtldqssevlgsgktltiqvkefgdagqytchkggevlshs<br>llllhkkedgiwstdilkdqkepknktflrceaknysgrftcwwlttistdltfsvkssrgssdpqgvtcgaatlsaervrgd<br>nkeyeysvecqedsacpaaeeslpievmvdavhklkyenytssffirdiikpdppknlqlkplknsrqvevsweypdt<br>wstphsyfshfcvqvqgkskrekkdwftdktsatvicrknasisvraqdryyssswsewasvpcsggggsggggsgg<br>ggsrnlpvatpdpgmfpclhhsqnllraysnmlqkarqtlefypctseeidheditkdktstveaclpleltkneqclnsre<br>tsfitngsclasrktsfmmalclssiyedlkmyqvefktmnakllmdpkrqifldqnmlavidelmqalnfnsetvpqk<br>ssleepdfyktkiklcillhafriravtidrvmsylnassggpGPAGLYAQpgsEVQLVESGGGLVQPG<br>NSLRLSCAASGFTFSKFGMSWVRQAPGKGLEWVSSISGSGRDTLYAESVKGRF<br>TISRDNAKTTLYLQMNSLRPEDTAVYYCTIGGSLSVSSQGTLVTVSSggggsggggs<br>sggggsggggsggggsggggsQSVLTQPPSVSGAPGQRVTISCSGSRSNIGSNTVKWYQ<br>QLPGTAPKLLIYYNDQRPSGVPDRFSGSKSGTSASLAITGLQAEDEADYYCQS<br>YDRYTHPALLFGTGTKVTVLgqpkaapsvtlfppsseelqankatlyclisdfypgavtvawkadsspv<br>kagvetttpskqsnnkyaassylsltpeqwkshrsyscqvthegstvektvaptecs** |
| 529 | WW0771 | iwelkkdvyvveldwypdapgemvvitcdtpeedgitwtldqssevlgsgktltiqvkefgdagqytchkggevlshs<br>llllhkkedgiwstdilkdqkepknktflrceaknysgrftcwwlttistdltfsvkssrgssdpqgvtcgaatlsaervrgd<br>nkeyeysvecqedsacpaaeeslpievmvdavhklkyenytssffirdiikpdppknlqlkplknsrqvevsweypdt<br>wstphsyfshfcvqvqgkskrekkdwftdktsatvicrknasisvraqdryyssswsewasvpcsggggsggggsgg<br>ggsrvipvsgparclsqsrnllkttddmvktarekllkhysctaedidheditrdqtstlktclplelhhknesclatretsstttrgs<br>clppqktslmmticlgsiyedlkmyqtefqainaalqnhnhqqiildkgmlvaidelmqslnhngetlrqkppvgead<br>pyryvkmklcilllhafstrvvtinrvmgylssasgpGPAGLYAQpgsEVQLVESGGGLVQPGNSL<br>RLSCAASGFTFSKFGMSWVRQAPGKGLEWVSSISGSGRDTLYAESVKGRFTIS<br>RDNAKTTLYLQMNSLRPEDTAVYYCTIGGSLSVSSQGTLVTVSSggggsggggs<br>ggsggggsggggsggggsQSVLTQPPSVSGAPGQRVTISCSGSRSNIGdeTVKWYQQLP<br>GTAPKLLIYYNDQRPSGVPDRFSGSKSGTSASLAITGLQAEDEADYYCQSYDR<br>YTHPALLFGTGTKVTVLgqpkaapsvtlfppsseelqankatlyclisdfypgavtvawkadsspvkagv<br>etttpskqsnnkyaassylsltpeqwkshrsyscqvthegstvektvaptecs** |
| 530 | WW0772 | iwelkkdvyvveldwypdapgemvvitcdtpeedgitwtldqssevlgsgktltiqvkefgdagqytchkggevlshs<br>llllhkkedgiwstdilkdqkepknktflrceaknysgrftcwwlttistdltfsvkssrgssdpqgvtcgaatlsaervrgd<br>nkeyeysvecqedsacpaaeeslpievmvdavhklkyenytssffirdiikpdppknlqlkplknsrqvevsweypdt<br>wstphsyfshfcvqvqgkskrekkdwftdktsatvicrknasisvraqdryyssswsewasvpcsggggsggggsgg<br>ggsrnlpvatpdpgmfpclhhsqnllraysnmlqkarqtlefypctseeidheditkdktstveaclpleltkneqclnsre<br>tsfitngsclasrktsfmmalclssiyedlkmyqvefktmnakllmdpkrqifldqnmlavidelmqalnfnsetvpqk<br>ssleepdfyktkiklcillhafriravtidrvmsylnassggpGPAGLYAQpgsEVQLVESGGGLVQPG<br>NSLRLSCAASGFTFSKFGMSWVRQAPGKGLEWVSSISGSGRDTLYAESVKGRF<br>TISRDNAKTTLYLQMNSLRPEDTAVYYCTIGGSLSVSSQGTLVTVSSggggsggggs<br>sggggsggggsggggsggggsQSVLTQPPSVSGAPGQRVTISCSGSRSNIGdeTVKWYQQ<br>LPGTAPKLLIYYNDQRPSGVPDRFSGSKSGTSASLAITGLQAEDEADYYCQSY<br>DRYTHPALLFGTGTKVTVLgqpkaapsvtlfppsseelqankatlyclisdfypgavtvawkadsspvka<br>gvetttlpskqsnnkyaassylsltpeqwkshrsyscqvthegstvektvaptecs** |
| 531 | WW0796 | iwelkkdvyvveldwypdapgemvvitcdtpeedgitwtldqssevlgsgktltiqvkefgdagqytchkggevlshs<br>llllhkkedgiwstdilkdqkepknktflrceaknysgrftcwwlttistdltfsvkssrgssdpqgvtcgaatlsaervrgd<br>nkeyeysvecqedsacpaaeeslpievmvdavhklkyenytssffirdiikpdppknlqlkplknsrqvevsweypdt<br>wstphsyfshfcvqvqgkskrekkdwftdktsatvicrknasisvraqdryyssswsewasvpcsggggsggggsgg<br>ggsrvipvsgparclsqsrnllkttddmvktarekllkhysctaedidheditrdqtstlktclplelhhknesclatretsstttrgs<br>clppqktslmmticlgsiyedlkmyqtefqainaalqnhnhqqiildkgmlvaidelmqslnhngetlrqkppvgead<br>pyryvkmklcilllhafstrvvtinrvmgylssasgpALFKSSFPpgsEVQLVESGGGLVQPGNSLR<br>LSCAASGFTFSKFGMSWVRQAPGKGLEWVSSISGSGRDTLYAESVKGRFTISR<br>DNAKTTLYLQMNSLRPEDTAVYYCTIGGSLSVSSQGTLVTVSSggggsggggsggggs<br>sggggsggggsggggsggggsQSVLTQPPSVSGAPGQRVTISCSGSRSNIGSNTVKWYQQLPG |

| SEQ ID NO. | Name | Sequence |
|---|---|---|
| | | TAPKLLIYYNDQRPSGVPDRFSGSKSGTSASLAITGLQAEDEADYYCQSYDRY<br>THPALLFGTGTKVTVLggggsggggsggggsQVQLVESGGGVVQPGRSLRLSCAAS<br>GFTFSSYGMHWVRQAPGKGLEWVAFIRYeGSNKYYAeSVKGRFTISRDNSKN<br>TLYLQMNSLRAEDTAVYYCKTHGSHDNWGQGTMVTVSS** |
| 532 | WW0797 | iwelkkdvyvveldwypdapgemvvltcdtpeedgitwildqssevlgsgktItiqvkefgdagqytchkggevlshs<br>llllhkkedgiwstdilkdqkepknktflrceaknysgrftcwwIttistdIffsvkssrgssdpqgvtcgaatIsaervrgd<br>nkeyeysvecqedsacpaaeeslpievmvdavhklkyenytssffirdiikpdppknIqlkplknsrqvevsweypdt<br>wstphsyfshfcvqvqgkskrekkdwftdktsatvicrknasisvraqdryyssswsewasvpcsggggsggggsgg<br>ggsrnIpvatpdpgmfpclhhsqnlIraysnmlqkarqtlefypctseeidheditkdktstveacIpleltknescInsre<br>tsfitngsclasrktsfmmalcIssiyedlkmyqvefktmnakIlmdpkrqifldqnmlavidelmqaInfnsetvpqk<br>ssleepdfyktkiklcillhafriravtidrvmsylnassggpALFKSSFPpgsEVQLVESGGGLVQPGN<br>SLRLSCAASGFTFSKFGMSWVRQAPGKGLEWVSSISGSGRDTLYAESVKGRFT<br>ISRDNAKTTLYLQMNSLRPEDTAVYYCTIGGSLSVSSQGTLVTVSSggggsggggsg<br>gggsggggsggggsggggsQSVLTQPPSVSGAPGQRVTISCSGSRSNIGSNTVKWYQQL<br>PGTAPKLLIYYNDQRPSGVPDRFSGSKSGTSASLAITGLQAEDEADYYCQSYD<br>RYTHPALLFGTGTKVTVLggggsggggsggggsQVQLVESGGGVVQPGRSLRLSCA<br>ASGFTFSSYGMHWVRQAPGKGLEWVAFIRYeGSNKYYAeSVKGRFTISRDNSK<br>NTLYLQMNSLRAEDTAVYYCKTHGSHDNWGQGTMVTVSS** |
| 533 | WW0798 | iwelkkdvyvveldwypdapgemvvltcdtpeedgitwtldqssevlgsgktItiqvkefgdagqytchkggevlshs<br>llllhkkedgiwstdilkdqkepknktflrceaknysgrftcwwIttistdIffsvkssrgssdpqgvtcgaatIsaervrgd<br>nkeyeysvecqedsacpaaeeslpievmvdavhlayenytssffirdiikpdppknIqlkplknsrqvevsweypdt<br>wstphsyfshfcvqvqgkskrekkdwftdktsatvicrknasisvraqdryyssswsewasvpcsggggsggggsgg<br>ggsrvipvsgparcIsqsrnlIktttddmvktareklkhysctaedidheditrdqtstIktclplelhknesclatretsstttrgs<br>cIppqktsImmticlgsiyedlkmyqtefqainaalqnhnhqqiildkgmlvaidelmqslnhngetIrqkppvgead<br>pyrvkmklcillhafstrvvtinrvmgylssasggpALFKSSFPpgsEVQLVESGGGLVQPGNSLR<br>LSCAASGFTFSKFGMSWVRQAPGKGLEWVSSISGSGRDTLYAESVKGRFTISR<br>DNAKTTLYLQMNSLRPEDTAVYYCTIGGSLSVSSQGTLVTVSSggggsggggsggggg<br>sggggsggggsggggsQSVLTQPPSVSGAPGQRVTISCSGSRSNIGdeTVKWYQQLPGT<br>APKLLIYYNDQRPSGVPDRFSGSKSGTSASLAITGLQAEDEADYYCQSYDRYT<br>HPALLFGTGTKVTVLggggsggggsggggsQVQLVESGGGVVQPGRSLRLSCAASGF<br>TFSSYGMHWVRQAPGKGLEWVAFIRYeGSNKYYAeSVKGRFTISRDNSKNTL<br>YLQMNSLRAEDTAVYYCKTHGSHDNWGQGTMVTVSS** |
| 534 | WW0799 | iwelkkdvyvveldwypdapgemvvltcdtpeedgitwildqssevlgsgktItiqvkefgdagqytchkggevlshs<br>llllhkkedgiwstdilkdqkepknktflrceaknysgrftcwwIttistdIffsvkssrgssdpqgvtcgaatIsaervrgd<br>nkeyeysvecqedsacpaaeeslpievmvdavhlayenytssffirdiikpdppknIqlkplknsrqvevsweypdt<br>wstphsyfshfcvqvqgkskrekkdwftdktsatvicrknasisvraqdryyssswsewasvpcsggggsggggsgg<br>ggsrnIpvatpdpgmfpclhhsqnlIraysnmlqkarqtlefypctseeidheditkdktstveacIpleltknescInsre<br>tsfitngsclasrktsfmmalcIssiyedlkmyqvefktmnakIlmdpkrqifldqnmlavidelmqaInfnsetvpqk<br>ssleepdfyktkiklcillhafriravtidrvmsylnassggpALFKSSFPpgsEVQLVESGGGLVQPGN<br>SLRLSCAASGFTFSKFGMSWVRQAPGKGLEWVSSISGSGRDTLYAESVKGRFT<br>ISRDNAKTTLYLQMNSLRPEDTAVYYCTIGGSLSVSSQGTLVTVSSggggsggggsg<br>gggsggggsggggsggggsQSVLTQPPSVSGAPGQRVTISCSGSRSNIGdeTVKWYQQL<br>PGTAPKLLIYYNDQRPSGVPDRFSGSKSGTSASLAITGLQAEDEADYYCQSYD<br>RYTHPALLFGTGTKVTVLggggsggggsggggsQVQLVESGGGVVQPGRSLRLSCA<br>ASGFTFSSYGMHWVRQAPGKGLEWVAFIRYeGSNKYYAeSVKGRFTISRDNSK<br>NTLYLQMNSLRAEDTAVYYCKTHGSHDNWGQGTMVTVSS** |
| 535 | WW0800 | iwelkkdvyvveldwypdapgemvvitcdtpeedgitwildqssevlgsgktltiqvkefgdagqytchkggevlshs<br>llllhkkedgiwstdilkdqkepknkffirceaknysgrftcwlttistdltfsvkssrgssdpqgvtcgaatlsaervrgd<br>nkeyeysvecqedsacpaaeeslpievmvdavhklkyenytssffirdiikpdppknlqlkplknsrqvevsweypdt<br>wstphsyfshfcvqvqgkskrekkdwftdktsatvicrknasisvraqdryyssswsewasvpcsggggsggggsgg<br>ggsrvipvsgparclsqsrnllktttddmvktareklkhysctaedidheditrdqtstlktclplelhknesclatretsstttrgs<br>clppqktslmmticlgsiyedlkmyqtefqainaalqnhnhqqiildkgmlvaidelmqslnhngetlrqkppvgead<br>pyrvkmklcillhafstrvvtinrvmgylssasggpALFKSSFPpgsEVQLVESGGGLVQPGNSLR<br>LSCAASGFTFSKFGMSWVRQAPGKGLEWVSSISGSGRDTLYAESVKGRFTISR<br>DNAKTTLYLQMNSLRPEDTAVYYCTIGGSLSVSSQGTLVTVSSggggsggggsgggg<br>sggggsggggsggggsQSVLTQPPSVSGAPGQRVTISCSGSRSNIGSNTVKWYQQLPG<br>TAPKLLIYYNDQRPSGVPDRFSGSKSGTSASLAITGLQAEDEADYYCQSYDRY<br>THPALLFGTGIKVTVLgqpkaapsvtlfppsseelqankatlycliscifypgavtvawkadsspvkagvett<br>tpskqsnnkyaassylsltpeqwkshrsyscqvthegstvektvaptecs** |
| 536 | WW0801 | iwelkkdvyvveldwypdapgemvvitcdtpeedgitwildqssevlgsgktltiqvkefgdagqytchkggevlshs<br>llllhkkedgiwstdilkdqkepknkifirceaknysgrftcwlttistdltfsvkssrgssdpqgvtcgaatlsaervrgd<br>nkeyeysvecqedsacpaaeeslpievmvdavhklkyenytssffirdiikpdppknlqlkplknsrqvevsweypdt<br>wstphsyfshfcvqvqgkskrekkdwftdktsatvicrknasisvraqdryyssswsewasvpcsggggsggggsgg<br>ggsrnlpvatpdpgmfpclhhsqnllraysnmlqkarqtlefypctseeidheditkdktstveaclpleltkneclnsre<br>tsfitngsclasrktsfmmalclssiyedlkmyqvefktmnakllmdpkrqifldqnmlavidelmqalnfnsetvpqk<br>ssleepdfyktkiklcillhafriravtidrvmsylnassggpALFKSSFPpgsEVQLVESGGGLVQPGN<br>SLRLSCAASGFTFSKFGMSWVRQAPGKGLEWVSSISGSGRDTLYAESVKGRFT<br>ISRDNAKTTLYLQMNSLRPEDTAVYYCTIGGSLSVSSQGTLVTVSSggggsggggsg |

| SEQ ID NO. | Name | Sequence |
|---|---|---|
| | | gggsggggsggggsggggsggggsQSVLTQPPSVSGAPGQRVTISCSGSRSNIGSNTVKWYQQL<br>PGTAPKLLIYYNDQRPSGVPDRFSGSKSGTSASLAITGLQAEDEADYYCQSYD<br>RYTHPALLFGTGIKVTVLgqpkaapsvtlfppsseelqankatlyclisdfypgavtvawkadsspvkag<br>vettlpskqsnnkyaassylsltpeqwkshrsyscqvthegstvektvaptecs** |
| 537 | WW0802 | iwelkkdvyvveldwypdapgemvvitcdtpeedgitwildqssevlgsgktltiqvkefgdagqytchkggevlshs<br>llllhkkedgiwstdilkdqkepknktflrceaknysgrftcwwlttistdltfsvkssrgssdpqgvtcgaatlsaervrgd<br>nkeyeysvecqedsacpaaeeslpievmvdavhklkyenytssffirdiikpdppknlqlkplknsrqvevsweypdt<br>wstphsyfshfcvqvqgkskrekkchvftdktsatvicrknasisvraqdryyssswsewasvpcsggggsggggsgg<br>ggsrvipvsgparclsqsrnllkttddmvktareklkhysctaedidheditrdqtstlktclplelhknesclatretssttrgs<br>clppqktslmmticlgsiyedlkmyqtefqainaalqnhnhqqiildkgmlvaidelmqslnhngetlrqkppvgead<br>pyrvkmklcillhafstrvvtinrvmgylssasggpALFKSSFPpgsEVQLVESGGGLVQPGNSLR<br>LSCAASGFTFSKFGMSWVRQAPGKGLEWVSSISGSGRDTLYAESVKGRFTISR<br>DNAKTTLYLQMNSLRPEDTAVYYCTIGGSLSVSSQGTLVTVSSggggsggggsggggs<br>sggggsggggsggggsQSVLTQPPSVSGAPGQRVTISCSGSRSNIGdeTVKWYQQLPGT<br>APKLLIYYNDQRPSGVPDRFSGSKSGTSASLAITGLQAEDEADYYCQSYDRYT<br>HPALLFGTGTKVTVLgqpkaapsvtlfppsseelqankativclisdfypgavtvawkadsspvkagvetttt<br>pskqsnnkyaassylsltpeqwkshrsyscqvthegstvektvaptecs** |
| 538 | WW0803 | iwelkkdvyvveldwypdapgemvvitcdtpeedgitwfldqssevlgsgktltiqvkefgdagqytchkggevlshs<br>llllhkkedgiwstdilkdqkepknkffirceaknysgrftcwwlttistdltfsvkssrgssdpqgvtcgaatlsaervrgd<br>nkeyeysvecqedsacpaaeeslpievmvdavhklkyenytssffirdiikpdppknlqlkplknsrqvevsweypdt<br>wstphsyfshfcvqvqgkskrekkdwftdktsatvicrknasisvraqdryyssswsewasvpcsggggsggggsgg<br>ggsrnlpvatpdpgmfpclhhsqnllraysnmlqkarqtlefypctseeidheditkdktstveaclpleltknesclnsre<br>tsfitngsclasrktsfmmalclssiyedlkmyqvefktmnakllmdpkrqifldqnmlavidelmqalnfnsetvpqk<br>ssleepdfyktkiklcillhafriravtidrvmsylnassggpALFKSSFPpgsEVQLVESGGGLVQPGN<br>SLRLSCAASGFTFSKFGMSWVRQAPGKGLEWVSSISGSGRDTLYAESVKGRFT<br>ISRDNAKTTLYLQMNSLRPEDTAVYYCTIGGSLSVSSQGTLVTVSSggggsggggsg<br>gggsggggsggggsggggsQSVLTQPPSVSGAPGQRVTISCSGSRSNIGdeTVKWYQQL<br>PGTAPKLLIYYNDQRPSGVPDRFSGSKSGTSASLAITGLQAEDEADYYCQSYD<br>RYTHPALLFGTGTKVTVLgqpkaapsvtlfppsseelqankatlyclisdfypgavtvawkadsspvkag<br>vettlpskqsnnkyaassylsltpeqwkshrsyscqvthegstvektvaptecs** |
| 539 | WW0643 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSGGPGPAGLYAQPGSCDLPHTYNLRNKRALKVLAQMRRLTPL<br>SCLKDRKDFGFPLEKVDAQQIQKAQSIPVLRDLTQQILNLFASKDSSAAWNAT<br>LLDSFCNDLHQQLNDLQGCLMQQVGVQESPLTQEDSLLAVRIYFHRITVFLRE<br>KKHSPCAWEVVRAEVWRALSSSANVLGRLREEKASGGPGPAGLYAQPGSEV<br>QLVESGGGLVQPGNSLRLSCAASGFTFSKFGMSWVRQAPGKGLEWVSSISGS<br>GRDTLYAESVKGRFTISRDNAKTTLYLQMNSLRPEDTAVYYCTIGGSLSVSSQ<br>GTLVTVSS |
| 540 | WW0644 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSGGPALFKSSFPPGSCDLPHTYNLRNKRALKVLAQMRRLTPLS<br>CLKDRKDFGFPLEKVDAQQIQKAQSIPVLRDLTQQILNLFASKDSSAAWNATL<br>LDSFCNDLHQQLNDLQGCLMQQVGVQESPLTQEDSLLAVRIYFHRITVFLREK<br>KHSPCAWEVVRAEVWRALSSSANVLGRLREEKASGGPALFKSSFPPGSEVQL<br>VESGGGLVQPGNSLRLSCAASGFTFSKFGMSWVRQAPGKGLEWVSSISGSGR<br>DTLYAESVKGRFTISRDNAKTTLYLQMNSLRPEDTAVYYCTIGGSLSVSSQGT<br>LVTVSS |
| 541 | WW0645 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSGGPGPAGLYAQPGSCNLSQTHSLNNRRTLMLMAQMRRISPFS<br>CLKDRHDFEFPQEEFDGNQFQKAQAISVLHEMMQQTFNLFSTKNSSAAWDET<br>LLEKFYIELFQQMNDLEACVIQEVGVEETPLMNEDSILAVKKYFQRITLYLME<br>KKYSPCAWEVVRAEIMRSLSFSTNLQKRLRRKDSGGPGPAGLYAQPGSEVQL<br>VESGGGLVQPGNSLRLSCAASGFTFSKFGMSWVRQAPGKGLEWVSSISGSGR<br>DTLYAESVKGRFTISRDNAKTTLYLQMNSLRPEDTAVYYCTIGGSLSVSSQGT<br>LVTVSS |
| 542 | WW0646 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSGGPALFKSSFPPGSCNLSQTHSLNNRRTLMLMAQMRRISPFSC<br>LKDRHDFEFPQEEFDGNQFQKAQAISVLHEMMQQTFNLFSTKNSSAAWDETL<br>LEKFYIELFQQMNDLEACVIQEVGVEETPLMNEDSILAVKKYFQRITLYLMEK<br>KYSPCAWEVVRAEIMRSLSFSTNLQKRLRRKDSGGPALFKSSFPPGSEVLVES<br>GGGLVQPGNSLRLSCAASGFTFSKFGMSWVRQAPGKGLEWVSSISGSGRDTL<br>YAESVKGRFTISRDNAKTTLYLQMNSLRPEDTAVYYCTIGGSLSVSSQGTLVT<br>VSS |

| SEQ ID NO. | Name | Sequence |
|---|---|---|
| 543 | WW0647 | CDLPHTYNLRNKRALKVLAQMRRLTPLSCLKDRKDFGFPLEKVDAQQIQKAQ SIPVLRDLTQQILNLFASKDSSAAWNATLLDSFCNDLHQQLNDLQGCLMQQV GVQESPLTQEDSLLAVRIYFHRITVFLREKKHSPCAWEVVRAEVWRALSSSAN VLGRLREEKAHHHHHH |
| 544 | WW0648 | CNLSQTHSLNNRRTLMLMAQMRRISPFSCLKDRHDFEFPQEEFDGNQFQKAQ AISVLHEMMQQTFNLFSTKNSSAAWDETLLEKFYIELFQQMNDLEACVIQEVG VEETPLMNEDSILAVKKYFQRITLYLMEKKYSPCAWEVVRAEIMRSLSFSTNL QKRLRRKDHHHHHH |
| 545 | WW0781 | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSGGPGPAGLYAQPGSCDLPQTHSLGSRRTLMLLAQMRRISLFS CLKDRHDFGFPQEEFGNQFQKAETIPVLHEMIQQIFNLFSTKDSSAAWDETLLD KFYTELYQQLNDLEACVIQGVGVEETPLMKEDSILAVRKYFQRITLYLKEKKY SPCAWEVVRAEIMRSFSLSTNLQESLRSKESGGPGPAGLYAQPGSEVQLVESG GGLVQPGNSLRLSCAASGFTFSKFGMSWVRQAPGKGLEWVSSISGSGRDTLY AESVKGRFTISRDNAKTTLYLQMNSLRPEDTAVYYCTIGGSLSVSSQGTLVTV SS |
| 546 | WW0782 | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSGGPGPAGLYAQPGSCNLSQTHSLNNRRTLMLMAQMRRISPFS CLKDRHDFEFPQEEFDGNQFQKAQAISVLHEMMQQTFNLFSTKDSSAAWDET LLEKFYIELFQQMNDLEACVIQEVGVEETPLMNEDSILAVKKYFQRITLYLME KKYSPCAWEVVRAEIMRSLSFSTNLQKRLRRKDSGGPGPAGLYAQPGSEVQL VESGGGLVQPGNSLRLSCAASGFTFSKFGMSWVRQAPGKGLEWVSSISGSGR DTLYAESVKGRFTISRDNAKTTLYLQMNSLRPEDTAVYYCTIGGSLSVSSQGT LVTVSS |
| 547 | WW0783 | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSGGPGPAGLYAQPGSCDLPQTHSLNNRRTLMLMAQMRRISPFS CLKDRHDFEFPQEEFDGNQFQKAQAISVLHEMMQQTFNLFSTKDSSAAWDET LLEKFYIELFQQMNDLEACVIQEVGVEETPLMNEDSILAVKKYFQRITLYLME KKYSPCAWEVVRAEIMRSLSFSTNLQKRLRRKDSGGPGPAGLYAQPGSEVQL VESGGGLVQPGNSLRLSCAASGFTFSKFGMSWVRQAPGKGLEWVSSISGSGR DTLYAESVKGRFTISRDNAKTTLYLQMNSLRPEDTAVYYCTIGGSLSVSSQGT LVTVSS |
| 548 | WW0784 | CDLPQTHSLGSRRTLMLLAQMRRISLFSCLKDRHDFGFPQEEFGNQFQKAETIP VLHEMIQQIFNLFSTKDSSAAWDETLLDKFYTELYQQLNDLEACVIQGVGVEE TPLMKEDSILAVRKYFQRITLYLKEKKYSPCAWEVVRAEIMRSFSLSTNLQESL RSKEHHHHHH |
| 549 | WW0785 | CNLSQTHSLNNRRTLMLMAQMRRISPFSCLKDRHDFEFPQEEFDGNQFQKAQ AISVLHEMMQQTFNLFSTKDSSAAWDETLLEKFYIELFQQMNDLEACVIQEVG VEETPLMNEDSILAVKKYFQRITLYLMEKKYSPCAWEVVRAEIMRSLSFSTNL QKRLRRKDHHHHHH |
| 550 | WW0786 | CDLPQTHSLNNRRTLMLMAQMRRISPFSCLKDRHDFEFPQEEFDGNQFQKAQ AISVLHEMMQQTFNLFSTKDSSAAWDETLLEKFYIELFQQMNDLEACVIQEVG VEETPLMNEDSILAVKKYFQRITLYLMEKKYSPCAWEVVRAEIMRSLSFSTNL QKRLRRKDHHHHHH |
| 551 | WW0815 | EAHKSEIAHRYNDLGEQHFKGLVLIAFSQYLQKCSYDEHAKLVQEVTDFAKT CVADESAANCDKSLHTLFGDKLCAIPNLRENYGELADCCTKQEPERNECFLQH KDDNPSLPPFERPEAEAMCTSFKENPTTFMGHYLHEVARRHPYFYAPELLYYA EQYNEILTQCCAEADKESCLTPKLDGVKEKALVSSVRQRMKCSSMQKFGERA FKAWAVARLSQTFPNADFAEITKLATDLTKVNKECCHGDLLECADDRAELAK YMCENQATISSKLQTCCDKPLLKKAHCLSEVEHDTMPADLPAIAADFVEDQE VCKNYAEAKDVFLGTFLYEYSRRHPDYSVSLLLRLAKKYEATLEKCCAEANP PACYGTVLAEFQPLVEEPKNLVKTNCDLYEKLGEYGFQNAILVRYTQKAPQV STPTLVEAARNLGRVGTKCCTLPEDQRLPCVEDYLSAILNRVCLLHEKTPVSE HVTKCCSGSLVERRPCFSALTVDETYVPKEFKAETFTFHSDICTLPEKEKQIKK QTALAELVKHKPKATAEQLKTVMDDFAQFLDTCCKAADKDTCFSTEGPNLVT RCKDALASGGPALFKSSFPPGSCDLPQTHNLRNKRALTLLVQMRRLSPLSCLK DRKDFGFPQEKVDAQQIKKAQAIPVLSELTQQILNIFTSKDSSAAWNTTLLDSF CNDLHQQLNDLQGCLMQQVGVQEFPLTQEDALLAVRKYFHRITVYLREKKH SPCAWEVVRAEVWRALSSSANVLGRLREEKSGGPALFKSSFPPGSEAHKSEIA HRYNDLGEQHFKGLVLIAFSQYLQKCSYDEHAKLVQEVTDFAKTCVADESAA NCDKSLHTLFGDKLCAIPNLRENYGELADCCTKQEPERNECFLQHKDDNPSLP PFERPEAEAMCTSFKENPTTFMGHYLHEVARRHPYFYAPELLYYAEQYNEILT |

| SEQ ID NO. | Name | Sequence |
|---|---|---|
|  |  | QCCAEADKESCLTPKLDGVKEKALVSSVRQRMKCSSMQKFGERAFKAWAVA RLSQTFPNADFAEITKLATDLTKVNKECCHGDLLECADDRAELAKYMCENQA TISSKLQTCCDKPLLKKAHCLSEVEHDTMPADLPAIAADFVEDQEVCKNYAEA KDVFLGTFLYEYSRRHPDYSVSLLLRLAKKYEATLEKCCAEANPPACYGTVL AEFQPLVEEPKNLVKTNCDLYEKLGEYGFQNAILVRYTQKAPQVSTPTLVEAA RNLGRVGTKCCTLPEDQRLPCVEDYLSAILNRVCLLHEKTPVSEHVTKCCSGS LVERRPCFSALTVDETYVPKEFKAETFTFHSDICTLPEKEKQIKKQTALAELVK HKPKATAEQLKTVMDDFAQFLDTCCKAADKDTCFSTEGPNLVTRCKDALAH HHHHH |
| 552 | WW0816 | EAHKSEIAHRYNDLGEQHFKGLVLIAFSQYLQKCSYDEHAKLVQEVTDFAKT CVADESAANCDKSLHTLFGDKLCAIPNLRENYGELADCCTKQEPERNECFLQH KDDNPSLPPFERPEAEAMCTSFKENPTTFMGHYLHEVARRHPYFYAPELLYYA EQYNEILTQCCAEADKESCLTPKLDGVKEKALVSSVRQRMKCSSMQKFGERA FKAWAVARLSQTFPNADFAEITKLATDLTKVNKECCHGDLLECADDRAELAK YMCENQATISSKLQTCCDKPLLKKAHCLSEVEHDTMPADLPAIAADFVEDQE VCKNYAEAKDVFLGTFLYEYSRRHPDYSVSLLLRLAKKYEATLEKCCAEANP PACYGTVLAEFQPLVEEPKNLVKTNCDLYEKLGEYGFQNAILVRYTQKAPQV STPTLVEAARNLGRVGTKCCTLPEDQRLPCVEDYLSAILNRVCLLHEKTPVSE HVTKCCSGSLVERRPCFSALTVDETYVPKEFKAETFTFHSDICTLPEKEKQIKK QTALAELVKHKPKATAEQLKTVMDDFAQFLDTCCKAADKDTCFSTEGPNLVT RCKDALASGGPALFKSSFPPGSCDLPHTYNLRNKRALKVLAQMRRLTPLSCLK DRKDFGFPLEKVDAQQIQKAQSIPVLRDLTQQILNLFASKDSSAAWNATLLDS FCNDLHQQLNDLQGCLMQQVGVQESPLTQEDSLLAVRIYFHRITVFLREKKHS PCAWEVVRAEVWRALSSSANVLGRLREEKASGGPALFKSSFPPGSEAHKSEIA HRYNDLGEQHFKGLVLIAFSQYLQKCSYDEHAKLVQEVTDFAKTCVADESAA NCDKSLHTLFGDKLCAIPNLRENYGELADCCTKQEPERNECFLQHKDDNPSLP PFERPEAEAMCTSFKENPTTFMGHYLHEVARRHPYFYAPELLYYAEQYNEILT QCCAEADKESCLTPKLDGVKEKALVSSVRQRMKCSSMQKFGERAFKAWAVA RLSQTFPNADFAEITKLATDLTKVNKECCHGDLLECADDRAELAKYMCENQA TISSKLQTCCDKPLLKKAHCLSEVEHDTMPADLPAIAADFVEDQEVCKNYAEA KDVFLGTFLYEYSRRHPDYSVSLLLRLAKKYEATLEKCCAEANPPACYGTVL AEFQPLVEEPKNLVKTNCDLYEKLGEYGFQNAILVRYTQKAPQVSTPTLVEAA RNLGRVGTKCCTLPEDQRLPCVEDYLSAILNRVCLLHEKTPVSEHVTKCCSGS LVERRPCFSALTVDETYVPKEFKAETFTFHSDICTLPEKEKQIKKQTALAELVK HKPKATAEQLKTVMDDFAQFLDTCCKAADKDTCFSTEGPNLVTRCKDALAH HHHHH |
| 553 | WW0817 | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSSGGPALFKSSFPPGSCDLPQTHNLRNKRALTLLVQMRRLSPLSC LKDRKDFGFPQEKVDAQQlKKAQAIPVLSELTQQILNIFTSKDSSAAWNTTLLD SFCNDLHQQLNDLQGCLMQQVGVQEFPLTQEDALLAVRKYFHRITVYLREKK HSPCAWEVVRAEVWRALSSSANVLGRLREEKSGGPALFKSSFPPGSEAHKSEI AHRYNDLGEQHFKGLVLIAFSQYLQKCSYDEHAKLVQEVTDFAKTCVADESA ANCDKSLHTLFGDKLCAIPNLRENYGELADCCTKQEPERNECFLQHKDDNPSL PPFERPEAEAMCTSFKENPTTFMGHYLHEVARRHPYFYAPELLYYAEQYNEIL TQCCAEADKESCLTPKLDGVKEKALVSSVRQRMKCSSMQKFGERAFKAWAV ARLSQlFPNADFAEITKLATDLTKVNKECCHGDLLECADDRAELAKYMCENQ ATISSKLQTCCDKPLLKKAHCLSEVEHDTMPADLPAIAADFVEDQEVCKNYAE AKDVFLGIFLYEYSRRHPDYSVSLLLRLAKKYEATLEKCCAEANPPACYGTV LAEFQPLVEEPKNLVKTNCDLYEKLGEYGFQNAILVRYTQKAPQVSTPTLVEA ARNLGRVGTKCCTLPEDQRLPCVEDYLSAILNRVCLLHEKTPVSEHVTKCCSG SLVERRPCFSALTVDETYVPKEFKAETFTFHSDICTLPEKEKQIKKQTALAELV KHKPKATAEQLKTVMDDFAQFLDTCCKAADKDTCFSTEGPNLVTRCKDALA HHHHHH |
| 554 | WW0818 | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSSGGPALFKSSFPPGSCDLPHTYNLRNKRALKVLAQMRRLTPLS CLKDRKDFGFPLEKVDAQQIQKAQSIPVLRDLTQQILNLFASKDSSAAWNATL LDSFCNDLHQQLNDLQGCLMQQVGVQESPLTQEDSLLAVRIYFHRITVFLREK KHSPCAWEVVRAEVWRALSSSANVLGRLREEKASGGPALFKSSFPPGSEAHK SEIAHRYNDLGEQHFKGLVLIAFSQYLQKCSYDEHAKLVQEVTDFAKTCVAD ESAANCDKSLHTLFGDKLCAIPNLRENYGELADCCTKQEPERNECFLQHKDD NPSLPPFERPEAEAMCTSFKENPTTFMGHYLHEVARRHPYFYAPELLYYAEQY NEILTQCCAEADKESCLTPKLDGVKEKALVSSVRQRMKCSSMQKFGERAFKA WAVARLSQTFPNADFAEITKLATDLTKVNKECCHGDLLECADDRAELAKYM CENQATISSKLQTCCDKPLLKKAHCLSEVEHDTMPADLPAIAADFVEDQEVCK NYAEAKDVFLGTFLYEYSRRHPDYSVSLLLRLAKKYEATLEKCCAEANPPAC YGTVLAEFQPLVEEPKNLVKTNCDLYEKLGEYGFQNAILVRYTQKAPQVSTPT LVEAARNLGRVGTKCCTLPEDQRLPCVEDYLSAILNRVCLLHEKTPVSEHVTK CCSGSLVERRPCFSALTVDETYVPKEFKAETFTFHSDICTLPEKEKQIKKQTAL |

Sequence Table

| SEQ ID NO. | Name | Sequence |
|---|---|---|
| | | AELVKHKPKATAEQLKTVMDDFAQFLDTCCKAADKDTCFSTEGPNLVTRCK<br>DALAHHHHHH |
| 555 | WW0819 | EAHKSEIAHRYNDLGEQHFKGLVLIAFSQYLQKCSYDEHAKLVQEVTDFAKT<br>CVADESAANCDKSLHTLFGDKLCAIPNLRENYGELADCCTKQEPERNECFLQH<br>KDDNPSLPPFERPEAEAMCTSFKENPTTFMGHYLHEVARRHPYFYAPELLYYA<br>EQYNEILTQCCAEADKESCLTPKLDGVKEKALVSSVRQRMKCSSMQKFGERA<br>FKAWAVARLSQTFPNADFAEITKLATDLTKVNKECCHGDLLECADDRAELAK<br>YMCENQATISSKLQTCCDKPLLKKAHCLSEVEHDTMPADLPAIAADFVEDQE<br>VCKNYAEAKDVFLGTFLYEYSRRHPDYSVSLLLRLAKKYEATLEKCCAEANP<br>PACYGTVLAEFQPLVEEPKNLVKTNCDLYEKLGEYGFQNAILVRYTQKAPQV<br>STPTLVEAARNLGRVGTKCCTLPEDQRLPCVEDYLSAILNRVCLLHEKTPVSE<br>HVTKCCSGSLVERRPCFSALTVDETYVPKEFKAETFTFHSDICTLPEKEKQIKK<br>QTALAELVKHKPKATAEQLKTVMDDFAQFLDTCCKAADKDTCFSTEGPNLVT<br>RCKDALASGGPALFKSSFPPGSCDLPQTHNLRNKRALTLLVQMRRLSPLSCLK<br>DRKDFGFPQEKVDAQQIKKAQAIPVLSELTQQILNIFTSKDSSAAWNTTLLDSF<br>CNDLHQQLNDLQGCLMQQVGVQEFPLTQEDALLAVRKYFHRITVYLREKKH<br>SPCAWEVVRAEVWRALSSSANVLGRLREEKSGGPALFKSSFPPGSEVQLVESG<br>GGLVQPGNSLRLSCAASGFTFSKFGMSWVRQAPGKGLEWVSSISGSGRDTLY<br>AESVKGRFTISRDNAKTTLYLQMNSLRPEDTAVYYCTIGGSLSVSSQGTLVTV<br>SSHHHHHH |
| 556 | WW0820 | EAHKSEIAHRYNDLGEQHFKGLVLIAFSQYLQKCSYDEHAKLVQEVTDFAKT<br>CVADESAANCDKSLHTLFGDKLCAIPNLRENYGELADCCTKQEPERNECFLQH<br>KDDNPSLPPFERPEAEAMCTSFKENPTTFMGHYLHEVARRHPYFYAPELLYYA<br>EQYNEILTQCCAEADKESCLTPKLDGVKEKALVSSVRQRMKCSSMQKFGERA<br>FKAWAVARLSQTFPNADFAEITKLATDLTKVNKECCHGDLLECADDRAELAK<br>YMCENQATISSKLQTCCDKPLLKKAHCLSEVEHDTMPADLPAIAADFVEDQE<br>VCKNYAEAKDVFLGTFLYEYSRRHPDYSVSLLLRLAKKYEATLEKCCAEANP<br>PACYGTVLAEFQPLVEEPKNLVKTNCDLYEKLGEYGFQNAILVRYTQKAPQV<br>STPTLVEAARNLGRVGTKCCTLPEDQRLPCVEDYLSAILNRVCLLHEKTPVSE<br>HVTKCCSGSLVERRPCFSALTVDETYVPKEFKAETFTFHSDICTLPEKEKQIKK<br>QTALAELVKHKPKATAEQLKTVMDDFAQFLDTCCKAADKDTCFSTEGPNLVT<br>RCKDALASGGPALFKSSFPPGSCDLPHTYNLRNKRALKVLAQMRRLTPLSCLK<br>DRKDFGFPLEKVDAQQIQKAQSIPVLRDLTQQILNLFASKDSSAAWNATLLDS<br>FCNDLHQQLNDLQGCLMQQVGVQESPLTQEDSLLAVRIYFHRITVFLREKKHS<br>PCAWEVVRAEVWRALSSSANVLGRLREEKASGGPALFKSSFPPGSEVQLVESG<br>GGLVQPGNSLRLSCAASGFTFSKFGMSWVRQAPGKGLEWVSSISGSGRDTLY<br>AESVKGRFTISRDNAKTTLYLQMNSLRPEDTAVYYCTIGGSLSVSSQGTLVTV<br>SSHHHHHH |
| 557 | WW0821 | DAHKSEVAHRFKDLGEENFKALVLIAFAQYLQQCPFEDHVKLVNEVTEFAKT<br>CVADESAENCDKSLHTLFGDKLCTVATLRETYGEMADCCAKQEPERNECFLQ<br>HKDDNPNLPRLVRPEVDVMCTAFHDNEETFLKKYLYEIARRHPYFYAPELLFF<br>AKRYKAAFTECCQAADKAACLLPKLDELRDEGKASSAKQRLKCASLQKFGER<br>AFKAWAVARLSQRFPKAEFAEVSKLVTDLTKVHTECCHGDLLECADDRADL<br>AKYICENQDSISSKLKECCEKPLLEKSHCIAEVENDEMPADLPSLAADFVESKD<br>VCKNYAEAKDVFLGMFLYEYARRHPDYSVVLLLRLAKTYETTLEKCCAAAD<br>PHECYAKVFDEFKPLVEEPQNLIKQNCELFEQLGEYKFQNALLVRYTKKVPQV<br>STPTLVEVSRNLGKVGSKCCKHPEAKRMPCAEDYLSVVLNQLCVLHEKTPVS<br>DRVTKCCTESLVNRRPCFSALEVDETYVPKEFNAETFTFHADICTLSEKERQIK<br>KQTALVELVKHKPKATKEQLKAVMDDFAAFVEKCCKADDKETCFAEEGKKL<br>VAASQAALGLSGGPALFKSSFPPGSCDLPQTHSLGSRRTLMLLAQMRRISLFSC<br>LKDRHDFGFPQEEFGNQFQKAETIPVLHEMIQQIFNLFSTKDSSAAWDETLLDK<br>FYTELYQQLNDLEACVIQGVGVTETPLMKEDSILAVRKYFQRITLYLKEKKYS<br>PCAWEVVRAEIMRSFSLSTNLQESLRSKESGGPALFKSSFPPGSDAHKSEVAHR<br>FKDLGEENFKALVLIAFAQYLQQCPFEDHVKLVNEVTEFAKTCVADESAENC<br>DKSLHTLFGDKLCTVATLRETYGEMADCCAKQEPERNECFLQHKDDNPNLPR<br>LVRPEVDVMCTAFHDNEETFLKKYLYEIARRHPYFYAPELLFFAKRYKAAFTE<br>CCQAADKAACLLPKLDELRDEGKASSAKQRLKCASLQKFGERAFKAWAVAR<br>LSQRFPKAEFAEVSKLVTDLTKVHTECCHGDLLECADDRADLAKYICENQDSI<br>SSKLKECCEKPLLEKSHCIAEVENDEMPADLPSLAADFVESKDVCKNYAEAKD<br>VFLGMFLYEYARRHPDYSVVLLLRLAKTYETTLEKCCAAADPHECYAKVFDE<br>FKPLVEEPQNLIKQNCELFEQLGEYKFQNALLVRYTKKVPQVSTPTLVEVSRN<br>LGKVGSKCCKHPEAKRMPCAEDYLSVVLNQLCVLHEKTPVSDRVTKCCTESL<br>VNRRPCFSALEVDETYVPKEFNAETFTFHADICTLSEKERQIKKQTALVELVKH<br>KPKATKEQLKAVMDDFAAFVEKCCKADDKETCFAEEGKKLVAASQAALGL |
| 558 | WW0822 | DAHKSEVAHRFKDLGEENFKALVLIAFAQYLQQCPFEDHVKLVNEVTEFAKT<br>CVADESAENCDKSLHTLFGDKLCTVATLRETYGEMADCCAKQEPERNECFLQ<br>HKDDNPNLPRLVRPEVDVMCTAFHDNEETFLKKYLYEIARRHPYFYAPELLFF<br>AKRYKAAFTECCQAADKAACLLPKLDELRDEGKASSAKQRLKCASLQKFGER<br>AFKAWAVARLSQRFPKAEFAEVSKLVTDLTKVHTECCHGDLLECADDRADL |

| Sequence Table | | |
|---|---|---|
| SEQ ID NO. | Name | Sequence |
| | | AKYICENQDSISSKLKECCEKPLLEKSHCIAEVENDEMPADLPSLAADFVESKD VCKNYAEAKDVFLGMFLYEYARRHPDYSVVLLLRLAKTYETTLEKCCAAAD PHECYAKVFDEFKPLVEEPQNLIKQNCELFEQLGEYKFQNALLVRYTKKVPQV STPTLVEVSRNLGKVGSKCCKHPEAKRMPCAEDYLSVVLNQLCVLHEKTPVS DRVTKCCTESLVNRRPCFSALEVDETYVPKEFNAETFTFHADICTLSEKERQIK KQTALVELVKHKPKATKEQLKAVMDDFAAFVEKCCKADDKETCFAEEGKKL VAASQAALGLSGGPALFKSSFPPGSCNLSQTHSLNNRRTLMLMAQMRRISPFS CLKDRHDFEFPQEEFDGNQFQKAQAISVLHEMMQQTFNLFSTKNSSAAWDET LLEKFYIELFQQMNDLEACVIQEVGVEETPLMNEDSILAVKKYFQRITLYLME KKYSPCAWEVVRAEIMRSLSFSTNLQKRLRRKDSGGPALFKSSFPPGSDAHKS EVAHRFKDLGEENFKALVLIAFAQYLQQCPFEDHVKLVNEVTEFAKTCVADE SAENCDKSLHTLFGDKLCTVATLRETYGEMADCCAKQEPERNECFLQHKDDN PNLPRLVRPEVDVMCTAFHDNEETFLKKYLYEIARRHPYFYAPELLFFAKRYK AAFTECCQAADKAACLLPKLDELRDEGKASSAKQRLKCASLQKFGERAFKA WAVARLSQRFPKAEFAEVSKLVTDLTKVHTECCHGDLLECADDRADLAKYIC ENQDSISSKLKECCEKPLLEKSHCIAEVENDEMPADLPSLAADFVESKDVCKN YAEAKDVFLGMFLYEYARRHPDYSVVLLLRLAKTYETTLEKCCAAADPHECY AKVFDEFKPLVEEPQNLIKQNCELFEQLGEYKFQNALLVRYTKKVPQVSTPTL VEVSRNLGKVGSKCCKHPEAKRMPCAEDYLSVVLNQLCVLHEKTPVSDRVT KCCTESLVNRRPCFSALEVDETYVPKEFNAETFTFHADICTLSEKERQIKKQTA LVELVKHKPKATKEQLKAVMDDFAAFVEKCCKADDKETCFAEEGKKLVAAS QAALGL |
| 559 | WW0831 | DAHKSEVAHRFKDLGEENFKALVLIAFAQYLQQCPFEDHVKLVNEVTEFAKT CVADESAENCDKSLHTLFGDKLCTVATLRETYGEMADCCAKQEPERNECFLQ HKDDNPNLPRLVRPEVDVMCTAFHDNEETFLKKYLYEIARRHPYFYAPELLFF AKRYKAAFTECCQAADKAACLLPKLDELRDEGKASSAKQRLKCASLQKFGER AFKAWAVARLSQRFPKAEFAEVSKLVTDLTKVHTECCHGDLLECADDRADL AKYICENQDSISSKLKECCEKPLLEKSHCIAEVENDEMPADLPSLAADFVESKD VCKNYAEAKDVFLGMFLYEYARRHPDYSVVLLLRLAKTYETTLEKCCAAAD PHECYAKVFDEFKPLVEEPQNLIKQNCELFEQLGEYKFQNALLVRYTKKVPQV STPTLVEVSRNLGKVGSKCCKHPEAKRMPCAEDYLSVVLNQLCVLHEKTPVS DRVTKCCTESLVNRRPCFSALEVDETYVPKEFNAETFTFHADICTLSEKERQIK KQTALVELVKHKPKATKEQLKAVMDDFAAFVEKCCKADDKETCFAEEGKKL VAASQAALGLSGGPALFKSSFPPGSCDLPQTHSLGNRRALILLAQMRRISPFSC LKDRHDFEFPQEEFDDKQFQKAQAISVLHEMIQQTFNLFSTKDSSAALDETLL DEFYIELDQQLNDLESCVMQEVGVIESPLMYEDSILAVRKYFQRITLYLTEKKY SSCAWEVVRAEIMRSFSLSINLQKRLKSKESGGPALFKSSFPPGSDAHKSEVAH RFKDLGEENFKALVLIAFAQYLQQCPFEDHVKLVNEVTEFAKTCVADESAEN CDKSLHTLFGDKLCTVATLRETYGEMADCCAKQEPERNECFLQHKDDNPNLP RLVRPEVDVMCTAFHDNEETFLKKYLYEIARRHPYFYAPELLFFAKRYKAAFT ECCQAADKAACLLPKLDELRDEGKASSAKQRLKCASLQKFGERAFKAWAVA RLSQRFPKAEFAEVSKLVTDLTKVHTECCHGDLLECADDRADLAKYICENQD SISSKLKECCEKPLLEKSHCIAEVENDEMPADLPSLAADFVESKDVCKNYAEA KDVFLGMFLYEYARRHPDYSVVLLLRLAKTYETTLEKCCAAADPHECYAKVF DEFKPLVEEPQNLIKQNCELFEQLGEYKFQNALLVRYTKKVPQVSTPTLVEVS RNLGKVGSKCCKHPEAKRMPCAEDYLSVVLNQLCVLHEKTPVSDRVTKCCTE SLVNRRPCFSALEVDETYVPKEFNAETFTFHADICTLSEKERQIKKQTALVELV KHKPKATKEQLKAVMDDFAAFVEKCCKADDKETCFAEEGKKLVAASQAALG L |
| 560 | WW0832 | DAHKSEVAHRFKDLGEENFKALVLIAFAQYLQQCPFEDHVKLVNEVTEFAKT CVADESAENCDKSLHTLFGDKLCTVATLRETYGEMADCCAKQEPERNECFLQ HKDDNPNLPRLVRPEVDVMCTAFHDNEETFLKKYLYEIARRHPYFYAPELLFF AKRYKAAFTECCQAADKAACLLPKLDELRDEGKASSAKQRLKCASLQKFGER AFKAWAVARLSQRFPKAEFAEVSKLVTDLTKVHTECCHGDLLECADDRADL AKYICENQDSISSKLKECCEKPLLEKSHCIAEVENDEMPADLPSLAADFVESKD VCKNYAEAKDVFLGMFLYEYARRHPDYSVVLLLRLAKTYETTLEKCCAAAD PHECYAKVFDEFKPLVEEPQNLIKQNCELFEQLGEYKFQNALLVRYTKKVPQV STPTLVEVSRNLGKVGSKCCKHPEAKRMPCAEDYLSVVLNQLCVLHEKTPVS DRVTKCCTESLVNRRPCFSALEVDETYVPKEFNAETFTFHADICTLSEKERQIK KQTALVELVKHKPKATKEQLKAVMDDFAAFVEKCCKADDKETCFAEEGKKL VAASQAALGLSGGPALFKSSFPPGSCDLPQTHSLGNRRALILLAQMGRISHFSC LKDRYDFGFPQEVFDGNQFQKAQAISAFHEMIQQTFNLFSTKDSSAAWDETLL DKFYIELFQQLNDLEACVTQEVGVEEIALMNEDSILAVRKYFQRITLYLMGKK YSPCAWEVVRAEIMRSFSFSTNLQKGLRRKDSGGPALFKSSFPPGSDAHKSEV AHRFKDLGEENFKALVLIAFAQYLQQCPFEDHVKLVNEVTEFAKTCVADESA ENCDKSLHTLFGDKLCTVATLRETYGEMADCCAKQEPERNECFLQHKDDNPN LPRLVRPEVDVMCTAFHDNEETFLKKYLYEIARRHPYFYAPELLFFAKRYKAA FTECCQAADKAACLLPKLDELRDEGKASSAKQRLKCASLQKFGERAFKAWA VARLSQRFPKAEFAEVSKLVTDLTKVHTECCHGDLLECADDRADLAKYICEN QDSISSKLKECCEKPLLEKSHCIAEVENDEMPADLPSLAADFVESKDVCKNYA EAKDVFLGMFLYEYARRHPDYSVVLLLRLAKTYETTLEKCCAAADPHECYAK |

Sequence Table

| SEQ ID NO. | Name | Sequence |
|---|---|---|
| | | VFDEFKPLVEEPQNLIKQNCELFEQLGEYKFQNALLVRYTKKVPQVSTPTLVE VSRNLGKVGSKCCKHPEAKRMPCAEDYLSVVLNQLCVLHEKTPVSDRVTKC CTESLVNRRPCFSALEVDETYVPKEFNAETFTFHADICTLSEKERQIKKQTALV ELVKHKPKATKEQLKAVMDDFAAFVEKCCKADDKETCFAEEGKKLVAASQA ALGL |
| 561 | WW0833 | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSSGGPALFKSSFPPGSCDLPQTHSLGNRRALILLAQMRRISPFSCL KDRHDFEFPQEEFDDKQFQKAQAISVLHEMIQQTFNLFSTKDSSAALDETLLD EFYIELDQQLNDLESCVMQEVGVIESPLMYEDSILAVRKYFQRITLYLTEKKYS SCAWEVVRAEIMRSFSLSINLQKRLKSKESGGPALFKSSFPPGSEVQLVESGGG LVQPGNSLRLSCAASGFTFSKFGMSWVRQAPGKGLEWVSSISGSGRDTLYAES VKGRFTISRDNAKTTLYLQMNSLRPEDTAVYYCTIGGSLSVSSQGTLVTVSS |
| 562 | WW0834 | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSSGGPALFKSSFPPGSCDLPQTHSLGNRRALILLAQMGRISHFSCL KDRYDFGFPQEVFDGNQFQKAQAISAFHEMIQQTFNLFSTKDSSAAWDETLLD KFYIELFQQLNDLEACVTQEVGVEEIALMNEDSILAVRKYFQRITLYLMGKKY SPCAWEVVRAEIMRSFSFSTNLQKGLRRKDSGGPALFKSSFPPGSEVQLVESGG GLVQPGNSLRLSCAASGFTFSKFGMSWVRQAPGKGLEWVSSISGSGRDTLYA ESVKGRFTISRDNAKTTLYLQMNSLRPEDTAVYYCTIGGSLSVSSQGTLVTVSS |
| 563 | WW0737 | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSSGGPGPAGLYAQPGSINYKQLQLQERTNIRKCQELLEQLNGKIN LTYRADFKIPMEMTEKMQKSYTAFAIQEMLQNVFLVFRNNFSSTGWNETIVV RLLDELHQQTVFLKTVLEEKQEERLTWEMSSTALHLKSYYWRVQRYLKLMK YNSYAWMVVRAEIFRNFLIIRRLTRNFQNSGGPGPAGLYAQPGSEVQLVESGG GLVQPGNSLRLSCAASGFTFSKFGMSWVRQAPGKGLEWVSSISGSGRDTLYA ESVKGRFTISRDNAKTTLYLQMNSLRPEDTAVYYCTIGGSLSVSSQGTLVTVSS |
| 564 | WW0738 | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSSGGPALFKSSFPPGSINYKQLQLQERTNIRKCQELLEQLNGKINL TYRADFKIPMEMTEKMQKSYTAFAIQEMLQNVFLVFRNNFSSTGWNETIVVR LLDELHQQTVFLKTVLEEKQEERLTWEMSSTALHLKSYYWRVQRYLKLMKY NSYAWMVVRAEIFRNFLIIRRLTRNFQNSGGPALFKSSFPPGSEVQLVESGGGL VQPGNSLRLSCAASGFTFSKFGMSWVRQAPGKGLEWVSSISGSGRDTLYAESV KGRFTISRDNAKTTLYLQMNSLRPEDTAVYYCTIGGSLSVSSQGTLVTVSS |
| 565 | WW0739 | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSSGGPGPAGLYAQPGSINYKQLQLQERTNIRKSQELLEQLNGKIN LTYRADFKIPMEMTEKMQKSYTAFAIQEMLQNVFLVFRNNFSSTGWNETIVV RLLDELHQQTVFLKTVLEEKQEERLTWEMSSTALHLKSYYWRVQRYLKLMK YNSYAWMVVRAEIFRNFLIIRRLTRNFQNSGGPGPAGLYAQPGSEVQLVESGG GLVQPGNSLRLSCAASGFTFSKFGMSWVRQAPGKGLEWVSSISGSGRDTLYA ESVKGRFTISRDNAKTTLYLQMNSLRPEDTAVYYCTIGGSLSVSSQGTLVTVSS |
| 566 | WW0740 | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSSGGPALFKSSFPPGSINYKQLQLQERTNIRKSQELLEQLNGKINL TYRADFKIPMEMTEKMQKSYTAFAIQEMLQNVFLVFRNNFSSTGWNETIVVR LLDELHQQTVFLKTVLEEKQEERLTWEMSSTALHLKSYYWRVQRYLKLMKY NSYAWMVVRAEIFRNFLIIRRLTRNFQNSGGPALFKSSFPPGSEVQLVESGGGL VQPGNSLRLSCAASGFTFSKFGMSWVRQAPGKGLEWVSSISGSGRDTLYAESV KGRFTISRDNAKTTLYLQMNSLRPEDTAVYYCTIGGSLSVSSQGTLVTVSS |
| 567 | WW0741 | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSSGGPGPAGLYAQPGSMSYNLLGFLQRSSNFQCQKLLWQLNGR LEYCLKDRMNFDIPEEIKQLQQFQKEDAALTIYEMLQNIFAIFRQDSSSTGWNE TIVENLLANVYHQINHLKTVLEEKLEKEDFTRGKLMSSLHLKRYYGRILHYLK AKEYSHCAWTIVRVEILRNFYFINRLTGYLRNSGGPGPAGLYAQPGSEVQLVE SGGGLVQPGNSLRLSCAASGFTFSKFGMSWVRQAPGKGLEWVSSISGSGRDTL YAESVKGRFTISRDNAKTTLYLQMNSLRPEDTAVYYCTIGGSLSVSSQGTLVT VSS |
| 568 | WW0742 | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSSGGPALFKSSFPPGSMSYNLLGFLQRSSNFQCQKLLWQLNGRL |

| SEQ ID NO. | Name | Sequence |
|---|---|---|
| | | EYCLKDRMNFDIPEEIKQLQQFQKEDAALTIYEMLQNIFAIFRQDSSTGWNET IVENLLANVYHQINHLKTVLEEKLEKEDFTRGKLMSSLHLKRYYGRILHYLKA KEYSHCAWTIVRVEILRNFYFINRLTGYLRNSGGPALFKSSFPPGSEVQLVESG GGLVQPGNSLRLSCAASGFTFSKFGMSWVRQAPGKGLEWVSSISGSGRDTLY AESVKGRFTISRDNAKTTLYLQMNSLRPEDTAVYYCTIGGSLSVSSQGTLVTV SS |
| 569 | WW0743 | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSSGGPGPAGLYAQPGSMSYNLLGFLQRSSNFQSQKLLWQLNGR LEYCLKDRMNFDIPEEIKQLQQFQKEDAALTIYEMLQNIFAIFRQDSSTGWNE TIVENLLANVYHQINHLKTVLEEKLEKEDFTRGKLMSSLHLKRYYGRILHYLK AKEYSHCAWTIVRVEILRNFYFINRLTGYLRNSGGPGPAGLYAQPGSEVQLVE SGGGLVQPGNSLRLSCAASGFTFSKFGMSWVRQAPGKGLEWVSSISGSGRDTL YAESVKGRFTISRDNAKTTLYLQMNSLRPEDTAVYYCTIGGSLSVSSQGTLVT VSS |
| 570 | WW0744 | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSSGGPALFKSSFPPGSMSYNLLGFLQRSSNFQSQKLLWQLNGRL EYCLKDRMNFDIPEEIKQLQQFQKEDAALTIYEMLQNIFAIFRQDSSTGWNET IVENLLANVYHQINHLKTVLEEKLEKEDFTRGKLMSSLHLKRYYGRILHYLKA KEYSHCAWTIVRVEILRNFYFINRLTGYLRNSGGPALFKSSFPPGSEVQLVESG GGLVQPGNSLRLSCAASGFTFSKFGMSWVRQAPGKGLEWVSSISGSGRDTLY AESVKGRFTISRDNAKTTLYLQMNSLRPEDTAVYYCTIGGSLSVSSQGTLVTV SS |
| 571 | WW0745 | INYKQLQLQERTNIRKCQELLEQLNGKINLTYRADFKIPMEMTEKMQKSYTAF AIQEMLQNVFLVFRNNFSSTGWNETIVVRLLDELHQQTVFLKTVLEEKQEERL TWEMSSTALHLKSYYWRVQRYLKLMKYNSYAWMVVRAEIFRNFLIIRRLTR NFQNHHHHHH |
| 572 | WW0746 | INYKQLQLQERTNIRKSQELLEQLNGKINLTYRADFKIPMEMTEKMQKSYTAF AIQEMLQNVFLVFRNNFSSTGWNETIVVRLLDELHQQTVFLKTVLEEKQEERL TWEMSSTALHLKSYYWRVQRYLKLMKYNSYAWMVVRAEIFRNFLIIRRLTR NFQNHHHHHH |
| 573 | WW0747 | MSYNLLGFLQRSSNFQCQKLLWQLNGRLEYCLKDRMNFDIPEEIKQLQQFQK EDAALTIYEMLQNIFAIFRQDSSTGWNETIVENLLANVYHQINHLKTVLEEKL EKEDFTRGKLMSSLHLKRYYGRILHYLKAKEYSHCAWTIVRVEILRNFYFINR LTGYLRNHHHHHH |
| 574 | WW0748 | MSYNLLGFLQRSSNFQSQKLLWQLNGRLEYCLKDRMNFDIPEEIKQLQQFQKE DAALTIYEMLQNIFAIFRQDSSTGWNETIVENLLANVYHQINHLKTVLEEKLE KEDFTRGKLMSSLHLKRYYGRILHYLKAKEYSHCAWTIVRVEILRNFYFINRL TGYLRNHHHHHH |
| 575 | WW0787 | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSSGGPGPAGLYAQPGSMSYNLLGFLQRSSNFQCQKLLWQLNGR LEYCLKDRMNFDIPEEIKQLQQFQKEDAALTIYEMLQNIFAIFRQDSSTGWQE TIVENLLANVYHQINHLKTVLEEKLEKEDFTRGKLMSSLHLKRYYGRILHYLK AKEYSHCAWTIVRVEILRNFYFINRLTGYLRNSGGPGPAGLYAQPGSEVQLVE SGGGLVQPGNSLRLSCAASGFTFSKFGMSWVRQAPGKGLEWVSSISGSGRDTL YAESVKGRFTISRDNAKTTLYLQMNSLRPEDTAVYYCTIGGSLSVSSQGTLVT VSS |
| 576 | WW0788 | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSSGGPGPAGLYAQPGSMSYNLLGFLQRSSNFQSQKLLWQLNGR LEYCLKDRMNFDIPEEIKQLQQFQKEDAALTIYEMLQNIFAIFRQDSSTGWQE TIVENLLANVYHQINHLKTVLEEKLEKEDFTRGKLMSSLHLKRYYGRILHYLK AKEYSHCAWTIVRVEILRNFYFINRLTGYLRNSGGPGPAGLYAQPGSEVQLVE SGGGLVQPGNSLRLSCAASGFTFSKFGMSWVRQAPGKGLEWVSSISGSGRDTL YAESVKGRFTISRDNAKTTLYLQMNSLRPEDTAVYYCTIGGSLSVSSQGTLVT VSS |
| 577 | WW0789 | MSYNLLGFLQRSSNFQCQKLLWQLNGRLEYCLKDRMNFDIPEEIKQLQQFQK EDAALTIYEMLQNIFAIFRQDSSTGWQETIVENLLANVYHQINHLKTVLEEKL EKEDFTRGKLMSSLHLKRYYGRILHYLKAKEYSHCAWTIVRVEILRNFYFINR LTGYLRNHHHHHH |

-continued

Sequence Table

| SEQ ID NO. | Name | Sequence |
|---|---|---|
| 578 | WW0790 | MSYNLLGFLQRSSNFQSQKLLWQLNGRLEYCLKDRMNFDIPEEIKQLQQFQKE DAALTIYEMLQNIFAIFRQDSSTGWQETIVENLLANVYHQINHLKTVLEEKLE KEDFTRGKLMSSLHLKRYYGRILHYLKAKEYSHCAWTIVRVEILRNFYFINRL TGYLRNHHHHHH |
| 579 | WW0729 | APTSSSTKKTQLQLEHLLLDLQMILNGINNYKNPKLTRMLTFKFYMPKKATEL KHLQCLEEELKPLEEVLNLAQSKNFHLRPRDLISNINIVLELKGSETTFMCEY ADETATIVEFLNRWITFCQSIISTLTSGGPGGGGSGGGGPGSEVQLVESGGGLVQ PGNSLRLSCAASGFTFSKFGMSWVRQAPGKGLEWVSSISGSGRDTLYAESVKG RFTISRDNAKTTLYLQMNSLRPEDTAVYYCTIGGSLSVSSQGTLVTVSSGGGGS GGGGSGGGGSGGGGSGGGGSGGGGSSGGPGGGGSGGGGPGSEVQLVESGGGL VQPGGSLRLSCAASGFTFSSYTLAWVRQAPGKGLEWVAAIDSSSYTYSPDTVR GRFTISRDNAKNSLYLQMNSLRAEDTAVYYCARDSNWDALDYWGQGTTVTV SSASTKGPSVFPLAPSSKSTSGGTAALGCLVKDYFPEPVTVSWNSGALTSGVH TFPAVLQSSGLYSLSSVVTVPSSSLGTQTYICNVNHKPSNTKVDKRVEPKSC |
| 580 | WW0734 | APTSSSTKKTQLQLEHLLLDLQMILNGINNYKNPKLTRMLTFKFYMPKKATEL KHLQCLEEELKPLEEVLNLAQSKNFHLRPRDLISNINIVLELKGSETTFMCEY ADETATIVEFLNRWITFCQSIISTLTSGGPGPAGMKGLPGSEVQLVESGGGLVQ PGNSLRLSCAASGFTFSKFGMSWVRQAPGKGLEWVSSISGSGRDTLYAESVKG RFTISRDNAKTTLYLQMNSLRPEDTAVYYCTIGGSLSVSSQGTLVTVSSGGGGS GGGGSGGGGSGGGGSGGGGSGGGGSGGGGSGGGGSEVQLVESGGGL VQPGGSLRLSCAASGFTFSSYTLAWVRQAPGKGLEWVAAIDSSSYTYSPDTVR GRFTISRDNAKNSLYLQMNSLRAEDTAVYYCARDSNWDALDYWGQGTTVTV SSASTKGPSVFPLAPSSKSTSGGTAALGCLVKDYFPEPVTVSWNSGALTSGVH TFPAVLQSSGLYSLSSVVTVPSSSLGTQTYICNVNHKPSNTKVDKRVEPKSC |
| 581 | WW0735 | APTSSSTKKTQLQLEHLLLDLQMILNGINNYKNPKLTRMLTFKFYMPKKATEL KHLQCLEEELKPLEEVLNLAQSKNFHLRPRDLISNINIVLELKGSETTFMCEY ADETATIVEFLNRWITFCQSIISTLTSGGPGPAGLYAQPGSEVQLVESGGGLVQP GNSLRLSCAASGFTFSKFGMSWVRQAPGKGLEWVSSISGSGRDTLYAESVKG RFTISRDNAKTTLYLQMNSLRPEDTAVYYCTIGGSLSVSSQGTLVTVSSGGGGS GGGGSGGGGSGGGGSGGGGSGGGGSGGGGSGGGGSEVQLVESGGGL VQPGGSLRLSCAASGFTFSSYTLAWVRQAPGKGLEWVAAIDSSSYTYSPDTVR GRFTISRDNAKNSLYLQMNSLRAEDTAVYYCARDSNWDALDYWGQGTTVTV SSASTKGPSVFPLAPSSKSTSGGTAALGCLVKDYFPEPVTVSWNSGALTSGVH TFPAVLQSSGLYSLSSVVTVPSSSLGTQTYICNVNHKPSNTKVDKRVEPKSC |
| 582 | WW0736 | APTSSSTKKTQLQLEHLLLDLQMILNGINNYKNPKLTRMLTFKFYMPKKATEL KHLQCLEEELKPLEEVLNLAQSKNFHLRPRDLISNINIVLELKGSETTFMCEY ADETATIVEFLNRWITFCQSIISTLTSGGPALFKSSFPPGSEVQLVESGGGLVQP GNSLRLSCAASGFTFSKFGMSWVRQAPGKGLEWVSSISGSGRDTLYAESVKG RFTISRDNAKTTLYLQMNSLRPEDTAVYYCTIGGSLSVSSQGTLVTVSSGGGGS GGGGSGGGGSGGGGSGGGGSGGGGSGGGGSGGGGSEVQLVESGGGL VQPGGSLRLSCAASGFTFSSYTLAWVRQAPGKGLEWVAAIDSSSYTYSPDTVR GRFTISRDNAKNSLYLQMNSLRAEDTAVYYCARDSNWDALDYWGQGTTVTV SSASTKGPSVFPLAPSSKSTSGGTAALGCLVKDYFPEPVTVSWNSGALTSGVH TFPAVLQSSGLYSLSSVVTVPSSSLGTQTYICNVNHKPSNTKVDKRVEPKSC |
| 583 | WW0792 | EVQLVESGGGLVQPGGSLRLSCAASGFTFSSYTLAWVRQAPGKGLEWVAAID SSSYTYSPDTVRGRFTISRDNAKNSLYLQMNSLRAEDTAVYYCARDSNWDAL DYWGQGTTVTVSSASTKGPSVFPLAPSSKSTSGGTAALGCLVKDYFPEPVTVS WNSGALTSGVHTFPAVLQSSGLYSLSSVVTVPSSSLGTQTYICNVNHKPSNTK VDKRVEPKSCHHHHHH |
| 584 | WW0061 | APTSSSTKKTQLQLEHLLLDLQMILNGINNYKNPKLTRMLTFKFYMPKKATEL KHLQCLEEELKPLEEVLNLAQSKNFHLRPRDLISNINIVLELKGSETTFMCEY ADETATIVEFLNRWITFCQSIISTLTSGGPGPAGMKGLPGSEVQLVESGGGLVQ PGNSLRLSCAASGFTFSKFGMSWVRQAPGKGLEWVSSISGSGRDTLYAESVKG RFTISRDNAKTTLYLQMNSLRPEDTAVYYCTIGGSLSVSSQGTLVTVSSHHHH HH |
| 585 | ACP293 (WW0237) | QVQLQESGGGLVQTGGSLRLSCTTSGTIFSGYTMGWYRQAPGEQRELVAVISG GGDTNYADSVKGRFTISRDNTKDTMYLQMNSLKPEDTAVYYCYSREVTPPW KLYWGQGTQVTVSSAAAYPYDVPDYGSHHHHHH |
| 586 | ACP294 (WW0238) | QVQLQESGGGLVQEGGSLRLSCAASERIFSTDVMGWYRQAAEKQRELVAVVS ARGTTNYLDAVKGRFTISRDNARNTLTLQMNDLKPEDTASYYCYVRETTSPW RIYWGQGTQVTVSSAAAYPYDVPDYGSHHHHHH |
| 587 | ACP295 (WW0239) | QVQLQESGGGLVQAGGSLRLSCAASGSIFSANAMGWYRQAPGKQRELVAVIS SGGSTNYADSVKGRFTISRDNAKNTVYLQMNSLKPEDTAVYYCMYSGSYYY TPNDYWGQGTQVTVSSAAAYPYDVPDYGSHHHHHH |

-continued

| SEQ ID NO. | Name | Sequence |
|---|---|---|
| 588 | ACP315 (WW0368) | EVQLLESGGGLVQPGGSLRLSCAASGSIFSANAMGWYRQAPGKQRELVAVISS GGSTNYADSVKGRFTISRDNSKNTVYLQMNSLRAEDTAVYYCMYSGSYYYTP NDYWGQGTLVTVSSAAAYPYDVPDYGSHHHHHH |
| 589 | ACP316 (WW0369) | EVQLLESGGGLVQPGGSLRLSCAASGSIFSANAMGWYRQAPGKGLELVAVISS GGSTNYADSVKGRFTISRDNSKNTVYLQMNSLRAEDTAVYYCMYSGSYYYTP NDYWGQGTLVTVSSAAAYPYDVPDYGSHHHHHH |
| 590 | ACP317 (WW0370) | EVQLLESGGGLVQPGGSLRLSCAASGSIFSANAMGWYRQAPGKGLEWVSVIS SGGSTNYADSVKGRFTISRDNSKNTLYLQMNSLRAEDTAVYYCMYSGSYYYT PNDYWGQGTLVTVSSAAAYPYDVPDYGSHHHHHH |
| 591 | ACP318 (WW0371) | QVQLLESGGGLVQPGGSLRLSCAASGSIFSANAMGWYRQAPGKQRELVAVIS SGGSTNYADSVKGRFTISRDNSKNTVYLQMNSLRAEDTAVYYCMYSGSYYYT PNDYWGQGTLVTVSSAAAYPYDVPDYGSHHHHHH |
| 592 | ACP319 (WW0372) | EVQLLESGGGLVQPGGSLRLSCAASGSIFSANAMGWYRQAPGKGRELVAVISS GGSTNYADSVKGRFTISRDNSKNTVYLQMNSLRAEDTAVYYCMYSGSYYYTP NDYWGQGTLVTVSSAAAYPYDVPDYGSHHHHHH |
| 593 | ACP320 (WW0373) | QVQLLESGGGLVQAGGSLRLSCAASGSIFSANAMGWYRQAPGKQRELVAVIS SGGSTNYADSVKGRFTISRDNSKNTVYLQMNSLRAEDTAVYYCMYSGSYYYT PNDYWGQGTLVTVSSAAAYPYDVPDYGSHHHHHH |
| 594 | ACP321 (WW0374) | EVQLLESGGGLVQPGGSLRLSCAASERIFSTDVMGWYRQAPGKQRELVAVVS ARGTTNYLDAVKGRFTISRDNSKNTLYLQMNSLRAEDTAVYYCYVRETTSPW RIYWGQGTLVTVSSAAAYPYDVPDYGSHHHHHH |
| 595 | ACP322 (WW0375) | EVQLLESGGGLVQPGGSLRLSCAASERIFSTDVMGWYRQAPGKGLELVAVVS ARGTTNYLDAVKGRFTISRDNSKNTLYLQMNSLRAEDTAVYYCYVRETTSPW RIYWGQGTLVTVSSAAAYPYDVPDYGSHHHHHH |
| 596 | ACP323 (WW0376) | EVQLLESGGGLVQPGGSLRLSCAASERIFSTDVMGWYRQAPGKGLEWVSVVS ARGTTNYLDAVKGRFTISRDNSKNTLYLQMNSLRAEDTAVYYCYVRETTSPW RIYWGQGTLVTVSSAAAYPYDVPDYGSHHHHHH |
| 597 | ACP324 (WW0377) | QVQLLESGGGLVQPGGSLRLSCAASERIFSTDVMGWYRQAPGKQRELVAVVS ARGTTNYLDAVKGRFTISRDNSKNTLYLQMNSLRAEDTAVYYCYVRETTSPW RIYWGQGTLVTVSSAAAYPYDVPDYGSHHHHHH |
| 598 | ACP325 (WW0378) | EVQLLESGGGLVQPGGSLRLSCAASERIFSTDVMGWYRQAPGKGRELVAVVS ARGTTNYLDSVKGRFTISRDNSKNTLYLQMNSLRAEDTAVYYCYVRETTSPW RIYWGQGTLVTVSSAAAYPYDVPDYGSHHHHHH |
| 599 | ACP326 (WW0379) | QVQLLESGGGLVQEGGSLRLSCAASERIFSTDVMGWYRQAAGKQRELVAVVS ARGTTNYLDAVKGRFTISRDNSKNTLYLQMNSLRAEDTASYYCYVRETTSPW RIYWGQGTLVTVSSAAAYPYDVPDYGSHHHHHH |
| 600 | ACP327 (WW0380) | EVQLLESGGGLVQPGGSLRLSCAASERIFSTDVMGWYRQAPGKGLELVAVVS ARGTTNYLDSVKGRFTISRDNSKNTLYLQMNSLRAEDTAVYYCYVRETTSPW RIYWGQGTLVTVSSAAAYPYDVPDYGSHHHHHH |
| 601 | ACP328 (WW0381) | EVQLLESGGGLVQPGGSLRLSCATSGTIFSGYTMGWYRQAPGKQRELVAVISG GGDTNYADSVKGRFTISRDNSKDTMYLQMNSLRAEDTAVYYCYSREVTPPW KLYWGQGTLVTVSSAAAYPYDVPDYGSHHHHHH |
| 602 | ACP329 (WW0382) | EVQLLESGGGLVQPGGSLRLSCATSGTIFSGYTMGWYRQAPGKGLELVAVISG GGDTNYADSVKGRFTISRDNSKDTMYLQMNSLRAEDTAVYYCYSREVTPPW KLYWGQGTLVTVSSAAAYPYDVPDYGSHHHHHH |
| 603 | ACP330 (WW0383) | EVQLLESGGGLVQPGGSLRLSCAASGTIFSGYTMGWYRQAPGKGLEWVSVIS GGGDTNYADSVKGRFTISRDNSKNTLYLQMNSLRAEDTAVYYCYSREVTPPW KLYWGQGTLVTVSSAAAYPYDVPDYGSHHHHHH |
| 604 | ACP331 (WW0384) | QVQLLESGGGLVQPGGSLRLSCATSGTIFSGYTMGWYRQAPGKQRELVAVIS GGGDTNYADSVKGRFTISRDNSKDTMYLQMNSLRAEDTAVYYCYSREVTPP WKLYWGQGTLVTVSSAAAYPYDVPDYGSHHHHHH |
| 605 | ACP332 (WW0385) | EVQLLESGGGLVQPGGSLRLSCATSGTIFSGYTMGWYRQAPGKQRELVAVISG GGDTNYADSVKGRFTISRDNSKNTMYLQMNSLRAEDTAVYYCYSREVTPPW KLYWGQGTLVTVSSAAAYPYDVPDYGSHHHHHH |

-continued

| SEQ ID NO. | Name | Sequence |
|---|---|---|
| 606 | ACP333 (WW0386) | EVQLLESGGGLVQPGGSLRLSCATSGTIFSGYTMGWYRQAPGKGRELVAVISG GGDTNYADSVKGRFTISRDNSKNTMYLQMNSLRAEDTAVYYCYSREVTPPW KLYWGQGTLVTVSSAAAYPYDVPDYGSHHHHHH |
| 607 | ACP334 (WW0387) | QVQLLESGGGLVQTGGSLRLSCATSGTIFSGYTMGWYRQAPGKQRELVAVIS GGGDTNYADSVKGRFTISRDNSKDTMYLQMNSLRAEDTAVYYCYSREVTPP WKLYWGQGTLVTVSSAAAYPYDVPDYGSHHHHHH |
| 608 | ACP335 (WW0388_ | EVQLLESGGGLVQPGGSLRLSCATSGTIFSGYTMGWYRQAPGKGLELVAVISG GGDTNYADSVKGRFTISRDNSKNTMYLQMNSLRAEDTAVYYCYSREVTPPW KLYWGQGTLVTVSSAAAYPYDVPDYGSHHHHHH |
| 609 | MMP14_1 | GPAGLYAQ |
| 610 | MMP9_1 | GPAGMKGL |
| 611 | FAPa_1 | PGGPAGIG |
| 612 | CTSL1_1 | ALFKSSFP |
| 613 | CTSL1_2 | ALFFSSPP |
| 614 | ADAM17_1 | LAQRLRSS |
| 615 | ADAM17_2 | LAQKLKSS |
| 616 | ALU30-1 | GALFKSSFPSGGGPAGLYAQGGSGKGGSGK |
| 617 | ALU30-2 | RGSGGGPAGLYAQGSGGGPAGLYAQGGSGK |
| 618 | ALU30-3 | KGGGPAGLYAQGPAGLYAQGPAGLYAQGSR |
| 619 | ALU30-4 | RGGPAGLYAQGGPAGLYAQGGGPAGLYAQK |
| 620 | ALU30-5 | KGGALFKSSFPGGPAGIGPLAQKLKSSGGS |
| 621 | ALU30-6 | SGGPGGPAGIGALFKSSFPLAQKLKSSGGG |
| 622 | ALU30-7 | RGPLAQKLKSSALFKSSFPGGPAGIGGGGK |
| 623 | ALU30-8 | GGGALFKSSFPLAQKLKSSPGGPAGIGGGR |
| 624 | ALU30-9 | RGPGGPAGIGPLAQKLKSSALFKSSFPGGG |
| 625 | ALU30-10 | RGGPLAQKLKSSPGGPAGIGALFKSSFPGK |
| 626 | ALU30-11 | RSGGPAGLYAQALFKSSFPLAQKLKSSGGG |
| 627 | ALU30-12 | GGPLAQKLKSSALFKSSFPGPAGLYAQGGR |
| 628 | ALU30-13 | GGALFKSSFPGPAGLYAQPLAQKLKSSGGK |
| 629 | ALU30-14 | RGGALFKSSFPLAQKLKSSGPAGLYAQGGK |
| 630 | ALU30-15 | RGGGPAGLYAQPLAQKLKSSALFKSSFPGG |
| 631 | ALU30-16 | SGPLAQKLKSSGPAGLYAQALFKSSFPGSK |
| 632 | ALU30-17 | KGGPGGPAGIGPLAQRLRSSALFKSSFPGR |
| 633 | ALU30-18 | KSGPGGPAGIGALFFSSPPLAQKLKSSGGR |
| 634 | ALU30-19 | SGGFPRSGGSFNPRTFGSKRKRRGSRGGGG |

INCORPORATION BY REFERENCE

The entire disclosures of all patent and non-patent publications cited herein are each incorporated by reference in their entireties for all purposes.

Other Embodiments

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in this application, in applications claiming priority from this application, or in related applications. Such claims, whether directed to a different invention or to the same invention, and whether broader, narrower, equal, or different in scope in comparison to the original claims, also are regarded as included within the subject matter of the inventions of the present disclosure.

The invention claimed is:

1. A fusion polypeptide having the formula of: [D]-[L1]-[A]-[L2']-[H], wherein,
   [A] is an interferon alpha (IFNa) polypeptide, a mutein, or an active fragment thereof,
   [D] is a blocking moiety,
   [H] is a half-life extension moiety,
   [L1] is a protease-cleavable polypeptide linker comprising the amino acid sequence of SEQ ID NO: 609, 612, or 615, and
   [L2'] is a protease-cleavable polypeptide linker comprising the amino acid sequence of SEQ ID NO: 609, 612, or 615,
   wherein the blocking moiety and the half-life extension moiety each independently comprise human serum albumin (HSA) or an antibody or antibody fragment that binds the HSA.

2. The fusion polypeptide of claim 1, wherein the IFa polypeptide comprises a murine interferon alpha 1 (mIFNa1), murine interferon alpha 11 (mIFNa11), human interferon alpha 2b (IFNA2b), murine interferon alpha 11 (mIFNa11), interferon alpha 8 (IFNA8), interferon alpha 14 (IFNA14), interferon alpha 16 (IFNA16), or a mutein thereof.

3. The fusion polypeptide of claim 2, wherein the IFNa polypeptide comprises the amino acid sequence of SEQ ID NO: 193, 548, 549 or 550.

4. The fusion polypeptide of claim 1, wherein each of the blocking moiety and the half-life extension moiety comprises HSA.

5. The fusion polypeptide of claim 1, wherein each of the blocking moiety and the half-life extension moiety comprises the antibody or antibody fragment that binds HSA.

6. The fusion polypeptide of claim 1, wherein one of the blocking moiety and the half-life extension moiety comprises HSA and the other one of the blocking moiety and the half-life extension moiety comprises the antibody or antibody fragment that binds HSA.

7. The fusion polypeptide of claim 1, wherein each of [L1] and [L2'] comprises SEQ ID NO: 609.

8. The fusion polypeptide of claim 7, wherein at least one of the blocking moiety and the half-life extension moiety comprises the antibody or antibody fragment that binds HSA, and the antibody or antibody fragment has the amino acid sequence of residues 1 to 116 of SEQ ID NO: 427.

9. The fusion polypeptide of claim 8, wherein the IFNa polypeptide comprises the amino acid sequence of SEQ ID NO: 193, 548, 549 or 550.

10. The fusion polypeptide of claim 7, comprising the amino acid sequence of SEQ ID NO: 424, 427, 539, 541, 545, 546 or 547.

11. The fusion polypeptide of claim 1, wherein each of [L1] and [L2'] comprises SEQ ID NO: 612.

12. The fusion polypeptide of claim 11, wherein at least one of the blocking moiety and the half-life extension moiety comprises the antibody or antibody fragment that binds HSA, and the antibody or antibody fragment has the amino acid sequence of residues 1 to 116 of SEQ ID NO: 427.

13. The fusion polypeptide of claim 11, wherein the IFNa polypeptide comprises an amino acid sequence of SEQ ID NO: 193, 548, 549 or 550.

14. The fusion polypeptide of claim 11, comprising the amino acid sequence selected from the group consisting of SEQ ID NO: 425, 428, 540, 542, and 551-562.

15. The fusion polypeptide of claim 1, wherein each of [L1] and [L2'] comprises SEQ ID NO: 615.

16. The fusion polypeptide of claim 15, wherein at least one of the blocking moiety and the half-life extension moiety comprises the antibody or antibody fragment that binds HSA, and the antibody or antibody fragment has the amino acid sequence of residues 1 to 116 of SEQ ID NO: 427.

17. The fusion polypeptide of claim 15, wherein the IFNa polypeptide comprises the amino acid sequence of SEQ ID NO: 193, 548, 549 or 550.

18. The fusion polypeptide of claim 15, comprising the amino acid sequence SEQ ID NO: 426 or 429.

19. A fusion polypeptide comprising the amino acid sequence of SEQ ID NO: 427.

20. A fusion polypeptide comprising the amino acid sequence of SEQ ID NO: 428.

21. A fusion polypeptide comprising the amino acid sequence of SEQ ID NO: 429.

22. A nucleic acid encoding the fusion polypeptide of claim 1.

23. A nucleic acid encoding the fusion polypeptide of claim 19.

24. A nucleic acid encoding the fusion polypeptide of claim 20.

25. A nucleic acid encoding the fusion polypeptide of claim 21.

26. A pharmaceutical composition comprising the fusion polypeptide of claim 1.

27. A pharmaceutical composition comprising the fusion polypeptide of claim 19.

28. A pharmaceutical composition comprising the fusion polypeptide of claim 20.

29. A pharmaceutical composition comprising the fusion polypeptide of claim 21.

* * * * *

```
                       SEQUENCE LISTING

Sequence total quantity: 647
SEQ ID NO: 1            moltype = AA  length = 153
FEATURE                 Location/Qualifiers
source                  1..153
                        mol_type = protein
                        organism = Homo sapiens
SEQUENCE: 1
MYRMQLLSCI ALSLALVTNS APTSSSTKKT QLQLEHLLLD LQMILNGINN YKNPKLTRML    60
TFKFYMPKKA TELKHLQCLE EELKPLEEVL NLAQSKNFHL RPRDLISNIN VIVLELKGSE   120
TTFMCEYADE TATIVEFLNR WITFCQSIIS TLT                                153

SEQ ID NO: 2            moltype = AA  length = 609
FEATURE                 Location/Qualifiers
source                  1..609
                        mol_type = protein
                        organism = Homo sapiens
SEQUENCE: 2
MKWVTFISLL FLFSSAYSRG VFRRDAHKSE VAHRFKDLGE ENFKALVLIA FAQYLQQCPF    60
EDHVKLVNEV TEFAKTCVAD ESAENCDKSL HTLFGDKLCT VATLRETYGE MADCCAKQEP   120
ERNECFLQHK DDNPNLPRLV RPEVDVMCTA FHDNEETFLK KYLYEIARRH PYFYAPELLF   180
FAKRYKAAFT ECCQAADKAA CLLPKLDELR DEGKASSAKQ GLKCASLQKF GERAFKAWAV   240
ARLSQRFPKA EFAEVSKLVT DLTKVHTECC HGDLLECADD RADLAKYICE NQDSISSKLK   300
ECCEKPLLEK SHCIAEVEND EMPADLPSLA ADFVGSKDVC KNYAEAKDVF LGMFLYEYAR   360
RHPDYSVVLL LRLAKTYETT LEKCCAAADP HECYAKVFDE FKPLVEEPQN LIKQNCELFE   420
QLGEYKFQNA LLVRYTKKVP QVSTPTLVEV SRNLGKVGSK CCKHPEAKRM PCAEDCLSVF   480
LNQLCVLHEK TPVSDRVTKC CTESLVNGRP CFSALEVDET YVPKEFNAET FTFHADICTL   540
SEKERQIKKQ TALVELVKHK PKATKEQLKA VMDDFAAFVE KCCKADDKET CFAEEGKKLV   600
AASQAALGL                                                          609

SEQ ID NO: 3            moltype = AA  length = 8
FEATURE                 Location/Qualifiers
REGION                  1..8
                        note = MMP7 cleavage domain sequence
source                  1..8
                        mol_type = protein
                        organism = unidentified
SEQUENCE: 3
KRALGLPG                                                             8

SEQ ID NO: 4            moltype = AA  length = 40
FEATURE                 Location/Qualifiers
REGION                  1..40
                        note = MMP7 cleavage domain sequence
source                  1..40
                        mol_type = protein
                        organism = unidentified
SEQUENCE: 4
DEDEDEDEDE DEDEDERPLA LWRSDRDRDR DRDRDRDRDR                          40

SEQ ID NO: 5            moltype = AA  length = 5
FEATURE                 Location/Qualifiers
VARIANT                 3
                        note = S or T
VARIANT                 4
                        note = L or I
VARIANT                 5
                        note = S or T
REGION                  1..5
                        note = MMP9 cleavage domain sequence
source                  1..5
```

```
                              mol_type = protein
                              organism = unidentified
SEQUENCE: 5
PRSLS                                                                          5

SEQ ID NO: 6                  moltype = AA  length = 5
FEATURE                       Location/Qualifiers
REGION                        1..5
                              note = MMP9 cleavage domain sequence
source                        1..5
                              mol_type = protein
                              organism = unidentified
SEQUENCE: 6
LEATA                                                                          5

SEQ ID NO: 7                  moltype = AA  length = 10
FEATURE                       Location/Qualifiers
REGION                        1..10
                              note = MMP11 cleavage domain sequence
source                        1..10
                              mol_type = protein
                              organism = unidentified
SEQUENCE: 7
GGAANLVRGG                                                                    10

SEQ ID NO: 8                  moltype = AA  length = 10
FEATURE                       Location/Qualifiers
REGION                        1..10
                              note = MMP14 cleavage domain sequence
source                        1..10
                              mol_type = protein
                              organism = unidentified
SEQUENCE: 8
SGRIGFLRTA                                                                    10

SEQ ID NO: 9                  moltype = AA  length = 6
FEATURE                       Location/Qualifiers
REGION                        1..6
                              note = MMP cleavage domain sequence
source                        1..6
                              mol_type = protein
                              organism = unidentified
SEQUENCE: 9
PLGLAG                                                                         6

SEQ ID NO: 10                 moltype = AA  length = 6
FEATURE                       Location/Qualifiers
REGION                        1..6
                              note = MMP cleavage domain sequence
source                        1..6
                              mol_type = protein
                              organism = unidentified
SEQUENCE: 10
PLGLAX                                                                         6

SEQ ID NO: 11                 moltype = AA  length = 6
FEATURE                       Location/Qualifiers
MOD_RES                       4
                              note = Cysteine(me)
REGION                        1..6
                              note = MMP cleavage domain sequence
source                        1..6
                              mol_type = protein
                              organism = unidentified
SEQUENCE: 11
PLGXAG                                                                         6

SEQ ID NO: 12                 moltype = AA  length = 8
FEATURE                       Location/Qualifiers
REGION                        1..8
                              note = MMP cleavage domain sequence
source                        1..8
                              mol_type = protein
                              organism = unidentified
SEQUENCE: 12
ESPAYYTA                                                                       8

SEQ ID NO: 13                 moltype = AA  length = 6
FEATURE                       Location/Qualifiers
```

```
REGION                    1..6
                          note = MMP cleavage domain sequence
source                    1..6
                          mol_type = protein
                          organism = unidentified
SEQUENCE: 13
RLQLKL                                                                          6

SEQ ID NO: 14             moltype = AA  length = 7
FEATURE                   Location/Qualifiers
REGION                    1..7
                          note = MMP cleavage domain sequence
source                    1..7
                          mol_type = protein
                          organism = unidentified
SEQUENCE: 14
RLQLKAC                                                                         7

SEQ ID NO: 15             moltype = AA  length = 7
FEATURE                   Location/Qualifiers
MOD_RES                   3
                          note = Citrulline
MOD_RES                   5
                          note = Homo-Phenylalanine
REGION                    1..7
                          note = MMP2, MMP9, MMP14 cleavage domain sequence
source                    1..7
                          mol_type = protein
                          organism = unidentified
SEQUENCE: 15
EPXGXYL                                                                         7

SEQ ID NO: 16             moltype = AA  length = 5
FEATURE                   Location/Qualifiers
REGION                    1..5
                          note = Urokinase plasminogen activator (uPA) cleavage
                            domainsequence
source                    1..5
                          mol_type = protein
                          organism = unidentified
SEQUENCE: 16
SGRSA                                                                           5

SEQ ID NO: 17             moltype = AA  length = 4
FEATURE                   Location/Qualifiers
REGION                    1..4
                          note = Urokinase plasminogen activator (uPA) cleavage
                            domainsequence
source                    1..4
                          mol_type = protein
                          organism = unidentified
SEQUENCE: 17
DAFK                                                                            4

SEQ ID NO: 18             moltype = AA  length = 5
FEATURE                   Location/Qualifiers
REGION                    1..5
                          note = Urokinase plasminogen activator (uPA) cleavage
                            domainsequence
source                    1..5
                          mol_type = protein
                          organism = unidentified
SEQUENCE: 18
GGGRR                                                                           5

SEQ ID NO: 19             moltype = AA  length = 4
FEATURE                   Location/Qualifiers
REGION                    1..4
                          note = Lysosomal Enzyme cleavage domain sequence
source                    1..4
                          mol_type = protein
                          organism = unidentified
SEQUENCE: 19
GFLG                                                                            4

SEQ ID NO: 20             moltype = AA  length = 4
FEATURE                   Location/Qualifiers
REGION                    1..4
                          note = Lysosomal Enzyme cleavage domain sequence
```

```
source                  1..4
                        mol_type = protein
                        organism = unidentified
SEQUENCE: 20
ALAL                                                                    4

SEQ ID NO: 21           moltype =    length =
SEQUENCE: 21
000

SEQ ID NO: 22           moltype =    length =
SEQUENCE: 22
000

SEQ ID NO: 23           moltype = AA   length = 5
FEATURE                 Location/Qualifiers
MOD_RES                 3
                        note = Cysteine(Et)
REGION                  1..5
                        note = Cathepsin D cleavage domain sequence
source                  1..5
                        mol_type = protein
                        organism = unidentified
SEQUENCE: 23
PIXFF                                                                   5

SEQ ID NO: 24           moltype = AA   length = 8
FEATURE                 Location/Qualifiers
REGION                  1..8
                        note = Cathepsin K cleavage domain sequence
source                  1..8
                        mol_type = protein
                        organism = unidentified
SEQUENCE: 24
GGPRGLPG                                                                8

SEQ ID NO: 25           moltype = AA   length = 6
FEATURE                 Location/Qualifiers
REGION                  1..6
                        note = Prostate Specific Antigen cleavage domain sequence
source                  1..6
                        mol_type = protein
                        organism = unidentified
SEQUENCE: 25
HSSKLQ                                                                  6

SEQ ID NO: 26           moltype = AA   length = 7
FEATURE                 Location/Qualifiers
REGION                  1..7
                        note = Prostate Specific Antigen cleavage domain sequence
source                  1..7
                        mol_type = protein
                        organism = unidentified
SEQUENCE: 26
HSSKLQL                                                                 7

SEQ ID NO: 27           moltype = AA   length = 9
FEATURE                 Location/Qualifiers
REGION                  1..9
                        note = Prostate Specific Antigen cleavage domain sequence
source                  1..9
                        mol_type = protein
                        organism = unidentified
SEQUENCE: 27
HSSKLQEDA                                                               9

SEQ ID NO: 28           moltype = AA   length = 10
FEATURE                 Location/Qualifiers
REGION                  1..10
                        note = Herpes Simplex Virus Protease cleavage domainsequence
source                  1..10
                        mol_type = protein
                        organism = unidentified
SEQUENCE: 28
LVLASSSFGY                                                              10

SEQ ID NO: 29           moltype = AA   length = 10
FEATURE                 Location/Qualifiers
REGION                  1..10
```

```
                    note = HIV Protease cleavage domain sequence
source              1..10
                    mol_type = protein
                    organism = unidentified
SEQUENCE: 29
GVSQNYPIVG                                                              10

SEQ ID NO: 30       moltype = AA   length = 10
FEATURE             Location/Qualifiers
REGION              1..10
                    note = CMV Protease cleavage domain sequence
source              1..10
                    mol_type = protein
                    organism = unidentified
SEQUENCE: 30
GVVQASCRLA                                                              10

SEQ ID NO: 31       moltype =    length =
SEQUENCE: 31
000

SEQ ID NO: 32       moltype = AA   length = 6
FEATURE             Location/Qualifiers
REGION              1..6
                    note = Thrombin cleavage domain sequence
source              1..6
                    mol_type = protein
                    organism = unidentified
SEQUENCE: 32
DPRSFL                                                                  6

SEQ ID NO: 33       moltype = AA   length = 6
FEATURE             Location/Qualifiers
REGION              1..6
                    note = Thrombin cleavage domain sequence
source              1..6
                    mol_type = protein
                    organism = unidentified
SEQUENCE: 33
PPRSFL                                                                  6

SEQ ID NO: 34       moltype = AA   length = 4
FEATURE             Location/Qualifiers
REGION              1..4
                    note = Caspase-3 cleavage domain sequence
source              1..4
                    mol_type = protein
                    organism = unidentified
SEQUENCE: 34
DEVD                                                                    4

SEQ ID NO: 35       moltype = AA   length = 5
FEATURE             Location/Qualifiers
REGION              1..5
                    note = Caspase-3 cleavage domain sequence
source              1..5
                    mol_type = protein
                    organism = unidentified
SEQUENCE: 35
DEVDP                                                                   5

SEQ ID NO: 36       moltype = AA   length = 8
FEATURE             Location/Qualifiers
REGION              1..8
                    note = Caspase-3 cleavage domain sequence
source              1..8
                    mol_type = protein
                    organism = unidentified
SEQUENCE: 36
KGSGDVEG                                                                8

SEQ ID NO: 37       moltype = AA   length = 6
FEATURE             Location/Qualifiers
REGION              1..6
                    note = Interleukin 1-beta converting enzyme cleavage
                     domainsequence
source              1..6
                    mol_type = protein
                    organism = unidentified
```

```
SEQUENCE: 37
GWEHDG                                                                        6

SEQ ID NO: 38            moltype = AA  length = 7
FEATURE                  Location/Qualifiers
REGION                   1..7
                         note = Enterokinase cleavage domain sequence
source                   1..7
                         mol_type = protein
                         organism = unidentified
SEQUENCE: 38
EDDDDKA                                                                       7

SEQ ID NO: 39            moltype = AA  length = 9
FEATURE                  Location/Qualifiers
REGION                   1..9
                         note = FAP cleavage domain sequence
source                   1..9
                         mol_type = protein
                         organism = unidentified
SEQUENCE: 39
KQEQNPGST                                                                     9

SEQ ID NO: 40            moltype = AA  length = 6
FEATURE                  Location/Qualifiers
REGION                   1..6
                         note = Kallikrein 2 cleavage domain sequence
source                   1..6
                         mol_type = protein
                         organism = unidentified
SEQUENCE: 40
GKAFRR                                                                        6

SEQ ID NO: 41            moltype = AA  length = 4
FEATURE                  Location/Qualifiers
REGION                   1..4
                         note = Plasmin cleavage domain sequence
source                   1..4
                         mol_type = protein
                         organism = unidentified
SEQUENCE: 41
DAFK                                                                          4

SEQ ID NO: 42            moltype = AA  length = 4
FEATURE                  Location/Qualifiers
REGION                   1..4
                         note = Plasmin cleavage domain sequence
source                   1..4
                         mol_type = protein
                         organism = unidentified
SEQUENCE: 42
DVLK                                                                          4

SEQ ID NO: 43            moltype = AA  length = 4
FEATURE                  Location/Qualifiers
REGION                   1..4
                         note = Plasmin cleavage domain sequence
source                   1..4
                         mol_type = protein
                         organism = unidentified
SEQUENCE: 43
DAFK                                                                          4

SEQ ID NO: 44            moltype = AA  length = 7
FEATURE                  Location/Qualifiers
REGION                   1..7
                         note = TOP cleavage domain sequence
source                   1..7
                         mol_type = protein
                         organism = unidentified
SEQUENCE: 44
ALLLALL                                                                       7

SEQ ID NO: 45            moltype = AA  length = 652
FEATURE                  Location/Qualifiers
source                   1..652
                         mol_type = protein
                         organism = synthetic construct
SEQUENCE: 45
```

```
QVQLQESGGG LVQAGGSLRL SCAASGRIFS IDIMSWYRQA PGKQRELVAR ITRGGTISYD    60
DSVKGRFTIS RDNAKNTVYL QMNSLKPEDT GVYYCNALYG TDYWGKGTQV TVSSGGGGSG   120
GGGSGGGGSA PTSSSTKKTQ LQLEHLLLDL QMILNGINNY KNPKLTRMLT FKFYMPKKAT   180
ELKHLQCLEE ELKPLEEVLN LAQSKNFHLR PRDLISNINV IVLELKGSET TFMCEYADET   240
ATIVEFLNRW ITFCQSIIST LTSGGPGPAG MKGLPGSEV LVESGGGLVQ PGNSLRLSCA    300
ASGFTFSKFG MSWVRQAPGK GLEWVSSISG SGRDTLYAES VKGRFTISRD NAKTTLYLQM   360
NSLRPEDTAV YYCTIGGSLS VSSQGTLVTV SSGGGGSGGG GSGGGGSEVQ LVESGGGLVQ   420
PGGSLRLSCA ASGFTSSYT LAWVRQAPGK GLEWVAAIDS SSYTYSPDTV RGRFTISRDN    480
AKNSLYLQMN SLRAEDTAVY YCARDSNWDA LDYWGQGTTV TVSSGGGGSG GGSGGGGSD    540
IQMTQSPSSL SASVGDRVTI TCKASQNVGT NVGWYQQKPG KAPKALIYSA SFRYSGVPSR   600
FSGSGSGTDF TLTISSLQPE DFATYYCQQY YTYPYTFGGG TKVEIKHHHH HH           652

SEQ ID NO: 46           moltype = AA  length = 652
FEATURE                 Location/Qualifiers
source                  1..652
                        mol_type = protein
                        organism = synthetic construct
SEQUENCE: 46
QVQLQESGGG LVQAGGSLRL SCAASGRIFS IDIMSWYRQA PGKQRELVAR ITRGGTISYD    60
DSVKGRFTIS RDNAKNTVYL QMNSLKPEDT GVYYCNALYG TDYWGKGTQV TVSSGGGGSG   120
GGGSGGGGSE VQLVESGGGL VQPGGSLRLS CAASGFTFSS YTLAWVRQAP GKGLEWVAAI   180
DSSSYTYSPD TVRGRFTISR DNAKNSLYLQ MNSLRAEDTA VYYCARDSNW DALDYWGQGT   240
TVTVSSGGGG SGGGGSGGGG SDIQMTQSPS SLSASVGDRV TITCKASQNV GTNVGWYQQK   300
PGKAPKALIY SASFRYSGVP SRFSGSGSGT DFTLTISSLQ PEDFATYYCQ QYYTYPYTFG   360
GGTKVEIKGG GGSGGGGSGG GGSEVQLVES GGGLVQPGNS LRLSCAASGF TFSKFGMSWV   420
RQAPGKGLEW VSSISGSGRD TLYAESVKGR FTISRDNAKT TLYLQMNSLR PEDTAVYYCT   480
IGGSLSVSSQ GTLVTVSSSG GPGPAGMKGL PGSAPTSSST KKTQLQLEHL LLDLQMILNG   540
INNYKNPKLT RMLTFKFYMP KKATELKHLQ CLEEELKPLE EVLNLAQSKN FHLRPRDLIS   600
NINVIVLELK GSETTFMCEY ADETATIVEF LNRWITFCQS IISTLTHHHH HH           652

SEQ ID NO: 47           moltype = AA  length = 553
FEATURE                 Location/Qualifiers
source                  1..553
                        mol_type = protein
                        organism = synthetic construct
SEQUENCE: 47
EVQLVESGGG LVQPGGSLRL SCAASGFTFS SYTLAWVRQA PGKGLEWVAA IDSSSYTYSP    60
DTVRGRFTIS RDNAKNSLYL QMNSLRAEDT AVYYCARDSN WDALDYWGQG TTVTVSSGGG   120
GSGGGGSGGG GSDIQMTQSP SSLSASVGDR VTITCKASQN VGTNVGWYQQ KPGKAPKALI   180
YSASFRYSGV PSRFSGSGSG TDFTLTISSL QPEDFATYYC QQYYTYPYTF GGGTKVEIKG   240
GGGSGGGGS GGGSGGGGSG GGGSGGGGSS GGPGPAGMKG LPGSAPTSSS TKKTQLQLEH   300
LLLDLQMILN GINNYKNPKL TRMLTFKFYM PKKATELKHL QCLEEELKPL EEVLNLAQSK   360
NFHLRPRDLI SNINVIVLEL KGSETTFMCE YADETATIVE FLNRWITFCQ SIISTLTSGG   420
PGPAGMKGLP GSEVQLVESG GGLVQPGNSL RLSCAASGFT FSKFGMSWVR QAPGKGLEWV   480
SSISGSGRDT LYAESVKGRF TISRDNAKTT LYLQMNSLRP EDTAVYYCTI GGSLSVSSQG   540
TLVTVSSHHH HH                                                       553

SEQ ID NO: 48           moltype = AA  length = 553
FEATURE                 Location/Qualifiers
source                  1..553
                        mol_type = protein
                        organism = synthetic construct
SEQUENCE: 48
EVQLVESGGG LVQPGGSLRL SCAASGFTFS SYTLAWVRQA PGKGLEWVAA IDSSSYTYSP    60
DTVRGRFTIS RDNAKNSLYL QMNSLRAEDT AVYYCARDSN WDALDYWGQG TTVTVSSGGG   120
GSGGGGSGGG GSDIQMTQSP SSLSASVGDR VTITCKASQN VGTNVGWYQQ KPGKAPKALI   180
YSASFRYSGV PSRFSGSGSG TDFTLTISSL QPEDFATYYC QQYYTYPYTF GGGTKVEIKG   240
GGGSGGGGS GGGSGGGGSG GGSGGGGSE VQLVESGGGL VQPGNSLRLS CAASGFTFSK   300
FGMSWVRQAP GKGLEWVSSI SGSGRDTLYA ESVKGRFTIS RDNAKTTLYL QMNSLRPEDT   360
AVYYCTIGGS LSVSSQGTLV TVSSGGGGSG GGGSGGGGS GGPGPAGMKG LPGSAPTSSS   420
TKKTQLQLEH LLLDLQMILN GINNYKNPKL TRMLTFKFYM PKKATELKHL QCLEEELKPL   480
EEVLNLAQSK NFHLRPRDLI SNINVIVLEL KGSETTFMCE YADETATIVE FLNRWITFCQ   540
SIISTLTHHH HH                                                       553

SEQ ID NO: 49           moltype = AA  length = 553
FEATURE                 Location/Qualifiers
source                  1..553
                        mol_type = protein
                        organism = synthetic construct
SEQUENCE: 49
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTSGGPGPA GMKGLPGSEV QLVESGGGLV QPGNSLRLSC AASGFTFSKF   180
GMSWVRQAPG KGLEWVSSIS SGSGRDTLYAE SVKGRFTISR DNAKTTLYLQ MNSLRPEDTA   240
VYYCTIGGSL SVSSQGTLVT VSSGGGGSGG GGSGGGGSGG GGSGGGGSGG GGSGGPGPA   300
GMKGLPGSEV QLVESGGGLV QPGGSLRLSC AASGFTSSY TLAWVRQAPG KGLEWVAAID   360
SSSYTYSPDT VRGRFTISRD NAKNSLYLQM NSLRAEDTAV YYCARDSNWD ALDYWGQGTT   420
VTVSSGGGGS GGGGSGGGGS DIQMTQSPSS LSASVGDRVT ITCKASQNVG TNVGWYQQKP   480
GKAPKALIYS ASFRYSGVPS RFSGSGSGTD FTLTISSLQP EDFATYYCQQ YYTYPYTFGG   540
```

```
GTKVEIKHHH HHH                                                                    553

SEQ ID NO: 50            moltype = AA   length = 682
FEATURE                  Location/Qualifiers
source                   1..682
                         mol_type = protein
                         organism = synthetic construct
SEQUENCE: 50
QVQLQESGGG LVQAGGSLRL SCAASGRIFS IDIMSWYRQA PGKQRELVAR ITRGGTISYD    60
DSVKGRFTIS RDNAKNTVYL QMNSLKPEDT GVYYCNALYG TDYWGKGTQV TVSSGGGGSG   120
GGGSGGGGSA PTSSSTKKTQ LQLEHLLLDL QMILNGINNY KNPKLTRMLT FKFYMPKKAT   180
ELKHLQCLEE ELKPLEEVLN LAQSKNFHLR PRDLISNINV IVLELKGSET TFMCEYADET   240
ATIVEFLNRW ITFCQSIIST LTSGGPGPAG MKGLPGSEVQ LVESGGGLVQ PGNSLRLSCA   300
ASGFTFSKFG MSWVRQAPGK GLEWVSSISG SGRDTLYAES VKGRFTISRD NAKTTLYLQM   360
NSLRPEDTAV YYCTIGGSLS VSSQGTLVTV SSGGGGSGGG GSGGGGSGGG GSGGGGSGGG   420
GSSGGPGPAG MKGLPGSEVQ LVESGGGLVQ PGGSLRLSCA ASGFTFSSYT LAWVRQAPGK   480
GLEWVAAIDS SSYTYSPDTV RGRFTISRDN AKNSLYLQMN SLRAEDTAVY YCARDSNWDA   540
LDYWGQGTTV TVSSGGGGSG GGGSGGGGSD IQMTQSPSSL SASVGDRVTI TCKASQNVGT   600
NVGWYQQKPG KAPKALIYSA SFRYSGVPSR FSGSGSGTDF TLTISSLQPE DFATYYCQQY   660
YTYPYTFGGG TKVEIKHHHH HH                                           682

SEQ ID NO: 51            moltype = AA   length = 667
FEATURE                  Location/Qualifiers
source                   1..667
                         mol_type = protein
                         organism = synthetic construct
SEQUENCE: 51
QVQLQESGGG LVQAGGSLRL SCAASGRIFS IDIMSWYRQA PGKQRELVAR ITRGGTISYD    60
DSVKGRFTIS RDNAKNTVYL QMNSLKPEDT GVYYCNALYG TDYWGKGTQV TVSSGGGGSG   120
GGGSGGGGSA PTSSSTKKTQ LQLEHLLLDL QMILNGINNY KNPKLTRMLT FKFYMPKKAT   180
ELKHLQCLEE ELKPLEEVLN LAQSKNFHLR PRDLISNINV IVLELKGSET TFMCEYADET   240
ATIVEFLNRW ITFCQSIIST LTSGGPGPAG MKGLPGSEVQ LVESGGGLVQ PGNSLRLSCA   300
ASGFTFSKFG MSWVRQAPGK GLEWVSSISG SGRDTLYAES VKGRFTISRD NAKTTLYLQM   360
NSLRPEDTAV YYCTIGGSLS VSSQGTLVTV SSGGGGSGGG GSGGGGSGGG GSGGGGSGGG   420
GSEVQLVESG GGLVQPGGSL RLSCAASGFT FSSYTLAWVR QAPGKGLEWV AAIDSSSYTY   480
SPDTVRGRFT ISRDNAKNSL YLQMNSLRAE DTAVYYCARD SNWDALDYWG QGTTVTVSSS   540
GGPGPAGMKG LPGSDIQMTQ SPSSLSASVG DRVTITCKAS QNVGTNVGWY QQKPGKAPKA   600
LIYSASFRYS GVPSRFSGSG SGTDFTLTIS SLQPEDFATY YCQQYYTYPY TFGGGTKVEI   660
KHHHHHH                                                            667

SEQ ID NO: 52            moltype = AA   length = 682
FEATURE                  Location/Qualifiers
source                   1..682
                         mol_type = protein
                         organism = synthetic construct
SEQUENCE: 52
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTSGGPGPA GMKGLPGSGG GGSGGGGSGG GGSGGGGSEV              180
QLVESGGGLV QPGGSLRLSC AASGFTFSSY TLAWVRQAPG KGLEWVAAID SSSYTYSPDT   240
VRGRFTISRD NAKNSLYLQM NSLRAEDTAV YYCARDSNWD ALDYWGQGTT VTVSSGGGGS   300
GGGGSGGGGS DIQMTQSPSS LSASVGDRVT ITCKASQNVG TNVGWYQQKP GKAPKALIYS   360
ASFRYSGVPS RFSGSGSGTD FTLTISSLQP EDFATYYCQQ YYTYPYTFGG GTKVEIKGGG   420
GSGGGGSGGG GSEVQLVESG GGLVQPGNSL RLSCAASGFT FSKFGMSWVR QAPGKGLEWV   480
SSISGSGRDT LYAESVKGRF TISRDNAKTT LYLQMNSLRP EDTAVYYCTI GGSLSVSSQG   540
TLVTVSSGGG GSGGGGSGGG GSQVQLQESG GGLVQAGGSL RLSCAASGRI FSIDIMSWYR   600
QAPGKQRELV ARITRGGTIS YDDSVKGRFT ISRDNAKNTV YLQMNSLKPE DTGVYYCNAL   660
YGTDYWGKGT QVTVSSHHHH HH                                           682

SEQ ID NO: 53            moltype = AA   length = 393
FEATURE                  Location/Qualifiers
source                   1..393
                         mol_type = protein
                         organism = synthetic construct
SEQUENCE: 53
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTSGGPGPA GMKGLPGSEV QLVESGGGLV QPGGSLRLSC AASGFTFSSY   180
TLAWVRQAPG KGLEWVAAID SSSYTYSPDT VRGRFTISRD NAKNSLYLQM NSLRAEDTAV   240
YYCARDSNWD ALDYWGQGTT VTVSSGGGGS GGGGSGGGGS DIQMTQSPSS LSASVGDRVT   300
ITCKASQNVG TNVGWYQQKP GKAPKALIYS ASFRYSGVPS RFSGSGSGTD FTLTISSLQP   360
EDFATYYCQQ YYTYPYTFGG GTKVEIKHHH HHH                                393

SEQ ID NO: 54            moltype = AA   length = 423
FEATURE                  Location/Qualifiers
source                   1..423
                         mol_type = protein
                         organism = synthetic construct
SEQUENCE: 54
```

```
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR 120
WITFCQSIIS TLTSGGPGPA GMKGLPGSGG GGSGGGGSGG GGSGGGGSGG GGSGGGGSEV 180
QLVESGGGLV QPGGSLRLSC AASGFTSSY  TLAWVRQAPG KGLEWVAAID SSSYTYSPDT 240
VRGRFTISRD NAKNSLYLQM NSLRAEDTAV YYCARDSNWD ALDYWGQGTT VTVSSGGGGS 300
GGGGSGGGGS DIQMTQSPSS LSASVGDRVT ITCKASQNVG TNVGWYQQKP GKAPKALIYS 360
ASFRYSGVPS RFSGSGSGTD FTLTISSLQP EDFATYYCQQ YYTYPYTFGG GTKVEIKHHH 420
HHH                                                              423

SEQ ID NO: 55           moltype = AA  length = 682
FEATURE                 Location/Qualifiers
source                  1..682
                        mol_type = protein
                        organism = synthetic construct
SEQUENCE: 55
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR 120
WITFCQSIIS TLTSGGPGPA GMKGLPGSGG GGSGGGGSGG GGSGGGGSGG GGSGGGGSEV 180
QLVESGGGLV QPGGSLRLSC AASGFTSSY  TLAWVRQAPG KGLEWVAAID SSSYTYSPDT 240
VRGRFTISRD NAKNSLYLQM NSLRAEDTAV YYCARDSNWD ALDYWGQGTT VTVSSGGGGS 300
GGGGSGGGGS DIQMTQSPSS LSASVGDRVT ITCKASQNVG TNVGWYQQKP GKAPKALIYS 360
ASFRYSGVPS RFSGSGSGTD FTLTISSLQP EDFATYYCQQ YYTYPYTFGG GTKVEIKGGG 420
PGPAGMKGLP GSEVQLVESG GGLVQPGNSL RLSCAASGFT FSKFGMSWVR QAPGKGLEWV 480
SSISGSGRDT LYAESVKGRF TISRDNAKTT LYLQMNSLRP EDTAVYYCTI GGSLSVSSQG 540
TLVTVSSGGG GSGGGGSGGG GSQVQLQESG GGLVQAGGSL RLSCAASGRI FSIDIMSWYR 600
QAPGKQRELV ARITRGGTIS YDDSVKGRFT ISRDNAKNTV YLQMNSLKPE DTGVYYCNAL 660
YGTDYWGKGT QVTVSSHHHH HH                                         682

SEQ ID NO: 56           moltype = AA  length = 682
FEATURE                 Location/Qualifiers
source                  1..682
                        mol_type = protein
                        organism = synthetic construct
SEQUENCE: 56
QVQLQESGGG LAQAGGSLSL SCAASGFTVS NSVMAWYRQT PGKQREFVAI INSVGSTNYA  60
DSVKGRFTIS RDNAKNTVYL QMNNLKPEDT AVYYCNRNFD RIYWGQGTQV TVSSSGGPGP 120
AGMKGLPGSE VQLVESGGGL VQPGGSLRLS CAASGFTFSS YTLAWVRQAP GKGLEWVAAI 180
DSSSYTYSPD TVRGRFTISR DNAKNSLYLQ MNSLRAEDTA VYYCARDSNW DALDYWGQGT 240
TVTVSSGGGG SGGGGSGGGG SDIQMTQSPS SLSASVGDRV TITCKASQNV GTNVGWYQQK 300
PGKAPKALIY SASFRYSGVP SRFSGSGSGT DFTLTISSLQ PEDFATYYCQ QYYTYPYTFG 360
GGTKVEIKGG GGSGGGGSGG GGSGGGGSGG GGSGGGGSGG GPGPAGMKGL PGSEVQLVES 420
GGGLVQPGNS LRLSCAASGF TFSKFGMSWV RQAPGKGLEW VSSISGSGRD TLYAESVKGR 480
FTISRDNAKT TLYLQMNSLR PEDTAVYYCT IGGSLSVSSQ GTLVTVSSGG PGPAGMKGL 540
PGSAPTSSST KKTQLQLEHL LLDLQMILNG INNYKNPKLT RMLTFKFYMP KKATELKHLQ 600
CLEEELKPLE EVLNLAQSKN FHLRPRDLIS NINVIVLELK GSETTFMCEY ADETATIVEF 660
LNRWITFCQS IISTLTHHHH HH                                         682

SEQ ID NO: 57           moltype = AA  length = 393
FEATURE                 Location/Qualifiers
source                  1..393
                        mol_type = protein
                        organism = synthetic construct
SEQUENCE: 57
EVQLVESGGG LVQPGGSLRL SCAASGFTFS SYTLAWVRQA PGKGLEWVAA IDSSSYTYSP  60
DTVRGRFTIS RDNAKNSLYL QMNSLRAEDT AVYYCARDSN WDALDYWGQG TTVTVSSGGG 120
GSGGGGSGGG GSDIQMTQSP SSLSASVGDR VTITCKASQN VGTNVGWYQQ KPGKAPKALI 180
YSASFRYSGV PSRFSGSGSG TDFTLTISSL QPEDFATYYC QQYYTYPYTF GGGTKVEIKS 240
GGPGPAGMKG LPGSAPTSSS TKKTQLQLEH LLLDLQMILN GINNYKNPKL TRMLTFKFYM 300
PKKATELKHL QCLEEELKPL EEVLNLAQSK NFHLRPRDLI SNINVIVLEL KGSETTFMCE 360
YADETATIVE FLNRWITFCQ SIISTLTHHH HHH                             393

SEQ ID NO: 58           moltype = AA  length = 423
FEATURE                 Location/Qualifiers
source                  1..423
                        mol_type = protein
                        organism = synthetic construct
SEQUENCE: 58
EVQLVESGGG LVQPGGSLRL SCAASGFTFS SYTLAWVRQA PGKGLEWVAA IDSSSYTYSP  60
DTVRGRFTIS RDNAKNSLYL QMNSLRAEDT AVYYCARDSN WDALDYWGQG TTVTVSSGGG 120
GSGGGGSGGG GSDIQMTQSP SSLSASVGDR VTITCKASQN VGTNVGWYQQ KPGKAPKALI 180
YSASFRYSGV PSRFSGSGSG TDFTLTISSL QPEDFATYYC QQYYTYPYTF GGGTKVEIKG 240
GGGSGGGGSG GGGSGGGGSG GGGSGGGGSS GGPGPAGMKG LPGSAPTSSS TKKTQLQLEH 300
LLLDLQMILN GINNYKNPKL TRMLTFKFYM PKKATELKHL QCLEEELKPL EEVLNLAQSK 360
NFHLRPRDLI SNINVIVLEL KGSETTFMCE YADETATIVE FLNRWITFCQ SIISTLTHHH 420
HHH                                                              423

SEQ ID NO: 59           moltype = AA  length = 669
FEATURE                 Location/Qualifiers
source                  1..669
```

```
                        mol_type = protein
                        organism = synthetic construct
SEQUENCE: 59
QVQLQESGGG  LVQAGGSLRL  SCAASGRIFS  IDIMSWYRQA  PGKQRELVAR  ITRGGTISYD    60
DSVKGRFTIS  RDNAKNTVYL  QMNSLKPEDT  GVYYCNALYG  TDYWGKGTQV  TVSSGGGGSG   120
GGGSGGGGSA  PTSSSTKKTQ  LQLEHLLLDL  QMILNGINNY  KNPKLTRMLT  FKFYMPKKAT   180
ELKHLQCLEE  ELKPLEEVLN  LAQSKNFHLR  PRDLISNINV  IVLELKGSET  TFMCEYADET   240
ATIVEFLNRW  ITFCQSIIST  LTSGGPGPAG  MKGLPGSEVQ  LVESGGGLVQ  PGNSLRLSCA   300
ASGFTFSKFG  MSWVRQAPGK  GLEWVSSISG  SGRDTLYAES  VKGRFTISRD  NAKTTLYLQM   360
NSLRPEDTAV  YYCTIGGSLS  VSSQGTLVTV  SSGGGGSGGG  GSGGGGSGGG  GSQVQLQQSG   420
AELVRPGTSV  KVSCKASGYA  FTNYLIEWVK  QRPGQGLEWI  GVINPGSGGT  NYNEKFKGKA   480
TLTADKSSST  AYMQLSSLTS  DDSAVYFCAR  WRGDGYYAYF  DVWGAGTTVT  VSSGGGGSGG   540
GGGSGGGSDI  VLTQSPASLA  VSLGQRATIS  CKASQSVDYD  GDSYMNWYQQ  KPGQPPKLLI   600
YAASNLESGI  PARFSGSGSG  TDFTLNIHPV  EEEDAATYYC  QQSNEDPYTF  GGGTKLEIKH   660
HHHHHEPEA                                                               669

SEQ ID NO: 60           moltype = AA   length = 669
FEATURE                 Location/Qualifiers
source                  1..669
                        mol_type = protein
                        organism = synthetic construct
SEQUENCE: 60
QVQLQESGGG  LVQAGGSLRL  SCAASGRIFS  IDIMSWYRQA  PGKQRELVAR  ITRGGTISYD    60
DSVKGRFTIS  RDNAKNTVYL  QMNSLKPEDT  GVYYCNALYG  TDYWGKGTQV  TVSSGGGGSG   120
GGGSGGGGSA  PTSSSTKKTQ  LQLEHLLLDL  QMILNGINNY  KNPKLTRMLT  FKFYMPKKAT   180
ELKHLQCLEE  ELKPLEEVLN  LAQSKNFHLR  PRDLISNINV  IVLELKGSET  TFMCEYADET   240
ATIVEFLNRW  ITFCQSIIST  LTSGGPGPAG  MKGLPGSEVQ  LVESGGGLVQ  PGNSLRLSCA   300
ASGFTFSKFG  MSWVRQAPGK  GLEWVSSISG  SGRDTLYAES  VKGRFTISRD  NAKTTLYLQM   360
NSLRPEDTAV  YYCTIGGSLS  VSSQGTLVTV  SSGGGGSGGG  GSGGGGSGGG  GSDIVLTQSP   420
ASLAVSLGQR  ATISCKASQS  VDYDGDSYMN  WYQQKPGQPP  KLLIYAASNL  ESGIPARFSG   480
SGSGTDFTLN  IHPVEEEDAA  TYYCQQSNED  PYTFGGGTKL  EIKGGGGSGG  GGSGGGGSQV   540
QLQQSGAELV  RPGTSVKVSC  KASGYAFTNY  LIEWVKQRPG  QGLEWIGVIN  PGSGGTNYNE   600
KFKGKATLTA  DKSSSTAYMQ  LSSLTSDDSA  VYFCARWRGD  GYYAYFDVWG  AGTTVTVSSH   660
HHHHHEPEA                                                               669

SEQ ID NO: 61           moltype = AA   length = 689
FEATURE                 Location/Qualifiers
source                  1..689
                        mol_type = protein
                        organism = synthetic construct
SEQUENCE: 61
APTSSSTKKT  QLQLEHLLLD  LQMILNGINN  YKNPKLTRML  TFKFYMPKKA  TELKHLQCLE    60
EELKPLEEVL  NLAQSKNFHL  RPRDLISNIN  VIVLELKGSE  TTFMCEYADE  TATIVEFLNR   120
WITFCQSIIS  TLTSGGPGPA  GMKGLPGSGG  GGSGGGGSGG  GGSGGGGSGG  GGSQVQLQQS   180
GAELVRPGTS  VKVSCKASGY  AFTNYLIEWV  KQRPGQGLEW  IGVINPGSGG  TNYNEKFKGK   240
ATLTADKSSS  TAYMQLSSLT  SDDSAVYFCA  RWRGDGYYAY  FDVWGAGTTV  TVSSGGGGSG   300
GGGSGGGGSD  IVLTQSPASL  AVSLGQRATI  SCKASQSVDY  DGDSYMNWYQ  QKPGQPPKLL   360
IYAASNLESG  IPARFSGSGS  GTDFTLNIHP  VEEEDAATYY  CQQSNEDPYT  FGGGTKLEIK   420
GGGGSGGGGS  GGGGSEVQLV  ESGGGLVQPG  NSLRLSCAAS  GFTFSKFGMS  WVRQAPGKGL   480
EWVSSISGSG  RDTLYAESVK  GRFTISRDNA  KTTLYLQMNS  LRPEDTAVYY  CTIGGSLSVS   540
SQGTLVTVSS  GGGGSGGGGS  GGGGSQVQLQ  ESGGGLVQAG  GSLRLSCAAS  GRIFSIDIMS   600
WYRQAPGKQR  ELVARITRGG  TISYDDSVKG  RFTISRDNAK  NTVYLQMNSL  KPEDTGVYYC   660
NALYGTDYWG  KGTQVTVSSH  HHHHHEPEA                                       689

SEQ ID NO: 62           moltype = AA   length = 689
FEATURE                 Location/Qualifiers
source                  1..689
                        mol_type = protein
                        organism = synthetic construct
SEQUENCE: 62
APTSSSTKKT  QLQLEHLLLD  LQMILNGINN  YKNPKLTRML  TFKFYMPKKA  TELKHLQCLE    60
EELKPLEEVL  NLAQSKNFHL  RPRDLISNIN  VIVLELKGSE  TTFMCEYADE  TATIVEFLNR   120
WITFCQSIIS  TLTSGGPGPA  GMKGLPGSGG  GGSGGGGSGG  GGSGGGGSGG  GGSDIVLTQS   180
PASLAVSLGQ  RATISCKASQ  SVDYDGDSYM  NWYQQKPGQP  PKLLIYAASN  LESGIPARFS   240
GSGSGTDFTL  NIHPVEEEDA  ATYYCQQSNE  DPYTFGGGTK  LEIKGGGGSG  GGGSGGGGSQ   300
VQLQQSGAEL  VRPGTSVKVS  CKASGYAFTN  YLIEWVKQRP  GQGLEWIGVI  NPGSGGTNYN   360
EKFKGKATLT  ADKSSSTAYM  QLSSLTSDDS  AVYFCARWRG  DGYYAYFDVW  GAGTTVTVSS   420
GGGGSGGGGS  GGGGSEVQLV  ESGGGLVQPG  NSLRLSCAAS  GFTFSKFGMS  WVRQAPGKGL   480
EWVSSISGSG  RDTLYAESVK  GRFTISRDNA  KTTLYLQMNS  LRPEDTAVYY  CTIGGSLSVS   540
SQGTLVTVSS  GGGGSGGGGS  GGGGSQVQLQ  ESGGGLVQAG  GSLRLSCAAS  GRIFSIDIMS   600
WYRQAPGKQR  ELVARITRGG  TISYDDSVKG  RFTISRDNAK  NTVYLQMNSL  KPEDTGVYYC   660
NALYGTDYWG  KGTQVTVSSH  HHHHHEPEA                                       689

SEQ ID NO: 63           moltype = AA   length = 272
FEATURE                 Location/Qualifiers
source                  1..272
                        mol_type = protein
                        organism = unidentified
SEQUENCE: 63
```

```
MDSYLLMWGL LTFIMVPGCQ AELCDDDPPE IPHATFKAMA YKEGTMLNCE CKRGFRRIKS  60
GSLYMLCTGN SSHSSWDNQC QCTSSATRNT TKQVTPQPEE QKERKTTEMQ SPMQPVDQAS 120
LPGHCREPPP WENEATERIY HFVVGQMVYY QCVQGYRALH RGPAESVCKM THGKTRWTQP 180
QLICTGEMET SQFPGEEKPQ ASPEGRPESE TSCLVTTTDF QIQTEMAATM ETSIFTTEYQ 240
VAVAGCVFLL ISVLLLSGLT WQRRQRKSRR TI                              272

SEQ ID NO: 64            moltype = AA  length = 551
FEATURE                  Location/Qualifiers
REGION                   1..551
                         note = IL2Rb sequence
source                   1..551
                         mol_type = protein
                         organism = unidentified
SEQUENCE: 64
MAAPALSWRL PLLILLLPLA TSWASAAVNG TSQFTCFYNS RANISCVWSQ DGALQDTSCQ  60
VHAWPDRRRW NQTCELLPVS QASWACNLIL GAPDSQKLTT VDIVTLRVLC REGVRWRVMA 120
IQDFKPFENL RLMAPISLQV VHVETHRCNI SWEISQASHY FERHLEFEAR TLSPGHTWEE 180
APLLTLKQKQ EWICLETLTP DTQYEFQVRV KPLQGEFTTW SPWSQPLAFR TKPAALGKDT 240
IPWLGHLLVG LSGAFGFIIL VYLLINCRNT GPWLKKVLKC NTPDPSKFFS QLSSEHGGDV 300
QKWLSSPFPS SSFSPGGLAP EISPLEVLER DKVTQLLLQQ DKVPEPASLS SNHSLTSCFT 360
NQGYFFFHLP DALEIEACQV YFTYDPYSEE DPDEGVAGAP TGSSPQPLQP LSGEDDAYCT 420
FPSRDDLLLF SPSLLGGPSP PSTAPGGSGA GEERMPPSLQ ERVPRDWDPQ PLGPPTGVP 480
DLVDFQPPPE LVLREAGEEV PDAGPREGVS FPWSRPPGQG EFRALNARLP LNTDAYLSLQ 540
ELQGQDPTHL V                                                    551

SEQ ID NO: 65            moltype = AA  length = 369
FEATURE                  Location/Qualifiers
REGION                   1..369
                         note = IL2Rg sequence
source                   1..369
                         mol_type = protein
                         organism = unidentified
SEQUENCE: 65
MLKPSLPFTS LLFLQLPLLG VGLNTTILTP NGNEDTTADF LTTMPTDSL SVSTLPLPEV  60
QCFVFNVEYM NCTWNSSSEP QPTNLTHYW YKNSNDNDKVQ KCSHYLFSEE ITSGCQLQKK 120
EIHLYQTFVV QLQDPREPRR QATQMLKLQN LVIPWAPENL TLHKLSESQL ELNWNNRFLN 180
HCLEHLVQYR TDWDHSWTEQ SVDYRHKFSL PSVDGQKRYT FRVRSRFNPL CGSAQHWSEW 240
SHPIHWGSNT SKENPPLFAL EAVVISVGSM GLIISLLCVY FWLERTMPRI PTLKNLEDLV 300
TEYHGNFSAW SGVSKGLAES LQPDYSERLC LVSEIPPKGG ALGEGPGASP CNQHSPYWAP 360
PCYTLKPET                                                       369

SEQ ID NO: 66            moltype = AA  length = 520
FEATURE                  Location/Qualifiers
source                   1..520
                         mol_type = protein
                         organism = synthetic construct
SEQUENCE: 66
IWELKKDVYV VELDWYPDAP GEMVVLTCDT PEEDGITWTL DQSSEVLGSG KTLTIQVKEF  60
GDAGQYTCHK GGEVLSHSLL LLHKKEDGIW STDILKDQKE PKNKTFLRCE AKNYSGRFTC 120
WWLTTISTDL TFSVKSSRGS SDPQGVTCGA ATLSAERVRG DNKEYEYSVE CQEDSACPAA 180
EESLPIEVMV DAVHKLKYEN YTSSFFIRDI IKPDPPKNLQ LKPLKNSRQV EVSWEYPDTW 240
STPHSYFSLT FCVQVQGKSK REKKDRVFTD KTSATVICRK NASISVRAQD RYYSSSWSEW 300
ASVPCSGGGG SGGGGSGGGG SRVIPVSGPA RCLSQSRNLL KTTDDMVKTA REKLKHYSCT 360
AEDIDHEDIT RDQTSTLKTC LPLELHKNES CLATRETSST TRGSCLPPQK TSLMMTLCLG 420
SIYEDLKMYQ TEFQAINAAL QNHNHQQIIL DKGMLVAIDE LMQSLNHNGE TLRQKPPVGE 480
ADPYRVKMKL CILLHAFSTR VVTINRVMGY LSSAHHHHHH                      520

SEQ ID NO: 67            moltype = AA  length = 524
FEATURE                  Location/Qualifiers
source                   1..524
                         mol_type = protein
                         organism = synthetic construct
SEQUENCE: 67
IWELKKDVYV VELDWYPDAP GEMVVLTCDT PEEDGITWTL DQSSEVLGSG KTLTIQVKEF  60
GDAGQYTCHK GGEVLSHSLL LLHKKEDGIW STDILKDQKE PKNKTFLRCE AKNYSGRFTC 120
WWLTTISTDL TFSVKSSRGS SDPQGVTCGA ATLSAERVRG DNKEYEYSVE CQEDSACPAA 180
EESLPIEVMV DAVHKLKYEN YTSSFFIRDI IKPDPPKNLQ LKPLKNSRQV EVSWEYPDTW 240
STPHSYFSLT FCVQVQGKSK REKKDRVFTD KTSATVICRK NASISVRAQD RYYSSSWSEW 300
ASVPCSGGGG SGGGGSGGGG SRNLPVATPD PGMFPCLHHS QNLLRAVSNM LQKARQTLEF 360
YPCTSEEIDH EDITKDKTST VEACLPLELT KNESCLNSRE TSFITNGSCL ASRKTSFMMA 420
LCLSSIYEDL KMYQVEFKTM NAKLLMDPKR QIFLDQNMLA VIDELMQALN FNSETVPQKS 480
SLEEPDFYKT KIKLCILLHA FRIRAVTIDR VMSYLNASHH HHHH                 524

SEQ ID NO: 68            moltype = AA  length = 940
FEATURE                  Location/Qualifiers
source                   1..940
                         mol_type = protein
                         organism = synthetic construct
SEQUENCE: 68
```

```
QSVLTQPPSV SGAPGQRVTI SCSGSRSNIG SNTVKWYQQL PGTAPKLLIY YNDQRPSGVP     60
DRFSGSKSGT SASLAITGLQ AEDEADYYCQ SYDRYTHPAL LFGTGTKVTV LGGGGSGGGG    120
SGGGGSQVQL VESGGGVVQP GRSLRLSCAA SGFTFSSYGM HWVRQAPGKG LEWVAFIRYD    180
GSNKYYADSV KGRFTISRDN SKNTLYLQMN SLRAEDTAVY YCKTHGSHDN WGQGTMVTVS    240
SGGGGSGGGG SGGGGSGGGG SSGGPGPAGM KGLPGSIWEL KKDVYVVELD              300
WYPDAPGEMV VLTCDTPEED GITWTLDQSS EVLGSGKTLT IQVKEFGDAG QYTCHKGGEV    360
LSHSLLLLHK KEDGIWSTDI LKDQKEPKNK TFLRCEAKNY SGRFTCWWLT TISTDLTFSV    420
KSSRGSSDPQ GVTCGAATLS AERVRGDNKE YEYSVECQED SACPAAEESL PIEVMVDAVH    480
KLKYENYTSS FFIRDIIKPD PPKNLQLKPL KNSRQVEVSW EYPDTWSTPH SYFSLTFCVQ    540
VQGKSKREKK DRVFTDKTSA TVICRKNASI SVRAQDRYYS SSWSEWASVP CSGGGGSGGG    600
GSGGGGSRVI PVSGPARCLS QSRNLLKTTD DMVKTAREKL KHYSCTAEDI DHEDITRDQT    660
STLKTCLPLE LHKNESCLAT RETSSTTRGS CLPPQKTSLM MTLCLGSIYE DLKMYQTEFQ    720
AINAALQNHN HQQIILDKGM LVAIDELMQS LNHNGETLRQ KPPVGEADPY RVKMKLCILL    780
HAFSTRVVTI NRVMGYLSSA SGGPGPAGMK GLPGSEVQLV ESGGGLVQPG NSLRLSCAAS    840
GFTFSKFGMS WVRQAPGKGL EWVSSISGSG RDTLYAESVK GRFTISRDNA KTTLYLQMNS    900
LRPEDTAVYY CTIGGSLSVS SQGTLVTVSS HHHHHHEPEA                          940

SEQ ID NO: 69           moltype = AA   length = 1069
FEATURE                 Location/Qualifiers
source                  1..1069
                        mol_type = protein
                        organism = synthetic construct
SEQUENCE: 69
QSVLTQPPSV SGAPGQRVTI SCSGSRSNIG SNTVKWYQQL PGTAPKLLIY YNDQRPSGVP     60
DRFSGSKSGT SASLAITGLQ AEDEADYYCQ SYDRYTHPAL LFGTGTKVTV LGGGGSGGGG    120
SGGGGSQVQL VESGGGVVQP GRSLRLSCAA SGFTFSSYGM HWVRQAPGKG LEWVAFIRYD    180
GSNKYYADSV KGRFTISRDN SKNTLYLQMN SLRAEDTAVY YCKTHGSHDN WGQGTMVTVS    240
SGGGGSGGGG SGGGGSGGGG SSGGPGPAGM KGLPGSIWEL KKDVYVVELD              300
WYPDAPGEMV VLTCDTPEED GITWTLDQSS EVLGSGKTLT IQVKEFGDAG QYTCHKGGEV    360
LSHSLLLLHK KEDGIWSTDI LKDQKEPKNK TFLRCEAKNY SGRFTCWWLT TISTDLTFSV    420
KSSRGSSDPQ GVTCGAATLS AERVRGDNKE YEYSVECQED SACPAAEESL PIEVMVDAVH    480
KLKYENYTSS FFIRDIIKPD PPKNLQLKPL KNSRQVEVSW EYPDTWSTPH SYFSLTFCVQ    540
VQGKSKREKK DRVFTDKTSA TVICRKNASI SVRAQDRYYS SSWSEWASVP CSGGGGSGGG    600
GSGGGGSRVI PVSGPARCLS QSRNLLKTTD DMVKTAREKL KHYSCTAEDI DHEDITRDQT    660
STLKTCLPLE LHKNESCLAT RETSSTTRGS CLPPQKTSLM MTLCLGSIYE DLKMYQTEFQ    720
AINAALQNHN HQQIILDKGM LVAIDELMQS LNHNGETLRQ KPPVGEADPY RVKMKLCILL    780
HAFSTRVVTI NRVMGYLSSA SGGPGPAGMK GLPGSEVQLV ESGGGLVQPG NSLRLSCAAS    840
GFTFSKFGMS WVRQAPGKGL EWVSSISGSG RDTLYAESVK GRFTISRDNA KTTLYLQMNS    900
LRPEDTAVYY CTIGGSLSVS SQGTLVTVSS GGGGSGGGGS GGGGSQVQLQ ESGGGLAQAG    960
GSLSLSCAAS GFTVSNSVMA WYRQTPGKQR EFVAIINSVG STNYADSVKG RFTISRDNAK   1020
NTVYLQMNNL KPEDTAVYVC NRNFDRIYWG QGTQVTVSSH HHHHHEPEA               1069

SEQ ID NO: 70           moltype = AA   length = 1069
FEATURE                 Location/Qualifiers
source                  1..1069
                        mol_type = protein
                        organism = synthetic construct
SEQUENCE: 70
QVQLQESGGG LAQAGGSLSL SCAASGFTVS NSVMAWYRQT PGKQREFVAI INSVGSTNYA     60
DSVKGRFTIS RDNAKNTVYL QMNNLKPEDT AVYVCNRNFD RIYWGQGTQV TVSSGGGGSG    120
GGGSGGGGSQ SVLTQPPSVS GAPGQRVTIS CSGSRSNIGS NTVKWYQQLP GTAPKLLIYY    180
NDQRPSGVPD RFSGSKSGTS ASLAITGLQA EDEADYYCQS YDRYTHPALL FGTGTKVTVL    240
GGGGSGGGGS GGGGSQVQLV ESGGGVVQPG RSLRLSCAAS GFTFSSYGMH WVRQAPGKGL    300
EWVAFIRYDG SNKYYADSVK GRFTISRDNS KNTLYLQMNS LRAEDTAVYY CKTHGSHDNW    360
GQGTMVTVSS GGGGSGGGGS GGGGSGGGGS GGGGSGGGGS SGGPGPAGMK GLPGSIWELK    420
KDVYVVELDW YPDAPGEMVV LTCDTPEEDG ITWTLDQSSE VLGSGKTLTI QVKEFGDAGQ    480
YTCHKGGEVL SHSLLLLHKK EDGIWSTDIL KDQKEPKNKT FLRCEAKNYS GRFTCWWLTT    540
ISTDLTFSVK SSRGSSDPQG VTCGAATLSA ERVRGDNKEY EYSVECQEDS ACPAAEESLP    600
IEVMVDAVHK LKYENYTSSF FIRDIIKPDP PKNLQLKPLK NSRQVEVSWE YPDTWSTPHS    660
YFSLTFCVQV QGKSKREKKD RVFTDKTSAT VICRKNASIS VRAQDRYYSS SWSEWASVPC    720
SGGGGSGGGG SGGGGSRVIP VSGPARCLSQ SRNLLKTTDD MVKTAREKLK HYSCTAEDID    780
HEDITRDQTS TLKTCLPLEL HKNESCLATR ETSSTTRGSC LPPQKTSLMM TLCLGSIYED    840
LKMYQTEFQA INAALQNHNH QQIILDKGML VAIDELMQSL NHNGETLRQK PPVGEADPYR    900
VKMKLCILLH AFSTRVVTIN RVMGYLSSAS GGPGPAGMKG LPGSEVQLVE SGGGLVQPGN    960
SLRLSCAASG FTFSKFGMSW VRQAPGKGLE WVSSISGSGR DTLYAESVKG RFTISRDNAK   1020
TTLYLQMNSL RPEDTAVYYC TIGGSLSVSS QGTLVTVSSH HHHHHEPEA               1069

SEQ ID NO: 71           moltype = AA   length = 940
FEATURE                 Location/Qualifiers
source                  1..940
                        mol_type = protein
                        organism = synthetic construct
SEQUENCE: 71
EVQLVESGGG LVQPGNSLRL SCAASGFTFS KFGMSWVRQA PGKGLEWVSS ISGSGRDTLY     60
AESVKGRFTI SRDNAKTTLY LQMNSLRPED TAVYYCTIGG SLSVSSQGTL VTVSSGGGGS    120
GGGGSGGGGS QSVLTQPPSV SGAPGQRVTI SCSGSRSNIG SNTVKWYQQL PGTAPKLLIY    180
YNDQRPSGVP DRFSGSKSGT SASLAITGLQ AEDEADYYCQ SYDRYTHPAL LFGTGTKVTV    240
LGGGGSGGGG SGGGGSQVQL VESGGGVVQP GRSLRLSCAA SGFTFSSYGM HWVRQAPGKG    300
LEWVAFIRYD GSNKYYADSV KGRFTISRDN SKNTLYLQMN SLRAEDTAVY YCKTHGSHDN    360
```

```
WGQGTMVTVS  SGGGGSGGGG  SGGGGSGGGG  SSGGPGPAGM  KGLPGSIWEL   420
KKDVYVVELD  WYPDAPGEMV  VLTCDTPEED  GITWTLDQSS  EVLGSGKTLT  IQVKEFGDAG   480
QYTCHKGGEV  LSHSLLLLHK  KEDGIWSTDI  LKDQKEPKNK  TFLRCEAKNY  SGRFTCWWLT   540
TISTDLTFSV  KSSRGSSDPQ  GVTCGAATLS  AERVRGDNKE  YEYSVECQED  SACPAAEESL   600
PIEVMVDAVH  KLKYENYTSS  FFIRDIIKPD  PPKNLQLKPL  KNSRQVEVSW  EYPDTWSTPH   660
SYFSLTFCVQ  VQGKSKREKK  DRVFTDKTSA  TVICRKNASI  SVRAQDRYYS  SSWSEWASVP   720
CSGGGGSGGG  GSGGGGSRVI  PVSGPARCLS  QSRNLLKTTD  DMVKTAREKL  KHYSCTAEDI   780
DHEDITRDQT  STLKTCLPLE  LHKNESCLAT  RETSSTTRGS  CLPPQKTSLM  MTLCLGSIYE   840
DLKMYQTEFQ  AINAALQNHN  HQQIILDKGM  LVAIDELMQS  LNHNGETLRQ  KPPVGEADPY   900
RVKMKLCILL  HAFSTRVVTI  NRVMGYLSSA  HHHHHHEPEA                           940

SEQ ID NO: 72               moltype = AA  length = 940
FEATURE                     Location/Qualifiers
source                      1..940
                            mol_type = protein
                            organism = synthetic construct
SEQUENCE: 72
EVQLVESGGG  LVQPGNSLRL  SCAASGFTFS  KFGMSWVRQA  PGKGLEWVSS  ISGSGRDTLY    60
AESVKGRFTI  SRDNAKTTLY  LQMNSLRPED  TAVYYCTIGG  SLSVSSQGTL  VTVSSSGGPG   120
PAGMKGLPGS  IWELKKDVYV  VELDWYPDAP  GEMVVLTCDT  PEEDGITWTL  DQSSEVLGSG   180
KTLTIQVKEF  GDAGQYTCHK  GGEVLSHSLL  LLHKKEDGIW  STDILKDQKE  PKNKTFLRCE   240
AKNYSGRFTC  WWLTTISTDL  TFSVKSSRGS  SDPQGVTCGA  ATLSAERVRG  DNKEYEYSVE   300
CQEDSACPAA  EESLPIEVMV  DAVHKLKYEN  YTSSFFIRDI  IKPDPPKNLQ  LKPLKNSRQV   360
EVSWEYPDTW  STPHSYFSLT  FCVQVQGKSK  REKKDRVFTD  KTSATVICRK  NASISVRAQD   420
RYYSSSWSEW  ASVPCSGGGG  SGGGGSGGGG  SRVIPVSGPA  RCLSQSRNLL  KTTDDMVKTA   480
REKLKHYSCT  AEDIDHEDIT  RDQTSTLKTC  LPLELHKNES  CLATRETSST  TRGSCLPPQK   540
TSLMMTLCLG  SIYEDLKMYQ  TEFQAINAAL  QNHNHQQIIL  DKGMLVAIDE  LMQSLNHNGE   600
TLRQKPPVGE  ADPYRVKMKL  CILLHAFSTR  VVTINRVMGY  LSSASGGPGP  AGMKGLPGSG   660
GGGSGGGGSG  GGGSGGGGSQ  SVLTQPPSVS  GAPGQRVTIS  CSGSRSNIGS  NTVKWYQQLP   720
GTAPKLLIYY  NDQRPSGVPD  RFSGSKSGTS  ASLAITGLQA  EDEADYYCQS  YDRYTHPALL   780
YDRYTHPALL  FGTGTKVTVL  GGGGSGGGGS  GGGGSQVQLV  ESGGGVVQPG  RSLRLSCAAS   840
GFTFSSYGMH  WVRQAPGKGL  EWVAFIRYDG  SNKYYADSVK  GRFTISRDNS  KNTLYLQMNS   900
LRAEDTAVYY  CKTHGSHDNW  GQGTMVTVSS  HHHHHHEPEA                           940

SEQ ID NO: 73               moltype = AA  length = 940
FEATURE                     Location/Qualifiers
source                      1..940
                            mol_type = protein
                            organism = synthetic construct
SEQUENCE: 73
IWELKKDVYV  VELDWYPDAP  GEMVVLTCDT  PEEDGITWTL  DQSSEVLGSG  KTLTIQVKEF    60
GDAGQYTCHK  GGEVLSHSLL  LLHKKEDGIW  STDILKDQKE  PKNKTFLRCE  AKNYSGRFTC   120
WWLTTISTDL  TFSVKSSRGS  SDPQGVTCGA  ATLSAERVRG  DNKEYEYSVE  CQEDSACPAA   180
EESLPIEVMV  DAVHKLKYEN  YTSSFFIRDI  IKPDPPKNLQ  LKPLKNSRQV  EVSWEYPDTW   240
STPHSYFSLT  FCVQVQGKSK  REKKDRVFTD  KTSATVICRK  NASISVRAQD  RYYSSSWSEW   300
ASVPCSGGGG  SGGGGSGGGG  SRVIPVSGPA  RCLSQSRNLL  KTTDDMVKTA  REKLKHYSCT   360
AEDIDHEDIT  RDQTSTLKTC  LPLELHKNES  CLATRETSST  TRGSCLPPQK  TSLMMTLCLG   420
SIYEDLKMYQ  TEFQAINAAL  QNHNHQQIIL  DKGMLVAIDE  LMQSLNHNGE  TLRQKPPVGE   480
ADPYRVKMKL  CILLHAFSTR  VVTINRVMGY  LSSASGGPGP  AGMKGLPGSG  GGGSGGGGSG   540
GGGSGGGGSG  GGGSGGGGSQ  SVLTQPPSVS  GAPGQRVTIS  CSGSRSNIGS  NTVKWYQQLP   600
GTAPKLLIYY  NDQRPSGVPD  RFSGSKSGTS  ASLAITGLQA  EDEADYYCQS  YDRYTHPALL   660
FGTGTKVTVL  GGGGSGGGGS  GGGGSQVQLV  ESGGGVVQPG  RSLRLSCAAS  GFTFSSYGMH   720
WVRQAPGKGL  EWVAFIRYDG  SNKYYADSVK  GRFTISRDNS  KNTLYLQMNS  LRAEDTAVYY   780
CKTHGSHDNW  GQGTMVTVSS  GGGGSGGGGS  GGGGSEVQLV  ESGGGLVQPG  NSLRLSCAAS   840
GFTFSKFGMS  WVRQAPGKGL  EWVSSISGSG  RDTLYAESVK  GRFTISRDNA  KTTLYLQMNS   900
LRPEDTAVYY  CTIGGSLSVS  SQGTLVTVSS  HHHHHHEPEA                           940

SEQ ID NO: 74               moltype = AA  length = 328
FEATURE                     Location/Qualifiers
source                      1..328
                            mol_type = protein
                            organism = Homo sapiens
SEQUENCE: 74
MCHQQLVISW  FSLVFLASPL  VAIWELKKDV  YVVELDWYPD  APGEMVVLTC  DTPEEDGITW    60
TLDQSSEVLG  SGKTLTIQVK  EFGDAGQYTC  HKGGEVLSHS  LLLLHKKEDG  IWSTDILKDQ   120
KEPKNKTFLR  CEAKNYSGRF  TCWWLTTIST  DLTFSVKSSR  GSSDPQGVTC  GAATLSAERV   180
RGDNKEYEYS  VECQEDSACP  AAEESLPIEV  MVDAVHKLKY  ENYTSSFFIR  DIIKPDPPKN   240
LQLKPLKNSR  QVEVSWEYPD  TWSTPHSYFS  LTFCVQVQGK  SKREKKDRVF  TDKTSATVIC   300
RKNASISVRA  QDRYYSSSWS  EWASVPCS                                         328

SEQ ID NO: 75               moltype = AA  length = 215
FEATURE                     Location/Qualifiers
source                      1..215
                            mol_type = protein
                            organism = Mus musculus
SEQUENCE: 75
MCQSRYLLFL  ATLALLNHLS  LARVIPVSGP  ARCLSQSRNL  LKTTDDMVKT  AREKLKHYSC    60
TAEDIDHEDI  TRDQTSTLKT  CLPLELHKNE  SCLATRETSS  TTRGSCLPPQ  KTSLMMTLCL   120
GSIYEDLKMY  QTEFQAINAA  LQNHNHQQII  LDKGMLVAID  ELMQSLNHNG  ETLRQKPPVG   180
```

```
EADPYRVKMK LCILLHAFST RVVTINRVMG YLSSA                              215

SEQ ID NO: 76            moltype = AA  length = 862
FEATURE                  Location/Qualifiers
REGION                   1..862
                         note = IL12Rb-2 sequence
source                   1..862
                         mol_type = protein
                         organism = unidentified
SEQUENCE: 76
MAHTFRGCSL AFMFIITWLL IKAKIDACKR GDVTVKPSHV ILLGSTVNIT CSLKPRQGCF    60
HYSRRNKLIL YKFDRRINFH HGHSLNSQVT GLPLGTTLFV CKLACINSDE IQICGAEIFV   120
GVAPEQPQNL SCIQKGEQGT VACTWERGRD THLYTEYTLQ LSGPKNLTWQ KQCKDIYCDY   180
LDFGINLTPE SPESNFTAKV TAVNSLGSSS SLPSTFTFLD IVRPLPPWDI RIKFQKASVS   240
RCTLYWRDEG LVLLNRLRYR PSNSRLWNMV NVTKAKGRHD LLDDKPFTEY EFQISSKLHL   300
YKGSWSDWSE SLRAQTPEEE PTGMLDVWYM KRHIDYSRQQ ISLFWKNLSV SEARGKILHY   360
QVTLQELTGG KAMTQNITGH TSWTTVIPRT GNWAVAVSAA NSKGSSLPTR INIMNLCEAG   420
LLAPRQVSAN SEGMDNILVT WQPPRKDPSA VQEYVVEWRE LHPGGDTQVP LNWLRSRPYN   480
VSALISENIK SYICYEIRVY ALSGDQGGCS SILGNSKHKA PLSGPHINAI TEEKGSILIS   540
WNSIPVQEQM GCLLHYRIYW KERDSNSQPQ LCEIPYRVSQ NSHPINSLQP RVTYVLWMTA   600
LTAAGESSHG NEREFCLQGK ANWMAFVAPS ICIAIIMVGI FSTHYFQQKV FVLLAALRPQ   660
WCSREIPDPA NSTCAKKYPI AEEKTQLPLD RLLIDWPTPE DPEPLVISEV LHQVTPVFRH   720
PPCSNWPQRE KGIQHQASE KDMMHSASSP PPPRALQAES RQLVDLYKVL ESRGSDPKPE    780
NPACPWTVLP AGDLPTHDGY LPSNIDDLPS HEAPLADSLE ELEPQHISLS VFPSSSLHPL   840
TFSCGDKLTL DQLKMRCDSL ML                                            862

SEQ ID NO: 77            moltype = AA  length = 662
FEATURE                  Location/Qualifiers
REGION                   1..662
                         note = IL12Rb-1 sequence
source                   1..662
                         mol_type = protein
                         organism = unidentified
SEQUENCE: 77
MEPLVTWVVP LLFLFLLSRQ GAACRTSECC FQDPPYPDAD SGSASGPRDL RCYRISSDRY    60
ECSWQYEGPT AGVSHFLRCC LSSGRCCYFA AGSATRLQFS DQAGVSVLYT VTLWVESWAR   120
NQTEKSPEVT LQLYNSVKYE PPLGDIKVSK LAGQLRMEWE TPDNQVGAEV QFRHRTPSSP   180
WKLGDCGPQD DDTESCLCPL EMNVAQEFQL RRRQLGSQGS SWSKWSSPVC VPPENPPQPG   240
VRFSVEQLGQ DGRRRLTLKE QPTQLELPEG CQGLAPGTEV TYRLQLHMLS CPCKAKATRT   300
LHLGKMPYLS GAAYNVAVIS SNQFGPGLNQ TWHIPADTHT EPVALNISVG TNGTTMYWPA   360
RAQSMTYCIE WQPVGQDGGL ATCSLTAPQD PDPAGMATYS WSRESGAMGQ EKCYYITIFA   420
SAHPEKLTLW STVLSTYHFG GNASAAGTPH HVSVKNHSLD SVSVDWAPSL LSTCPGVLKE   480
YVVRCRDEDS KQVSEHPVQP TETQVTLSGL RAGVAYTVQV RADTAWLRGV WSQPQRFSIE   540
VQVSDWLIFF ASLGSFLSIL LVGVLGYLGL NRAARHLCPP LPTPCASSAI EFPGGKETWQ   600
WINPVDFQEE ASLQEALVVE MSWDKGERTE PLEKTELPEG APELALDTEL SLEDGDRCKA   660
KM                                                                  662

SEQ ID NO: 78            moltype = AA  length = 328
FEATURE                  Location/Qualifiers
source                   1..328
                         mol_type = protein
                         organism = Homo sapiens
SEQUENCE: 78
MCHQQLVISW FSLVFLASPL VAIWELKKDV YVVELDWYPD APGEMVVLTC DTPEEDGITW    60
TLDQSSEVLG SGKTLTIQVK EFGDAGQYTC HKGGEVLSHS LLLLHKKEDG IWSTDILKDQ   120
KEPKNKTFLR CEAKNYSGRF TCWWLTTIST DLTFSVKSSR GSSDPQGVTC GAATLSAERV   180
RGDNKEYEYS VECQEDSACP AAEESLPIEV MVDAVHKLKY ENYTSSFFIR DIIKPDDPKN   240
LQLKPLKNSR QVEVSWEYPD TWSTPHSYFS LTFCVQVQGK SKREKKDRVF TDKTSATVIC   300
RKNASISVRA QDRYYSSSWS EWASVPCS                                      328

SEQ ID NO: 79            moltype = AA  length = 335
FEATURE                  Location/Qualifiers
source                   1..335
                         mol_type = protein
                         organism = Mus musculus
SEQUENCE: 79
MCPQKLTISW FAIVLLVSPL MAMWELEKDV YVVEVDWTPD APGETVNLTC DTPEEDDITW    60
TSDQRHGVIG SGKTLTITVK EFLDAGQYTC HKGGETLSHS HLLLHKKENG IWSTEILKNF   120
KNKTFLKCEA PNYSGRFTCS WLVQRNMDLK FNIKSSSSSP DSRAVTCGMA SLSAEKVTLD   180
QRDYEKYSVS CQEDVTCPTA EETLPIELAL EARQQNKYEN YSTSFFIRDI IKPDDPKNLQ   240
MKPLKNSQVE VSWEYPDSWS TPHSYFSLKF FVRIQRKKEK MKETEEGCNQ KGAFLVEKTS   300
TEVQCKGGNV CVQAQDRYYN SSCSKWACVP CRVRS                              335

SEQ ID NO: 80            moltype = AA  length = 399
FEATURE                  Location/Qualifiers
source                   1..399
                         mol_type = protein
                         organism = synthetic construct
SEQUENCE: 80
```

```
EVQLVESGGG LVQPGNSLRL SCAASGFTFS KFGMSWVRQA PGKGLEWVSS ISGSGRDTLY    60
AESVKGRFTI SRDNAKTTLY LQMNSLRPED TAVYYCTIGG SLSVSSQGTL VTVSSSGGPG   120
PAGMKGLPGS HGTVIESLES LNNYFNSSGI DVEEKSLFLD IWRNWQKDGD MKILQSQIIS   180
FYLRLFEVLK DNQAISNNIS VIESHLITTF FSNSKAKKDA FMSIAKFEVN NPQVQRQAFN   240
ELIRVVHQLL PESSLRKRKR SRCSGGPGPA GMKGLPGSEV QLVESGGGLV QPGNSLRLSC   300
AASGFTFSKF GMSWVRQAPG KGLEWVSSIS GSGRDTLYAE SVKGRFTISR DNAKTTLYLQ   360
MNSLRPEDTA VYYCTIGGSL SVSSQGTLVT VSSHHHHHH                          399

SEQ ID NO: 81           moltype = AA  length = 547
FEATURE                 Location/Qualifiers
source                  1..547
                        mol_type = protein
                        organism = synthetic construct
SEQUENCE: 81
EVQLVESGGG LVQPGNSLRL SCAASGFTFS KFGMSWVRQA PGKGLEWVSS ISGSGRDTLY    60
AESVKGRFTI SRDNAKTTLY LQMNSLRPED TAVYYCTIGG SLSVSSQGTL VTVSSSGGPG   120
PAGMKGLPGS HGTVIESLES LNNYFNSSGI DVEEKSLFLD IWRNWQKDGD MKILQSQIIS   180
FYLRLFEVLK DNQAISNNIS VIESHLITTF FSNSKAKKDA FMSIAKFEVN NPQVQRQAFN   240
ELIRVVHQLL PESSLRKRKR SRCSGGPGPA GMKGLPGSHG TVIESLESLN NYFNSSGIDV   300
EEKSLFLDIW RNWQKDGDMK ILQSQIISFY LRLFEVLKDN QAISNNISVI ESHLITTFFS   360
NSKAKKDAFM SIAKFEVNNP QVQRQAFNEL IRVVHQLLPE SSLRKRKRSR CSGGPGPAGM   420
KGLPGSEVQL VESGGGLVQP GNSLRLSCAA SGFTFSKFGM SWVRQAPGKG LEWVSSISGS   480
GRDTLYAESV KGRFTISRDN AKTTLYLQMN SLRPEDTAVY YCTIGGSLSV SSQGTLVTVS   540
SHHHHHH                                                             547

SEQ ID NO: 82           moltype = AA  length = 547
FEATURE                 Location/Qualifiers
source                  1..547
                        mol_type = protein
                        organism = synthetic construct
SEQUENCE: 82
EVQLVESGGG LVQPGNSLRL SCAASGFTFS KFGMSWVRQA PGKGLEWVSS ISGSGRDTLY    60
AESVKGRFTI SRDNAKTTLY LQMNSLRPED TAVYYCTIGG SLSVSSQGTL VTVSSSGGPG   120
PAGMKGLPGS HGTVIESLES LNNYFNSSGI DVEEKSLFLD IWRNWQKDGD MKILQSQIIS   180
FYLRLFEVLK DNQAISNNIS VIESHLITTF FSNSKAKKDA FMSIAKFEVN NPQVQRQAFN   240
ELIRVVHQLL PESSLRKRKR SRCGGGGSGG GGSGGGGSHG TVIESLESLN NYFNSSGIDV   300
EEKSLFLDIW RNWQKDGDMK ILQSQIISFY LRLFEVLKDN QAISNNISVI ESHLITTFFS   360
NSKAKKDAFM SIAKFEVNNP QVQRQAFNEL IRVVHQLLPE SSLRKRKRSR CSGGPGPAGM   420
KGLPGSEVQL VESGGGLVQP GNSLRLSCAA SGFTFSKFGM SWVRQAPGKG LEWVSSISGS   480
GRDTLYAESV KGRFTISRDN AKTTLYLQMN SLRPEDTAVY YCTIGGSLSV SSQGTLVTVS   540
SHHHHHH                                                             547

SEQ ID NO: 83           moltype = AA  length = 166
FEATURE                 Location/Qualifiers
source                  1..166
                        mol_type = protein
                        organism = Homo sapiens
SEQUENCE: 83
MKYTSYILAF QLCIVLGSLG CYCQDPYVKE AENLKKYFNA GHSDVADNGT LFLGILKNWK    60
EESDRKIMQS QIVSFYFKLF KNFKDDQSIQ KSVETIKEDM NVKFFNSNKK KRDDFEKLTN   120
YSVTDLNVQR KAIHELIQVM AELSPAAKTG KRKRSQMLFR GRRASQ                  166

SEQ ID NO: 84           moltype = AA  length = 155
FEATURE                 Location/Qualifiers
source                  1..155
                        mol_type = protein
                        organism = Mus musculus
SEQUENCE: 84
MNATHCILAL QLFLMAVSGC YCHGTVIESL ESLNNYFNSS GIDVEEKSLF LDIWRNWQKD    60
GDMKILQSQI ISFYLRLFEV LKDNQAISNN ISVIESHLIT TFFSNSKAKK DAFMSIAKFE   120
VNNPQVQRQA FNELIRVVHQ LLPESSLRKR KRSRC                              155

SEQ ID NO: 85           moltype = AA  length = 699
FEATURE                 Location/Qualifiers
source                  1..699
                        mol_type = protein
                        organism = synthetic construct
SEQUENCE: 85
MDMRVPAQLL GLLLLWLRGA RCEVQLVESG GGLVQPGNSL RLSCAASGFT FSKFGMSWVR    60
QAPGKGLEWV SSISGSGRDT LYAESVKGRF TISRDNAKTT LYLQMNSLRP EDTAVYYCTI   120
GGSLSVSSQG TLVTVSSSGG PGPAGMKGLP GSHGTVIESL ESLNNYFNSS GIDVEEKSLF   180
LDIWRNWQKD GDMKILQSQI ISFYLRLFEV LKDNQAISNN ISVIESHLIT TFFSNSKAKK   240
DAFMSIAKFE VNNPQVQRQA FNELIRVVHQ LLPESSLRKR KRSRCSGGPG PAGMKGLPGS   300
EVQLVESGGG LVQPGNSLRL SCAASGFTFS KFGMSWVRQA PGKGLEWVSS ISGSGRDTLY   360
AESVKGRFTI SRDNAKTTLY LQMNSLRPED TAVYYCTIGG SLSVSSQGTL VTVSSSGGPG   420
PAGMKGLPGS HGTVIESLES LNNYFNSSGI DVEEKSLFLD IWRNWQKDGD MKILQSQIIS   480
FYLRLFEVLK DNQAISNNIS VIESHLITTF FSNSKAKKDA FMSIAKFEVN NPQVQRQAFN   540
ELIRVVHQLL PESSLRKRKR SRCSGGPGPA GMKGLPGSEV QLVESGGGLV QPGNSLRLSC   600
AASGFTFSKF GMSWVRQAPG KGLEWVSSIS GSGRDTLYAE SVKGRFTISR DNAKTTLYLQ   660
```

```
MNSLRPEDTA VYYCTIGGSL SVSSQGTLVT VSSHHHHHH                           699

SEQ ID NO: 86             moltype = AA  length = 436
FEATURE                   Location/Qualifiers
source                    1..436
                          mol_type = protein
                          organism = synthetic construct
SEQUENCE: 86
EVQLVESGGG LVQPGNSLRL SCAASGFTFS KFGMSWVRQA PGKGLEWVSS ISGSGRDTLY    60
AESVKGRFTI SRDNAKTTLY LQMNSLRPED TAVYYCTIGG SLSVSSQGTL VTVSSSGGPG    120
PAGMKGLPGS CDLPQTHNLR NKRALTLLVQ MRRLSPLSCL KDRKDFGFPQ EKVDAQQIKK    180
AQAIPVLSEL TQQILNIFTS KDSSAAWNTT LLDSFCNDLH QQLNDLQGCL MQQVGVQEFP    240
LTQEDALLAV RKYFHRITVY LREKKHSPCA WEVVRAEVWR ALSSSANVLG RLREEKSGGP    300
GPAGMKGLPG SEVQLVESGG GLVQPGNSLR LSCAASGFTF SKFGMSWVRQ APGKGLEWVS    360
SISGSGRDTL YAESVKGRFT ISRDNAKTTL YLQMNSLRPE DTAVYYCTIG GSLSVSSQGT    420
LVTVSSHHHH HHEPEA                                                   436

SEQ ID NO: 87             moltype = AA  length = 428
FEATURE                   Location/Qualifiers
source                    1..428
                          mol_type = protein
                          organism = synthetic construct
SEQUENCE: 87
EVQLVESGGG LVQPGNSLRL SCAASGFTFS KFGMSWVRQA PGKGLEWVSS ISGSGRDTLY    60
AESVKGRFTI SRDNAKTTLY LQMNSLRPED TAVYYCTIGG SLSVSSQGTL VTVSSSGGPG    120
PAGMKGLPGS CDLPQTHNLR NKRALTLLVQ MRRLSPLSCL KDRKDFGFPQ EKVDAQQIKK    180
AQAIPVLSEL TQQILNIFTS KDSSAAWNTT LLDSFCNDLH QQLNDLQGCL MQQVGVQEFP    240
LTQEDALLAV RKYFHRITVY LREKKHSPCA WEVVRAEVWR ALSSSANVSG GPGPAGMKGL    300
PGSEVQLVES GGGLVQPGNS LRLSCAASGF TFSKFGMSWV RQAPGKGLEW VSSISGSGRD    360
TLYAESVKGR FTISRDNAKT TLYLQMNSLR PEDTAVYYCT IGGSLSVSSQ GTLVTVSSHH    420
HHHHEPEA                                                            428

SEQ ID NO: 88             moltype = AA  length = 489
FEATURE                   Location/Qualifiers
REGION                    1..489
                          note = IFNgR1 sequence
source                    1..489
                          mol_type = protein
                          organism = unidentified
SEQUENCE: 88
MALLFLLPLV MQGVSRAEMG TADLGPSSVP TPTNVTIESY NMNPIVYWEY QIMPQVPVFT    60
VEVKNYGVKN SEWIDACINI SHHYCNISDH VGDPSNSLWV RVKARVGQKE SAYAKSEEFA    120
VCRDGKIGPP KLDIRKEEKQ IMIDIFHPSV FVNGDEQEVD YDPETTCYIR VYNVYVRMNG    180
SEIQYKILTQ KEDDCDEIQC QLAIPVSSLN SQYCVSAEGV LHVWGVTTEK SKEVCITIFN    240
SSIKGSLWIP VVAALLLFLV LSLVFICFYI KKINPLKEKS IILPKSLISV VRSATLETKP    300
ESKYVSLITS YQPFSLEKEV VCEEPLSPAT VPGMHTEDNP GKVEHTEELS SITEVVTTEE    360
NIPDVVPGSH LTPIERESSS PLSSNQSEPG SIALNSYHSR NCSESDHSRN GFDTDSSCLE    420
SHSSLSDSEF PPNNKGEIKT EGQELITVIK APTSFGYDKP HVLVDLLVDD SGKESLIGYR    480
PTEDSKEFS                                                           489

SEQ ID NO: 89             moltype = AA  length = 337
FEATURE                   Location/Qualifiers
REGION                    1..337
                          note = IFNgR2 sequence
source                    1..337
                          mol_type = protein
                          organism = unidentified
SEQUENCE: 89
MRPTLLWSLL LLLGVFAAAA AAPPDPLSQL PAPQHPKIRL YNAEQVLSWE PVALSNSTRP    60
VVYQVQFKYT DSKWFTADIM SIGVNCTQIT ATECDFTAAS PSAGFPMDFN VTLRLRAELG    120
ALHSAWVTMP WFQHYRNVTV GPPENIEVTP GEGSLIIRFS SPPDIADTST AFFCYVHYW    180
EKGGIQQVKG PFRSNSISLD NLKPSRVYCL QVQAQLLWNK SNIFRVGHLS NISCYETMAD    240
ASTELQQVIL ISVGTFSLLS VLAGACFFLV LKYRGLIKYW FHTPPSIPLQ IEEYLKDPTQ    300
PILEALDKDS SPKDDVWDSV SIISFPEKEQ EDVLQTL                             337

SEQ ID NO: 90             moltype = AA  length = 528
FEATURE                   Location/Qualifiers
source                    1..528
                          mol_type = protein
                          organism = synthetic construct
SEQUENCE: 90
QVQLQESGGG LVQAGGSLRL SCAASGRIFS IDIMSWYRQA PGKQRELVAR ITRGGTISYD    60
DSVKGRFTIS RDNAKNTVYL QMNSLKPEDT GVYYCNALYG TDYWGKGTQV TVSSGGGGSG    120
GGGSGGGGSE VQLVESGGGL VQPGNSLRLS CAASGFTFSK FGMSWVRQAP GKGLEWVSSI    180
SGSGRDTLYA ESVKGRFTIS RDNAKTTLYL QMNSLRPEDT AVYYCTIGGS LSVSSQGTLV    240
TVSSSGGPGP AGMKGLPGSH GTVIESLESL NNYFNSSGID VEEKSLFLDI WRNWQKDGDM    300
KILQSQIISF YLRLFEVLKD NQAISNNISV IESHLITTFF SNSKAKKDAF MSIAKFEVNN    360
PQVQRQAFNE LIRVVHQLLP ESSLRKRKRS RCSGGPGPAG MKGLPGSEVQ LVESGGGLVQ    420
PGNSLRLSCA ASGFTFSKFG MSWVRQAPGK GLEWVSSISG SGRDTLYAES VKGRFTISRD    480
```

```
NAKTTLYLQM NSLRPEDTAV YYCTIGGSLS VSSQGTLVTV SSHHHHHH              528

SEQ ID NO: 91           moltype = AA  length = 658
FEATURE                 Location/Qualifiers
source                  1..658
                        mol_type = protein
                        organism = synthetic construct
SEQUENCE: 91
EVQLVESGGG LVQPGNSLRL SCAASGFTFS KFGMSWVRQA PGKGLEWVSS ISGSGRDTLY   60
AESVKGRFTI SRDNAKTTLY LQMNSLRPED TAVYYCTIGG SLSVSSQGTL VTVSSSGGPG  120
PAGMKGLPGS HGTVIESLES LNNYFNSSGI DVEEKSLFLD IWRNWQKDGD MKILQSQIIS  180
FYLRLFEVLK DNQAISNNIS VIESHLITTF FSNSKAKKDA FMSIAKFEVN NPQVQRQAFN  240
ELIRVVHQLL PESSLRKRKR SRCSGGPGPA GMKGLPGSEV QLVESGGGLV QPGNSLRLSC  300
AASGFTFSKF GMSWVRQAPG KGLEWVSSIS GSGRDTLYAE SVKGRFTISR DNAKTTLYLQ  360
MNSLRPEDTA VYYCTIGGSL SVSSQGTLVT VSSSGGPGPA GMKGLPGSEV QLVESGGGLV  420
QPGNSLRLSC AASGFTFSKF GMSWVRQAPG KGLEWVSSIS GSGRDTLYAE SVKGRFTISR  480
DNAKTTLYLQ MNSLRPEDTA VYYCTIGGSL SVSSQGTLVT VSSGGGGSGG GGSGGGGSQV  540
QLQESGGGLV QAGGSLRLSC AASGRIFSID IMSWYRQESG KQRELVARIT RGGTISYDDS  600
VKGRFTISRD NAKNTVYLQM NSLKPEDTGV YYCNALYGTD YWGKGTQVTV SSHHHHHH    658

SEQ ID NO: 92           moltype = AA  length = 1337
FEATURE                 Location/Qualifiers
source                  1..1337
                        mol_type = protein
                        organism = synthetic construct
SEQUENCE: 92
EAHKSEIAHR YNDLGEQHFK GLVLIAFSQY LQKCSYDEHA KLVQEVTDFA KTCVADESAA   60
NCDKSLHTLF GDKLCAIPNL RENYGELADC CTKQEPERNE CFLQHKDDNP SLPPFERPEA  120
EAMCTSFKEN PTTFMGHYLH EVARRHPYFY APELLYYAEQ YNEILTQCCA EADKESCLTP  180
KLDGVKEKAL VSSVRQRMKC SSMQKFGERA FKAWAVARLS QTFPNADFAE ITKLATDLTK  240
VNKECCHGDL LECADDRAEL AKYMCENQAT ISSKLQTCCD KPLLKKAHCL SEVEHDTMPA  300
DLPAIAADFV EDQEVCKNYA EAKDVFLGTF LYEYSRRHPD YSVSLLLRLA KKYEATLEKC  360
CAEANPPACY GTVLAEFQPL VEEPKNLVKT NCDLYEKLGE YGFQNAILVR YTQKAPQVST  420
PTLVEAARNL GRVGTKCCTL PEDQRLPCVE DYLSAILNRV CLLHEKTPVS EHVTKCCSGS  480
LVERRPCFSA LTVDETYVPK EFKAETFTFH SDICTLPEKE KQIKKQTALA ELVKHKPKAT  540
AEQLKTVMDD FAQFLDTCCK AADKDTCFST EGPNLVTRCK DALASGGPGP AGMKGLPGSH  600
GTVIESLESL NNYFNSSGID VEEKSLFLDI WRNWQKDGDM KILQSQIISF YLRLFEVLKD  660
NQAISNNISV IESHLITTFF SNSKAKKDAF MSIAKFEVNN PQVQRQAFNE LIRVVHQLLP  720
ESSLRKRKRS RCSGGPGPAG MKGLPGSEAH KSEIAHRYND LGEQHFKGLV LIAFSQYLQK  780
CSYDEHAKLV QEVTDFAKTC VADESAANCD KSLHTLFGDK LCAIPNLREN YGELADCCTK  840
QEPERNECFL QHKDDNPSLP PFERPEAEAM CTSFKENPTT FMGHYLHEVA RRHPYFYAPE  900
LLYYAEQYNE ILTQCCAEAD KESCLTPKLD GVKEKALVSS VRQRMKCSSM QKFGERAFKA  960
WAVARLSQTF PNADFAEITK LATDLTKVNK ECCHGDLLEC ADDRAELAKY MCENQATISS 1020
KLQTCCDKPL LKKAHCLSEV EHDTMPADLP AIAAADFVEDQ EVCKNYAEAK DVFLGTFLYE 1080
YSRRHPDYSV SLLLRLAKKY EATLEKCCAE ANPPACYGTV LAEFQPLVEE PKNLVKTNCD 1140
LYEKLGEYGF QNAILVRYTQ KAPQVSTPTL VEAARNLGRV GTKCCTLPED QRLPCVEDYL 1200
SAILNRVCLL HEKTPVSEHV TKCCSGSLVE RRPCFSALTV DETYVPKEFK AETFTFHSDI 1260
CTLPEKEKQI KKQTALAELV KHKPKATAEQ LKTVMDDFAQ FLDTCCKAAD KDTCFSTEGP 1320
NLVTRCKDAL AHHHHHH                                                1337

SEQ ID NO: 93           moltype = AA  length = 1485
FEATURE                 Location/Qualifiers
source                  1..1485
                        mol_type = protein
                        organism = synthetic construct
SEQUENCE: 93
EAHKSEIAHR YNDLGEQHFK GLVLIAFSQY LQKCSYDEHA KLVQEVTDFA KTCVADESAA   60
NCDKSLHTLF GDKLCAIPNL RENYGELADC CTKQEPERNE CFLQHKDDNP SLPPFERPEA  120
EAMCTSFKEN PTTFMGHYLH EVARRHPYFY APELLYYAEQ YNEILTQCCA EADKESCLTP  180
KLDGVKEKAL VSSVRQRMKC SSMQKFGERA FKAWAVARLS QTFPNADFAE ITKLATDLTK  240
VNKECCHGDL LECADDRAEL AKYMCENQAT ISSKLQTCCD KPLLKKAHCL SEVEHDTMPA  300
DLPAIAADFV EDQEVCKNYA EAKDVFLGTF LYEYSRRHPD YSVSLLLRLA KKYEATLEKC  360
CAEANPPACY GTVLAEFQPL VEEPKNLVKT NCDLYEKLGE YGFQNAILVR YTQKAPQVST  420
PTLVEAARNL GRVGTKCCTL PEDQRLPCVE DYLSAILNRV CLLHEKTPVS EHVTKCCSGS  480
LVERRPCFSA LTVDETYVPK EFKAETFTFH SDICTLPEKE KQIKKQTALA ELVKHKPKAT  540
AEQLKTVMDD FAQFLDTCCK AADKDTCFST EGPNLVTRCK DALASGGPGP AGMKGLPGSH  600
GTVIESLESL NNYFNSSGID VEEKSLFLDI WRNWQKDGDM KILQSQIISF YLRLFEVLKD  660
NQAISNNISV IESHLITTFF SNSKAKKDAF MSIAKFEVNN PQVQRQAFNE LIRVVHQLLP  720
ESSLRKRKRS RCGGGGSGGG GSGGGGSHGT VIESLESLNN YFNSSGIDVE EKSLFLDIWR  780
NWQKDGDMKI LQSQIISFYL RLFEVLKDNQ AISNNISVIE SHLITTFFSN SKAKKDAFMS  840
IAKFEVNNPQ VQRQAFNELI RVVHQLLPES SLRKRKRSRC SGGPGPAGMK GLPGSEAHKS  900
EIAHRYNDLG EQHFKGLVLI AFSQYLQKCS YDEHAKLVQE VTDFAKTCVA DESAANCDKS  960
LHTLFGDKLC AIPNLRENYG ELADCCTKQE PERNECFLQH KDDNPSLPPF ERPEAEAMCT 1020
SFKENPTTFM GHYLHEVARR HPYFYAPELL YYAEQYNEIL TQCCAEADKE SCLTPKLDGV 1080
KEKALVSSVR QRMKCSSMQK FGERAFKAWA VARLSQTFPN ADFAEITKLA TDLTKVNKEC 1140
CHGDLLECAD DRAELAKYMC ENQATISSKL QTCCDKPLLK KAHCLSEVEH DTMPADLPAI 1200
AADFVEDQEV CKNYAEAKDV FLGTFLYEYS RRHPDYSVSL LLRLAKKYEA TLEKCCAEAN 1260
PPACYGTVLA EFQPLVEEPK NLVKTNCDLY EKLGEYGFQN AILVRYTQKA PQVSTPTLVE 1320
AARNLGRVGT KCCTLPEDQR LPCVEDYLSA ILNRVCLLHE KTPVSEHVTK CCSGSLVERR 1380
```

```
PCFSALTVDE TYVPKEFKAE TFTFHSDICT LPEKEKQIKK QTALAELVKH KPKATAEQLK    1440
TVMDDFAQFL DTCCKAADKD TCFSTEGPNL VTRCKDALAH HHHHH                    1485

SEQ ID NO: 94           moltype = AA   length = 698
FEATURE                 Location/Qualifiers
source                  1..698
                        mol_type = protein
                        organism = synthetic construct
SEQUENCE: 94
MDMRVPAQLL GLLLLWLRGA RCQVQLQESG GGLVQAGGSL RLSCAASGRI FSIDIMSWYR    60
QAPGKQRELV ARITRGGTIS YDDSVKGRFT ISRDNAKNTV YLQMNSLKPE DTGVYYCNAL    120
YGTDYWGKGT QVTVSSGGGG SGGGGSGGGG SEVQLVESGG GLVQPGNSLR LSCAASGFTF    180
SKFGMSWVRQ APGKGLEWVS SISGSGRDTL YAESVKGRFT ISRDNAKTTL YLQMNSLRPE    240
DTAVYYCTIG GSLSVSSQGT LVTVSSSGGP GPAGMKGLPG SHGTVIESLE SLNNYFNSSG    300
IDVEEKSLFL DIWRNWQKDG DMKILQSQII SFYLRLFEVL KDNQAISNNI SVIESHLITT    360
FFSNSKAKKD AFMSIAKFEV NNPQVQRQAF NELIRVVHQL LPESSLRKRK RSRCGGGGSG    420
GGGSGGGGSH GTVIESLESL NNYFNSSGID VEEKSLFLDI WRNWQKDGDM KILQSQIISF    480
YLRLFEVLKD NQAISNNISV IESHLITTFF SNSKAKKDAF MSIAKFEVNN PQVQRQAFNE    540
LIRVVHQLLP ESSLRKRKRS RCSGGPGPAG MKGLPGSEVQ LVESGGGLVQ PGNSLRLSCA    600
ASGFTFSKFG MSWVRQAPGK GLEWVSSISG SGRDTLYAES VKGRFTISRD NAKTTLYLQM    660
NSLRPEDTAV YYCTIGGSLS VSSQGTLVTV SSHHHHHH                            698

SEQ ID NO: 95           moltype = AA   length = 699
FEATURE                 Location/Qualifiers
source                  1..699
                        mol_type = protein
                        organism = synthetic construct
SEQUENCE: 95
MDMRVPAQLL GLLLLWLRGA RCEVQLVESG GGLVQPGNSL RLSCAASGFT FSKFGMSWVR    60
QAPGKGLEWV SSISGSGRDT LYAESVKGRF TISRDNAKTT LYLQMNSLRP EDTAVYYCTI    120
GGSLSVSSQG TLVTVSSSGG PGPAGMKGLP GSHGTVIESL ESLNNYFNSS GIDVEEKSLF    180
LDIWRNWQKD GDMKILQSQI ISFYLRLFEV LKDNQAISNN ISVIESHLIT TFFSNSKAKK    240
DAFMSIAKFE VNNPQVQRQA FNELIRVVHQ LLPESSLRKR KRSCGGPG PAGMKGLPGS      300
EVQLVESGGG LVQPGNSLRL SCAASGFTFS KFGMSWVRQA PGKGLEWVSS ISGSGRDTLY    360
AESVKGRFTI SRDNAKTTLY LQMNSLRPED TAVYYCTIGG SLSVSSQGTL VTVSSSGGPG    420
PAGMKGLPGS HGTVIESLES LNNYFNSSGI DVEEKSLFLD IWRNWQKDGD MKILQSQIIS    480
FYLRLFEVLK DNQAISNNIS VIESHLITTF FSNSKAKKDA FMSIAKFEVN NPQVQRQAFN    540
ELIRVVHQLL PESSLRKRKR SRCSGGPGPA GMKGLPGSEV QLVESGGGLV QPGNSLRLSC    600
AASGFTFSKF GMSWVRQAPG KGLEWVSSIS GSGRDTLYAE SVKGRFTISR DNAKTTLYLQ    660
MNSLRPEDTA VYYCTIGGSL SVSSQGTLVT VSSHHHHHH                           699

SEQ ID NO: 96           moltype = AA   length = 554
FEATURE                 Location/Qualifiers
source                  1..554
                        mol_type = protein
                        organism = synthetic construct
SEQUENCE: 96
MDMRVPAQLL GLLLLWLRGA RCQVQLQESG GGLAQAGGSL SLSCAASGFT VSNSVMAWYR    60
QTPGKQREFV AIINSVGSTN YADSVKGRFT ISRDNAKNTV YLQMNNLKPE DTAVYVCNRN    120
FDRIYWGQGT QVTVSSGGGG SGGGGSGGGG SEVQLVESGG GLVQPGNSLR LSCAASGFTF    180
SKFGMSWVRQ APGKGLEWVS SISGSGRDTL YAESVKGRFT ISRDNAKTTL YLQMNSLRPE    240
DTAVYYCTIG GSLSVSSQGT LVTVSSSGGP GPAGMKGLPG SHGTVIESLE SLNNYFNSSG    300
IDVEEKSLFL DIWRNWQKDG DMKILQSQII SFYLRLFEVL KDNQAISNNI SVIESHLITT    360
FFSNSKAKKD AFMSIAKFEV NNPQVQRQAF NELIRVVHQL LPESSLRKRK RSRCSGGPGP    420
AGMKGLPGSE VQLVESGGGL VQPGNSLRLS CAASGFTFSK FGMSWVRQAP GKGLEWVSSI    480
SGSGRDTLYA ESVKGRFTIS RDNAKTTLYL QMNSLRPEDT AVYYCTIGGS LSVSSQGTLV    540
TVSSHHHHHH EPEA                                                     554

SEQ ID NO: 97           moltype = AA   length = 554
FEATURE                 Location/Qualifiers
source                  1..554
                        mol_type = protein
                        organism = synthetic construct
SEQUENCE: 97
MDMRVPAQLL GLLLLWLRGA RCEVQLVESG GGLVQPGNSL RLSCAASGFT FSKFGMSWVR    60
QAPGKGLEWV SSISGSGRDT LYAESVKGRF TISRDNAKTT LYLQMNSLRP EDTAVYYCTI    120
GGSLSVSSQG TLVTVSSSGG PGPAGMKGLP GSHGTVIESL ESLNNYFNSS GIDVEEKSLF    180
LDIWRNWQKD GDMKILQSQI ISFYLRLFEV LKDNQAISNN ISVIESHLIT TFFSNSKAKK    240
DAFMSIAKFE VNNPQVQRQA FNELIRVVHQ LLPESSLRKR KRSCGGPG PAGMKGLPGS      300
EVQLVESGGG LVQPGNSLRL SCAASGFTFS KFGMSWVRQA PGKGLEWVSS ISGSGRDTLY    360
AESVKGRFTI SRDNAKTTLY LQMNSLRPED TAVYYCTIGG SLSVSSQGTL VTVSSGGGGS    420
GGGGSGGGGS QVQLQESGGG LAQAGGSLSL SCAASGFTVS NSVMAWYRQT PGKQREFVAI    480
INSVGSTNYA DSVKGRFTIS RDNAKNTVYL QMNNLKPEDT AVYVCNRNFD RIYWGQGTQV    540
TVSSHHHHHH EPEA                                                     554

SEQ ID NO: 98           moltype = AA   length = 702
FEATURE                 Location/Qualifiers
source                  1..702
                        mol_type = protein
```

```
                        organism = synthetic construct
SEQUENCE: 98
MDMRVPAQLL GLLLLWLRGA RCEVQLVESG GGLVQPGNSL RLSCAASGFT FSKFGMSWVR     60
QAPGKGLEWV SSISGSGRDT LYAESVKGRF TISRDNAKTT LYLQMNSLRP EDTAVYYCTI    120
GGSLSVSSQG TLVTVSSSGG PGPAGMKGLP GSHGTVIESL ESLNNYFNSS GIDVEEKSLF    180
LDIWRNWQKD GDMKILQSQI ISFYLRLFEV LKDNQAISNN ISVIESHLIT TFFSNSKAKK    240
DAFMSIAKFE VNNPQVQRQA FNELIRVVHQ LLPESSLRKR KRSRCSGGPG PAGMKGLPGS    300
HGTVIESLES LNNYFSSSGI DVEEKSLFLD IWRNWQKDGD MKILQSQIIS FYLRLFEVLK    360
DNQAISNNIS VIESHLITTF FSNSKAKKDA FMSIAKFEVN NPQVQRQAFN ELIRVVHQLL    420
PESSLRKRKR SRCSGGPGPA GMKGLPGSEV QLVESGGGLV QPGNSLRLSC AASGFTFSKF    480
GMSWVRQAPG KGLEWVSSIS GSGRDTLYAE SVKGRFTISR DNAKTTLYLQ MNSLRPEDTA    540
VYYCTIGGSL SVSSQGTLVT VSSGGGGSGG GGSGGGGSQV QLQESGGGLV QAGGSLRLSC    600
AASGRIFSID IMSWYRQAPG KQRELVARIT RGGTISYDDS VKGRFTISRD NAKNTVYLQM    660
NSLKPEDTGV YYCNALYGTD YWGKGTQVTV SSHHHHHHEP EA                      702

SEQ ID NO: 99            moltype = AA  length = 702
FEATURE                  Location/Qualifiers
source                   1..702
                         mol_type = protein
                         organism = synthetic construct
SEQUENCE: 99
MDMRVPAQLL GLLLLWLRGA RCQVQLQESG GGLAQAGGSL SLSCAASGFT VSNSVMAWYR     60
QTPGKQREFV AIINSVGSTN YADSVKGRFT ISRDNAKNTV YLQMNNLKPE DTAVYVCNRN    120
FDRIYWQGT QVTVSSGGGG SGGGGSGGGG SEVQLVESGG GLVQPGNSLR LSCAASGFTF    180
SKFGMSWVRQ APGKGLEWVS SISGSGRDTL YAESVKGRFT ISRDNAKTTL YLQMNSLRPE    240
DTAVYYCTIG GSLSVSSQGT LVTVSSSGGP GPAGMKGLPG SHGTVIESLE SLNNYFNSSG    300
IDVEEKSLFL DIWRNWQKDG DMKILQSQII SFYLRLFEVL KDNQAISNNI SVIESHLITT    360
FFSNSKAKKD AFMSIAKFEV NNPQVQRQAF NELIRVVHQL LPESSLRKRK RSRCSGGPGP    420
AGMKGLPGSH GTVIESLESL NNYFNSSGID VEEKSLFLDI WRNWQKDGDM KILQSQIISF    480
YLRLFEVLKD NQAISNNISV IESHLITTFF SNSKAKKDAF MSIAKFEVNN PQVQRQAFNE    540
LIRVVHQLLP ESSLRKRKRS RCSGGPGPAG MKGLPGSEVQ LVESGGGLVQ PGNSLRLSCA    600
ASGFTFSKFG MSWVRQAPGK GLEWVSSISG SGRDTLYAES VKGRFTISRD NAKTTLYLQM    660
NSLRPEDTAV YYCTIGGSLS VSSQGTLVTV SSHHHHHHEP EA                      702

SEQ ID NO: 100           moltype = AA  length = 702
FEATURE                  Location/Qualifiers
source                   1..702
                         mol_type = protein
                         organism = synthetic construct
SEQUENCE: 100
MDMRVPAQLL GLLLLWLRGA RCEVQLVESG GGLVQPGNSL RLSCAASGFT FSKFGMSWVR     60
QAPGKGLEWV SSISGSGRDT LYAESVKGRF TISRDNAKTT LYLQMNSLRP EDTAVYYCTI    120
GGSLSVSSQG TLVTVSSSGG PGPAGMKGLP GSHGTVIESL ESLNNYFNSS GIDVEEKSLF    180
LDIWRNWQKD GDMKILQSQI ISFYLRLFEV LKDNQAISNN ISVIESHLIT TFFSNSKAKK    240
DAFMSIAKFE VNNPQVQRQA FNELIRVVHQ LLPESSLRKR KRSRCSGGPG PAGMKGLPGS    300
HGTVIESLES LNNYFNSSGI DVEEKSLFLD IWRNWQKDGD MKILQSQIIS FYLRLFEVLK    360
DNQAISNNIS VIESHLITTF FSNSKAKKDA FMSIAKFEVN NPQVQRQAFN ELIRVVHQLL    420
PESSLRKRKR SRCSGGPGPA GMKGLPGSEV QLVESGGGLV QPGNSLRLSC AASGFTFSKF    480
GMSWVRQAPG KGLEWVSSIS GSGRDTLYAE SVKGRFTISR DNAKTTLYLQ MNSLRPEDTA    540
VYYCTIGGSL SVSSQGTLVT VSSGGGGSGG GGSGGGGSQV QLQESGGGLA QAGGSLSLSC    600
AASGFTVSNS VMAWYRQTPG KQREFVAIIN SVGSTNYADS VKGRFTISRD NAKTTLYLQM    660
NNLKPEDTAV YVCNRNFDRI YWGQGTQVTV SSHHHHHHEP EA                      702

SEQ ID NO: 101           moltype = AA  length = 832
FEATURE                  Location/Qualifiers
source                   1..832
                         mol_type = protein
                         organism = synthetic construct
SEQUENCE: 101
MDMRVPAQLL GLLLLWLRGA RCEVQLVESG GGLVQPGNSL RLSCAASGFT FSKFGMSWVR     60
QAPGKGLEWV SSISGSGRDT LYAESVKGRF TISRDNAKTT LYLQMNSLRP EDTAVYYCTI    120
GGSLSVSSQG TLVTVSSSGG PGPAGMKGLP GSHGTVIESL ESLNNYFNSS GIDVEEKSLF    180
LDIWRNWQKD GDMKILQSQI ISFYLRLFEV LKDNQAISNN ISVIESHLIT TFFSNSKAKK    240
DAFMSIAKFE VNNPQVQRQA FNELIRVVHQ LLPESSLRKR KRSRCSGGPG PAGMKGLPGS    300
HGTVIESLES LNNYFNSSGI DVEEKSLFLD IWRNWQKDGD MKILQSQIIS FYLRLFEVLK    360
DNQAISNNIS VIESHLITTF FSNSKAKKDA FMSIAKFEVN NPQVQRQAFN ELIRVVHQLL    420
PESSLRKRKR SRCSGGPGPA GMKGLPGSEV QLVESGGGLV QPGNSLRLSC AASGFTFSKF    480
GMSWVRQAPG KGLEWVSSIS GSGRDTLYAE SVKGRFTISR DNAKTTLYLQ MNSLRPEDTA    540
VYYCTIGGSL SVSSQGTLVT VSSGGGGSGG GGSGGGGSEV QLVESGGGLV QPGGSLRLSC    600
AASGFTFSSY AMSWVRQAPG KGLEWVSAIS GSGGSTYYAD SVKGRFTISR DNSKNTLYLQ    660
MNSLRAEDTA VYYCARGVGA FRPYRKHEWG QGTLVTVSRG GGGSGGGGS GGGSSSELTQ    720
DPAVSVALGQ TVRITCQGDS LRSYYASWYQ QKPGQAPVLV IYGKNNRPSG IPDRFSGSSS    780
GNTASLTTTG AQAEDEADYY CNSSPFEHNL VVFGGGTKLT VLHHHHHHEP EA            832

SEQ ID NO: 102           moltype = AA  length = 276
FEATURE                  Location/Qualifiers
source                   1..276
                         mol_type = protein
                         organism = synthetic construct
```

```
SEQUENCE: 102
MDMRVPAQLL GLLLLWLRGA RCEVQLVESG GGLVQPGGSL RLSCAASGFT FSSYAMSWVR      60
QAPGKGLEWV SAISGSGGST YYADSVKGRF TISRDNSKNT LYLQMNSLRA EDTAVYYCAR     120
GVGAFRPYRK HEWGQGTLVT VSRGGGGSGG GGSGGGGSSS ELTQDPAVSV ALGQTVRITC     180
QGDSLRSYYA SWYQQKPGQA PVLVIYGKNN RPSGIPDRFS GSSSGNTASL TTTGAQAEDE     240
ADYYCNSSPF EHNLVVFGGG TKLTVLHHHH HHEPEA                              276

SEQ ID NO: 103              moltype = AA  length = 573
FEATURE                     Location/Qualifiers
source                      1..573
                            mol_type = protein
                            organism = synthetic construct
SEQUENCE: 103
MDMRVPAQLL GLLLLWLRGA RCEVQLVESG GGLVQPGNSL RLSCAASGFT FSKFGMSWVR      60
QAPGKGLEWV SSISGSGRDT LYAESVKGRF TISRDNAKTT LYLQMNSLRP EDTAVYYCTI     120
GGSLSVSSQG TLVTVSSSGG PGPAGMKGLP GSHGTVIESL ESLNNYFNSS GIDVEEKSLF     180
LDIWRNWQKD GDMKILQSQI ISFYLRLFEV LKDNQAISNN ISVIESHLIT TFFSNSKAKK     240
DAFMSIAKFE VNNPQVQRQA FNELIRVVHQ LLPESSLRKR KRSRCSGGPG PAGMKGLPGS     300
EVQLVESGGG LVQPGNSLRL SCAASGFTFS KFGMSWVRQA PGKGLEWVSS ISGSGRDTLY     360
AESVKGRFTI SRDNAKTTLY LQMNSLRPED TAVYYCTIGG SLSVSSQGTL VTVSSSGGPG     420
PAGMKGLPGS HGTVIESLES LNNYFNSSGI DVEEKSLFLD IWRNWQKDGD MKILQSQIIS     480
FYLRLFEVLK DNQAISNNIS VIESHLITTF FSNSKAKKDA FMSIAKFEVN NPQVQRQAFN     540
ELIRVVHQLL PESSLRKRKR SRCHHHHHHE PEA                                 573

SEQ ID NO: 104              moltype = AA  length = 573
FEATURE                     Location/Qualifiers
source                      1..573
                            mol_type = protein
                            organism = synthetic construct
SEQUENCE: 104
MDMRVPAQLL GLLLLWLRGA RCHGTVIESL ESLNNYFNSS GIDVEEKSLF LDIWRNWQKD      60
GDMKILQSQI ISFYLRLFEV LKDNQAISNN ISVIESHLIT TFFSNSKAKK DAFMSIAKFE     120
VNNPQVQRQA FNELIRVVHQ LLPESSLRKR KRSRCSGGPG PAGMKGLPGS EVQLVESGGG     180
LVQPGNSLRL SCAASGFTFS KFGMSWVRQA PGKGLEWVSS ISGSGRDTLY AESVKGRFTI     240
SRDNAKTTLY LQMNSLRPED TAVYYCTIGG SLSVSSQGTL VTVSSSGGPG PAGMKGLPGS     300
HGTVIESLES LNNYFNSSGI DVEEKSLFLD IWRNWQKDGD MKILQSQIIS FYLRLFEVLK     360
DNQAISNNIS VIESHLITTF FSNSKAKKDA FMSIAKFEVN NPQVQRQAFN ELIRVVHQLL     420
PESSLRKRKR SRCSGGPGPA GMKGLPGSEV QLVESGGGLV QPGNSLRLSC AASGFTFSKF     480
GMSWVRQAPG KGLEWVSSIS GSGRDTLYAE SVKGRFTISR DNAKTTLYLQ MNSLRPEDTA     540
VYYCTIGGSL SVSSQGTLVT VSSHHHHHHE PEA                                 573

SEQ ID NO: 105              moltype = AA  length = 1511
FEATURE                     Location/Qualifiers
source                      1..1511
                            mol_type = protein
                            organism = synthetic construct
SEQUENCE: 105
MDMRVPAQLL GLLLLWLRGA RCHGTVIESL ESLNNYFNSS GIDVEEKSLF LDIWRNWQKD      60
GDMKILQSQI ISFYLRLFEV LKDNQAISNN ISVIESHLIT TFFSNSKAKK DAFMSIAKFE     120
VNNPQVQRQA FNELIRVVHQ LLPESSLRKR KRSCGGPG PAGMKGLPGS EAHKSEIAHR     180
YNDLGEQHFK GLVLIAFSQY LQKCSYDEHA KLVQEVTDFA KTCVADESAA NCDKSLHTLF     240
GDKLCAIPNL RENYGELADC CTKQEPERNE CFLQHKDDNP SLPPFERPEA EAMCTSFKEN     300
PTTFMGHYLH EVARRHPYFY APELLYYAEQ YNEILTQCCA EADKESCLTP KLDGVKEKAL     360
VSSVRQRMKC SSMQKFGERA FKAWAVARLS QTFPNADFAE ITKLATDLTK VNKECCHGDL     420
LECADDRAEL AKYMCENQAT ISSKLQTCCD KPLLKKAHCL SEVEHDTMPA DLPAIAADFV     480
EDQEVCKNYA EAKDVFLGTF LYEYSRRHPD YSVSLLLRLA KKYEATLEKC CAEANPPACY     540
GTVLAEFQPL VEEPKNLVKT NCDLYEKLGE YGFQNAILVR YTQKAPQVST PTLVEAARNL     600
GRVGTKCCTL PEDQRLPCVE DYLSAILNRV CLLHEKTPVS EHVTKCCSGS LVERRPCFSA     660
LTVDETYVPK EFKAETFTPH SDICTLPEKE KQIKKQTALA ELVKHKPKAT AEQLKTVMDD     720
FAQFLDTCCK AADKDTCFST EGPNLVTRCK DALASGGPGP AGMKGLPGSH GTVIESLESL     780
NNYFNSSGID VEEKSLFLDI WRNWQKDGDM KILQSQIISF YLRLFEVLKD NQAISNNISV     840
IESHLITTFF SNSKAKKDAF MSIAKFEVNN PQVQRQAFNE LIRVVHQLLP ESSLRKRKRS     900
RCSGGPGPAG MKGLPGSEAH KSEIAHRYND LGEQHFKGLV LIAFSQYLQK CSYDEHAKLV     960
QEVTDFAKTC VADESAANCD KSLHTLFGDK LCAIPNLREN YGELADCCTK QEPERNECFL    1020
QHKDDNPSLP PFERPEAEAM CTSFKENPTT FMGHYLHEVA RRHPYFYAPE LLYYAEQYNE    1080
ILTQCCAEAD KESCLTPKLD GVKEKALVSS VRQRMKCSSM QKFGERAFKA WAVARLSQTF    1140
PNADFAEITK LATDLTKVNK ECCHGDLLEC ADDRAELAKY MCENQATISS KLQTCCDKPL    1200
LKKAHCLSEV EHDTMPADLP AIAADFVEDQ EVCKNYAEAK DVFLGTFLYE YSRRHPDYSV    1260
SLLLRLAKKY EATLEKCCAE ANPPACYGTV LAEFQPLVEE PKNLVKTNCD LYEKLGEYGF    1320
QNAILVRYTQ KAPQVSTPTL VEAARNLGRV GTKCCTLPED QRLPCVEDYL SAILNRVCLL    1380
HEKTPVSEHV TKCCSGSLVE RRPCFSALTV DETYVPKEFK AETFTFHSDI CTLPEKEKQI    1440
KKQTALAELV KHKPKATAEQ LKTVMDDFAQ FLDTCCKAAD KDTCFSTEGP NLVTRCKDAL    1500
AHHHHHHEPE A                                                        1511

SEQ ID NO: 106              moltype = AA  length = 1511
FEATURE                     Location/Qualifiers
source                      1..1511
                            mol_type = protein
                            organism = synthetic construct
```

```
SEQUENCE: 106
MDMRVPAQLL GLLLLWLRGA RCEAHKSEIA HRYNDLGEQH FKGLVLIAFS QYLQKCSYDE    60
HAKLVQEVTD FAKTCVADES AANCDKSLHT LFGDKLCAIP NLRENYGELA DCCTKQEPER   120
NECFLQHKDD NPSLPPFERP EAEAMCTSFK ENPTTFMGHY LHEVARRHPY FYAPELLYYA   180
EQYNEILTQC CAEADKESCL TPKLDGVKEK ALVSSVRQRM KCSSMQKFGE RAFKAWAVAR   240
LSQTFPNADF AEITKLATDL TKVNKECCHG DLLECADDRA ELAKYMCENQ ATISSKLQTC   300
CDKPLLKKAH CLSEVEHDTM PADLPAIAAD FVEDQEVCKN YAEAKDVFLG TFLYEYSRRH   360
PDYSVSLLLR LAKKYEATLE KCCAEANPPA CYGTVLAEFQ PLVEEPKNLV KTNCDLYEKL   420
GEYGFQNAIL VRYTQKAPQV STPTLVEAAR NLGRVGTKCC TLPEDQRLPC VEDYLSAILN   480
RVCLLHEKTP VSEHVTKCCS GSLVERRPCF SALTVDETYV PKEFKAETFT FHSDICTLPE   540
KEKQIKKQTA LAELVKHKPK ATAEQLKTVM DDFAQFLDTC CKAADKDTCF STEGPNLVTR   600
CKDALASGGP GPAGMKGLPG SHGTVIESLE SLNNYFNSSG IDVEEKSLFL DIWRNWQKDG   660
DMKILQSQII SFYLRLFEVL KDNQAISNNI SVIESHLITT FFSNSKAKKD AFMSIAKFEV   720
NNPQVQRQAF NELIRVVHQL LPESSLRKRK RSRCSGGPGP AGMKGLPGSE AHKSEIAHRY   780
NDLGEQHFKG LVLIAFSQYL QKCSYDEHAK LVQEVTDFAK TCVADESAAN CDKSLHTLFG   840
DKLCAIPNLR ENYGELADCC TKQEPERNEC FLQHKDDNPS LPPFERPEAE AMCTSFKENP   900
TTFMGHYLHE VARRHPYFYA PELLYYAEQY NEILTQCCAE ADKESCLTPK LDGVKEKALV   960
SSVRQRMKCS SMQKFGERAF KAWAVARLSQ TFPNADFAEI TKLATDLTKV NKECCHGDLL  1020
ECADDRAELA KYMCENQATI SSKLQTCCDK PLLKKAHCLS EVEHDTMPAD LPAIAADFVE  1080
DQEVCKNYAE AKDVFLGTFL YEYSRRHPDY SVSLLLRLAK KYEATLEKCC AEANPPACYG  1140
TVLAEFQPLV EEPKNLVKTN CDLYEKLGEY GFQNAILVRY TQKAPQVSTP TLVEAARNLG  1200
RVGTKCCTLP EDQRLPCVED YLSAILNRVC LLHEKTPVSE HVTKCCSGSL VERRPCFSAL  1260
TVDETYVPKE FKAETFTFHS DICTLPEKEK QIKKQTALAE LVKHKPKATA EQLKTVMDDF  1320
AQFLDTCCKA ADKDTCFSTE GPNLVTRCKD ALASGGPGPA GMKGLPGSHG TVIESLESLN  1380
NYFNSSGIDV EEKSLFLDIW RNWQKDGDMK ILQSQIISFY LRLFEVLKDN QAISNNISVI  1440
ESHLITTFFS NSKAKKDAFM SIAKFEVNNP QVQRQAFNEL IRVVHQLLPE SSLRKRKRSR  1500
CHHHHHHEPE A                                                      1511

SEQ ID NO: 107           moltype = AA  length = 2110
FEATURE                  Location/Qualifiers
source                   1..2110
                         mol_type = protein
                         organism = synthetic construct
SEQUENCE: 107
MDMRVPAQLL GLLLLWLRGA RCEAHKSEIA HRYNDLGEQH FKGLVLIAFS QYLQKCSYDE    60
HAKLVQEVTD FAKTCVADES AANCDKSLHT LFGDKLCAIP NLRENYGELA DCCTKQEPER   120
NECFLQHKDD NPSLPPFERP EAEAMCTSFK ENPTTFMGHY LHEVARRHPY FYAPELLYYA   180
EQYNEILTQC CAEADKESCL TPKLDGVKEK ALVSSVRQRM KCSSMQKFGE RAFKAWAVAR   240
LSQTFPNADF AEITKLATDL TKVNKECCHG DLLECADDRA ELAKYMCENQ ATISSKLQTC   300
CDKPLLKKAH CLSEVEHDTM PADLPAIAAD FVEDQEVCKN YAEAKDVFLG TFLYEYSRRH   360
PDYSVSLLLR LAKKYEATLE KCCAEANPPA CYGTVLAEFQ PLVEEPKNLV KTNCDLYEKL   420
GEYGFQNAIL VRYTQKAPQV STPTLVEAAR NLGRVGTKCC TLPEDQRLPC VEDYLSAILN   480
RVCLLHEKTP VSEHVTKCCS GSLVERRPCF SALTVDETYV PKEFKAETFT FHSDICTLPE   540
KEKQIKKQTA LAELVKHKPK ATAEQLKTVM DDFAQFLDTC CKAADKDTCF STEGPNLVTR   600
CKDALASGGP GPAGMKGLPG SHGTVIESLE SLNNYFNSSG IDVEEKSLFL DIWRNWQKDG   660
DMKILQSQII SFYLRLFEVL KDNQAISNNI SVIESHLITT FFSNSKAKKD AFMSIAKFEV   720
NNPQVQRQAF NELIRVVHQL LPESSLRKRK RSRCSGGPGP AGMKGLPGSE AHKSEIAHRY   780
NDLGEQHFKG LVLIAFSQYL QKCSYDEHAK LVQEVTDFAK TCVADESAAN CDKSLHTLFG   840
DKLCAIPNLR ENYGELADCC TKQEPERNEC FLQHKDDNPS LPPFERPEAE AMCTSFKENP   900
TTFMGHYLHE VARRHPYFYA PELLYYAEQY NEILTQCCAE ADKESCLTPK LDGVKEKALV   960
SSVRQRMKCS SMQKFGERAF KAWAVARLSQ TFPNADFAEI TKLATDLTKV NKECCHGDLL  1020
ECADDRAELA KYMCENQATI SSKLQTCCDK PLLKKAHCLS EVEHDTMPAD LPAIAADFVE  1080
DQEVCKNYAE AKDVFLGTFL YEYSRRHPDY SVSLLLRLAK KYEATLEKCC AEANPPACYG  1140
TVLAEFQPLV EEPKNLVKTN CDLYEKLGEY GFQNAILVRY TQKAPQVSTP TLVEAARNLG  1200
RVGTKCCTLP EDQRLPCVED YLSAILNRVC LLHEKTPVSE HVTKCCSGSL VERRPCFSAL  1260
TVDETYVPKE FKAETFTFHS DICTLPEKEK QIKKQTALAE LVKHKPKATA EQLKTVMDDF  1320
AQFLDTCCKA ADKDTCFSTE GPNLVTRCKD ALASGGPGPA GMKGLPGSHG TVIESLESLN  1380
NYFNSSGIDV EEKSLFLDIW RNWQKDGDMK ILQSQIISFY LRLFEVLKDN QAISNNISVI  1440
ESHLITTFFS NSKAKKDAFM SIAKFEVNNP QVQRQAFNEL IRVVHQLLPE SSLRKRKRSR  1500
CSGGPGPAGM KGLPGSEAHK SEIAHRYNDL GEQHFKGLVL IAFSQYLQKC SYDEHAKLVQ  1560
EVTDFAKTCV ADESAANCDK SLHTLFGDKL CAIPNLRENY GELADCCTKQ EPERNECFLQ  1620
HKDDNPSLPP FERPEAEAMC TSFKENPTTF MGHYLHEVAR RHPYFYAPEL LYYAEQYNEI  1680
LTQCCAEADK ESCLTPKLDG VKEKALVSSV RQRMKCSSMQ KFGERAFKAW AVARLSQTFP  1740
NADFAEITKL ATDLTKVNKE CCHGDLLECA DDRAELAKYM CENQATISSK LQTCCDKPLL  1800
KKAHCLSEVE HDTMPADLPA IAADFVEDQE VCKNYAEAKD VFLGTFLYEY SRRHPDYSVS  1860
LLLRLAKKYE ATLEKCCAEA NPPACYGTVL AEFQPLVEEP KNLVKTNCDL YEKLGEYGFQ  1920
NAILVRYTQK APQVSTPTLV EAARNLGRVG TKCCTLPEDQ RLPCVEDYLS AILNRVCLLH  1980
EKTPVSEHVT KCCSGSLVER RPCFSALTVD ETYVPKEFKA ETFTFHSDIC TLPEKEKQIK  2040
KQTALAELVK HKPKATAEQL KTVMDDFAQF LDTCCKAADK DTCFSTEGPN LVTRCKDALA  2100
HHHHHHEPEA                                                        2110

SEQ ID NO: 108           moltype = AA  length = 2120
FEATURE                  Location/Qualifiers
source                   1..2120
                         mol_type = protein
                         organism = synthetic construct
SEQUENCE: 108
MDMRVPAQLL GLLLLWLRGA RCEAHKSEIA HRYNDLGEQH FKGLVLIAFS QYLQKCSYDE    60
HAKLVQEVTD FAKTCVADES AANCDKSLHT LFGDKLCAIP NLRENYGELA DCCTKQEPER   120
```

```
NECFLQHKDD NPSLPPFERP EAEAMCTSFK ENPTTFMGHY LHEVARRHPY FYAPELLYYA    180
EQYNEILTQC CAEADKESCL TPKLDGVKEK ALVSSVRQRM KCSSMQKFGE RAFKAWAVAR    240
LSQTFPNADF AEITKLATDL TKVNKECCHG DLLECADDRA ELAKYMCENQ ATISSKLQTC    300
CDKPLLKKAH CLSEVEHDTM PADLPAIAAD FVEDQEVCKN YAEAKDVFLG TFLYEYSRRH    360
PDYSVSLLLR LAKKYEATLE KCCAEANPPA CYGTVLAEFQ PLVEEPKNLV KTNCDLYEKL    420
GEYGFQNAIL VRYTQKAPQV STPTLVEAAR NLGRVGTKCC TLPEDQRLPC VEDYLSAILN    480
RVCLLHEKTP VSEHVTKCCS GSLVERRPCF SALTVDETYV PKEFKAETFT FHSDICTLPE    540
KEKQIKKQTA LAELVKHKPK ATAEQLKTVM DDFAQFLDTC CKAADKDTCF STEGPNLVTR    600
CKDALASGGP GPAGMKGLPG SHGTVIESLE SLNNYFNSSG IDVEEKSLFL DIWRNWQKDG    660
DMKILQSQII SFYLRLFEVL KDNQAISNNI SVIESHLITT FFSNSKAKKD AFMSIAKFEV    720
NNPQVQRQAF NELIRVVHQL LPESSLRKRK RSRCSGGPGP AGMKGLPGSS GGGSEAHKSE    780
IAHRYNDLGE QHFKGLVLIA FSQYLQKCSY DEHAKLVQEV TDFAKTCVAD ESAANCDKSL    840
HTLFGDKLCA IPNLRENYGE LADCCTKQEP ERNECFLQHK DDNPSLPPFE RPEAEAMCTS    900
FKENPTTFMG HYLHEVARRH PYFYAPELLY YAEQYNEILT QCCAEADKES CLTPKLDGVK    960
EKALVSSVRQ RMKCSSMQKF GERAFKAWAV ARLSQTFPNA DFAEITKLAT DLTKVNKECC   1020
HGDLLECADD RAELAKYMCE NQATISSKLQ TCCDKPLLKK AHCLSEVEHD TMPADLPAIA   1080
ADFVEDQEVC KNYAEAKDVF LGTFLYEYSR RHPDYSVSLL LRLAKKYEAT LEKCCAEANP   1140
PACYGTVLAE FQPLVEEPKN LVKTNCDLYE KLGEYGFQNA ILVRYTQKAP QVSTPTLVEA   1200
ARNLGRVGTK CCTLPEDQRL PCVEDYLSAI LNRVCLLHEK TPVSEHVTKC CSGSLVERRP   1260
CFSALTVDET YVPKEFKAET FTFHSDICTL PEKEKQIKKQ TALAELVKHK PKATAEQLKT   1320
VMDDFAQFLD TCCKAADKDT CFSTEGPNLV TRCKDALAGG GGSSGGPGPA GMKGLPGSHG   1380
TVIESLESLN NYFNSSGIDV EEKSLFLDIW RNWQKDGDMK ILQSQIISFY LRLFEVLKDN   1440
QAISNNISVI ESHLITTFFS NSKAKKDAFM SIAKFEVNNP QVQRQAFNEL IRVVHQLLPE   1500
SSLRKRKRSR CSGGPGPAGM KGLPGSEAHK SEIAHRYNDL GEQHFKGLVL IAFSQYLQKC   1560
SYDEHAKLVQ EVTDFAKTCV ADESAANCDK SLHTLFGDKL CAIPNLRENY GELADCCTKQ   1620
EPERNECFLQ HKDDNPSLPP FERPEAEAMC TSFKENPTTF MGHYLHEVAR RHPYFYAPEL   1680
LYYAEQYNEI LTQCCAEADK ESCLTPKLDG VKEKALVSSV RQRMKCSSMQ KFGERAFKAW   1740
AVARLSQTFP NADFAEITKL ATDLTKVNKE CCHGDLLECA DDRAELAKYM CENQATISSK   1800
LQTCCDKPLL KKAHCLSEVE HDTMPADLPA IAADFVEDQE VCKNYAEAKD VFLGTFLYEY   1860
SRRHPDYSVS LLLRLAKKYE ATLEKCCAEA NPPACYGTVL AEFQPLVEEP KNLVKTNCDL   1920
YEKLGEYGFQ NAILVRYTQK APQVSTPTLV EAARNLGRVG TKCCTLPEDQ RLPCVEDYLS   1980
AILNRVCLLH EKTPVSEHVT KCCSGSLVER RPCFSALTVD ETYVPKEFKA ETFTFHSDIC   2040
TLPEKEKQIK KQTALAELVK HKPKATAEQL KTVMDDFAQF LDTCCKAADK DTCFSTEGPN   2100
LVTRCKDALA HHHHHHEPEA                                              2120

SEQ ID NO: 109         moltype = AA  length = 2130
FEATURE                Location/Qualifiers
source                 1..2130
                       mol_type = protein
                       organism = synthetic construct
SEQUENCE: 109
MDMRVPAQLL GLLLLWLRGA RCEAHKSEIA HRYNDLGEQH FKGLVLIAFS QYLQKCSYDE     60
HAKLVQEVTD FAKTCVADES AANCDKSLHT LFGDKLCAIP NLRENYGELA DCCTKQEPER    120
NECFLQHKDD NPSLPPFERP EAEAMCTSFK ENPTTFMGHY LHEVARRHPY FYAPELLYYA    180
EQYNEILTQC CAEADKESCL TPKLDGVKEK ALVSSVRQRM KCSSMQKFGE RAFKAWAVAR    240
LSQTFPNADF AEITKLATDL TKVNKECCHG DLLECADDRA ELAKYMCENQ ATISSKLQTC    300
CDKPLLKKAH CLSEVEHDTM PADLPAIAAD FVEDQEVCKN YAEAKDVFLG TFLYEYSRRH    360
PDYSVSLLLR LAKKYEATLE KCCAEANPPA CYGTVLAEFQ PLVEEPKNLV KTNCDLYEKL    420
GEYGFQNAIL VRYTQKAPQV STPTLVEAAR NLGRVGTKCC TLPEDQRLPC VEDYLSAILN    480
RVCLLHEKTP VSEHVTKCCS GSLVERRPCF SALTVDETYV PKEFKAETFT FHSDICTLPE    540
KEKQIKKQTA LAELVKHKPK ATAEQLKTVM DDFAQFLDTC CKAADKDTCF STEGPNLVTR    600
CKDALASGGP GPAGMKGLPG SHGTVIESLE SLNNYFNSSG IDVEEKSLFL DIWRNWQKDG    660
DMKILQSQII SFYLRLFEVL KDNQAISNNI SVIESHLITT FFSNSKAKKD AFMSIAKFEV    720
NNPQVQRQAF NELIRVVHQL LPESSLRKRK RSRCSGGPGP AGMKGLPGSG GGGSGGGSE     780
AHKSEIAHRY NDLGEQHFKG LVLIAFSQYL QKCSYDEHAK LVQEVTDFAK TCVADESAAN    840
CDKSLHTLFG DKLCAIPNLR ENYGELADCC TKQEPERNEC FLQHKDDNPS LPPFERPEAE    900
AMCTSFKENP TTFMGHYLHE VARRHPYFYA PELLYYAEQY NEILTQCCAE ADKESCLTPK    960
LDGVKEKALV SSVRQRMKCS SMQKFGERAF KAWAVARLSQ TFPNADFAEI TKLATDLTKV   1020
NKECCHGDLL ECADDRAELA KYMCENQATI SSKLQTCCDK PLLKKAHCLS EVEHDTMPAD   1080
LPAIAADFVE DQEVCKNYAE AKDVFLGTFL YEYSRRHPDY SVSLLLRLAK KYEATLEKCC   1140
AEANPPACYG TVLAEFQPLV EEPKNLVKTN CDLYEKLGEY GFQNAILVRY TQKAPQVSTP   1200
TLVEAARNLG RVGTKCCTLP EDQRLPCVED YLSAILNRVC LLHEKTPVSE HVTKCCSGSL   1260
VERRPCFSAL TVDETYVPKE FKAETFTFHS DICTLPEKEK QIKKQTALAE LVKHKPKATA   1320
EQLKTVMDDF AQFLDTCCKA ADKDTCFSTE GPNLVTRCKD ALAGGGGSGG GGSSGGPGPA   1380
GMKGLPGSHG TVIESLESLN NYFNSSGIDV EEKSLFLDIW RNWQKDGDMK ILQSQIISFY   1440
LRLFEVLKDN QAISNNISVI ESHLITTFFS NSKAKKDAFM SIAKFEVNNP QVQRQAFNEL   1500
IRVVHQLLPE SSLRKRKRSR CSGGPGPAGM KGLPGSEAHK SEIAHRYNDL GEQHFKGLVL   1560
IAFSQYLQKC SYDEHAKLVQ EVTDFAKTCV ADESAANCDK SLHTLFGDKL CAIPNLRENY   1620
GELADCCTKQ EPERNECFLQ HKDDNPSLPP FERPEAEAMC TSFKENPTTF MGHYLHEVAR   1680
RHPYFYAPEL LYYAEQYNEI LTQCCAEADK ESCLTPKLDG VKEKALVSSV RQRMKCSSMQ   1740
KFGERAFKAW AVARLSQTFP NADFAEITKL ATDLTKVNKE CCHGDLLECA DDRAELAKYM   1800
CENQATISSK LQTCCDKPLL KKAHCLSEVE HDTMPADLPA IAADFVEDQE VCKNYAEAKD   1860
VFLGTFLYEY SRRHPDYSVS LLLRLAKKYE ATLEKCCAEA NPPACYGTVL AEFQPLVEEP   1920
KNLVKTNCDL YEKLGEYGFQ NAILVRYTQK APQVSTPTLV EAARNLGRVG TKCCTLPEDQ   1980
RLPCVEDYLS AILNRVCLLH EKTPVSEHVT KCCSGSLVER RPCFSALTVD ETYVPKEFKA   2040
ETFTFHSDIC TLPEKEKQIK KQTALAELVK HKPKATAEQL KTVMDDFAQF LDTCCKAADK   2100
DTCFSTEGPN LVTRCKDALA HHHHHHEPEA                                   2130

SEQ ID NO: 110         moltype = AA  length = 703
```

```
FEATURE                 Location/Qualifiers
source                  1..703
                        mol_type = protein
                        organism = synthetic construct
SEQUENCE: 110
MDMRVPAQLL GLLLLWLRGA RCEVQLVESG GGLVQPGNSL RLSCAASGFT FSKFGMSWVR   60
QAPGKGLEWV SSISGSGRDT LYAESVKGRF TISRDNAKTT LYLQMNSLRP EDTAVYYCTI  120
GGSLSVSSQG TLVTVSSGGG GSGGGSGGGG GSHGTVIESL ESLNNYFNSS GIDVEEKSLF  180
LDIWRNWQKD GDMKILQSQI ISFYLRLFEV LKDNQAISNN ISVIESHLIT TFFSNSKAKK  240
DAFMSIAKFE VNNPQVQRQA FNELIRVVHQ LLPESSLRKR KRSRCGGGGS GGGGSGGGGS  300
EVQLVESGGG LVQPGNSLRL SCAASGFTFS KFGMSWVRQA PGKGLEWVSS ISGSGRDTLY  360
AESVKGRFTI SRDNAKTTLY LQMNSLRPED TAVYYCTIGG SLSVSSQGTL VTVSSGGGGS  420
GGGGSGGGGS HGTVIESLES LNNYFNSSGI DVEEKSLFLD IWRNWQKDGD MKILQSQIIS  480
FYLRLFEVLK DNQAISNNIS VIESHLITTF FSNSKAKKDA FMSIAKFEVN NPQVQRQAFN  540
ELIRVVHQLL PESSLRKRKR SRCGGGGSGG GGSGGGGSEV QLVESGGGLV QPGNSLRLSC  600
AASGFTFSKF GMSWVRQAPG KGLEWVSSIS GSGRDTLYAE SVKGRFTISR DNAKTTLYLQ  660
MNSLRPEDTA VYYCTIGGSL SVSSQGTLVT VSSHHHHHHE PEA                   703

SEQ ID NO: 111          moltype = AA   length = 832
FEATURE                 Location/Qualifiers
source                  1..832
                        mol_type = protein
                        organism = synthetic construct
SEQUENCE: 111
MDMRVPAQLL GLLLLWLRGA RCEVQLVESG GGLVQPGNSL RLSCAASGFT FSKFGMSWVR   60
QAPGKGLEWV SSISGSGRDT LYAESVKGRF TISRDNAKTT LYLQMNSLRP EDTAVYYCTI  120
GGSLSVSSQG TLVTVSSSGG PGPAGMKGLP GSHGTVIESL ESLNNYFNSS GIDVEEKSLF  180
LDIWRNWQKD GDMKILQSQI ISFYLRLFEV LKDNQAISNN ISVIESHLIT TFFSNSKAKK  240
DAFMSIAKFE VNNPQVQRQA FNELIRVVHQ LLPESSLRKR KRSRCGGGPG PAGMKGLPGS  300
EVQLVESGGG LVQPGNSLRL SCAASGFTFS KFGMSWVRQA PGKGLEWVSS ISGSGRDTLY  360
AESVKGRFTI SRDNAKTTLY LQMNSLRPED TAVYYCTIGG SLSVSSQGTL VTVSSSGGPG  420
PAGMKGLPGS HGTVIESLES LNNYFNSSGI DVEEKSLFLD IWRNWQKDGD MKILQSQIIS  480
FYLRLFEVLK DNQAISNNIS VIESHLITTF FSNSKAKKDA FMSIAKFEVN NPQVQRQAFN  540
ELIRVVHQLL PESSLRKRKR SRCSGGPGPA GMKGLPGSEV QLVESGGGLV QPGNSLRLSC  600
AASGFTFSKF GMSWVRQAPG KGLEWVSSIS GSGRDTLYAE SVKGRFTISR DNAKTTLYLQ  660
MNSLRPEDTA VYYCTIGGSL SVSSQGTLVT VSSGGGGSGG GGSGGGGSQV QLQESGGGLA  720
QAGGSLSLSC AASGFTVSNS VMAWYRQTPG KQREFVAIIN SVGSTNYADS VKGRFTISRD  780
NAKNTVYLQM NNLKPEDTAV YVCNRNFDRI YWGQGTQVTV SSHHHHHHEP EA          832

SEQ ID NO: 112          moltype = AA   length = 832
FEATURE                 Location/Qualifiers
source                  1..832
                        mol_type = protein
                        organism = synthetic construct
SEQUENCE: 112
MDMRVPAQLL GLLLLWLRGA RCQVQLQESG GGLAQAGGSL SLSCAASGFT VSNSVMAWYR   60
QTPGKQREFV AIINSVGSTN YADSVKGRFT ISRDNAKNTV YLQMNNLKPE DTAVYVCNRN  120
FDRIYWGQGT QVTVSSGGGG SGGGGSGGGG SEVQLVESGG GLVQPGNSLR LSCAASGFTF  180
SKFGMSWVRQ APGKGLEWVS SISGSGRDTL YAESVKGRFT ISRDNAKTTL YLQMNSLRPE  240
DTAVYYCTIG GSLSVSSQGT LVTVSSSGGP GPAGMKGLPG SHGTVIESLE SLNNYFNSSG  300
IDVEEKSLFL DIWRNWQKDG DMKILQSQII SFYLRLFEVL KDNQAISNNI SVIESHLITT  360
FFSNSKAKKD AFMSIAKFEV NNPQVQRQAF NELIRVVHQL LPESSLRKRK RSRCSGGPGP  420
AGMKGLPGSE VQLVESGGGL VQPGNSLRLS CAASGFTFSK FGMSWVRQAP GKGLEWVSSI  480
SGSGRDTLYA ESVKGRFTIS RDNAKTTLYL QMNSLRPEDT AVYYCTIGGS LSVSSQGTLV  540
TVSSSGGPGP AGMKGLPGSH GTVIESLESL NNYFNSSGID VEEKSLFLDI WRNWQKDGDM  600
KILQSQIISF YLRLFEVLKD NQAISNNISI IESHLITTFF SNSKAKKDAF MSIAKFEVNN  660
PQVQRQAFNE LIRVVHQLLP ESSLRKRKRS RCSGGPGPAG MKGLPGSEVQ LVESGGGLVQ  720
PGNSLRLSCA ASGFTFSKFG MSWVRQAPGK GLEWVSSISG SGRDTLYAES VKGRFTISRD  780
NAKTTLYLQM NSLRPEDTAV YYCTIGGSLS VSSQGTLVTV SSHHHHHHEP EA          832

SEQ ID NO: 113          moltype = AA   length = 549
FEATURE                 Location/Qualifiers
source                  1..549
                        mol_type = protein
                        organism = synthetic construct
SEQUENCE: 113
MDMRVPAQLL GLLLLWLRGA RCRVIPVSGP ARCLSQSRNL LKTTDDMVKT AREKLKHYSC   60
TAEDIDHEDI TRDQTSTLKT CLPLELHKNE SCLATRETSS TTRGSCLPPQ KTSLMMTLCL  120
GSIYEDLKMY QTEFQAINAA LQNHNHQQII LDKGMLVAID ELMQSLNHNG ETLRQKPPVG  180
EADPYRVKMK LCILLHAFST RVVTINRVMG YLSSASGGPG PAGMKGLPGS MWELEKDYVV  240
VEVDWTPDAP GETVNLTCDT PEEDDITWTS DQRHGVIGSG KTLTITVKEF LDAGQYTCHK  300
GGETLSHSHL LLHKKENGIW STEILKNFKN KTFLKCEAPN YSGRFTCSWL VQRNMDLKFN  360
IKSSSSSPDS RAVTCGMASL SAEKVTLDQR DYEKYSVSCQ EDVTCPTAEE TLPIELALEA  420
RQQNKYENYS TSFFIRDIIK PDPPKNLQMK PLKNSQVEVS WEYPDSWSTP HSYFSLKFFV  480
RIQRKKEKMK ETEEGCNQKG AFLVEKTSTE VQCKGGNVCV QAQDRYYNSS CSKWACVPCR  540
VRSHHHHHH                                                          549

SEQ ID NO: 114          moltype = AA   length = 579
FEATURE                 Location/Qualifiers
```

```
source                  1..579
                        mol_type = protein
                        organism = synthetic construct
SEQUENCE: 114
MDMRVPAQLL GLLLLWLRGA RCRVIPVSGP ARCLSQSRNL LKTTDDMVKT AREKLKHYSC    60
TAEDIDHEDI TRDQTSTLKT CLPLELHKNE SCLATRETSS TTRGSCLPPQ KTSLMMTLCL   120
GSIYEDLKMY QTEFQAINAA LQNHNHQQII LDKGMLVAID ELMQSLNHNG ETLRQKPPVG   180
EADPYRVKMK LCILLHAFST RVVTINRVMG YLSSAGGGGS GGGGSGGGGS SGGPGPAGMK   240
GLPGSGGGGS GGGGSGGGGS MWELEKDVYV VEVDWTPDAP GETVNLTCDT PEEDDITWTS   300
DQRHGVIGSG KTLTITVKEF LDAGQYTCHK GGETLSHSHL LLHKKENGIW STEILKNFKN   360
KTFLKCEAPN YSGRFTCSWL VQRNMDLKFN IKSSSSSPDS RAVTCGMASL SAEKVTLDQR   420
DYEKYSVSCQ EDVTCPTAEE TLPIELALEA RQQNKYENYS TSFFIRDIIK PDPPKNLQMK   480
PLKNSQVEVS WEYPDSWSTP HSYFSLKFFV RIQRKKEKMK ETEEGCNQKG AFLVEKTSTE   540
VQCKGGNVCV QAQDRYYNSS CSKWACVPCR VRSHHHHHH                         579

SEQ ID NO: 115          moltype = AA  length = 809
FEATURE                 Location/Qualifiers
source                  1..809
                        mol_type = protein
                        organism = synthetic construct
SEQUENCE: 115
MDMRVPAQLL GLLLLWLRGA RCEVQLVESG GGLVQPGNSL RLSCAASGFT FSKFGMSWVR    60
QAPGKGLEWV SSISGSGRDT LYAESVKGRF TISRDNAKTT LYLQMNSLRP EDTAVYYCTI   120
GGSLSVSSQG TLVTVSSSGG PGPAGMKGLP GSMWELEKDV YVVEVDWTPD APGETVNLTC   180
DTPEEDDITW TSDQRHGVIG SGKTLTITVK EFLDAGQYTC HKGGETLSHS HLLLHKKENG   240
IWSTEILKNF KNKTFLKCEA PNYSGRFTCS WLVQRNMDLK FNIKSSSSSP DSRAVTCGMA   300
SLSAEKVTLD QRDYEKYSVS CQEDVTCPTA EETLPIELAL EARQQNKYEN YSTSFFIRDI   360
IKPDPPKNLQ MKPLKNSQVE VSWEYPDSWS TPHSYFSLKF FVRIQRKKEK MKETEEGCNQ   420
KGAFLVEKTS TEVQCKGGNV CVQAQDRYYN SSCSKWACVP CRVRSGGGGS GGGGSGGGGS   480
RVIPVSGPAR CLSQSRNLLK TTDDMVKTAR EKLKHYSCTA EDIDHEDITR DQTSTLKTCL   540
PLELHKNESC LATRETSSTT RGSCLPPQKT SLMMTLCLGS IYEDLKMYQT EFQAINAALQ   600
NHNHQQIILD KGMLVAIDEL MQSLNHNGET LRQKPPVGEA DPYRVKMKLC ILLHAFSTRV   660
VTINRVMGYL SSASGGPGPA GMKGLPGSEV QLVESGGGLV QPGNSLRLSC AASGFTFSKF   720
GMSWVRQAPG KGLEWVSSIS GSGRDTLYAE SVKGRFTISR DNAKTTLYLQ MNSLRPEDTA   780
VYYCTIGGSL SVSSQGTLVT VSSHHHHHH                                   809

SEQ ID NO: 116          moltype = AA  length = 938
FEATURE                 Location/Qualifiers
source                  1..938
                        mol_type = protein
                        organism = synthetic construct
SEQUENCE: 116
MDMRVPAQLL GLLLLWLRGA RCQVQLQESG GGLVQAGGSL RLSCAASGRI FSIDIMSWYR    60
QAPGKQRELV ARITRGGTIS YDDSVKGRFT ISRDNAKNTV YLQMNSLKPE DTGVYYCNAL   120
YGTDYWGKGT QVTVSSGGGG SGGGGSGGGG SEVQLVESGG GLVQPGNSLR LSCAASGFTF   180
SKFGMSWVRQ APGKGLEWVS SISGSGRDTL YAESVKGRFT ISRDNAKTTL YLQMNSLRPE   240
DTAVYYCTIG GSLSVSSQGT LVTVSSSGGP GPAGMKGLPG SMWELEKDVY VVEVDWTPDA   300
PGETVNLTCD TPEEDDITWT SDQRHGVIGS GKTLTITVKE FLDAGQYTCH KGGETLSHSH   360
LLLHKKENGI WSTEILKNFK NKTFLKCEAP NYSGRFTCSW LVQRNMDLKF NIKSSSSSPD   420
SRAVTCGMAS LSAEKVTLDQ RDYEKYSVSC QEDVTCPTAE ETLPIELALE ARQQNKYENY   480
STSFFIRDII KPDPPKNLQM KPLKNSQVEV SWEYPDSWST PHSYFSLKFF VRIQRKKEKM   540
KETEEGCNQK GAFLVEKTST EVQCKGGNVC VQAQDRYYNS SCSKWACVPC RVRSGGGGSG   600
GGGSGGGGSR VIPVSGPARC LSQSRNLLKT TDDMVKTARE KLKHYSCTAE DIDHEDITRD   660
QTSTLKTCLP LELHKNESCL ATRETSSTTR GSCLPPQKTS LMMTLCLGSI YEDLKMYQTE   720
FQAINAALQN HNHQQIILDK GMLVAIDELM QSLNHNGETL RQKPPVGEAD PYRVKMKLCI   780
LLHAFSTRVV TINRVMGYLS SASGGPGPAG MKGLPGSEVQ LVESGGGLVQ PGNSLRLSCA   840
ASGFTFSKFG MSWVRQAPGK GLEWVSSISG SGRDTLYAES VKGRFTISRD NAKTTLYLQM   900
NSLRPEDTAV YYCTIGGSLS VSSQGTLVTV SSHHHHHH                          938

SEQ ID NO: 117          moltype = AA  length = 938
FEATURE                 Location/Qualifiers
source                  1..938
                        mol_type = protein
                        organism = synthetic construct
SEQUENCE: 117
MDMRVPAQLL GLLLLWLRGA RCQVQLQESG GGLVQAGGSL RLSCAASGRI FSIDIMSWYR    60
QAPGKQRELV ARITRGGTIS YDDSVKGRFT ISRDNAKNTV YLQMNSLKPE DTGVYYCNAL   120
YGTDYWGKGT QVTVSSGGGG SGGGGSGGGG SEVQLVESGG GLVQPGNSLR LSCAASGFTF   180
SKFGMSWVRQ APGKGLEWVS SISGSGRDTL YAESVKGRFT ISRDNAKTTL YLQMNSLRPE   240
DTAVYYCTIG GSLSVSSQGT LVTVSSSGGP GPAGMKGLPG SMWELEKDVY VVEVDWTPDA   300
PGETVNLTCD TPEEDDITWT SDQRHGVIGS GKTLTITVKE FLDAGQYTCH KGGETLSHSH   360
LLLHKKENGI WSTEILKNFK NKTFLKCEAP NYSGRFTCSW LVQRNMDLKF NIKSSSSSPD   420
SRAVTCGMAS LSAEKVTLDQ RDYEKYSVSC QEDVTCPTAE ETLPIELALE ARQQNKYENY   480
STSFFIRDII KPDPPKNLQM KPLKNSQVEV SWEYPDSWST PHSYFSLKFF VRIQRKKEKM   540
KETEEGCNQK GAFLVEKTST EVQCKGGNVC VQAQDRYYNS SCSKWACVPC RVRSGGGGSG   600
GGGSGGGGSR VIPVSGPARC LSQSRNLLKT TDDMVKTARE KLKHYSCTAE DIDHEDITRD   660
QTSTLKTCLP LELHKNESCL ATRETSSTTR GSCLPPQKTS LMMTLCLGSI YEDLKMYQTE   720
FQAINAALQN HNHQQIILDK GMLVAIDELM QSLNHNGETL RQKPPVGEAD PYRVKMKLCI   780
LLHAFSTRVV TINRVMGYLS SASGGPGPAG MKGLPGSEVQ LVESGGGLVQ PGNSLRLSCA   840
```

```
ASGFTFSKFG MSWVRQAPGK GLEWVSSISG SGRDTLYAES VKGRFTISRD NAKTTLYLQM    900
NSLRPEDTAV YYCTIGGSLS VSSQGTLVTV SSHHHHHH                            938

SEQ ID NO: 118         moltype = AA  length = 938
FEATURE                Location/Qualifiers
source                 1..938
                       mol_type = protein
                       organism = synthetic construct
SEQUENCE: 118
MDMRVPAQLL GLLLLWLRGA RCEVQLVESG GGLVQPGNSL RLSCAASGFT FSKFGMSWVR     60
QAPGKGLEWV SSISGSGRDT LYAESVKGRF TISRDNAKTT LYLQMNSLRP EDTAVYYCTI    120
GGSLSVSSQG TLVTVSSSGG PGPAGMKGLP GSMWELEKDV YVVEVDWTPD APGETVNLTC    180
DTPEEDDITW TSDQRHGVIG SGKTLTITVK EFLDAGQYTC HKGGETLSHS HLLLHKKENG    240
IWSTEILKNF KNKTFLKCEA PNYSGRFTCS WLVQRNMDLK FNIKSSSSSP DSRAVTCGMA    300
SLSAEKVTLD QRDYEKYSVS CQEDVTCPTA EETLPIELAL EARQQNKYEN YSTSFFIRDI    360
IKPDPPKNLQ MKPLKNSQVE VSWEYPDSWS TPHSYFSLKF FVRIQRKKEK MKETEEGCNQ    420
KGAFLVEKTS TEVQCKGGNV CVQAQDRYYN SSCSKWACVP CRVRSGGGGS GGGGSGGGGS    480
RVIPVSGPAR CLSQSRNLLK TTDDMVKTAR EKLKHYSCTA EDIDHEDITR DQTSTLKTCL    540
PLELHKNESC LATRETSSTT RGSCLPPQKT SLMMTLCLGS IYEDLKMYQT EFQAINAALQ    600
NHNHQQIILD KGMLVAIDEL MQSLNHNGET LRQKPPVGEA DPYRVKMKLC ILLHAFSTRV    660
VTINRVMGYL SSASGGPGPA GMKGLPGSEV QLVESGGGLV QPGNSLRLSC AASGFTFSKF    720
GMSWVRQAPG KGLEWVSSIS GSGRDTLYAE SVKGRFTISR DNAKTTLYLQ MNSLRPEDTA    780
VYYCTIGGSL SVSSQGTLVT VSSGGGGSGG GGSGGGGSQV QLQESGGGLV QAGGSLRLSC    840
AASGRIFSID IMSWYRQAPG KQRELVARIT RGGTISYDDS VKGRFTISRD NAKNTVYLQM    900
NSLKPEDTGV YYCNALYGTD YWGKGTQVTV SSHHHHHH                            938

SEQ ID NO: 119         moltype = AA  length = 962
FEATURE                Location/Qualifiers
source                 1..962
                       mol_type = protein
                       organism = synthetic construct
SEQUENCE: 119
MDMRVPAQLL GLLLLWLRGA RCIWELKKDV YVVELDWYPD APGEMVVLTC DTPEEDGITW     60
TLDQSSEVLG SGKTLTIQVK EFGDAGQYTC HKGGEVLSHS LLLLHKKEDG IWSTDILKDQ    120
KEPKNKTFLR CEAKNYSGRF TCWWLTTIST DLTFSVKSSR GSSDPQGVTC GAATLSAERV    180
RGDNKEYEYS VECQEDSACP AAEESLPIEV MVDAVHKLKY ENYTSSFFIR DIIKPDPPKN    240
LQLKPLKNSR QVEVSWEYPD TWSTPHSYFS LTFCVQVQGK SKREKKDRVF TDKTSATVIC    300
RKNASISVRA QDRYYSSSWS EWASVPCSGG GGSGGGGSGG GGSRVIPVSG PARCLSQSRN    360
LLKTTDDMVK TAREKLKHYS CTAEDIDHED ITRDQTSTLK TCLPLELHKN ESCLATRETS    420
STTRGSCLPP QKTSLMMTLC LGSIYEDLKM YQTEFQAINA ALQNHNHQQI ILDKGMLVAI    480
DELMQSLNHN GETLRQKPPV GEADPYRVKM KLCILLHAFS TRVVTINRVM GYLSSAGGGG    540
SGGGSGGGGS SGGGSGGGGS SGGGSGGGGS SGGGSGGGGS SQSVLTQPPS VSGAPGQRVT    600
ISCSGSRSNI GSNTVKWYQQ LPGTAPKLLI YYNDQRPSGV PDRFSGSKSG TSASLAITGL    660
QAEDEADYYC QSYDRYTHPA LLFGTGTKVT VLGGGGSGGG GSGGGGSQVQ LVESGGGVVQ    720
PGRSLRLSCA ASGFTFSSYG MHWVRQAPGK GLEWVAFIRY DGSNKYYADS VKGRFTISRD    780
NSKNTLYLQM NSLRAEDTAV YYCKTHGSHD NWGQGTMVTV SSGGGGSGGG GSGGGGSEVQ    840
LVESGGGLVQ PGNSLRLSCA ASGFTFSKFG MSWVRQAPGK GLEWVSSISG SGRDTLYAES    900
VKGRFTISRD NAKTTLYLQM NSLRPEDTAV YYCTIGGSLS VSSQGTLVTV SSHHHHHHEP    960
EA                                                                  962

SEQ ID NO: 120         moltype = AA  length = 832
FEATURE                Location/Qualifiers
source                 1..832
                       mol_type = protein
                       organism = synthetic construct
SEQUENCE: 120
MDMRVPAQLL GLLLLWLRGA RCIWELKKDV YVVELDWYPD APGEMVVLTC DTPEEDGITW     60
TLDQSSEVLG SGKTLTIQVK EFGDAGQYTC HKGGEVLSHS LLLLHKKEDG IWSTDILKDQ    120
KEPKNKTFLR CEAKNYSGRF TCWWLTTIST DLTFSVKSSR GSSDPQGVTC GAATLSAERV    180
RGDNKEYEYS VECQEDSACP AAEESLPIEV MVDAVHKLKY ENYTSSFFIR DIIKPDPPKN    240
LQLKPLKNSR QVEVSWEYPD TWSTPHSYFS LTFCVQVQGK SKREKKDRVF TDKTSATVIC    300
RKNASISVRA QDRYYSSSWS EWASVPCSGG GGSGGGGSGG GGSRVIPVSG PARCLSQSRN    360
LLKTTDDMVK TAREKLKHYS CTAEDIDHED ITRDQTSTLK TCLPLELHKN ESCLATRETS    420
STTRGSCLPP QKTSLMMTLC LGSIYEDLKM YQTEFQAINA ALQNHNHQQI ILDKGMLVAI    480
DELMQSLNHN GETLRQKPPV GEADPYRVKM KLCILLHAFS TRVVTINRVM GYLSSASGGP    540
GPAGMKGLPG SGGGGSGGGG SGGGGSGGGG SGGGGSGGGG SQSVLTQPPS VSGAPGQRVT    600
ISCSGSRSNI GSNTVKWYQQ LPGTAPKLLI YYNDQRPSGV PDRFSGSKSG TSASLAITGL    660
QAEDEADYYC QSYDRYTHPA LLFGTGTKVT VLGGGGSGGG GSGGGGSQVQ LVESGGGVVQ    720
PGRSLRLSCA ASGFTFSSYG MHWVRQAPGK GLEWVAFIRY DGSNKYYADS VKGRFTISRD    780
NSKNTLYLQM NSLRAEDTAV YYCKTHGSHD NWGQGTMVTV SSHHHHHHEP EA            832

SEQ ID NO: 121         moltype = AA  length = 1091
FEATURE                Location/Qualifiers
source                 1..1091
                       mol_type = protein
                       organism = synthetic construct
SEQUENCE: 121
MDMRVPAQLL GLLLLWLRGA RCIWELKKDV YVVELDWYPD APGEMVVLTC DTPEEDGITW     60
TLDQSSEVLG SGKTLTIQVK EFGDAGQYTC HKGGEVLSHS LLLLHKKEDG IWSTDILKDQ    120
```

```
KEPKNKTFLR CEAKNYSGRF TCWWLTTIST DLTFSVKSSR GSSDPQGVTC GAATLSAERV  180
RGDNKEYEYS VECQEDSACP AAEESLPIEV MVDAVHKLKY ENYTSSFFIR DIIKPDPPKN  240
LQLKPLKNSR QVEVSWEYPD TWSTPHSYFS LTFCVQVQGK SKREKKDRVF TDKTSATVIC  300
RKNASISVRA QDRYYSSSWS EWASVPCSGG GGSGGGGSGG GGSRVIPVSG PARCLSQSRN  360
LLKTTDDMVK TAREKLKHYS CTAEDIDHED ITRDQTSTLK TCLPLELHKN ESCLATRETS  420
STTRGSCLPP QKTSLMMTLC LGSIYEDLKM YQTEFQAINA ALQNHNHQQI ILDKGMLVAI  480
DELMQSLNHN GETLRQKPPV GEADPYRVKM KLCILLHAFS TRVVTINRVM GYLSSASGGP  540
GPAGMKGLPG SGGGGSGGGG SGGGGSGGGG SGGGGSGGGG SQSVLTQPPS VSGAPGQRVT  600
ISCSGSRSNI GSNTVKWYQQ LPGTAPKLLI YYNDQRPSGV PDRFSGSKSG TSASLAITGL  660
QAEDEADYYC QSYDRYTHPA LLFGTGTKVT VLGGGGSGGG GSGGGGSGVQ LVESGGGVVQ  720
PGRSLRLSCA ASGFTFSSYG MHWVRQAPGK GLEWVAFIRY DGSNKYYADS VKGRFTISRD  780
NSKNTLYLQM NSLRAEDTAV YYCKTHGSHD NWGQGTMVTV SSGGGGSGGG GSGGGGSEVQ  840
LVESGGGLVQ PGNSLRLSCA ASGFTFSKFG MSWVRQAPGK GLEWVSSISG SGRDTLYAES  900
VKGRFTISRD NAKTTLYLQM NSLRPEDTAV YYCTIGGSLS VSSQGTLVTV SSGGGGSGGG  960
GSGGGGSQVQ LQESGGGLAQ AGGSLSLSCA ASGFTVSNSV MAWYRQTPGK QREFVAIINS 1020
VGSTNYADSV KGRFTISRDN AKNTVYLQMN NLKPEDTAVY VCNRNFDRIY WGQGTQVTVS 1080
SHHHHHHEPE A                                                     1091

SEQ ID NO: 122          moltype = AA  length = 1091
FEATURE                 Location/Qualifiers
source                  1..1091
                        mol_type = protein
                        organism = synthetic construct
SEQUENCE: 122
MDMRVPAQLL GLLLLWLRGA RCQVQLQESG GGLAQAGGSL SLSCAASGFT VSNSVMAWYR   60
QTPGKQREFV AIINSVGSTN YADSVKGRFT ISRDNAKNTV YLQMNNLKPE DTAVYVCNRN  120
FDRIYWGQGT QVTVSSGGGG SGGGGSGGGG SIWELKKDVY VVELDWYPDA PGEMVVLTCD  180
TPEEDGITWT LDQSSEVLGS GKTLTIQVKE FGDAGQYTCH KGGEVLSHSL LLLHKKEDGI  240
WSTDILKDQK EPKNKTFLRC EAKNYSGRFT CWWLTTISTD LTFSVKSSRG SSDPQGVTCG  300
AATLSAERVR GDNKEYEYSV ECQEDSACPA AEESLPIEVM VDAVHKLKYE NYTSSFFIRD  360
IIKPDPPKNL QLKPLKNSRQ VEVSWEYPDT WSTPHSYFSL TFCVQVQGKS KREKKDRVFT  420
DKTSATVICR KNASISVRAQ DRYYSSSWSE WASVPCSGGG GSGGGGSGGG GSRVIPVSGP  480
ARCLSQSRNL LKTTDDMVKT AREKLKHYSC TAEDIDHEDI TRDQTSTLKT CLPLELHKNE  540
SCLATRETSS TTRGSCLPPQ KTSLMMTLCL GSIYEDLKMY QTEFQAINAA LQNHNHQQII  600
LDKGMLVAID ELMQSLNHNG ETLRQKPPVG EADPYRVKMK LCILLHAFST RVVTINRVMG  660
YLSSASGGPG PAGMKGLPGS GGGGSGGGGS GGGGSGGGGS GGGGSGGGGS QSVLTQPPSV  720
SGAPGQRVTI SCSGSRSNIG SNTVKWYQQL PGTAPKLLIY YNDQRPSGVP DRFSGSKSGT  780
SASLAITGLQ AEDEADYYCQ SYDRYTHPAL LFGTGTKVTV LGGGGSGGGG SGGGGSGVQL  840
VESGGGVVQP GRSLRLSCAA SGFTFSSYGM HWVRQAPGKG LEWVAFIRYD GSNKYYADSV  900
KGRFTISRDN SKNTLYLQMN SLRAEDTAVY YCKTHGSHDN WGQGTMVTVS SGGGGSGGGG  960
SGGGGSEVQL VESGGGLVQP GNSLRLSCAA SGFTFSKFGM SWVRQAPGKG LEWVSSISGS 1020
GRDTLYAESV KGRFTISRDN AKTTLYLQMN SLRPEDTAVY YCTIGGSLSV SSQGTLVTVS 1080
SHHHHHHEPE A                                                     1091

SEQ ID NO: 123          moltype = AA  length = 1091
FEATURE                 Location/Qualifiers
source                  1..1091
                        mol_type = protein
                        organism = synthetic construct
SEQUENCE: 123
MDMRVPAQLL GLLLLWLRGA RCQVQLQESG GGLAQAGGSL SLSCAASGFT VSNSVMAWYR   60
QTPGKQREFV AIINSVGSTN YADSVKGRFT ISRDNAKNTV YLQMNNLKPE DTAVYVCNRN  120
FDRIYWGQGT QVTVSSSGGP GPAGMKGLPG SIWELKKDVY VVELDWYPDA PGEMVVLTCD  180
TPEEDGITWT LDQSSEVLGS GKTLTIQVKE FGDAGQYTCH KGGEVLSHSL LLLHKKEDGI  240
WSTDILKDQK EPKNKTFLRC EAKNYSGRFT CWWLTTISTD LTFSVKSSRG SSDPQGVTCG  300
AATLSAERVR GDNKEYEYSV ECQEDSACPA AEESLPIEVM VDAVHKLKYE NYTSSFFIRD  360
IIKPDPPKNL QLKPLKNSRQ VEVSWEYPDT WSTPHSYFSL TFCVQVQGKS KREKKDRVFT  420
DKTSATVICR KNASISVRAQ DRYYSSSWSE WASVPCSGGG GSGGGGSGGG GSRVIPVSGP  480
ARCLSQSRNL LKTTDDMVKT AREKLKHYSC TAEDIDHEDI TRDQTSTLKT CLPLELHKNE  540
SCLATRETSS TTRGSCLPPQ KTSLMMTLCL GSIYEDLKMY QTEFQAINAA LQNHNHQQII  600
LDKGMLVAID ELMQSLNHNG ETLRQKPPVG EADPYRVKMK LCILLHAFST RVVTINRVMG  660
YLSSASGGPG PAGMKGLPGS GGGGSGGGGS GGGGSGGGGS GGGGSGGGGS QSVLTQPPSV  720
SGAPGQRVTI SCSGSRSNIG SNTVKWYQQL PGTAPKLLIY YNDQRPSGVP DRFSGSKSGT  780
SASLAITGLQ AEDEADYYCQ SYDRYTHPAL LFGTGTKVTV LGGGGSGGGG SGGGGSGVQL  840
VESGGGVVQP GRSLRLSCAA SGFTFSSYGM HWVRQAPGKG LEWVAFIRYD GSNKYYADSV  900
KGRFTISRDN SKNTLYLQMN SLRAEDTAVY YCKTHGSHDN WGQGTMVTVS SGGGGSGGGG  960
SGGGGSEVQL VESGGGLVQP GNSLRLSCAA SGFTFSKFGM SWVRQAPGKG LEWVSSISGS 1020
GRDTLYAESV KGRFTISRDN AKTTLYLQMN SLRPEDTAVY YCTIGGSLSV SSQGTLVTVS 1080
SHHHHHHEPE A                                                     1091

SEQ ID NO: 124          moltype = AA  length = 674
FEATURE                 Location/Qualifiers
source                  1..674
                        mol_type = protein
                        organism = synthetic construct
SEQUENCE: 124
MDMRVPAQLL GLLLLWLRGA RCAPTSSSTK KTQLQLEHLL LDLQMILNGI NNYKNPKLTR   60
MLTFKFYMPK KATELKHLQC LEEELKPLEE VLNLAQSKNF HLRPRDLISN INVIVLELKG  120
SETTFMCEYA DETATIVEFL NRWITFCQSI ISTLTSGGPG PAGMKGLPGS EVQLVESGGG  180
```

```
LVQPGGSLRL SCAASGFTFS SYTLAWVRQA PGKGLEWVAA IDSSSYTYSP DTVRGRFTIS  240
RDNAKNSLYL QMNSLRAEDT AVYYCARDSN WDALDYWGQG TTVTVSSGGG GSGGGGSGGG  300
GSDIQMTQSP SSLSASVGDR VTITCKASQN VGTNVGWYQQ KPGKAPKALI YSASFRYSGV  360
PSRFSGSGSG TDFTLTISSL QPEDFATYYC QQYYTYPYTF GGGTKVEIKG GGGSGGGGSG  420
GGGSVQLVE SGGGLVQPGN SLRLSCAASG FTFSKFGMSW VRQAPGKGLE WVSSISGSGR  480
DTLYAESVKG RFTISRDNAK TTLYLQMNSL RPEDTAVYYC TIGGSLSVSS QGTLVTVSSG  540
GGGSGGGGS GGGSQVQLQE SGGGLVQAGG SLRLSCAASG RIFSIDIMSW YRQAPGKQRE  600
LVARITRGGT ISYDDSVKGR FTISRDNAKN TVYLQMNSLK PEDTGVYYCN ALYGTDYWGK  660
GTQVTVSSHH HHHH                                                  674

SEQ ID NO: 125           moltype = AA  length = 674
FEATURE                  Location/Qualifiers
source                   1..674
                         mol_type = protein
                         organism = synthetic construct
SEQUENCE: 125
MDMRVPAQLL GLLLLWLRGA RCQVQLQESG GGLVQAGGSL RLSCAASGRI FSIDIMSWYR  60
QAPGKQRELV ARITRGGTIS YDDSVKGRFT ISRDNAKNTV YLQMNSLKPE DTGVYYCNAL  120
YGTDYWGKGT QVTVSSGGP GPAGMKGLPG SEVQLVESGG GLVQPGNSLR LSCAASGFTF  180
SKFGMSWVRQ APGKGLEWVS SISGSGRDTL YAESVKGRFT ISRDNAKTTL YLQMNSLRPE  240
DTAVYYCTIG GSLSVSSQGT LVTVSSGGP GPAGMKGLPG SEVQLVESGG GLVQPGGSLR  300
LSCAASGFTF SSYTLAWVRQ APGKGLEWVA AIDSSSYTYS PDTVRGRFTI SRDNAKNSLY  360
LQMNSLRAED TAVYYCARDS NWDALDYWG GTTVTVSSGG GGSGGGGSGG GGSDIQMTQS  420
PSSLSASVGD RVTITCKASQ NVGTNVGWYQ QKPGKAPKAL IYSASFRYSG VPSRFSGSGS  480
GTDFTLTISS LQPEDFATYY CQQYYTYPYT FGGGTKVEIK SGGPGPAGMK GLPGSAPTSS  540
STKKTQLQLE HLLLDLQMIL NGINNYKNPK LTRMLTFKFY MPKKATELKH LQCLEEELKP  600
LEEVLNLAQS KNFHLRPRDL ISNINIVILE LKGSETTFMC EYADETATIV EFLNRWITFC  660
QSIISTLTHH HHHH                                                  674

SEQ ID NO: 126           moltype = AA  length = 425
FEATURE                  Location/Qualifiers
source                   1..425
                         mol_type = protein
                         organism = synthetic construct
SEQUENCE: 126
MDMRVPAQLL GLLLLWLRGA RCELCDDDPP EIPHATFKAM AYKEGTMLNC ECKRGFRRIK  60
SGSLYMLCTG NSSHSSWDNQ CQCTSSATRN TTKQVTPQPE EQKERKTTEM QSPMQPVDQA  120
SLPGHCREPP PWENEATERI YHFVVGQMVY YQCVQGYRAL HRGPAESVCK MTHGKTRWTQ  180
PQLICTGEME TSQFPGEEKP QASPEGRPES ETSCLVTTTD FQIQTEMAAT METSIFTTEY  240
QGGGGSGGGG SGGGGSGGGG SGGGGSGGG SSGGPGPAGM KGLPGSAPTS SSTKKTQLQL  300
EHLLLDLQMI LNGINNYKNP KLTRMLTFKF YMPKKATELK HLQCLEEELK PLEEVLNLAQ  360
SKNFHLRPRD LISNINIVIL ELKGSETTFM CEYADETATI VEFLNRWITF CQSIISTLTH  420
HHHHH                                                            425

SEQ ID NO: 127           moltype = AA  length = 425
FEATURE                  Location/Qualifiers
source                   1..425
                         mol_type = protein
                         organism = synthetic construct
SEQUENCE: 127
MDMRVPAQLL GLLLLWLRGA RCAPTSSSTK KTQLQLEHLL LDLQMILNGI NNYKNPKLTR  60
MLTFKFYMPK KATELKHLQC LEEELKPLEE VLNLAQSKNF HLRPRDLISN INIVILELKG  120
SETTFMCEYA DETATIVEFL NRWITFCQSI ISTLTSGGPG PAGMKGLPGS GGGGSGGGGS  180
GGGGSGGGGS GGGGSGGGS ELCDDDPPEI PHATFKAMAY KEGTMLNCEC KRGFRRIKSG  240
SLYMLCTGNS SHSSWDNQCQ CTSSATRNTT KQVTPQPEEQ KERKTTEMQS PMQPVDQASL  300
PGHCREPPPW ENEATERIYH FVVGQMVYYQ CVQGYRALHR GPAESVCKMT HGKTRWTQPQ  360
LICTGEMETS QFPGEEKPQA SPEGRPESET SCLVTTTDFQ IQTEMAATME TSIFTTEYQH  420
HHHHH                                                            425

SEQ ID NO: 128           moltype = AA  length = 555
FEATURE                  Location/Qualifiers
source                   1..555
                         mol_type = protein
                         organism = synthetic construct
SEQUENCE: 128
MDMRVPAQLL GLLLLWLRGA RCEVQLVESG GGLVQPGNSL RLSCAASGFT FSKFGMSWVR  60
QAPGKGLEWV SSISGSGRDT LYAESVKGRF TISRDNAKTT LYLQMNSLRP EDTAVYYCTI  120
GGSLSVSSQG TLVTVSSGGG GSGGGGSGGG GSELCDDDPP EIPHATFKAM AYKEGTMLNC  180
ECKRGFRRIK SGSLYMLCTG NSSHSSWDNQ CQCTSSATRN TTKQVTPQPE EQKERKTTEM  240
QSPMQPVDQA SLPGHCREPP PWENEATERI YHFVVGQMVY YQCVQGYRAL HRGPAESVCK  300
MTHGKTRWTQ PQLICTGEME TSQFPGEEKP QASPEGRPES ETSCLVTTTD FQIQTEMAAT  360
METSIFTTEY QGGGGSGGGG SGGGGSGGGG SGGGGSGGGG SSGGPGPAGM KGLPGSAPTS  420
SSTKKTQLQL EHLLLDLQMI LNGINNYKNP KLTRMLTFKF YMPKKATELK HLQCLEEELK  480
PLEEVLNLAQ SKNFHLRPRD LISNINIVIL ELKGSETTFM CEYADETATI VEFLNRWITF  540
CQSIISTLTH HHHHH                                                 555

SEQ ID NO: 129           moltype = AA  length = 555
FEATURE                  Location/Qualifiers
source                   1..555
```

```
                        mol_type = protein
                        organism = synthetic construct
SEQUENCE: 129
MDMRVPAQLL GLLLLWLRGA RCAPTSSSTK KTQLQLEHLL LDLQMILNGI NNYKNPKLTR    60
MLTFKFYMPK KATELKHLQC LEEELKPLEE VLNLAQSKNF HLRPRDLISN INVIVLELKG   120
SETTFMCEYA DETATIVEFL NRWITFCQSI ISTLTSGGPG PAGMKGLPGS GGGGSGGGGS   180
GGGGSGGGGS GGGGSGGGGS ELCDDDPPEI PHATFKAMAY KEGTMLNCEC KRGFRRIKSG   240
SLYMLCTGNS SHSSWDNQCQ CTSSATRNTT KQVTPQPEEQ KERKTTEMQS PMQPVDQASL   300
PGHCREPPPW ENEATERIYH FVVGQMVYYQ CVQGYRALHR GPAESVCKMT HGKTRWTQPQ   360
LICTGEMETS QFPGEEKPQA SPEGRPESET SCLVTTTDFQ IQTEMAATME TSIFTTEYQG   420
GGGSGGGGSG GGGSEVQLVE SGGGLVQPGN SLRLSCAASG FTFSKFGMSW VRQAPGKGLE   480
WVSSISGSGR DTLYAESVKG RFTISRDNAK TTLYLQMNSL RPEDTAVYYC TIGGSLSVSS   540
QGTLVTVSSH HHHHH                                                   555

SEQ ID NO: 130          moltype = AA  length = 555
FEATURE                 Location/Qualifiers
source                  1..555
                        mol_type = protein
                        organism = synthetic construct
SEQUENCE: 130
MDMRVPAQLL GLLLLWLRGA RCAPTSSSTK KTQLQLEHLL LDLQMILNGI NNYKNPKLTR    60
MLTFKFYMPK KATELKHLQC LEEELKPLEE VLNLAQSKNF HLRPRDLISN INVIVLELKG   120
SETTFMCEYA DETATIVEFL NRWITFCQSI ISTLTSGGPG PAGMKGLPGS GGGGSGGGGS   180
GGGGSGGGGS GGGGSGGGGS ELCDDDPPEI PHATFKAMAY KEGTMLNCEC KRGFRRIKSG   240
SLYMLCTGNS SHSSWDNQCQ CTSSATRNTT KQVTPQPEEQ KERKTTEMQS PMQPVDQASL   300
PGHCREPPPW ENEATERIYH FVVGQMVYYQ CVQGYRALHR GPAESVCKMT HGKTRWTQPQ   360
LICTGEMETS QFPGEEKPQA SPEGRPESET SCLVTTTDFQ IQTEMAATME TSIFTTEYQG   420
GGPGPAGMKG LPGSEVQLVE SGGGLVQPGN SLRLSCAASG FTFSKFGMSW VRQAPGKGLE   480
WVSSISGSGR DTLYAESVKG RFTISRDNAK TTLYLQMNSL RPEDTAVYYC TIGGSLSVSS   540
QGTLVTVSSH HHHHH                                                   555

SEQ ID NO: 131          moltype = AA  length = 575
FEATURE                 Location/Qualifiers
source                  1..575
                        mol_type = protein
                        organism = synthetic construct
SEQUENCE: 131
MDMRVPAQLL GLLLLWLRGA RCEVQLVESG GGLVQPGNSL RLSCAASGFT FSKFGMSWVR    60
QAPGKGLEWV SSISGSGRDT LYAESVKGRF TISRDNAKTT LYLQMNSLRP EDTAVYYCTI   120
GGSLSVSSQG TLVTVSSSGG PGPAGMKGLP GSEVQLVESG GGLVQPGGSL RLSCAASGFT   180
FSSYTLAWVR QAPGKGLEWV AAIDSSSYTY SPDTVRGRFT ISRDNAKNSL YLQMNSLRAE   240
DTAVYYCARD SNWDALDYWG QGTTVTVSSG GGGSGGGGSG GGGSDIQMTQ SPSSLSASVG   300
DRVTITCKAS QNVGTNVGWY QQKPGKAPKA LIYSASFRYS GVPSRFSGSG SGTDFTLTIS   360
SLQPEDFATY YCQQYYTYPY TFGGGTKVEI KGGGGSGGGG SGGGGSGGGG SGGGGSGGGG   420
SSGGPGPAGM KGLPGSAPTS SSTKKTQLQL EHLLLDLQMI LNGINNYKNP KLTRMLTFKF   480
YMPKKATELK HLQCLEEELK PLEEVLNLAQ SKNFHLRPRD LISNINVIVL ELKGSETTFM   540
CEYADETATI VEFLNRWITF CQSIISTLTH HHHHH                              575

SEQ ID NO: 132          moltype = AA  length = 704
FEATURE                 Location/Qualifiers
source                  1..704
                        mol_type = protein
                        organism = synthetic construct
SEQUENCE: 132
MDMRVPAQLL GLLLLWLRGA RCAPTSSSTK KTQLQLEHLL LDLQMILNGI NNYKNPKLTR    60
MLTFKFYMPK KATELKHLQC LEEELKPLEE VLNLAQSKNF HLRPRDLISN INVIVLELKG   120
SETTFMCEYA DETATIVEFL NRWITFCQSI ISTLTSGGPG PAGMKGLPGS GGGGSGGGGS   180
GGGGSGGGGS GGGGSGGGGS EVQLVESGGG LVQPGGSLRL SCAASGFTFS SYTLAWVRQA   240
PGKGLEWVAA IDSSSYTYSP DTVRGRFTIS RDNAKNSLYL QMNSLRAEDT AVYYCARDSN   300
WDALDYWGQG TTVTVSSGG PGPAGMKGLP GSDIQMTQSP SSLSASVGDR VTITCKASQN    360
VGTNVGWYQQ KPGKAPKALI YSASFRYSGV PSRFSGSGSG TDFTLTISSL QPEDFATYYC   420
QQYYTYPYTF GGGTKVEIKG GGGSGGGGSG GGGSEVQLVE SGGGLVQPGN SLRLSCAASG   480
FTFSKFGMSW VRQAPGKGLE WVSSISGSGR DTLYAESVKG RFTISRDNAK TTLYLQMNSL   540
RPEDTAVYYC TIGGSLSVSS QGTLVTVSSG GGGSGGGGSG GGGSQVQLQE SGGGLVQAGG   600
SLRLSCAASG RIFSIDIMSW YRQAPGKQRE LVARITRGGT ISYDDSVKGR FTISRDNAKN   660
TVYLQMNSLK PEDTGVYYCN ALYGTDYWGK GTQVTVSSHH HHHH                   704

SEQ ID NO: 133          moltype = AA  length = 689
FEATURE                 Location/Qualifiers
source                  1..689
                        mol_type = protein
                        organism = synthetic construct
SEQUENCE: 133
MDMRVPAQLL GLLLLWLRGA RCQVQLQESG GGLVQAGGSL RLSCAASGRI FSIDIMSWYR    60
QAPGKQRELV ARITRGGTIS YDDSVKGRFT ISRDNAKNTV YLQMNSLKPE DTGVYYCNAL   120
YGTDYWGKGT QVTVSGGGG SGGGGSGGGG SAPTSSSTKK TQLQLEHLLL DLQMILNGIN    180
NYKNPKLTRM LTFKFYMPKK ATELKHLQCL EEELKPLEEV LNLAQSKNFH LRPRDLISNI   240
NVIVLELKGS ETTFMCEYAD ETATIVEFLN RWITFCQSII STLTSGGPGP AGMKGLPGSE   300
VQLVESGGGL VQPGNSLRLS CAASGFTFSK FGMSWVRQAP GKGLEWVSSI SGSGRDTLYA   360
```

| | | |
|---|---|---|
| ESVKGRFTIS RDNAKTTLYL QMNSLRPEDT AVYYCTIGGS LSVSSQGTLV TVSSGGGGSG | | 420 |
| GGGSGGGGSG GGGSGGGGSG GGGSEVQLVE SGGGLVQPGG SLRLSCAASG FTFSSYTLAW | | 480 |
| VRQAPGKGLE WVAAIDSSSY TYSPDTVRGR FTISRDNAKN SLYLQMNSLR AEDTAVYYCA | | 540 |
| RDSNWDALDY WGQGTTVTVS SGGGGSGGGG SGGGGSDIQM TQSPSSLSAS VGDRVTITCK | | 600 |
| ASQNVGTNVG WYQQKPGKAP KALIYSASFR YSGVPSRFSG SGSGTDFTLT ISSLQPEDFA | | 660 |
| TYYCQQYYTY PYTFGGGTKV EIKHHHHHH | | 689 |

SEQ ID NO: 134      moltype = AA   length = 545
FEATURE             Location/Qualifiers
source              1..545
                    mol_type = protein
                    organism = synthetic construct
SEQUENCE: 134

| | | |
|---|---|---|
| MDMRVPAQLL GLLLLWLRGA RCAPTSSSTK KTQLQLEHLL LDLQMILNGI NNYKNPKLTR | | 60 |
| MLTFKFYMPK KATELKHLQC LEEELKPLEE VLNLAQSKNF HLRPRDLISN INVIVLELKG | | 120 |
| SETTFMCEYA DETATIVEFL NRWITFCQSI ISTLTSGGPG PAGMKGLPGS EVQLVESGGG | | 180 |
| LVQPGGSLRL SCAASGFTFS SYTLAWVRQA PGKGLEWVAA IDSSSYTYSP DTVRGRFTIS | | 240 |
| RDNAKNSLYL QMNSLRAEDT AVYYCARDSN WDALDYWGQG TTVTVSSGGG GSGGGGSGGG | | 300 |
| GSDIQMTQSP SSLSASVGDR VTITCKASQN VGTNVGWYQQ KPGKAPKALI YSASFRYSGV | | 360 |
| PSRFSGSGSG TDFTLTISSL QPEDFATYYC QQYYTYPYTF GGGTKVEIKG GGGSGGGGSG | | 420 |
| GGGSEVQLVE SGGGLVQPGN SLRLSCAASG FTFSKFGMSW VRQAPGKGLE WVSSISGSGR | | 480 |
| DTLYAESVKG RFTISRDNAK TTLYLQMNSL RPEDTAVYYC TIGGSLSVSS QGTLVTVSSH | | 540 |
| HHHHH | | 545 |

SEQ ID NO: 135      moltype = AA   length = 575
FEATURE             Location/Qualifiers
source              1..575
                    mol_type = protein
                    organism = synthetic construct
SEQUENCE: 135

| | | |
|---|---|---|
| MDMRVPAQLL GLLLLWLRGA RCAPTSSSTK KTQLQLEHLL LDLQMILNGI NNYKNPKLTR | | 60 |
| MLTFKFYMPK KATELKHLQC LEEELKPLEE VLNLAQSKNF HLRPRDLISN INVIVLELKG | | 120 |
| SETTFMCEYA DETATIVEFL NRWITFCQSI ISTLTSGGPG PAGMKGLPGS GGGGSGGGGS | | 180 |
| GGGGSGGGGS GGGGSGGGGS EVQLVESGGG LVQPGGSLRL SCAASGFTFS SYTLAWVRQA | | 240 |
| PGKGLEWVAA IDSSSYTYSP DTVRGRFTIS RDNAKNSLYL QMNSLRAEDT AVYYCARDSN | | 300 |
| WDALDYWGQG TTVTVSSGGG GSGGGGSGGG GSDIQMTQSP SSLSASVGDR VTITCKASQN | | 360 |
| VGTNVGWYQQ KPGKAPKALI YSASFRYSGV PSRFSGSGSG TDFTLTISSL QPEDFATYYC | | 420 |
| QQYYTYPYTF GGGTKVEIKG GGSGGGGSG GGGSEVQLVE SGGGLVQPGN SLRLSCAASG | | 480 |
| FTFSKFGMSW VRQAPGKGLE WVSSISGSGR DTLYAESVKG RFTISRDNAK TTLYLQMNSL | | 540 |
| RPEDTAVYYC TIGGSLSVSS QGTLVTVSSH HHHH | | 575 |

SEQ ID NO: 136      moltype = AA   length = 421
FEATURE             Location/Qualifiers
source              1..421
                    mol_type = protein
                    organism = synthetic construct
SEQUENCE: 136

| | | |
|---|---|---|
| MDMRVPAQLL GLLLLWLRGA RCEVQLVESG GGLVQPGNSL RLSCAASGFT FSKFGMSWVR | | 60 |
| QAPGKGLEWV SSISGSGRDT LYAESVKGRF TISRDNAKTT LYLQMNSLRP EDTAVYYCTI | | 120 |
| GGSLSVSSQG TLVTVSSSGG PGPAGMKGLP GSAPTSSSTK KTQLQLEHLL LDLQMILNGI | | 180 |
| NNYKNPKLTR MLTFKFYMPK KATELKHLQC LEEELKPLEE VLNLAQSKNF HLRPRDLISN | | 240 |
| INVIVLELKG SETTFMCEYA DETATIVEFL NRWITFCQSI ISTLTSGGPG PAGMKGLPGS | | 300 |
| EVQLVESGGG LVQPGNSLRL SCAASGFTFS KFGMSWVRQA PGKGLEWVSS ISGSGRDTLY | | 360 |
| AESVKGRFTI SRDNAKTTLY LQMNSLRPED TAVYYCTIGG SLSVSSQGTL VTVSSHHHHH | | 420 |
| H | | 421 |

SEQ ID NO: 137      moltype = AA   length = 806
FEATURE             Location/Qualifiers
source              1..806
                    mol_type = protein
                    organism = synthetic construct
SEQUENCE: 137

| | | |
|---|---|---|
| MDMRVPAQLL GLLLLWLRGA RCQVQLQESG GGLVQAGGSL RLSCAASGRI FSIDIMSWYR | | 60 |
| QAPGKQRELV ARITRGGTIS YDDSVKGRFT ISRDNAKNTV YLQMNSLKPE DTGVYYCNAL | | 120 |
| YGTDYWGKGT QVTVSSGSGS GSGSGSGSGS GSEVQLVESG GGLVQPGNSL RLSCAASGFT | | 180 |
| FSKFGMSWVR QAPGKGLEWV SSISGSGRDT LYAESVKGRF TISRDNAKTT LYLQMNSLRP | | 240 |
| EDTAVYYCTI GGSLSVSSQG TLVTVSSGSG SGSGSGSGSG SGSQVQLQES GGGLVQAGGS | | 300 |
| LRLSCAASGR IFSIDIMSWY RQAPGKQREL VARITRGGTI SYDDSVKGRF TISRDNAKNT | | 360 |
| VYLQMNSLKP EDTGVYYCNA LYGTDYWGKG TQVTVSSGSG SGSGSGSGSG SGSEVQLVES | | 420 |
| GGGLVQPGGS LRLSCAASGF TFSSYTLAWV RQAPGKGLEW VAAIDSSSYT YSPDTVRGRF | | 480 |
| TISRDNAKNS LYLQMNSLRA EDTAVYYCAR DSNWDALDYW GQGTTVTVSS GGGGSGGGGS | | 540 |
| GGGGSDIQMT QSPSSLSASV GDRVTITCKA SQNVGTNVGW YQQKPGKAPK ALIYSASFRY | | 600 |
| SGVPSRFSGS GSGTDFTLTI SSLQPEDFAT YYCQQYYTYP YTFGGGTKVE IKSGGPGPAG | | 660 |
| MKGLPGSAPT SSSTKKTQLQ LEHLLLDLQM ILNGINNYKN PKLTRMLTFK FYMPKKATEL | | 720 |
| KHLQCLEEEL KPLEEVLNLA QSKNFHLRPR DLISNINVIV LELKGSETTF MCEYADETAT | | 780 |
| IVEFLNRWIT FCQSIISTLT HHHHHH | | 806 |

SEQ ID NO: 138      moltype = AA   length = 676
FEATURE             Location/Qualifiers

```
source                   1..676
                         mol_type = protein
                         organism = synthetic construct
SEQUENCE: 138
MDMRVPAQLL GLLLLWLRGA RCQVQLQESG GGLVQAGGSL RLSCAASGRI FSIDIMSWYR    60
QAPGKQRELV ARITRGGTIS YDDSVKGRFT ISRDNAKNTV YLQMNSLKPE DTGVYYCNAL   120
YGTDYWGKGT QVTVSSGSGS GSGSGSGSGS GSEVQLVESG GGLVQPGNSL RLSCAASGFT   180
FSKFGMSWVR QAPGKGLEWV SSISGSGRDT LYAESVKGRF TISRDNAKTT LYLQMNSLRP   240
EDTAVYYCTI GGSLSVSSQG TLVTVSSGSG SGSGSGSGSG SGSEVQLVES GGGLVQPGGS   300
LRLSCAASGF TFSSYTLAWV RQAPGKGLEW VAAIDSSSYT YSPDTVRGRF TISRDNAKNS   360
LYLQMNSLRA EDTAVYYCAR DSNWDALDYW GQGTTVTVSS GGGGSGGGGS GGGGSDIQMT   420
QSPSSLSASV GDRVTITCKA SQNVGTNVGW YQQKPGKAPK ALIYSASFRY SGVPSRFSGS   480
GSGTDFTLTI SSLQPEDFAT YYCQQYYTYP YTFGGGTKVE IKSGGPGPAG MKGLPGSAPT   540
SSSTKKTQLQ LEHLLLDLQM ILNGINNYKN PKLTRMLTFK FYMPKKATEL KHLQCLEEEL   600
KPLEEVLNLA QSKNFHLRPR DLISNINVIV LELKGSETTF MCEYADETAT IVEFLNRWIT   660
FCQSIISTLT HHHHHH                                                  676

SEQ ID NO: 139           moltype = AA  length = 421
FEATURE                  Location/Qualifiers
source                   1..421
                         mol_type = protein
                         organism = synthetic construct
SEQUENCE: 139
MDMRVPAQLL GLLLLWLRGA RCQVQLQESG GGLVQAGGSL RLSCAASGRI FSIDIMSWYR    60
QAPGKQRELV ARITRGGTIS YDDSVKGRFT ISRDNAKNTV YLQMNSLKPE DTGVYYCNAL   120
YGTDYWGKGT QVTVSSGSGS GSGSGSGSGS GSEVQLVESG GGLVQPGNSL RLSCAASGFT   180
FSKFGMSWVR QAPGKGLEWV SSISGSGRDT LYAESVKGRF TISRDNAKTT LYLQMNSLRP   240
EDTAVYYCTI GGSLSVSSQG TLVTVSSGGG PGPAGMKGLP GSAPTSSSTK KTQLQLEHLL   300
LDLQMILNGI NNYKNPKLTR MLTFKFYMPK KATELKHLQC LEEELKPLEE VLNLAQSKNF   360
HLRPRDLISN INVIVLELKG SETTFMCEYA DETATIVEFL NRWITFCQSI ISTLTHHHHH   420
H                                                                  421

SEQ ID NO: 140           moltype = AA  length = 420
FEATURE                  Location/Qualifiers
source                   1..420
                         mol_type = protein
                         organism = synthetic construct
SEQUENCE: 140
MDMRVPAQLL GLLLLWLRGA RCQVQLQESG GGLVQAGGSL RLSCAASGRI FSIDIMSWYR    60
QAPGKQRELV ARITRGGTIS YDDSVKGRFT ISRDNAKNTV YLQMNSLKPE DTGVYYCNAL   120
YGTDYWGKGT QVTVSSGGP GPAGMKGLPG SAPTSSSTKK TQLQLEHLLL DLQMILNGIN   180
NYKNPKLTRM LTFKFYMPKK ATELKHLQCL EEELKPLEEV LNLAQSKNFH LRPRDLISNI   240
NVIVLELKGS ETTFMCEYAD ETATIVEFLN RWITFCQSII STLTSGGPGP AGMKGLPGSE   300
VQLVESGGGL VQPGNSLRLS CAASGFTFSK FGMSWVRQAP GKGLEWVSSI SGSGRDTLYA   360
ESVKGRFTIS RDNAKTTLYL QMNSLRPEDT AVYYCTIGGS LSVSSQGTLV TVSSHHHHHH   420

SEQ ID NO: 141           moltype = AA  length = 550
FEATURE                  Location/Qualifiers
source                   1..550
                         mol_type = protein
                         organism = synthetic construct
SEQUENCE: 141
MDMRVPAQLL GLLLLWLRGA RCQVQLQESG GGLVQAGGSL RLSCAASGRI FSIDIMSWYR    60
QAPGKQRELV ARITRGGTIS YDDSVKGRFT ISRDNAKNTV YLQMNSLKPE DTGVYYCNAL   120
YGTDYWGKGT QVTVSSGGGS SGGGGSGGGG SEVQLVESGG GLVQPGNSLR LSCAASGFTF   180
SKFGMSWVRQ APGKGLEWVS SISGSGRDTL YAESVKGRFT ISRDNAKTTL YLQMNSLRPE   240
DTAVYYCTIG GSLSVSSQGT LVTVSSGGPG PAGMKGLPGS APTSSSTKKT QLQLEHLLL    300
DLQMILNGIN NYKNPKLTRM LTFKFYMPKK ATELKHLQCL EEELKPLEEV LNLAQSKNFH   360
LRPRDLISNI NVIVLELKGS ETTFMCEYAD ETATIVEFLN RWITFCQSII STLTSGGPGP   420
AGMKGLPGSE VQLVESGGGL VQPGNSLRLS CAASGFTFSK FGMSWVRQAP GKGLEWVSSI   480
SGSGRDTLYA ESVKGRFTIS RDNAKTTLYL QMNSLRPEDT AVYYCTIGGS LSVSSQGTLV   540
TVSSHHHHHH                                                         550

SEQ ID NO: 142           moltype = AA  length = 420
FEATURE                  Location/Qualifiers
source                   1..420
                         mol_type = protein
                         organism = synthetic construct
SEQUENCE: 142
MDMRVPAQLL GLLLLWLRGA RCQVQLQESG GGLVQAGGSL RLSCAASGRI FSIDIMSWYR    60
QAPGKQRELV ARITRGGTIS YDDSVKGRFT ISRDNAKNTV YLQMNSLKPE DTGVYYCNAL   120
YGTDYWGKGT QVTVSSGGGG SGGGGSGGGG SAPTSSSTKK TQLQLEHLLL DLQMILNGIN   180
NYKNPKLTRM LTFKFYMPKK ATELKHLQCL EEELKPLEEV LNLAQSKNFH LRPRDLISNI   240
NVIVLELKGS ETTFMCEYAD ETATIVEFLN RWITFCQSII STLTSGGPGP AGMKGLPGSE   300
VQLVESGGGL VQPGNSLRLS CAASGFTFSK FGMSWVRQAP GKGLEWVSSI SGSGRDTLYA   360
ESVKGRFTIS RDNAKTTLYL QMNSLRPEDT AVYYCTIGGS LSVSSQGTLV TVSSHHHHHH   420

SEQ ID NO: 143           moltype = AA  length = 290
FEATURE                  Location/Qualifiers
```

```
source                   1..290
                         mol_type = protein
                         organism = synthetic construct
SEQUENCE: 143
MDMRVPAQLL GLLLLWLRGA RCQVQLQESG GGLVQAGGSL RLSCAASGRI FSIDIMSWYR   60
QAPGKQRELV ARITRGGTIS YDDSVKGRFT ISRDNAKNTV YLQMNSLKPE DTGVYYCNAL  120
YGTDYWGKGT QVTVSSGGGG SGGGGSGGGG SAPTSSSTKK TQLQLEHLLL DLQMILNGIN  180
NYKNPKLTRM LTFKFYMPKK ATELKHLQCL EEELKPLEEV LNLAQSKNFH LRPRDLISNI  240
NVIVLELKGS ETTFMCEYAD ETATIVEFLN RWITFCQSII STLTHHHHHH            290

SEQ ID NO: 144           moltype = AA  length = 291
FEATURE                  Location/Qualifiers
source                   1..291
                         mol_type = protein
                         organism = synthetic construct
SEQUENCE: 144
MDMRVPAQLL GLLLLWLRGA RCAPTSSSTK KTQLQLEHLL LDLQMILNGI NNYKNPKLTR   60
MLTFKFYMPK KATELKHLQC LEEELKPLEE VLNLAQSKNF HLRPRDLISN INVIVLELKG  120
SETTFMCEYA DETATIVEFL NRWITFCQSI ISTLTSGGPG PAGMKGLPGS EVQLVESGGG  180
LVQPGNSLRL SCAASGFTFS KFGMSWVRQA PGKGLEWVSS ISGSGRDTLY AESVKGRFTI  240
SRDNAKTTLY LQMNSLRPED TAVYYCTIGG SLSVSSQGTL VTVSSHHHHH H           291

SEQ ID NO: 145           moltype = AA  length = 689
FEATURE                  Location/Qualifiers
source                   1..689
                         mol_type = protein
                         organism = synthetic construct
SEQUENCE: 145
MDMRVPAQLL GLLLLWLRGA RCQVQLQESG GGLVQAGGSL RLSCAASGRI FSIDIMSWYR   60
QAPGKQRELV ARITRGGTIS YDDSVKGRFT ISRDNAKNTV YLQMNSLKPE DTGVYYCNAL  120
YGTDYWGKGT QVTVSSSGGP GPAGMKGLPG SAPTSSSTKK TQLQLEHLLL DLQMILNGIN  180
NYKNPKLTRM LTFKFYMPKK ATELKHLQCL EEELKPLEEV LNLAQSKNFH LRPRDLISNI  240
NVIVLELKGS ETTFMCEYAD ETATIVEFLN RWITFCQSII STLTSGGPGP AGMKGLPGSE  300
VQLVESGGGL VQPGNSLRLS CAASGFTFSK FGMSWVRQAP GKGLEWVSSI SGSGRDTLYA  360
ESVKGRFTIS RDNAKTTLYL QMNSLRPEDT AVYYCTIGGS LSVSSQGTLV TVSSGGGGSG  420
GGGSGGGGSG GGGSGGGGSG GGGSEVQLVE SGGGLVQPGG SLRLSCAASG FTFSSYTLAW  480
VRQAPGKGLE WVAAIDSSSY TYSPDTVRGR FTISRDNAKN SLYLQMNSLR AEDTAVYYCA  540
RDSNWDALDY WGQGTTVTVS SGGGGSGGGG SGGGGSDIQM TQSPSSLSAS VGDRVTITCK  600
ASQNVGTNVG WYQQKPGKAP KALIYSASFR YSGVPSRFSG SGSGTDFTLT ISSLQPEDFA  660
TYYCQQYYTY PYTFGGGTKV EIKHHHHHH                                   689

SEQ ID NO: 146           moltype = AA  length = 704
FEATURE                  Location/Qualifiers
source                   1..704
                         mol_type = protein
                         organism = synthetic construct
SEQUENCE: 146
MDMRVPAQLL GLLLLWLRGA RCAPTSSSTK KTQLQLEHLL LDLQMILNGI NNYKNPKLTR   60
MLTFKFYMPK KATELKHLQC LEEELKPLEE VLNLAQSKNF HLRPRDLISN INVIVLELKG  120
SETTFMCEYA DETATIVEFL NRWITFCQSI ISTLTSGGPG PAGMKGLPGS GGGGSGGGGS  180
GGGGSGGGGS GGGGSGGGGS EVQLVESGGG LVQPGNSLRL SCAASGFTFS SYTLAWVRQA  240
PGKGLEWVAA IDSSSYTYSP DTVRGRFTIS RDNAKNSLYL QMNSLRAEDT AVYYCARDSN  300
WDALDYWGQG TTVTVSSGGG GSGGGGSGGG GSDIQMTQSP SSLSASVGDR VTITCKASQN  360
VGTNVGWYQQ KPGKAPKALI YSASFRYSGV PSRFSGSGSG TDFTLTISSL QPEDFATYYC  420
QQYYTYPYTF GGGTKVEIKG GGGSGGGGS GGGSEVQLVQPGN SLRLSCAASG  480
FTFSKFGMSW VRQAPGKGLE WVSSISGSGR DTLYAESVKG RFTISRDNAK TTLYLQMNSL  540
RPEDTAVYYC TIGGSLSVSS QGTLVTVSSG GGGSGGGGSG GGGSQVQLQE SGGGLAQAGG  600
SLSLSCAASG FTVSNSVMAW YRQTPGKQRE FVAIINSVGS TNYADSVKGR FTISRDNAKN  660
TVYLQMNNLK PEDTAVYVCN RNFDRIYWGQ GTQVTVSSHH HHHH                  704

SEQ ID NO: 147           moltype = AA  length = 674
FEATURE                  Location/Qualifiers
source                   1..674
                         mol_type = protein
                         organism = synthetic construct
SEQUENCE: 147
MDMRVPAQLL GLLLLWLRGA RCQVQLQESG GGLAQAGGSL SLSCAASGFT VSNSVMAWYR   60
QTPGKQREFV AIINSVGSTN YADSVKGRFT ISRDNAKNTV YLQMNNLKPE DTAVYVCNRN  120
FDRIYWGQGT QVTVSSAPTS SSTKKTQLQL EHLLLDLQMI LNGINNYKNP KLTRMLTFKF  180
YMPKKATELK HLQCLEEELK PLEEVLNLAQ SKNFHLRPRD LISNINVIVL ELKGSETTFM  240
CEYADETATI VEFLNRWITF CQSIISTLTS GGPGPAGMKG LPGSEVQLVE SGGGLVQPGN  300
SLRLSCAASG FTFSKFGMSW VRQAPGKGLE WVSSISGSGR DTLYAESVKG RFTISRDNAK  360
TTLYLQMNSL RPEDTAVYYC TIGGSLSVSS QGTLVTVSSG GGGSGGGGSG GGGSGGGGSG  420
GGGSGGGGSE VQLVESGGGL VQPGGSLRLS CAASGFTFSS YTLAWVRQAP GKGLEWVAAI  480
DSSSYTYSPD TVRGRFTISR DNAKNSLYLQ MNSLRAEDTA VYYCARDSNW DALDYWGQGT  540
TVTVSSGGGG SGGGGSGGGG SDIQMTQSPS SLSASVGDRV TITCKASQNV GTNVGWYQQK  600
PGKAPKALIY SASFRYSGVP SRFSGSGSGT DFTLTISSLQ PEDFATYYCQ QYYTYPYTFG  660
GGTKVEIKHH HHHH                                                   674
```

```
SEQ ID NO: 148            moltype = AA   length = 704
FEATURE                   Location/Qualifiers
source                    1..704
                          mol_type = protein
                          organism = synthetic construct
SEQUENCE: 148
MDMRVPAQLL GLLLLWLRGA RCEVQLVESG GGLVQPGGSL RLSCAASGFT FSSYTLAWVR    60
QAPGKGLEWV AAIDSSSYTY SPDTVRGRFT ISRDNAKNSL YLQMNSLRAE DTAVYYCARD   120
SNWDALDYWG QGTTVTVSSG GGGSGGGGSG GGGSDIQMTQ SPSSLSASVG DRVTITCKAS   180
QNVGTNVGWY QQKPGKAPKA LIYSASFRYS GVPSRFSGSG SGTDFTLTIS SLQPEDFATY   240
YCQQYYTYPY TFGGGTKVEI KGGGGSGGGG SGGGGSGGGG SGGGGSGGGG SSGGPGPAGM   300
KGLPGSAPTS SSTKKTQLQL EHLLLDLQMI LNGINNYKNP KLTRMLTFKF YMPKKATELK   360
HLQCLEEELK PLEEVLNLAQ SKNFHLRPRD LISNINVIVL ELKGSETTFM CEYADETATI   420
VEFLNRWITF CQSIISTLTS GGPGPAGMKG LPGSEVQLVE SGGGLVQPGN SLRLSCAASG   480
FTFSKFGMSW VRQAPGKGLE WVSSISGSGR DTLYAESVKG RFTISRDNAK TTLYLQMNSL   540
RPEDTAVYYC TIGGSLSVSS QGTLVTVSSG GGGSGGGGSG GGGSQVQLQE SGGGLAQAGG   600
SLSLSCAASG FTVSNSVMAW YRQTPGKQRE FVAIINSVGS TNYADSVKGR FTISRDNAKN   660
TVYLQMNNLK PEDTAVYVCN RNFDRIYWGQ GTQVTVSSHH HHHH               704

SEQ ID NO: 149            moltype = AA   length = 704
FEATURE                   Location/Qualifiers
source                    1..704
                          mol_type = protein
                          organism = synthetic construct
SEQUENCE: 149
MDMRVPAQLL GLLLLWLRGA RCQVQLQESG GGLAQAGGSL SLSCAASGFT VSNSVMAWYR    60
QTPGKQREFV AIINSVGSTN YADSVKGRFT ISRDNAKNTV YLQMNNLKPE DTAVYVCNRN   120
FDRIYWGQGT QVTVSSGGGG SGGGGSGGGG SEVQLVESGG GLVQPGNSLR LSCAASGFTF   180
SKFGMSWVRQ APGKGLEWVS SISGSGRDTL YAESVKGRFT ISRDNAKTTL YLQMNSLRPE   240
DTAVYYCTIG GSLSVSSQGT LVTVSSSGGP GPAGMKGLPG SEVQLVESGG GLVQPGGSLR   300
LSCAASGFTF SSYTLAWVRQ APGKGLEWVA AIDSSSYTYS PDTVRGRFTI SRDNAKNSLY   360
LQMNSLRAED TAVYYCARDS NWDALDYWGQ GTTVTVSSGG GGSGGGGSGG GGSDIQMTQS   420
PSSLSASVGD RVTITCKASQ NVGTNVGWYQ QKPGKAPKAL IYSASFRYSG VPSRFSGSGS   480
GTDFTLTISS LQPEDFATYY CQQYYTYPYT FGGGTKVEIK GGGGSGGGGS GGGGSGGGGS   540
GGGGSGGGGS SGGPGPAGMK GLPGSAPTSS STKKTQLQLE HLLLDLQMIL NGINNYKNPK   600
LTRMLTFKFY MPKKATELKH LQCLEEELKP LEEVLNLAQS KNFHLRPRDL ISNINVIVLE   660
LKGSETTFMC EYADETATIV EFLNRWITFC QSIISTLTHH HHHH               704

SEQ ID NO: 150            moltype = AA   length = 689
FEATURE                   Location/Qualifiers
source                    1..689
                          mol_type = protein
                          organism = synthetic construct
SEQUENCE: 150
MDMRVPAQLL GLLLLWLRGA RCEVQLVESG GGLVQPGGSL RLSCAASGFT FSSYTLAWVR    60
QAPGKGLEWV AAIDSSSYTY SPDTVRGRFT ISRDNAKNSL YLQMNSLRAE DTAVYYCARD   120
SNWDALDYWG QGTTVTVSSG GGGSGGGGSG GGGSDIQMTQ SPSSLSASVG DRVTITCKAS   180
QNVGTNVGWY QQKPGKAPKA LIYSASFRYS GVPSRFSGSG SGTDFTLTIS SLQPEDFATY   240
YCQQYYTYPY TFGGGTKVEI KGGGGSGGGG SGGGGSGGGG SGGGGSGGGG SEVQLVESGG   300
GLVQPGNSLR LSCAASGFTF SKFGMSWVRQ APGKGLEWVS SISGSGRDTL YAESVKGRFT   360
ISRDNAKTTL YLQMNSLRPE DTAVYYCTIG GSLSVSSQGT LVTVSSSGGP GPAGMKGLPG   420
SAPTSSSTKK TQLQLEHLLL DLQMILNGIN NYKNPKLTRM LTFKYMPKK ATELKHLQCL   480
EEELKPLEEV LNLAQSKNFH LRPRDLISNI NVIVLELKGS ETTFMCEYAD ETATIVEFLN   540
RWITFCQSII STLTGGGSG GGGSGGGGSQ VQLQESGGGL AQAGGSLSLS CAASGFTVSN   600
SVMAWYRQTP GKQREFVAII NSVGSTNYAD SVKGRFTISR DNAKNTVYLQ MNNLKPEDTA   660
VYVCNRNFDR IYWGQGTQVT VSSHHHHHH                                 689

SEQ ID NO: 151            moltype = AA   length = 700
FEATURE                   Location/Qualifiers
source                    1..700
                          mol_type = protein
                          organism = synthetic construct
SEQUENCE: 151
MDMRVPAQLL GLLLLWLRGA RCQVQLQESG GGLVQAGGSL RLSCAASGRI FSIDIMSWYR    60
QAPGKQRELV ARITRGGTIS YDDSVKGRFT ISRDNAKNTV YLQMNSLKPE DTGVYYCNAL   120
YGTDYWGKGT QVTVSSGGGG SGGGGSGGGG SAPTSSSTKK TQLQLEHLLL DLQMILNGIN   180
NYKNPKLTRM LTFKFYMPKK ATELKHLQCL EEELKPLEEV LNLAQSKNFH LRPRDLISNI   240
NVIVLELKGS ETTFMCEYAD ETATIVEFLN RWITFCQSII STLTSGGPGP AGMKGLPGSG   300
GETGPAAPGS EVQLVESGGG LVQPGNSLRL SCAASGFTFS KFGMSWVRQA PGKGLEWVSS   360
ISGSGRDTLY AESVKGRFTI SRDNAKTTLY LQMNSLRPED TAVYYCTIGG SLSVSSQGTL   420
VTVSSGGGGS GGGGSGGGGS GGGGSGGGGS GGGGSEVQLV ESGGGLVQPG GSLRLSCAAS   480
GFTFSSYTLA WVRQAPGKGL EWVAAIDSSS YTYSPDTVRG RFTISRDNAK NSLYLQMNSL   540
RAEDTAVYYC ARDSNWDALD YWGQGTTVTV SSGGGGSGGG GSGGGGSDIQ MTQSPSSLSA   600
SVGDRVTITC KASQNVGTNV GWYQQKPGKA PKALIYSASF RYSGVPSRFS GSGSGTDFTL   660
TISSLQPEDF ATYYCQQYYT YPYTFGGGTK VEIKHHHHHH                      700

SEQ ID NO: 152            moltype = AA   length = 276
FEATURE                   Location/Qualifiers
source                    1..276
```

```
                        mol_type = protein
                        organism = synthetic construct
SEQUENCE: 152
MDMRVPAQLL GLLLLWLRGA RCEVQLVESG GGLVQPGGSL RLSCAASGFT FSSYAMSWVR    60
QAPGKGLEWV SAISGSGGST YYADSVKGRF TISRDNSKNT LYLQMNSLRA EDTAVYYCAR   120
GVGAFRPYRK HEWGQGTLVT VSRGGGGSGG GGSGGGGSSS ELTQDPAVSV ALGQTVRITC   180
QGDSLRSYYA SWYQQKPGQA PVLVIYGKNN RPSGIPDRFS GSSSGNTASL TTTGAQAEDE   240
ADYYCNSSPF EHNLVVFGGG TKLTVLHHHH HHEPEA                            276

SEQ ID NO: 153          moltype = AA  length = 279
FEATURE                 Location/Qualifiers
source                  1..279
                        mol_type = protein
                        organism = synthetic construct
SEQUENCE: 153
MDMRVPAQLL GLLLLWLRGA RCQVQLQQSG AELVRPGTSV KVSCKASGYA FTNYLIEWVK    60
QRPGQGLEWI GVINPGSGGT NYNEKFKGKA TLTADKSSST AYMQLSSLTS DDSAVYFCAR   120
WRGDGYYAYF DVWGAGTTVT VSSGGGGSGG GGSGGGGSDI VLTQSPASLA VSLGQRATIS   180
CKASQSVDYD GDSYMNWYQQ KPGQPPKLLI YAASNLESGI PARFSGSGSG TDFTLNIHPV   240
EEEEDAATYYC QQSNEDPYTF GGGTKLEIKH HHHHHEPEA                        279

SEQ ID NO: 154          moltype = AA  length = 279
FEATURE                 Location/Qualifiers
source                  1..279
                        mol_type = protein
                        organism = synthetic construct
SEQUENCE: 154
MDMRVPAQLL GLLLLWLRGA RCQVQLQQSG AELVRPGTSV KVSCKASGYA FTNYLIEWVK    60
QRPGQGLEWI GVINPGSGGT NYNEKFKGKA TLTADKSSST AYMQLSSLTS DDSAVYFCAR   120
WRGDGYYAYF DVWGAGTTVT VSSSGGGPGPA GMKGLPGSDI VLTQSPASLA VSLGQRATIS   180
CKASQSVDYD GDSYMNWYQQ KPGQPPKLLI YAASNLESGI PARFSGSGSG TDFTLNIHPV   240
EEEEDAATYYC QQSNEDPYTF GGGTKLEIKH HHHHHEPEA                        279

SEQ ID NO: 155          moltype = AA  length = 279
FEATURE                 Location/Qualifiers
source                  1..279
                        mol_type = protein
                        organism = synthetic construct
SEQUENCE: 155
MDMRVPAQLL GLLLLWLRGA RCDIVLTQSP ASLAVSLGQR ATISCKASQS VDYDGDSYMN    60
WYQQKPGQPP KLLIYAASNL ESGIPARFSG SGSGTDFTLN IHPVEEEDAA TYYCQQSNED   120
PYTFGGGTKL EIKGGGGSGG GGSGGGGSQV QLQQSGAELV RPGTSVKVSC KASGYAFTNY   180
LIEWVKQRPG QGLEWIGVIN PGSGGTNYNE KFKGKATLTA DKSSSTAYMQ LSSLTSDDSA   240
VYFCARWRGD GYYAYFDVWG AGTTVTVSSH HHHHHEPEA                         279

SEQ ID NO: 156          moltype = AA  length = 279
FEATURE                 Location/Qualifiers
source                  1..279
                        mol_type = protein
                        organism = synthetic construct
SEQUENCE: 156
MDMRVPAQLL GLLLLWLRGA RCDIVLTQSP ASLAVSLGQR ATISCKASQS VDYDGDSYMN    60
WYQQKPGQPP KLLIYAASNL ESGIPARFSG SGSGTDFTLN IHPVEEEDAA TYYCQQSNED   120
PYTFGGGTKL EIKSGGPGPA GMKGLPGSQV QLQQSGAELV RPGTSVKVSC KASGYAFTNY   180
LIEWVKQRPG QGLEWIGVIN PGSGGTNYNE KFKGKATLTA DKSSSTAYMQ LSSLTSDDSA   240
VYFCARWRGD GYYAYFDVWG AGTTVTVSSH HHHHHEPEA                         279

SEQ ID NO: 157          moltype = AA  length = 295
FEATURE                 Location/Qualifiers
source                  1..295
                        mol_type = protein
                        organism = synthetic construct
SEQUENCE: 157
MDMRVPAQLL GLLLLWLRGA RCAPTSSSTK KTQLQLEHLL LDLQMILNGI NNYKNPKLTR    60
MLTFKFYMPK KATELKHLQC LEEELKPLEE VLNLAQSKNF HLRPRDLISN INVIVLELKG   120
SETTFMCEYA DETATIVEFL NRWITFCQSI ISTLTGGGGS GGGGSGGGGS EVQLVESGGG   180
LVQPGNSLRL SCAASGFTFS KFGMSWVRQA PGKGLEWVSS ISGSGRDTLY AESVKGRFTI   240
SRDNAKTTLY LQMNSLRPED TAVYYCTIGG SLSVSSQGTL VTVSSHHHHH HEPEA        295

SEQ ID NO: 158          moltype = AA  length = 765
FEATURE                 Location/Qualifiers
source                  1..765
                        mol_type = protein
                        organism = synthetic construct
SEQUENCE: 158
MDMRVPAQLL GLLLLWLRGA RCAPTSSSTK KTQLQLEHLL LDLQMILNGI NNYKNPKLTR    60
MLTFKFYMPK KATELKHLQC LEEELKPLEE VLNLAQSKNF HLRPRDLISN INVIVLELKG   120
SETTFMCEYA DETATIVEFL NRWITFCQSI ISTLTGGGGS GGGGSGGGGS DAHKSEVAHR   180
FKDLGEENFK ALVLIAFAQY LQQCPFEDHV KLVNEVTEFA KTCVADESAE NCDKSLHTLF   240
```

```
GDKLCTVATL RETYGEMADC CAKQEPERNE CFLQHKDDNP NLPRLVRPEV DVMCTAFHDN    300
EETFLKKYLY EIARRHPYFY APELLFFAKR YKAAFTECCQ AADKAACLLP KLDELRDEGK    360
ASSAKQRLKC ASLQKFGERA FKAWAVARLS QRFPKAEFAE VSKLVTDLTK VHTECCHGDL    420
LECADDRADL AKYICENQDS ISSKLKECCE KPLLEKSHCI AEVENDEMPA DLPSLAADFV    480
ESKDVCKNYA EAKDVFLGMF LYEYARRHPD YSVVLLLRLA KTYETTLEKC CAAADPHECY    540
AKVFDEFKPL VEEPQNLIKQ NCELFEQLGE YKFQNALLVR YTKKVPQVST PTLVEVSRNL    600
GKVGSKCCKH PEAKRMPCAE DYLSVVLNQL CVLHEKTPVS DRVTKCCTES LVNRRPCFSA    660
LEVDETYVPK EFNAETFTFH ADICTLSEKE RQIKKQTALV ELVKHKPKAT KEQLKAVMDD    720
FAAFVEKCCK ADDKETCFAE EGKKLVAASQ AALGLHHHHH HEPEA                    765

SEQ ID NO: 159          moltype = AA   length = 765
FEATURE                 Location/Qualifiers
source                  1..765
                        mol_type = protein
                        organism = synthetic construct
SEQUENCE: 159
MDMRVPAQLL GLLLLWLRGA RCAPTSSSTK KTQLQLEHLL LDLQMILNGI NNYKNPKLTR     60
MLTFKFYMPK KATELKHLQC LEEELKPLEE VLNLAQSKNF HLRPRDLISN INVIVLELKG    120
SETTFMCEYA DETATIVEFL NRWITFCQSI ISTLTGGGGS GGGGSGGGGS DAHKSEVAHR    180
FKDLGEENFK ALVLIAFAQY LQQCPFEDHV KLVNEVTEFA KTCVADESAE NCDKSLHTLF    240
GDKLCTVATL RETYGEMADC CAKQEPERNE CFLQHKDDNP NLPRLVRPEV DVMCTAFHDN    300
EETFLKKYLY EIARRHPYFY APELLFFAKR YKAAFTECCQ AADKAACLLP KLDELRDEGK    360
ASSAKQRLKC ASLQKFGERA FKAWAVARLS QRFPKAEFAE VSKLVTDLTK VHTECCHGDL    420
LECADDRADL AKYICENQDS ISSKLKECCE KPLLEKSHCI AEVENDEMPA DLPSLAADFV    480
ESKDVCKNYA EAKDVFLGMF LYEYARRHPD YSVVLLLRLA KTYETTLEKC CAAADPHECY    540
AKVFDEFKPL VEEPQNLIKQ NCELFEQLGE YKFQNALLVR YTKKVPQVST PTLVEVSRNL    600
GKVGSKCCKH PEAKRMPCAE DYLSVVLNQL CVLHEKTPVS DRVTKCCTES LVNRRPCFSA    660
LEVDETYVPK EFNAETFTFH ADICTLSEKE RQIKKQTALV ELVKHKPKAT KEQLKAVMDD    720
FAAFVEKCCK ADDKETCFAE EGKKLVAASQ AALGLHHHHH HEPEA                    765

SEQ ID NO: 160          moltype = AA   length = 765
FEATURE                 Location/Qualifiers
source                  1..765
                        mol_type = protein
                        organism = synthetic construct
SEQUENCE: 160
MDMRVPAQLL GLLLLWLRGA RCAPTSSSTK KTQLQLEHLL LDLQMILNGI NNYKNPKLTR     60
MLTFKFYMPK KATELKHLQC LEEELKPLEE VLNLAQSKNF HLRPRDLISN INVIVLELKG    120
SETTFMCEYA DETATIVEFL NRWITFCQSI ISTLTSGGPG PAGMKGLPGS DAHKSEVAHR    180
FKDLGEENFK ALVLIAFAQY LQQCPFEDHV KLVNEVTEFA KTCVADESAE NCDKSLHTLF    240
GDKLCTVATL RETYGEMADC CAKQEPERNE CFLQHKDDNP NLPRLVRPEV DVMCTAFHDN    300
EETFLKKYLY EIARRHPYFY APELLFFAKR YKAAFTECCQ AADKAACLLP KLDELRDEGK    360
ASSAKQRLKC ASLQKFGERA FKAWAVARLS QRFPKAEFAE VSKLVTDLTK VHTECCHGDL    420
LECADDRADL AKYICENQDS ISSKLKECCE KPLLEKSHCI AEVENDEMPA DLPSLAADFV    480
ESKDVCKNYA EAKDVFLGMF LYEYARRHPD YSVVLLLRLA KTYETTLEKC CAAADPHECY    540
AKVFDEFKPL VEEPQNLIKQ NCELFEQLGE YKFQNALLVR YTKKVPQVST PTLVEVSRNL    600
GKVGSKCCKH PEAKRMPCAE DYLSVVLNQL CVLHEKTPVS DRVTKCCTES LVNRRPCFSA    660
LEVDETYVPK EFNAETFTFH ADICTLSEKE RQIKKQTALV ELVKHKPKAT KEQLKAVMDD    720
FAAFVEKCCK ADDKETCFAE EGKKLVAASQ AALGLHHHHH HEPEA                    765

SEQ ID NO: 161          moltype = AA   length = 708
FEATURE                 Location/Qualifiers
source                  1..708
                        mol_type = protein
                        organism = synthetic construct
SEQUENCE: 161
MDMRVPAQLL GLLLLWLRGA RCAPTSSSTK KTQLQLEHLL LDLQMILNGI NNYKNPKLTR     60
MLTFKFYMPK KATELKHLQC LEEELKPLEE VLNLAQSKNF HLRPRDLISN INVIVLELKG    120
SETTFMCEYA DETATIVEFL NRWITFCQSI ISTLTSGGPG PAGMKGLPGS EVQLVESGGG    180
LVQPGNSLRL SCAASGFTFS KFGMSWVRQA PGKGLEWVSS ISGSGRDTLY AESVKGRFTI    240
SRDNAKTTLY LQMNSLRPED TAVYYCTIGG SLSVSSQGTL VTVSSGGGGS GGGGSGGGGS    300
GGGGSGGGGS GGGGSSGGPG PAGMKGLPGS EVQLVESGGG LVQPGGSLRL SCAASGFTFS    360
SYTLAWVRQA PGKGLEWVAA IDSSSYTYSP DTVRGRFTIS RDNAKNSLYL QMNSLRAEDT    420
AVYYCARDSN WDALDYWGQG TTVTVSSGGG GSGGGGSGGG GSDIQMTQSP SSLSASVGDR    480
VTITCKASQN VGTNVGWYQQ KPGKAPKALI YSASFRYSGV PSRFSGSGSG TDFTLTISSL    540
QPEDFATYYC QQYYTYPYTF GGGTKVEIKG GGGSGGGGSG GGGSQVQLQE SGGGLAQAGG    600
SLSLSCAASG FTVSNSVMAW YRQTPGKQRE FVAIINSVGS TNYADSVKGR FTISRDNAKN    660
TVYLQMNNLK PEDTAVYVCN RNFDRIYWGQ GTQVTVSSHH HHHHEPEA                 708

SEQ ID NO: 162          moltype = AA   length = 708
FEATURE                 Location/Qualifiers
source                  1..708
                        mol_type = protein
                        organism = synthetic construct
SEQUENCE: 162
MDMRVPAQLL GLLLLWLRGA RCQVQLQESG GGLAQAGGSL SLSCAASGFT VSNSVMAWYR     60
QTPGKQREFV AIINSVGSTN YADSVKGRFT ISRDNAKNTV YLQMNNLKPE DTAVYVCNRN    120
FDRIYWGQGT QVTVSSGGGG SGGGGSGGGG SAPTSSSTKK TQLQLEHLLL DLQMILNGIN    180
NYKNPKLTRM LTFKFYMPKK ATELKHLQCL EEELKPLEEV LNLAQSKNFH LRPRDLISNI    240
```

```
NVIVLELKGS ETTFMCEYAD ETATIVEFLN RWITFCQSII STLTSGGPGP AGMKGLPGSE   300
VQLVESGGGL VQPGNSLRLS CAASGFTFSK FGMSWVRQAP GKGLEWVSSI SGSGRDTLYA   360
ESVKGRFTIS RDNAKTTLYL QMNSLRPEDT AVYYCTIGGS LSVSSQGTLV TVSSGGGGSG   420
GGGSGGGGSG GGGSGGGGSG GGGSSGGPGP AGMKGLPGSE VQLVESGGGL VQPGGSLRLS   480
CAASGFTFSS YTLAWVRQAP GKGLEWVAAI DSSSYTYSPD TVRGRFTISR DNAKNSLYLQ   540
MNSLRAEDTA VYYCARDSNW DALDYWGQGT TVTVSSGGGG SGGGGSGGGG SDIQMTQSPS   600
SLSASVGDRV TITCKASQNV GTNVGWYQQK PGKAPKALIY SASFRYSGVP SRFSGSGSGT   660
DFTLTISSLQ PEDFATYYCQ QYYTYPYTFG GGTKVEIKHH HHHHEPEA               708

SEQ ID NO: 163          moltype = AA  length = 708
FEATURE                 Location/Qualifiers
source                  1..708
                        mol_type = protein
                        organism = synthetic construct
SEQUENCE: 163
MDMRVPAQLL GLLLLWLRGA RCQVQLQESG GGLAQAGGSL SLSCAASGFT VSNSVMAWYR   60
QTPGKQREFV AIINSVGSTN YADSVKGRFT ISRDNAKNTV YLQMNNLKPE DTAVYYCNRN  120
FDRIYWGQGT QVTVSSSGGP GPAGMKGLPG SAPTSSSTKK TQLQLEHLLL DLQMILNGIN  180
NYKNPKLTRM LTFKFYMPKK ATELKHLQCL EEELKPLEEV LNLAQSKNFH LRPRDLISNI  240
NVIVLELKGS ETTFMCEYAD ETATIVEFLN RWITFCQSII STLTSGGPGP AGMKGLPGSE  300
VQLVESGGGL VQPGNSLRLS CAASGFTFSK FGMSWVRQAP GKGLEWVSSI SGSGRDTLYA  360
ESVKGRFTIS RDNAKTTLYL QMNSLRPEDT AVYYCTIGGS LSVSSQGTLV TVSSGGGGSG  420
GGGSGGGGSG GGGSGGGGSG GGGSSGGPGP AGMKGLPGSE VQLVESGGGL VQPGGSLRLS  480
CAASGFTFSS YTLAWVRQAP GKGLEWVAAI DSSSYTYSPD TVRGRFTISR DNAKNSLYLQ  540
MNSLRAEDTA VYYCARDSNW DALDYWGQGT TVTVSSGGGG SGGGGSGGGG SDIQMTQSPS  600
SLSASVGDRV TITCKASQNV GTNVGWYQQK PGKAPKALIY SASFRYSGVP SRFSGSGSGT  660
DFTLTISSLQ PEDFATYYCQ QYYTYPYTFG GGTKVEIKHH HHHHEPEA               708

SEQ ID NO: 164          moltype = AA  length = 161
FEATURE                 Location/Qualifiers
source                  1..161
                        mol_type = protein
                        organism = synthetic construct
SEQUENCE: 164
MDMRVPAQLL GLLLLWLRGA RCAPTSSSTK KTQLQLEHLL LDLQMILNGI NNYKNPKLTR   60
MLTFKFYMPK KATELKHLQC LEEELKPLEE VLNLAQSKNF HLRPRDLISN INVIVLELKG  120
SETTFMCEYA DETATIVEFL NRWITFCQSI ISTLTHHHHH H                      161

SEQ ID NO: 165          moltype = AA  length = 708
FEATURE                 Location/Qualifiers
source                  1..708
                        mol_type = protein
                        organism = synthetic construct
SEQUENCE: 165
MDMRVPAQLL GLLLLWLRGA RCAPTSSSTK KTQLQLEHLL LDLQMILNGI NNYKNPKLTR   60
MLTFKFYMPK KATELKHLQC LEEELKPLEE VLNLAQSKNF HLRPRDLISN INVIVLELKG  120
SETTFMCEYA DETATIVEFL NRWITFCQSI ISTLTSGGPG PAGMKGLPGS EVQLVESGGG  180
LVQPGNSLRL SCAASGFTFS KFGMSWVRQA PGKGLEWVSS ISGSGRDTLY AESVKGRFTI  240
SRDNAKTTLY LQMNSLRPED TAVYYCTIGG SLSVSSQGTL VTVSSGGGGS GGGGSGGGGS  300
GGGGSGGGGS GGGGSSGGPG PAGMKGLPGS EVQLVESGGG LVQPGGSLRL SCAASGFTFS  360
SYTLAWVRQA PGKGLEWVAA IDSSSYTYSP DTVRGRFTIS RDNAKNSLYL QMNSLRAEDT  420
AVYYCARDSN WDALDYWGQG TTVTVSSGGG GSGGGGSGGG GSDIQMTQSP SSLSASVGDR  480
VTITCKASQN VGTNVGWYQQ KPGKAPKALI YSASFRYSGV PSRFSGSGSG TDFTLTISSL  540
QPEDFATYYC QQYYTYPYTF GGGTKVEIKG GGGSGGGGSG GGGSQVQLQE SGGGLVQAGG  600
SLRLSCAASG RIFSIDIMSW YRQAPGKQRE LVARITRGGT ISYDDSVKGR FTISRDNAKN  660
TVYLQMNSLK PEDTGVYYCN ALYGTDYWGK GTQVTVSSHH HHHHEPEA               708

SEQ ID NO: 166          moltype = AA  length = 708
FEATURE                 Location/Qualifiers
source                  1..708
                        mol_type = protein
                        organism = synthetic construct
SEQUENCE: 166
MDMRVPAQLL GLLLLWLRGA RCQVQLQESG GGLVQAGGSL RLSCAASGRI FSIDIMSWYR   60
QAPGKQRELV ARITRGGTIS YDDSVKGRFT ISRDNAKNTV YLQMNSLKPE DTGVYYCNAL  120
YGTDYWGKGT QVTVSSGGGG SGGGGSGGGG SAPTSSSTKK TQLQLEHLLL DLQMILNGIN  180
NYKNPKLTRM LTFKFYMPKK ATELKHLQCL EEELKPLEEV LNLAQSKNFH LRPRDLISNI  240
NVIVLELKGS ETTFMCEYAD ETATIVEFLN RWITFCQSII STLTSGGPGP AGMKGLPGSE  300
VQLVESGGGL VQPGNSLRLS CAASGFTFSK FGMSWVRQAP GKGLEWVSSI SGSGRDTLYA  360
ESVKGRFTIS RDNAKTTLYL QMNSLRPEDT AVYYCTIGGS LSVSSQGTLV TVSSGGGGSG  420
GGGSGGGGSG GGGSGGGGSG GGGSSGGPGP AGMKGLPGSE VQLVESGGGL VQPGGSLRLS  480
CAASGFTFSS YTLAWVRQAP GKGLEWVAAI DSSSYTYSPD TVRGRFTISR DNAKNSLYLQ  540
MNSLRAEDTA VYYCARDSNW DALDYWGQGT TVTVSSGGGG SGGGGSGGGG SDIQMTQSPS  600
SLSASVGDRV TITCKASQNV GTNVGWYQQK PGKAPKALIY SASFRYSGVP SRFSGSGSGT  660
DFTLTISSLQ PEDFATYYCQ QYYTYPYTFG GGTKVEIKHH HHHHEPEA               708

SEQ ID NO: 167          moltype = AA  length = 708
FEATURE                 Location/Qualifiers
source                  1..708
```

```
                        mol_type = protein
                        organism = synthetic construct
SEQUENCE: 167
MDMRVPAQLL  GLLLLWLRGA  RCQVQLQESG  GGLVQAGGSL  RLSCAASGRI  FSIDIMSWYR   60
QAPGKQRELV  ARITRGGTIS  YDDSVKGRFT  ISRDNAKNTV  YLQMNSLKPE  DTGVYYCNAL  120
YGTDYWGKGT  QVTVSSSGGP  GPAGMKGLPG  SAPTSSSTKK  TQLQLEHLLL  DLQMILNGIN  180
NYKNPKLTRM  LTFKFYMPKK  ATELKHLQCL  EEELKPLEEV  LNLAQSKNFH  LRPRDLISNI  240
NVIVLELKGS  ETTFMCEYAD  ETATIVEFLN  RWITFCQSII  STLTSGGPGP  AGMKGLPGSE  300
VQLVESGGGL  VQPGNSLRLS  CAASGFTFSK  FGMSWVRQAP  GKGLEWVSSI  SGSGRDTLYA  360
ESVKGRFTIS  RDNAKTTLYL  QMNSLRPEDT  AVYYCTIGGS  LSVSSQGTLV  TVSSGGGGSG  420
GGGSGGGGSG  GGGSGGGGSG  GGGSSGGPGP  AGMKGLPGSE  VQLVESGGGL  VQPGGSLRLS  480
CAASGFTFSS  YTLAWVRQAP  GKGLEWVAAI  DSSSYTYSPD  TVRGRFTISR  DNAKNSLYLQ  540
MNSLRAEDTA  VYYCARDSNW  DALDYWGQGT  TVTVSSGGGG  SGGGGSGGGG  SDIQMTQSPS  600
SLSASVGDRV  TITCKASQNV  GTNVGWYQQK  PGKAPKALIY  SASFRYSGVP  SRFSGSGSGT  660
DFTLTISSLQ  PEDFATYYCQ  QYYTYPYTFG  GGTKVEIKHH  HHHHEPEA           708

SEQ ID NO: 168          moltype = AA   length = 450
FEATURE                 Location/Qualifiers
source                  1..450
                        mol_type = protein
                        organism = synthetic construct
SEQUENCE: 168
MDMRVPAQLL  GLLLLWLRGA  RCEVQLVESG  GGLVQPGNSL  RLSCAASGFT  FSKFGMSWVR   60
QAPGKGLEWV  SSISGSGRDT  LYAESVKGRF  TISRDNAKTT  LYLQMNSLRP  EDTAVYYCTI  120
GGSLSVSSQG  TLVTVSSSGG  PGPAGMKGLP  GSCDLPQTHN  LRNKRALTLL  VQMRRLSPLS  180
CLKDRKDFGF  PQEKVDAQQI  KKAQAIPVLS  ELTQQILNIF  TSKDSSAAWN  TTLLDSFCND  240
LHQQLNDLQG  CLMQQVGVQE  FPLTQEDALL  AVRKYFHRIT  VYLREKKHSP  CAWEVVRAEV  300
WRALSSSANV  SGGPGPAGMK  GLPGSEVQLV  ESGGGLVQPG  NSLRLSCAAS  GFTFSKFGMS  360
WVRQAPGKGL  EWVSSISGSG  RDTLYAESVK  GRFTISRDNA  KTTLYLQMNS  LRPEDTAVYY  420
CTIGGSLSVS  SQGTLVTVSS  HHHHHHEPEA                                  450

SEQ ID NO: 169          moltype = AA   length = 198
FEATURE                 Location/Qualifiers
source                  1..198
                        mol_type = protein
                        organism = synthetic construct
SEQUENCE: 169
MDMRVPAQLL  GLLLLWLRGA  RCCDLPQTHN  LRNKRALTLL  VQMRRLSPLS  CLKDRKDFGF   60
PQEKVDAQQI  KKAQAIPVLS  ELTQQILNIF  TSKDSSAAWN  TTLLDSFCND  LHQQLNDLQG  120
CLMQQVGVQE  FPLTQEDALL  AVRKYFHRIT  VYLREKKHSP  CAWEVVRAEV  WRALSSSANV  180
LGRLREEKHH  HHHHEPEA                                                198

SEQ ID NO: 170          moltype = AA   length = 328
FEATURE                 Location/Qualifiers
source                  1..328
                        mol_type = protein
                        organism = synthetic construct
SEQUENCE: 170
MDMRVPAQLL  GLLLLWLRGA  RCEVQLVESG  GGLVQPGNSL  RLSCAASGFT  FSKFGMSWVR   60
QAPGKGLEWV  SSISGSGRDT  LYAESVKGRF  TISRDNAKTT  LYLQMNSLRP  EDTAVYYCTI  120
GGSLSVSSQG  TLVTVSSSGG  PGPAGMKGLP  GSCDLPQTHN  LRNKRALTLL  VQMRRLSPLS  180
CLKDRKDFGF  PQEKVDAQQI  KKAQAIPVLS  ELTQQILNIF  TSKDSSAAWN  TTLLDSFCND  240
LHQQLNDLQG  CLMQQVGVQE  FPLTQEDALL  AVRKYFHRIT  VYLREKKHSP  CAWEVVRAEV  300
WRALSSSANV  LGRLREEKHH  HHHHEPEA                                    328

SEQ ID NO: 171          moltype = AA   length = 328
FEATURE                 Location/Qualifiers
source                  1..328
                        mol_type = protein
                        organism = synthetic construct
SEQUENCE: 171
MDMRVPAQLL  GLLLLWLRGA  RCCDLPQTHN  LRNKRALTLL  VQMRRLSPLS  CLKDRKDFGF   60
PQEKVDAQQI  KKAQAIPVLS  ELTQQILNIF  TSKDSSAAWN  TTLLDSFCND  LHQQLNDLQG  120
CLMQQVGVQE  FPLTQEDALL  AVRKYFHRIT  VYLREKKHSP  CAWEVVRAEV  WRALSSSANV  180
LGRLREEKSG  GPGPAGMKGL  PGSEVQLVES  GGGLVQPGNS  LRLSCAASGF  TFSKFGMSWV  240
RQAPGKGLEW  VSSISGSGRD  TLYAESVKGR  FTISRDNAKT  TLYLQMNSLR  PEDTAVYYCT  300
IGGSLSVSSQ  GTLVTVSSHH  HHHHEPEA                                    328

SEQ ID NO: 172          moltype = AA   length = 1396
FEATURE                 Location/Qualifiers
source                  1..1396
                        mol_type = protein
                        organism = synthetic construct
SEQUENCE: 172
MDMRVPAQLL  GLLLLWLRGA  RCEAHKSEIA  HRYNDLGEQH  FKGLVLIAFS  QYLQKCSYDE   60
HAKLVQEVTD  FAKTCVADES  AANCDKSLHT  LFGDKLCAIP  NLRENYGELA  DCCTKQEPER  120
NECFLQHKDD  NPSLPPFERP  EAEAMCTSFK  ENPTTFMGHY  LHEVARRHPY  FYAPELLYYA  180
EQYNEILTQC  CAEADKESCL  TPKLDGVKEK  ALVSSVRQRM  KCSSMQKFGE  RAFKAWAVAR  240
LSQTFPNADF  AEITKLATDL  TKVNKECCHG  DLLECADDRA  ELAKYMCENQ  ATISSKLQTC  300
```

```
CDKPLLKKAH CLSEVEHDTM PADLPAIAAD FVEDQEVCKN YAEAKDVFLG TFLYEYSRRH   360
PDYSVSLLLR LAKKYEATLE KCCAEANPPA CYGTVLAEFQ PLVEEPKNLV KTNCDLYEKL   420
GEYGFQNAIL VRYTQKAPQV STPTLVEAAR NLGRVGTKCC TLPEDQRLPC VEDYLSAILN   480
RVCLLHEKTP VSEHVTKCCS GSLVERRPCF SALTVDETYV PKEFKAETFT FHSDICTLPE   540
KEKQIKKQTA LAELVKHKPK ATAEQLKTVM DDFAQFLDTC CKAADKDTCF STEGPNLVTR   600
CKDALASGGP GPAGMKGLPG SCDLPQTHNL RNKRALTLLV QMRRLSPLSC LKDRKDFGFP   660
QEKVDAQQIK KAQAIPVLSE LTQQILNIFT SKDSSAAWNT TLLDSFCNDL HQQLNDLQGC   720
LMQQVGVQEF PLTQEDALLA VRKYFHRITV YLREKKHSPC AWEVVRAEVW RALSSSANVL   780
GRLREEKSGG PGPAGMKGLP GSEAHKSEIA HRYNDLGEPH FKGLVLIAFS QYLQKCSYDE   840
HAKLVQEVTD FAKTCVADES AANCDKSLHT LFGDKLCAIP NLRENYGELA DCCTKQEPER   900
NECFLQHKDD NPSLPPFERP EAEAMCTSFK ENPTTFMGHY LHEVARRHPY FYAPELLYYA   960
EQYNEILTQC CAEADKESCL TPKLDGVKEK ALVSSVRQRM KCSSMQKFGE RAFKAWAVAR  1020
LSQTFPNADF AEITKLATDL TKVNKECCHG DLLECADDRA ELAKYMCENQ ATISSKLQTC  1080
CDKPLLKKAH CLSEVEHDTM PADLPAIAAD FVEDQEVCKN YAEAKDVFLG TFLYEYSRRH  1140
PDYSVSLLLR LAKKYEATLE KCCAEANPPA CYGTVLAEFQ PLVEEPKNLV KTNCDLYEKL  1200
GEYGFQNAIL VRYTQKAPQV STPTLVEAAR NLGRVGTKCC TLPEDQRLPC VEDYLSAILN  1260
RVCLLHEKTP VSEHVTKCCS GSLVERRPCF SALTVDETYV PKEFKAETFT FHSDICTLPE  1320
KEKQIKKQTA LAELVKHKPK ATAEQLKTVM DDFAQFLDTC CKAADKDTCF STEGPNLVTR  1380
CKDALAHHHH HHEPEA                                                  1396

SEQ ID NO: 173         moltype = AA   length = 797
FEATURE                Location/Qualifiers
source                 1..797
                       mol_type = protein
                       organism = synthetic construct
SEQUENCE: 173
MDMRVPAQLL GLLLLWLRGA RCEAHKSEIA HRYNDLGEQH FKGLVLIAFS QYLQKCSYDE    60
HAKLVQEVTD FAKTCVADES AANCDKSLHT LFGDKLCAIP NLRENYGELA DCCTKQEPER   120
NECFLQHKDD NPSLPPFERP EAEAMCTSFK ENPTTFMGHY LHEVARRHPY FYAPELLYYA   180
EQYNEILTQC CAEADKESCL TPKLDGVKEK ALVSSVRQRM KCSSMQKFGE RAFKAWAVAR   240
LSQTFPNADF AEITKLATDL TKVNKECCHG DLLECADDRA ELAKYMCENQ ATISSKLQTC   300
CDKPLLKKAH CLSEVEHDTM PADLPAIAAD FVEDQEVCKN YAEAKDVFLG TFLYEYSRRH   360
PDYSVSLLLR LAKKYEATLE KCCAEANPPA CYGTVLAEFQ PLVEEPKNLV KTNCDLYEKL   420
GEYGFQNAIL VRYTQKAPQV STPTLVEAAR NLGRVGTKCC TLPEDQRLPC VEDYLSAILN   480
RVCLLHEKTP VSEHVTKCCS GSLVERRPCF SALTVDETYV PKEFKAETFT FHSDICTLPE   540
KEKQIKKQTA LAELVKHKPK ATAEQLKTVM DDFAQFLDTC CKAADKDTCF STEGPNLVTR   600
CKDALASGGP GPAGMKGLPG SCDLPQTHNL RNKRALTLLV QMRRLSPLSC LKDRKDFGFP   660
QEKVDAQQIK KAQAIPVLSE LTQQILNIFT SKDSSAAWNT TLLDSFCNDL HQQLNDLQGC   720
LMQQVGVQEF PLTQEDALLA VRKYFHRITV YLREKKHSPC AWEVVRAEVW RALSSSANVL   780
GRLREEKHHH HHEPEA                                                   797

SEQ ID NO: 174         moltype = AA   length = 797
FEATURE                Location/Qualifiers
source                 1..797
                       mol_type = protein
                       organism = synthetic construct
SEQUENCE: 174
MDMRVPAQLL GLLLLWLRGA RCCDLPQTHN LRNKRALTLL VQMRRLSPLS CLKDRKDFGF    60
PQEKVDAQQI KKAQAIPVLS ELTQQILNIF TSKDSSAAWN TTLLDSFCND LHQQLNDLQG   120
CLMQQVGVQE FPLTQEDALL AVRKYFHRIT VYLREKKHSP CAWEVVRAEV WRALSSSANV   180
LGRLREEKSG GPGPAGMKGL PGSEAHKSEI AHRYNDLGEP HFKGLVLIAF SQYLQKCSYD   240
EHAKLVQEVT DFAKTCVADE SAANCDKSLH TLFGDKLCAI PNLRENYGEL ADCCTKQEPE   300
RNECFLQHKD DNPSLPPFER PEAEAMCTSF KENPTTFMGH YLHEVARRHP YFYAPELLYY   360
AEQYNEILTQ CCAEADKESC LTPKLDGVKE KALVSSVRQR MKCSSMQKFG ERAFKAWAVA   420
RLSQTFPNAD FAEITKLATD LTKVNKECCH GDLLECADDR AELAKYMCEN QATISSKLQT   480
CCDKPLLKKA HCLSEVEHDT MPADLPAIAA DFVEDQEVCK NYAEAKDVFL GTFLYEYSRR   540
HPDYSVSLLL RLAKKYEATL EKCCAEANPP ACYGTVLAEF QPLVEEPKNL VKTNCDLYEK   600
LGEYGFQNAI LVRYTQKAPQ VSTPTLVEAA RNLGRVGTKC CTLPEDQRLP CVEDYLSAIL   660
NRVCLLHEKT PVSEHVTKCC SGSLVERRPC FSALTVDETY VPKEFKAETF TFHSDICTLP   720
EKEKQIKKQT ALAELVKHKP KATAEQLKTV MDDFAQFLDT CCKAADKDTC FSTEGPNLVT   780
RCKDALAHHH HHHEPEA                                                  797

SEQ ID NO: 175         moltype = AA   length = 587
FEATURE                Location/Qualifiers
source                 1..587
                       mol_type = protein
                       organism = synthetic construct
SEQUENCE: 175
MDMRVPAQLL GLLLLWLRGA RCQVQLQESG GGLAQAGGSL SLSCAASGFT VSNSVMAWYR    60
QTPGKQREFV AIINSVGSTN YADSVKGRFT ISRDNAKNTV YLQMNNLKPE DTAVYVCNRN   120
FDRIYWGQGT QVTVSSGGGG SGGGGSGGGG SEVQLVESGG GLVQPGNSLR LSCAASGFTF   180
SKFGMSWVRQ APGKGLEWVS SISGSGRDTL YAESVKGRFT ISRDNAKTTL YLQMNSLRPE   240
DTAVYYCTIG GSLSVSSQGT LVTVSSSGGP GPAGMKGLPG SCDLPQTHNL RNKRALTLLV   300
QMRRLSPLSC LKDRKDFGFP QEKVDAQQIK KAQAIPVLSE LTQQILNIFT SKDSSAAWNT   360
TLLDSFCNDL HQQLNDLQGC LMQQVGVQEF PLTQEDALLA VRKYFHRITV YLREKKHSPC   420
AWEVVRAEVW RALSSSANVL GRLREEKSGG PGPAGMKGLP GSEVQLVESG GGLVQPGNSL   480
RLSCAASGFT FSKFGMSWVR QAPGKGLEWV SSISGSGRDT LYAESVKGRF TISRDNAKTT   540
LYLQMNSLRP EDTAVYYCTI GGSLSVSSQG TLVTVSSHHH HHHEPEA                 587
```

```
SEQ ID NO: 176            moltype = AA  length = 587
FEATURE                   Location/Qualifiers
source                    1..587
                          mol_type = protein
                          organism = synthetic construct
SEQUENCE: 176
MDMRVPAQLL GLLLLWLRGA RCEVQLVESG GGLVQPGNSL RLSCAASGFT FSKFGMSWVR   60
QAPGKGLEWV SSISGSGRDT LYAESVKGRF TISRDNAKTT LYLQMNSLRP EDTAVYYCTI  120
GGSLSVSSQG TLVTVSSSGG PGPAGMKGLP GSCDLPQTHN LRNKRALTLL VQMRRLSPLS  180
CLKDRKDFGF PQEKVDAQQI KKAQAIPVLS ELTQQILNIF TSKDSSAAWN TTLLDSFCND  240
LHQQLNDLQG CLMQQVGVQE FPLTQEDALL AVRKYFHRIT VYLREKKHSP CAWEVVRAEV  300
WRALSSSANV LGRLREEKSG GPGPAGMKGL PGSEVQLVES GGGLVQPGNS LRLSCAASGF  360
TFSKFGMSWV RQAPGKGLEW VSSISGSGRD TLYAESVKGR FTISRDNAKT TLYLQMNSLR  420
PEDTAVYYCT IGGSLSVSSQ GTLVTVSSGG GGSGGGGSGG GGSQVQLQES GGGLAQAGGS  480
LSLSCAASGF TVSNSVMAWY RQTPGKQREF VAIINSVGST NYADSVKGRF TISRDNAKNT  540
VYLQMNNLKP EDTAVYVCNR NFDRIYWGQG TQVTVSSHHH HHHEPEA              587

SEQ ID NO: 177            moltype = AA  length = 458
FEATURE                   Location/Qualifiers
source                    1..458
                          mol_type = protein
                          organism = synthetic construct
SEQUENCE: 177
MDMRVPAQLL GLLLLWLRGA RCEVQLVESG GGLVQPGNSL RLSCAASGFT FSKFGMSWVR   60
QAPGKGLEWV SSISGSGRDT LYAESVKGRF TISRDNAKTT LYLQMNSLRP EDTAVYYCTI  120
GGSLSVSSQG TLVTVSSGGG GSGGGGSGGG GSCDLPQTHN LRNKRALTLL VQMRRLSPLS  180
CLKDRKDFGF PQEKVDAQQI KKAQAIPVLS ELTQQILNIF TSKDSSAAWN TTLLDSFCND  240
LHQQLNDLQG CLMQQVGVQE FPLTQEDALL AVRKYFHRIT VYLREKKHSP CAWEVVRAEV  300
WRALSSSANV LGRLREEKGG GGSGGGGSGG GGSEVQLVES GGGLVQPGNS LRLSCAASGF  360
TFSKFGMSWV RQAPGKGLEW VSSISGSGRD TLYAESVKGR FTISRDNAKT TLYLQMNSLR  420
PEDTAVYYCT IGGSLSVSSQ GTLVTVSSHH HHHHEPEA                        458

SEQ ID NO: 178            moltype = AA  length = 579
FEATURE                   Location/Qualifiers
source                    1..579
                          mol_type = protein
                          organism = synthetic construct
SEQUENCE: 178
MDMRVPAQLL GLLLLWLRGA RCAPTSSSTK KTQLQLEHLL LDLQMILNGI NNYKNPKLTR   60
MLTFKFYMPK KATELKHLQC LEEELKPLEE VLNLAQSKNF HLRPRDLISN INVIVLELKG  120
SETTFMCEYA DETATIVEFL NRWITFCQSI ISTLTSGGPG PAGLYAQPGS EVQLVESGGG  180
LVQPGNSLRL SCAASGFTFS KFGMSWVRQA PGKGLEWVSS ISGSGRDTLY AESVKGRFTI  240
SRDNAKTTLY LQMNSLRPED TAVYYCTIGG SLSVSSQGTL VTVSSGGGGS GGGGSGGGGS  300
GGGGSGGGGS GGGGSSGGPG PAGLYAQPGS EVQLVESGGG LVQPGGSLRL SCAASGFTFS  360
SYTLAWVRQA PGKGLEWVAA IDSSSYTYSP DTVRGRFTIS RDNAKNSLYL QMNSLRAEDT  420
AVYYCARDSN WDALDYWGQG TTVTVSSGGG GSGGGGSGGG GSDIQMTQSP SSLSASVGDR  480
VTITCKASQN VGTNVGWYQQ KPGKAPKALI YSASFRYSGV PSRFSGSGSG TDFTLTISSL  540
QPEDFATYYC QQYYTYPYTF GGGTKVEIKH HHHHHEPEA                       579

SEQ ID NO: 179            moltype = AA  length = 579
FEATURE                   Location/Qualifiers
source                    1..579
                          mol_type = protein
                          organism = synthetic construct
SEQUENCE: 179
MDMRVPAQLL GLLLLWLRGA RCAPTSSSTK KTQLQLEHLL LDLQMILNGI NNYKNPKLTR   60
MLTFKFYMPK KATELKHLQC LEEELKPLEE VLNLAQSKNF HLRPRDLISN INVIVLELKG  120
SETTFMCEYA DETATIVEFL NRWITFCQSI ISTLTSGGPP GGPAGIGPGS EVQLVESGGG  180
LVQPGNSLRL SCAASGFTFS KFGMSWVRQA PGKGLEWVSS ISGSGRDTLY AESVKGRFTI  240
SRDNAKTTLY LQMNSLRPED TAVYYCTIGG SLSVSSQGTL VTVSSGGGGS GGGGSGGGGS  300
GGGGSGGGGS GGGGSSGGPP GGPAGIGPGS EVQLVESGGG LVQPGGSLRL SCAASGFTFS  360
SYTLAWVRQA PGKGLEWVAA IDSSSYTYSP DTVRGRFTIS RDNAKNSLYL QMNSLRAEDT  420
AVYYCARDSN WDALDYWGQG TTVTVSSGGG GSGGGGSGGG GSDIQMTQSP SSLSASVGDR  480
VTITCKASQN VGTNVGWYQQ KPGKAPKALI YSASFRYSGV PSRFSGSGSG TDFTLTISSL  540
QPEDFATYYC QQYYTYPYTF GGGTKVEIKH HHHHHEPEA                       579

SEQ ID NO: 180            moltype = AA  length = 579
FEATURE                   Location/Qualifiers
source                    1..579
                          mol_type = protein
                          organism = synthetic construct
SEQUENCE: 180
MDMRVPAQLL GLLLLWLRGA RCAPTSSSTK KTQLQLEHLL LDLQMILNGI NNYKNPKLTR   60
MLTFKFYMPK KATELKHLQC LEEELKPLEE VLNLAQSKNF HLRPRDLISN INVIVLELKG  120
SETTFMCEYA DETATIVEFL NRWITFCQSI ISTLTSGGPA LFKSSFPPGS EVQLVESGGG  180
LVQPGNSLRL SCAASGFTFS KFGMSWVRQA PGKGLEWVSS ISGSGRDTLY AESVKGRFTI  240
SRDNAKTTLY LQMNSLRPED TAVYYCTIGG SLSVSSQGTL VTVSSGGGGS GGGGSGGGGS  300
GGGGSGGGGS GGGGSSGGPA LFKSSFPPGS EVQLVESGGG LVQPGGSLRL SCAASGFTFS  360
SYTLAWVRQA PGKGLEWVAA IDSSSYTYSP DTVRGRFTIS RDNAKNSLYL QMNSLRAEDT  420
```

```
AVYYCARDSN WDALDYWGQG TTVTVSSGGG GSGGGGSGGG GSDIQMTQSP SSLSASVGDR    480
VTITCKASQN VGTNVGWYQQ KPGKAPKALI YSASFRYSGV PSRFSGSGSG TDFTLTISSL    540
QPEDFATYYC QQYYTYPYTF GGGTKVEIKH HHHHHEPEA                          579

SEQ ID NO: 181          moltype = AA   length = 581
FEATURE                 Location/Qualifiers
source                  1..581
                        mol_type = protein
                        organism = synthetic construct
SEQUENCE: 181
MDMRVPAQLL GLLLLWLRGA RCAPTSSSTK KTQLQLEHLL LDLQMILNGI NNYKNPKLTR    60
MLTFKFYMPK KATELKHLQC LEEELKPLEE VLNLAQSKNF HLRPRDLISN INVIVLELKG    120
SETTFMCEYA DETATIVEFL NRWITFCQSI ISTLTSGGPP LAQKLKSSPG SEVQLVESGG    180
GLVQPGNSLR LSCAASGFTF SKFGMSWVRQ APGKGLEWVS SISGSGRDTL YAESVKGRFT    240
ISRDNAKTTL YLQMNSLRPE DTAVYYCTIG GSLVSSQGT LVTVSSGGGG SGGGGSGGGG    300
SGGGGSGGGG SGGGGSSGGP PLAQKLKSSP GSEVQLVESG GGLVQPGGSL RLSCAASGFT    360
FSSYTLAWVR QAPGKGLEWV AAIDSSSYTY SPDTVRGRFT ISRDNAKNSL YLQMNSLRAE    420
DTAVYYCARD SNWDALDYWG QGTTVTVSSG GGGSGGGGSG GGGSDIQMTQ SPSSLSASVG    480
DRVTITCKAS QNVGTNVGWY QQKPGKAPKA LIYSASFRYS GVPSRFSGSG SGTDFTLTIS    540
SLQPEDFATY YCQQYYTYPY TFGGGTKVEI KHHHHHHEPE A                       581

SEQ ID NO: 182          moltype = AA   length = 613
FEATURE                 Location/Qualifiers
source                  1..613
                        mol_type = protein
                        organism = synthetic construct
SEQUENCE: 182
MDMRVPAQLL GLLLLWLRGA RCAPTSSSTK KTQLQLEHLL LDLQMILNGI NNYKNPKLTR    60
MLTFKFYMPK KATELKHLQC LEEELKPLEE VLNLAQSKNF HLRPRDLISN INVIVLELKG    120
SETTFMCEYA DETATIVEFL NRWITFCQSI ISTLTSGGPP GGPAGIGALF KSSFPPLAQK    180
LKSSPGSEVQ LVESGGGLVQ PGNSLRLSCA ASGFTFSKFG MSWVRQAPGK GLEWVSSISG    240
SGRDTLYAES VKGRFTISRD NAKTTLYLQM NSLRPEDTAV YYCTIGGSLS VSSQGTLVTV    300
SSGGGGSGGG GSGGGGSGGG GSGGGGSGGG GSSGGPPGGP AGIGALFKSS FPPLAQKLKS    360
SPGSEVQLVE SGGGLVQPGG SLRLSCAASG FTFSSYTLAW VRQAPGKGLE WVAAIDSSSY    420
TYSPDTVRGR FTISRDNAKN SLYLQMNSLR AEDTAVYYCA RDSNWDALDY WGQGTTVTVS    480
SGGGGSGGGG SGGGGSDIQM TQSPSSLSAS VGDRVTITCK ASQNVGTNVG WYQQKPGKAP    540
KALIYSASFR YSGVPSRFSG SGSGTDFTLT ISSLQPEDFA TYYCQQYYTY PYTFGGGTKV    600
EIKHHHHHHE PEA                                                     613

SEQ ID NO: 183          moltype =      length =
SEQUENCE: 183
000

SEQ ID NO: 184          moltype =      length =
SEQUENCE: 184
000

SEQ ID NO: 185          moltype =      length =
SEQUENCE: 185
000

SEQ ID NO: 186          moltype =      length =
SEQUENCE: 186
000

SEQ ID NO: 187          moltype =      length =
SEQUENCE: 187
000

SEQ ID NO: 188          moltype =      length =
SEQUENCE: 188
000

SEQ ID NO: 189          moltype =      length =
SEQUENCE: 189
000

SEQ ID NO: 190          moltype =      length =
SEQUENCE: 190
000

SEQ ID NO: 191          moltype = AA   length = 267
FEATURE                 Location/Qualifiers
source                  1..267
                        mol_type = protein
                        organism = synthetic construct
SEQUENCE: 191
MDMRVPAQLL GLLLLWLRGA RCEVQLVESG GGLVQPGGSL RLSCAASGFT FSSYTLAWVR    60
QAPGKGLEWV AAIDSSSYTY SPDTVRGRFT ISRDNAKNSL YLQMNSLRAE DTAVYYCARD    120
```

```
SNWDALDYWG QGTTVTVSSG GGGSGGGGSG GGGSDIQMTQ SPSSLSASVG DRVTITCKAS    180
QNVGTNVGWY QQKPGKAPKA LIYSASFRYS GVPSRFSGSG SGTDFTLTIS SLQPEDFATY    240
YCQQYYTYPY TFGGGTKVEI KHHHHHH                                        267

SEQ ID NO: 192          moltype = AA  length = 269
FEATURE                 Location/Qualifiers
source                  1..269
                        mol_type = protein
                        organism = synthetic construct
SEQUENCE: 192
MDMRVPAQLL GLLLLWLRGA RCQSVLTQPP SVSGAPGQRV TISCSGSRSN IGSNTVKWYQ     60
QLPGTAPKLL IYYNDQRPSG VPDRFSGSKS GTSASLAITG LQAEDEADYY CQSYDRYTHP    120
ALLFGTGTKV TVLGGGGSGG GGSGGGGSQV QLVESGGGVV QPGRSLRLSC AASGFTFSSY    180
GMHWVRQAPG KGLEWVAFIR YDGSNKYYAD SVKGRFTISR DNSKNTLYLQ MNSLRAEDTA    240
VYYCKTHGSH DNWGQGTMVT VSSHHHHHH                                      269

SEQ ID NO: 193          moltype = AA  length = 171
FEATURE                 Location/Qualifiers
source                  1..171
                        mol_type = protein
                        organism = synthetic construct
SEQUENCE: 193
CDLPQTHSLG SRRTLMLLAQ MRRISLFSCL KDRHDFGFPQ EEFGNQFQKA ETIPVLHEMI     60
QQIFNLFSTK DSSAAWDETL LDKFYTELYQ QLNDLEACVI QGVGVTETPL MKEDSILAVR    120
KYFQRITLYL KEKKYSPCAW EVVRAEIMRS FSLSTNLQES LRSKEHHHHH H             171

SEQ ID NO: 194          moltype = AA  length = 520
FEATURE                 Location/Qualifiers
source                  1..520
                        mol_type = protein
                        organism = synthetic construct
SEQUENCE: 194
IWELKKDVYV VELDWYPDAP GEMVVLTCDT PEEDGITWTL DQSSEVLGSG KTLTIQVKEF     60
GDAGQYTCHK GGEVLSHSLL LLHKKEDGIW STDILKDQKE PKNKTFLRCE AKNYSGRFTC    120
WWLTTISTDL TFSVKSSRGS SDPQGVTCGA ATLSAERVRG DNKEYEYSVE CQEDSACPAA    180
EESLPIEVMV DAVHKLKYEN YTSSFFIRDI IKPDPPKNLQ LKPLKNSRQV EVSWEYPDTW    240
STPHSYFSLT FCVQVQGKSK REKKDRVFTD KTSATVICRK NASISVRAQD RYYSSSWSEW    300
ASVPCSGGGG SGGGGSGGGG SRVIPVSGPA RCLSQSRNLL KTTDDMVKTA REKLKHYSCT    360
AEDIDHEDIT RDQTSTLKTC LPLELHKNES CLATRETSST TRGSCLPPQK TSLMMTLCLG    420
SIYEDLKMYQ TEFQAINAAL QNHNHQQIIL DKGMLVAIDE LMQSLNHNGE TLRQKPPVGE    480
ADPYRVKMKL CILLHAFSTR VVTINRVMGY LSSAHHHHHH                          520

SEQ ID NO: 195          moltype = AA  length = 141
FEATURE                 Location/Qualifiers
source                  1..141
                        mol_type = protein
                        organism = synthetic construct
SEQUENCE: 195
QVQLQESGGG LVQAGGSLRL SCAASGRTFS SVYDMGWFRQ APGKDREFVA RITESARNTR     60
YADSVRGRFT ISRDNAKNTV YLQMNNLELE DAAVYYCAAD PQTVVVGTPD YWGQGTQVTV    120
SSAAAYPYDV PDYGSHHHHH H                                              141

SEQ ID NO: 196          moltype = AA  length = 247
FEATURE                 Location/Qualifiers
source                  1..247
                        mol_type = protein
                        organism = synthetic construct
SEQUENCE: 196
QSVLTQPPSV SGAPGQRVTI SCTGSSSNIG SNTVKWYQQL PGTAPKLLIY GNDQRPSGVP     60
DRFSGSKSGT SASLAITGLQ AEDEADYYCQ SYDRYTHPAY VFGTGTKVTV LGGGGSGGGG    120
SGGGGSQVQL VESGGGVVQP GRSLRLSCAA SGFTFSSYGM HWVRQAPGKG LEWVAFIRYD    180
GSNKYYADSV KGRFTISRDN SKNTLYLQMN SLRAEDTAVY YCKTHGSHDN WGQGTMVTVS    240
SHHHHHH                                                              247

SEQ ID NO: 197          moltype = AA  length = 247
FEATURE                 Location/Qualifiers
source                  1..247
                        mol_type = protein
                        organism = synthetic construct
SEQUENCE: 197
QSVLTQPPSV SGAPGQRVTI SCTGSSSNIG SNTVKWYQQL PGTAPKLLIY YNDQRPSGVP     60
DRFSGSKSGT SASLAITGLQ AEDEADYYCQ SYDRYTHPAY VFGTGTKVTV LGGGGSGGGG    120
SGGGGSQVQL VESGGGVVQP GRSLRLSCAA SGFTFSSYGM HWVRQAPGKG LEWVAFIRYD    180
GSNKYYADSV KGRFTISRDN SKNTLYLQMN SLRAEDTAVY YCKTHGSHDN WGQGTMVTVS    240
SHHHHHH                                                              247

SEQ ID NO: 198          moltype = AA  length = 247
FEATURE                 Location/Qualifiers
source                  1..247
```

```
                            mol_type = protein
                            organism = synthetic construct
SEQUENCE: 198
QSVLTQPPSV SGAPGQRVTI SCSGSRSNIG SNTVKWYQQL PGTAPKLLIY YNDQRPSGVP    60
DRFSGSKSGT SASLAITGLQ AEDEADYYCQ SYDRYTHPAL LFGTGTKVTV LGGGGSGGGG   120
SGGGGSQVQL VESGGGVVQP GRSLRLSCAA SGFTFSSYAM HWVRQAPGKG LEWVAVISYD   180
GSNKYYADSV KGRFTISRDN SKNTLYLQMN SLRAEDTAVY YCARHGSHDN WGQGTMVTVS   240
SHHHHHH                                                            247

SEQ ID NO: 199           moltype = AA   length = 247
FEATURE                  Location/Qualifiers
source                   1..247
                         mol_type = protein
                         organism = synthetic construct
SEQUENCE: 199
QSVLTQPPSV SGAPGQRVTI SCSGSRSNIG SNTVKWYQQL PGTAPKLLIY YNDQRPSGVP    60
DRFSGSKSGT SASLAITGLQ AEDEADYYCQ SYDRYTHPAL LFGTGTKVTV LGGGGSGGGG   120
SGGGGSQVQL VESGGGVVQP GRSLRLSCAA SGFTFSSYGM HWVRQAPGKG LEWVAFIRYE   180
GSNKYYADSV KGRFTISRDN SKNTLYLQMN SLRAEDTAVY YCKTHGSHDN WGQGTMVTVS   240
SHHHHHH                                                            247

SEQ ID NO: 200           moltype = AA   length = 247
FEATURE                  Location/Qualifiers
source                   1..247
                         mol_type = protein
                         organism = synthetic construct
SEQUENCE: 200
QSVLTQPPSV SGAPGQRVTI SCSGSRSNIG SNTVKWYQQL PGTAPKLLIY YNDQRPSGVP    60
DRFSGSKSGT SASLAITGLQ AEDEADYYCQ SYDRYTHPAL LFGTGTKVTV LGGGGSGGGG   120
SGGGGSQVQL VESGGGVVQP GRSLRLSCAA SGFTFSSYGM HWVRQAPGKG LEWVAFIRYD   180
GSNKYYAESV KGRFTISRDN SKNTLYLQMN SLRAEDTAVY YCKTHGSHDN WGQGTMVTVS   240
SHHHHHH                                                            247

SEQ ID NO: 201           moltype = AA   length = 247
FEATURE                  Location/Qualifiers
source                   1..247
                         mol_type = protein
                         organism = synthetic construct
SEQUENCE: 201
QSVLTQPPSV SGAPGQRVTI SCSGSRSNIG SQTVKWYQQL PGTAPKLLIY YNDQRPSGVP    60
DRFSGSKSGT SASLAITGLQ AEDEADYYCQ SYERYTHPAL LFGTGTKVTV LGGGGSGGGG   120
SGGGGSQVQL VESGGGVVQP GRSLRLSCAA SGFTFSSYGM HWVRQAPGKG LEWVAFIRYD   180
GSNKYYADSV KGRFTISRDN SKNTLYLQMN SLRAEDTAVY YCKTHGSHDN WGQGTMVTVS   240
SHHHHHH                                                            247

SEQ ID NO: 202           moltype = AA   length = 247
FEATURE                  Location/Qualifiers
source                   1..247
                         mol_type = protein
                         organism = synthetic construct
SEQUENCE: 202
QSVLTQPPSV SGAPGQRVTI SCSGSRSNIG SQTVKWYQQL PGTAPKLLIY YNDQRPSGVP    60
DRFSGSKSGT SASLAITGLQ AEDEADYYCQ SYSRYTHPAL LFGTGTKVTV LGGGGSGGGG   120
SGGGGSQVQL VESGGGVVQP GRSLRLSCAA SGFTFSSYGM HWVRQAPGKG LEWVAFIRYD   180
GSNKYYADSV KGRFTISRDN SKNTLYLQMN SLRAEDTAVY YCKTHGSHDN WGQGTMVTVS   240
SHHHHHH                                                            247

SEQ ID NO: 203           moltype = AA   length = 247
FEATURE                  Location/Qualifiers
source                   1..247
                         mol_type = protein
                         organism = synthetic construct
SEQUENCE: 203
QSVLTQPPSV SGAPGQRVTI SCSGSESNIG SNTVKWYQQL PGTAPKLLIY YNDQRPSGVP    60
DRFSGSKSGT SASLAITGLQ AEDEADYYCQ SYDRYTHPAL LFGTGTKVTV LGGGGSGGGG   120
SGGGGSQVQL VESGGGVVQP GRSLRLSCAA SGFTFSSYGM HWVRQAPGKG LEWVAFIRYD   180
GSNKYYADSV KGRFTISRDN SKNTLYLQMN SLRAEDTAVY YCKTHGSHDN WGQGTMVTVS   240
SHHHHHH                                                            247

SEQ ID NO: 204           moltype = AA   length = 247
FEATURE                  Location/Qualifiers
source                   1..247
                         mol_type = protein
                         organism = synthetic construct
SEQUENCE: 204
QSVLTQPPSV SGAPGQRVTI SCSGSSSNIG SNTVKWYQQL PGTAPKLLIY YNDQRPSGVP    60
DRFSGSKSGT SASLAITGLQ AEDEADYYCQ SYDRYTHPAL LFGTGTKVTV LGGGGSGGGG   120
SGGGGSQVQL VESGGGVVQP GRSLRLSCAA SGFTFSSYGM HWVRQAPGKG LEWVAFIRYD   180
GSNKYYADSV KGRFTISRDN SKNTLYLQMN SLRAEDTAVY YCKTHGSHDN WGQGTMVTVS   240
```

```
SHHHHHH                                                                             247

SEQ ID NO: 205              moltype = AA   length = 247
FEATURE                     Location/Qualifiers
source                      1..247
                            mol_type = protein
                            organism = synthetic construct
SEQUENCE: 205
QSVLTQPPSV SGAPGQRVTI SCSGSRSNIG DNTVKWYQQL PGTAPKLLIY YNDQRPSGVP    60
DRFSGSKSGT SASLAITGLQ AEDEADYYCQ SYDRYTHPAL LFGTGTKVTV LGGGGSGGGG   120
SGGGGSQVQL VESGGGVVQP GRSLRLSCAA SGFTFSSYGM HWVRQAPGKG LEWVAFIRYD   180
GSNKYYADSV KGRFTISRDN SKNTLYLQMN SLRAEDTAVY YCKTHGSHDN WGQGTMVTVS   240
SHHHHHH                                                            247

SEQ ID NO: 206              moltype = AA   length = 247
FEATURE                     Location/Qualifiers
source                      1..247
                            mol_type = protein
                            organism = synthetic construct
SEQUENCE: 206
QSVLTQPPSV SGAPGQRVTI SCSGSRSNIG ENTVKWYQQL PGTAPKLLIY YNDQRPSGVP    60
DRFSGSKSGT SASLAITGLQ AEDEADYYCQ SYDRYTHPAL LFGTGTKVTV LGGGGSGGGG   120
SGGGGSQVQL VESGGGVVQP GRSLRLSCAA SGFTFSSYGM HWVRQAPGKG LEWVAFIRYD   180
GSNKYYADSV KGRFTISRDN SKNTLYLQMN SLRAEDTAVY YCKTHGSHDN WGQGTMVTVS   240
SHHHHHH                                                            247

SEQ ID NO: 207              moltype = AA   length = 247
FEATURE                     Location/Qualifiers
source                      1..247
                            mol_type = protein
                            organism = synthetic construct
SEQUENCE: 207
QSVLTQPPSV SGAPGQRVTI SCSGSRSNIG SDTVKWYQQL PGTAPKLLIY YNDQRPSGVP    60
DRFSGSKSGT SASLAITGLQ AEDEADYYCQ SYDRYTHPAL LFGTGTKVTV LGGGGSGGGG   120
SGGGGSQVQL VESGGGVVQP GRSLRLSCAA SGFTFSSYGM HWVRQAPGKG LEWVAFIRYD   180
GSNKYYADSV KGRFTISRDN SKNTLYLQMN SLRAEDTAVY YCKTHGSHDN WGQGTMVTVS   240
SHHHHHH                                                            247

SEQ ID NO: 208              moltype = AA   length = 247
FEATURE                     Location/Qualifiers
source                      1..247
                            mol_type = protein
                            organism = synthetic construct
SEQUENCE: 208
QSVLTQPPSV SGAPGQRVTI SCSGSRSNIG SETVKWYQQL PGTAPKLLIY YNDQRPSGVP    60
DRFSGSKSGT SASLAITGLQ AEDEADYYCQ SYDRYTHPAL LFGTGTKVTV LGGGGSGGGG   120
SGGGGSQVQL VESGGGVVQP GRSLRLSCAA SGFTFSSYGM HWVRQAPGKG LEWVAFIRYD   180
GSNKYYADSV KGRFTISRDN SKNTLYLQMN SLRAEDTAVY YCKTHGSHDN WGQGTMVTVS   240
SHHHHHH                                                            247

SEQ ID NO: 209              moltype = AA   length = 247
FEATURE                     Location/Qualifiers
source                      1..247
                            mol_type = protein
                            organism = synthetic construct
SEQUENCE: 209
QSVLTQPPSV SGAPGQRVTI SCSGSRSNIG SNDVKWYQQL PGTAPKLLIY YNDQRPSGVP    60
DRFSGSKSGT SASLAITGLQ AEDEADYYCQ SYDRYTHPAL LFGTGTKVTV LGGGGSGGGG   120
SGGGGSQVQL VESGGGVVQP GRSLRLSCAA SGFTFSSYGM HWVRQAPGKG LEWVAFIRYD   180
GSNKYYADSV KGRFTISRDN SKNTLYLQMN SLRAEDTAVY YCKTHGSHDN WGQGTMVTVS   240
SHHHHHH                                                            247

SEQ ID NO: 210              moltype = AA   length = 247
FEATURE                     Location/Qualifiers
source                      1..247
                            mol_type = protein
                            organism = synthetic construct
SEQUENCE: 210
QSVLTQPPSV SGAPGQRVTI SCSGSRSNIG SNTVDWYQQL PGTAPKLLIY YNDQRPSGVP    60
DRFSGSKSGT SASLAITGLQ AEDEADYYCQ SYDRYTHPAL LFGTGTKVTV LGGGGSGGGG   120
SGGGGSQVQL VESGGGVVQP GRSLRLSCAA SGFTFSSYGM HWVRQAPGKG LEWVAFIRYD   180
GSNKYYADSV KGRFTISRDN SKNTLYLQMN SLRAEDTAVY YCKTHGSHDN WGQGTMVTVS   240
SHHHHHH                                                            247

SEQ ID NO: 211              moltype = AA   length = 247
FEATURE                     Location/Qualifiers
source                      1..247
                            mol_type = protein
                            organism = synthetic construct
```

```
SEQUENCE: 211
QSVLTQPPSV SGAPGQRVTI SCSGSRSNIG SNTVEWYQQL PGTAPKLLIY YNDQRPSGVP    60
DRFSGSKSGT SASLAITGLQ AEDEADYYCQ SYDRYTHPAL LFGTGTKVTV LGGGGSGGGG   120
SGGGGSQVQL VESGGGVVQP GRSLRLSCAA SGFTFSSYGM HWVRQAPGKG LEWVAFIRYD   180
GSNKYYADSV KGRFTISRDN SKNTLYLQMN SLRAEDTAVY YCKTHGSHDN WGQGTMVTVS   240
SHHHHHH                                                             247

SEQ ID NO: 212          moltype = AA  length = 247
FEATURE                 Location/Qualifiers
source                  1..247
                        mol_type = protein
                        organism = synthetic construct
SEQUENCE: 212
QSVLTQPPSV SGAPGQRVTI SCSGSRSNIG SNTVKWYQQL PGTAPKLLIY YNDQDPSGVP    60
DRFSGSKSGT SASLAITGLQ AEDEADYYCQ SYDRYTHPAL LFGTGTKVTV LGGGGSGGGG   120
SGGGGSQVQL VESGGGVVQP GRSLRLSCAA SGFTFSSYGM HWVRQAPGKG LEWVAFIRYD   180
GSNKYYADSV KGRFTISRDN SKNTLYLQMN SLRAEDTAVY YCKTHGSHDN WGQGTMVTVS   240
SHHHHHH                                                             247

SEQ ID NO: 213          moltype = AA  length = 247
FEATURE                 Location/Qualifiers
source                  1..247
                        mol_type = protein
                        organism = synthetic construct
SEQUENCE: 213
QSVLTQPPSV SGAPGQRVTI SCSGSRSNIG SNTVKWYQQL PGTAPKLLIY YNDQEPSGVP    60
DRFSGSKSGT SASLAITGLQ AEDEADYYCQ SYDRYTHPAL LFGTGTKVTV LGGGGSGGGG   120
SGGGGSQVQL VESGGGVVQP GRSLRLSCAA SGFTFSSYGM HWVRQAPGKG LEWVAFIRYD   180
GSNKYYADSV KGRFTISRDN SKNTLYLQMN SLRAEDTAVY YCKTHGSHDN WGQGTMVTVS   240
SHHHHHH                                                             247

SEQ ID NO: 214          moltype = AA  length = 247
FEATURE                 Location/Qualifiers
source                  1..247
                        mol_type = protein
                        organism = synthetic construct
SEQUENCE: 214
QSVLTQPPSV SGAPGQRVTI SCSGSRSNIG SNTVKWYQQL PGTAPKLLIY YNDQRPDGVP    60
DRFSGSKSGT SASLAITGLQ AEDEADYYCQ SYDRYTHPAL LFGTGTKVTV LGGGGSGGGG   120
SGGGGSQVQL VESGGGVVQP GRSLRLSCAA SGFTFSSYGM HWVRQAPGKG LEWVAFIRYD   180
GSNKYYADSV KGRFTISRDN SKNTLYLQMN SLRAEDTAVY YCKTHGSHDN WGQGTMVTVS   240
SHHHHHH                                                             247

SEQ ID NO: 215          moltype = AA  length = 247
FEATURE                 Location/Qualifiers
source                  1..247
                        mol_type = protein
                        organism = synthetic construct
SEQUENCE: 215
QSVLTQPPSV SGAPGQRVTI SCSGSRSNIG SNTVKWYQQL PGTAPKLLIY YNDQRPSGVP    60
DRFSGSKSGT SASLAITGLQ AEDEADYYCQ SYDEYTHPAL LFGTGTKVTV LGGGGSGGGG   120
SGGGGSQVQL VESGGGVVQP GRSLRLSCAA SGFTFSSYGM HWVRQAPGKG LEWVAFIRYD   180
GSNKYYADSV KGRFTISRDN SKNTLYLQMN SLRAEDTAVY YCKTHGSHDN WGQGTMVTVS   240
SHHHHHH                                                             247

SEQ ID NO: 216          moltype = AA  length = 247
FEATURE                 Location/Qualifiers
source                  1..247
                        mol_type = protein
                        organism = synthetic construct
SEQUENCE: 216
QSVLTQPPSV SGAPGQRVTI SCSGSRSNIG SNTVKWYQQL PGTAPKLLIY YNDQRPSGVP    60
DRFSGSKSGT SASLAITGLQ AEDEADYYCQ SYDRYTDPAL LFGTGTKVTV LGGGGSGGGG   120
SGGGGSQVQL VESGGGVVQP GRSLRLSCAA SGFTFSSYGM HWVRQAPGKG LEWVAFIRYD   180
GSNKYYADSV KGRFTISRDN SKNTLYLQMN SLRAEDTAVY YCKTHGSHDN WGQGTMVTVS   240
SHHHHHH                                                             247

SEQ ID NO: 217          moltype = AA  length = 247
FEATURE                 Location/Qualifiers
source                  1..247
                        mol_type = protein
                        organism = synthetic construct
SEQUENCE: 217
QSVLTQPPSV SGAPGQRVTI SCSGSESNIG SNTVKWYQQL PGTAPKLLIY YNDQEPSGVP    60
DRFSGSKSGT SASLAITGLQ AEDEADYYCQ SYDEYTHPAL LFGTGTKVTV LGGGGSGGGG   120
SGGGGSQVQL VESGGGVVQP GRSLRLSCAA SGFTFSSYGM HWVRQAPGKG LEWVAFIRYD   180
GSNKYYADSV KGRFTISRDN SKNTLYLQMN SLRAEDTAVY YCKTHGSHDN WGQGTMVTVS   240
SHHHHHH                                                             247
```

```
SEQ ID NO: 218            moltype = AA   length = 247
FEATURE                   Location/Qualifiers
source                    1..247
                          mol_type = protein
                          organism = synthetic construct
SEQUENCE: 218
QSVLTQPPSV SGAPGQRVTI SCSGSESNIG SNDVKWYQQL PGTAPKLLIY YNDQRPSGVP    60
DRFSGSKSGT SASLAITGLQ AEDEADYYCQ SYDRYTHPAL LFGTGTKVTV LGGGGSGGGG   120
SGGGGSQVQL VESGGGVVQP GRSLRLSCAA SGFTFSSYGM HWVRQAPGKG LEWVAFIRYD   180
GSNKYYADSV KGRFTISRDN SKNTLYLQMN SLRAEDTAVY YCKTHGSHDN WGQGTMVTVS   240
SHHHHHH                                                             247

SEQ ID NO: 219            moltype = AA   length = 247
FEATURE                   Location/Qualifiers
source                    1..247
                          mol_type = protein
                          organism = synthetic construct
SEQUENCE: 219
QSVLTQPPSV SGAPGQRVTI SCSGSRSNIG SNTVKWYQQL PGTAPKLLIY YNDQRPSGVP    60
DRFSGSKSGT SASLAITGLQ AEDEADYYCQ SYDRYTHPAL LFGTGTKVTV LGGGGSGGGG   120
SGGGGSQVQL VESGGGVVQP GRSLRLSCAA SGFTFESYGM HWVRQAPGKG LEWVAFIRYD   180
GSNKYYADSV KGRFTISRDN SKNTLYLQMN SLRAEDTAVY YCKTHGSHDN WGQGTMVTVS   240
SHHHHHH                                                             247

SEQ ID NO: 220            moltype = AA   length = 247
FEATURE                   Location/Qualifiers
source                    1..247
                          mol_type = protein
                          organism = synthetic construct
SEQUENCE: 220
QSVLTQPPSV SGAPGQRVTI SCSGSRSNIG SNTVKWYQQL PGTAPKLLIY YNDQRPSGVP    60
DRFSGSKSGT SASLAITGLQ AEDEADYYCQ SYDRYTHPAL LFGTGTKVTV LGGGGSGGGG   120
SGGGGSQVQL VESGGGVVQP GRSLRLSCAA SGFTFSEYGM HWVRQAPGKG LEWVAFIRYD   180
GSNKYYADSV KGRFTISRDN SKNTLYLQMN SLRAEDTAVY YCKTHGSHDN WGQGTMVTVS   240
SHHHHHH                                                             247

SEQ ID NO: 221            moltype = AA   length = 247
FEATURE                   Location/Qualifiers
source                    1..247
                          mol_type = protein
                          organism = synthetic construct
SEQUENCE: 221
QSVLTQPPSV SGAPGQRVTI SCSGSRSNIG SNTVKWYQQL PGTAPKLLIY YNDQRPSGVP    60
DRFSGSKSGT SASLAITGLQ AEDEADYYCQ SYDRYTHPAL LFGTGTKVTV LGGGGSGGGG   120
SGGGGSQVQL VESGGGVVQP GRSLRLSCAA SGFTFSDYGM HWVRQAPGKG LEWVAFIRYD   180
GSNKYYADSV KGRFTISRDN SKNTLYLQMN SLRAEDTAVY YCKTHGSHDN WGQGTMVTVS   240
SHHHHHH                                                             247

SEQ ID NO: 222            moltype = AA   length = 247
FEATURE                   Location/Qualifiers
source                    1..247
                          mol_type = protein
                          organism = synthetic construct
SEQUENCE: 222
QSVLTQPPSV SGAPGQRVTI SCSGSRSNIG SNTVKWYQQL PGTAPKLLIY YNDQRPSGVP    60
DRFSGSKSGT SASLAITGLQ AEDEADYYCQ SYDRYTHPAL LFGTGTKVTV LGGGGSGGGG   120
SGGGGSQVQL VESGGGVVQP GRSLRLSCAA SGFTFSSYGM HWVRQAPGKG LEWVAFIEYD   180
GSNKYYADSV KGRFTISRDN SKNTLYLQMN SLRAEDTAVY YCKTHGSHDN WGQGTMVTVS   240
SHHHHHH                                                             247

SEQ ID NO: 223            moltype = AA   length = 247
FEATURE                   Location/Qualifiers
source                    1..247
                          mol_type = protein
                          organism = synthetic construct
SEQUENCE: 223
QSVLTQPPSV SGAPGQRVTI SCSGSRSNIG SNTVKWYQQL PGTAPKLLIY YNDQRPSGVP    60
DRFSGSKSGT SASLAITGLQ AEDEADYYCQ SYDRYTHPAL LFGTGTKVTV LGGGGSGGGG   120
SGGGGSQVQL VESGGGVVQP GRSLRLSCAA SGFTFSSYGM HWVRQAPGKG LEWVAFIDYD   180
GSNKYYADSV KGRFTISRDN SKNTLYLQMN SLRAEDTAVY YCKTHGSHDN WGQGTMVTVS   240
SHHHHHH                                                             247

SEQ ID NO: 224            moltype = AA   length = 247
FEATURE                   Location/Qualifiers
source                    1..247
                          mol_type = protein
                          organism = synthetic construct
SEQUENCE: 224
QSVLTQPPSV SGAPGQRVTI SCSGSRSNIG SNTVKWYQQL PGTAPKLLIY YNDQRPSGVP    60
```

```
DRFSGSKSGT SASLAITGLQ AEDEADYYCQ SYDRYTHPAL LFGTGTKVTV LGGGGSGGGG    120
SGGGGSQVQL VESGGGVVQP GRSLRLSCAA SGFTFSSYGM HWVRQAPGKG LEWVAFIRYD    180
GSNDYYADSV KGRFTISRDN SKNTLYLQMN SLRAEDTAVY YCKTHGSHDN WGQGTMVTVS    240
SHHHHHH                                                              247

SEQ ID NO: 225           moltype = AA  length = 247
FEATURE                  Location/Qualifiers
source                   1..247
                         mol_type = protein
                         organism = synthetic construct
SEQUENCE: 225
QSVLTQPPSV SGAPGQRVTI SCSGSRSNIG SNTVKWYQQL PGTAPKLLIY YNDQRPSGVP     60
DRFSGSKSGT SASLAITGLQ AEDEADYYCQ SYDRYTHPAL LFGTGTKVTV LGGGGSGGGG    120
SGGGGSQVQL VESGGGVVQP GRSLRLSCAA SGFTFSSYGM HWVRQAPGKG LEWVAFIRYD    180
GSNEYYADSV KGRFTISRDN SKNTLYLQMN SLRAEDTAVY YCKTHGSHDN WGQGTMVTVS    240
SHHHHHH                                                              247

SEQ ID NO: 226           moltype = AA  length = 247
FEATURE                  Location/Qualifiers
source                   1..247
                         mol_type = protein
                         organism = synthetic construct
SEQUENCE: 226
QSVLTQPPSV SGAPGQRVTI SCSGSRSNIG SNTVKWYQQL PGTAPKLLIY YNDQRPSGVP     60
DRFSGSKSGT SASLAITGLQ AEDEADYYCQ SYDRYTHPAL LFGTGTKVTV LGGGGSGGGG    120
SGGGGSQVQL VESGGGVVQP GRSLRLSCAA SGFTFSSYGM HWVRQAPGKG LEWVAFIRYD    180
GSNKYYADSV EGRFTISRDN SKNTLYLQMN SLRAEDTAVY YCKTHGSHDN WGQGTMVTVS    240
SHHHHHH                                                              247

SEQ ID NO: 227           moltype = AA  length = 247
FEATURE                  Location/Qualifiers
source                   1..247
                         mol_type = protein
                         organism = synthetic construct
SEQUENCE: 227
QSVLTQPPSV SGAPGQRVTI SCSGSRSNIG SNTVKWYQQL PGTAPKLLIY YNDQRPSGVP     60
DRFSGSKSGT SASLAITGLQ AEDEADYYCQ SYDRYTHPAL LFGTGTKVTV LGGGGSGGGG    120
SGGGGSQVQL VESGGGVVQP GRSLRLSCAA SGFTFSSYGM HWVRQAPGKG LEWVAFIRYD    180
GSNKYYADSV KGRFTISRDN SKNTLYLQMN SLRAEDTAVY YCKTHGSEDN WGQGTMVTVS    240
SHHHHHH                                                              247

SEQ ID NO: 228           moltype = AA  length = 247
FEATURE                  Location/Qualifiers
source                   1..247
                         mol_type = protein
                         organism = synthetic construct
SEQUENCE: 228
QSVLTQPPSV SGAPGQRVTI SCSGSRSNIG SNTVKWYQQL PGTAPKLLIY YNDQRPSGVP     60
DRFSGSKSGT SASLAITGLQ AEDEADYYCQ SYDRYTHPAL LFGTGTKVTV LGGGGSGGGG    120
SGGGGSQVQL VESGGGVVQP GRSLRLSCAA SGFTFSSYGM HWVRQAPGKG LEWVAFIEYD    180
GSNKYYADSV EGRFTISRDN SKNTLYLQMN SLRAEDTAVY YCKTHGSHDN WGQGTMVTVS    240
SHHHHHH                                                              247

SEQ ID NO: 229           moltype = AA  length = 247
FEATURE                  Location/Qualifiers
source                   1..247
                         mol_type = protein
                         organism = synthetic construct
SEQUENCE: 229
QSVLTQPPSV SGAPGQRVTI SCSGSRSNIG SNTVKWYQQL PGTAPKLLIY YNDQRPSGVP     60
DRFSGSKSGT SASLAITGLQ AEDEADYYCQ SYDRYTHPAL LFGTGTKVTV LGGGGSGGGG    120
SGGGGSQVQL VESGGGVVQP GRSLRLSCAA SGFTFSSYGM HWVRQAPGKG LEWVAFIEYD    180
GSNKYYADSV EGRFTISRDN SKNTLYLQMN SLRAEDTAVY YCKTHGSEDN WGQGTMVTVS    240
SHHHHHH                                                              247

SEQ ID NO: 230           moltype = AA  length = 247
FEATURE                  Location/Qualifiers
source                   1..247
                         mol_type = protein
                         organism = synthetic construct
SEQUENCE: 230
QSVLTQPPSV SGAPGQRVTI SCSGSRSNIG SNTVKWYQQL PGTAPKLLIY YNDQRPSGVP     60
DRFSGSKSGT SASLAITGLQ AEDEADYYCQ SYDRYTHPAL LFGTGTKVTV LGGGGSGGGG    120
SGGGGSQVQL VESGGGVVQP GRSLRLSCAA SGFTFSSYGM HWVRQAPGKG LEWVAFIRYD    180
GSNKYYADSV KGRFTISRDN SKNTLYLQMN SLRAEDTAVY YCKTHGSHDN WGQGTMVTVS    240
SHHHHHH                                                              247

SEQ ID NO: 231           moltype = AA  length = 306
FEATURE                  Location/Qualifiers
```

```
source                  1..306
                        mol_type = protein
                        organism = synthetic construct
SEQUENCE: 231
IWELKKDVYV VELDWYPDAP GEMVVLTCDT PEEDGITWTL DQSSEVLGSG KTLTIQVKEF    60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSACPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RYYSSSWSEW   300
ASVPCS                                                              306

SEQ ID NO: 232          moltype = AA  length = 137
FEATURE                 Location/Qualifiers
source                  1..137
                        mol_type = protein
                        organism = synthetic construct
SEQUENCE: 232
QVQLQESGGG LVQTGGSLRL SCTTSGTIFS GYTMGWYRQA PGEQRELVAV ISGGGDTNYA    60
DSVKGRFTIS RDNTKDTMYL QMNSLKPEDT AVYYCYSREV TPPWKLYWGQ GTQVTVSSAA   120
AYPYDVPDYG SHHHHHH                                                  137

SEQ ID NO: 233          moltype = AA  length = 137
FEATURE                 Location/Qualifiers
source                  1..137
                        mol_type = protein
                        organism = synthetic construct
SEQUENCE: 233
QVQLQESGGG LVQEGGSLRL SCAASERIFS TDVMGWYRQA AEKQRELVAV VSARGTTNYL    60
DAVKGRFTIS RDNARNTLTL QMNDLKPEDT ASYYCYVRET TSPWRIYWGQ GTQVTVSSAA   120
AYPYDVPDYG SHHHHHH                                                  137

SEQ ID NO: 234          moltype = AA  length = 138
FEATURE                 Location/Qualifiers
source                  1..138
                        mol_type = protein
                        organism = synthetic construct
SEQUENCE: 234
QVQLQESGGG LVQAGGSLRL SCAASGSIFS ANAMGWYRQA PGKQRELVAV ISSGGSTNYA    60
DSVKGRFTIS RDNAKNTVYL QMNSLKPEDT AVYYCMYSGS YYYTPNDYWG QGTQVTVSSA   120
AAYPYDVPDY GSHHHHHH                                                 138

SEQ ID NO: 235          moltype = AA  length = 245
FEATURE                 Location/Qualifiers
source                  1..245
                        mol_type = protein
                        organism = synthetic construct
SEQUENCE: 235
EVQLVESGGG LVQPGGSLRL SCAASGFTFS SYTLAWVRQA PGKGLEWVAA IDSSSYTYSP    60
DTVRGRFTIS RDNAKNSLYL QMNSLRAEDT AVYYCARDSN WDALDYWGQG TTVTVSSGGG   120
GSGGGGSGGG GSDIQMTQSP SSLSASVGDR VTITCKASQN VGTNVGWYQQ KPGKAPKALI   180
YSASFRYSGV PSRFSGSGSG TDFTLTISSL QPEDFATYYC QQYYTYPYTF GGGTKVEIKH   240
HHHHH                                                               245

SEQ ID NO: 236          moltype = AA  length = 138
FEATURE                 Location/Qualifiers
source                  1..138
                        mol_type = protein
                        organism = synthetic construct
SEQUENCE: 236
EVQLLESGGG LVQPGGSLRL SCAASGSIFS ANAMGWYRQA PGKQRELVAV ISSGGSTNYA    60
DSVKGRFTIS RDNSKNTVYL QMNSLRAEDT AVYYCMYSGS YYYTPNDYWG QGTLVTVSSA   120
AAYPYDVPDY GSHHHHHH                                                 138

SEQ ID NO: 237          moltype = AA  length = 138
FEATURE                 Location/Qualifiers
source                  1..138
                        mol_type = protein
                        organism = synthetic construct
SEQUENCE: 237
EVQLLESGGG LVQPGGSLRL SCAASGSIFS ANAMGWYRQA PGKGLELVAV ISSGGSTNYA    60
DSVKGRFTIS RDNSKNTVYL QMNSLRAEDT AVYYCMYSGS YYYTPNDYWG QGTLVTVSSA   120
AAYPYDVPDY GSHHHHHH                                                 138

SEQ ID NO: 238          moltype = AA  length = 138
FEATURE                 Location/Qualifiers
source                  1..138
                        mol_type = protein
                        organism = synthetic construct
SEQUENCE: 238
```

```
EVQLLESGGG LVQPGGSLRL SCAASGSIFS ANAMGWVRQA PGKGLEWVSV ISSGGSTNYA      60
DSVKGRFTIS RDNSKNTLYL QMNSLRAEDT AVYYCMYSGS YYYTPNDYWG QGTLVTVSSA     120
AAYPYDVPDY GSHHHHHH                                                  138

SEQ ID NO: 239          moltype = AA   length = 138
FEATURE                 Location/Qualifiers
source                  1..138
                        mol_type = protein
                        organism = synthetic construct
SEQUENCE: 239
QVQLLESGGG LVQPGGSLRL SCAASGSIFS ANAMGWYRQA PGKQRELVAV ISSGGSTNYA      60
DSVKGRFTIS RDNSKNTVYL QMNSLRAEDT AVYYCMYSGS YYYTPNDYWG QGTLVTVSSA     120
AAYPYDVPDY GSHHHHHH                                                  138

SEQ ID NO: 240          moltype = AA   length = 138
FEATURE                 Location/Qualifiers
source                  1..138
                        mol_type = protein
                        organism = synthetic construct
SEQUENCE: 240
EVQLLESGGG LVQPGGSLRL SCAASGSIFS ANAMGWYRQA PGKGRELVAV ISSGGSTNYA      60
DSVKGRFTIS RDNSKNTVYL QMNSLRAEDT AVYYCMYSGS YYYTPNDYWG QGTLVTVSSA     120
AAYPYDVPDY GSHHHHHH                                                  138

SEQ ID NO: 241          moltype = AA   length = 138
FEATURE                 Location/Qualifiers
source                  1..138
                        mol_type = protein
                        organism = synthetic construct
SEQUENCE: 241
QVQLLESGGG LVQAGGSLRL SCAASGSIFS ANAMGWYRQA PGKQRELVAV ISSGGSTNYA      60
DSVKGRFTIS RDNSKNTVYL QMNSLRAEDT AVYYCMYSGS YYYTPNDYWG QGTLVTVSSA     120
AAYPYDVPDY GSHHHHHH                                                  138

SEQ ID NO: 242          moltype = AA   length = 137
FEATURE                 Location/Qualifiers
source                  1..137
                        mol_type = protein
                        organism = synthetic construct
SEQUENCE: 242
EVQLLESGGG LVQPGGSLRL SCAASERIFS TDVMGWYRQA PGKQRELVAV VSARGTTNYL      60
DAVKGRFTIS RDNSKNTLYL QMNSLRAEDT AVYYCYVRET TSPWRIYWGQ GTLVTVSSAA     120
AYPYDVPDYG SHHHHHH                                                   137

SEQ ID NO: 243          moltype = AA   length = 137
FEATURE                 Location/Qualifiers
source                  1..137
                        mol_type = protein
                        organism = synthetic construct
SEQUENCE: 243
EVQLLESGGG LVQPGGSLRL SCAASERIFS TDVMGWYRQA PGKGLELVAV VSARGTTNYL      60
DAVKGRFTIS RDNSKNTLYL QMNSLRAEDT AVYYCYVRET TSPWRIYWGQ GTLVTVSSAA     120
AYPYDVPDYG SHHHHHH                                                   137

SEQ ID NO: 244          moltype = AA   length = 137
FEATURE                 Location/Qualifiers
source                  1..137
                        mol_type = protein
                        organism = synthetic construct
SEQUENCE: 244
EVQLLESGGG LVQPGGSLRL SCAASERIFS TDVMGWVRQA PGKGLEWVSV VSARGTTNYL      60
DAVKGRFTIS RDNSKNTLYL QMNSLRAEDT AVYYCYVRET TSPWRIYWGQ GTLVTVSSAA     120
AYPYDVPDYG SHHHHHH                                                   137

SEQ ID NO: 245          moltype = AA   length = 137
FEATURE                 Location/Qualifiers
source                  1..137
                        mol_type = protein
                        organism = synthetic construct
SEQUENCE: 245
QVQLLESGGG LVQPGGSLRL SCAASERIFS TDVMGWYRQA PGKQRELVAV VSARGTTNYL      60
DAVKGRFTIS RDNSKNTLYL QMNSLRAEDT AVYYCYVRET TSPWRIYWGQ GTLVTVSSAA     120
AYPYDVPDYG SHHHHHH                                                   137

SEQ ID NO: 246          moltype = AA   length = 137
FEATURE                 Location/Qualifiers
source                  1..137
                        mol_type = protein
                        organism = synthetic construct
```

```
SEQUENCE: 246
EVQLLESGGG LVQPGGSLRL SCAASERIFS TDVMGWYRQA PGKGRELVAV VSARGTTNYL   60
DSVKGRFTIS RDNSKNTLYL QMNSLRAEDT AVYYCYVRET TSPWRIYWGQ GTLVTVSSAA  120
AYPYDVPDYG SHHHHHH                                                137

SEQ ID NO: 247          moltype = AA  length = 137
FEATURE                 Location/Qualifiers
source                  1..137
                        mol_type = protein
                        organism = synthetic construct
SEQUENCE: 247
QVQLLESGGG LVQEGGSLRL SCAASERIFS TDVMGWYRQA AGKQRELVAV VSARGTTNYL   60
DAVKGRFTIS RDNSKNTLYL QMNSLRAEDT ASYYCYVRET TSPWRIYWGQ GTLVTVSSAA  120
AYPYDVPDYG SHHHHHH                                                137

SEQ ID NO: 248          moltype = AA  length = 137
FEATURE                 Location/Qualifiers
source                  1..137
                        mol_type = protein
                        organism = synthetic construct
SEQUENCE: 248
EVQLLESGGG LVQPGGSLRL SCAASERIFS TDVMGWYRQA PGKGLELVAV VSARGTTNYL   60
DSVKGRFTIS RDNSKNTLYL QMNSLRAEDT AVYYCYVRET TSPWRIYWGQ GTLVTVSSAA  120
AYPYDVPDYG SHHHHHH                                                137

SEQ ID NO: 249          moltype = AA  length = 137
FEATURE                 Location/Qualifiers
source                  1..137
                        mol_type = protein
                        organism = synthetic construct
SEQUENCE: 249
EVQLLESGGG LVQPGGSLRL SCATSGTIFS GYTMGWYRQA PGKQRELVAV ISGGGDTNYA   60
DSVKGRFTIS RDNSKDTMYL QMNSLRAEDT AVYYCYSREV TPPWKLYWGQ GTLVTVSSAA  120
AYPYDVPDYG SHHHHHH                                                137

SEQ ID NO: 250          moltype = AA  length = 137
FEATURE                 Location/Qualifiers
source                  1..137
                        mol_type = protein
                        organism = synthetic construct
SEQUENCE: 250
EVQLLESGGG LVQPGGSLRL SCATSGTIFS GYTMGWYRQA PGKGLELVAV ISGGGDTNYA   60
DSVKGRFTIS RDNSKDTMYL QMNSLRAEDT AVYYCYSREV TPPWKLYWGQ GTLVTVSSAA  120
AYPYDVPDYG SHHHHHH                                                137

SEQ ID NO: 251          moltype = AA  length = 137
FEATURE                 Location/Qualifiers
source                  1..137
                        mol_type = protein
                        organism = synthetic construct
SEQUENCE: 251
EVQLLESGGG LVQPGGSLRL SCAASGTIFS GYTMGWVRQA PGKGLEWVSV ISGGGDTNYA   60
DSVKGRFTIS RDNSKNTLYL QMNSLRAEDT AVYYCYSREV TPPWKLYWGQ GTLVTVSSAA  120
AYPYDVPDYG SHHHHHH                                                137

SEQ ID NO: 252          moltype = AA  length = 137
FEATURE                 Location/Qualifiers
source                  1..137
                        mol_type = protein
                        organism = synthetic construct
SEQUENCE: 252
QVQLLESGGG LVQPGGSLRL SCATSGTIFS GYTMGWYRQA PGKQRELVAV ISGGGDTNYA   60
DSVKGRFTIS RDNSKDTMYL QMNSLRAEDT AVYYCYSREV TPPWKLYWGQ GTLVTVSSAA  120
AYPYDVPDYG SHHHHHH                                                137

SEQ ID NO: 253          moltype = AA  length = 137
FEATURE                 Location/Qualifiers
source                  1..137
                        mol_type = protein
                        organism = synthetic construct
SEQUENCE: 253
EVQLLESGGG LVQPGGSLRL SCATSGTIFS GYTMGWYRQA PGKQRELVAV ISGGGDTNYA   60
DSVKGRFTIS RDNSKNTMYL QMNSLRAEDT AVYYCYSREV TPPWKLYWGQ GTLVTVSSAA  120
AYPYDVPDYG SHHHHHH                                                137

SEQ ID NO: 254          moltype = AA  length = 137
FEATURE                 Location/Qualifiers
source                  1..137
                        mol_type = protein
```

```
                        organism = synthetic construct
SEQUENCE: 254
EVQLLESGGG LVQPGGSLRL SCATSGTIFS GYTMGWYRQA PGKGRELVAV ISGGGDTNYA        60
DSVKGRFTIS RDNSKNTMYL QMNSLRAEDT AVYYCYSREV TPPWKLYWGQ GTLVTVSSAA       120
AYPYDVPDYG SHHHHHH                                                     137

SEQ ID NO: 255          moltype = AA  length = 137
FEATURE                 Location/Qualifiers
source                  1..137
                        mol_type = protein
                        organism = synthetic construct
SEQUENCE: 255
QVQLLESGGG LVQTGGSLRL SCATSGTIFS GYTMGWYRQA PGKQRELVAV ISGGGDTNYA        60
DSVKGRFTIS RDNSKDTMYL QMNSLRAEDT AVYYCYSREV TPPWKLYWGQ GTLVTVSSAA       120
AYPYDVPDYG SHHHHHH                                                     137

SEQ ID NO: 256          moltype = AA  length = 137
FEATURE                 Location/Qualifiers
source                  1..137
                        mol_type = protein
                        organism = synthetic construct
SEQUENCE: 256
EVQLLESGGG LVQPGGSLRL SCATSGTIFS GYTMGWYRQA PGKGLELVAV ISGGGDTNYA        60
DSVKGRFTIS RDNSKNTMYL QMNSLRAEDT AVYYCYSREV TPPWKLYWGQ GTLVTVSSAA       120
AYPYDVPDYG SHHHHHH                                                     137

SEQ ID NO: 257          moltype = AA  length = 245
FEATURE                 Location/Qualifiers
source                  1..245
                        mol_type = protein
                        organism = synthetic construct
SEQUENCE: 257
EVQLVESGGG LVQPGGSLRL SCAASGFTFS SYTLAWVRQA PGKGLEWVAA IDSSSYTYSP        60
DTVRGRFTIS RDNAKNSLYL QMNSLRAEDT AVYYCARDSN WDALDYWGQG TTVTVSSGGG       120
GSGGGGSGGG GSDIQMTQSP SSLSASVGDR VTITCKAREK LWSAVAWYQQ KPGKAPKALI       180
YSASFRYSGV PSRFSGSGSG TDFTLTISSL QPEDFATYYC QQYYTYPYTF GGGTKVEIKH       240
HHHHH                                                                  245

SEQ ID NO: 258          moltype = AA  length = 245
FEATURE                 Location/Qualifiers
source                  1..245
                        mol_type = protein
                        organism = synthetic construct
SEQUENCE: 258
EVQLVESGGG LVQPGGSLRL SCAASGFTFS SYTLAWVRQA PGKGLEWVAA IDSSSYTYSP        60
DTVRGRFTIS RDNAKNSLYL QMNSLRAEDT AVYYCARDSN WDALDYWGQG TTVTVSSGGG       120
GSGGGGSGGG GSDIQMTQSP SSLSASVGDR VTITCKAREK LWSAVAWYQQ KPGKAPKSLI       180
YSASFRYSGV PSRFSGSGSG TDFTLTISSL QPEDFATYYC QQYYTYPYTF GGGTKVEIKH       240
HHHHH                                                                  245

SEQ ID NO: 259          moltype = AA  length = 245
FEATURE                 Location/Qualifiers
source                  1..245
                        mol_type = protein
                        organism = synthetic construct
SEQUENCE: 259
EVQLVESGGG LVQPGGSLRL SCAASGFTFS SYTLAWVRQA PGKGLEWVAA IDSSSYTYSP        60
DTVRGRFTIS RDNAKNSLYL QMNSLRAEDT AVYYCARDSN WDALDYWGQG TTVTVSSGGG       120
GSGGGGSGGG GSDIQMTQSP SSLSASVGDR VTITCKVTEK VWGNVAWYQQ KPGKAPISLI       180
YSPSLRKSGV PSRFSGSGSG TDFTLTISSL QPEDFATYYC QQYYTYPYTF GGGTKVEIKH       240
HHHHH                                                                  245

SEQ ID NO: 260          moltype = AA  length = 245
FEATURE                 Location/Qualifiers
source                  1..245
                        mol_type = protein
                        organism = synthetic construct
SEQUENCE: 260
EVQLVESGGG LVQPGGSLRL SCAASGFTFS SYTLAWVRQA PGKGLEWVAA IDSSSYTYSP        60
DTVRGRFTIS RDNAKNSLYL QMNSLRAEDT AVYYCARDSN WDALDYWGQG TTVTVSSGGG       120
GSGGGGSGGG GSDIQMTQSP SSLSASVGDR VTITCKSSEK LWANVAWYQQ KPGKAPKALI       180
YSASFRYSGV PSRFSGSGSG TDFTLTISSL QPEDFATYYC QQYYTYPYTF GGGTKVEIKH       240
HHHHH                                                                  245

SEQ ID NO: 261          moltype = AA  length = 245
FEATURE                 Location/Qualifiers
source                  1..245
                        mol_type = protein
                        organism = synthetic construct
```

```
SEQUENCE: 261
EVQLVESGGG LVQPGGSLRL SCAASGFTFS SYTLAWVRQA PGKGLEWVAA IDSSSYTYSP    60
DTVRGRFTIS RDNAKNSLYL QMNSLRAEDT AVYYCARDSN WDALDYWGQG TTVTVSSGGG   120
GSGGGGSGGG GSDIQMTQSP SSLSASVGDR VTITCKSSEK LWANVAWYQQ KPGKAPKSLI   180
YSASFRYSGV PSRFSGSGSG TDFTLTISSL QPEDFATYYC QQYYTYPYTF GGGTKVEIKH   240
HHHHH                                                               245

SEQ ID NO: 262          moltype = AA  length = 214
FEATURE                 Location/Qualifiers
source                  1..214
                        mol_type = protein
                        organism = synthetic construct
SEQUENCE: 262
DIQMTQSPSS LSASVGDRVT ITCKASQNVG TNVGWYQQKP GKAPKALIYS ASFRYSGVPS    60
RFSGSGSGTD FTLTISSLQP EDFATYYCQQ YYTYPYTFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 263          moltype = AA  length = 214
FEATURE                 Location/Qualifiers
source                  1..214
                        mol_type = protein
                        organism = synthetic construct
SEQUENCE: 263
DIQMTQSPSS LSASVGDRVT ITCKAREKLW SAVAWYQQKP GKAPKSLIYS ASFRYSGVPS    60
RFSGSGSGTD FTLTISSLQP EDFATYYCQQ YYTYPYTFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 264          moltype = AA  length = 214
FEATURE                 Location/Qualifiers
source                  1..214
                        mol_type = protein
                        organism = synthetic construct
SEQUENCE: 264
DIQMTQSPSS LSASVGDRVT ITCKVTEKVW GNVAWYQQKP GKAPISLIYS PSLRKSGVPS    60
RFSGSGSGTD FTLTISSLQP EDFATYYCQQ YYTYPYTFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 265          moltype = AA  length = 363
FEATURE                 Location/Qualifiers
source                  1..363
                        mol_type = protein
                        organism = synthetic construct
SEQUENCE: 265
DIQMTQSPSS LSASVGDRVT ITCKAREKLW SAVAWYQQKP GKAPKSLIYS ASFRYSGVPS    60
RFSGSGSGTD FTLTISSLQP EDFATYYCQQ YYTYPYTFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGECGGGGSG GGGSGGGGSG GGGSGGGGSG   240
GGGSEVQLLE SGGGLVQPGG SLRLSCAASG SIFSANAMGW YRQAPGQRE LVAVISSGGS    300
TNYADSVKGR FTISRDNSKN TVYLQMNSLR AEDTAVYYCM YSGSYYYTPN DYWGQGTLVT   360
VSS                                                                 363

SEQ ID NO: 266          moltype = AA  length = 363
FEATURE                 Location/Qualifiers
source                  1..363
                        mol_type = protein
                        organism = synthetic construct
SEQUENCE: 266
DIQMTQSPSS LSASVGDRVT ITCKAREKLW SAVAWYQQKP GKAPKSLIYS ASFRYSGVPS    60
RFSGSGSGTD FTLTISSLQP EDFATYYCQQ YYTYPYTFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGECGGGGSG GGGSGGGGSG GGGSGGGGSG   240
GGGSEVQLLE SGGGLVQPGG SLRLSCAASG SIFSANAMGW YRQAPGKGLE LVAVISSGGS   300
TNYADSVKGR FTISRDNSKN TVYLQMNSLR AEDTAVYYCM YSGSYYYTPN DYWGQGTLVT   360
VSS                                                                 363

SEQ ID NO: 267          moltype = AA  length = 363
FEATURE                 Location/Qualifiers
source                  1..363
                        mol_type = protein
                        organism = synthetic construct
SEQUENCE: 267
DIQMTQSPSS LSASVGDRVT ITCKVTEKVW GNVAWYQQKP GKAPISLIYS PSLRKSGVPS    60
RFSGSGSGTD FTLTISSLQP EDFATYYCQQ YYTYPYTFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGECGGGGSG GGGSGGGGSG GGGSGGGGSG   240
GGGSEVQLLE SGGGLVQPGG SLRLSCAASG SIFSANAMGW YRQAPGKQRE LVAVISSGGS   300
```

```
TNYADSVKGR FTISRDNSKN TVYLQMNSLR AEDTAVYYCM YSGSYYYTPN DYWGQGTLVT    360
VSS                                                                 363

SEQ ID NO: 268          moltype = AA  length = 363
FEATURE                 Location/Qualifiers
source                  1..363
                        mol_type = protein
                        organism = synthetic construct
SEQUENCE: 268
DIQMTQSPSS LSASVGDRVT ITCKVTEKVW GNVAWYQQKP GKAPISLIYS PSLRKSGVPS    60
RFSGSGSGTD FTLTISSLQP EDFATYYCQQ YYTYPYTFGG GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGECGGGGSG GGGSGGGGSG GGGSGGGGSG    240
GGGSEVQLLE SGGGLVQPGG SLRLSCAASG SIFSANAMGW YRQAPGKGLE LVAVISSGGS    300
TNYADSVKGR FTISRDNSKN TVYLQMNSLR AEDTAVYYCM YSGSYYYTPN DYWGQGTLVT    360
VSS                                                                 363

SEQ ID NO: 269          moltype = AA  length = 214
FEATURE                 Location/Qualifiers
source                  1..214
                        mol_type = protein
                        organism = synthetic construct
SEQUENCE: 269
DIQMTQSPSS LSASVGDRVT ITCKSSEKLW ANVAWYQQKP GKAPKSLIYS ASFRYSGVPS    60
RFSGSGSGTD FTLTISSLQP EDFATYYCQQ YYTYPYTFGG GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 270          moltype = AA  length = 214
FEATURE                 Location/Qualifiers
source                  1..214
                        mol_type = protein
                        organism = synthetic construct
SEQUENCE: 270
DIQMTQSPSS LSASVGDRVT ITCKSSEKLW ANVAWYQQKP GKAPKLLIYS ASFRYSGVPS    60
RFSGSGSGTD FTLTISSLQP EDFATYYCQQ YYTYPYTFGG GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 271          moltype = AA  length = 214
FEATURE                 Location/Qualifiers
source                  1..214
                        mol_type = protein
                        organism = synthetic construct
SEQUENCE: 271
DIQMTQSPSS LSASVGDRVT ITCKAREKLW SAVAWYQQKP GKAPKLLIYS ASFRYSGVPS    60
RFSGSGSGTD FTLTISSLQP EDFATYYCQQ YYTYPYTFGG GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 272          moltype = AA  length = 547
FEATURE                 Location/Qualifiers
source                  1..547
                        mol_type = protein
                        organism = synthetic construct
SEQUENCE: 272
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR    120
WITFCQSIIS TLTSGGPGPA GLYAQPGSEV QLVESGGGLV QPGNSLRLSC AASGFTFSKF    180
GMSWVRQAPG KGLEWVSSIS GSGRDTLYAE SVKGRFTISR DNAKTTLYLQ MNSLRPEDTA    240
VYYCTIGGSL SVSSQGTLVT VSSGGGGSGG GGSGGGGSGG GGSGGGGSGG GGSSGGPGPA    300
GLYAQPGSEV QLVESGGGLV QPGGSLRLSC AASGFTFSSY TLAWVRQAPG KGLEWVAAID    360
SSSYTYSPDT VRGRFTISRD NAKNSLYLQM NSLRAEDTAV YYCARDSNWD ALDYWGQGTT    420
VTVSSGGGGS GGGGSGGGGS DIQMTQSPSS LSASVGDRVT ITCKSSEKLW ANVAWYQQKP    480
GKAPKALIYS ASFRYSGVPS RFSGSGSGTD FTLTISSLQP EDFATYYCQQ YYTYPYTFGG    540
GTKVEIK                                                             547

SEQ ID NO: 273          moltype = AA  length = 547
FEATURE                 Location/Qualifiers
source                  1..547
                        mol_type = protein
                        organism = synthetic construct
SEQUENCE: 273
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR    120
WITFCQSIIS TLTSGGPGPA GLYAQPGSEV QLVESGGGLV QPGNSLRLSC AASGFTFSKF    180
GMSWVRQAPG KGLEWVSSIS GSGRDTLYAE SVKGRFTISR DNAKTTLYLQ MNSLRPEDTA    240
VYYCTIGGSL SVSSQGTLVT VSSGGGGSGG GGSGGGGSGG GGSGGGGSGG GGSSGGPGPA    300
GLYAQPGSEV QLVESGGGLV QPGGSLRLSC AASGFTFSSY TLAWVRQAPG KGLEWVAAID    360
```

```
SSSYTYSPDT VRGRFTISRD NAKNSLYLQM NSLRAEDTAV YYCARDSNWD ALDYWGQGTT  420
VTVSSGGGGS GGGGSGGGGS DIQMTQSPSS LSASVGDRVT ITCKSSEKLW ANVAWYQQKP  480
GKAPKSLIYS ASFRYSGVPS RFSGSGSGTD FTLTISSLQP EDFATYYCQQ YYTYPYTFGG  540
GTKVEIK                                                           547

SEQ ID NO: 274          moltype = AA  length = 547
FEATURE                 Location/Qualifiers
source                  1..547
                        mol_type = protein
                        organism = synthetic construct
SEQUENCE: 274
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GLYAQPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPGPA  300
GLYAQPGSEV QLVESGGGLV QPGGSLRLSC AASGFTFSSY TLAWVRQAPG KGLEWVAAID  360
SSSYTYSPDT VRGRFTISRD NAKNSLYLQM NSLRAEDTAV YYCARDSNWD ALDYWGQGTT  420
VTVSSGGGGS GGGGSGGGGS DIQMTQSPSS LSASVGDRVT ITCKSSEKLW ANVAWYQQKP  480
GKAPKLLIYS ASFRYSGVPS RFSGSGSGTD FTLTISSLQP EDFATYYCQQ YYTYPYTFGG  540
GTKVEIK                                                           547

SEQ ID NO: 275          moltype = AA  length = 547
FEATURE                 Location/Qualifiers
source                  1..547
                        mol_type = protein
                        organism = synthetic construct
SEQUENCE: 275
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GLYAQPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPGPA  300
GLYAQPGSEV QLVESGGGLV QPGGSLRLSC AASGFTFSSY TLAWVRQAPG KCLEWVAAID  360
SSSYTYSPDT VRGRFTISRD NAKNSLYLQM NSLRAEDTAV YYCARDSNWD ALDYWGQGTT  420
VTVSSGGGGS GGGGSGGGGS DIQMTQSPSS LSASVGDRVT ITCKSSEKLW ANVAWYQQKP  480
GKAPKSLIYS ASFRYSGVPS RFSGSGSGTD FTLTISSLQP EDFATYYCQQ YYTYPYTFGC  540
GTKVEIK                                                           547

SEQ ID NO: 276          moltype = AA  length = 547
FEATURE                 Location/Qualifiers
source                  1..547
                        mol_type = protein
                        organism = synthetic construct
SEQUENCE: 276
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GLYAQPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPGPA  300
GLYAQPGSEV QLVESGGGLV QPGGSLRLSC AASGFTFSSY TLAWVRQAPG KCLEWVAAID  360
SSSYTYSPDT VRGRFTISRD NAKNSLYLQM NSLRAEDTAV YYCARDSNWD ALDYWGQGTT  420
VTVSSGGGGS GGGGSGGGGS DIQMTQSPSS LSASVGDRVT ITCKSSEKLW ANVAWYQQKP  480
GKAPKLLIYS ASFRYSGVPS RFSGSGSGTD FTLTISSLQP EDFATYYCQQ YYTYPYTFGC  540
GTKVEIK                                                           547

SEQ ID NO: 277          moltype = AA  length = 547
FEATURE                 Location/Qualifiers
source                  1..547
                        mol_type = protein
                        organism = synthetic construct
SEQUENCE: 277
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GLYAQPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPGPA  300
GLYAQPGSEV QLVESGGGLV QPGGSLRLSC AASGFTFSSY TLAWVRQAPG KGLEWVAAID  360
SSSYTYSPDT VRGRFTISRD NAKNSLYLQM NSLRAEDTAV YYCARDSNWD ALDYWGCGTT  420
VTVSSGGGGS GGGGSGGGGS DIQMTQSPSS LSASVGDRVT ITCKSSEKLW ANVAWYQQKP  480
GKCPKALIYS ASFRYSGVPS RFSGSGSGTD FTLTISSLQP EDFATYYCQQ YYTYPYTFGG  540
GTKVEIK                                                           547

SEQ ID NO: 278          moltype = AA  length = 547
FEATURE                 Location/Qualifiers
source                  1..547
                        mol_type = protein
                        organism = synthetic construct
SEQUENCE: 278
```

```
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTSGGPGPA GLYAQPGSEV QLVESGGGLV QPGNSLRLSC AASGFTFSKF   180
GMSWVRQAPG KGLEWVSSIS GSGRDTLYAE SVKGRFTISR DNAKTTLYLQ MNSLRPEDTA   240
VYYCTIGGSL SVSSQGTLVT VSSGGGGSGG GGSGGGGSGG GGSSGGPGPA              300
GLYAQPGSEV QLVESGGGLV QPGGSLRLSC AASGFTFSSY TLAWVRQAPG KGLEWVAAID   360
SSSYTYSPDT VRGRFTISRD NAKNSLYLQM NSLRAEDTAV YYCARDSNWD ALDYWGQGTT   420
VTVSSSGGPG PAGLYAQPGS DIQMTQSPSS LSASVGDRVT ITCKAREKLW SAVAWYQQKP   480
GKAPKLLIYS ASFRYSGVPS RFSGSGSGTD FTLTISSLQP EDFATYYCQQ YYTYPYTFGG   540
GTKVEIK                                                             547

SEQ ID NO: 279         moltype = AA  length = 547
FEATURE                Location/Qualifiers
source                 1..547
                       mol_type = protein
                       organism = synthetic construct
SEQUENCE: 279
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTSGGPGPA GLYAQPGSEV QLVESGGGLV QPGNSLRLSC AASGFTFSKF   180
GMSWVRQAPG KGLEWVSSIS GSGRDTLYAE SVKGRFTISR DNAKTTLYLQ MNSLRPEDTA   240
VYYCTIGGSL SVSSQGTLVT VSSGGGGSGG GGSGGGGSGG GGSSGGPGPA              300
GLYAQPGSEV QLVESGGGLV QPGGSLRLSC AASGFTFSSY TLAWVRQAPG KGLEWVAAID   360
SSSYTYSPDT VRGRFTISRD NAKNSLYLQM NSLRAEDTAV YYCARDSNWD ALDYWGQGTT   420
VTVSSGGGGS GGGGSGGGGS DIQMTQSPSS LSASVGDRVT ITCKAREKLW SAVAWYQQKP   480
GKAPKLLIYS ASFRYSGVPS RFSGSGSGTD FTLTISSLQP EDFATYYCQQ YYTYPYTFGG   540
GTKVEIK                                                             547

SEQ ID NO: 280         moltype = AA  length = 547
FEATURE                Location/Qualifiers
source                 1..547
                       mol_type = protein
                       organism = synthetic construct
SEQUENCE: 280
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTSGGPGPA GLYAQPGSEV QLVESGGGLV QPGNSLRLSC AASGFTFSKF   180
GMSWVRQAPG KGLEWVSSIS GSGRDTLYAE SVKGRFTISR DNAKTTLYLQ MNSLRPEDTA   240
VYYCTIGGSL SVSSQGTLVT VSSGGGGSGG GGSGGGGSGG GGSSGGPGPA              300
GLYAQPGSEV QLVESGGGLV QPGGSLRLSC AASGFTFSSY TLAWVRQAPG KCLEWVAAID   360
SSSYTYSPDT VRGRFTISRD NAKNSLYLQM NSLRAEDTAV YYCARDSNWD ALDYWGQGTT   420
VTVSSGGGGS GGGGSGGGGS DIQMTQSPSS LSASVGDRVT ITCKAREKLW SAVAWYQQKP   480
GKAPKLLIYS ASFRYSGVPS RFSGSGSGTD FTLTISSLQP EDFATYYCQQ YYTYPYTFGC   540
GTKVEIK                                                             547

SEQ ID NO: 281         moltype = AA  length = 547
FEATURE                Location/Qualifiers
source                 1..547
                       mol_type = protein
                       organism = synthetic construct
SEQUENCE: 281
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTSGGPALF KSSFPPGSEV QLVESGGGLV QPGNSLRLSC AASGFTFSKF   180
GMSWVRQAPG KGLEWVSSIS GSGRDTLYAE SVKGRFTISR DNAKTTLYLQ MNSLRPEDTA   240
VYYCTIGGSL SVSSQGTLVT VSSGGGGSGG GGSGGGGSGG GGSGGGGSGG GGSSGGPALF   300
KSSFPPGSEV QLVESGGGLV QPGGSLRLSC AASGFTFSSY TLAWVRQAPG KGLEWVAAID   360
SSSYTYSPDT VRGRFTISRD NAKNSLYLQM NSLRAEDTAV YYCARDSNWD ALDYWGQGTT   420
VTVSSGGGGS GGGGSGGGGS DIQMTQSPSS LSASVGDRVT ITCKAREKLW SAVAWYQQKP   480
GKAPKSLIYS ASFRYSGVPS RFSGSGSGTD FTLTISSLQP EDFATYYCQQ YYTYPYTFGG   540
GTKVEIK                                                             547

SEQ ID NO: 282         moltype = AA  length = 547
FEATURE                Location/Qualifiers
source                 1..547
                       mol_type = protein
                       organism = synthetic construct
SEQUENCE: 282
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTSGGPALF KSSFPPGSEV QLVESGGGLV QPGNSLRLSC AASGFTFSKF   180
GMSWVRQAPG KGLEWVSSIS GSGRDTLYAE SVKGRFTISR DNAKTTLYLQ MNSLRPEDTA   240
VYYCTIGGSL SVSSQGTLVT VSSGGGGSGG GGSGGGGSGG GGSGGGGSGG GGSSGGPALF   300
KSSFPPGSEV QLVESGGGLV QPGGSLRLSC AASGFTFSSY TLAWVRQAPG KGLEWVAAID   360
SSSYTYSPDT VRGRFTISRD NAKNSLYLQM NSLRAEDTAV YYCARDSNWD ALDYWGQGTT   420
VTVSSGGGGS GGGGSGGGGS DIQMTQSPSS LSASVGDRVT ITCKVTEKVW GNVAWYQQKP   480
GKAPISLIYS PSLRKSGVPS RFSGSGSGTD FTLTISSLQP EDFATYYCQQ YYTYPYTFGG   540
GTKVEIK                                                             547
```

```
SEQ ID NO: 283            moltype = AA  length = 547
FEATURE                   Location/Qualifiers
source                    1..547
                          mol_type = protein
                          organism = synthetic construct
SEQUENCE: 283
APTSSSTKKT QLQLEHLLLD LQMILNGINN YKNPKLTRML TFKFYMPKKA TELKHLQCLE   60
EELKPLEEVL NLAQSKNFHL RPRDLISNIN VIVLELKGSE TTFMCEYADE TATIVEFLNR  120
WITFCQSIIS TLTSGGPALF KSSFPPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPALF  300
KSSFPPGSEV QLVESGGGLV QPGGSLRLSC AASGFTFSSY TLAWVRQAPG KCLEWVAAID  360
SSSYTYSPDT VRGRFTISRD NAKNSLYLQM NSLRAEDTAV YYCARDSNWD ALDYWGCGTT  420
VTVSSGGGGS GGGGSGGGGS DIQMTQSPSS LSASVGDRVT ITCKAREKLW SAVAWYQQKP  480
GKAPKSLIYS ASFRYSGVPS RFSGSGSGTD FTLTISSLQP EDFATYYCQQ YYTYPYTFGC  540
GTKVEIK                                                            547

SEQ ID NO: 284            moltype = AA  length = 547
FEATURE                   Location/Qualifiers
source                    1..547
                          mol_type = protein
                          organism = synthetic construct
SEQUENCE: 284
APTSSSTKKT QLQLEHLLLD LQMILNGINN YKNPKLTRML TFKFYMPKKA TELKHLQCLE   60
EELKPLEEVL NLAQSKNFHL RPRDLISNIN VIVLELKGSE TTFMCEYADE TATIVEFLNR  120
WITFCQSIIS TLTSGGPALF KSSFPPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPALF  300
KSSFPPGSEV QLVESGGGLV QPGGSLRLSC AASGFTFSSY TLAWVRQAPG KGLEWVAAID  360
SSSYTYSPDT VRGRFTISRD NAKNSLYLQM NSLRAEDTAV YYCARDSNWD ALDYWGCGTT  420
VTVSSGGGGS GGGGSGGGGS DIQMTQSPSS LSASVGDRVT ITCKAREKLW SAVAWYQQKP  480
GKCPKALIYS ASFRYSGVPS RFSGSGSGTD FTLTISSLQP EDFATYYCQQ YYTYPYTFGG  540
GTKVEIK                                                            547

SEQ ID NO: 285            moltype = AA  length = 547
FEATURE                   Location/Qualifiers
source                    1..547
                          mol_type = protein
                          organism = synthetic construct
SEQUENCE: 285
APTSSSTKKT QLQLEHLLLD LQMILNGINN YKNPKLTRML TFKFYMPKKA TELKHLQCLE   60
EELKPLEEVL NLAQSKNFHL RPRDLISNIN VIVLELKGSE TTFMCEYADE TATIVEFLNR  120
WITFCQSIIS TLTSGGPALF KSSFPPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPALF  300
KSSFPPGSEV QLVESGGGLV QPGGSLRLSC AASGFTFSSY TLAWVRQAPG KCLEWVAAID  360
SSSYTYSPDT VRGRFTISRD NAKNSLYLQM NSLRAEDTAV YYCARDSNWD ALDYWGCGTT  420
VTVSSGGGGS GGGGSGGGGS DIQMTQSPSS LSASVGDRVT ITCKVTEKVW GNVAWYQQKP  480
GKAPISLIYS PSLRKSGVPS RFSGSGSGTD FTLTISSLQP EDFATYYCQQ YYTYPYTFGC  540
GTKVEIK                                                            547

SEQ ID NO: 286            moltype = AA  length = 528
FEATURE                   Location/Qualifiers
source                    1..528
                          mol_type = protein
                          organism = synthetic construct
SEQUENCE: 286
APTSSSTKKT QLQLEHLLLD LQMILNGINN YKNPKLTRML TFKFYMPKKA TELKHLQCLE   60
EELKPLEEVL NLAQSKNFHL RPRDLISNIN VIVLELKGSE TTFMCEYADE TATIVEFLNR  120
WITFCQSIIS TLTSGGPALF KSSFPPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPALF  300
KSSFPPGSEV QLVESGGGLV QPGGSLRLSC AASGFTFSSY TLAWVRQAPG KGLEWVAAID  360
SSSYTYSPDT VRGRFTISRD NAKNSLYLQM NSLRAEDTAV YYCARDSNWD ALDYWGQGTT  420
VTVSSASTKG PSVFPLAPSS KSTSGGTAAL GCLVKDYFPE PVTVSWNSGA LTSGVHTFPA  480
VLQSSGLYSL SSVVTVPSSS LGTQTYICNV NHKPSNTKVD KRVEPKSC               528

SEQ ID NO: 287            moltype = AA  length = 642
FEATURE                   Location/Qualifiers
source                    1..642
                          mol_type = protein
                          organism = synthetic construct
SEQUENCE: 287
ESKYGPPCPP CPAPEFLGGP SVFLFPPKPK DTLMISRTPE VTCVVVDVSQ EDPEVQFNWY   60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGKS GGPALFKSSF  240
PPGSAPTSSS TKKTQLQLEH LLLDLQMILN GINNYKNPKL TRMLTFKFYM PKKATELKHL  300
QCLEEELKPL EEVLNLAQSK NFHLRPRDLI SNINVIVLEL KGSETTFMCE YADETATIVE  360
```

```
FLNRWITFCQ SIISTLTGGG GSGGGGSGGG GSGGGGSGGG GSGGGGSSGG PALFKSSFPP   420
GSEVQLVESG GGLVQPGGSL RLSCAASGFT FSSYTLAWVR QAPGKGLEWV AAIDSSSYTY   480
SPDTVRGRFT ISRDNAKNSL YLQMNSLRAE DTAVYYCARD SNWDALDYWG QGTTVTVSSA   540
STKGPSVFPL APSSKSTSGG TAALGCLVKD YFPEPVTVSW NSGALTSGVH TFPAVLQSSG   600
LYSLSSVVTV PSSSLGTQTY ICNVNHKPSN TKVDKRVEPK SC                     642

SEQ ID NO: 288          moltype = AA   length = 661
FEATURE                 Location/Qualifiers
source                  1..661
                        mol_type = protein
                        organism = synthetic construct
SEQUENCE: 288
ESKYGPPCPP CPAPEFLGGP SVFLFPPKPK DTLMISRTPE VTCVVVDVSQ EDPEVQFNWY    60
VDGVEVHNAK TKPREEQFNS TYRVVSVLTV LHQDWLNGKE YKCKVSNKGL PSSIEKTISK   120
AKGQPREPQV YTLPPSQEEM TKNQVSLTCL VKGFYPSDIA VEWESNGQPE NNYKTTPPVL   180
DSDGSFFLYS RLTVDKSRWQ EGNVFSCSVM HEALHNHYTQ KSLSLSLGKS GGPALFKSSF   240
PPGSAPTSSS TKKTQLQLEH LLLDLQMILN GINNYKNPKL TRMLTFKFYM PKKATELKHL   300
QCLEEELKPL EEVLNLAQSK NFHLRPRDLI SNINVIVLEL KGSETTFMCE YADETATIVE   360
FLNRWITFCQ SIISTLTGGG GSGGGGSGGG GSGGGGSGGG GSGGGGSSGG PALFKSSFPP   420
GSEVQLVESG GGLVQPGGSL RLSCAASGFT FSSYTLAWVR QAPGKGLEWV AAIDSSSYTY   480
SPDTVRGRFT ISRDNAKNSL YLQMNSLRAE DTAVYYCARD SNWDALDYWG QGTTVTVSSG   540
GGGSGGGGSG GGGSDIQMTQ SPSSLSASVG DRVTITCKAR EKLWSAVAWY QQKPGKAPKS   600
LIYSASFRYS GVPSRFSGSG SGTDFTLTIS SLQPEDFATY YCQQYYTYPY TFGGGTKVEI   660
K                                                                  661

SEQ ID NO: 289          moltype = AA   length = 661
FEATURE                 Location/Qualifiers
source                  1..661
                        mol_type = protein
                        organism = synthetic construct
SEQUENCE: 289
ESKYGPPCPP CPAPEFLGGP SVFLFPPKPK DTLMISRTPE VTCVVVDVSQ EDPEVQFNWY    60
VDGVEVHNAK TKPREEQFNS TYRVVSVLTV LHQDWLNGKE YKCKVSNKGL PSSIEKTISK   120
AKGQPREPQV YTLPPSQEEM TKNQVSLTCL VKGFYPSDIA VEWESNGQPE NNYKTTPPVL   180
DSDGSFFLYS RLTVDKSRWQ EGNVFSCSVM HEALHNHYTQ KSLSLSLGKS GGPALFKSSF   240
PPGSAPTSSS TKKTQLQLEH LLLDLQMILN GINNYKNPKL TRMLTFKFYM PKKATELKHL   300
QCLEEELKPL EEVLNLAQSK NFHLRPRDLI SNINVIVLEL KGSETTFMCE YADETATIVE   360
FLNRWITFCQ SIISTLTGGG GSGGGGSGGG GSGGGGSGGG GSGGGGSSGG PALFKSSFPP   420
GSEVQLVESG GGLVQPGGSL RLSCAASGFT FSSYTLAWVR QAPGKGLEWV AAIDSSSYTY   480
SPDTVRGRFT ISRDNAKNSL YLQMNSLRAE DTAVYYCARD SNWDALDYWG QGTTVTVSSG   540
GGGSGGGGSG GGGSDIQMTQ SPSSLSASVG DRVTITCKVT EKVWGNVAWY QQKPGKAPIS   600
LIYSPSLRKS GVPSRFSGSG SGTDFTLTIS SLQPEDFATY YCQQYYTYPY TFGGGTKVEI   660
K                                                                  661

SEQ ID NO: 290          moltype = AA   length = 661
FEATURE                 Location/Qualifiers
source                  1..661
                        mol_type = protein
                        organism = synthetic construct
SEQUENCE: 290
ESKYGPPCPP CPAPEFLGGP SVFLFPPKPK DTLMISRTPE VTCVVVDVSQ EDPEVQFNWY    60
VDGVEVHNAK TKPREEQFNS TYRVVSVLTV LHQDWLNGKE YKCKVSNKGL PSSIEKTISK   120
AKGQPREPQV YTLPPSQEEM TKNQVSLTCL VKGFYPSDIA VEWESNGQPE NNYKTTPPVL   180
DSDGSFFLYS RLTVDKSRWQ EGNVFSCSVM HEALHNHYTQ KSLSLSLGKS GGPALFKSSF   240
PPGSAPTSSS TKKTQLQLEH LLLDLQMILN GINNYKNPKL TRMLTFKFYM PKKATELKHL   300
QCLEEELKPL EEVLNLAQSK NFHLRPRDLI SNINVIVLEL KGSETTFMCE YADETATIVE   360
FLNRWITFCQ SIISTLTGGG GSGGGGSGGG GSGGGGSGGG GSGGGGSSGG PALFKSSFPP   420
GSEVQLVESG GGLVQPGGSL RLSCAASGFT FSSYTLAWVR QAPGKCLEWV AAIDSSSYTY   480
SPDTVRGRFT ISRDNAKNSL YLQMNSLRAE DTAVYYCARD SNWDALDYWG QGTTVTVSSG   540
GGGSGGGGSG GGGSDIQMTQ SPSSLSASVG DRVTITCKAR EKLWSAVAWY QQKPGKAPKS   600
LIYSASFRYS GVPSRFSGSG SGTDFTLTIS SLQPEDFATY YCQQYYTYPY TFGCGTKVEI   660
K                                                                  661

SEQ ID NO: 291          moltype = AA   length = 661
FEATURE                 Location/Qualifiers
source                  1..661
                        mol_type = protein
                        organism = synthetic construct
SEQUENCE: 291
ESKYGPPCPP CPAPEFLGGP SVFLFPPKPK DTLMISRTPE VTCVVVDVSQ EDPEVQFNWY    60
VDGVEVHNAK TKPREEQFNS TYRVVSVLTV LHQDWLNGKE YKCKVSNKGL PSSIEKTISK   120
AKGQPREPQV YTLPPSQEEM TKNQVSLTCL VKGFYPSDIA VEWESNGQPE NNYKTTPPVL   180
DSDGSFFLYS RLTVDKSRWQ EGNVFSCSVM HEALHNHYTQ KSLSLSLGKS GGPALFKSSF   240
PPGSAPTSSS TKKTQLQLEH LLLDLQMILN GINNYKNPKL TRMLTFKFYM PKKATELKHL   300
QCLEEELKPL EEVLNLAQSK NFHLRPRDLI SNINVIVLEL KGSETTFMCE YADETATIVE   360
FLNRWITFCQ SIISTLTGGG GSGGGGSGGG GSGGGGSGGG GSGGGGSSGG PALFKSSFPP   420
GSEVQLVESG GGLVQPGGSL RLSCAASGFT FSSYTLAWVR QAPGKGLEWV AAIDSSSYTY   480
SPDTVRGRFT ISRDNAKNSL YLQMNSLRAE DTAVYYCARD SNWDALDYWG CGTTVTVSSG   540
GGGSGGGGSG GGGSDIQMTQ SPSSLSASVG DRVTITCKAR EKLWSAVAWY QQKPGKCPKA   600
```

```
LIYSASFRYS GVPSRFSGSG SGTDFTLTIS SLQPEDFATY YCQQYYTYPY TFGGGTKVEI   660
K                                                                  661

SEQ ID NO: 292            moltype = AA  length = 661
FEATURE                   Location/Qualifiers
source                    1..661
                          mol_type = protein
                          organism = synthetic construct
SEQUENCE: 292
ESKYGPPCPP CPAPEFLGGP SVFLFPPKPK DTLMISRTPE VTCVVVDVSQ EDPEVQFNWY   60
VDGVEVHNAK TKPREEQFNS TYRVVSVLTV LHQDWLNGKE YKCKVSNKGL PSSIEKTISK   120
AKGQPREPQV YTLPPSQEEM TKNQVSLTCL VKGFYPSDIA VEWESNGQPE NNYKTTPPVL   180
DSDGSFFLYS RLTVDKSRWQ EGNVFSCSVM HEALHNHYTQ KSLSLSLGKS GGPALFKSSF   240
PPGSAPTSSS TKKTQLQLEH LLLDLQMILN GINNYKNPKL TRMLTFKFYM PKKATELKHL   300
QCLEEELKPL EEVLNLAQSK NFHLRPRDLI SNINVIVLEL KGSETTFMCE YADETATIVE   360
FLNRWITFCQ SIISTLTGGG GSGGGGSGGG GSGGGGSGGG GSGGGGSSGG PALFKSSFPP   420
GSEVQLVESG GGLVQPGGSL RLSCAASGFT FSSYTLAWVR QAPGKCLEWV AAIDSSSYTY   480
SPDTVRGRFT ISRDNAKNSL YLQMNSLRAE DTAVYYCARD SNWDALDYWG QGTTVTVSSG   540
GGGSGGGGSG GGGSDIQMTQ SPSSLSASVG DRVTITCKVT EKVWGNVAWY QQKPGKAPIS   600
LIYSPSLRKS GVPSRFSGSG SGTDFTLTIS SLQPEDFATY YCQQYYTYPY TFGCGTKVEI   660
K                                                                  661

SEQ ID NO: 293            moltype = AA  length = 661
FEATURE                   Location/Qualifiers
source                    1..661
                          mol_type = protein
                          organism = synthetic construct
SEQUENCE: 293
ESKYGPPCPP CPAPEFLGGP SVFLFPPKPK DTLMISRTPE VTCVVVDVSQ EDPEVQFNWY   60
VDGVEVHNAK TKPREEQFNS TYRVVSVLTV LHQDWLNGKE YKCKVSNKGL PSSIEKTISK   120
AKGQPREPQV YTLPPSQEEM TKNQVSLTCL VKGFYPSDIA VEWESNGQPE NNYKTTPPVL   180
DSDGSFFLYS RLTVDKSRWQ EGNVFSCSVM HEALHNHYTQ KSLSLSLGKS GGPALFKSSF   240
PPGSAPTSSS TKKTQLQLEH LLLDLQMILN GINNYKNPKL TRMLTFKFYM PKKATELKHL   300
QCLEEELKPL EEVLNLAQSK NFHLRPRDLI SNINVIVLEL KGSETTFMCE YADETATIVE   360
FLNRWITFCQ SIISTLTGGG GSGGGGSGGG GSGGGGSGGG GSGGGGSSGG PALFKSSFPP   420
GSEVQLVESG GGLVQPGGSL RLSCAASGFT FSSYTLAWVR QAPGKGLEWV AAIDSSSYTY   480
SPDTVRGRFT ISRDNAKNSL YLQMNSLRAE DTAVYYCARD SNWDALDYWG CGTTVTVSSG   540
GGGSGGGGSG GGGSDIQMTQ SPSSLSASVG DRVTITCKVT EKVWGNVAWY QQKPGKCPIS   600
LIYSPSLRKS GVPSRFSGSG SGTDFTLTIS SLQPEDFATY YCQQYYTYPY TFGGGTKVEI   660
K                                                                  661

SEQ ID NO: 294            moltype = AA  length = 659
FEATURE                   Location/Qualifiers
source                    1..659
                          mol_type = protein
                          organism = synthetic construct
SEQUENCE: 294
VPRDCGCKPC ICTVPEVSSV FIFPPKPKDV LTITLTPKVT CVVVDISKDD PEVQFSWFVD   60
DVEVHTAQTQ PREEQFNSTF RSVSELPIMH QDWLNGKEFK CRVNSAAFPA PIEKTISKTK   120
GRPKAPQVYT IPPPKEQMAK DKVSLTCMIT DFFPEDITVE WQWNGQPAEN YKNTQPIMDT   180
DGSYFVYSKL NVQKSNWEAG NTFTCSVLHE GLHNHHTEKS LSHSPGKSGG PALFKSSFPP   240
GSAPTSSSTK KTQLQLEHLL LDLQMILNGI NNYKNPKLTR MLTFKFYMPK KATELKHLQC   300
LEEELKPLEE VLNLAQSKNF HLRPRDLISN INVIVLELKG SETTFMCEYA DETATIVEFL   360
NRWITFCQSI ISTLTGGGGS GGGGSGGGGS GGGGSGGGGS GGGGSSGGPA LFKSSFPPGS   420
EVQLVESGGG LVQPGGSLRL SCAASGFTFS SYTLAWVRQA PGKGLEWVAA IDSSSYTYSP   480
DTVRGRFTIS RDNAKNSLYL QMNSLRAEDT AVYYCARDSN WDALDYWGQG TTVTVSSGGG   540
GSGGGGSGGG GSDIQMTQSP SSLSASVGDR VTITCKAREK LWSAVAWYQQ KPGKAPKSLI   600
YSASFRYSGV PSRFSGSGSG TDFTLTISSL QPEDFATYYC QQYYTYPYTF GGGTKVEIK    659

SEQ ID NO: 295            moltype = AA  length = 659
FEATURE                   Location/Qualifiers
source                    1..659
                          mol_type = protein
                          organism = synthetic construct
SEQUENCE: 295
VPRDCGCKPC ICTVPEVSSV FIFPPKPKDV LTITLTPKVT CVVVDISKDD PEVQFSWFVD   60
DVEVHTAQTQ PREEQFNSTF RSVSELPIMH QDWLNGKEFK CRVNSAAFPA PIEKTISKTK   120
GRPKAPQVYT IPPPKEQMAK DKVSLTCMIT DFFPEDITVE WQWNGQPAEN YKNTQPIMDT   180
DGSYFVYSKL NVQKSNWEAG NTFTCSVLHE GLHNHHTEKS LSHSPGKSGG PALFKSSFPP   240
GSAPTSSSTK KTQLQLEHLL LDLQMILNGI NNYKNPKLTR MLTFKFYMPK KATELKHLQC   300
LEEELKPLEE VLNLAQSKNF HLRPRDLISN INVIVLELKG SETTFMCEYA DETATIVEFL   360
NRWITFCQSI ISTLTGGGGS GGGGSGGGGS GGGGSGGGGS GGGGSSGGPA LFKSSFPPGS   420
EVQLVESGGG LVQPGGSLRL SCAASGFTFS SYTLAWVRQA PGKGLEWVAA IDSSSYTYSP   480
DTVRGRFTIS RDNAKNSLYL QMNSLRAEDT AVYYCARDSN WDALDYWGQG TTVTVSSGGG   540
GSGGGGSGGG GSDIQMTQSP SSLSASVGDR VTITCKVTEK VWGNVAWYQQ KPGKAPISLI   600
YSPSLRKSGV PSRFSGSGSG TDFTLTISSL QPEDFATYYC QQYYTYPYTF GGGTKVEIK    659

SEQ ID NO: 296            moltype = AA  length = 659
FEATURE                   Location/Qualifiers
```

```
source                      1..659
                            mol_type = protein
                            organism = synthetic construct
SEQUENCE: 296
VPRDCGCKPC ICTVPEVSSV FIFPPKPKDV LTITLTPKVT CVVVDISKDD PEVQFSWFVD    60
DVEVHTAQTQ PREEQFNSTF RSVSELPIMH QDWLNGKEFK CRVNSAAFPA PIEKTISKTK   120
GRPKAPQVYT IPPPKEQMAK DKVSLTCMIT DFFPEDITVE WQWNGQPAEN YKNTQPIMDT   180
DGSYFVYSKL NVQKSNWEAG NTFTCSVLHE GLHNHHTEKS LSHSPGKSGG PALFKSSFPP   240
GSAPTSSSTK KTQLQLEHLL LDLQMILNGI NNYKNPKLTR MLTFKFYMPK KATELKHLQC   300
LEEELKPLEE VLNLAQSKNF HLRPRDLISN INVIVLELKG SETTFMCEYA DETATIVEFL   360
NRWITFCQSI ISTLTGGGGS GGGGSGGGGS GGGGSGGGGS GGGGSSGGPA LFKSSFPPGS   420
EVQLVESGGG LVQPGGSLRL SCAASGFTFS SYTLAWVRQA PGKCLEWVAA IDSSSYTYSP   480
DTVRGRFTIS RDNAKNSLYL QMNSLRAEDT AVYYCARDSN WDALDYWGQG TTVTVSSGGG   540
GSGGGGGSGGG GSDIQMTQSP SSLSASVGDR VTITCKAREK LWSAVAWYQQ KPGKAPKSLI   600
YSASFRYSGV PSRFSGSGSG TDFTLTISSL QPEDFATYYC QQYYTYPYTF GCGTKVEIK    659

SEQ ID NO: 297              moltype = AA  length = 659
FEATURE                     Location/Qualifiers
source                      1..659
                            mol_type = protein
                            organism = synthetic construct
SEQUENCE: 297
VPRDCGCKPC ICTVPEVSSV FIFPPKPKDV LTITLTPKVT CVVVDISKDD PEVQFSWFVD    60
DVEVHTAQTQ PREEQFNSTF RSVSELPIMH QDWLNGKEFK CRVNSAAFPA PIEKTISKTK   120
GRPKAPQVYT IPPPKEQMAK DKVSLTCMIT DFFPEDITVE WQWNGQPAEN YKNTQPIMDT   180
DGSYFVYSKL NVQKSNWEAG NTFTCSVLHE GLHNHHTEKS LSHSPGKSGG PALFKSSFPP   240
GSAPTSSSTK KTQLQLEHLL LDLQMILNGI NNYKNPKLTR MLTFKFYMPK KATELKHLQC   300
LEEELKPLEE VLNLAQSKNF HLRPRDLISN INVIVLELKG SETTFMCEYA DETATIVEFL   360
NRWITFCQSI ISTLTGGGGS GGGGSGGGGS GGGGSGGGGS GGGGSSGGPA LFKSSFPPGS   420
EVQLVESGGG LVQPGGSLRL SCAASGFTFS SYTLAWVRQA PGKCLEWVAA IDSSSYTYSP   480
DTVRGRFTIS RDNAKNSLYL QMNSLRAEDT AVYYCARDSN WDALDYWGCG TTVTVSSGGG   540
GSGGGGGSGGG GSDIQMTQSP SSLSASVGDR VTITCKAREK LWSAVAWYQQ KPGKCPKALI   600
YSASFRYSGV PSRFSGSGSG TDFTLTISSL QPEDFATYYC QQYYTYPYTF GGGTKVEIK    659

SEQ ID NO: 298              moltype = AA  length = 659
FEATURE                     Location/Qualifiers
source                      1..659
                            mol_type = protein
                            organism = synthetic construct
SEQUENCE: 298
VPRDCGCKPC ICTVPEVSSV FIFPPKPKDV LTITLTPKVT CVVVDISKDD PEVQFSWFVD    60
DVEVHTAQTQ PREEQFNSTF RSVSELPIMH QDWLNGKEFK CRVNSAAFPA PIEKTISKTK   120
GRPKAPQVYT IPPPKEQMAK DKVSLTCMIT DFFPEDITVE WQWNGQPAEN YKNTQPIMDT   180
DGSYFVYSKL NVQKSNWEAG NTFTCSVLHE GLHNHHTEKS LSHSPGKSGG PALFKSSFPP   240
GSAPTSSSTK KTQLQLEHLL LDLQMILNGI NNYKNPKLTR MLTFKFYMPK KATELKHLQC   300
LEEELKPLEE VLNLAQSKNF HLRPRDLISN INVIVLELKG SETTFMCEYA DETATIVEFL   360
NRWITFCQSI ISTLTGGGGS GGGGSGGGGS GGGGSGGGGS GGGGSSGGPA LFKSSFPPGS   420
EVQLVESGGG LVQPGGSLRL SCAASGFTFS SYTLAWVRQA PGKCLEWVAA IDSSSYTYSP   480
DTVRGRFTIS RDNAKNSLYL QMNSLRAEDT AVYYCARDSN WDALDYWGQG TTVTVSSGGG   540
GSGGGGGSGGG GSDIQMTQSP SSLSASVGDR VTITCKVTEK VWGNVAWYQQ KPGKAPISLI   600
YSPSLRKSGV PSRFSGSGSG TDFTLTISSL QPEDFATYYC QQYYTYPYTF GCGTKVEIK    659

SEQ ID NO: 299              moltype = AA  length = 659
FEATURE                     Location/Qualifiers
source                      1..659
                            mol_type = protein
                            organism = synthetic construct
SEQUENCE: 299
VPRDCGCKPC ICTVPEVSSV FIFPPKPKDV LTITLTPKVT CVVVDISKDD PEVQFSWFVD    60
DVEVHTAQTQ PREEQFNSTF RSVSELPIMH QDWLNGKEFK CRVNSAAFPA PIEKTISKTK   120
GRPKAPQVYT IPPPKEQMAK DKVSLTCMIT DFFPEDITVE WQWNGQPAEN YKNTQPIMDT   180
DGSYFVYSKL NVQKSNWEAG NTFTCSVLHE GLHNHHTEKS LSHSPGKSGG PALFKSSFPP   240
GSAPTSSSTK KTQLQLEHLL LDLQMILNGI NNYKNPKLTR MLTFKFYMPK KATELKHLQC   300
LEEELKPLEE VLNLAQSKNF HLRPRDLISN INVIVLELKG SETTFMCEYA DETATIVEFL   360
NRWITFCQSI ISTLTGGGGS GGGGSGGGGS GGGGSGGGGS GGGGSSGGPA LFKSSFPPGS   420
EVQLVESGGG LVQPGGSLRL SCAASGFTFS SYTLAWVRQA PGKGLEWVAA IDSSSYTYSP   480
DTVRGRFTIS RDNAKNSLYL QMNSLRAEDT AVYYCARDSN WDALDYWGCG TTVTVSSGGG   540
GSGGGGGSGGG GSDIQMTQSP SSLSASVGDR VTITCKVTEK VWGNVAWYQQ KPGKCPISLI   600
YSPSLRKSGV PSRFSGSGSG TDFTLTISSL QPEDFATYYC QQYYTYPYTF GGGTKVEIK    659

SEQ ID NO: 300              moltype = AA  length = 662
FEATURE                     Location/Qualifiers
source                      1..662
                            mol_type = protein
                            organism = synthetic construct
SEQUENCE: 300
MDMRVPAQLL GLLLLWLRGA RCVPRDCGCK PCICTVPEVS SVFIFPPKPK DVLTITLTPK    60
VTCVVVDISK DDPEVQFSWF VDDVEVHTAQ TQPREEQFNS TFRSVSELPI MHQDWLNGKE   120
FKCRVNSAAF PAPIEKTISK TKGRPKAPQV YTIPPPKEQM AKDKVSLTCM ITDFFPEDIT   180
```

```
VEWQWNGQPA ENYKNTQPIM DTDGSYFVYS KLNVQKSNWE AGNTFTCSVL HEGLHNHHTE    240
KSLSHSPGKS GGPALFKSSF PPGSAPTSSS TKKTQLQLEH LLLDLQMILN GINNYKNPKL    300
TRMLTFKFYM PKKATELKHL QCLEEELKPL EEVLNLAQSK NFHLRPRDLI SNINIVLEL    360
KGSETTFMCE YADETATIVE FLNRWITFCQ SIISTLTGGG GSGGGGSGGG GSGGGGSGGG    420
GSGGGSSGG PALFKSSFPP GSEVQLVESG GGLVQPGGSL RLSCAASGFT FSSYTLAWVR    480
QAPGKGLEWV AAIDSSSYTY SPDTVRGRFT ISRDNAKNSL YLQMNSLRAE DTAVYYCARD    540
SNWDALDYWG QGTTVTVSSA STKGPSVFPL APSSKSTSGG TAALGCLVKD YFPEPVTVSW    600
NSGALTSGVH TFPAVLQSSG LYSLSSVVTV PSSSLGTQTY ICNVNHKPSN TKVDKRVEPK    660
SC                                                                 662

SEQ ID NO: 301            moltype = AA  length = 214
FEATURE                   Location/Qualifiers
source                    1..214
                          mol_type = protein
                          organism = synthetic construct
SEQUENCE: 301
DIQMTQSPSS LSASVGDRVT ITCKVTEKVW GNVAWYQQKP GKAPISLIYS PSLRKSGVPS    60
RFSGSGSGTD FTLTISSLQP EDFATYYCQQ YYTYPYTFGG GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                               214

SEQ ID NO: 302            moltype = AA  length = 661
FEATURE                   Location/Qualifiers
source                    1..661
                          mol_type = protein
                          organism = synthetic construct
SEQUENCE: 302
ESKYGPPCPP CPAPEFLGGP SVFLFPPKPK DTLMISRTPE VTCVVVDVSQ EDPEVQFNWY    60
VDGVEVHNAK TKPREEQFNS TYRVVSVLTV LHQDWLNGKE YKCKVSNKGL PSSIEKTISK    120
AKGQPREPQV YTLPPSQEEM TKNQVSLTCL VKGFYPSDIA VEWESNGQPE NNYKTTPPVL    180
DSDGSFFLYS RLTVDKSRWQ EGNVFSCSVM HEALHNHYTQ KSLSLSLGKS GGPGPAGLYA    240
QPGSAPTSSS TKKTQLQLEH LLLDLQMILN GINNYKNPKL TRMLTFKFYM PKKATELKHL    300
QCLEEELKPL EEVLNLAQSK NFHLRPRDLI SNINIVLEL KGSETTFMCE YADETATIVE    360
FLNRWITFCQ SIISTLTGGG GSGGGGSGGG GSGGGGSGGG GSGGGGSGGG PGPAGLYAQP    420
GSEVQLVESG GGLVQPGGSL RLSCAASGFT FSSYTLAWVR QAPGKCLEWV AAIDSSSYTY    480
SPDTVRGRFT ISRDNAKNSL YLQMNSLRAE DTAVYYCARD SNWDALDYWG QGTTVTVSSG    540
GGGSGGGGSG GGGSDIQMTQ SPSSLSASVG DRVTITCKAS QNVGTNVGWY QQKPGKAPKA    600
LIYSASFRYS GVPSRFSGSG SGTDFTLTIS SLQPEDFATY YCQQYYTYPY TFGCGTKVEI    660
K                                                                  661

SEQ ID NO: 303            moltype = AA  length = 661
FEATURE                   Location/Qualifiers
source                    1..661
                          mol_type = protein
                          organism = synthetic construct
SEQUENCE: 303
ESKYGPPCPP CPAPEFLGGP SVFLFPPKPK DTLMISRTPE VTCVVVDVSQ EDPEVQFNWY    60
VDGVEVHNAK TKPREEQFNS TYRVVSVLTV LHQDWLNGKE YKCKVSNKGL PSSIEKTISK    120
AKGQPREPQV YTLPPSQEEM TKNQVSLTCL VKGFYPSDIA VEWESNGQPE NNYKTTPPVL    180
DSDGSFFLYS RLTVDKSRWQ EGNVFSCSVM HEALHNHYTQ KSLSLSLGKS GGPGPAGLYA    240
QPGSAPTSSS TKKTQLQLEH LLLDLQMILN GINNYKNPKL TRMLTFKFYM PKKATELKHL    300
QCLEEELKPL EEVLNLAQSK NFHLRPRDLI SNINIVLEL KGSETTFMCE YADETATIVE    360
FLNRWITFCQ SIISTLTGGG GSGGGGSGGG GSGGGGSGGG GSGGGGSGGG PGPAGLYAQP    420
GSEVQLVESG GGLVQPGGSL RLSCAASGFT FSSYTLAWVR QAPGKGLEWV AAIDSSSYTY    480
SPDTVRGRFT ISRDNAKNSL YLQMNSLRAE DTAVYYCARD SNWDALDYWG CGTTVTVSSG    540
GGGSGGGGSG GGGSDIQMTQ SPSSLSASVG DRVTITCKAS QNVGTNVGWY QQKPGKCPKA    600
LIYSASFRYS GVPSRFSGSG SGTDFTLTIS SLQPEDFATY YCQQYYTYPY TFGGGTKVEI    660
K                                                                  661

SEQ ID NO: 304            moltype = AA  length = 661
FEATURE                   Location/Qualifiers
source                    1..661
                          mol_type = protein
                          organism = synthetic construct
SEQUENCE: 304
ESKYGPPCPP CPAPEFLGGP SVFLFPPKPK DTLMISRTPE VTCVVVDVSQ EDPEVQFNWY    60
VDGVEVHNAK TKPREEQFNS TYRVVSVLTV LHQDWLNGKE YKCKVSNKGL PSSIEKTISK    120
AKGQPREPQV YTLPPSQEEM TKNQVSLTCL VKGFYPSDIA VEWESNGQPE NNYKTTPPVL    180
DSDGSFFLYS RLTVDKSRWQ EGNVFSCSVM HEALHNHYTQ KSLSLSLGKS GGPGPAGLYA    240
QPGSAPTSSS TKKTQLQLEH LLLDLQMILN GINNYKNPKL TRMLTFKFYM PKKATELKHL    300
QCLEEELKPL EEVLNLAQSK NFHLRPRDLI SNINIVLEL KGSETTFMCE YADETATIVE    360
FLNRWITFCQ SIISTLTGGG GSGGGGSGGG GSGGGGSGGG GSGGGGSGGG PGPAGLYAQP    420
GSEVQLVESG GGLVQPGGSL RLSCAASGFT FSSYTLAWVR QAPGKCLEWV AAIDSSSYTY    480
SPDTVRGRFT ISRDNAKNSL YLQMNSLRAE DTAVYYCARD SNWDALDYWG QGTTVTVSSG    540
GGGSGGGGSG GGGSDIQMTQ SPSSLSASVG DRVTITCKAR EKLWSAVAWY QQKPGKAPKA    600
LIYSASFRYS GVPSRFSGSG SGTDFTLTIS SLQPEDFATY YCQQYYTYPY TFGCGTKVEI    660
K                                                                  661

SEQ ID NO: 305            moltype = AA  length = 661
```

```
FEATURE                 Location/Qualifiers
source                  1..661
                        mol_type = protein
                        organism = synthetic construct
SEQUENCE: 305
ESKYGPPCPP  CPAPEFLGGP  SVFLFPPKPK  DTLMISRTPE  VTCVVVDVSQ  EDPEVQFNWY   60
VDGVEVHNAK  TKPREEQFNS  TYRVVSVLTV  LHQDWLNGKE  YKCKVSNKGL  PSSIEKTISK  120
AKGQPREPQV  YTLPPSQEEM  TKNQVSLTCL  VKGFYPSDIA  VEWESNGQPE  NNYKTTPPVL  180
DSDGSFFLYS  RLTVDKSRWQ  EGNVFSCSVM  HEALHNHYTQ  KSLSLSLGKS  GGPGPAGLYA  240
QPGSAPTSSS  TKKTQLQLEH  LLLDLQMILN  GINNYKNPKL  TRMLTFKFYM  PKKATELKHL  300
QCLEEELKPL  EEVLNLAQSK  NFHLRPRDLI  SNINVIVLEL  KGSETTFMCE  YADETATIVE  360
FLNRWITFCQ  SIISTLTGGG  GSGGGGSGGG  GSGGGGSGGG  GSGGGGSSGG  PGPAGLYAQP  420
GSEVQLVESG  GGLVQPGGSL  RLSCAASGFT  FSSYTLAWVR  QAPGKGLEWV  AAIDSSSYTY  480
SPDTVRGRFT  ISRDNAKNSL  YLQMNSLRAE  DTAVYYCARD  SNWDALDYWG  CGTTVTVSSG  540
GGGSGGGGSG  GGGSDIQMTQ  SPSSLSASVG  DRVTITCKAR  EKLWSAVAWY  QQKPGKCPKA  600
LIYSASFRYS  GVPSRFSGSG  SGTDFTLTIS  SLQPEDFATY  YCQQYYTYPY  TFGGGTKVEI  660
K                                                                      661

SEQ ID NO: 306          moltype = AA   length = 661
FEATURE                 Location/Qualifiers
source                  1..661
                        mol_type = protein
                        organism = synthetic construct
SEQUENCE: 306
ESKYGPPCPP  CPAPEFLGGP  SVFLFPPKPK  DTLMISRTPE  VTCVVVDVSQ  EDPEVQFNWY   60
VDGVEVHNAK  TKPREEQFNS  TYRVVSVLTV  LHQDWLNGKE  YKCKVSNKGL  PSSIEKTISK  120
AKGQPREPQV  YTLPPSQEEM  TKNQVSLTCL  VKGFYPSDIA  VEWESNGQPE  NNYKTTPPVL  180
DSDGSFFLYS  RLTVDKSRWQ  EGNVFSCSVM  HEALHNHYTQ  KSLSLSLGKS  GGPGPAGLYA  240
QPGSAPTSSS  TKKTQLQLEH  LLLDLQMILN  GINNYKNPKL  TRMLTFKFYM  PKKATELKHL  300
QCLEEELKPL  EEVLNLAQSK  NFHLRPRDLI  SNINVIVLEL  KGSETTFMCE  YADETATIVE  360
FLNRWITFCQ  SIISTLTGGG  GSGGGGSGGG  GSGGGGSGGG  GSGGGGSSGG  PGPAGLYAQP  420
GSEVQLVESG  GGLVQPGGSL  RLSCAASGFT  FSSYTLAWVR  QAPGKCLEWV  AAIDSSSYTY  480
SPDTVRGRFT  ISRDNAKNSL  YLQMNSLRAE  DTAVYYCARD  SNWDALDYWG  QGTTVTVSSG  540
GGGSGGGGSG  GGGSDIQMTQ  SPSSLSASVG  DRVTITCKVT  EKVWGNVAWY  QQKPGKAPIS  600
LIYSPSLRKS  GVPSRFSGSG  SGTDFTLTIS  SLQPEDFATY  YCQQYYTYPY  TFGCGTKVEI  660
K                                                                      661

SEQ ID NO: 307          moltype = AA   length = 661
FEATURE                 Location/Qualifiers
source                  1..661
                        mol_type = protein
                        organism = synthetic construct
SEQUENCE: 307
ESKYGPPCPP  CPAPEFLGGP  SVFLFPPKPK  DTLMISRTPE  VTCVVVDVSQ  EDPEVQFNWY   60
VDGVEVHNAK  TKPREEQFNS  TYRVVSVLTV  LHQDWLNGKE  YKCKVSNKGL  PSSIEKTISK  120
AKGQPREPQV  YTLPPSQEEM  TKNQVSLTCL  VKGFYPSDIA  VEWESNGQPE  NNYKTTPPVL  180
DSDGSFFLYS  RLTVDKSRWQ  EGNVFSCSVM  HEALHNHYTQ  KSLSLSLGKS  GGPGPAGLYA  240
QPGSAPTSSS  TKKTQLQLEH  LLLDLQMILN  GINNYKNPKL  TRMLTFKFYM  PKKATELKHL  300
QCLEEELKPL  EEVLNLAQSK  NFHLRPRDLI  SNINVIVLEL  KGSETTFMCE  YADETATIVE  360
FLNRWITFCQ  SIISTLTGGG  GSGGGGSGGG  GSGGGGSGGG  GSGGGGSSGG  PGPAGLYAQP  420
GSEVQLVESG  GGLVQPGGSL  RLSCAASGFT  FSSYTLAWVR  QAPGKGLEWV  AAIDSSSYTY  480
SPDTVRGRFT  ISRDNAKNSL  YLQMNSLRAE  DTAVYYCARD  SNWDALDYWG  CGTTVTVSSG  540
GGGSGGGGSG  GGGSDIQMTQ  SPSSLSASVG  DRVTITCKVT  EKVWGNVAWY  QQKPGKCPIS  600
LIYSPSLRKS  GVPSRFSGSG  SGTDFTLTIS  SLQPEDFATY  YCQQYYTYPY  TFGGGTKVEI  660
K                                                                      661

SEQ ID NO: 308          moltype = AA   length = 541
FEATURE                 Location/Qualifiers
source                  1..541
                        mol_type = protein
                        organism = synthetic construct
SEQUENCE: 308
ESKYGPPCPP  CPAPEFLGGP  SVFLFPPKPK  DTLMISRTPE  VTCVVVDVSQ  EDPEVQFNWY   60
VDGVEVHNAK  TKPREEQFNS  TYRVVSVLTV  LHQDWLNGKE  YKCKVSNKGL  PSSIEKTISK  120
AKGQPREPQV  YTLPPSQEEM  TKNQVSLTCL  VKGFYPSDIA  VEWESNGQPE  NNYKTTPPVL  180
DSDGSFFLYS  RLTVDKSRWQ  EGNVFSCSVM  HEALHNHYTQ  KSLSLSLGKS  GGPGPAGLYA  240
QPGSAPTSSS  TKKTQLQLEH  LLLDLQMILN  GINNYKNPKL  TRMLTFKFYM  PKKATELKHL  300
QCLEEELKPL  EEVLNLAQSK  NFHLRPRDLI  SNINVIVLEL  KGSETTFMCE  YADETATIVE  360
FLNRWITFCQ  SIISTLTGGG  GSGGGGSGGG  GSGGGGSGGG  GSGGGGSSGG  PGPAGLYAQP  420
GSEVQLLESG  GGLVQPGGSL  RLSCAASGSI  FSANAMGWYR  QAPGKQRELV  AVISSGGSTN  480
YADSVKGRFT  ISRDNSKNTV  YLQMNSLRAE  DTAVYYCMYS  GSYYYTPNDY  WGQGTLVTVS  540
S                                                                      541

SEQ ID NO: 309          moltype = AA   length = 547
FEATURE                 Location/Qualifiers
source                  1..547
                        mol_type = protein
                        organism = synthetic construct
SEQUENCE: 309
```

```
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTSGGPGPA GLYAQPGSEV QLVESGGGLV QPGNSLRLSC AASGFTSKF    180
GMSWVRQAPG KGLEWVSSIS GSGRDTLYAE SVKGRFTISR DNAKTTLYLQ MNSLRPEDTA   240
VYYCTIGGSL SVSSQGTLVT VSSGGGGSGG GGSGGGGSGG GGSSGGPGPA              300
GLYAQPGSEV QLVESGGGLV QPGGSLRLSC AASGFTSSY  TLAWVRQAPG KCLEWVAAID   360
SSSYTYSPDT VRGRFTISRD NAKNSLYLQM NSLRAEDTAV YYCARDSNWD ALDYWGQGTT   420
VTVSSGGGGS GGGGSGGGGS DIQMTQSPSS LSASVGDRVT ITCKAREKLW SAVAWYQQKP   480
GKAPKSLIYS ASFRYSGVPS RFSGSGSGTD FTLTISSLQP EDFATYYCQQ YYTYPYTFGC   540
GTKVEIK                                                             547

SEQ ID NO: 310          moltype = AA  length = 661
FEATURE                 Location/Qualifiers
source                  1..661
                        mol_type = protein
                        organism = synthetic construct
SEQUENCE: 310
ESKYGPPCPP CPAPEFLGGP SVFLFPPKPK DTLMISRTPE VTCVVVDVSQ EDPEVQFNWY    60
VDGVEVHNAK TKPREEQFNS TYRVVSVLTV LHQDWLNGKE YKCKVSNKGL PSSIEKTISK   120
AKGQPREPQV YTLPPSQEEM TKNQVSLTCL VKGFYPSDIA VEWESNGQPE NNYKTTPPVL   180
DSDGSFFLYS RLTVDKSRWQ EGNVFSCSVM HEALHNHYTQ KSLSLSLGKS GGPGPAGLYA   240
QPGSGPAPTSSS TKKTQLQLEH LLLDLQMILN GINNYKNPKL TRMLTFKFYM PKKATELKHL   300
QCLEEELKPL EEVLNLAQSK NFHLRPRDLI SNINVIVLEL KGSETTFMCE YADETATIVE   360
FLNRWITFCQ SIISTLTGGG GSGGGGSGGG GSGGGGSGGG GSGGGGSSGG PGPAGLYAQP   420
GSEVQLVESG GGLVQPGGSL RLSCAASGFT FSSYTLAWVR QAPGKCLEWV AAIDSSSYTY   480
SPDTVRGRFT ISRDNAKNSL YLQMNSLRAE DTAVYYCARD SNWDALDYWG QGTTVTVSSG   540
GGGSGGGGSG GGGSDIQMTQ SPSSLSASVG DRVTITCKAR EKLWSAVAWY QQKPGKAPKS   600
LIYSASFRYS GVPSRFSGSG SGTDFTLTIS SLQPEDFATY YCQQYYTYPY TFGCGTKVEI   660
K                                                                   661

SEQ ID NO: 311          moltype = AA  length = 811
FEATURE                 Location/Qualifiers
source                  1..811
                        mol_type = protein
                        organism = synthetic construct
SEQUENCE: 311
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTSGGPGPA GLYAQPGSGG GGSGGGGSGG GGSGGGGSGG GGSGGGGSEL   180
CDDDPPEIPH ATFKAMAYKE GTMLNCECKR GFRRIKSGSL YMLCTGNSSH SSWDNQCQCT   240
SSATRNTTKQ VTPQPEEQKE RKTTEMQSPM QPVDQASLPG HCREPPPWEN EATERIYHFV   300
VGQMVYYQCV QGYRALHRGP AESVCKMTHG KTRWTQPQLI CTGEMETSQF PGEEKPQASP   360
EGRPESETSS LVTTTDFQIQ TEMAATMETS IFTTEYQSGG PGPAGLYAQP GSEVQLVESG   420
GGLVQPGNSL RLSCAASGFT FSKFGMSWVR QAPGKGLEWV SSISGSGRDT LYAESVKGRF   480
TISRDNAKTT LYLQMNSLRP EDTAVYYCTI GGSLSVSSQG TLVTVSSGGG GSGGGGSGGG   540
GSGGGGSGGG GSGGGGSSGG PGPAGLYAQP GSEVQLVESG GGLVQPGGSL RLSCAASGFT   600
FSSYTLAWVR QAPGKCLEWV AAIDSSSYTY SPDTVRGRFT ISRDNAKNSL YLQMNSLRAE   660
DTAVYYCARD SNWDALDYWG QGTTVTVSSG GGGSGGGGSG GGGSDIQMTQ SPSSLSASVG   720
DRVTITCKAR EKLWSAVAWY QQKPGKAPKS LIYSASFRYS GVPSRFSGSG SGTDFTLTIS   780
SLQPEDFATY YCQQYYTYPY TFGCGTKVEI K                                  811

SEQ ID NO: 312          moltype = AA  length = 811
FEATURE                 Location/Qualifiers
source                  1..811
                        mol_type = protein
                        organism = synthetic construct
SEQUENCE: 312
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTSGGPGPA GLYAQPGSGG GGSGGGGSGG GGSGGGGSGG GGSGGGGSEL   180
CDDDPPEIPH ATFKAMAYKE GTMLNCECKR GFRRIKSGSL YMLCTGNSSH SSWDNQCQCT   240
SSATRNTTKQ VTPQPEEQKE RKTTEMQSPM QPVDQASLPG HCREPPPWEN EATERIYHFV   300
VGQMVYYQCV QGYRALHRGP AESVCKMTHG KTRWTQPQLI CTGEMETSQF PGEEKPQASP   360
EGRPESETSS LVTTTDFQIQ TEMAATMETS IFTTEYQSGG PGPAGLYAQP GSEVQLVESG   420
GGLVQPGNSL RLSCAASGFT FSKFGMSWVR QAPGKGLEWV SSISGSGRDT LYAESVKGRF   480
TISRDNAKTT LYLQMNSLRP EDTAVYYCTI GGSLSVSSQG TLVTVSSGGG GSGGGGSGGG   540
GSGGGGSGGG GSGGGGSSGG PGPAGLYAQP GSEVQLVESG GGLVQPGGSL RLSCAASGFT   600
FSSYTLAWVR QAPGKGLEWV AAIDSSSYTY SPDTVRGRFT ISRDNAKNSL YLQMNSLRAE   660
DTAVYYCARD SNWDALDYWG CGTTVTVSSG GGGSGGGGSG GGGSDIQMTQ SPSSLSASVG   720
DRVTITCKAR EKLWSAVAWY QQKPGKCPKA LIYSASFRYS GVPSRFSGSG SGTDFTLTIS   780
SLQPEDFATY YCQQYYTYPY TFGGGTKVEI K                                  811

SEQ ID NO: 313          moltype = AA  length = 811
FEATURE                 Location/Qualifiers
source                  1..811
                        mol_type = protein
                        organism = synthetic construct
SEQUENCE: 313
APTSSSTKKT QLQLEHLLLD LQMILNGINN YKNPKLTRML TFKFYMPKKA TELKHLQCLE    60
```

```
EELKPLEEVL NLAQSKNFHL RPRDLISNIN VIVLELKGSE TTFMCEYADE TATIVEFLNR    120
WITFCQSIIS TLTSGGPGPA GLYAQPGSGG GGSGGGGSGG GGSGGGGSGG GGSGGGGSEL    180
CDDDPPEIPH ATFKAMAYKE GTMLNCECKR GFRRIKSGSL YMLCTGNSSH SSWDNQCQCT    240
SSATRNTTKQ VTPQPEEQKE RKTTEMQSPM QPVDQASLPG HCREPPPWEN EATERIYHFV    300
VGQMVYYQCV QGYRALHRGP AESVCKMTHG KTRWTQPQLI CTGEMETSQF PGEEKPQASP    360
EGRPESETSS LVTTTDFQIQ TEMAATMETS IFTTEYQSGG PGPAGLYAQP GSEVQLVESG    420
GGLVQPGNSL RLSCAASGFT FSKFGMSWVR QAPGKGLEWV SSISGSGRDT LYAESVKGRF    480
TISRDNAKTT LYLQMNSLRP EDTAVYYCTI GGSLSVSSQG TLVTVSSGGG GSGGGGSGGG    540
GSGGGGSGGG GSGGGGSSGG PGPAGLYAQP GSEVQLVESG GGLVQPGGSL RLSCAASGFT    600
FSSYTLAWVR QAPGKCLEWV AAIDSSSYTY SPDTVRGRFT ISRDNAKNSL YLQMNSLRAE    660
DTAVYYCARD SNWDALDYWG QGTTVTVSSG GGGSGGGGSG GGGSDIQMTQ SPSSLSASVG    720
DRVTITCKVT EKVWGNVAWY QQKPGKAPIS LIYSPSLRKS GVPSRFSGSG SGTDFTLTIS    780
SLQPEDFATY YCQQYYTYPY TFGCGTKVEI K                                   811

SEQ ID NO: 314          moltype = AA   length = 811
FEATURE                 Location/Qualifiers
source                  1..811
                        mol_type = protein
                        organism = synthetic construct
SEQUENCE: 314
APTSSSTKKT QLQLEHLLLD LQMILNGINN YKNPKLTRML TFKFYMPKKA TELKHLQCLE     60
EELKPLEEVL NLAQSKNFHL RPRDLISNIN VIVLELKGSE TTFMCEYADE TATIVEFLNR    120
WITFCQSIIS TLTSGGPGPA GLYAQPGSGG GGSGGGGSGG GGSGGGGSGG GGSGGGGSEL    180
CDDDPPEIPH ATFKAMAYKE GTMLNCECKR GFRRIKSGSL YMLCTGNSSH SSWDNQCQCT    240
SSATRNTTKQ VTPQPEEQKE RKTTEMQSPM QPVDQASLPG HCREPPPWEN EATERIYHFV    300
VGQMVYYQCV QGYRALHRGP AESVCKMTHG KTRWTQPQLI CTGEMETSQF PGEEKPQASP    360
EGRPESETSS LVTTTDFQIQ TEMAATMETS IFTTEYQSGG PGPAGLYAQP GSEVQLVESG    420
GGLVQPGNSL RLSCAASGFT FSKFGMSWVR QAPGKGLEWV SSISGSGRDT LYAESVKGRF    480
TISRDNAKTT LYLQMNSLRP EDTAVYYCTI GGSLSVSSQG TLVTVSSGGG GSGGGGSGGG    540
GSGGGGSGGG GSGGGGSSGG PGPAGLYAQP GSEVQLVESG GGLVQPGGSL RLSCAASGFT    600
FSSYTLAWVR QAPGKGLEWV AAIDSSSYTY SPDTVRGRFT ISRDNAKNSL YLQMNSLRAE    660
DTAVYYCARD SNWDALDYWG CGTTVTVSSG GGGSGGGGSG GGGSDIQMTQ SPSSLSASVG    720
DRVTITCKVT EKVWGNVAWY QQKPGKCPIS LIYSPSLRKS GVPSRFSGSG SGTDFTLTIS    780
SLQPEDFATY YCQQYYTYPY TFGGGTKVEI K                                   811

SEQ ID NO: 315          moltype = AA   length = 691
FEATURE                 Location/Qualifiers
source                  1..691
                        mol_type = protein
                        organism = synthetic construct
SEQUENCE: 315
APTSSSTKKT QLQLEHLLLD LQMILNGINN YKNPKLTRML TFKFYMPKKA TELKHLQCLE     60
EELKPLEEVL NLAQSKNFHL RPRDLISNIN VIVLELKGSE TTFMCEYADE TATIVEFLNR    120
WITFCQSIIS TLTSGGPGPA GLYAQPGSGG GGSGGGGSGG GGSGGGGSGG GGSGGGGSEL    180
CDDDPPEIPH ATFKAMAYKE GTMLNCECKR GFRRIKSGSL YMLCTGNSSH SSWDNQCQCT    240
SSATRNTTKQ VTPQPEEQKE RKTTEMQSPM QPVDQASLPG HCREPPPWEN EATERIYHFV    300
VGQMVYYQCV QGYRALHRGP AESVCKMTHG KTRWTQPQLI CTGEMETSQF PGEEKPQASP    360
EGRPESETSS LVTTTDFQIQ TEMAATMETS IFTTEYQSGG PGPAGLYAQP GSEVQLVESG    420
GGLVQPGNSL RLSCAASGFT FSKFGMSWVR QAPGKGLEWV SSISGSGRDT LYAESVKGRF    480
TISRDNAKTT LYLQMNSLRP EDTAVYYCTI GGSLSVSSQG TLVTVSSGGG GSGGGGSGGG    540
GSGGGGSGGG GSGGGGSSGG PGPAGLYAQP GSEVQLVESG GGLVQPGGSL RLSCAASGSI    600
FSANAMGWYR QAPGKQRELV AVISSGGSTN YADSVKGRFT ISRDNSKNTV YLQMNSLRAE    660
DTAVYYCMYS GSYYYTPNDY WGQGTLVTVS S                                   691

SEQ ID NO: 316          moltype = AA   length = 691
FEATURE                 Location/Qualifiers
source                  1..691
                        mol_type = protein
                        organism = synthetic construct
SEQUENCE: 316
APTSSSTKKT QLQLEHLLLD LQMILNGINN YKNPKLTRML TFKFYMPKKA TELKHLQCLE     60
EELKPLEEVL NLAQSKNFHL RPRDLISNIN VIVLELKGSE TTFMCEYADE TATIVEFLNR    120
WITFCQSIIS TLTSGGPGPA GLYAQPGSGG GGSGGGGSGG GGSGGGGSGG GGSGGGGSEL    180
CDDDPPEIPH ATFKAMAYKE GTMLNCECKR GFRRIKSGSL YMLCTGNSSH SSWDNQCQCT    240
SSATRNTTKQ VTPQPEEQKE RKTTEMQSPM QPVDQASLPG HCREPPPWEN EATERIYHFV    300
VGQMVYYQCV QGYRALHRGP AESVCKMTHG KTRWTQPQLI CTGEMETSQF PGEEKPQASP    360
EGRPESETSS LVTTTDFQIQ TEMAATMETS IFTTEYQSGG PGPAGLYAQP GSEVQLVESG    420
GGLVQPGNSL RLSCAASGFT FSKFGMSWVR QAPGKGLEWV SSISGSGRDT LYAESVKGRF    480
TISRDNAKTT LYLQMNSLRP EDTAVYYCTI GGSLSVSSQG TLVTVSSGGG GSGGGGSGGG    540
GSGGGGSGGG GSGGGGSSGG PGPAGLYAQP GSEVQLLESG GGLVQPGGSL RLSCAASGSI    600
FSANAMGWYR QAPGKGLELV AVISSGGSTN YADSVKGRFT ISRDNSKNTV YLQMNSLRAE    660
DTAVYYCMYS GSYYYTPNDY WGQGTLVTVS S                                   691

SEQ ID NO: 317          moltype = AA   length = 792
FEATURE                 Location/Qualifiers
source                  1..792
                        mol_type = protein
                        organism = synthetic construct
SEQUENCE: 317
```

```
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTSGGPGPA GLYAQPGSGG GGSGGGGSGG GGSGGGGSEL              180
CDDDPPEIPH ATFKAMAYKE GTMLNCECKR GFRRIKSGSL YMLCTGNSSH SSWDNQCQCT   240
SSATRNTTKQ VTPQPEEQKE RKTTEMQSPM QPVDQASLPG HCREPPPWEN EATERIYHFV   300
VGQMVYYQCV QGYRALHRGP AESVCKMTHG KTRWTQPQLI CTGEMETSQF PGEEKPQASP   360
EGRPESETSS LVTTTDFQIQ TEMAATMETS IFTTEYQSGG PGPAGLYAQP GSEVQLVESG   420
GGLVQPGNSL RLSCAASGFT FSKFGMSWVR QAPGKGLEWV SSISGSGRDT LYAESVKGRF   480
TISRDNAKTT LYLQMNSLRP EDTAVYYCTI GGSLSVSSQG TLVTVSSGGG GSGGGGSGGG   540
GSGGGGSGGG GSGGGGSSGG PGPAGLYAQP GSEVQLVESG GGLVQPGGSL RLSCAASGFT   600
FSSYTLAWVR QAPGKGLEWV AAIDSSSYTY SPDTVRGRFT ISRDNAKNSL YLQMNSLRAE   660
DTAVYYCARD SNWDALDYWG QGTTVTVSSA STKGPSVFPL APSSKSTSGG TAALGCLVKD   720
YPPEPVTVSW NSGALTSGVH TFPAVLQSSG LYSLSSVVTV PSSSLGTQTY ICNVNHKPSN   780
TKVDKRVEPK SC                                                      792

SEQ ID NO: 318        moltype = AA  length = 676
FEATURE               Location/Qualifiers
source                1..676
                      mol_type = protein
                      organism = synthetic construct
SEQUENCE: 318
EVQLVESGGG LVQPGGSLRL SCAASGFTFS SYTLAWVRQA PGKCLEWVAA IDSSSYTYSP    60
DTVRGRFTIS RDNAKNSLYL QMNSLRAEDT AVYYCARDSN WDALDYWGQG TTVTVSSGGG   120
GSGGGGSGGG GSDIQMTQSP SSLSASVGDR VTITCKAREK LWSAVAWYQQ KPGKAPKSLI   180
YSASFRYSGV PSRFSGSGSG TDFTLTISSL QPEDFATYYC QQYYTYPYTF GCGTKVEIKS   240
GGPGPAGLYA QPGSGGGGSG GGGSGGGGSG GGGSEVQLVE SGGGLVQPGN              300
SLRLSCAASG FTFSKFGMSW VRQAPGKGLE WVSSISGSGR DTLYAESVKG RFTISRDNAK   360
TTLYLQMNSL RPEDTAVYYC TIGGSLSVSS QGTLVTVSSS GGPGPAGLYA QPGSTFKFYM   420
PKKATELKHL QCLEEELKPL EEVLNLAQSK NFHLRPRDLI SNINVIVLEL KGSETTFMCE   480
YADETATIVE FLNRWITFCQ SIISTLTGGS SSTKKTQLQL EHLLLDLQMI LNGINNYKNP   540
KLTRMLSGGP GPAGLYAQPG SEVQLVESGG GLVQPGNSLR LSCAASGFTF SKFGMSWVRQ   600
APGKGLEWVS SISGSGRDTL YAESVKGRFT ISRDNAKTTL YLQMNSLRPE DTAVYYCTIG   660
GSLSVSSQGT LVTVSS                                                  676

SEQ ID NO: 319        moltype = AA  length = 676
FEATURE               Location/Qualifiers
source                1..676
                      mol_type = protein
                      organism = synthetic construct
SEQUENCE: 319
EVQLVESGGG LVQPGGSLRL SCAASGFTFS SYTLAWVRQA PGKGLEWVAA IDSSSYTYSP    60
DTVRGRFTIS RDNAKNSLYL QMNSLRAEDT AVYYCARDSN WDALDYWCG TTVTVSSGGG    120
GSGGGGSGGG GSDIQMTQSP SSLSASVGDR VTITCKAREK LWSAVAWYQQ KPGKCPKSLI   180
YSASFRYSGV PSRFSGSGSG TDFTLTISSL QPEDFATYYC QQYYTYPYTF GGGTKVEIKS   240
GGPGPAGLYA QPGSGGGGSG GGGSGGGGSG GGGSEVQLVE SGGGLVQPGN              300
SLRLSCAASG FTFSKFGMSW VRQAPGKGLE WVSSISGSGR DTLYAESVKG RFTISRDNAK   360
TTLYLQMNSL RPEDTAVYYC TIGGSLSVSS QGTLVTVSSS GGPGPAGLYA QPGSTFKFYM   420
PKKATELKHL QCLEEELKPL EEVLNLAQSK NFHLRPRDLI SNINVIVLEL KGSETTFMCE   480
YADETATIVE FLNRWITFCQ SIISTLTGGS SSTKKTQLQL EHLLLDLQMI LNGINNYKNP   540
KLTRMLSGGP GPAGLYAQPG SEVQLVESGG GLVQPGNSLR LSCAASGFTF SKFGMSWVRQ   600
APGKGLEWVS SISGSGRDTL YAESVKGRFT ISRDNAKTTL YLQMNSLRPE DTAVYYCTIG   660
GSLSVSSQGT LVTVSS                                                  676

SEQ ID NO: 320        moltype = AA  length = 676
FEATURE               Location/Qualifiers
source                1..676
                      mol_type = protein
                      organism = synthetic construct
SEQUENCE: 320
EVQLVESGGG LVQPGGSLRL SCAASGFTFS SYTLAWVRQA PGKCLEWVAA IDSSSYTYSP    60
DTVRGRFTIS RDNAKNSLYL QMNSLRAEDT AVYYCARDSN WDALDYWGQG TTVTVSSGGG   120
GSGGGGSGGG GSDIQMTQSP SSLSASVGDR VTITCKVTEK VWGNVAWYQQ KPGKAPISLI   180
YSPSLRKSGV PSRFSGSGSG TDFTLTISSL QPEDFATYYC QQYYTYPYTF GCGTKVEIKS   240
GGPGPAGLYA QPGSGGGGSG GGGSGGGGSG GGGSEVQLVE SGGGLVQPGN              300
SLRLSCAASG FTFSKFGMSW VRQAPGKGLE WVSSISGSGR DTLYAESVKG RFTISRDNAK   360
TTLYLQMNSL RPEDTAVYYC TIGGSLSVSS QGTLVTVSSS GGPGPAGLYA QPGSTFKFYM   420
PKKATELKHL QCLEEELKPL EEVLNLAQSK NFHLRPRDLI SNINVIVLEL KGSETTFMCE   480
YADETATIVE FLNRWITFCQ SIISTLTGGS SSTKKTQLQL EHLLLDLQMI LNGINNYKNP   540
KLTRMLSGGP GPAGLYAQPG SEVQLVESGG GLVQPGNSLR LSCAASGFTF SKFGMSWVRQ   600
APGKGLEWVS SISGSGRDTL YAESVKGRFT ISRDNAKTTL YLQMNSLRPE DTAVYYCTIG   660
GSLSVSSQGT LVTVSS                                                  676

SEQ ID NO: 321        moltype = AA  length = 676
FEATURE               Location/Qualifiers
source                1..676
                      mol_type = protein
                      organism = synthetic construct
SEQUENCE: 321
EVQLVESGGG LVQPGGSLRL SCAASGFTFS SYTLAWVRQA PGKGLEWVAA IDSSSYTYSP    60
```

```
DTVRGRFTIS RDNAKNSLYL QMNSLRAEDT AVYYCARDSN WDALDYWGCG TTVTVSSGGG   120
GSGGGGSGGG GSDIQMTQSP SSLSASVGDR VTITCKVTEK VWGNVAWYQQ KPGKCPISLI   180
YSPSLRKSGV PSRFSGSGSG TDFTLTISSL QPEDFATYYC QQYYTYPYTF GGGTKVEIKS   240
GGPGPAGLYA QPGSGGGGSG GGGSGGGGSG GGGSGGGGSG GGGSEVQLVE SGGGLVQPGN   300
SLRLSCAASG FTFSKFGMSW VRQAPGKGLE WVSSISGSGR DTLYAESVKG RFTISRDNAK   360
TTLYLQMNSL RPEDTAVYYC TIGGSLSVSS QGTLVTVSSS GGPGPAGLYA QPGSTFKFYM   420
PKKATELKHL QCLEEELKPL EEVLNLAQSK NFHLRPRDLI SNINVIVLEL KGSETTFMCE   480
YADETATIVE FLNRWITFCQ SIISTLTGGS SSTKKTQLQL EHLLLDLQMI LNGINNYKNP   540
KLTRMLSGGP GPAGLYAQPG SEVQLVESGG GLVQPGNSLR LSCAASGFTF SKFGMSWVRQ   600
APGKGLEWVS SISGSGRDTL YAESVKGRFT ISRDNAKTTL YLQMNSLRPE DTAVYYCTIG   660
GSLSVSSQGT LVTVSS                                                   676

SEQ ID NO: 322         moltype = AA  length = 556
FEATURE                Location/Qualifiers
source                 1..556
                       mol_type = protein
                       organism = synthetic construct
SEQUENCE: 322
EVQLLESGGG LVQPGGSLRL SCAASGSIFS ANAMGWYRQA PGKQRELVAV ISSGGSTNYA   60
DSVKGRFTIS RDNSKNTVYL QMNSLRAEDT AVYYCMYSGS YYYTPNDYWG QGTLVTVSSS   120
GGPGPAGLYA QPGSGGGGSG GGGSGGGGSG GGGSGGGGSG GGGSEVQLVE SGGGLVQPGN   180
SLRLSCAASG FTFSKFGMSW VRQAPGKGLE WVSSISGSGR DTLYAESVKG RFTISRDNAK   240
TTLYLQMNSL RPEDTAVYYC TIGGSLSVSS QGTLVTVSSS GGPGPAGLYA QPGSTFKFYM   300
PKKATELKHL QCLEEELKPL EEVLNLAQSK NFHLRPRDLI SNINVIVLEL KGSETTFMCE   360
YADETATIVE FLNRWITFCQ SIISTLTGGS SSTKKTQLQL EHLLLDLQMI LNGINNYKNP   420
KLTRMLSGGP GPAGLYAQPG SEVQLVESGG GLVQPGNSLR LSCAASGFTF SKFGMSWVRQ   480
APGKGLEWVS SISGSGRDTL YAESVKGRFT ISRDNAKTTL YLQMNSLRPE DTAVYYCTIG   540
GSLSVSSQGT LVTVSS                                                   556

SEQ ID NO: 323         moltype = AA  length = 556
FEATURE                Location/Qualifiers
source                 1..556
                       mol_type = protein
                       organism = synthetic construct
SEQUENCE: 323
EVQLLESGGG LVQPGGSLRL SCAASGSIFS ANAMGWYRQA PGKGLELVAV ISSGGSTNYA   60
DSVKGRFTIS RDNSKNTVYL QMNSLRAEDT AVYYCMYSGS YYYTPNDYWG QGTLVTVSSS   120
GGPGPAGLYA QPGSGGGGSG GGGSGGGGSG GGGSGGGGSG GGGSEVQLVE SGGGLVQPGN   180
SLRLSCAASG FTFSKFGMSW VRQAPGKGLE WVSSISGSGR DTLYAESVKG RFTISRDNAK   240
TTLYLQMNSL RPEDTAVYYC TIGGSLSVSS QGTLVTVSSS GGPGPAGLYA QPGSTFKFYM   300
PKKATELKHL QCLEEELKPL EEVLNLAQSK NFHLRPRDLI SNINVIVLEL KGSETTFMCE   360
YADETATIVE FLNRWITFCQ SIISTLTGGS SSTKKTQLQL EHLLLDLQMI LNGINNYKNP   420
KLTRMLSGGP GPAGLYAQPG SEVQLVESGG GLVQPGNSLR LSCAASGFTF SKFGMSWVRQ   480
APGKGLEWVS SISGSGRDTL YAESVKGRFT ISRDNAKTTL YLQMNSLRPE DTAVYYCTIG   540
GSLSVSSQGT LVTVSS                                                   556

SEQ ID NO: 324         moltype = AA  length = 657
FEATURE                Location/Qualifiers
source                 1..657
                       mol_type = protein
                       organism = synthetic construct
SEQUENCE: 324
EVQLVESGGG LVQPGGSLRL SCAASGFTFS SYTLAWVRQA PGKGLEWVAA IDSSSYTYSP   60
DTVRGRFTIS RDNAKNSLYL QMNSLRAEDT AVYYCARDSN WDALDYWGQG TTVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKRVEPKSC SGGPGPAGLY AQPGSGGGGS   240
GGGGSGGGGS GGGGSGGGGS GGGGSEVQLV ESGGGLVQPG NSLRLSCAAS GFTFSKFGMS   300
WVRQAPGKGL EWVSSISGSG RDTLYAESVK GRFTISRDNA KTTLYLQMNS LRPEDTAVYY   360
CTIGGSLSVS SQGTLVTVSS GGPGPAGLY AQPGSTFKFY MPKKATELKH LQCLEEELKP   420
LEEVLNLAQS KNFHLRPRDL ISNINVIVLE LKGSETTFMC EYADETATIV EFLNRWITFC   480
QSIISTLTGG SSSTKKTQLQ LEHLLLDLQM ILNGINNYKN PKLTRMLSGG PGPAGLYAQP   540
GSEVQLVESG GGLVQPGNSL RLSCAASGFT FSKFGMSWVR QAPGKGLEWV SSISGSGRDT   600
LYAESVKGRF TISRDNAKTT LYLQMNSLRP EDTAVYYCTI GGSLSVSSQG TLVTVSS      657

SEQ ID NO: 325         moltype = AA  length = 640
FEATURE                Location/Qualifiers
source                 1..640
                       mol_type = protein
                       organism = synthetic construct
SEQUENCE: 325
VPRDCGCKPC ICTVPEVSSV FIFPPKPKDV LTITLTPKVT CVVVDISKDD PEVQFSWFVD   60
DVEVHTAQTQ PREEQFNSTF RSVSELPIMH QDWLNGKEFK CRVNSAAFPA PIEKTISKTK   120
GRPKAPQVYT IPPPKEQMAK DKVSLTCMIT DFFPEDITVE WQWNGQPAEN YKNTQPIMDT   180
DGSYFVYSKL NVQKSNWEAG NTFTCSVLHE GLHNHHTEKS LSHSPGKSGG PGPAGLYAQP   240
GSAPTSSSTK KTQLQLEHLL LDLQMILNGI NNYKNPKLTR MLTFKFYMPK KATELKHLQC   300
LEEELKPLEE VLNLAQSKNF HLRPRDLISN INVIVLELKG SETTFMCEYA DETATIVEFL   360
NRWITFCQSI ISTLTGGGGS GGGGSGGGGS GGGGSGGGGS GGGGSGGGPG PAGLYAQPGS   420
EVQLVESGGG LVQPGGSLRL SCAASGFTFS SYTLAWVRQA PGKGLEWVAA IDSSSYTYSP   480
DTVRGRFTIS RDNAKNSLYL QMNSLRAEDT AVYYCARDSN WDALDYWGQG TTVTVSSAST   540
```

```
KGPSVFPLAP SSKSTSGGTA ALGCLVKDYF PEPVTVSWNS GALTSGVHTF PAVLQSSGLY  600
SLSSVVTVPS SSLGTQTYIC NVNHKPSNTK VDKRVEPKSC                       640

SEQ ID NO: 326           moltype = AA  length = 659
FEATURE                  Location/Qualifiers
source                   1..659
                         mol_type = protein
                         organism = synthetic construct
SEQUENCE: 326
VPRDCGCKPC ICTVPEVSSV FIFPPKPKDV LTITLTPKVT CVVVDISKDD PEVQFSWFVD  60
DVEVHTAQTQ PREEQFNSTF RSVSELPIMH QDWLNGKEFK CRVNSAAFPA PIEKTISKTK  120
GRPKAPQVYT IPPPKEQMAK DKVSLTCMIT DFFPEDITVE WQWNGQPAEN YKNTQPIMDT  180
DGSYFVYSKL NVQKSNWEAG NTFTCSVLHE GLHNHHTEKS LSHSPGKSGG PGPAGLYAQP  240
GSAPTSSSTK KTQLQLEHLL LDLQMILNGI NNYKNPKLTR MLTFKFYMPK KATELKHLQC  300
LEEELKPLEE VLNLAQSKNF HLRPRDLISN INVIVLELKG SETTFMCEYA DETATIVEFL  360
NRWITFCQSI ISTLTGGGGS GGGGSGGGGS GGGGSGGGGS GGGGSSGGPG PAGLYAQPGS  420
EVQLVESGGG LVQPGGSLRL SCAASGFTFS SYTLAWVRQA PGKCLEWVAA IDSSSYTYSP  480
DTVRGRFTIS RDNAKNSLYL QMNSLRAEDT AVYYCARDSN WDALDYWGQG TTVTVSSGGG  540
GSGGGGSGGG GSDIQMTQSP SSLSASVGDR VTITCKAREK LWSAVAWYQQ KPGKAPKALI  600
YSASFRYSGV PSRFSGSGSG TDFTLTISSL QPEDFATYYC QQYYTYPYTF GCGTKVEIK   659

SEQ ID NO: 327           moltype = AA  length = 659
FEATURE                  Location/Qualifiers
source                   1..659
                         mol_type = protein
                         organism = synthetic construct
SEQUENCE: 327
VPRDCGCKPC ICTVPEVSSV FIFPPKPKDV LTITLTPKVT CVVVDISKDD PEVQFSWFVD  60
DVEVHTAQTQ PREEQFNSTF RSVSELPIMH QDWLNGKEFK CRVNSAAFPA PIEKTISKTK  120
GRPKAPQVYT IPPPKEQMAK DKVSLTCMIT DFFPEDITVE WQWNGQPAEN YKNTQPIMDT  180
DGSYFVYSKL NVQKSNWEAG NTFTCSVLHE GLHNHHTEKS LSHSPGKSGG PGPAGLYAQP  240
GSAPTSSSTK KTQLQLEHLL LDLQMILNGI NNYKNPKLTR MLTFKFYMPK KATELKHLQC  300
LEEELKPLEE VLNLAQSKNF HLRPRDLISN INVIVLELKG SETTFMCEYA DETATIVEFL  360
NRWITFCQSI ISTLTGGGGS GGGGSGGGGS GGGGSGGGGS GGGGSSGGPG PAGLYAQPGS  420
EVQLVESGGG LVQPGGSLRL SCAASGFTFS SYTLAWVRQA PGKCLEWVAA IDSSSYTYSP  480
DTVRGRFTIS RDNAKNSLYL QMNSLRAEDT AVYYCARDSN WDALDYWGQG TTVTVSSGGG  540
GSGGGGSGGG GSDIQMTQSP SSLSASVGDR VTITCKAREK LWSAVAWYQQ KPGKAPKSLI  600
YSASFRYSGV PSRFSGSGSG TDFTLTISSL QPEDFATYYC QQYYTYPYTF GCGTKVEIK   659

SEQ ID NO: 328           moltype = AA  length = 659
FEATURE                  Location/Qualifiers
source                   1..659
                         mol_type = protein
                         organism = synthetic construct
SEQUENCE: 328
VPRDCGCKPC ICTVPEVSSV FIFPPKPKDV LTITLTPKVT CVVVDISKDD PEVQFSWFVD  60
DVEVHTAQTQ PREEQFNSTF RSVSELPIMH QDWLNGKEFK CRVNSAAFPA PIEKTISKTK  120
GRPKAPQVYT IPPPKEQMAK DKVSLTCMIT DFFPEDITVE WQWNGQPAEN YKNTQPIMDT  180
DGSYFVYSKL NVQKSNWEAG NTFTCSVLHE GLHNHHTEKS LSHSPGKSGG PGPAGLYAQP  240
GSAPTSSSTK KTQLQLEHLL LDLQMILNGI NNYKNPKLTR MLTFKFYMPK KATELKHLQC  300
LEEELKPLEE VLNLAQSKNF HLRPRDLISN INVIVLELKG SETTFMCEYA DETATIVEFL  360
NRWITFCQSI ISTLTGGGGS GGGGSGGGGS GGGGSGGGGS GGGGSSGGPG PAGLYAQPGS  420
EVQLVESGGG LVQPGGSLRL SCAASGFTFS SYTLAWVRQA PGKGLEWVAA IDSSSYTYSP  480
DTVRGRFTIS RDNAKNSLYL QMNSLRAEDT AVYYCARDSN WDALDYWGCG TTVTVSSGGG  540
GSGGGGSGGG GSDIQMTQSP SSLSASVGDR VTITCKAREK LWSAVAWYQQ KPGKCPKALI  600
YSASFRYSGV PSRFSGSGSG TDFTLTISSL QPEDFATYYC QQYYTYPYTF GGGTKVEIK   659

SEQ ID NO: 329           moltype = AA  length = 659
FEATURE                  Location/Qualifiers
source                   1..659
                         mol_type = protein
                         organism = synthetic construct
SEQUENCE: 329
VPRDCGCKPC ICTVPEVSSV FIFPPKPKDV LTITLTPKVT CVVVDISKDD PEVQFSWFVD  60
DVEVHTAQTQ PREEQFNSTF RSVSELPIMH QDWLNGKEFK CRVNSAAFPA PIEKTISKTK  120
GRPKAPQVYT IPPPKEQMAK DKVSLTCMIT DFFPEDITVE WQWNGQPAEN YKNTQPIMDT  180
DGSYFVYSKL NVQKSNWEAG NTFTCSVLHE GLHNHHTEKS LSHSPGKSGG PGPAGLYAQP  240
GSAPTSSSTK KTQLQLEHLL LDLQMILNGI NNYKNPKLTR MLTFKFYMPK KATELKHLQC  300
LEEELKPLEE VLNLAQSKNF HLRPRDLISN INVIVLELKG SETTFMCEYA DETATIVEFL  360
NRWITFCQSI ISTLTGGGGS GGGGSGGGGS GGGGSGGGGS GGGGSSGGPG PAGLYAQPGS  420
EVQLVESGGG LVQPGGSLRL SCAASGFTFS SYTLAWVRQA PGKCLEWVAA IDSSSYTYSP  480
DTVRGRFTIS RDNAKNSLYL QMNSLRAEDT AVYYCARDSN WDALDYWGQG TTVTVSSGGG  540
GSGGGGSGGG GSDIQMTQSP SSLSASVGDR VTITCKVTEK VWGNVAWYQQ KPGKAPISLI  600
YSPSLRKSGV PSRFSGSGSG TDFTLTISSL QPEDFATYYC QQYYTYPYTF GCGTKVEIK   659

SEQ ID NO: 330           moltype = AA  length = 659
FEATURE                  Location/Qualifiers
source                   1..659
                         mol_type = protein
```

```
                       organism = synthetic construct
SEQUENCE: 330
VPRDCGCKPC ICTVPEVSSV FIFPPKPKDV LTITLTPKVT CVVVDISKDD PEVQFSWFVD   60
DVEVHTAQTQ PREEQFNSTF RSVSELPIMH QDWLNGKEFK CRVNSAAFPA PIEKTISKTK  120
GRPKAPQVYT IPPPKEQMAK DKVSLTCMIT DFFPEDITVE WQWNGQPAEN YKNTQPIMDT  180
DGSYFVYSKL NVQKSNWEAG NTFTCSVLHE GLHNHHTEKS LSHSPGKSGG PGPAGLYAQP  240
GSAPTSSSTK KTQLQLEHLL LDLQMILNGI NNYKNPKLTR MLTFKFYMPK KATELKHLQC  300
LEEELKPLEE VLNLAQSKNF HLRPRDLISN INVIVLELKG SETTFMCEYA DETATIVEFL  360
NRWITFCQSI ISTLTGGGGS GGGGSGGGGS GGGGSGGGGS GGGGSSGGPG PAGLYAQPGS  420
EVQLVESGGG LVQPGGSLRL SCAASGFTFS SYTLAWVRQA PGKGLEWVAA IDSSSYTYSP  480
DTVRGRFTIS RDNAKNSLYL QMNSLRAEDT AVYYCARDSN WDALDYWGCG TTVTVSSGGG  540
GSGGGGSGGG GSDIQMTQSP SSLSASVGDR VTITCKVTEK VWGNVAWYQQ KPGKCPISLI  600
YSPSLRKSGV PSRFSGSGSG TDFTLTISSL QPEDFATYYC QQYYTYPYTF GGGTKVEIK   659

SEQ ID NO: 331          moltype = AA  length = 539
FEATURE                 Location/Qualifiers
source                  1..539
                        mol_type = protein
                        organism = synthetic construct
SEQUENCE: 331
VPRDCGCKPC ICTVPEVSSV FIFPPKPKDV LTITLTPKVT CVVVDISKDD PEVQFSWFVD   60
DVEVHTAQTQ PREEQFNSTF RSVSELPIMH QDWLNGKEFK CRVNSAAFPA PIEKTISKTK  120
GRPKAPQVYT IPPPKEQMAK DKVSLTCMIT DFFPEDITVE WQWNGQPAEN YKNTQPIMDT  180
DGSYFVYSKL NVQKSNWEAG NTFTCSVLHE GLHNHHTEKS LSHSPGKSGG PGPAGLYAQP  240
GSAPTSSSTK KTQLQLEHLL LDLQMILNGI NNYKNPKLTR MLTFKFYMPK KATELKHLQC  300
LEEELKPLEE VLNLAQSKNF HLRPRDLISN INVIVLELKG SETTFMCEYA DETATIVEFL  360
NRWITFCQSI ISTLTGGGGS GGGGSGGGGS GGGGSGGGGS GGGGSSGGPG PAGLYAQPGS  420
EVQLLESGGG LVQPGGSLRL SCAASGSIFS ANAMGWYRQA PGKQRELVAV ISSGGSTNYA  480
DSVKGRFTIS RDNSKNTVYL QMNSLRAEDT AVYYCMYSGS YYYTPNDYWG QGTLVTVSS   539

SEQ ID NO: 332          moltype = AA  length = 463
FEATURE                 Location/Qualifiers
source                  1..463
                        mol_type = protein
                        organism = synthetic construct
SEQUENCE: 332
ELCDDDPPEI PHATFKAMAY KEGTMLNCEC KRGFRRIKSG SLYMLCTGNS SHSSWDNQCQ   60
CTSSATRNTT KQVTPQPEEQ KERKTTEMQS PMQPVDQASL PGHCREPPPW ENEATERIYH  120
FVVGQMVYYQ CVQGYRALHR GPAESVCKMT HGKTRWTQPQ LICTGEMETS QFPGEEKPQA  180
SPEGRPESET SSLVTTTDFQ IQTEMAATME TSIFTTEYQG GGGSGGGGSG GGGSGGGGSG  240
GGGSGGGGSD IQMTQSPSSL SASVGDRVTI TCKAREKLWS AVAWYQQKPG KAPKSLIYSA  300
SFRYSGVPSR FSGSGSGTDF TLTISSLQPE DFATYYCQQY YTYPYTFGGG TKVEIKRTVA  360
APSVFIFPPS DEQLKSGTAS VVCLLNNFYP REAKVQWKVD NALQSGNSQE SVTEQDSKDS  420
TYSLSSTLTL SKADYEKHKV YACEVTHQGL SSPVTKSFNR GEC                   463

SEQ ID NO: 333          moltype = AA  length = 463
FEATURE                 Location/Qualifiers
source                  1..463
                        mol_type = protein
                        organism = synthetic construct
SEQUENCE: 333
ELCDDDPPEI PHATFKAMAY KEGTMLNCEC KRGFRRIKSG SLYMLCTGNS SHSSWDNQCQ   60
CTSSATRNTT KQVTPQPEEQ KERKTTEMQS PMQPVDQASL PGHCREPPPW ENEATERIYH  120
FVVGQMVYYQ CVQGYRALHR GPAESVCKMT HGKTRWTQPQ LICTGEMETS QFPGEEKPQA  180
SPEGRPESET SSLVTTTDFQ IQTEMAATME TSIFTTEYQG GGGSGGGGSG GGGSGGGGSG  240
GGGSGGGGSD IQMTQSPSSL SASVGDRVTI TCKVTEKVWG NVAWYQQKPG KAPISLIYSP  300
SLRKSGVPSR FSGSGSGTDF TLTISSLQPE DFATYYCQQY YTYPYTFGGG TKVEIKRTVA  360
APSVFIFPPS DEQLKSGTAS VVCLLNNFYP REAKVQWKVD NALQSGNSQE SVTEQDSKDS  420
TYSLSSTLTL SKADYEKHKV YACEVTHQGL SSPVTKSFNR GEC                   463

SEQ ID NO: 334          moltype = AA  length = 811
FEATURE                 Location/Qualifiers
source                  1..811
                        mol_type = protein
                        organism = synthetic construct
SEQUENCE: 334
APTSSSTKKT QLQLEHLLLD LQMILNGINN YKNPKLTRML TFKFYMPKKA TELKHLQCLE   60
EELKPLEEVL NLAQSKNFHL RPRDLISNIN VIVLELKGSE TTFMCEYADE TATIVEFLNR  120
WITFCQSIIS TLTSGGPGPA GLYAQPGSGG GGSGGGGSGG GGSGGGGSEV              180
QLVESGGGLV QPGGSLRLSC AASGFTFSSY TLAWVRQAPG KCLEWVAAID SSSYTYSPDT  240
VRGRFTISRD NAKNSLYLQM NSLRAEDTAV YYCARDSNWD ALDYWGQTT  VTVSSGGGGS  300
GGGGSGGGGS DIQMTQSPSS LSASVGDRVT ITCKAREKLW SAVAWYQQKP GKAPKSLIYS  360
ASFRYSGVPS RFSGSGSGTD FTLTISSLQP EDFATYYCQQ YYTYPYTFGC GTKVEIKGGG  420
GSGGGGSGGG GSGGGGSGGG GSGGGGSGGG GSELCDDDPP EIPHATFKAM             480
AYKEGTMLNC ECKRGFRRIK SGSLYMLCTG NSSHSSWDNQ CQCTSSATRN TTKQVTPQPE  540
EQKERKTTEM QSPMQPVDQA SLPGHCREPP PWENEATERI YHFVVGQMVY YQCVQGYRAL  600
HRGPAESVCK MTHGKTRWTQ PQLICTGEME TSQFPGEEKP QASPEGRPES ETSSLVTTTD  660
FQIQTEMAAT METSIFTTEY QSGGPGPAGL YAQPGSEVQL VESGGGLVQP GNSLRLSCAA  720
SGFTFSKFGM SWVRQAPGKG LEWVSSISGS GRDTLYAESV KGRFTISRDN AKTTLYLQMN  780
```

```
SLRPEDTAVY YCTIGGSLSV SSQGTLVTVS S                                   811

SEQ ID NO: 335          moltype = AA   length = 811
FEATURE                 Location/Qualifiers
source                  1..811
                        mol_type = protein
                        organism = synthetic construct
SEQUENCE: 335
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR    120
WITFCQSIIS TLTSGGPGPA GLYAQPGSGG GGSGGGGSGG GGSGGGGSGG GGSGGGGSEV    180
QLVESGGGLV QPGGSLRLSC AASGFTFSSY TLAWVRQAPG KGLEWVAAID SSSYTYSPDT    240
VRGRFTISRD NAKNSLYLQM NSLRAEDTAV YYCARDSNWD ALDYWGCGTT VTVSSGGGGS    300
GGGGSGGGGS DIQMTQSPSS LSASVGDRVT ITCKAREKLW SAVAWYQQKP GKCPKALIYS    360
ASFRYSGVPS RFSGSGSGTD FTLTISSLQP EDFATYYCQQ YYTYPYTFGG GTKVEIKGGG    420
GSGGGGSGGG GSGGGGSGGG GSGGGGSGGG GSELCDDDPP EIPHATFKAM              480
AYKEGTMLNC ECKRGFRRIK SGSLYMLCTG NSSHSSWDNQ CQCTSSATRN TTKQVTPQPE    540
EQKERKTTEM QSPMQPVDQA SLPGHCREPP PWENEATERI YHFVVGQMVY YQCVQGYRAL    600
HRGPAESVCK MTHGKTRWTQ PQLICTGEME TSQFPGEEKP QASPEGRPES ETSSLVTTTD    660
FQIQTEMAAT METSIFTTEY QSGGPGPAGL YAQPGSEVQL VESGGGLVQP GNSLRLSCAA    720
SGFTFSKFGM SWVRQAPGKG LEWVSSISGS GRDTLYAESV KGRFTISRDN AKTTLYLQMN    780
SLRPEDTAVY YCTIGGSLSV SSQGTLVTVS S                                  811

SEQ ID NO: 336          moltype = AA   length = 811
FEATURE                 Location/Qualifiers
source                  1..811
                        mol_type = protein
                        organism = synthetic construct
SEQUENCE: 336
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR    120
WITFCQSIIS TLTSGGPGPA GLYAQPGSGG GGSGGGGSGG GGSGGGGSGG GGSGGGGSEV    180
QLVESGGGLV QPGGSLRLSC AASGFTFSSY TLAWVRQAPG KCLEWVAAID SSSYTYSPDT    240
VRGRFTISRD NAKNSLYLQM NSLRAEDTAV YYCARDSNWD ALDYWGQGTT VTVSSGGGGS    300
GGGGSGGGGS DIQMTQSPSS LSASVGDRVT ITCKVTEKVW GNVAWYQQKP GKAPISLIYS    360
PSLRKSGVPS RFSGSGSGTD FTLTISSLQP EDFATYYCQQ YYTYPYTFGC GTKVEIKGGG    420
GSGGGGSGGG GSGGGGSGGG GSGGGGSGGG GSELCDDDPP EIPHATFKAM              480
AYKEGTMLNC ECKRGFRRIK SGSLYMLCTG NSSHSSWDNQ CQCTSSATRN TTKQVTPQPE    540
EQKERKTTEM QSPMQPVDQA SLPGHCREPP PWENEATERI YHFVVGQMVY YQCVQGYRAL    600
HRGPAESVCK MTHGKTRWTQ PQLICTGEME TSQFPGEEKP QASPEGRPES ETSSLVTTTD    660
FQIQTEMAAT METSIFTTEY QSGGPGPAGL YAQPGSEVQL VESGGGLVQP GNSLRLSCAA    720
SGFTFSKFGM SWVRQAPGKG LEWVSSISGS GRDTLYAESV KGRFTISRDN AKTTLYLQMN    780
SLRPEDTAVY YCTIGGSLSV SSQGTLVTVS S                                  811

SEQ ID NO: 337          moltype = AA   length = 811
FEATURE                 Location/Qualifiers
source                  1..811
                        mol_type = protein
                        organism = synthetic construct
SEQUENCE: 337
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR    120
WITFCQSIIS TLTSGGPGPA GLYAQPGSGG GGSGGGGSGG GGSGGGGSGG GGSGGGGSEV    180
QLVESGGGLV QPGGSLRLSC AASGFTFSSY TLAWVRQAPG KGLEWVAAID SSSYTYSPDT    240
VRGRFTISRD NAKNSLYLQM NSLRAEDTAV YYCARDSNWD ALDYWGQGTT VTVSSGGGGS    300
GGGGSGGGGS DIQMTQSPSS LSASVGDRVT ITCKVTEKVW GNVAWYQQKP GKCPISLIYS    360
PSLRKSGVPS RFSGSGSGTD FTLTISSLQP EDFATYYCQQ YYTYPYTFGG GTKVEIKGGG    420
GSGGGGSGGG GSGGGGSGGG GSGGGGSGGG GSELCDDDPP EIPHATFKAM              480
AYKEGTMLNC ECKRGFRRIK SGSLYMLCTG NSSHSSWDNQ CQCTSSATRN TTKQVTPQPE    540
EQKERKTTEM QSPMQPVDQA SLPGHCREPP PWENEATERI YHFVVGQMVY YQCVQGYRAL    600
HRGPAESVCK MTHGKTRWTQ PQLICTGEME TSQFPGEEKP QASPEGRPES ETSSLVTTTD    660
FQIQTEMAAT METSIFTTEY QSGGPGPAGL YAQPGSEVQL VESGGGLVQP GNSLRLSCAA    720
SGFTFSKFGM SWVRQAPGKG LEWVSSISGS GRDTLYAESV KGRFTISRDN AKTTLYLQMN    780
SLRPEDTAVY YCTIGGSLSV SSQGTLVTVS S                                  811

SEQ ID NO: 338          moltype = AA   length = 691
FEATURE                 Location/Qualifiers
source                  1..691
                        mol_type = protein
                        organism = synthetic construct
SEQUENCE: 338
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR    120
WITFCQSIIS TLTSGGPGPA GLYAQPGSGG GGSGGGGSGG GGSGGGGSGG GGSGGGGSEV    180
QLLESGGGLV QPGGSLRLSC AASGIFSAN   AMGWYRQAPG KQRELVAVIS SGGSTNYADS    240
VKGRFTISRD NSKNTVYLQM NSLRAEDTAV YYCMYSGSYY YTPNDYWGQG TLVTVSSGGG    300
GSGGGGSGGG GSGGGGSGGG GSGGGGSGGG GSELCDDDPP EIPHATFKAM              360
AYKEGTMLNC ECKRGFRRIK SGSLYMLCTG NSSHSSWDNQ CQCTSSATRN TTKQVTPQPE    420
EQKERKTTEM QSPMQPVDQA SLPGHCREPP PWENEATERI YHFVVGQMVY YQCVQGYRAL    480
```

```
HRGPAESVCK MTHGKTRWTQ PQLICTGEME TSQFPGEEKP QASPEGRPES ETSSLVTTTD    540
FQIQTEMAAT METSIFTTEY QSGGPGPAGL YAQPGSEVQL VESGGGLVQP GNSLRLSCAA    600
SGFTFSKFGM SWVRQAPGKG LEWVSSISGS GRDTLYAESV KGRFTISRDN AKTTLYLQMN    660
SLRPEDTAVY YCTIGGSLSV SSQGTLVTVS S                                   691

SEQ ID NO: 339           moltype = AA   length = 691
FEATURE                  Location/Qualifiers
source                   1..691
                         mol_type = protein
                         organism = synthetic construct
SEQUENCE: 339
APTSSSTKKT QLQLEHLLLD LQMILNGINN YKNPKLTRML TFKFYMPKKA TELKHLQCLE     60
EELKPLEEVL NLAQSKNFHL RPRDLISNIN VIVLELKGSE TTFMCEYADE TATIVEFLNR    120
WITFCQSIIS TLTSGGPGPA GLYAQPGSGG GGSGGGGSGG GGSGGGGSGG GGSGGGGSEV    180
QLLESGGGLV QPGGSLRLSC AASGIFSAN AMGWYRQAPG KGLELVAVIS SGGSTNYADS     240
VKGRFTISRD NSKNTVYLQM NSLRAEDTAV YYCMYSGSYY YTPNDYWGQG TLVTVSSGGG    300
GSGGGGSGGG GSGGGGSGGG GSGGGGSGGG GSGGGGSGGG GSELCDDDPP EIPHATFKAM    360
AYKEGTMLNC ECKRGFRRIK SGSLYMLCTG NSSHSSWDNQ CQCTSSATRN TTKQVTPQPE    420
EQKERKTTEM QSPMQPVDQA SLPGHCREPP PWENEATERI YHFVVGQMVY YQCVQGYRAL    480
HRGPAESVCK MTHGKTRWTQ PQLICTGEME TSQFPGEEKP QASPEGRPES ETSSLVTTTD    540
FQIQTEMAAT METSIFTTEY QSGGPGPAGL YAQPGSEVQL VESGGGLVQP GNSLRLSCAA    600
SGFTFSKFGM SWVRQAPGKG LEWVSSISGS GRDTLYAESV KGRFTISRDN AKTTLYLQMN    660
SLRPEDTAVY YCTIGGSLSV SSQGTLVTVS S                                   691

SEQ ID NO: 340           moltype = AA   length = 811
FEATURE                  Location/Qualifiers
source                   1..811
                         mol_type = protein
                         organism = synthetic construct
SEQUENCE: 340
EVQLVESGGG LVQPGNSLRL SCAASGFTFS KFGMSWVRQA PGKGLEWVSS ISGSGRDTLY     60
AESVKGRFTI SRDNAKTTLY LQMNSLRPED TAVYYCTIGG SLSVSSQGTL VTVSSSGGPG    120
PAGLYAQPGS EVQLVESGGG LVQPGGSLRL SCAASGFTFS SYTLAWVRQA PGKCLEWVAA    180
IDSSSYTYSP DTVRGRFTIS RDNAKNSLYL QMNSLRAEDT AVYYCARDSN WDALDYWGCG    240
TTVTVSSGGG GSGGGGSGGG GSDIQMTQSP SSLSASVGDR VTITCKAREK LWSAVAWYQQ    300
KPGKAPKSLI YSASFRYSGV PSRFSGSGSG TDFTLTISSL QPEDFATYYC QQYYTYPYTF    360
GCGTKVEIKG GGGSGGGGSG GGGSGGGGSG GGGSGGGGSG GGGSGGGGSG GGSELCDDD    420
PPEIPHATFK AMAYKEGTML NCECKRGFRR IKSGSLYMLC TGNSSHSSWD NQCQCTSSAT    480
RNTTKQVTPQ PEEQKERKTT EMQSPMQPVD QASLPGHCRE PPPWENEATE RIYHFVVGQM    540
VYYQCVQGYR ALHRGPAESV CKMTHGKTRW TQPQLICTGE METSQFPGEE KPQASPEGRP    600
ESETSSLVTT TDFQIQTEMA ATMETSIFTT EYQGGGGSGG GGSGGGGSGG GGSGGGGSGG    660
GGSSGGPGPA GLYAQPGSAP TSSSTKKTQL QLEHLLLDLQ MILNGINNYK NPKLTRMLTF    720
KFYMPKKATE LKHLQCLEEE LKPLEEVLNL AQSKNFHLRP RDLISNINVI VLELKGSETT    780
FMCEYADETA TIVEFLNRWI TFCQSIISTL T                                   811

SEQ ID NO: 341           moltype = AA   length = 811
FEATURE                  Location/Qualifiers
source                   1..811
                         mol_type = protein
                         organism = synthetic construct
SEQUENCE: 341
EVQLVESGGG LVQPGNSLRL SCAASGFTFS KFGMSWVRQA PGKGLEWVSS ISGSGRDTLY     60
AESVKGRFTI SRDNAKTTLY LQMNSLRPED TAVYYCTIGG SLSVSSQGTL VTVSSSGGPG    120
PAGLYAQPGS EVQLVESGGG LVQPGGSLRL SCAASGFTFS SYTLAWVRQA PGKGLEWVAA    180
IDSSSYTYSP DTVRGRFTIS RDNAKNSLYL QMNSLRAEDT AVYYCARDSN WDALDYWGCG    240
TTVTVSSGGG GSGGGGSGGG GSDIQMTQSP SSLSASVGDR VTITCKAREK LWSAVAWYQQ    300
KPGKCPKALI YSASFRYSGV PSRFSGSGSG TDFTLTISSL QPEDFATYYC QQYYTYPYTF    360
GGGTKVEIKG GGGSGGGGSG GGGSGGGGSG GGGSGGGGSG GGGSGGGGSG GGSELCDDD    420
PPEIPHATFK AMAYKEGTML NCECKRGFRR IKSGSLYMLC TGNSSHSSWD NQCQCTSSAT    480
RNTTKQVTPQ PEEQKERKTT EMQSPMQPVD QASLPGHCRE PPPWENEATE RIYHFVVGQM    540
VYYQCVQGYR ALHRGPAESV CKMTHGKTRW TQPQLICTGE METSQFPGEE KPQASPEGRP    600
ESETSSLVTT TDFQIQTEMA ATMETSIFTT EYQGGGGSGG GGSGGGGSGG GGSGGGGSGG    660
GGSSGGPGPA GLYAQPGSAP TSSSTKKTQL QLEHLLLDLQ MILNGINNYK NPKLTRMLTF    720
KFYMPKKATE LKHLQCLEEE LKPLEEVLNL AQSKNFHLRP RDLISNINVI VLELKGSETT    780
FMCEYADETA TIVEFLNRWI TFCQSIISTL T                                   811

SEQ ID NO: 342           moltype = AA   length = 811
FEATURE                  Location/Qualifiers
source                   1..811
                         mol_type = protein
                         organism = synthetic construct
SEQUENCE: 342
EVQLVESGGG LVQPGNSLRL SCAASGFTFS KFGMSWVRQA PGKGLEWVSS ISGSGRDTLY     60
AESVKGRFTI SRDNAKTTLY LQMNSLRPED TAVYYCTIGG SLSVSSQGTL VTVSSSGGPG    120
PAGLYAQPGS EVQLVESGGG LVQPGGSLRL SCAASGFTFS SYTLAWVRQA PGKCLEWVAA    180
IDSSSYTYSP DTVRGRFTIS RDNAKNSLYL QMNSLRAEDT AVYYCARDSN WDALDYWGQG    240
TTVTVSSGGG GSGGGGSGGG GSDIQMTQSP SSLSASVGDR VTITCKVTEK VWGNVAWYQQ    300
KPGKAPISLI YSPSLRKSGV PSRFSGSGSG TDFTLTISSL QPEDFATYYC QQYYTYPYTF    360
GCGTKVEIKG GGGSGGGGSG GGGSGGGGSG GGGSGGGGSG GGSELCDDD    420
```

```
PPEIPHATFK AMAYKEGTML NCECKRGFRR IKSGSLYMLC TGNSSHSSWD NQCQCTSSAT    480
RNTTKQVTPQ PEEQKERKTT EMQSPMQPVD QASLPGHCRE PPPWENEATE RIYHFVVGQM    540
VYYQCVQGYR ALHRGPAESV CKMTHGKTRW TQPQLICTGE METSQFPGEE KPQASPEGRP    600
ESETSSLVTT TDFQIQTEMA ATMETSIFTT EYQGGGGSGG GGSGGGGSGG GGSGGGGSGG    660
GGSSGGPGPA GLYAQPGSAP TSSSTKKTQL QLEHLLLDLQ MILNGINNYK NPKLTRMLTF    720
KFYMPKKATE LKHLQCLEEE LKPLEEVLNL AQSKNFHLRP RDLISNINVI VLELKGSETT    780
FMCEYADETA TIVEFLNRWI TFCQSIISTL T                                  811

SEQ ID NO: 343              moltype = AA   length = 811
FEATURE                     Location/Qualifiers
source                      1..811
                            mol_type = protein
                            organism = synthetic construct
SEQUENCE: 343
EVQLVESGGG LVQPGNSLRL SCAASGFTFS KFGMSWVRQA PGKGLEWVSS ISGSGRDTLY     60
AESVKGRFTI SRDNAKTTLY LQMNSLRPED TAVYYCTIGG SLSVSSQGTL VTVSSSGGPG    120
PAGLYAQPGS EVQLVESGGG LVQPGGSLRL SCAASGFTFS SYTLAWVRQA PGKGLEWVAA    180
IDSSSYTYSP DTVRGRFTIS RDNAKNSLYL QMNSLRAEDT AVYYCARDSN WDALDYWGCG    240
TTVTVSSGGG GSGGGGSGGG GSDIQMTQSP SSLSASVGDR VTITCKVTEK VWGNVAWYQQ    300
KPGKCPISLI YSPSLRKSGV PSRFSGSGSG TDFTLTISSL QPEDFATYYC QQYYTYPYTF    360
GGGTKVEIKG GGGSGGGGSG GGGSGGGGSG GGGSGGGGSG GGGSELCDDD              420
PPEIPHATFK AMAYKEGTML NCECKRGFRR IKSGSLYMLC TGNSSHSSWD NQCQCTSSAT    480
RNTTKQVTPQ PEEQKERKTT EMQSPMQPVD QASLPGHCRE PPPWENEATE RIYHFVVGQM    540
VYYQCVQGYR ALHRGPAESV CKMTHGKTRW TQPQLICTGE METSQFPGEE KPQASPEGRP    600
ESETSSLVTT TDFQIQTEMA ATMETSIFTT EYQGGGGSGG GGSGGGGSGG GGSGGGGSGG    660
GGSSGGPGPA GLYAQPGSAP TSSSTKKTQL QLEHLLLDLQ MILNGINNYK NPKLTRMLTF    720
KFYMPKKATE LKHLQCLEEE LKPLEEVLNL AQSKNFHLRP RDLISNINVI VLELKGSETT    780
FMCEYADETA TIVEFLNRWI TFCQSIISTL T                                  811

SEQ ID NO: 344              moltype = AA   length = 691
FEATURE                     Location/Qualifiers
source                      1..691
                            mol_type = protein
                            organism = synthetic construct
SEQUENCE: 344
EVQLVESGGG LVQPGNSLRL SCAASGFTFS KFGMSWVRQA PGKGLEWVSS ISGSGRDTLY     60
AESVKGRFTI SRDNAKTTLY LQMNSLRPED TAVYYCTIGG SLSVSSQGTL VTVSSSGGPG    120
PAGLYAQPGS EVQLLESGGG LVQPGGSLRL SCAASGSIFS ANAMGWYRQA PGKQRELVAV    180
ISSGGSTNYA DSVKGRFTIS RDNSKNTVYL QMNSLRAEDT AVYYCMYSGS YYYTPNDYWG    240
QGTLVTVSSG GGGSGGGGSG GGSGGGGSG GGGSGGGGSG GGGSELCDDD               300
PPEIPHATFK AMAYKEGTML NCECKRGFRR IKSGSLYMLC TGNSSHSSWD NQCQCTSSAT    360
RNTTKQVTPQ PEEQKERKTT EMQSPMQPVD QASLPGHCRE PPPWENEATE RIYHFVVGQM    420
VYYQCVQGYR ALHRGPAESV CKMTHGKTRW TQPQLICTGE METSQFPGEE KPQASPEGRP    480
ESETSSLVTT TDFQIQTEMA ATMETSIFTT EYQGGGGSGG GGSGGGGSGG GGSGGGGSGG    540
GGSSGGPGPA GLYAQPGSAP TSSSTKKTQL QLEHLLLDLQ MILNGINNYK NPKLTRMLTF    600
KFYMPKKATE LKHLQCLEEE LKPLEEVLNL AQSKNFHLRP RDLISNINVI VLELKGSETT    660
FMCEYADETA TIVEFLNRWI TFCQSIISTL T                                  691

SEQ ID NO: 345              moltype = AA   length = 691
FEATURE                     Location/Qualifiers
source                      1..691
                            mol_type = protein
                            organism = synthetic construct
SEQUENCE: 345
EVQLVESGGG LVQPGNSLRL SCAASGFTFS KFGMSWVRQA PGKGLEWVSS ISGSGRDTLY     60
AESVKGRFTI SRDNAKTTLY LQMNSLRPED TAVYYCTIGG SLSVSSQGTL VTVSSSGGPG    120
PAGLYAQPGS EVQLLESGGG LVQPGGSLRL SCAASGSIFS ANAMGWYRQA PGKGLELVAV    180
ISSGGSTNYA DSVKGRFTIS RDNSKNTVYL QMNSLRAEDT AVYYCMYSGS YYYTPNDYWG    240
QGTLVTVSSG GGGSGGGGSG GGSGGGGSG GGGSGGGGSG GGGSELCDDD               300
PPEIPHATFK AMAYKEGTML NCECKRGFRR IKSGSLYMLC TGNSSHSSWD NQCQCTSSAT    360
RNTTKQVTPQ PEEQKERKTT EMQSPMQPVD QASLPGHCRE PPPWENEATE RIYHFVVGQM    420
VYYQCVQGYR ALHRGPAESV CKMTHGKTRW TQPQLICTGE METSQFPGEE KPQASPEGRP    480
ESETSSLVTT TDFQIQTEMA ATMETSIFTT EYQGGGGSGG GGSGGGGSGG GGSGGGGSGG    540
GGSSGGPGPA GLYAQPGSAP TSSSTKKTQL QLEHLLLDLQ MILNGINNYK NPKLTRMLTF    600
KFYMPKKATE LKHLQCLEEE LKPLEEVLNL AQSKNFHLRP RDLISNINVI VLELKGSETT    660
FMCEYADETA TIVEFLNRWI TFCQSIISTL T                                  691

SEQ ID NO: 346              moltype = AA   length = 696
FEATURE                     Location/Qualifiers
source                      1..696
                            mol_type = protein
                            organism = synthetic construct
SEQUENCE: 346
APTSSSTKKT QLQLEHLLLD LQMILNGINN YKNPKLTRML TFKFYMPKKA TELKHLQCLE     60
EELKPLEEVL NLAQSKNFHL RPRDLISNIN VIVLELKGSE TTFMCEYADE TATIVEFLNR    120
WITFCQSIIS TLTSGGPGPA GLYAQPGSEV QLVESGGGLV QPGNSLRLSC AASGFTFSKF    180
GMSWVRQAPG KGLEWVSSIS GSGRDTLYAE SVKGRFTISR DNAKTTLYLQ MNSLRPEDTA    240
VYYCTIGGSL SVSSQGTLVT VSSGGGGSGG GGSGGGGSGG GGSGGGGSGG GGSSGGPGPA    300
GLYAQPGSEV QLVESGGGLV QPGGSLRLSC AASGFTFSSY TLAWVRQAPG KCLEWVAAID    360
```

```
SSSYTYSPDT VRGRFTISRD NAKNSLYLQM NSLRAEDTAV YYCARDSNWD ALDYWGQGTT    420
VTVSSGGGGS GGGGSGGGGS DIQMTQSPSS LSASVGDRVT ITCKAREKLW SAVAWYQQKP    480
GKAPKSLIYS ASFRYSGVPS RFSGSGSGTD FTLTISSLQP EDFATYYCQQ YYTYPYTFGC    540
GTKVEIKGGG GSGGGGSGGG GSGGGGSGGG GSGGGGSEVQ LLESGGGLVQ PGGSLRLSCA    600
ASGSIFSANA MGWYRQAPGK QRELVAVISS GGSTNYADSV KGRFTISRDN SKNTVYLQMN    660
SLRAEDTAVY YCMYSGSYYY TPNDYWGQGT LVTVSS                              696

SEQ ID NO: 347          moltype = AA   length = 696
FEATURE                 Location/Qualifiers
source                  1..696
                        mol_type = protein
                        organism = synthetic construct
SEQUENCE: 347
APTSSSTKKT QLQLEHLLLD LQMILNGINN YKNPKLTRML TFKFYMPKKA TELKHLQCLE     60
EELKPLEEVL NLAQSKNFHL RPRDLISNIN VIVLELKGSE TTFMCEYADE TATIVEFLNR    120
WITFCQSIIS TLTSGGPGPA GLYAQPGSEV QLVESGGGLV QPGNSLRLSC AASGFTFSKF    180
GMSWVRQAPG KGLEWVSSIS GSGRDTLYAE SVKGRFTISR DNAKTTLYLQ MNSLRPEDTA    240
VYYCTIGGSL SVSSQGTLVT VSSGGGGSGG GGSGGGGSGG GGSGGGGSGG GGSSGGPGPA    300
GLYAQPGSEV QLVESGGGLV QPGGSLRLSC AASGFTFSSY TLAWVRQAPG KGLEWVAAID    360
SSSYTYSPDT VRGRFTISRD NAKNSLYLQM NSLRAEDTAV YYCARDSNWD ALDYWGCGTT    420
VTVSSGGGGS GGGGSGGGGS DIQMTQSPSS LSASVGDRVT ITCKAREKLW SAVAWYQQKP    480
GKCPKALIYS ASFRYSGVPS RFSGSGSGTD FTLTISSLQP EDFATYYCQQ YYTYPYTFGG    540
GTKVEIKGGG GSGGGGSGGG GSGGGGSGGG GSGGGGSEVQ LLESGGGLVQ PGGSLRLSCA    600
ASGSIFSANA MGWYRQAPGK QRELVAVISS GGSTNYADSV KGRFTISRDN SKNTVYLQMN    660
SLRAEDTAVY YCMYSGSYYY TPNDYWGQGT LVTVSS                              696

SEQ ID NO: 348          moltype = AA   length = 696
FEATURE                 Location/Qualifiers
source                  1..696
                        mol_type = protein
                        organism = synthetic construct
SEQUENCE: 348
APTSSSTKKT QLQLEHLLLD LQMILNGINN YKNPKLTRML TFKFYMPKKA TELKHLQCLE     60
EELKPLEEVL NLAQSKNFHL RPRDLISNIN VIVLELKGSE TTFMCEYADE TATIVEFLNR    120
WITFCQSIIS TLTSGGPGPA GLYAQPGSEV QLVESGGGLV QPGNSLRLSC AASGFTFSKF    180
GMSWVRQAPG KGLEWVSSIS GSGRDTLYAE SVKGRFTISR DNAKTTLYLQ MNSLRPEDTA    240
VYYCTIGGSL SVSSQGTLVT VSSGGGGSGG GGSGGGGSGG GGSGGGGSGG GGSSGGPGPA    300
GLYAQPGSEV QLVESGGGLV QPGGSLRLSC AASGFTFSSY TLAWVRQAPG KCLEWVAAID    360
SSSYTYSPDT VRGRFTISRD NAKNSLYLQM NSLRAEDTAV YYCARDSNWD ALDYWGQGTT    420
VTVSSGGGGS GGGGSGGGGS DIQMTQSPSS LSASVGDRVT ITCKVTEKVW GNVAWYQQKP    480
GKAPISLIYS PSLRKSGVPS RFSGSGSGTD FTLTISSLQP EDFATYYCQQ YYTYPYTFGC    540
GTKVEIKGGG GSGGGGSGGG GSGGGGSGGG GSGGGGSEVQ LLESGGGLVQ PGGSLRLSCA    600
ASGSIFSANA MGWYRQAPGK QRELVAVISS GGSTNYADSV KGRFTISRDN SKNTVYLQMN    660
SLRAEDTAVY YCMYSGSYYY TPNDYWGQGT LVTVSS                              696

SEQ ID NO: 349          moltype = AA   length = 696
FEATURE                 Location/Qualifiers
source                  1..696
                        mol_type = protein
                        organism = synthetic construct
SEQUENCE: 349
APTSSSTKKT QLQLEHLLLD LQMILNGINN YKNPKLTRML TFKFYMPKKA TELKHLQCLE     60
EELKPLEEVL NLAQSKNFHL RPRDLISNIN VIVLELKGSE TTFMCEYADE TATIVEFLNR    120
WITFCQSIIS TLTSGGPGPA GLYAQPGSEV QLVESGGGLV QPGNSLRLSC AASGFTFSKF    180
GMSWVRQAPG KGLEWVSSIS GSGRDTLYAE SVKGRFTISR DNAKTTLYLQ MNSLRPEDTA    240
VYYCTIGGSL SVSSQGTLVT VSSGGGGSGG GGSGGGGSGG GGSGGGGSGG GGSSGGPGPA    300
GLYAQPGSEV QLVESGGGLV QPGGSLRLSC AASGFTFSSY TLAWVRQAPG KGLEWVAAID    360
SSSYTYSPDT VRGRFTISRD NAKNSLYLQM NSLRAEDTAV YYCARDSNWD ALDYWGCGTT    420
VTVSSGGGGS GGGGSGGGGS DIQMTQSPSS LSASVGDRVT ITCKVTEKVW GNVAWYQQKP    480
GKCPISLIYS PSLRKSGVPS RFSGSGSGTD FTLTISSLQP EDFATYYCQQ YYTYPYTFGG    540
GTKVEIKGGG GSGGGGSGGG GSGGGGSGGG GSGGGGSEVQ LLESGGGLVQ PGGSLRLSCA    600
ASGSIFSANA MGWYRQAPGK QRELVAVISS GGSTNYADSV KGRFTISRDN SKNTVYLQMN    660
SLRAEDTAVY YCMYSGSYYY TPNDYWGQGT LVTVSS                              696

SEQ ID NO: 350          moltype = AA   length = 696
FEATURE                 Location/Qualifiers
source                  1..696
                        mol_type = protein
                        organism = synthetic construct
SEQUENCE: 350
APTSSSTKKT QLQLEHLLLD LQMILNGINN YKNPKLTRML TFKFYMPKKA TELKHLQCLE     60
EELKPLEEVL NLAQSKNFHL RPRDLISNIN VIVLELKGSE TTFMCEYADE TATIVEFLNR    120
WITFCQSIIS TLTSGGPGPA GLYAQPGSEV QLVESGGGLV QPGNSLRLSC AASGFTFSKF    180
GMSWVRQAPG KGLEWVSSIS GSGRDTLYAE SVKGRFTISR DNAKTTLYLQ MNSLRPEDTA    240
VYYCTIGGSL SVSSQGTLVT VSSGGGGSGG GGSGGGGSGG GGSGGGGSGG GGSSGGPGPA    300
GLYAQPGSEV QLVESGGGLV QPGGSLRLSC AASGFTFSSY TLAWVRQAPG KCLEWVAAID    360
SSSYTYSPDT VRGRFTISRD NAKNSLYLQM NSLRAEDTAV YYCARDSNWD ALDYWGQGTT    420
VTVSSGGGGS GGGGSGGGGS DIQMTQSPSS LSASVGDRVT ITCKAREKLW SAVAWYQQKP    480
GKAPKSLIYS ASFRYSGVPS RFSGSGSGTD FTLTISSLQP EDFATYYCQQ YYTYPYTFGC    540
```

```
GTKVEIKGGG GSGGGGSGGG GSGGGGSGGG GSGGGGSEVQ LLESGGGLVQ PGGSLRLSCA   600
ASGSIFSANA MGWYRQAPGK GLELVAVISS GGSTNYADSV KGRFTISRDN SKNTVYLQMN   660
SLRAEDTAVY YCMYSGSYYY TPNDYWGQGT LVTVSS                             696

SEQ ID NO: 351          moltype = AA   length = 696
FEATURE                 Location/Qualifiers
source                  1..696
                        mol_type = protein
                        organism = synthetic construct
SEQUENCE: 351
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTSGGPGPA GLYAQPGSEV QLVESGGGLV QPGNSLRLSC AASGFTFSKF   180
GMSWVRQAPG KGLEWVSSIS GSGRDTLYAE SVKGRFTISR DNAKTTLYLQ MNSLRPEDTA   240
VYYCTIGGSL SVSSQGTLVT VSSGGGGSGG GGSGGGGSGG GGSGGGGSGG GGSSGGPGPA   300
GLYAQPGSEV QLVESGGGLV QPGGSLRLSC AASGFTFSSY TLAWVRQAPG KGLEWVAAID   360
SSSYTYSPDT VRGRFTISRD NAKNSLYLQM NSLRAEDTAV YYCARDSNWD ALDYWGCGTT   420
VTVSSGGGGS GGGGSGGGGS DIQMTQSPSS LSASVGDRVT ITCKAREKLW SAVAWYQQKP   480
GKCPKALIYS ASFRYSGVPS RFSGSGSGTD FTLTISSLQP EDFATYYCQQ YYTYPYTFGG   540
GTKVEIKGGG GSGGGGSGGG GSGGGGSGGG GSGGGGSEVQ LLESGGGLVQ PGGSLRLSCA   600
ASGSIFSANA MGWYRQAPGK GLELVAVISS GGSTNYADSV KGRFTISRDN SKNTVYLQMN   660
SLRAEDTAVY YCMYSGSYYY TPNDYWGQGT LVTVSS                             696

SEQ ID NO: 352          moltype = AA   length = 696
FEATURE                 Location/Qualifiers
source                  1..696
                        mol_type = protein
                        organism = synthetic construct
SEQUENCE: 352
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTSGGPGPA GLYAQPGSEV QLVESGGGLV QPGNSLRLSC AASGFTFSKF   180
GMSWVRQAPG KGLEWVSSIS GSGRDTLYAE SVKGRFTISR DNAKTTLYLQ MNSLRPEDTA   240
VYYCTIGGSL SVSSQGTLVT VSSGGGGSGG GGSGGGGSGG GGSSGGPGPA               300
GLYAQPGSEV QLVESGGGLV QPGGSLRLSC AASGFTFSSY TLAWVRQAPG KCLEWVAAID   360
SSSYTYSPDT VRGRFTISRD NAKNSLYLQM NSLRAEDTAV YYCARDSNWD ALDYWGQGTT   420
VTVSSGGGGS GGGGSGGGGS DIQMTQSPSS LSASVGDRVT ITCKVTEKVW GNVAWYQQKP   480
GKAPISLIYS PSLRKSGVPS RFSGSGSGTD FTLTISSLQP EDFATYYCQQ YYTYPYTFGC   540
GTKVEIKGGG GSGGGGSGGG GSGGGGSGGG GSGGGGSEVQ LLESGGGLVQ PGGSLRLSCA   600
ASGSIFSANA MGWYRQAPGK GLELVAVISS GGSTNYADSV KGRFTISRDN SKNTVYLQMN   660
SLRAEDTAVY YCMYSGSYYY TPNDYWGQGT LVTVSS                             696

SEQ ID NO: 353          moltype = AA   length = 696
FEATURE                 Location/Qualifiers
source                  1..696
                        mol_type = protein
                        organism = synthetic construct
SEQUENCE: 353
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTSGGPGPA GLYAQPGSEV QLVESGGGLV QPGNSLRLSC AASGFTFSKF   180
GMSWVRQAPG KGLEWVSSIS GSGRDTLYAE SVKGRFTISR DNAKTTLYLQ MNSLRPEDTA   240
VYYCTIGGSL SVSSQGTLVT VSSGGGGSGG GGSGGGGSGG GGSGGGGSGG GGSSGGPGPA   300
GLYAQPGSEV QLVESGGGLV QPGGSLRLSC AASGFTFSSY TLAWVRQAPG KGLEWVAAID   360
SSSYTYSPDT VRGRFTISRD NAKNSLYLQM NSLRAEDTAV YYCARDSNWD ALDYWGCGTT   420
VTVSSGGGGS GGGGSGGGGS DIQMTQSPSS LSASVGDRVT ITCKVTEKVW GNVAWYQQKP   480
GKCPISLIYS PSLRKSGVPS RFSGSGSGTD FTLTISSLQP EDFATYYCQQ YYTYPYTFGG   540
GTKVEIKGGG GSGGGGSGGG GSGGGGSGGG GSGGGGSEVQ LLESGGGLVQ PGGSLRLSCA   600
ASGSIFSANA MGWYRQAPGK GLELVAVISS GGSTNYADSV KGRFTISRDN SKNTVYLQMN   660
SLRAEDTAVY YCMYSGSYYY TPNDYWGQGT LVTVSS                             696

SEQ ID NO: 354          moltype = AA   length = 6
FEATURE                 Location/Qualifiers
source                  1..6
                        mol_type = protein
                        organism = synthetic construct
SEQUENCE: 354
HHHHHH                                                                6

SEQ ID NO: 355          moltype = AA   length = 547
FEATURE                 Location/Qualifiers
source                  1..547
                        mol_type = protein
                        organism = synthetic construct
SEQUENCE: 355
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTSGGPGPA GLYAQPGSEV QLVESGGGLV QPGNSLRLSC AASGFTFSKF   180
GMSWVRQAPG KGLEWVSSIS GSGRDTLYAE SVKGRFTISR DNAKTTLYLQ MNSLRPEDTA   240
```

```
VYYCTIGGSL SVSSQGTLVT VSSGGGGSGG GGSGGGGSGG GGSGGGGSGG GGSSGGPGPA   300
GLYAQPGSEV QLVESGGGLV QPGGSLRLSC AASGFTFSSY TLAWVRQAPG KCLEWVAAID   360
SSSYTYSPDT VRGRFTISRD NAKNSLYLQM NSLRAEDTAV YYCARDSNWD ALDYWGQGTT   420
VTVSSGGGGS GGGGSGGGGS DIQMTQSPSS LSASVGDRVT ITCKASQNVG TNVGWYQQKP   480
GKAPKALIYS ASFRYSGVPS RFSGSGSGTD FTLTISSLQP EDFATYYCQQ YYTYPYTFGC   540
GTKVEIK                                                            547

SEQ ID NO: 356        moltype = AA  length = 547
FEATURE               Location/Qualifiers
source                1..547
                      mol_type = protein
                      organism = synthetic construct
SEQUENCE: 356
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTSGGPGPA GLYAQPGSEV QLVESGGGLV QPGNSLRLSC AASGFTFSKF   180
GMSWVRQAPG KGLEWVSSIS GSGRDTLYAE SVKGRFTISR DNAKTTLYLQ MNSLRPEDTA   240
VYYCTIGGSL SVSSQGTLVT VSSGGGGSGG GGSGGGGSGG GGSGGGGSGG GGSSGGPGPA   300
GLYAQPGSEV QLVESGGGLV QPGGSLRLSC AASGFTFSSY TLAWVRQAPG KGLEWVAAID   360
SSSYTYSPDT VRGRFTISRD NAKNSLYLQM NSLRAEDTAV YYCARDSNWD ALDYWGCGTT   420
VTVSSGGGGS GGGGSGGGGS DIQMTQSPSS LSASVGDRVT ITCKASQNVG TNVGWYQQKP   480
GKCPKALIYS ASFRYSGVPS RFSGSGSGTD FTLTISSLQP EDFATYYCQQ YYTYPYTFGG   540
GTKVEIK                                                            547

SEQ ID NO: 357        moltype = AA  length = 547
FEATURE               Location/Qualifiers
source                1..547
                      mol_type = protein
                      organism = synthetic construct
SEQUENCE: 357
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTSGGPGPA GLYAQPGSEV QLVESGGGLV QPGNSLRLSC AASGFTFSKF   180
GMSWVRQAPG KGLEWVSSIS GSGRDTLYAE SVKGRFTISR DNAKTTLYLQ MNSLRPEDTA   240
VYYCTIGGSL SVSSQGTLVT VSSGGGGSGG GGSGGGGSGG GGSGGGGSGG GGSSGGPGPA   300
GLYAQPGSEV QLVESGGGLV QPGGSLRLSC AASGFTFSSY TLAWVRQAPG KCLEWVAAID   360
SSSYTYSPDT VRGRFTISRD NAKNSLYLQM NSLRAEDTAV YYCARDSNWD ALDYWGQGTT   420
VTVSSGGGGS GGGGSGGGGS DIQMTQSPSS LSASVGDRVT ITCKAREKLW SAVAWYQQKP   480
GKAPKALIYS ASFRYSGVPS RFSGSGSGTD FTLTISSLQP EDFATYYCQQ YYTYPYTFGC   540
GTKVEIK                                                            547

SEQ ID NO: 358        moltype = AA  length = 547
FEATURE               Location/Qualifiers
source                1..547
                      mol_type = protein
                      organism = synthetic construct
SEQUENCE: 358
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTSGGPGPA GLYAQPGSEV QLVESGGGLV QPGNSLRLSC AASGFTFSKF   180
GMSWVRQAPG KGLEWVSSIS GSGRDTLYAE SVKGRFTISR DNAKTTLYLQ MNSLRPEDTA   240
VYYCTIGGSL SVSSQGTLVT VSSGGGGSGG GGSGGGGSGG GGSGGGGSGG GGSSGGPGPA   300
GLYAQPGSEV QLVESGGGLV QPGGSLRLSC AASGFTFSSY TLAWVRQAPG KGLEWVAAID   360
SSSYTYSPDT VRGRFTISRD NAKNSLYLQM NSLRAEDTAV YYCARDSNWD ALDYWGCGTT   420
VTVSSGGGGS GGGGSGGGGS DIQMTQSPSS LSASVGDRVT ITCKAREKLW SAVAWYQQKP   480
GKCPKALIYS ASFRYSGVPS RFSGSGSGTD FTLTISSLQP EDFATYYCQQ YYTYPYTFGG   540
GTKVEIK                                                            547

SEQ ID NO: 359        moltype = AA  length = 547
FEATURE               Location/Qualifiers
source                1..547
                      mol_type = protein
                      organism = synthetic construct
SEQUENCE: 359
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTSGGPGPA GLYAQPGSEV QLVESGGGLV QPGNSLRLSC AASGFTFSKF   180
GMSWVRQAPG KGLEWVSSIS GSGRDTLYAE SVKGRFTISR DNAKTTLYLQ MNSLRPEDTA   240
VYYCTIGGSL SVSSQGTLVT VSSGGGGSGG GGSGGGGSGG GGSGGGGSGG GGSSGGPGPA   300
GLYAQPGSEV QLVESGGGLV QPGGSLRLSC AASGFTFSSY TLAWVRQAPG KCLEWVAAID   360
SSSYTYSPDT VRGRFTISRD NAKNSLYLQM NSLRAEDTAV YYCARDSNWD ALDYWGQGTT   420
VTVSSGGGGS GGGGSGGGGS DIQMTQSPSS LSASVGDRVT ITCKVTEKVW GNVAWYQQKP   480
GKAPISLIYS PSLRKSGVPS RFSGSGSGTD FTLTISSLQP EDFATYYCQQ YYTYPYTFGC   540
GTKVEIK                                                            547

SEQ ID NO: 360        moltype = AA  length = 547
FEATURE               Location/Qualifiers
source                1..547
                      mol_type = protein
```

```
                        organism = synthetic construct
SEQUENCE: 360
APTSSSTKKT QLQLEHLLLD LQMILNGINN YKNPKLTRML TFKFYMPKKA TELKHLQCLE     60
EELKPLEEVL NLAQSKNFHL RPRDLISNIN VIVLELKGSE TTFMCEYADE TATIVEFLNR    120
WITFCQSIIS TLTSGGPGPA GLYAQPGSEV QLVESGGGLV QPGNSLRLSC AASGFTFSKF    180
GMSWVRQAPG KGLEWVSSIS GSGRDTLYAE SVKGRFTISR DNAKTTLYLQ MNSLRPEDTA    240
VYYCTIGGSL SVSSQGTLVT VSSGGGGSGG GGSGGGGSGG GGSGGGGSGG GGSSGGPGPA    300
GLYAQPGSEV QLVESGGGLV QPGGSLRLSC AASGFTSSY  TLAWRQAPG  KGLEWVAAID    360
SSSYTYSPDT VRGRFTISRD NAKNSLYLQM NSLRAEDTA  YYCARDSNWD ALDYWGCGIR    420
VTVSSGGGGS GGGGSGGGGS DIQMTQSPSS LSASVGDRVT ITCKVTEKVW GNVAWYQQKP    480
GKCPISLIYS PSLRKSGVPS RFSGSGSGTD FTLTISSLQP EDFATYYCQQ YYTYPYTFGG    540
GTKVEIK                                                              547

SEQ ID NO: 361          moltype = AA   length = 427
FEATURE                 Location/Qualifiers
source                  1..427
                        mol_type = protein
                        organism = synthetic construct
SEQUENCE: 361
APTSSSTKKT QLQLEHLLLD LQMILNGINN YKNPKLTRML TFKFYMPKKA TELKHLQCLE     60
EELKPLEEVL NLAQSKNFHL RPRDLISNIN VIVLELKGSE TTFMCEYADE TATIVEFLNR    120
WITFCQSIIS TLTSGGPGPA GLYAQPGSEV QLVESGGGLV QPGNSLRLSC AASGFTFSKF    180
GMSWVRQAPG KGLEWVSSIS GSGRDTLYAE SVKGRFTISR DNAKTTLYLQ MNSLRPEDTA    240
VYYCTIGGSL SVSSQGTLVT VSSGGGGSGG GGSGGGGSGG GGSGGGGSGG GGSSGGPGPA    300
GLYAQPGSEV QLLESGGGLV QPGGSLRLSC AASGSIFSAN AMGWYRQAPG KQRELVAVIS    360
SGGSTNYADS VKGRFTISRD NSKNTVYLQM NSLRAEDTAV YYCMYSGSYY YTPNDYWGQG    420
TLVTVSS                                                              427

SEQ ID NO: 362          moltype = AA   length = 528
FEATURE                 Location/Qualifiers
source                  1..528
                        mol_type = protein
                        organism = synthetic construct
SEQUENCE: 362
APTSSSTKKT QLQLEHLLLD LQMILNGINN YKNPKLTRML TFKFYMPKKA TELKHLQCLE     60
EELKPLEEVL NLAQSKNFHL RPRDLISNIN VIVLELKGSE TTFMCEYADE TATIVEFLNR    120
WITFCQSIIS TLTSGGPGPA GLYAQPGSEV QLVESGGGLV QPGNSLRLSC AASGFTFSKF    180
GMSWVRQAPG KGLEWVSSIS GSGRDTLYAE SVKGRFTISR DNAKTTLYLQ MNSLRPEDTA    240
VYYCTIGGSL SVSSQGTLVT VSSGGGGSGG GGSGGGGSGG GGSGGGGSGG GGSSGGPGPA    300
GLYAQPGSEV QLVESGGGLV QPGGSLRLSC AASGFTFSSY TLAWRQAPG  KGLEWVAAID    360
SSSYTYSPDT VRGRFTISRD NAKNSLYLQM NSLRAEDTAV YYCARDSNWD ALDYWGQGTT    420
VTVSSASTKG PSVFPLAPSS KSTSGGTAAL GCLVKDYFPE PVTVSWNSGA LTSGVHTFPA    480
VLQSSGLYSL SSVVTVPSSS LGTQTYICNV NHKPSNTKVD KRVEPKSC                 528

SEQ ID NO: 363          moltype = AA   length = 642
FEATURE                 Location/Qualifiers
source                  1..642
                        mol_type = protein
                        organism = synthetic construct
SEQUENCE: 363
ESKYGPPCPP CPAPEFLGGP SVFLFPPKPK DTLMISRTPE VTCVVVDVSQ EDPEVQFNWY     60
VDGVEVHNAK TKPREEQFNS TYRVVSVLTV LHQDWLNGKE YKCKVSNKGL PSSIEKTISK    120
AKGQPREPQV YTLPPSQEEM TKNQVSLTCL VKGFYPSDIA VEWESNGQPE NNYKTTPPVL    180
DSDGSFFLYS RLTVDKSRWQ EGNVFSCSVM HEALHNHYTQ KSLSLSLGKS GGPGPAGLYA    240
QPGSAPTSSS TKKTQLQLEH LLLDLQMILN GINNYKNPKL TRMLTFKFYM PKKATELKHL    300
QCLEEELKPL EEVLNLAQSK NFHLRPRDLI SNINVIVLEL KGSETTFMCE YADETATIVE    360
FLNRWITFCQ SIISTLTGGG GSGGGGSGGG GSGGGGSGGG GSGGGGSSGG PGPAGLYAQP    420
GSEVQLVESG GGLVQPGGSL RLSCAASGFT FSSYTLAWVR QAPGKGLEWV AAIDSSSYTY    480
SPDTVRGRFT ISRDNAKNSL YLQMNSLRAE DTAVYYCARD NDALDYWG    QGTTVTVSSA    540
STKGPSVFPL APSSKSTSGG TAALGCLVKD YFPEPVTVSW NSGALTSGVH TFPAVLQSSG    600
LYSLSSVVTV PSSSLGTQTY ICNVNHKPSN TKVDKRVEPK SC                       642

SEQ ID NO: 364          moltype = AA   length = 245
FEATURE                 Location/Qualifiers
source                  1..245
                        mol_type = protein
                        organism = synthetic construct
SEQUENCE: 364
EVQLVESGGG LVQPGGSLRL SCAASGFTFS SYTLAWVRQA PGKGLEWVAA IDSSSYTYSP     60
DTVRGRFTIS RDNAKNSLYL QMNSLRAEDT AVYYCARDSN WDALDYWGQG TTVTVSSSGG    120
PGPAGLYAQP GSDIQMTQSP SSLSASVGDR VTITCKVTEK VWGNVAWYQQ KPGKAPISLI    180
YSPSLRKSGV PSRFSGSGSG TDFTLTISSL QPEDFATYYC QQYYTYPYTF GGGTKVEIKH    240
HHHHH                                                                245

SEQ ID NO: 365          moltype = AA   length = 245
FEATURE                 Location/Qualifiers
source                  1..245
                        mol_type = protein
                        organism = synthetic construct
```

```
SEQUENCE: 365
EVQLVESGGG LVQPGGSLRL SCAASGFTFS SYTLAWVRQA PGKGLEWVAA IDSSSYTYSP    60
DTVRGRFTIS RDNAKNSLYL QMNSLRAEDT AVYYCARDSN WDALDYWGQG TTVTVSSSGG   120
PGPAGLYAQP GSDIQMTQSP SSLSASVGDR VTITCKAREK LWSAVAWYQQ KPGKAPKALI   180
YSASFRYSGV PSRFSGSGSG TDFTLTISSL QPEDFATYYC QQYYTYPYTF GGGTKVEIKH   240
HHHHH                                                              245

SEQ ID NO: 366          moltype = AA  length = 245
FEATURE                 Location/Qualifiers
source                  1..245
                        mol_type = protein
                        organism = synthetic construct
SEQUENCE: 366
EVQLVESGGG LVQPGGSLRL SCAASGFTFS SYTLAWVRQA PGKGLEWVAA IDSSSYTYSP    60
DTVRGRFTIS RDNAKNSLYL QMNSLRAEDT AVYYCARDSN WDALDYWGQG TTVTVSSSGG   120
PGPAGLYAQP GSDIQMTQSP SSLSASVGDR VTITCKAREK LWSAVAWYQQ KPGKAPKSLI   180
YSASFRYSGV PSRFSGSGSG TDFTLTISSL QPEDFATYYC QQYYTYPYTF GGGTKVEIKH   240
HHHHH                                                              245

SEQ ID NO: 367          moltype = AA  length = 609
FEATURE                 Location/Qualifiers
source                  1..609
                        mol_type = protein
                        organism = synthetic construct
SEQUENCE: 367
EVQLVESGGG LVQPGNSLRL SCAASGFTFS KFGMSWVRQA PGKGLEWVSS ISGSGRDTLY    60
AESVKGRFTI SRDNAKTTLY LQMNSLRPED TAVYYCTIGG SLSVSSQGTL VTVSSSGGPG   120
PAGMKGLPGS RVIPVSGPAR CLSQSRNLLK TTDDMVKTAR EKLKHYSCTA EDIDHEDITR   180
DQTSTLKTCL PLELHKNESC LATRETSSTT RGSCLPPQKT SLMMTLCLGS IYEDLKMYQT   240
EFQAINAALQ NHNHQQIILD KGMLVAIDEL MQSLNHNGET LRQKPPVGEA DPYRVKMKLC   300
ILLHAFSTRV VTINRVMGYL SSASGGPGPA GMKGLPGSGG GGSGGGGSGG GGSGGGGSGG   360
GGSGGGGSQS VLTQPPSVSG APGQRVTISC SGSRSNIGSN TVKWYQQLPG TAPKLLIYYN   420
DQRPSGVPDR FSGSKSGTSA SLAITGLQAE DEADYYCQSY DRYTHPALLF GTGTKVTVLG   480
GGGSGGGGSG GGGSQVQLVE SGGGVVQPGR SLRLSCAASG FTFSSYGMHW VRQAPGKGLE   540
WVAFIRYDGS NKYYADSVKG RFTISRDNSK NTLYLQMNSL RAEDTAVYYC KTHGSHDNWG   600
QGTMVTVSS                                                          609

SEQ ID NO: 368          moltype = AA  length = 930
FEATURE                 Location/Qualifiers
source                  1..930
                        mol_type = protein
                        organism = synthetic construct
SEQUENCE: 368
EVQLVESGGG LVQPGNSLRL SCAASGFTFS KFGMSWVRQA PGKGLEWVSS ISGSGRDTLY    60
AESVKGRFTI SRDNAKTTLY LQMNSLRPED TAVYYCTIGG SLSVSSQGTL VTVSSSGGPG   120
PAGMKGLPGS IWELKKDVYV VELDWYPDAP GEMVVLTCDT PEEDGITWTL DQSSEVLGSG   180
KTLTIQVKEF GDAGQYTCHK GGEVLSHSLL LLHKKEDGIW STDILKDQKE PKNKTFLRCE   240
AKNYSGRFTC WWLTTISTDL TFSVKSSRGS SDPQGVTCGA ATLSAERVRG DNKEYEYSVE   300
CQEDSASPAA EESLPIEVMV DAVHKLKYEN YTSSFFIRDI IKPDPPKNLQ LKPLKNSRQV   360
EVSWEYPDTW STPHSYFSLT FCVQVQGKSK REKKDRVFTD KTSATVICRK NASISVRAQD   420
RYYSSSWSEW ASVPCSGGGG SGGGGSGGGG SRVIPVSGPA RCLSQSRNLL KTTDDMVKTA   480
REKLKHYSCT AEDIDHEDIT RDQTSTLKTC LPLELHKNES SLATRETSST TRGSCLPPQK   540
TSLMMTLCLG SIYEDLKMYQ TEFQAINAAL QNHNHQQIIL DKGMLVAIDE LMQSLNHNGE   600
TLRQKPPVGE ADPYRVKMKL CILLHAFSTR VVTINRVMGY LSSASGGPGP AGMKGLPGSG   660
GGGSGGGGSG GGGSGGGGSG GGGSGGGGSQ SVLTQPPSVS GAPGQRVTIS CSGSRSNIGS   720
NTVKWYQQLP GTAPKLLIYY NDQRPSGVPD RFSGSKSGTS ASLAITGLQA EDEADYYCQS   780
YDRYTHPALL FGTGTKVTVL GGGGSGGGGS GGGGSQVQLV ESGGGVVQPG RSLRLSCAAS   840
GFTFSSYGMH WVRQAPGKGL EWVAFIRYDG SNKYYADSVK GRFTISRDNS KNTLYLQMNS   900
LRAEDTAVYY CKTHGSHDNW GQGTMVTVSS                                   930

SEQ ID NO: 369          moltype = AA  length = 935
FEATURE                 Location/Qualifiers
source                  1..935
                        mol_type = protein
                        organism = synthetic construct
SEQUENCE: 369
EVQLVESGGG LVQPGNSLRL SCAASGFTFS KFGMSWVRQA PGKGLEWVSS ISGSGRDTLY    60
AESVKGRFTI SRDNAKTTLY LQMNSLRPED TAVYYCTIGG SLSVSSQGTL VTVSSSGGPG   120
PAGMKGLPGS IWELKKDVYV VELDWYPDAP GEMVVLTCDT PEEDGITWTL DQSSEVLGSG   180
KTLTIQVKEF GDAGQYTCHK GGEVLSHSLL LLHKKEDGIW STDILKDQKE PKNKTFLRCE   240
AKNYSGRFTC WWLTTISTDL TFSVKSSRGS SDPQGVTCGA ATLSAERVRG DNKEYEYSVE   300
CQEDSACPAA EESLPIEVMV DAVHKLKYEN YTSSFFIRDI IKPDPPKNLQ LKPLKNSRQV   360
EVSWEYPDTW STPHSYFSLT FCVQVQGKSK REKKDRVFTD KTSATVICRK NASISVRAQD   420
RYYSSSWSEW ASVPCSGGGG SGGGGSGGGG SRVIP VSGPARCLSQ SRNLLKTTDD   480
MVKTAREKLK HYSCTAEDID HEDITRDQTS TLKTCLPLEL HKNESCLATR ETSSTTRGSC   540
LPPQKTSLMM TLCLGSIYED LKMYQTEFQA INAALQNHNH QQIILDKGML VAIDELMQSL   600
NHNGETLRQK PPVGEADPYR VKMKLCILLH AFSTRVVTIN RVMGYLSSAS GGPGPAGMKG   660
LPGSGGGGSG GGGSGGGGSG GGGSGGGGSG GGGSQSVLTQ PPSVSGAPGQ RVTISCSGSR   720
SNIGSNTVKW YQQLPGTAPK LLIYYNDQRP SGVPDRFSGS KSGTSASLAI TGLQAEDEAD   780
```

```
YYCQSYDRYT HPALLFGTGT KVTVLGGGGS GGGGSGGGGS QVQLVESGGG VVQPGRSLRL  840
SCAASGFTFS SYGMHWVRQA PGKGLEWVAF IRYDGSNKYY ADSVKGRFTI SRDNSKNTLY  900
LQMNSLRAED TAVYYCKTHG SHDNWGQGTM VTVSS                            935

SEQ ID NO: 370            moltype = AA   length = 930
FEATURE                   Location/Qualifiers
source                    1..930
                          mol_type = protein
                          organism = synthetic construct
SEQUENCE: 370
EVQLVESGGG LVQPGNSLRL SCAASGFTFS KFGMSWVRQA PGKGLEWVSS ISGSGRDTLY   60
AESVKGRFTI SRDNAKTTLY LQMNSLRPED TAVYYCTIGG SLSVSSQGTL VTVSSSGGPG  120
PAGMKGLPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRVIPVSGPA RCLSQSRNLL KTTDDMVKTA  480
REKLKHYSCT AEDIDHEDIT RDQTSTLKTC LPLELHKNES CLATRETSST TRGSCLPPQK  540
TSLMMTLCLG SIYEDLKMYQ TEFQAINAAL QNHNHQQIIL DKGMLVAIDE LMQSLNHNGE  600
TLRQKPPVGE ADPYRVKMKL CILLHAFSTR VVTINRVMGY LSSASGGPGP AGMKGLPGSG  660
GGGSGGGGSG GGGSGGGGSG GGGSGGGGSQ SVLTQPPSVS GAPGQRVTIS CSGSRSNIGS  720
NTVKWYQQLP GTAPKLLIYY NDQRPSGVPD RFSGSKSGTS ASLAITGLQA EDEADYYCQS  780
YDRYTHPALL FGCGTKVTVL GGGGSGGGGS GGGGSQVQLV ESGGGVVQPG RSLRLSCAAS  840
GFTFSSYGMH WVRQAPGKCL EWVAFIRYDG SNKYYADSVK GRFTISRDNS KNTLYLQMNS  900
LRAEDTAVYY CKTHGSHDNW GQGTMVTVSS                                  930

SEQ ID NO: 371            moltype = AA   length = 930
FEATURE                   Location/Qualifiers
source                    1..930
                          mol_type = protein
                          organism = synthetic construct
SEQUENCE: 371
EVQLVESGGG LVQPGNSLRL SCAASGFTFS KFGMSWVRQA PGKGLEWVSS ISGSGRDTLY   60
AESVKGRFTI SRDNAKTTLY LQMNSLRPED TAVYYCTIGG SLSVSSQGTL VTVSSSGGPG  120
PAGMKGLPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRVIPVSGPA RCLSQSRNLL KTTDDMVKTA  480
REKLKHYSCT AEDIDHEDIT RDQTSTLKTC LPLELHKNES CLATRETSST TRGSCLPPQK  540
TSLMMTLCLG SIYEDLKMYQ TEFQAINAAL QNHNHQQIIL DKGMLVAIDE LMQSLNHNGE  600
TLRQKPPVGE ADPYRVKMKL CILLHAFSTR VVTINRVMGY LSSASGGPGP AGMKGLPGSG  660
GGGSGGGGSG GGGSGGGGSG GGGSGGGGSQ SVLTQPPSVS GAPGQRVTIS CSGSRSNIGS  720
NTVKWYQQLP GTCPKLLIYY NDQRPSGVPD RFSGSKSGTS ASLAITGLQA EDEADYYCQS  780
YDRYTHPALL FGTGTKVTVL GGGGSGGGGS GGGGSQVQLV ESGGGVVQPG RSLRLSCAAS  840
GFTFSSYGMH WVRQAPGKGL EWVAFIRYDG SNKYYADSVK GRFTISRDNS KNTLYLQMNS  900
LRAEDTAVYY CKTHGSHDNW GCGTMVTVSS                                  930

SEQ ID NO: 372            moltype = AA   length = 553
FEATURE                   Location/Qualifiers
source                    1..553
                          mol_type = protein
                          organism = synthetic construct
SEQUENCE: 372
APTSSSTKKT QLQLEHLLLD LQMILNGINN YKNPKLTRML TFKFYMPKKA TELKHLQCLE   60
EELKPLEEVL NLAQSKNFHL RPRDLISNIN VIVLELKGSE TTFMCEYADE TATIVEFLNR  120
WITFCQSIIS TLTSGGPGPA GMKGLPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPGPA  300
GMKGLPGSEV QLVESGGGLV QPGGSLRLSC AASGFTFSSY TLAWVRQAPG KGLEWVAAID  360
SSSYTYSPDT VRGRFTISRD NAKNSLYLQM NSLRAEDTAV YCARDSNWD ALDYWGQGTT  420
VTVSSGGGGS GGGGSGGGGS DIQMTQSPSS LSASVGDRVT ITCKASQNVG TNVGWYQQKP  480
GKAPKALIYS ASFRYSGVPS RFSGSGSGTD FTLTISSLQP EDFATYYCQQ YYTYPYTFGG  540
GTKVEIKHHH HHH                                                    553

SEQ ID NO: 373            moltype = AA   length = 444
FEATURE                   Location/Qualifiers
source                    1..444
                          mol_type = protein
                          organism = synthetic construct
SEQUENCE: 373
APTSSSTKKT QLQLEHLLLD LQMILNGINN YKNPKLTRML TFKFYMPKKA TELKHLQCLE   60
EELKPLEEVL NLAQSKNFHL RPRDLISNIN VIVLELKGSE TTFMCEYADE TATIVEFLNR  120
WITFCQSIIS TLTSGGPGPA GMKGLPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPGPA  300
GMKGLPGQVQ LQESGGGLVQ TGGSLRLSCT TSGTIFSGYT MGWYRQAPGE QRELVAVISG  360
```

```
GGDTNYADSV KGRFTISRDN TKDTMYLQMN SLKPEDTAVY YCYSREVTPP WKLYWGQGTQ  420
VTVSSAAAYP YDVPDYGSHH HHHH                                        444

SEQ ID NO: 374           moltype = AA  length = 444
FEATURE                  Location/Qualifiers
source                   1..444
                         mol_type = protein
                         organism = synthetic construct
SEQUENCE: 374
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GMKGLPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPGPA  300
GMKGLPGQVQ LQESGGGLVQ EGGSLRLSCA ASERIFSTDV MGWYRQAAEK QRELVAVVSA  360
RGTTNYLDAV KGRFTISRDN ARNTLTLQMN DLKPEDTASY YCYVRETTSP WRIYWGQGTQ  420
VTVSSAAAYP YDVPDYGSHH HHHH                                        444

SEQ ID NO: 375           moltype = AA  length = 445
FEATURE                  Location/Qualifiers
source                   1..445
                         mol_type = protein
                         organism = synthetic construct
SEQUENCE: 375
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GMKGLPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPGPA  300
GMKGLPGQVQ LQESGGGLVQ AGGSLRLSCA ASGSIFSANA MGWYRQAPGK QRELVAVISS  360
GGSTNYADSV KGRFTISRDN AKNTVYLQMN SLKPEDTAVY YCMYSGSYYY TPNDYWGQGT  420
QVTVSSAAAY PYDVPDYGSH HHHH                                        445

SEQ ID NO: 376           moltype = AA  length = 557
FEATURE                  Location/Qualifiers
source                   1..557
                         mol_type = protein
                         organism = synthetic construct
SEQUENCE: 376
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GMKGLPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPGPA  300
GMKGLPGSEV QLVESGGGLV QPGGSLRLSC AASGFTFSSY TLAWVRQAPG KGLEWVAAID  360
SSSSYTYSPDT VRGRFTISRD NAKNSLYLQM NSLRAEDTAV YYCARDSNWD ALDYWGQGTT  420
VTVSSSGGPG PAGMKGLPGS DIQMTQSPSS LSASVGDRVT ITCKASQNVG TNVGWYQQKP  480
GKAPKALIYS ASFRYSGVPS RFSGSGSGTD FTLTISSLQP EDFATYYCQQ YYTYPYTFGG  540
GTKVEIKHHH HHHEPEA                                                557

SEQ ID NO: 377           moltype = AA  length = 557
FEATURE                  Location/Qualifiers
source                   1..557
                         mol_type = protein
                         organism = synthetic construct
SEQUENCE: 377
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GMKGLPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPGPA  300
GMKGLPGSEV QLVESGGGLV QPGGSLRLSC AASGFTFSSY TLAWVRQAPG KGLEWVAAID  360
SSSSYTYSPDT VRGRFTISRD NAKNSLYLQM NSLRAEDTAV YYCARDSNWD ALDYWGQGTT  420
VTVSSGGGGS GGGGSGGGGS DIQMTQSPSS LSASVGDRVT ITCKASQNVG TNVGWYQQKP  480
GKAPKLLIYS ASFRYSGVPS RFSGSGSGTD FTLTISSLQP EDFATYYCQQ YYTYPYTFGG  540
GTKVEIKHHH HHHEPEA                                                557

SEQ ID NO: 378           moltype = AA  length = 557
FEATURE                  Location/Qualifiers
source                   1..557
                         mol_type = protein
                         organism = synthetic construct
SEQUENCE: 378
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GMKGLPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPGPA  300
GMKGLPGSEV QLVESGGGLV QPGGSLRLSC AASGFTFSSY TLAWVRQAPG KGLEWVAAID  360
```

```
SSSYTYSPDT VRGRFTISRD NAKNSLYLQM NSLRAEDTAV YYCARDSNWD ALDYWGQGTT      420
VTVSSGGGGS GGGGSGGGGS DIQMTQSPSS LSASVGDRVT ITCKASQNVG TNVGWYQQKP      480
GKAPKGLIYS ASFRYSGVPS RFSGSGSGTD FTLTISSLQP EDFATYYCQQ YYTYPYTFGG      540
GTKVEIKHHH HHHEPEA                                                    557

SEQ ID NO: 379          moltype = AA  length = 557
FEATURE                 Location/Qualifiers
source                  1..557
                        mol_type = protein
                        organism = synthetic construct
SEQUENCE: 379
APTSSSTKKT QLQLEHLLLD LQMILNGINN YKNPKLTRML TFKFYMPKKA TELKHLQCLE       60
EELKPLEEVL NLAQSKNFHL RPRDLISNIN VIVLELKGSE TTFMCEYADE TATIVEFLNR      120
WITFSQSIIS TLTSGGPGPA GMKGLPGSEV QLVESGGGLV QPGNSLRLSC AASGFTFSKF      180
GMSWVRQAPG KGLEWVSSIS GSGRDTLYAE SVKGRFTISR DNAKTTLYLQ MNSLRPEDTA      240
VYYCTIGGSL SVSSQGTLVT VSSGGGGSGG GGSGGGGSGG GGSGGGGSGG GGSSGGPGPA      300
GMKGLPGSEV QLVESGGGLV QPGGSLRLSC AASGFTFSSY TLAWVRQAPG KGLEWVAAID      360
SSSYTYSPDT VRGRFTISRD NAKNSLYLQM NSLRAEDTAV YYCARDSNWD ALDYWGQGTT      420
VTVSSGGGGS GGGGSGGGGS DIQMTQSPSS LSASVGDRVT ITCKASQNVG TNVGWYQQKP      480
GKAPKALIYS ASFRYSGVPS RFSGSGSGTD FTLTISSLQP EDFATYYCQQ YYTYPYTFGG      540
GTKVEIKHHH HHHEPEA                                                    557

SEQ ID NO: 380          moltype = AA  length = 1027
FEATURE                 Location/Qualifiers
source                  1..1027
                        mol_type = protein
                        organism = synthetic construct
SEQUENCE: 380
APTSSSTKKT QLQLEHLLLD LQMILNGINN YKNPKLTRML TFKFYMPKKA TELKHLQCLE       60
EELKPLEEVL NLAQSKNFHL RPRDLISNIN VIVLELKGSE TTFMCEYADE TATIVEFLNR      120
WITFCQSIIS TLTSGGPGPA GMKGLPGSDA HKSEVAHRFK DLGEENFKAL VLIAFAQYLQ      180
QCPFEDHVKL VNEVTEFAKT CVADESAENC DKSLHTLFGD KLCTVATLRE TYGEMADCCA      240
KQEPERNECF LQHKDDNPNL PRLVRPEVDV MCTAFHDNEE TFLKKYLYEI ARRHPYFYAP      300
ELLFFAKRYK AAFTECCQAA DKAACLLPKL DELRDEGKAS SAKQRLKCAS LQKFGERAFK      360
AWAVARLSQR FPKAEFAEVS KLVTDLTKVH TECCHGDLLE CADDRADLAK YICENQDSIS      420
SKLKECCEKP LLEKSHCIAE VENDEMPADL PSLAADFVES KDVCKNYAEA KDVFLGMFLY      480
EYARRHPDYS VVLLLRLAKT YETTLEKCCA AADPHECYAK VFDEFKPLVE EPQNLIKQNC      540
ELFEQLGEYK FQNALLVRYT KKVPQVSTPT LVEVSRNLGK VGSKCCKHPE AKRMPCAEDY      600
LSVVLNQLCV LHEKTPVSDR VTKCCTESLV NRRPCFSALE VDETYVPKEF NAETFTFHAD      660
ICTLSEKERQ IKKQTALVEL VKHKPKATKE QLKAVMDDFA AFVEKCCKAD DKETCFAEEG      720
KKLVAASQAA LGLGGGGSGG GGSGGGGSGG GGSGGGGSGG GGSSGGPGPA GMKGLPGSEV      780
QLVESGGGLV QPGGSLRLSC AASGFTFSSY TLAWVRQAPG KGLEWVAAID SSSYTYSPDT      840
VRGRFTISRD NAKNSLYLQM NSLRAEDTAV YYCARDSNWD ALDYWGQGTT VTVSSGGGGS      900
GGGGSGGGGS DIQMTQSPSS LSASVGDRVT ITCKASQNVG TNVGWYQQKP GKAPKALIYS      960
ASFRYSGVPS RFSGSGSGTD FTLTISSLQP EDFATYYCQQ YYTYPYTFGG GTKVEIKHHH     1020
HHHEPEA                                                              1027

SEQ ID NO: 381          moltype = AA  length = 1022
FEATURE                 Location/Qualifiers
source                  1..1022
                        mol_type = protein
                        organism = synthetic construct
SEQUENCE: 381
APTSSSTKKT QLQLEHLLLD LQMILNGINN YKNPKLTRML TFKFYMPKKA TELKHLQCLE       60
EELKPLEEVL NLAQSKNFHL RPRDLISNIN VIVLELKGSE TTFMCEYADE TATIVEFLNR      120
WITFCQSIIS TLTSGGPGPA GMKGLPGSEA HKSEIAHRYN DLGEQHFKGL VLIAFSQYLQ      180
KCSYDEHAKL VQEVTDFAKT CVADESAANC DKSLHTLFGD KLCAIPNLRE NYGELADCCT      240
KQEPERNECF LQHKDDNPSL PPFERPEAEA MCTSFKENPT TFMGHYLHEV ARRHPYFYAP      300
ELLYYAEQYN EILTQCCAEA DKESCLTPKL DGVKEKALVS SVRQRMKCSS MQKFGERAFK      360
AWAVARLSQT FPNADFAEIT KLATDLTKVN KECCHGDLLE CADDRAELAK YMCENQATIS      420
SKLQTCCDKP LLKKAHCLSE VEHDTMPADL PAIAADFVED QEVCKNYAEA KDVFLGTFLY      480
EYSRRHPDYS VSLLLRLAKK YEATLEKCCA EANPPACYGT VLAEFQPLVE EPKNLVKTNC      540
DLYEKLGEYG FQNAILVRYT QKAPQVSTPT LVEAARNLGR VGTKCCTLPE DQRLPCVEDY      600
LSAILNRVCL LHEKTPVSEH VTKCCSGSLV ERRPCFSALT VDETYVPKEF KAETFTFHSD      660
ICTLPEKEKQ IKKQTALAEL VKHKPKATAE QLKTVMDDFA QFLDTCCKAA DKDTCFSTEG      720
PNLVTRCKDA LAGGGGSGGG GSGGGGSGGG GSGGGGSGGG GSSGGPGPAG MKGLPGSEVQ      780
LVESGGGLVQ PGGSLRLSCA ASGFTFSSYT LAWVRQAPGK GLEWVAAIDS SSYTYSPDTV      840
RGRFTISRDN AKNSLYLQMN SLRAEDTAVY YCARDSNWDA LDYWGQGTTV TVSSGGGGSG      900
GGGSGGGGSD IQMTQSPSSL SASVGDRVTI TCKASQNVGT NVGWYQQKPG KAPKALIYSA      960
SFRYSGVPSR FSGSGSGTDF TLTISSLQPE DFATYYCQQY YTYPYTFGGG TKVEIKHHHH     1020
HH                                                                   1022

SEQ ID NO: 382          moltype = AA  length = 1336
FEATURE                 Location/Qualifiers
source                  1..1336
                        mol_type = protein
                        organism = synthetic construct
SEQUENCE: 382
EAHKSEIAHR YNDLGEQHFK GLVLIAFSQY LQKCSYDEHA KLVQEVTDFA KTCVADESAA       60
```

```
NCDKSLHTLF GDKLCAIPNL RENYGELADC CTKQEPERNE CFLQHKDDNP SLPPFERPEA    120
EAMCTSFKEN PTTFMGHYLH EVARRHPYFY APELLYYAEQ YNEILTQCCA EADKESCLTP    180
KLDGVKEKAL VSSVRQRMKC SSMQKFGERA FKAWAVARLS QTFPNADFAE ITKLATDLTK    240
VNKECCHGDL LECADDRAEL AKYMCENQAT ISSKLQTCCD KPLLKKAHCL SEVEHDTMPA    300
DLPAIAADFV EDQEVCKNYA EAKDVFLGTF LYEYSRRHPD YSVSLLLRLA KKYEATLEKC    360
CAEANPPACY GTVLAEFQPL VEEPKNLVKT NCDLYEKLGE YGFQNAILVR YTQKAPQVST    420
PTLVEAARNL GRVGTKCCTL PEDQRLPCVE DYLSAILNRV CLLHEKTPVS EHVTKCCSGS    480
LVERRPCFSA LTVDETYVPK EFKAETFTFH SDICTLPEKE KQIKKQTALA ELVKHKPKAT    540
AEQLKTVMDD FAQFLDTCCK AADKDTCFST EGPNLVTRCK DALASGGPGP AGMKGLPGST    600
FKFYMPKKAT ELKHLQCLEE ELKPLEEVLN LAQSKNFHLR PRDLISNINV IVLELKGSET    660
TFMCEYADET ATIVEFLNRW ITFCQSIIST LTGGSSSTKK TQLQLEHLLL DLQMILNGIN    720
NYKNPKLTRM LSGGPGPAGM KGLPGSEAHK SEIAHRYNDL GEQHFKGLVL IAFSQYLQKC    780
SYDEHAKLVQ EVTDFAKTCV ADESAANCDK SLHTLFGDKL CAIPNLRENY GELADCCTKQ    840
EPERNECFLQ HKDDNPSLPP FERPEAEAMC TSFKENPTTF MGHYLHEVAR RHPYFYAPEL    900
LYYAEQYNEI LTQCCAEADK ESCLTPKLDG VKEKALVSSV RQRMKCSSMQ KFGERAFKAW    960
AVARLSQTFP NADFAEITKL ATDLTKVNKE CCHGDLLECA DDRAELAKYM CENQATISSK   1020
LQTCCDKPLL KKAHCLSEVE HDTMPADLPA IAADFVEDQE VCKNYAEAKD VFLGTFLYEY   1080
SRRHPDYSVS LLLRLAKKYE ATLEKCCAEA NPPACYGTVL AEFQPLVEEP KNLVKTNCDL   1140
YEKLGEYGFQ NAILVRYTQK APQVSTPTLV EAARNLGRVG TKCCTLPEDQ RLPCVEDYLS   1200
AILNRVCLLH EKTPVSEHVT KCCSGSLVER RPCFSALTVD ETYVPKEFKA ETFTFHSDIC   1260
TLPEKEKQIK KQTALAELVK HKPKATAEQL KTVMDDFAQF LDTCCKAADK DTCFSTEGPN   1320
LVTRCKDALA HHHHHH                                                  1336

SEQ ID NO: 383           moltype = AA   length = 817
FEATURE                  Location/Qualifiers
source                   1..817
                         mol_type = protein
                         organism = synthetic construct
SEQUENCE: 383
APTSSSTKKT QLQLEHLLLD LQMILNGINN YKNPKLTRML TFKFYMPKKA TELKHLQCLE     60
EELKPLEEVL NLAQSKNFHL RPRDLISNIN VIVLELKGSE TTFMCEYADE TATIVEFLNR    120
WITFCQSIIS TLTSGGPGPA GMKGLPGSEV QLVESGGGLV QPGNSLRLSC AASGFTFSKF    180
GMSWVRQAPG KGLEWVSSIS GSGRDTLYAE SVKGRFTISR DNAKTTLYLQ MNSLRPEDTA    240
VYYCTIGGSL SVSSQGTLVT VSSGGGGSGG GGSGGGGSGG GGSSGGPGPA                300
GMKGLPGSEV QLVESGGGLV QPGGSLRLSC AASGFTFSSY TLAWVRQAPG KGLEWVAAID    360
SSSSYTYSPDT VRGRFTISRD NAKNSLYLQM NSLRAEDTAV YYCARDSNWD ALDYWGQGTT    420
VTVSSGGGGS GGGGSGGGGS DIQMTQSPSS LSASVGDRVT ITCKASQNVG TNVGWYQQKP    480
GKAPKALIYS ASFRYSGVPS RFSGSGSGTD FTLTISSLQP EDFATYYCQQ YYTYPYTFGG    540
GTKVEIKSGG PGPAGMKGLP GSGGGGSGGG GSGGGGSGGG GSGGGGSGGG GSELCDDDPP    600
EIPHATFKAM AYKEGTMLNC ECKRGFRRIK SGSLYMLCTG NSSHSSWDNQ CQCTSSATRN    660
TTKQVTPQPE EQKERKTTEM QSPMQPVDQA SLPGHCREPP PWENEATERI YHFVVGQMVY    720
YQCVQGYRAL HRGPAESVCK MTHGKTRWTQ PQLICTGEME TSQFPGEEKP QASPEGRPES    780
ETSCLVTTTD FQIQTEMAAT METSIFTTEY QHHHHHH                              817

SEQ ID NO: 384           moltype = AA   length = 817
FEATURE                  Location/Qualifiers
source                   1..817
                         mol_type = protein
                         organism = synthetic construct
SEQUENCE: 384
ELCDDDPPEI PHATFKAMAY KEGTMLNCEC KRGFRRIKSG SLYMLCTGNS SHSSWDNQCQ     60
CTSSATRNTT KQVTPQPEEQ KERKTTEMQS PMQPVDQASL PGHCREPPPW ENEATERIYH    120
FVVGQMVYYQ CVQGYRALHR GPAESVCKMT HGKTRWTQPQ LICTGEMETS QFPGEEKPQA    180
SPEGRPESET SCLVTTTDFQ IQTEMAATME TSIFTTEYQG GGGSGGGGSG GGGSGGGGSG    240
GGGGSGGGGS GGPGPAGMKG LPGSAPTSSS TKKTQLQLEH LLLDLQMILN GINNYKNPKL    300
TRMLTFKFYM PKKATELKHL QCLEEELKPL EEVLNLAQSK NFHLRPRDLI SNINVIVLEL    360
KGSETTFMCE YADETATIVE FLNRWITFCQ SIISTLTSGG PGPAGMKGLP GSEVQLVESG    420
GGLVQPGNSL RLSCAASGFT FSKFGMSWVR QAPGKGLEWV SSISGSGRDT LYAESVKGRF    480
TISRDNAKTT LYLQMNSLRP EDTAVYYCTI GGSLSVSSQG TLVTVSSGGG GSGGGGSGGG    540
GSGGGGSGGG GSGGGGSSGG PGPAGMKGLP GSEVQLVESG GGLVQPGGSL RLSCAASGFT    600
FSSYTLAWVR QAPGKGLEWV AAIDSSSYTY SPDTVRGRFT ISRDNAKNSL YLQMNSLRAE    660
DTAVYYCARD SNWDALDYWG QGTTVTVSSG GGGSGGGGSG GGGSDIQMTQ SPSSLSASVG    720
DRVTITCKAS QNVGTNVGWY QQKPGKAPKA LIYSASFRYS GVPSRFSGSG SGTDFTLTIS    780
SLQPEDFATY YCQQYYTYPY TFGGGTKVEI KHHHHHH                              817

SEQ ID NO: 385           moltype = AA   length = 817
FEATURE                  Location/Qualifiers
source                   1..817
                         mol_type = protein
                         organism = synthetic construct
SEQUENCE: 385
APTSSSTKKT QLQLEHLLLD LQMILNGINN YKNPKLTRML TFKFYMPKKA TELKHLQCLE     60
EELKPLEEVL NLAQSKNFHL RPRDLISNIN VIVLELKGSE TTFMCEYADE TATIVEFLNR    120
WITFCQSIIS TLTSGGPGPA GMKGLPGSGG GGSGGGGSGG GGSGGGGSGG GGSGGGGSEL    180
CDDDPPEIPH ATFKAMAYKE GTMLNCECKR GFRRIKSGSL YMLCTGNSSH SSWDNQCQCT    240
SSATRNTTKQ VTPQPEEQKE RKTTEMQSPM QPVDQASLPG HCREPPPWEN EATERIYHFV    300
VGQMVYYQCV QGYRALHRGP AESVCKMTHG KTRWTQPQLI CTGEMETSQF PGEEKPQASP    360
EGRPESETSC LVTTTDFQIQ TEMAATMETS IFTTEYQSGG PGPAGMKGLP GSEVQLVESG    420
GGLVQPGNSL RLSCAASGFT FSKFGMSWVR QAPGKGLEWV SSISGSGRDT LYAESVKGRF    480
```

```
TISRDNAKTT LYLQMNSLRP EDTAVYYCTI GGSLSVSSQG TLVTVSSGGG GSGGGGSGGG    540
GSGGGGSGGG GSGGGGSSGG PGPAGMKGLP GSEVQLVESG GGLVQPGGSL RLSCAASGFT    600
FSSYTLAWVR QAPGKGLEWV AAIDSSSYTY SPDTVRGRFT ISRDNAKNSL YLQMNSLRAE    660
DTAVYYCARD SNWDALDYWG QGTTVTVSSG GGGSGGGGSG GGGSDIQMTQ SPSSLSASVG    720
DRVTITCKAS QNVGTNVGWY QQKPGKAPKA LIYSASFRYS GVPSRFSGSG SGTDFTLTIS    780
SLQPEDFATY YCQQYYTYPY TFGGGTKVEI KHHHHHH                             817

SEQ ID NO: 386         moltype = AA  length = 682
FEATURE                Location/Qualifiers
source                 1..682
                       mol_type = protein
                       organism = synthetic construct
SEQUENCE: 386
EVQLVESGGG LVQPGNSLRL SCAASGFTFS KFGMSWVRQA PGKGLEWVSS ISGSGRDTLY     60
AESVKGRFTI SRDNAKTTLY LQMNSLRPED TAVYYCTIGG SLSVSSQGTL VTVSSSGGPG    120
PAGMKGLPGS TFKFYMPKKA TELKHLQCLE EELKPEEVL NLAQSKNFHL RPRDLISNIN     180
VIVLELKGSE TTFMCEYADE TATIVEFLNR WITFCQSIIS TLTGGSSSTK KTQLQLEHLL    240
LDLQMILNGI NNYKNPKLTR MLSGGPGPAG MKGLPGSEVQ LVESGGGLVQ PGNSLRLSCA    300
ASGFTFSKFG MSWVRQAPGK GLEWVSSISG SGRDTLYAES VKGRFTISRD NAKTTLYLQM    360
NSLRPEDTAV YYCTIGGSLS VSSQGTLVTV SSGGGGSGGG GSGGGGSGGG GSGGGGSGGG    420
GSSGGPGPAG MKGLPGSEVQ LVESGGGLVQ PGGSLRLSCA ASGFTFSSYT LAWVRQAPGK    480
GLEWVAAIDS SSYTYSPDTV RGRFTISRDN AKNSLYLQMN SLRAEDTAVY YCARDSNWDA    540
LDYWGQGTTV TVSSGGGGSG GGGSGGGGSD IQMTQSPSSL SASVGDRVTI TCKASQNVGT    600
NVGWYQQKPG KAPKALIYSA SFRYSGVPSR FSGSGSGTDF TLTISSLQPE DFATYYCQQY    660
YTYPYTFGGG TKVEIKHHHH HH                                             682

SEQ ID NO: 387         moltype = AA  length = 682
FEATURE                Location/Qualifiers
source                 1..682
                       mol_type = protein
                       organism = synthetic construct
SEQUENCE: 387
EVQLVESGGG LVQPGSLRL SCAASGFTFS SYTLAWVRQA PGKGLEWVAA IDSSSYTYSP      60
DTVRGRFTIS RDNAKNSLYL QMNSLRAEDT AVYYCARDSN WDALDYWGQG TTVTVSSGGG    120
GSGGGGSGGG GSDIQMTQSP SSLSASVGDR VTITCKASQN VGTNVGWYQQ KPGKAPKALI    180
YSASFRYSGV PSRFSGSGSG TDFTLTISSL QPEDFATYYC QQYYTYPYTF GGGTKVEIKS    240
GGPGPAGMKG LPGSGGGGSG GGGSGGGGSG GGGSGGGGSG GGGSEVQLVE SGGGLVQPGN    300
SLRLSCAASG FTFSKFGMSW VRQAPGKGLE WVSSISGSGR DTLYAESVKG RFTISRDNAK    360
TTLYLQMNSL RPEDTAVYYC TIGGSLSVSS QGTLVTVSSS GGPGPAGMKG LPGSTFKFYM    420
PKKATELKHL QCLEEELKPL EEVLNLAQSK NFHLRPRDLI SNINVIVLEL KGSETTFMCE    480
YADETATIVE FLNRWITFCQ SIISTLTGGS SSTKKTQLQL EHLLLDLQMI LNGINNYKNP    540
KLTRMLSGGP GPAGMKGLPG SEVQLVESGG GLVQPGNSLR LSCAASGFTF SKFGMSWVRQ    600
APGKGLEWVS SISGSGRDTL YAESVKGRFT ISRDNAKTTL YLQMNSLRPE DTAVYYCTIG    660
GSLSVSSQGT LVTVSSHHHH HH                                             682

SEQ ID NO: 388         moltype = AA  length = 553
FEATURE                Location/Qualifiers
source                 1..553
                       mol_type = protein
                       organism = synthetic construct
SEQUENCE: 388
APTSSSTKKT QLQLEHLLLD LQMILNGINN YKNPKLTRML TFKFYMPKKA TELKHLQCLE     60
EELKPEEVL NLAQSKNFHL RPRDLISNIN VIVLELKGSE TTFMCEYADE TATIVEFLNR     120
WITFCQSIIS TLTGGPGPA GMKGLPGSEV QLVESGGGLV QPGNSLRLSC AASGFTFSKF     180
GMSWVRQAPG KGLEWVSSIS GSGRDTLYAE SVKGRFTISR DNAKTTLYLQ MNSLRPEDTA    240
VYYCTIGGSL SVSSQGTLVT VSSGGGGSGG GGSGGGGSGG GGSGGGGSGG GGSSGGPGPA    300
GMKGLPGSEV QLVESGGGLV QPGGSLRLSC AASGFTFSSY TLAWVRQAPG KGLEWVAAID    360
SSSYTYSPDT VRGRFTISRD NAKNSLYLQM NSLRAEDTAV YYCARDSNWD ALDYWGQGTT    420
VTVSSGGGGS GGGGSGGGGS DIQMTQSPSS LSASVGDRVT ITCKASQNVG TNVGWYQQKP    480
GKAPKSLIYS ASFRYSGVPS RFSGSGSGTD FTLTISSLQP EDFATYYCQQ YYTYPYTFGG    540
GTKVEIKHHH HHH                                                       553

SEQ ID NO: 389         moltype = AA  length = 553
FEATURE                Location/Qualifiers
source                 1..553
                       mol_type = protein
                       organism = synthetic construct
SEQUENCE: 389
APTSSSTKKT QLQLEHLLLD LQMILNGINN YKNPKLTRML TFKFYMPKKA TELKHLQCLE     60
EELKPEEVL NLAQSKNFHL RPRDLISNIN VIVLELKGSE TTFMCEYADE TATIVEFLNR     120
WITFCQSIIS TLTGGPGPA GMKGLPGSEV QLVESGGGLV QPGNSLRLSC AASGFTFSKF     180
GMSWVRQAPG KGLEWVSSIS GSGRDTLYAE SVKGRFTISR DNAKTTLYLQ MNSLRPEDTA    240
VYYCTIGGSL SVSSQGTLVT VSSGGGGSGG GGSGGGGSGG GGSGGGGSGG GGSSGGPGPA    300
GMKGLPGSEV QLVESGGGLV QPGGSLRLSC AASGFTFSSY TLAWVRQAPG KGLEWVAAID    360
SSSYTYSPDT VRGRFTISRD NAKNSLYLQM NSLRAEDTAV YYCARDSNWD ALDYWGQGTT    420
VTVSSGGGGS GGGGSGGGGS DIQMTQSPSS LSASVGDRVT ITCKASQNVG TNVGWYQQKP    480
GQAPRLLIYS ASFRYSGVPS RFSGSGSGTD FTLTISSLQP EDFATYYCQQ YYTYPYTFGG    540
GTKVEIKHHH HHH                                                       553
```

```
SEQ ID NO: 390            moltype = AA  length = 667
FEATURE                   Location/Qualifiers
source                    1..667
                          mol_type = protein
                          organism = synthetic construct
SEQUENCE: 390
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTSGGPGPA GMKGLPGSES KYGPPCPPCP APEFLGGPSV FLFPPKPKDT   180
LMISRTPEVT CVVVDVSQED PEVQFNWYVD GVEVHNAKTK PREEQFNSTY RVVSVLTVLH   240
QDWLNGKEYK CKVSNKGLPS SIEKTISKAK GQPREPQVYT LPPSQEEMTK NQVSLTCLVK   300
GFYPSDIAVE WESNGQPENN YKTTPPVLDS DGSFFLYSRL TVDKSRWQEG NVFSCSVMHE   360
ALHNHYTQKS LSLSLGKGGG GSGGGGSGGG GSGGGGSGGG GSGGGGSSGG PGPAGMKGLP   420
GSEVQLVESG GGLVQPGGSL RLSCAASGFT FSSYTLAWVR QAPGKGLEWV AAIDSSSYTY   480
SPDTVRGRFT ISRDNAKNSL YLQMNSLRAE DTAVYYCARD SNWDALDYWG QGTTVTVSSG   540
GGGSGGGGSG GGGSDIQMTQ SPSSLSASVG DRVTITCKAS QNVGTNVGWY QQKPGKAPKA   600
LIYSASFRYS GVPSRFSGSG SGTDFTLTIS SLQPEDFATY YCQQYYTYPY TFGGGTKVEI   660
KHHHHHH                                                             667

SEQ ID NO: 391            moltype = AA  length = 667
FEATURE                   Location/Qualifiers
source                    1..667
                          mol_type = protein
                          organism = synthetic construct
SEQUENCE: 391
ESKYGPPCPP CPAPEFLGGP SVFLFPPKPK DTLMISRTPE VTCVVVDVSQ EDPEVQFNWY    60
VDGVEVHNAK TKPREEQFNS TYRVVSVLTV LHQDWLNGKE YKCKVSNKGL PSSIEKTISK   120
AKGQPREPQV YTLPPSQEEM TKNQVSLTCL VKGFYPSDIA VEWESNGQPE NNYKTTPPVL   180
DSDGSFFLYS RLTVDKSRWQ EGNVFSCSVM HEALHNHYTQ KSLSLSLGKS GGPGPAGMKG   240
LPGSAPTSSS TKKTQLQLEH LLLDLQMILN GINNYKNPKL TRMLTFKFYM PKKATELKHL   300
QCLEEELKPL EEVLNLAQSK NFHLRPRDLI SNINVIVLEL KGSETTFMCE YADETATIVE   360
FLNRWITFCQ SIISTLTGGG GSGGGGSGGG GSGGGGSGGG GSGGGGSSGG PGPAGMKGLP   420
GSEVQLVESG GGLVQPGGSL RLSCAASGFT FSSYTLAWVR QAPGKGLEWV AAIDSSSYTY   480
SPDTVRGRFT ISRDNAKNSL YLQMNSLRAE DTAVYYCARD SNWDALDYWG QGTTVTVSSG   540
GGGSGGGGSG GGGSDIQMTQ SPSSLSASVG DRVTITCKAS QNVGTNVGWY QQKPGKAPKA   600
LIYSASFRYS GVPSRFSGSG SGTDFTLTIS SLQPEDFATY YCQQYYTYPY TFGGGTKVEI   660
KHHHHHH                                                             667

SEQ ID NO: 392            moltype = AA  length = 667
FEATURE                   Location/Qualifiers
source                    1..667
                          mol_type = protein
                          organism = synthetic construct
SEQUENCE: 392
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTSGGPGPA GMKGLPGSGG GGSGGGGSGG GGSGGGGSEV   180
QLVESGGGLV QPGGSLRLSC AASGFTFSSY TLAWVRQAPG KGLEWVAAID SSSYTYSPDT   240
VRGRFTISRD NAKNSLYLQM NSLRAEDTAV YYCARDSNWD ALDYWGQGTT VTVSSGGGGS   300
GGGGSGGGGS DIQMTQSPSS LSASVGDRVT ITCKASQNVG TNVGWYQQKP GKAPKALIYS   360
ASFRYSGVPS RFSGSGSGTD FTLTISSLQP EDFATYYCQQ YYTYPYTFGG GTKVEIKSGG   420
PGPAGMKGLP GSESKYGPPC PPCPAPEFLG GPSVFLFPPK PKDTLMISRT PEVTCVVVDV   480
SQEDPEVQFN WYVDGVEVHN AKTKPREEQF NSTYRVVSVL TVLHQDWLNG KEYKCKVSNK   540
GLPSSIEKTI SKAKGQPREP QVYTLPPSQE EMTKNQVSLT CLVKGFYPSD IAVEWESNGQ   600
PENNYKTTPP VLDSDGSFFL YSRLTVDKSR WQEGNVFSCS VMHEALHNHY TQKSLSLSLG   660
KHHHHHH                                                             667

SEQ ID NO: 393            moltype = AA  length = 665
FEATURE                   Location/Qualifiers
source                    1..665
                          mol_type = protein
                          organism = synthetic construct
SEQUENCE: 393
VPRDCGCKPC ICTVPEVSSV FIFPPKPKDV LTITLTPKVT CVVVDISKDD PEVQFSWFVD    60
DVEVHTAQTQ PREEQFNSTF RSVSELPIMH QDWLNGKEFK CRVNSAAFPA PIEKTISKTK   120
GRPKAPQVYT IPPPKEQMAK DKVSLTCMIT DFFPEDITVE WQWNGQPAEN YKNTQPIMDT   180
DGSYFVYSKL NVQKSNWEAG NTFTCSVLHE GLHNHHTEKS LSHSPGKSGG PGPAGMKGLP   240
GSAPTSSSTK KTQLQLEHLL LDLQMILNGI NNYKNPKLML TFKFYMPKME KATELKHLQC   300
LEEELKPLEE VLNLAQSKNF HLRPRDLISN INVIVLELKG SETTFMCEYA DETATIVEFL   360
NRWITFCQSI ISTLTGGGGS GGGGSGGGGS GGGGSGGGGS GGGGSSGGPG PAGMKGLPGS   420
EVQLVESGGG LVQPGGSLRL SCAASGFTFS SYTLAWVRQA PGKGLEWVAA IDSSSYTYSP   480
DTVRGRFTIS RDNAKNSLYL QMNSLRAEDT AVYYCARDSN WDALDYWGQG TTVTVSSGGG   540
GSGGGGSGGG GSDIQMTQSP SSLSASVGDR VTITCKASQN VGTNVGWYQQ KPGKAPKALI   600
YSASFRYSGV PSRFSGSGSG TDFTLTISSL QPEDFATYYC QQYYTYPYTF GGGTKVEIKH   660
HHHHH                                                               665

SEQ ID NO: 394            moltype = AA  length = 547
FEATURE                   Location/Qualifiers
source                    1..547
```

```
                       mol_type = protein
                       organism = synthetic construct
SEQUENCE: 394
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTSGGPGPA GLYAQPGSEV QLVESGGGLV QPGNSLRLSC AASGFTFSKF   180
GMSWVRQAPG KGLEWVSSIS GSGRDTLYAE SVKGRFTISR DNAKTTLYLQ MNSLRPEDTA   240
VYYCTIGGSL SVSSQGTLVT VSSGGGGSGG GGSGGGGSGG GGSGGGGSGG GGSSGGPGPA   300
GLYAQPGSEV QLVESGGGLV QPGGSLRLSC AASGFTFSSY TLAWVRQAPG KGLEWVAAID   360
SSSYTYSPDT VRGRFTISRD NAKNSLYLQM NSLRAEDTAV YYCARDSNWD ALDYWGQGTT   420
VTVSSSGGPG PAGLYAQPGS DIQMTQSPSS LSASVGDRVT ITCKAREKLW SAVAWYQQKP   480
GKAPKSLIYS ASFRYSGVPS RFSGSGSGTD FTLTISSLQP EDFATYYCQQ YYTYPYTFGG   540
GTKVEIK                                                            547

SEQ ID NO: 395         moltype = AA  length = 547
FEATURE                Location/Qualifiers
source                 1..547
                       mol_type = protein
                       organism = synthetic construct
SEQUENCE: 395
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTSGGPGPA GLYAQPGSEV QLVESGGGLV QPGNSLRLSC AASGFTFSKF   180
GMSWVRQAPG KGLEWVSSIS GSGRDTLYAE SVKGRFTISR DNAKTTLYLQ MNSLRPEDTA   240
VYYCTIGGSL SVSSQGTLVT VSSGGGGSGG GGSGGGGSGG GGSGGGGSGG GGSSGGPGPA   300
GLYAQPGSEV QLVESGGGLV QPGGSLRLSC AASGFTFSSY TLAWVRQAPG KGLEWVAAID   360
SSSYTYSPDT VRGRFTISRD NAKNSLYLQM NSLRAEDTAV YYCARDSNWD ALDYWGQGTT   420
VTVSSGGGGS GGGGSGGGGS DIQMTQSPSS LSASVGDRVT ITCKAREKLW SAVAWYQQKP   480
GKAPKSLIYS ASFRYSGVPS RFSGSGSGTD FTLTISSLQP EDFATYYCQQ YYTYPYTFGG   540
GTKVEIK                                                            547

SEQ ID NO: 396         moltype = AA  length = 547
FEATURE                Location/Qualifiers
source                 1..547
                       mol_type = protein
                       organism = synthetic construct
SEQUENCE: 396
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTSGGPGPA GLYAQPGSEV QLVESGGGLV QPGNSLRLSC AASGFTFSKF   180
GMSWVRQAPG KGLEWVSSIS GSGRDTLYAE SVKGRFTISR DNAKTTLYLQ MNSLRPEDTA   240
VYYCTIGGSL SVSSQGTLVT VSSGGGGSGG GGSGGGGSGG GGSGGGGSGG GGSSGGPGPA   300
GLYAQPGSEV QLVESGGGLV QPGGSLRLSC AASGFTFSSY TLAWVRQAPG KGLEWVAAID   360
SSSYTYSPDT VRGRFTISRD NAKNSLYLQM NSLRAEDTAV YYCARDSNWD ALDYWGQGTT   420
VTVSSSGGPG PAGLYAQPGS DIQMTQSPSS LSASVGDRVT ITCKVTEKVW GNVAWYQQKP   480
GKAPISLIYS PSLRKSGVPS RFSGSGSGTD FTLTISSLQP EDFATYYCQQ YYTYPYTFGG   540
GTKVEIK                                                            547

SEQ ID NO: 397         moltype = AA  length = 547
FEATURE                Location/Qualifiers
source                 1..547
                       mol_type = protein
                       organism = synthetic construct
SEQUENCE: 397
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTSGGPGPA GLYAQPGSEV QLVESGGGLV QPGNSLRLSC AASGFTFSKF   180
GMSWVRQAPG KGLEWVSSIS GSGRDTLYAE SVKGRFTISR DNAKTTLYLQ MNSLRPEDTA   240
VYYCTIGGSL SVSSQGTLVT VSSGGGGSGG GGSGGGGSGG GGSGGGGSGG GGSSGGPGPA   300
GLYAQPGSEV QLVESGGGLV QPGGSLRLSC AASGFTFSSY TLAWVRQAPG KGLEWVAAID   360
SSSYTYSPDT VRGRFTISRD NAKNSLYLQM NSLRAEDTAV YYCARDSNWD ALDYWGQGTT   420
VTVSSGGGGS GGGGSGGGGS DIQMTQSPSS LSASVGDRVT ITCKVTEKVW GNVAWYQQKP   480
GKAPISLIYS PSLRKSGVPS RFSGSGSGTD FTLTISSLQP EDFATYYCQQ YYTYPYTFGG   540
GTKVEIK                                                            547

SEQ ID NO: 398         moltype = AA  length = 427
FEATURE                Location/Qualifiers
source                 1..427
                       mol_type = protein
                       organism = synthetic construct
SEQUENCE: 398
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTSGGPGPA GLYAQPGSEV QLVESGGGLV QPGNSLRLSC AASGFTFSKF   180
GMSWVRQAPG KGLEWVSSIS GSGRDTLYAE SVKGRFTISR DNAKTTLYLQ MNSLRPEDTA   240
VYYCTIGGSL SVSSQGTLVT VSSGGGGSGG GGSGGGGSGG GGSGGGGSGG GGSSGGPGPA   300
GLYAQPGSEV QLLESGGGLV QPGGSLRLSC AASGSIFSAN AMGWYRQAPG KGLELVAVIS   360
SGGSTNYADS VKGRFTISRD NSKNTVYLQM NSLRAEDTAV YYCMYSGSYY YTPNDYWGQG   420
TLVTVSS                                                            427
```

```
SEQ ID NO: 399           moltype = AA  length = 426
FEATURE                  Location/Qualifiers
source                   1..426
                         mol_type = protein
                         organism = synthetic construct
SEQUENCE: 399
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTSGGPGPA GLYAQPGSEV QLVESGGGLV QPGNSLRLSC AASGFTFSKF   180
GMSWVRQAPG KGLEWVSSIS SGRDTLYAE SVKGRFTISR DNAKTTLYLQ MNSLRPEDTA    240
VYYCTIGGSL SVSSQGTLVT VSSGGGGSGG GGSGGGGSGG GGSGGGGSGG GGSSGGPGPA   300
GLYAQPGSEV QLLESGGGLV QPGGSLRLSC AASERIFSTD VMGWYRQAPG KQRELVAVVS   360
ARGTTNYLDA VKGRFTISRD NSKNTLYLQM NSLRAEDTAV YYCVRETTS PWRIYWGQGT    420
LVTVSS                                                              426

SEQ ID NO: 400           moltype = AA  length = 811
FEATURE                  Location/Qualifiers
source                   1..811
                         mol_type = protein
                         organism = synthetic construct
SEQUENCE: 400
ELCDDDPPEI PHATFKAMAY KEGTMLNCEC KRGFRRIKSG SLYMLCTGNS SHSSWDNQCQ    60
CTSSATRNTT KQVTPQPEEQ KERKTTEMQS PMQPVDQASL PGHCREPPPW ENEATERIYH   120
FVVGQMVYYQ CVQGYRALHR GPAESVCKMT HGKTRWTQPQ LICTGEMETS QFPGEEKPQA   180
SPEGRPESET SSLVTTTDFQ IQTEMAATME TSIFTTEYQG GGGSGGGGSG GGGSGGGGSG   240
GGGSGGGGSS GGPGPAGLYA QPGSAPTSSS TKKTQLQLEH LLLDLQMILN GINNYKNPKL   300
TRMLTFKFYM PKKATELKHL QCLEEELKPL EEVLNLAQSK NFHLRPRDLI SNINVIVLEL   360
KGSETTFMCE YADETATIVE FLNRWITFCQ SIISTLTSGG PGPAGLYAQP GSEVQLVESG   420
GGLVQPGNSL RLSCAASGFT FSKFGMSWVR QAPGKGLEWV SSISGSGRDT LYAESVKGRF   480
TISRDNAKTT LYLQMNSLRP EDTAVYYCTI GGSLSVSSQG TLVTVSSGGG GSGGGGSGGG   540
GSGGGGSGGG GSGGGGSSGG PGPAGLYAQP GSEVQLVESG GGLVQPGGSL RLSCAASGFT   600
FSSYTLAWVR QAPGKGLEWV AAIDSSSYTY SPDTVRGRFT ISRDNAKNSL YLQMNSLRAE   660
DTAVYYCARD SNWDALDYWG QGTTVTVSSS GGPGPAGLYA QPGSDIQMTQ SPSSLSASVG   720
DRVTITCKAR EKLWSAVAWY QQKPGKAPKS LIYSASFRYS GVPSRFSGSG SGTDFTLTIS   780
SLQPEDFATY YCQQYYTYPY TFGGGTKVEI K                                  811

SEQ ID NO: 401           moltype = AA  length = 811
FEATURE                  Location/Qualifiers
source                   1..811
                         mol_type = protein
                         organism = synthetic construct
SEQUENCE: 401
ELCDDDPPEI PHATFKAMAY KEGTMLNCEC KRGFRRIKSG SLYMLCTGNS SHSSWDNQCQ    60
CTSSATRNTT KQVTPQPEEQ KERKTTEMQS PMQPVDQASL PGHCREPPPW ENEATERIYH   120
FVVGQMVYYQ CVQGYRALHR GPAESVCKMT HGKTRWTQPQ LICTGEMETS QFPGEEKPQA   180
SPEGRPESET SSLVTTTDFQ IQTEMAATME TSIFTTEYQG GGGSGGGGSG GGGSGGGGSG   240
GGGSGGGGSS GGPGPAGLYA QPGSAPTSSS TKKTQLQLEH LLLDLQMILN GINNYKNPKL   300
TRMLTFKFYM PKKATELKHL QCLEEELKPL EEVLNLAQSK NFHLRPRDLI SNINVIVLEL   360
KGSETTFMCE YADETATIVE FLNRWITFCQ SIISTLTSGG PGPAGLYAQP GSEVQLVESG   420
GGLVQPGNSL RLSCAASGFT FSKFGMSWVR QAPGKGLEWV SSISGSGRDT LYAESVKGRF   480
TISRDNAKTT LYLQMNSLRP EDTAVYYCTI GGSLSVSSQG TLVTVSSGGG GSGGGGSGGG   540
GSGGGGSGGG GSGGGGSSGG PGPAGLYAQP GSEVQLVESG GGLVQPGGSL RLSCAASGFT   600
FSSYTLAWVR QAPGKGLEWV AAIDSSSYTY SPDTVRGRFT ISRDNAKNSL YLQMNSLRAE   660
DTAVYYCARD SNWDALDYWG QGTTVTVSSG GGSGGGGSGG GGSDIQMTQ SPSSLSASVG    720
DRVTITCKAR EKLWSAVAWY QQKPGKAPKS LIYSASFRYS GVPSRFSGSG SGTDFTLTIS   780
SLQPEDFATY YCQQYYTYPY TFGGGTKVEI K                                  811

SEQ ID NO: 402           moltype = AA  length = 811
FEATURE                  Location/Qualifiers
source                   1..811
                         mol_type = protein
                         organism = synthetic construct
SEQUENCE: 402
ELCDDDPPEI PHATFKAMAY KEGTMLNCEC KRGFRRIKSG SLYMLCTGNS SHSSWDNQCQ    60
CTSSATRNTT KQVTPQPEEQ KERKTTEMQS PMQPVDQASL PGHCREPPPW ENEATERIYH   120
FVVGQMVYYQ CVQGYRALHR GPAESVCKMT HGKTRWTQPQ LICTGEMETS QFPGEEKPQA   180
SPEGRPESET SSLVTTTDFQ IQTEMAATME TSIFTTEYQG GGGSGGGGSG GGGSGGGGSG   240
GGGSGGGGSS GGPGPAGLYA QPGSAPTSSS TKKTQLQLEH LLLDLQMILN GINNYKNPKL   300
TRMLTFKFYM PKKATELKHL QCLEEELKPL EEVLNLAQSK NFHLRPRDLI SNINVIVLEL   360
KGSETTFMCE YADETATIVE FLNRWITFCQ SIISTLTSGG PGPAGLYAQP GSEVQLVESG   420
GGLVQPGNSL RLSCAASGFT FSKFGMSWVR QAPGKGLEWV SSISGSGRDT LYAESVKGRF   480
TISRDNAKTT LYLQMNSLRP EDTAVYYCTI GGSLSVSSQG TLVTVSSGGG GSGGGGSGGG   540
GSGGGGSGGG GSGGGGSSGG PGPAGLYAQP GSEVQLVESG GGLVQPGGSL RLSCAASGFT   600
FSSYTLAWVR QAPGKGLEWV AAIDSSSYTY SPDTVRGRFT ISRDNAKNSL YLQMNSLRAE   660
DTAVYYCARD SNWDALDYWG QGTTVTVSSS GGPGPAGLYA QPGSDIQMTQ SPSSLSASVG   720
DRVTITCKVT EKVWGNVAWY QQKPGKAPIS LIYSPSLRKS GVPSRFSGSG SGTDFTLTIS   780
SLQPEDFATY YCQQYYTYPY TFGGGTKVEI K                                  811
```

| SEQ ID NO: 403 | moltype = AA length = 811 |
| --- | --- |
| FEATURE | Location/Qualifiers |
| source | 1..811 |
| | mol_type = protein |
| | organism = synthetic construct |

SEQUENCE: 403
```
ELCDDDPPEI PHATFKAMAY KEGTMLNCEC KRGFRRIKSG SLYMLCTGNS SHSSWDNQCQ    60
CTSSATRNTT KQVTPQPEEQ KERKTTEMQS PMQPVDQASL PGHCREPPPW ENEATERIYH   120
FVVGQMVYYQ CVQGYRALHR GPAESVCKMT HGKTRWTQPQ LICTGEMETS QFPGEEKPQA   180
SPEGRPESET SSLVTTTDFQ IQTEMAATME TSIFTTEYQG GGGSGGGGSG GGGSGGGGSG   240
GGGSGGGGSS GGPGPAGLYA QPGSAPTSSS TKKTQLQLEH LLLDLQMILN GINNYKNPKL   300
TRMLTFKFYM PKKATELKHL QCLEEELKPL EEVLNLAQSK NFHLRPRDLI SNINVIVLEL   360
KGSETTFMCE YADETATIVE FLNRWITFCQ SIISTLTSGG PGPAGLYAQP GSEVQLVESG   420
GGLVQPGNSL RLSCAASGFT FSKFGMSWVR QAPGKGLEWV SSISGSGRDT LYAESVKGRF   480
TISRDNAKTT LYLQMNSLRP EDTAVYYCTI GGSLSVSSQG TLVTVSSGGG GSGGGGSGGG   540
GSGGGGSGGG GSGGGGSSGG PGPAGLYAQP GSEVQLVESG GGLVQPGGSL RLSCAASGFT   600
FSSYTLAWVR QAPGKGLEWV AAIDSSSYTY SPDTVRGRFT ISRDNAKNSL YLQMNSLRAE   660
DTAVYYCARD SNWDALDYWG QGTTVTVSSG GGGSGGGGSG GGGSDIQMTQ SPSSLSASVG   720
DRVTITCKVT EKVWGNVAWY QQKPGKAPIS LIYSPSLRKS GVPSRFSGSG SGTDFTLTIS   780
SLQPEDFATY YCQQYYTYPY TFGGGTKVEI K                                 811
```

| SEQ ID NO: 404 | moltype = AA length = 691 |
| --- | --- |
| FEATURE | Location/Qualifiers |
| source | 1..691 |
| | mol_type = protein |
| | organism = synthetic construct |

SEQUENCE: 404
```
ELCDDDPPEI PHATFKAMAY KEGTMLNCEC KRGFRRIKSG SLYMLCTGNS SHSSWDNQCQ    60
CTSSATRNTT KQVTPQPEEQ KERKTTEMQS PMQPVDQASL PGHCREPPPW ENEATERIYH   120
FVVGQMVYYQ CVQGYRALHR GPAESVCKMT HGKTRWTQPQ LICTGEMETS QFPGEEKPQA   180
SPEGRPESET SSLVTTTDFQ IQTEMAATME TSIFTTEYQG GGGSGGGGSG GGGSGGGGSG   240
GGGSGGGGSS GGPGPAGLYA QPGSAPTSSS TKKTQLQLEH LLLDLQMILN GINNYKNPKL   300
TRMLTFKFYM PKKATELKHL QCLEEELKPL EEVLNLAQSK NFHLRPRDLI SNINVIVLEL   360
KGSETTFMCE YADETATIVE FLNRWITFCQ SIISTLTSGG PGPAGLYAQP GSEVQLVESG   420
GGLVQPGNSL RLSCAASGFT FSKFGMSWVR QAPGKGLEWV SSISGSGRDT LYAESVKGRF   480
TISRDNAKTT LYLQMNSLRP EDTAVYYCTI GGSLSVSSQG TLVTVSSGGG GSGGGGSGGG   540
GSGGGGSGGG GSGGGGSSGG PGPAGLYAQP GSEVQLLESG GGLVQPGGSL RLSCAASGSI   600
FSANAMGWYR QAPGKGLELV AVISSGGSTN YADSVKGRFT ISRDNSKNTV YLQMNSLRAE   660
DTAVYYCMYS GSYYYTPNDY WGQGTLVTVS S                                 691
```

| SEQ ID NO: 405 | moltype = AA length = 690 |
| --- | --- |
| FEATURE | Location/Qualifiers |
| source | 1..690 |
| | mol_type = protein |
| | organism = synthetic construct |

SEQUENCE: 405
```
ELCDDDPPEI PHATFKAMAY KEGTMLNCEC KRGFRRIKSG SLYMLCTGNS SHSSWDNQCQ    60
CTSSATRNTT KQVTPQPEEQ KERKTTEMQS PMQPVDQASL PGHCREPPPW ENEATERIYH   120
FVVGQMVYYQ CVQGYRALHR GPAESVCKMT HGKTRWTQPQ LICTGEMETS QFPGEEKPQA   180
SPEGRPESET SSLVTTTDFQ IQTEMAATME TSIFTTEYQG GGGSGGGGSG GGGSGGGGSG   240
GGGSGGGGSS GGPGPAGLYA QPGSAPTSSS TKKTQLQLEH LLLDLQMILN GINNYKNPKL   300
TRMLTFKFYM PKKATELKHL QCLEEELKPL EEVLNLAQSK NFHLRPRDLI SNINVIVLEL   360
KGSETTFMCE YADETATIVE FLNRWITFCQ SIISTLTSGG PGPAGLYAQP GSEVQLVESG   420
GGLVQPGNSL RLSCAASGFT FSKFGMSWVR QAPGKGLEWV SSISGSGRDT LYAESVKGRF   480
TISRDNAKTT LYLQMNSLRP EDTAVYYCTI GGSLSVSSQG TLVTVSSGGG GSGGGGSGGG   540
GSGGGGSGGG GSGGGGSSGG PGPAGLYAQP GSEVQLLESG GGLVQPGGSL RLSCAASERI   600
FSTDVMGWYR QAPGKQRELV AVVSARGTTN YLDAVKGRFT ISRDNSKNTL YLQMNSLRAE   660
DTAVYYCYVR ETTSPWRIYW GQGTLVTVSS                                   690
```

| SEQ ID NO: 406 | moltype = AA length = 661 |
| --- | --- |
| FEATURE | Location/Qualifiers |
| source | 1..661 |
| | mol_type = protein |
| | organism = synthetic construct |

SEQUENCE: 406
```
ESKYGPPCPP CPAPEFLGGP SVFLFPPKPK DTLMISRTPE VTCVVVDVSQ EDPEVQFNWY    60
VDGVEVHNAK TKPREEQFNS TYRVVSVLTV LHQDWLNGKE YKCKVSNKGL PSSIEKTISK   120
AKGQPREPQV YTLPPSQEEM TKNQVSLTCL VKGFYPSDIA VEWESNGQPE NNYKTTPPVL   180
DSDGSFFLYS RLTVDKSRWQ EGNVFSCSVM HEALHNHYTQ KSLSLSLGKS GGPGPAGLYA   240
QPGSAPTSSS TKKTQLQLEH LLLDLQMILN GINNYKNPKL TRMLTFKFYM PKKATELKHL   300
QCLEEELKPL EEVLNLAQSK NFHLRPRDLI SNINVIVLEL KGSETTFMCE YADETATIVE   360
FLNRWITFCQ SIISTLTGGG GSGGGGSGGG GSGGGGSSGG PGPAGLYAQP             420
GSEVQLVESG GGLVQPGGSL RLSCAASGFT FSSYTLAWVR QAPGKGLEWV AAIDSSSYTY   480
SPDTVRGRFT ISRDNAKNSL YLQMNSLRAE DTAVYYCARD SNWDALDYWG QGTTVTVSSS   540
GGPGPAGLYA QPGSDIQMTQ SPSSLSASVG DRVTITCKAR EKLWSAVAWY QQKPGKAPKS   600
LIYSASFRYS GVPSRFSGSG SGTDFTLTIS SLQPEDFATY YCQQYYTYPY TFGGGTKVEI   660
K                                                                 661
```

| SEQ ID NO: 407 | moltype = AA length = 661 |
| --- | --- |

```
FEATURE                 Location/Qualifiers
source                  1..661
                        mol_type = protein
                        organism = synthetic construct
SEQUENCE: 407
ESKYGPPCPP  CPAPEFLGGP  SVFLFPPKPK  DTLMISRTPE  VTCVVVDVSQ  EDPEVQFNWY   60
VDGVEVHNAK  TKPREEQFNS  TYRVVSVLTV  LHQDWLNGKE  YKCKVSNKGL  PSSIEKTISK  120
AKGQPREPQV  YTLPPSQEEM  TKNQVSLTCL  VKGFYPSDIA  VEWESNGQPE  NNYKTTPPVL  180
DSDGSFFLYS  RLTVDKSRWQ  EGNVFSCSVM  HEALHNHYTQ  KSLSLSLGKS  GGPGPAGLYA  240
QPGSAPTSSS  TKKTQLQLEH  LLLDLQMILN  GINNYKNPKL  TRMLTFKFYM  PKKATELKHL  300
QCLEEELKPL  EEVLNLAQSK  NFHLRPRDLI  SNINVIVLEL  KGSETTFMCE  YADETATIVE  360
FLNRWITFCQ  SIISTLTGGG  GSGGGGSGGG  GSGGGGSGGG  GSGGGGSSGG  PGPAGLYAQP  420
GSEVQLVESG  GGLVQPGGSL  RLSCAASGFT  FSSYTLAWVR  QAPGKGLEWV  AAIDSSSYTY  480
SPDTVRGRFT  ISRDNAKNSL  YLQMNSLRAE  DTAVYYCARD  SNWDALDYWG  QGTTVTVSSG  540
GGGSGGGGSG  GGGSDIQMTQ  SPSSLSASVG  DRVTITCKAR  EKLWSAVAWY  QQKPGKAPKS  600
LIYSASFRYS  GVPSRFSGSG  SGTDFTLTIS  SLQPEDFATY  YCQQYYTYPY  TFGGGTKVEI  660
K                                                                      661

SEQ ID NO: 408          moltype = AA  length = 661
FEATURE                 Location/Qualifiers
source                  1..661
                        mol_type = protein
                        organism = synthetic construct
SEQUENCE: 408
ESKYGPPCPP  CPAPEFLGGP  SVFLFPPKPK  DTLMISRTPE  VTCVVVDVSQ  EDPEVQFNWY   60
VDGVEVHNAK  TKPREEQFNS  TYRVVSVLTV  LHQDWLNGKE  YKCKVSNKGL  PSSIEKTISK  120
AKGQPREPQV  YTLPPSQEEM  TKNQVSLTCL  VKGFYPSDIA  VEWESNGQPE  NNYKTTPPVL  180
DSDGSFFLYS  RLTVDKSRWQ  EGNVFSCSVM  HEALHNHYTQ  KSLSLSLGKS  GGPGPAGLYA  240
QPGSAPTSSS  TKKTQLQLEH  LLLDLQMILN  GINNYKNPKL  TRMLTFKFYM  PKKATELKHL  300
QCLEEELKPL  EEVLNLAQSK  NFHLRPRDLI  SNINVIVLEL  KGSETTFMCE  YADETATIVE  360
FLNRWITFCQ  SIISTLTGGG  GSGGGGSGGG  GSGGGGSGGG  GSGGGGSSGG  PGPAGLYAQP  420
GSEVQLVESG  GGLVQPGGSL  RLSCAASGFT  FSSYTLAWVR  QAPGKGLEWV  AAIDSSSYTY  480
SPDTVRGRFT  ISRDNAKNSL  YLQMNSLRAE  DTAVYYCARD  SNWDALDYWG  QGTTVTVSSS  540
GGPGPAGLYA  QPGSDIQMTQ  SPSSLSASVG  DRVTITCKVT  EKVWGNVAWY  QQKPGKAPIS  600
LIYSPSLRKS  GVPSRFSGSG  SGTDFTLTIS  SLQPEDFATY  YCQQYYTYPY  TFGGGTKVEI  660
K                                                                      661

SEQ ID NO: 409          moltype = AA  length = 661
FEATURE                 Location/Qualifiers
source                  1..661
                        mol_type = protein
                        organism = synthetic construct
SEQUENCE: 409
ESKYGPPCPP  CPAPEFLGGP  SVFLFPPKPK  DTLMISRTPE  VTCVVVDVSQ  EDPEVQFNWY   60
VDGVEVHNAK  TKPREEQFNS  TYRVVSVLTV  LHQDWLNGKE  YKCKVSNKGL  PSSIEKTISK  120
AKGQPREPQV  YTLPPSQEEM  TKNQVSLTCL  VKGFYPSDIA  VEWESNGQPE  NNYKTTPPVL  180
DSDGSFFLYS  RLTVDKSRWQ  EGNVFSCSVM  HEALHNHYTQ  KSLSLSLGKS  GGPGPAGLYA  240
QPGSAPTSSS  TKKTQLQLEH  LLLDLQMILN  GINNYKNPKL  TRMLTFKFYM  PKKATELKHL  300
QCLEEELKPL  EEVLNLAQSK  NFHLRPRDLI  SNINVIVLEL  KGSETTFMCE  YADETATIVE  360
FLNRWITFCQ  SIISTLTGGG  GSGGGGSGGG  GSGGGGSGGG  GSGGGGSSGG  PGPAGLYAQP  420
GSEVQLVESG  GGLVQPGGSL  RLSCAASGFT  FSSYTLAWVR  QAPGKGLEWV  AAIDSSSYTY  480
SPDTVRGRFT  ISRDNAKNSL  YLQMNSLRAE  DTAVYYCARD  SNWDALDYWG  QGTTVTVSSG  540
GGGSGGGGSG  GGGSDIQMTQ  SPSSLSASVG  DRVTITCKVT  EKVWGNVAWY  QQKPGKAPIS  600
LIYSPSLRKS  GVPSRFSGSG  SGTDFTLTIS  SLQPEDFATY  YCQQYYTYPY  TFGGGTKVEI  660
K                                                                      661

SEQ ID NO: 410          moltype = AA  length = 541
FEATURE                 Location/Qualifiers
source                  1..541
                        mol_type = protein
                        organism = synthetic construct
SEQUENCE: 410
ESKYGPPCPP  CPAPEFLGGP  SVFLFPPKPK  DTLMISRTPE  VTCVVVDVSQ  EDPEVQFNWY   60
VDGVEVHNAK  TKPREEQFNS  TYRVVSVLTV  LHQDWLNGKE  YKCKVSNKGL  PSSIEKTISK  120
AKGQPREPQV  YTLPPSQEEM  TKNQVSLTCL  VKGFYPSDIA  VEWESNGQPE  NNYKTTPPVL  180
DSDGSFFLYS  RLTVDKSRWQ  EGNVFSCSVM  HEALHNHYTQ  KSLSLSLGKS  GGPGPAGLYA  240
QPGSAPTSSS  TKKTQLQLEH  LLLDLQMILN  GINNYKNPKL  TRMLTFKFYM  PKKATELKHL  300
QCLEEELKPL  EEVLNLAQSK  NFHLRPRDLI  SNINVIVLEL  KGSETTFMCE  YADETATIVE  360
FLNRWITFCQ  SIISTLTGGG  GSGGGGSGGG  GSGGGGSGGG  GSGGGGSSGG  PGPAGLYAQP  420
GSEVQLLESG  GGLVQPGGSL  RLSCAASGSI  FSANAMGWYR  QAPGKGLELV  AVISSGGSTN  480
YADSVKGRFT  ISRDNSKNTV  YLQMNSLRAE  DTAVYYCMYS  GSYYYTPNDY  WGQGTLVTVS  540
S                                                                      541

SEQ ID NO: 411          moltype = AA  length = 540
FEATURE                 Location/Qualifiers
source                  1..540
                        mol_type = protein
                        organism = synthetic construct
SEQUENCE: 411
```

```
ESKYGPPCPP CPAPEFLGGP SVFLFPPKPK DTLMISRTPE VTCVVVDVSQ EDPEVQFNWY   60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGKS GGPGPAGLYA  240
QPGSAPTSSS TKKTQLQLEH LLLDLQMILN GINNYKNPKL TRMLTFKFYM PKKATELKHL  300
QCLEEELKPL EEVLNLAQSK NFHLRPRDLI SNINIVIVLEL KGSETTFMCE YADETATIVE  360
FLNRWITFCQ SIISTLTGGG GSGGGGSGGG GSGGGGSGGG GSGGGGSGG PGPAGLYAQP  420
GSEVQLLESG GGLVQPGGSL RLSCAASERI FSTDVMGWYR QAPGKQRELV AVVSARGTTN  480
YLDAVKGRFT ISRDNSKNTL YLQMNSLRAE DTAVYYCYVR ETTSPWRIYW GQGTLVTVSS  540

SEQ ID NO: 412           moltype = AA   length = 925
FEATURE                  Location/Qualifiers
source                   1..925
                         mol_type = protein
                         organism = synthetic construct
SEQUENCE: 412
ESKYGPPCPP CPAPEFLGGP SVFLFPPKPK DTLMISRTPE VTCVVVDVSQ EDPEVQFNWY   60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGKS GGPGPAGLYA  240
QPGSELCDDD PPEIPHATFK AMAYKEGTML NCECKRGFRR IKSGSLYMLC TGNSSHSSWD  300
NQCQCTSSAT RNTTKQVTPQ PEEQKERKTT EMQSPMQPVD QASLPGHCRE PPPWENEATE  360
RIYHFVVGQM VYYQCVQGYR ALHRGPAESV CKMTHGKTRW TQPQLICTGE METSQFPGEE  420
KPQASPEGRP ESETSSLVTT TDFQIQTEMA ATMETSIFTT EYQGGGGSGG GGSGGGGSGG  480
GGSGGGGSGG GGSSGGPGPA GLYAQPGSAP TSSSTKKTQL QLEHLLLDLQ MILNGINNYK  540
NPKLTRMLTF KFYMPKKATE LKHLQCLEEE LKPLEEVLNL AQSKNFHLRP RDLISNINVI  600
VLELKGSETT FMCEYADETA TIVEFLNRWI TFCQSIISTL TGGGGSGGGG SGGGGSGGGG  660
SGGGGSGGGG SSGGPGPAGL YAQPGSEVQL VESGGGLVQP GGSLRLSCAA SGFTFSSYTL  720
AWVRQAPGKG LEWVAAIDSS SYTYSPDTVR GRFTISRDNA KNSLYLQMNS LRAEDTAVYY  780
CARDSNWDAL DYWGQGTTVT VSSSGGPGPA GLYAQPGSDI QMTQSPSSLS ASVGDRVTIT  840
CKAREKLWSA VAWYQQKPGK APKSLIYSAS FRYSGVPSRF SGSGSGTDFT LTISSLQPED  900
FATYYCQQYY TYPYTFGGGT KVEIK                                      925

SEQ ID NO: 413           moltype = AA   length = 925
FEATURE                  Location/Qualifiers
source                   1..925
                         mol_type = protein
                         organism = synthetic construct
SEQUENCE: 413
ESKYGPPCPP CPAPEFLGGP SVFLFPPKPK DTLMISRTPE VTCVVVDVSQ EDPEVQFNWY   60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGKS GGPGPAGLYA  240
QPGSELCDDD PPEIPHATFK AMAYKEGTML NCECKRGFRR IKSGSLYMLC TGNSSHSSWD  300
NQCQCTSSAT RNTTKQVTPQ PEEQKERKTT EMQSPMQPVD QASLPGHCRE PPPWENEATE  360
RIYHFVVGQM VYYQCVQGYR ALHRGPAESV CKMTHGKTRW TQPQLICTGE METSQFPGEE  420
KPQASPEGRP ESETSSLVTT TDFQIQTEMA ATMETSIFTT EYQGGGGSGG GGSGGGGSGG  480
GGSGGGGSGG GGSSGGPGPA GLYAQPGSAP TSSSTKKTQL QLEHLLLDLQ MILNGINNYK  540
NPKLTRMLTF KFYMPKKATE LKHLQCLEEE LKPLEEVLNL AQSKNFHLRP RDLISNINVI  600
VLELKGSETT FMCEYADETA TIVEFLNRWI TFCQSIISTL TGGGGSGGGG SGGGGSGGGG  660
SGGGGSGGGG SSGGPGPAGL YAQPGSEVQL VESGGGLVQP GGSLRLSCAA SGFTFSSYTL  720
AWVRQAPGKG LEWVAAIDSS SYTYSPDTVR GRFTISRDNA KNSLYLQMNS LRAEDTAVYY  780
CARDSNWDAL DYWGQGTTVT VSSSGGGGSGG GGSGGGGSDI QMTQSPSSLS ASVGDRVTIT  840
CKAREKLWSA VAWYQQKPGK APKSLIYSAS FRYSGVPSRF SGSGSGTDFT LTISSLQPED  900
FATYYCQQYY TYPYTFGGGT KVEIK                                      925

SEQ ID NO: 414           moltype = AA   length = 925
FEATURE                  Location/Qualifiers
source                   1..925
                         mol_type = protein
                         organism = synthetic construct
SEQUENCE: 414
ESKYGPPCPP CPAPEFLGGP SVFLFPPKPK DTLMISRTPE VTCVVVDVSQ EDPEVQFNWY   60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGKS GGPGPAGLYA  240
QPGSELCDDD PPEIPHATFK AMAYKEGTML NCECKRGFRR IKSGSLYMLC TGNSSHSSWD  300
NQCQCTSSAT RNTTKQVTPQ PEEQKERKTT EMQSPMQPVD QASLPGHCRE PPPWENEATE  360
RIYHFVVGQM VYYQCVQGYR ALHRGPAESV CKMTHGKTRW TQPQLICTGE METSQFPGEE  420
KPQASPEGRP ESETSSLVTT TDFQIQTEMA ATMETSIFTT EYQGGGGSGG GGSGGGGSGG  480
GGSGGGGSGG GGSSGGPGPA GLYAQPGSAP TSSSTKKTQL QLEHLLLDLQ MILNGINNYK  540
NPKLTRMLTF KFYMPKKATE LKHLQCLEEE LKPLEEVLNL AQSKNFHLRP RDLISNINVI  600
VLELKGSETT FMCEYADETA TIVEFLNRWI TFCQSIISTL TGGGGSGGGG SGGGGSGGGG  660
SGGGGSGGGG SSGGPGPAGL YAQPGSEVQL VESGGGLVQP GGSLRLSCAA SGFTFSSYTL  720
AWVRQAPGKG LEWVAAIDSS SYTYSPDTVR GRFTISRDNA KNSLYLQMNS LRAEDTAVYY  780
CARDSNWDAL DYWGQGTTVT VSSSGGPGPA GLYAQPGSDI QMTQSPSSLS ASVGDRVTIT  840
CKVTEKVWGN VAWYQQKPGK APISLIYSPS LRKSGVPSRF SGSGSGTDFT LTISSLQPED  900
FATYYCQQYY TYPYTFGGGT KVEIK                                      925
```

```
SEQ ID NO: 415            moltype = AA  length = 925
FEATURE                   Location/Qualifiers
source                    1..925
                          mol_type = protein
                          organism = synthetic construct
SEQUENCE: 415
ESKYGPPCPP CPAPEFLGGP SVFLFPPKPK DTLMISRTPE VTCVVVDVSQ EDPEVQFNWY  60
VDGVEVHNAK TKPREEQFNS TYRVVSVLTV LHQDWLNGKE YKCKVSNKGL PSSIEKTISK 120
AKGQPREPQV YTLPPSQEEM TKNQVSLTCL VKGFYPSDIA VEWESNGQPE NNYKTTPPVL 180
DSDGSFFLYS RLTVDKSRWQ EGNVFSCSVM HEALHNHYTQ KSLSLSLGKS GGPGPAGLYA 240
QPGSELCDDD PPEIPHATFK AMAYKEGTML NCECKRGFRR IKSGSLYMLC TGNSSHSSWD 300
NQCQCTSSAT RNTTKQVTPQ PEEQKERKTT EMQSPMQPVD QASLPGHCRE PPPWENEATE 360
RIYHFVVGQM VYYQCVQGYR ALHRGPAESV CKMTHGKTRW TQPQLICTGE METSQFPGEE 420
KPQASPEGRP ESETSSLVTT TDFQIQTEMA ATMETSIFTT EYQGGGGSGG GGSGGGGSGG 480
GGSGGGGSGG GGSSGGPGPA GLYAQPGSAP TSSSTKKTQL QLEHLLLDLQ MILNGINNYK 540
NPKLTRMLTF KFYMPKKATE LKHLQCLEEE LKPLEEVLNL AQSKNFHLRP RDLISNINVI 600
VLELKGSETT FMCEYADETA TIVEFLNRWI TFCQSIISTL TGGGGSGGGG SGGGGSGGGG 660
SGGGGSGGGG SSGGPGPAGL YAQPGSEVQL VESGGGLVQP GGSLRLSCAA SGFTFSSYTL 720
AWVRQAPGKG LEWVAAIDSS SYTYSPDTVR GRFTISRDNA KNSLYLQMNS LRAEDTAVYY 780
CARDSNWDAL DYWGQGTTVT VSSGGGGSGG GGSGGGGSDI QMTQSPSSLS ASVGDRVTIT 840
CKVTEKVWGN VAWYQQKPGK APISLIYSPS LRKSGVPSRF SGSGSGTDFT LTISSLQPED 900
FATYYCQQYY TYPYTFGGGT KVEIK                                     925

SEQ ID NO: 416            moltype = AA  length = 805
FEATURE                   Location/Qualifiers
source                    1..805
                          mol_type = protein
                          organism = synthetic construct
SEQUENCE: 416
ESKYGPPCPP CPAPEFLGGP SVFLFPPKPK DTLMISRTPE VTCVVVDVSQ EDPEVQFNWY  60
VDGVEVHNAK TKPREEQFNS TYRVVSVLTV LHQDWLNGKE YKCKVSNKGL PSSIEKTISK 120
AKGQPREPQV YTLPPSQEEM TKNQVSLTCL VKGFYPSDIA VEWESNGQPE NNYKTTPPVL 180
DSDGSFFLYS RLTVDKSRWQ EGNVFSCSVM HEALHNHYTQ KSLSLSLGKS GGPGPAGLYA 240
QPGSELCDDD PPEIPHATFK AMAYKEGTML NCECKRGFRR IKSGSLYMLC TGNSSHSSWD 300
NQCQCTSSAT RNTTKQVTPQ PEEQKERKTT EMQSPMQPVD QASLPGHCRE PPPWENEATE 360
RIYHFVVGQM VYYQCVQGYR ALHRGPAESV CKMTHGKTRW TQPQLICTGE METSQFPGEE 420
KPQASPEGRP ESETSSLVTT TDFQIQTEMA ATMETSIFTT EYQGGGGSGG GGSGGGGSGG 480
GGSGGGGSGG GGSSGGPGPA GLYAQPGSAP TSSSTKKTQL QLEHLLLDLQ MILNGINNYK 540
NPKLTRMLTF KFYMPKKATE LKHLQCLEEE LKPLEEVLNL AQSKNFHLRP RDLISNINVI 600
VLELKGSETT FMCEYADETA TIVEFLNRWI TFCQSIISTL TGGGGSGGGG SGGGGSGGGG 660
SGGGGSGGGG SSGGPGPAGL YAQPGSEVQL LESGGGLVQP GGSLRLSCAA SGSIFSANAM 720
GWYRQAPGKG LELVAVISSG GSTNYADSVK GRFTISRDNS KNTVYLQMNS LRAEDTAVYY 780
CMYSGSYYYT PNDYWGQGTL VTVSS                                     805

SEQ ID NO: 417            moltype = AA  length = 804
FEATURE                   Location/Qualifiers
source                    1..804
                          mol_type = protein
                          organism = synthetic construct
SEQUENCE: 417
ESKYGPPCPP CPAPEFLGGP SVFLFPPKPK DTLMISRTPE VTCVVVDVSQ EDPEVQFNWY  60
VDGVEVHNAK TKPREEQFNS TYRVVSVLTV LHQDWLNGKE YKCKVSNKGL PSSIEKTISK 120
AKGQPREPQV YTLPPSQEEM TKNQVSLTCL VKGFYPSDIA VEWESNGQPE NNYKTTPPVL 180
DSDGSFFLYS RLTVDKSRWQ EGNVFSCSVM HEALHNHYTQ KSLSLSLGKS GGPGPAGLYA 240
QPGSELCDDD PPEIPHATFK AMAYKEGTML NCECKRGFRR IKSGSLYMLC TGNSSHSSWD 300
NQCQCTSSAT RNTTKQVTPQ PEEQKERKTT EMQSPMQPVD QASLPGHCRE PPPWENEATE 360
RIYHFVVGQM VYYQCVQGYR ALHRGPAESV CKMTHGKTRW TQPQLICTGE METSQFPGEE 420
KPQASPEGRP ESETSSLVTT TDFQIQTEMA ATMETSIFTT EYQGGGGSGG GGSGGGGSGG 480
GGSGGGGSGG GGSSGGPGPA GLYAQPGSAP TSSSTKKTQL QLEHLLLDLQ MILNGINNYK 540
NPKLTRMLTF KFYMPKKATE LKHLQCLEEE LKPLEEVLNL AQSKNFHLRP RDLISNINVI 600
VLELKGSETT FMCEYADETA TIVEFLNRWI TFCQSIISTL TGGGGSGGGG SGGGGSGGGG 660
SGGGGSGGGG SSGGPGPAGL YAQPGSEVQL LESGGGLVQP GGSLRLSCAA SERIFSTDVM 720
GWYRQAPGKQ RELVAVVSAR GTTNYLDAVK GRFTISRDNS KNTLYLQMNS LRAEDTAVYY 780
CYVRETTSPW RIYWGQGTLV TVSS                                      804

SEQ ID NO: 418            moltype = AA  length = 245
FEATURE                   Location/Qualifiers
source                    1..245
                          mol_type = protein
                          organism = synthetic construct
SEQUENCE: 418
EVQLVESGGG LVQPGGSLRL SCAASGFTFS SYTLAWVRQA PGKGLEWVAA IDSSSYTYSP  60
DTVRGRFTIS RDNAKNSLYL QMNSLRAEDT AVYYCARDSN WDALDYWGQG TTVTVSSGGG 120
GSGGGGSGGG GSDIQMTQSP SSLSASVGDR VTITCKASQN VGTNVGWYQQ KPGKAPKSLI 180
YSASFRYSGV PSRFSGSGSG TDFTLTISSL QPEDFATYYC QQYYTYPYTF GGGTKVEIKH 240
HHHHH                                                           245

SEQ ID NO: 419            moltype = AA  length = 245
FEATURE                   Location/Qualifiers
```

```
source                   1..245
                         mol_type = protein
                         organism = synthetic construct
SEQUENCE: 419
EVQLVESGGG LVQPGGSLRL SCAASGFTFS SYTLAWVRQA PGKGLEWVAA IDSSSYTYSP    60
DTVRGRFTIS RDNAKNSLYL QMNSLRAEDT AVYYCARDSN WDALDYWGQG TTVTVSSSGG   120
PGPAGLYAQP GSDIQMTQSP SSLSASVGDR VTITCKASQN VGTNVGWYQQ KPGKAPKALI   180
YSASFRYSGV PSRFSGSGSG TDFTLTISSL QPEDFATYYC QQYYTYPYTF GGGTKVEIKH   240
HHHHH                                                               245

SEQ ID NO: 420           moltype = AA  length = 245
FEATURE                  Location/Qualifiers
source                   1..245
                         mol_type = protein
                         organism = synthetic construct
SEQUENCE: 420
EVQLVESGGG LVQPGGSLRL SCAASGFTFS SYTLAWVRQA PGKGLEWVAA IDSSSYTYSP    60
DTVRGRFTIS RDNAKNSLYL QMNSLRAEDT AVYYCARDSN WDALDYWGQG TTVTVSSSGG   120
PGPAGLYAQP GSDIQMTQSP SSLSASVGDR VTITCKASQN VGTNVGWYQQ KPGKAPKSLI   180
YSASFRYSGV PSRFSGSGSG TDFTLTISSL QPEDFATYYC QQYYTYPYTF GGGTKVEIKH   240
HHHHH                                                               245

SEQ ID NO: 421           moltype = AA  length = 612
FEATURE                  Location/Qualifiers
source                   1..612
                         mol_type = protein
                         organism = synthetic construct
SEQUENCE: 421
LVEEPKNLVK TNCDLYEKLG EYGFQNAILV RYTQKAPQVS TPTLVEAARN LGRVGTKCCT    60
LPEDQRLPCV EDYLSAILNR VCLLHEKTPV SEHVTKCCSG SLVERRPCFS ALTVDETYVP   120
KEFKAETFTF HSDICTLPEK EKQIKKQTAL AELVKHKPKA TAEQLKTVMD DFAQFLDTCC   180
KAADKDTCFS TEGPNLVTRC KDALASGGPG PAGMKGLPGS CDLPQTHNLR NKRALTLLVQ   240
MRRLSPLSCL KDRKDFGFPQ EKVDAQQIKK AQAIPVLSEL TQQILNIFTS KDSSAAWNTT   300
LLDSFCNDLH QQLNDLQGCL MQQVGVQEFP LTQEDALAVR KYFHRITVY LREKKHSPCA    360
WEVVRAEVWR ALSSSANVLG RLREEKSGGP GPAGMKGLPG SLVEEPKNLV KTNCDLYEKL   420
GEYGFQNAIL VRYTQKAPQV STPTLVEAAR NLGRVGTKCC TLPEDQRLPC VEDYLSAILN   480
RVCLLHEKTP VSEHVTKCCS GSLVERRPCF SALTVDETYV PKEFKAETFT FHSDICTLPE   540
KEKQIKKQTA LAELVKHKPK ATAEQLKTVM DDFAQFLDTC CKAADKDTCF STEGPNLVTR   600
CKDALAHHHH HH                                                       612

SEQ ID NO: 422           moltype = AA  length = 1030
FEATURE                  Location/Qualifiers
source                   1..1030
                         mol_type = protein
                         organism = synthetic construct
SEQUENCE: 422
EAHKSEIAHR YNDLGEQHFK GLVLIAFSQY LQKCSYDEHA KLVQEVTDFA KTCVADESAA    60
NCDKSLHTLF GDKLCAIPNL RENYGELADC CTKQEPERNE CFLQHKDDNP SLPPFERPEA   120
EAMCTSFKEN PTTFMGHYLH EVARRHPYFY APELLYYAEQ YNEILTQCCA EADKESCLTP   180
KLDGVKEKAL VSSVRQGGGG SGGGGSGGSL VEEPKNLVKT NCDLYEKLGE YGFQNAILVR   240
YTQKAPQVST PTLVEAARNL GRVGTKCCTL PEDQRLPCVE DYLSAILNRV CLLHEKTPVS   300
EHVTKCCSGS LVERRPCFSA LTVDETYVPK EFKAETFTFH SDICTLPEKE KQIKKQTALA   360
ELVKHKPKAT AEQLKTVMDD FAQFLDTCCK AADKDTCFST EGPNLVTRCK DALASGGPGP   420
AGMKGLPGSC DLPQTHNLRN KRALTLLVQM RRLSPLSCLK DRKDFGFPQE KVDAQQIKKA   480
QAIPVLSELT QQILNIFTSK DSSAAWNTTL LDSFCNDLHQ QLNDLQGCLM QQVGVQEFPL   540
TQEDALLAVR KYFHRITVYL REKKHSPCAW EVVRAEVWRA LSSSANVLGR LREEKSGGPG   600
PAGMKGLPGS EAHKSEIAHR YNDLGEQHFK GLVLIAFSQY LQKCSYDEHA KLVQEVTDFA   660
KTCVADESAA NCDKSLHTLF GDKLCAIPNL RENYGELADC CTKQEPERNE CFLQHKDDNP   720
SLPPFERPEA EAMCTSFKEN PTTFMGHYLH EVARRHPYFY APELLYYAEQ YNEILTQCCA   780
EADKESCLTP KLDGVKEKAL VSSVRQGGGG SGGGGSGGSL VEEPKNLVKT NCDLYEKLGE   840
YGFQNAILVR YTQKAPQVST PTLVEAARNL GRVGTKCCTL PEDQRLPCVE DYLSAILNRV   900
CLLHEKTPVS EHVTKCCSGS LVERRPCFSA LTVDETYVPK EFKAETFTFH SDICTLPEKE   960
KQIKKQTALA ELVKHKPKAT AEQLKTVMDD FAQFLDTCCK AADKDTCFST EGPNLVTRCK  1020
DALAHHHHHH                                                         1030

SEQ ID NO: 423           moltype = AA  length = 466
FEATURE                  Location/Qualifiers
source                   1..466
                         mol_type = protein
                         organism = synthetic construct
SEQUENCE: 423
EVQLVESGGG LVQPGNSLRL SCAASGFTFS KFGMSWVRQA PGKGLEWVSS ISGSGRDTLY    60
AESVKGRFTI SRDNAKTTLY LQMNSLRPED TAVYYCTIGG SLSVSSQGTL VTVSSGGGGS   120
GGGSGGPGPA GMKGLPGSGG GGSGGGSCDL PQTHNLRNKR ALTLLVQMRR LSPLSCLKDR   180
KDFGFPQEKV DAQQIKKAQA IPVLSELTQQ ILNIFTSKDS SAAWNTTLLD SFCNDLHQQL   240
NDLQGCLMQQ VGVQEFPLTQ EDALLAVRKY FHRITVYLRE KKHSPCAWEV VRAEVWRALS   300
SSANVLGRLR EEKGGGGSGG GSGGPGPAGM KGLPGSGGGG SGGGSEVQLV ESGGGLVQPG   360
NSLRLSCAAS GFTFSKFGMS WVRQAPGKGL EWVSSISGSG RDTLYAESVK GRFTISRDNA   420
KTTLYLQMNS LRPEDTAVYY CTIGGSLSVS SQGTLVTVSS HHHHHH                 466
```

```
SEQ ID NO: 424          moltype = AA  length = 426
FEATURE                 Location/Qualifiers
source                  1..426
                        mol_type = protein
                        organism = synthetic construct
SEQUENCE: 424
EVQLVESGGG LVQPGNSLRL SCAASGFTFS KFGMSWVRQA PGKGLEWVSS ISGSGRDTLY    60
AESVKGRFTI SRDNAKTTLY LQMNSLRPED TAVYYCTIGG SLSVSSQGTL VTVSSSGGPG   120
PAGLYAQPGS CDLPQTHNLR NKRALTLLVQ MRRLSPLSCL KDRKDFGFPQ EKVDAQQIKK   180
AQAIPVLSEL TQQILNIFTS KDSSAAWNTT LLDSFCNDLH QQLNDLQGCL MQQVGVQEFP   240
LTQEDALLAV RKYFHRITVY LREKKHSPCA WEVVRAEVWR ALSSSANVLG RLREEKSGGP   300
GPAGLYAQPG SEVQLVESGG GLVQPGNSLR LSCAASGFTF SKFGMSWVRQ APGKGLEWVS   360
SISGSGRDTL YAESVKGRFT ISRDNAKTTL YLQMNSLRPE DTAVYYCTIG GSLSVSSQGT   420
LVTVSS                                                              426

SEQ ID NO: 425          moltype = AA  length = 426
FEATURE                 Location/Qualifiers
source                  1..426
                        mol_type = protein
                        organism = synthetic construct
SEQUENCE: 425
EVQLVESGGG LVQPGNSLRL SCAASGFTFS KFGMSWVRQA PGKGLEWVSS ISGSGRDTLY    60
AESVKGRFTI SRDNAKTTLY LQMNSLRPED TAVYYCTIGG SLSVSSQGTL VTVSSSGGPA   120
LFKSSFPPGS CDLPQTHNLR NKRALTLLVQ MRRLSPLSCL KDRKDFGFPQ EKVDAQQIKK   180
AQAIPVLSEL TQQILNIFTS KDSSAAWNTT LLDSFCNDLH QQLNDLQGCL MQQVGVQEFP   240
LTQEDALLAV RKYFHRITVY LREKKHSPCA WEVVRAEVWR ALSSSANVLG RLREEKSGGP   300
ALFKSSFPPG SEVQLVESGG GLVQPGNSLR LSCAASGFTF SKFGMSWVRQ APGKGLEWVS   360
SISGSGRDTL YAESVKGRFT ISRDNAKTTL YLQMNSLRPE DTAVYYCTIG GSLSVSSQGT   420
LVTVSS                                                              426

SEQ ID NO: 426          moltype = AA  length = 428
FEATURE                 Location/Qualifiers
source                  1..428
                        mol_type = protein
                        organism = synthetic construct
SEQUENCE: 426
EVQLVESGGG LVQPGNSLRL SCAASGFTFS KFGMSWVRQA PGKGLEWVSS ISGSGRDTLY    60
AESVKGRFTI SRDNAKTTLY LQMNSLRPED TAVYYCTIGG SLSVSSQGTL VTVSSSGGPP   120
LAQKLKSSPG SCDLPQTHNL RNKRALTLLV QMRRLSPLSC LKDRKDFGFP QEKVDAQQIK   180
KAQAIPVLSE LTQQILNIFT SKDSSAAWNT TLLDSFCNDL HQQLNDLQGC LMQQVGVQEF   240
PLTQEDALLA VRKYFHRITV YLREKKHSPC AWEVVRAEVW RALSSSANVL GRLREEKSGG   300
PPLAQKLKSS PGSEVQLVES GGGLVQPGNS LRLSCAASGF TFSKFGMSWV RQAPGKGLEW   360
VSSISGSGRD TLYAESVKGR FTISRDNAKT TLYLQMNSLR PEDTAVYYCT IGGSLSVSSQ   420
GTLVTVSS                                                            428

SEQ ID NO: 427          moltype = AA  length = 425
FEATURE                 Location/Qualifiers
source                  1..425
                        mol_type = protein
                        organism = synthetic construct
SEQUENCE: 427
EVQLVESGGG LVQPGNSLRL SCAASGFTFS KFGMSWVRQA PGKGLEWVSS ISGSGRDTLY    60
AESVKGRFTI SRDNAKTTLY LQMNSLRPED TAVYYCTIGG SLSVSSQGTL VTVSSSGGPG   120
PAGLYAQPGS CDLPQTHSLG SRRTLMLLAQ MRRISLFSCL KDRHDFGFPQ EEFGNQFQKA   180
ETIPVLHEMI QQIFNLFSTK DSSAAWDETL LDKFYTELYQ QLNDLEACVI QGVGVTETPL   240
MKEDSILAVR KYFQRITLYL KEKKYSPCAW EVVRAEIMRS FSLSTNLQES LRSKESGGPG   300
PAGLYAQPGS EVQLVESGGG LVQPGNSLRL SCAASGFTFS KFGMSWVRQA PGKGLEWVSS   360
ISGSGRDTLY AESVKGRFTI SRDNAKTTLY LQMNSLRPED TAVYYCTIGG SLSVSSQGTL   420
VTVSS                                                               425

SEQ ID NO: 428          moltype = AA  length = 425
FEATURE                 Location/Qualifiers
source                  1..425
                        mol_type = protein
                        organism = synthetic construct
SEQUENCE: 428
EVQLVESGGG LVQPGNSLRL SCAASGFTFS KFGMSWVRQA PGKGLEWVSS ISGSGRDTLY    60
AESVKGRFTI SRDNAKTTLY LQMNSLRPED TAVYYCTIGG SLSVSSQGTL VTVSSSGGPA   120
LFKSSFPPGS CDLPQTHSLG SRRTLMLLAQ MRRISLFSCL KDRHDFGFPQ EEFGNQFQKA   180
ETIPVLHEMI QQIFNLFSTK DSSAAWDETL LDKFYTELYQ QLNDLEACVI QGVGVTETPL   240
MKEDSILAVR KYFQRITLYL KEKKYSPCAW EVVRAEIMRS FSLSTNLQES LRSKESGGPA   300
LFKSSFPPGS EVQLVESGGG LVQPGNSLRL SCAASGFTFS KFGMSWVRQA PGKGLEWVSS   360
ISGSGRDTLY AESVKGRFTI SRDNAKTTLY LQMNSLRPED TAVYYCTIGG SLSVSSQGTL   420
VTVSS                                                               425

SEQ ID NO: 429          moltype = AA  length = 427
FEATURE                 Location/Qualifiers
source                  1..427
```

```
                         mol_type = protein
                         organism = synthetic construct
SEQUENCE: 429
EVQLVESGGG LVQPGNSLRL SCAASGFTFS KFGMSWVRQA PGKGLEWVSS ISGSGRDTLY    60
AESVKGRFTI SRDNAKTTLY LQMNSLRPED TAVYYCTIGG SLSVSSQGTL VTVSSSGGPP   120
LAQKLKSSPG SCDLPQTHSL GSRRTLMLLA QMRRISLFSC LKDRHDFGFP QEEFGNQFQK   180
AETIPVLHEM IQQIFNLFST KDSSAAWDET LLDKFYTELY QQLNDLEACV IQGVGVTETP   240
LMKEDSILAV RKYFQRITLY LKEKKYSPCA WEVVRAEIMR SFSLSTNLQE SLRSKESGGP   300
PLAQKLKSSP GSEVQLVESG GGLVQPGNSL RLSCAASGFT FSKFGMSWVR QAPGKGLEWV   360
SSISGSGRDT LYAESVKGRF TISRDNAKTT LYLQMNSLRP EDTAVYYCTI GGSLSVSSQG   420
TLVTVSS                                                             427

SEQ ID NO: 430          moltype = AA  length = 728
FEATURE                 Location/Qualifiers
source                  1..728
                        mol_type = protein
                        organism = synthetic construct
SEQUENCE: 430
EVQLVESGGG LVQPGNSLRL SCAASGFTFS KFGMSWVRQA PGKGLEWVSS ISGSGRDTLY    60
AESVKGRFTI SRDNAKTTLY LQMNSLRPED TAVYYCTIGG SLSVSSQGTL VTVSSSGGPG   120
PAGMKGLPGS HGTVIESLES LNNYFNSSGI DVEEKSLFLD IWRNWQKDGD MKILQSQIIS   180
FYLRLFEVLK DNQAISNNIS VIESHLITTF FSNSKAKKDA FMSIAKFEVN NPQVQRQAFN   240
ELIRVVHQLL PESSLRKRKR SRCSGGPGPA GMKGLPGSCD LPQTHNLRNK RALTLLVQMR   300
RLSPLSCLKD RKDFGFPQEK VDAQQIKKAQ AIPVLSELTQ QILNIFTSKD SSAAWNTTLL   360
DSFCNDLHQQ LNDLQGCLMQ QVGVQEFPLT QEDALLAVRK YFHRITVYLR EKKHSPCAWE   420
VVRAEVWRAL SSSANVLGRL REEKSGGPGP AGMKGLPGSH GTVIESLESL NNYFNSSGID   480
VEEKSLFLDI WRNWQKDGDM KILQSQIISF YLRLFEVLKD NQAISNNISV IESHLITTFF   540
SNSKAKKDAF MSIAKFEVNN PQVQRQAFNE LIRVVHQLLP ESSLRKRKRS RCSGGPGPAG   600
MKGLPGSEVQ LVESGGGLVQ PGNSLRLSCA ASGFTFSKFG MSWVRQAPGK GLEWVSSISG   660
SGRDTLYAES VKGRFTISRD NAKTTLYLQM NSLRPEDTAV YYCTIGGSLS VSSQGTLVTV   720
SSHHHHHH                                                            728

SEQ ID NO: 431          moltype = AA  length = 947
FEATURE                 Location/Qualifiers
source                  1..947
                        mol_type = protein
                        organism = synthetic construct
SEQUENCE: 431
LVEEPKNLVK TNCDLYEKLG EYGFQNAILV RYTQKAPQVS TPTLVEAARN LGRVGTKCCT    60
LPEDQRLPCV EDYLSAILNR VCLLHEKTPV SEHVTKCCSG SLVERRPCFS ALTVDETYVP   120
KEFKAETFTF HSDICTLPEK EKQIKKQTAL AELVKHKPKA TAEQLKTVMD DFAQFLDTCC   180
KAADKDTCFS TEGPNLVTRC KDALASGGPG PAGMKGLPGS HGTVIESLES LNNYFNSSGI   240
DVEEKSLFLD IWRNWQKDGD MKILQSQIIS FYLRLFEVLK DNQAISNNIS VIESHLITTF   300
FSNSKAKKDA FMSIAKFEVN NPQVQRQAFN ELIRVVHQLL PESSLRKRKR SRCSGGPGPA   360
GMKGLPGSLV EEPKNLVKTN CDLYEKLGEY GFQNAILVRY TQKAPQVSTP TLVEAARNLG   420
RVGTKCCTLP EDQRLPCVED YLSAILNRVC LLHEKTPVSE HVTKCCSGSL VERRPCFSAL   480
TVDETYVPKE FKAETFTFHS DICTLPEKEK QIKKQTALAE LVKHKPKATA EQLKTVMDDF   540
AQFLDTCCKA ADKDTCFSTE GPNLVTRCKD ALASGGPGPA GMKGLPGSHG TVIESLESLN   600
NYFNSSGIDV EEKSLFLDIW RNWQKDGDMK ILQSQIISFY LRLFEVLKDN QAISNNISVI   660
ESHLITTFFS NSKAKKDAFM SIAKFEVNNP QVQRQAFNEL IRVVHQLLPE SSLRKRKRSR   720
CSGGPGPAGM KGLPGSLVEE PKNLVKTNCD LYEKLGEYGF QNAILVRYTQ KAPQVSTPTL   780
VEAARNLGRV GTKCCTLPED QRLPCVEDYL SAILNRVCLL HEKTPVSEHV TKCCSGSLVE   840
RRPCFSALTV DETYVPKEFK AETFTFHSDI CTLPEKEKQI KKQTALAELV KHKPKATAEQ   900
LKTVMDDFAQ FLDTCCKAAD KDTCFSTEGP NLVTRCKDAL AHHHHHH                 947

SEQ ID NO: 432          moltype = AA  length = 1574
FEATURE                 Location/Qualifiers
source                  1..1574
                        mol_type = protein
                        organism = synthetic construct
SEQUENCE: 432
EAHKSEIAHR YNDLGEQHFK GLVLIAFSQY LQKCSYDEHA KLVQEVTDFA KTCVADESAA    60
NCDKSLHTLF GDKLCAIPNL RENYGELADC CTKQEPERNE CFLQHKDDNP SLPPFERPEA   120
EAMCTSFKEN PTTFMGHYLH EVARRHPYFY APELLYYAEQ YNEILTQCCA EADKESCLTP   180
KLDGVKEKAL VSSVRQGGGG SGGGGSGGSL VEEPKNLVKT NCDLYEKLGE YGFQNAILVR   240
YTQKAPQVST PTLVEAARNL GRVGTKCCTL PEDQRLPCVE DYLSAILNRV CLLHEKTPVS   300
EHVTKCCSGS LVERRPCFSA LTVDETYVPK EFKAETFTFH SDICTLPEKE KQIKKQTALA   360
ELVKHKPKAT AEQLKTVMDD FAQFLDTCCK AADKDTCFST EGPNLVTRCK DALASGGPGP   420
AGMKGLPGSH GTVIESLESL NNYFNSSGID VEEKSLFLDI WRNWQKDGDM KILQSQIISF   480
YLRLFEVLKD NQAISNNISV IESHLITTFF SNSKAKKDAF MSIAKFEVNN PQVQRQAFNE   540
LIRVVHQLLP ESSLRKRKRS RCSGGPGPAG MKGLPGSEAH KSEIAHRYND LGEQHFKGLV   600
LIAFSQYLQK CSYDEHAKLV QEVTDFAKTC VADESAANCD KSLHTLFGDK LCAIPNLREN   660
YGELADCCTK QEPERNECFL QHKDDNPSLP FERPEAEAM CTSFKENPTT FMGHYLHEVA    720
RRHPYFYAPE LLYYAEQYNE ILTQCCAEAD KESCLTPKLD GVKEKALVSS VRQGGGGSGG   780
GGSGGSLVEE PKNLVKTNCD LYEKLGEYGF QNAILVRYTQ KAPQVSTPTL VEAARNLGRV   840
GTKCCTLPED QRLPCVEDYL SAILNRVCLL HEKTPVSEHV TKCCSGSLVE RRPCFSALTV   900
DETYVPKEFK AETFTFHSDI CTLPEKEKQI KKQTALAELV KHKPKATAEQ LKTVMDDFAQ   960
FLDTCCKAAD KDTCFSTEGP NLVTRCKDAL ASGGPGPAGM KGLPGSHGTV IESLESLNNY  1020
FNSSGIDVEE KSLFLDIWRN WQKDGDMKIL QSQIISFYLR LFEVLKDNQA ISNNISVIES  1080
```

```
HLITTFFSNS KAKKDAFMSI AKFEVNNPQV QRQAFNELIR VVHQLLPESS LRKRKRSRCS  1140
GGPGPAGMKG LPGSEAHKSE IAHRYNDLGE QHFKGLVLIA FSQYLQKCSY DEHAKLVQEV  1200
TDFAKTCVAD ESAANCDKSL HTLFGDKLCA IPNLRENYGE LADCCTKQEP ERNECFLQHK  1260
DDNPSLPPFE RPEAEAMCTS FKENPTTFMG HYLHEVARRH PYFYAPELLY YAEQYNEILT  1320
QCCAEADKES CLTPKLDGVK EKALVSSVRQ GGGGSGGGGS GGSLVEEPKN LVKTNCDLYE  1380
KLGEYGFQNA ILVRYTQKAP QVSTPTLVEA ARNLGRVGTK CCTLPEDQRL PCVEDYLSAI  1440
LNRVCLLHEK TPVSEHVTKC CSGSLVERRP CFSALTVDET YVPKEFKAET FTFHSDICTL  1500
PEKEKQIKKQ TALAELVKHK PKATAEQLKT VMDDFAQFLD TCCKAADKDT CFSTEGPNLV  1560
TRCKDALAHH HHHH                                                   1574

SEQ ID NO: 433           moltype = AA  length = 745
FEATURE                  Location/Qualifiers
source                   1..745
                         mol_type = protein
                         organism = synthetic construct
SEQUENCE: 433
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSGGGGS  120
GGGGSGGPGPA GMKGLPGSGG GGSGGGSHGT VIESLESLNN YFNSSGIDVE EKSLFLDIWR  180
NWQKDGDMKI LQSQIISFYL RLFEVLKDNQ AISNNISVIE SHLITTFFSN SKAKKDAFMS  240
IAKFEVNNPQ VQRQAFNELI RVVHQLLPES SLRKRKRSRC GGGGSGGGSG GPGPAGMKGL  300
PGSGGGGSGG GSEVQLVESG GGLVQPGNSL RLSCAASGFT FSKFGMSWVR QAPGKGLEWV  360
SSISGSGRDT LYAESVKGRF TISRDNAKTT LYLQMNSLRP EDTAVYYCTI GGSLSVSSQG  420
TLVTVSSGGG GSGGGGSGGPG PAGMKGLPGS GGGGSGGGSH GTVIESLESL NNYFNSSGID  480
VEEKSLFLDI WRNWQKDGDM KILQSQIISF YLRLFEVLKD NQAISNNISV IESHLITTFF  540
SNSKAKKDAF MSIAKFEVNN PQVQRQAFNE LIRVVHQLLP ESSLRKRKRS RCGGGGSGGG  600
SGGPGPAGMK GLPGSGGGGS GGGSEVQLVE SGGGLVQPGN SLRLSCAASG FTFSKFGMSW  660
VRQAPGKGLE WVSSISGSGR DTLYAESVKG RFTISRDNAK TTLYLQMNSL RPEDTAVYYC  720
TIGGSLSVSS QGTLVTVSSH HHHH                                        745

SEQ ID NO: 434           moltype = AA  length = 936
FEATURE                  Location/Qualifiers
source                   1..936
                         mol_type = protein
                         organism = synthetic construct
SEQUENCE: 434
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSGGGGS  120
GGGGSGGGGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRVIPVSGPA RCLSQSRNLL KTTDDMVKTA  480
REKLKHYSCT AEDIDHEDIT RDQTSTLKTC LPLELHKNES CLATRETSST TRGSCLPPQK  540
TSLMMTLCLG SIYEDLKMYQ TEFQAINAAL QNHNHQQIIL DKGMLVAIDE LMQSLNHNGE  600
TLRQKPPVGE ADPYRVKMKL CILLHAFSTR VVTINRVMGY LSSAGGGGSG GGGSGGGGSG  660
GGGSGGGGSG GGGSGGGGSG GGGSGGGGSQ SVLTQPPSVS GAPGQRVTIS CSGSRSNIGS  720
NTVKWYQQLP GTAPKLLIYY NDQRPSGVPD RFSGSKSGTS ASLAITGLQA EDEADYYCQS  780
YDRYTHPALL FGTGTKVTVL GGGGSGGGGS GGGGSQVQLV ESGGGVVQPG RSLRLSCAAS  840
GFTFSSYGMH WVRQAPGKGL EWVAFIRYDG SNKYYADSVK GRFTISRDNS KNTLYLQMNS  900
LRAEDTAVYY CKTHGSHDNW GQGTMVTVSS HHHHHH                           936

SEQ ID NO: 435           moltype = AA  length = 1405
FEATURE                  Location/Qualifiers
source                   1..1405
                         mol_type = protein
                         organism = synthetic construct
SEQUENCE: 435
EAHKSEIAHR YNDLGEQHFK GLVLIAFSQY LQKCSYDEHA KLVQEVTDFA KTCVADESAA  60
NCDKSLHTLF GDKLCAIPNL RENYGELADC TKQEPERNE CFLQHKDDNP SLPPFERPEA  120
EAMCTSFKEN PTTFMGHYLH EVARRHPYFY APELLYYAEQ YNEILTQCCA EADKESCLTP  180
KLDGVKEKAL VSSVRQRMKC SSMQKFGERA FKAWAVARLS QTFPNADFAE ITKLATDLTK  240
VNKECCHGDL LECADDRAEL AKYMCENQAT ISSKLQTCCD KPLLKKAHCL SEVEHDTMPA  300
DLPAIAADFV EDQEVCKNYA EAKDVFLGTF LYEYSRRHPD YSVSLLLRLA KKYEATLEKC  360
CAEANPPACY GTVLAEFQPL VEEPKNLVKT NCDLYEKLGE YGFQNAILVR YTQKAPQVST  420
PTLVEAARNL GRVGTKCCTL PEDQRLPCVE DYLSAILNRV CLLHEKTPVS EHVTKCCSGS  480
LVERRPCFSA LTVDETYVPK EFKAETFTPH SDICTLPEKE KQIKKQTALA ELVKHKPKAT  540
AEQLKTVMDD FAQFLDTCCK AADKDTCFST EGPNLVTRCK DALASGGPGP AGMKGLPGSI  600
WELKKDVYVV ELDWYPDAPG EMVVLTCDTP EEDGITWTLD QSSEVLGSGK TLTIQVKEFG  660
DAGQYTCHKG GEVLSHSLL LLHKKEDGIWS TDILKDQKEP KNKTFLRCEA KNYSGRFTCW  720
WLTTISTDLT FSVKSSRGSS DPQGVTCGAA TLSAERVRGD NKEYEYSVEC QEDSACPAAE  780
ESLPIEVMVD AVHKLKYENY TSSFFIRDII KPDPPKNLQL KPLKNSRQVE VSWEYPDTWS  840
TPHSYFSLTF CVQVQGKSKR EKKDRVFTDK TSATVICRKN ASISVRAQYY YSSSWSEWA  900
SVPCSGGGGS GGGGSGGGGS RVIPVSGPAR CLSQSRNLLK TTDDMVKTAR EKLKHYSCTA  960
EDIDHEDITR DQTSTLKTCL PLELHKNESC LATRETSSTT RGSCLPPQKT SLMMTLCLGS  1020
IYEDLKMYQT EFQAINAALQ NHNHQQIILD KGMLVAIDEL MQSLNHNGET LRQKPPVGEA  1080
DPYRVKMKLC ILLHAFSTRV VTINRVMGYL SSAGGPGPA GMKGLPGSGG GGSGGGGSSG  1140
GGSGGGGSGG GGSGGGGSQS VLTQPPSVSG APGQRVTISC SGSRSNIGSN TVKWYQQLPG  1200
```

```
TAPKLLIYYN DQRPSGVPDR FSGSKSGTSA SLAITGLQAE DEADYYCQSY DRYTHPALLF   1260
GTGTKVTVLG GGGSGGGGSG GGGSQVQLVE SGGGVVQPGR SLRLSCAASG FTFSSYGMHW   1320
VRQAPGKGLE WVAFIRYDGS NKYYADSVKG RFTISRDNSK NTLYLQMNSL RAEDTAVYYC   1380
KTHGSHDNWG QGTMVTVSSH HHHHH                                        1405

SEQ ID NO: 436           moltype = AA  length = 1405
FEATURE                  Location/Qualifiers
source                   1..1405
                         mol_type = protein
                         organism = synthetic construct
SEQUENCE: 436
IWELKKDVYV VELDWYPDAP GEMVVLTCDT PEEDGITWTL DQSSEVLGSG KTLTIQVKEF   60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSACPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RYYSSSWSEW   300
ASVPCSGGGG SGGGGSGGGG SRVIPVSGPA RCLSQSRNLL KTTDDMVKTA REKLKHYSCT   360
AEDIDHEDIT RDQTSTLKTC LPLELHKNES CLATRETSST TRGSCLPPQK TSLMMTLCLG   420
SIYEDLKMYQ TEFQAINAAL QNHNHQQIIL DKGMLVAIDE LMQSLNHNGE TLRQKPPVGE   480
ADPYRVKMKL CILLHAFSTR VVTINRVMGY LSSASGGPGP AGMKGLPGSG GGGSGGGGSG   540
GGGSGGGGSG GGGSGGGGSQ SVLTQPPSVS GAPGQRVTIS CSGSRSNIGS NTVKWYQQLP   600
GTAPKLLIYY NDQRPSGVPD RFSGSKSGTS ASLAITGLQA EDEADYYCQS YDRYTHPALL   660
FGTGTKVTVL GGGGSGGGGS GGGSQVQLV ESGGGVVQPG RSLRLSCAAS GFTFSSYGMH    720
WVRQAPGKGL EWVAFIRYDG SNKYYADSVK GRFTISRDNS KNTLYLQMNS LRAEDTAVYY   780
CKTHGSHDNW GQGTMVTVSS SGGPGPAGMK GLPGSEAHKS EIAHRYNDLG EQHFKGLVLI   840
AFSQYLQKCS YDEHAKLVQE VTDFAKTCVA DESAANCDKS LHTLFGDKLC AIPNLRENYG   900
ELADCCTKQE PERNECFLQH KDDNPSLPPF ERPEAEAMCT SFKENPTTFM GHYLHEVARR   960
HPYFYAPELL YYAEQYNEIL TQCCAEADKE SCLTPKLDGV KEKALVSSVR QRMKCSSMQK   1020
FGERAFKAWA VARLSQTFPN ADFAEITKLA TDLTKVNKEC CHGDLLECAD DRAELAKYMC   1080
ENQATISSKL QTCCDKPLLK KAHCLSEVEH DTMPADLPAI AADFVEDQEV CKNYAEAKDV   1140
FLGTFLYEYS RRHPDYSVSL LLRLAKKYEA TLEKCCAEAN PPACYGTVLA EFQPLVEEPK   1200
NLVKTNCDLY EKLGEYGFQN AILVRYTQKA PQVSTPTLVE AARNLGRVGT KCCTLPEDQR   1260
LPCVEDYLSA ILNRVCLLHE KTPVSEHVTK CCSGSLVERR PCFSALTVDE TYVPKEFKAE   1320
TFTFHSDICT LPEKEKQIKK QTALAELVKH KPKATAEQLK TVMDDFAQFL DTCCKAADKD   1380
TCFSTEGPNL VTRCKDALAH HHHHH                                        1405

SEQ ID NO: 437           moltype = AA  length = 1048
FEATURE                  Location/Qualifiers
source                   1..1048
                         mol_type = protein
                         organism = synthetic construct
SEQUENCE: 437
VPRDCGCKPC ICTVPEVSSV FIFPPKPKDV LTITLTPKVT CVVVDISKDD PEVQFSWFVD   60
DVEVHTAQTQ PREEQFNSTF RSVSELPIMH QDWLNGKEFK CRVNSAAFPA PIEKTISKTK   120
GRPKAPQVYT IPPPKEQMAK DKVSLTCMIT DFFPEDITVE WQWNGQPAEN YKNTQPIMDT   180
DGSYFVYSKL NVQKSNWEAG NTFTCSVLHE GLHNHHTEKS LSHSPGKSGG PGPAGMKGLP   240
GSIWELKKDV YVVELDWYPD APGEMVVLTC DTPEEDGITW TLDQSSEVLG SGKTLTIQVK   300
EFGDAGQYTC HKGGEVLSHS LLLLHKKEDG IWSTDILKDQ KEPKNKTFLR CEAKNYSGRF   360
TCWWLTTIST DLTFSVKSSR GSSDPQGVTC GAATLSAERV RGDNKEYEYS VECQEDSACP   420
AAEESLPIEV MVDAVHKLKY ENYTSSFFIR DIIKPDPPKN LQLKPLKNSR QVEVSWEYPD   480
TWSTPHSYFS LTFCVQVQGK SKREKKDRVF TDKTSATVIC RKNASISVRA QDRYYSSSWS   540
EWASVPCSGG GGSGGGGSGG GGSRVIPVSG PARCLSQSRN LLKTTDDMVK TAREKLKHYS   600
CTAEDIDHED ITRDQTSTLK TCLPLELHKN ESCLATRETS STTRGSCLPP QKTSLMMTLC   660
LGSIYEDLKM YQTEFQAINA ALQNHNHQQI ILDKGMLVAI DELMQSLNHN GETLRQKPPV   720
GEADPYRVKM KLCILLHAFS TRVVTINRVM GYLSSASGGP GPAGMKGLPG SGGGGSGGGG   780
SGGGGSGGGG SGGGGSGGGG SQSVLTQPPS VSGAPGQRVT ISCSGSRSNI GSNTVKWYQQ   840
LPGTAPKLLI YYNDQRPSGV PDRFSGSKSG TSASLAITGL QAEDEADYYC QSYDRYTHPA   900
LLFGTGTKVT VLGGGGSGGG GSGGGGSQVQ LVESGGGVVQ PGRSLRLSCA ASGFTFSSYG   960
MHWVRQAPGK GLEWVAFIRY DGSNKYYADS VKGRFTISRD NSKNTLYLQM NSLRAEDTAV   1020
YYCKTHGSHD NWGQGTMVTV SSHHHHHH                                     1048

SEQ ID NO: 438           moltype = AA  length = 1048
FEATURE                  Location/Qualifiers
source                   1..1048
                         mol_type = protein
                         organism = synthetic construct
SEQUENCE: 438
IWELKKDVYV VELDWYPDAP GEMVVLTCDT PEEDGITWTL DQSSEVLGSG KTLTIQVKEF   60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSACPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RYYSSSWSEW   300
ASVPCSGGGG SGGGGSGGGG SRVIPVSGPA RCLSQSRNLL KTTDDMVKTA REKLKHYSCT   360
AEDIDHEDIT RDQTSTLKTC LPLELHKNES CLATRETSST TRGSCLPPQK TSLMMTLCLG   420
SIYEDLKMYQ TEFQAINAAL QNHNHQQIIL DKGMLVAIDE LMQSLNHNGE TLRQKPPVGE   480
ADPYRVKMKL CILLHAFSTR VVTINRVMGY LSSASGGPGP AGMKGLPGSG GGGSGGGGSG   540
GGGSGGGGSG GGSGGGGSQ SVLTQPPSVS GAPGQRVTIS CSGSRSNIGS NTVKWYQQLP    600
GTAPKLLIYY NDQRPSGVPD RFSGSKSGTS ASLAITGLQA EDEADYYCQS YDRYTHPALL   660
FGTGTKVTVL GGGGSGGGGS GGGSQVQLV ESGGGVVQPG RSLRLSCAAS GFTFSSYGMH    720
```

```
WVRQAPGKGL EWVAFIRYDG SNKYYADSVK GRFTISRDNS KNTLYLQMNS LRAEDTAVYY    780
CKTHGSHDNW GQGTMVTVSS SGGPGPAGMK GLPGSVPRDC GCKPCICTVP EVSSVFIFPP    840
KPKDVLTITL TPKVTCVVVD ISKDDPEVQF SWFVDDVEVH TAQTQPREEQ FNSTFRSVSE    900
LPIMHQDWLN GKEFKCRVNS AAFPAPIEKT ISKTKGRPKA PQVYTIPPPK EQMAKDKVSL    960
TCMITDFFPE DITVEWQWNG QPAENYKNTQ PIMDTDGSYF VYSKLNVQKS NWEAGNTFTC   1020
SVLHEGLHNH HTEKSLSHSP GKHHHHHH                                     1048

SEQ ID NO: 439          moltype = AA  length = 936
FEATURE                 Location/Qualifiers
source                  1..936
                        mol_type = protein
                        organism = synthetic construct
SEQUENCE: 439
EVQLVESGGG LVQPGNSLRL SCAASGFTFS KFGMSWVRQA PGKGLEWVSS ISGSGRDTLY     60
AESVKGRFTI SRDNAKTTLY LQMNSLRPED TAVYYCTIGG SLSVSSQGTL VTVSSSGGPG    120
PAGMKGLPGS IWELKKDVYV VELDWYPDAP GEMVVLTCDT PEEDGITWTL DQSSEVLGSG    180
KTLTIQVKEF GDAGQYTCHK GGEVLSHSLL LHKKEDGIW STDILKDQKE PKNKTFLRCE     240
AKNYSGRFTC WWLTTISTDL TFSVKSSRGS SDPQGVTCGA ATLSAERVRG DNKEYEYSVE    300
CQEDSACPAA EESLPIEVMV DAVHKLKYEN YTSSFFIRDI IKPDPPKNLQ LKPLKNSRQV    360
EVSWEYPDTW STPHSYFSLT FCVQVQGKSK REKKDRVFTD KTSATVICRK NASISVRAQD    420
RYYSSSWSEW ASVPCGGGG SGGGGSGGGG SRVIPVSGPA RCLSQSRNLL KTTDDMVKTA     480
REKLKHYSCT AEDIDHEDIT RDQTSTLKTC LPLELHKNES CLATRETSST TRGSCLPPQK    540
TSLMMTLCLG SIYEDLKMYQ TEFQAINAAL QNHNHQQIIL DKGMLVAIDE LMQSLNHNGE    600
TLRQKPPVGE ADPYRVKMKL CILLHAFSTR VVTINRVMGY LSSASGGPGP AGMKGLPGSG    660
GGGSGGGGSG GGGSGGGGSG GGGSGGGGSQ SVLTQPPSVS GAPGQRVTIS CSGSRSNIGS    720
NTVKWYQQLP GTAPKLLIYY NDQRPSGVPD RFSGSKSGTS ASLAITGLQA EDEADYYCQS    780
YDRYTHPALL FGTGTKVTVL SGGPGPAGMK GLPGSQVQLV ESGGGVVQPG RSLRLSCAAS    840
GFTFSSYGMH WVRQAPGKGL EWVAFIRYDG SNKYYADSVK GRFTISRDNS KNTLYLQMNS    900
LRAEDTAVYY CKTHGSHDNW GQGTMVTVSS HHHHHH                             936

SEQ ID NO: 440          moltype = AA  length = 817
FEATURE                 Location/Qualifiers
source                  1..817
                        mol_type = protein
                        organism = synthetic construct
SEQUENCE: 440
EVQLVESGGG LVQPGNSLRL SCAASGFTFS KFGMSWVRQA PGKGLEWVSS ISGSGRDTLY     60
AESVKGRFTI SRDNAKTTLY LQMNSLRPED TAVYYCTIGG SLSVSSQGTL VTVSSSGGPG    120
PAGMKGLPGS IWELKKDVYV VELDWYPDAP GEMVVLTCDT PEEDGITWTL DQSSEVLGSG    180
KTLTIQVKEF GDAGQYTCHK GGEVLSHSLL LHKKEDGIW STDILKDQKE PKNKTFLRCE     240
AKNYSGRFTC WWLTTISTDL TFSVKSSRGS SDPQGVTCGA ATLSAERVRG DNKEYEYSVE    300
CQEDSACPAA EESLPIEVMV DAVHKLKYEN YTSSFFIRDI IKPDPPKNLQ LKPLKNSRQV    360
EVSWEYPDTW STPHSYFSLT FCVQVQGKSK REKKDRVFTD KTSATVICRK NASISVRAQD    420
RYYSSSWSEW ASVPCGGGG SGGGGSGGGG SRVIPVSGPA RCLSQSRNLL KTTDDMVKTA     480
REKLKHYSCT AEDIDHEDIT RDQTSTLKTC LPLELHKNES CLATRETSST TRGSCLPPQK    540
TSLMMTLCLG SIYEDLKMYQ TEFQAINAAL QNHNHQQIIL DKGMLVAIDE LMQSLNHNGE    600
TLRQKPPVGE ADPYRVKMKL CILLHAFSTR VVTINRVMGY LSSASGGPGP AGMKGLPGSG    660
GGGSGGGGSG GGGSGGGGSG GGGSGGGGSQ VQLQESGGGL VQAGGSLRLS CAASGRTFSS    720
VYDMGWFRQA PGKDREFVAR ITESARNTRY ADSVRGRFTI SRDNAKNTVY LQMNNLELED    780
AAVYYCAADP QTVVVGTPDY WGQGTQVTVS SHHHHHH                            817

SEQ ID NO: 441          moltype = AA  length = 547
FEATURE                 Location/Qualifiers
source                  1..547
                        mol_type = protein
                        organism = synthetic construct
SEQUENCE: 441
APTSSSTKKT QLQLEHLLLD LQMILNGINN YKNPKLTRML TFKFYMPKKA TELKHLQCLE     60
EELKPLEEVL NLAQSKNFHL RPRDLISNIN IVLVELKGSA TTFMCEYADE TATIVEFLNR    120
WITFCQSIIS TLTSGGPALF KSSFPPGSEV QLVESGGGLV QPGNSLRLSC AASGFTFSKF    180
GMSWVRQAPG KGLEWVSSIS GSGRDTLYAE SVKGRFTISR DNAKTTLYLQ MNSLRPEDTA    240
VYYCTIGGSL SVSSQGTLVT VSSGGGGSGG GGSGGGGSGG GGSGGGGSGG GGSSGGPALF    300
KSSFPPGSEV QLVESGGGLV QPGGSLRLSC AASGFTFSSY TLAWVRQAPG KGLEWVAAID    360
SSSYTYSPDT VRGRFTISRD NAKNSLYLQM NSLRAEDTAV YYCARDSNWD ALDYWGCGTT    420
VTVSSGGGGS GGGGSGGGGS DIQMTQSPSS LSASVGDRVT ITCKVTEKVW GNVAWYQQKP    480
GKCPISLIYS PSLRKSGVPS RFSGSGSGTD FTLTISSLQP EDFATYYCQQ YYTYPYTFGG    540
GTKVEIK                                                             547

SEQ ID NO: 442          moltype = AA  length = 5
FEATURE                 Location/Qualifiers
REGION                  1..5
                        note = Sortase A cleavage site
source                  1..5
                        mol_type = protein
                        organism = unidentified
SEQUENCE: 442
LPXTG                                                                 5

SEQ ID NO: 443          moltype = AA  length = 25
```

| | |
|---|---|
| FEATURE | Location/Qualifiers |
| SITE | 1..25<br>note = This sequence may encompass 1-5 'Gly Gly Gly Gly Ser' repeating units |
| source | 1..25<br>mol_type = protein<br>organism = synthetic construct |

SEQUENCE: 443
GGGGSGGGGS GGGGSGGGGS GGGGS                              25

| | |
|---|---|
| SEQ ID NO: 444 | moltype = AA  length = 20 |
| FEATURE | Location/Qualifiers |
| SITE | 1..20<br>note = This sequence may encompass 1-5 'Gly Gly Gly Ser' repeating units |
| source | 1..20<br>mol_type = protein<br>organism = synthetic construct |

SEQUENCE: 444
GGGSGGGSGG GSGGGSGGGS                                    20

| | |
|---|---|
| SEQ ID NO: 445 | moltype = AA  length = 7 |
| FEATURE | Location/Qualifiers |
| REGION | 1..7<br>note = protease-cleavable sequence |
| source | 1..7<br>mol_type = protein<br>organism = unidentified |

SEQUENCE: 445
GPLGVRG                                                  7

| | |
|---|---|
| SEQ ID NO: 446 | moltype = AA  length = 8 |
| FEATURE | Location/Qualifiers |
| REGION | 1..8<br>note = protease-cleavable sequence |
| source | 1..8<br>mol_type = protein<br>organism = unidentified |

SEQUENCE: 446
IPVSLRSG                                                 8

| | |
|---|---|
| SEQ ID NO: 447 | moltype = AA  length = 8 |
| FEATURE | Location/Qualifiers |
| REGION | 1..8<br>note = protease-cleavable sequence |
| source | 1..8<br>mol_type = protein<br>organism = unidentified |

SEQUENCE: 447
VPLSLYSG                                                 8

| | |
|---|---|
| SEQ ID NO: 448 | moltype = AA  length = 10 |
| FEATURE | Location/Qualifiers |
| REGION | 1..10<br>note = protease-cleavable sequence |
| source | 1..10<br>mol_type = protein<br>organism = unidentified |

SEQUENCE: 448
SGESPAYYTA                                               10

| | |
|---|---|
| SEQ ID NO: 449 | moltype = AA  length = 5 |
| FEATURE | Location/Qualifiers |
| source | 1..5<br>mol_type = protein<br>organism = synthetic construct |

SEQUENCE: 449
GGGGS                                                    5

| | |
|---|---|
| SEQ ID NO: 450 | moltype = AA  length = 6 |
| FEATURE | Location/Qualifiers |
| source | 1..6<br>mol_type = protein<br>organism = synthetic construct |

SEQUENCE: 450
GSGSGS                                                   6

| | |
|---|---|
| SEQ ID NO: 451 | moltype = AA  length = 13 |
| FEATURE | Location/Qualifiers |

```
source                         1..13
                               mol_type = protein
                               organism = synthetic construct
SEQUENCE: 451
GSGGGSGGGS GGT                                                        13

SEQ ID NO: 452                 moltype = AA   length = 15
FEATURE                        Location/Qualifiers
source                         1..15
                               mol_type = protein
                               organism = synthetic construct
SEQUENCE: 452
GGGGSGGGGS GGGGS                                                      15

SEQ ID NO: 453                 moltype = AA   length = 20
FEATURE                        Location/Qualifiers
source                         1..20
                               mol_type = protein
                               organism = synthetic construct
SEQUENCE: 453
GGGGSGGGGS GGGGSGGGGS                                                 20

SEQ ID NO: 454                 moltype = AA   length = 934
FEATURE                        Location/Qualifiers
source                         1..934
                               mol_type = protein
                               organism = synthetic construct
SEQUENCE: 454
EVQLVESGGG LVQPGNSLRL SCAASGFTFS KFGMSWVRQA PGKGLEWVSS ISGSGRDTLY      60
AESVKGRFTI SRDNAKTTLY LQMNSLRPED TAVYYCTIGG SLSVSSQGTL VTVSSSGGPG     120
PAGLYAQPGS IWELKKDVYV VELDWYPDAP GEMVVLTCDT PEEDGITWTL DQSSEVLGSG     180
KTLTIQVKEF GDAGQYTCHK GGEVLSHSLL LLHKKEDGIW STDILKDQKE PKNKTFLRCE     240
AKNYSGRFTC WWLTTISTDL TFSVKSSRGS SDPQGVTCGA ATLSAERVRG DNKEYEYSVE     300
CQEDSACPAA EESLPIEVMV DAVHKLKYEN YTSSFFIRDI KPDPPKNLQ LKPLKNSRQV      360
EVSWEYPDTW STPHSYFSLT FCVQVQGKSK REKKDRVFTD KTSATVICRK NASISVRAQD     420
RYYSSSWSEW ASVPCSGGGG SGGGGSGGGG SRNLPVATPD PGMFPCLHHS QNLLRAVSNM     480
LQKARQTLEF YPCTSEEIDH EDITKDKTST VEACLPLELT KNESCLNSRE TSFITNGSCL     540
ASRKTSFMMA LCLSSIYEDL KMYQVEFKTM NAKLLMDPKR QIFLDQNMLA VIDELMQALN     600
FNSETVPQKS SLEEPDFYKT KIKLCILLHA FRIRAVTIDR VMSYLNASSG GPGPAGLYAQ     660
PGSGGGGSGG GGSGGGGSGG GGSGGGGSGG GGSQSVLTQP PSVSGAPGQR VTISCSGSRS     720
NIGSNTVKWY QQLPGTAPKL LIYYNDQRPS GVPDRFSGSK SGTSASLAIT GLQAEDEADY     780
YCQSYDRYTH PALLFGTGTK VTVLGGGGSG GGGSGGGGSQ VQLVESGGGV VQPGRSLRLS     840
CAASGFTFSS YGMHWVRQAP GKGLEWVAFI RYDGSNKYYA DSVKGRFTIS RDNSKNTLYL     900
QMNSLRAEDT AVYYCKTHGS HDNWGQGTMV TVSS                                934

SEQ ID NO: 455                 moltype = AA   length = 930
FEATURE                        Location/Qualifiers
source                         1..930
                               mol_type = protein
                               organism = synthetic construct
SEQUENCE: 455
EVQLVESGGG LVQPGNSLRL SCAASGFTFS KFGMSWVRQA PGKGLEWVSS ISGSGRDTLY      60
AESVKGRFTI SRDNAKTTLY LQMNSLRPED TAVYYCTIGG SLSVSSQGTL VTVSSSGGPA     120
LFKSSFPPGS IWELKKDVYV VELDWYPDAP GEMVVLTCDT PEEDGITWTL DQSSEVLGSG     180
KTLTIQVKEF GDAGQYTCHK GGEVLSHSLL LLHKKEDGIW STDILKDQKE PKNKTFLRCE     240
AKNYSGRFTC WWLTTISTDL TFSVKSSRGS SDPQGVTCGA ATLSAERVRG DNKEYEYSVE     300
CQEDSACPAA EESLPIEVMV DAVHKLKYEN YTSSFFIRDI IKPDPPKNLQ LKPLKNSRQV     360
EVSWEYPDTW STPHSYFSLT FCVQVQGKSK REKKDRVFTD KTSATVICRK NASISVRAQD     420
RYYSSSWSEW ASVPCSGGGG SGGGGSGGGG SRVIPVSGPA RCLSQSRNLL KTTDDMVKTA     480
REKLKHYSCT AEDIDHEDIT RDQTSTLKTC LPLELHKNES CLATRETSST TRGSCLPPQK     540
TSLMMTLCLG SIYEDLKMYQ TEFQAINAAL QNHHQQIIL DKGMLVAIDE LMQSLNHNGE      600
TLRQKPPVGE ADPYRVKMKL CILLHAFSTR VVTINRVMGY LSSASGGPAL FKSSFPPGSG     660
GGGGSGGSG GGGSGGGGSG GGSGGGGSQ SVLTQPPSVS GAPGQRVTIS CSGSRSNIGS       720
NTVKWYQQLP GTAPKLLIYY NDQRPSGVPD RFSGSKSGTS ASLAITGLQA EDEADYYCQS     780
YDRYTHPALL FGTGTKVTVL GGGGSGGGGS GGGGSQVQLV ESGGGVVQPG RSLRLSCAAS     840
GFTFSSYGMH WVRQAPGKGL EWVAFIRYDG SNKYYADSVK GRFTISRDNS KNTLYLQMNS     900
LRAEDTAVYY CKTHGSHDNW GQGTMVTVSS                                     930

SEQ ID NO: 456                 moltype = AA   length = 934
FEATURE                        Location/Qualifiers
source                         1..934
                               mol_type = protein
                               organism = synthetic construct
SEQUENCE: 456
EVQLVESGGG LVQPGNSLRL SCAASGFTFS KFGMSWVRQA PGKGLEWVSS ISGSGRDTLY      60
AESVKGRFTI SRDNAKTTLY LQMNSLRPED TAVYYCTIGG SLSVSSQGTL VTVSSSGGPA     120
LFKSSFPPGS IWELKKDVYV VELDWYPDAP GEMVVLTCDT PEEDGITWTL DQSSEVLGSG     180
KTLTIQVKEF GDAGQYTCHK GGEVLSHSLL LLHKKEDGIW STDILKDQKE PKNKTFLRCE     240
AKNYSGRFTC WWLTTISTDL TFSVKSSRGS SDPQGVTCGA ATLSAERVRG DNKEYEYSVE     300
```

```
CQEDSACPAA EESLPIEVMV DAVHKLKYEN YTSSFFIRDI IKPDPPKNLQ LKPLKNSRQV    360
EVSWEYPDTW STPHSYFSLT FCVQVQGKSK REKKDRVFTD KTSATVICRK NASISVRAQD    420
RYYSSSWSEW ASVPCSGGGG SGGGGSGGGG SRNLPVATPD PGMFPCLHHS QNLLRAVSNM    480
LQKARQTLEF YPCTSEEIDH EDITKDKTST VEACLPLELT KNESCLNSRE TSFITNGSCL    540
ASRKTSFMMA LCLSSIYEDL KMYQVEFKTM NAKLLMDPKR QIFLDQNMLA VIDELMQALN    600
FNSETVPQKS SLEEPDFYKT KIKLCILLHA FRIRAVTIDR VMSYLNASSG GPALFKSSFP    660
PGSGGGGSGG GGSGGGGSGG GGSGGGGSGG GGSQSVLTQP PSVSGAPGQR VTISCSGSRS    720
NIGSNTVKWY QQLPGTAPKL LIYYNDQRPS GVPDRFSGSK SGTSASLAIT GLQAEDEADY    780
YCQSYDRYTH PALLFGTGTK VTVLGGGGSG GGGSGGGGSQ VQLVESGGGV VQPGRSLRLS    840
CAASGFTFSS YGMHWVRQAP GKGLEWVAFI RYDGSNKYYA DSVKGRFTIS RDNSKNTLYL    900
QMNSLRAEDT AVYYCKTHGS HDNWGQGTMV TVSS                              934

SEQ ID NO: 457          moltype = AA  length = 930
FEATURE                 Location/Qualifiers
source                  1..930
                        mol_type = protein
                        organism = synthetic construct
SEQUENCE: 457
EVQLVESGGG LVQPGNSLRL SCAASGFTFS KFGMSWVRQA PGKGLEWVSS ISGSGRDTLY     60
AESVKGRFTI SRDNAKTTLY LQMNSLRPED TAVYYCTIGG SLSVSSQGTL VTVSSSGGPG    120
PAGLYAQPGS IWELKKDVYV VELDWYPDAP GEMVVLTCDT PEEDGITWTL DQSSEVLGSG    180
KTLTIQVKEF GDAGQYTCHK GGEVLSHSLL LLHKKEDGIW STDILKDQKE PKNKTFLRCE    240
AKNYSGRFTC WWLTTISTDL TFSVKSSRGS SDPQGVTCGA ATLSAERVRG DNKEYEYSVE    300
CQEDSACPAA EESLPIEVMV DAVHKLKYEN YTSSFFIRDI IKPDPPKNLQ LKPLKNSRQV    360
EVSWEYPDTW STPHSYFSLT FCVQVQGKSK REKKDRVFTD KTSATVICRK NASISVRAQD    420
RYYSSSWSEW ASVPCSGGGG SGGGGSGGGG SRVIPVSGPA RCLSQSRNLL KTTDDMVKTA    480
REKLKHYSCT AEDIDHEDIT RDQTSTLKTC LPLELHKNES CLATRETSST TRGSCLPPQK    540
TSLMMTLCLG SIYEDLKMYQ TEFQAINAAL QNHNHQQIIL DKGMLVAIDE LMQSLNHNGE    600
TLRQKPPVGE ADPYRVKMKL CILLHAFSTR VVTINRVMGY LSSASGGPGP AGLYAQPGSG    660
GGGSGGGGSG GGGSGGGGSG GGGSGGGGSQ SVLTQPPSVS GAPGQRVTIS CSGSRSNIGS    720
NTVKWYQQLP GTAPKLLIYY NDQRPSGVPD RFSGSKSGTS ASLAITGLQA EDEADYYCQS    780
YDRYTHPALL FGTGTKVTVL GGGGSGGGGS GGGGSQVQLV ESGGGVVQPG RSLRLSCAAS    840
GFTFSSYGMH WVRQAPGKGL EWVAFIRYEG SNKYYAESVK GRFTISRDNS KNTLYLQMNS    900
LRAEDTAVYY CKTHGSHDNW GQGTMVTVSS                                    930

SEQ ID NO: 458          moltype = AA  length = 934
FEATURE                 Location/Qualifiers
source                  1..934
                        mol_type = protein
                        organism = synthetic construct
SEQUENCE: 458
EVQLVESGGG LVQPGNSLRL SCAASGFTFS KFGMSWVRQA PGKGLEWVSS ISGSGRDTLY     60
AESVKGRFTI SRDNAKTTLY LQMNSLRPED TAVYYCTIGG SLSVSSQGTL VTVSSSGGPG    120
PAGLYAQPGS IWELKKDVYV VELDWYPDAP GEMVVLTCDT PEEDGITWTL DQSSEVLGSG    180
KTLTIQVKEF GDAGQYTCHK GGEVLSHSLL LLHKKEDGIW STDILKDQKE PKNKTFLRCE    240
AKNYSGRFTC WWLTTISTDL TFSVKSSRGS SDPQGVTCGA ATLSAERVRG DNKEYEYSVE    300
CQEDSACPAA EESLPIEVMV DAVHKLKYEN YTSSFFIRDI IKPDPPKNLQ LKPLKNSRQV    360
EVSWEYPDTW STPHSYFSLT FCVQVQGKSK REKKDRVFTD KTSATVICRK NASISVRAQD    420
RYYSSSWSEW ASVPCSGGGG SGGGGSGGGG SRNLPVATPD PGMFPCLHHS QNLLRAVSNM    480
LQKARQTLEF YPCTSEEIDH EDITKDKTST VEACLPLELT KNESCLNSRE TSFITNGSCL    540
ASRKTSFMMA LCLSSIYEDL KMYQVEFKTM NAKLLMDPKR QIFLDQNMLA VIDELMQALN    600
FNSETVPQKS SLEEPDFYKT KIKLCILLHA FRIRAVTIDR VMSYLNASSG GPGPAGLYAQ    660
PGSGGGGSGG GGSGGGGSGG GGSGGGGSGG GGSQSVLTQP PSVSGAPGQR VTISCSGSRS    720
NIGSNTVKWY QQLPGTAPKL LIYYNDQRPS GVPDRFSGSK SGTSASLAIT GLQAEDEADY    780
YCQSYDRYTH PALLFGTGTK VTVLGGGGSG GGGSGGGGSQ VQLVESGGGV VQPGRSLRLS    840
CAASGFTFSS YGMHWVRQAP GKGLEWVAFI RYEGSNKYYA ESVKGRFTIS RDNSKNTLYL    900
QMNSLRAEDT AVYYCKTHGS HDNWGQGTMV TVSS                              934

SEQ ID NO: 459          moltype = AA  length = 930
FEATURE                 Location/Qualifiers
source                  1..930
                        mol_type = protein
                        organism = synthetic construct
SEQUENCE: 459
EVQLVESGGG LVQPGNSLRL SCAASGFTFS KFGMSWVRQA PGKGLEWVSS ISGSGRDTLY     60
AESVKGRFTI SRDNAKTTLY LQMNSLRPED TAVYYCTIGG SLSVSSQGTL VTVSSSGGPG    120
PAGLYAQPGS IWELKKDVYV VELDWYPDAP GEMVVLTCDT PEEDGITWTL DQSSEVLGSG    180
KTLTIQVKEF GDAGQYTCHK GGEVLSHSLL LLHKKEDGIW STDILKDQKE PKNKTFLRCE    240
AKNYSGRFTC WWLTTISTDL TFSVKSSRGS SDPQGVTCGA ATLSAERVRG DNKEYEYSVE    300
CQEDSACPAA EESLPIEVMV DAVHKLKYEN YTSSFFIRDI IKPDPPKNLQ LKPLKNSRQV    360
EVSWEYPDTW STPHSYFSLT FCVQVQGKSK REKKDRVFTD KTSATVICRK NASISVRAQD    420
RYYSSSWSEW ASVPCSGGGG SGGGGSGGGG SRVIPVSGPA RCLSQSRNLL KTTDDMVKTA    480
REKLKHYSCT AEDIDHEDIT RDQTSTLKTC LPLELHKNES CLATRETSST TRGSCLPPQK    540
TSLMMTLCLG SIYEDLKMYQ TEFQAINAAL QNHNHQQIIL DKGMLVAIDE LMQSLNHNGE    600
TLRQKPPVGE ADPYRVKMKL CILLHAFSTR VVTINRVMGY LSSASGGPGP AGLYAQPGSG    660
GGGSGGGGSG GGGSGGGGSG GGGSGGGGSQ SVLTQPPSVS GAPGQRVTIS CSGSRSNIGS    720
ETVKWYQQLP GTAPKLLIYY NDQRPSGVPD RFSGSKSGTS ASLAITGLQA EDEADYYCQS    780
YDRYTHPALL FGTGTKVTVL GGGGSGGGGS GGGGSQVQLV ESGGGVVQPG RSLRLSCAAS    840
GFTFSSYGMH WVRQAPGKGL EWVAFIRYEG SNKYYAESVK GRFTISRDNS KNTLYLQMNS    900
```

```
                                          -continued

LRAEDTAVYY CKTHGSHDNW GQGTMVTVSS                                          930

SEQ ID NO: 460              moltype = AA  length = 934
FEATURE                     Location/Qualifiers
source                      1..934
                            mol_type = protein
                            organism = synthetic construct
SEQUENCE: 460
EVQLVESGGG LVQPGNSLRL SCAASGFTFS KFGMSWVRQA PGKGLEWVSS ISGSGRDTLY          60
AESVKGRFTI SRDNAKTTLY LQMNSLRPED TAVYYCTIGG SLSVSSQGTL VTVSSSGGPG         120
PAGLYAQPGS IWELKKDVYV VELDWYPDAP GEMVVLTCDT PEEDGITWTL DQSSEVLGSG         180
KTLTIQVKEF GDAGQYTCHK GGEVLSHSLL LLHKKEDGIW STDILKDQKE PKNKTFLRCE         240
AKNYSGRFTC WWLTTISTDL TFSVKSSRGS SDPQGVTCGA ATLSAERVRG DNKEYEYSVE         300
CQEDSACPAA EESLPIEVMV DAVHKLKYEN YTSSFFIRDI IKPDPPKNLQ LKPLKNSRQV         360
EVSWEYPDTW STPHSYFSLT FCVQVQGKSK REKKDRVFTD KTSATVICRK NASISVRAQD         420
RYYSSSWSEW ASVPCSGGGG SGGGGSGGGG SRNLPVATPD PGMFPCLHHS QNLLRAVSNM         480
LQKARQTLEF YPCTSEEIDH EDITKDKTST VEACLPLELT KNESCLNSRE TSFITNGSCL         540
ASRKTSFMMA LCLSSIYEDL KMYQVEFKTM NAKLLMDPKR QIFLDQNMLA IDELMQALN          600
FNSETVPQKS SLEEPDFYKT KIKLCILLHA FRIRAVTIDR VMSYLNASSG GPGPAGLYAQ         660
PGSGGGGSGG GGSGGGGSGG GGSGGGGSGG GGSQSVLTQP PSVSGAPGQR VTISCSGSRS         720
NIGSETVKWY QQLPGTAPKL LIYYNDQRPS GVPDRFSGSK SGTSASLAIT GLQAEDEADY         780
YCQSYDRYTH PALLFGTGTK VTVLGGGGSG GGGSGGGGSQ VQLVESGGGV VQPGRSLRLS         840
CAASGFTFSS YGMHWVRQAP GKGLEWVAFI RYEGSNKYYA ESVKGRFTIS RDNSKNTLYL         900
QMNSLRAEDT AVYYCKTHGS HDNWGQGTMV TVSS                                    934

SEQ ID NO: 461              moltype = AA  length = 930
FEATURE                     Location/Qualifiers
source                      1..930
                            mol_type = protein
                            organism = synthetic construct
SEQUENCE: 461
EVQLVESGGG LVQPGNSLRL SCAASGFTFS KFGMSWVRQA PGKGLEWVSS ISGSGRDTLY          60
AESVKGRFTI SRDNAKTTLY LQMNSLRPED TAVYYCTIGG SLSVSSQGTL VTVSSSGGPG         120
PAGLYAQPGS IWELKKDVYV VELDWYPDAP GEMVVLTCDT PEEDGITWTL DQSSEVLGSG         180
KTLTIQVKEF GDAGQYTCHK GGEVLSHSLL LLHKKEDGIW STDILKDQKE PKNKTFLRCE         240
AKNYSGRFTC WWLTTISTDL TFSVKSSRGS SDPQGVTCGA ATLSAERVRG DNKEYEYSVE         300
CQEDSACPAA EESLPIEVMV DAVHKLKYEN YTSSFFIRDI IKPDPPKNLQ LKPLKNSRQV         360
EVSWEYPDTW STPHSYFSLT FCVQVQGKSK REKKDRVFTD KTSATVICRK NASISVRAQD         420
RYYSSSWSEW ASVPCSGGGG SGGGGSGGGG SRVIPVSGPA RCLSQSRNLL KTTDDMVKTA         480
REKLKHYSCT AEDIDHEDIT RDQTSTLKTC LPLELHKNES CLATRETSST TRGSCLPPQK         540
TSLMMTLCLG SIYEDLKMYQ TEFQAINAAL QNHNHQQIIL DKGMLVAIDE LMQSLNHNGE         600
TLRQKPPVGE ADPYRVKMKL CILLHAFSTR VVTINRVMGY LSSASGGPGP AGLYAQPGSG         660
GGGSGGGGSG GGGSGGGGSG GGGSGGGGSG SVLTQPPSVS GAPGQRVTIS CSGSRSNIGD         720
NTVKWYQQLP GTAPKLLIYY NDQRPSGVPD RFSGSKSGTS ASLAITGLQA EDEADYYCQS         780
YDRYTHPALL FGTGTKVTVL GGGGSGGGGS GGGGSQVQLV ESGGGVVQPG RSLRLSCAAS         840
GFTFSSYGMH WVRQAPGKGL EWVAFIRYEG SNKYYAESVK GRFTISRDNS KNTLYLQMNS         900
LRAEDTAVYY CKTHGSHDNW GQGTMVTVSS                                         930

SEQ ID NO: 462              moltype = AA  length = 934
FEATURE                     Location/Qualifiers
source                      1..934
                            mol_type = protein
                            organism = synthetic construct
SEQUENCE: 462
EVQLVESGGG LVQPGNSLRL SCAASGFTFS KFGMSWVRQA PGKGLEWVSS ISGSGRDTLY          60
AESVKGRFTI SRDNAKTTLY LQMNSLRPED TAVYYCTIGG SLSVSSQGTL VTVSSSGGPG         120
PAGLYAQPGS IWELKKDVYV VELDWYPDAP GEMVVLTCDT PEEDGITWTL DQSSEVLGSG         180
KTLTIQVKEF GDAGQYTCHK GGEVLSHSLL LLHKKEDGIW STDILKDQKE PKNKTFLRCE         240
AKNYSGRFTC WWLTTISTDL TFSVKSSRGS SDPQGVTCGA ATLSAERVRG DNKEYEYSVE         300
CQEDSACPAA EESLPIEVMV DAVHKLKYEN YTSSFFIRDI IKPDPPKNLQ LKPLKNSRQV         360
EVSWEYPDTW STPHSYFSLT FCVQVQGKSK REKKDRVFTD KTSATVICRK NASISVRAQD         420
RYYSSSWSEW ASVPCSGGGG SGGGGSGGGG SRNLPVATPD PGMFPCLHHS QNLLRAVSNM         480
LQKARQTLEF YPCTSEEIDH EDITKDKTST VEACLPLELT KNESCLNSRE TSFITNGSCL         540
ASRKTSFMMA LCLSSIYEDL KMYQVEFKTM NAKLLMDPKR QIFLDQNMLA VIDELMQALN         600
FNSETVPQKS SLEEPDFYKT KIKLCILLHA FRIRAVTIDR VMSYLNASSG GPGPAGLYAQ         660
PGSGGGGSGG GGSGGGGSGG GGSGGGGSGG GGSQSVLTQP PSVSGAPGQR VTISCSGSRS         720
NIGDNTVKWY QQLPGTAPKL LIYYNDQRPS GVPDRFSGSK SGTSASLAIT GLQAEDEADY         780
YCQSYDRYTH PALLFGTGTK VTVLGGGGSG GGGSGGGGSQ VQLVESGGGV VQPGRSLRLS         840
CAASGFTFSS YGMHWVRQAP GKGLEWVAFI RYEGSNKYYA ESVKGRFTIS RDNSKNTLYL         900
QMNSLRAEDT AVYYCKTHGS HDNWGQGTMV TVSS                                    934

SEQ ID NO: 463              moltype = AA  length = 930
FEATURE                     Location/Qualifiers
source                      1..930
                            mol_type = protein
                            organism = synthetic construct
SEQUENCE: 463
EVQLVESGGG LVQPGNSLRL SCAASGFTFS KFGMSWVRQA PGKGLEWVSS ISGSGRDTLY          60
AESVKGRFTI SRDNAKTTLY LQMNSLRPED TAVYYCTIGG SLSVSSQGTL VTVSSSGGPG         120
```

```
PAGLYAQPGS IWELKKDVYV VELDWYPDAP GEMVVLTCDT PEEDGITWTL DQSSEVLGSG   180
KTLTIQVKEF GDAGQYTCHK GGEVLSHSLL LLHKKEDGIW STDILKDQKE PKNKTFLRCE   240
AKNYSGRFTC WWLTTISTDL TFSVKSSRGS SDPQGVTCGA ATLSAERVRG DNKEYEYSVE   300
CQEDSACPAA EESLPIEVMV DAVHKLKYEN YTSSFFIRDI IKPDPPKNLQ LKPLKNSRQV   360
EVSWEYPDTW STPHSYFSLT FCVQVQGKSK REKKDRVFTD KTSATVICRK NASISVRAQD   420
RYYSSSWSEW ASVPCSGGGG SGGGGSGGGG SRVIPVSGPA RCLSQSRNLL KTTDDMVKTA   480
REKLKHYSCT AEDIDHEDIT RDQTSTLKTC LPLELHKNES CLATRETSST TRGSCLPPQK   540
TSLMMTLCLG SIYEDLKMYQ TEFQAINAAL QNHNHQQIIL DKGMLVAIDE LMQSLNHNGE   600
TLRQKPPVGE ADPYRVKMKL CILLHAFSTR VVTINRVMGY LSSASGGPGP AGLYAQPGSG   660
GGGSGGGGSG GGGSGGGGSG GGGSGGGGSQ SVLTQPPSVS GAPGQRVTIS CSGSRSNIGD   720
ETVKWYQQLP GTAPKLLIYY NDQRPSGVPD RFSGSKSGTS ASLAITGLQA EDEADYYCQS   780
YDRYTHPALL FGTGTKVTVL GGGGSGGGGS GGGGSQVLV ESGGGVVQPG RSLRLSCAAS    840
GFTFSSYGMH WVRQAPGKGL EWVAFIRYDG SNKYYADSVK GRFTISRDNS KNTLYLQMNS   900
LRAEDTAVYY CKTHGSHDNW GQGTMVTVSS                                    930

SEQ ID NO: 464        moltype = AA  length = 934
FEATURE               Location/Qualifiers
source                1..934
                      mol_type = protein
                      organism = synthetic construct
SEQUENCE: 464
EVQLVESGGG LVQPGNSLRL SCAASGFTFS KFGMSWVRQA PGKGLEWVSS ISGSGRDTLY    60
AESVKGRFTI SRDNAKTTLY LQMNSLRPED TAVYYCTIGG SLSVSSQGTL VTVSSSGGPG   120
PAGLYAQPGS IWELKKDVYV VELDWYPDAP GEMVVLTCDT PEEDGITWTL DQSSEVLGSG   180
KTLTIQVKEF GDAGQYTCHK GGEVLSHSLL LLHKKEDGIW STDILKDQKE PKNKTFLRCE   240
AKNYSGRFTC WWLTTISTDL TFSVKSSRGS SDPQGVTCGA ATLSAERVRG DNKEYEYSVE   300
CQEDSACPAA EESLPIEVMV DAVHKLKYEN YTSSFFIRDI IKPDPPKNLQ LKPLKNSRQV   360
EVSWEYPDTW STPHSYFSLT FCVQVQGKSK REKKDRVFTD KTSATVICRK NASISVRAQD   420
RYYSSSWSEW ASVPCSGGGG SGGGGSGGGG SRNLPVATPD PGMFPCLHHS QNLLRAVSNM   480
LQKARQTLEF YPCTSEEIDH EDITKDKTST VEACLPLELT KNESCLNSRE TSFITNGSCL   540
ASRKTSFMMA LCLSSIYEDL KMYQVEFKTM NAKLLMDPKR QIFLDQNMLA VIDELMQALN   600
FNSETVPQKS SLEEPDFYKT KIKLCILLHA FRIRAVTIDR VMSYLNASSG GPGPAGLYAQ   660
PGSGGGGSGG GGSGGGGSGG GGSGGGGSGG GGSQSVLTQP PSVSGAPGQR VTISCSGSRS   720
NIGDETVKWY QQLPGTAPKL LIYYNDQRPS GVPDRFSGSK SGTSASLAIT GLQAEDEADY   780
YCQSYDRYTH PALLFGTGTK VTVLGGGGSG GGGSGGGGSQ VQLVESGGGV VQPGRSLRLS   840
CAASGFTFSS YGMHWVRQAP GKGLEWVAFI RYDGSNKYYA DSVKGRFTIS RDNSKNTLYL   900
QMNSLRAEDT AVYYCKTHGS HDNWGQGTMV TVSS                               934

SEQ ID NO: 465        moltype = AA  length = 930
FEATURE               Location/Qualifiers
source                1..930
                      mol_type = protein
                      organism = synthetic construct
SEQUENCE: 465
EVQLVESGGG LVQPGNSLRL SCAASGFTFS KFGMSWVRQA PGKGLEWVSS ISGSGRDTLY    60
AESVKGRFTI SRDNAKTTLY LQMNSLRPED TAVYYCTIGG SLSVSSQGTL VTVSSSGGPG   120
PAGLYAQPGS IWELKKDVYV VELDWYPDAP GEMVVLTCDT PEEDGITWTL DQSSEVLGSG   180
KTLTIQVKEF GDAGQYTCHK GGEVLSHSLL LLHKKEDGIW STDILKDQKE PKNKTFLRCE   240
AKNYSGRFTC WWLTTISTDL TFSVKSSRGS SDPQGVTCGA ATLSAERVRG DNKEYEYSVE   300
CQEDSACPAA EESLPIEVMV DAVHKLKYEN YTSSFFIRDI IKPDPPKNLQ LKPLKNSRQV   360
EVSWEYPDTW STPHSYFSLT FCVQVQGKSK REKKDRVFTD KTSATVICRK NASISVRAQD   420
RYYSSSWSEW ASVPCSGGGG SGGGGSGGGG SRVIPVSGPA RCLSQSRNLL KTTDDMVKTA   480
REKLKHYSCT AEDIDHEDIT RDQTSTLKTC LPLELHKNES CLATRETSST TRGSCLPPQK   540
TSLMMTLCLG SIYEDLKMYQ TEFQAINAAL QNHNHQQIIL DKGMLVAIDE LMQSLNHNGE   600
TLRQKPPVGE ADPYRVKMKL CILLHAFSTR VVTINRVMGY LSSASGGPGP AGLYAQPGSG   660
GGGSGGGGSG GGGSGGGGSG GGGSGGGGSQ SVLTQPPSVS GAPGQRVTIS CSGSRSNIGD   720
ETVKWYQQLP GTAPKLLIYY NDQRPSGVPD RFSGSKSGTS ASLAITGLQA EDEADYYCQS   780
YDRYTHPALL FGTGTKVTVL GGGGSGGGGS GGGGSQVLV ESGGGVVQPG RSLRLSCAAS    840
GFTFSSYGMH WVRQAPGKGL EWVAFIRYEG SNKYYAESVK GRFTISRDNS KNTLYLQMNS   900
LRAEDTAVYY CKTHGSHDNW GQGTMVTVSS                                    930

SEQ ID NO: 466        moltype = AA  length = 934
FEATURE               Location/Qualifiers
source                1..934
                      mol_type = protein
                      organism = synthetic construct
SEQUENCE: 466
EVQLVESGGG LVQPGNSLRL SCAASGFTFS KFGMSWVRQA PGKGLEWVSS ISGSGRDTLY    60
AESVKGRFTI SRDNAKTTLY LQMNSLRPED TAVYYCTIGG SLSVSSQGTL VTVSSSGGPG   120
PAGLYAQPGS IWELKKDVYV VELDWYPDAP GEMVVLTCDT PEEDGITWTL DQSSEVLGSG   180
KTLTIQVKEF GDAGQYTCHK GGEVLSHSLL LLHKKEDGIW STDILKDQKE PKNKTFLRCE   240
AKNYSGRFTC WWLTTISTDL TFSVKSSRGS SDPQGVTCGA ATLSAERVRG DNKEYEYSVE   300
CQEDSACPAA EESLPIEVMV DAVHKLKYEN YTSSFFIRDI IKPDPPKNLQ LKPLKNSRQV   360
EVSWEYPDTW STPHSYFSLT FCVQVQGKSK REKKDRVFTD KTSATVICRK NASISVRAQD   420
RYYSSSWSEW ASVPCSGGGG SGGGGSGGGG SRNLPVATPD PGMFPCLHHS QNLLRAVSNM   480
LQKARQTLEF YPCTSEEIDH EDITKDKTST VEACLPLELT KNESCLNSRE TSFITNGSCL   540
ASRKTSFMMA LCLSSIYEDL KMYQVEFKTM NAKLLMDPKR QIFLDQNMLA VIDELMQALN   600
FNSETVPQKS SLEEPDFYKT KIKLCILLHA FRIRAVTIDR VMSYLNASSG GPGPAGLYAQ   660
PGSGGGGSGG GGSGGGGSGG GGSGGGGSGG GGSQSVLTQP PSVSGAPGQR VTISCSGSRS   720
```

```
NIGDETVKWY QQLPGTAPKL LIYYNDQRPS GVPDRFSGSK SGTSASLAIT GLQAEDEADY    780
YCQSYDRYTH PALLFGTGTK VTVLGGGGSG GGGSGGGGSQ VQLVESGGGV VQPGRSLRLS    840
CAASGFTFSS YGMHWVRQAP GKGLEWVAFI RYEGSNKYYA ESVKGRFTIS RDNSKNTLYL    900
QMNSLRAEDT AVYYCKTHGS HDNWGQGTMV TVSS                                934

SEQ ID NO: 467          moltype = AA   length = 930
FEATURE                 Location/Qualifiers
source                  1..930
                        mol_type = protein
                        organism = synthetic construct
SEQUENCE: 467
EVQLVESGGG LVQPGNSLRL SCAASGFTFS KFGMSWVRQA PGKGLEWVSS ISGSGRDTLY     60
AESVKGRFTI SRDNAKTTLY LQMNSLRPED TAVYYCTIGG SLSVSSQGTL VTVSSSGGPG    120
PAGLYAQPGS IWELKKDVYV VELDWYPDAP GEMVVLTCDT PEEDGITWTL DQSSEVLGSG    180
KTLTIQVKEF GDAGQYTCHK GGEVLSHSLL LLHKKEDGIW STDILKDQKE PKNKTFLRCE    240
AKNYSGRFTC WWLTTISTDL TFSVKSSRGS SDPQGVTCGA ATLSAERVRG DNKEYEYSVE    300
CQEDSACPAA EESLPIEVMV DAVHKLKYEN YTSSFFIRDI IKPDPPKNLQ LKPLKNSRQV    360
EVSWEYPDTW STPHSYFSLT FCVQVQGKSK REKKDRVFTD KTSATVICRK NASISVRAQD    420
RYYSSSWSEW ASVPCSGGGG SGGGGSGGGG SRVIPVSGPA RCLSQSRNLL KTTDDMVKTA    480
REKLKHYSCT AEDIDHEDIT RDQTSTLKTC LPLELHKNES CLATRETSST TRGSCLPPQK    540
TSLMMTLCLG SIYEDLKMYQ TEFQAINAAL QNHNHQQIIL DKGMLVAIDE LMQSLNHNGE    600
TLRQKPPVGE ADPYRVKMKL CILLHAFSTR VVTINRVMGY LSSASGGPGP AGLYAQPGSG    660
GGGSGGGGSG GGGSGGGGSG GGGSGGGGSQ SVLTQPPSVS GAPGQRVTIS CSGSESNIGS    720
NDVKWYQQLP GTAPKLLIYY NDQRPSGVPD RFSGSKSGTS ASLAITGLQA EDEADYYCQS    780
YDRYTHPALL FGTGTKVTVL GGGGSGGGGS GGGGSQVQLV ESGGGVVPPG RSLRLSCAAS    840
GFTFSSYGMH WVRQAPGKGL EWVAFIRYDG SNKYYADSVK GRFTISRDNS KNTLYLQMNS    900
LRAEDTAVYY CKTHGSHDNW GQGTMVTVSS                                     930

SEQ ID NO: 468          moltype = AA   length = 934
FEATURE                 Location/Qualifiers
source                  1..934
                        mol_type = protein
                        organism = synthetic construct
SEQUENCE: 468
EVQLVESGGG LVQPGNSLRL SCAASGFTFS KFGMSWVRQA PGKGLEWVSS ISGSGRDTLY     60
AESVKGRFTI SRDNAKTTLY LQMNSLRPED TAVYYCTIGG SLSVSSQGTL VTVSSSGGPG    120
PAGLYAQPGS IWELKKDVYV VELDWYPDAP GEMVVLTCDT PEEDGITWTL DQSSEVLGSG    180
KTLTIQVKEF GDAGQYTCHK GGEVLSHSLL LLHKKEDGIW STDILKDQKE PKNKTFLRCE    240
AKNYSGRFTC WWLTTISTDL TFSVKSSRGS SDPQGVTCGA ATLSAERVRG DNKEYEYSVE    300
CQEDSACPAA EESLPIEVMV DAVHKLKYEN YTSSFFIRDI IKPDPPKNLQ LKPLKNSRQV    360
EVSWEYPDTW STPHSYFSLT FCVQVQGKSK REKKDRVFTD KTSATVICRK NASISVRAQD    420
RYYSSSWSEW ASVPCSGGGG SGGGGSGGGG SRNLPVATPD PGMFPCLHHS QNLLRAVSNM    480
LQKARQTLEF YPCTSEEIDH EDITKDKTST VEACLPLELT KNESCLNSRE TSFITNGSCL    540
ASRKTSFMMA LCLSSIYEDL KMYQVEFKTN NAKLLMDPKR QIFLDQNMLA VIDELMQALN    600
FNSETVPQKS SLEEPDFYKT KIKLCILLHA FRIRAVTIDR VMSYLNASSG GPGPAGLYAQ    660
PGSGGGGSGG GGSGGGGSGG GGSGGGGSGG GGSQSVLTQP PSVSGAPGQR VTISCSGSES    720
NIGSNDVKWY QQLPGTAPKL LIYYNDQRPS GVPDRFSGSK SGTSASLAIT GLQAEDEADY    780
YCQSYDRYTH PALLFGTGTK VTVLGGGGSG GGGSGGGGSQ VQLVESGGGV VQPGRSLRLS    840
CAASGFTFSS YGMHWVRQAP GKGLEWVAFI RYDGSNKYYA DSVKGRFTIS RDNSKNTLYL    900
QMNSLRAEDT AVYYCKTHGS HDNWGQGTMV TVSS                                934

SEQ ID NO: 469          moltype = AA   length = 930
FEATURE                 Location/Qualifiers
source                  1..930
                        mol_type = protein
                        organism = synthetic construct
SEQUENCE: 469
EVQLVESGGG LVQPGNSLRL SCAASGFTFS KFGMSWVRQA PGKGLEWVSS ISGSGRDTLY     60
AESVKGRFTI SRDNAKTTLY LQMNSLRPED TAVYYCTIGG SLSVSSQGTL VTVSSSGGPG    120
PAGLYAQPGS IWELKKDVYV VELDWYPDAP GEMVVLTCDT PEEDGITWTL DQSSEVLGSG    180
KTLTIQVKEF GDAGQYTCHK GGEVLSHSLL LLHKKEDGIW STDILKDQKE PKNKTFLRCE    240
AKNYSGRFTC WWLTTISTDL TFSVKSSRGS SDPQGVTCGA ATLSAERVRG DNKEYEYSVE    300
CQEDSACPAA EESLPIEVMV DAVHKLKYEN YTSSFFIRDI IKPDPPKNLQ LKPLKNSRQV    360
EVSWEYPDTW STPHSYFSLT FCVQVQGKSK REKKDRVFTD KTSATVICRK NASISVRAQD    420
RYYSSSWSEW ASVPCSGGGG SGGGGSGGGG SRVIPVSGPA RCLSQSRNLL KTTDDMVKTA    480
REKLKHYSCT AEDIDHEDIT RDQTSTLKTC LPLELHKNES CLATRETSST TRGSCLPPQK    540
TSLMMTLCLG SIYEDLKMYQ TEFQAINAAL QNHNHQQIIL DKGMLVAIDE LMQSLNHNGE    600
TLRQKPPVGE ADPYRVKMKL CILLHAFSTR VVTINRVMGY LSSASGGPGP AGLYAQPGSG    660
GGGSGGGGSG GGGSGGGGSG GGGSGGGGSQ SVLTQPPSVS GAPGQRVTIS CSGSRSNIGE    720
NTVKWYQQLP GTAPKLLIYY NDQRPSGVPD RFSGSKSGTS ASLAITGLQA EDEADYYCQS    780
YDRYTHPALL FGTGTKVTVL GGGGSGGGGS GGGGSQVQLV ESGGGVVPPG RSLRLSCAAS    840
GFTFSSYGMH WVRQAPGKGL EWVAFIRYEG SNKYYAESVK GRFTISRDNS KNTLYLQMNS    900
LRAEDTAVYY CKTHGSHDNW GQGTMVTVSS                                     930

SEQ ID NO: 470          moltype = AA   length = 934
FEATURE                 Location/Qualifiers
source                  1..934
                        mol_type = protein
                        organism = synthetic construct
```

```
SEQUENCE: 470
EVQLVESGGG LVQPGNSLRL SCAASGFTFS KFGMSWVRQA PGKGLEWVSS ISGSGRDTLY    60
AESVKGRFTI SRDNAKTTLY LQMNSLRPED TAVYYCTIGG SLSVSSQGTL VTVSSSGGPG   120
PAGLYAQPGS IWELKKDVYV VELDWYPDAP GEMVVLTCDT PEEDGITWTL DQSSEVLGSG   180
KTLTIQVKEF GDAGQYTCHK GGEVLSHSLL LLHKKEDGIW STDILKDQKE PKNKTFLRCE   240
AKNYSGRFTC WWLTTISTDL TFSVKSSRGS SDPQGVTCGA ATLSAERVRG DNKEYEYSVE   300
CQEDSACPAA EESLPIEVMV DAVHKLKYEN YTSSFFIRDI IKPDPPKNLQ LKPLKNSRQV   360
EVSWEYPDTW STPHSYFSLT FCVQVQGKSK REKKDRVFTD KTSATVICRK NASISVRAQD   420
RYYSSSWSEW ASVPCSGGGG SGGGGSGGGG SRNLPVATPD PGMFPCLHHS QNLLRAVSNM   480
LQKARQTLEF YPCTSEEIDH EDITKDKTST VEACLPLELT KNESCLNSRE TSFITNGSCL   540
ASRKTSFMMA LCLSSIYEDL KMYQVEFKTM NAKLLMDPKR QIFLDQNMLA VIDELMQALN   600
FNSETVPQKS SLEEPDFYKT KIKLCILLHA FRIRAVTIDR VMSYLNASSG GPGPAGLYAQ   660
PGSGGGGSGG GGSGGGGSGG GGSGGGGSGG GGSQSVLTQP PSVSGAPGQR VTISCSGSRS   720
NIGENTVKWY QQLPGTAPKL LIYYNDQRPS GVPDRFSGSK SGTSASLAIT GLQAEDEADY   780
YCQSYDRYTH PALLFGTGTK VTVLGGGGSG GGGSGGGGSQ VQLVESGGGV VQPGRSLRLS   840
CAASGFTFSS YGMHWVRQAP GKGLEWVAFI RYEGSNKYYA ESVKGRFTIS RDNSKNTLYL   900
QMNSLRAEDT AVYYCKTHGS HDNWGQGTMV TVSS                              934

SEQ ID NO: 471          moltype = AA   length = 930
FEATURE                 Location/Qualifiers
source                  1..930
                        mol_type = protein
                        organism = synthetic construct
SEQUENCE: 471
EVQLVESGGG LVQPGNSLRL SCAASGFTFS KFGMSWVRQA PGKGLEWVSS ISGSGRDTLY    60
AESVKGRFTI SRDNAKTTLY LQMNSLRPED TAVYYCTIGG SLSVSSQGTL VTVSSSGGPG   120
PAGLYAQPGS IWELKKDVYV VELDWYPDAP GEMVVLTCDT PEEDGITWTL DQSSEVLGSG   180
KTLTIQVKEF GDAGQYTCHK GGEVLSHSLL LLHKKEDGIW STDILKDQKE PKNKTFLRCE   240
AKNYSGRFTC WWLTTISTDL TFSVKSSRGS SDPQGVTCGA ATLSAERVRG DNKEYEYSVE   300
CQEDSACPAA EESLPIEVMV DAVHKLKYEN YTSSFFIRDI IKPDPPKNLQ LKPLKNSRQV   360
EVSWEYPDTW STPHSYFSLT FCVQVQGKSK REKKDRVFTD KTSATVICRK NASISVRAQD   420
RYYSSSWSEW ASVPCSGGGG SGGGGSGGGG SRVIPVSGPA RCLSQSRNLL KTTDDMVKTA   480
REKLKHYSCT AEDIDHEDIT RDQTSTLKTC LPLELHKNES CLATRETSST TRGSCLPPQK   540
TSLMMTLCLG SIYEDLKMYQ TEFQAINAAL QNHNHQQIIL DKGMLVAIDE LMQSLNHNGE   600
TLRQKPPVGE ADPYRVKMKL CILLHAFSTR VVTINRVMGY LSSASGGPGP AGLYAQPGSG   660
GGGSGGGGSG GGGSGGGGSG GGGSGGGGSQ SVLTQPPSVS GAPGQRVTIS CSGSRSNIGE   720
ETVKWYQQLP GTAPKLLIYY NDQRPSGVPD RFSGSKSGTS ASLAITGLQA EDEADYYCQS   780
YDRYTHPALL FGTGTKVTVL GGGGSGGGGS GGGGSQVQLV ESGGGVVQPG RSLRLSCAAS   840
GFTFSSYGMH WVRQAPGKGL EWVAFIRYDG SNKYYADSVK GRFTISRDNS KNTLYLQMNS   900
LRAEDTAVYY CKTHGSHDNW GQGTMVTVSS                                   930

SEQ ID NO: 472          moltype = AA   length = 934
FEATURE                 Location/Qualifiers
source                  1..934
                        mol_type = protein
                        organism = synthetic construct
SEQUENCE: 472
EVQLVESGGG LVQPGNSLRL SCAASGFTFS KFGMSWVRQA PGKGLEWVSS ISGSGRDTLY    60
AESVKGRFTI SRDNAKTTLY LQMNSLRPED TAVYYCTIGG SLSVSSQGTL VTVSSSGGPG   120
PAGLYAQPGS IWELKKDVYV VELDWYPDAP GEMVVLTCDT PEEDGITWTL DQSSEVLGSG   180
KTLTIQVKEF GDAGQYTCHK GGEVLSHSLL LLHKKEDGIW STDILKDQKE PKNKTFLRCE   240
AKNYSGRFTC WWLTTISTDL TFSVKSSRGS SDPQGVTCGA ATLSAERVRG DNKEYEYSVE   300
CQEDSACPAA EESLPIEVMV DAVHKLKYEN YTSSFFIRDI IKPDPPKNLQ LKPLKNSRQV   360
EVSWEYPDTW STPHSYFSLT FCVQVQGKSK REKKDRVFTD KTSATVICRK NASISVRAQD   420
RYYSSSWSEW ASVPCSGGGG SGGGGSGGGG SRNLPVATPD PGMFPCLHHS QNLLRAVSNM   480
LQKARQTLEF YPCTSEEIDH EDITKDKTST VEACLPLELT KNESCLNSRE TSFITNGSCL   540
ASRKTSFMMA LCLSSIYEDL KMYQVEFKTM NAKLLMDPKR QIFLDQNMLA VIDELMQALN   600
FNSETVPQKS SLEEPDFYKT KIKLCILLHA FRIRAVTIDR VMSYLNASSG GPGPAGLYAQ   660
PGSGGGGSGG GGSGGGGSGG GGSGGGGSGG GGSQSVLTQP PSVSGAPGQR VTISCSGSRS   720
NIGEETVKWY QQLPGTAPKL LIYYNDQRPS GVPDRFSGSK SGTSASLAIT GLQAEDEADY   780
YCQSYDRYTH PALLFGTGTK VTVLGGGGSG GGGSGGGGSQ VQLVESGGGV VQPGRSLRLS   840
CAASGFTFSS YGMHWVRQAP GKGLEWVAFI RYDGSNKYYA DSVKGRFTIS RDNSKNTLYL   900
QMNSLRAEDT AVYYCKTHGS HDNWGQGTMV TVSS                              934

SEQ ID NO: 473          moltype = AA   length = 930
FEATURE                 Location/Qualifiers
source                  1..930
                        mol_type = protein
                        organism = synthetic construct
SEQUENCE: 473
EVQLVESGGG LVQPGNSLRL SCAASGFTFS KFGMSWVRQA PGKGLEWVSS ISGSGRDTLY    60
AESVKGRFTI SRDNAKTTLY LQMNSLRPED TAVYYCTIGG SLSVSSQGTL VTVSSSGGPG   120
PAGLYAQPGS IWELKKDVYV VELDWYPDAP GEMVVLTCDT PEEDGITWTL DQSSEVLGSG   180
KTLTIQVKEF GDAGQYTCHK GGEVLSHSLL LLHKKEDGIW STDILKDQKE PKNKTFLRCE   240
AKNYSGRFTC WWLTTISTDL TFSVKSSRGS SDPQGVTCGA ATLSAERVRG DNKEYEYSVE   300
CQEDSACPAA EESLPIEVMV DAVHKLKYEN YTSSFFIRDI IKPDPPKNLQ LKPLKNSRQV   360
EVSWEYPDTW STPHSYFSLT FCVQVQGKSK REKKDRVFTD KTSATVICRK NASISVRAQD   420
RYYSSSWSEW ASVPCSGGGG SGGGGSGGGG SRVIPVSGPA RCLSQSRNLL KTTDDMVKTA   480
REKLKHYSCT AEDIDHEDIT RDQTSTLKTC LPLELHKNES CLATRETSST TRGSCLPPQK   540
```

```
TSLMMTLCLG  SIYEDLKMYQ  TEFQAINAAL  QNHNHQQIIL  DKGMLVAIDE  LMQSLNHNGE   600
TLRQKPPVGE  ADPYRVKMKL  CILLHAFSTR  VVTINRVMGY  LSSASGGPGP  AGLYAQPGSG   660
GGGSGGGGSG  GGGSGGGGSG  GGGSGGGGSQ  SVLTQPPSVS  GAPGQRVTIS  CSGSRSNIGS   720
ETVKWYQQLP  GTAPKLLIYY  NDQRPSGVPD  RFSGSKSGTS  ASLAITGLQA  EDEADYYCQS   780
YDRYTHPALL  FGTGTKVTVL  GGGGSGGGGS  GGGGSQVQLV  ESGGGVVQPG  RSLRLSCAAS   840
GFTFSSYGMH  WVRQAPGKGL  EWVAFIRYEG  SNKYYADSVK  GRFTISRDNS  KNTLYLQMNS   900
LRAEDTAVYY  CKTHGSHDNW  GQGTMVTVSS                                      930

SEQ ID NO: 474          moltype = AA  length = 934
FEATURE                 Location/Qualifiers
source                  1..934
                        mol_type = protein
                        organism = synthetic construct
SEQUENCE: 474
EVQLVESGGG  LVQPGNSLRL  SCAASGFTFS  KFGMSWVRQA  PGKGLEWVSS  ISGSGRDTLY    60
AESVKGRFTI  SRDNAKTTLY  LQMNSLRPED  TAVYYCTIGG  SLSVSSQGTL  VTVSSSGGPG   120
PAGLYAQPGS  IWELKKDVYV  VELDWYPDAP  GEMVVLTCDT  PEEDGITWTL  DQSSEVLGSG   180
KTLTIQVKEF  GDAGQYTCHK  GGEVLSHSLL  LLHKKEDGIW  STDILKDQKE  PKNKTFLRCE   240
AKNYSGRFTC  WWLTTISTDL  TFSVKSSRGS  SDPQGVTCGA  ATLSAERVRG  DNKEYEYSVE   300
CQEDSACPAA  EESLPIEVMV  DAVHKLKYEN  YTSSFFIRDI  IKPDPPKNLQ  LKPLKNSRQV   360
EVSWEYPDTW  STPHSYFSLT  FCVQVQGKSK  REKKDRVFTD  KTSATVICRK  NASISVRAQD   420
RYYSSSWSEW  ASVPCSGGGG  SGGGGSGGGG  SRNLPMPGKS  PGMFPCLHHS  QNLLRAVSNM   480
LQKARQTLEF  YPCTSEEIDH  EDITKDKTST  VEACLPLELT  KNESCLNSRE  TSFITNGSCL   540
ASRKTSFMMA  LCLSSIYEDL  KMYQVEFKTM  NAKLLMDPKR  QIFLDQNMLA  VIDELMQALN   600
FNSETVPQKS  SLEEPDFYKT  KIKLCILLHA  FRIRAVTIDR  VMSYLNASSG  GPGPAGLYAQ   660
PGSGGGGSGG  GGGSGGGGSG  GGSQSVLTQP  PSVSGAPGQR  VTISCSGSRS   720
NIGSETVKWY  QQLPGTAPKL  LIYYNDQRPS  GVPDRFSGSK  SGTSASLAIT  GLQAEDEADY   780
YCQSYDRYTH  PALLFGTGTK  VTVLGGGGSG  GGGSGGGGSQ  VQLVESGGGV  VQPGRSLRLS   840
CAASGFTFSS  YGMHWVRQAP  GKGLEWVAFI  RYEGSNKYYA  DSVKGRFTIS  RDNSKNTLYL   900
QMNSLRAEDT  AVYYCKTHGS  HDNWGQGTMV  TVSS                                934

SEQ ID NO: 475          moltype = AA  length = 930
FEATURE                 Location/Qualifiers
source                  1..930
                        mol_type = protein
                        organism = synthetic construct
SEQUENCE: 475
EVQLVESGGG  LVQPGNSLRL  SCAASGFTFS  KFGMSWVRQA  PGKGLEWVSS  ISGSGRDTLY    60
AESVKGRFTI  SRDNAKTTLY  LQMNSLRPED  TAVYYCTIGG  SLSVSSQGTL  VTVSSSGGPA   120
LFKSSFPPGS  IWELKKDVYV  VELDWYPDAP  GEMVVLTCDT  PEEDGITWTL  DQSSEVLGSG   180
KTLTIQVKEF  GDAGQYTCHK  GGEVLSHSLL  LLHKKEDGIW  STDILKDQKE  PKNKTFLRCE   240
AKNYSGRFTC  WWLTTISTDL  TFSVKSSRGS  SDPQGVTCGA  ATLSAERVRG  DNKEYEYSVE   300
CQEDSACPAA  EESLPIEVMV  DAVHKLKYEN  YTSSFFIRDI  IKPDPPKNLQ  LKPLKNSRQV   360
EVSWEYPDTW  STPHSYFSLT  FCVQVQGKSK  REKKDRVFTD  KTSATVICRK  NASISVRAQD   420
RYYSSSWSEW  ASVPCSGGGG  SGGGGSGGGG  SRVIPVSGPA  RCLSQSRNLL  KTTDDMVKTA   480
REKLKHYSCT  AEDIDHEDIT  RDQTSTLKTC  LPLELHKNES  CLATRETSST  TRGSCLPPQK   540
TSLMMTLCLG  SIYEDLKMYQ  TEFQAINAAL  QNHNHQQIIL  DKGMLVAIDE  LMQSLNHNGE   600
TLRQKPPVGE  ADPYRVKMKL  CILLHAFSTR  VVTINRVMGY  LSSASGGPAL  FKSSFPPGSG   660
GGGSGGGGSG  GGGSGGGGSG  GGGSGGGGSQ  SVLTQPPSVS  GAPGQRVTIS  CSGSRSNIGS   720
NTVKWYQQLP  GTAPKLLIYY  NDQRPSGVPD  RFSGSKSGTS  ASLAITGLQA  EDEADYYCQS   780
YDRYTHPALL  FGTGTKVTVL  GGGGSGGGGS  GGGGSQVQLV  ESGGGVVQPG  RSLRLSCAAS   840
GFTFSSYGMH  WVRQAPGKGL  EWVAFIRYEG  SNKYYAESVK  GRFTISRDNS  KNTLYLQMNS   900
LRAEDTAVYY  CKTHGSHDNW  GQGTMVTVSS                                      930

SEQ ID NO: 476          moltype = AA  length = 934
FEATURE                 Location/Qualifiers
source                  1..934
                        mol_type = protein
                        organism = synthetic construct
SEQUENCE: 476
EVQLVESGGG  LVQPGNSLRL  SCAASGFTFS  KFGMSWVRQA  PGKGLEWVSS  ISGSGRDTLY    60
AESVKGRFTI  SRDNAKTTLY  LQMNSLRPED  TAVYYCTIGG  SLSVSSQGTL  VTVSSSGGPA   120
LFKSSFPPGS  IWELKKDVYV  VELDWYPDAP  GEMVVLTCDT  PEEDGITWTL  DQSSEVLGSG   180
KTLTIQVKEF  GDAGQYTCHK  GGEVLSHSLL  LLHKKEDGIW  STDILKDQKE  PKNKTFLRCE   240
AKNYSGRFTC  WWLTTISTDL  TFSVKSSRGS  SDPQGVTCGA  ATLSAERVRG  DNKEYEYSVE   300
CQEDSACPAA  EESLPIEVMV  DAVHKLKYEN  YTSSFFIRDI  IKPDPPKNLQ  LKPLKNSRQV   360
EVSWEYPDTW  STPHSYFSLT  FCVQVQGKSK  REKKDRVFTD  KTSATVICRK  NASISVRAQD   420
RYYSSSWSEW  ASVPCSGGGG  SGGGGSGGGG  SRNLPMPGKS  PGMFPCLHHS  QNLLRAVSNM   480
LQKARQTLEF  YPCTSEEIDH  EDITKDKTST  VEACLPLELT  KNESCLNSRE  TSFITNGSCL   540
ASRKTSFMMA  LCLSSIYEDL  KMYQVEFKTM  NAKLLMDPKR  QIFLDQNMLA  VIDELMQALN   600
FNSETVPQKS  SLEEPDFYKT  KIKLCILLHA  FRIRAVTIDR  VMSYLNASSG  GPALFKSSFP   660
PGSGGGGSGG  GGSGGGGSGG  GGSGGGGSGG  GGSQSVLTQP  PSVSGAPGQR  VTISCSGSRS   720
NIGSNTVKWY  QQLPGTAPKL  LIYYNDQRPS  GVPDRFSGSK  SGTSASLAIT  GLQAEDEADY   780
YCQSYDRYTH  PALLFGTGTK  VTVLGGGGSG  GGGSGGGGSQ  VQLVESGGGV  VQPGRSLRLS   840
CAASGFTFSS  YGMHWVRQAP  GKGLEWVAFI  RYEGSNKYYA  ESVKGRFTIS  RDNSKNTLYL   900
QMNSLRAEDT  AVYYCKTHGS  HDNWGQGTMV  TVSS                                934

SEQ ID NO: 477          moltype = AA  length = 930
FEATURE                 Location/Qualifiers
```

```
source                  1..930
                        mol_type = protein
                        organism = synthetic construct
SEQUENCE: 477
EVQLVESGGG LVQPGNSLRL SCAASGFTFS KFGMSWVRQA PGKGLEWVSS ISGSGRDTLY    60
AESVKGRFTI SRDNAKTTLY LQMNSLRPED TAVYYCTIGG SLSVSSQGTL VTVSSSGGPA   120
LPFKSSFPPGS IWELKKDVYV VELDWYPDAP GEMVVLTCDT PEEDGITWTL DQSSEVLGSG   180
KTLTIQVKEF GDAGQYTCHK GGEVLSHSLL LLHKKEDGIW STDILKDQKE PKNKTFLRCE   240
AKNYSGRFTC WWLTTISTDL TFSVKSSRGS SDPQGVTCGA ATLSAERVRG DNKEYEYSVE   300
CQEDSACPAA EESLPIEVMV DAVHKLKYEN YTSSFFIRDI IKPDPPKNLQ LKPLKNSRQV   360
EVSWEYPDTW STPHSYFSLT FCVQVQGKSK REKKDRVFTD KTSATVICRK NASISVRAQD   420
RYYSSSWSEW ASVPCSGGGG SGGGGSGGGG SRVIPVSGPA RCLSQSRNLL KTTDDMVKTA   480
REKLKHYSCT AEDIDHEDIT RDQTSTLKTC LPLELHKNES CLATRETSST TRGSCLPPQK   540
TSLMMTLCLG SIYEDLKMYQ TEFQAINAAL QNHNHQQIIL DKGMLVAIDE LMQSLNHNGE   600
TLRQKPPVGE ADPYRVKMKL CILLHAFSTR VVTINRVMGY LSSASGGPAL FKSSFPPGSG   660
GGGSGGGGSG GGGSGGGGSG GGGSGGGGSQ SVLTQPPSVS GAPGQRVTIS CSGSRSNIGS   720
ETVKWYQQLP GTAPKLLIYY NDQRPSGVPD RFSGSKSGTS ASLAITGLQA EDEADYYCQS   780
YDRYTHPALL FGTGTKVTVL GGGGSGGGGS GGGGSGGGSQ VLVESGGGVV QPGRSLRLSC   840
CAASGFTFSS YGMHWVRQAP GKGLEWVAFI RYEGSNKYYA ESVKGRFTIS RDNSKNTLYL   900
QMNSLRAEDT AVYYCKTHGS HDNWGQGTMV TVSS                                 930

SEQ ID NO: 478          moltype = AA  length = 930
FEATURE                 Location/Qualifiers
source                  1..930
                        mol_type = protein
                        organism = synthetic construct
SEQUENCE: 478
EVQLVESGGG LVQPGNSLRL SCAASGFTFS KFGMSWVRQA PGKGLEWVSS ISGSGRDTLY    60
AESVKGRFTI SRDNAKTTLY LQMNSLRPED TAVYYCTIGG SLSVSSQGTL VTVSSSGGPA   120
LPFKSSFPPGS IWELKKDVYV VELDWYPDAP GEMVVLTCDT PEEDGITWTL DQSSEVLGSG   180
KTLTIQVKEF GDAGQYTCHK GGEVLSHSLL LLHKKEDGIW STDILKDQKE PKNKTFLRCE   240
AKNYSGRFTC WWLTTISTDL TFSVKSSRGS SDPQGVTCGA ATLSAERVRG DNKEYEYSVE   300
CQEDSACPAA EESLPIEVMV DAVHKLKYEN YTSSFFIRDI IKPDPPKNLQ LKPLKNSRQV   360
EVSWEYPDTW STPHSYFSLT FCVQVQGKSK REKKDRVFTD KTSATVICRK NASISVRAQD   420
RYYSSSWSEW ASVPCSGGGG SGGGGSGGGG SRVIPVSGPA RCLSQSRNLL KTTDDMVKTA   480
REKLKHYSCT AEDIDHEDIT RDQTSTLKTC LPLELHKNES CLATRETSST TRGSCLPPQK   540
TSLMMTLCLG SIYEDLKMYQ TEFQAINAAL QNHNHQQIIL DKGMLVAIDE LMQSLNHNGE   600
TLRQKPPVGE ADPYRVKMKL CILLHAFSTR VVTINRVMGY LSSASGGPAL FKSSFPPGSG   660
GGGSGGGGSG GGGSGGGGSG GGGSGGGGSQ SVLTQPPSVS GAPGQRVTIS CSGSRSNIGD   720
NTVKWYQQLP GTAPKLLIYY NDQRPSGVPD RFSGSKSGTS ASLAITGLQA EDEADYYCQS   780
YDRYTHPALL FGTGTKVTVL GGGGSGGGGS GGGGSGGGSQ VLVESGGGVV QPGRSLRLSC   840
CAASGFTFSS YGMHWVRQAP GKGLEWVAFI RYEGSNKYYA ESVKGRFTIS RDNSKNTLYL   900
QMNSLRAEDT AVYYCKTHGS HDNWGQGTMV TVSS                                 930

SEQ ID NO: 479          moltype = AA  length = 934
FEATURE                 Location/Qualifiers
source                  1..934
                        mol_type = protein
                        organism = synthetic construct
SEQUENCE: 479
EVQLVESGGG LVQPGNSLRL SCAASGFTFS KFGMSWVRQA PGKGLEWVSS ISGSGRDTLY    60
AESVKGRFTI SRDNAKTTLY LQMNSLRPED TAVYYCTIGG SLSVSSQGTL VTVSSSGGPA   120
LPFKSSFPPGS IWELKKDVYV VELDWYPDAP GEMVVLTCDT PEEDGITWTL DQSSEVLGSG   180
KTLTIQVKEF GDAGQYTCHK GGEVLSHSLL LLHKKEDGIW STDILKDQKE PKNKTFLRCE   240
AKNYSGRFTC WWLTTISTDL TFSVKSSRGS SDPQGVTCGA ATLSAERVRG DNKEYEYSVE   300
CQEDSACPAA EESLPIEVMV DAVHKLKYEN YTSSFFIRDI IKPDPPKNLQ LKPLKNSRQV   360
EVSWEYPDTW STPHSYFSLT FCVQVQGKSK REKKDRVFTD KTSATVICRK NASISVRAQD   420
RYYSSSWSEW ASVPCSGGGG SGGGGSGGGG SRNLPVATPD PGMFPCLHHS QNLLRAVSNM   480
LQKARQTLEF YPCTSEEIDH EDITKDKTST VEACLPLELT KNESCLNSRE TSFITNGSCL   540
ASRKTSFMMA LCLSSIYEDL KMYQVEFKTM NAKLLMDPKR QIFLDQNMLA VIDELMQALN   600
FNSETVPQKS SLEEPDFYKT KIKLCILLHA FRIRAVTIDR VMSYLNASSG GPALFKSSFP   660
PGSGGGGSGG GGSGGGGSGG GGSGGGGSGG GGSQSVLTQP PSVSGAPGQR VTISCSGSRS   720
NIGDNTVKWY QQLPGTAPKL LIYYNDQRPS GVPDRFSGSK SGTSASLAIT GLQAEDEADY   780
YCQSYDRYTH PALLFGTGTK VTVLGGGGSG GGGSGGGGSQ VQLVESGGGV VQPGRSLRLS   840
CAASGFTFSS YGMHWVRQAP GKGLEWVAFI RYEGSNKYYA ESVKGRFTIS RDNSKNTLYL   900
QMNSLRAEDT AVYYCKTHGS HDNWGQGTMV TVSS                                 934

SEQ ID NO: 480          moltype = AA  length = 930
FEATURE                 Location/Qualifiers
source                  1..930
                        mol_type = protein
                        organism = synthetic construct
SEQUENCE: 480
EVQLVESGGG LVQPGNSLRL SCAASGFTFS KFGMSWVRQA PGKGLEWVSS ISGSGRDTLY    60
AESVKGRFTI SRDNAKTTLY LQMNSLRPED TAVYYCTIGG SLSVSSQGTL VTVSSSGGPA   120
LPFKSSFPPGS IWELKKDVYV VELDWYPDAP GEMVVLTCDT PEEDGITWTL DQSSEVLGSG   180
KTLTIQVKEF GDAGQYTCHK GGEVLSHSLL LLHKKEDGIW STDILKDQKE PKNKTFLRCE   240
AKNYSGRFTC WWLTTISTDL TFSVKSSRGS SDPQGVTCGA ATLSAERVRG DNKEYEYSVE   300
CQEDSACPAA EESLPIEVMV DAVHKLKYEN YTSSFFIRDI IKPDPPKNLQ LKPLKNSRQV   360
```

```
EVSWEYPDTW STPHSYFSLT FCVQVQGKSK REKKDRVFTD KTSATVICRK NASISVRAQD    420
RYYSSSWSEW ASVPCSGGGG SGGGGSGGGG SRVIPVSGPA RCLSQSRNLL KTTDDMVKTA    480
REKLKHYSCT AEDIDHEDIT RDQTSTLKTC LPLELHKNES CLATRETSST TRGSCLPPQK    540
TSLMMTLCLG SIYEDLKMYQ TEFQAINAAL QNHNHQQIIL DKGMLVAIDE LMQSLNHNGE    600
TLRQKPPVGE ADPYRVKMKL CILLHAFSTR VVTINRVMGY LSSASGGPAL FKSSFPPGSG    660
GGGSGGGGSG GGGSGGGGSG GGGSGGGGSQ SVLTQPPSVS GAPGQRVTIS CSGSRSNIGD    720
ETVKWYQQLP GTAPKLLIYY NDQRPSGVPD RFSGSKSGTS ASLAITGLQA EDEADYYCQS    780
YDRYTHPALL FGTGTKVTVL GGGGSGGGGS GGGGSQVQLV ESGGGVVQPG RSLRLSCAAS    840
GFTFSSYGMH WVRQAPGKGL EWVAFIRYDG SNKYYADSVK GRFTISRDNS KNTLYLQMNS    900
LRAEDTAVYY CKTHGSHDNW GQGTMVTVSS                                    930

SEQ ID NO: 481          moltype = AA  length = 934
FEATURE                 Location/Qualifiers
source                  1..934
                        mol_type = protein
                        organism = synthetic construct
SEQUENCE: 481
EVQLVESGGG LVQPGNSLRL SCAASGFTFS KFGMSWVRQA PGKGLEWVSS ISGSGRDTLY     60
AESVKGRFTI SRDNAKTTLY LQMNSLRPED TAVYYCTIGG SLSVSSQGTL VTVSSSGGPA    120
LFKSSFPPGS IWELKKDVYV VELDWYPDAP GEMVVLTCDT PEEDGITWTL DQSSEVLGSG    180
KTLTIQVKEF GDAGQYTCHK GGEVLSHSLL LLHKKEDGIW STDILKDQKE PKNKTFLRCE    240
AKNYSGRFTC WWLTTISTDL TFSVKSSRGS SDPQGVTCGA ATLSAERVRG DNKEYEYSVE    300
CQEDSACPAA EESLPIEVMV DAVHKLKYEN YTSSFFIRDI IKPDPPKNLQ LKPLKNSRQV    360
EVSWEYPDTW STPHSYFSLT FCVQVQGKSK REKKDRVFTD KTSATVICRK NASISVRAQD    420
RYYSSSWSEW ASVPCSGGGG SGGGGSGGGG SRNLPVATPD PGMFPCLHHS QNLLRAVSNM    480
LQKARQTLEF YPCTSEEIDH EDITKDKTST VEACLPIEVM VIDELMQALN               540
ASRKTSFMMA LCLSSIYEDL KMYQVEFKTM NAKLLMDPKR QIFLDQNMLA VIDELMQALN    600
FNSETVPQKS SLEEPDFYKT KIKLCILLHA FRIRAVTIDR VMSYLNASSG GPALFKSSFP    660
PGSGGGGSGG GGSGGGGSGG GGSGGGGSGG GGSQSVLTQP PSVSGAPGQR VTISCSGSRS    720
NIGDETVKWY QQLPGTAPKL LIYYNDQRPS GVPDRFSGSK SGTSASLAIT GLQAEDEADY    780
YCQSYDRYTH PALLFGTGTK VTVLGGGGSG GGGSGGGGSQ VQLVESGGGV VQPGRSLRLS    840
CAASGFTFSS YGMHWVRQAP GKGLEWVAFI RYDGSNKYYA DSVKGRFTIS RDNSKNTLYL    900
QMNSLRAEDT AVYYCKTHGS HDNWGQGTMV TVSS                               934

SEQ ID NO: 482          moltype = AA  length = 930
FEATURE                 Location/Qualifiers
source                  1..930
                        mol_type = protein
                        organism = synthetic construct
SEQUENCE: 482
EVQLVESGGG LVQPGNSLRL SCAASGFTFS KFGMSWVRQA PGKGLEWVSS ISGSGRDTLY     60
AESVKGRFTI SRDNAKTTLY LQMNSLRPED TAVYYCTIGG SLSVSSQGTL VTVSSSGGPA    120
LFKSSFPPGS IWELKKDVYV VELDWYPDAP GEMVVLTCDT PEEDGITWTL DQSSEVLGSG    180
KTLTIQVKEF GDAGQYTCHK GGEVLSHSLL LLHKKEDGIW STDILKDQKE PKNKTFLRCE    240
AKNYSGRFTC WWLTTISTDL TFSVKSSRGS SDPQGVTCGA ATLSAERVRG DNKEYEYSVE    300
CQEDSACPAA EESLPIEVMV DAVHKLKYEN YTSSFFIRDI IKPDPPKNLQ LKPLKNSRQV    360
EVSWEYPDTW STPHSYFSLT FCVQVQGKSK REKKDRVFTD KTSATVICRK NASISVRAQD    420
RYYSSSWSEW ASVPCSGGGG SGGGGSGGGG SRVIPVSGPA RCLSQSRNLL KTTDDMVKTA    480
REKLKHYSCT AEDIDHEDIT RDQTSTLKTC LPLELHKNES CLATRETSST TRGSCLPPQK    540
TSLMMTLCLG SIYEDLKMYQ TEFQAINAAL QNHNHQQIIL DKGMLVAIDE LMQSLNHNGE    600
TLRQKPPVGE ADPYRVKMKL CILLHAFSTR VVTINRVMGY LSSASGGPAL FKSSFPPGSG    660
GGGSGGGGSG GGGSGGGGSG GGGSGGGGSQ SVLTQPPSVS GAPGQRVTIS CSGSRSNIGD    720
ETVKWYQQLP GTAPKLLIYY NDQRPSGVPD RFSGSKSGTS ASLAITGLQA EDEADYYCQS    780
YDRYTHPALL FGTGTKVTVL GGGGSGGGGS GGGGSQVQLV ESGGGVVQPG RSLRLSCAAS    840
GFTFSSYGMH WVRQAPGKGL EWVAFIRYEG SNKYYAESVK GRFTISRDNS KNTLYLQMNS    900
LRAEDTAVYY CKTHGSHDNW GQGTMVTVSS                                    930

SEQ ID NO: 483          moltype = AA  length = 934
FEATURE                 Location/Qualifiers
source                  1..934
                        mol_type = protein
                        organism = synthetic construct
SEQUENCE: 483
EVQLVESGGG LVQPGNSLRL SCAASGFTFS KFGMSWVRQA PGKGLEWVSS ISGSGRDTLY     60
AESVKGRFTI SRDNAKTTLY LQMNSLRPED TAVYYCTIGG SLSVSSQGTL VTVSSSGGPA    120
LFKSSFPPGS IWELKKDVYV VELDWYPDAP GEMVVLTCDT PEEDGITWTL DQSSEVLGSG    180
KTLTIQVKEF GDAGQYTCHK GGEVLSHSLL LLHKKEDGIW STDILKDQKE PKNKTFLRCE    240
AKNYSGRFTC WWLTTISTDL TFSVKSSRGS SDPQGVTCGA ATLSAERVRG DNKEYEYSVE    300
CQEDSACPAA EESLPIEVMV DAVHKLKYEN YTSSFFIRDI IKPDPPKNLQ LKPLKNSRQV    360
EVSWEYPDTW STPHSYFSLT FCVQVQGKSK REKKDRVFTD KTSATVICRK NASISVRAQD    420
RYYSSSWSEW ASVPCSGGGG SGGGGSGGGG SRNLPVATPD PGMFPCLHHS QNLLRAVSNM    480
LQKARQTLEF YPCTSEEIDH EDITKDKTST VEACLPLELT KNESCLNSRE TSFITNGSCL    540
ASRKTSFMMA LCLSSIYEDL KMYQVEFKTM NAKLLMDPKR QIFLDQNMLA VIDELMQALN    600
FNSETVPQKS SLEEPDFYKT KIKLCILLHA FRIRAVTIDR VMSYLNASSG GPALFKSSFP    660
PGSGGGGSGG GGSGGGGSGG GGSGGGGSGG GGSQSVLTQP PSVSGAPGQR VTISCSGSRS    720
NIGDETVKWY QQLPGTAPKL LIYYNDQRPS GVPDRFSGSK SGTSASLAIT GLQAEDEADY    780
YCQSYDRYTH PALLFGTGTK VTVLGGGGSG GGGSGGGGSQ VQLVESGGGV VQPGRSLRLS    840
CAASGFTFSS YGMHWVRQAP GKGLEWVAFI RYEGSNKYYA ESVKGRFTIS RDNSKNTLYL    900
QMNSLRAEDT AVYYCKTHGS HDNWGQGTMV TVSS                               934
```

```
SEQ ID NO: 484          moltype = AA  length = 930
FEATURE                 Location/Qualifiers
source                  1..930
                        mol_type = protein
                        organism = synthetic construct
SEQUENCE: 484
EVQLVESGGG LVQPGNSLRL SCAASGFTFS KFGMSWVRQA PGKGLEWVSS ISGSGRDTLY    60
AESVKGRFTI SRDNAKTTLY LQMNSLRPED TAVYYCTIGG SLSVSSQGTL VTVSSSGGPA   120
LFKSSFPPGS IWELKKDVYV VELDWYPDAP GEMVVLTCDT PEEDGITWTL DQSSEVLGSG   180
KTLTIQVKEF GDAGQYTCHK GGEVLSHSLL LLHKKEDGIW STDILKDQKE PKNKTFLRCE   240
AKNYSGRFTC WWLTTISTDL TFSVKSSRGS SDPQGVTCGA ATLSAERVRG DNKEYEYSVE   300
CQEDSACPAA EESLPIEVMV DAVHKLKYEN YTSSFFIRDI IKPDPPKNLQ LKPLKNSRQV   360
EVSWEYPDTW STPHSYFSLT FCVQVQGKSK REKKDRVFTD KTSATVICRK NASISVRAQD   420
RYYSSSWSEW ASVPCSGGGG SGGGGSGGGG SRVIPVSGPA RCLSQSRNLL KTTDDMVKTA   480
REKLKHYSCT AEDIDHEDIT RDQTSTLKTC LPLELHKNES CLATRETSST TRGSCLPPQK   540
TSLMMTLCLG SIYEDLKMYQ TEFQAINAAL QNHNHQQIIL DKGMLVAIDE LMQSLNHNGE   600
TLRQKPPVGE ADPYRVKMKL CILLHAFSTR VVTINRVMGY LSSASGGPAL FKSSFPPGSG   660
GGGSGGGSG GGGSGGGGSG GGGSGGGSQ SVLTQPPSVS GAPGQRVTIS CSGSESNIGS    720
NDVKWYQQLP GTAPKLLIYY NDQRPSGVPD RFSGSKSGTS ASLAITGQLA EDEADYYCQS   780
YDRYTHPALL FGTGTKVTVL GGGGSGGGGS GGGGSQVQLV ESGGGVVQPG RSLRLSCAAS   840
GPTFSSYGMH WVRQAPGKGL EWVAFIRYDG SNKYYADSVK GRFTISRDNS KNTLYLQMNS   900
LRAEDTAVYY CKTHGSHDNW GQGTMVTVSS                                   930

SEQ ID NO: 485          moltype = AA  length = 934
FEATURE                 Location/Qualifiers
source                  1..934
                        mol_type = protein
                        organism = synthetic construct
SEQUENCE: 485
EVQLVESGGG LVQPGNSLRL SCAASGFTFS KFGMSWVRQA PGKGLEWVSS ISGSGRDTLY    60
AESVKGRFTI SRDNAKTTLY LQMNSLRPED TAVYYCTIGG SLSVSSQGTL VTVSSSGGPA   120
LFKSSFPPGS IWELKKDVYV VELDWYPDAP GEMVVLTCDT PEEDGITWTL DQSSEVLGSG   180
KTLTIQVKEF GDAGQYTCHK GGEVLSHSLL LLHKKEDGIW STDILKDQKE PKNKTFLRCE   240
AKNYSGRFTC WWLTTISTDL TFSVKSSRGS SDPQGVTCGA ATLSAERVRG DNKEYEYSVE   300
CQEDSACPAA EESLPIEVMV DAVHKLKYEN YTSSFFIRDI IKPDPPKNLQ LKPLKNSRQV   360
EVSWEYPDTW STPHSYFSLT FCVQVQGKSK REKKDRVFTD KTSATVICRK NASISVRAQD   420
RYYSSSWSEW ASVPCSGGGG SGGGGSGGGG SRNLPLPSPD PGMFPCLHHS QNLLRAVSNM   480
LQKARQTLEF YPCTSEEIDH EDITKDTKST VEACLPLELT KNESCLNSRE TSFITNGSCL   540
ASRKTSFMMA LCLSSIYEDL KMYQVEFKTM NAKLLMDPKR QIFLDQNMLA VIDELMQALN   600
FNSETVPQKS SLEEPDFYKT KIKLCILLHA FRIRAVTIDR VMSYLNASSG GPALFKSSFP   660
PGSGGGGSGG GGSGGGGSGG GGSGGGGSGG GGSQSVLTQP PSVSGAPGQR VTISCSGSES   720
NIGSNDVKWY QQLPGTAPKL LIYYNDQRPS GVPDRFSGSK SGTSASLAIT GLQAEDEADY   780
YCQSYDRYTH PALLFGTGTK VTVLGGGGSG GGGSGGGGSQ VQLVESGGGV VQPGRSLRLS   840
CAASGFTFSS YGMHWVRQAP GKGLEWVAFI RYDGSNKYYA DSVKGRFTIS RDNSKNTLYL   900
QMNSLRAEDT AVYYCKTHGS HDNWGQGTMV TVSS                              934

SEQ ID NO: 486          moltype = AA  length = 930
FEATURE                 Location/Qualifiers
source                  1..930
                        mol_type = protein
                        organism = synthetic construct
SEQUENCE: 486
EVQLVESGGG LVQPGNSLRL SCAASGFTFS KFGMSWVRQA PGKGLEWVSS ISGSGRDTLY    60
AESVKGRFTI SRDNAKTTLY LQMNSLRPED TAVYYCTIGG SLSVSSQGTL VTVSSSGGPA   120
LFKSSFPPGS IWELKKDVYV VELDWYPDAP GEMVVLTCDT PEEDGITWTL DQSSEVLGSG   180
KTLTIQVKEF GDAGQYTCHK GGEVLSHSLL LLHKKEDGIW STDILKDQKE PKNKTFLRCE   240
AKNYSGRFTC WWLTTISTDL TFSVKSSRGS SDPQGVTCGA ATLSAERVRG DNKEYEYSVE   300
CQEDSACPAA EESLPIEVMV DAVHKLKYEN YTSSFFIRDI IKPDPPKNLQ LKPLKNSRQV   360
EVSWEYPDTW STPHSYFSLT FCVQVQGKSK REKKDRVFTD KTSATVICRK NASISVRAQD   420
RYYSSSWSEW ASVPCSGGGG SGGGGSGGGG SRVIPVSGPA RCLSQSRNLL KTTDDMVKTA   480
REKLKHYSCT AEDIDHEDIT RDQTSTLKTC LPLELHKNES CLATRETSST TRGSCLPPQK   540
TSLMMTLCLG SIYEDLKMYQ TEFQAINAAL QNHNHQQIIL DKGMLVAIDE LMQSLNHNGE   600
TLRQKPPVGE ADPYRVKMKL CILLHAFSTR VVTINRVMGY LSSASGGPAL FKSSFPPGSG   660
GGGSGGGSG GGGSGGGGSG GGGSGGGSQ SVLTQPPSVS GAPGQRVTIS CSGSRSNIGE    720
NTVKWYQQLP GTAPKLLIYY NDQRPSGVPD RFSGSKSGTS ASLAITGQLA EDEADYYCQS   780
YDRYTHPALL FGTGTKVTVL GGGGSGGGGS GGGGSQVQLV ESGGGVVQPG RSLRLSCAAS   840
GFTFSSYGMH WVRQAPGKGL EWVAFIRYEG SNKYYAESVK GRFTISRDNS KNTLYLQMNS   900
LRAEDTAVYY CKTHGSHDNW GQGTMVTVSS                                   930

SEQ ID NO: 487          moltype = AA  length = 934
FEATURE                 Location/Qualifiers
source                  1..934
                        mol_type = protein
                        organism = synthetic construct
SEQUENCE: 487
EVQLVESGGG LVQPGNSLRL SCAASGFTFS KFGMSWVRQA PGKGLEWVSS ISGSGRDTLY    60
AESVKGRFTI SRDNAKTTLY LQMNSLRPED TAVYYCTIGG SLSVSSQGTL VTVSSSGGPA   120
LFKSSFPPGS IWELKKDVYV VELDWYPDAP GEMVVLTCDT PEEDGITWTL DQSSEVLGSG   180
```

```
KTLTIQVKEF GDAGQYTCHK GGEVLSHSLL LLHKKEDGIW STDILKDQKE PKNKTFLRCE    240
AKNYSGRFTC WWLTTISTDL TFSVKSSRGS SDPQGVTCGA ATLSAERVRG DNKEYEYSVE    300
CQEDSACPAA EESLPIEVMV DAVHKLKYEN YTSSFFIRDI IKPDPPKNLQ LKPLKNSRQV    360
EVSWEYPDTW STPHSYFSLT FCVQVQGKSK REKKDRVFTD KTSATVICRK NASISVRAQD    420
RYYSSSWSEW ASVPCSGGGG SGGGGSGGGG SRNLPVATPD PGMFPCLHHS QNLLRAVSNM    480
LQKARQTLEF YPCTSEEIDH EDITKDKTST VEACLPLELT KNESCLNSRE TSFITNGSCL    540
ASRKTSFMMA LCLSSIYEDL KMYQVEFKTM NAKLLMDPKR QIFLDQNMLA VIDELMQALN    600
FNSETVPQKS SLEEPDFYKT KIKLCILLHA FRIRAVTIDR VMSYLNASSG GPALFKSSFP    660
PGSGGGGSGG GGSGGGGSGG GGSQSVLTQP PSVSGAPGQR VTISCSGSRS              720
NIGENTVKWY QQLPGTAPKL LIYYNDQRPS GVPDRFSGSK SGTSASLAIT GLQAEDEADY    780
YCQSYDRYTH PALLFGTGTK VTVLGGGGSG GGGSGGGGSQ VQLVESGGGV VQPGRSLRLS    840
CAASGFTFSS YGMHWVRQAP GKGLEWVAFI RYEGSNKYYA ESVKGRFTIS RDNSKNTLYL    900
QMNSLRAEDT AVYYCKTHGS HDNWGQGTMV TVSS                               934

SEQ ID NO: 488          moltype = AA   length = 930
FEATURE                 Location/Qualifiers
source                  1..930
                        mol_type = protein
                        organism = synthetic construct
SEQUENCE: 488
EVQLVESGGG LVQPGNSLRL SCAASGFTFS KFGMSWVRQA PGKGLEWVSS ISGSGRDTLY     60
AESVKGRFTI SRDNAKTTLY LQMNSLRPED TAVYYCTIGG SLSVSSQGTL VTVSSSGGPA    120
LFKSSFPPGS IWELKKDVYV VELDWYPDAP GEMVVLTCDT PEEDGITWTL DQSSEVLGSG    180
KTLTIQVKEF GDAGQYTCHK GGEVLSHSLL LLHKKEDGIW STDILKDQKE PKNKTFLRCE    240
AKNYSGRFTC WWLTTISTDL TFSVKSSRGS SDPQGVTCGA ATLSAERVRG DNKEYEYSVE    300
CQEDSACPAA EESLPIEVMV DAVHKLKYEN YTSSFFIRDI IKPDPPKNLQ LKPLKNSRQV    360
EVSWEYPDTW STPHSYFSLT FCVQVQGKSK REKKDRVFTD KTSATVICRK NASISVRAQD    420
RYYSSSWSEW ASVPCSGGGG SGGGGSGGGG SRVIPVSGPA RCLSQSRNLL KTTDDMVKTA    480
REKLKHYSCT AEDIDHEDIT RDQTSTLKTC LPLELHKNES CLATRETSST TRGSCLPPQK    540
TSLMMTLCLG SIYEDLKMYQ TEFQAINAAL QNHNHQQIIL DKGMLVAIDE LMQSLNHNGE    600
TLRQKPPVGE ADPYRVKMKL CILLHAFSTR VVTINRVMGY LSSASGGPAL FKSSFPPGSG    660
GGGSGGGGSG GGSGGGGSG GGSGGGGSQ SVLTQPPSVS GAPGQRVTIS CSGSRSNIGE      720
ETVKWYQQLP GTAPKLLIYY NDQRPSGVPD RFSGSKSGTS ASLAITGLQA EDEADYYCQS    780
YDRYTHPALL FGTGTKVTVL GGGGSGGGGS GGGGSQVLVT ESGGGVVQPG RSLRLSCAAS    840
GFTFSSYGMH WVRQAPGKGL EWVAFIRYDG SNKYYADSVK GRFTISRDNS KNTLYLQMNS    900
LRAEDTAVYY CKTHGSHDNW GQGTMVTVSS                                    930

SEQ ID NO: 489          moltype = AA   length = 934
FEATURE                 Location/Qualifiers
source                  1..934
                        mol_type = protein
                        organism = synthetic construct
SEQUENCE: 489
EVQLVESGGG LVQPGNSLRL SCAASGFTFS KFGMSWVRQA PGKGLEWVSS ISGSGRDTLY     60
AESVKGRFTI SRDNAKTTLY LQMNSLRPED TAVYYCTIGG SLSVSSQGTL VTVSSSGGPA    120
LFKSSFPPGS IWELKKDVYV VELDWYPDAP GEMVVLTCDT PEEDGITWTL DQSSEVLGSG    180
KTLTIQVKEF GDAGQYTCHK GGEVLSHSLL LLHKKEDGIW STDILKDQKE PKNKTFLRCE    240
AKNYSGRFTC WWLTTISTDL TFSVKSSRGS SDPQGVTCGA ATLSAERVRG DNKEYEYSVE    300
CQEDSACPAA EESLPIEVMV DAVHKLKYEN YTSSFFIRDI IKPDPPKNLQ LKPLKNSRQV    360
EVSWEYPDTW STPHSYFSLT FCVQVQGKSK REKKDRVFTD KTSATVICRK NASISVRAQD    420
RYYSSSWSEW ASVPCSGGGG SGGGGSGGGG SRNLPVATPD PGMFPCLHHS QNLLRAVSNM    480
LQKARQTLEF YPCTSEEIDH EDITKDKTST VEACLPLELT KNESCLNSRE TSFITNGSCL    540
ASRKTSFMMA LCLSSIYEDL KMYQVEFKTM NAKLLMDPKR QIFLDQNMLA VIDELMQALN    600
FNSETVPQKS SLEEPDFYKT KIKLCILLHA FRIRAVTIDR VMSYLNASSG GPALFKSSFP    660
PGSGGGGSGG GGSGGGGSGG GGSQSVLTQP PSVSGAPGQR VTISCSGSRS              720
NIGEETVKWY QQLPGTAPKL LIYYNDQRPS GVPDRFSGSK SGTSASLAIT GLQAEDEADY    780
YCQSYDRYTH PALLFGTGTK VTVLGGGGSG GGGSGGGGSQ VQLVESGGGV VQPGRSLRLS    840
CAASGFTFSS YGMHWVRQAP GKGLEWVAFI RYDGSNKYYA DSVKGRFTIS RDNSKNTLYL    900
QMNSLRAEDT AVYYCKTHGS HDNWGQGTMV TVSS                               934

SEQ ID NO: 490          moltype = AA   length = 930
FEATURE                 Location/Qualifiers
source                  1..930
                        mol_type = protein
                        organism = synthetic construct
SEQUENCE: 490
EVQLVESGGG LVQPGNSLRL SCAASGFTFS KFGMSWVRQA PGKGLEWVSS ISGSGRDTLY     60
AESVKGRFTI SRDNAKTTLY LQMNSLRPED TAVYYCTIGG SLSVSSQGTL VTVSSSGGPA    120
LFKSSFPPGS IWELKKDVYV VELDWYPDAP GEMVVLTCDT PEEDGITWTL DQSSEVLGSG    180
KTLTIQVKEF GDAGQYTCHK GGEVLSHSLL LLHKKEDGIW STDILKDQKE PKNKTFLRCE    240
AKNYSGRFTC WWLTTISTDL TFSVKSSRGS SDPQGVTCGA ATLSAERVRG DNKEYEYSVE    300
CQEDSACPAA EESLPIEVMV DAVHKLKYEN YTSSFFIRDI IKPDPPKNLQ LKPLKNSRQV    360
EVSWEYPDTW STPHSYFSLT FCVQVQGKSK REKKDRVFTD KTSATVICRK NASISVRAQD    420
RYYSSSWSEW ASVPCSGGGG SGGGGSGGGG SRVIPVSGPA RCLSQSRNLL KTTDDMVKTA    480
REKLKHYSCT AEDIDHEDIT RDQTSTLKTC LPLELHKNES CLATRETSST TRGSCLPPQK    540
TSLMMTLCLG SIYEDLKMYQ TEFQAINAAL QNHNHQQIIL DKGMLVAIDE LMQSLNHNGE    600
TLRQKPPVGE ADPYRVKMKL CILLHAFSTR VVTINRVMGY LSSASGGPAL FKSSFPPGSG    660
GGGSGGGGSG GGGSGGGGSG GGSGGGGSQ SVLTQPPSVS GAPGQRVTIS CSGSRSNIGS     720
ETVKWYQQLP GTAPKLLIYY NDQRPSGVPD RFSGSKSGTS ASLAITGLQA EDEADYYCQS    780
```

```
YDRYTHPALL FGTGTKVTVL GGGGSGGGGS GGGGSQVQLV ESGGGVVQPG RSLRLSCAAS   840
GFTFSSYGMH WVRQAPGKGL EWVAFIRYEG SNKYYADSVK GRFTISRDNS KNTLYLQMNS   900
LRAEDTAVYY CKTHGSHDNW GQGTMVTVSS                                   930

SEQ ID NO: 491           moltype = AA   length = 934
FEATURE                  Location/Qualifiers
source                   1..934
                         mol_type = protein
                         organism = synthetic construct
SEQUENCE: 491
EVQLVESGGG LVQPGNSLRL SCAASGFTFS KFGMSWVRQA PGKGLEWVSS ISGSGRDTLY    60
AESVKGRFTI SRDNAKTTLY LQMNSLRPED TAVYYCTIGG SLSVSSQGTL VTVSSSGGPA   120
LFKSSFPPGS IWELKKDVYV VELDWYPDAP GEMVVLTCDT PEEDGITWTL DQSSEVLGSG   180
KTLTIQVKEF GDAGQYTCHK GGEVLSHSLL LLHKKEDGIW STDILKDQKE PKNKTFLRCE   240
AKNYSGRFTC WWLTTISTDL TFSVKSSRGS SDPQGVTCGA ATLSAERVRG DNKEYEYSVE   300
CQEDSACPAA EESLPIEVMV DAVHKLKYEN YTSSFFIRDI IKPDPPKNLQ LKPLKNSRQV   360
EVSWEYPDTW STPHSYFSLT FCVQVQGKSK REKKDRVFTD KTSATVICRK NASISVRAQD   420
RYYSSSWSEW ASVPCSGGGG SGGGGSGGGG SRNLPVATPD PGMFPCLHHS QNLLRAVSNM   480
LQKARQTLEF YPCTSEEIDH EDITKDKTST VEACLPLELT KNESCLNSRE TSFITNGSCL   540
ASRKTSFMMA LCLSSIYEDL KMYQVEFKTM NAKLLMDPKR QIFLDQNMLA VIDELMQALN   600
FNSETVPQKS SLEEPDFYKT KIKLCILLHA FRIRAVTIDR VMSYLNASSG GPALFKSSFP   660
PGSGGGGSGG GGSGGGGSGG GGSQSVLTQP PSVSGAPGQR VTISCSGSRS   720
NIGSETVKWY QQLPGTAPKL LIYYNDQRPS GVPDRFSGSK SGTSASLAIT GLQAEDEADY   780
YCQSYDRYTH PALLFGTGTK VTVLGGGGSG GGGSGGGGSQ VQLVESGGGV VQPGRSLRLS   840
CAASGFTFSS YGMHWVRQAP GKGLEWVAFI RYEGSNKYYA DSVKGRFTIS RDNSKNTLYL   900
QMNSLRAEDT AVYYCKTHGS HDNWGQGTMV TVSS                              934

SEQ ID NO: 492           moltype = AA   length = 906
FEATURE                  Location/Qualifiers
source                   1..906
                         mol_type = protein
                         organism = synthetic construct
SEQUENCE: 492
EVQLVESGGG LVQPGNSLRL SCAASGFTFS KFGMSWVRQA PGKGLEWVSS ISGSGRDTLY    60
AESVKGRFTI SRDNAKTTLY LQMNSLRPED TAVYYCTIGG SLSVSSQGTL VTVSSSGGPG   120
PAGLYAQPGS IWELKKDVYV VELDWYPDAP GEMVVLTCDT PEEDGITWTL DQSSEVLGSG   180
KTLTIQVKEF GDAGQYTCHK GGEVLSHSLL LLHKKEDGIW STDILKDQKE PKNKTFLRCE   240
AKNYSGRFTC WWLTTISTDL TFSVKSSRGS SDPQGVTCGA ATLSAERVRG DNKEYEYSVE   300
CQEDSACPAA EESLPIEVMV DAVHKLKYEN YTSSFFIRDI IKPDPPKNLQ LKPLKNSRQV   360
EVSWEYPDTW STPHSYFSLT FCVQVQGKSK REKKDRVFTD KTSATVICRK NASISVRAQD   420
RYYSSSWSEW ASVPCSGGGG SGGGGSGGGG SRVIPVSGPA RCLSQSRNLL KTTDDMVKTA   480
REKLKHYSCT AEDIDHEDIT RDQTSTLKTC LPLELHKNES CLATRETSST TRGSCLPPQK   540
TSLMMTLCLG SIYEDLKMYQ TEFQAINAAL NNHHQQIIL DKGMLVAIDE LMQSLNHNGE   600
TLRQKPPVGE ADPYRVKMKL CILLHAFSTR VVTINRVMGY LSSASGGPGP AGLYAQPGSG   660
GGGSGGGGSG GGGSGGGGSG GGGSGGGGSQ SVLTQPPSVS GAPGQRVTIS CSGSRSNIGS   720
NTVKWYQQLP GTAPKLLIYY NDQRPSGVPD RFSGSKSGTS ASLAITGLQA EDEADYYCQS   780
YDRYTHPALL FGTGTKVTVL GQPKAAPSVT LFPPSSEELQ ANKATLVCLI SDFYPGAVTV   840
AWKADSSPVK AGVETTTPSK QSNNKYAASS YLSLTPEQWK SHRSYSCQVT HEGSTVEKTV   900
APTECS                                                             906

SEQ ID NO: 493           moltype = AA   length = 910
FEATURE                  Location/Qualifiers
source                   1..910
                         mol_type = protein
                         organism = synthetic construct
SEQUENCE: 493
EVQLVESGGG LVQPGNSLRL SCAASGFTFS KFGMSWVRQA PGKGLEWVSS ISGSGRDTLY    60
AESVKGRFTI SRDNAKTTLY LQMNSLRPED TAVYYCTIGG SLSVSSQGTL VTVSSSGGPG   120
PAGLYAQPGS IWELKKDVYV VELDWYPDAP GEMVVLTCDT PEEDGITWTL DQSSEVLGSG   180
KTLTIQVKEF GDAGQYTCHK GGEVLSHSLL LLHKKEDGIW STDILKDQKE PKNKTFLRCE   240
AKNYSGRFTC WWLTTISTDL TFSVKSSRGS SDPQGVTCGA ATLSAERVRG DNKEYEYSVE   300
CQEDSACPAA EESLPIEVMV DAVHKLKYEN YTSSFFIRDI IKPDPPKNLQ LKPLKNSRQV   360
EVSWEYPDTW STPHSYFSLT FCVQVQGKSK REKKDRVFTD KTSATVICRK NASISVRAQD   420
RYYSSSWSEW ASVPCSGGGG SGGGGSGGGG SRNLPVATPD PGMFPCLHHS QNLLRAVSNM   480
LQKARQTLEF YPCTSEEIDH EDITKDKTST VEACLPLELT KNESCLNSRE TSFITNGSCL   540
ASRKTSFMMA LCLSSIYEDL KMYQVEFKTM NAKLLMDPKR QIFLDQNMLA VIDELMQALN   600
FNSETVPQKS SLEEPDFYKT KIKLCILLHA FRIRAVTIDR VMSYLNASSG GPGPAGLYAQ   660
PGSGGGGSGG GGSGGGGSGG GGSGGGGSGG GGSQSVLTQP PSVSGAPGQR VTISCSGSRS   720
NIGSNTVKWY QQLPGTAPKL LIYYNDQRPS GVPDRFSGSK SGTSASLAIT GLQAEDEADY   780
YCQSYDRYTH PALLFGTGTK VTVLGQPKAA PSVTLFPPSS EELQANKATL VCLISDFYPG   840
AVTVAWKADS SPVKAGVETT TPSKQSNNKY AASSYLSLTP EQWKSHRSYS CQVTHEGSTV   900
EKTVAPTECS                                                         910

SEQ ID NO: 494           moltype = AA   length = 906
FEATURE                  Location/Qualifiers
source                   1..906
                         mol_type = protein
                         organism = synthetic construct
SEQUENCE: 494
```

```
EVQLVESGGG LVQPGNSLRL SCAASGFTFS KFGMSWVRQA PGKGLEWVSS ISGSGRDTLY    60
AESVKGRFTI SRDNAKTTLY LQMNSLRPED TAVYYCTIGG SLSVSSQGTL VTVSSSGGPG   120
PAGLYAQPGS IWELKKDVYV VELDWYPDAP GEMVVLTCDT PEEDGITWTL DQSSEVLGSG   180
KTLTIQVKEF GDAGQYTCHK GGEVLSHSLL LLHKKEDGIW STDILKDQKE PKNKTFLRCE   240
AKNYSGRFTC WWLTTISTDL TFSVKSSRGS SDPQGVTCGA ATLSAERVRG DNKEYEYSVE   300
CQEDSACPAA EESLPIEVMV DAVHKLKYEN YTSSFFIRDI IKPDPPKNLQ LKPLKNSRQV   360
EVSWEYPDTW STPHSYFSLT FCVQVQGKSK REKKDRVFTD KTSATVICRK NASISVRAQD   420
RYYSSSWSEW ASVPCSGGGG SGGGGSGGGG SRVIPVSGPA RCLSQSRNLL KTTDDMVKTA   480
REKLKHYSCT AEDIDHEDIT RDQTSTLKTC LPLELHKNES CLATRETSST TRGSCLPPQK   540
TSLMMTLCLG SIYEDLKMYQ TEFQAINAAL QNHNHQQIIL DKGMLVAIDE LMQSLNHNGE   600
TLRQKPPVGE ADPYRVKMKL CILLHAFSTR VVTINRVMGY LSSASGGPGP AGLYAQPGSG   660
GGGSGGGGSG GGGSGGGGSG GGGSGGGSQ SVLTQPPSVS GAPGQRVTIS CSGSRSNIGS   720
ETVKWYQQLP GTAPKLLIYY NDQRPSGVPD RFSGSKSGTS ASLAITGLQA EDEADYYCQS   780
YDRYTHPALL FGTGTKVTVL GQPKAAPSVT LFPPSSEELQ ANKATLVCLI SDFYPGAVTV   840
AWKADSSPVK AGVETTTPSK QSNNKYAASS YLSLTPEQWK SHRSYSCQVT HEGSTVEKTV   900
APTECS                                                              906

SEQ ID NO: 495          moltype = AA  length = 910
FEATURE                 Location/Qualifiers
source                  1..910
                        mol_type = protein
                        organism = synthetic construct
SEQUENCE: 495
EVQLVESGGG LVQPGNSLRL SCAASGFTFS KFGMSWVRQA PGKGLEWVSS ISGSGRDTLY    60
AESVKGRFTI SRDNAKTTLY LQMNSLRPED TAVYYCTIGG SLSVSSQGTL VTVSSSGGPG   120
PAGLYAQPGS IWELKKDVYV VELDWYPDAP GEMVVLTCDT PEEDGITWTL DQSSEVLGSG   180
KTLTIQVKEF GDAGQYTCHK GGEVLSHSLL LLHKKEDGIW STDILKDQKE PKNKTFLRCE   240
AKNYSGRFTC WWLTTISTDL TFSVKSSRGS SDPQGVTCGA ATLSAERVRG DNKEYEYSVE   300
CQEDSACPAA EESLPIEVMV DAVHKLKYEN YTSSFFIRDI IKPDPPKNLQ LKPLKNSRQV   360
EVSWEYPDTW STPHSYFSLT FCVQVQGKSK REKKDRVFTD KTSATVICRK NASISVRAQD   420
RYYSSSWSEW ASVPCSGGGG SGGGGSGGGG SRNLPVATPD PGMFPCLHHS QNLLRAVSNM   480
LQKARQTLEF YPCTSEEIDH EDITKDKTST VEACLPLELT KNESCLNSRE TSFITNGSCL   540
ASRKTSFMMA LCLSSIYEDL KMYQVEFKTM NAKLLMDPKR QIFLDQNMLA VIDELMQALN   600
FNSETVPQKS SLEEPDFYKT KIKLCILLHA FRIRAVTIDR VMSYLNASSG GPGPAGLYAQ   660
PGSGGGGSGG GGSGGGGSGG GGSGGGGSGG GGSQSVLTQP PSVSGAPGQR VTISCSGSRS   720
NIGSETVKWY QQLPGTAPKL LIYYNDQRPS GVPDRFSGSK SGTSASLAIT GLQAEDEADY   780
YCQSYDRYTH PALLFGTGTK VTVLGQPKAA PSVTLFPPSS EELQANKATL VCLISDFYPG   840
AVTVAWKADS SPVKAGVETT TPSKQSNNKY AASSYLSLTP EQWKSHRSYS CQVTHEGSTV   900
EKTVAPTECS                                                         910

SEQ ID NO: 496          moltype = AA  length = 906
FEATURE                 Location/Qualifiers
source                  1..906
                        mol_type = protein
                        organism = synthetic construct
SEQUENCE: 496
EVQLVESGGG LVQPGNSLRL SCAASGFTFS KFGMSWVRQA PGKGLEWVSS ISGSGRDTLY    60
AESVKGRFTI SRDNAKTTLY LQMNSLRPED TAVYYCTIGG SLSVSSQGTL VTVSSSGGPG   120
PAGLYAQPGS IWELKKDVYV VELDWYPDAP GEMVVLTCDT PEEDGITWTL DQSSEVLGSG   180
KTLTIQVKEF GDAGQYTCHK GGEVLSHSLL LLHKKEDGIW STDILKDQKE PKNKTFLRCE   240
AKNYSGRFTC WWLTTISTDL TFSVKSSRGS SDPQGVTCGA ATLSAERVRG DNKEYEYSVE   300
CQEDSACPAA EESLPIEVMV DAVHKLKYEN YTSSFFIRDI IKPDPPKNLQ LKPLKNSRQV   360
EVSWEYPDTW STPHSYFSLT FCVQVQGKSK REKKDRVFTD KTSATVICRK NASISVRAQD   420
RYYSSSWSEW ASVPCSGGGG SGGGGSGGGG SRVIPVSGPA RCLSQSRNLL KTTDDMVKTA   480
REKLKHYSCT AEDIDHEDIT RDQTSTLKTC LPLELHKNES CLATRETSST TRGSCLPPQK   540
TSLMMTLCLG SIYEDLKMYQ TEFQAINAAL QNHNHQQIIL DKGMLVAIDE LMQSLNHNGE   600
TLRQKPPVGE ADPYRVKMKL CILLHAFSTR VVTINRVMGY LSSASGGPGP AGLYAQPGSG   660
GGGSGGGGSG GGGSGGGGSG GGGSGGGSQ SVLTQPPSVS GAPGQRVTIS CSGSRSNIGD   720
NTVKWYQQLP GTAPKLLIYY NDQRPSGVPD RFSGSKSGTS ASLAITGLQA EDEADYYCQS   780
YDRYTHPALL FGTGTKVTVL GQPKAAPSVT LFPPSSEELQ ANKATLVCLI SDFYPGAVTV   840
AWKADSSPVK AGVETTTPSK QSNNKYAASS YLSLTPEQWK SHRSYSCQVT HEGSTVEKTV   900
APTECS                                                              906

SEQ ID NO: 497          moltype = AA  length = 910
FEATURE                 Location/Qualifiers
source                  1..910
                        mol_type = protein
                        organism = synthetic construct
SEQUENCE: 497
EVQLVESGGG LVQPGNSLRL SCAASGFTFS KFGMSWVRQA PGKGLEWVSS ISGSGRDTLY    60
AESVKGRFTI SRDNAKTTLY LQMNSLRPED TAVYYCTIGG SLSVSSQGTL VTVSSSGGPG   120
PAGLYAQPGS IWELKKDVYV VELDWYPDAP GEMVVLTCDT PEEDGITWTL DQSSEVLGSG   180
KTLTIQVKEF GDAGQYTCHK GGEVLSHSLL LLHKKEDGIW STDILKDQKE PKNKTFLRCE   240
AKNYSGRFTC WWLTTISTDL TFSVKSSRGS SDPQGVTCGA ATLSAERVRG DNKEYEYSVE   300
CQEDSACPAA EESLPIEVMV DAVHKLKYEN YTSSFFIRDI IKPDPPKNLQ LKPLKNSRQV   360
EVSWEYPDTW STPHSYFSLT FCVQVQGKSK REKKDRVFTD KTSATVICRK NASISVRAQD   420
RYYSSSWSEW ASVPCSGGGG SGGGGSGGGG SRNLPVATPD PGMFPCLHHS QNLLRAVSNM   480
LQKARQTLEF YPCTSEEIDH EDITKDKTST VEACLPLELT KNESCLNSRE TSFITNGSCL   540
ASRKTSFMMA LCLSSIYEDL KMYQVEFKTM NAKLLMDPKR QIFLDQNMLA VIDELMQALN   600
```

```
FNSETVPQKS SLEEPDFYKT KIKLCILLHA FRIRAVTIDR VMSYLNASSG GPGPAGLYAQ  660
PGSGGGGSGG GGSGGGGSGG GGSGGGGSGG GGSQSVLTQP PSVSGAPGQR VTISCSGSRS  720
NIGDNTVKWY QQLPGTAPKL LIYYNDQRPS GVPDRFSGSK SGTSASLAIT GLQAEDEADY  780
YCQSYDRYTH PALLFGTGTK VTVLGQPKAA PSVTLFPPSS EELQANKATL VCLISDFYPG  840
AVTVAWKADS SPVKAGVETT TPSKQSNNKY AASSYLSLTP EQWKSHRSYS CQVTHEGSTV  900
EKTVAPTECS                                                       910

SEQ ID NO: 498          moltype = AA  length = 906
FEATURE                 Location/Qualifiers
source                  1..906
                        mol_type = protein
                        organism = synthetic construct
SEQUENCE: 498
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGLYAQPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRVIPVSGPA RCLSQSRNLL KTTDDMVKTA  480
REKLKHYSCT AEDIDHEDIT RDQTSTLKTC LPLELHKNES CLATRETSST TRGSCLPPQK  540
TSLMMTLCLG SIYEDLKMYQ TEFQAINAAL QNHNHQQIIL DKGMLVAIDE LMQSLNHNGE  600
TLRQKPPVGE ADPYRVKMKL CILLHAFSTR VVTINRVMGY LSSASGGPGP AGLYAQPGSG  660
GGGSGGGGSG GGGSGGGGSG GGGSGGGGSQ SVLTQPPSVS GAPGQRVTIS CSGSRSNIGD  720
ETVKWYQQLP GTAPKLLIYY NDQRPSGVPD RFSGSKSGTS ASLAITGLQA EDEADYYCQS  780
YDRYTHPALL FGTGTKVTVL GQPKAAPSVT LFPPSSEELQ ANKATLVCLI SDFYPGAVTV  840
AWKADSSPVK AGVETTTPSK QSNNKYAASS YLSLTPEQWK SHRSYSCQVT HEGSTVEKTV  900
APTECS                                                           906

SEQ ID NO: 499          moltype = AA  length = 910
FEATURE                 Location/Qualifiers
source                  1..910
                        mol_type = protein
                        organism = synthetic construct
SEQUENCE: 499
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGLYAQPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRNLPVATPD PGMFPCLHHS QNLLRAVSNM  480
LQKARQTLEF YPCTSEEIDH EDITKDKTST VEACLPLELT KNESCLNSRE TSFITNGSCL  540
ASRKTSFMMA LCLSSIYEDL KMYQVEFKTM NAKLLMDPKR QIFLDQNMLA VIDELMQALN  600
FNSETVPQKS SLEEPDFYKT KIKLCILLHA FRIRAVTIDR VMSYLNASSG GPGPAGLYAQ  660
PGSGGGGSGG GGSGGGGSGG GGSGGGGSGG GGSQSVLTQP PSVSGAPGQR VTISCSGSRS  720
NIGDETVKWY QQLPGTAPKL LIYYNDQRPS GVPDRFSGSK SGTSASLAIT GLQAEDEADY  780
YCQSYDRYTH PALLFGTGTK VTVLGQPKAA PSVTLFPPSS EELQANKATL VCLISDFYPG  840
AVTVAWKADS SPVKAGVETT TPSKQSNNKY AASSYLSLTP EQWKSHRSYS CQVTHEGSTV  900
EKTVAPTECS                                                       910

SEQ ID NO: 500          moltype = AA  length = 906
FEATURE                 Location/Qualifiers
source                  1..906
                        mol_type = protein
                        organism = synthetic construct
SEQUENCE: 500
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGLYAQPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRVIPVSGPA RCLSQSRNLL KTTDDMVKTA  480
REKLKHYSCT AEDIDHEDIT RDQTSTLKTC LPLELHKNES CLATRETSST TRGSCLPPQK  540
TSLMMTLCLG SIYEDLKMYQ TEFQAINAAL QNHNHQQIIL DKGMLVAIDE LMQSLNHNGE  600
TLRQKPPVGE ADPYRVKMKL CILLHAFSTR VVTINRVMGY LSSASGGPGP AGLYAQPGSG  660
GGGSGGGGSG GGGSGGGGSG GGGSGGGGSQ SVLTQPPSVS GAPGQRVTIS CSGSESNIGS  720
NDVKWYQQLP GTAPKLLIYY NDQRPSGVPD RFSGSKSGTS ASLAITGLQA EDEADYYCQS  780
YDRYTHPALL FGTGTKVTVL GQPKAAPSVT LFPPSSEELQ ANKATLVCLI SDFYPGAVTV  840
AWKADSSPVK AGVETTTPSK QSNNKYAASS YLSLTPEQWK SHRSYSCQVT HEGSTVEKTV  900
APTECS                                                           906

SEQ ID NO: 501          moltype = AA  length = 910
FEATURE                 Location/Qualifiers
source                  1..910
```

```
                            mol_type = protein
                            organism = synthetic construct
SEQUENCE: 501
EVQLVESGGG LVQPGNSLRL SCAASGFTFS KFGMSWVRQA PGKGLEWVSS ISGSGRDTLY    60
AESVKGRFTI SRDNAKTTLY LQMNSLRPED TAVYYCTIGG SLSVSSQGTL VTVSSSGGPG   120
PAGLYAQPGS IWELKKDVYV VELDWYPDAP GEMVVLTCDT PEEDGITWTL DQSSEVLGSG   180
KTLTIQVKEF GDAGQYTCHK GGEVLSHSLL LLHKKEDGIW STDILKDQKE PKNKTFLRCE   240
AKNYSGRFTC WWLTTISTDL TFSVKSSRGS SDPQGVTCGA ATLSAERVRG DNKEYEYSVE   300
CQEDSACPAA EESLPIEVMV DAVHKLKYEN YTSSFFIRDI IKPDPPKNLQ LKPLKNSRQV   360
EVSWEYPDTW STPHSYFSLT FCVQVQGKSK REKKDRVFTD KTSATVICRK NASISVRAQD   420
RYYSSSWSEW ASVPCSGGGG SGGGGSGGGG SRNLPVATPD PGMFPCLHHS QNLLRAVSNM   480
LQKARQTLEF YPCTSEEIDH EDITKDKTST VEACLPLELT KNESCLNSRE TSFITNGSCL   540
ASRKTSFMMA LCLSSIYEDL KMYQVEFKTM NAKLLMDPKR QIFLDQNMLA VIDELMQALN   600
FNSETVPQKS SLEEPDFYKT KIKLCILLHA FRIRAVTIDR VMSYLNASSG GPGPAGLYAQ   660
PGSGGGGSGG GGSGGGGSGG GGSGGGGSGG GGSQSVLTQP PSVSGAPGQR VTISCSGSES   720
NIGSNDVKWY QQLPGTAPKL LIYYNDQRPS GVPDRFSGSK SGTSASLAIT GLQAEDEADY   780
YCQSYDRYTH PALLFGTGTK VTVLGQPKAA PSVTLFPPSS EELQANKATL VCLISDFYPG   840
AVTVAWKADS SPVKAGVETT TPSKQSNNKY AASSYLSLTP EQWKSHRSYS CQVTHEGSTV   900
EKTVAPTECS                                                         910

SEQ ID NO: 502          moltype = AA  length = 906
FEATURE                 Location/Qualifiers
source                  1..906
                        mol_type = protein
                        organism = synthetic construct
SEQUENCE: 502
EVQLVESGGG LVQPGNSLRL SCAASGFTFS KFGMSWVRQA PGKGLEWVSS ISGSGRDTLY    60
AESVKGRFTI SRDNAKTTLY LQMNSLRPED TAVYYCTIGG SLSVSSQGTL VTVSSSGGPG   120
PAGLYAQPGS IWELKKDVYV VELDWYPDAP GEMVVLTCDT PEEDGITWTL DQSSEVLGSG   180
KTLTIQVKEF GDAGQYTCHK GGEVLSHSLL LLHKKEDGIW STDILKDQKE PKNKTFLRCE   240
AKNYSGRFTC WWLTTISTDL TFSVKSSRGS SDPQGVTCGA ATLSAERVRG DNKEYEYSVE   300
CQEDSACPAA EESLPIEVMV DAVHKLKYEN YTSSFFIRDI IKPDPPKNLQ LKPLKNSRQV   360
EVSWEYPDTW STPHSYFSLT FCVQVQGKSK REKKDRVFTD KTSATVICRK NASISVRAQD   420
RYYSSSWSEW ASVPCSGGGG SGGGGSGGGG SRVIPVSGPA RCLSQSRNLL KTTDDMVKTA   480
REKLKHYSCT AEDIDHEDIT RDQTSTLKTC LPLELHKNES CLATRETSST TRGSCLPPQK   540
TSLMMTLCLG SIYEDLKMYQ TEFQAINAAL QNHHQQIIL DKGMLVAIDE LMQSLNHNGE    600
TLRQKPPVGE ADPYRVKMKL CILLHAFSTR VVTINRVMGY LSSASGGPGP AGLYAQPGSG   660
GGGSGGGGSG GGGSGGGGSG GGGSGGGGSQ SVLTQPPSVS GAPGQRVTIS CSGSRSNIGE   720
NTVKWYQQLP GTAPKLLIYY NDQRPSGVPD RFSGSKSGTS ASLAITGLQA EDEADYYCQS   780
YDRYTHPALL FGTGTKVTVL GQPKAAPSVT LFPPSSEELQ ANKATLVCLI SDFYPGAVTV   840
AWKADSSPVK AGVETTTPSK QSNNKYAASS YLSLTPEQWK SHRSYSCQVT HEGSTVEKTV   900
APTECS                                                             906

SEQ ID NO: 503          moltype = AA  length = 910
FEATURE                 Location/Qualifiers
source                  1..910
                        mol_type = protein
                        organism = synthetic construct
SEQUENCE: 503
EVQLVESGGG LVQPGNSLRL SCAASGFTFS KFGMSWVRQA PGKGLEWVSS ISGSGRDTLY    60
AESVKGRFTI SRDNAKTTLY LQMNSLRPED TAVYYCTIGG SLSVSSQGTL VTVSSSGGPG   120
PAGLYAQPGS IWELKKDVYV VELDWYPDAP GEMVVLTCDT PEEDGITWTL DQSSEVLGSG   180
KTLTIQVKEF GDAGQYTCHK GGEVLSHSLL LLHKKEDGIW STDILKDQKE PKNKTFLRCE   240
AKNYSGRFTC WWLTTISTDL TFSVKSSRGS SDPQGVTCGA ATLSAERVRG DNKEYEYSVE   300
CQEDSACPAA EESLPIEVMV DAVHKLKYEN YTSSFFIRDI IKPDPPKNLQ LKPLKNSRQV   360
EVSWEYPDTW STPHSYFSLT FCVQVQGKSK REKKDRVFTD KTSATVICRK NASISVRAQD   420
RYYSSSWSEW ASVPCSGGGG SGGGGSGGGG SRNLPVATPD PGMFPCLHHS QNLLRAVSNM   480
LQKARQTLEF YPCTSEEIDH EDITKDKTST VEACLPLELT KNESCLNSRE TSFITNGSCL   540
ASRKTSFMMA LCLSSIYEDL KMYQVEFKTM NAKLLMDPKR QIFLDQNMLA VIDELMQALN   600
FNSETVPQKS SLEEPDFYKT KIKLCILLHA FRIRAVTIDR VMSYLNASSG GPGPAGLYAQ   660
PGSGGGGSGG GGSGGGGSGG GGSGGGGSGG GGSQSVLTQP PSVSGAPGQR VTISCSGSRS   720
NIGENTVKWY QQLPGTAPKL LIYYNDQRPS GVPDRFSGSK SGTSASLAIT GLQAEDEADY   780
YCQSYDRYTH PALLFGTGTK VTVLGQPKAA PSVTLFPPSS EELQANKATL VCLISDFYPG   840
AVTVAWKADS SPVKAGVETT TPSKQSNNKY AASSYLSLTP EQWKSHRSYS CQVTHEGSTV   900
EKTVAPTECS                                                         910

SEQ ID NO: 504          moltype = AA  length = 906
FEATURE                 Location/Qualifiers
source                  1..906
                        mol_type = protein
                        organism = synthetic construct
SEQUENCE: 504
EVQLVESGGG LVQPGNSLRL SCAASGFTFS KFGMSWVRQA PGKGLEWVSS ISGSGRDTLY    60
AESVKGRFTI SRDNAKTTLY LQMNSLRPED TAVYYCTIGG SLSVSSQGTL VTVSSSGGPG   120
PAGLYAQPGS IWELKKDVYV VELDWYPDAP GEMVVLTCDT PEEDGITWTL DQSSEVLGSG   180
KTLTIQVKEF GDAGQYTCHK GGEVLSHSLL LLHKKEDGIW STDILKDQKE PKNKTFLRCE   240
AKNYSGRFTC WWLTTISTDL TFSVKSSRGS SDPQGVTCGA ATLSAERVRG DNKEYEYSVE   300
CQEDSACPAA EESLPIEVMV DAVHKLKYEN YTSSFFIRDI IKPDPPKNLQ LKPLKNSRQV   360
EVSWEYPDTW STPHSYFSLT FCVQVQGKSK REKKDRVFTD KTSATVICRK NASISVRAQD   420
```

```
RYYSSSWSEW ASVPCSGGGG SGGGGSGGGG SRVIPVSGPA RCLSQSRNLL KTTDDMVKTA  480
REKLKHYSCT AEDIDHEDIT RDQTSTLKTC LPLELHKNES CLATRETSST TRGSCLPPQK  540
TSLMMTLCLG SIYEDLKMYQ TEFQAINAAL QNHHQQIIL DKGMLVAIDE LMQSLNHNGE  600
TLRQKPPVGE ADPYRVKMKL CILLHAFSTR VVTINRVMGY LSSASGGPGP AGLYAQPGSG  660
GGGSGGGSG GGGSGGGGSG GGGSGGGGSQ SVLTQPPSVS GAPGQRVTIS CSGSRSNIGE  720
ETVKWYQQLP GTAPKLLIYY NDQRPSGVPD RFSGSKSGTS ASLAITGLQA EDEADYYCQS  780
YDRYTHPALL FGTGTKVTVL GQPKAAPSVT LFPPSSEELQ ANKATLVCLI SDFYPGAVTV  840
AWKADSSPVK AGVETTTPSK QSNNKYAASS YLSLTPEQWK SHRSYSCQVT HEGSTVEKTV  900
APTECS                                                              906

SEQ ID NO: 505          moltype = AA  length = 910
FEATURE                 Location/Qualifiers
source                  1..910
                        mol_type = protein
                        organism = synthetic construct
SEQUENCE: 505
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGLYAQPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRNLPVATPD PGMFPCLHHS QNLLRAVSNM  480
LQKARQTLEF YPCTSEEIDH EDITKDKTST VEACLPLELT KNESCLNSRE TSFITNGSCL  540
ASRKTSFMMA LCLSSIYEDL KMYQVEFKTM NAKLLMDQPK QIFLDQNMLA VIDELMQALN  600
FNSETVPQKS SLEEPDFYKT KIKLCILLHA FRIRAVTIDR VMSYLNASSG GPGPAGLYAQ  660
PGSGGGGSGG GGSGGGGSGG GGSQSVLTQP PSVSGAPGQR VTISCSGSRS  720
NIGEETVKWY QQLPGTAPKL LIYYNDQRPS GVPDRFSGSK SGTSASLAIT GLQAEDEADY  780
YCQSYDRYTH PALLFGTGTK VTVLGQPKAA PSVTLFPPSS EELQANKATL VCLISDFYPG  840
AVTVAWKADS SPVKAGVETT TPSKQSNNKY AASSYLSLTP EQWKSHRSYS CQVTHEGSTV  900
EKTVAPTECS                                                          910

SEQ ID NO: 506          moltype = AA  length = 906
FEATURE                 Location/Qualifiers
source                  1..906
                        mol_type = protein
                        organism = synthetic construct
SEQUENCE: 506
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPA  120
LFKSSFPPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRVIPVSGPA RCLSQSRNLL KTTDDMVKTA  480
REKLKHYSCT AEDIDHEDIT RDQTSTLKTC LPLELHKNES CLATRETSST TRGSCLPPQK  540
TSLMMTLCLG SIYEDLKMYQ TEFQAINAAL QNHHQQIIL DKGMLVAIDE LMQSLNHNGE  600
TLRQKPPVGE ADPYRVKMKL CILLHAFSTR VVTINRVMGY LSSASGGPAL FKSSFPPGSG  660
GGGSGGGSG GGGSGGGGSG GGSGGGGSQ SVLTQPPSVS GAPGQRVTIS CSGSRSNIGS  720
NTVKWYQQLP GTAPKLLIYY NDQRPSGVPD RFSGSKSGTS ASLAITGLQA EDEADYYCQS  780
YDRYTHPALL FGTGTKVTVL GQPKAAPSVT LFPPSSEELQ ANKATLVCLI SDFYPGAVTV  840
AWKADSSPVK AGVETTTPSK QSNNKYAASS YLSLTPEQWK SHRSYSCQVT HEGSTVEKTV  900
APTECS                                                              906

SEQ ID NO: 507          moltype = AA  length = 910
FEATURE                 Location/Qualifiers
source                  1..910
                        mol_type = protein
                        organism = synthetic construct
SEQUENCE: 507
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPA  120
LFKSSFPPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRNLPVATPD PGMFPCLHHS QNLLRAVSNM  480
LQKARQTLEF YPCTSEEIDH EDITKDKTST VEACLPLELT KNESCLNSRE TSFITNGSCL  540
ASRKTSFMMA LCLSSIYEDL KMYQVEFKTM NAKLLMDPKR QIFLDQNMLA VIDELMQALN  600
FNSETVPQKS SLEEPDFYKT KIKLCILLHA FRIRAVTIDR VMSYLNASSG GPALFKSSFP  660
PGSGGGGSGG GGSGGGGSGG GGSQSVLTQP PSVSGAPGQR VTISCSGSRS  720
NIGSNTVKWY QQLPGTAPKL LIYYNDQRPS GVPDRFSGSK SGTSASLAIT GLQAEDEADY  780
YCQSYDRYTH PALLFGTGTK VTVLGQPKAA PSVTLFPPSS EELQANKATL VCLISDFYPG  840
AVTVAWKADS SPVKAGVETT TPSKQSNNKY AASSYLSLTP EQWKSHRSYS CQVTHEGSTV  900
EKTVAPTECS                                                          910
```

| SEQ ID NO: 508 | moltype = AA length = 906 |
| FEATURE | Location/Qualifiers |
| source | 1..906 |
| | mol_type = protein |
| | organism = synthetic construct |

SEQUENCE: 508
```
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPA 120
LFKSSFPPGS IWELKKDVYV VELDWYPDAP GEMVVLTCDT PEEDGITWTL DQSSEVLGSG 180
KTLTIQVKEF GDAGQYTCHK GGEVLSHSLL LLHKKEDGIW STDILKDQKE PKNKTFLRCE 240
AKNYSGRFTC WWLTTISTDL TFSVKSSRGS SDPQGVTCGA ATLSAERVRG DNKEYEYSVE 300
CQEDSACPAA EESLPIEVMV DAVHKLKYEN YTSSFFIRDI IKPDPPKNLQ LKPLKNSRQV 360
EVSWEYPDTW STPHSYFSLT FCVQVQGKSK REKKDRVFTD KTSATVICRK NASISVRAQD 420
RYYSSSWSEW ASVPCSGGGG SGGGGSGGGG SRVIPVSGPA RCLSQSRNLL KTTDDMVKTA 480
REKLKHYSCT AEDIDHEDIT RDQTSTLKTC LPLELHKNES CLATRETSST TRGSCLPPQK 540
TSLMMTLCLG SIYEDLKMYQ TEFQAINAAL QNHNHQQIIL DKGMLVAIDE LMQSLNHNGE 600
TLRQKPPVGE ADPYRVKMKL CILLHAFSTR VVTINRVMGY LSSASGGPAL FKSSFPPGSG 660
GGGSGGGGSG GGGSGGGGSG GGGSGGGGSQ SVLTQPPSVS GAPGQRVTIS CSGSRSNIGS 720
ETVKWYQQLP GTAPKLLIYY NDQRPSGVPD RFSGSKSGTS ASLAITGLQA EDEADYYCQS 780
YDRYTHPALL FGTGTKVTVL GQPKAAPSVT LFPPSSEELQ ANKATLVCLI SDFYPGAVTV 840
AWKADSSPVK AGVETTTPSK QSNNKYAASS YLSLTPEQWK SHRSYSCQVT HEGSTVEKTV 900
APTECS                                                           906
```

| SEQ ID NO: 509 | moltype = AA length = 910 |
| FEATURE | Location/Qualifiers |
| source | 1..910 |
| | mol_type = protein |
| | organism = synthetic construct |

SEQUENCE: 509
```
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPA 120
LFKSSFPPGS IWELKKDVYV VELDWYPDAP GEMVVLTCDT PEEDGITWTL DQSSEVLGSG 180
KTLTIQVKEF GDAGQYTCHK GGEVLSHSLL LLHKKEDGIW STDILKDQKE PKNKTFLRCE 240
AKNYSGRFTC WWLTTISTDL TFSVKSSRGS SDPQGVTCGA ATLSAERVRG DNKEYEYSVE 300
CQEDSACPAA EESLPIEVMV DAVHKLKYEN YTSSFFIRDI IKPDPPKNLQ LKPLKNSRQV 360
EVSWEYPDTW STPHSYFSLT FCVQVQGKSK REKKDRVFTD KTSATVICRK NASISVRAQD 420
RYYSSSWSEW ASVPCSGGGG SGGGGSGGGG SRNLPVATPD PGMFPCLHHS QNLLRAVSNM 480
LQKARQTLEF YPCTSEEIDH EDITKDKTST VEACLPLELT KNESCLNSRE TSFITNGSCL 540
ASRKTSFMMA LCLSSIYEDL KMYQVEFKTM NAKLLMDPKR QIFLDQNMLA VIDELMQALN 600
FNSETVPQKS SLEEPDFYKT KIKLCILLHA FRIRAVTIDR VMSYLNASSG GPALFKSSFP 660
PGSGGGGSGG GGSGGGGSGG GGSGGGGSGG GGSQSVLTQP PSVSGAPGQR VTISCSGSRS 720
NIGSETVKWY QQLPGTAPKL LIYYNDQRPS GVPDRFSGSK SGTSASLAIT GLQAEDEADY 780
YCQSYDRYTH PALLFGTGTK VTVLGQPKAA PSVTLFPPSS EELQANKATL VCLISDFYPG 840
AVTVAWKADS SPVKAGVETT TPSKQSNNKY AASSYLSLTP EQWKSHRSYS CQVTHEGSTV 900
EKTVAPTECS                                                       910
```

| SEQ ID NO: 510 | moltype = AA length = 906 |
| FEATURE | Location/Qualifiers |
| source | 1..906 |
| | mol_type = protein |
| | organism = synthetic construct |

SEQUENCE: 510
```
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPA 120
LFKSSFPPGS IWELKKDVYV VELDWYPDAP GEMVVLTCDT PEEDGITWTL DQSSEVLGSG 180
KTLTIQVKEF GDAGQYTCHK GGEVLSHSLL LLHKKEDGIW STDILKDQKE PKNKTFLRCE 240
AKNYSGRFTC WWLTTISTDL TFSVKSSRGS SDPQGVTCGA ATLSAERVRG DNKEYEYSVE 300
CQEDSACPAA EESLPIEVMV DAVHKLKYEN YTSSFFIRDI IKPDPPKNLQ LKPLKNSRQV 360
EVSWEYPDTW STPHSYFSLT FCVQVQGKSK REKKDRVFTD KTSATVICRK NASISVRAQD 420
RYYSSSWSEW ASVPCSGGGG SGGGGSGGGG SRVIPVSGPA RCLSQSRNLL KTTDDMVKTA 480
REKLKHYSCT AEDIDHEDIT RDQTSTLKTC LPLELHKNES CLATRETSST TRGSCLPPQK 540
TSLMMTLCLG SIYEDLKMYQ TEFQAINAAL QNHNHQQIIL DKGMLVAIDE LMQSLNHNGE 600
TLRQKPPVGE ADPYRVKMKL CILLHAFSTR VVTINRVMGY LSSASGGPAL FKSSFPPGSG 660
GGGSGGGGSG GGGSGGGGSG GGSGGGGSQ SVLTQPPSVS GAPGQRVTIS CSGSRSNIGD 720
NTVKWYQQLP GTAPKLLIYY NDQRPSGVPD RFSGSKSGTS ASLAITGLQA EDEADYYCQS 780
YDRYTHPALL FGTGTKVTVL GQPKAAPSVT LFPPSSEELQ ANKATLVCLI SDFYPGAVTV 840
AWKADSSPVK AGVETTTPSK QSNNKYAASS YLSLTPEQWK SHRSYSCQVT HEGSTVEKTV 900
APTECS                                                           906
```

| SEQ ID NO: 511 | moltype = AA length = 910 |
| FEATURE | Location/Qualifiers |
| source | 1..910 |
| | mol_type = protein |
| | organism = synthetic construct |

SEQUENCE: 511
```
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPA 120
LFKSSFPPGS IWELKKDVYV VELDWYPDAP GEMVVLTCDT PEEDGITWTL DQSSEVLGSG 180
KTLTIQVKEF GDAGQYTCHK GGEVLSHSLL LLHKKEDGIW STDILKDQKE PKNKTFLRCE 240
```

```
AKNYSGRFTC WWLTTISTDL TFSVKSSRGS SDPQGVTCGA ATLSAERVRG DNKEYEYSVE   300
CQEDSACPAA EESLPIEVMV DAVHKLKYEN YTSSFFIRDI IKPDPPKNLQ LKPLKNSRQV   360
EVSWEYPDTW STPHSYFSLT FCVQVQGKSK REKKDRVFTD KTSATVICRK NASISVRAQD   420
RYYSSSWSEW ASVPCSGGGG SGGGGSGGGG SRNLPVATPD PGMFPCLHHS QNLLRAVSNM   480
LQKARQTLEF YPCTSEEIDH EDITKDKTST VEACLPLELT KNESCLNSRE TSFITNGSCL   540
ASRKTSFMMA LCLSSIYEDL KMYQVEFKTM NAKLLMDPKR QIFLDQNMLA VIDELMQALN   600
FNSETVPQKS SLEEPDFYKT KIKLCILLHA FRIRAVTIDR VMSYLNASSG GPALFKSSFP   660
PGSGGGGSGG GGSGGGGSGG GGSGGGGSGG GGSQSVLTQP PSVSGAPGQR VTISCSGSRS   720
NIGDNTVKWY QQLPGTAPKL LIYYNDQRPS GVPDRFSGSK SGTSASLAIT GLQAEDEADY   780
YCQSYDRYTH PALLFGTGTK VTVLGQPKAA PSVTLFPPSS EELQANKATL VCLISDFYPG   840
AVTVAWKADS SPVKAGVETT TPSKQSNNKY AASSYLSLTP EQWKSHRSYS CQVTHEGSTV   900
EKTVAPTECS                                                          910

SEQ ID NO: 512          moltype = AA  length = 906
FEATURE                 Location/Qualifiers
source                  1..906
                        mol_type = protein
                        organism = synthetic construct
SEQUENCE: 512
EVQLVESGGG LVQPGNSLRL SCAASGFTFS KFGMSWVRQA PGKGLEWVSS ISGSGRDTLY   60
AESVKGRFTI SRDNAKTTLY LQMNSLRPED TAVYYCTIGG SLSVSSQGTL VTVSSSGGPA   120
LFKSSFPPGS IWELKKDVYV VELDWYPDAP GEMVVLTCDT PEEDGITWTL DQSSEVLGSG   180
KTLTIQVKEF GDAGQYTCHK GGEVLSHSLL LLHKKEDGIW STDILKDQKE PKNKTFLRCE   240
AKNYSGRFTC WWLTTISTDL TFSVKSSRGS SDPQGVTCGA ATLSAERVRG DNKEYEYSVE   300
CQEDSACPAA EESLPIEVMV DAVHKLKYEN YTSSFFIRDI IKPDPPKNLQ LKPLKNSRQV   360
EVSWEYPDTW STPHSYFSLT FCVQVQGKSK REKKDRVFTD KTSATVICRK NASISVRAQD   420
RYYSSSWSEW ASVPCSGGGG SGGGGSGGGG SRVIPVSGPA RCLSQSRNLL KTTDDMVKTA   480
REKLKHYSCT AEDIDHEDIT RDQTSTLKTC LPLELHKNES CLATRETSST TRGSCLPPQK   540
TSLMMTLCLG SIYEDLKMYQ TEFQAINAAL QNHNHQQIIL DKGMLVAIDE LMQSLNHNGE   600
TLRQKPPVGE ADPYRVKMKL CILLHAFSTR VVTINRVMGY LSSASGGPAL FKSSFPPGSG   660
GGGSGGGGSG GGGSGGGGSG GGGSGGGGSQ SVLTQPPSVS GAPGQRVTIS CSGSRSNIGD   720
ETVKWYQQLP GTAPKLLIYY NDQRPSGVPD RFSGSKSGTS ASLAITGLQA EDEADYYCQS   780
YDRYTHPALL FGTGTKVTVL GQPKAAPSVT LFPPSSEELQ ANKATLVCLI SDFYPGAVTV   840
AWKADSSPVK AGVETTTPSK QSNNKYAASS YLSLTPEQWK SHRSYSCQVT HEGSTVEKTV   900
APTECS                                                              906

SEQ ID NO: 513          moltype = AA  length = 910
FEATURE                 Location/Qualifiers
source                  1..910
                        mol_type = protein
                        organism = synthetic construct
SEQUENCE: 513
EVQLVESGGG LVQPGNSLRL SCAASGFTFS KFGMSWVRQA PGKGLEWVSS ISGSGRDTLY   60
AESVKGRFTI SRDNAKTTLY LQMNSLRPED TAVYYCTIGG SLSVSSQGTL VTVSSSGGPA   120
LFKSSFPPGS IWELKKDVYV VELDWYPDAP GEMVVLTCDT PEEDGITWTL DQSSEVLGSG   180
KTLTIQVKEF GDAGQYTCHK GGEVLSHSLL LLHKKEDGIW STDILKDQKE PKNKTFLRCE   240
AKNYSGRFTC WWLTTISTDL TFSVKSSRGS SDPQGVTCGA ATLSAERVRG DNKEYEYSVE   300
CQEDSACPAA EESLPIEVMV DAVHKLKYEN YTSSFFIRDI IKPDPPKNLQ LKPLKNSRQV   360
EVSWEYPDTW STPHSYFSLT FCVQVQGKSK REKKDRVFTD KTSATVICRK NASISVRAQD   420
RYYSSSWSEW ASVPCSGGGG SGGGGSGGGG SRNLPVATPD PGMFPCLHHS QNLLRAVSNM   480
LQKARQTLEF YPCTSEEIDH EDITKDKTST VEACLPLELT KNESCLNSRE TSFITNGSCL   540
ASRKTSFMMA LCLSSIYEDL KMYQVEFKTM NAKLLMDPKR QIFLDQNMLA VIDELMQALN   600
FNSETVPQKS SLEEPDFYKT KIKLCILLHA FRIRAVTIDR VMSYLNASSG GPALFKSSFP   660
PGSGGGGSGG GGSGGGGSGG GGSGGGGSGG GGSQSVLTQP PSVSGAPGQR VTISCSGSRS   720
NIGDNTVKWY QQLPGTAPKL LIYYNDQRPS GVPDRFSGSK SGTSASLAIT GLQAEDEADY   780
YCQSYDRYTH PALLFGTGTK VTVLGQPKAA PSVTLFPPSS EELQANKATL VCLISDFYPG   840
AVTVAWKADS SPVKAGVETT TPSKQSNNKY AASSYLSLTP EQWKSHRSYS CQVTHEGSTV   900
EKTVAPTECS                                                          910

SEQ ID NO: 514          moltype = AA  length = 906
FEATURE                 Location/Qualifiers
source                  1..906
                        mol_type = protein
                        organism = synthetic construct
SEQUENCE: 514
EVQLVESGGG LVQPGNSLRL SCAASGFTFS KFGMSWVRQA PGKGLEWVSS ISGSGRDTLY   60
AESVKGRFTI SRDNAKTTLY LQMNSLRPED TAVYYCTIGG SLSVSSQGTL VTVSSSGGPA   120
LFKSSFPPGS IWELKKDVYV VELDWYPDAP GEMVVLTCDT PEEDGITWTL DQSSEVLGSG   180
KTLTIQVKEF GDAGQYTCHK GGEVLSHSLL LLHKKEDGIW STDILKDQKE PKNKTFLRCE   240
AKNYSGRFTC WWLTTISTDL TFSVKSSRGS SDPQGVTCGA ATLSAERVRG DNKEYEYSVE   300
CQEDSACPAA EESLPIEVMV DAVHKLKYEN YTSSFFIRDI IKPDPPKNLQ LKPLKNSRQV   360
EVSWEYPDTW STPHSYFSLT FCVQVQGKSK REKKDRVFTD KTSATVICRK NASISVRAQD   420
RYYSSSWSEW ASVPCSGGGG SGGGGSGGGG SRVIPVSGPA RCLSQSRNLL KTTDDMVKTA   480
REKLKHYSCT AEDIDHEDIT RDQTSTLKTC LPLELHKNES CLATRETSST TRGSCLPPQK   540
TSLMMTLCLG SIYEDLKMYQ TEFQAINAAL QNHNHQQIIL DKGMLVAIDE LMQSLNHNGE   600
TLRQKPPVGE ADPYRVKMKL CILLHAFSTR VVTINRVMGY LSSASGGPAL FKSSFPPGSG   660
GGGSGGGGSG GGGSGGGGSG GGGSGGGGSQ SVLTQPPSVS GAPGQRVTIS CSGSESNIGS   720
NDVKWYQQLP GTAPKLLIYY NDQRPSGVPD RFSGSKSGTS ASLAITGLQA EDEADYYCQS   780
YDRYTHPALL FGTGTKVTVL GQPKAAPSVT LFPPSSEELQ ANKATLVCLI SDFYPGAVTV   840
```

```
AWKADSSPVK AGVETTTPSK QSNNKYAASS YLSLTPEQWK SHRSYSCQVT HEGSTVEKTV    900
APTECS                                                              906

SEQ ID NO: 515          moltype = AA  length = 910
FEATURE                 Location/Qualifiers
source                  1..910
                        mol_type = protein
                        organism = synthetic construct
SEQUENCE: 515
EVQLVESGGG LVQPGNSLRL SCAASGFTFS KFGMSWVRQA PGKGLEWVSS ISGSGRDTLY    60
AESVKGRFTI SRDNAKTTLY LQMNSLRPED TAVYYCTIGG SLSVSSQGTL VTVSSSGGPA    120
LFKSSFPPGS IWELKKDVYV VELDWYPDAP GEMVVLTCDT PEEDGITWTL DQSSEVLGSG    180
KTLTIQVKEF GDAGQYTCHK GGEVLSHSLL LLHKKEDGIW STDILKDQKE PKNKTFLRCE    240
AKNYSGRFTC WWLTTISTDL TFSVKSSRGS SDPQGVTCGA ATLSAERVRG DNKEYEYSVE    300
CQEDSACPAA EESLPIEVMV DAVHKLKYEN YTSSFFIRDI IKPDPPKNLQ LKPLKNSRQV    360
EVSWEYPDTW STPHSYFSLT FCVQVQGKSK REKKDRVFTD KTSATVICRK NASISVRAQD    420
RYYSSSWSEW ASVPCSGGGG SGGGGSGGGG SRNLPVATPD PGMFPCLHHS QNLLRAVSNM    480
LQKARQTLEF YPCTSEEIDH EDITKDKTST VEACLPLELT KNESCLNSRE TSFITNGSCL    540
ASRKTSFMMA LCLSSIYEDL KMYQVEFKTM NAKLLMDPKR QIFLDQNMLA VIDELMQALN    600
FNSETVPQKS SLEEPDFYKT KIKLCILLHA FRIRAVTIDR VMSYLNASSG GPALFKSSFP    660
PGSGGGGSGG GGSGGGGSGG GGSGGGGSGG GGSQSVLTQP PSVSGAPGQR VTISCSGSES    720
NIGSNDVKWY QQLPGTAPKL LIYYNDQRPS GVPDRFSGSK SGTSASLAIT GLQAEDEADY    780
YCQSYDRYTH PALLFGTGTK VTVLGQPKAA PSVTLFPPSS EELQANKATL VCLISDFYPG    840
AVTVAWKADS SPVKAGVETT TPSKQSNNKY AASSYLSLTP EQWKSHRSYS CQVTHEGSTV    900
EKTVAPTECS                                                          910

SEQ ID NO: 516          moltype = AA  length = 906
FEATURE                 Location/Qualifiers
source                  1..906
                        mol_type = protein
                        organism = synthetic construct
SEQUENCE: 516
EVQLVESGGG LVQPGNSLRL SCAASGFTFS KFGMSWVRQA PGKGLEWVSS ISGSGRDTLY    60
AESVKGRFTI SRDNAKTTLY LQMNSLRPED TAVYYCTIGG SLSVSSQGTL VTVSSSGGPA    120
LFKSSFPPGS IWELKKDVYV VELDWYPDAP GEMVVLTCDT PEEDGITWTL DQSSEVLGSG    180
KTLTIQVKEF GDAGQYTCHK GGEVLSHSLL LLHKKEDGIW STDILKDQKE PKNKTFLRCE    240
AKNYSGRFTC WWLTTISTDL TFSVKSSRGS SDPQGVTCGA ATLSAERVRG DNKEYEYSVE    300
CQEDSACPAA EESLPIEVMV DAVHKLKYEN YTSSFFIRDI IKPDPPKNLQ LKPLKNSRQV    360
EVSWEYPDTW STPHSYFSLT FCVQVQGKSK REKKDRVFTD KTSATVICRK NASISVRAQD    420
RYYSSSWSEW ASVPCSGGGG SGGGGSGGGG SRVIPVSGPA RCLSQSRNLL KTTDDMVKTA    480
REKLKHYSCT AEDIDHEDIT RDQTSTLKTC LPLELHKNES CLATRETSST TRGSCLPPQK    540
TSLMMTLCLG SIYEDLKMYQ TEFQAINAAL QNHNHQQIIL DKGMLVAIDE LMQSLNHNGE    600
TLRQKPPVGE ADPYRVKMKL CILLHAFSTR VVTINRVMGY LSSASGGPAL FKSSFPPGSG    660
GGGSGGGGSG GGGSGGGGSG GGGSGGGGSQ SVLTQPPSVS GAPGQRVTIS CSGSRSNIGE    720
NTVKWYQQLP GTAPKLLIYY NDQRPSGVPD RFSGSKSGTS ASLAITGLQA EDEADYYCQS    780
YDRYTHPALL FGTGTKVTVL GQPKAAPSVT LFPPSSEELQ ANKATLVCLI SDFYPGAVTV    840
AWKADSSPVK AGVETTTPSK QSNNKYAASS YLSLTPEQWK SHRSYSCQVT HEGSTVEKTV    900
APTECS                                                              906

SEQ ID NO: 517          moltype = AA  length = 910
FEATURE                 Location/Qualifiers
source                  1..910
                        mol_type = protein
                        organism = synthetic construct
SEQUENCE: 517
EVQLVESGGG LVQPGNSLRL SCAASGFTFS KFGMSWVRQA PGKGLEWVSS ISGSGRDTLY    60
AESVKGRFTI SRDNAKTTLY LQMNSLRPED TAVYYCTIGG SLSVSSQGTL VTVSSSGGPA    120
LFKSSFPPGS IWELKKDVYV VELDWYPDAP GEMVVLTCDT PEEDGITWTL DQSSEVLGSG    180
KTLTIQVKEF GDAGQYTCHK GGEVLSHSLL LLHKKEDGIW STDILKDQKE PKNKTFLRCE    240
AKNYSGRFTC WWLTTISTDL TFSVKSSRGS SDPQGVTCGA ATLSAERVRG DNKEYEYSVE    300
CQEDSACPAA EESLPIEVMV DAVHKLKYEN YTSSFFIRDI IKPDPPKNLQ LKPLKNSRQV    360
EVSWEYPDTW STPHSYFSLT FCVQVQGKSK REKKDRVFTD KTSATVICRK NASISVRAQD    420
RYYSSSWSEW ASVPCSGGGG SGGGGSGGGG SRNLPMFPCL HHSQNLLRAVSNM           480
LQKARQTLEF YPCTSEEIDH EDITKDKTST VEACLPLELT KNESCLNSRE TSFITNGSCL    540
ASRKTSFMMA LCLSSIYEDL KMYQVEFKTM NAKLLMDPKR QIFLDQNMLA VIDELMQALN    600
FNSETVPQKS SLEEPDFYKT KIKLCILLHA FRIRAVTIDR VMSYLNASSG GPALFKSSFP    660
PGSGGGGSGG GGSGGGGSGG GGSGGGGSGG GGSQSVLTQP PSVSGAPGQR VTISCSGSRS    720
NIGENTVKWY QQLPGTAPKL LIYYNDQRPS GVPDRFSGSK SGTSASLAIT GLQAEDEADY    780
YCQSYDRYTH PALLFGTGTK VTVLGQPKAA PSVTLFPPSS EELQANKATL VCLISDFYPG    840
AVTVAWKADS SPVKAGVETT TPSKQSNNKY AASSYLSLTP EQWKSHRSYS CQVTHEGSTV    900
EKTVAPTECS                                                          910

SEQ ID NO: 518          moltype = AA  length = 906
FEATURE                 Location/Qualifiers
source                  1..906
                        mol_type = protein
                        organism = synthetic construct
SEQUENCE: 518
EVQLVESGGG LVQPGNSLRL SCAASGFTFS KFGMSWVRQA PGKGLEWVSS ISGSGRDTLY    60
```

```
AESVKGRFTI SRDNAKTTLY LQMNSLRPED TAVYYCTIGG SLSVSSQGTL VTVSSSGGPA    120
LFKSSFPPGS IWELKKDVYV VELDWYPDAP GEMVVLTCDT PEEDGITWTL DQSSEVLGSG    180
KTLTIQVKEF GDAGQYTCHK GGEVLSHSLL LLHKKEDGIW STDILKDQKE PKNKTFLRCE    240
AKNYSGRFTC WWLTTISTDL TFSVKSSRGS SDPQGVTCGA ATLSAERVRG DNKEYEYSVE    300
CQEDSACPAA EESLPIEVMV DAVHKLKYEN YTSSFFIRDI IKPDPPKNLQ LKPLKNSRQV    360
EVSWEYPDTW STPHSYFSLT FCVQVQGKSK REKKDRVFTD KTSATVICRK NASISVRAQD    420
RYYSSSWSEW ASVPCSGGGG SGGGGSGGGG SRVIPVSGPA RCLSQSRNLL KTTDDMVKTA    480
REKLKHYSCT AEDIDHEDIT RDQTSTLKTC LPLELHKNES CLATRETSST TRGSCLPPQK    540
TSLMMTLCLG SIYEDLKMYQ TEFQAINAAL QNHNHQQIIL DKGMLVAIDE LMQSLNHNGE    600
TLRQKPPVGE ADPYRVKMKL CILLHAFSTR VVTINRVMGY LSSASGGPAL FKSSFPPGSG    660
GGGSGGGGSG GGGSGGGGSQ SVLTQPPSVS GAPGQRVTIS CSGSRSNIGE    720
ETVKWYQQLP GTAPKLLIYY NDQRPSGVPD RFSGSKSGTS ASLAITGLQA EDEADYYCQS    780
YDRYTHPALL FGTGTKVTVL GQPKAAPSVT LFPPSSEELQ ANKATLVCLI SDFYPGAVTV    840
AWKADSSPVK AGVETTTPSK QSNNKYAASS YLSLTPEQWK SHRSYSCQVT HEGSTVEKTV    900
APTECS                                                                906

SEQ ID NO: 519          moltype = AA   length = 910
FEATURE                 Location/Qualifiers
source                  1..910
                        mol_type = protein
                        organism = synthetic construct
SEQUENCE: 519
EVQLVESGGG LVQPGNSLRL SCAASGFTFS KFGMSWVRQA PGKGLEWVSS ISGSGRDTLY    60
AESVKGRFTI SRDNAKTTLY LQMNSLRPED TAVYYCTIGG SLSVSSQGTL VTVSSSGGPA    120
LFKSSFPPGS IWELKKDVYV VELDWYPDAP GEMVVLTCDT PEEDGITWTL DQSSEVLGSG    180
KTLTIQVKEF GDAGQYTCHK GGEVLSHSLL LLHKKEDGIW STDILKDQKE PKNKTFLRCE    240
AKNYSGRFTC WWLTTISTDL TFSVKSSRGS SDPQGVTCGA ATLSAERVRG DNKEYEYSVE    300
CQEDSACPAA EESLPIEVMV DAVHKLKYEN YTSSFFIRDI IKPDPPKNLQ LKPLKNSRQV    360
EVSWEYPDTW STPHSYFSLT FCVQVQGKSK REKKDRVFTD KTSATVICRK NASISVRAQD    420
RYYSSSWSEW ASVPCSGGGG SGGGGSGGGG SRNLPVATPD PGMFPCLHHS QNLLRAVSNM    480
LQKARQTLEF YPCTSEEIDH EDITKDKTST VEACLPLELT KNESCLNSRE TSFITNGSCL    540
ASRKTSFMMA LCLSSIYEDL KMYQVEFKTM NAKLLMDPKR QIFLDQNMLA VIDELMQALN    600
FNSETVPQKS SLEEPDFYKT KIKLCILLHA FRIRAVTIDR VMSYLNASSG GPALFKSSFP    660
PGSGGGGSGG GGSGGGGSGG GGSQSVLTQP PSVSGAPGQR VTISCSGSRS    720
NIGEETVKWY QQLPGTAPKL LIYYNDQRPS GVPDRFSGSK SGTSASLAIT GLQAEDEADY    780
YCQSYDRYTH PALLFGTGTK VTVLGQPKAA PSVTLFPPSS EELQANKATL VCLISDFYPG    840
AVTVAWKADS SPVKAGVETT TPSKQSNNKY AASSYLSLTP EQWKSHRSYS CQVTHEGSTV    900
EKTVAPTECS                                                           910

SEQ ID NO: 520          moltype = AA   length = 218
FEATURE                 Location/Qualifiers
source                  1..218
                        mol_type = protein
                        organism = synthetic construct
SEQUENCE: 520
QVQLVESGGG VVQPGRSLRL SCAASGFTFS SYGMHWVRQA PGKGLEWVAF IRYDGSNKYY    60
ADSVKGRFTI SRDNSKNTLY LQMNSLRAED TAVYYCSHDN WGQGTM VTVSSASTKG    120
PSVFPLAPSS KSTSGGTAAL GCLVKDYFPE PVTVSWNSGA LTSGVHTFPA VLQSSGLYSL    180
SSVVTVPSSS LGTQTYICNV NHKPSNTKVD KRVEPKSC                             218

SEQ ID NO: 521          moltype = AA   length = 218
FEATURE                 Location/Qualifiers
source                  1..218
                        mol_type = protein
                        organism = synthetic construct
SEQUENCE: 521
QVQLVESGGG VVQPGRSLRL SCAASGFTFS SYGMHWVRQA PGKGLEWVAF IRYEGSNKYY    60
AESVKGRFTI SRDNSKNTLY LQMNSLRAED TAVYYCKTHG SHDNWGQGTM VTVSSASTKG    120
PSVFPLAPSS KSTSGGTAAL GCLVKDYFPE PVTVSWNSGA LTSGVHTFPA VLQSSGLYSL    180
SSVVTVPSSS LGTQTYICNV NHKPSNTKVD KRVEPKSC                             218

SEQ ID NO: 522          moltype = AA   length = 218
FEATURE                 Location/Qualifiers
source                  1..218
                        mol_type = protein
                        organism = synthetic construct
SEQUENCE: 522
QVQLVESGGG VVQPGRSLRL SCAASGFTFS SYGMHWVRQA PGKGLEWVAF IRYEGSNKYY    60
ADSVKGRFTI SRDNSKNTLY LQMNSLRAED TAVYYCKTHG SHDNWGQGTM VTVSSASTKG    120
PSVFPLAPSS KSTSGGTAAL GCLVKDYFPE PVTVSWNSGA LTSGVHTFPA VLQSSGLYSL    180
SSVVTVPSSS LGTQTYICNV NHKPSNTKVD KRVEPKSC                             218

SEQ ID NO: 523          moltype = AA   length = 915
FEATURE                 Location/Qualifiers
source                  1..915
                        mol_type = protein
                        organism = synthetic construct
SEQUENCE: 523
IWELKKDVYV VELDWYPDAP GEMVVLTCDT PEEDGITWTL DQSSEVLGSG KTLTIQVKEF    60
```

```
GDAGQYTCHK  GGEVLSHSLL  LLHKKEDGIW  STDILKDQKE  PKNKTFLRCE  AKNYSGRFTC   120
WWLTTISTDL  TFSVKSSRGS  SDPQGVTCGA  ATLSAERVRG  DNKEYEYSVE  CQEDSACPAA   180
EESLPIEVMV  DAVHKLKYEN  YTSSFFIRDI  IKPDPPKNLQ  LKPLKNSRQV  EVSWEYPDTW   240
STPHSYFSLT  FCVQVQGKSK  REKKDRVFTD  KTSATVICRK  NASISVRAQD  RYYSSSWSEW   300
ASVPCSGGGG  SGGGGSGGGG  SRVIPVSGPA  RCLSQSRNLL  KTTDDMVKTA  REKLKHYSCT   360
AEDIDHEDIT  RDQTSTLKTC  LPLELHKNES  CLATRETSST  TRGSCLPPQK  TSLMMTLCLG   420
SIYEDLKMYQ  TEFQAINAAL  QNHNHQQIIL  DKGMLVAIDE  LMQSLNHNGE  TLRQKPPVGE   480
ADPYRVKMKL  CILLHAFSTR  VVTINRVMGY  LSSASGGPGP  AGLYAQPGSE  VQLVESGGGL   540
VQPGNSLRLS  CAASGFTFSK  FGMSWVRQAP  GKGLEWVSSI  SGSGRDTLYA  ESVKGRFTIS   600
RDNAKTTLYL  QMNSLRPEDT  AVYYCTIGGS  LSVSSQGTLV  TVSSGGGGSG  GGGSGGGGSG   660
GGGSGGGGSG  GGGSQSVLTQ  PPSVSGAPGQ  RVTISCSGSR  SNIGSNTVKW  YQQLPGTAPK   720
LLIYYNDQRP  SGVPDRFSGS  KSGTSASLAI  TGLQAEDEAD  YYCQSYDRYT  HPALLFGTGT   780
KVTVLGGGGS  GGGGSGGGGS  QVQLVESGGG  VVQPGRSLRL  SCAASGFTFS  SYGMHWVRQA   840
PGKGLEWVAF  IRYEGSNKYY  AESVKGRFTI  SRDNSKNTLY  LQMNSLRAED  TAVYYCKTHG   900
SHDNWGQGTM  VTVSS                                                       915

SEQ ID NO: 524          moltype = AA   length = 919
FEATURE                 Location/Qualifiers
source                  1..919
                        mol_type = protein
                        organism = synthetic construct
SEQUENCE: 524
IWELKKDVYV  VELDWYPDAP  GEMVVLTCDT  PEEDGITWTL  DQSSEVLGSG  KTLTIQVKEF    60
GDAGQYTCHK  GGEVLSHSLL  LLHKKEDGIW  STDILKDQKE  PKNKTFLRCE  AKNYSGRFTC   120
WWLTTISTDL  TFSVKSSRGS  SDPQGVTCGA  ATLSAERVRG  DNKEYEYSVE  CQEDSACPAA   180
EESLPIEVMV  DAVHKLKYEN  YTSSFFIRDI  IKPDPPKNLQ  LKPLKNSRQV  EVSWEYPDTW   240
STPHSYFSLT  FCVQVQGKSK  REKKDRVFTD  KTSATVICRK  NASISVRAQD  RYYSSSWSEW   300
ASVPCSGGGG  SGGGGSGGGG  SRNLPVATPD  PGMFPCLHHS  QNLLRAVSNM  LQKARQTLEF   360
YPCTSEEIDH  EDITKDKTST  VEACLPLELT  KNESCLNSRE  TSFITNGSCL  ASRKTSFMMA   420
LCLSSIYEDL  KMYQVEFKTM  NAKLLMDPKR  QIFLDQNMLA  VIDELMQALN  FNSETVPQKS   480
SLEEPDFYKT  KIKLCILLHA  FRIRAVTIDR  VMSYLNASSG  GPGPAGLYAQ  PGSEVQLVES   540
GGGLVQPGNS  LRLSCAASGF  TFSKFGMSWV  RQAPGKGLEW  VSSISGSGRD  TLYAESVKGR   600
FTISRDNAKT  TLYLQMNSLR  PEDTAVYYCT  IGGSLSVSSQ  GTLVTVSSGG  GGSGGGGSGG   660
GGSGGGGSGG  GGSGGGGSQS  VLTQPPSVSG  APGQRVTISC  SGSRSNIGSN  TVKWYQQLPG   720
TAPKLLIYYN  DQRPSGVPDR  FSGSKSGTSA  SLAITGLQAE  DEADYYCQSY  DRYTHPALLF   780
GTGTKVTVLG  GGGSGGGGSG  GGGSQVQLVE  SGGGVVQPGR  SLRLSCAASG  FTFSSYGMHW   840
VRQAPGKGLE  WVAFIRYEGS  NKYYAESVKG  RFTISRDNSK  NTLYLQMNSL  RAEDTAVYYC   900
KTHGSHDNWG  QGTMVTVSS                                                   919

SEQ ID NO: 525          moltype = AA   length = 915
FEATURE                 Location/Qualifiers
source                  1..915
                        mol_type = protein
                        organism = synthetic construct
SEQUENCE: 525
IWELKKDVYV  VELDWYPDAP  GEMVVLTCDT  PEEDGITWTL  DQSSEVLGSG  KTLTIQVKEF    60
GDAGQYTCHK  GGEVLSHSLL  LLHKKEDGIW  STDILKDQKE  PKNKTFLRCE  AKNYSGRFTC   120
WWLTTISTDL  TFSVKSSRGS  SDPQGVTCGA  ATLSAERVRG  DNKEYEYSVE  CQEDSACPAA   180
EESLPIEVMV  DAVHKLKYEN  YTSSFFIRDI  IKPDPPKNLQ  LKPLKNSRQV  EVSWEYPDTW   240
STPHSYFSLT  FCVQVQGKSK  REKKDRVFTD  KTSATVICRK  NASISVRAQD  RYYSSSWSEW   300
ASVPCSGGGG  SGGGGSGGGG  SRVIPVSGPA  RCLSQSRNLL  KTTDDMVKTA  REKLKHYSCT   360
AEDIDHEDIT  RDQTSTLKTC  LPLELHKNES  CLATRETSST  TRGSCLPPQK  TSLMMTLCLG   420
SIYEDLKMYQ  TEFQAINAAL  QNHNHQQIIL  DKGMLVAIDE  LMQSLNHNGE  TLRQKPPVGE   480
ADPYRVKMKL  CILLHAFSTR  VVTINRVMGY  LSSASGGPGP  AGLYAQPGSE  VQLVESGGGL   540
VQPGNSLRLS  CAASGFTFSK  FGMSWVRQAP  GKGLEWVSSI  SGSGRDTLYA  ESVKGRFTIS   600
RDNAKTTLYL  QMNSLRPEDT  AVYYCTIGGS  LSVSSQGTLV  TVSSGGGGSG  GGGSGGGGSG   660
GGGSGGGGSG  GGGSQSVLTQ  PPSVSGAPGQ  RVTISCSGSR  SNIGDETVKW  YQQLPGTAPK   720
LLIYYNDQRP  SGVPDRFSGS  KSGTSASLAI  TGLQAEDEAD  YYCQSYDRYT  HPALLFGTGT   780
KVTVLGGGGS  GGGGSGGGGS  QVQLVESGGG  VVQPGRSLRL  SCAASGFTFS  SYGMHWVRQA   840
PGKGLEWVAF  IRYEGSNKYY  AESVKGRFTI  SRDNSKNTLY  LQMNSLRAED  TAVYYCKTHG   900
SHDNWGQGTM  VTVSS                                                       915

SEQ ID NO: 526          moltype = AA   length = 919
FEATURE                 Location/Qualifiers
source                  1..919
                        mol_type = protein
                        organism = synthetic construct
SEQUENCE: 526
IWELKKDVYV  VELDWYPDAP  GEMVVLTCDT  PEEDGITWTL  DQSSEVLGSG  KTLTIQVKEF    60
GDAGQYTCHK  GGEVLSHSLL  LLHKKEDGIW  STDILKDQKE  PKNKTFLRCE  AKNYSGRFTC   120
WWLTTISTDL  TFSVKSSRGS  SDPQGVTCGA  ATLSAERVRG  DNKEYEYSVE  CQEDSACPAA   180
EESLPIEVMV  DAVHKLKYEN  YTSSFFIRDI  IKPDPPKNLQ  LKPLKNSRQV  EVSWEYPDTW   240
STPHSYFSLT  FCVQVQGKSK  REKKDRVFTD  KTSATVICRK  NASISVRAQD  RYYSSSWSEW   300
ASVPCSGGGG  SGGGGSGGGG  SRNLPVATPD  PGMFPCLHHS  QNLLRAVSNM  LQKARQTLEF   360
YPCTSEEIDH  EDITKDKTST  VEACLPLELT  KNESCLNSRE  TSFITNGSCL  ASRKTSFMMA   420
LCLSSIYEDL  KMYQVEFKTM  NAKLLMDPKR  QIFLDQNMLA  VIDELMQALN  FNSETVPQKS   480
SLEEPDFYKT  KIKLCILLHA  FRIRAVTIDR  VMSYLNASSG  GPGPAGLYAQ  PGSEVQLVES   540
GGGLVQPGNS  LRLSCAASGF  TFSKFGMSWV  RQAPGKGLEW  VSSISGSGRD  TLYAESVKGR   600
FTISRDNAKT  TLYLQMNSLR  PEDTAVYYCT  IGGSLSVSSQ  GTLVTVSSGG  GGSGGGGSGG   660
```

```
GGSGGGGSGG GGSGGGGSQS VLTQPPSVSG APGQRVTISC SGSRSNIGDE TVKWYQQLPG    720
TAPKLLIYYN DQRPSGVPDR FSGSKSGTSA SLAITGLQAE DEADYYCQSY DRYTHPALLF    780
GTGTKVTVLG GGGSGGGGSG GGGSQVQLVE SGGGVVQPGR SLRLSCAASG FTFSSYGMHW    840
VRQAPGKGLE WVAFIRYEGS NKYYAESVKG RFTISRDNSK NTLYLQMNSL RAEDTAVYYC    900
KTHGSHDNWG QGTMVTVSS                                                 919

SEQ ID NO: 527         moltype = AA   length = 891
FEATURE                Location/Qualifiers
source                 1..891
                       mol_type = protein
                       organism = synthetic construct
SEQUENCE: 527
IWELKKDVYV VELDWYPDAP GEMVVLTCDT PEEDGITWTL DQSSEVLGSG KTLTIQVKEF     60
GDAGQYTCHK GGEVLSHSLL LLHKKEDGIW STDILKDQKE PKNKTFLRCE AKNYSGRFTC    120
WWLTTISTDL TFSVKSSRGS SDPQGVTCGA ATLSAERVRG DNKEYEYSVE CQEDSACPAA    180
EESLPIEVMV DAVHKLKYEN YTSSFFIRDI IKPDPPKNLQ LKPLKNSRQV EVSWEYPDTW    240
STPHSYFSLT FCVQVQGKSK REKKDRVFTD KTSATVICRK NASISVRAQD RYYSSSWSEW    300
ASVPCSGGGG SGGGGSGGGG SRVIPVSGPA RCLSQSRNLL KTTDDMVKTA REKLKHYSCT    360
AEDIDHEDIT RDQTSTLKTC LPLELHKNES CLATRETSST TRGSCLPPQK TSLMMTLCLG    420
SIYEDLKMYQ TEFQAINAAL QNHNHQQIIL DKGMLVAIDE LMQSLNHNGE TLRQKPPVGE    480
ADPYRVKMKL CILLHAFSTR VVTINRVMGY LSSASGGPGP AGLYAQPGSE VQLVESGGGL    540
VQPGNSLRLS CAASGFTFSK FGMSWVRQAP GKGLEWVSSI SGSGRDTLYA ESVKGRFTIS    600
RDNAKTTLYL QMNSLRPEDT AVYYCTIGGS LSVSSQGTLV TVSSGGGGSG GGGSGGGGSG    660
GGGSGGGGSG GGGSQSVLTQ PPSVSGAPGQ RVTISCSGSR SNIGSNTVKW YQQLPGTAPK    720
LLIYYNDQRP SGVPDRFSGS KSGTSASLAI TGLQAEDEAD YYCQSYDRYT HPALLFGTGT    780
KVTVLGQPKA APSVTLFPPS SEELQANKAT LVCLISDFYP GAVTVAWKAD SSPVKAGVET    840
TTPSKQSNNK YAASSYLSLT PEQWKSHRSY SCQVTHEGST VEKTVAPTEC S             891

SEQ ID NO: 528         moltype = AA   length = 895
FEATURE                Location/Qualifiers
source                 1..895
                       mol_type = protein
                       organism = synthetic construct
SEQUENCE: 528
IWELKKDVYV VELDWYPDAP GEMVVLTCDT PEEDGITWTL DQSSEVLGSG KTLTIQVKEF     60
GDAGQYTCHK GGEVLSHSLL LLHKKEDGIW STDILKDQKE PKNKTFLRCE AKNYSGRFTC    120
WWLTTISTDL TFSVKSSRGS SDPQGVTCGA ATLSAERVRG DNKEYEYSVE CQEDSACPAA    180
EESLPIEVMV DAVHKLKYEN YTSSFFIRDI IKPDPPKNLQ LKPLKNSRQV EVSWEYPDTW    240
STPHSYFSLT FCVQVQGKSK REKKDRVFTD KTSATVICRK NASISVRAQD RYYSSSWSEW    300
ASVPCSGGGG SGGGGSGGGG SRNLPVATPD PGMFPCLHHS QNLLRAVSNM LQKARQTLEF    360
YPCTSEEIDH EDITKDKTST VEACLPLELT KNESCLNSRE TSFITNGSCL ASRKTSFMMA    420
LCLSSIYEDL KMYQVEFKTM NAKLLMDPKR QIFLDQNMLA VIDELMQALN FNSETVPQKS    480
SLEEPDFYKT KIKLCILLHA FRIRAVTIDR VMSYLNASSG GPGPAGLYAQ PGSEVQLVES    540
GGGLVQPGNS LRLSCAASGF TFSKFGMSWV RQAPGKGLEW VSSISGSGRD TLYAESVKGR    600
FTISRDNAKT TLYLQMNSLR PEDTAVYYCT IGGSLSVSSQ GTLVTVSSGG GGSGGGGSGG    660
GGSGGGGSGG GGSGGGGSQS VLTQPPSVSG APGQRVTISC SGSRSNIGSN TVKWYQQLPG    720
TAPKLLIYYN DQRPSGVPDR FSGSKSGTSA SLAITGLQAE DEADYYCQSY DRYTHPALLF    780
GTGTKVTVLG QPKAAPSVTL FPPSSEELQA NKATLVCLIS DFYPGAVTVA WKADSSPVKA    840
GVETTTPSKQ SNNKYAASSY LSLTPEQWKS HRSYSCQVTH EGSTVEKTVA PTECS          895

SEQ ID NO: 529         moltype = AA   length = 891
FEATURE                Location/Qualifiers
source                 1..891
                       mol_type = protein
                       organism = synthetic construct
SEQUENCE: 529
IWELKKDVYV VELDWYPDAP GEMVVLTCDT PEEDGITWTL DQSSEVLGSG KTLTIQVKEF     60
GDAGQYTCHK GGEVLSHSLL LLHKKEDGIW STDILKDQKE PKNKTFLRCE AKNYSGRFTC    120
WWLTTISTDL TFSVKSSRGS SDPQGVTCGA ATLSAERVRG DNKEYEYSVE CQEDSACPAA    180
EESLPIEVMV DAVHKLKYEN YTSSFFIRDI IKPDPPKNLQ LKPLKNSRQV EVSWEYPDTW    240
STPHSYFSLT FCVQVQGKSK REKKDRVFTD KTSATVICRK NASISVRAQD RYYSSSWSEW    300
ASVPCSGGGG SGGGGSGGGG SRVIPVSGPA RCLSQSRNLL KTTDDMVKTA REKLKHYSCT    360
AEDIDHEDIT RDQTSTLKTC LPLELHKNES CLATRETSST TRGSCLPPQK TSLMMTLCLG    420
SIYEDLKMYQ TEFQAINAAL QNHNHQQIIL DKGMLVAIDE LMQSLNHNGE TLRQKPPVGE    480
ADPYRVKMKL CILLHAFSTR VVTINRVMGY LSSASGGPGP AGLYAQPGSE VQLVESGGGL    540
VQPGNSLRLS CAASGFTFSK FGMSWVRQAP GKGLEWVSSI SGSGRDTLYA ESVKGRFTIS    600
RDNAKTTLYL QMNSLRPEDT AVYYCTIGGS LSVSSQGTLV TVSSGGGGSG GGGSGGGGSG    660
GGGSGGGGSG GGGSQSVLTQ PPSVSGAPGQ RVTISCSGSR SNIGDETVKW YQQLPGTAPK    720
LLIYYNDQRP SGVPDRFSGS KSGTSASLAI TGLQAEDEAD YYCQSYDRYT HPALLFGTGT    780
KVTVLGQPKA APSVTLFPPS SEELQANKAT LVCLISDFYP GAVTVAWKAD SSPVKAGVET    840
TTPSKQSNNK YAASSYLSLT PEQWKSHRSY SCQVTHEGST VEKTVAPTEC S             891

SEQ ID NO: 530         moltype = AA   length = 895
FEATURE                Location/Qualifiers
source                 1..895
                       mol_type = protein
                       organism = synthetic construct
SEQUENCE: 530
IWELKKDVYV VELDWYPDAP GEMVVLTCDT PEEDGITWTL DQSSEVLGSG KTLTIQVKEF     60
```

```
GDAGQYTCHK GGEVLSHSLL LLHKKEDGIW STDILKDQKE PKNKTFLRCE AKNYSGRFTC      120
WWLTTISTDL TFSVKSSRGS SDPQGVTCGA ATLSAERVRG DNKEYEYSVE CQEDSACPAA      180
EESLPIEVMV DAVHKLKYEN YTSSFFIRDI IKPDPPKNLQ LKPLKNSRQV EVSWEYPDTW      240
STPHSYFSLT FCVQVQGKSK REKKDRVFTD KTSATVICRK NASISVRAQD RYYSSSWSEW      300
ASVPCSGGGG SGGGGSGGGG SRNLPVATPD PGMFPCLHHS QNLLRAVSNM LQKARQTLEF      360
YPCTSEEIDH EDITKDKTST VEACLPLELT KNESCLNSRE TSFITNGSCL ASRKTSFMMA      420
LCLSSIYEDL KMYQVEFKTM NAKLLMDPKR QIFLDQNMLA VIDELMQALN FNSETVPQKS      480
SLEEPDFYKT KIKLCILLHA FRIRAVTIDR VMSYLNASSG GPGPAGLYAQ PGSEVQLVES      540
GGGLVQPGNS LRLSCAASGF TFSKFGMSWV RQAPGKGLEW VSSISGSGRD TLYAESVKGR      600
FTISRDNAKT TLYLQMNSLR PEDTAVYYCT IGGSLSVSSQ GTLVTVSSGG GSGGGGSGG      660
GGSGGGGSGG GGSGGGGSQS VLTQPPSVSG APGQRVTISC SGSRSNIGDE TVKWYQQLPG      720
TAPKLLIYYN DQRPSGVPDR FSGSKSGTSA SLAITGLQAE DEADYYCQSY DRYTHPALLF      780
GTGTKVTVLG QPKAAPSVTL FPPSSEELQA NKATLVCLIS DFYPGAVTVA WKADSSPVKA      840
GVETTTPSKQ SNNKYAASSY LSLTPEQWKS HRSYSCQVTH EGSTVEKTVA PTECS          895

SEQ ID NO: 531           moltype = AA   length = 915
FEATURE                  Location/Qualifiers
source                   1..915
                         mol_type = protein
                         organism = synthetic construct
SEQUENCE: 531
IWELKKDVYV VELDWYPDAP GEMVVLTCDT PEEDGITWTL DQSSEVLGSG KTLTIQVKEF       60
GDAGQYTCHK GGEVLSHSLL LLHKKEDGIW STDILKDQKE PKNKTFLRCE AKNYSGRFTC      120
WWLTTISTDL TFSVKSSRGS SDPQGVTCGA ATLSAERVRG DNKEYEYSVE CQEDSACPAA      180
EESLPIEVMV DAVHKLKYEN YTSSFFIRDI IKPDPPKNLQ LKPLKNSRQV EVSWEYPDTW      240
STPHSYFSLT FCVQVQGKSK REKKDRVFTD KTSATVICRK NASISVRAQD RYYSSSWSEW      300
ASVPCSGGGG SGGGGSGGGG SRVIPVSGPA RCLSQSRNLL KTTDDMVKTA REKLKHYSCT      360
AEDIDHEDIT RDQTSTLKTC LPLELHKNES CLATRETSST TRGSCLPPQK TSLMMTLCLG      420
SIYEDLKMYQ TEFQAINAAL QNHNHQQIIL DKGMLVAIDE LMQSLNHNGE TLRQKPPVGE      480
ADPYRVKMKL CILLHAFSTR VVTINRVMGY LSSASGGPAL FKSSFPPGSE VQLVESGGGL      540
VQPGNSLRLS CAASGFTFSK FGMSWVRQAP GKGLEWVSSI SGSGRDTLYA ESVKGRFTIS      600
RDNAKTTLYL QMNSLRPEDT AVYYCTIGGS LSVSSQGTLV TVSSGGGGSG GGGSGGGGSG      660
GGGSGGGGSG GGGSQSVLTQ PPSVSGAPGQ RVTISCSGSR SNIGSNTVKW YQQLPGTAPK      720
LLIYYNDQRP SGVPDRFSGS KSGTSASLAI TGLQAEDEAD YYCQSYDRYT HPALLFGTGT      780
KVTVLGGGGS GGGGSGGGGS QVQLVESGGG VVQPGRSLRL SCAASGFTFS SYGMHWVRQA      840
PGKGLEWVAF IRYEGSNKYY AESVKGRFTI SRDNSKNTLY LQMNSLRAED TAVYYCKTHG      900
SHDNWGQGTM VTVSS                                                      915

SEQ ID NO: 532           moltype = AA   length = 919
FEATURE                  Location/Qualifiers
source                   1..919
                         mol_type = protein
                         organism = synthetic construct
SEQUENCE: 532
IWELKKDVYV VELDWYPDAP GEMVVLTCDT PEEDGITWTL DQSSEVLGSG KTLTIQVKEF       60
GDAGQYTCHK GGEVLSHSLL LLHKKEDGIW STDILKDQKE PKNKTFLRCE AKNYSGRFTC      120
WWLTTISTDL TFSVKSSRGS SDPQGVTCGA ATLSAERVRG DNKEYEYSVE CQEDSACPAA      180
EESLPIEVMV DAVHKLKYEN YTSSFFIRDI IKPDPPKNLQ LKPLKNSRQV EVSWEYPDTW      240
STPHSYFSLT FCVQVQGKSK REKKDRVFTD KTSATVICRK NASISVRAQD RYYSSSWSEW      300
ASVPCSGGGG SGGGGSGGGG SRNLPVATPD PGMFPCLHHS QNLLRAVSNM LQKARQTLEF      360
YPCTSEEIDH EDITKDKTST VEACLPLELT KNESCLNSRE TSFITNGSCL ASRKTSFMMA      420
LCLSSIYEDL KMYQVEFKTM NAKLLMDPKR QIFLDQNMLA VIDELMQALN FNSETVPQKS      480
SLEEPDFYKT KIKLCILLHA FRIRAVTIDR VMSYLNASSG GPALFKSSFP PGSEVQLVES      540
GGGLVQPGNS LRLSCAASGF TFSKFGMSWV RQAPGKGLEW VSSISGSGRD TLYAESVKGR      600
FTISRDNAKT TLYLQMNSLR PEDTAVYYCT IGGSLSVSSQ GTLVTVSSGG GSGGGGSGG      660
GGSGGGGSGG GGSGGGGSQS VLTQPPSVSG APGQRVTISC SGSRSNIGSN TVKWYQQLPG      720
TAPKLLIYYN DQRPSGVPDR FSGSKSGTSA SLAITGLQAE DEADYYCQSY DRYTHPALLF      780
GTGTKVTVLG GGGSGGGGSG GGGSQVQLVE SGGGVVQPGR SLRLSCAASG FTFSSYGMHW      840
VRQAPGKGLE WVAFIRYEGS NKYYAESVKG RFTISRDNSK NTLYLQMNSL RAEDTAVYYC      900
KTHGSHDNWG QGTMVTVSS                                                  919

SEQ ID NO: 533           moltype = AA   length = 915
FEATURE                  Location/Qualifiers
source                   1..915
                         mol_type = protein
                         organism = synthetic construct
SEQUENCE: 533
IWELKKDVYV VELDWYPDAP GEMVVLTCDT PEEDGITWTL DQSSEVLGSG KTLTIQVKEF       60
GDAGQYTCHK GGEVLSHSLL LLHKKEDGIW STDILKDQKE PKNKTFLRCE AKNYSGRFTC      120
WWLTTISTDL TFSVKSSRGS SDPQGVTCGA ATLSAERVRG DNKEYEYSVE CQEDSACPAA      180
EESLPIEVMV DAVHKLKYEN YTSSFFIRDI IKPDPPKNLQ LKPLKNSRQV EVSWEYPDTW      240
STPHSYFSLT FCVQVQGKSK REKKDRVFTD KTSATVICRK NASISVRAQD RYYSSSWSEW      300
ASVPCSGGGG SGGGGSGGGG SRVIPVSGPA RCLSQSRNLL KTTDDMVKTA REKLKHYSCT      360
AEDIDHEDIT RDQTSTLKTC LPLELHKNES CLATRETSST TRGSCLPPQK TSLMMTLCLG      420
SIYEDLKMYQ TEFQAINAAL QNHNHQQIIL DKGMLVAIDE LMQSLNHNGE TLRQKPPVGE      480
ADPYRVKMKL CILLHAFSTR VVTINRVMGY LSSASGGPAL FKSSFPPGSE VQLVESGGGL      540
VQPGNSLRLS CAASGFTFSK FGMSWVRQAP GKGLEWVSSI SGSGRDTLYA ESVKGRFTIS      600
RDNAKTTLYL QMNSLRPEDT AVYYCTIGGS LSVSSQGTLV TVSSGGGGSG GGGSGGGGSG      660
GGGSGGGGSG GGGSQSVLTQ PPSVSGAPGQ RVTISCSGSR SNIGDETVKW YQQLPGTAPK      720
```

```
LLIYYNDQRP SGVPDRFSGS KSGTSASLAI TGLQAEDEAD YYCQSYDRYT HPALLFGTGT    780
KVTVLGGGGS GGGGSGGGGS QVQLVESGGG VVQPGRSLRL SCAASGFTFS SYGMHWVRQA    840
PGKGLEWVAF IRYEGSNKYY AESVKGRFTI SRDNSKNTLY LQMNSLRAED TAVYYCKTHG    900
SHDNWGQGTM VTVSS                                                    915

SEQ ID NO: 534            moltype = AA  length = 919
FEATURE                   Location/Qualifiers
source                    1..919
                          mol_type = protein
                          organism = synthetic construct
SEQUENCE: 534
IWELKKDVYV VELDWYPDAP GEMVVLTCDT PEEDGITWTL DQSSEVLGSG KTLTIQVKEF     60
GDAGQYTCHK GGEVLSHSLL LLHKKEDGIW STDILKDQKE PKNKTFLRCE AKNYSGRFTC    120
WWLTTISTDL TFSVKSSRGS SDPQGVTCGA ATLSAERVRG DNKEYEYSVE CQEDSACPAA    180
EESLPIEVMV DAVHKLKYEN YTSSFFIRDI IKPDPPKNLQ LKPLKNSRQV EVSWEYPDTW    240
STPHSYFSLT FCVQVQGKSK REKKDRVFTD KTSATVICRK NASISVRAQD RYYSSSWSEW    300
ASVPCSGGGG SGGGGSGGGG SRNLPVATPD PGMFPCLHHS QNLLRAVSNM LQKARQTLEF    360
YPCTSEEIDH EDITKDKTST VEACLPLELT KNESCLNSRE TSFITNGSCL ASRKTSFMMA    420
LCLSSIYEDL KMYQVEFKTM NAKLLMDPKR QIFLDQNMLA VIDELMQALN FNSETVPQKS    480
SLEEPDFYKT KIKLCILLHA FRIRAVTIDR VMSYLNASSG GPALFKSSFP PGSEVQLVES    540
GGGLVQPGNS LRLSCAASGF TFSKFGMSWV RQAPGKGLEW VSSISGSGRD TLYAESVKGR    600
FTISRDNAKT TLYLQMNSLR PEDTAVYYCT IGGSLSVSSQ GTLVTVSSGG GGSGGGGSGG    660
GGSGGGGSGG GGSGGGGSQS VLTQPPSVSG APGQRVTISC SGSRSNIGDE TVKWYQQLPG    720
TAPKLLIYYN DQRPSGVPDR FSGSKSGTSA SLAITGLQAE DEADYYCQSY DRYTHPALLF    780
GTGTKVTVLG GGGSGGGGSG GGGSQVQLVE SGGGVVQPGR SLRLCAASG FTFSSYGMHW    840
VRQAPGKGLE WVAFIRYEGS NKYYAESVKG RFTISRDNSK NTLYLQMNSL RAEDTAVYYC    900
KTHGSHDNWG QGTMVTVSS                                                919

SEQ ID NO: 535            moltype = AA  length = 891
FEATURE                   Location/Qualifiers
source                    1..891
                          mol_type = protein
                          organism = synthetic construct
SEQUENCE: 535
IWELKKDVYV VELDWYPDAP GEMVVLTCDT PEEDGITWTL DQSSEVLGSG KTLTIQVKEF     60
GDAGQYTCHK GGEVLSHSLL LLHKKEDGIW STDILKDQKE PKNKTFLRCE AKNYSGRFTC    120
WWLTTISTDL TFSVKSSRGS SDPQGVTCGA ATLSAERVRG DNKEYEYSVE CQEDSACPAA    180
EESLPIEVMV DAVHKLKYEN YTSSFFIRDI IKPDPPKNLQ LKPLKNSRQV EVSWEYPDTW    240
STPHSYFSLT FCVQVQGKSK REKKDRVFTD KTSATVICRK NASISVRAQD RYYSSSWSEW    300
ASVPCSGGGG SGGGGSGGGG SRVIPVSGPA RCLSQSRNLL KTTDDMVKTA REKLKHYSCT    360
AEDIDHEDIT RDQTSTLKTC LPLELHKNES CLATRETSST TRGSCLPPQK TSLMMTLCLG    420
SIYEDLKMYQ TEFQAINAAL QNHNHQQIIL DKGMLVAIDE LMQSLNHNGE TLRQKPPVGE    480
ADPYRVKMKL CILLHAFSTR VVTINRVMGY LSSASGGPAL FKSSFPPGSE VQLVESGGGL    540
VQPGNSLRLS CAASGFTFSK FGMSWVRQAP GKGLEWVSSI SGSGRDTLYA ESVKGRFTIS    600
RDNAKTTLYL QMNSLRPEDT AVYYCTIGGS LSVSSQGTLV TVSSGGGGGS GGGGSGGGGS    660
GGGSGGGGS GGGSQSVLTQ PPSVSGAPGQ RVTISCSGSR SNIGSNTVKW YQQLPGTAPK    720
LLIYYNDQRP SGVPDRFSGS KSGTSASLAI TGLQAEDEAD YYCQSYDRYT HPALLFGTGT    780
KVTVLGQPKA APSVTLFPPS SEELQANKAT LVCLISDFYP GAVTVAWKAD SSPVKAGVET    840
TTPSKQSNNK YAASSYLSLT PEQWKSHRSY SCQVTHEGST VEKTVAPTEC S             891

SEQ ID NO: 536            moltype = AA  length = 895
FEATURE                   Location/Qualifiers
source                    1..895
                          mol_type = protein
                          organism = synthetic construct
SEQUENCE: 536
IWELKKDVYV VELDWYPDAP GEMVVLTCDT PEEDGITWTL DQSSEVLGSG KTLTIQVKEF     60
GDAGQYTCHK GGEVLSHSLL LLHKKEDGIW STDILKDQKE PKNKTFLRCE AKNYSGRFTC    120
WWLTTISTDL TFSVKSSRGS SDPQGVTCGA ATLSAERVRG DNKEYEYSVE CQEDSACPAA    180
EESLPIEVMV DAVHKLKYEN YTSSFFIRDI IKPDPPKNLQ LKPLKNSRQV EVSWEYPDTW    240
STPHSYFSLT FCVQVQGKSK REKKDRVFTD KTSATVICRK NASISVRAQD RYYSSSWSEW    300
ASVPCSGGGG SGGGGSGGGG SRNLPVATPD PGMFPCLHHS QNLLRAVSNM LQKARQTLEF    360
YPCTSEEIDH EDITKDKTST VEACLPLELT KNESCLNSRE TSFITNGSCL ASRKTSFMMA    420
LCLSSIYEDL KMYQVEFKTM NAKLLMDPKR QIFLDQNMLA VIDELMQALN FNSETVPQKS    480
SLEEPDFYKT KIKLCILLHA FRIRAVTIDR VMSYLNASSG GPALFKSSFP PGSEVQLVES    540
GGGLVQPGNS LRLSCAASGF TFSKFGMSWV RQAPGKGLEW VSSISGSGRD TLYAESVKGR    600
FTISRDNAKT TLYLQMNSLR PEDTAVYYCT IGGSLSVSSQ GTLVTVSSGG GGSGGGGSGG    660
GGSGGGGSGG GGSGGGGSQS VLTQPPSVSG APGQRVTISC SGSRSNIGSN TVKWYQQLPG    720
TAPKLLIYYN DQRPSGVPDR FSGSKSGTSA SLAITGLQAE DEADYYCQSY DRYTHPALLF    780
GTGTKVTVLG QPKAAPSVTL FPPSSEELQA NKATLVCLIS DFYPGAVTVA WKADSSPVKA    840
GVETTTPSKQ SNNKYAASSY LSLTPEQWKS HRSYSCQVTH EGSTVEKTVA PTECS         895

SEQ ID NO: 537            moltype = AA  length = 891
FEATURE                   Location/Qualifiers
source                    1..891
                          mol_type = protein
                          organism = synthetic construct
SEQUENCE: 537
IWELKKDVYV VELDWYPDAP GEMVVLTCDT PEEDGITWTL DQSSEVLGSG KTLTIQVKEF     60
```

```
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSACPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RYYSSSWSEW   300
ASVPCSGGGG SGGGGSGGGG SRVIPVSGPA RCLSQSRNLL KTTDDMVKTA REKLKHYSCT   360
AEDIDHEDIT RDQTSTLKTC LPLELHKNES CLATRETSST TRGSCLPPQK TSLMMTLCLG   420
SIYEDLKMYQ TEFQAINAAL QNHNHQQIIL DKGMLVAIDE LMQSLNHNGE TLRQKPPVGE   480
ADPYRVKMKL CILLHAFSTR VVTINRVMGY LSSASGGPAL FKSSFPPGSE VQLVESGGGL   540
VQPGNSLRLS CAASGFTFSK FGMSWVRQAP GKGLEWVSSI SGSGRDTLYA ESVKGRFTIS   600
RDNAKTTLYL QMNSLRPEDT AVYYCTIGGS LSVSSQGTLV TVSSGGGGSG GGGSGGGGSG   660
GGGSGGGGSG GGGSQSVLTQ PPSVSGAPGQ RVTISCSGSR SNIGDETVKW YQQLPGTAPK   720
LLIYYNDQRP SGVPDRFSGS KSGTSASLAI TGLQAEDEAD YYCQSYDRYT HPALLFGTGT   780
KVTVLGQPKA APSVTLFPPS SEELQANKAT LVCLISDFYP GAVTVAWKAD SSPVKAGVET   840
TTPSKQSNNK YAASSYLSLT PEQWKSHRSY SCQVTHEGST VEKTVAPTEC S            891

SEQ ID NO: 538          moltype = AA   length = 895
FEATURE                 Location/Qualifiers
source                  1..895
                        mol_type = protein
                        organism = synthetic construct
SEQUENCE: 538
IWELKKDVYV VELDWYPDAP GEMVVLTCDT PEEDGITWTL DQSSEVLGSG KTLTIQVKEF    60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSACPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RYYSSSWSEW   300
ASVPCSGGGG SGGGGSGGGG SRNLPVATPD PGMFPCLHHS QNLLRAVSNM LQKARQTLEF   360
YPCTSEEIDH EDITKDKTST VEACLPLELT KNESCLNSRE TSFITNGSCL ASRKTSFMMA   420
LCLSSIYEDL KMYQVEFKTM NAKLLMDPKR QIFLDQNMLA VIDELMQALN FNSETVPQKS   480
SLEEPDFYKT KIKLCILLHA FRIRAVTIDR VMSYLNASSG GPALFKSSFP PGSEVQLVES   540
GGGLVQPGNS LRLSCAASGF TFSKFGMSWV RQAPGKGLEW VSSISGSGRD TLYAESVKGR   600
FTISRDNAKT TLYLQMNSLR PEDTAVYYCT IGGSLSVSSQ GTLVTVSSGG GGSGGGGSGG   660
GGSGGGGSGG GGSGGGGSQS VLTQPPSVSG APGQRVTISC SGSRSNIGDE TVKWYQQLPG   720
TAPKLLIYYN DQRPSGVPDR FSGSKSGTSA SLAITGLQAE DEADYYCQSY DRYTHPALLF   780
GTGTKVTVLG QPKAAPSVTL FPPSSEELQA NKATLVCLIS DFYPGAVTVA WKADSSPVKA   840
GVETTTPSKQ SNNKYAASSY LSLTPEQWKS HRSYSCQVTH EGSTVEKTVA PTECS         895

SEQ ID NO: 539          moltype = AA   length = 427
FEATURE                 Location/Qualifiers
source                  1..427
                        mol_type = protein
                        organism = synthetic construct
SEQUENCE: 539
EVQLVESGGG LVQPGNSLRL SCAASGFTFS KFGMSWVRQA PGKGLEWVSS ISGSGRDTLY    60
AESVKGRFTI SRDNAKTTLY LQMNSLRPED TAVYYCTIGG SLSVSSQGTL VTVSSSGGPG   120
PAGLYAQPGS CDLPHTYNLR NKRALKVLAQ MRRLTPLSCL KDRKDFGFPL EKVDAQQIQK   180
AQSIPVLRDL TQQILNLFAS KDSSAAWNAT LLDSFCNDLH QQLNDLQGCL MQQVGVQESP   240
LTQEDSLLAV RIYFHRITVF LREKKHSPCA WEVVRAEVWR ALSSSANVLG RLREEKASGG   300
PGPAGLYAQP GSEVQLVESG GLVQPGNSL RLSCAASGFT FSKFGMSWVR QAPGKGLEWV   360
SSISGSGRDT LYAESVKGRF TISRDNAKTT LYLQMNSLRP EDTAVYYCTI GGSLSVSSQG   420
TLVTVSS                                                             427

SEQ ID NO: 540          moltype = AA   length = 427
FEATURE                 Location/Qualifiers
source                  1..427
                        mol_type = protein
                        organism = synthetic construct
SEQUENCE: 540
EVQLVESGGG LVQPGNSLRL SCAASGFTFS KFGMSWVRQA PGKGLEWVSS ISGSGRDTLY    60
AESVKGRFTI SRDNAKTTLY LQMNSLRPED TAVYYCTIGG SLSVSSQGTL VTVSSSGGPA   120
LFKSSFPPGS CDLPHTYNLR NKRALKVLAQ MRRLTPLSCL KDRKDFGFPL EKVDAQQIQK   180
AQSIPVLRDL TQQILNLFAS KDSSAAWNAT LLDSFCNDLH QQLNDLQGCL MQQVGVQESP   240
LTQEDSLLAV RIYFHRITVF LREKKHSPCA WEVVRAEVWR ALSSSANVLG RLREEKASGG   300
PALFKSSFPP GSEVQLVESG GLVQPGNSL RLSCAASGFT FSKFGMSWVR QAPGKGLEWV   360
SSISGSGRDT LYAESVKGRF TISRDNAKTT LYLQMNSLRP EDTAVYYCTI GGSLSVSSQG   420
TLVTVSS                                                             427

SEQ ID NO: 541          moltype = AA   length = 426
FEATURE                 Location/Qualifiers
source                  1..426
                        mol_type = protein
                        organism = synthetic construct
SEQUENCE: 541
EVQLVESGGG LVQPGNSLRL SCAASGFTFS KFGMSWVRQA PGKGLEWVSS ISGSGRDTLY    60
AESVKGRFTI SRDNAKTTLY LQMNSLRPED TAVYYCTIGG SLSVSSQGTL VTVSSSGGPG   120
PAGLYAQPGS CNLSQTHSLN NRRTLMLMAQ MRRISPFSCL KDRHDFEFPQ EEFDGNQFQK   180
AQAISVLHEM MQQTFNLFST KNSSAAWDET LLEKFYIELF QQMNDLEACV IQEVGVEETP   240
LMNEDSILAV KKYFQRITLY LMEKKYSPCA WEVVRAEIMR SLSFSTNLQK RLRRKDSGGP   300
GPAGLYAQPG SEVQLVESGG GLVQPGNSLR LSCAASGFTF SKFGMSWVRQ APGKGLEWVS   360
```

```
SISGSGRDTL YAESVKGRFT ISRDNAKTTL YLQMNSLRPE DTAVYYCTIG GSLSVSSQGT   420
LVTVSS                                                              426

SEQ ID NO: 542           moltype = AA  length = 426
FEATURE                  Location/Qualifiers
source                   1..426
                         mol_type = protein
                         organism = synthetic construct
SEQUENCE: 542
EVQLVESGGG LVQPGNSLRL SCAASGFTFS KFGMSWVRQA PGKGLEWVSS ISGSGRDTLY   60
AESVKGRFTI SRDNAKTTLY LQMNSLRPED TAVYYCTIGG SLSVSSQGTL VTVSSSGGPA   120
LFKSSFPPGS CNLSQTHSLN NRRTLMLMAQ MRRISPFSCL KDRHDFEFPQ EEFDGNQFQK   180
AQAISVLHEM MQQTFNLFST KNSSAAWDET LLEKFYIELF QQMNDLEACV IQEVGVEETP   240
LMNEDSILAV KKYFQRITLY LMEKKYSPCA WEVVRAEIMR SLSFSTNLQK RLRRKDSGGP   300
ALFKSSFPPG SEVQLVESGG GLVQPGNSLR LSCAASGFTF SKFGMSWVRQ APGKGLEWVS   360
SISGSGRDTL YAESVKGRFT ISRDNAKTTL YLQMNSLRPE DTAVYYCTIG GSLSVSSQGT   420
LVTVSS                                                              426

SEQ ID NO: 543           moltype = AA  length = 173
FEATURE                  Location/Qualifiers
source                   1..173
                         mol_type = protein
                         organism = synthetic construct
SEQUENCE: 543
CDLPHTYNLR NKRALKVLAQ MRRLTPLSCL KDRKDFGFPL EKVDAQQIQK AQSIPVLRDL   60
TQQILNLFAS KDSSAAWNAT LLDSFCNDLH QQLNDLQGCL MQQVGVQESP LTQEDSLLAV   120
RIYFHRITVF LREKKHSPCA WEVVRAEVWR ALSSSANVLG RLREEKAHHH HHH          173

SEQ ID NO: 544           moltype = AA  length = 172
FEATURE                  Location/Qualifiers
source                   1..172
                         mol_type = protein
                         organism = synthetic construct
SEQUENCE: 544
CNLSQTHSLN NRRTLMLMAQ MRRISPFSCL KDRHDFEFPQ EEFDGNQFQK AQAISVLHEM   60
MQQTFNLFST KNSSAAWDET LLEKFYIELF QQMNDLEACV IQEVGVEETP LMNEDSILAV   120
KKYFQRITLY LMEKKYSPCA WEVVRAEIMR SLSFSTNLQK RLRRKDHHHH HH           172

SEQ ID NO: 545           moltype = AA  length = 425
FEATURE                  Location/Qualifiers
source                   1..425
                         mol_type = protein
                         organism = synthetic construct
SEQUENCE: 545
EVQLVESGGG LVQPGNSLRL SCAASGFTFS KFGMSWVRQA PGKGLEWVSS ISGSGRDTLY   60
AESVKGRFTI SRDNAKTTLY LQMNSLRPED TAVYYCTIGG SLSVSSQGTL VTVSSSGGPG   120
PAGLYAQPGS CDLPQTHSLG SRRTLMLLAQ MRRISLFSCL KDRHDFGFPQ EEFGNQFQKA   180
ETIPVLHEMI QQIFNLFSTK DSSAAWNETL LDKFYTELYQ QLNDLEACVI QGVGVEETPL   240
MKEDSILAVR KYFQRITLYL KEKKYSPCAW EVVRAEIMRS FSLSTNLQES LRSKESGGPG   300
PAGLYAQPGS EVQLVESGGG LVQPGNSLRL SCAASGFTFS KFGMSWVRQA PGKGLEWVSS   360
ISGSGRDTLY AESVKGRFTI SRDNAKTTLY LQMNSLRPED TAVYYCTIGG SLSVSSQGTL   420
VTVSS                                                               425

SEQ ID NO: 546           moltype = AA  length = 426
FEATURE                  Location/Qualifiers
source                   1..426
                         mol_type = protein
                         organism = synthetic construct
SEQUENCE: 546
EVQLVESGGG LVQPGNSLRL SCAASGFTFS KFGMSWVRQA PGKGLEWVSS ISGSGRDTLY   60
AESVKGRFTI SRDNAKTTLY LQMNSLRPED TAVYYCTIGG SLSVSSQGTL VTVSSSGGPG   120
PAGLYAQPGS CNLSQTHSLN NRRTLMLMAQ MRRISPFSCL KDRHDFEFPQ EEFDGNQFQK   180
AQAISVLHEM MQQTFNLFST KDSSAAWDET LLEKFYIELF QQMNDLEACV IQEVGVEETP   240
LMNEDSILAV KKYFQRITLY LMEKKYSPCA WEVVRAEIMR SLSFSTNLQK RLRRKDSGGP   300
GPAGLYAQPG SEVQLVESGG GLVQPGNSLR LSCAASGFTF SKFGMSWVRQ APGKGLEWVS   360
SISGSGRDTL YAESVKGRFT ISRDNAKTTL YLQMNSLRPE DTAVYYCTIG GSLSVSSQGT   420
LVTVSS                                                              426

SEQ ID NO: 547           moltype = AA  length = 426
FEATURE                  Location/Qualifiers
source                   1..426
                         mol_type = protein
                         organism = synthetic construct
SEQUENCE: 547
EVQLVESGGG LVQPGNSLRL SCAASGFTFS KFGMSWVRQA PGKGLEWVSS ISGSGRDTLY   60
AESVKGRFTI SRDNAKTTLY LQMNSLRPED TAVYYCTIGG SLSVSSQGTL VTVSSSGGPG   120
PAGLYAQPGS CDLPQTHSLN NRRTLMLMAQ MRRISPFSCL KDRHDFEFPQ EEFDGNQFQK   180
AQAISVLHEM MQQTFNLFST KDSSAAWDET LLEKFYIELF QQMNDLEACV IQEVGVEETP   240
LMNEDSILAV KKYFQRITLY LMEKKYSPCA WEVVRAEIMR SLSFSTNLQK RLRRKDSGGP   300
```

```
GPAGLYAQPG SEVQLVESGG GLVQPGNSLR LSCAASGFTF SKFGMSWVRQ APGKGLEWVS    360
SISGSGRDTL YAESVKGRFT ISRDNAKTTL YLQMNSLRPE DTAVYYCTIG GSLSVSSQGT    420
LVTVSS                                                                426

SEQ ID NO: 548         moltype = AA   length = 171
FEATURE                Location/Qualifiers
source                 1..171
                       mol_type = protein
                       organism = synthetic construct
SEQUENCE: 548
CDLPQTHSLG SRRTLMLLAQ MRRISLFSCL KDRHDFGFPQ EEFGNQFQKA ETIPVLHEMI     60
QQIFNLFSTK DSSAAWDETL LDKFYTELYQ QLNDLEACVI QGVGVEETPL MKEDSILAVR    120
KYFQRITLYL KEKKYSPCAW EVVRAEIMRS FSLSTNLQES LRSKEHHHHH H             171

SEQ ID NO: 549         moltype = AA   length = 172
FEATURE                Location/Qualifiers
source                 1..172
                       mol_type = protein
                       organism = synthetic construct
SEQUENCE: 549
CNLSQTHSLN NRRTLMLMAQ MRRISPFSCL KDRHDFEFPQ EEFDGNQFQK AQAISVLHEM     60
MQQTFNLFST KDSSAAWDET LLEKFYIELF QQMNDLEACV IQEVGVEETP LMNEDSILAV    120
KKYFQRITLY LMEKKYSPCA WEVVRAEIMR SLSFSTNLQK RLRRKDHHHH HH            172

SEQ ID NO: 550         moltype = AA   length = 172
FEATURE                Location/Qualifiers
source                 1..172
                       mol_type = protein
                       organism = synthetic construct
SEQUENCE: 550
CDLPQTHSLN NRRTLMLMAQ MRRISPFSCL KDRHDFEFPQ EEFDGNQFQK AQAISVLHEM     60
MQQTFNLFST KDSSAAWDET LLEKFYIELF QQMNDLEACV IQEVGVEETP LMNEDSILAV    120
KKYFQRITLY LMEKKYSPCA WEVVRAEIMR SLSFSTNLQK RLRRKDHHHH HH            172

SEQ ID NO: 551         moltype = AA   length = 1370
FEATURE                Location/Qualifiers
source                 1..1370
                       mol_type = protein
                       organism = synthetic construct
SEQUENCE: 551
EAHKSEIAHR YNDLGEQHFK GLVLIAFSQY LQKCSYDEHA KLVQEVTDFA KTCVADESAA     60
NCDKSLHTLF GDKLCAIPNL RENYGELADC CTKQEPERNE CFLQHKDDNP SLPPFERPEA    120
EAMCTSFKEN PTTFMGHYLH EVARRHPYFY APELLYYAEQ YNEILTQCCA EADKESCLTP    180
KLDGVKEKAL VSSVRQRMKC SSMQKFGERA FKAWAVARLS QTFPNADFAE ITKLATDLTK    240
VNKECCHGDL LECADDRAEL AKYMCENQAT ISSKLQTCCD KPLLKAHCL SEVEHDTMPA     300
DLPAIAADFV EDQEVCKNYA EAKDVFLGTF LYEYSRRHPD YSVSLLLRLA KKYEATLEKC    360
CAEANPPACY GTVLAEFQPL VEEPKNLVKT NCDLYEKLGE YGFQNAILVR YTQKAPQVST    420
PTLVEAARNL GRVGTKCCTL PEDQRLPCVE DYLSAILNRV CLLHEKTPVS EHVTKCCSGS    480
LVERRPCFSA LTVDETYVPK EFKAETFTFH SDICTLPEKE KQIKKQTALA ELVKHKPKAT    540
AEQLKTVMDD FAQFLDTCCK AADKDTCFST EGPNLVTRCK DALASGGPAL FKSSFPPGSC    600
DLPQTHNLRN KRALTLLVQM RRLSPLSCLK DRKDFGFPQE KVDAQQIKKA QAIPVLSELT    660
QQILNIFTSK DSSAAWNTTL LDSFCNDLHQ QLNDLQGCLM QQVGVQEFPL TQEDALLAVR    720
KYFHRITVYL REKHSPCAW EVVRAEVWRA LSSSANVLGR LREEKSGGPA LFKSSFPPGS     780
EAHKSEIAHR YNDLGEQHFK GLVLIAFSQY LQKCSYDEHA KLVQEVTDFA KTCVADESAA    840
NCDKSLHTLF GDKLCAIPNL RENYGELADC CTKQEPERNE CFLQHKDDNP SLPPFERPEA    900
EAMCTSFKEN PTTFMGHYLH EVARRHPYFY APELLYYAEQ YNEILTQCCA EADKESCLTP    960
KLDGVKEKAL VSSVRQRMKC SSMQKFGERA FKAWAVARLS QTFPNADFAE ITKLATDLTK   1020
VNKECCHGDL LECADDRAEL AKYMCENQAT ISSKLQTCCD KPLLKAHCL SEVEHDTMPA    1080
DLPAIAADFV EDQEVCKNYA EAKDVFLGTF LYEYSRRHPD YSVSLLLRLA KKYEATLEKC   1140
CAEANPPACY GTVLAEFQPL VEEPKNLVKT NCDLYEKLGE YGFQNAILVR YTQKAPQVST   1200
PTLVEAARNL GRVGTKCCTL PEDQRLPCVE DYLSAILNRV CLLHEKTPVS EHVTKCCSGS   1260
LVERRPCFSA LTVDETYVPK EFKAETFTFH SDICTLPEKE KQIKKQTALA ELVKHKPKAT   1320
AEQLKTVMDD FAQFLDTCCK AADKDTCFST EGPNLVTRCK DALAHHHHHH              1370

SEQ ID NO: 552         moltype = AA   length = 1371
FEATURE                Location/Qualifiers
source                 1..1371
                       mol_type = protein
                       organism = synthetic construct
SEQUENCE: 552
EAHKSEIAHR YNDLGEQHFK GLVLIAFSQY LQKCSYDEHA KLVQEVTDFA KTCVADESAA     60
NCDKSLHTLF GDKLCAIPNL RENYGELADC CTKQEPERNE CFLQHKDDNP SLPPFERPEA    120
EAMCTSFKEN PTTFMGHYLH EVARRHPYFY APELLYYAEQ YNEILTQCCA EADKESCLTP    180
KLDGVKEKAL VSSVRQRMKC SSMQKFGERA FKAWAVARLS QTFPNADFAE ITKLATDLTK    240
VNKECCHGDL LECADDRAEL AKYMCENQAT ISSKLQTCCD KPLLKAHCL SEVEHDTMPA     300
DLPAIAADFV EDQEVCKNYA EAKDVFLGTF LYEYSRRHPD YSVSLLLRLA KKYEATLEKC    360
CAEANPPACY GTVLAEFQPL VEEPKNLVKT NCDLYEKLGE YGFQNAILVR YTQKAPQVST    420
PTLVEAARNL GRVGTKCCTL PEDQRLPCVE DYLSAILNRV CLLHEKTPVS EHVTKCCSGS    480
LVERRPCFSA LTVDETYVPK EFKAETFTFH SDICTLPEKE KQIKKQTALA ELVKHKPKAT    540
```

```
AEQLKTVMDD FAQFLDTCCK AADKDTCFST EGPNLVTRCK DALASGGGPAL FKSSFPPGSC    600
DLPHTYNLRN KRALKVLAQM RRLTPLSCLK DRKDFGFPLE KVDAQQIQKA QSIPVLRDLT    660
QQILNLFASK DSSAAWNATL LDSFCNDLHQ QLNDLQGCLM QQVGVQESPL TQEDSLLAVR    720
IYFHRITVFL REKKHSPCAW EVVRAEVWRA LSSSANVLGR LREEKASGGP ALFKSSFPPG    780
SEAHKSEIAH RYNDLGEQHF KGLVLIAFSQ YLQKCSYDEH AKLVQEVTDF AKTCVADESA    840
ANCDKSLHTL FGDKLCAIPN LRENYGELAD CCTKQEPERN ECFLQHKDDN PSLPPFERPE    900
AEAMCTSFKE NPTTFMGHYL HEVARRHPYF YAPELLYYAE QYNEILTQCC AEADKESCLT    960
PKLDGVKEKA LVSSVRQRMK CSSMQKFGER AFKAWAVARL SQTFPNADFA EITKLATDLT   1020
KVNKECCHGD LLECADDRAE LAKYMCENQA TISSKLQTCC DKPLLKKAHC LSEVEHDTMP   1080
ADLPAIAADF VEDQEVCKNY AEAKDVFLGT FLYEYSRRHP DYSVSLLLRL AKKYEATLEK   1140
CCAEANPPAC YGTVLAEFQP LVEEPKNLVK TNCDLYEKLG EYGFQNAILV RYTQKAPVQS   1200
TPTLVEAARN LGRVGTKCCT LPEDQRLPCV EDYLSAILNR VCLLHEKTPV SEHVTKCCSG   1260
SLVERRPCFS ALTVDETYVP KEFKAETFTF HSDICTLPEK EKQIKKQTAL AELVKHKPKA   1320
TAEQLKTVMD DFAQFLDTCC KAADKDTCFS TEGPNLVTRC KDALAHHHHH H            1371

SEQ ID NO: 553          moltype = AA  length = 901
FEATURE                 Location/Qualifiers
source                  1..901
                        mol_type = protein
                        organism = synthetic construct
SEQUENCE: 553
EVQLVESGGG LVQPGNSLRL SCAASGFTFS KFGMSWVRQA PGKGLEWVSS ISGSGRDTLY     60
AESVKGRFTI SRDNAKTTLY LQMNSLRPED TAVYYCTIGG SLSVSSQGTL VTVSSSGGPA    120
LFKSSFPPGS CDLPQTHNLR NKRALTLLVQ MRRLSPLSCL KDRKDFGFPQ EKVDAQQIKK    180
AQAIPVLSEL TQQILNIFTS KDSSAAWNTT LLDSFCNDLH QQLNDLQGCL MQQVGVQEFP    240
LTQEDALLAV RKYFHRITVY LREKKHSPCA WEVVRAEVWR ALSSSANVLG RLREEKSGGP    300
ALFKSSFPPG SEAHKSEIAH RYNDLGEQHF KGLVLIAFSQ YLQKCSYDEH AKLVQEVTDF    360
AKTCVADESA ANCDKSLHTL FGDKLCAIPN LRENYGELAD CCTKQEPERN ECFLQHKDDN    420
PSLPPFERPE AEAMCTSFKE NPTTFMGHYL HEVARRHPYF YAPELLYYAE QYNEILTQCC    480
AEADKESCLT PKLDGVKEKA LVSSVRQRMK CSSMQKFGER AFKAWAVARL SQTFPNADFA    540
EITKLATDLT KVNKECCHGD LLECADDRAE LAKYMCENQA TISSKLQTCC DKPLLKKAHC    600
LSEVEHDTMP ADLPAIAADF VEDQEVCKNY AEAKDVFLGT FLYEYSRRHP DYSVSLLLRL    660
AKKYEATLEK CCAEANPPAC YGTVLAEFQP LVEEPKNLVK TNCDLYEKLG EYGFQNAILV    720
RYTQKAPVQS TPTLVEAARN LGRVGTKCCT LPEDQRLPCV EDYLSAILNR VCLLHEKTPV    780
SEHVTKCCSG SLVERRPCFS ALTVDETYVP KEFKAETFTF HSDICTLPEK EKQIKKQTAL    840
AELVKHKPKA TAEQLKTVMD DFAQFLDTCC KAADKDTCFS TEGPNLVTRC KDALAHHHHH    900
H                                                                   901

SEQ ID NO: 554          moltype = AA  length = 902
FEATURE                 Location/Qualifiers
source                  1..902
                        mol_type = protein
                        organism = synthetic construct
SEQUENCE: 554
EVQLVESGGG LVQPGNSLRL SCAASGFTFS KFGMSWVRQA PGKGLEWVSS ISGSGRDTLY     60
AESVKGRFTI SRDNAKTTLY LQMNSLRPED TAVYYCTIGG SLSVSSQGTL VTVSSSGGPA    120
LFKSSFPPGS CDLPHTYNLR NKRALKVLAQ MRRLTPLSCL KDRKDFGFPL EKVDAQQIQK    180
AQSIPVLRDL TQQILNLFAS KDSSAAWNAT LLDSFCNDLH QQLNDLQGCL MQQVGVQESP    240
LTQEDSLLAV RIYFHRITVF LREKKHSPCA WEVVRAEVWR ALSSSANVLG RLREEKASGG    300
PALFKSSFPP GSEAHKSEIA HRYNDLGEQH FKGLVLIAFS QYLQKCSYDE HAKLVQEVTD    360
FAKTCVADES AANCDKSLHT LFGDKLCAIP NLRENYGELA DCCTKQEPER NECFLQHKDD    420
NPSLPPFERP EAEAMCTSFK ENPTTFMGHY LHEVARRHPY FYAPELLYYA EQYNEILTQC    480
CAEADKESCL TPKLDGVKEK ALVSSVRQRM KCSSMQKFGE RAFKAWAVAR LSQTFPNADF    540
AEITKLATDL TKVNKECCHG DLLECADDRA ELAKYMCENQ ATISSKLQTC CDKPLLKKAH    600
CLSEVEHDTM PADLPAIAAD FVEDQEVCKN YAEAKDVFLG TFLYEYSRRH PDYSVSLLLR    660
LAKKYEATLE KCCAEANPPA CYGTVLAEFQ PLVEEPKNLV KTNCDLYEKL GEYGFQNAIL    720
VRYTQKAPVQ STPTLVEAAR NLGRVGTKCC TLPEDQRLPC VEDYLSAILN RVCLLHEKTP    780
VSEHVTKCCS GSLVERRPCF SALTVDETYV PKEFKAETFT FHSDICTLPE KEKQIKKQTA    840
LAELVKHKPK ATAEQLKTVM DDFAQFLDTC CKAADKDTCF STEGPNLVTR CKDALAHHHH    900
HH                                                                  902

SEQ ID NO: 555          moltype = AA  length = 901
FEATURE                 Location/Qualifiers
source                  1..901
                        mol_type = protein
                        organism = synthetic construct
SEQUENCE: 555
EAHKSEIAHR YNDLGEQHFK GLVLIAFSQY LQKCSYDEHA KLVQEVTDFA KTCVADESAA     60
NCDKSLHTLF GDKLCAIPNL RENYGELADC CTKQEPERNE CFLQHKDDNP SLPPFERPEA    120
EAMCTSFKEN PTTFMGHYLH EVARRHPYFY APELLYYAEQ YNEILTQCCA EADKESCLTP    180
KLDGVKEKAL VSSVRQRMKC SSMQKFGERA FKAWAVARLS QTFPNADFAE ITKLATDLTK    240
VNKECCHGDL LECADDRAEL AKYMCENQAT ISSKLQTCCD KPLLKKAHCL SEVEHDTMPA    300
DLPAIAADFV EDQEVCKNYA EAKDVFLGTF LYEYSRRHPD YSVSLLLRLA KKYEATLEKC    360
CAEANPPACY GTVLAEFQPL VEEPKNLVKT NCDLYEKLGE YGFQNAILVR YTQKAPVQST    420
PTLVEAARNL GRVGTKCCTL PEDQRLPCVE DYLSAILNRV CLLHEKTPVS EHVTKCCSGS    480
LVERRPCFSA LTVDETYVPK EFKAETFTFH SDICTLPEKE KQIKKQTALA ELVKHKPKAT    540
AEQLKTVMDD FAQFLDTCCK AADKDTCFST EGPNLVTRCK DALASGGPAL FKSSFPPGSC    600
DLPQTHNLRN KRALTLLVQM RRLSPLSCLK DRKDFGFPQE KVDAQQIKKA QAIPVLSELT    660
QQILNIFTSK DSSAAWNTTL LDSFCNDLHQ QLNDLQGCLM QQVGVQEFPL TQEDALLAVR    720
```

```
KYFHRITVYL REKKHSPCAW EVVRAEVWRA LSSSANVLGR LREEKSGGPA LFKSSFPPGS    780
EVQLVESGGG LVQPGNSLRL SCAASGFTFS KFGMSWVRQA PGKGLEWVSS ISGSGRDTLY    840
AESVKGRFTI SRDNAKTTLY LQMNSLRPED TAVYYCTIGG SLSVSSQGTL VTVSSHHHHH    900
H                                                                    901

SEQ ID NO: 556          moltype = AA  length = 902
FEATURE                 Location/Qualifiers
source                  1..902
                        mol_type = protein
                        organism = synthetic construct
SEQUENCE: 556
EAHKSEIAHR YNDLGEQHFK GLVLIAFSQY LQKCSYDEHA KLVQEVTDFA KTCVADESAA     60
NCDKSLHTLF GDKLCAIPNL RENYGELADC CTKQEPERNE CFLQHKDDNP SLPPFERPEA    120
EAMCTSFKEN PTTFMGHYLH EVARRHPYFY APELLYYAEQ YNEILTQCCA EADKESCLTP    180
KLDGVKEKAL VSSVRQRMKC SSMQKFGERA FKAWAVARLS QTFPNADFAE ITKLATDLTK    240
VNKECCHGDL LECADDRAEL AKYMCENQAT ISSKLQTCCD KPLLKKAHCL SEVEHDTMPA    300
DLPAIAADFV EDQEVCKNYA EAKDVFLGTF LYEYSRRHPD YSVSLLLRLA KKYEATLEKC    360
CAEANPPACY GTVLAEFQPL VEEPKNLVKT NCDLYEKLGE YGFQNAILVR YTQKAPQVST    420
PTLVEAARNL GRVGTKCCTL PEDQRLPCVE DYLSAILNRV CLLHEKTPVS EHVTKCCSGS    480
LVERRPCFSA LTVDETYVPK EFKAETFTFH SDICTLPEKE KQIKKQTALA ELVKHKPKAT    540
AEQLKTVMDD FAQFLDTCCK AADKDTCFST EGPNLVTRCK DALASGGPAL FKSSFPPGSC    600
DLPHTYNLRN KRALKVLAQM RRLTPLSCLK DRKDFGFPPL KVDAQQIQKA QSIPVLRDLT    660
QQILNLFASK DSSAAWNATL LDSFCNDLHQ QLNDLQGCLM QQVGVQESPL TQEDSLLAVR    720
IYFHRITVFL REKKHSPCAW EVVRAEVWRA LSSSANVLGR LREEKASGGP ALFKSSFPPG    780
SEVQLVESGG GLVQPGNSLR LSCAASGFTF SKFGMSWVRQ APGKGLEWVS SISGSGRDTL    840
YAESVKGRFT ISRDNAKTTL YLQMNSLRPE DTAVYYCTIG GSLSVSSQGT LVTVSSHHHH    900
HH                                                                   902

SEQ ID NO: 557          moltype = AA  length = 1365
FEATURE                 Location/Qualifiers
source                  1..1365
                        mol_type = protein
                        organism = synthetic construct
SEQUENCE: 557
DAHKSEVAHR FKDLGEENFK ALVLIAFAQY LQQCPFEDHV KLVNEVTEFA KTCVADESAE     60
NCDKSLHTLF GDKLCTVATL RETYGEMADC CAKQEPERNE CFLQHKDDNP NLPRLVRPEV    120
DVMCTAFHDN EETFLKKYLY EIARRHPYFY APELLFFAKR YKAAFTECCQ AADKAACLLP    180
KLDELRDEGK ASSAKQRLKC ASLQKFGERA FKAWAVARLS QRFPKAEFAE VSKLVTDLTK    240
VHTECCHGDL LECADDRADL AKYICENQDS ISSKLKECCE KPLLEKSHCI AEVENDEMPA    300
DLPSLAADFV ESKDVCKNYA EAKDVFLGMF LYEYARRHPD YSVVLLLRLA KTYETTLEKC    360
CAAADPHECY AKVFDEFKPL VEEPQNLIKQ NCELFEQLGE YKFQNALLVR YTKKVPQVST    420
PTLVEVSRNL GKVGSKCCKH PEAKRMPCAE DYLSVVLNQL CVLHEKTPVS DRVTKCCTES    480
LVNRRPCFSA LEVDETYVPK EFNAETFTFH ADICTLSEKE RQIKKQTALV ELVKHKPKAT    540
KEQLKAVMDD FAAFVEKCCK ADDKETCFAE EGKKLVAASQ AALGLSGGPA LFKSSFPPGS    600
CDLPQTHSLG SRRTLMLLAQ MRRISLFSCL KDRHDFGFPQ EEFGNQFQKA ETIPVLHEMI    660
QQIFNLFSTK DSSAAWDETL LDKFYTELYQ QLNDLEACVI QGVGVTETPL MKEDSILAVR    720
KYFQRITLYL KEKKYSPCAW EVVRAEIMRS FSLSTNLQKS LRSKESGGPA LFKSSFPPGS    780
DAHKSEVAHR FKDLGEENFK ALVLIAFAQY LQQCPFEDHV KLVNEVTEFA KTCVADESAE    840
NCDKSLHTLF GDKLCTVATL RETYGEMADC CAKQEPERNE CFLQHKDDNP NLPRLVRPEV    900
DVMCTAFHDN EETFLKKYLY EIARRHPYFY APELLFFAKR YKAAFTECCQ AADKAACLLP    960
KLDELRDEGK ASSAKQRLKC ASLQKFGERA FKAWAVARLS QRFPKAEFAE VSKLVTDLTK   1020
VHTECCHGDL LECADDRADL AKYICENQDS ISSKLKECCE KPLLEKSHCI AEVENDEMPA   1080
DLPSLAADFV ESKDVCKNYA EAKDVFLGMF LYEYARRHPD YSVVLLLRLA KTYETTLEKC   1140
CAAADPHECY AKVFDEFKPL VEEPQNLIKQ NCELFEQLGE YKFQNALLVR YTKKVPQVST   1200
PTLVEVSRNL GKVGSKCCKH PEAKRMPCAE DYLSVVLNQL CVLHEKTPVS DRVTKCCTES   1260
LVNRRPCFSA LEVDETYVPK EFNAETFTFH ADICTLSEKE RQIKKQTALV ELVKHKPKAT   1320
KEQLKAVMDD FAAFVEKCCK ADDKETCFAE EGKKLVAASQ AALGL                  1365

SEQ ID NO: 558          moltype = AA  length = 1366
FEATURE                 Location/Qualifiers
source                  1..1366
                        mol_type = protein
                        organism = synthetic construct
SEQUENCE: 558
DAHKSEVAHR FKDLGEENFK ALVLIAFAQY LQQCPFEDHV KLVNEVTEFA KTCVADESAE     60
NCDKSLHTLF GDKLCTVATL RETYGEMADC CAKQEPERNE CFLQHKDDNP NLPRLVRPEV    120
DVMCTAFHDN EETFLKKYLY EIARRHPYFY APELLFFAKR YKAAFTECCQ AADKAACLLP    180
KLDELRDEGK ASSAKQRLKC ASLQKFGERA FKAWAVARLS QRFPKAEFAE VSKLVTDLTK    240
VHTECCHGDL LECADDRADL AKYICENQDS ISSKLKECCE KPLLEKSHCI AEVENDEMPA    300
DLPSLAADFV ESKDVCKNYA EAKDVFLGMF LYEYARRHPD YSVVLLLRLA KTYETTLEKC    360
CAAADPHECY AKVFDEFKPL VEEPQNLIKQ NCELFEQLGE YKFQNALLVR YTKKVPQVST    420
PTLVEVSRNL GKVGSKCCKH PEAKRMPCAE DYLSVVLNQL CVLHEKTPVS DRVTKCCTES    480
LVNRRPCFSA LEVDETYVPK EFNAETFTFH ADICTLSEKE RQIKKQTALV ELVKHKPKAT    540
KEQLKAVMDD FAAFVEKCCK ADDKETCFAE EGKKLVAASQ AALGLSGGPA LFKSSFPPGS    600
CNLSQTHSLN NRRTLMLMAQ MRRISPFSCL KDRHDFEFPQ EEFDGNQFQK AQAISVLHEM    660
MQQTFNLFST KNSSAAWDET LLEKFYIELF QQMNDLEACV IQEVGVEETP LMNEDSILAV    720
KKYFQRITLY LMEKKYSPCA WEVVRAEIMR SLSFSTNLQK RLRRKDSGGP ALFKSSFPPG    780
SDAHKSEVAH RFKDLGEENF KALVLIAFAQ YLQQCPFEDH VKLVNEVTEF AKTCVADESA    840
ENCDKSLHTL FGDKLCTVAT LRETYGEMAD CCAKQEPERN ECFLQHKDDN PNLPRLVRPE    900
```

```
VDVMCTAFHD NEETFLKKYL YEIARRHPYF YAPELLFFAK RYKAAFTECC QAADKAACLL    960
PKLDELRDEG KASSAKQRLK CASLQKFGER AFKAWAVARL SQRFPKAEFA EVSKLVTDLT   1020
KVHTECCHGD LLECADDRAD LAKYICENQD SISSSKLKECC EKPLLEKSHC IAEVENDEMP  1080
ADLPSLAADF VESKDVCKNY AEAKDVFLGM FLYEYARRHP DYSVVLLLRL AKTYETTLEK   1140
CCAAADPHEC YAKVFDEFKP LVEEPQNLIK QNCELFEQLG EYKFQNALLV RYTKKVPQVS   1200
TPTLVEVSRN LGKVGSKCCK HPEAKRMPCA EDYLSVVLNQ LCVLHEKTPV SDRVTKCCTE   1260
SLVNRRPCFS ALEVDETYVP KEFNAETFTF HADICTLSEK ERQIKKQTAL VELVKHKPKA   1320
TKEQLKAVMD DFAAFVEKCC KADDKETCFA EEGKKLVAAS QAALGL                 1366

SEQ ID NO: 559           moltype = AA  length = 1366
FEATURE                  Location/Qualifiers
source                   1..1366
                         mol_type = protein
                         organism = synthetic construct
SEQUENCE: 559
DAHKSEVAHR FKDLGEENFK ALVLIAFAQY LQQCPFEDHV KLVNEVTEFA KTCVADESAE     60
NCDKSLHTLF GDKLCTVATL RETYGEMADC CAKQEPERNE CFLQHKDDNP NLPRLVRPEV   120
DVMCTAFHDN EETFLKKYLY EIARRHPYFY APELLFFAKR YKAAFTECCQ AADKAACLLP   180
KLDELRDEGK ASSAKQRLKC ASLQKFGERA FKAWAVARLS QRFPKAEFAE VSKLVTDLTK   240
VHTECCHGDL LECADDRADL AKYICENQDS ISSKLKECCE KPLLEKSHCI AEVENDEMPA   300
DLPSLAADFV ESKDVCKNYA EAKDVFLGMF LYEYARRHPD YSVVLLLRLA KTYETTLEKC   360
CAAADPHECY AKVFDEFKPL VEEPQNLIKQ NCELFEQLGE YKFQNALLVR YTKKVPQVST   420
PTLVEVSRNL GKVGSKCCKH PEAKRMPCAE DYLSVVLNQL CVLHEKTPVS DRVTKCCTES   480
LVNRRPCFSA LEVDETYVPK EFNAETFTFH ADICTLSEKE RQIKKQTALV ELVKHKPKAT   540
KEQLKAVMDD FAAFVEKCCK ADDKETCFAE EGKKLVAASQ AALGLSGGPA LFKSSFPPGS   600
CDLPQTHSLG NRRALILLAQ MRRISPFSCL KDRHDFEPPQ EEFDDKQFQK AQAISVLHEM   660
IQQTFNLFST KDSSAALDET LLDEFYIELD QQLNDLESCV MQEVGVIESP LMYEDSILAV   720
RKYFQRITLY LTEKKYSSCA WEVVRAEIMR SFSLSINLQK RLKSKESGGP ALFKSSFPPG   780
SDAHKSEVAH RFKDLGEENF KALVLIAFAQ YLQQCPFEDH VKLVNEVTEF AKTCVADESA   840
ENCDKSLHTL FGDKLCTVAT LRETYGEMAD CCAKQEPERN ECFLQHKDDN PNLPRLVRPE   900
VDVMCTAFHD NEETFLKKYL YEIARRHPYF YAPELLFFAK RYKAAFTECC QAADKAACLL   960
PKLDELRDEG KASSAKQRLK CASLQKFGER AFKAWAVARL SQRFPKAEFA EVSKLVTDLT  1020
KVHTECCHGD LLECADDRAD LAKYICENQD SISSSKLKECC EKPLLEKSHC IAEVENDEMP 1080
ADLPSLAADF VESKDVCKNY AEAKDVFLGM FLYEYARRHP DYSVVLLLRL AKTYETTLEK  1140
CCAAADPHEC YAKVFDEFKP LVEEPQNLIK QNCELFEQLG EYKFQNALLV RYTKKVPQVS  1200
TPTLVEVSRN LGKVGSKCCK HPEAKRMPCA EDYLSVVLNQ LCVLHEKTPV SDRVTKCCTE  1260
SLVNRRPCFS ALEVDETYVP KEFNAETFTF HADICTLSEK ERQIKKQTAL VELVKHKPKA  1320
TKEQLKAVMD DFAAFVEKCC KADDKETCFA EEGKKLVAAS QAALGL                1366

SEQ ID NO: 560           moltype = AA  length = 1366
FEATURE                  Location/Qualifiers
source                   1..1366
                         mol_type = protein
                         organism = synthetic construct
SEQUENCE: 560
DAHKSEVAHR FKDLGEENFK ALVLIAFAQY LQQCPFEDHV KLVNEVTEFA KTCVADESAE    60
NCDKSLHTLF GDKLCTVATL RETYGEMADC CAKQEPERNE CFLQHKDDNP NLPRLVRPEV   120
DVMCTAFHDN EETFLKKYLY EIARRHPYFY APELLFFAKR YKAAFTECCQ AADKAACLLP   180
KLDELRDEGK ASSAKQRLKC ASLQKFGERA FKAWAVARLS QRFPKAEFAE VSKLVTDLTK   240
VHTECCHGDL LECADDRADL AKYICENQDS ISSKLKECCE KPLLEKSHCI AEVENDEMPA   300
DLPSLAADFV ESKDVCKNYA EAKDVFLGMF LYEYARRHPD YSVVLLLRLA KTYETTLEKC   360
CAAADPHECY AKVFDEFKPL VEEPQNLIKQ NCELFEQLGE YKFQNALLVR YTKKVPQVST   420
PTLVEVSRNL GKVGSKCCKH PEAKRMPCAE DYLSVVLNQL CVLHEKTPVS DRVTKCCTES   480
LVNRRPCFSA LEVDETYVPK EFNAETFTFH ADICTLSEKE RQIKKQTALV ELVKHKPKAT   540
KEQLKAVMDD FAAFVEKCCK ADDKETCFAE EGKKLVAASQ AALGLSGGPA LFKSSFPPGS   600
CDLPQTHSLG NRRALILLAQ MGRISHFSCL KDRYDFGFPQ EVFDGNQFQK AQAISAFHEM   660
IQQTFNLFST KDSSAAWDET LLDKFYIELF QQLNDLEACV TQEVGVEEIA LMNEDSILAV   720
RKYFQRITLY LMGKKYSPCA WEVVRAEIMR SFSFSTNLQK GLRRKDSGGP ALFKSSFPPG   780
SDAHKSEVAH RFKDLGEENF KALVLIAFAQ YLQQCPFEDH VKLVNEVTEF AKTCVADESA   840
ENCDKSLHTL FGDKLCTVAT LRETYGEMAD CCAKQEPERN ECFLQHKDDN PNLPRLVRPE   900
VDVMCTAFHD NEETFLKKYL YEIARRHPYF YAPELLFFAK RYKAAFTECC QAADKAACLL   960
PKLDELRDEG KASSAKQRLK CASLQKFGER AFKAWAVARL SQRFPKAEFA EVSKLVTDLT  1020
KVHTECCHGD LLECADDRAD LAKYICENQD SISSSKLKECC EKPLLEKSHC IAEVENDEMP 1080
ADLPSLAADF VESKDVCKNY AEAKDVFLGM FLYEYARRHP DYSVVLLLRL AKTYETTLEK  1140
CCAAADPHEC YAKVFDEFKP LVEEPQNLIK QNCELFEQLG EYKFQNALLV RYTKKVPQVS  1200
TPTLVEVSRN LGKVGSKCCK HPEAKRMPCA EDYLSVVLNQ LCVLHEKTPV SDRVTKCCTE  1260
SLVNRRPCFS ALEVDETYVP KEFNAETFTF HADICTLSEK ERQIKKQTAL VELVKHKPKA  1320
TKEQLKAVMD DFAAFVEKCC KADDKETCFA EEGKKLVAAS QAALGL                1366

SEQ ID NO: 561           moltype = AA  length = 426
FEATURE                  Location/Qualifiers
source                   1..426
                         mol_type = protein
                         organism = synthetic construct
SEQUENCE: 561
EVQLVESGGG LVQPGNSLRL SCAASGFTFS KFGMSWVRQA PGKGLEWVSS ISGSGRDTLY    60
AESVKGRFTI SRDNAKTTLY LQMNSLRPED TAVYYCTIGG SLSVSSQGTL VTVSSSGGPA   120
LFKSSFPPGS CDLPQTHSLG NRRALILLAQ MRRISPFSCL KDRHDFEPPQ EEFDDKQFQK   180
AQAISVLHEM IQQTFNLFST KDSSAALDET LLDEFYIELD QQLNDLESCV MQEVGVIESP   240
```

```
LMYEDSILAV RKYFQRITLY LTEKKYSSCA WEVVRAEIMR SFSLSINLQK RLKSKESGGP   300
ALFKSSFPPG SEVQLVESGG GLVQPGNSLR LSCAASGFTF SKFGMSWVRQ APGKGLEWVS   360
SISGSGRDTL YAESVKGRFT ISRDNAKTTL YLQMNSLRPE DTAVYYCTIG GSLSVSSQGT   420
LVTVSS                                                              426

SEQ ID NO: 562          moltype = AA   length = 426
FEATURE                 Location/Qualifiers
source                  1..426
                        mol_type = protein
                        organism = synthetic construct
SEQUENCE: 562
EVQLVESGGG LVQPGNSLRL SCAASGFTFS KFGMSWVRQA PGKGLEWVSS ISGSGRDTLY   60
AESVKGRFTI SRDNAKTTLY LQMNSLRPED TAVYYCTIGG SLSVSSQGTL VTVSSSGGPA   120
LFKSSFPPGS CDLPQTHSLG NRRALILLAQ MGRISHFSCL KDRYDFGFPQ EVFDGNQFQK   180
AQAISAFHEM IQQTFNLFST KDSSAAWDET LLDKFYIELF QQLNDLEACV TQEVGVEEIA   240
LMNEDSILAV RKYFQRITLY LMGKKYSPCA WEVVRAEIMR SFSFSTNLQK GLRRKDSGGP   300
ALFKSSFPPG SEVQLVESGG GLVQPGNSLR LSCAASGFTF SKFGMSWVRQ APGKGLEWVS   360
SISGSGRDTL YAESVKGRFT ISRDNAKTTL YLQMNSLRPE DTAVYYCTIG GSLSVSSQGT   420
LVTVSS                                                              426

SEQ ID NO: 563          moltype = AA   length = 421
FEATURE                 Location/Qualifiers
source                  1..421
                        mol_type = protein
                        organism = synthetic construct
SEQUENCE: 563
EVQLVESGGG LVQPGNSLRL SCAASGFTFS KFGMSWVRQA PGKGLEWVSS ISGSGRDTLY   60
AESVKGRFTI SRDNAKTTLY LQMNSLRPED TAVYYCTIGG SLSVSSQGTL VTVSSSGGPG   120
PAGLYAQPGS INYKQLQLQE RTNIRKCQEL LEQLNGKINL TYRADFKIPM EMTEKMQKSY   180
TAFAIQEMLQ NVFLVFRNNF SSTGWNETIV VRLLDELHQQ TVFLKTVLEE KQEERLTWEM   240
SSTALHLKSY YWRVQRYLKL MKYNSYAWMV VRAEIFRNFL IIRRLTRNFQ NSGGPGPAGL   300
YAQPGSEVQL VESGGGLVQP GNSLRLSCAA SGFTFSKFGM SWVRQAPGKG LEWVSSISGS   360
GRDTLYAESV KGRFTISRDN AKTTLYLQMN SLRPEDTAVY YCTIGGSLSV SSQGTLVTVS   420
S                                                                   421

SEQ ID NO: 564          moltype = AA   length = 421
FEATURE                 Location/Qualifiers
source                  1..421
                        mol_type = protein
                        organism = synthetic construct
SEQUENCE: 564
EVQLVESGGG LVQPGNSLRL SCAASGFTFS KFGMSWVRQA PGKGLEWVSS ISGSGRDTLY   60
AESVKGRFTI SRDNAKTTLY LQMNSLRPED TAVYYCTIGG SLSVSSQGTL VTVSSSGGPA   120
LFKSSFPPGS INYKQLQLQE RTNIRKCQEL LEQLNGKINL TYRADFKIPM EMTEKMQKSY   180
TAFAIQEMLQ NVFLVFRNNF SSTGWNETIV VRLLDELHQQ TVFLKTVLEE KQEERLTWEM   240
SSTALHLKSY YWRVQRYLKL MKYNSYAWMV VRAEIFRNFL IIRRLTRNFQ NSGGPALFKS   300
SFPPGSEVQL VESGGGLVQP GNSLRLSCAA SGFTFSKFGM SWVRQAPGKG LEWVSSISGS   360
GRDTLYAESV KGRFTISRDN AKTTLYLQMN SLRPEDTAVY YCTIGGSLSV SSQGTLVTVS   420
S                                                                   421

SEQ ID NO: 565          moltype = AA   length = 421
FEATURE                 Location/Qualifiers
source                  1..421
                        mol_type = protein
                        organism = synthetic construct
SEQUENCE: 565
EVQLVESGGG LVQPGNSLRL SCAASGFTFS KFGMSWVRQA PGKGLEWVSS ISGSGRDTLY   60
AESVKGRFTI SRDNAKTTLY LQMNSLRPED TAVYYCTIGG SLSVSSQGTL VTVSSSGGPG   120
PAGLYAQPGS INYKQLQLQE RTNIRKSQEL LEQLNGKINL TYRADFKIPM EMTEKMQKSY   180
TAFAIQEMLQ NVFLVFRNNF SSTGWNETIV VRLLDELHQQ TVFLKTVLEE KQEERLTWEM   240
SSTALHLKSY YWRVQRYLKL MKYNSYAWMV VRAEIFRNFL IIRRLTRNFQ NSGGPGPAGL   300
YAQPGSEVQL VESGGGLVQP GNSLRLSCAA SGFTFSKFGM SWVRQAPGKG LEWVSSISGS   360
GRDTLYAESV KGRFTISRDN AKTTLYLQMN SLRPEDTAVY YCTIGGSLSV SSQGTLVTVS   420
S                                                                   421

SEQ ID NO: 566          moltype = AA   length = 421
FEATURE                 Location/Qualifiers
source                  1..421
                        mol_type = protein
                        organism = synthetic construct
SEQUENCE: 566
EVQLVESGGG LVQPGNSLRL SCAASGFTFS KFGMSWVRQA PGKGLEWVSS ISGSGRDTLY   60
AESVKGRFTI SRDNAKTTLY LQMNSLRPED TAVYYCTIGG SLSVSSQGTL VTVSSSGGPA   120
LFKSSFPPGS INYKQLQLQE RTNIRKSQEL LEQLNGKINL TYRADFKIPM EMTEKMQKSY   180
TAFAIQEMLQ NVFLVFRNNF SSTGWNETIV VRLLDELHQQ TVFLKTVLEE KQEERLTWEM   240
SSTALHLKSY YWRVQRYLKL MKYNSYAWMV VRAEIFRNFL IIRRLTRNFQ NSGGPALFKS   300
SFPPGSEVQL VESGGGLVQP GNSLRLSCAA SGFTFSKFGM SWVRQAPGKG LEWVSSISGS   360
GRDTLYAESV KGRFTISRDN AKTTLYLQMN SLRPEDTAVY YCTIGGSLSV SSQGTLVTVS   420
S                                                                   421
```

```
SEQ ID NO: 567          moltype = AA  length = 426
FEATURE                 Location/Qualifiers
source                  1..426
                        mol_type = protein
                        organism = synthetic construct
SEQUENCE: 567
EVQLVESGGG LVQPGNSLRL SCAASGFTFS KFGMSWVRQA PGKGLEWVSS ISGSGRDTLY     60
AESVKGRFTI SRDNAKTTLY LQMNSLRPED TAVYYCTIGG SLSVSSQGTL VTVSSSGGPG    120
PAGLYAQPGS MSYNLLGFLQ RSSNFQCQKL LWQLNGRLEY CLKDRMNFDI PEEIKQLQQF    180
QKEDAALTIY EMLQNIFAIF RQDSSSTGWN ETIVENLLAN VYHQINHLKT VLEEKLEKED    240
FTRGKLMSSL HLKRYYGRIL HYLKAKEYSH CAWTIVRVEI LRNFYFINRL TGYLRNSGGP    300
GPAGLYAQPG SEVQLVESGG GLVQPGNSLR LSCAASGFTF SKFGMSWVRQ APGKGLEWVS    360
SISGSGRDTL YAESVKGRFT ISRDNAKTTL YLQMNSLRPE DTAVYYCTIG GSLSVSSQGT    420
LVTVSS                                                               426

SEQ ID NO: 568          moltype = AA  length = 426
FEATURE                 Location/Qualifiers
source                  1..426
                        mol_type = protein
                        organism = synthetic construct
SEQUENCE: 568
EVQLVESGGG LVQPGNSLRL SCAASGFTFS KFGMSWVRQA PGKGLEWVSS ISGSGRDTLY     60
AESVKGRFTI SRDNAKTTLY LQMNSLRPED TAVYYCTIGG SLSVSSQGTL VTVSSSGGPA    120
LFKSSFPPGS MSYNLLGFLQ RSSNFQCQKL LWQLNGRLEY CLKDRMNFDI PEEIKQLQQF    180
QKEDAALTIY EMLQNIFAIF RQDSSSTGWN ETIVENLLAN VYHQINHLKT VLEEKLEKED    240
FTRGKLMSSL HLKRYYGRIL HYLKAKEYSH CAWTIVRVEI LRNFYFINRL TGYLRNSGGP    300
ALFKSSFPPG SEVQLVESGG GLVQPGNSLR LSCAASGFTF SKFGMSWVRQ APGKGLEWVS    360
SISGSGRDTL YAESVKGRFT ISRDNAKTTL YLQMNSLRPE DTAVYYCTIG GSLSVSSQGT    420
LVTVSS                                                               426

SEQ ID NO: 569          moltype = AA  length = 426
FEATURE                 Location/Qualifiers
source                  1..426
                        mol_type = protein
                        organism = synthetic construct
SEQUENCE: 569
EVQLVESGGG LVQPGNSLRL SCAASGFTFS KFGMSWVRQA PGKGLEWVSS ISGSGRDTLY     60
AESVKGRFTI SRDNAKTTLY LQMNSLRPED TAVYYCTIGG SLSVSSQGTL VTVSSSGGPG    120
PAGLYAQPGS MSYNLLGFLQ RSSNFQSQKL LWQLNGRLEY CLKDRMNFDI PEEIKQLQQF    180
QKEDAALTIY EMLQNIFAIF RQDSSSTGWN ETIVENLLAN VYHQINHLKT VLEEKLEKED    240
FTRGKLMSSL HLKRYYGRIL HYLKAKEYSH CAWTIVRVEI LRNFYFINRL TGYLRNSGGP    300
GPAGLYAQPG SEVQLVESGG GLVQPGNSLR LSCAASGFTF SKFGMSWVRQ APGKGLEWVS    360
SISGSGRDTL YAESVKGRFT ISRDNAKTTL YLQMNSLRPE DTAVYYCTIG GSLSVSSQGT    420
LVTVSS                                                               426

SEQ ID NO: 570          moltype = AA  length = 426
FEATURE                 Location/Qualifiers
source                  1..426
                        mol_type = protein
                        organism = synthetic construct
SEQUENCE: 570
EVQLVESGGG LVQPGNSLRL SCAASGFTFS KFGMSWVRQA PGKGLEWVSS ISGSGRDTLY     60
AESVKGRFTI SRDNAKTTLY LQMNSLRPED TAVYYCTIGG SLSVSSQGTL VTVSSSGGPA    120
LFKSSFPPGS MSYNLLGFLQ RSSNFQSQKL LWQLNGRLEY CLKDRMNFDI PEEIKQLQQF    180
QKEDAALTIY EMLQNIFAIF RQDSSSTGWN ETIVENLLAN VYHQINHLKT VLEEKLEKED    240
FTRGKLMSSL HLKRYYGRIL HYLKAKEYSH CAWTIVRVEI LRNFYFINRL TGYLRNSGGP    300
ALFKSSFPPG SEVQLVESGG GLVQPGNSLR LSCAASGFTF SKFGMSWVRQ APGKGLEWVS    360
SISGSGRDTL YAESVKGRFT ISRDNAKTTL YLQMNSLRPE DTAVYYCTIG GSLSVSSQGT    420
LVTVSS                                                               426

SEQ ID NO: 571          moltype = AA  length = 167
FEATURE                 Location/Qualifiers
source                  1..167
                        mol_type = protein
                        organism = synthetic construct
SEQUENCE: 571
INYKQLQLQE RTNIRKCQEL LEQLNGKINL TYRADFKIPM EMTEKMQKSY TAFAIQEMLQ     60
NVFLVFRNNF SSTGWNETIV VRLLDELHQQ TVFLKTVLEE KQEERLTWEM SSTALHLKSY    120
YWRVQRYLKL MKYNSYAWMV VRAEIFRNFL IIRRLTRNFQ NHHHHHH                  167

SEQ ID NO: 572          moltype = AA  length = 167
FEATURE                 Location/Qualifiers
source                  1..167
                        mol_type = protein
                        organism = synthetic construct
SEQUENCE: 572
INYKQLQLQE RTNIRKSQEL LEQLNGKINL TYRADFKIPM EMTEKMQKSY TAFAIQEMLQ     60
NVFLVFRNNF SSTGWNETIV VRLLDELHQQ TVFLKTVLEE KQEERLTWEM SSTALHLKSY    120
```

```
YWRVQRYLKL MKYNSYAWMV VRAEIFRNFL IIRRLTRNFQ NHHHHHH              167

SEQ ID NO: 573          moltype = AA  length = 172
FEATURE                 Location/Qualifiers
source                  1..172
                        mol_type = protein
                        organism = synthetic construct
SEQUENCE: 573
MSYNLLGFLQ RSSNFQCQKL LWQLNGRLEY CLKDRMNFDI PEEIKQLQQF QKEDAALTIY   60
EMLQNIFAIF RQDSSSTGWN ETIVENLLAN VYHQINHLKT VLEEKLEKED FTRGKLMSSL  120
HLKRYYGRIL HYLKAKEYSH CAWTIVRVEI LRNFYFINRL TGYLRNHHHH HH          172

SEQ ID NO: 574          moltype = AA  length = 172
FEATURE                 Location/Qualifiers
source                  1..172
                        mol_type = protein
                        organism = synthetic construct
SEQUENCE: 574
MSYNLLGFLQ RSSNFQSQKL LWQLNGRLEY CLKDRMNFDI PEEIKQLQQF QKEDAALTIY   60
EMLQNIFAIF RQDSSSTGWN ETIVENLLAN VYHQINHLKT VLEEKLEKED FTRGKLMSSL  120
HLKRYYGRIL HYLKAKEYSH CAWTIVRVEI LRNFYFINRL TGYLRNHHHH HH          172

SEQ ID NO: 575          moltype = AA  length = 426
FEATURE                 Location/Qualifiers
source                  1..426
                        mol_type = protein
                        organism = synthetic construct
SEQUENCE: 575
EVQLVESGGG LVQPGNSLRL SCAASGFTFS KFGMSWVRQA PGKGLEWVSS ISGSGRDTLY   60
AESVKGRFTI SRDNAKTTLY LQMNSLRPED TAVYYCTIGG SLSVSSQGTL VTVSSSGGPG  120
PAGLYAQPGS MSYNLLGFLQ RSSNFQCQKL LWQLNGRLEY CLKDRMNFDI PEEIKQLQQF  180
QKEDAALTIY EMLQNIFAIF RQDSSSTGWQ ETIVENLLAN VYHQINHLKT VLEEKLEKED  240
FTRGKLMSSL HLKRYYGRIL HYLKAKEYSH CAWTIVRVEI LRNFYFINRL TGYLRNSGGP  300
GPAGLYAQPG SEVQLVESGG GLVQPGNSLR LSCAASGFTF SKFGMSWVRQ APGKGLEWVS  360
SISGSGRDTL YAESVKGRFT ISRDNAKTTL YLQMNSLRPE DTAVYYCTIG GSLSVSSQGT  420
LVTVSS                                                             426

SEQ ID NO: 576          moltype = AA  length = 426
FEATURE                 Location/Qualifiers
source                  1..426
                        mol_type = protein
                        organism = synthetic construct
SEQUENCE: 576
EVQLVESGGG LVQPGNSLRL SCAASGFTFS KFGMSWVRQA PGKGLEWVSS ISGSGRDTLY   60
AESVKGRFTI SRDNAKTTLY LQMNSLRPED TAVYYCTIGG SLSVSSQGTL VTVSSSGGPG  120
PAGLYAQPGS MSYNLLGFLQ RSSNFQSQKL LWQLNGRLEY CLKDRMNFDI PEEIKQLQQF  180
QKEDAALTIY EMLQNIFAIF RQDSSSTGWQ ETIVENLLAN VYHQINHLKT VLEEKLEKED  240
FTRGKLMSSL HLKRYYGRIL HYLKAKEYSH CAWTIVRVEI LRNFYFINRL TGYLRNSGGP  300
GPAGLYAQPG SEVQLVESGG GLVQPGNSLR LSCAASGFTF SKFGMSWVRQ APGKGLEWVS  360
SISGSGRDTL YAESVKGRFT ISRDNAKTTL YLQMNSLRPE DTAVYYCTIG GSLSVSSQGT  420
LVTVSS                                                             426

SEQ ID NO: 577          moltype = AA  length = 172
FEATURE                 Location/Qualifiers
source                  1..172
                        mol_type = protein
                        organism = synthetic construct
SEQUENCE: 577
MSYNLLGFLQ RSSNFQCQKL LWQLNGRLEY CLKDRMNFDI PEEIKQLQQF QKEDAALTIY   60
EMLQNIFAIF RQDSSSTGWQ ETIVENLLAN VYHQINHLKT VLEEKLEKED FTRGKLMSSL  120
HLKRYYGRIL HYLKAKEYSH CAWTIVRVEI LRNFYFINRL TGYLRNHHHH HH          172

SEQ ID NO: 578          moltype = AA  length = 172
FEATURE                 Location/Qualifiers
source                  1..172
                        mol_type = protein
                        organism = synthetic construct
SEQUENCE: 578
MSYNLLGFLQ RSSNFQSQKL LWQLNGRLEY CLKDRMNFDI PEEIKQLQQF QKEDAALTIY   60
EMLQNIFAIF RQDSSSTGWQ ETIVENLLAN VYHQINHLKT VLEEKLEKED FTRGKLMSSL  120
HLKRYYGRIL HYLKAKEYSH CAWTIVRVEI LRNFYFINRL TGYLRNHHHH HH          172

SEQ ID NO: 579          moltype = AA  length = 528
FEATURE                 Location/Qualifiers
source                  1..528
                        mol_type = protein
                        organism = synthetic construct
SEQUENCE: 579
APTSSSTKKT QLQLEHLLLD LQMILNGINN YKNPKLTRML TFKFYMPKKA TELKHLQCLE   60
```

```
EELKPLEEVL NLAQSKNFHL RPRDLISNIN VIVLELKGSE TTFMCEYADE TATIVEFLNR    120
WITFCQSIIS TLTSGGPGGG GSGGGPGSEV QLVESGGGLV QPGNSLRLSC AASGFTFSKF    180
GMSWVRQAPG KGLEWVSSIS GSGRDTLYAE SVKGRFTISR DNAKTTLYLQ MNSLRPEDTA    240
VYYCTIGGSL SVSSQGTLVT VSSGGGGSGG GSGGGGSGG GGSGGGGSGG GGSSGGPGGG    300
GSGGGPGSEV QLVESGGGLV QPGGSLRLSC AASGFTFSSY TLAWVRQAPG KGLEWVAAID    360
SSSYTYSPDT VRGRFTISRD NAKNSLYLQM NSLRAEDTAV YYCARDSNWD ALDYWGQGTT    420
VTVSSASTKG PSVFPLAPSS KSTSGGTAAL GCLVKDYFPE PVTVSWNSGA LTSGVHTFPA    480
VLQSSGLYSL SSVVTVPSSS LGTQTYICNV NHKPSNTKVD KRVEPKSC                 528

SEQ ID NO: 580           moltype = AA   length = 528
FEATURE                  Location/Qualifiers
source                   1..528
                         mol_type = protein
                         organism = synthetic construct
SEQUENCE: 580
APTSSSTKKT QLQLEHLLLD LQMILNGINN YKNPKLTRML TFKFYMPKKA TELKHLQCLE     60
EELKPLEEVL NLAQSKNFHL RPRDLISNIN VIVLELKGSE TTFMCEYADE TATIVEFLNR    120
WITFCQSIIS TLTSGGPGPA GMKGLPGSEV QLVESGGGLV QPGNSLRLSC AASGFTFSKF    180
GMSWVRQAPG KGLEWVSSIS GSGRDTLYAE SVKGRFTISR DNAKTTLYLQ MNSLRPEDTA    240
VYYCTIGGSL SVSSQGTLVT VSSGGGGSGG GSGGGGSGG GGSGGGGSGG GGSGGGGSGG    300
GGSGGGGSEV QLVESGGGLV QPGGSLRLSC AASGFTFSSY TLAWVRQAPG KGLEWVAAID    360
SSSYTYSPDT VRGRFTISRD NAKNSLYLQM NSLRAEDTAV YYCARDSNWD ALDYWGQGTT    420
VTVSSASTKG PSVFPLAPSS KSTSGGTAAL GCLVKDYFPE PVTVSWNSGA LTSGVHTFPA    480
VLQSSGLYSL SSVVTVPSSS LGTQTYICNV NHKPSNTKVD KRVEPKSC                 528

SEQ ID NO: 581           moltype = AA   length = 528
FEATURE                  Location/Qualifiers
source                   1..528
                         mol_type = protein
                         organism = synthetic construct
SEQUENCE: 581
APTSSSTKKT QLQLEHLLLD LQMILNGINN YKNPKLTRML TFKFYMPKKA TELKHLQCLE     60
EELKPLEEVL NLAQSKNFHL RPRDLISNIN VIVLELKGSE TTFMCEYADE TATIVEFLNR    120
WITFCQSIIS TLTSGGPGPA GLYAQPGSEV QLVESGGGLV QPGNSLRLSC AASGFTFSKF    180
GMSWVRQAPG KGLEWVSSIS GSGRDTLYAE SVKGRFTISR DNAKTTLYLQ MNSLRPEDTA    240
VYYCTIGGSL SVSSQGTLVT VSSGGGGSGG GSGGGGSGG GGSGGGGSGG GGSGGGGSGG    300
GGSGGGGSEV QLVESGGGLV QPGGSLRLSC AASGFTFSSY TLAWVRQAPG KGLEWVAAID    360
SSSYTYSPDT VRGRFTISRD NAKNSLYLQM NSLRAEDTAV YYCARDSNWD ALDYWGQGTT    420
VTVSSASTKG PSVFPLAPSS KSTSGGTAAL GCLVKDYFPE PVTVSWNSGA LTSGVHTFPA    480
VLQSSGLYSL SSVVTVPSSS LGTQTYICNV NHKPSNTKVD KRVEPKSC                 528

SEQ ID NO: 582           moltype = AA   length = 528
FEATURE                  Location/Qualifiers
source                   1..528
                         mol_type = protein
                         organism = synthetic construct
SEQUENCE: 582
APTSSSTKKT QLQLEHLLLD LQMILNGINN YKNPKLTRML TFKFYMPKKA TELKHLQCLE     60
EELKPLEEVL NLAQSKNFHL RPRDLISNIN VIVLELKGSE TTFMCEYADE TATIVEFLNR    120
WITFCQSIIS TLTSGGPALF KSSFPPGSEV QLVESGGGLV QPGNSLRLSC AASGFTFSKF    180
GMSWVRQAPG KGLEWVSSIS GSGRDTLYAE SVKGRFTISR DNAKTTLYLQ MNSLRPEDTA    240
VYYCTIGGSL SVSSQGTLVT VSSGGGGSGG GSGGGGSGG GGSGGGGSGG GGSGGGGSGG    300
GGSGGGGSEV QLVESGGGLV QPGGSLRLSC AASGFTFSSY TLAWVRQAPG KGLEWVAAID    360
SSSYTYSPDT VRGRFTISRD NAKNSLYLQM NSLRAEDTAV YYCARDSNWD ALDYWGQGTT    420
VTVSSASTKG PSVFPLAPSS KSTSGGTAAL GCLVKDYFPE PVTVSWNSGA LTSGVHTFPA    480
VLQSSGLYSL SSVVTVPSSS LGTQTYICNV NHKPSNTKVD KRVEPKSC                 528

SEQ ID NO: 583           moltype = AA   length = 226
FEATURE                  Location/Qualifiers
source                   1..226
                         mol_type = protein
                         organism = synthetic construct
SEQUENCE: 583
EVQLVESGGG LVQPGGSLRL SCAASGFTFS SYTLAWVRQA PGKGLEWVAA IDSSSYTYSP     60
DTVRGRFTIS RDNAKNSLYL QMNSLRAEDT AVYYCARDSN WDALDYWGQG TTVTVSSAST    120
KGPSVFPLAP SSKSTSGGTA ALGCLVKDYF PEPVTVSWNS GALTSGVHTF PAVLQSSGLY    180
SLSSVVTVPS SSLGTQTYIC NVNHKPSNTK VDKRVEPKSC HHHHHH                   226

SEQ ID NO: 584           moltype = AA   length = 269
FEATURE                  Location/Qualifiers
source                   1..269
                         mol_type = protein
                         organism = synthetic construct
SEQUENCE: 584
APTSSSTKKT QLQLEHLLLD LQMILNGINN YKNPKLTRML TFKFYMPKKA TELKHLQCLE     60
EELKPLEEVL NLAQSKNFHL RPRDLISNIN VIVLELKGSE TTFMCEYADE TATIVEFLNR    120
WITFCQSIIS TLTSGGPGPA GMKGLPGSEV QLVESGGGLV QPGNSLRLSC AASGFTFSKF    180
GMSWVRQAPG KGLEWVSSIS GSGRDTLYAE SVKGRFTISR DNAKTTLYLQ MNSLRPEDTA    240
VYYCTIGGSL SVSSQGTLVT VSSHHHHHH                                      269
```

```
SEQ ID NO: 585         moltype = AA   length = 137
FEATURE                Location/Qualifiers
source                 1..137
                       mol_type = protein
                       organism = synthetic construct
SEQUENCE: 585
QVQLQESGGG LVQTGGSLRL SCTTSGTIFS GYTMGWYRQA PGEQRELVAV ISGGGDTNYA    60
DSVKGRFTIS RDNTKDTMYL QMNSLKPEDT AVYYCSREV TPPWKLYWGQ GTQVTVSSAA   120
AYPYDVPDYG SHHHHHH                                                 137

SEQ ID NO: 586         moltype = AA   length = 137
FEATURE                Location/Qualifiers
source                 1..137
                       mol_type = protein
                       organism = synthetic construct
SEQUENCE: 586
QVQLQESGGG LVQEGGSLRL SCAASERIFS TDVMGWYRQA AEKQRELVAV VSARGTTNYL    60
DAVKGRFTIS RDNARNTLTL QMNDLKPEDT ASYYCVRET TSPWRIYWGQ GTQVTVSSAA   120
AYPYDVPDYG SHHHHHH                                                 137

SEQ ID NO: 587         moltype = AA   length = 138
FEATURE                Location/Qualifiers
source                 1..138
                       mol_type = protein
                       organism = synthetic construct
SEQUENCE: 587
QVQLQESGGG LVQAGGSLRL SCAASGSIFS ANAMGWYRQA PGKQRELVAV ISSGGSTNYA    60
DSVKGRFTIS RDNAKNTVYL QMNSLKPEDT AVYYCMYSGS YYYTPNDYWG QGTQVTVSSA   120
AAYPYDVPDY GSHHHHHH                                                138

SEQ ID NO: 588         moltype = AA   length = 138
FEATURE                Location/Qualifiers
source                 1..138
                       mol_type = protein
                       organism = synthetic construct
SEQUENCE: 588
EVQLLESGGG LVQPGGSLRL SCAASGSIFS ANAMGWYRQA PGKQRELVAV ISSGGSTNYA    60
DSVKGRFTIS RDNSKNTVYL QMNSLRAEDT AVYYCMYSGS YYYTPNDYWG QGTLVTVSSA   120
AAYPYDVPDY GSHHHHHH                                                138

SEQ ID NO: 589         moltype = AA   length = 138
FEATURE                Location/Qualifiers
source                 1..138
                       mol_type = protein
                       organism = synthetic construct
SEQUENCE: 589
EVQLLESGGG LVQPGGSLRL SCAASGSIFS ANAMGWYRQA PGKGLELVAV ISSGGSTNYA    60
DSVKGRFTIS RDNSKNTVYL QMNSLRAEDT AVYYCMYSGS YYYTPNDYWG QGTLVTVSSA   120
AAYPYDVPDY GSHHHHHH                                                138

SEQ ID NO: 590         moltype = AA   length = 138
FEATURE                Location/Qualifiers
source                 1..138
                       mol_type = protein
                       organism = synthetic construct
SEQUENCE: 590
EVQLLESGGG LVQPGGSLRL SCAASGSIFS ANAMGWVRQA PGKGLEWVSV ISSGGSTNYA    60
DSVKGRFTIS RDNSKNTLYL QMNSLRAEDT AVYYCMYSGS YYYTPNDYWG QGTLVTVSSA   120
AAYPYDVPDY GSHHHHHH                                                138

SEQ ID NO: 591         moltype = AA   length = 138
FEATURE                Location/Qualifiers
source                 1..138
                       mol_type = protein
                       organism = synthetic construct
SEQUENCE: 591
QVQLLESGGG LVQPGGSLRL SCAASGSIFS ANAMGWYRQA PGKQRELVAV ISSGGSTNYA    60
DSVKGRFTIS RDNSKNTVYL QMNSLRAEDT AVYYCMYSGS YYYTPNDYWG QGTLVTVSSA   120
AAYPYDVPDY GSHHHHHH                                                138

SEQ ID NO: 592         moltype = AA   length = 138
FEATURE                Location/Qualifiers
source                 1..138
                       mol_type = protein
                       organism = synthetic construct
SEQUENCE: 592
EVQLLESGGG LVQPGGSLRL SCAASGSIFS ANAMGWYRQA PGKGRELVAV ISSGGSTNYA    60
DSVKGRFTIS RDNSKNTVYL QMNSLRAEDT AVYYCMYSGS YYYTPNDYWG QGTLVTVSSA   120
```

```
AAYPYDVPDY GSHHHHHH                                                          138

SEQ ID NO: 593            moltype = AA   length = 138
FEATURE                   Location/Qualifiers
source                    1..138
                          mol_type = protein
                          organism = synthetic construct
SEQUENCE: 593
QVQLLESGGG LVQAGGSLRL SCAASGSIFS ANAMGWYRQA PGKQRELVAV ISSGGSTNYA              60
DSVKGRFTIS RDNSKNTVYL QMNSLRAEDT AVYYCMYSGS YYYTPNDYWG QGTLVTVSSA             120
AAYPYDVPDY GSHHHHHH                                                          138

SEQ ID NO: 594            moltype = AA   length = 137
FEATURE                   Location/Qualifiers
source                    1..137
                          mol_type = protein
                          organism = synthetic construct
SEQUENCE: 594
EVQLLESGGG LVQPGGSLRL SCAASERIFS TDVMGWYRQA PGKQRELVAV VSARGTTNYL              60
DAVKGRFTIS RDNSKNTLYL QMNSLRAEDT AVYYCYVRET TSPWRIYWGQ GTLVTVSSAA             120
AYPYDVPDYG SHHHHHH                                                           137

SEQ ID NO: 595            moltype = AA   length = 137
FEATURE                   Location/Qualifiers
source                    1..137
                          mol_type = protein
                          organism = synthetic construct
SEQUENCE: 595
EVQLLESGGG LVQPGGSLRL SCAASERIFS TDVMGWYRQA PGKGLELVAV VSARGTTNYL              60
DAVKGRFTIS RDNSKNTLYL QMNSLRAEDT AVYYCYVRET TSPWRIYWGQ GTLVTVSSAA             120
AYPYDVPDYG SHHHHHH                                                           137

SEQ ID NO: 596            moltype = AA   length = 137
FEATURE                   Location/Qualifiers
source                    1..137
                          mol_type = protein
                          organism = synthetic construct
SEQUENCE: 596
EVQLLESGGG LVQPGGSLRL SCAASERIFS TDVMGWVRQA PGKGLEWVSV VSARGTTNYL              60
DAVKGRFTIS RDNSKNTLYL QMNSLRAEDT AVYYCYVRET TSPWRIYWGQ GTLVTVSSAA             120
AYPYDVPDYG SHHHHHH                                                           137

SEQ ID NO: 597            moltype = AA   length = 137
FEATURE                   Location/Qualifiers
source                    1..137
                          mol_type = protein
                          organism = synthetic construct
SEQUENCE: 597
QVQLLESGGG LVQPGGSLRL SCAASERIFS TDVMGWYRQA PGKQRELVAV VSARGTTNYL              60
DAVKGRFTIS RDNSKNTLYL QMNSLRAEDT AVYYCYVRET TSPWRIYWGQ GTLVTVSSAA             120
AYPYDVPDYG SHHHHHH                                                           137

SEQ ID NO: 598            moltype = AA   length = 137
FEATURE                   Location/Qualifiers
source                    1..137
                          mol_type = protein
                          organism = synthetic construct
SEQUENCE: 598
EVQLLESGGG LVQPGGSLRL SCAASERIFS TDVMGWYRQA PGKGRELVAV VSARGTTNYL              60
DSVKGRFTIS RDNSKNTLYL QMNSLRAEDT AVYYCYVRET TSPWRIYWGQ GTLVTVSSAA             120
AYPYDVPDYG SHHHHHH                                                           137

SEQ ID NO: 599            moltype = AA   length = 137
FEATURE                   Location/Qualifiers
source                    1..137
                          mol_type = protein
                          organism = synthetic construct
SEQUENCE: 599
QVQLLESGGG LVQEGGSLRL SCAASERIFS TDVMGWYRQA AGKQRELVAV VSARGTTNYL              60
DAVKGRFTIS RDNSKNTLYL QMNSLRAEDT ASYYCYVRET TSPWRIYWGQ GTLVTVSSAA             120
AYPYDVPDYG SHHHHHH                                                           137

SEQ ID NO: 600            moltype = AA   length = 137
FEATURE                   Location/Qualifiers
source                    1..137
                          mol_type = protein
                          organism = synthetic construct
SEQUENCE: 600
EVQLLESGGG LVQPGGSLRL SCAASERIFS TDVMGWYRQA PGKGLELVAV VSARGTTNYL              60
```

```
DSVKGRFTIS RDNSKNTLYL QMNSLRAEDT AVYYCYVRET TSPWRIYWGQ GTLVTVSSAA    120
AYPYDVPDYG SHHHHHH                                                  137

SEQ ID NO: 601          moltype = AA  length = 137
FEATURE                 Location/Qualifiers
source                  1..137
                        mol_type = protein
                        organism = synthetic construct
SEQUENCE: 601
EVQLLESGGG LVQPGGSLRL SCATSGTIFS GYTMGWYRQA PGKQRELVAV ISGGGDTNYA    60
DSVKGRFTIS RDNSKDTMYL QMNSLRAEDT AVYYCSREV TPPWKLYWGQ GTLVTVSSAA     120
AYPYDVPDYG SHHHHHH                                                  137

SEQ ID NO: 602          moltype = AA  length = 137
FEATURE                 Location/Qualifiers
source                  1..137
                        mol_type = protein
                        organism = synthetic construct
SEQUENCE: 602
EVQLLESGGG LVQPGGSLRL SCATSGTIFS GYTMGWYRQA PGKGLELVAV ISGGGDTNYA    60
DSVKGRFTIS RDNSKDTMYL QMNSLRAEDT AVYYCSREV TPPWKLYWGQ GTLVTVSSAA     120
AYPYDVPDYG SHHHHHH                                                  137

SEQ ID NO: 603          moltype = AA  length = 137
FEATURE                 Location/Qualifiers
source                  1..137
                        mol_type = protein
                        organism = synthetic construct
SEQUENCE: 603
EVQLLESGGG LVQPGGSLRL SCAASGTIFS GYTMGWVRQA PGKGLEWVSV ISGGGDTNYA    60
DSVKGRFTIS RDNSKNTLYL QMNSLRAEDT AVYYCSREV TPPWKLYWGQ GTLVTVSSAA     120
AYPYDVPDYG SHHHHHH                                                  137

SEQ ID NO: 604          moltype = AA  length = 137
FEATURE                 Location/Qualifiers
source                  1..137
                        mol_type = protein
                        organism = synthetic construct
SEQUENCE: 604
QVQLLESGGG LVQPGGSLRL SCATSGTIFS GYTMGWYRQA PGKQRELVAV ISGGGDTNYA    60
DSVKGRFTIS RDNSKDTMYL QMNSLRAEDT AVYYCSREV TPPWKLYWGQ GTLVTVSSAA     120
AYPYDVPDYG SHHHHHH                                                  137

SEQ ID NO: 605          moltype = AA  length = 137
FEATURE                 Location/Qualifiers
source                  1..137
                        mol_type = protein
                        organism = synthetic construct
SEQUENCE: 605
EVQLLESGGG LVQPGGSLRL SCATSGTIFS GYTMGWYRQA PGKQRELVAV ISGGGDTNYA    60
DSVKGRFTIS RDNSKNTMYL QMNSLRAEDT AVYYCSREV TPPWKLYWGQ GTLVTVSSAA     120
AYPYDVPDYG SHHHHHH                                                  137

SEQ ID NO: 606          moltype = AA  length = 137
FEATURE                 Location/Qualifiers
source                  1..137
                        mol_type = protein
                        organism = synthetic construct
SEQUENCE: 606
EVQLLESGGG LVQPGGSLRL SCATSGTIFS GYTMGWYRQA PGKGRELVAV ISGGGDTNYA    60
DSVKGRFTIS RDNSKNTMYL QMNSLRAEDT AVYYCSREV TPPWKLYWGQ GTLVTVSSAA     120
AYPYDVPDYG SHHHHHH                                                  137

SEQ ID NO: 607          moltype = AA  length = 137
FEATURE                 Location/Qualifiers
source                  1..137
                        mol_type = protein
                        organism = synthetic construct
SEQUENCE: 607
QVQLLESGGG LVQTGGSLRL SCATSGTIFS GYTMGWYRQA PGKQRELVAV ISGGGDTNYA    60
DSVKGRFTIS RDNSKDTMYL QMNSLRAEDT AVYYCSREV TPPWKLYWGQ GTLVTVSSAA     120
AYPYDVPDYG SHHHHHH                                                  137

SEQ ID NO: 608          moltype = AA  length = 137
FEATURE                 Location/Qualifiers
source                  1..137
                        mol_type = protein
                        organism = synthetic construct
SEQUENCE: 608
```

```
EVQLLESGGG LVQPGGSLRL SCATSGTIFS GYTMGWYRQA PGKGLELVAV ISGGGDTNYA    60
DSVKGRFTIS RDNSKNTMYL QMNSLRAEDT AVYYCYSREV TPPWKLYWGQ GTLVTVSSAA   120
AYPYDVPDYG SHHHHHH                                                  137

SEQ ID NO: 609              moltype = AA   length = 8
FEATURE                     Location/Qualifiers
source                      1..8
                            mol_type = protein
                            organism = synthetic construct
SEQUENCE: 609
GPAGLYAQ                                                              8

SEQ ID NO: 610              moltype = AA   length = 8
FEATURE                     Location/Qualifiers
source                      1..8
                            mol_type = protein
                            organism = synthetic construct
SEQUENCE: 610
GPAGMKGL                                                              8

SEQ ID NO: 611              moltype = AA   length = 8
FEATURE                     Location/Qualifiers
source                      1..8
                            mol_type = protein
                            organism = synthetic construct
SEQUENCE: 611
PGGPAGIG                                                              8

SEQ ID NO: 612              moltype = AA   length = 8
FEATURE                     Location/Qualifiers
source                      1..8
                            mol_type = protein
                            organism = synthetic construct
SEQUENCE: 612
ALFKSSFP                                                              8

SEQ ID NO: 613              moltype = AA   length = 8
FEATURE                     Location/Qualifiers
source                      1..8
                            mol_type = protein
                            organism = synthetic construct
SEQUENCE: 613
ALFFSSPP                                                              8

SEQ ID NO: 614              moltype = AA   length = 8
FEATURE                     Location/Qualifiers
source                      1..8
                            mol_type = protein
                            organism = synthetic construct
SEQUENCE: 614
LAQRLRSS                                                              8

SEQ ID NO: 615              moltype = AA   length = 8
FEATURE                     Location/Qualifiers
source                      1..8
                            mol_type = protein
                            organism = synthetic construct
SEQUENCE: 615
LAQKLKSS                                                              8

SEQ ID NO: 616              moltype = AA   length = 30
FEATURE                     Location/Qualifiers
source                      1..30
                            mol_type = protein
                            organism = synthetic construct
SEQUENCE: 616
GALFKSSFPS GGGPAGLYAQ GGSGKGGSGK                                     30

SEQ ID NO: 617              moltype = AA   length = 30
FEATURE                     Location/Qualifiers
source                      1..30
                            mol_type = protein
                            organism = synthetic construct
SEQUENCE: 617
RGSGGGPAGL YAQGSGGGPA GLYAQGGSGK                                     30

SEQ ID NO: 618              moltype = AA   length = 30
FEATURE                     Location/Qualifiers
source                      1..30
```

```
                        mol_type = protein
                        organism = synthetic construct
SEQUENCE: 618
KGGGPAGLYA QGPAGLYAQG PAGLYAQGSR                                   30

SEQ ID NO: 619          moltype = AA   length = 30
FEATURE                 Location/Qualifiers
source                  1..30
                        mol_type = protein
                        organism = synthetic construct
SEQUENCE: 619
RGGPAGLYAQ GGPAGLYAQG GGPAGLYAQK                                   30

SEQ ID NO: 620          moltype = AA   length = 30
FEATURE                 Location/Qualifiers
source                  1..30
                        mol_type = protein
                        organism = synthetic construct
SEQUENCE: 620
KGGALFKSSF PGGPAGIGPL AQKLKSSGGS                                   30

SEQ ID NO: 621          moltype = AA   length = 30
FEATURE                 Location/Qualifiers
source                  1..30
                        mol_type = protein
                        organism = synthetic construct
SEQUENCE: 621
SGGPGGPAGI GALFKSSFPL AQKLKSSGGG                                   30

SEQ ID NO: 622          moltype = AA   length = 30
FEATURE                 Location/Qualifiers
source                  1..30
                        mol_type = protein
                        organism = synthetic construct
SEQUENCE: 622
RGPLAQKLKS SALFKSSFPG GPAGIGGGGK                                   30

SEQ ID NO: 623          moltype = AA   length = 30
FEATURE                 Location/Qualifiers
source                  1..30
                        mol_type = protein
                        organism = synthetic construct
SEQUENCE: 623
GGGALFKSSF PLAQKLKSSP GGPAGIGGGR                                   30

SEQ ID NO: 624          moltype = AA   length = 30
FEATURE                 Location/Qualifiers
source                  1..30
                        mol_type = protein
                        organism = synthetic construct
SEQUENCE: 624
RGPGGPAGIG PLAQKLKSSA LFKSSFPGGG                                   30

SEQ ID NO: 625          moltype = AA   length = 30
FEATURE                 Location/Qualifiers
source                  1..30
                        mol_type = protein
                        organism = synthetic construct
SEQUENCE: 625
RGGPLAQKLK SSPGGPAGIG ALFKSSFPGK                                   30

SEQ ID NO: 626          moltype = AA   length = 30
FEATURE                 Location/Qualifiers
source                  1..30
                        mol_type = protein
                        organism = synthetic construct
SEQUENCE: 626
RSGGPAGLYA QALFKSSFPL AQKLKSSGGG                                   30

SEQ ID NO: 627          moltype = AA   length = 30
FEATURE                 Location/Qualifiers
source                  1..30
                        mol_type = protein
                        organism = synthetic construct
SEQUENCE: 627
GGPLAQKLKS SALFKSSFPG PAGLYAQGGR                                   30

SEQ ID NO: 628          moltype = AA   length = 30
FEATURE                 Location/Qualifiers
```

```
source                    1..30
                          mol_type = protein
                          organism = synthetic construct
SEQUENCE: 628
GGALFKSSFP GPAGLYAQPL AQKLKSSGGK                                              30

SEQ ID NO: 629            moltype = AA  length = 30
FEATURE                   Location/Qualifiers
source                    1..30
                          mol_type = protein
                          organism = synthetic construct
SEQUENCE: 629
RGGALFKSSF PLAQKLKSSG PAGLYAQGGK                                              30

SEQ ID NO: 630            moltype = AA  length = 30
FEATURE                   Location/Qualifiers
source                    1..30
                          mol_type = protein
                          organism = synthetic construct
SEQUENCE: 630
RGGGPAGLYA QPLAQKLKSS ALFKSSFPGG                                              30

SEQ ID NO: 631            moltype = AA  length = 30
FEATURE                   Location/Qualifiers
source                    1..30
                          mol_type = protein
                          organism = synthetic construct
SEQUENCE: 631
SGPLAQKLKS SGPAGLYAQA LFKSSFPGSK                                              30

SEQ ID NO: 632            moltype = AA  length = 30
FEATURE                   Location/Qualifiers
source                    1..30
                          mol_type = protein
                          organism = synthetic construct
SEQUENCE: 632
KGGPGGPAGI GPLAQRLRSS ALFKSSFPGR                                              30

SEQ ID NO: 633            moltype = AA  length = 30
FEATURE                   Location/Qualifiers
source                    1..30
                          mol_type = protein
                          organism = synthetic construct
SEQUENCE: 633
KSGPGGPAGI GALFFSSPPL AQKLKSSGGR                                              30

SEQ ID NO: 634            moltype = AA  length = 30
FEATURE                   Location/Qualifiers
source                    1..30
                          mol_type = protein
                          organism = synthetic construct
SEQUENCE: 634
SGGFPRSGGS FNPRTFGSKR KRRGSRGGGG                                              30

SEQ ID NO: 635            moltype = AA  length = 934
FEATURE                   Location/Qualifiers
source                    1..934
                          mol_type = protein
                          organism = synthetic construct
SEQUENCE: 635
EVQLVESGGG LVQPGNSLRL SCAASGFTFS KFGMSWVRQA PGKGLEWVSS ISGSGRDTLY             60
AESVKGRFTI SRDNAKTTLY LQMNSLRPED TAVYYCTIGG SLSVSSQGTL VTVSSSGGPA            120
LFKSSFPPGS IWELKKDVYV VELDWYPDAP GEMVVLTCDT PEEDGITWTL DQSSEVLGSG            180
KTLTIQVKEF GDAGQYTCHK GGEVLSHSLL LLHKKEDGIW STDILKDQKE PKNKTFLRCE            240
AKNYSGRFTC WWLTTISTDL TFSVKSSRGS SDPQGVTCGA ATLSAERVRG DNKEYEYSVE            300
CQEDSACPAA EESLPIEVMV DAVHKLKYEN YTSSFFIRDI IKPDPPKNLQ LKPLKNSRQV            360
EVSWEYPDTW STPHSYFSLT FCVQVQGKSK REKKDRVFTD KTSATVICRK NASISVRAQD            420
RYYSSSWSEW ASVPCSGGGG SGGGGSGGGG SRNLPVATPD PGMFPCLHHS QNLLRAVSNM            480
LQKARQTLEF YPCTSEEIDH EDITKDKTST VEACLPLELT KNESCLNSRE TSFITNGSCL            540
ASRKTSFMMA LCLSSIYEDL KMYQVEFKTM NAKLLMDPKR QIFLDQNMLA VIDELMQALN            600
FNSETVPQKS SLEEPDFYKT KIKLCILLHA FRIRAVTIDR VMSYLNASSG GPALFKSSFP            660
PGSGGGGSGG GGSGGGGSGG GGSGGGGSGG GGSQSVLTQP PSVSGAPGQR VTISCSGSRS            720
NIGSETVKWY QQLPGTAPKL LIYYNDQRPS GVPDRFSGSK SGTSASLAIT GLQAEDEADY            780
YCQSYDRYTH PALLFGTGTK VTVLGGGGSG GGGSGGGGSQ VQLVESGGGV VQPGRSLRLS            840
CAASGFTFSS YGMHWVRQAP GKGLEWVAFI RYEGSNKYYA ESVKGRFTIS RDNSKNTLYL            900
QMNSLRAEDT AVYYCKTHGS HDNWGQGTMV TVSS                                       934

SEQ ID NO: 636            moltype = AA  length = 553
FEATURE                   Location/Qualifiers
```

```
                                    -continued source                  1..553
                        mol_type = protein
                        organism = synthetic construct
SEQUENCE: 636
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTSGGPGPA GMKGLPGSEV QLVESGGGLV QPGNSLRLSC AASGFTFSKF   180
GMSWVRQAPG KGLEWVSSIS GSGRDTLYAE SVKGRFTISR DNAKTTLYLQ MNSLRPEDTA   240
VYYCTIGGSL SVSSQGTLVT VSSGGGGSGG GGSGGGGSGG GGSGGGGSGG GGSGGGGSGG   300
GGSGGGGSEV QLVESGGGLV QPGGSLRLSC AASGFTFSSY TLAWVRQAPG KGLEWVAAID   360
SSSYTYSPDT VRGRFTISRD NAKNSLYLQM NSLRAEDTAV YYCARDSNWD ALDYWGQGTT   420
VTVSSGGGGS GGGGSGGGGS DIQMTQSPSS LSASVGDRVT ITCKASQNVG TNVGWYQQKP   480
GKAPKALIYS ASFRYSGVPS RFSGSGSGTD FTLTISSLQP EDFATYYCQQ YYTYPYTFGG   540
GTKVEIKHHH HHH                                                     553

SEQ ID NO: 637          moltype = AA  length = 665
FEATURE                 Location/Qualifiers
source                  1..665
                        mol_type = protein
                        organism = synthetic construct
SEQUENCE: 637
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTSGGPGPA GMKGLPGSVP RDCGCKPCIC TVPEVSSVFI FPPKPKDVLT   180
ITLTPKVTCV VVDISKDDPE VQFSWFVDDV EVHTAQTQPR EEQFNSTFRS VSELPIMHQD   240
WLNGKEPKCR VNSAAPPAPI EKTISKTKGR PKAPQVYTIP PKEQMAKDK VSLTCMITDF    300
FPEDITVEWQ WNGQPAENYK NTQPIMDTDG SYFVYSKLNV QKSNWEAGNT FTCSVLHEGL   360
HNHHTEKSLS HSPGKGGGGS GGGGSGGGGS GGGGSGGGGS GGGGSSGGPG PAGMKGLPGS   420
EVQLVESGGG LVQPGGSLRL SCAASGFTFS SYTLAWVRQA PGKGLEWVAA IDSSSYTYSP   480
DTVRGRFTIS RDNAKNSLYL QMNSLRAEDT AVYYCARDSN WDALDYWGQG TTVTVSSGGG   540
GSGGGGSGGG GSDIQMTQSP SSLSASVGDR VTITCKASQN VGTNVGWYQQ KPGKAPKALI   600
YSASFRYSGV PSRFSGSGSG TDFTLTISSL QPEDFATYYC QQYYTYPYTF GGGTKVEIKH   660
HHHHH                                                              665

SEQ ID NO: 638          moltype = AA  length = 665
FEATURE                 Location/Qualifiers
source                  1..665
                        mol_type = protein
                        organism = synthetic construct
SEQUENCE: 638
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTSGGPGPA GMKGLPGSGG GGSGGGGSGG GGSGGGGSGG GGSGGGGSEV   180
QLVESGGGLV QPGGSLRLSC AASGFTFSSY TLAWVRQAPG KGLEWVAAID SSSYTYSPDT   240
VRGRFTISRD NAKNSLYLQM NSLRAEDTAV YYCARDSNWD ALDYWGQGTT VTVSSGGGGS   300
GGGGSGGGGS DIQMTQSPSS LSASVGDRVT ITCKASQNVG TNVGWYQQKP GKAPKALIYS   360
ASFRYSGVPS RFSGSGSGTD FTLTISSLQP EDFATYYCQQ YYTYPYTFGG GTKVEIKSGG   420
PGPAGMKGLP GSVPRDCGCK PCICTVPEVS SVFIFPPKPK DVLTITLTPK VTCVVVDISK   480
DDPEVQFSWF VDDVEVHTAQ TQPREEQFNS TFRSVSELPI MHQDWLNGKE FKCRVNSAAF   540
PAPIEKTISK TKGRPKAPQV YTIPPPKEQM AKDKVSLTCM ITDFFPEDIT VEWQWNGQPA   600
ENYKNTQPIM DTDGSYFVYS KLNVQKSNWE AGNTFTCSVL HEGLHNHHTE KSLSHSPGKH   660
HHHHH                                                              665

SEQ ID NO: 639          moltype = AA  length = 558
FEATURE                 Location/Qualifiers
source                  1..558
                        mol_type = protein
                        organism = synthetic construct
SEQUENCE: 639
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTGGGSGGG SGGGSGGGSE VQLVESGGGL VQPGNSLRLS CAASGFTFSK   180
FGMSWVRQAP GKGLEWVSSI SGSGRDTLYA ESVKGRFTIS RDNAKTTLYL QMNSLRPEDT   240
AVYYCTIGGS LSVSSQGTLV TVSSGGGGS GGGSGGGGSG GGGSSGGPGP              300
AGMKGLPGSE VQLVESGGGL VQPGGSLRLS CAASGFTFSS YTLAWVRQAP GKGLEWVAAI   360
DSSSYTYSPD TVRGRFTISR DNAKNSLYLQ MNSLRAEDTA VYYCARDSNW DALDYWGQGT   420
TVTVSSGGGG SGGGGSGGGG SDIQMTQSPS SLSASVGDRV TITCKASQNV GTNVGWYQQK   480
PGKAPKALIY SASFRYSGVP SRFSGSGSGT DFTLTISSLQ PEDFATYYCQ QYYTYPYTFG   540
GGTKVEIKHH HHHHEPEA                                                558

SEQ ID NO: 640          moltype = AA  length = 273
FEATURE                 Location/Qualifiers
source                  1..273
                        mol_type = protein
                        organism = synthetic construct
SEQUENCE: 640
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTSGGPGPA GMKGLPGSEV QLVESGGGLV QPGNSLRLSC AASGFTFSKF   180
```

```
GMSWVRQAPG KGLEWVSSIS GSGRDTLYAE SVKGRFTISR DNAKTTLYLQ MNSLRPEDTA   240
VYYCTIGGSL SVSSQGTLVT VSSHHHHHHE PEA                                273

SEQ ID NO: 641          moltype = AA  length = 659
FEATURE                 Location/Qualifiers
source                  1..659
                        mol_type = protein
                        organism = synthetic construct
SEQUENCE: 641
VPRDCGCKPC ICTVPEVSSV FIFPPKPKDV LTITLTPKVT CVVVDISKDD PEVQFSWFVD   60
DVEVHTAQTQ PREEQFNSTF RSVSELPIMH QDWLNGKEFK CRVNSAAFPA PIEKTISKTK   120
GRPKAPQVYT IPPPKEQMAK DKVSLTCMIT DFFPEDITVE WQWNGQPAEN YKNTQPIMDT   180
DGSYFVYSKL NVQKSNWEAG NTFTCSVLHE GLHNHHTEKS LSHSPGKSGG PGPAGLYAQP   240
GSAPTSSSTK KTQLQLEHLL LDLQMILNGI NNYKNPKLTR MLTFKFYMPK KATELKHLQC   300
LEEELKPLEE VLNLAQSKNF HLRPRDLISN INVIVLELKG SETTFMCEYA DETATIVEFL   360
NRWITFCQSI ISTLTGGGGS GGGGSGGGGS GGGGSGGGGS GGGGSSGGPG PAGLYAQPGS   420
EVQLVESGGG LVQPGGSLRL SCAASGFTFS SYTLAWVRQA PGKGLEWVAA IDSSSYTYSP   480
DTVRGRFTIS RDNAKNSLYL QMNSLRAEDT AVYYCARDSN WDALDYWGQG TTVTVSSGGG   540
PGPAGLYAQP GSDIQMTQSP SSLSASVGDR VTITCKAREK LWSAVAWYQQ KPGKAPKSLI   600
YSASFRYSGV PSRFSGSGSG TDFTLTISSL QPEDFATYYC QQYYTYPYTF GGGTKVEIK    659

SEQ ID NO: 642          moltype = AA  length = 659
FEATURE                 Location/Qualifiers
source                  1..659
                        mol_type = protein
                        organism = synthetic construct
SEQUENCE: 642
VPRDCGCKPC ICTVPEVSSV FIFPPKPKDV LTITLTPKVT CVVVDISKDD PEVQFSWFVD   60
DVEVHTAQTQ PREEQFNSTF RSVSELPIMH QDWLNGKEFK CRVNSAAFPA PIEKTISKTK   120
GRPKAPQVYT IPPPKEQMAK DKVSLTCMIT DFFPEDITVE WQWNGQPAEN YKNTQPIMDT   180
DGSYFVYSKL NVQKSNWEAG NTFTCSVLHE GLHNHHTEKS LSHSPGKSGG PGPAGLYAQP   240
GSAPTSSSTK KTQLQLEHLL LDLQMILNGI NNYKNPKLTR MLTFKFYMPK KATELKHLQC   300
LEEELKPLEE VLNLAQSKNF HLRPRDLISN INVIVLELKG SETTFMCEYA DETATIVEFL   360
NRWITFCQSI ISTLTGGGGS GGGGSGGGGS GGGGSGGGGS GGGGSSGGPG PAGLYAQPGS   420
EVQLVESGGG LVQPGGSLRL SCAASGFTFS SYTLAWVRQA PGKGLEWVAA IDSSSYTYSP   480
DTVRGRFTIS RDNAKNSLYL QMNSLRAEDT AVYYCARDSN WDALDYWGQG TTVTVSSGGG   540
GSGGGGSGGG GSDIQMTQSP SSLSASVGDR VTITCKAREK LWSAVAWYQQ KPGKAPKSLI   600
YSASFRYSGV PSRFSGSGSG TDFTLTISSL QPEDFATYYC QQYYTYPYTF GGGTKVEIK    659

SEQ ID NO: 643          moltype = AA  length = 659
FEATURE                 Location/Qualifiers
source                  1..659
                        mol_type = protein
                        organism = synthetic construct
SEQUENCE: 643
VPRDCGCKPC ICTVPEVSSV FIFPPKPKDV LTITLTPKVT CVVVDISKDD PEVQFSWFVD   60
DVEVHTAQTQ PREEQFNSTF RSVSELPIMH QDWLNGKEFK CRVNSAAFPA PIEKTISKTK   120
GRPKAPQVYT IPPPKEQMAK DKVSLTCMIT DFFPEDITVE WQWNGQPAEN YKNTQPIMDT   180
DGSYFVYSKL NVQKSNWEAG NTFTCSVLHE GLHNHHTEKS LSHSPGKSGG PGPAGLYAQP   240
GSAPTSSSTK KTQLQLEHLL LDLQMILNGI NNYKNPKLTR MLTFKFYMPK KATELKHLQC   300
LEEELKPLEE VLNLAQSKNF HLRPRDLISN INVIVLELKG SETTFMCEYA DETATIVEFL   360
NRWITFCQSI ISTLTGGGGS GGGGSGGGGS GGGGSGGGGS GGGGSSGGPG PAGLYAQPGS   420
EVQLVESGGG LVQPGGSLRL SCAASGFTFS SYTLAWVRQA PGKGLEWVAA IDSSSYTYSP   480
DTVRGRFTIS RDNAKNSLYL QMNSLRAEDT AVYYCARDSN WDALDYWGQG TTVTVSSGGG   540
PGPAGLYAQP GSDIQMTQSP SSLSASVGDR VTITCKVTEK VWGNVAWYQQ KPGKAPISLI   600
YSPSLRKSGV PSRFSGSGSG TDFTLTISSL QPEDFATYYC QQYYTYPYTF GGGTKVEIK    659

SEQ ID NO: 644          moltype = AA  length = 659
FEATURE                 Location/Qualifiers
source                  1..659
                        mol_type = protein
                        organism = synthetic construct
SEQUENCE: 644
VPRDCGCKPC ICTVPEVSSV FIFPPKPKDV LTITLTPKVT CVVVDISKDD PEVQFSWFVD   60
DVEVHTAQTQ PREEQFNSTF RSVSELPIMH QDWLNGKEFK CRVNSAAFPA PIEKTISKTK   120
GRPKAPQVYT IPPPKEQMAK DKVSLTCMIT DFFPEDITVE WQWNGQPAEN YKNTQPIMDT   180
DGSYFVYSKL NVQKSNWEAG NTFTCSVLHE GLHNHHTEKS LSHSPGKSGG PGPAGLYAQP   240
GSAPTSSSTK KTQLQLEHLL LDLQMILNGI NNYKNPKLTR MLTFKFYMPK KATELKHLQC   300
LEEELKPLEE VLNLAQSKNF HLRPRDLISN INVIVLELKG SETTFMCEYA DETATIVEFL   360
NRWITFCQSI ISTLTGGGGS GGGGSGGGGS GGGGSGGGGS GGGGSSGGPG PAGLYAQPGS   420
EVQLVESGGG LVQPGGSLRL SCAASGFTFS SYTLAWVRQA PGKGLEWVAA IDSSSYTYSP   480
DTVRGRFTIS RDNAKNSLYL QMNSLRAEDT AVYYCARDSN WDALDYWGQG TTVTVSSGGG   540
GSGGGGSGGG GSDIQMTQSP SSLSASVGDR VTITCKVTEK VWGNVAWYQQ KPGKAPISLI   600
YSPSLRKSGV PSRFSGSGSG TDFTLTISSL QPEDFATYYC QQYYTYPYTF GGGTKVEIK    659

SEQ ID NO: 645          moltype = AA  length = 539
FEATURE                 Location/Qualifiers
source                  1..539
                        mol_type = protein
```

```
                            organism = synthetic construct
SEQUENCE: 645
VPRDCGCKPC ICTVPEVSSV FIFPPKPKDV LTITLTPKVT CVVVDISKDD PEVQFSWFVD    60
DVEVHTAQTQ PREEQFNSTF RSVSELPIMH QDWLNGKEFK CRVNSAAFPA PIEKTISKTK   120
GRPKAPQVYT IPPPKEQMAK DKVSLTCMIT DFFPEDITVE WQWNGQPAEN YKNTQPIMDT   180
DGSYFVYSKL NVQKSNWEAG NTFTCSVLHE GLHNHHTEKS LSHSPGKSGG PGPAGLYAQP   240
GSAPTSSSTK KTQLQLEHLL LDLQMILNGI NNYKNPKLTR MLTFKFYMPK KATELKHLQC   300
LEEELKPLEE VLNLAQSKNF HLRPRDLISN INVIVLELKG SETTFMCEYA DETATIVEFL   360
NRWITFCQSI ISTLTGGGGS GGGGSGGGGS GGGGSGGGGS GGGGSSGGPG PAGLYAQPGS   420
EVQLLESGGG LVQPGGSLRL SCAASGSIFS ANAMGWYRQA PGKGLELVAV ISSGGSTNYA   480
DSVKGRFTIS RDNSKNTVYL QMNSLRAEDT AVYYCMYSGS YYYTPNDYWG QGTLVTVSS    539

SEQ ID NO: 646          moltype = AA  length = 538
FEATURE                 Location/Qualifiers
source                  1..538
                        mol_type = protein
                        organism = synthetic construct
SEQUENCE: 646
VPRDCGCKPC ICTVPEVSSV FIFPPKPKDV LTITLTPKVT CVVVDISKDD PEVQFSWFVD    60
DVEVHTAQTQ PREEQFNSTF RSVSELPIMH QDWLNGKEFK CRVNSAAFPA PIEKTISKTK   120
GRPKAPQVYT IPPPKEQMAK DKVSLTCMIT DFFPEDITVE WQWNGQPAEN YKNTQPIMDT   180
DGSYFVYSKL NVQKSNWEAG NTFTCSVLHE GLHNHHTEKS LSHSPGKSGG PGPAGLYAQP   240
GSAPTSSSTK KTQLQLEHLL LDLQMILNGI NNYKNPKLTR MLTFKFYMPK KATELKHLQC   300
LEEELKPLEE VLNLAQSKNF HLRPRDLISN INVIVLELKG SETTFMCEYA DETATIVEFL   360
NRWITFCQSI ISTLTGGGGS GGGGSGGGGS GGGGSGGGGS GGGGSSGGPG PAGLYAQPGS   420
EVQLLESGGG LVQPGGSLRL SCAASERIFS TDVMGWYRQA PGKQRELVAV VSARGTTNYL   480
DAVKGRFTIS RDNSKNTLYL QMNSLRAEDT AVYYCYVRET TSPWRIYWGQ GTLVTVSS    538

SEQ ID NO: 647          moltype = AA  length = 930
FEATURE                 Location/Qualifiers
source                  1..930
                        mol_type = protein
                        organism = synthetic construct
SEQUENCE: 647
EVQLVESGGG LVQPGNSLRL SCAASGFTFS KFGMSWVRQA PGKGLEWVSS ISGSGRDTLY    60
AESVKGRFTI SRDNAKTTLY LQMNSLRPED TAVYYCTIGG SLSVSSQGTL VTVSSSGGPG   120
PAGLYAQPGS IWELKKDVYV VELDWYPDAP GEMVVLTCDT PEEDGITWTL DQSSEVLGSG   180
KTLTIQVKEF GDAGQYTCHK GGEVLSHSLL LLHKKEDGIW STDILKDQKE PKNKTFLRCE   240
AKNYSGRFTC WWLTTISTDL TFSVKSSRGS SDPQGVTCGA ATLSAERVRG DNKEYEYSVE   300
CQEDSACPAA EESLPIEVMV DAVHKLKYEN YTSSFFIRDI IKPDPPKNLQ LKPLKNSRQV   360
EVSWEYPDTW STPHSYFSLT FCVQVQGKSK REKKDRVFTD KTSATVICRK NASISVRAQD   420
RYYSSSWSEW ASVPCSGGGG SGGGGSGGGG SRVIPVSGPA RCLSQSRNLL KTTDDMVKTA   480
REKLKHYSCT AEDIDHEDIT RDQTSTLKTC LPLELHKNES CLATRETSST TRGSCLPPQK   540
TSLMMTLCLG SIYEDLKMYQ TEFQAINAAL QNHNHQQIIL DKGMLVAIDE LMQSLNHNGE   600
TLRQKPPVGE ADPYRVKMKL CILLHAFSTR VVTINRVMGY LSSASGGPGP AGLYAQPGSG   660
GGGSGGGGSG GGGSGGGGSG GGGSGGGSQ SVLTQPPSVS GAPGQRVTIS CSGSRSNIGS   720
NTVKWYQQLP GTAPKLLIYY NDQRPSGVPD RFSGSKSGTS ASLAITGLQA EDEADYYCQS   780
YDRYTHPALL FGTGTKVTVL GGGGSGGGGS GGGGSQVQLV ESGGGVVQPG RSLRLSCAAS   840
GFTFSSYGMH WVRQAPGKGL EWVAFIRYDG SNKYYADSVK GRFTISRDNS KNTLYLQMNS   900
LRAEDTAVYY CKTHGSHDNW GQGTMVTVSS                                   930
```